US012691068B2

(12) United States Patent
Zhang et al.

(10) Patent No.: US 12,691,068 B2
(45) **Date of Patent: *Jul. 28, 2026**

(54) MODULAR LIPID COMPOUNDS AND TWO-TO THREE-COMPONENT LIPID NANOPARTICLE COMPOSITIONS

(71) Applicant: SunVax mRNA Therapeutics Inc., Beverly, MA (US)

(72) Inventors: Libin Zhang, Lynnfield, MA (US); Yingzhong Li, Reading, MA (US)

(73) Assignee: Sun Vax mRNA Therapeutics Inc., Beverly, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/396,075

(22) Filed: Dec. 26, 2023

(65) Prior Publication Data

US 2024/0261223 A1 Aug. 8, 2024

Related U.S. Application Data

(60) Provisional application No. 63/477,252, filed on Dec. 27, 2022.

(51) Int. Cl.

| | |
|---|---|
| ***A61K 9/127*** | (2025.01) |
| ***A61K 9/1271*** | (2025.01) |
| ***A61K 9/1272*** | (2025.01) |
| ***C07C 231/02*** | (2006.01) |
| ***C07D 211/34*** | (2006.01) |
| ***C07D 251/04*** | (2006.01) |
| ***C12N 15/113*** | (2010.01) |

(52) U.S. Cl.

CPC .......... *A61K 9/1272* (2013.01); *A61K 9/1271* (2013.01); *C07C 231/02* (2013.01); *C07D 211/34* (2013.01); *C07D 251/04* (2013.01); *C12N 15/113* (2013.01); *C12N 2310/11* (2013.01); *C12N 2310/14* (2013.01)

(58) Field of Classification Search

CPC ...... A61K 9/1272; A61K 9/1271; A61K 9/00; A61K 9/5123; C07C 231/02; C07D 211/34; C07D 251/04; C12N 15/113; C12N 2310/11; C12N 2310/14; C07H 7/033

See application file for complete search history.

(56) References Cited

U.S. PATENT DOCUMENTS

| | | | | |
|---|---|---|---|---|
| 6,020,526 A * | 2/2000 | Schwartz ............. | C07K 5/0815 562/561 |
| 2017/0007709 A1 | 1/2017 | Kurosawa et al. | |
| 2022/0162521 A1 | 5/2022 | Drummond et al. | |
| 2023/0390402 A1 | 12/2023 | Liu et al. | |

FOREIGN PATENT DOCUMENTS

| | | | |
|---|---|---|---|
| CN | 109 549 934 B | 3/2021 |
| CN | 114 904 002 A | 8/2022 |
| KR | 10-2023-0124927 A | 8/2023 |
| WO | 99/29705 A2 | 6/1999 |
| WO | 2016/203025 A1 | 12/2016 |
| WO | 2020/190750 A1 | 9/2020 |
| WO | 2023/064599 A1 | 4/2023 |
| WO | 2023/196527 A2 | 10/2023 |

OTHER PUBLICATIONS

Dehghan et al. (Monatshefte für Chemie—Chemical Monthly 2020, 151, 397-404).*

Brown et al. (Nucleic Acids Research, 2020, vol. 48, No. 21 11827-11844).*

Jing et al., "Steric groups fusion strategy for green multi-resonance emitters toward efficient OLEDs with narrowband emission," Dyes and Pigments 219 (2023) 111520, https://doi.org/10.1016/j.dyepig.2023.111520, 7 pages.

Yu et al., "Impact of crosslinking agents with steric cyclic groups on the properties of polymer-dispersed liquid crystals," Phys. Chem. Chem. Phys., 2024, 26, pp. 7388-7739, DOI: 10.1039/d3cp05683j.

Kappes, Thomas et al: "The tetrabenzylglucosyloxycarbonyl(B Gloc)-group-A carbohydrate-derived enzyme-labile urethane protecting group", Carbohydrate Research, Dec. 1, 1997 (Dec. 1, 1997), pp. 341-349.

Furuta, Tomoyuki et al: "Nutrient-Based Chemical Library as a Source of Energy Metabolism Modulators", ACS Chemical Biology, vol. 14, No. 9, Aug. 22, 2019 (Aug. 22, 2019), pp. 1860-1865.

Vass, E. et al: "Spectroscopic evidence of beta-turn in N-glycated peptidomimetics related to leucine-enkephalin", Spectrochimica Acta Part A: Molecular and Biomolecular Spectroscopy, vol. 56, No. 12, Nov. 1, 2000 (Nov. 1, 2000), pp. 2479-2489.

Jullien, Ludovic et al: "The "Chundle" Approach to Molecular Channels Synthesis of a Macrocycle-Based Molecular Bundle", Tetrahedron Letters, vol. 29, No. 31 (1988), pp. 3803-3806.

Jullien, Ludovic, et al. "An Approach to Channel Type Molecular Structures. 1. Synthesis of Bouquet-Shaped Molecules Based on an [18]-O6 Polyether Macrocycle.", Journal of Inclusion Phenomena and Molecular Recognition in Chemistry, The Pedersen Memorial Issue (Jan. 1, 1992), pp. 55-74.

Yang, Sunny Y. et al: "Real-time and quantitative fluorescent live-cell imaging with quadruplex-specific red-edge probe (G4-REP)", Biochimica Et Biophysica Acta, vol. 1861, No. 5, Dec. 10, 2016, pp. 1312-1320.

(Continued)

*Primary Examiner* — Michael G. Hartley
*Assistant Examiner* — Melissa J Perreira
(74) *Attorney, Agent, or Firm* — ROTHWELL, FIGG, ERNST & MANBECK, P.C.

(57) ABSTRACT

Novel delivery nanoparticles composes of two-, or three-component lipid compounds. Compositions comprising such lipid compounds, and related methods of their use are disclosed. Nanoparticle compositions include at least one novel modular lipid as well as additional lipids such as ionizable lipids, and phospholipids. Nanoparticle compositions further including biologically active agents, such as siRNA or mRNA, are useful in the delivery of said biologically active agents to subjects in need thereof.

14 Claims, 15 Drawing Sheets

(56) References Cited

OTHER PUBLICATIONS

Sato, Koji et al: "Syntheses of new peptidic glycoclusters derived from β-alanine: di-and trimerized glycoclusters and glycocluster-clusters.", Carbohydrate Research, vol. 341, No. 7, May 22, 2006, pp. 836-845.
Zhang, Jundong et al: "Identification of Inhibitors of Heparin-Growth Factor Interactions from Combinatorial Libraries of Four-Component Condensation Reactions", Bioorganic & Medicinal Chemistry, vol. 9, No. 4, Apr. 1, 2001, pp. 825-836.
International Search Report and Written Opinion for PCT/US2023/085919 dated Dec. 11, 2024 (33 pages).
Written Opinion issued for International Application No. PCT/US2023/085919 on May 20, 2025, 19 pages.
International Preliminary Report on Patentability issued for International Application No. PCT/US2023/085919 on Jul. 15, 2025, 20 pages.

* cited by examiner

MODULAR LIPID COMPOUNDS AND TWO-TO THREE-COMPONENT LIPID NANOPARTICLE COMPOSITIONS

CROSS-REFERENCE TO RELATED APPLICATION

This application claims priority benefit of U.S. Provisional Appl. No. 63/477,252 filed on Dec. 27, 2022, the disclosures of which are incorporated herein by reference in their entireties.

TECHNICAL FIELD

The present disclosure provides novel lipids, lipid nanoparticle compositions, and related methods of their synthesis and uses.

BACKGROUND

Treatment of diseases using biologically active substances such as small molecule drugs, proteins, and nucleic acids, including DNA and RNA, represent promising alternatives to conventional approaches for vaccination or treatment of diseases because of their potential for higher potency, rapid development, low-cost manufacture, and safe administration.

A recent development in the field uses bipolar lipids, such as phosphor-lipids or amine-lipids, which assemble into monolayers or sphere, to deliver drugs, such as therapeutic proteins, compounds, or nucleic acids. During the last two decades, numerous bipolar lipids along with helper lipids, referred to as lipid nanoparticles (LNP), were developed for delivery of nucleic acids, especially for delivery of ribonucleic acids (RNA). Currently, various RNA vaccine platforms against infectious diseases, hereditary diseases, and several types of cancer have demonstrated encouraging results in both animal models and humans. Notably, such platforms including the mRNA COVID vaccines require use of a four component LNP delivery system to achieve a prophylactic effect in humans.

However, while recent developments in this field have addressed some issues such as the relative instability and low cell permeability leading to reduced expression in vivo, delivery of these biologically active substances still presents safety concerns. For example, safety concerns using the conventional four-component lipid nanoparticle (LNP) delivery system include local and systemic inflammation, biodistribution and persistence of expressed immunogens, stimulation of auto-reactive antibodies, and potential toxic effects of delivery system components. Additionally, achieving adequate antigen expression for protection or immunomodulation using four-component LNPs for delivery of therapeutic mRNAs remains a medical challenge and unmet need.

Thus, there exists a need to develop compounds, compositions, and methods that improve stability, facilitate internalization, increase target affinity of nucleic acid therapeutics, and reduce safety issues.

SUMMARY OF THE INVENTION

The present disclosure provides novel lipids, LNP compositions, methods of synthesis, and methods of using novel lipids and compositions of the present disclosure.

In one aspect, the present disclosure provides a nanoparticle composition comprising an ionizable lipid component and a saccharide lipid component.

In one aspect, the present disclosure provides a two-component LNP composition, wherein the two lipid components are an modular lipid component and a stabilizer lipid component, wherein the stabilizer lipid component is a saccharide lipid compound or a PEG lipid, wherein the modular lipid component comprises from about 0.5 mol % to about 99.5 mol % of the total lipid present in the particle, or any subranges thereof, e.g., 0.5-9.5, 1-10, 11-20, 21-30, 31-40, 41-50, 51-60, 61-70, 71-80, 81-90, 91-99, 2-20, 21-40, 41-60, 61-80, 2-98, 5-25, 26-45, 46-65, 70-95, 3-30, 31-60, 61-90, 10-80, 15-85, 55.5-99.5 mol %, or any range or value within any of the recited ranges, and wherein stabilizer lipid component comprises from about 0.5 mol % to about 99.5 mol % of the total lipid present in the particle, or any subranges thereof, e.g., 0.5-9.5, 1-10, 11-20, 21-30, 31-40, 41-50, 51-60, 61-70, 71-80, 81-90, 91-99, 2-20, 21-40, 41-60, 61-80, 2-98, 5-25, 26-45, 46-65, 70-95, 3-30, 31-60, 61-90, 10-80, 15-85, 55.5-99.5 mol %, or any range or value within any of the recited ranges.

In one aspect, the present disclosure provides a three-component LNP composition, wherein the three lipid components are a modular lipid or ionizable lipid component, a stabilizer lipid component, and a phospholipid component, wherein the stabilizer lipid component is a saccharide lipid compound or a PEG lipid, wherein the phospholipid component comprises from about 5 to 60 mol % of the total lipid present in the particle, or any subranges thereof, e.g. 5 to 15, 10 to 20, 15 to 25, 20 to 30, 25 to 35, 30 to 40, 35 to 45, 40 to 50, 45 to 55, 50 to 60, 5 to 25, 15 to 35, 25 to 45, 35 to 55, or 10 to 50 mol %, wherein the stabilizer lipid component comprises from about 0.2 to 80 mol % of the total lipid present in the particle or any subranges thereof, e.g. 0.2 to 5.5, 5.5 to 10, 7.5 to 15, 10 to 20, 15 to 25, 20 to 30, 25 to 35, 30 to 40, 35 to 45, 38 to 50, 42 to 55, 45 to 60, 48 to 65, 50 to 70, 55 to 75, 60 to 80, or 70 to 80 mol %, wherein the modular lipid or ionizable lipid component comprises from about 5 to 80 mol % of the total lipid present in the particle, or any subranges thereof, e.g. 5 to 15, 10 to 20, 15 to 25, 20 to 30, 25 to 35, 30 to 40, 35 to 45, 40 to 50, 45 to 55, 50 to 60, 55 to 65, 60 to 70, 65 to 75, 70 to 80, 5 to 25, 15 to 35, 25 to 45, 35 to 55, 10 to 50, 20 to 60, 30 to 70, or 40 to 80 mol %.

In one aspect, the present disclosure provides a three-component LNP composition, wherein the three lipid components are a modular lipid component, a ionizable lipid component, and a phospholipid component, wherein the stabilizer lipid component is a saccharide lipid compound or a PEG lipid, wherein the phospholipid component comprises from about 15 mol % to about 55 mol % of the total lipid present in the particle, or any subranges thereof, e.g. 15 to 20, 18 to 25, 20 to 30, 22 to 35, 25 to 40, 28 to 45, 30 to 50, 33 to 55, 35 to 40, 40 to 45, 45 to 50, or 50 to 55 mol %, wherein the modular lipid component comprises from about 3 mol % to about 25 mol % of the total lipid present in the particle, or any subranges thereof, e.g. 3 to 10, 5 to 15, 8 to 20, 12 to 25, 15 to 30, 20 to 35, 25 to 40, 30 to 45, or 35 to 50 mol % wherein the ionizable lipid component comprises from about 30 mol % to about 80 mol % of the total lipid present in the particle, or any subranges thereof, e.g. 30 to 40, 35 to 45, 38 to 50, 42 to 55, 45 to 60, 48 to 65, 50 to 70, 55 to 75, 60 to 80, 32 to 42, 38 to 48, 40 to 50, 45 to 55, 48 to 58, 55 to 65, 58 to 68, 62 to 72, or 70 to 80 mol %.

In one aspect, the present disclosure provides modular LNP (mLNP) compositions comprising compounds of Formula (I):

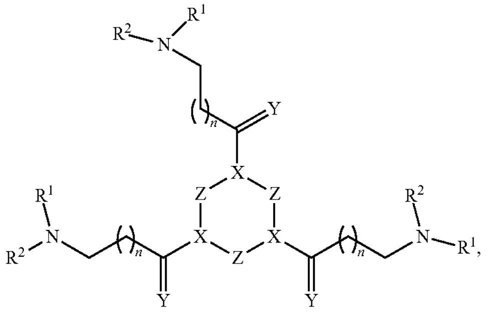

(I)

wherein an integer from 0-10, e.g., 0, 1, 2, 3, 4, 5, 6, 7, 8, 9, or 10, or any subrange selected from within the range of 0-10, e.g., 2-9, 3-8, 4-7, 1-5, 1-4, 5-9, etc.;

each of $R^1$ and $R^2$ is independently selected from H, C1-C24 alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

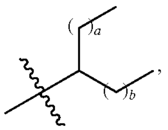
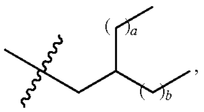
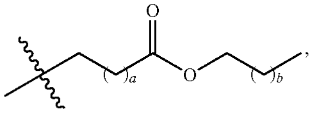
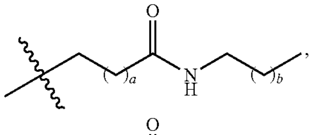
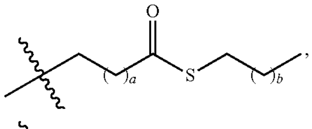
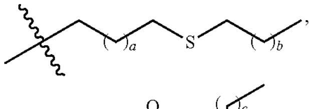
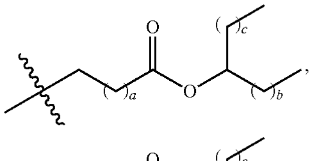
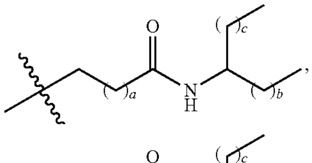
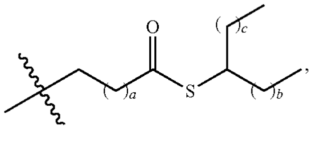

-continued

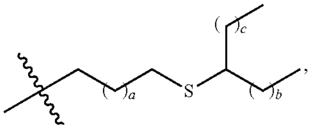
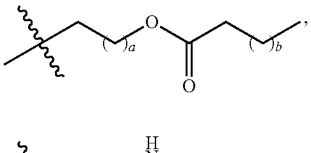
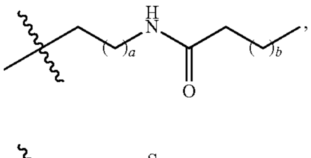
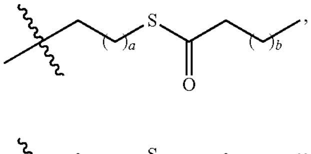
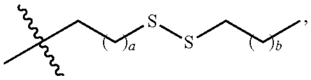
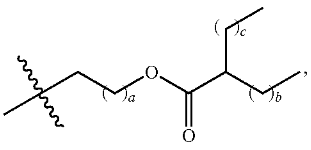
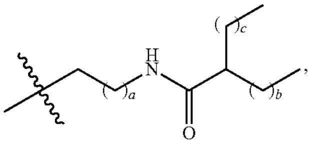
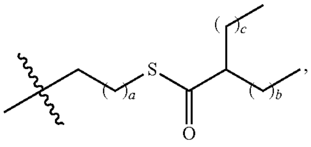
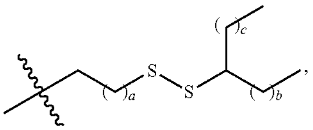
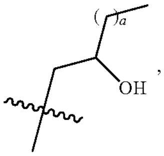
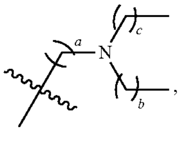
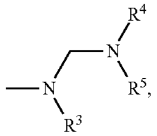

a, b and c are each independently an integer from 1-24;

each X is independently selected from CH, or N;

each Y is independently selected from $CH_2$, NH, O, or S; and each Z is independently selected from $CH_2$, NH, O, or S.

In certain aspects, compounds of Formula II may include, for example, the following compounds:

(Ia)

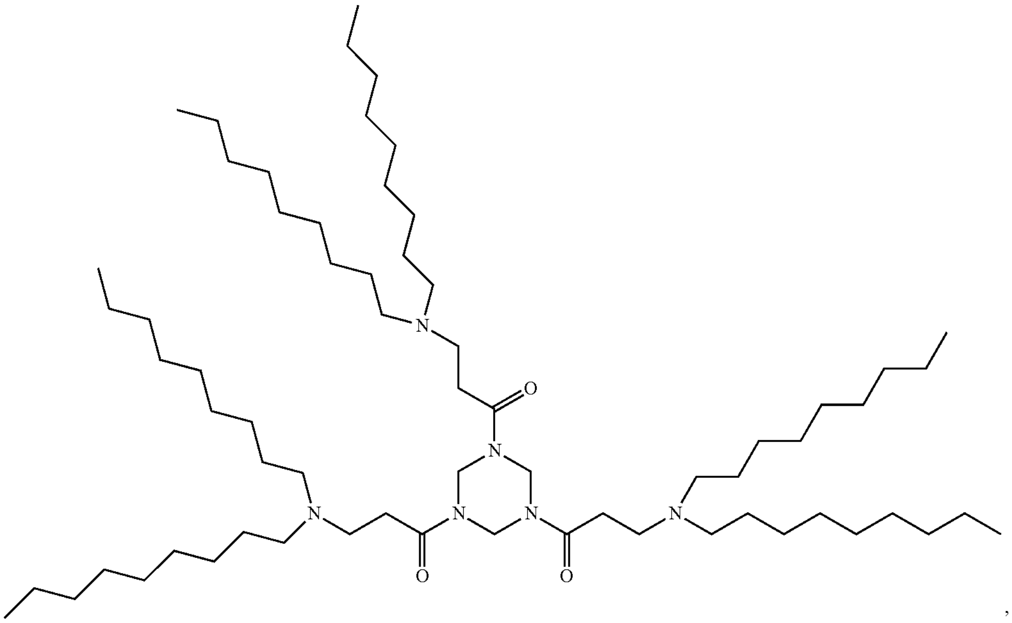

, (Ib)

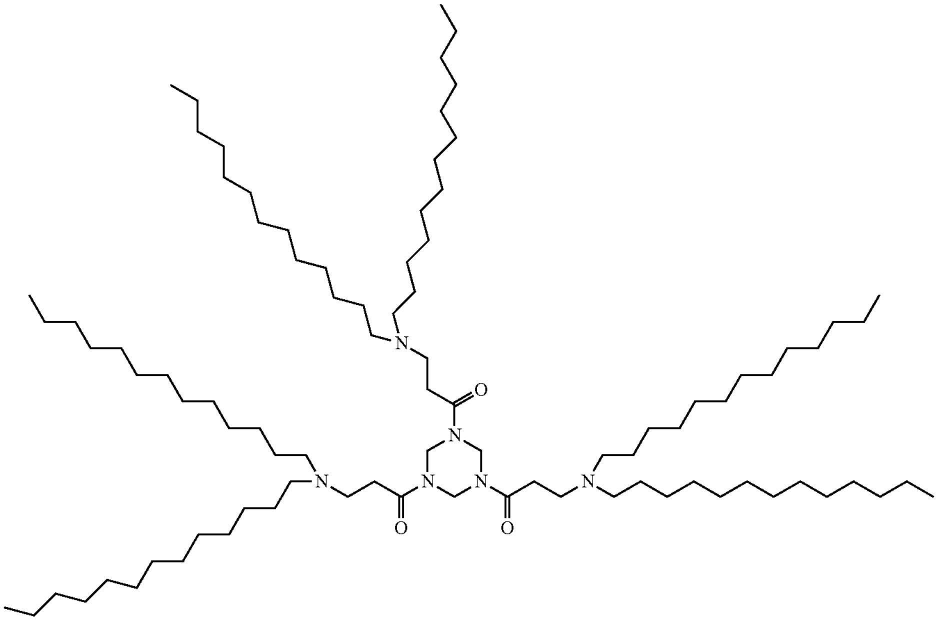

or a salt or isomer thereof.

In one aspect, the present disclosure provides mLNP compositions comprising compounds of Formula (II):

(II)

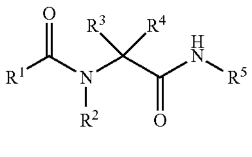

or a salt or isomer thereof, wherein each of $R^1$, $R^4$ and $R^5$ is independently selected from $C_2$-$C_{24}$ alkyl, $C_2$-$C_{24}$ alkenyl, $C_2$-$C_{24}$ alkynyl, substituted $C_2$-$C_{24}$ alkyl, substituted alkenyl, substituted alkynyl, substituted acyl, substituted carbocyclyl, substituted heterocyclyl, substituted aryl, substituted heteroaryl, poly(ethylene glycol) (PEG),

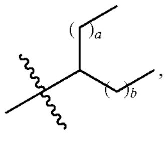

,

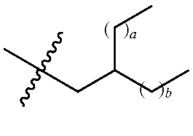

,

-continued
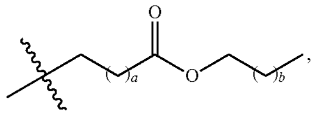
,
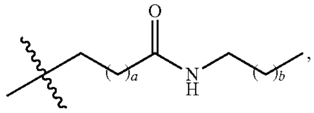
,
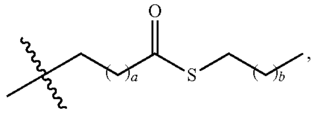
,
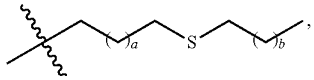
,
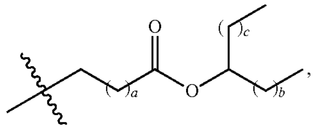
,
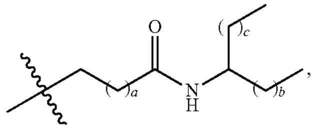
,
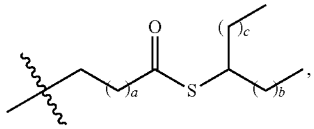
,
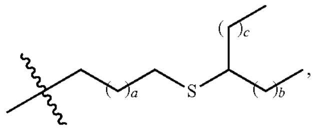
,
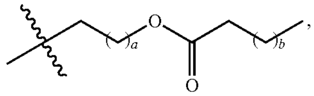
,
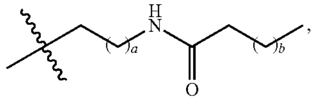
,
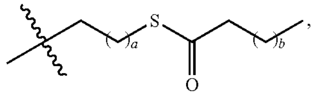
,
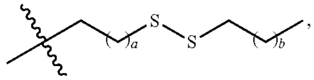
,
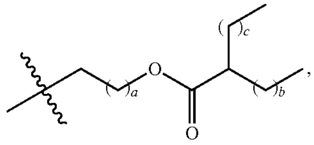
,
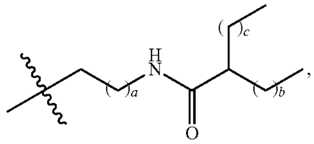
,
-continued
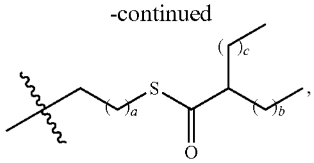
,
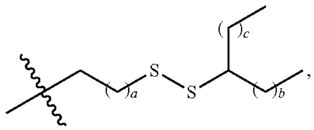
,
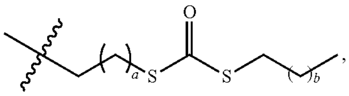
,
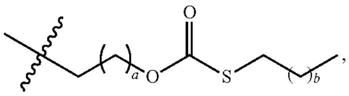
,
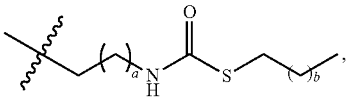
,
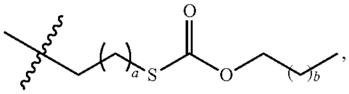
,
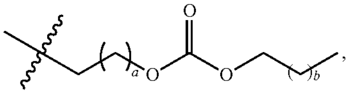
,
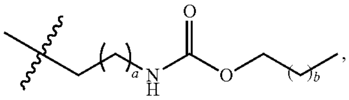
,
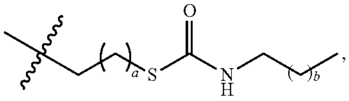
,
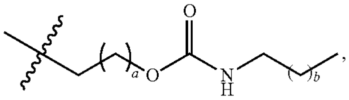
,
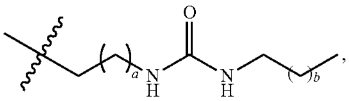
,
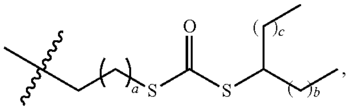
,
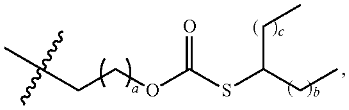
,
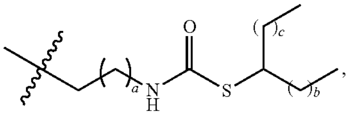
,
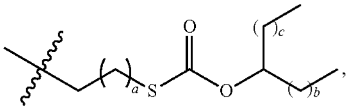
,
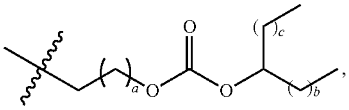
, -continued
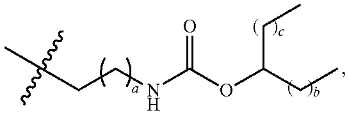,
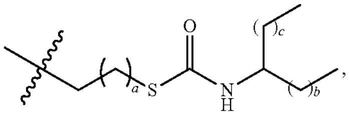,
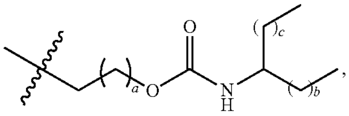,
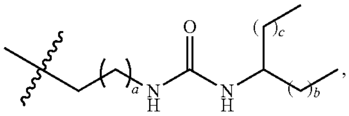, 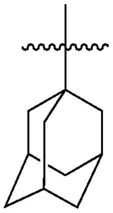,
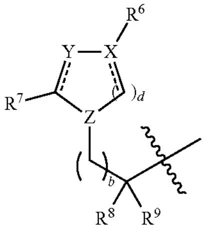, 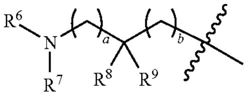,
each of $R^2$ and $R^3$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl, poly(ethylene glycol) (PEG),
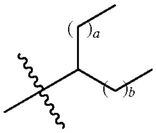, 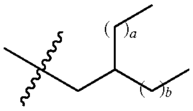,
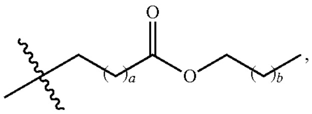,
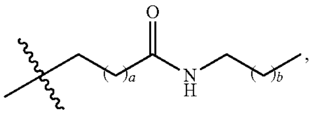,
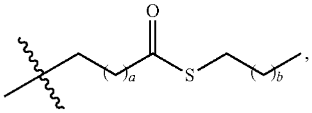,
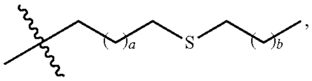,
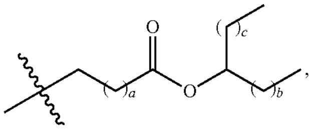,
-continued
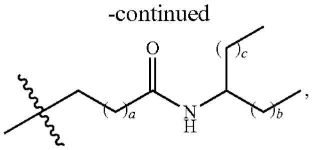,
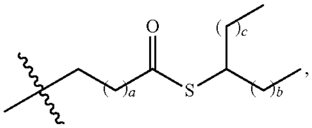,
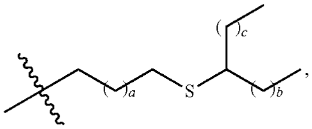,
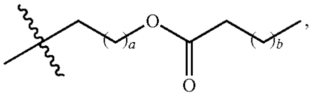,
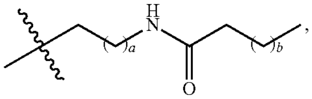,
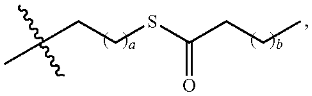,
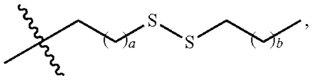,
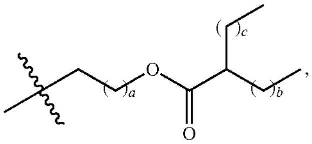,
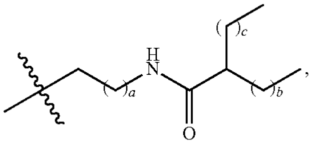,
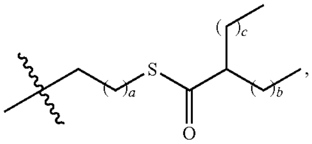,
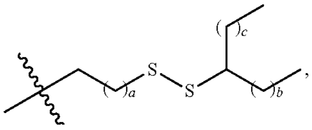,
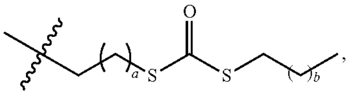,
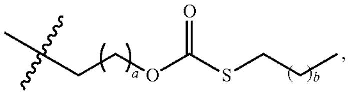,
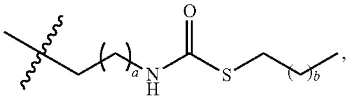,
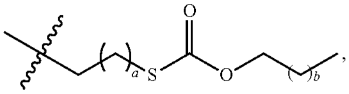, -continued
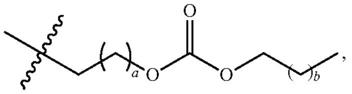
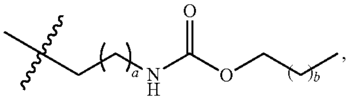
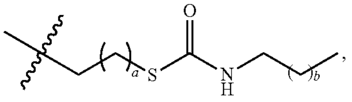
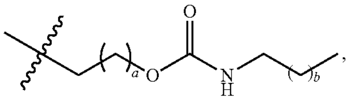
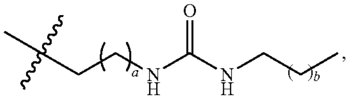
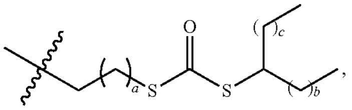
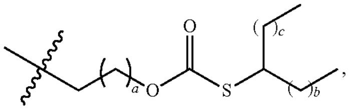
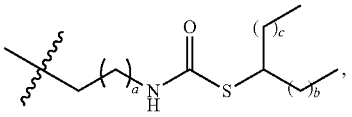
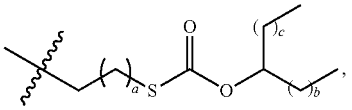
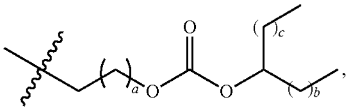
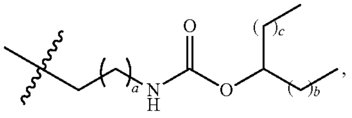
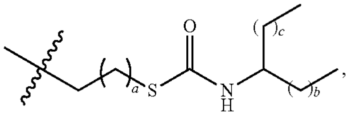
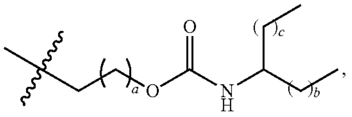
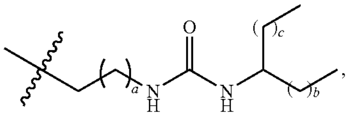
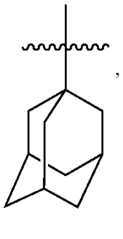
-continued
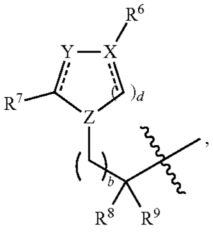
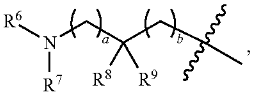
a, b and c are each independently an integer from 0-24;
each of $R^6$, $R^7$, $R^8$, $R^9$ is independently selected from H, C1-C24 alkyl, C1-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl,
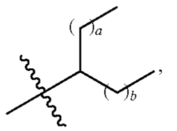
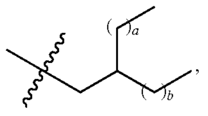
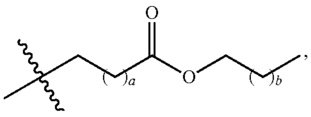
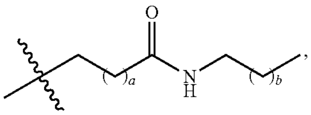
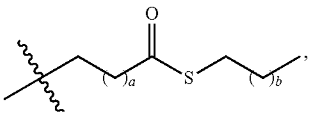
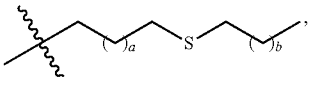
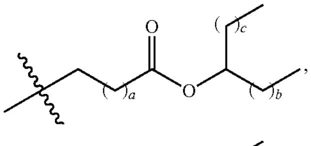
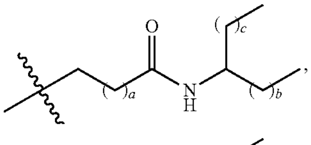
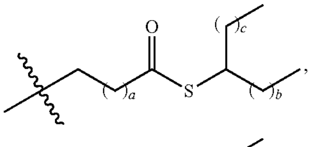
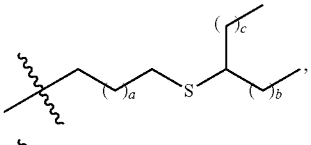
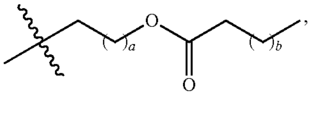

-continued
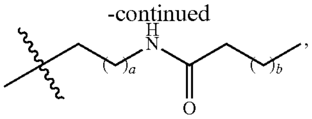
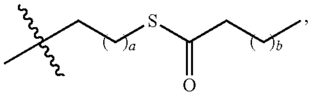
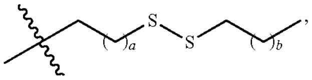
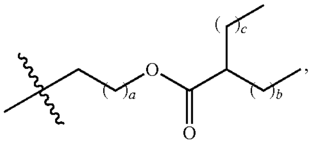
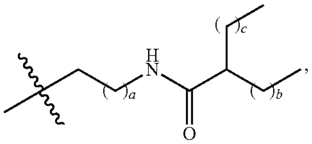
-continued
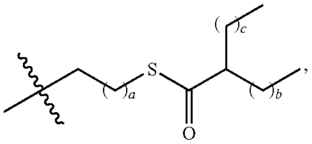
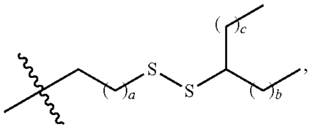
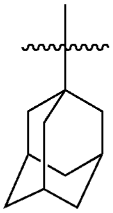
a, b and c are each independently an integer from 0-24; each X is independently selected from CH or N; each Y is independently selected from $CH_2$, NH, O, or S; and each Z is independently selected from CH or N.
In certain aspects, compounds of Formula II may include, for example, the following compounds:
(IIa)
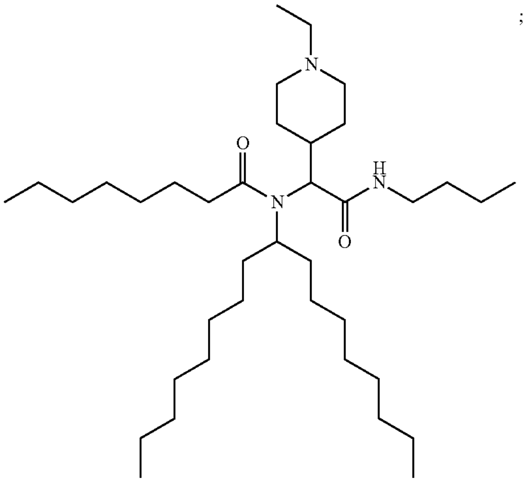
; or
(IIb)
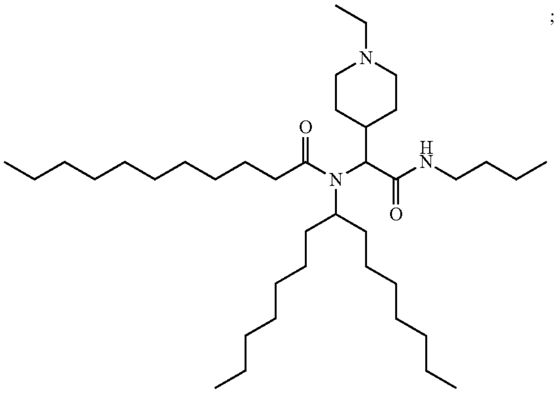
;
(IIc)
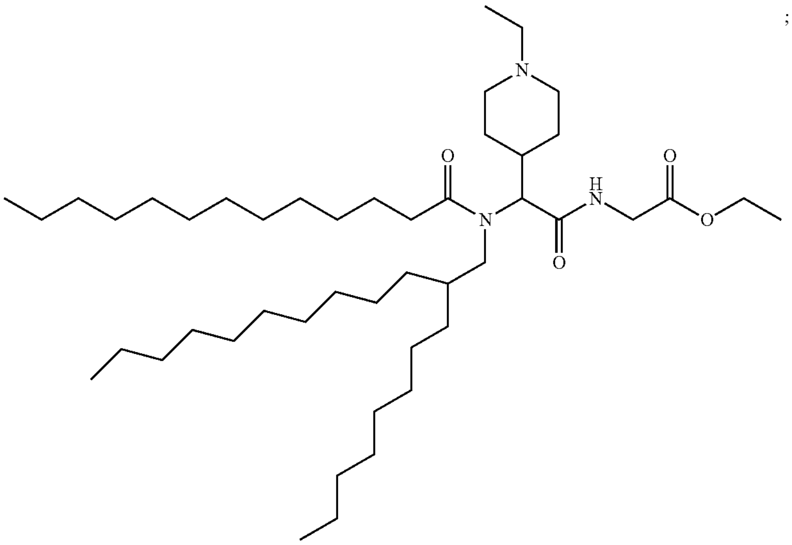
;

-continued (IId)

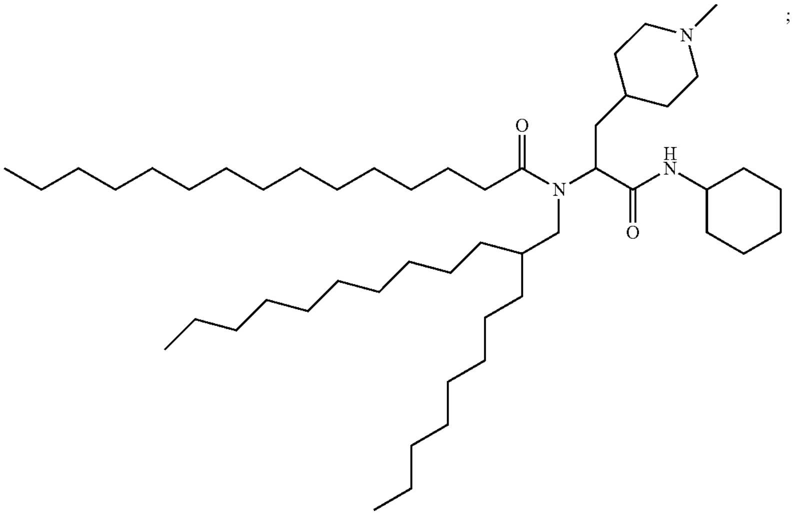

;

(IIe)

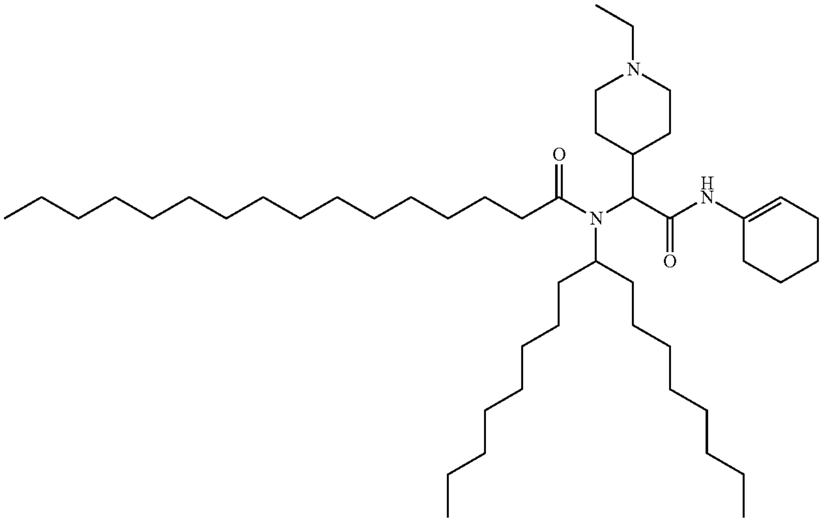

.

In one aspect, the present disclosure provides novel saccharide lipids.

In one aspect, the present disclosure provides mLNP compositions comprising compounds of Formula (III):

(III)

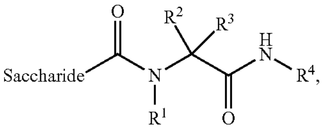

or a salt or isomer thereof, wherein each of $R^1$, $R^2$, $R^3$, $R^4$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl, poly(ethylene glycol) (PEG),

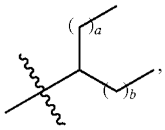

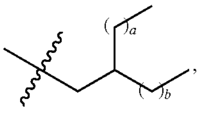

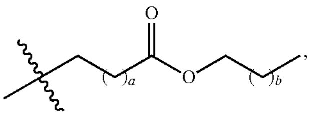

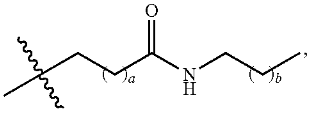

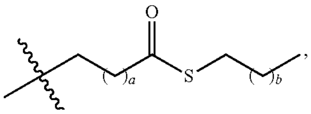

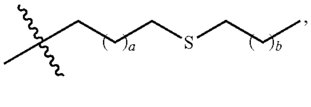

-continued
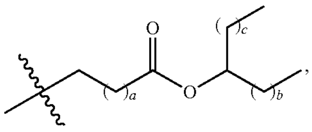
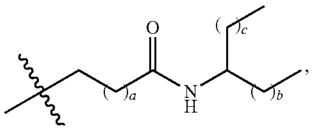
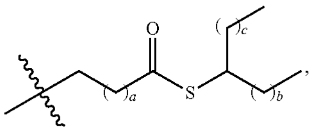
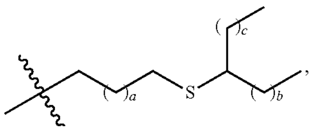
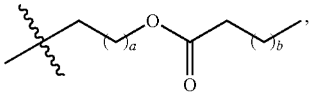
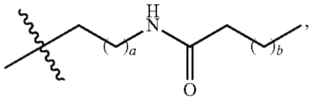
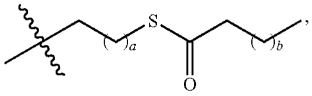
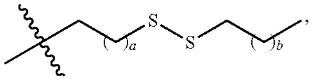
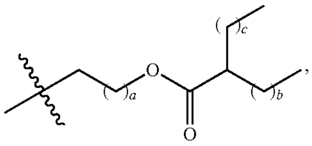
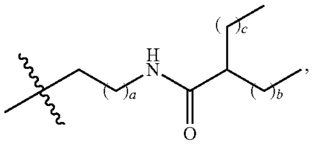
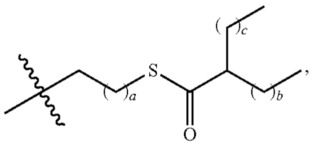
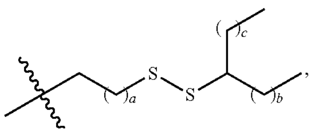
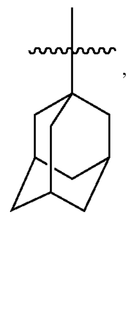
-continued
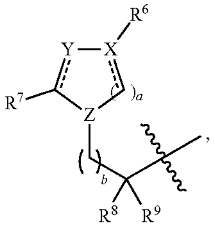
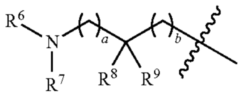
a, b and e are each independently an integer from 0-24;
each of $R^6$, $R^7$, $R^8$, $R^9$ is independently selected from H, C1-C24 alkyl, C1-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl,
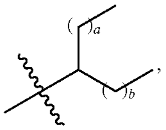
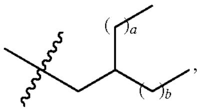
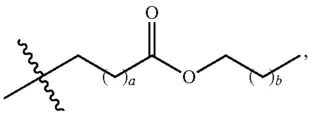
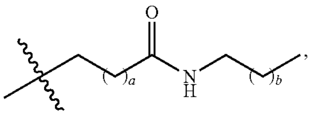
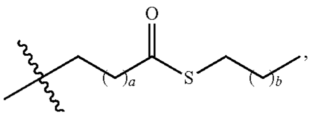
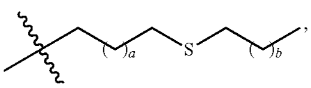
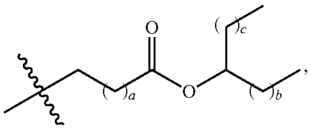
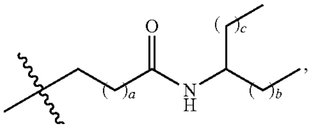
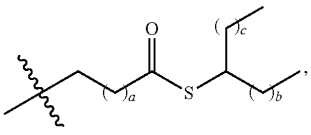
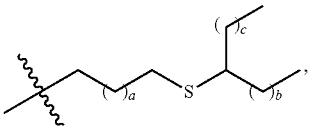
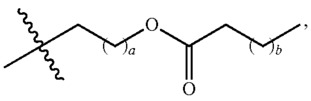

-continued

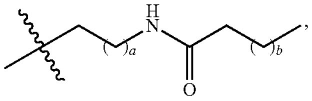

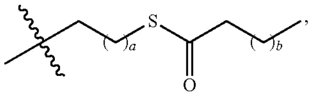

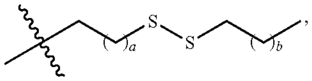

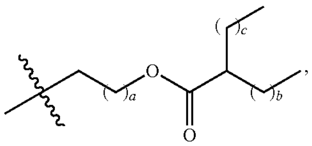

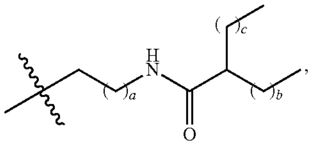

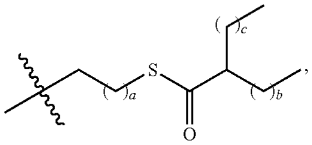

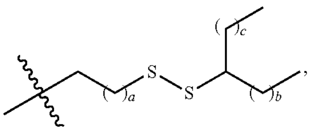

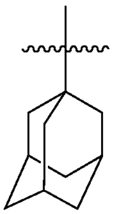

a, b and c are each independently an integer from 0-24;

each X is independently selected from CH or N;

each Y is independently selected from $CH_2$, NH, O, or S;

each Z is independently selected from CH or N;

and wherein the saccharide is selected from monosaccharides, disaccharides, oligosaccharides, and polysaccharides.

In certain aspects, compounds of Formula III may include, for example, the following compounds:

(III)(a)

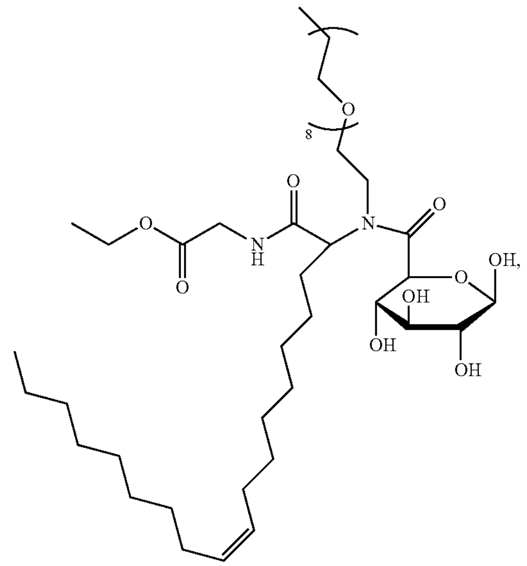

P1_E2

(III)(b)

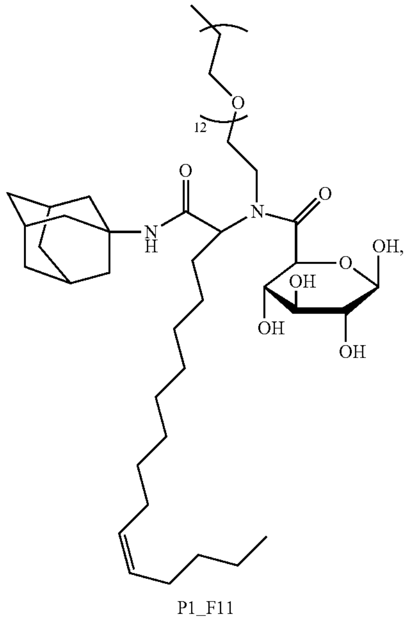

P1_F11

-continued
(III)(c)
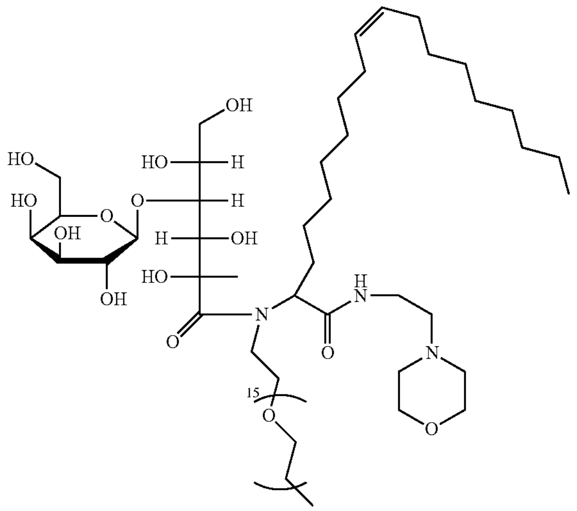
P1_C6
(III)(d)
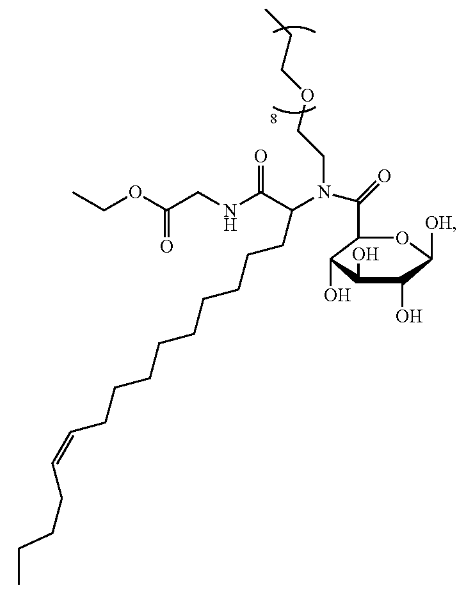
P1_E8
-continued
(III)(e)
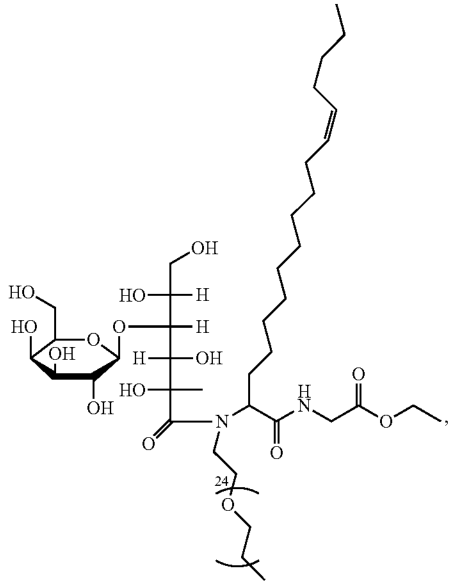
P1_D8
(III)(f)
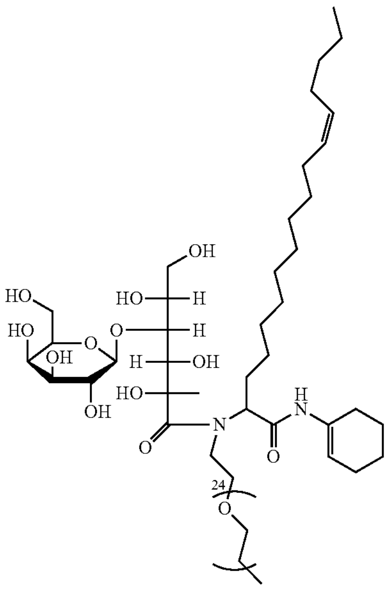
P1_D9
In one aspect, the present disclosure provides compounds of Formula (IV):
(IV)
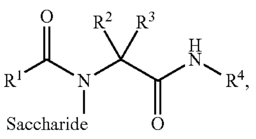
or a salt or isomer thereof, wherein
each of $R^1$, $R^2$, $R^3$, $R^4$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl, poly(ethylene glycol) (PEG),

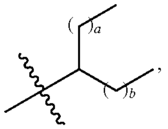
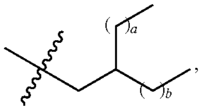
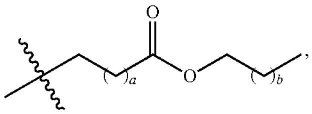
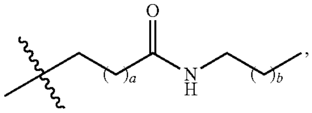
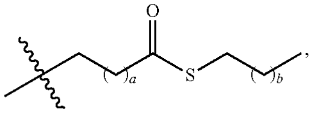
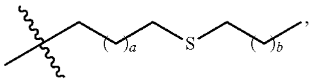
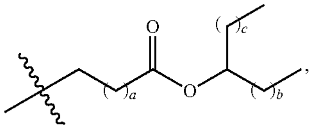
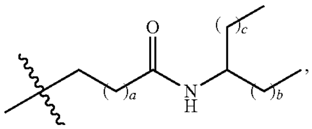
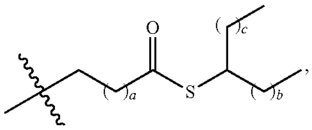
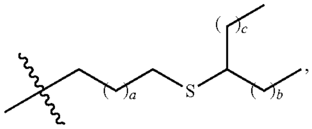
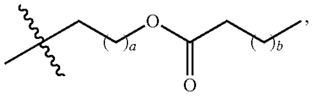
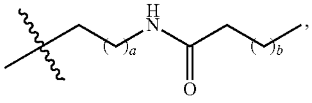
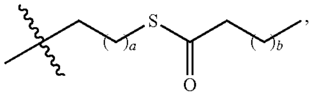
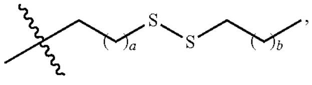
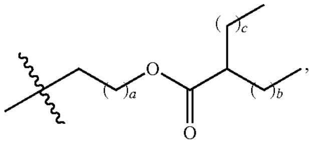

-continued

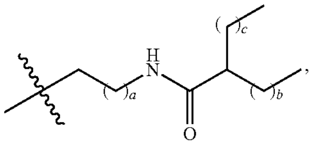
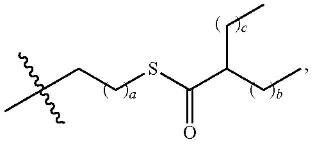
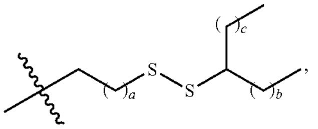
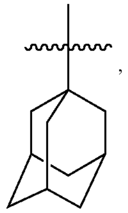
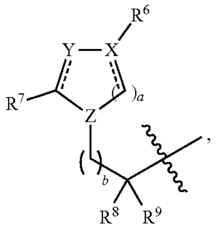
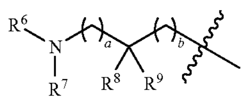

a, b and c are each independently an integer from 0-24;

each of $R^6$, $R^7$, $R^8$, $R^9$ is independently selected from H, C1-C24 alkyl, C1-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl,

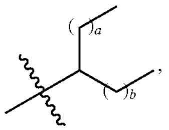
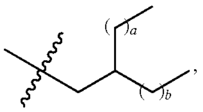
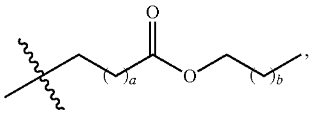
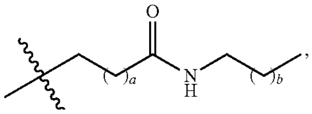
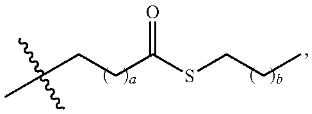
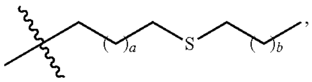
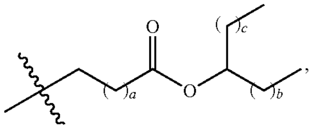

-continued

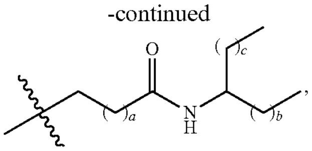

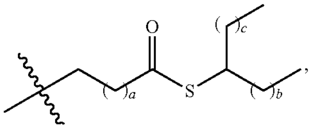

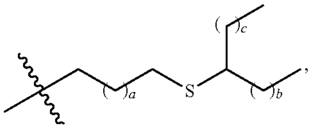

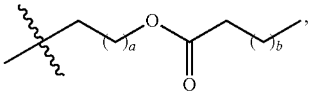

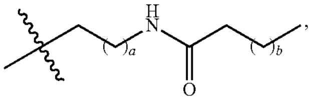

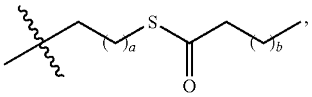

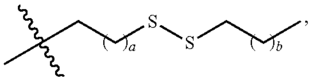

-continued

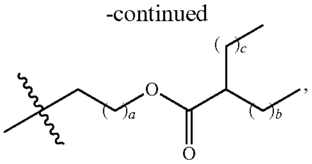

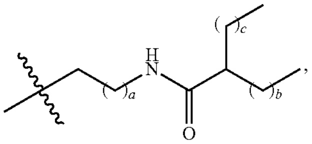

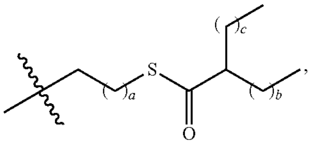

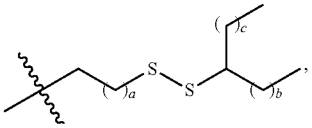

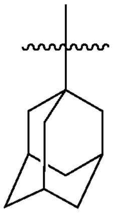

a, b and c are each independently an integer from 0-24;

each X is independently selected from CH or N;

each Y is independently selected from $CH_2$, NH, O, or S;

each Z is independently selected from CH or N;

each saccharide is independently selected from monosaccharides, disaccharides, oligosaccharides, and polysaccharides.

In certain aspects, compounds of Formula IV may include, for example, the following compound:

(IV)(a)

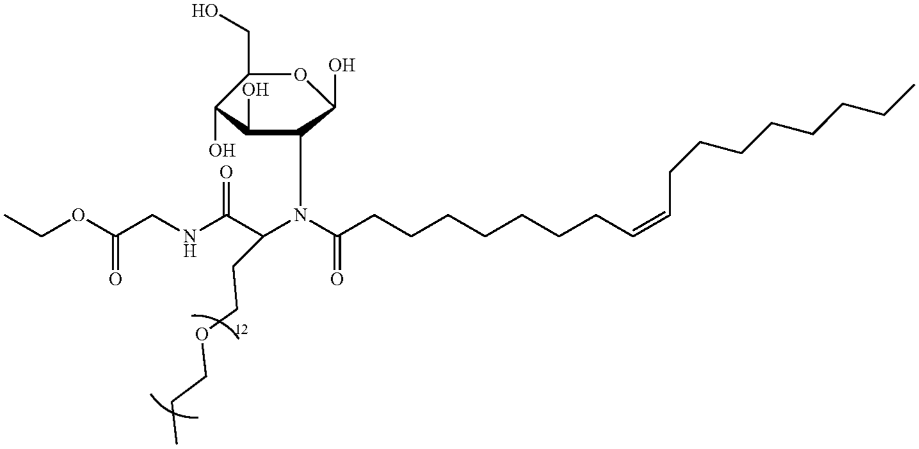

-continued (IV)(b)

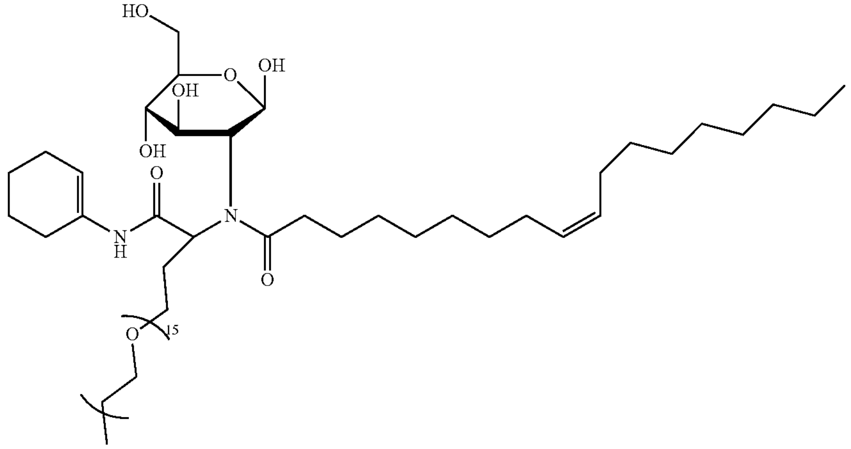

(IV)(c)

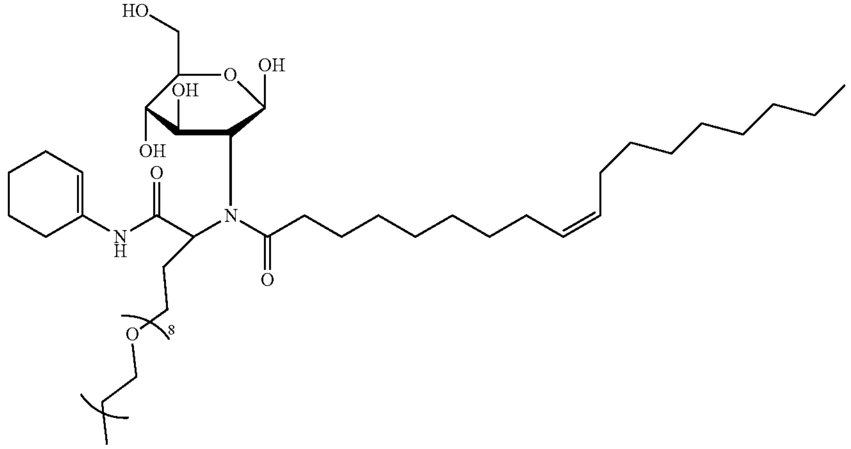

Monosaccharides useful in the composition of the disclosure include include trioses (ketotriose, aldotriose), tetroses (ketotetrose, aldotetroses), pentoses (ribulose, xylulose, ribose, arabinose, xylose, lyxose, deoxyribose), hexoses (psicose, fructose, sorbose, tagatose, allose, altrose, glucose, mannose, fucose, fuculose, rhamnose, heptose, octose, nonose, gulose, idose, galactose, talose), sedoheptulose.

Disaccharides include sucrose, lactose, maltose, trehalose, turanose, cellobiose. Oligosaccharides include raffinose, melezitose, maltotriose, acarbose, stachyose, fructooligosaccharide, galactooligosaccharides, mannanoligosaccharides.

Polysaccharides include ployglycitol, n-acetylglucosamine, chitin.

In one aspect, the present disclosure provides modular lipids comprising two or more functional groups and at least one linker between at least two functional groups. In some aspects, the functional groups are selected from a cationic or ionizable lipid, a phospholipid, a saccharide lipid, a lipid raft, a stabilizer lipid, a bipolar compound having hydrophobic and hydrophilic ends, a steric group, a sterol-containing group, a folate-containing group, an N-acetylgalactosamine (GalNAc)-containing group, an oligopeptide group, an oligonucleotide group, or a combination thereof.

In one aspect, the present disclosure provides a method for synthesizing a modular lipid comprising a cationic ionizable group and a sterol-containing or sterol derivatives group, the method comprising performing four component reaction of an acid compound, an amine compound, an aldehyde/ketone compound, and an isocyanide compound as follows:

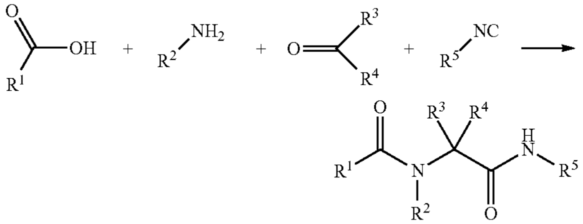

wherein each of $R^1$, $R^4$ and $R^5$ is independently selected from $C_2$-$C_{24}$ alkyl, $C_2$-$C_{24}$ alkenyl, $C_2$-$C_{24}$ alkynyl, substituted $C_2$-$C_{24}$ alkyl, substituted alkenyl, substituted alkynyl, substituted acyl, substituted carbocyclyl, substituted heterocyclyl, substituted aryl, substituted heteroaryl, poly(ethylene glycol) (PEG),

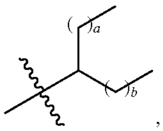 , 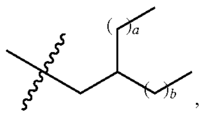 ,

-continued
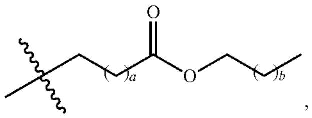,
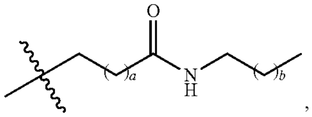,
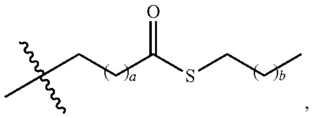,
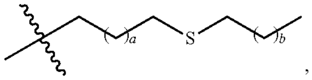,
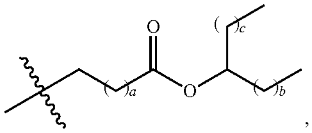,
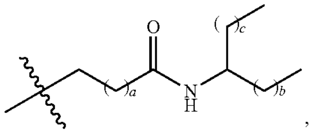,
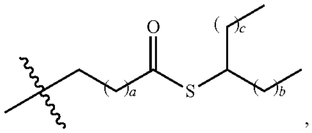,
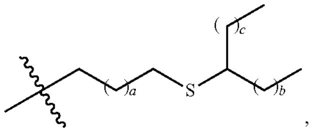,
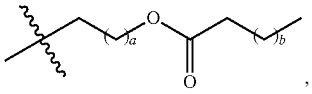,
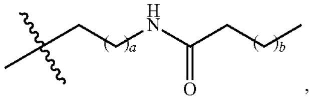,
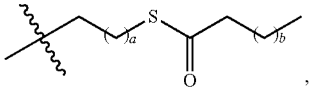,
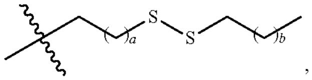,
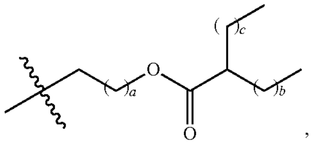,
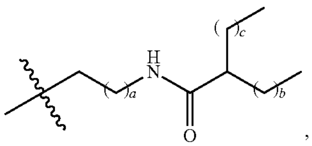,
-continued
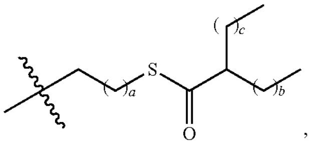,
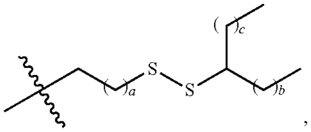,
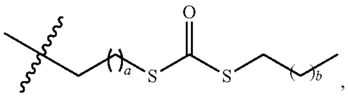,
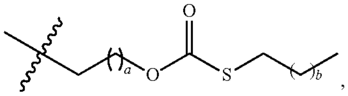,
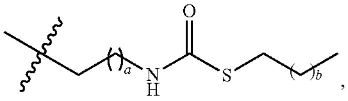,
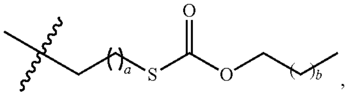,
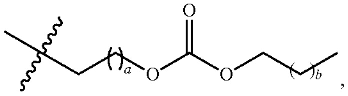,
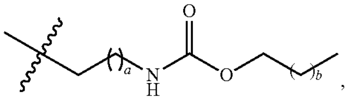,
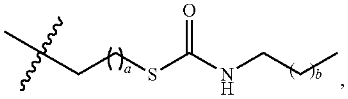,
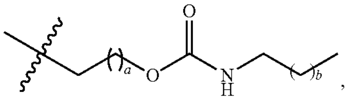,
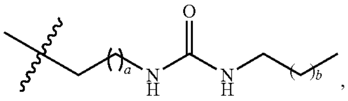,
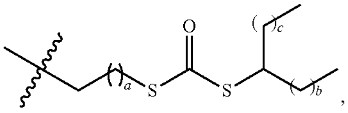,
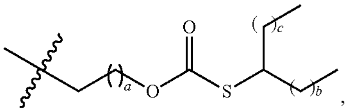,
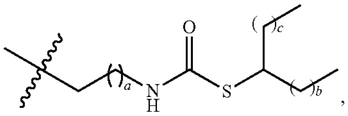,
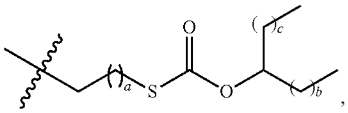,
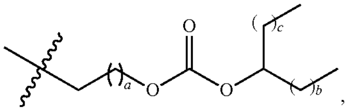, -continued
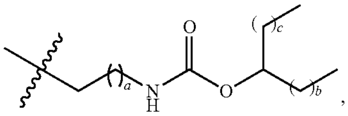,
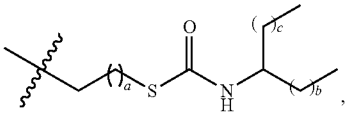,
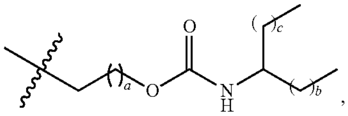,
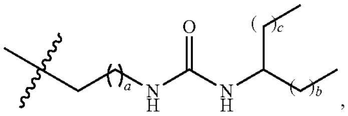, 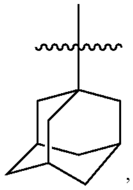,
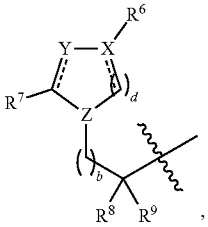, 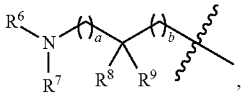,
wherein each of $R^2$ and $R^3$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl, poly(ethylene glycol) (PEG) and
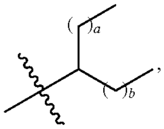, 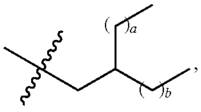,
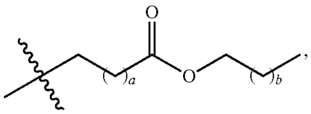,
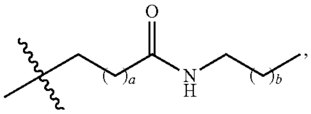,
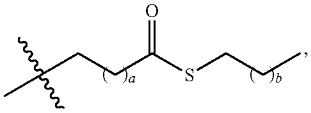,
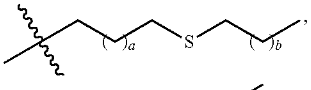,
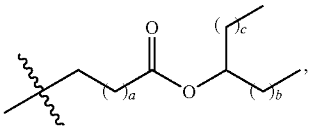,
-continued
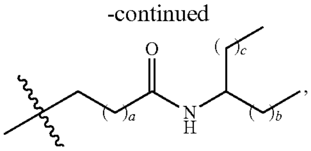,
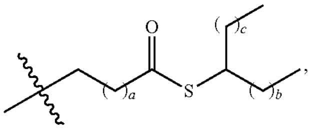,
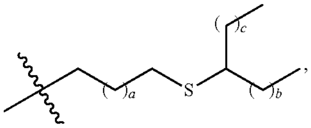,
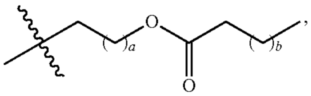,
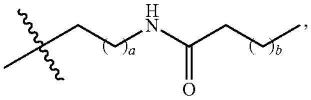,
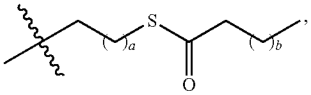,
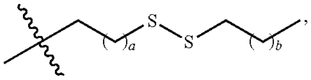,
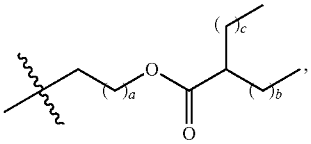,
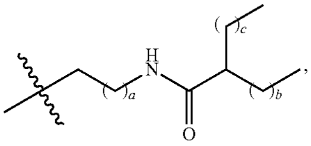,
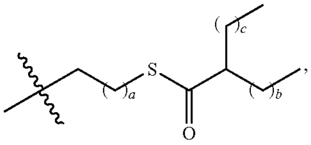,
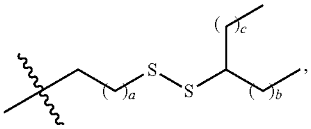,
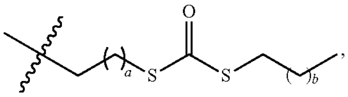,
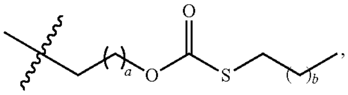,
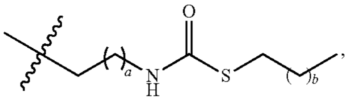,
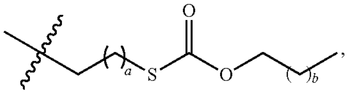, -continued
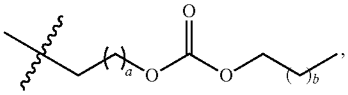,
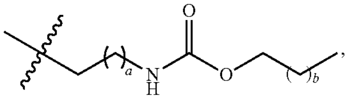,
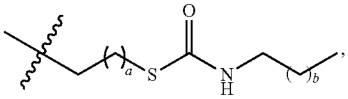,
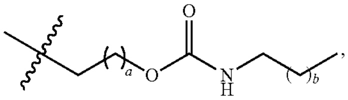,
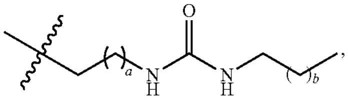,
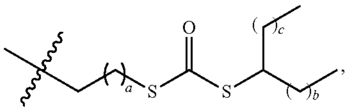,
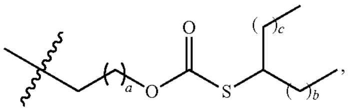,
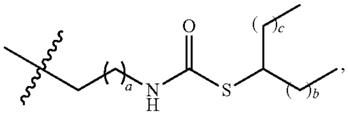,
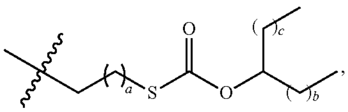,
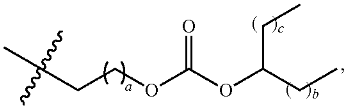,
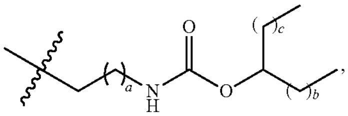,
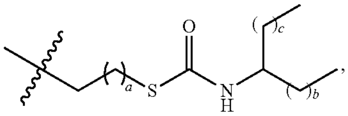,
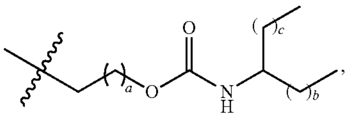,
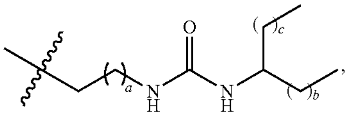, 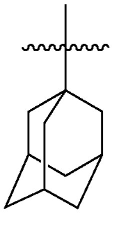,
-continued
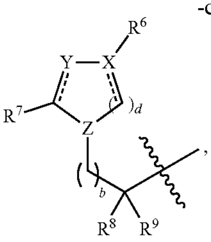, 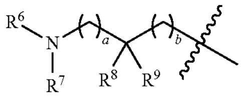,
wherein each $R^6$, $R^7$, $R^8$ and $R^9$ is independently selected from H, C1-C24 alkyl, C1-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl,
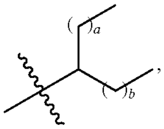, 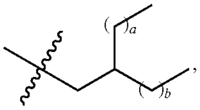,
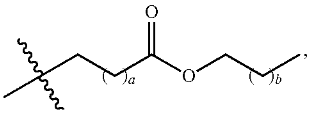,
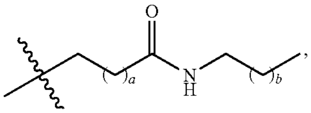,
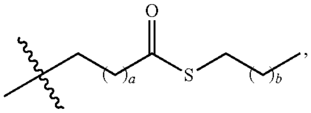,
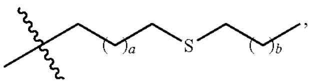,
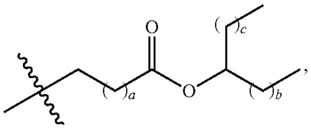,
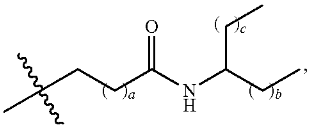,
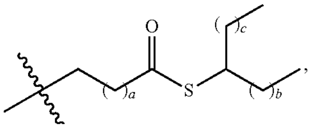,
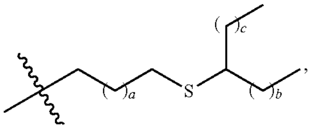,
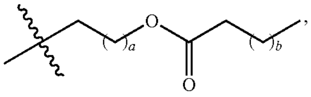,
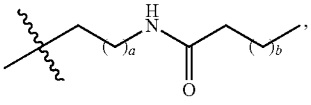, -continued

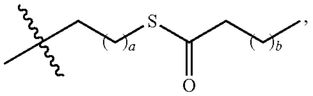

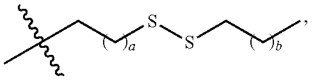

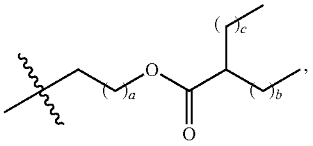

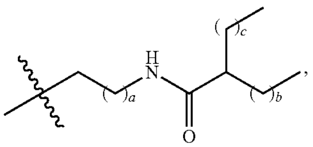

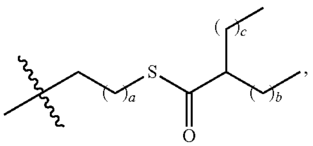

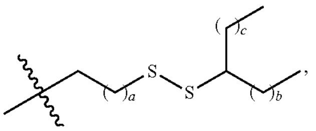

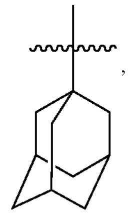

a, b, c, and d are each independently an integer from 0-24;

each X is independently selected from CH or N;

each Y is independently selected from $CH_2$, NH, O, or S; and each Z is independently selected from CH or N.

In one aspect, the present disclosure provides a modular lipid of Formula V, VI, VII, VIII, IX, or X:

V

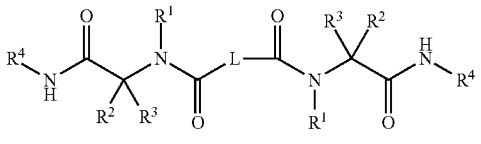

VI

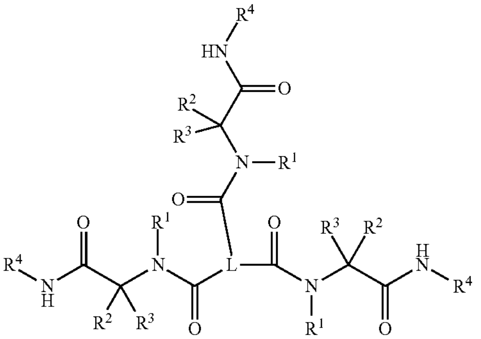

-continued

VII

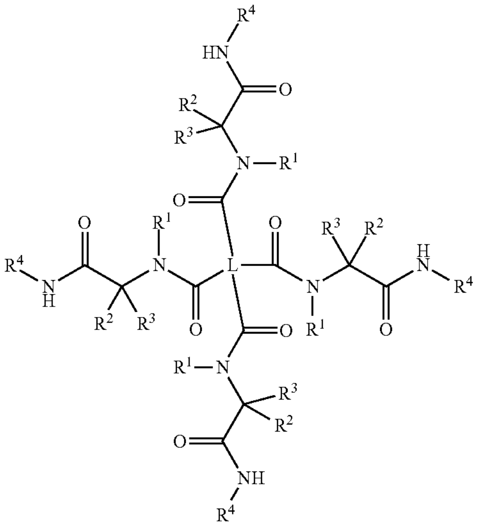

VIII

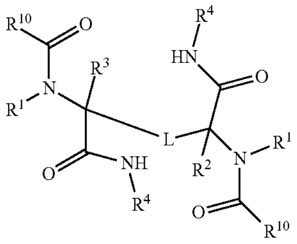

IX

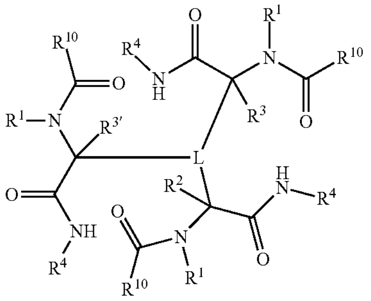

X

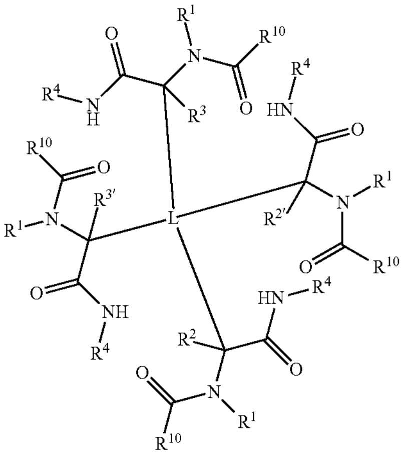

or a salt or isomer thereof, wherein each $R^1$, $R^4$, and $R^{10}$ is independently selected from $C_2$-$C_{24}$ alkyl, $C_2$-$C_{24}$ alkenyl, $C_2$-$C_{24}$ alkynyl, substituted $C_2$-$C_{24}$ alkyl, substituted alkenyl, substituted alkynyl, substituted acyl, substituted carbocyclyl, substituted heterocyclyl, substituted aryl, substituted heteroaryl, poly(ethylene glycol) (PEG),
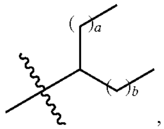,
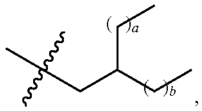,
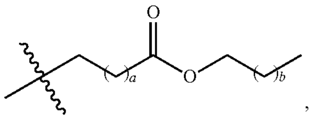,
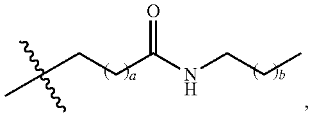,
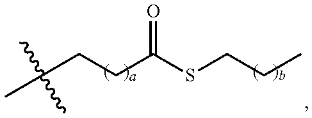,
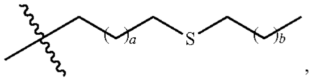,
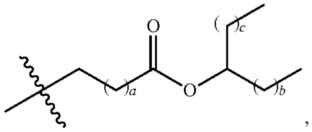,
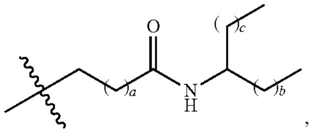,
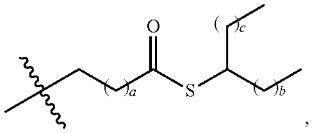,
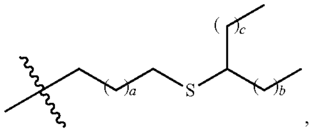,
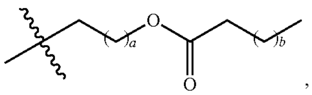,
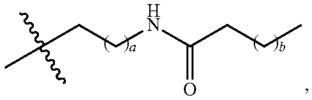,
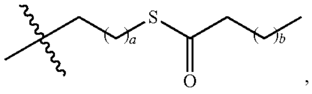,
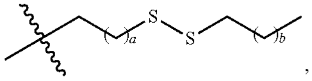,
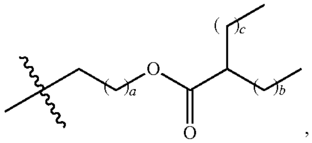,
-continued
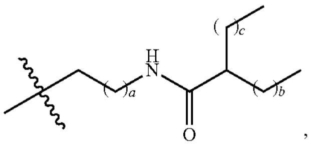,
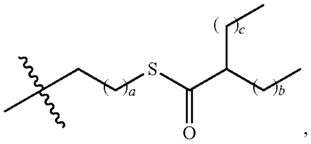,
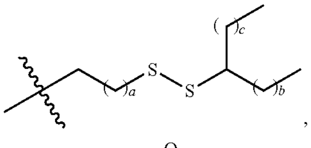,
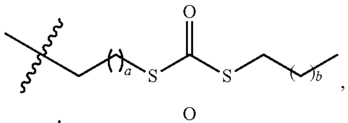,
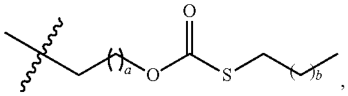,
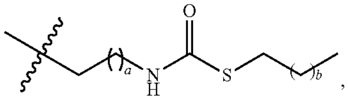,
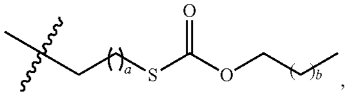,
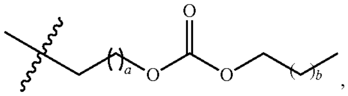,
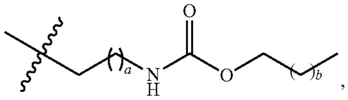,
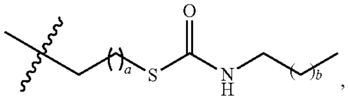,
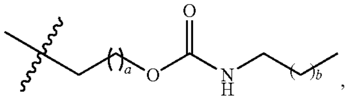,
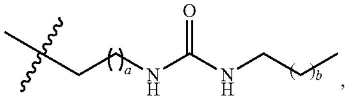,
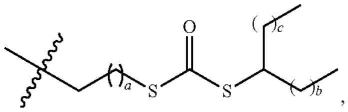,
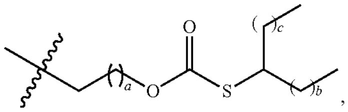,
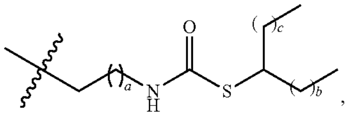, -continued
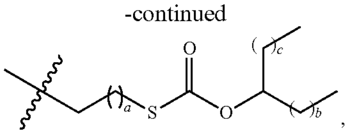,
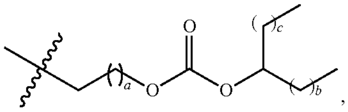,
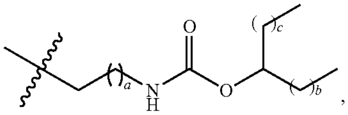,
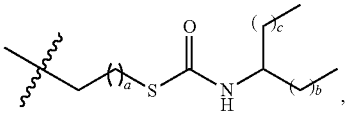,
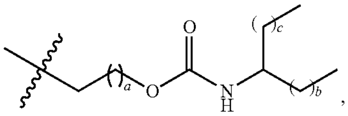,
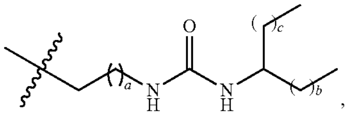, 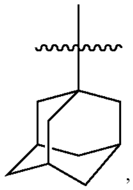,
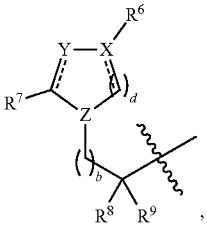, 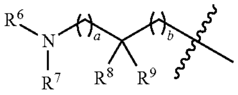
each $R^2$, $R^{2'}$, $R^3$ and $R^{3'}$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl, poly(ethylene glycol) (PBG) and
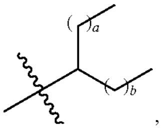, 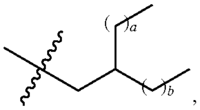,
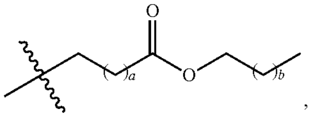,
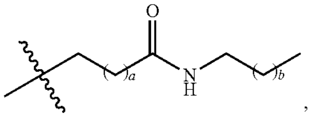,
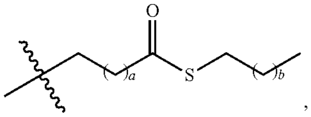,
-continued
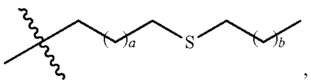,
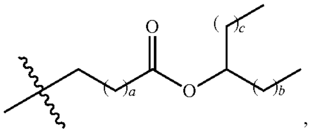,
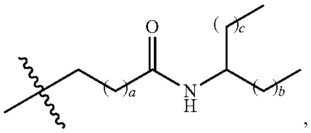,
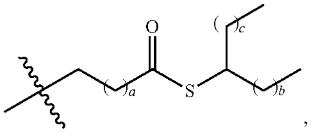,
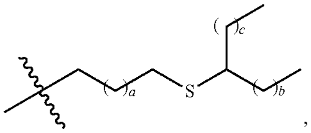,
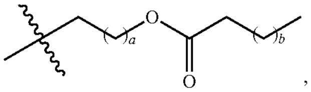,
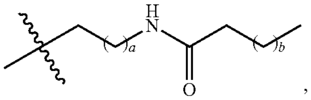,
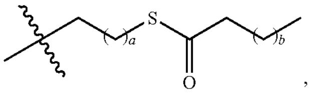,
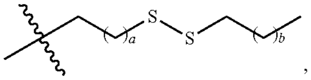,
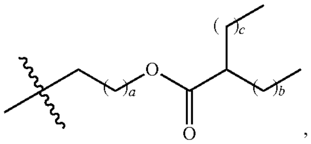,
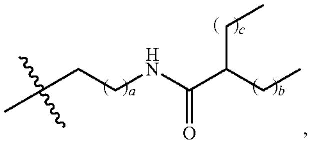,
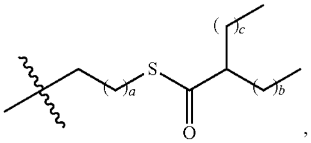,
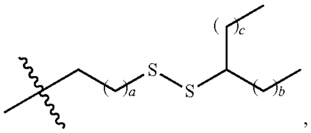,
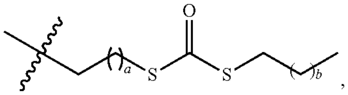, -continued
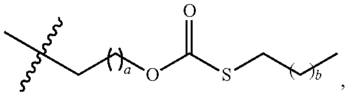,
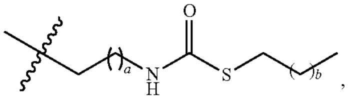,
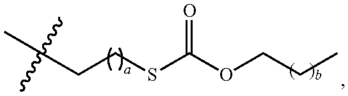,
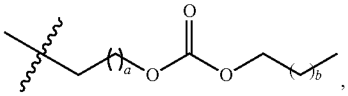,
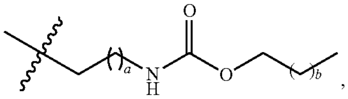,
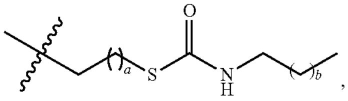,
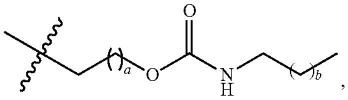,
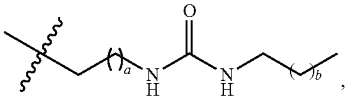,
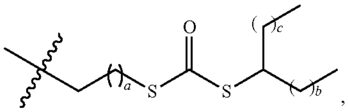,
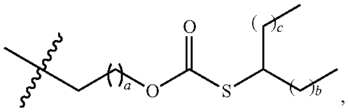,
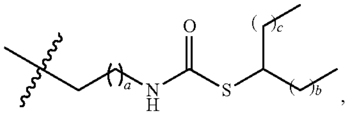,
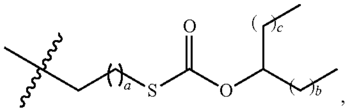,
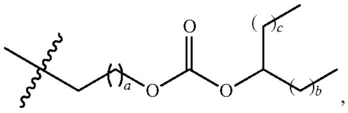,
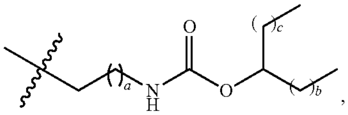,
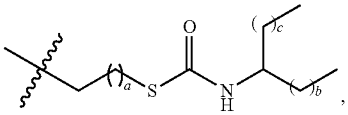,
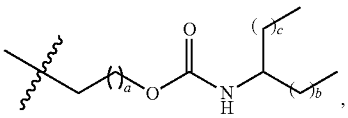,
-continued
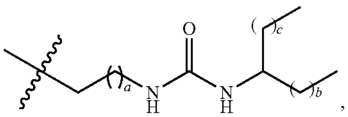, 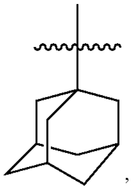,
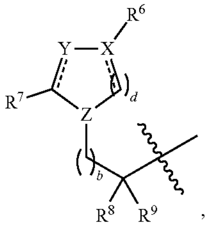, 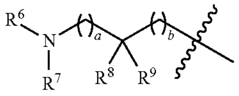
each L is independently selected from alkyl, alkenyl, alkynyl, substituted alkyl, substituted alkenyl, substituted alkynyl, substituted acyl, substituted carbocyclyl, substituted heterocyclyl, substituted aryl, substituted heteroaryl, poly (ethylene glycol) (PEG) and
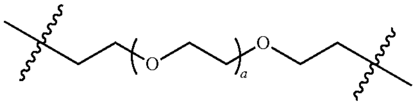,
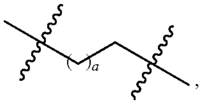,
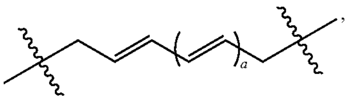,
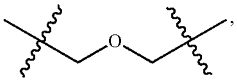, 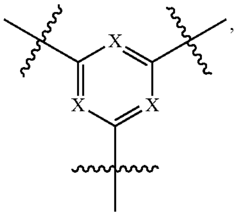,
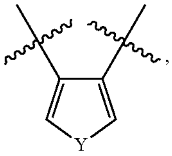, 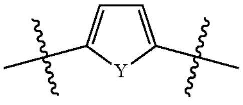,
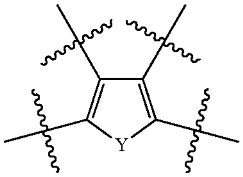, 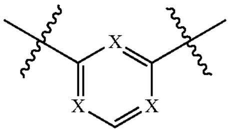,
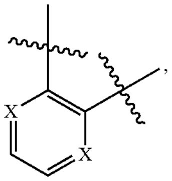, 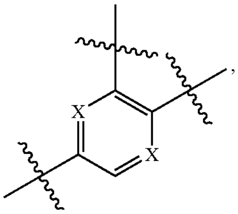

-continued
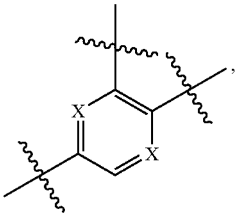,
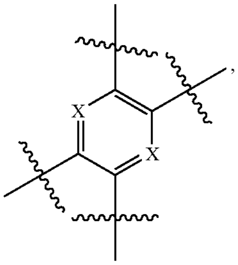,
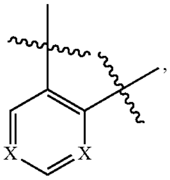,
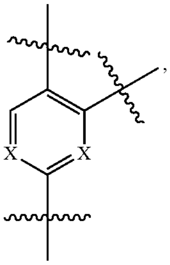,
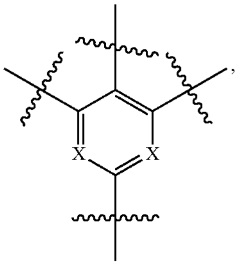,
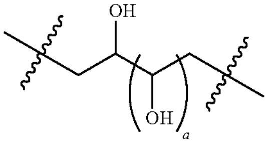,
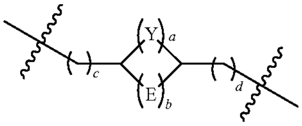,
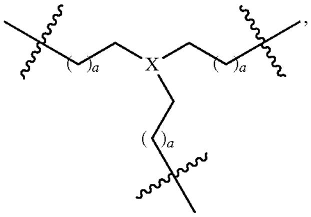,
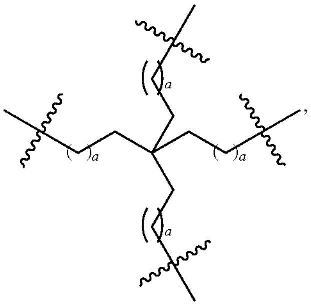,
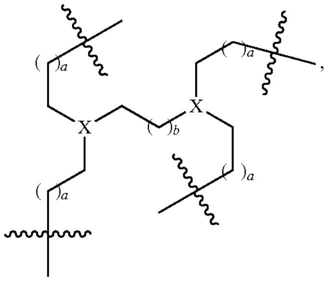,
-continued
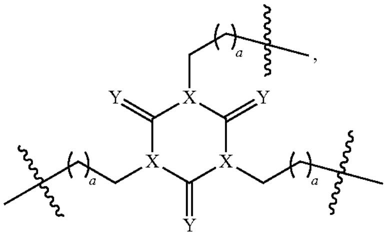,
each $R^6$, $R^7$, $R^8$ and $R^9$ is independently selected from H, C1-C24 alkyl, C1-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl,
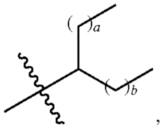,
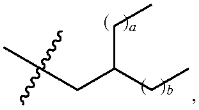,
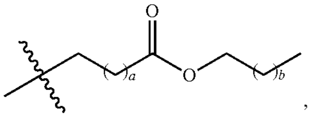,
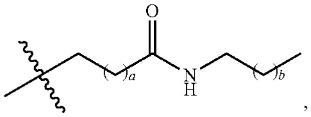,
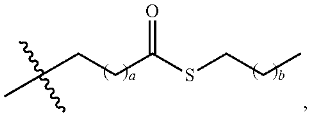,
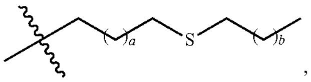,
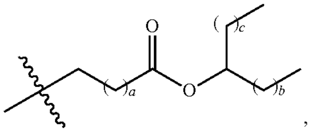,
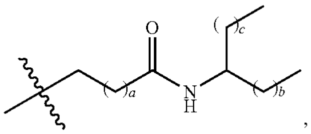,
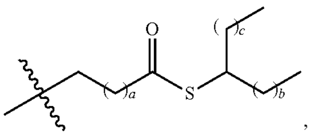,
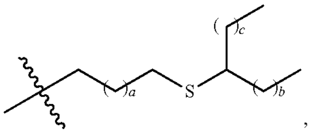,
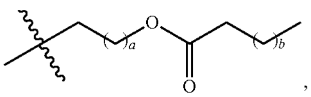, -continued

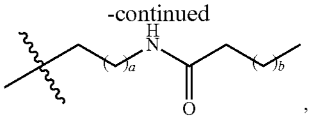
,
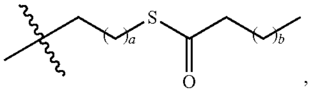
,
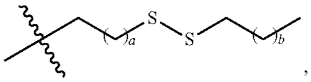
,
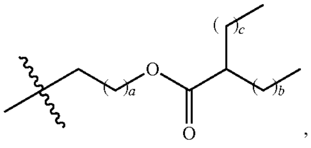
,
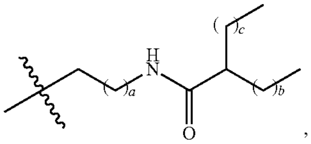
,
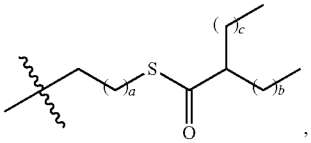
,
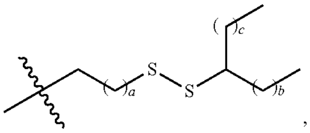
,
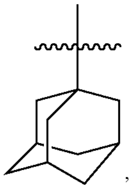
, a, b, c, and d are each independently an integer from 0-24;
each E is independently selected from $CH_2$, NH, O, or S;
each X is independently selected from CH or N;
each Y is independently selected from $CH_2$, NH, O, or S;
each Z is independently selected from CH or N.

In one aspect, the present disclosure provides methods for synthesizing a modular lipid of Formula V, VI and VII comprising performing the following four component reaction:

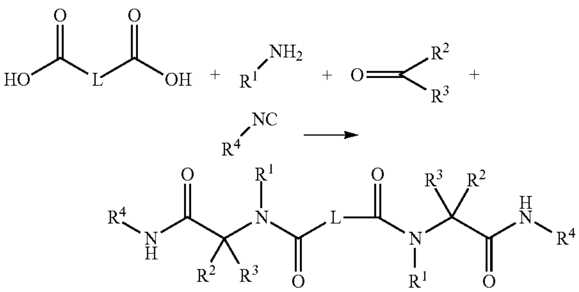
V

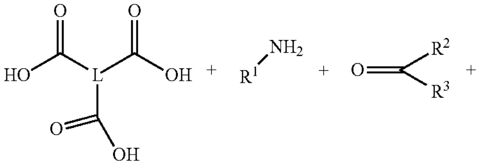

-continued

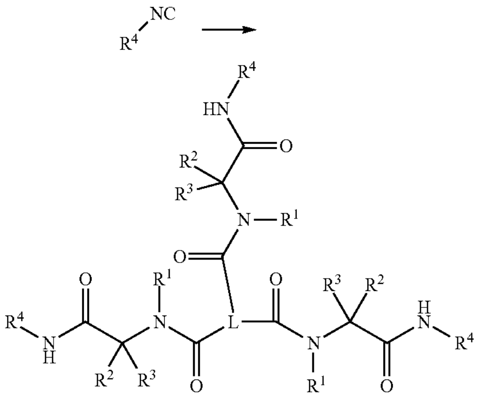
VI

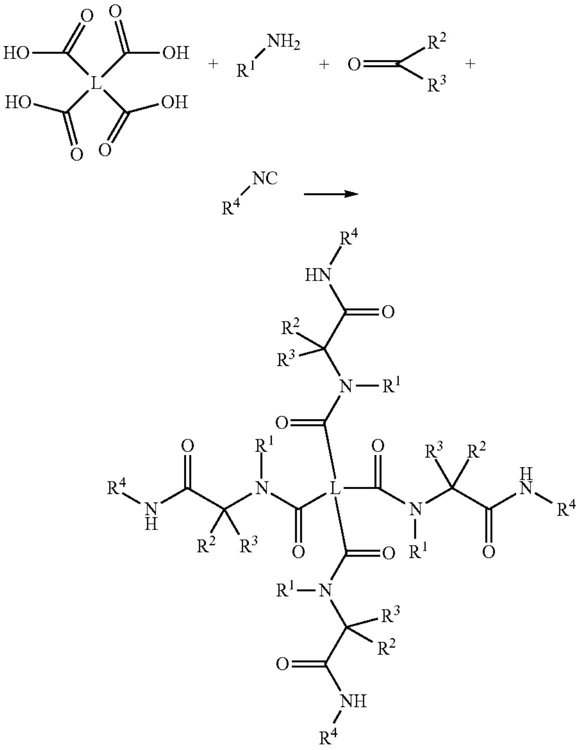
VII or a salt or isomer thereof, wherein each $R^1$ and $R^4$ is independently selected from $C_2$-$C_{24}$ alkyl, $C_2$-$C_{24}$ alkenyl, $C_2$-$C_{24}$ alkynyl, substituted $C_2$-$C_{24}$ alkyl, substituted alkenyl, substituted alkynyl, substituted acyl, substituted carbocyclyl, substituted heterocyclyl, substituted aryl, substituted heteroaryl, poly(ethylene glycol) (PEG),

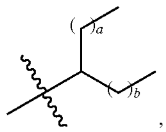
,
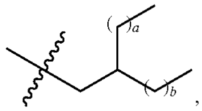
,
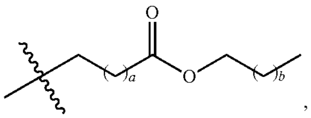
,

-continued
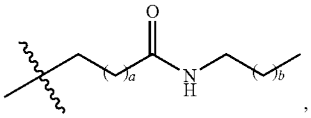
,
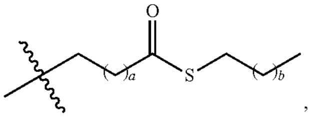
,
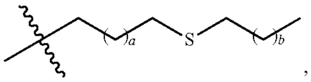
,
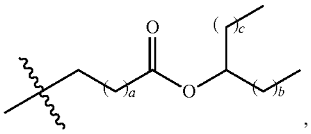
,
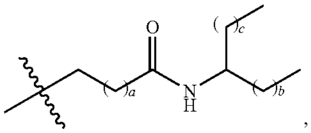
,
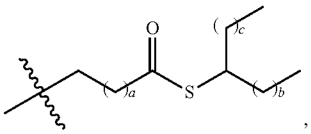
,
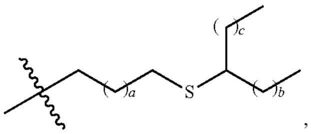
,
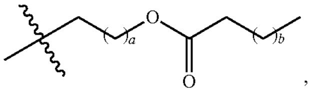
,
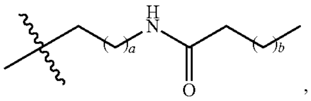
,
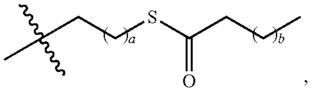
,
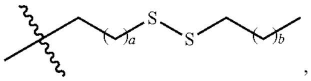
,
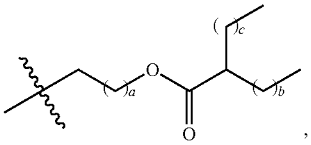
,
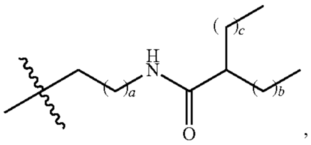
,
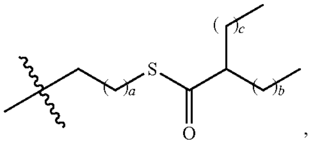
,
-continued
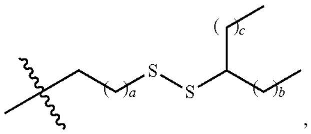
,
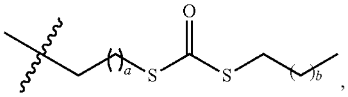
,
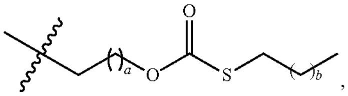
,
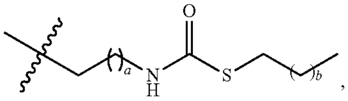
,
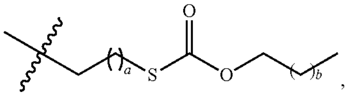
,
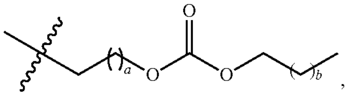
,
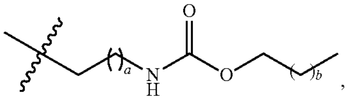
,
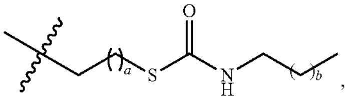
,
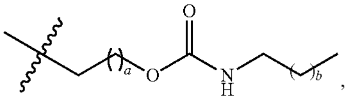
,
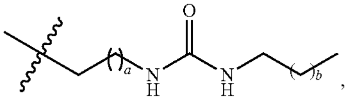
,
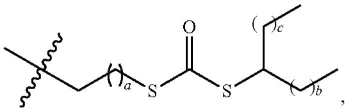
,
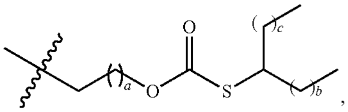
,
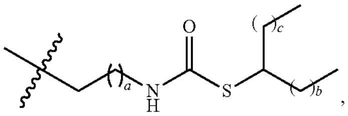
,
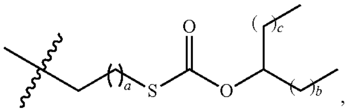
,
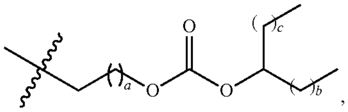
,
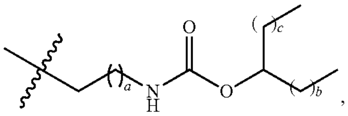
, -continued
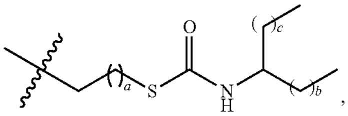
,
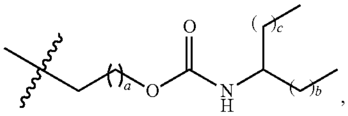
,
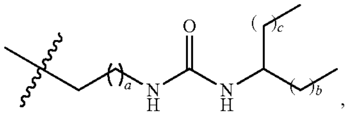
,
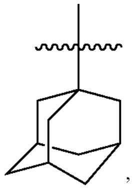
,
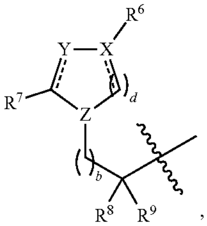
,
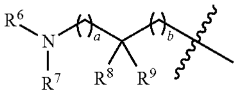
each $R^2$ and $R^3$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl, poly(ethylene glycol) (PEG) and
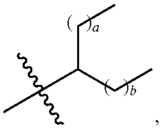
,
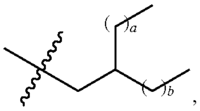
,
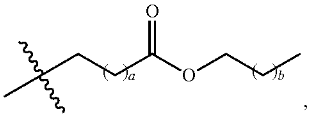
,
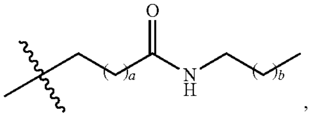
,
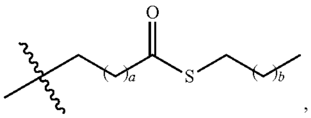
,
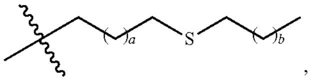
,
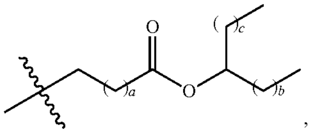
,
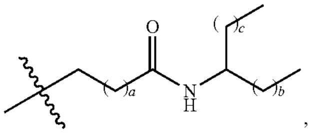
,
-continued
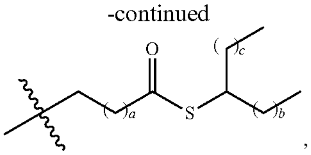
,
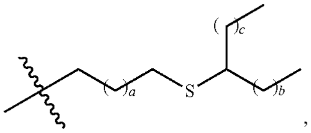
,
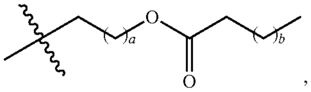
,
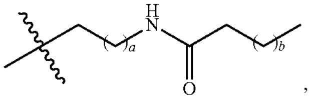
,
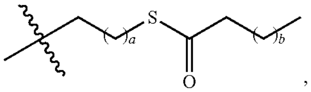
,
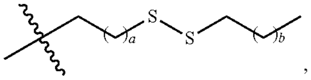
,
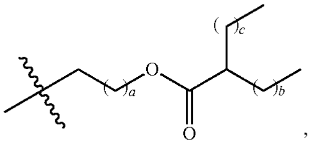
,
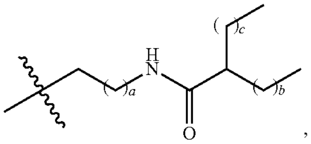
,
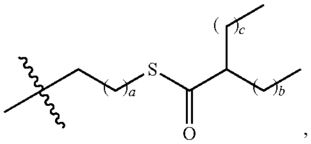
,
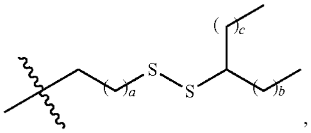
,
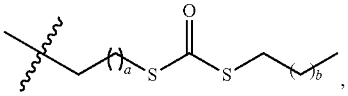
,
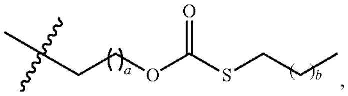
,
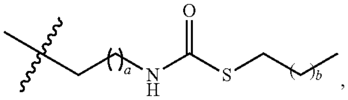
,
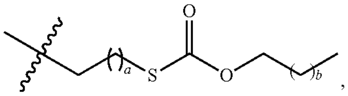
,
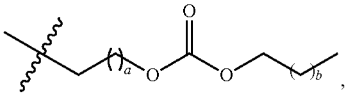
, -continued
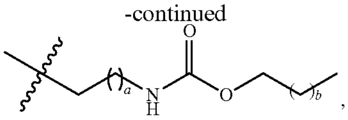,
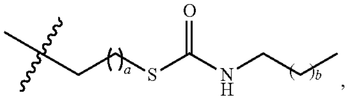,
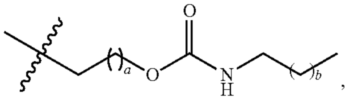,
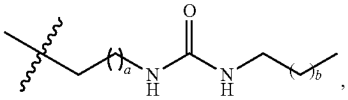,
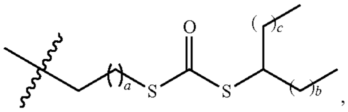,
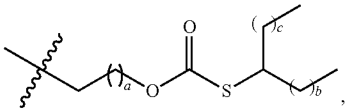,
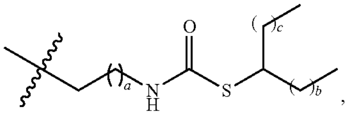,
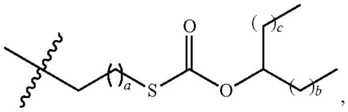,
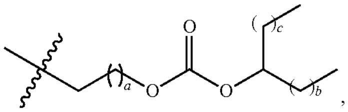,
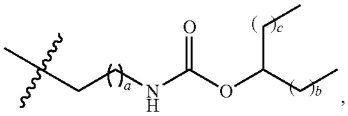,
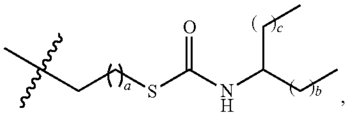,
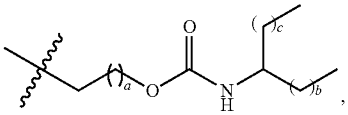,
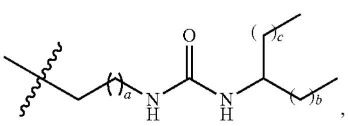, 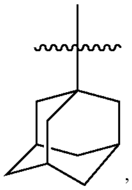,
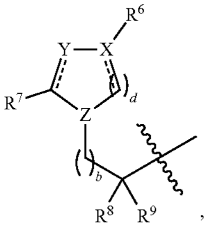, 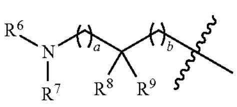
each L is independently selected from alkyl, alkenyl, alkynyl, substituted alkyl, substituted alkenyl, substituted alkynyl, substituted acyl, substituted carbocyclyl, substituted heterocyclyl, substituted aryl, substituted heteroaryl, poly (ethylene glycol) (PEG) and
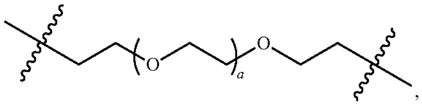,
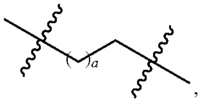, 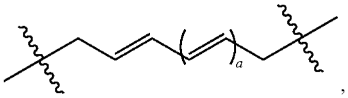,
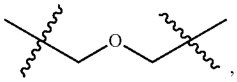, 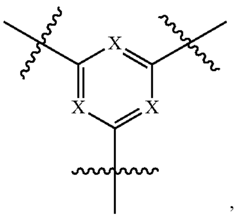,
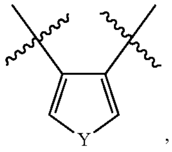, 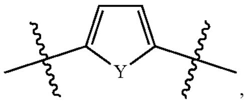,
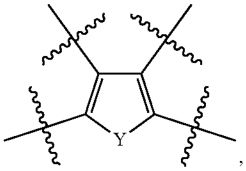, 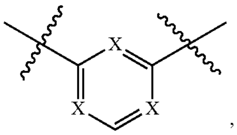,
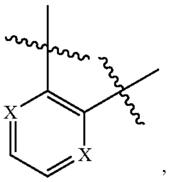, 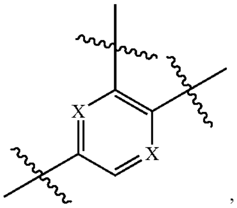,
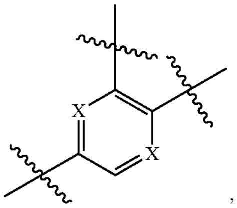, 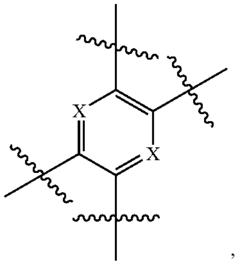,
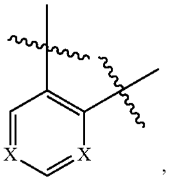, 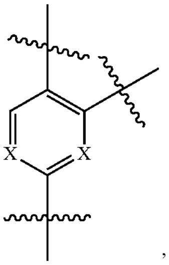, -continued
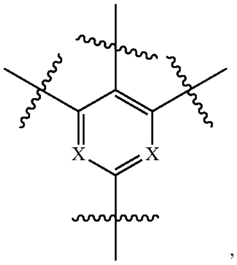
,
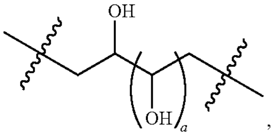
,
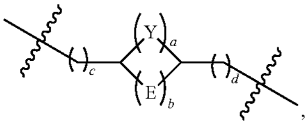
,
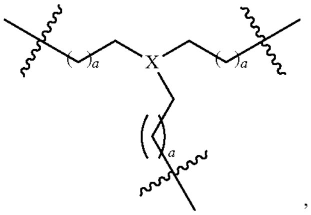
,
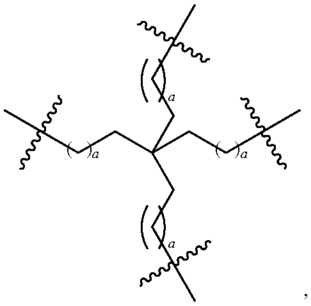
,
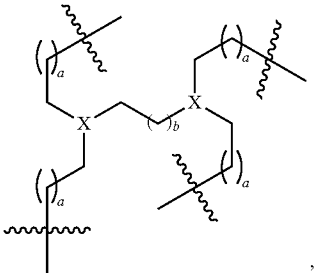
,
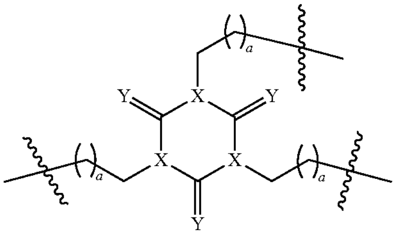
$R^6$, $R^7$, $R^8$ and $R^9$ are each independently selected from H, C1-C24 alkyl, $C_1$-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl,
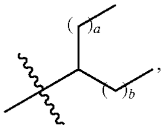
,
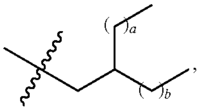
,
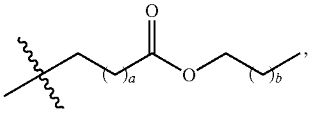
,
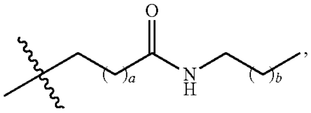
,
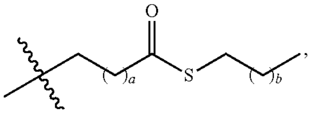
,
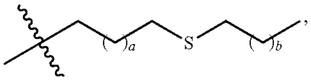
,
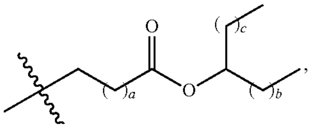
,
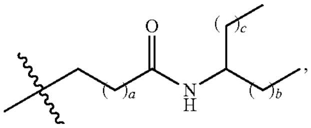
,
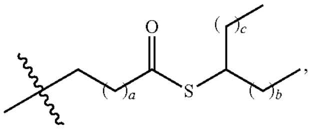
,
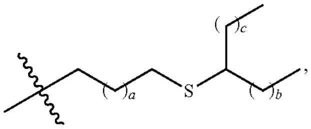
,
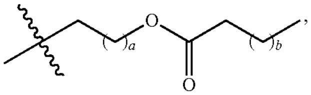
,
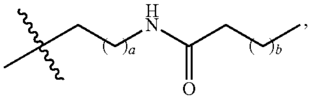
,
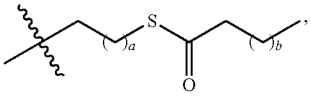
,
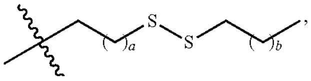
,
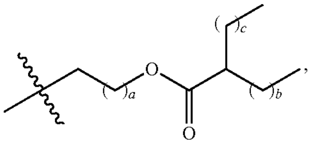
, -continued

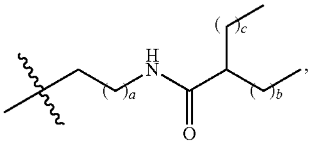

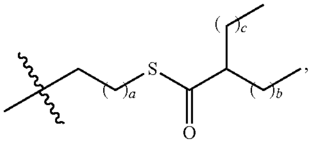

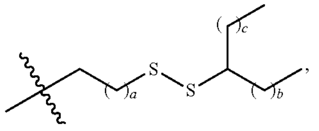

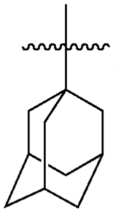

a, b, c and d are each independently an integer from 0-24;

each E is independently selected from $CH_2$, NH, O, or S;

each X is independently selected from CH or N;

each Y is independently selected from $CH_2$, NH, O, or S;

each Z is independently selected from CH or N.

In one aspect, the present disclosure provides methods for synthesizing a modular lipid of Formulae VIII, IX and X comprising performing the following four component reaction:

VIII

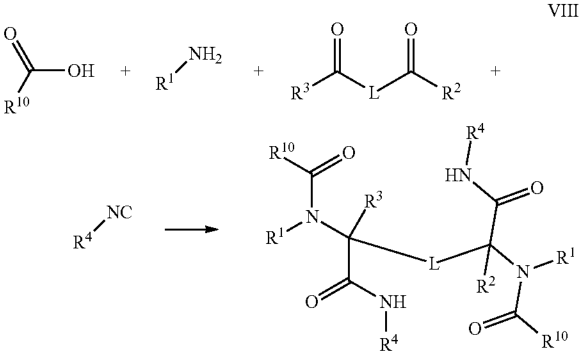

IX

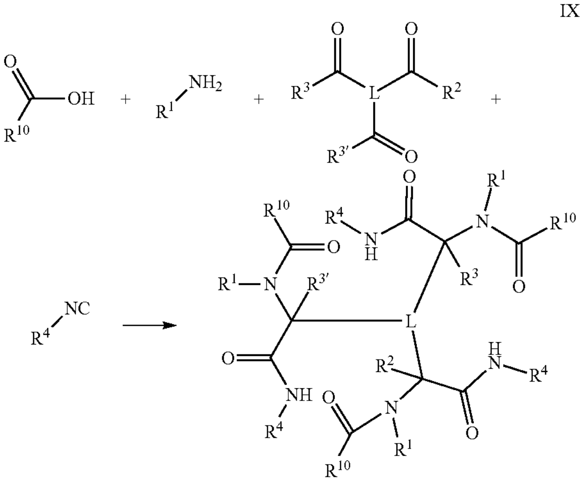

-continued

X

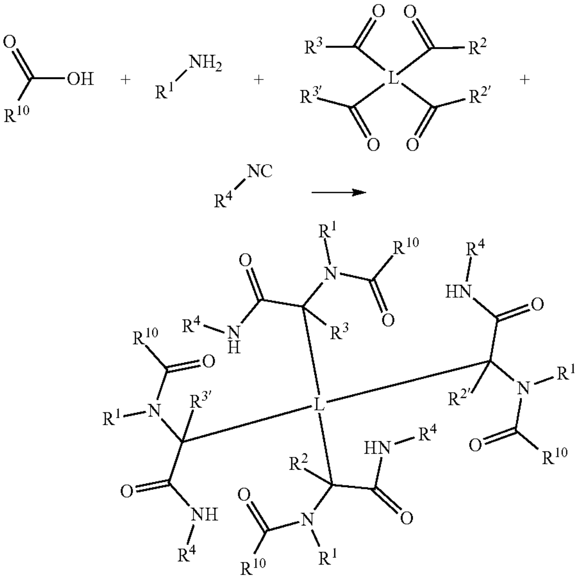

or a salt or isomer thereof, wherein each $R^1$, $R^4$, and $R^{10}$, is independently selected from $C_2$-$C_{24}$ alkyl, $C_2$-$C_{24}$ alkenyl, $C_2$-$C_{24}$ alkynyl, substituted $C_2$-$C_{24}$ alkyl, substituted alkenyl, substituted alkynyl, substituted acyl, substituted carbocyclyl, substituted heterocyclyl, substituted aryl, substituted heteroaryl, poly(ethylene glycol) (PEG),

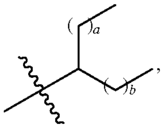

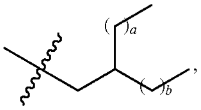

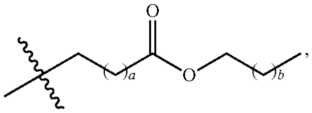

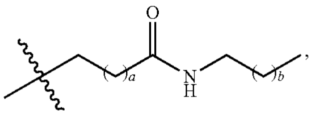

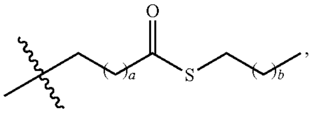

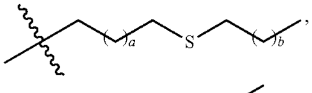

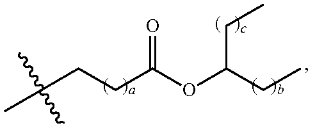

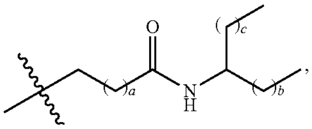

-continued
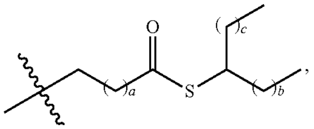
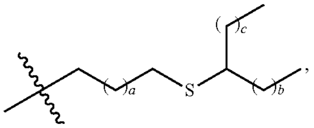
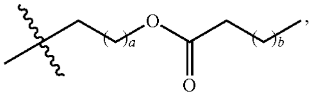
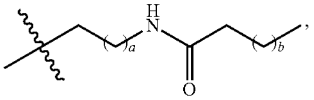
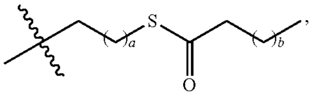
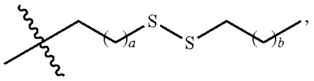
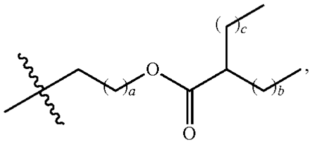
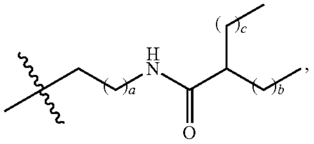
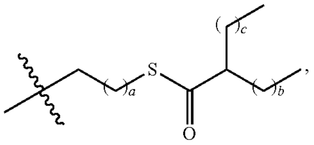
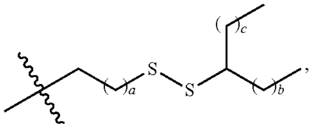
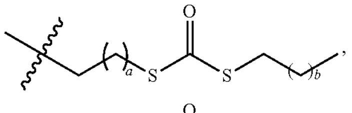
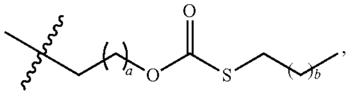
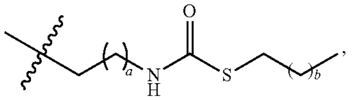
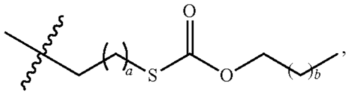
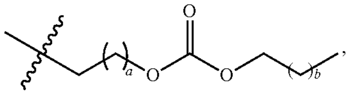
-continued
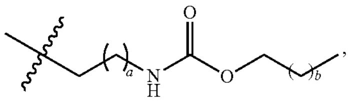
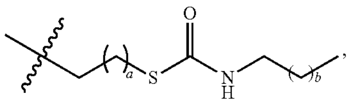
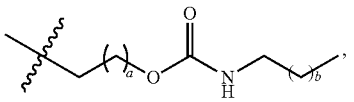
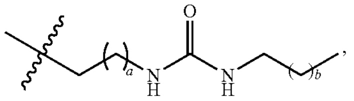
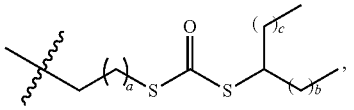
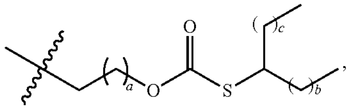
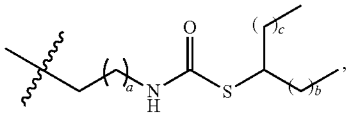
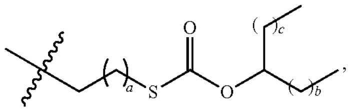
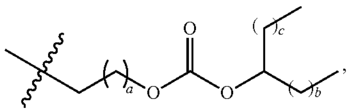
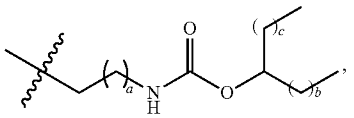
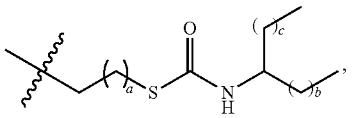
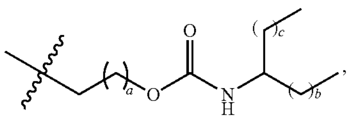
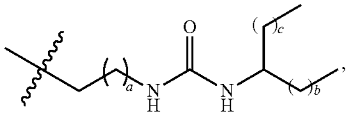
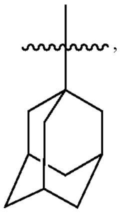

-continued
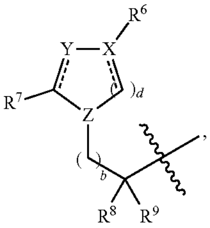,
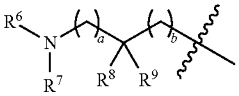
each $R^2$, $R^{2'}$, $R^3$ and $R^{3'}$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl, poly(ethylene glycol) (PBG) and
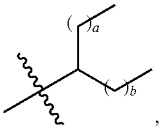,
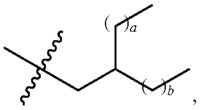,
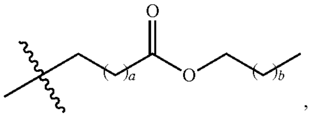,
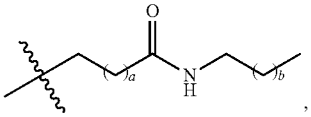,
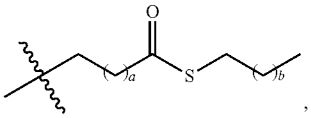,
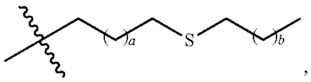,
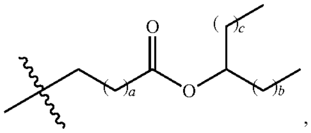,
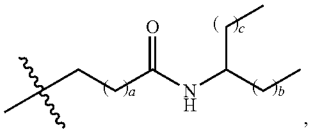,
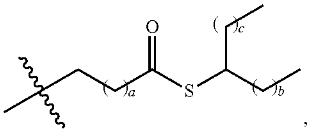,
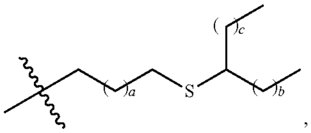,
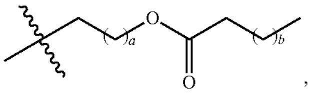,
-continued
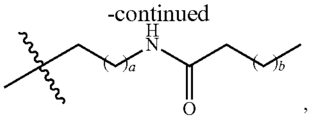,
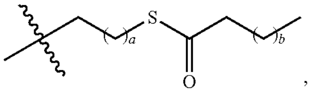,
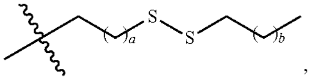,
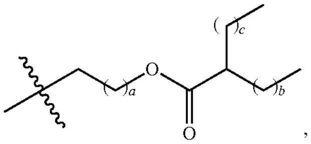,
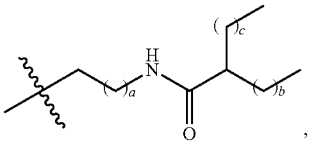,
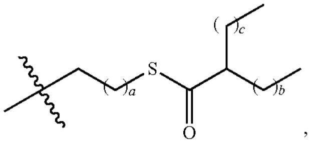,
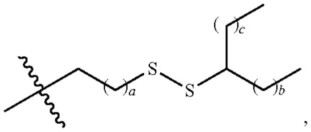,
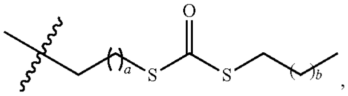,
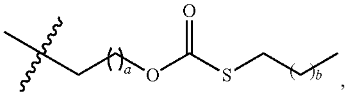,
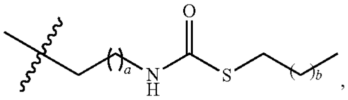,
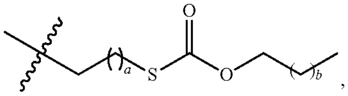,
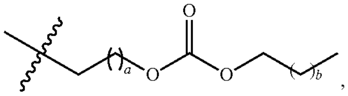,
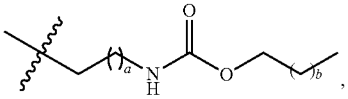,
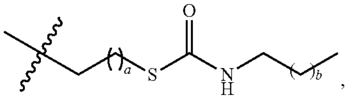,
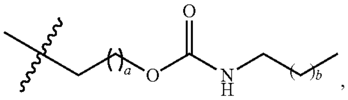,
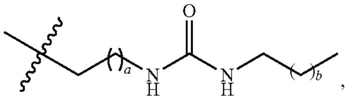, -continued
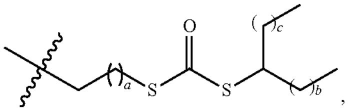,
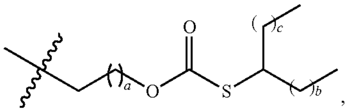,
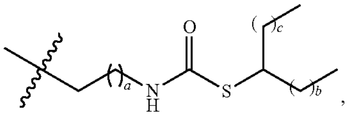,
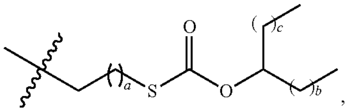,
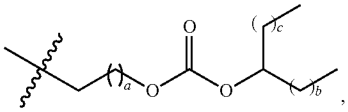,
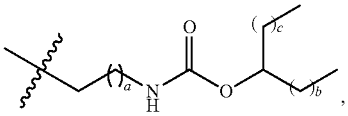,
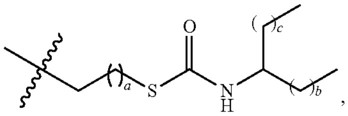,
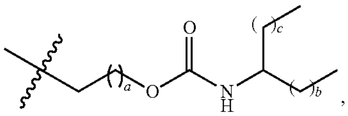,
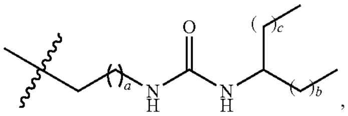, 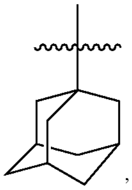,
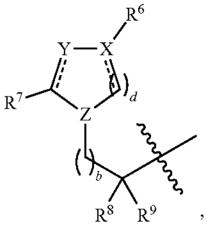, 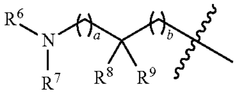
each L is independently selected from alkyl, alkenyl, alkynyl, substituted alkyl, substituted alkenyl, substituted alkynyl, substituted acyl, substituted carbocyclyl, substituted heterocyclyl, substituted aryl, substituted heteroaryl, poly (ethylene glycol) (PEG) and
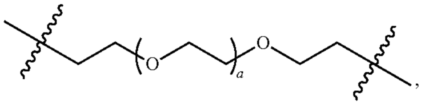,
-continued
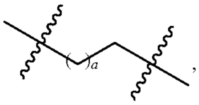, 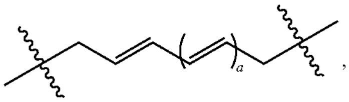,
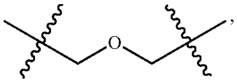, 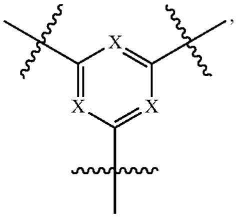,
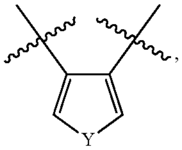, 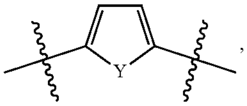,
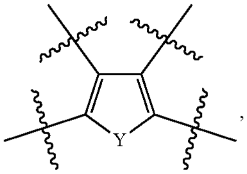, 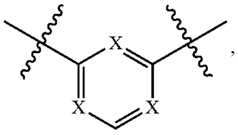,
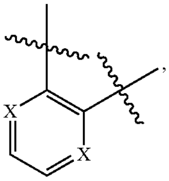, 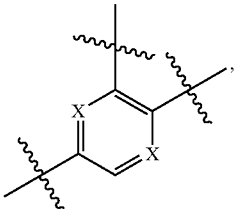,
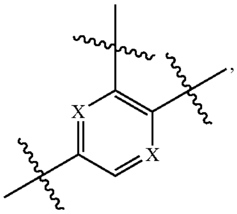, 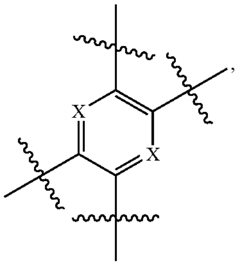,
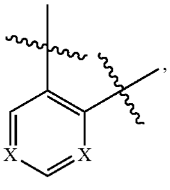, 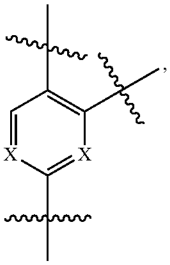,
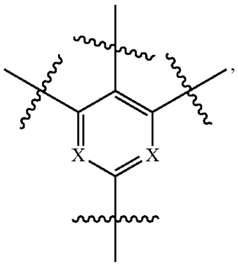, 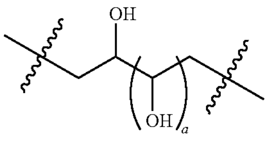, -continued
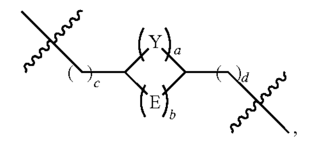
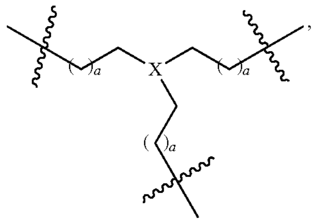
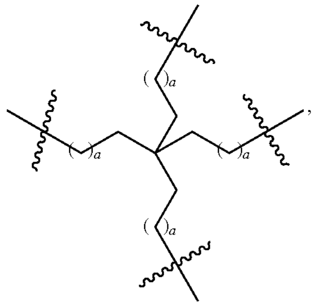
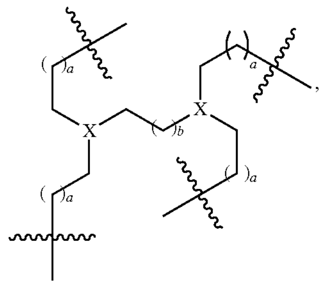
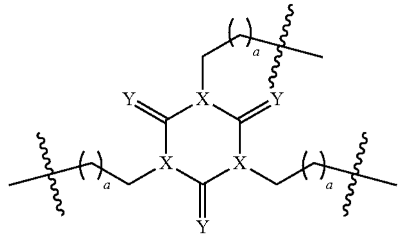
$R^6$, $R^7$, $R^8$ and $R^9$ are each independently selected from H, C1-C24 alkyl, C1-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl,
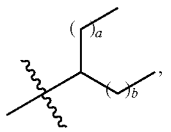
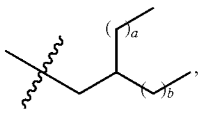
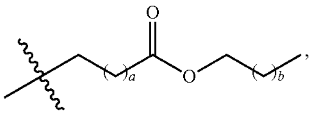
-continued
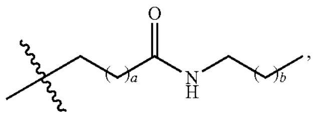
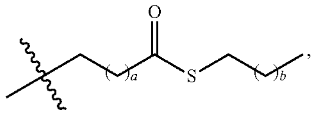
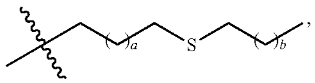
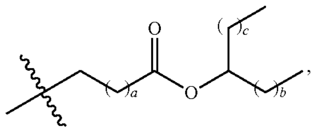
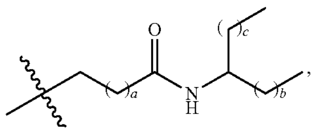
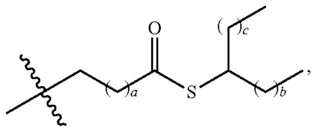
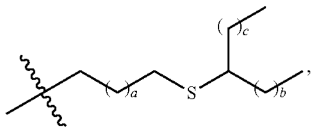
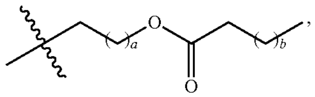
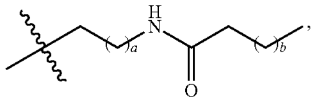
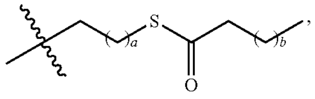
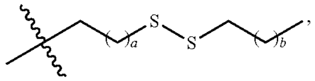
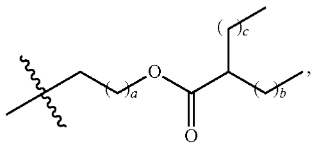
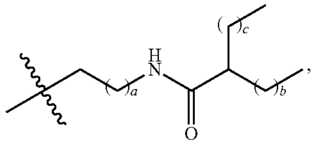
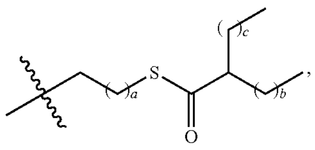

-continued
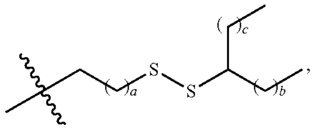
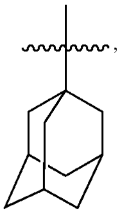
a, b, c and d are each independently an integer from 0-24;
each E is independently selected from $CH_2$, NH, O, or S;
each X is independently selected from CH or N;
each Y is independently selected from $CH_2$, NH, O, or S;
each Z is independently selected from CH or N.
A modular lipid, wherein the lipid is:
P161F6
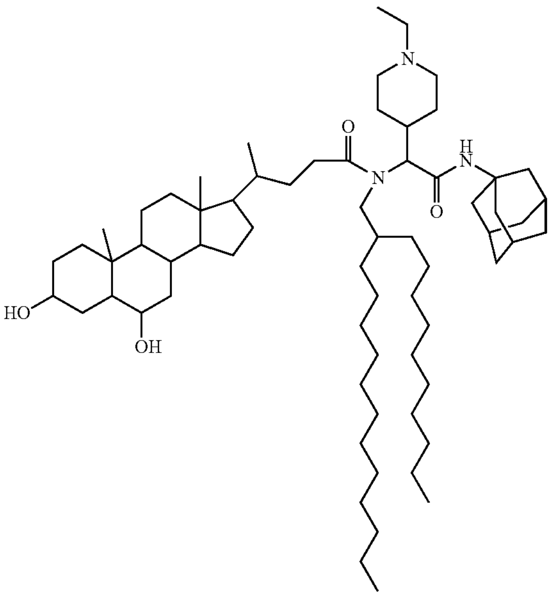
P161F5
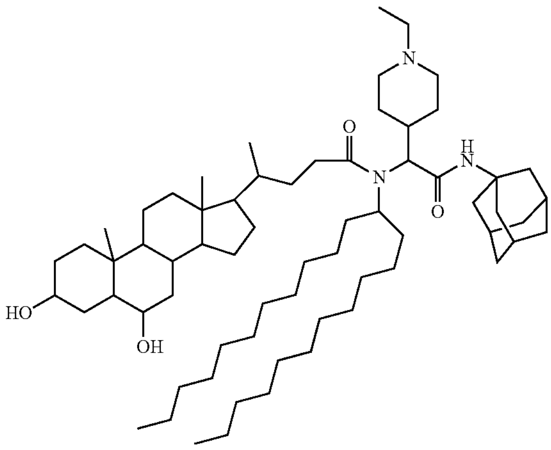
P161F12
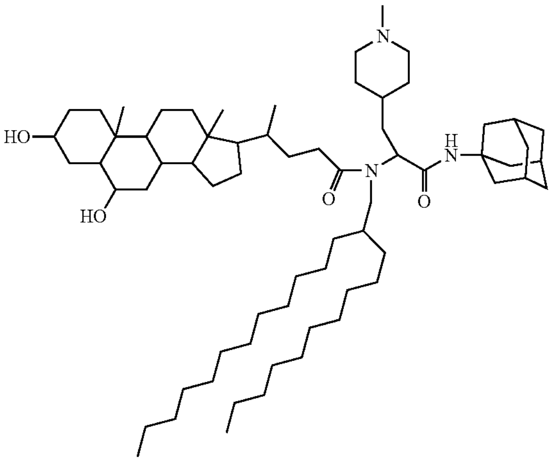
P161F10
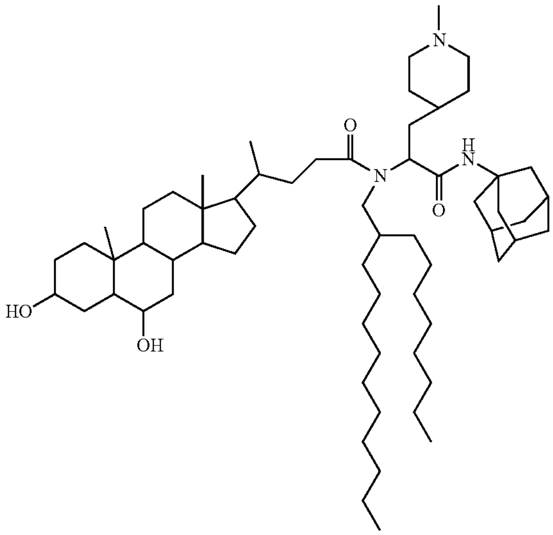

-continued
P287A12
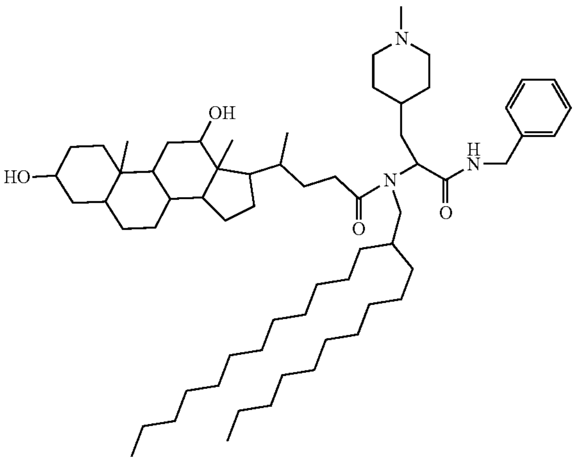
P287C12
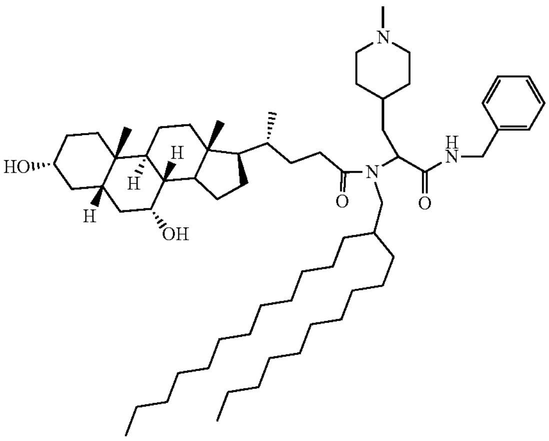
HP3G5
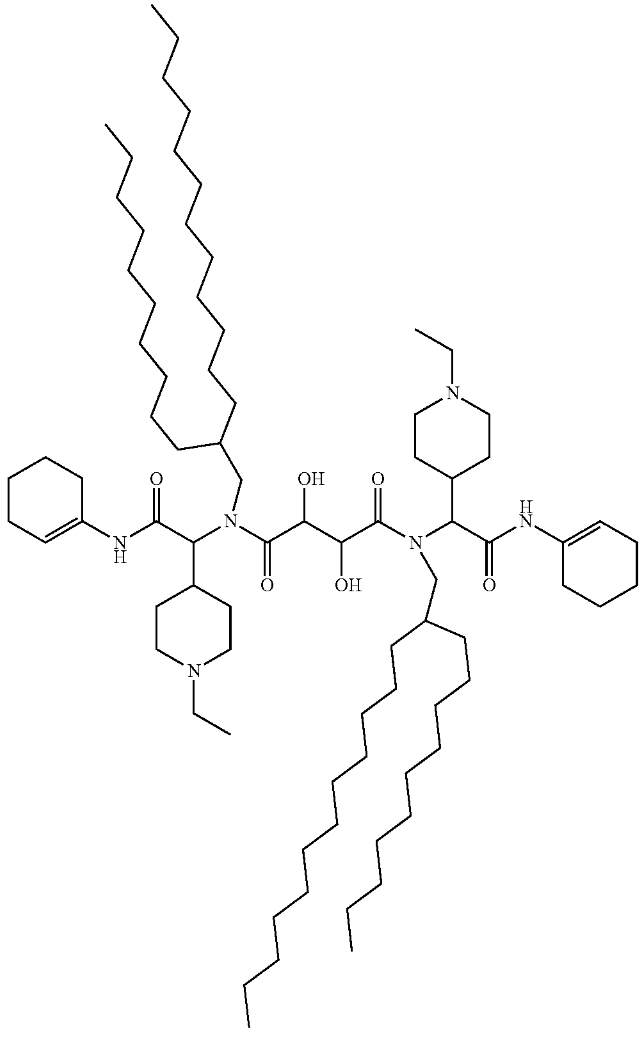

-continued
HP3H5
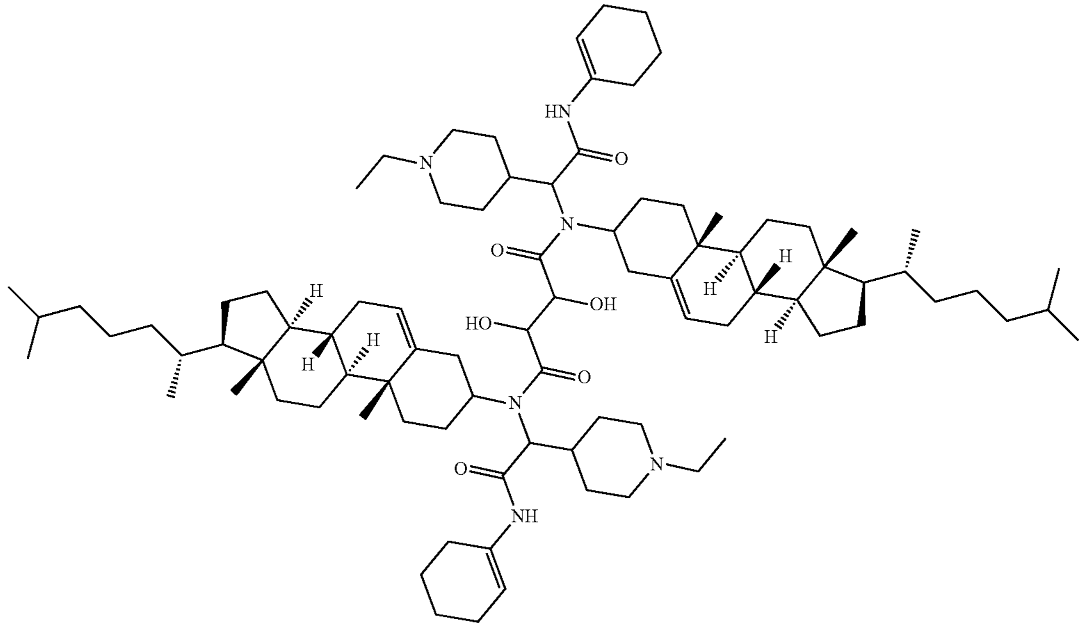
SP1E2
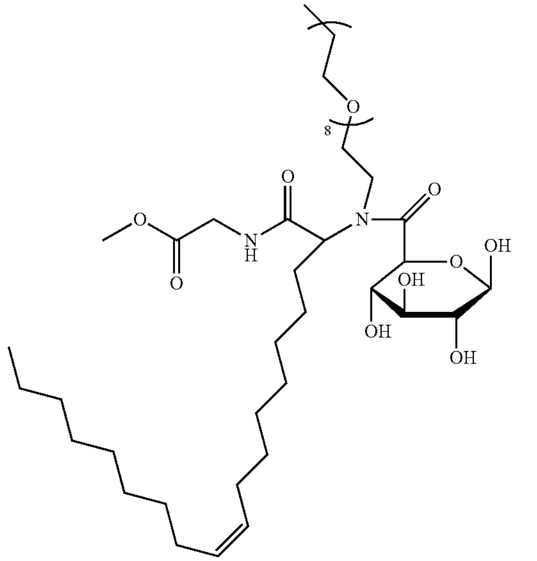
SP1F2
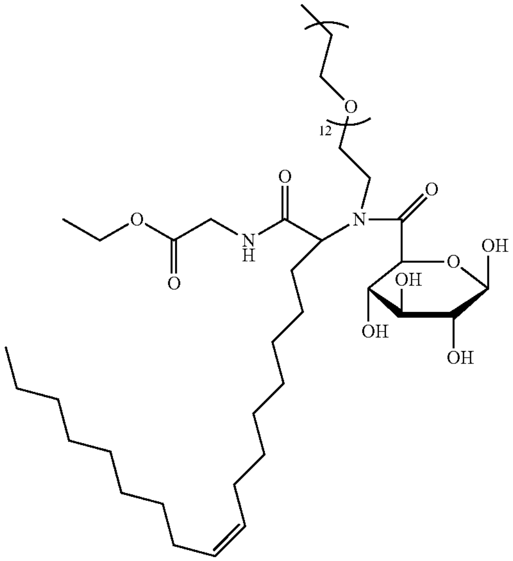
SP1F11
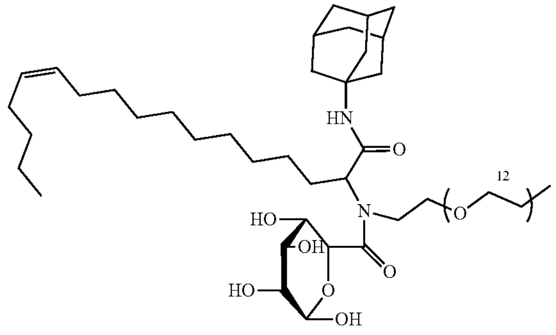
SP1E8
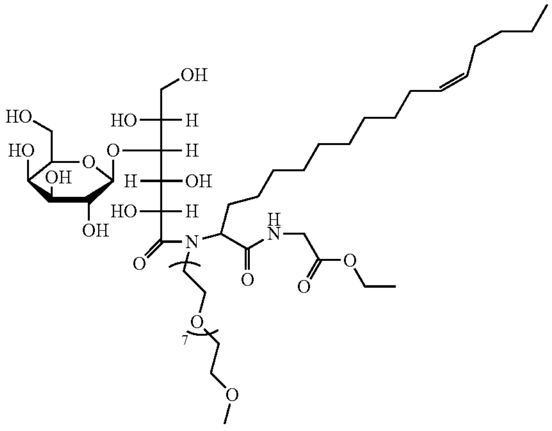

-continued
SP1E2K
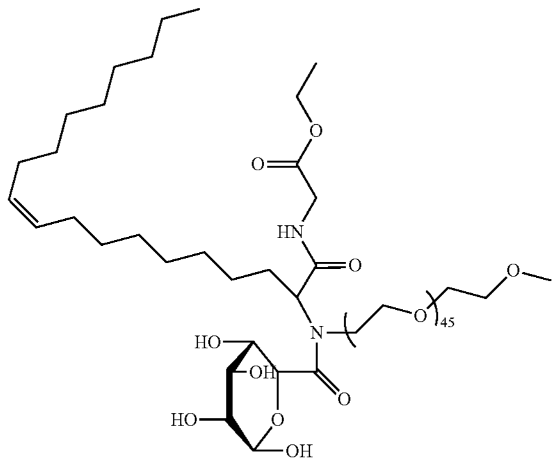
SP1E2KI
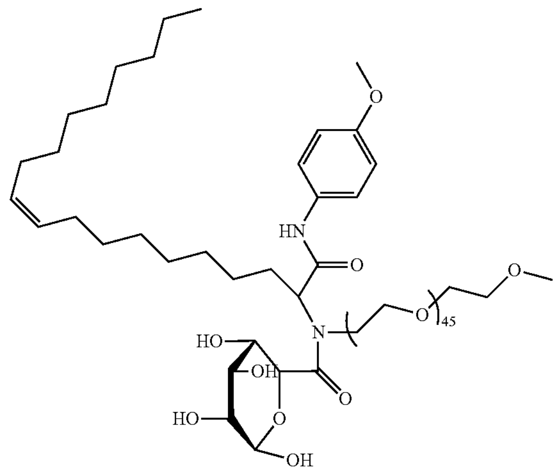
SP2B12
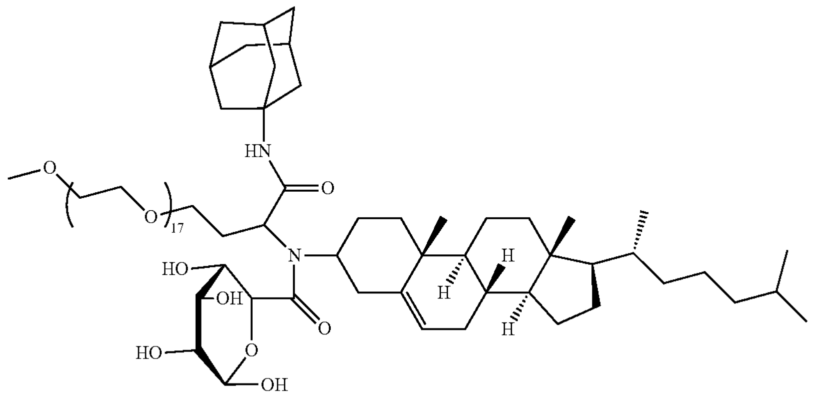
SP2A3
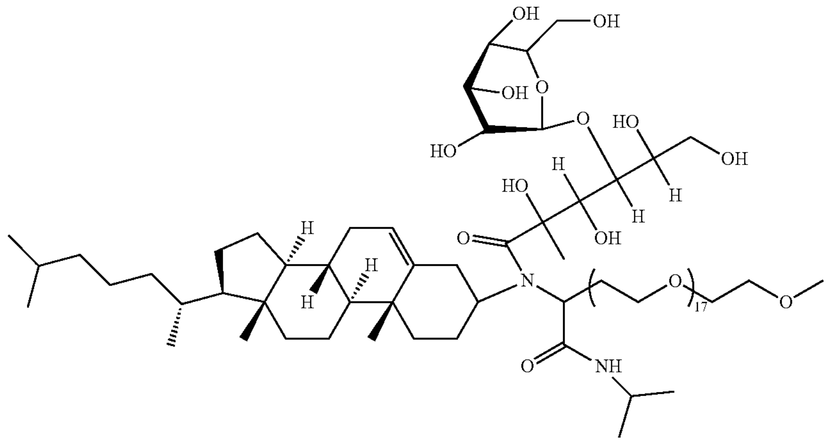

-continued
SP4A7
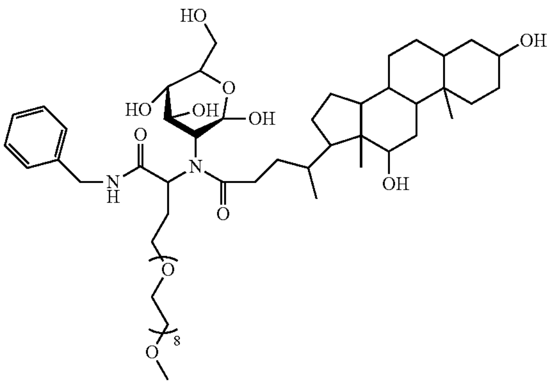
SP6A1
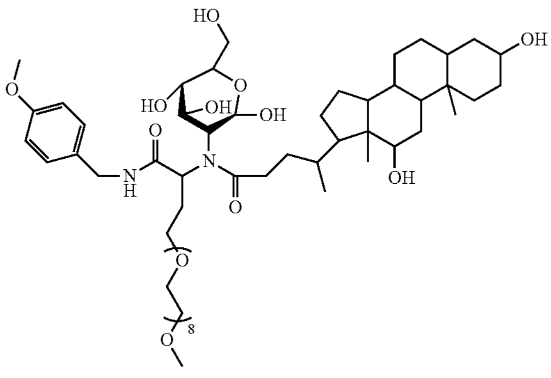
SP11A6
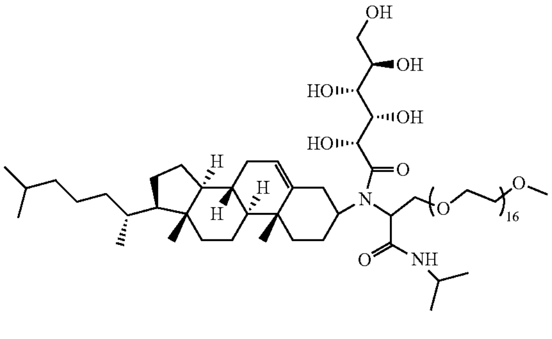
SP11H6
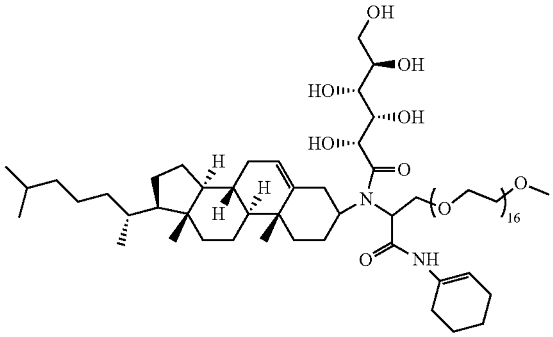
SP11H3
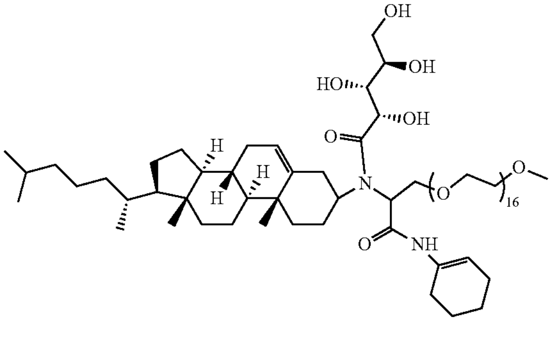
SP11A12
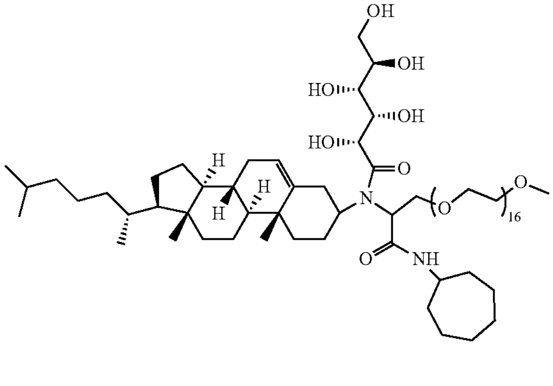

-continued

SP1E2-PEG3

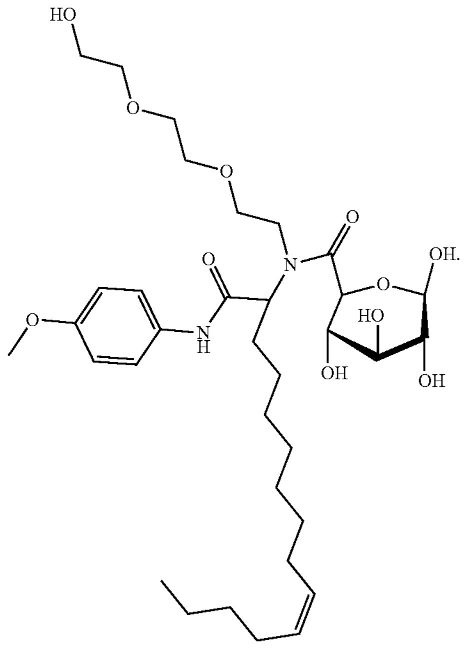

In one aspect, the present disclosure provides a nanoparticle composition comprising a modular lipid component, a stabilizer lipid component, and/or a phospholipid component, optionally wherein the nanoparticle composition is a two-component composition or a three-component composition. In some aspects, the stabilizer lipid component is the saccharide lipid compound of the disclosure or a PEG lipid. In some aspects, a two-component LNP contains a modular lipid and a PEG lipid which could be saccharide lipid (containing a PEG group).

In one aspect, the present disclosure provides a nanoparticle composition comprising a modular lipid component, a phospholipid component, and a saccharide lipid component.

In one aspect, the present disclosure provides two- or three-component nanoparticle compositions and uses thereof including novel saccharide LNP (mLNP) compositions and nanoparticle compositions comprising at least one modular lipid that provide better transfection efficiency of nucleic acid as compared to traditional four components LNP systems.

In one aspect, the present disclosure provides a nanoparticle composition and a use thereof or method for delivering a payload (e.g. a biologically active agent nucleic acid) to a cell (e.g., a cell) by administering a nanoparticle composition comprising at least one saccharide lipid or modular lipid of the present disclosure.

In one aspect, the present disclosure provides a nanoparticle composition and a use thereof or method for delivering a payload (e.g. a biologically active agent nucleic acid) to a cell (e.g., a cell) by administering a nanoparticle composition comprising at least one saccharide lipid, modular lipid of the present disclosure and at least one ionizable lipid.

In one aspect, the present disclosure provides a nanoparticle composition and a use thereof or method for delivering a payload (e.g. a biologically active agent nucleic acid) to a cell (e.g., a cell) by administering a nanoparticle composition comprising at least one saccharide lipid or modular lipid of the present disclosure, at least one ionizable lipid, and at least one phospholipid.

In one aspect, the present disclosure provides uses and methods of using the two- or three-component compositions to deliver at least one payload to a subject in need thereof or to a biological sample. In some aspects, the use or method of the present disclosure is a prophylactic, diagnostic, or therapeutic use or method. In some aspects, upon administration to a subject in a therapeutically effective amount, provides a therapeutic benefit to the subject.

In one aspect, the present disclosure provides a two component composition including the two components in the following relative mole percentages: 1 to 99 mole % of saccharide lipid; and 1 to 99 mole % of ionizable lipid.

In one aspect, the present disclosure provides a nanoparticle composition comprising a modular lipid component, a phospholipid component, and a saccharide lipid component. In some aspects, the modular lipid component comprises a linker, a cationic ionizable group and a lipid raft group.

In one aspect, the present disclosure provides a three component composition including the three components in the following relative mole percentages: 0.2 to 80 mole % of saccharide lipid; 5 to 80 mole % of ionizable lipid; and 5 to 60 mole % of phospholipid.

In one aspect, the payload is a conventional mRNA or self-amplifying mRNA encoding the polypeptide of interest, whereby the mRNA is capable of being translated in the cell to produce the polypeptide. In another aspect, the payload is a DNA encoding the gene of interest, whereby the cell becomes capable of expressing the introduced gene. In another aspect, payload is a siRNA or antisense RNA capable of modulating the expression of a gene of interest, whereby the cell decreases expression of the gene of interest. In one aspect, at least one of the ionizable lipids is an ionizable lipid of the disclosure, such as a compound of Formula I including any species therein and derivatives thereof. In one aspect, at least one of the saccharide lipids is a compound of Formulas III or IV including any species therein and derivatives thereof. In one aspect, the nanoparticle composition comprise at least two different saccharide lipids. In one aspect, the nanoparticle composition comprise both saccharide lipids of Formulas III and IV. In one aspect, the nanoparticle composition comprise a modular lipid of the disclosure.

In another aspect, the present disclosure provides a nanoparticle composition comprising (i) at least one ionizable lipid, (ii) a phospholipid moiety, (iii) a saccharide lipid, (iv) a payload, or any combination thereof. In one aspect, the phospholipid moiety may be selected from the non-limiting group consisting of 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin. In one aspect, at least one of the ionizable lipids is a compound of Formula I, include species thereof such as Ia, Ib, etc. In one aspect, at least one of the ionizable lipids is a compound of Formula II, include species thereof such as IIa, IIb, IIc, IId, IIe, etc. In one aspect, at least one of the saccharide lipids is a compound of Formulas III or IV, including species thereof. In one aspect, the nanoparticle composition comprise at least two different saccharide lipids. In one aspect, the nanoparticle composition comprise both saccharide lipids of Formulas III or IV, including species thereof.

In another aspect, the present disclosure provides methods of synthesizing a compound of Formulae (I), (II), (III), and/or (IV) include species thereof such as Ia, Ib, IIa, IIb, IIc, IId, IIe, etc.

In another aspect, the ionizable lipid is:

P83B4

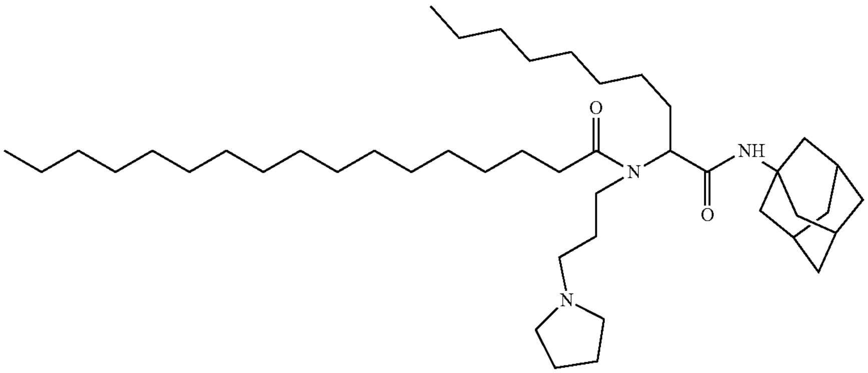

P83C4

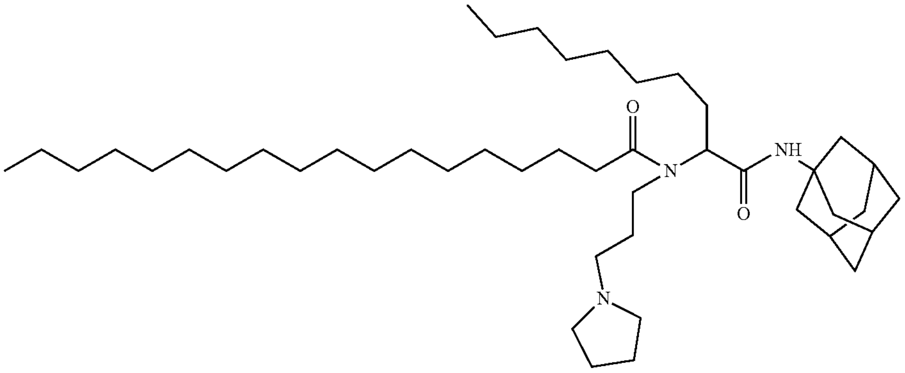

-continued
P83A4
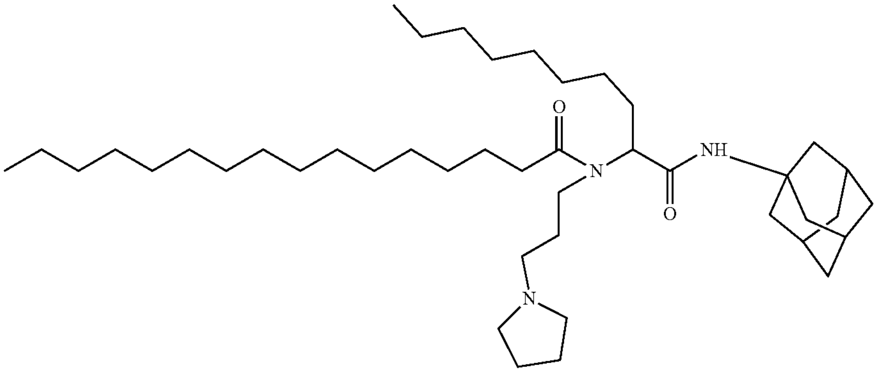
P94B4
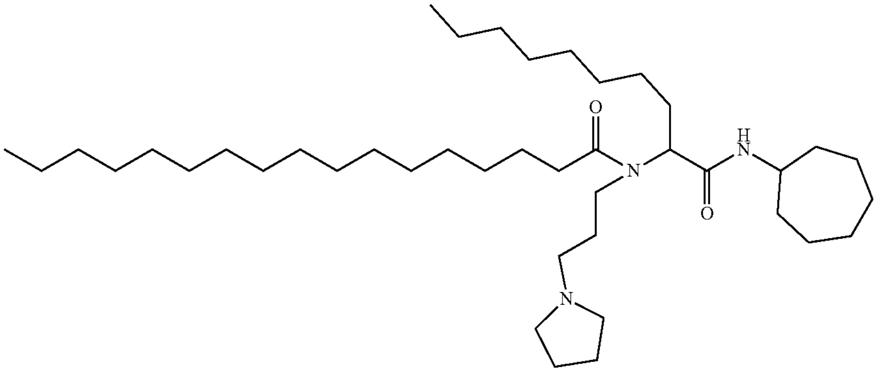
P94C4
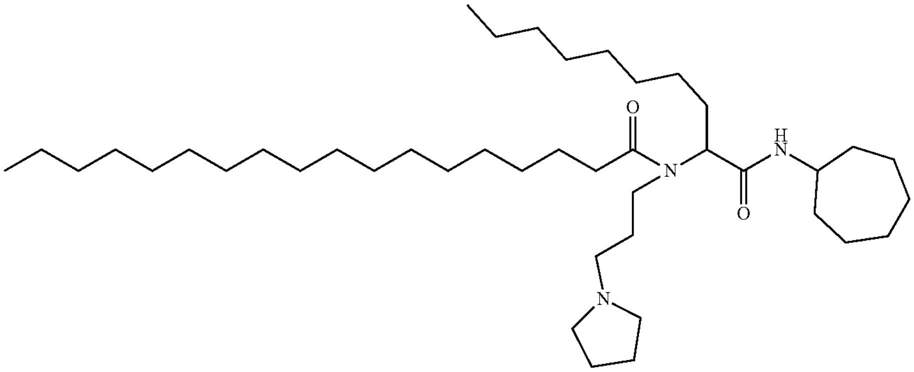
P95G12
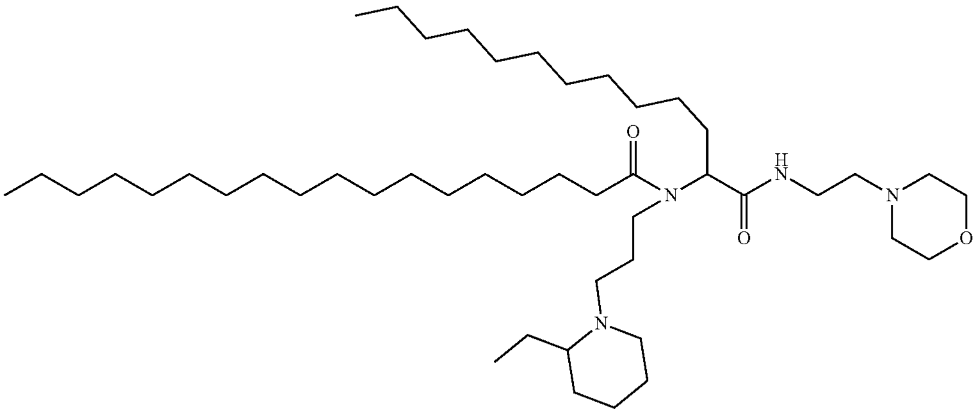

-continued
P110C10
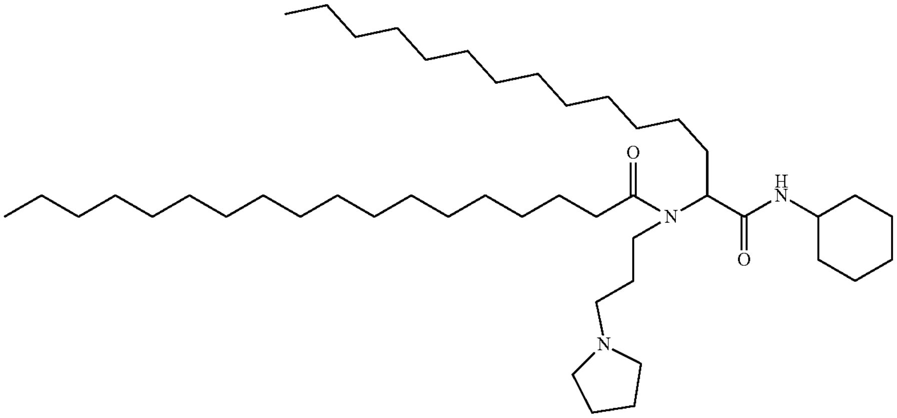
P366B5
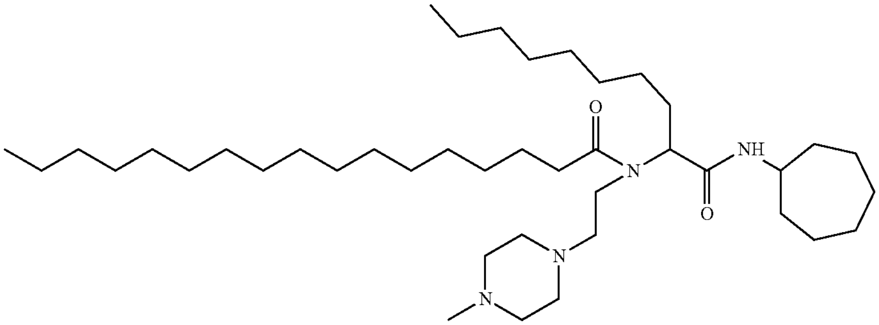
P366B6
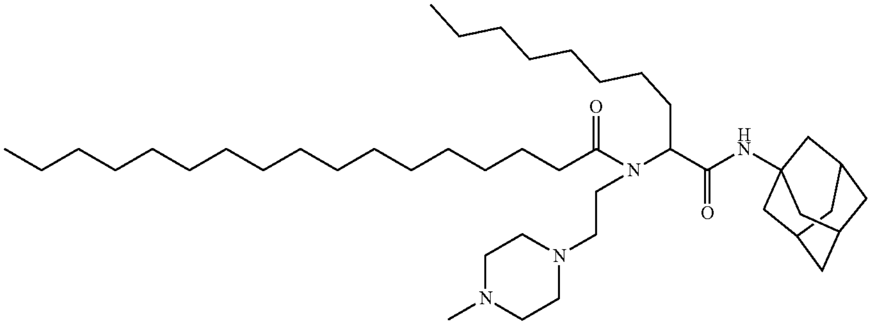
P110C10
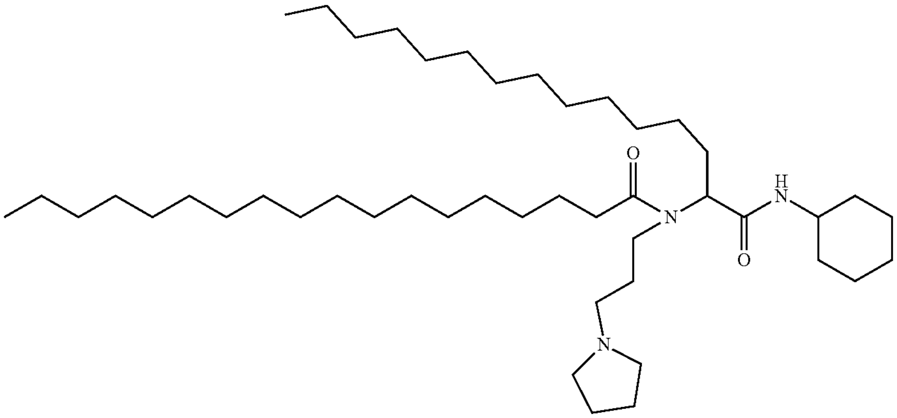

-continued
P366B5
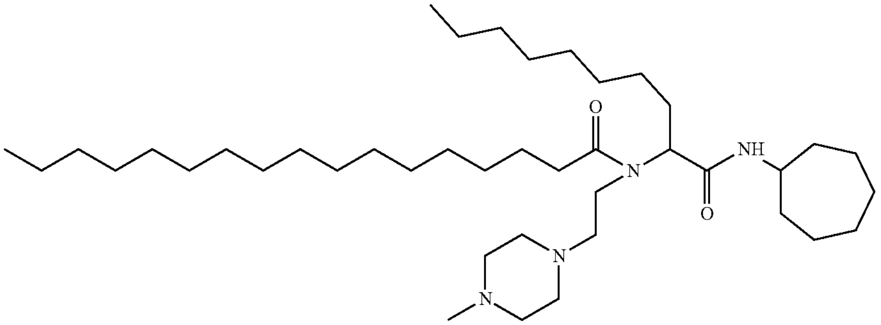
P366B6
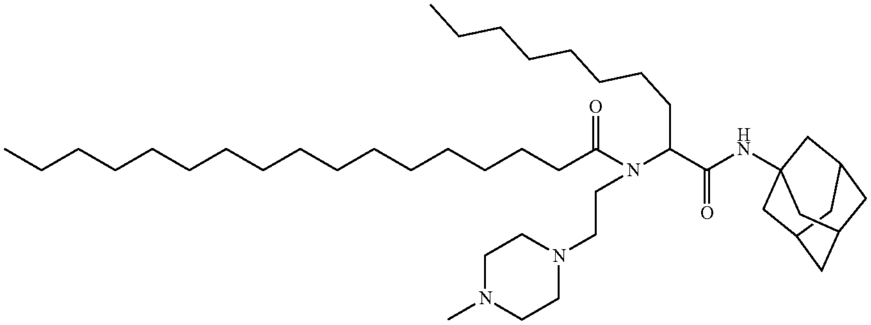
P366B12
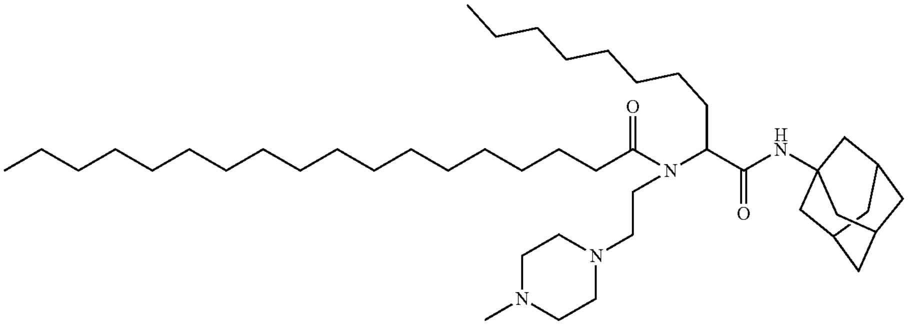
P366C1
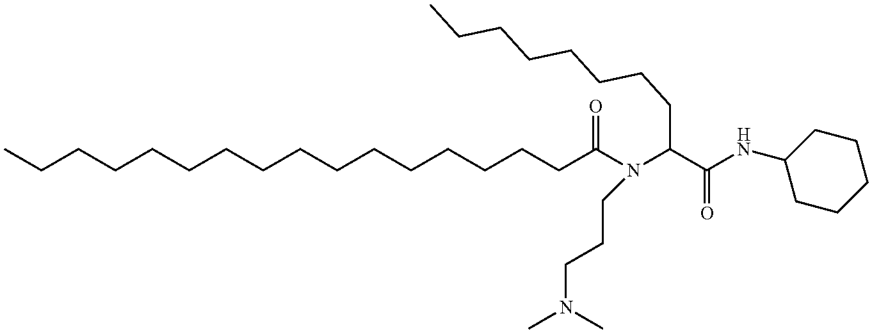

-continued
P366C4
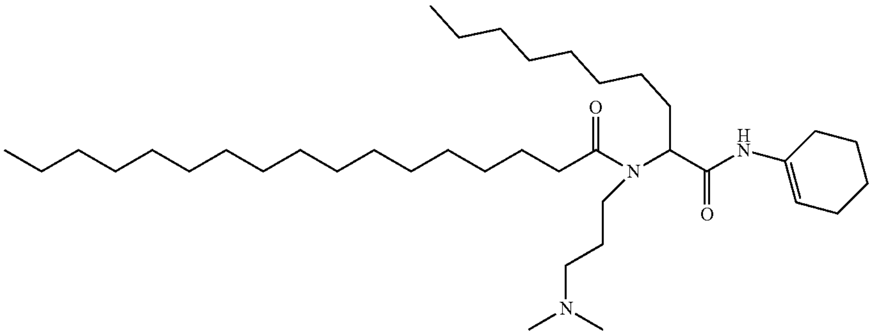
P366C6
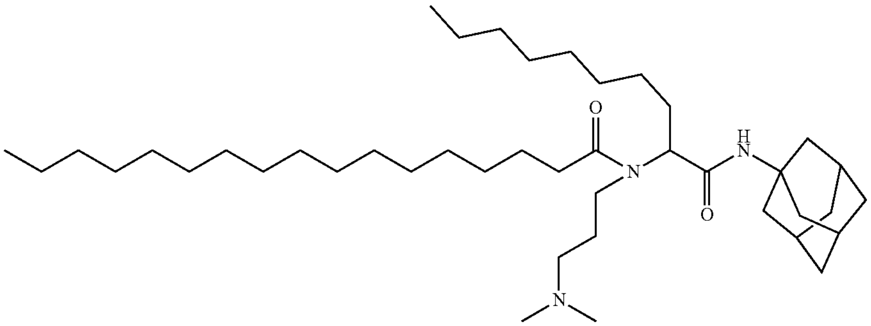
P366C7
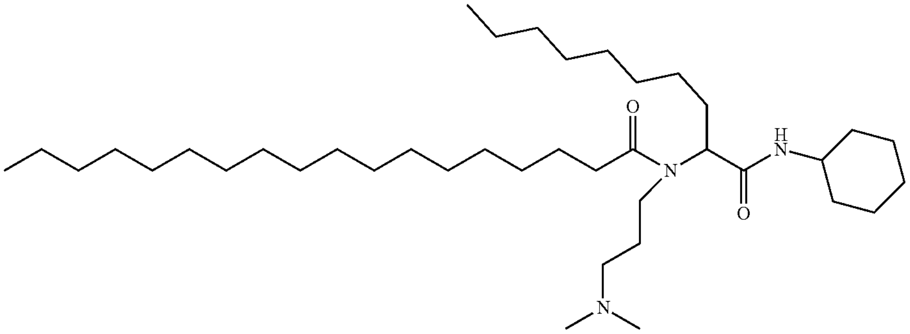
P366C11
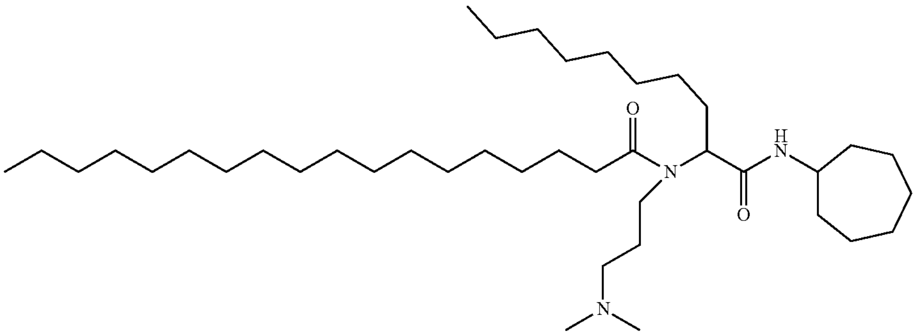

-continued
P366C12
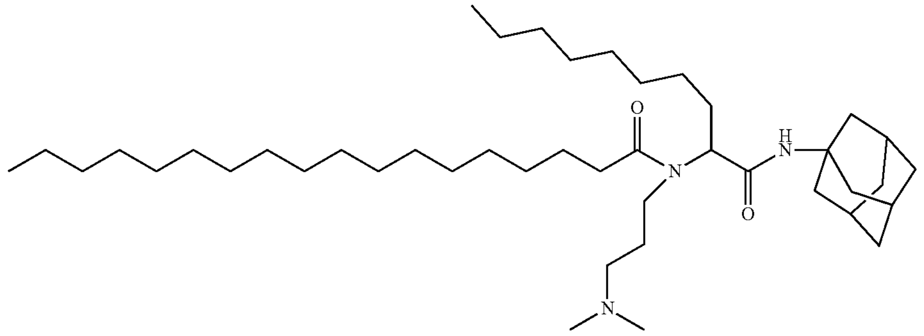
PC66D11
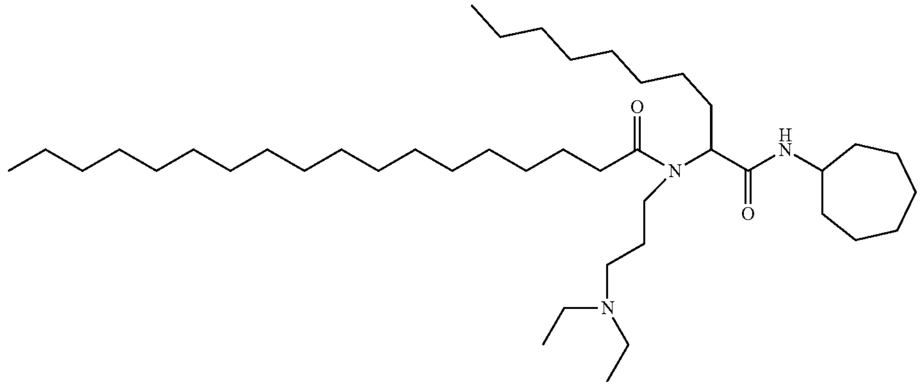
P366D12
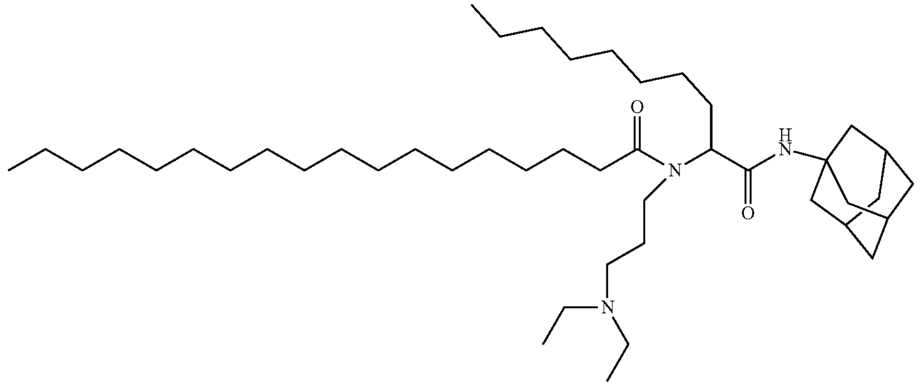
P368C5
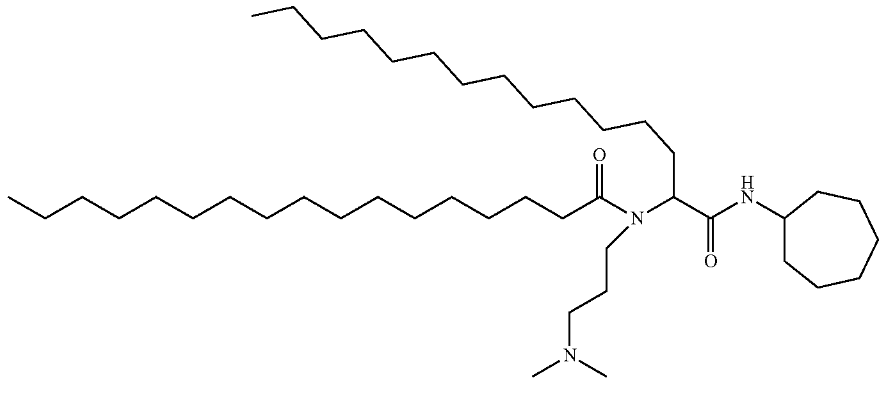

-continued
P368C12
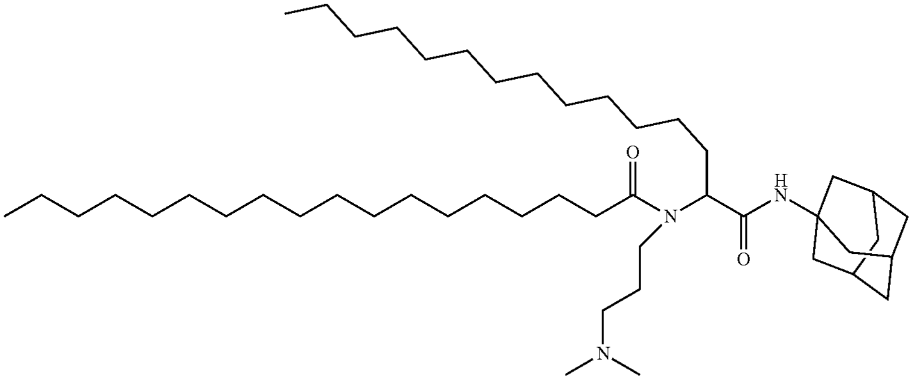
P368D12
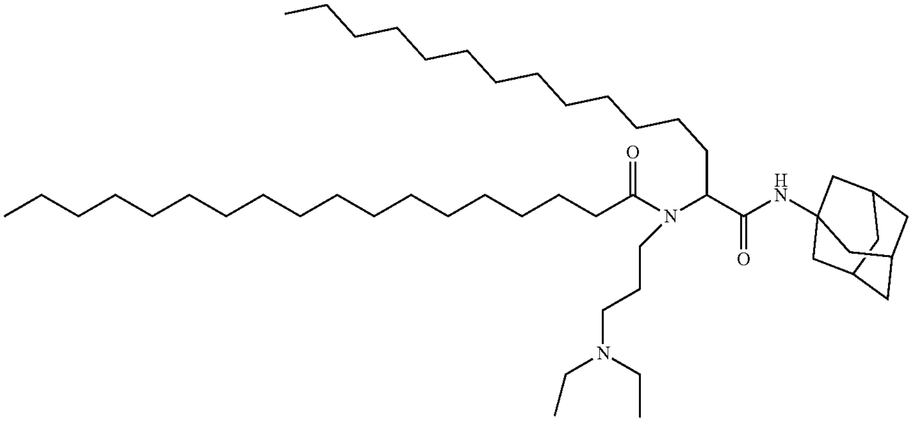
P370D6
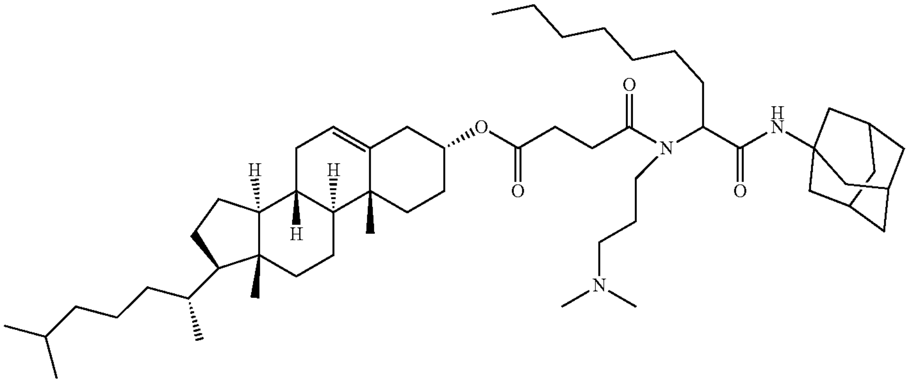
P371A6
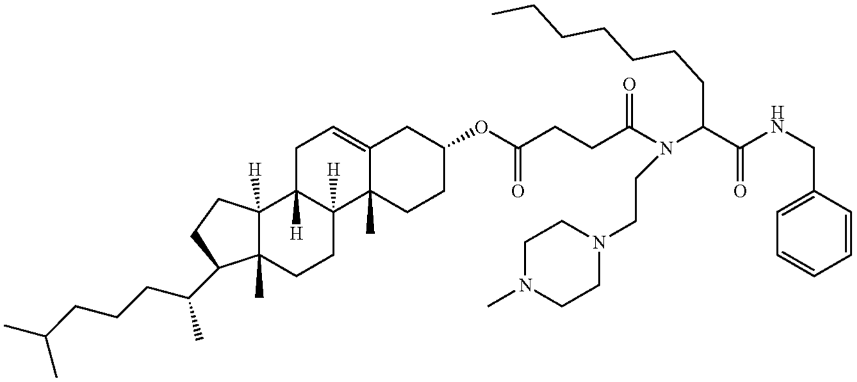

-continued
P371D6
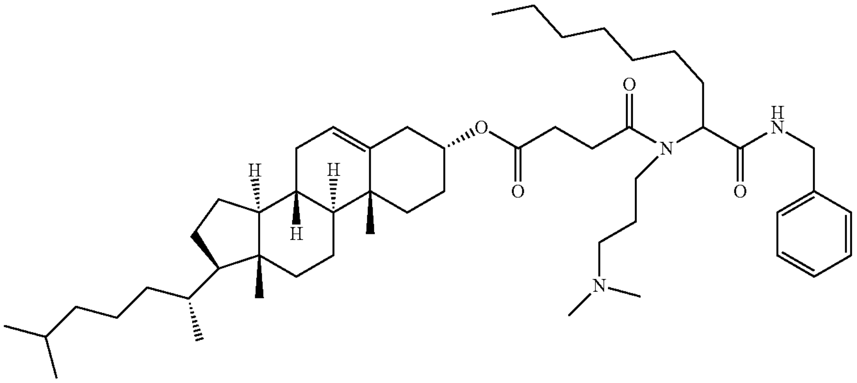
P374F7
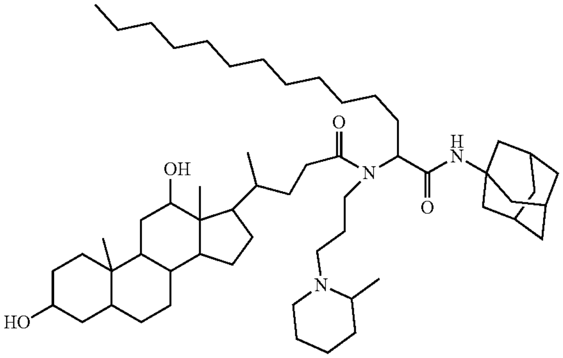
P376F1
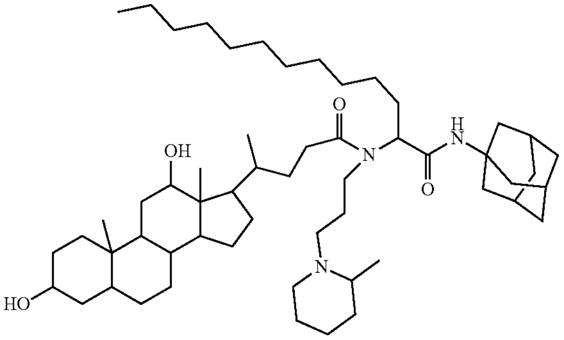
P380D1
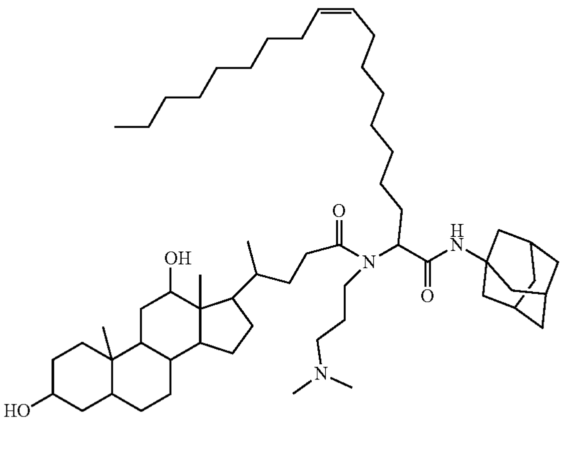
P380E1
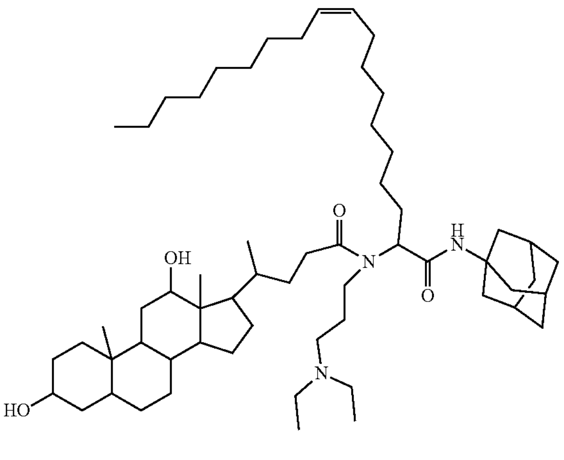

-continued
P380F1
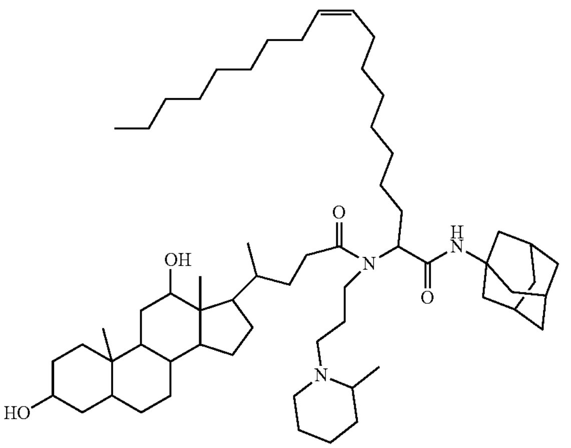
P380F4
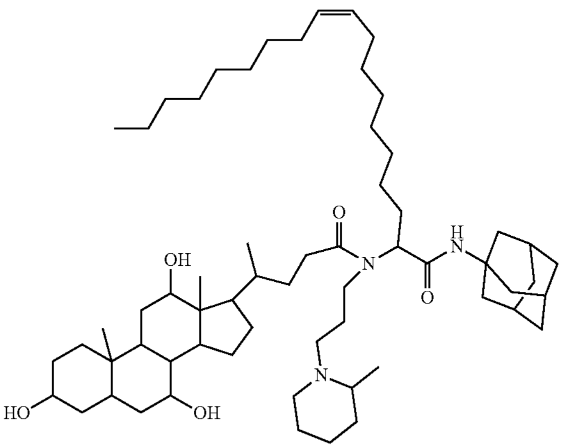
P381F1
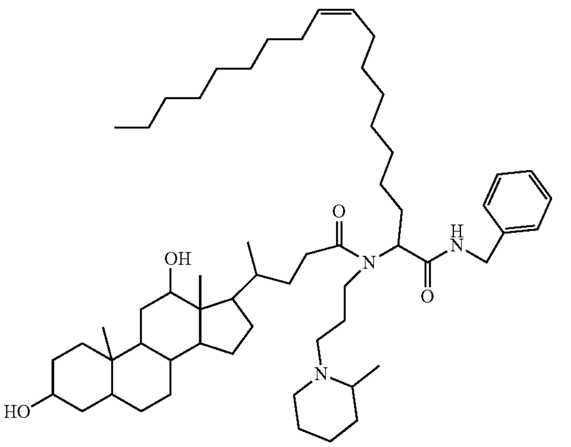
P383A9
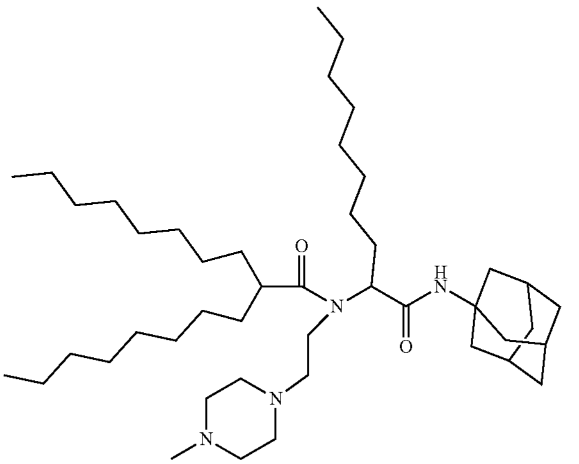
P383B10
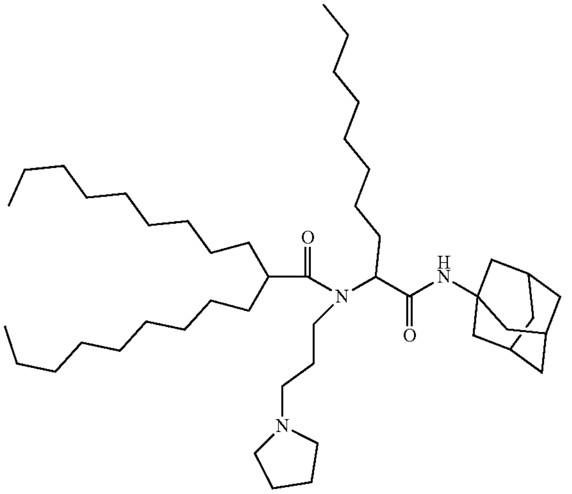
P386D12
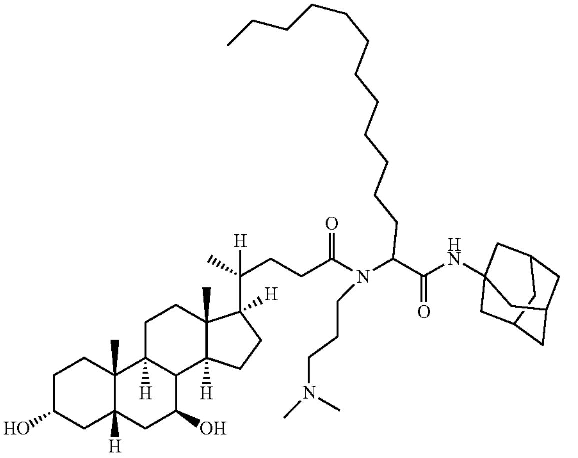

-continued
P387A2
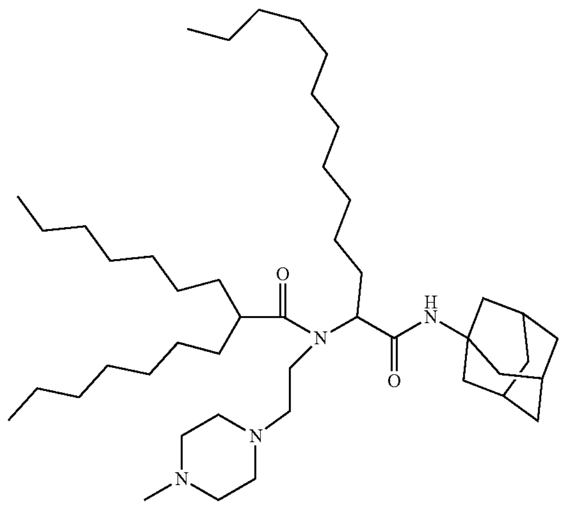
P390E12
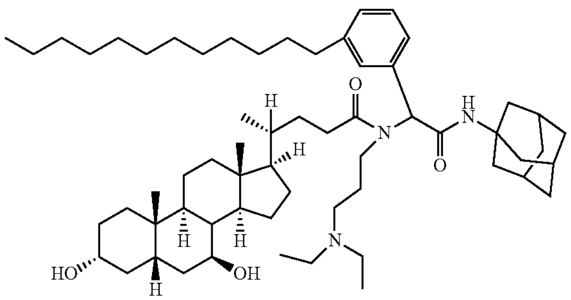
P394A7
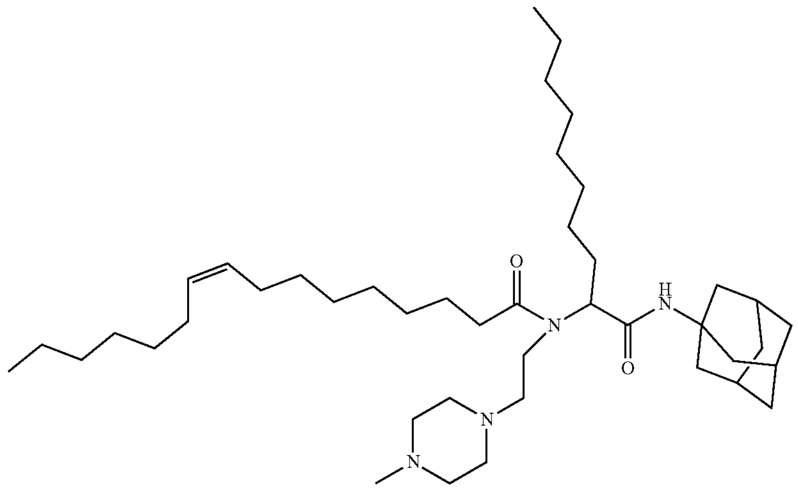
P394D7
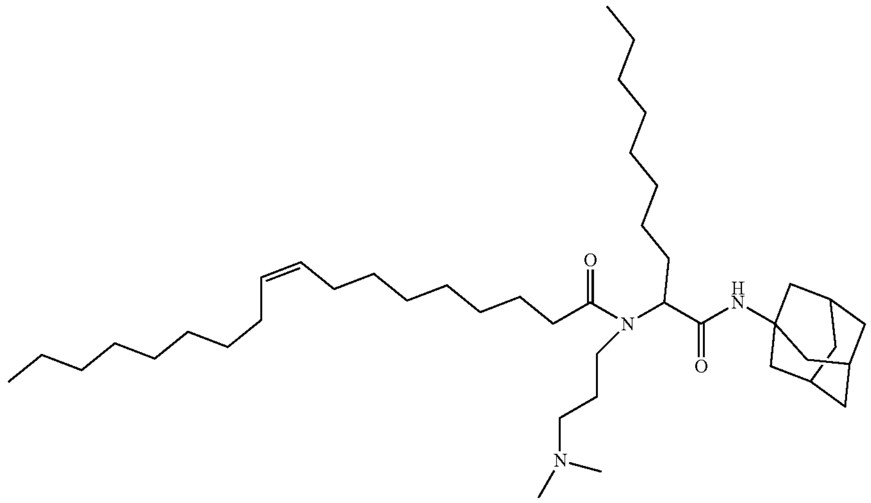

-continued
P394D12
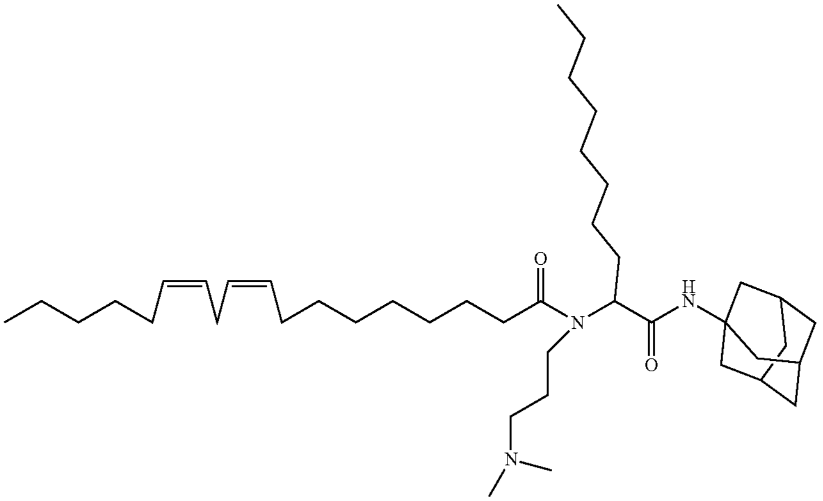
P394H8
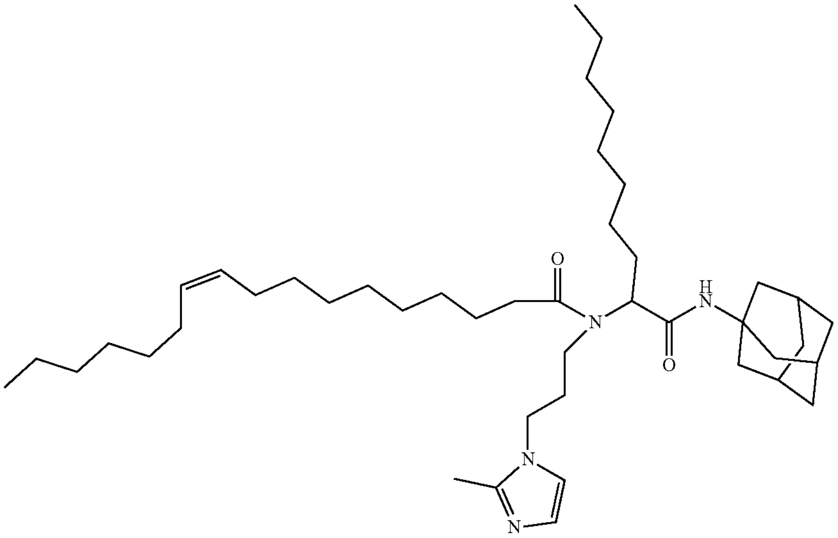
P394H9
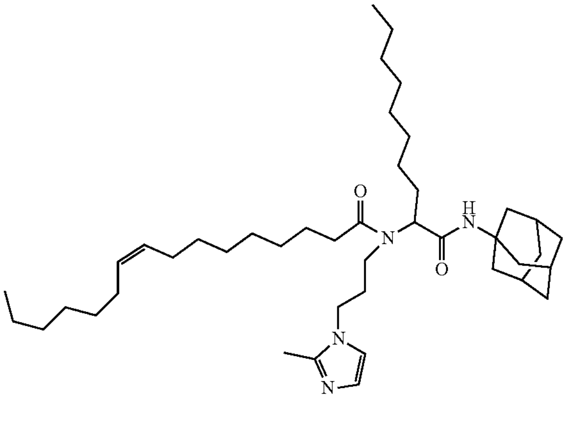
P398D1
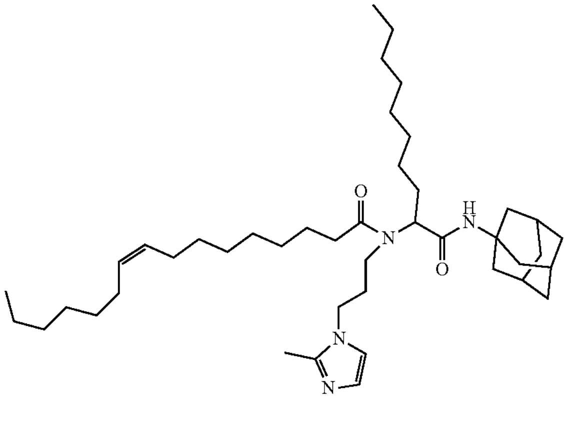

-continued
P398D6
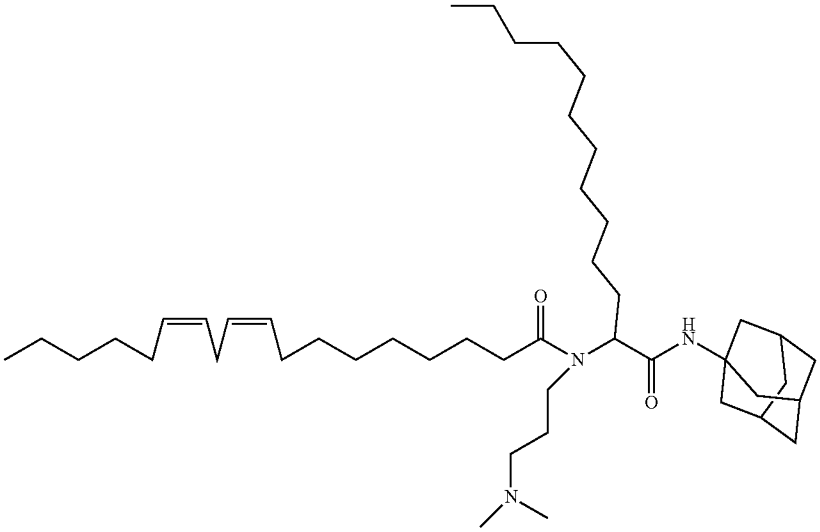
P398D7
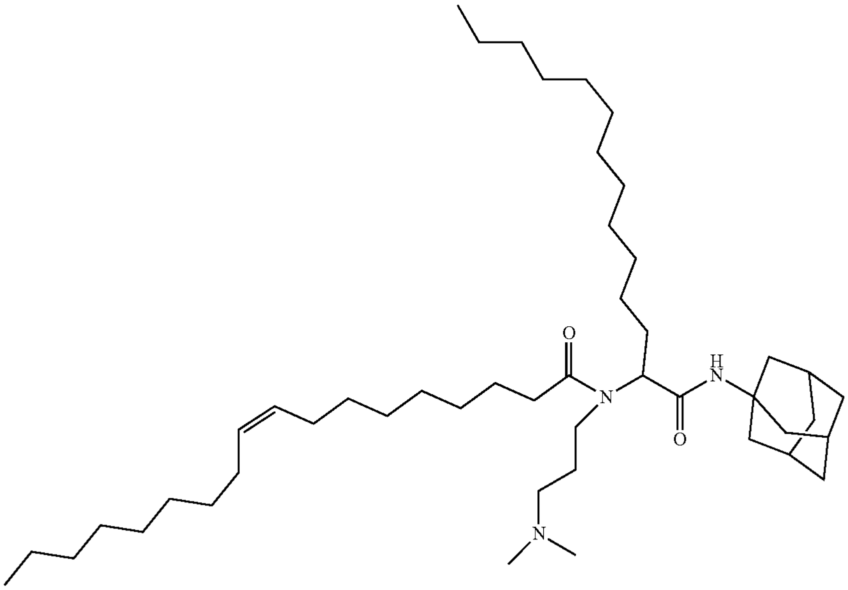
P398D8
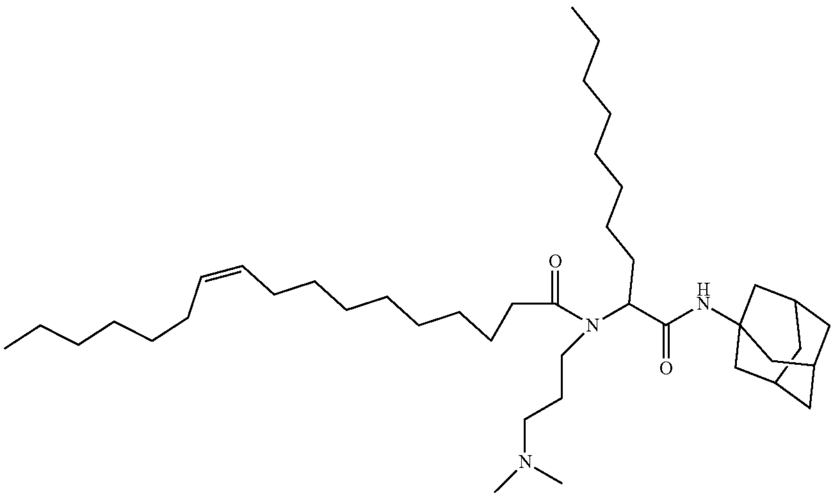

-continued
P398D9
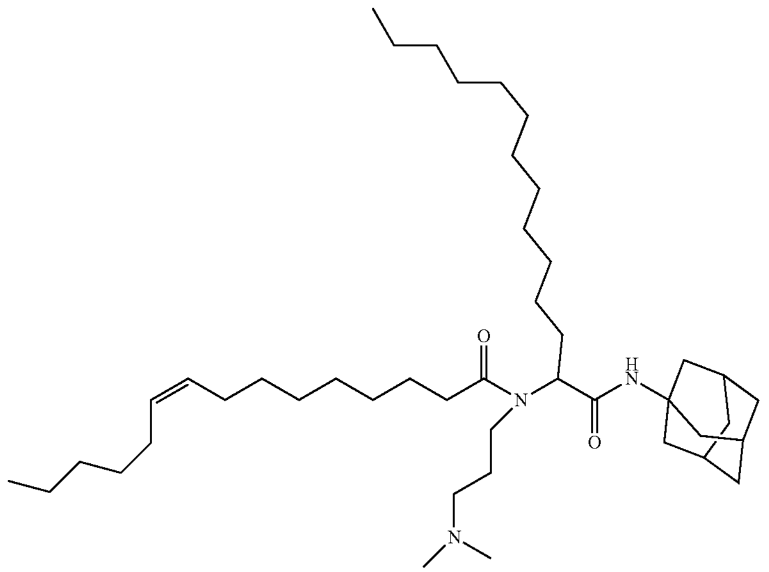
P398D12
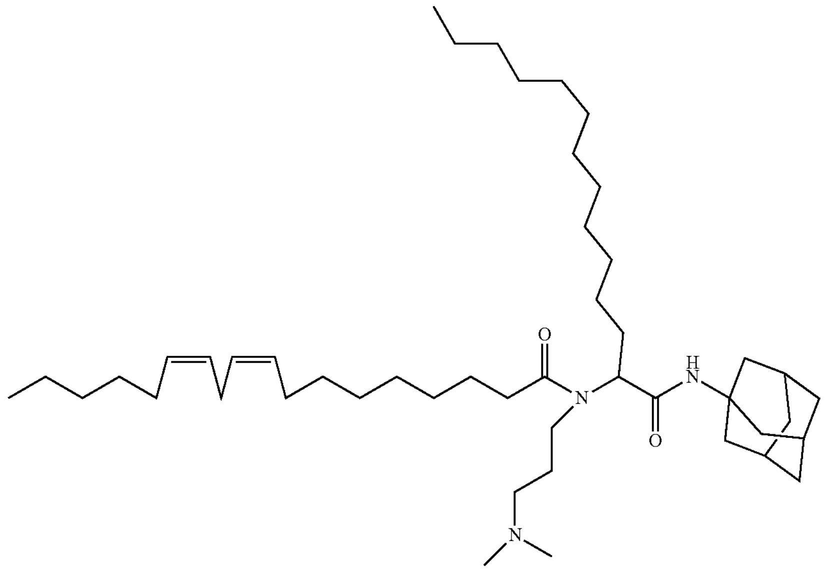

-continued
P398E1
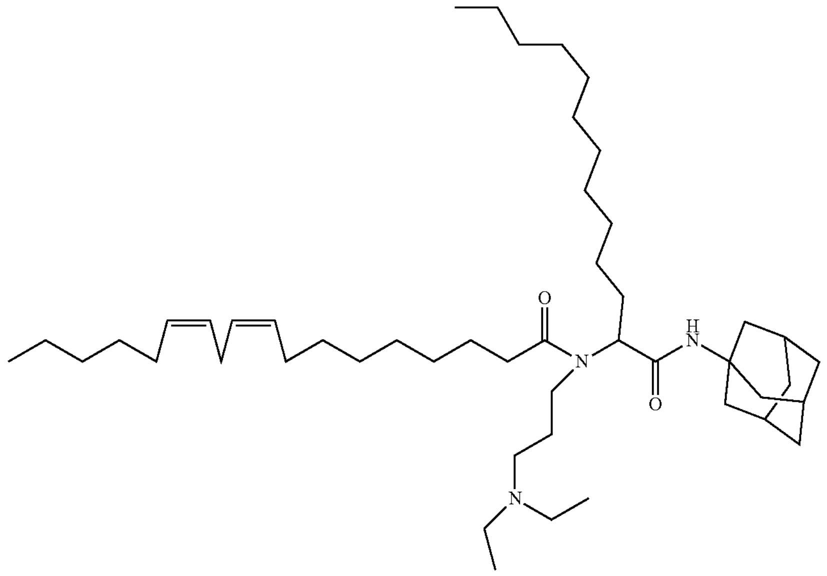
P399A1
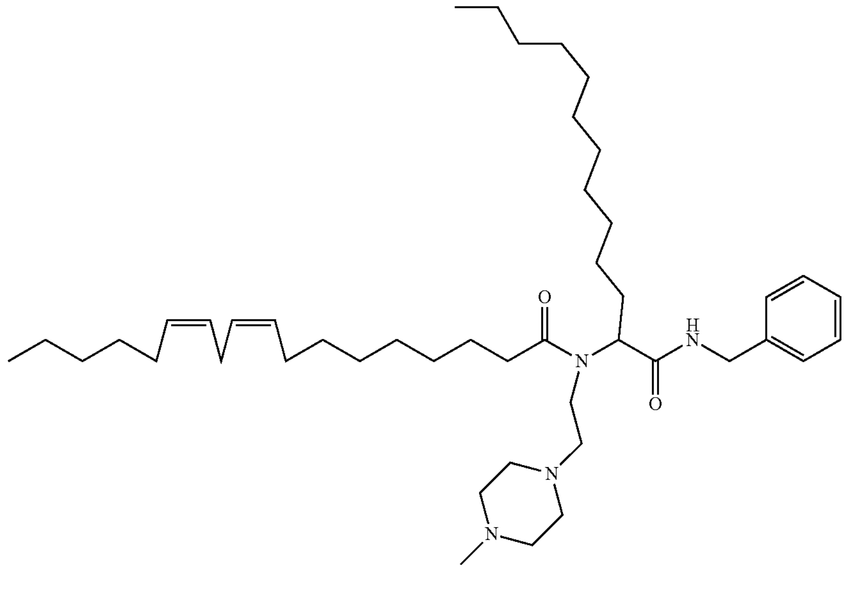

-continued
P399A9
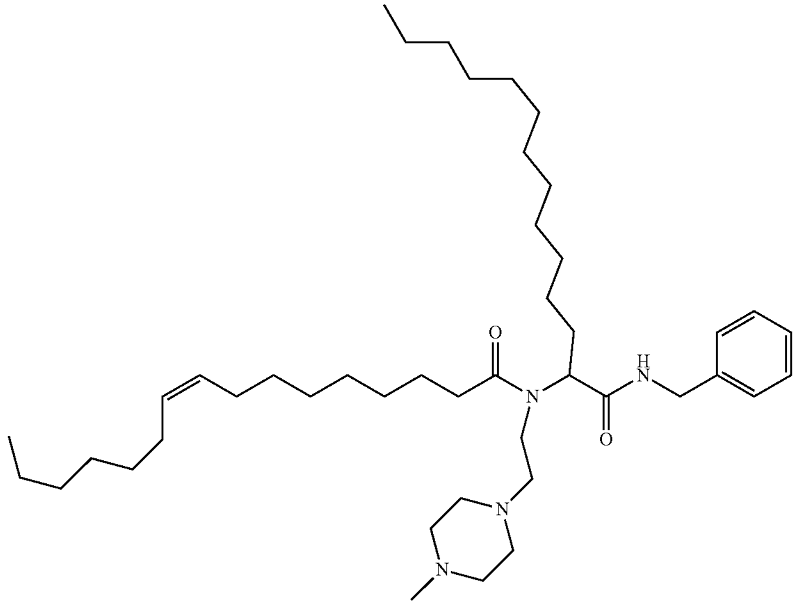
P399E1
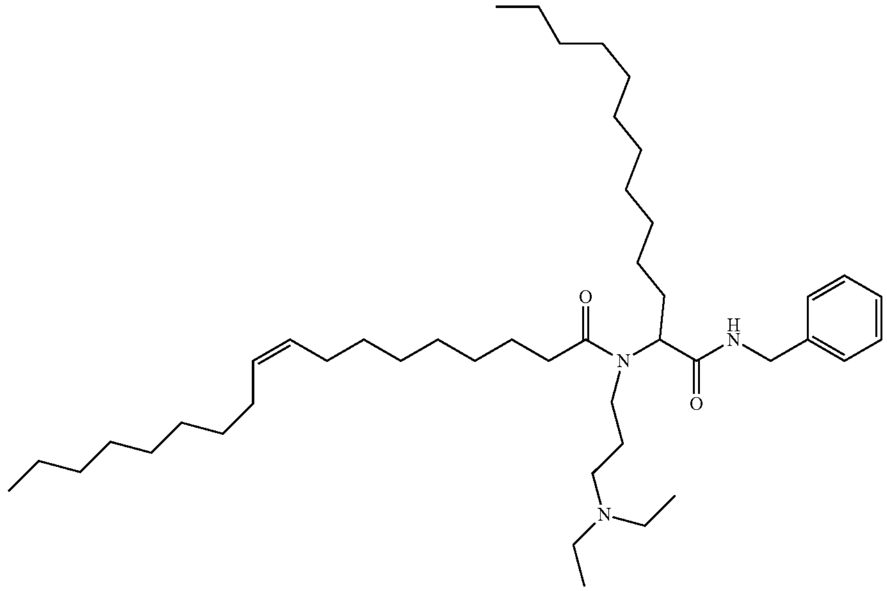

P399F1
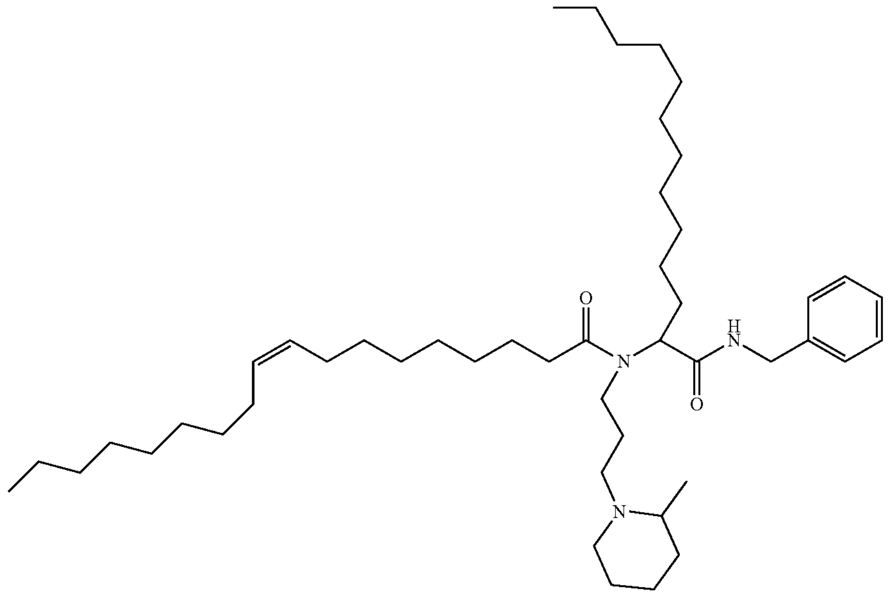
P399F12
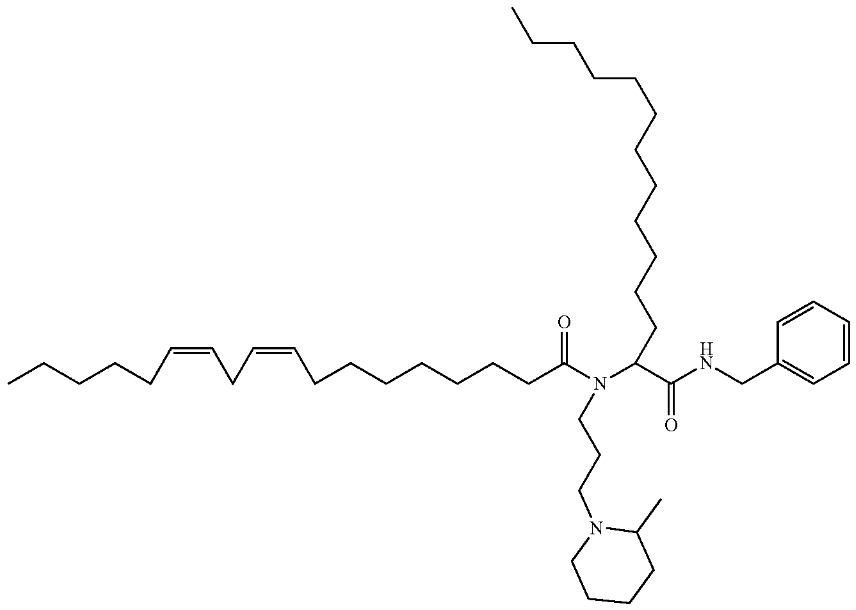

-continued
P399H1
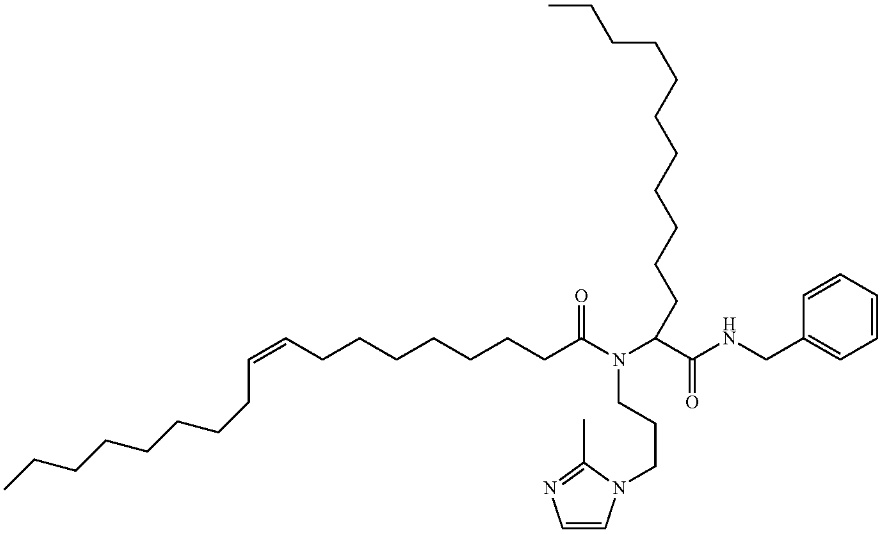
P399H3
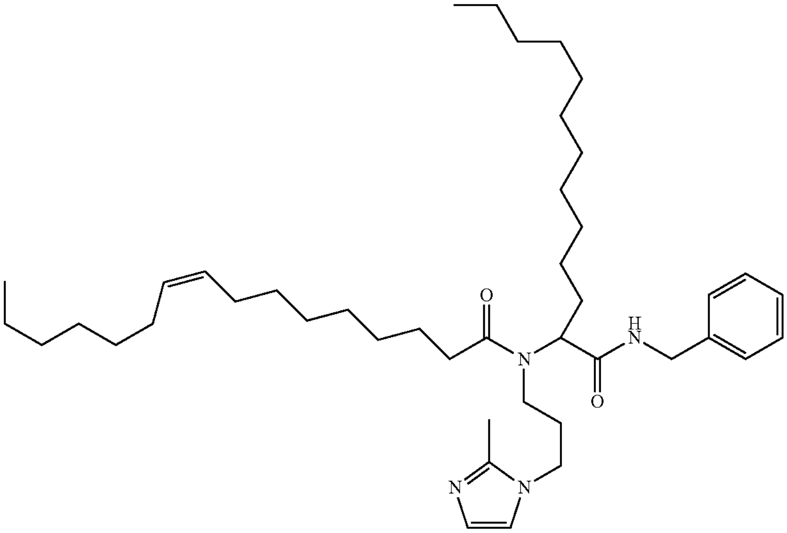
P400A3
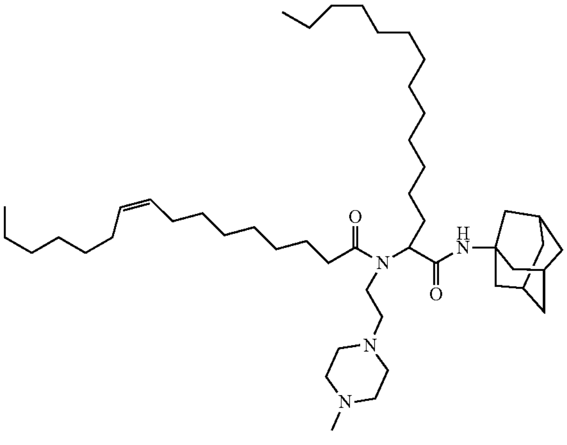
P400A4
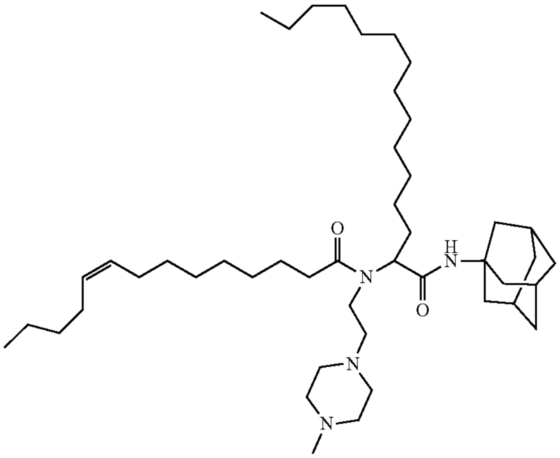

-continued
P400D12
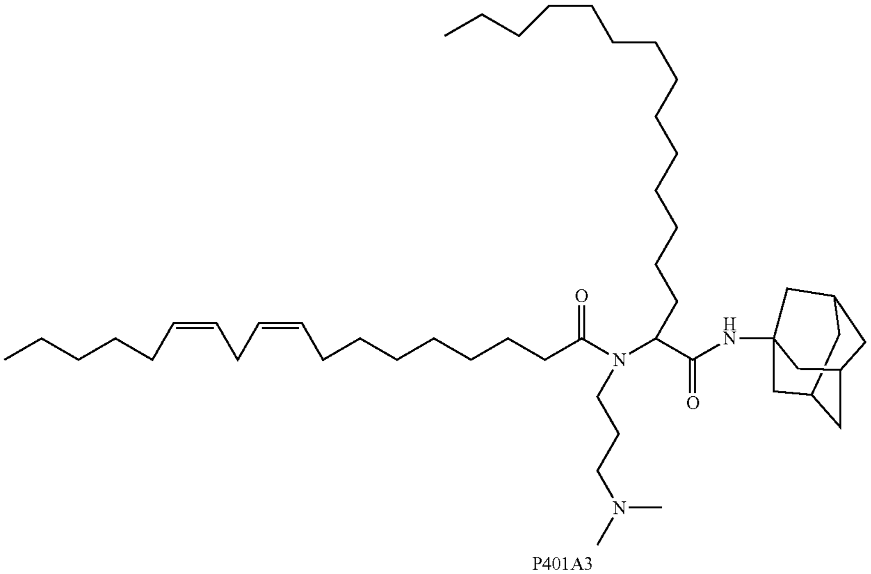
P401A3
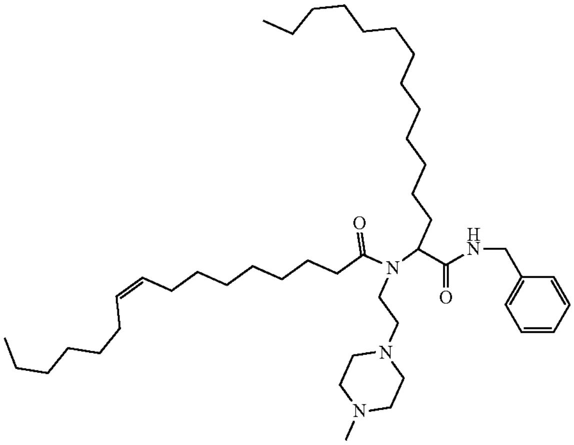
P401A4
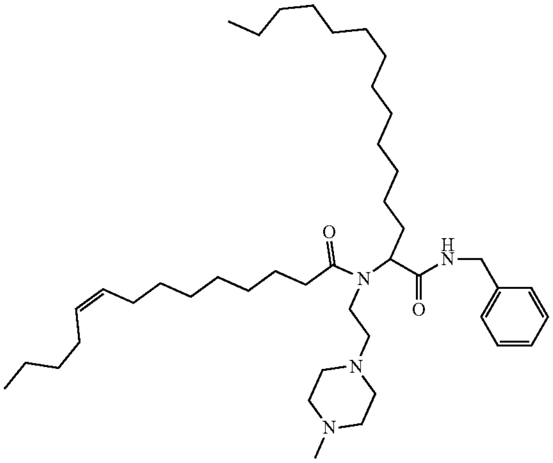
P401A6
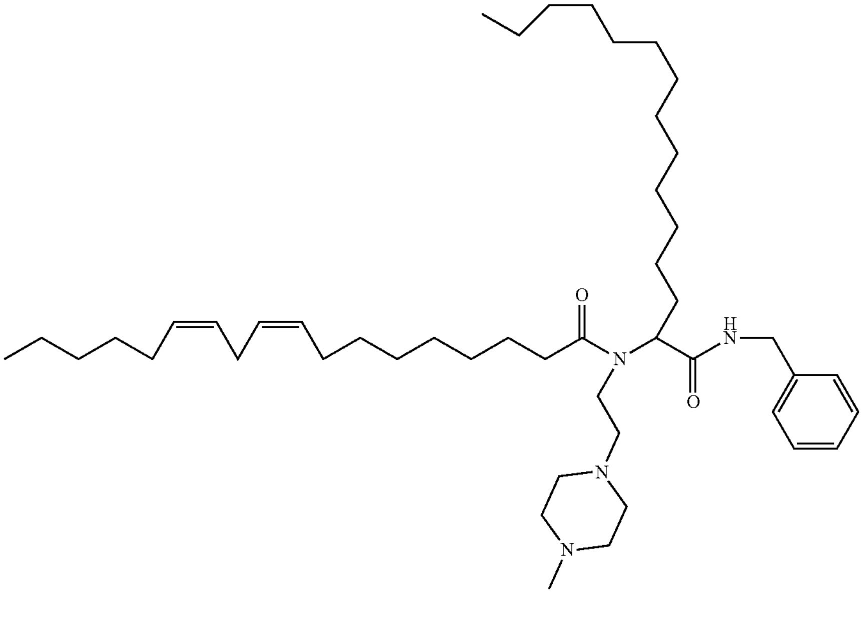

-continued
P401D1
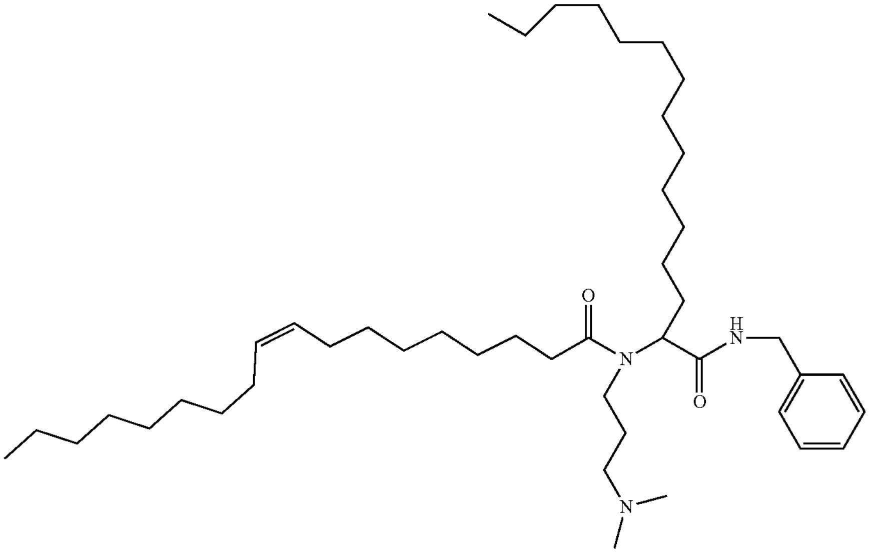
P401E1
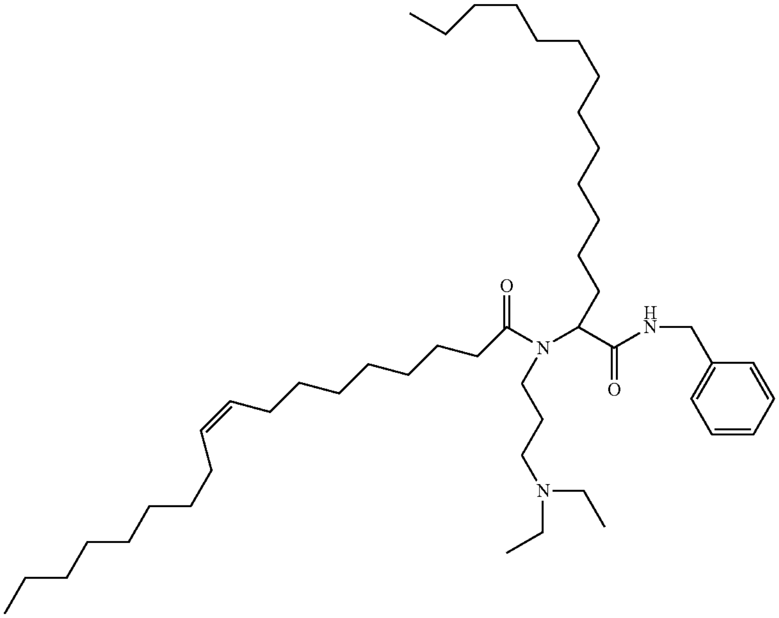
P401E9
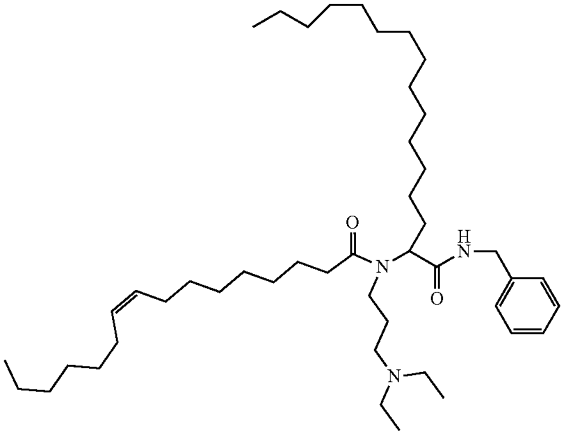
P401E10
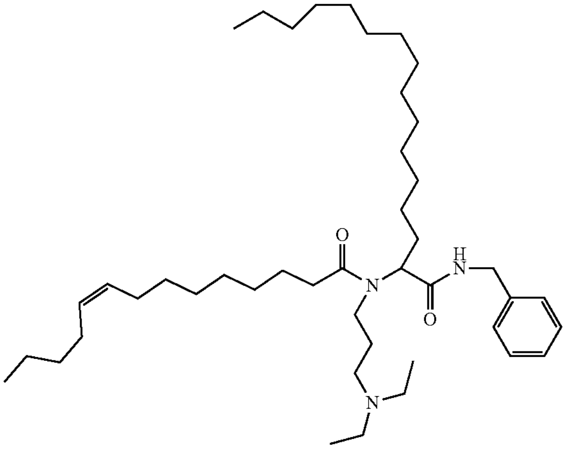

-continued
P401E12
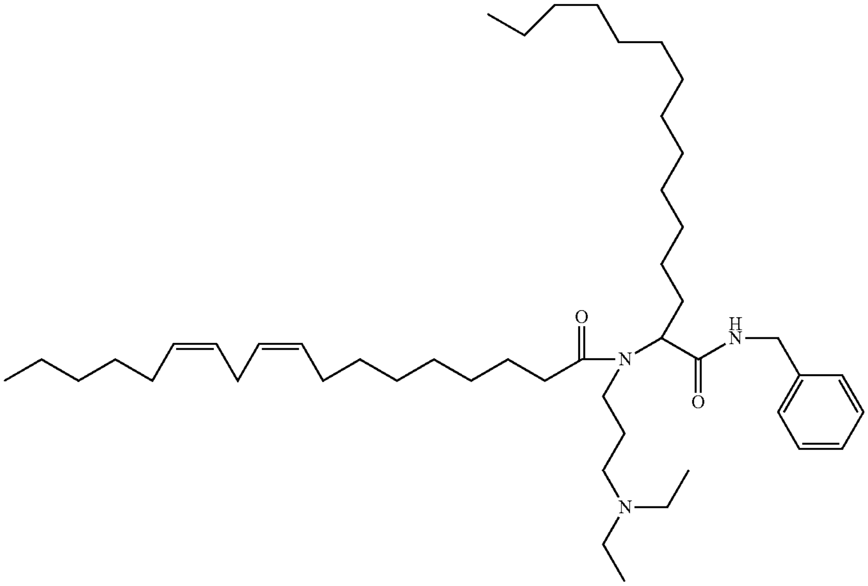
P401H12
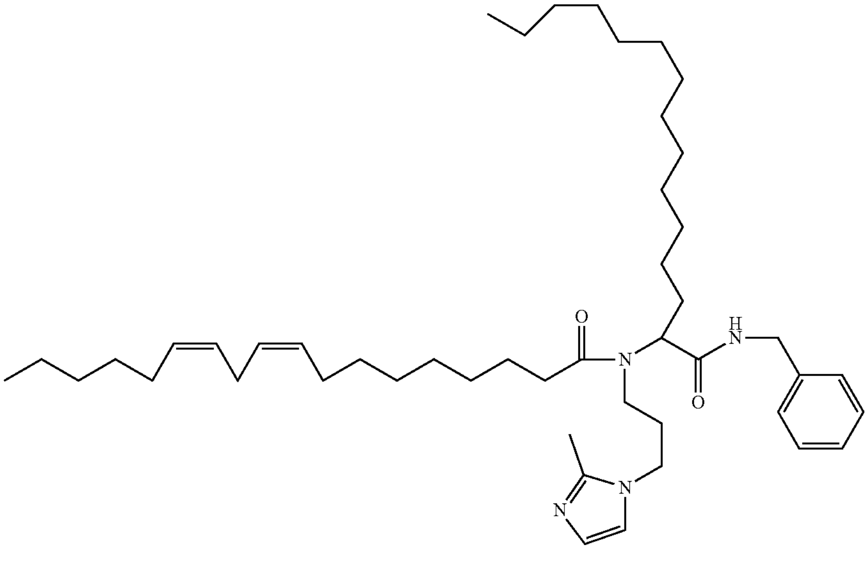
P402A7
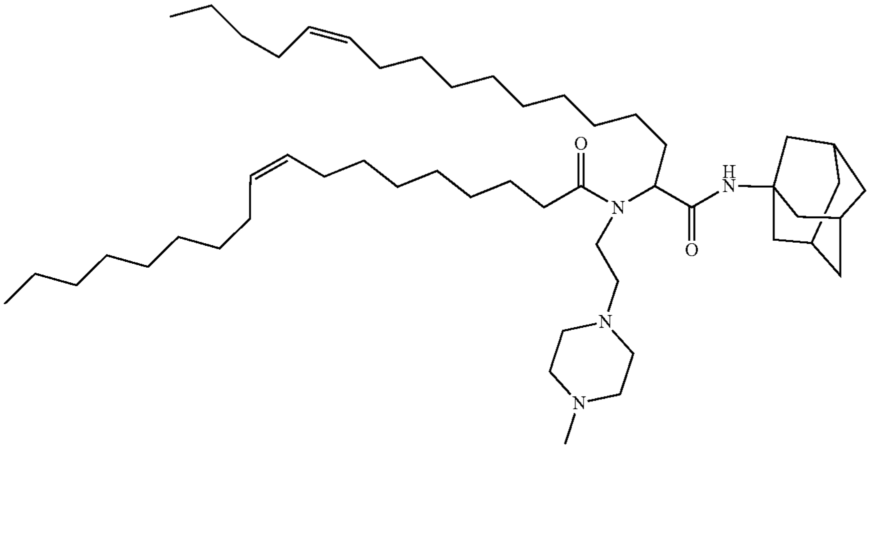

-continued
P402A9
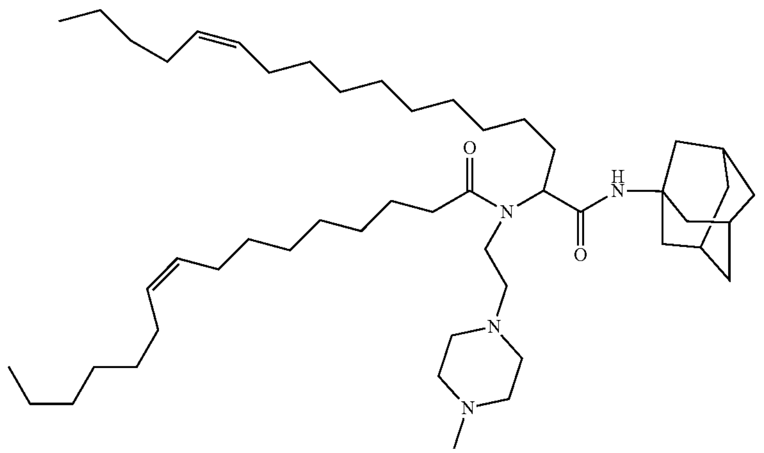
P402D7
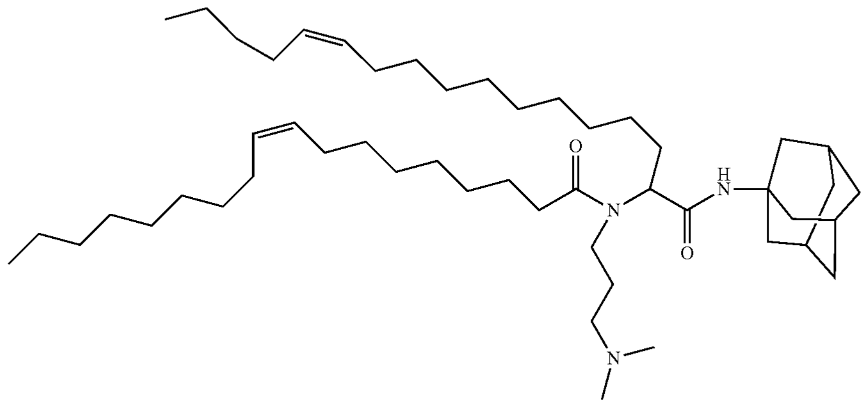
P402D9
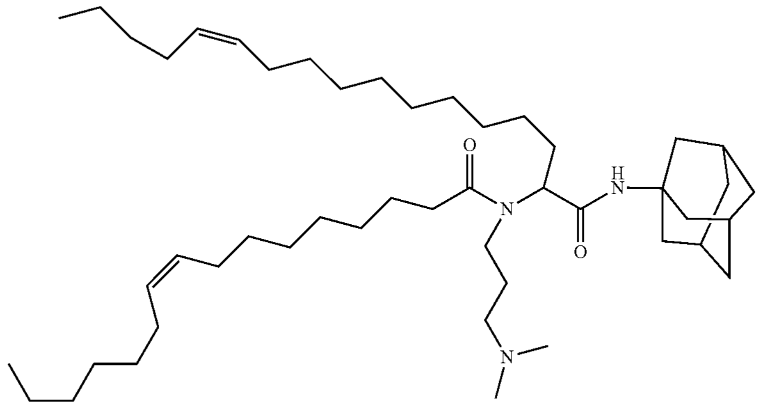
P402D12
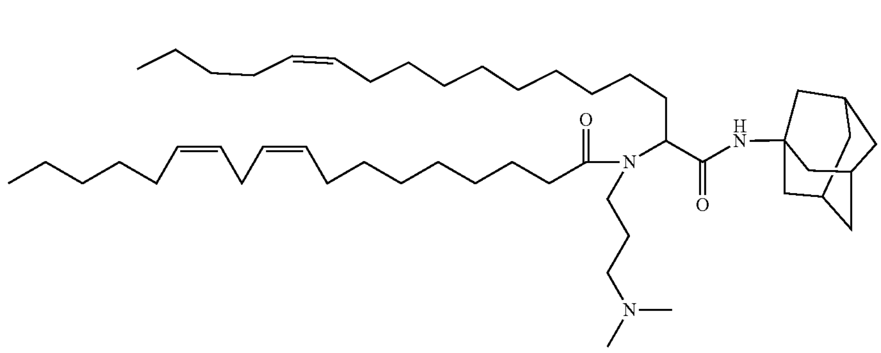

-continued
P402E12
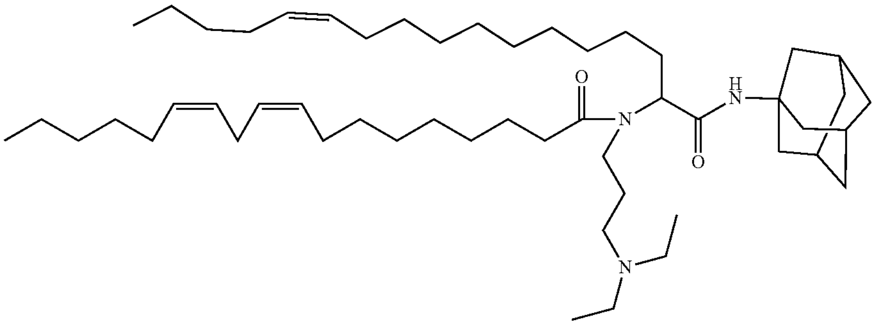
P403A7
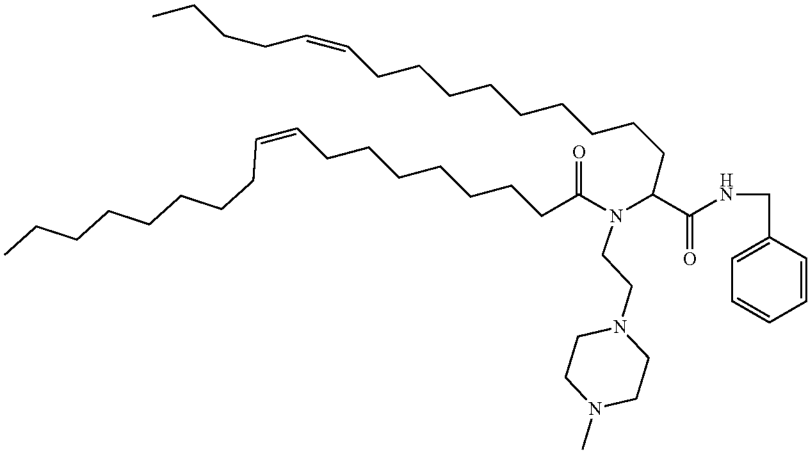
P403A9
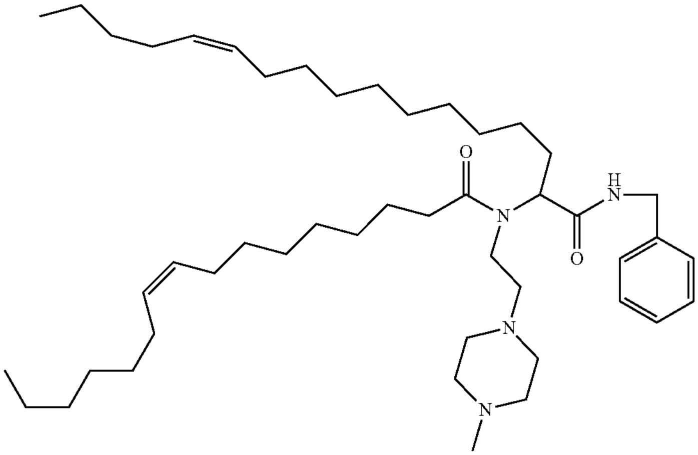
P403H7
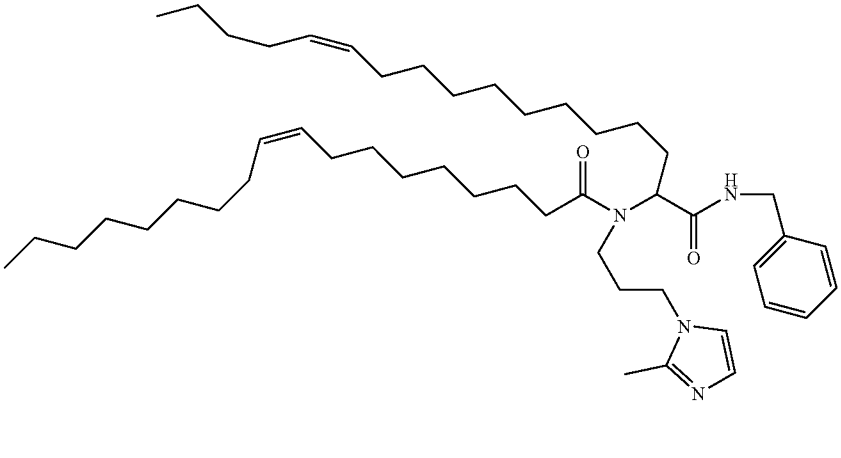

-continued
P403H10
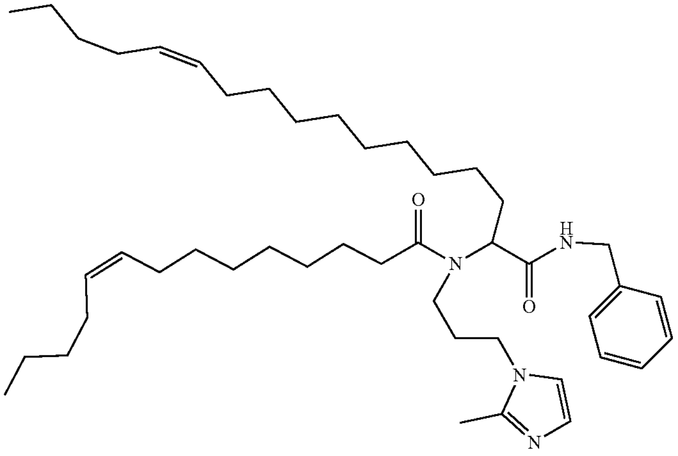
P404D1
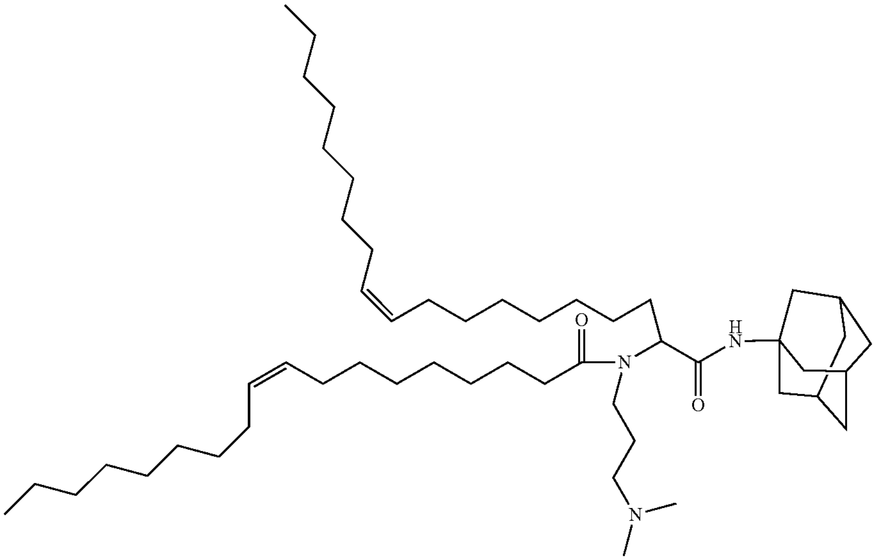
P404D3
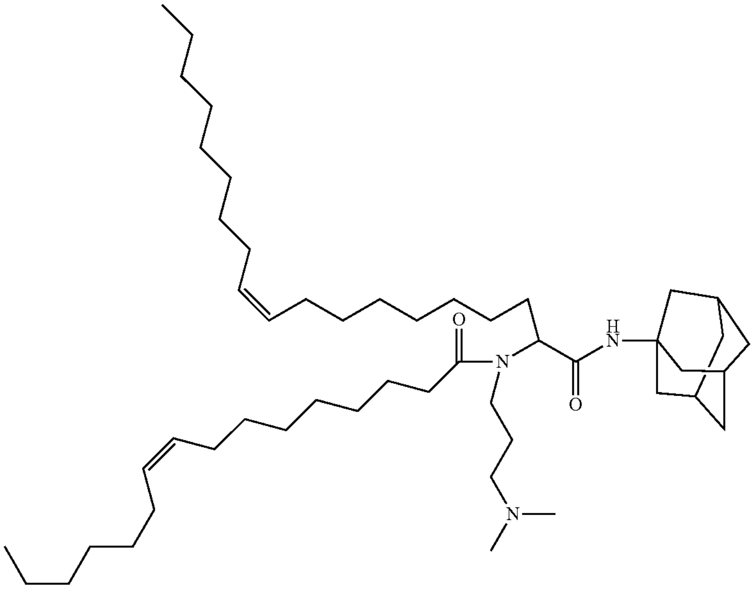

-continued
P404D6
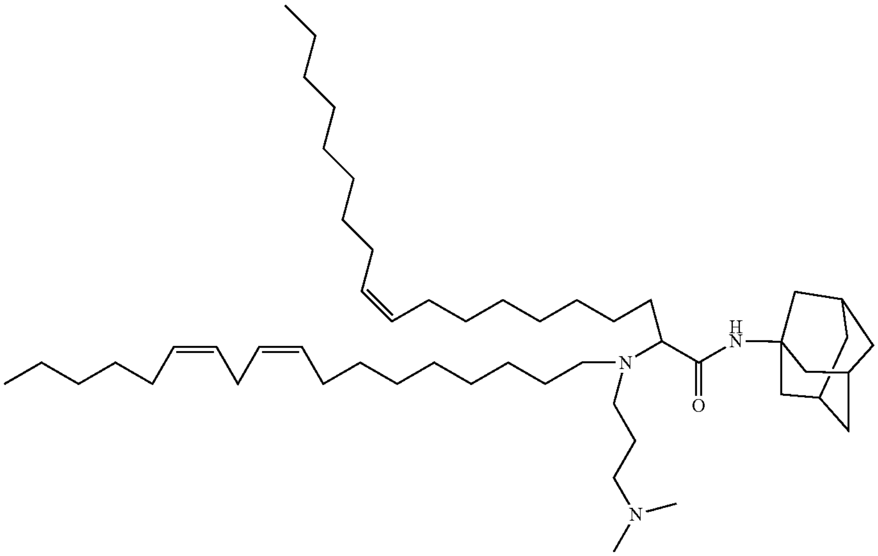
P404E1
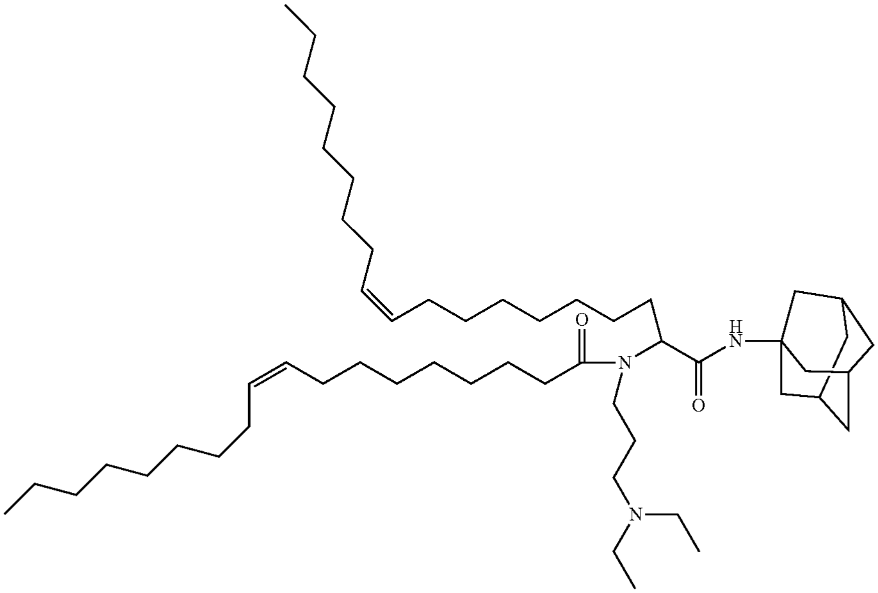

-continued
P405E3
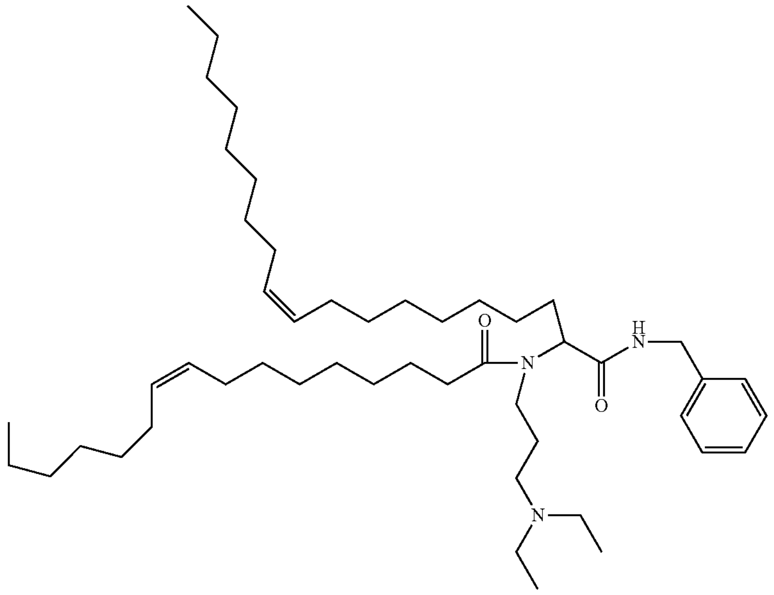
P406A6
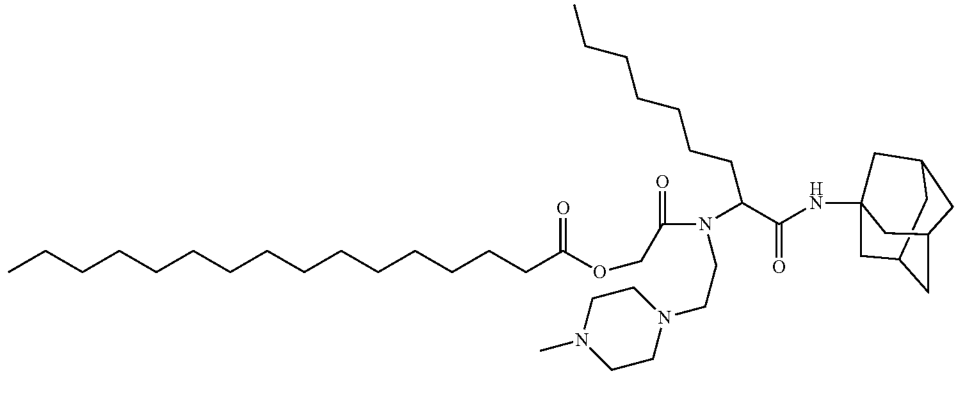
P406A12
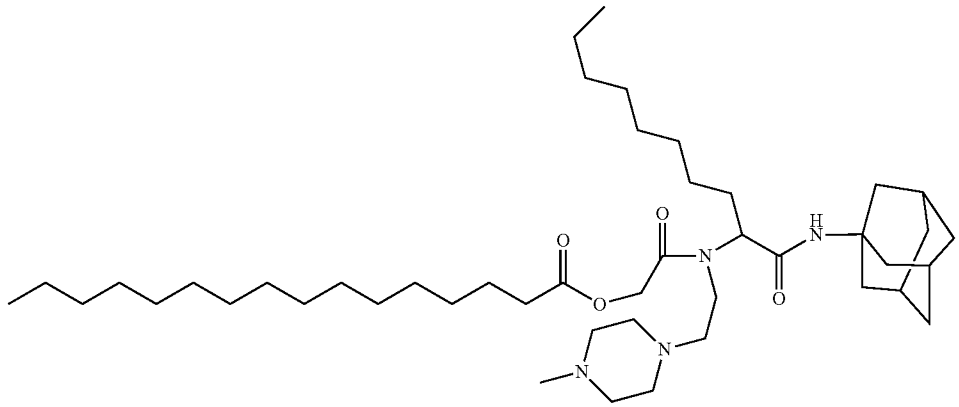

-continued
P406E12
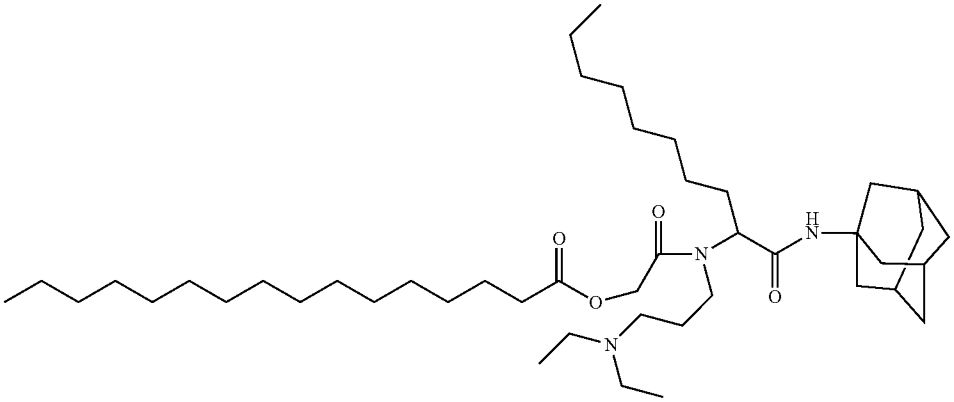
P406F12
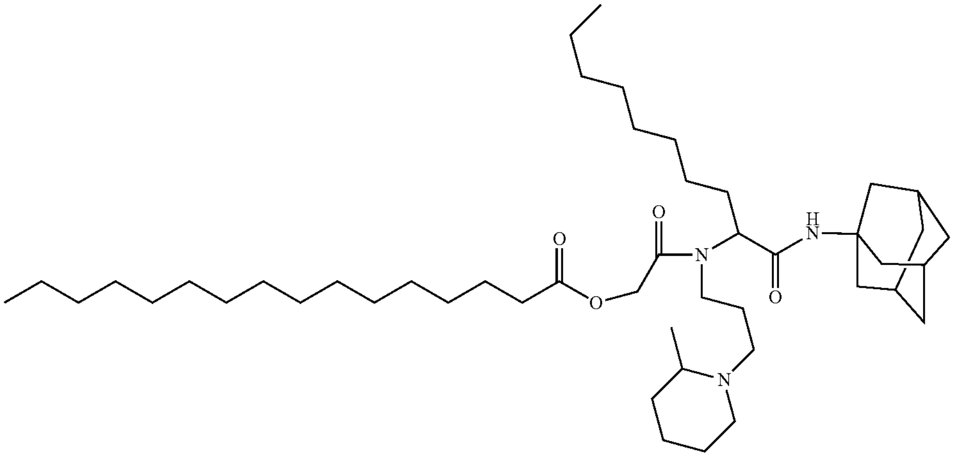
P406H6
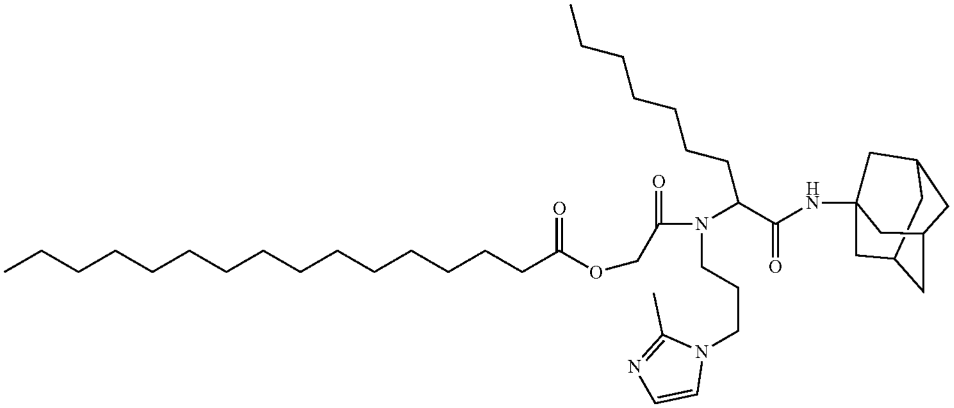

-continued
P406H10
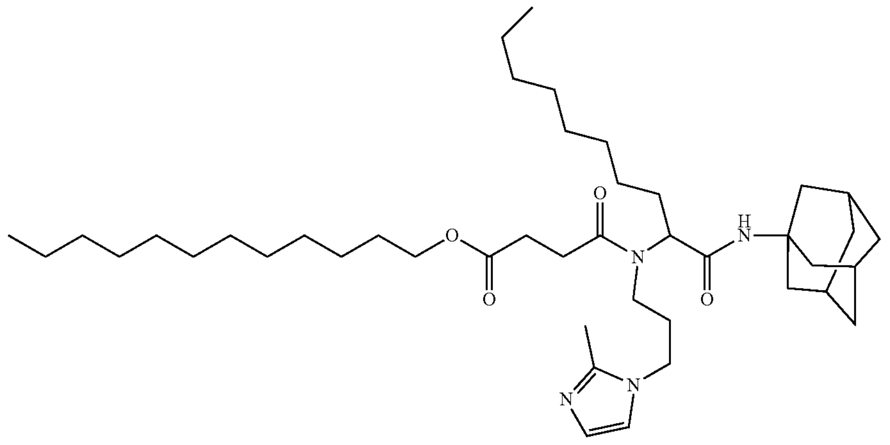
P406H12
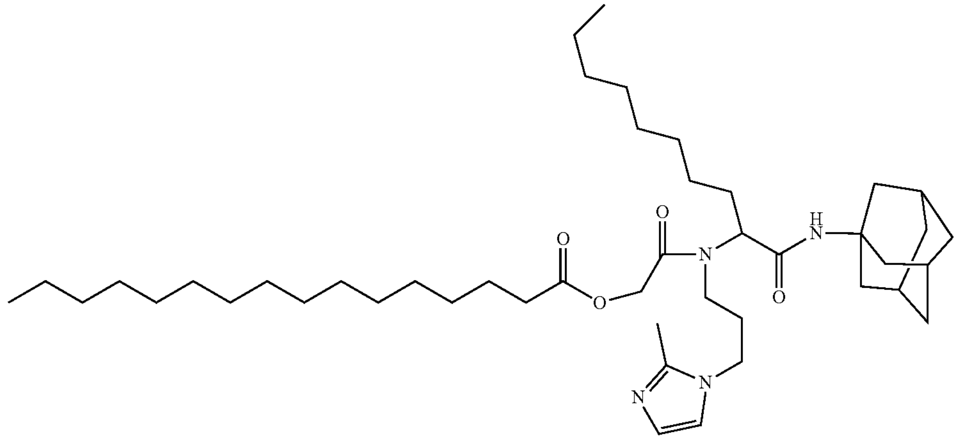
P407D12
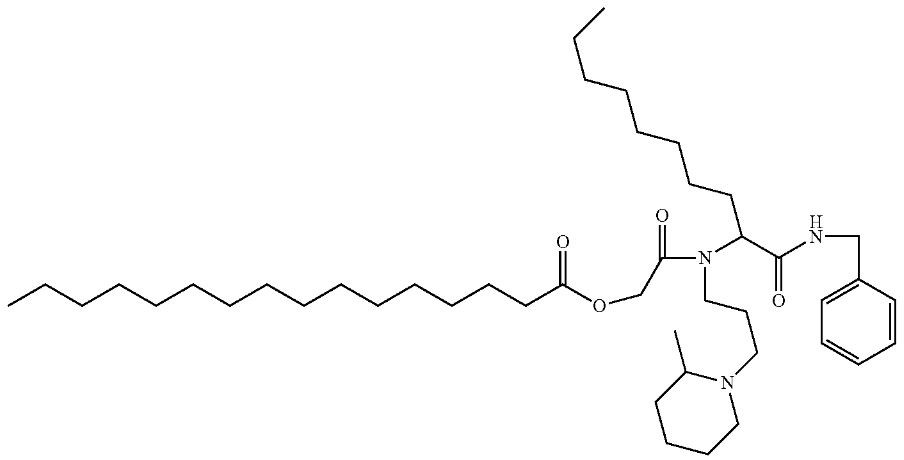

-continued
P407F12
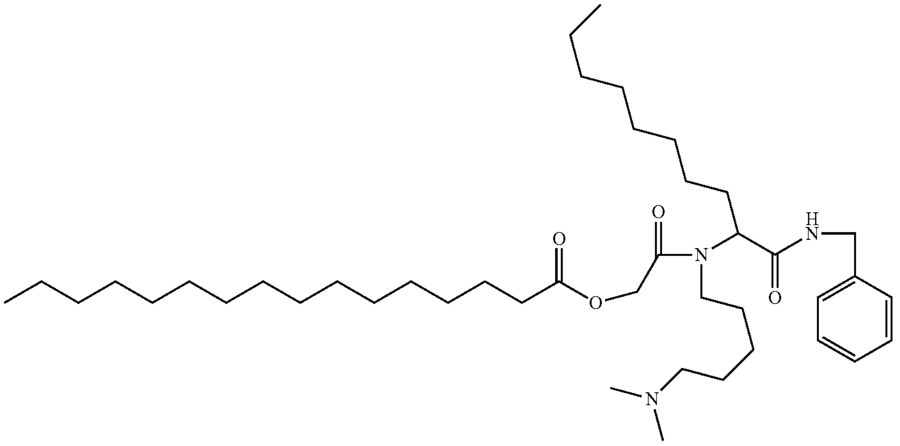
P408H4
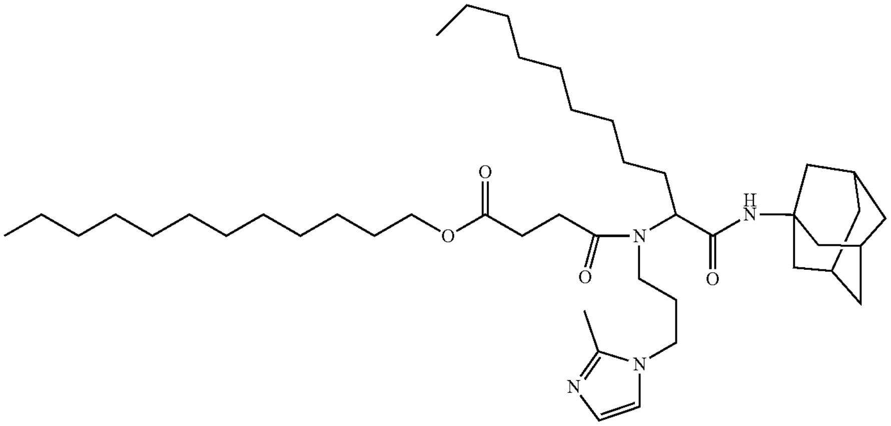
P410A6
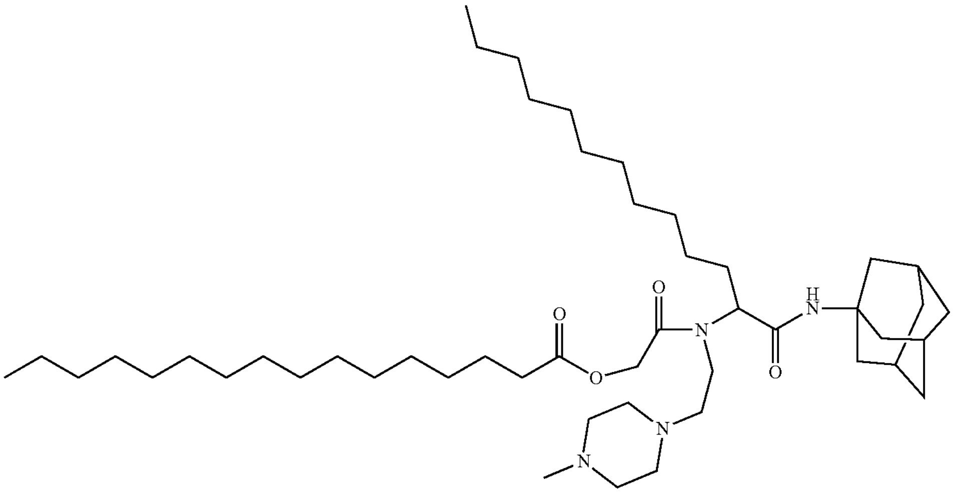

-continued
P410A10
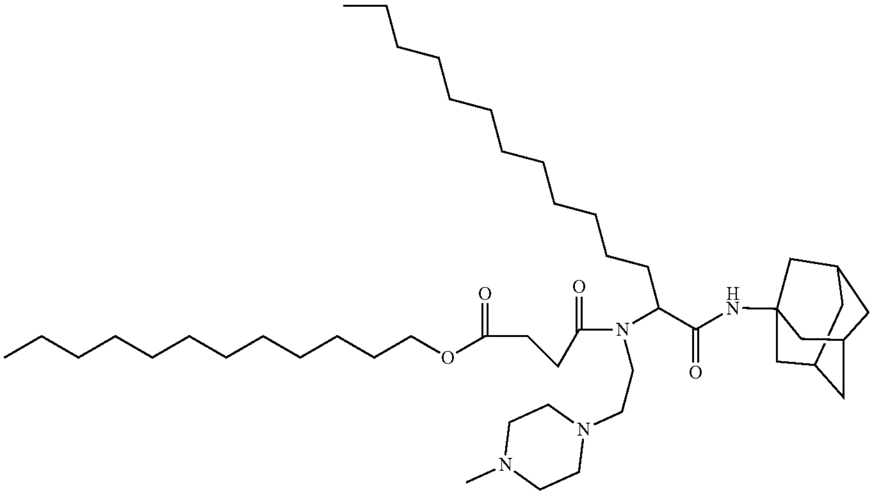
P410D4
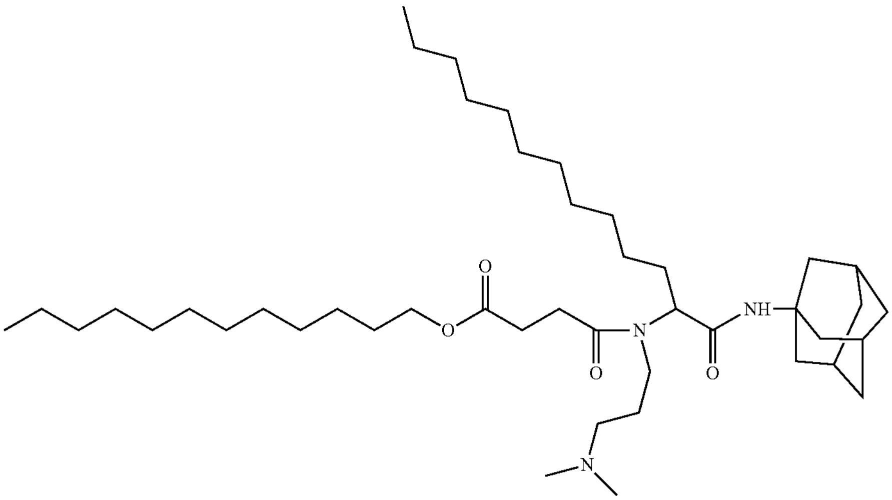
P410D12
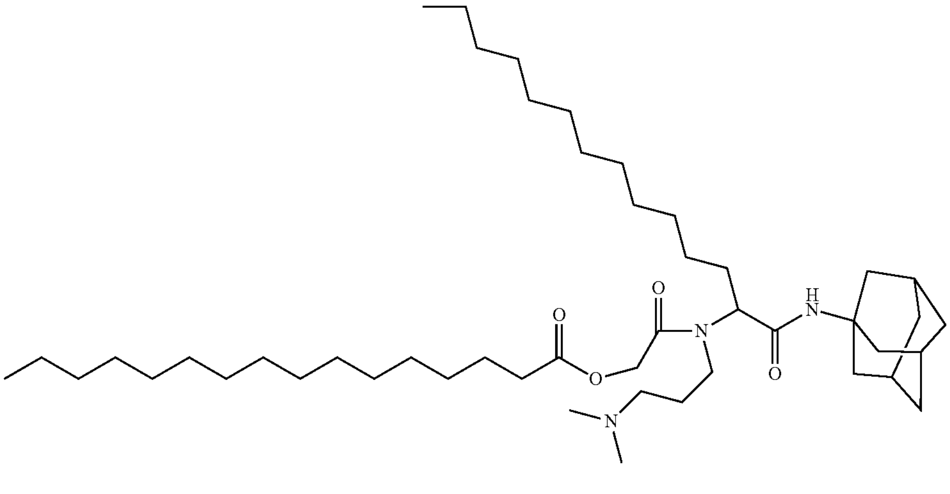

-continued
P410E12
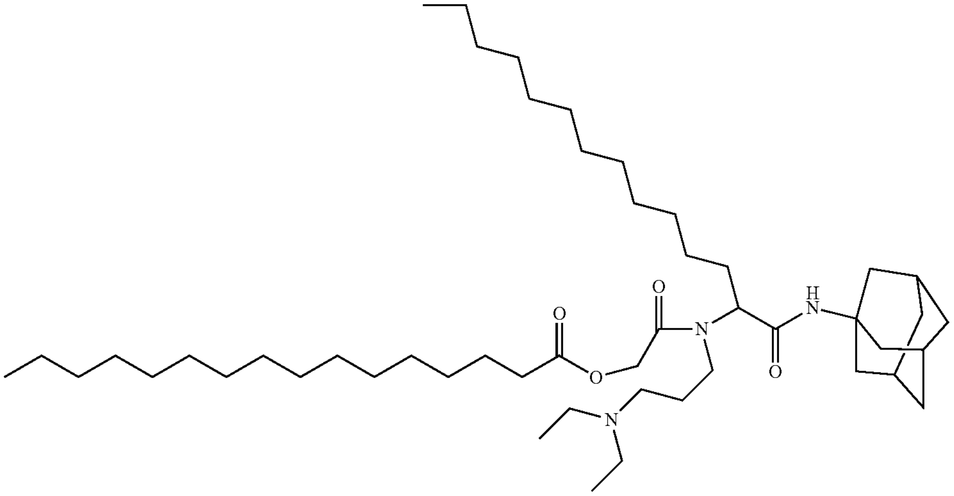
P410F12
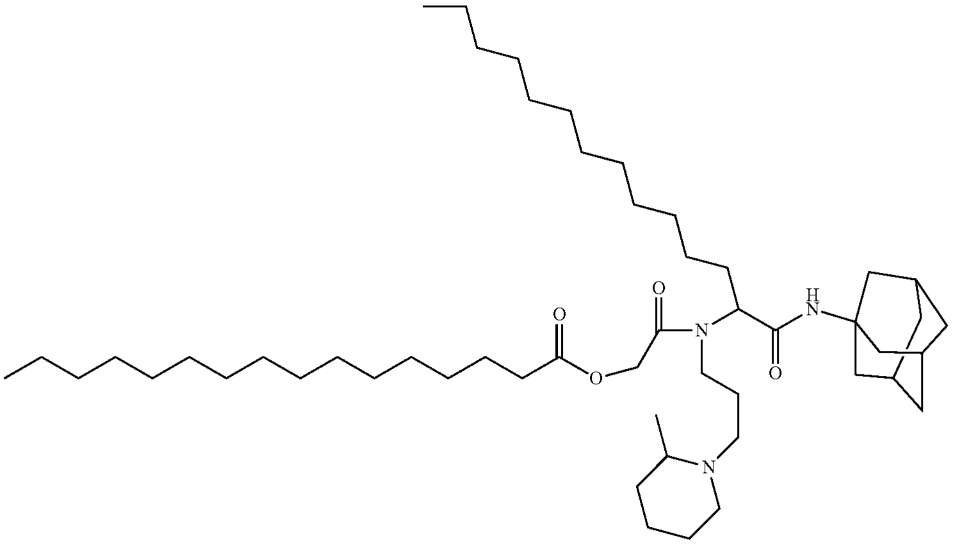
P410H4
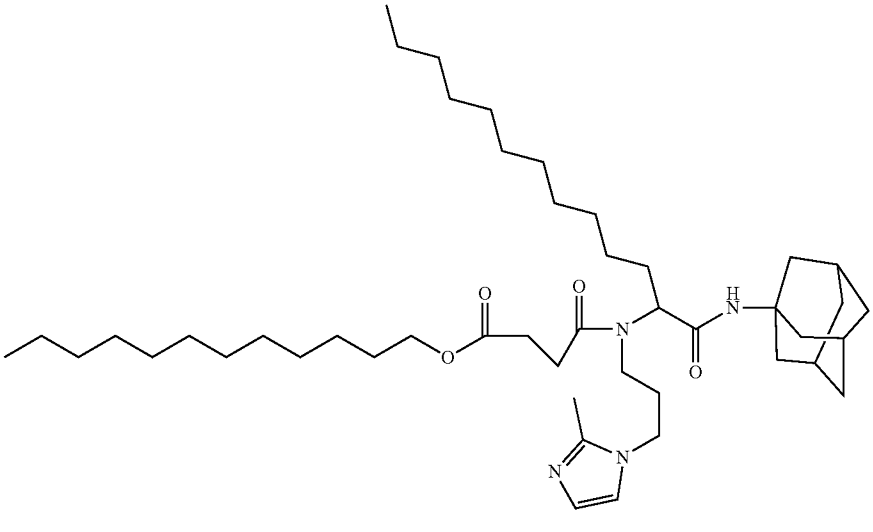

P410H6
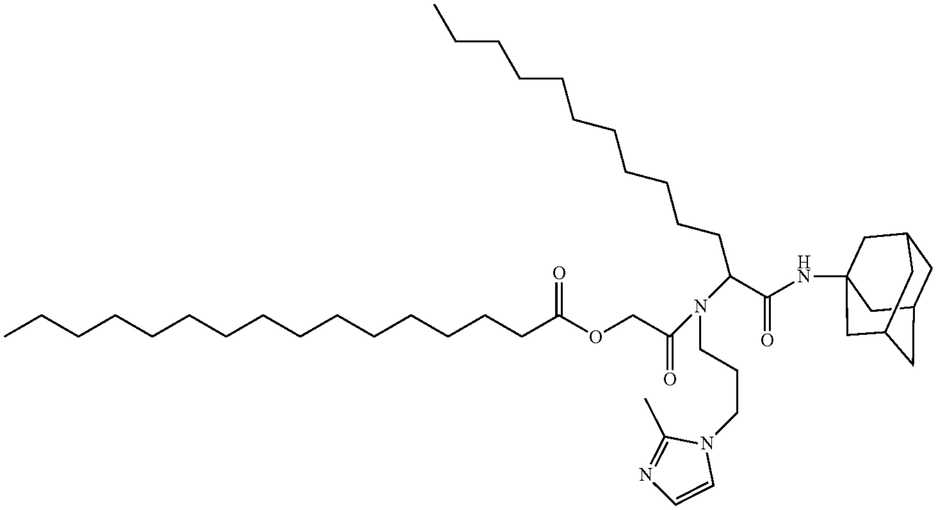
P410H8
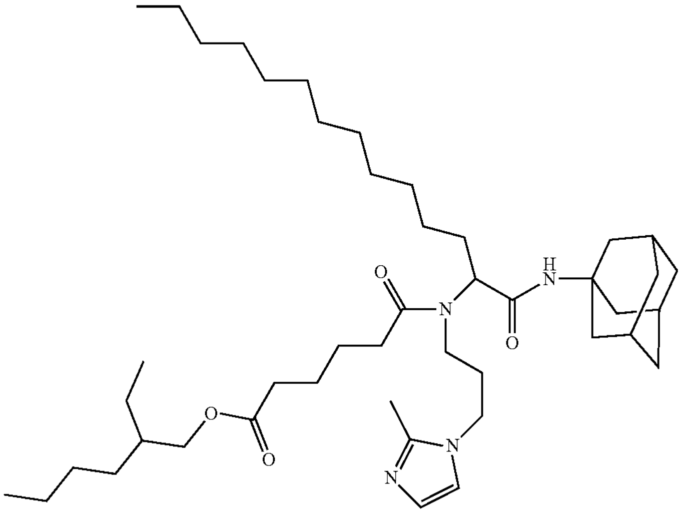
P410H10
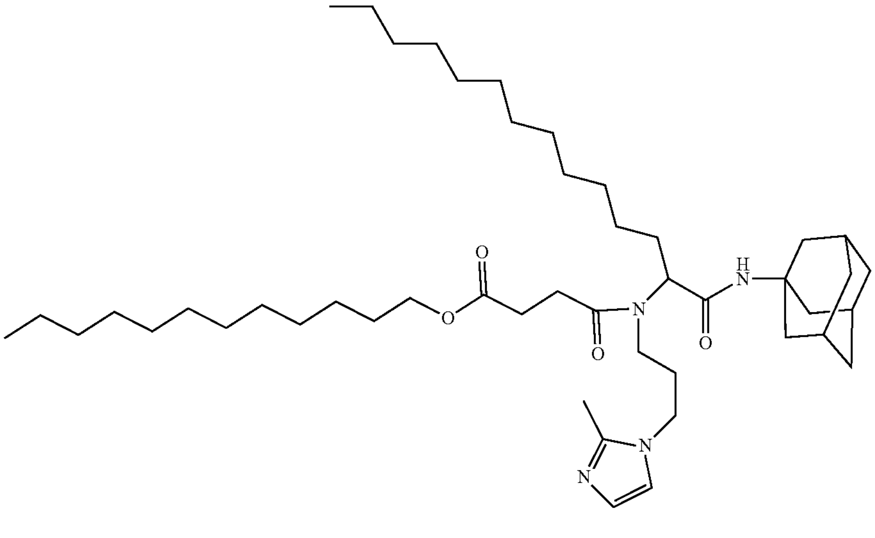

-continued
P411C6
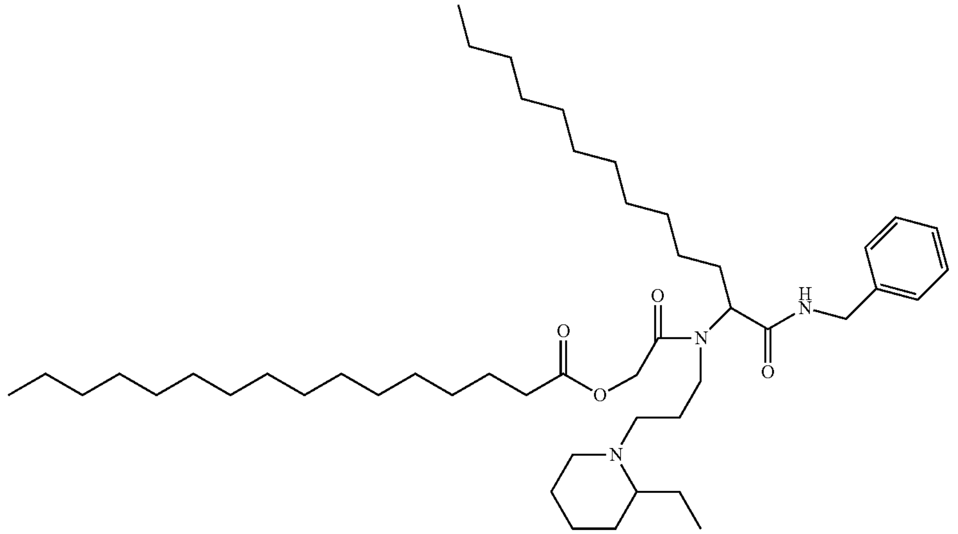
P411C12
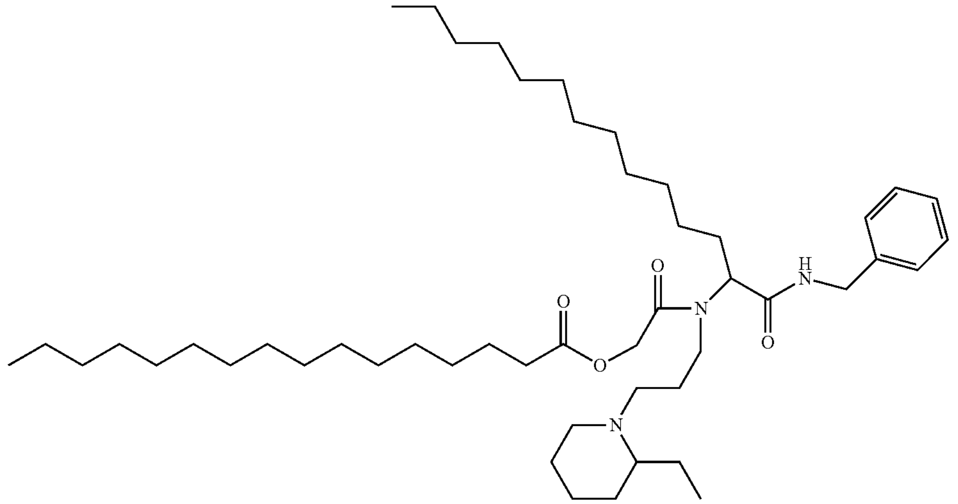
P411F12
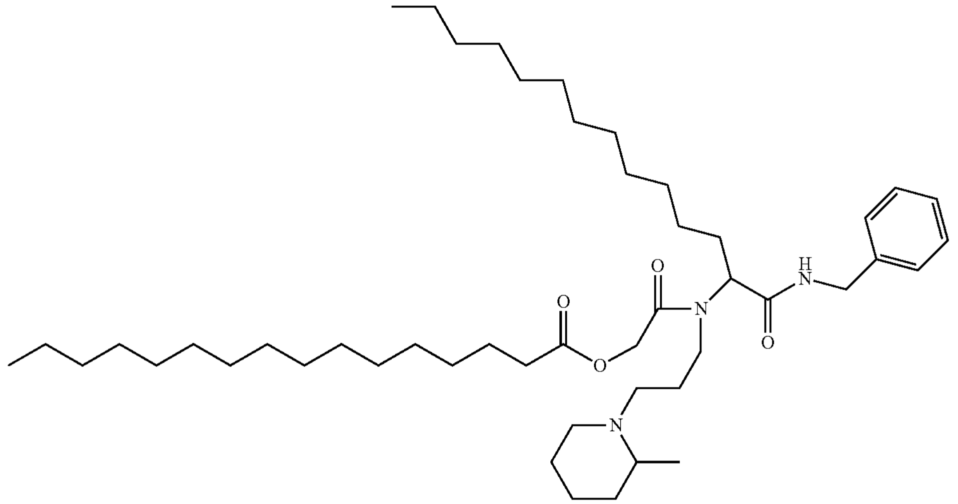

-continued
P411H6
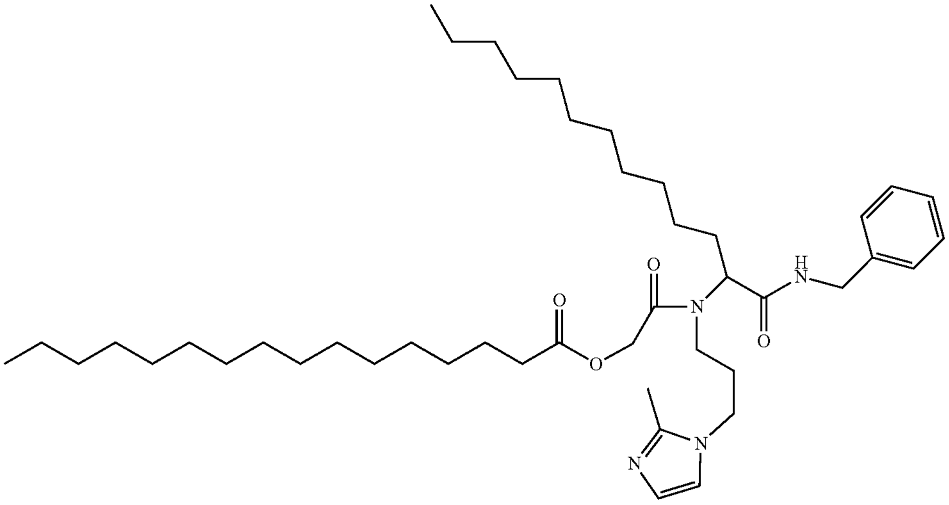
P411H10
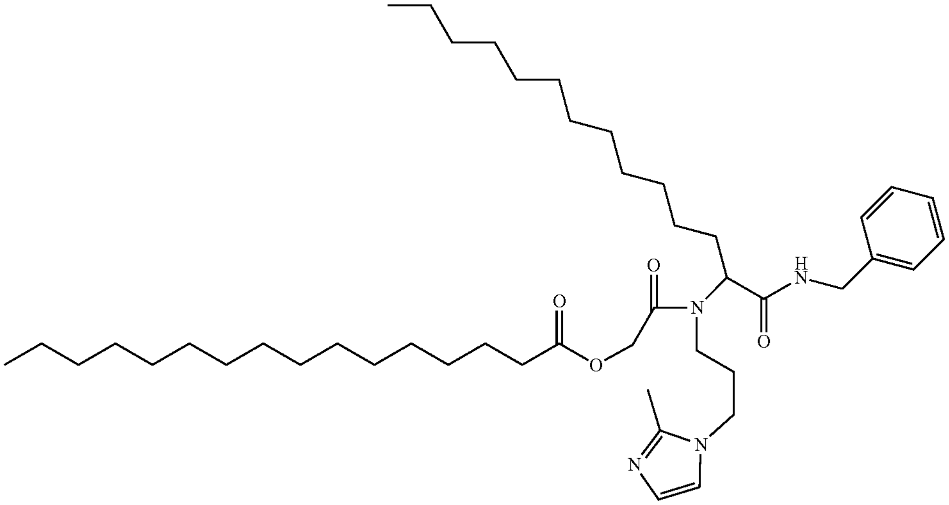
P411H12
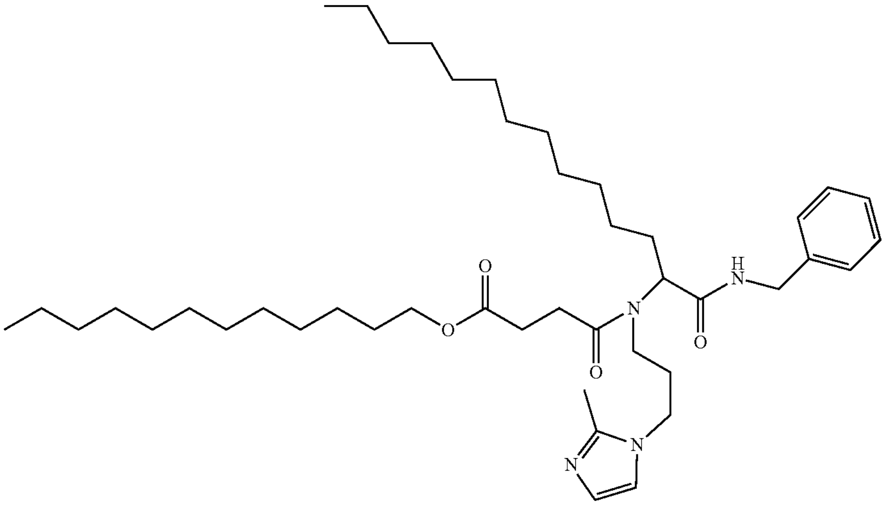

-continued
P412A6
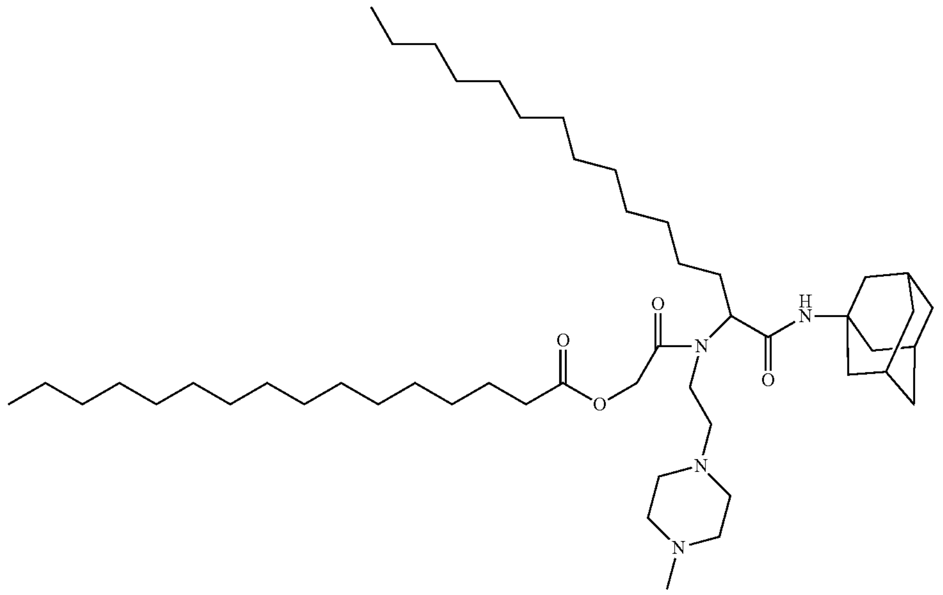
P412D6
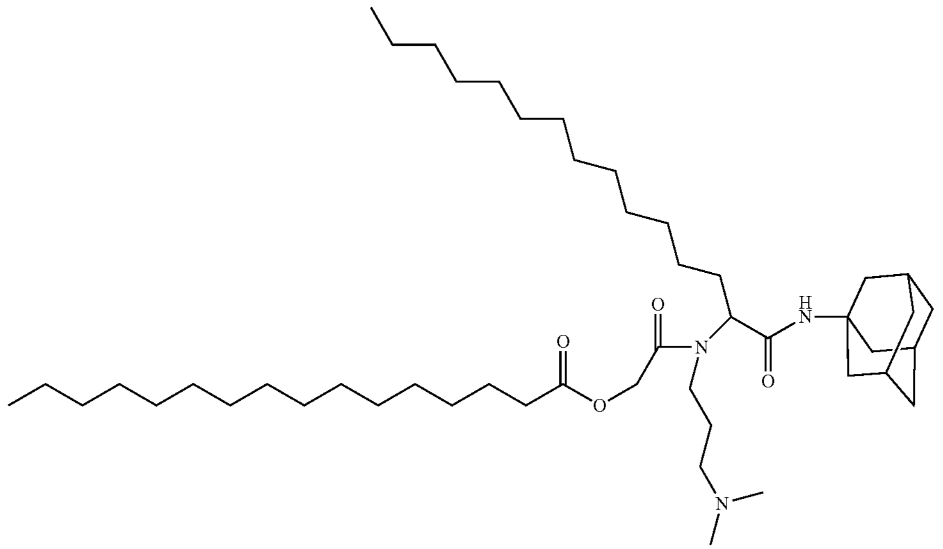

-continued
P412D10
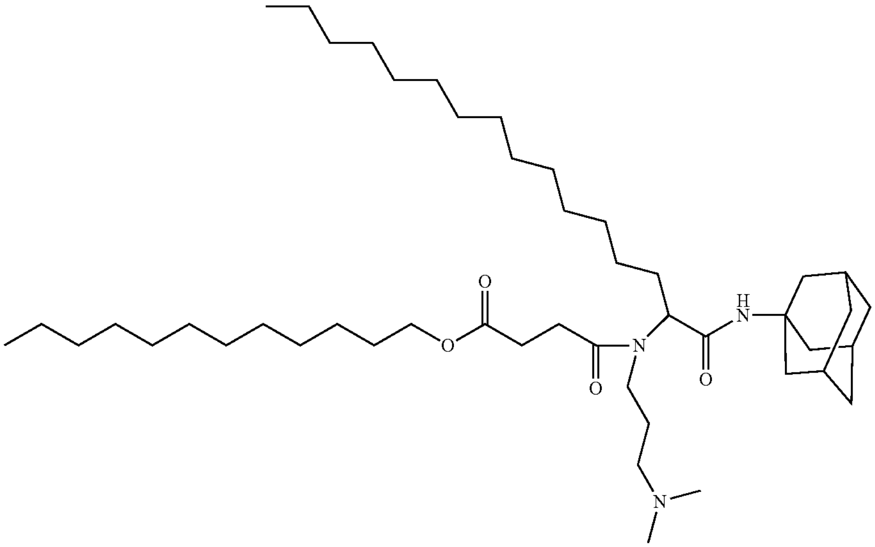
P412D12
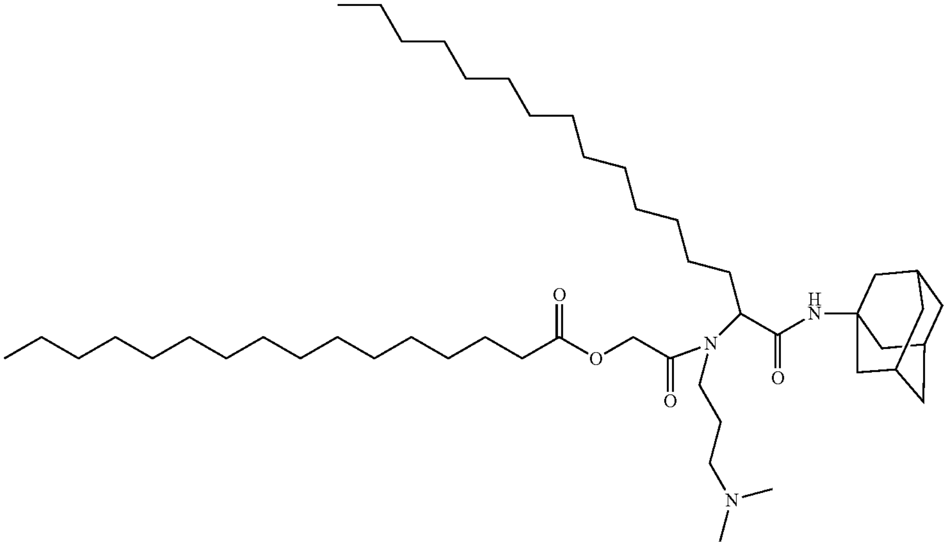
P412H2
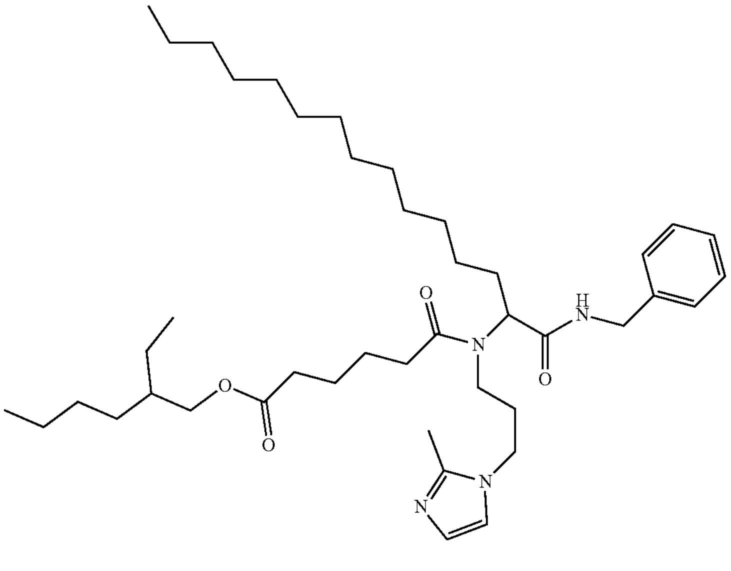

-continued
P412H4
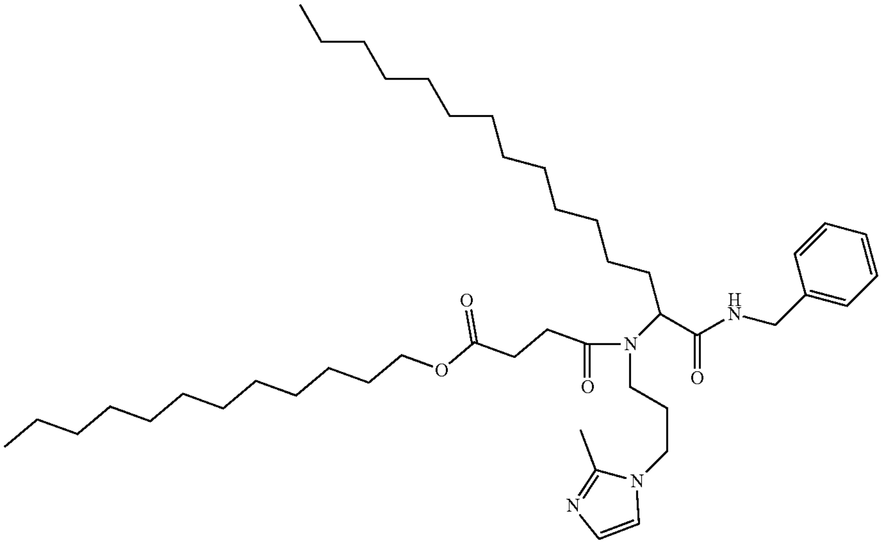
P412H6
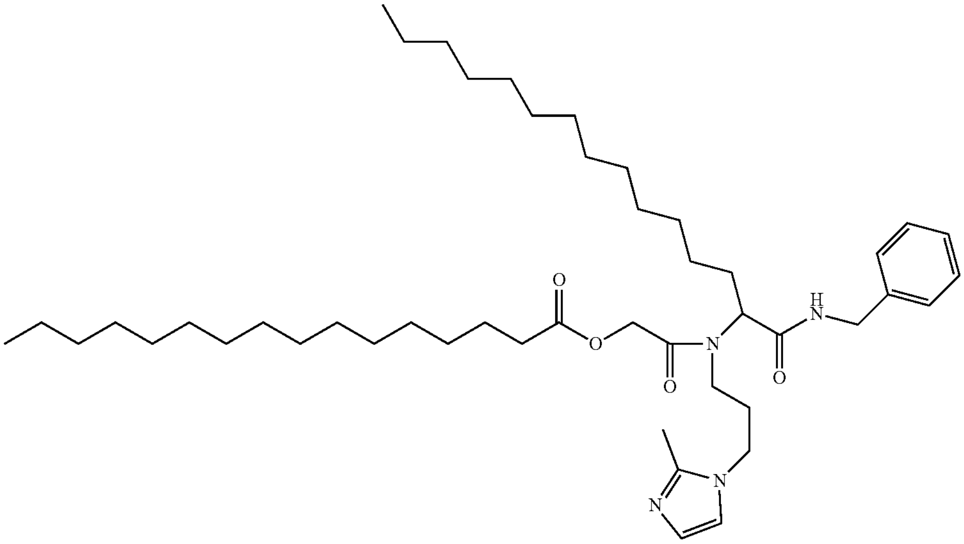
P412H10
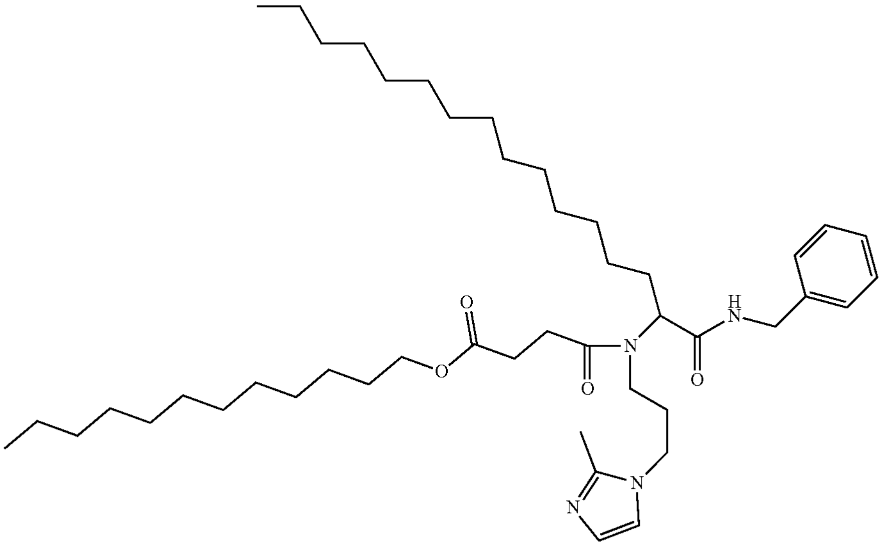

-continued
P414A10
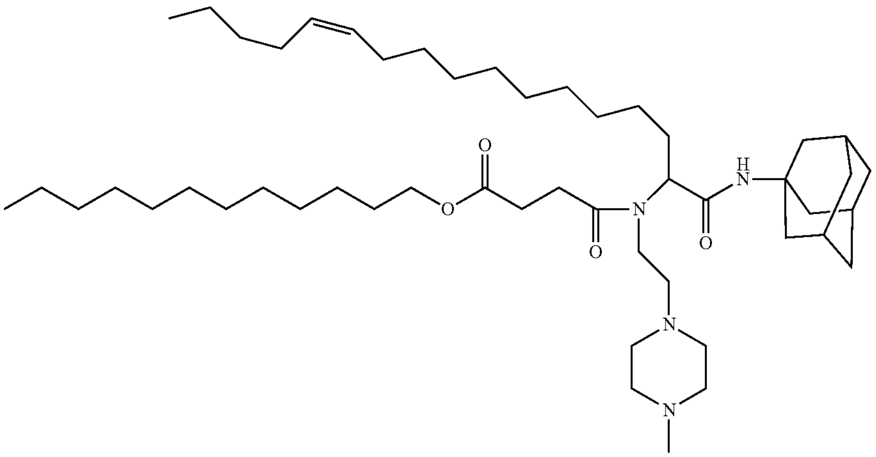
P414A11
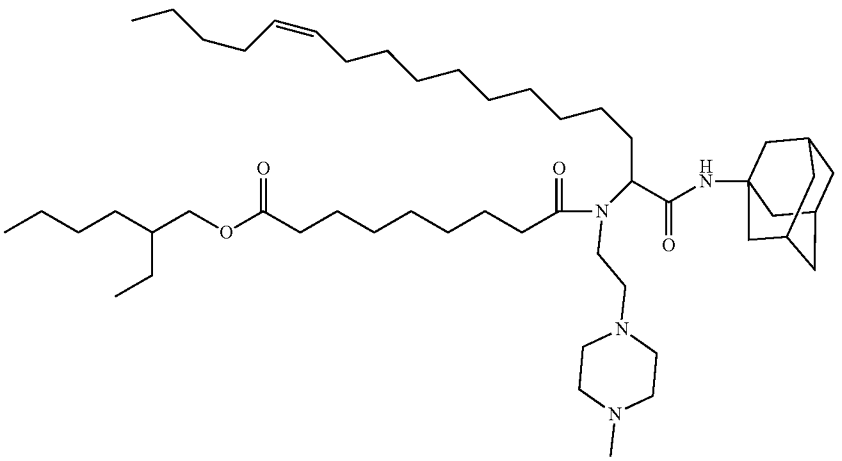
P414A12
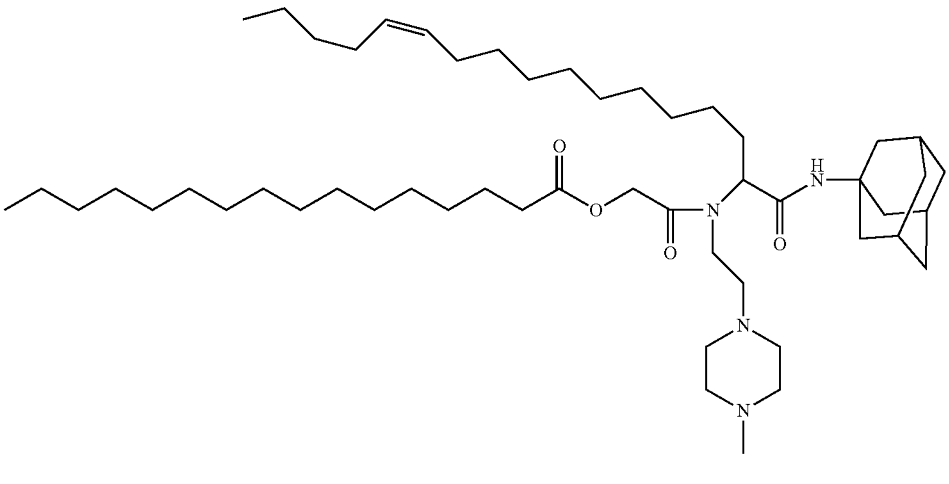

-continued
P414D12
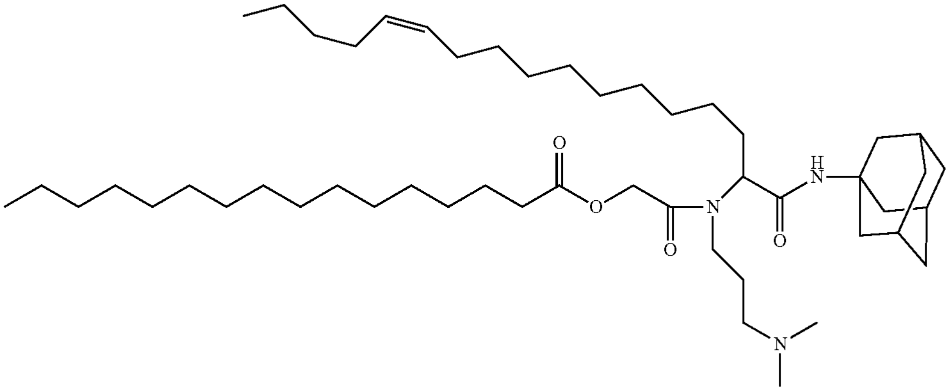
P414E12
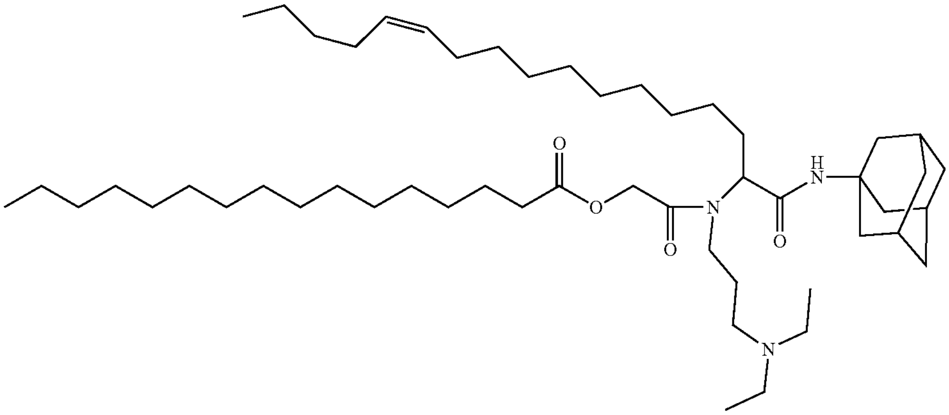
P415A12
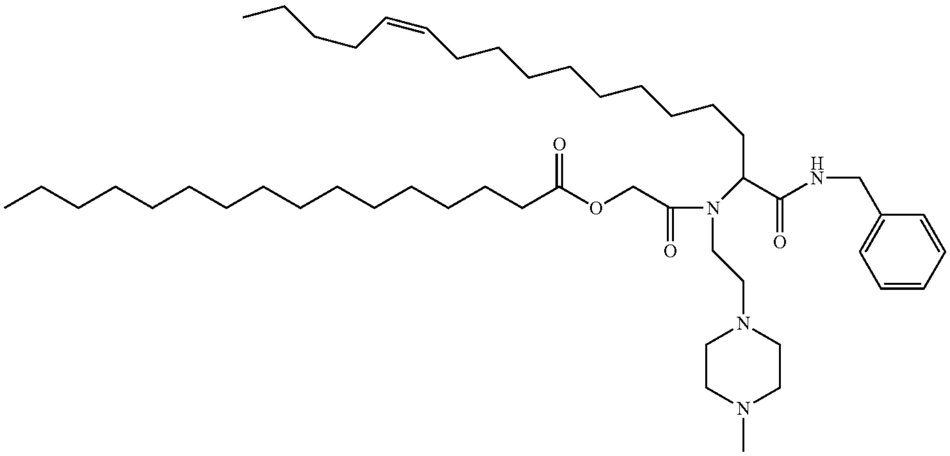

-continued
P415C12
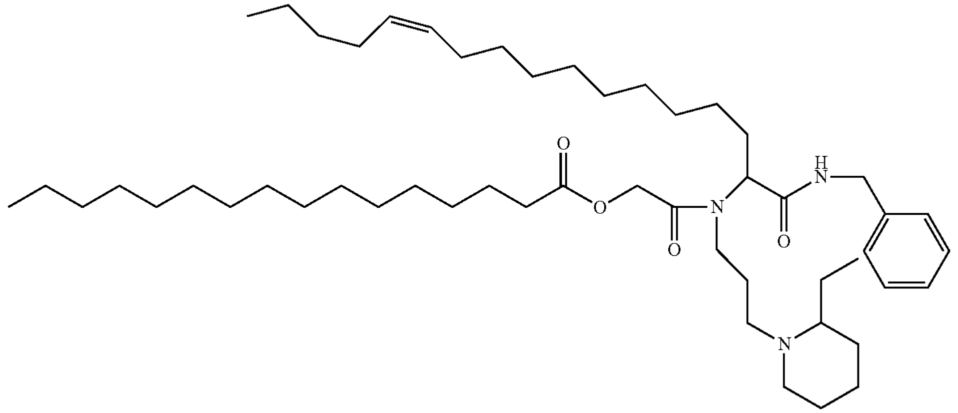
P415F12
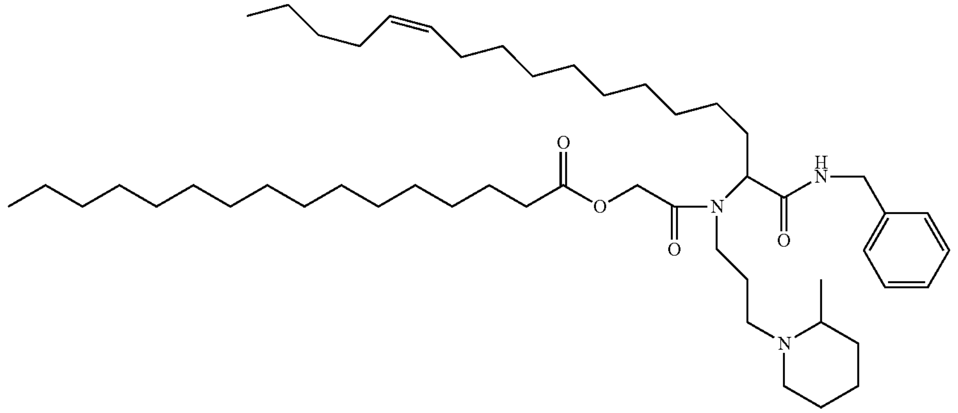
P416D4
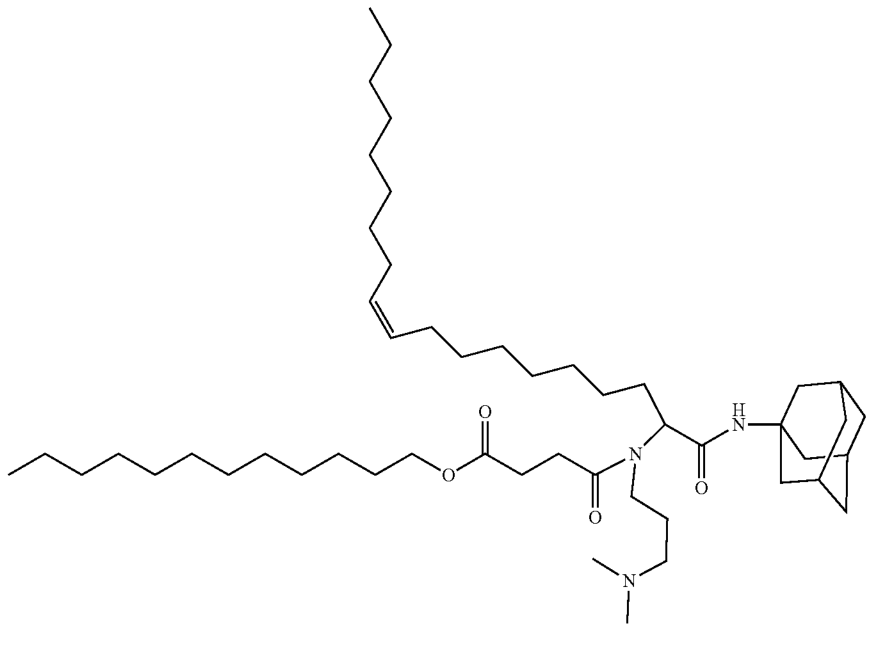

-continued
P416D6
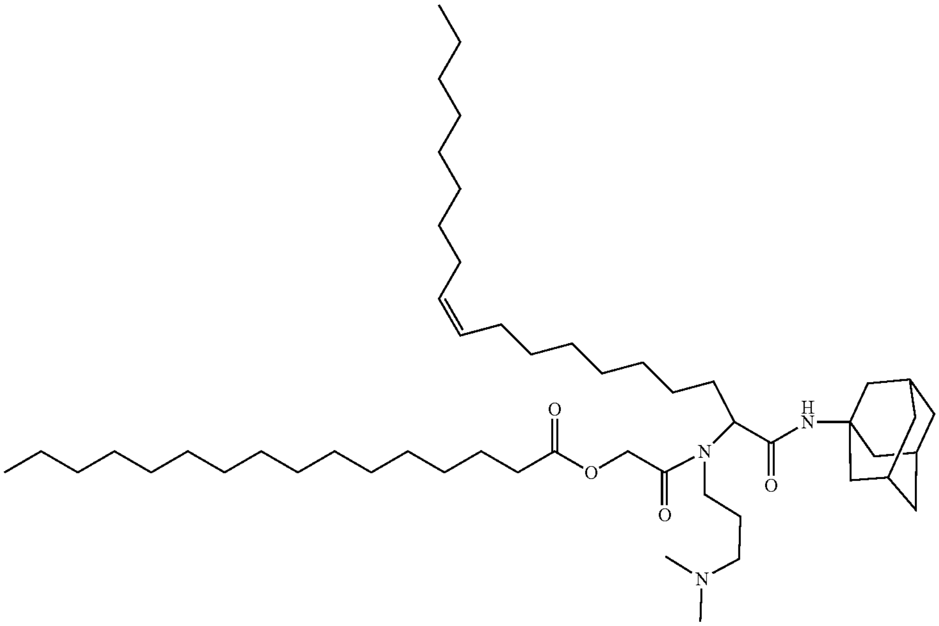
P416E4
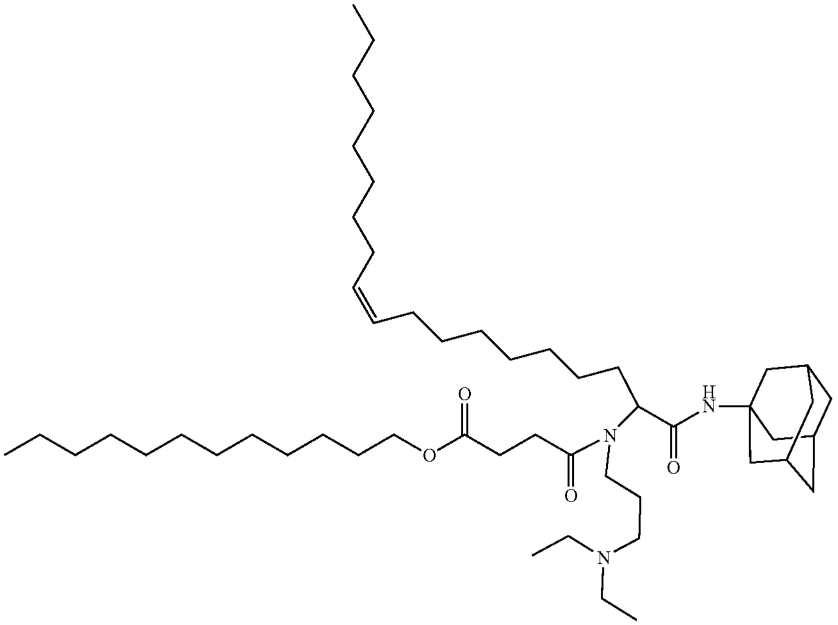

-continued
P416E6
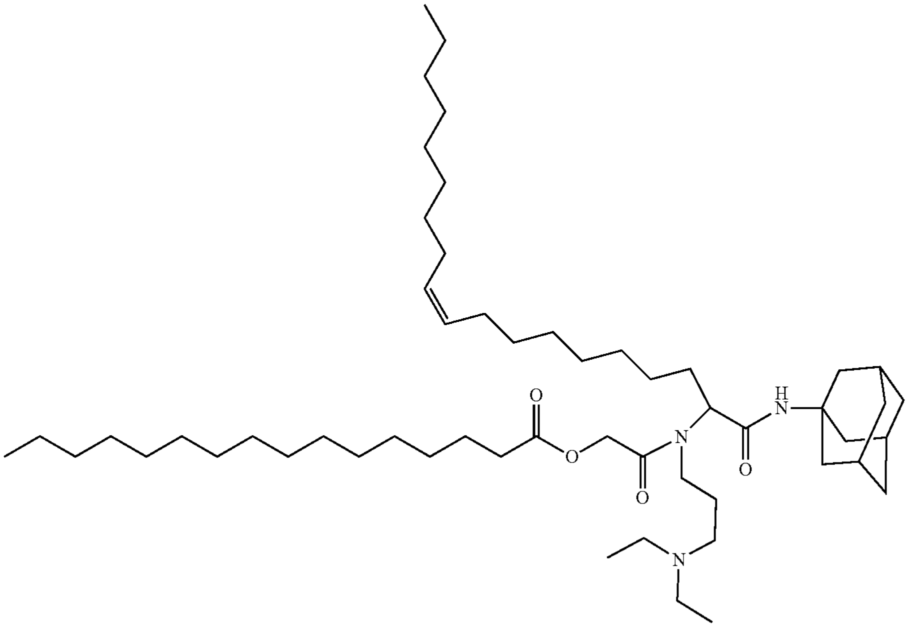
P417A4
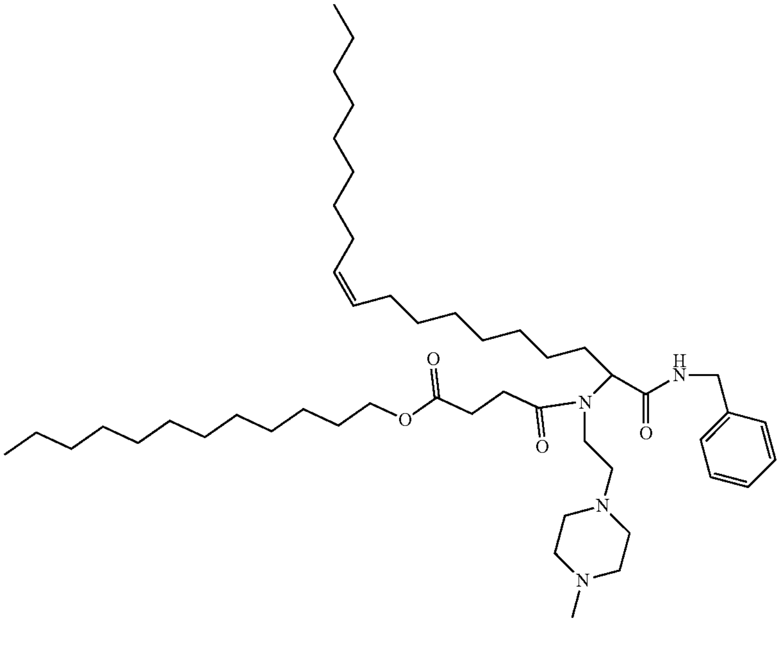

-continued
P417D6
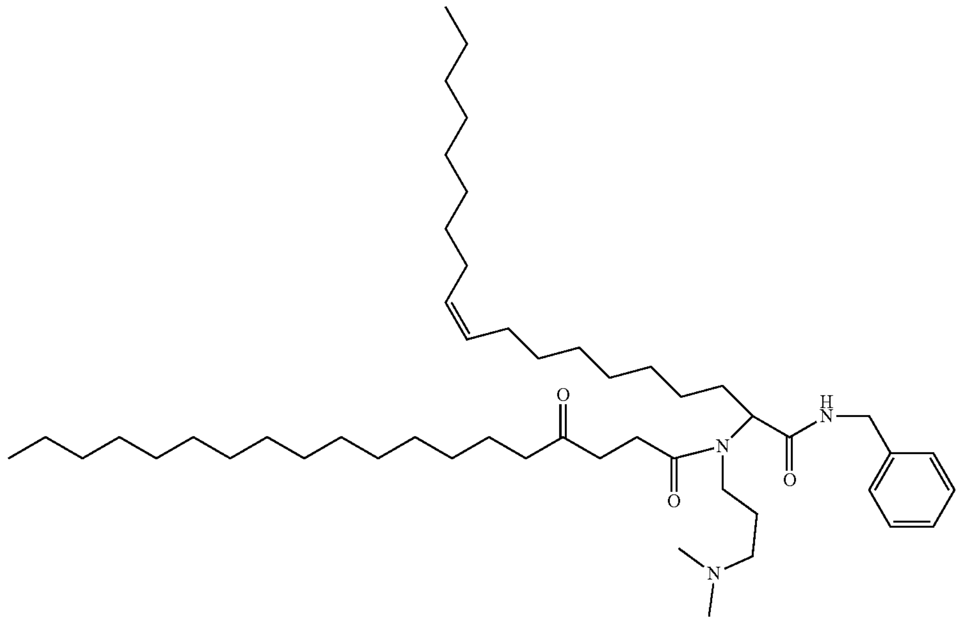
P417E4
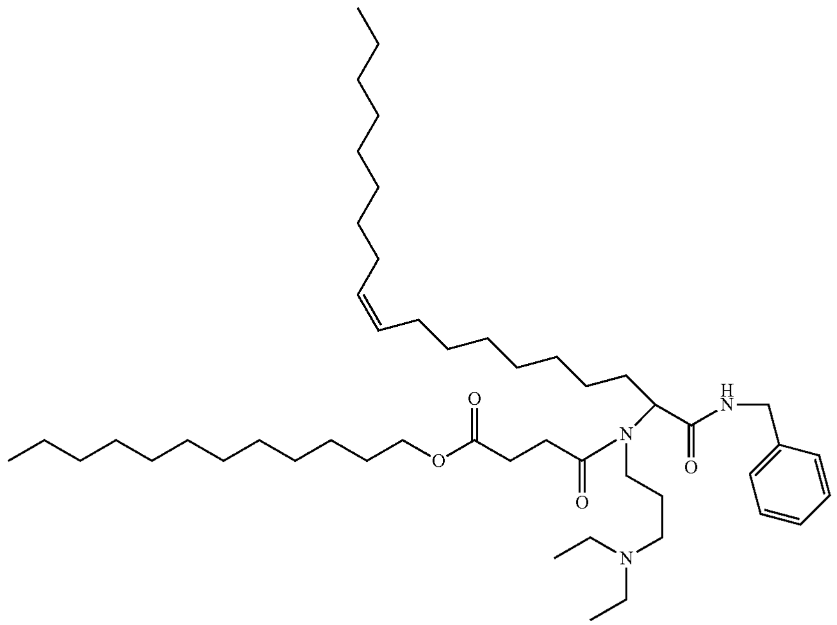

-continued
P417E6
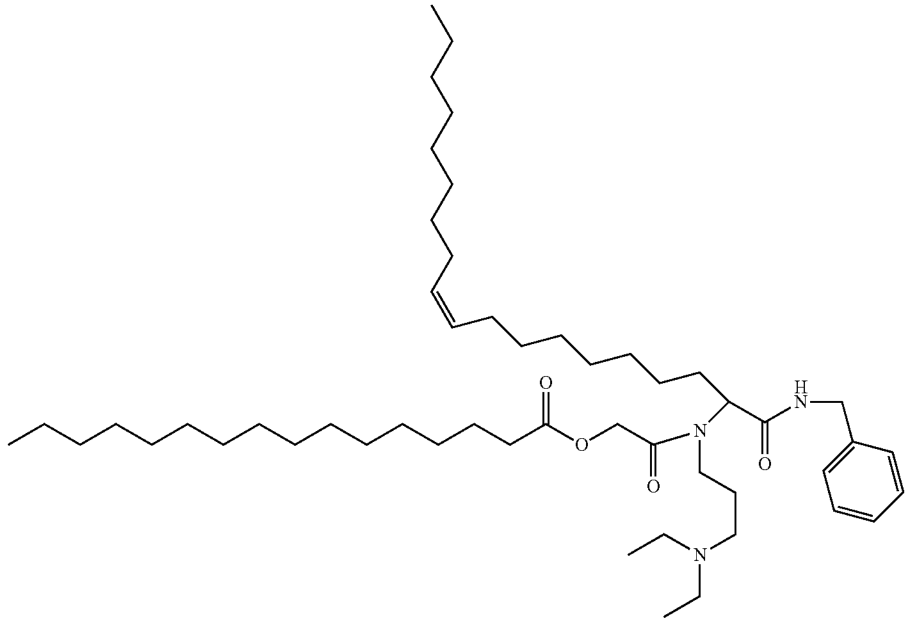
P417F4
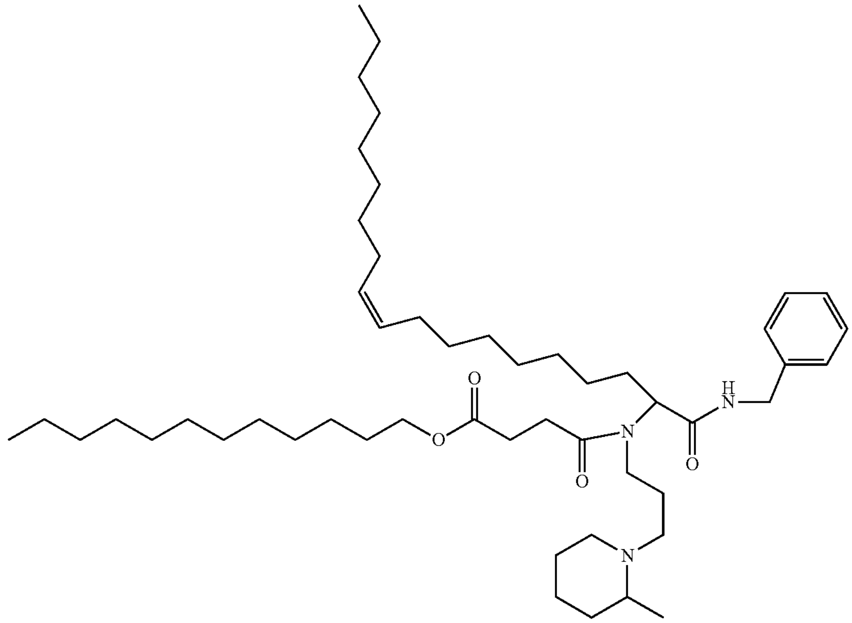

-continued
P417H2
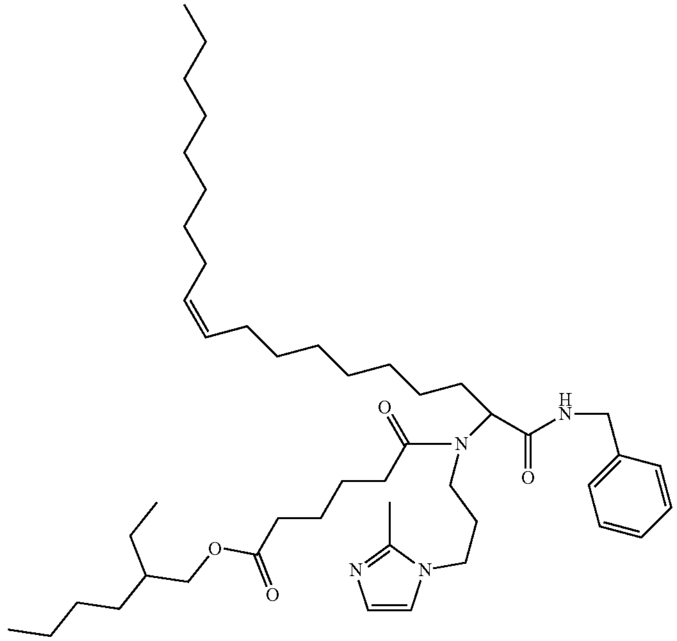
P417H4
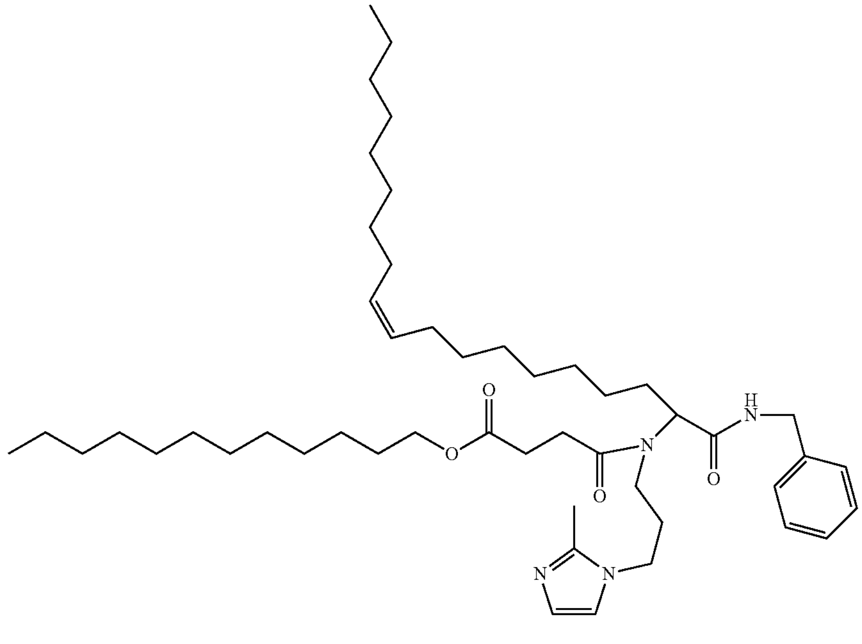

-continued
P417H6
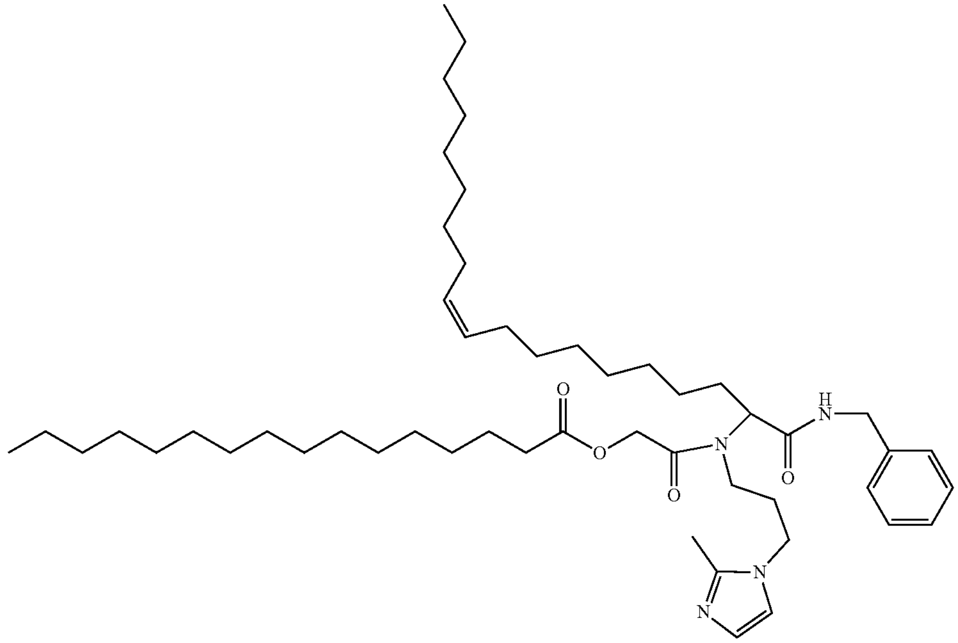
P423A2
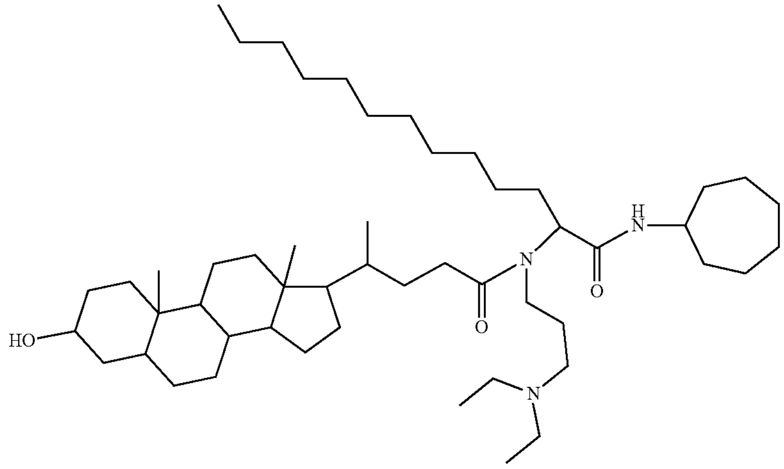
P423C7
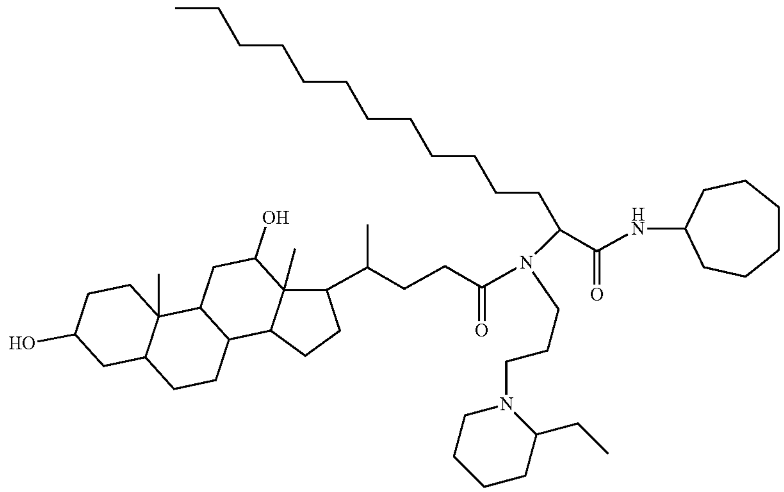

-continued
P429D1
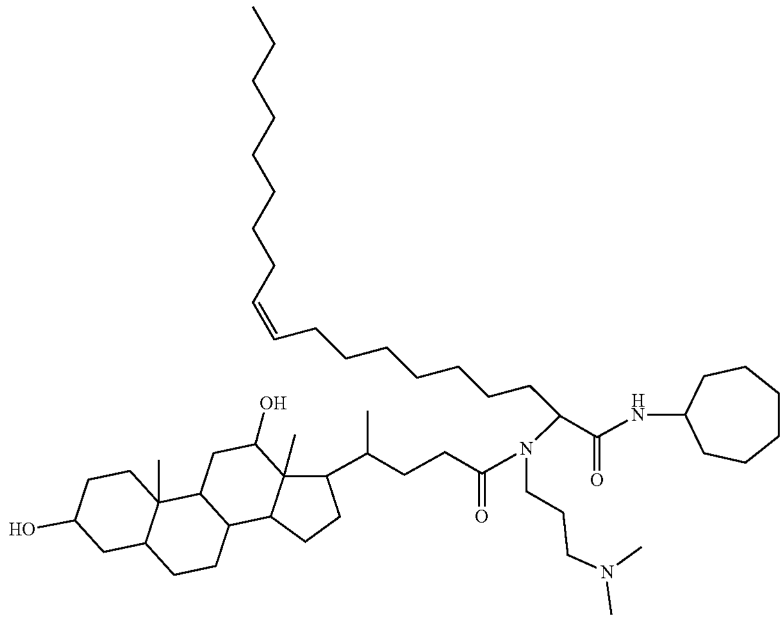
P441D1
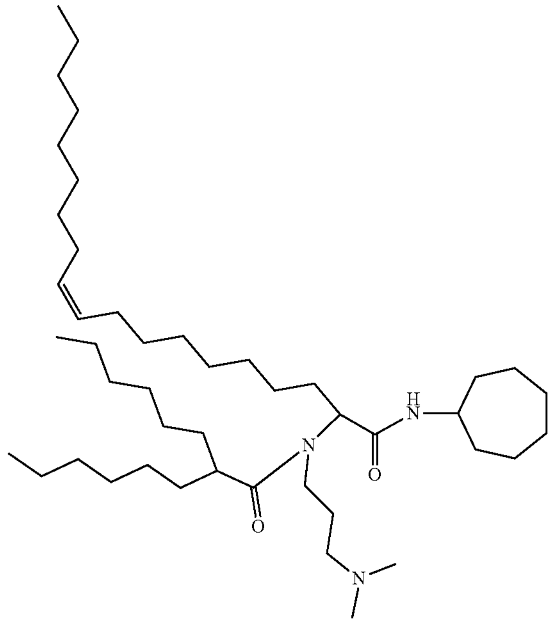

-continued
P442H1
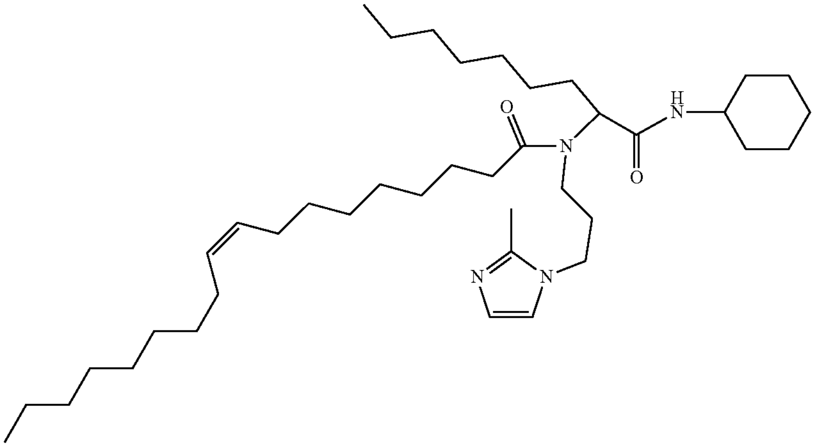
P442H7
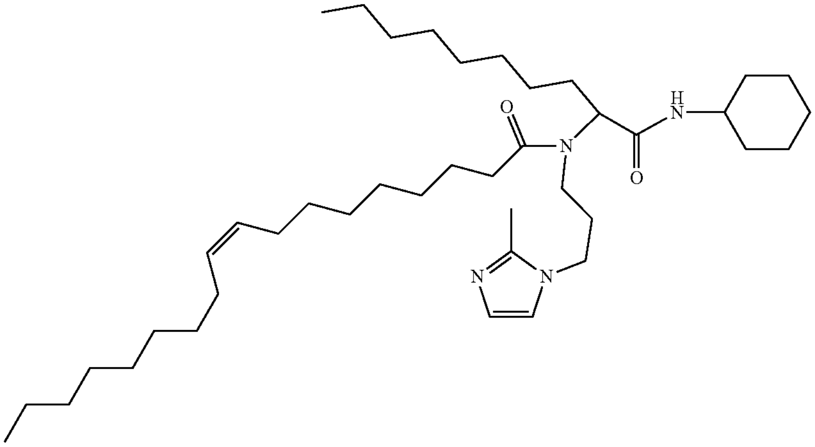
P443H1
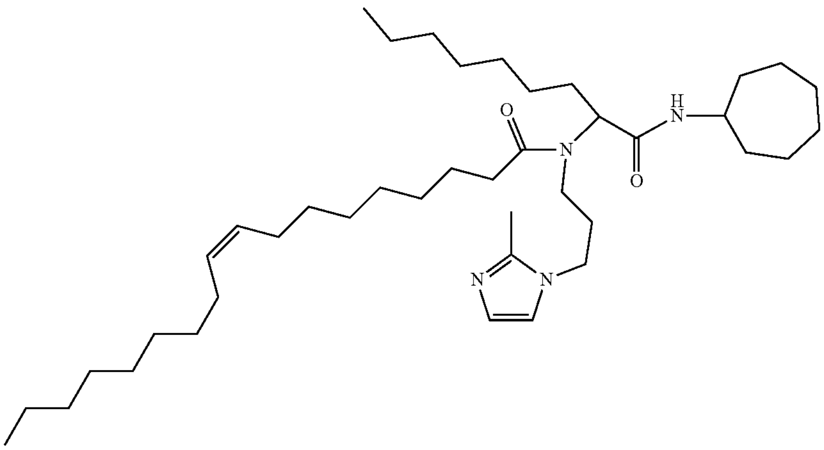

-continued
P443A1
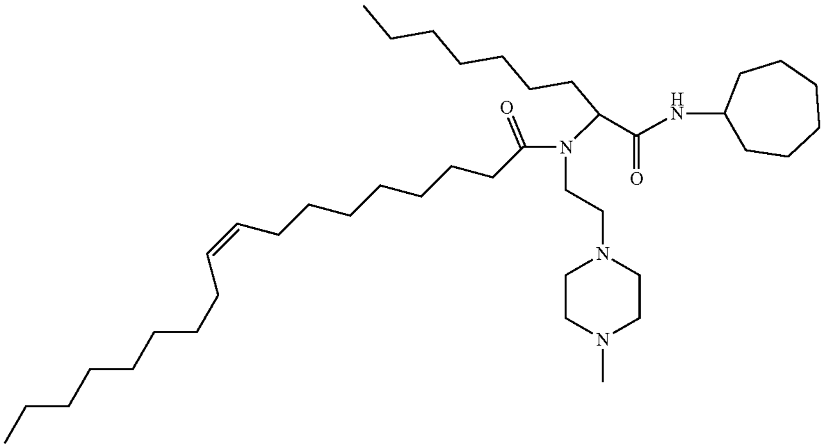
P443A7
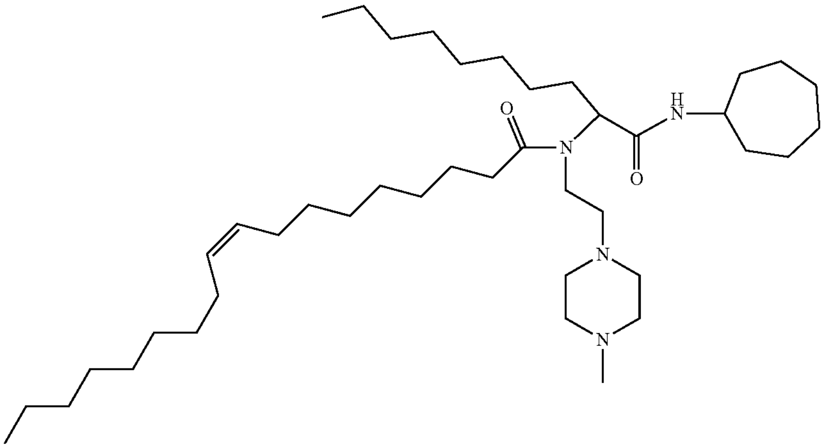
P446H7
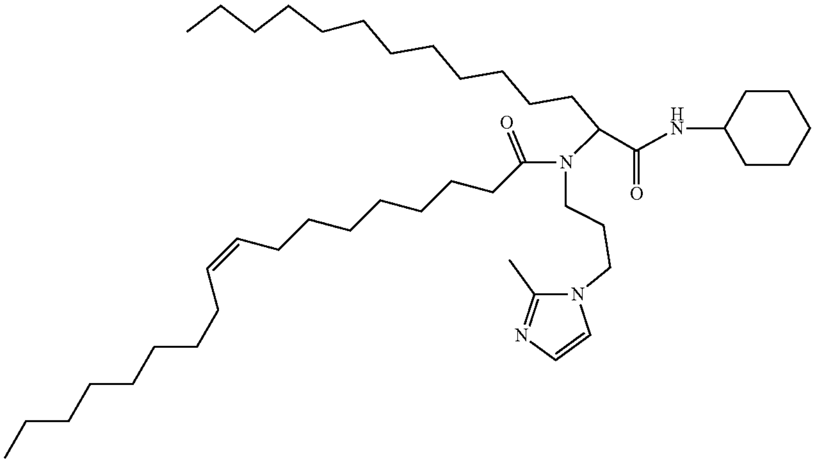

-continued
P446D7
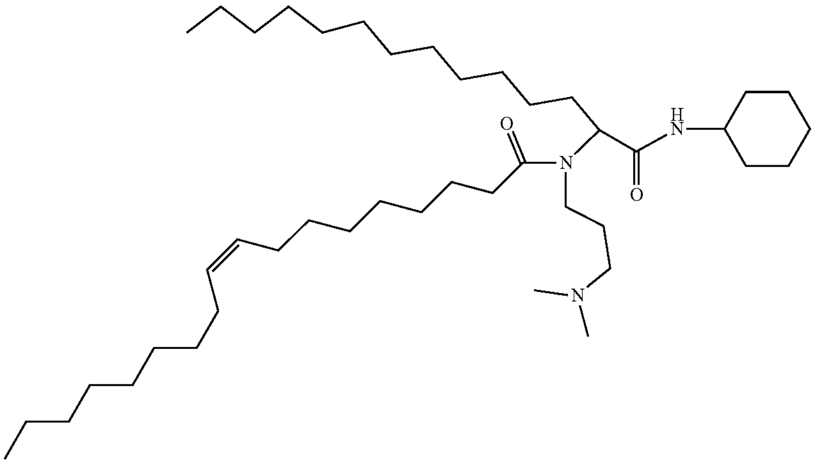
P446D12
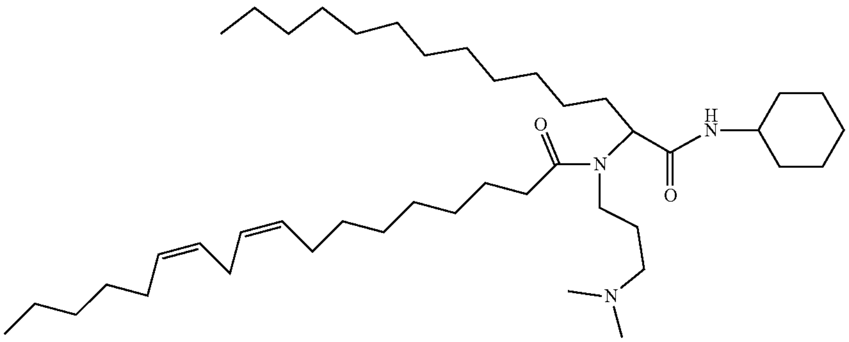
P447A1
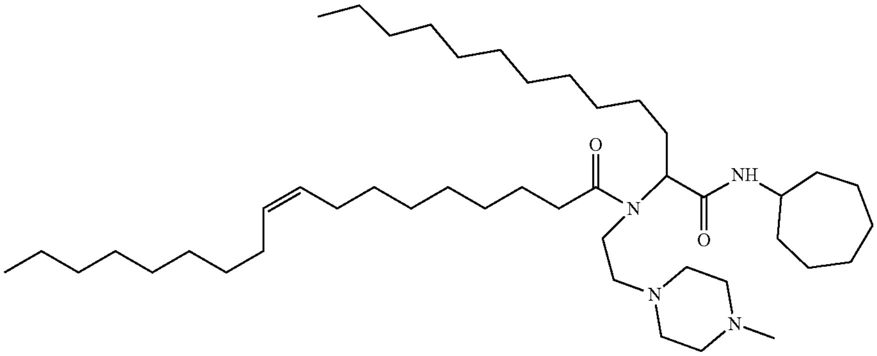
P447A6
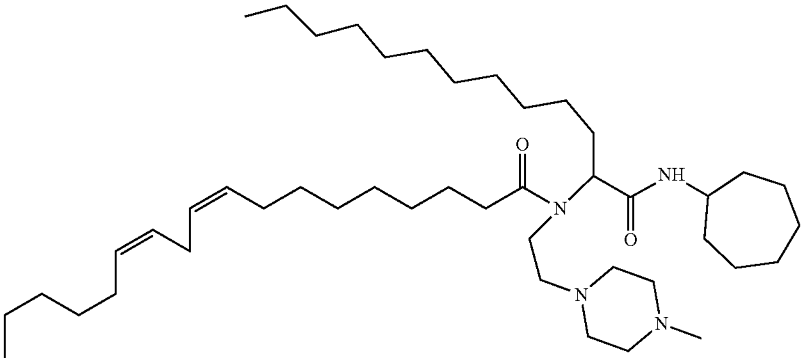

-continued
P447A7
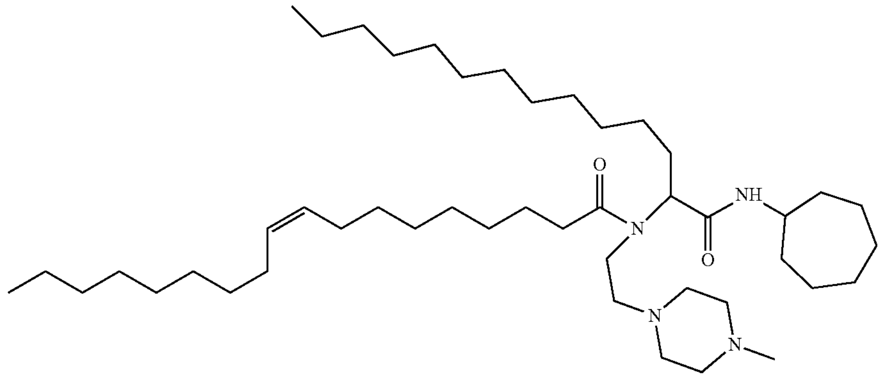
P447A9
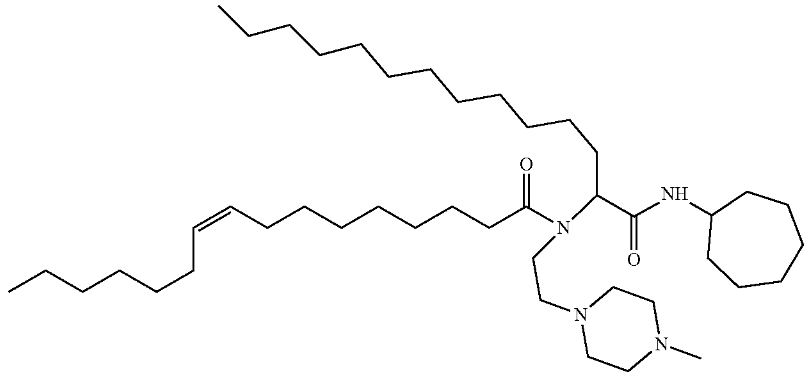
P447A12
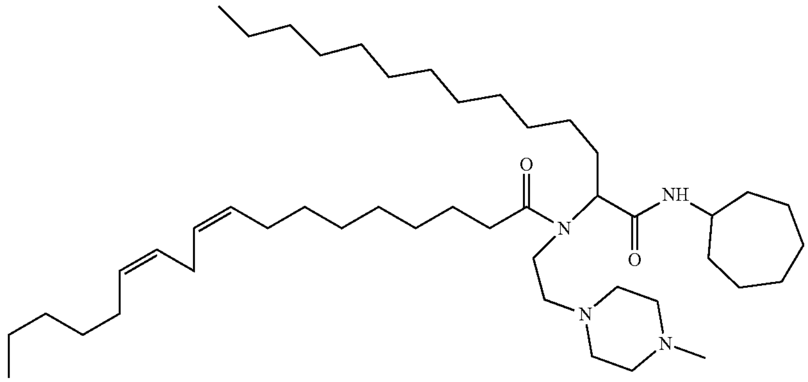
P447D1
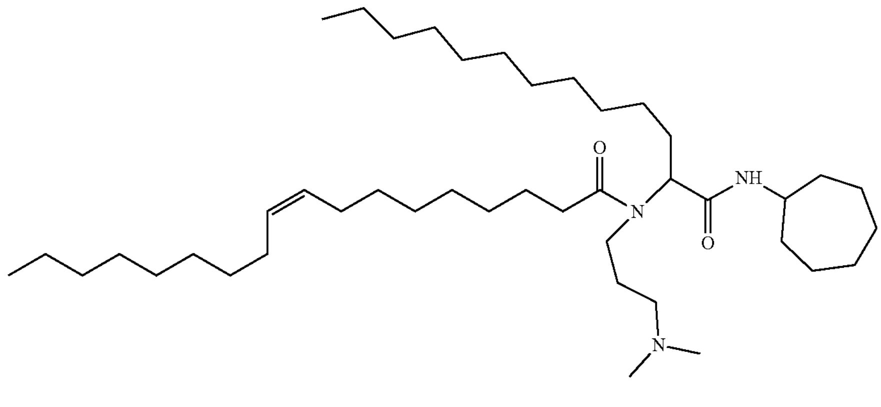

-continued
P447D6
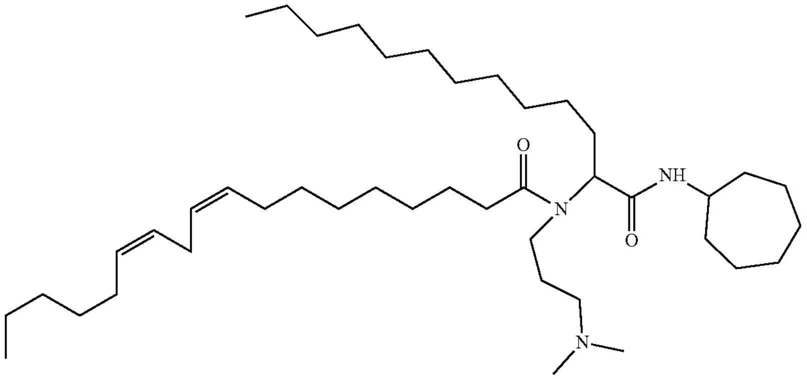
P447D7
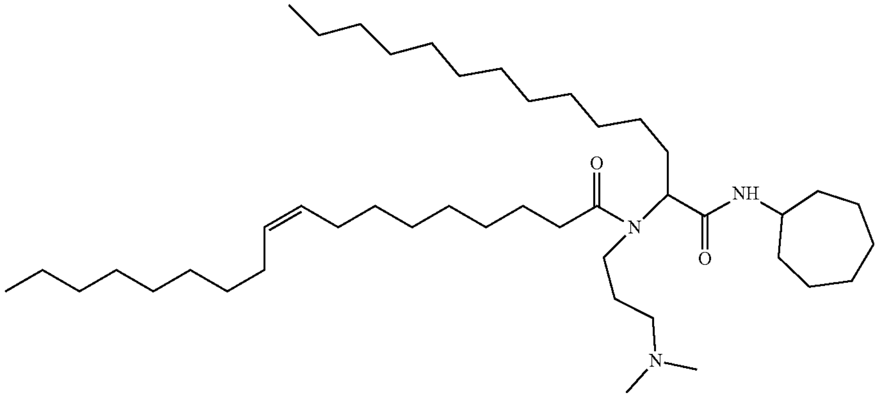
P447D12
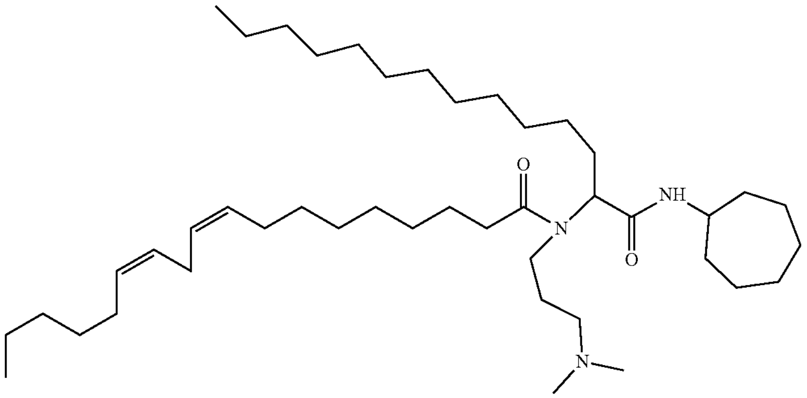
P447H1
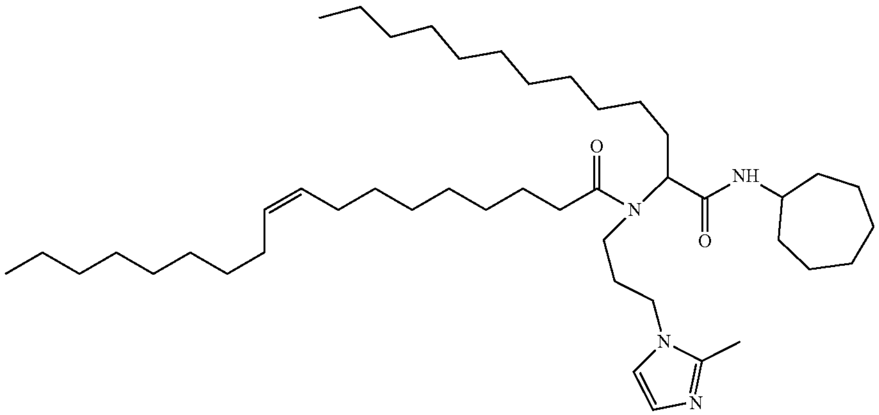

-continued
P447H3
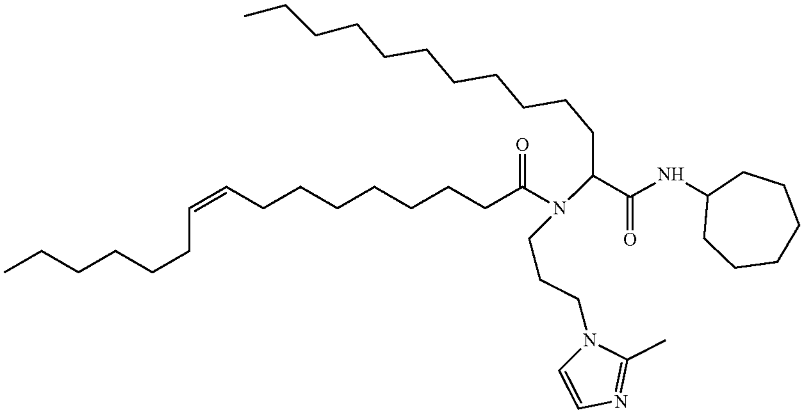
P447H7
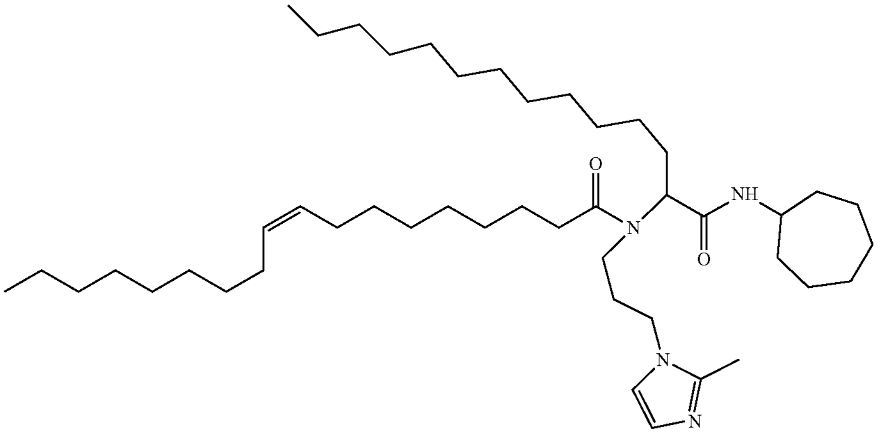
P447H9
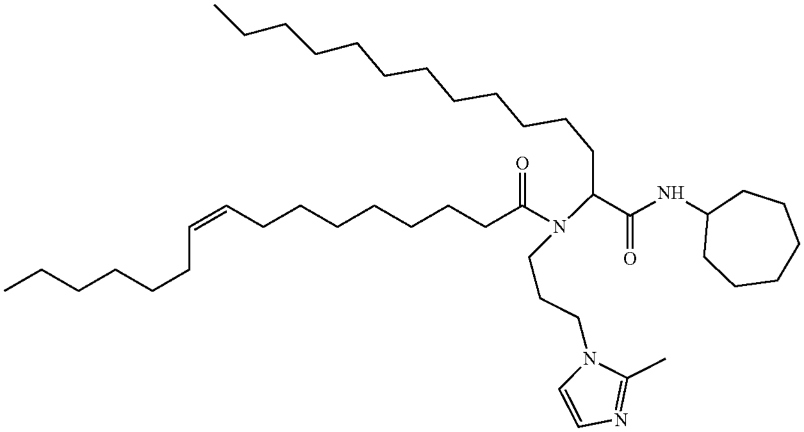

-continued
P447H10
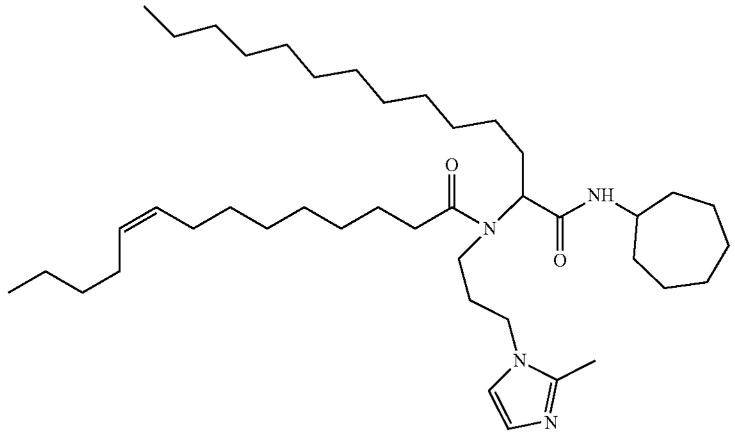
P447H12
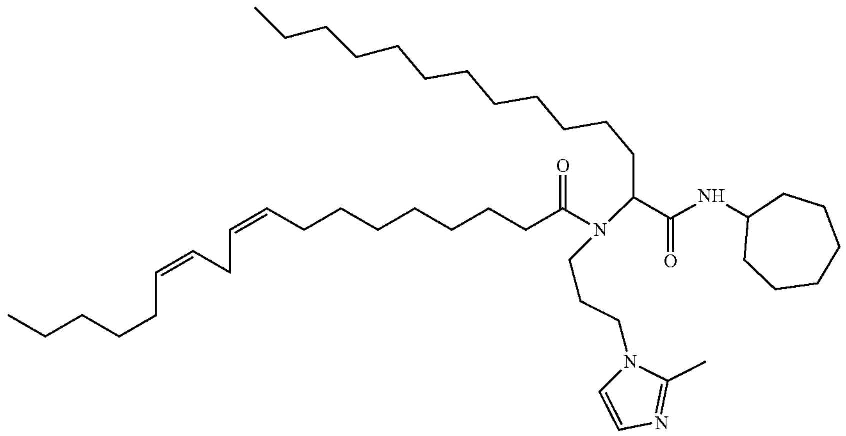
P448A1
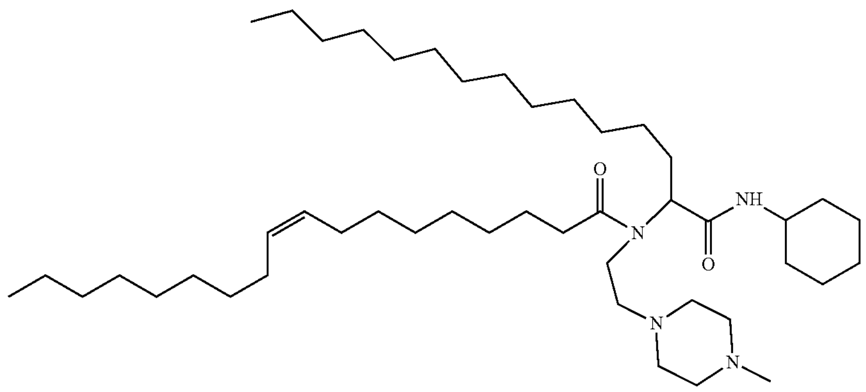

-continued
P448A6
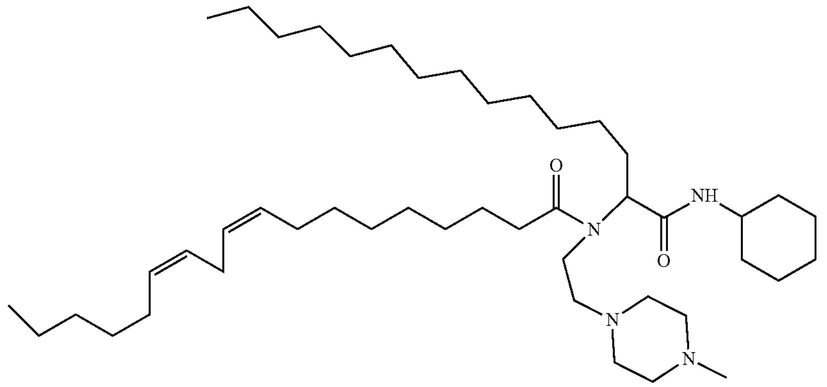
P448D7
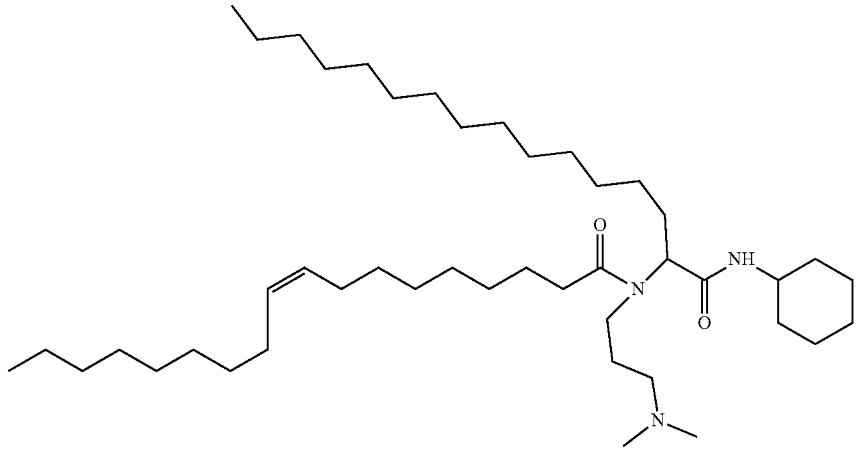
P448H7
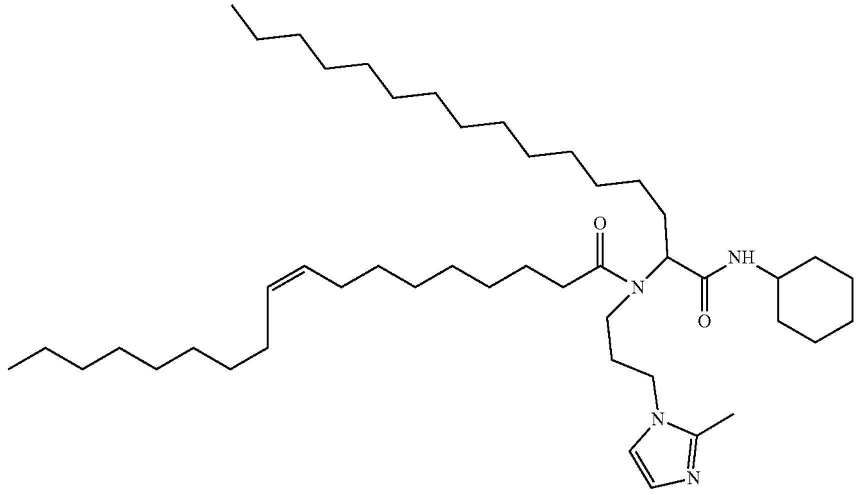

-continued
P448H9
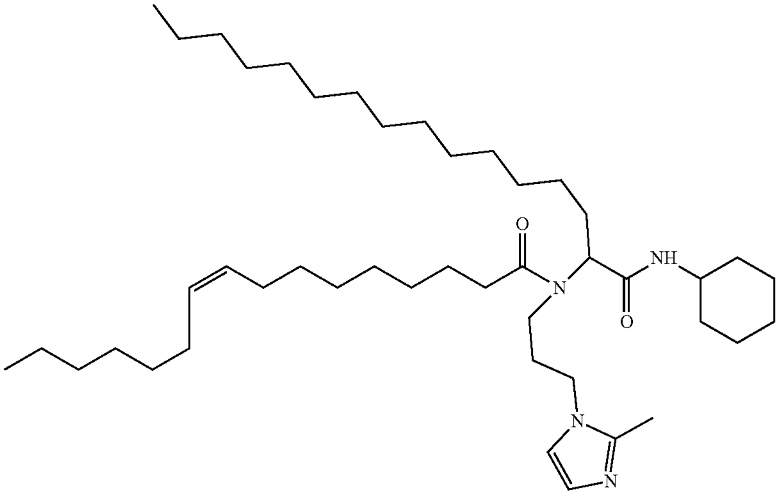
P449A3
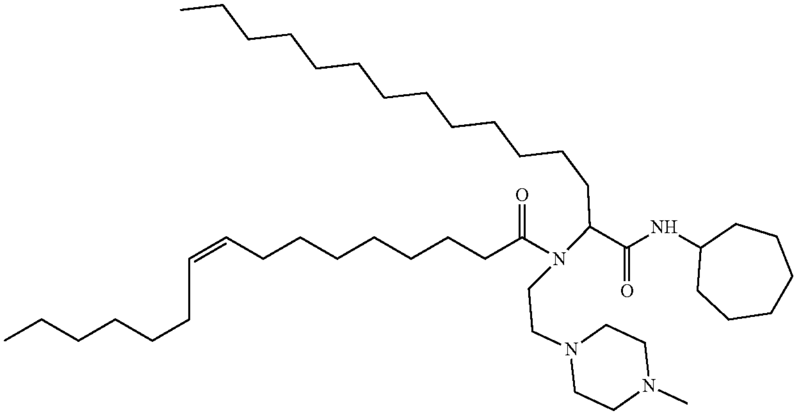
P449A6
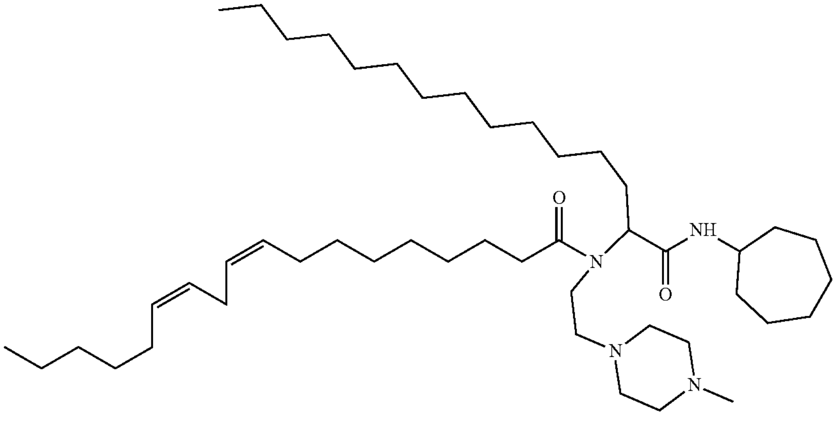

-continued
P449A12
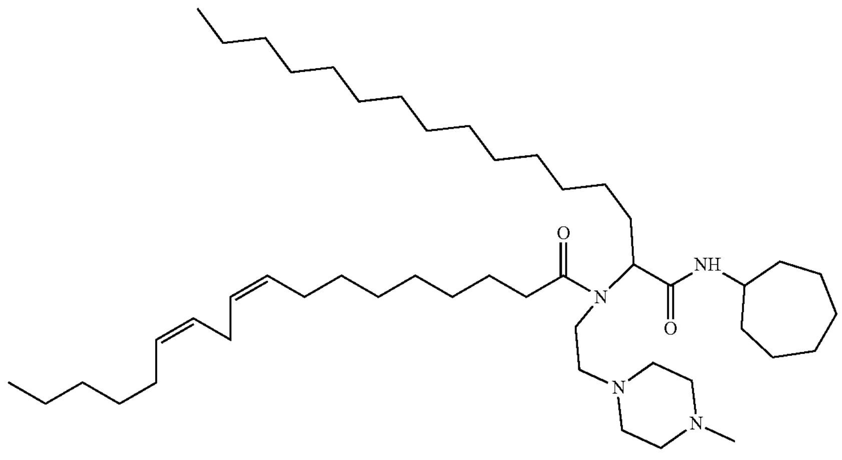
P449D1
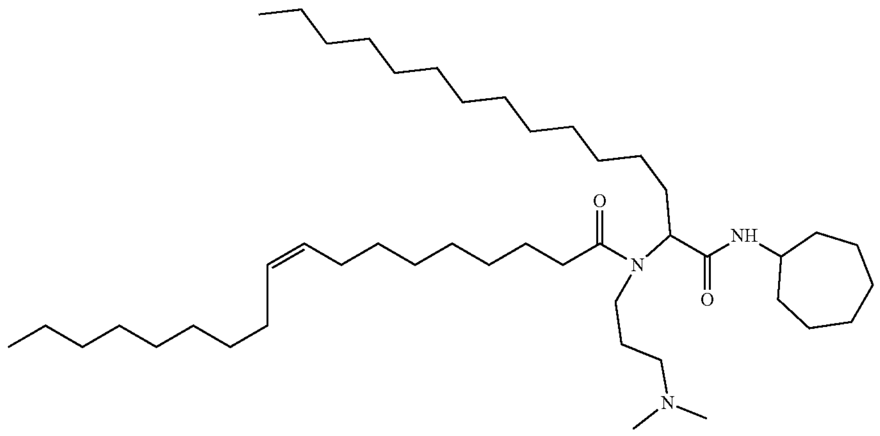
P448H7
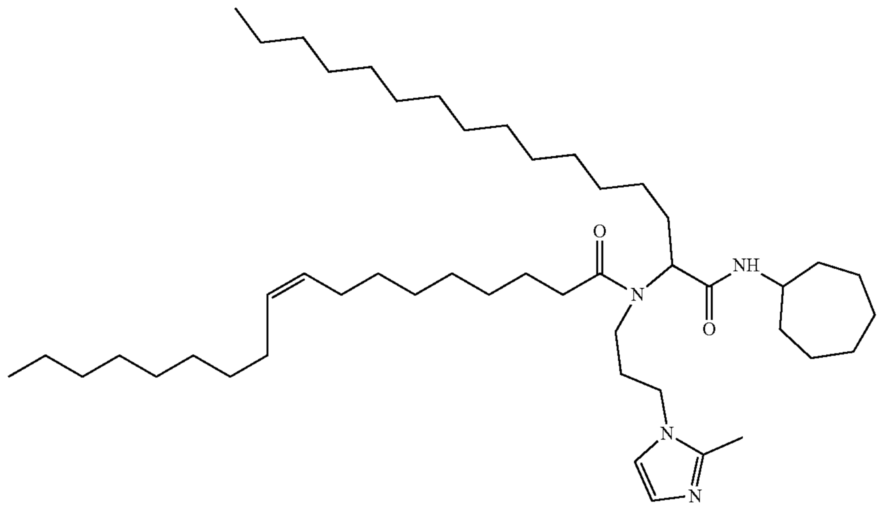

-continued
P451A7
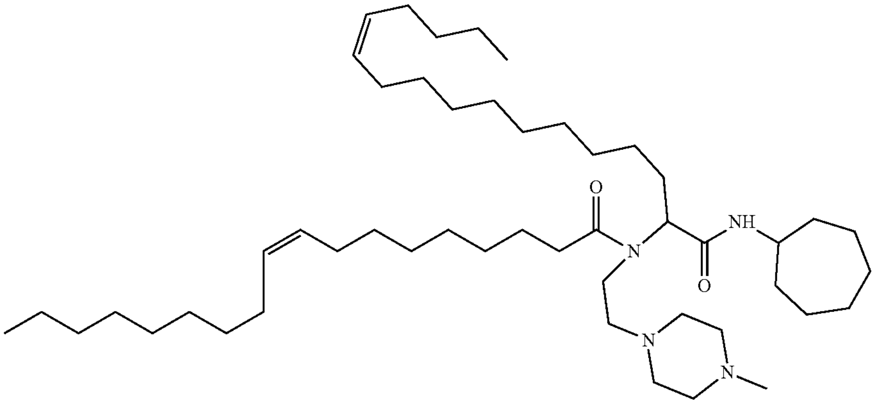
P451A9
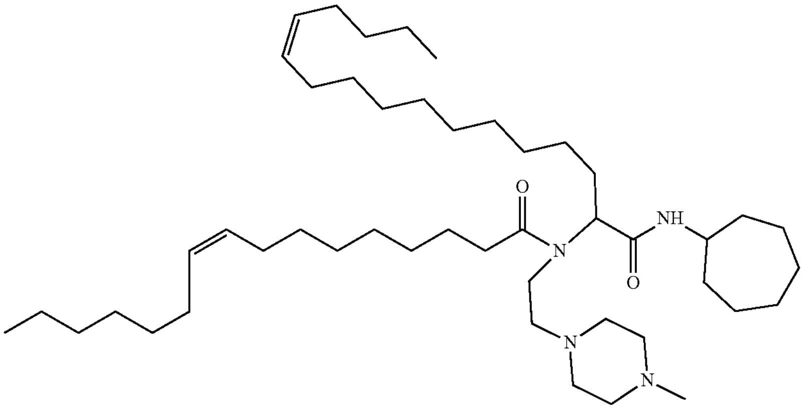
P451A10
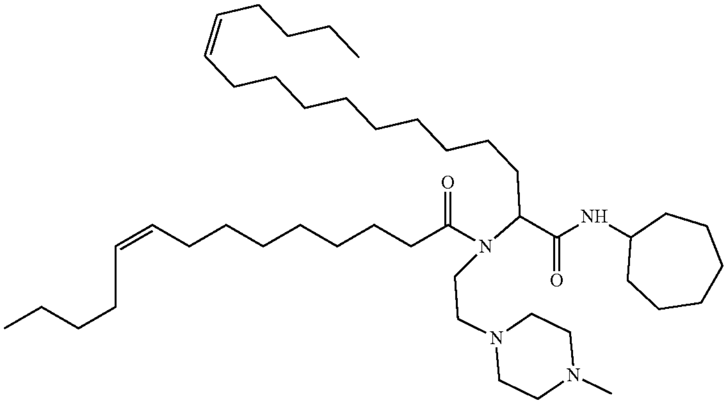
P451A12
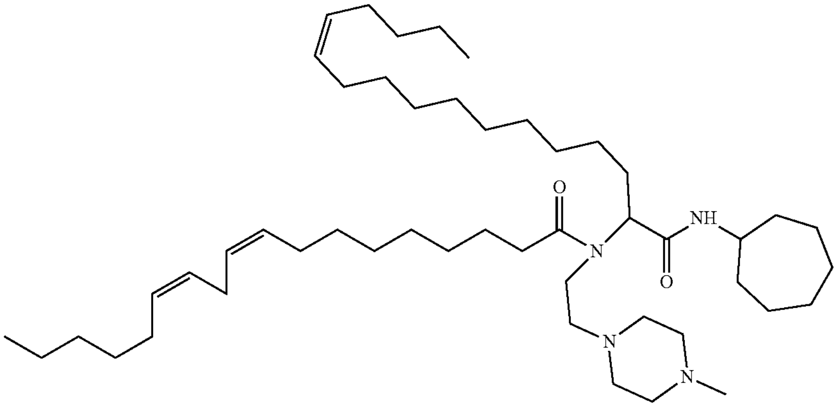

-continued
P451D12
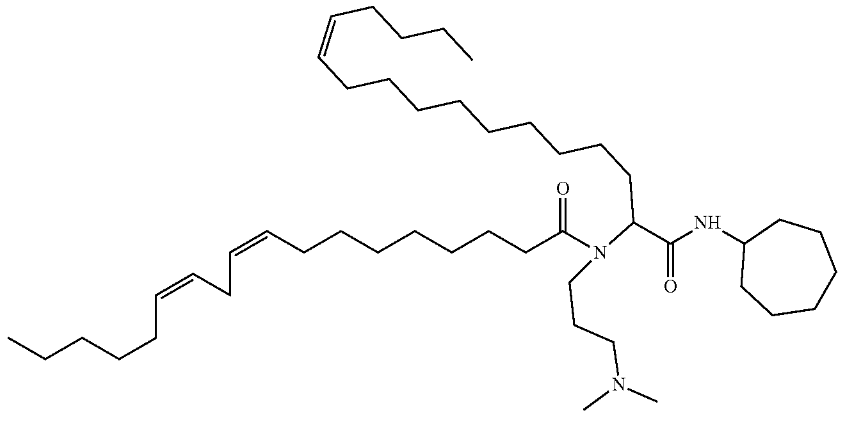
P451H7
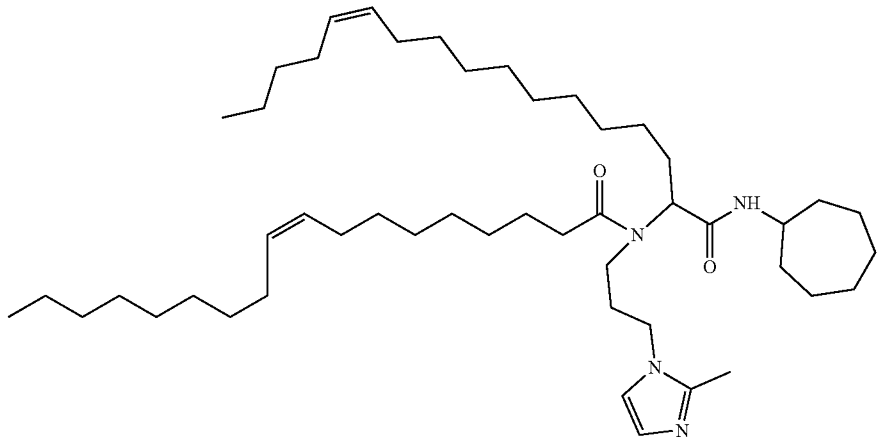
P451H9
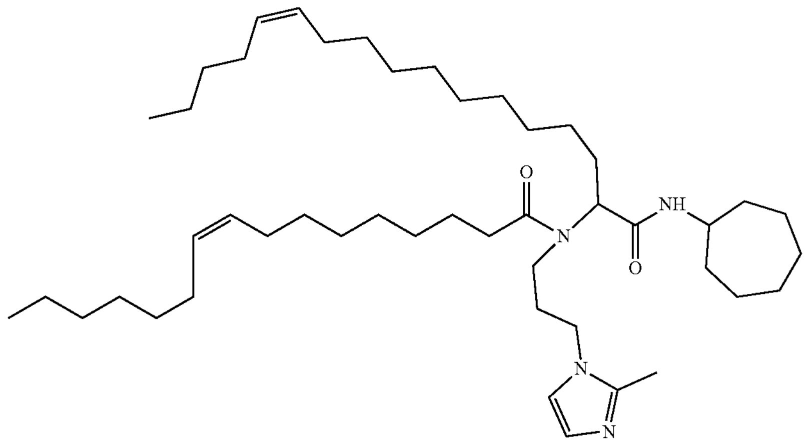

-continued
P453A4
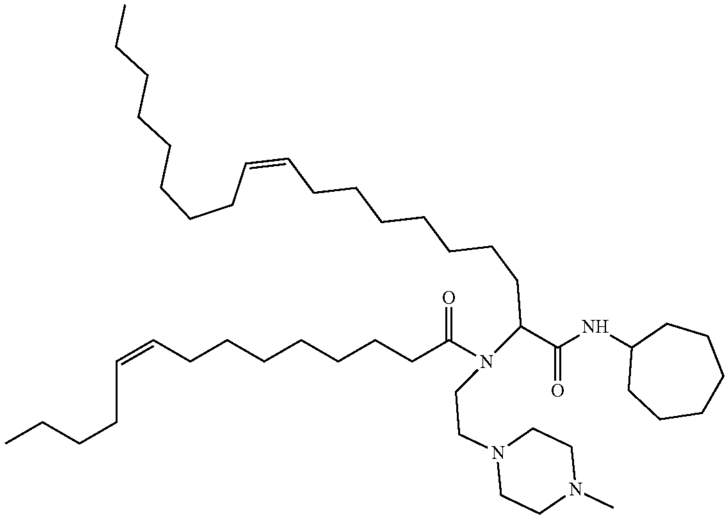
P453A6
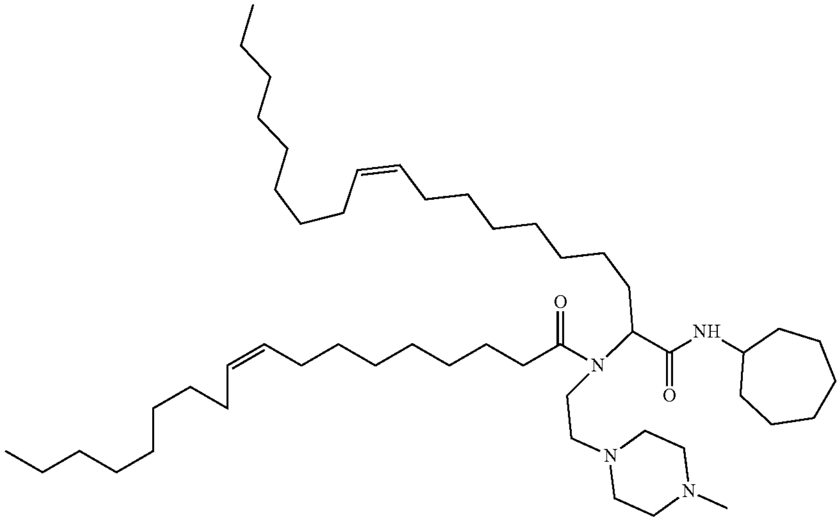
P453H1
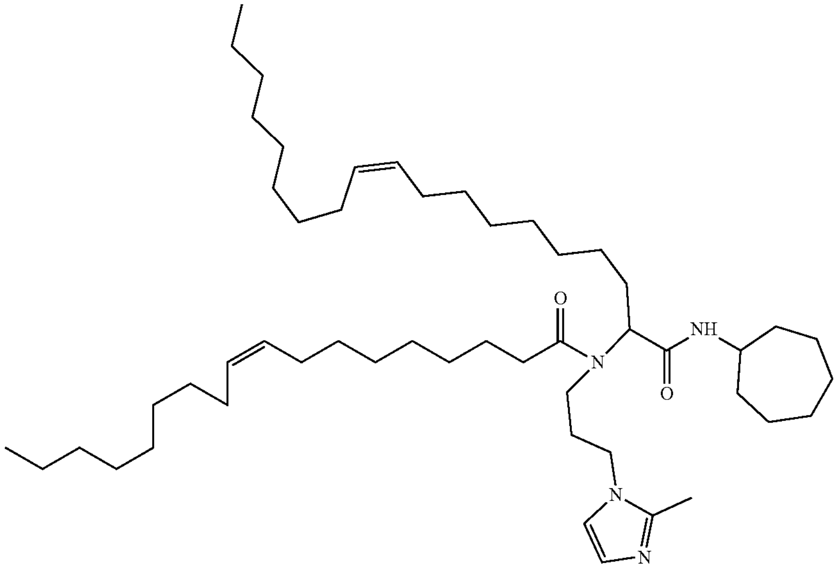

-continued
P453H3
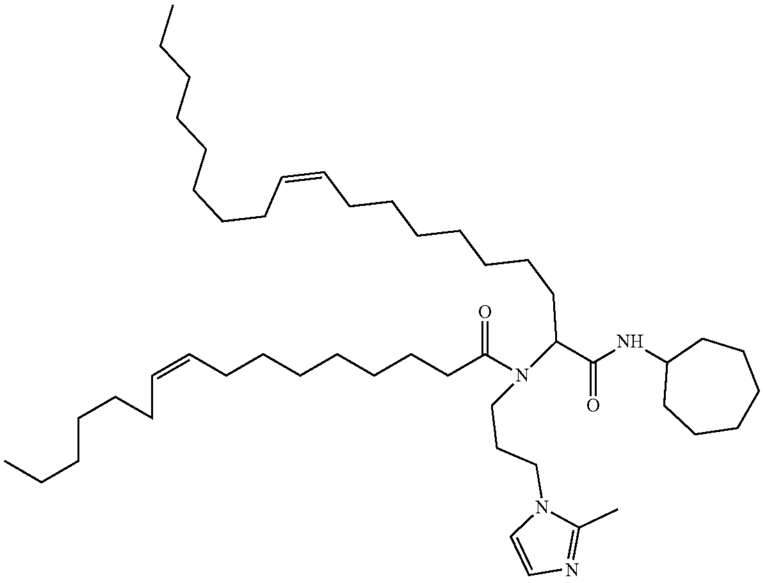
P454A6
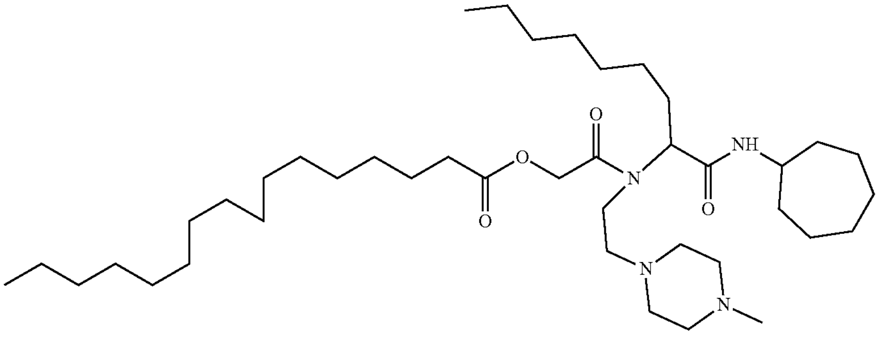
P454A12
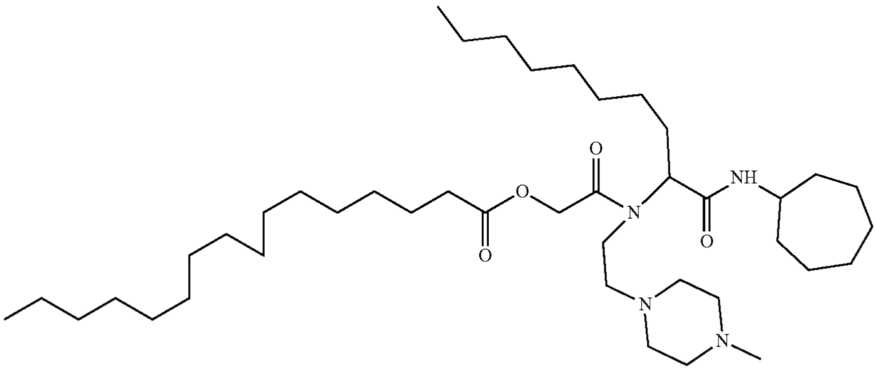

-continued
P454B12
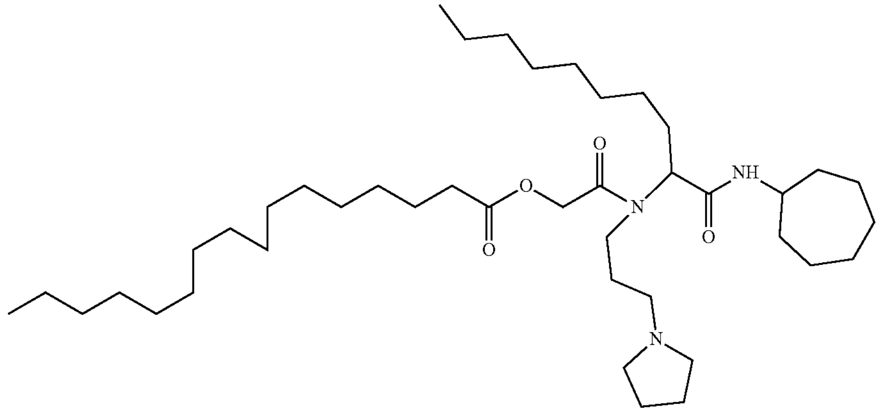
P454C12
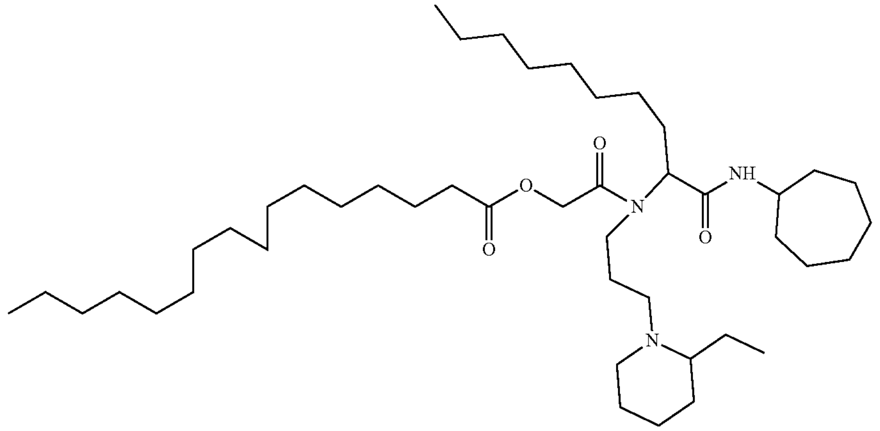
P454D12
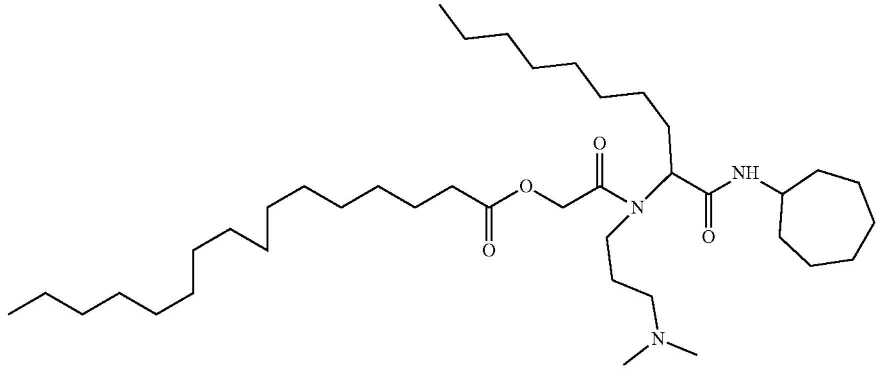
P454E12
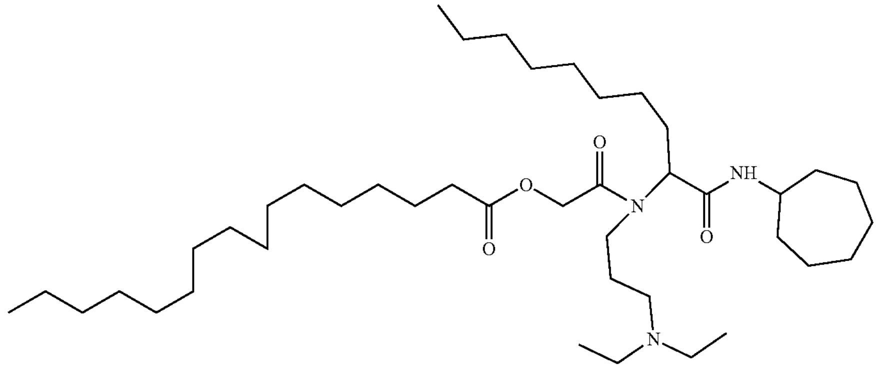

-continued
P454F12
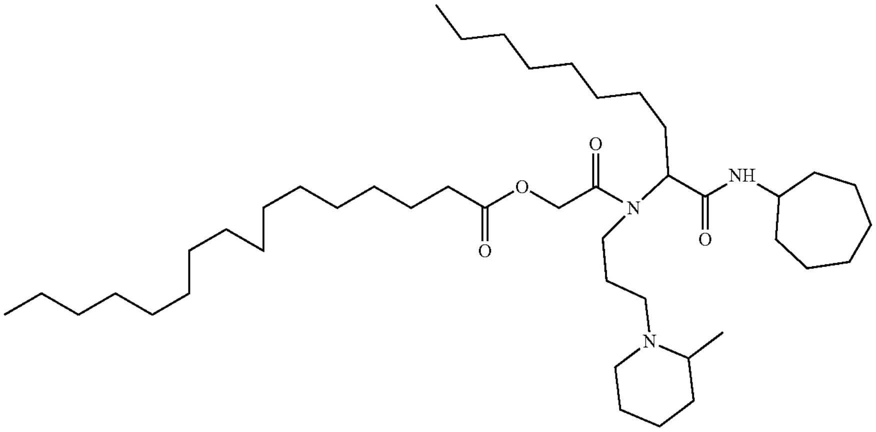
P454H6
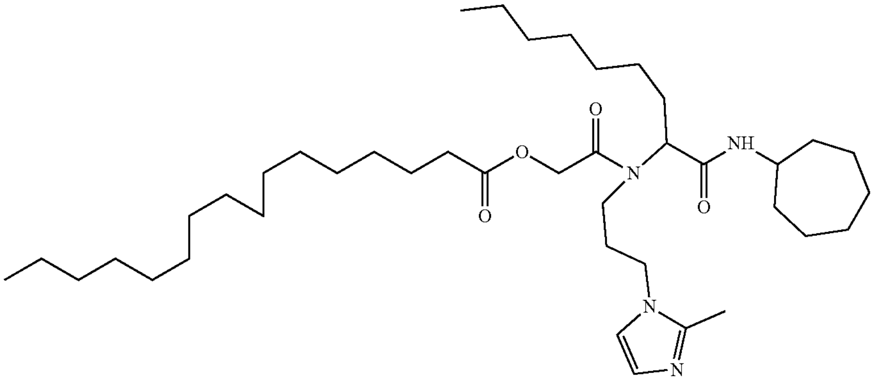
P455A6
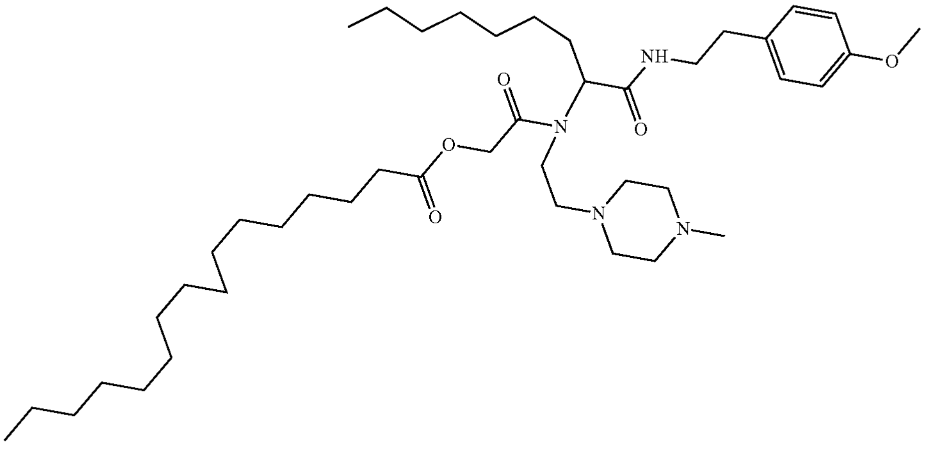

-continued
P455A12
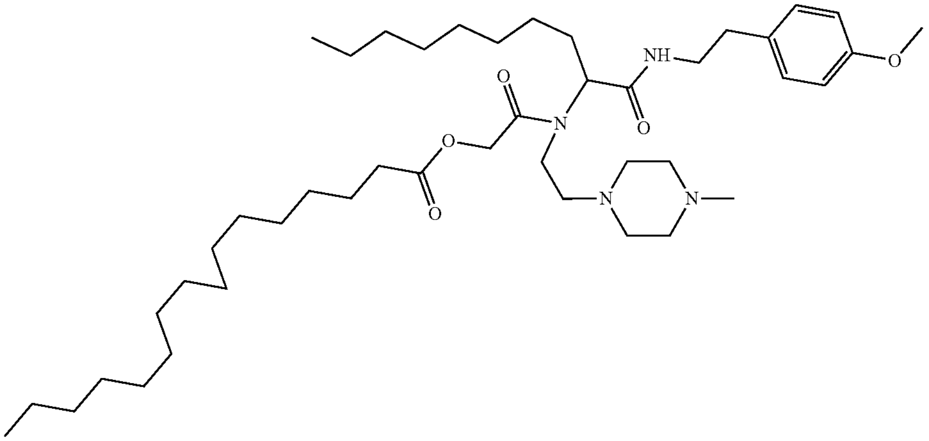
P455C12
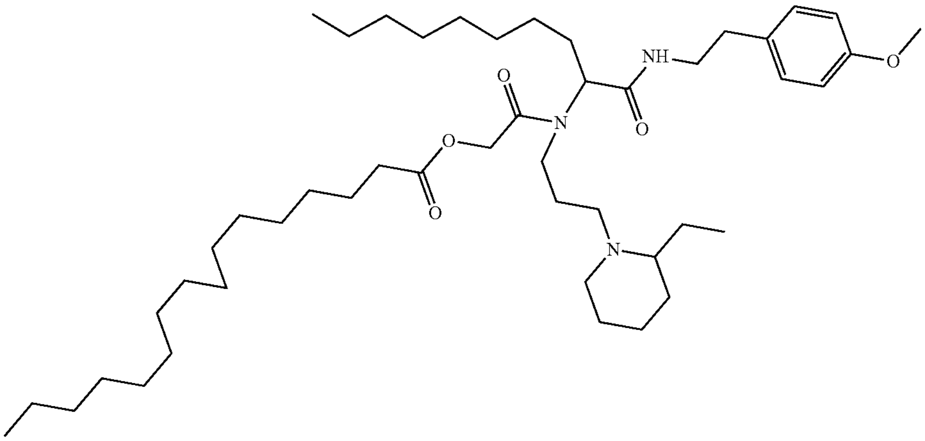
P455D12
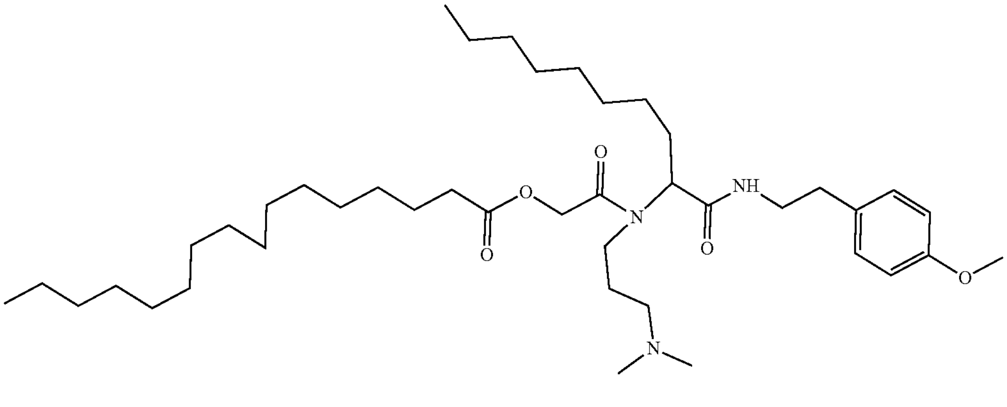

-continued
P455F12
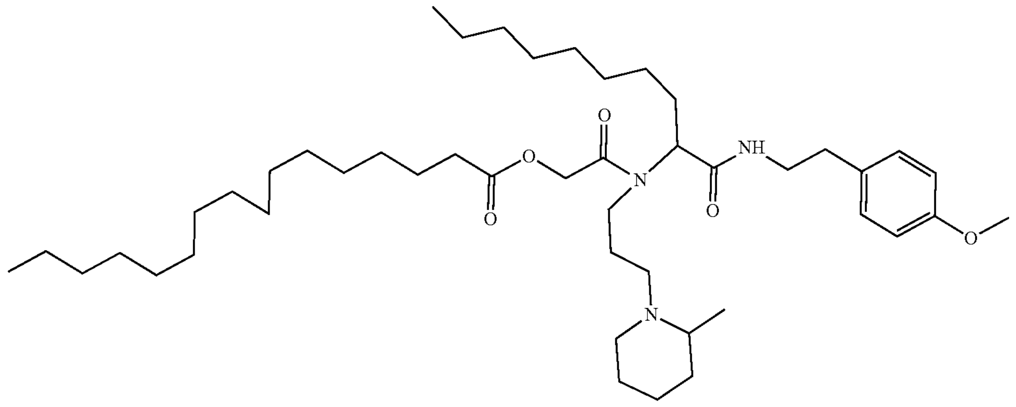
P458A10
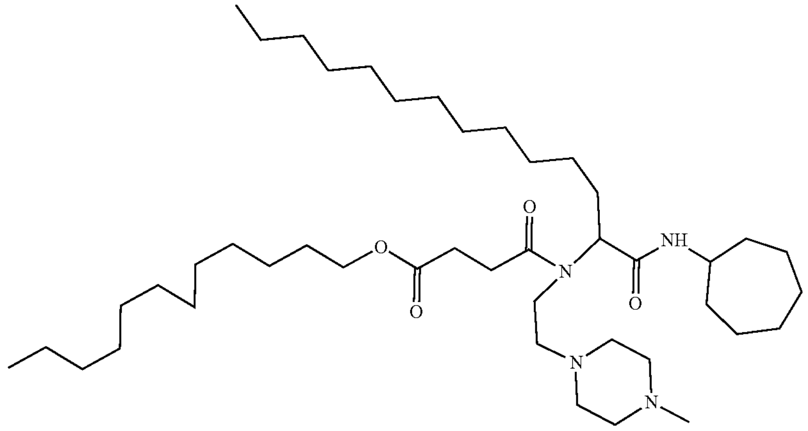
P458A11
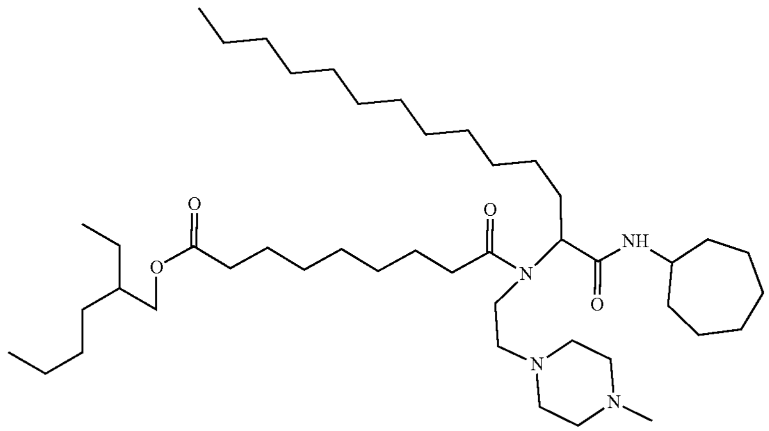

-continued
P458A12
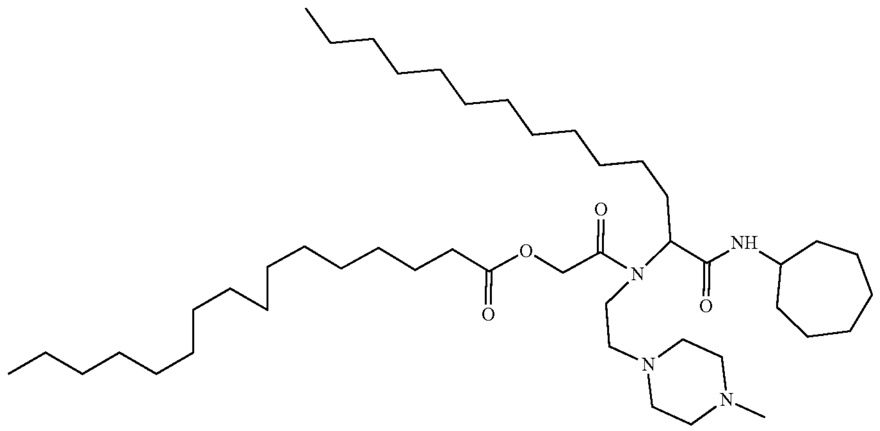
P458B12
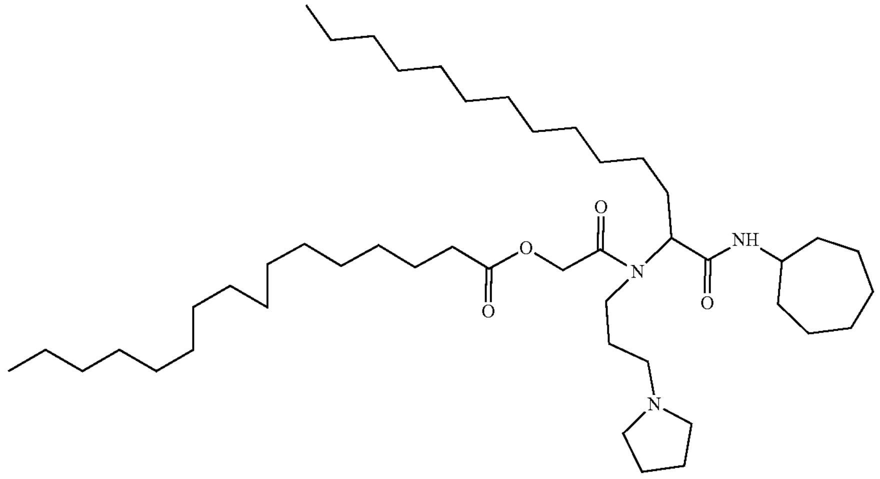
P458C12
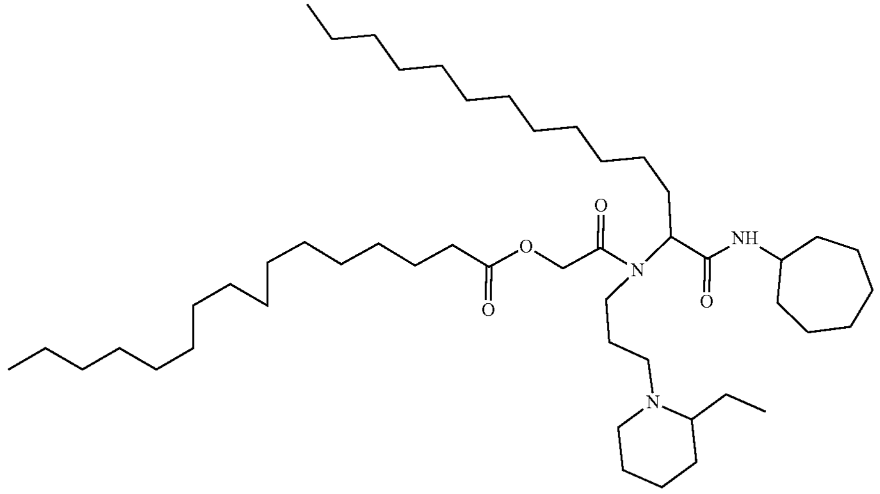

-continued
P458D12
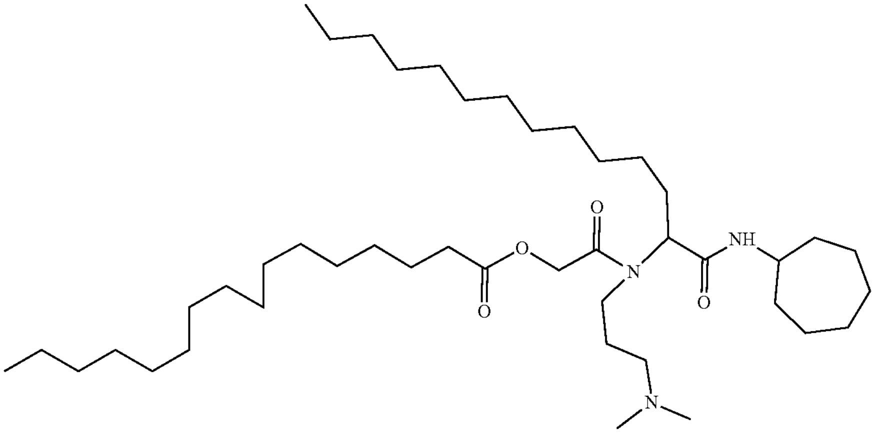
P458F12
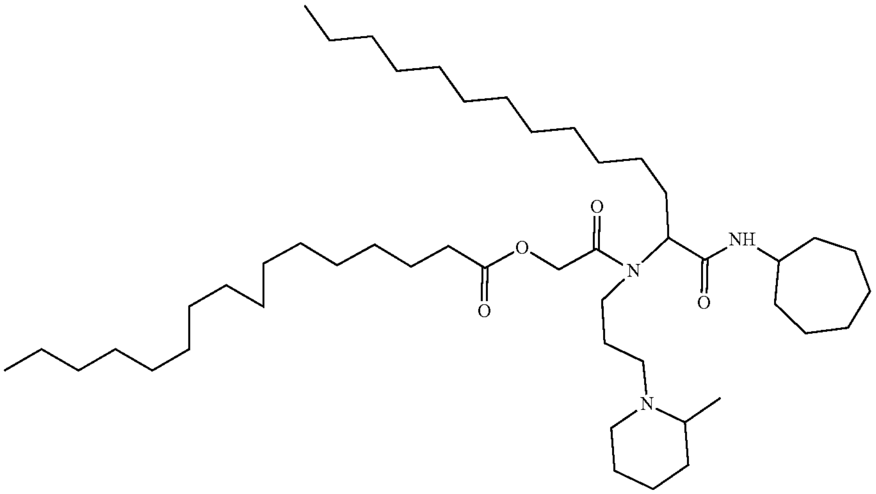
P459C6
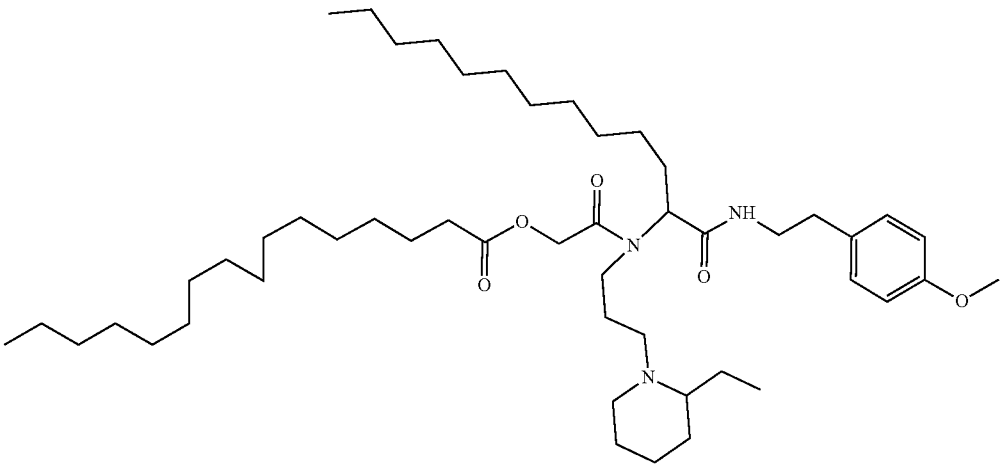

-continued
P459C12
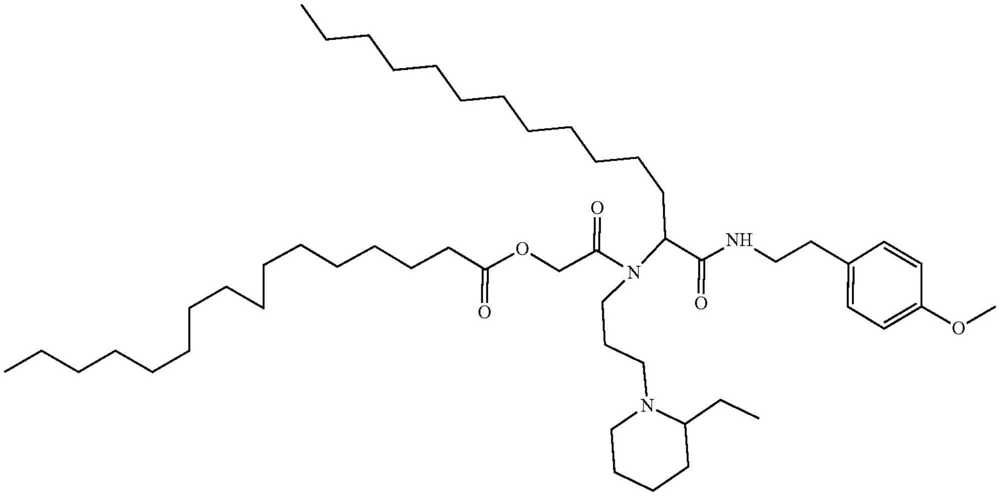
P459F4
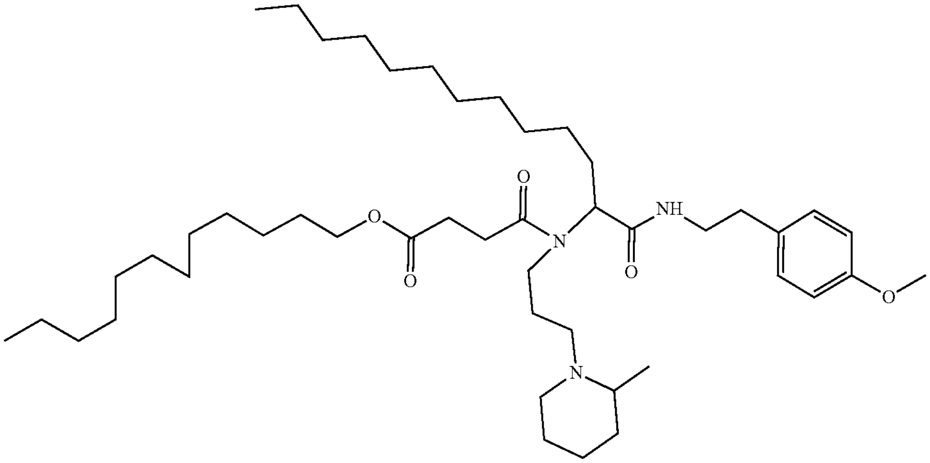
P459F6
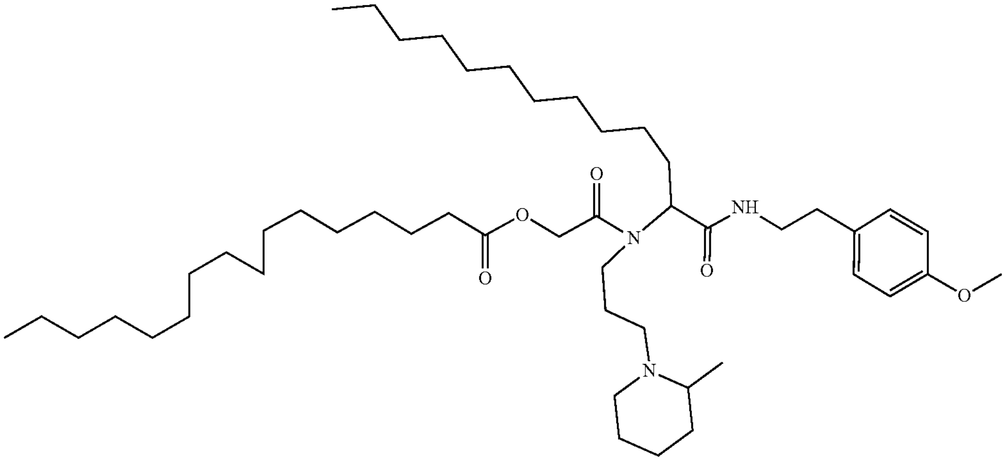

-continued
P460A5
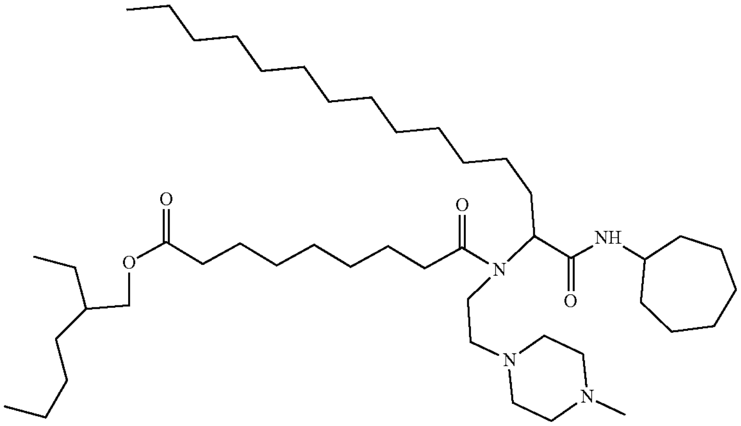
P460A6
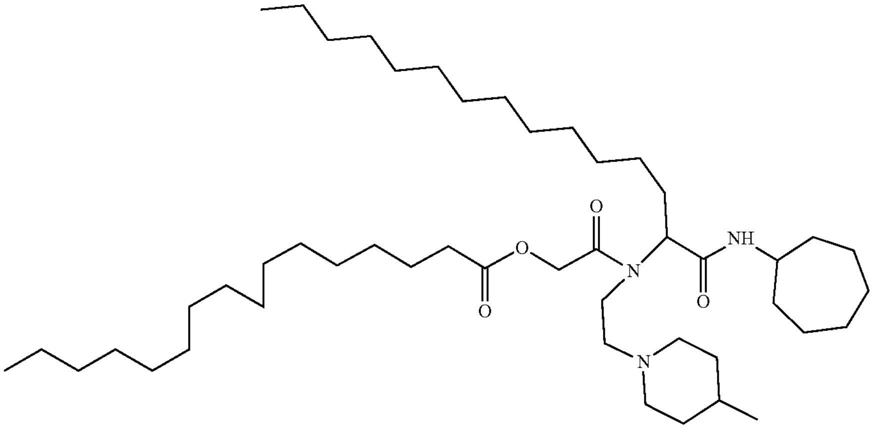
P460A11
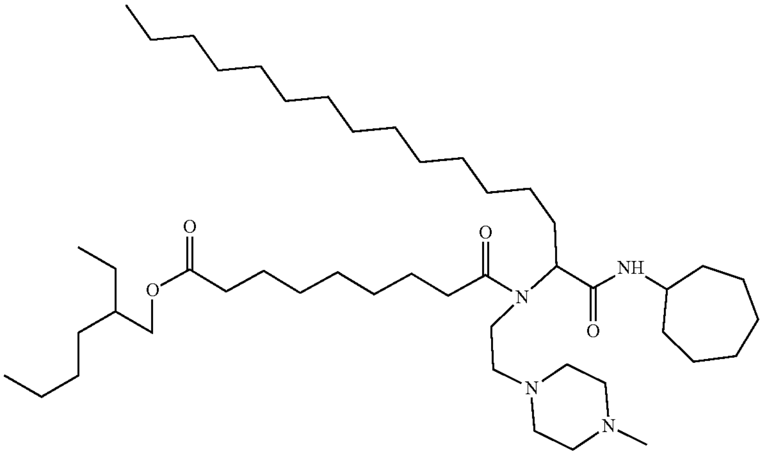

-continued
P461A2
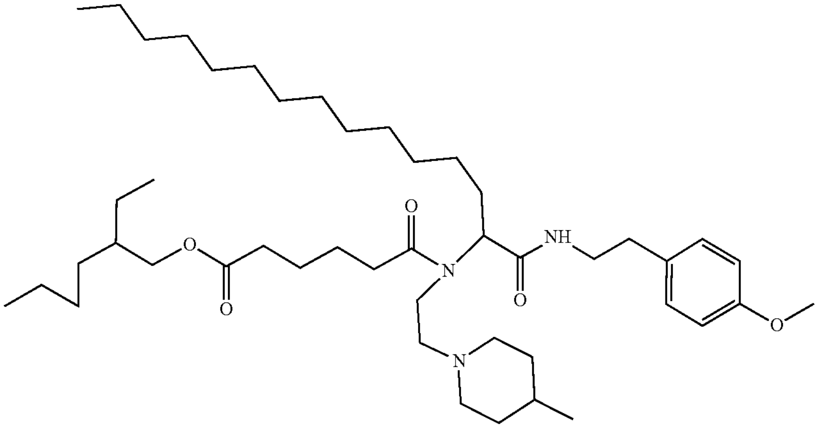
P461A5
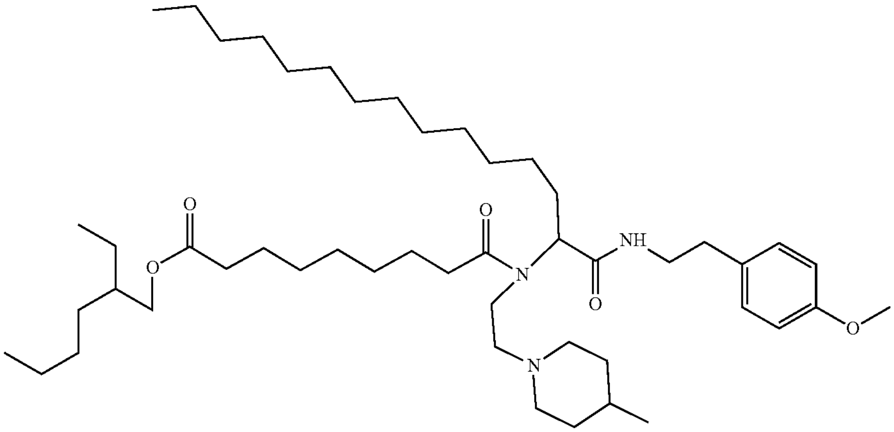
P460A11
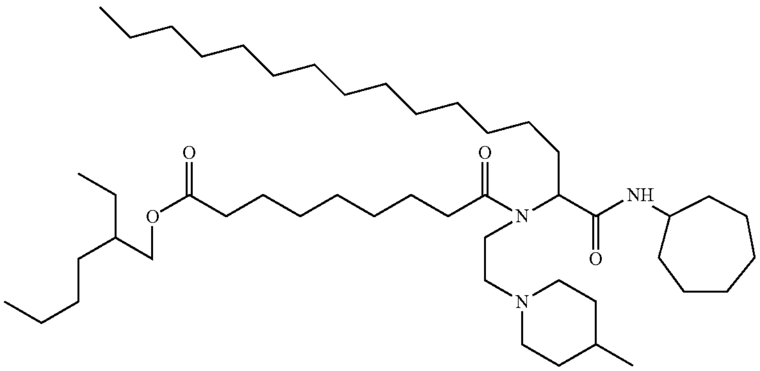

-continued
P461A2
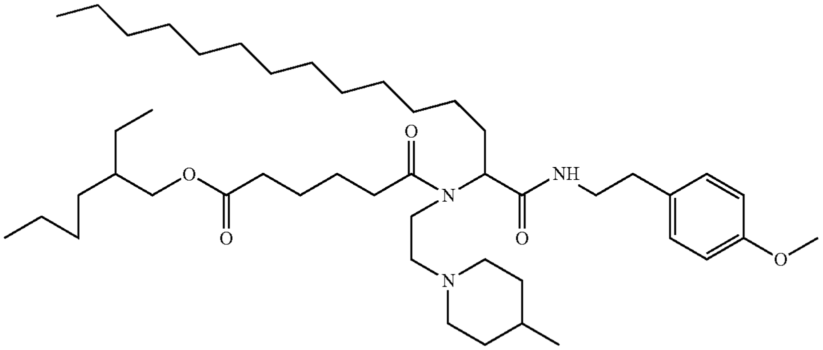
P461A5
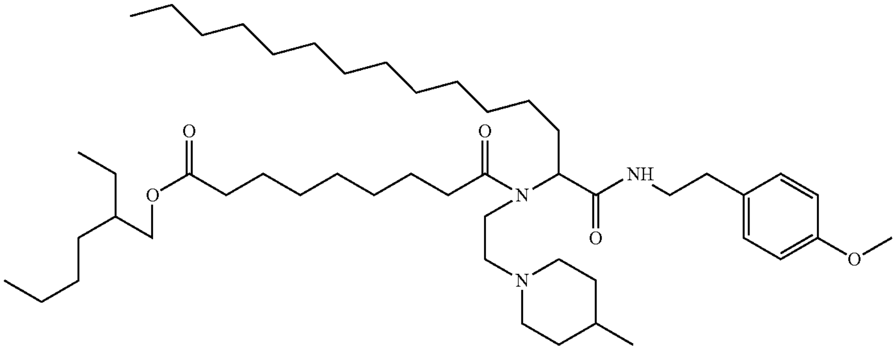
P461H6
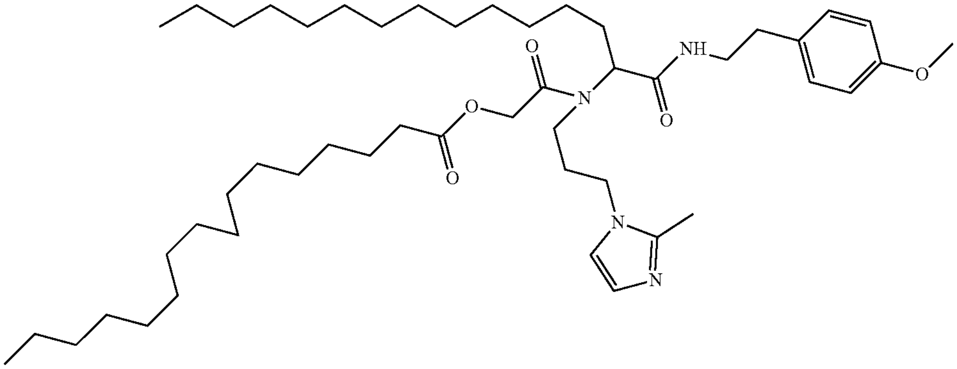
P461H12
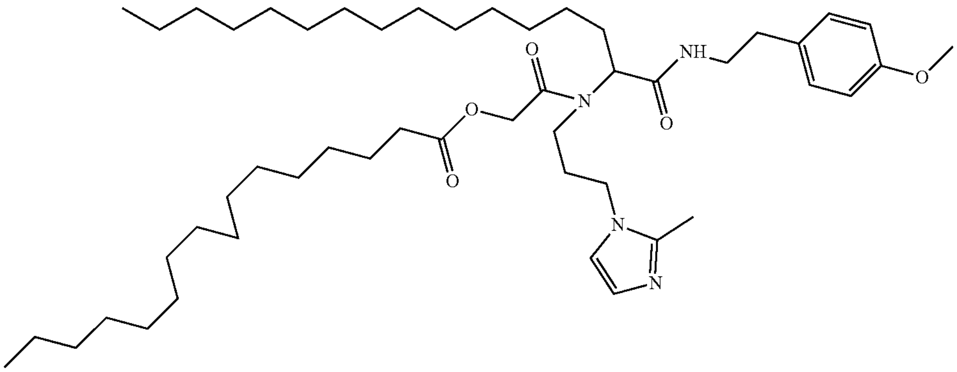

-continued
P462A10
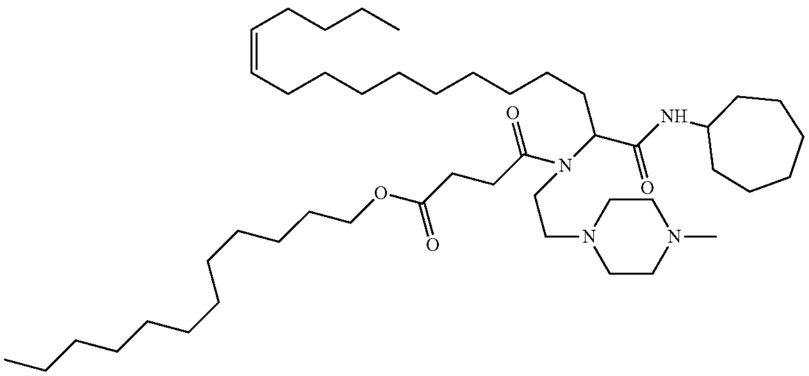
P462A11
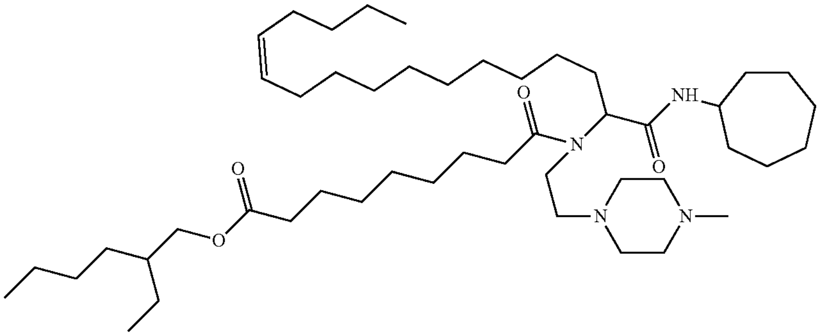
P462A12
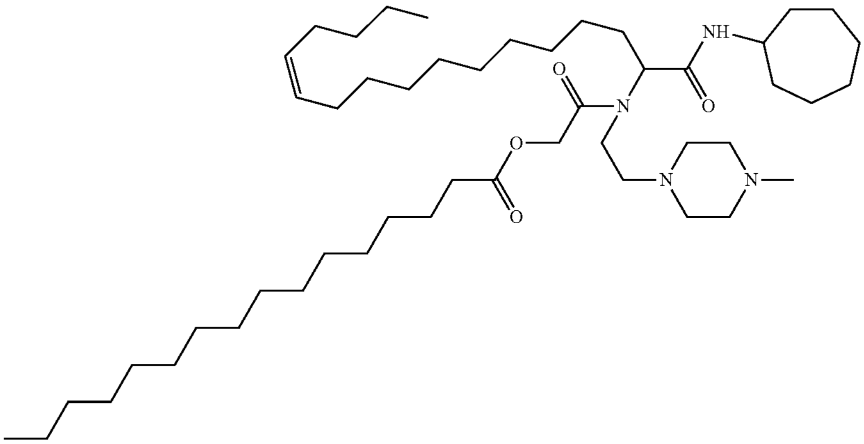
P462C12
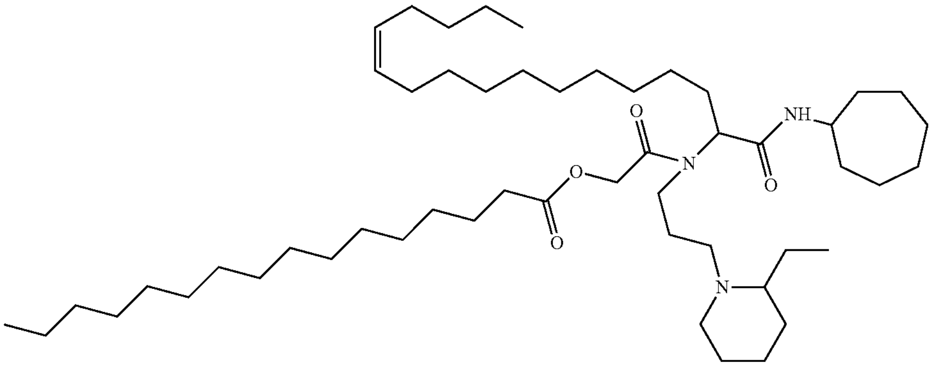

-continued
P462E10
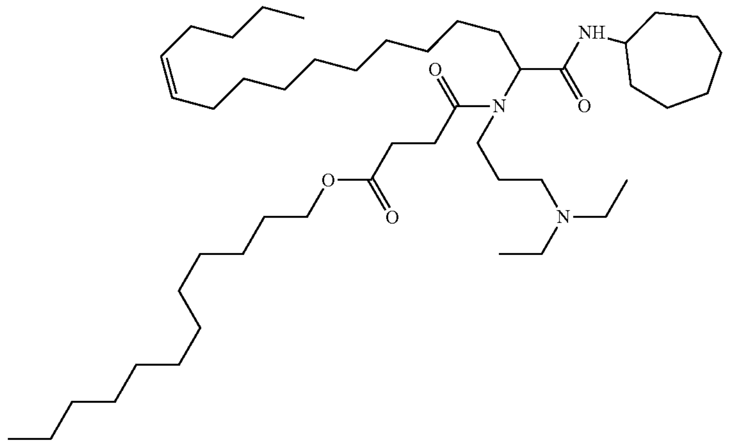
P462E11
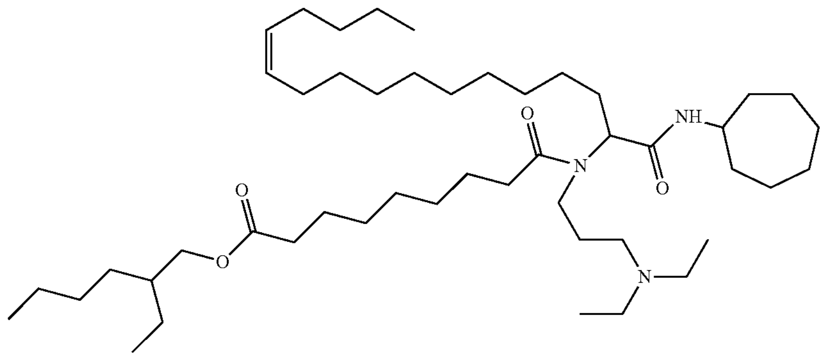
P462E12
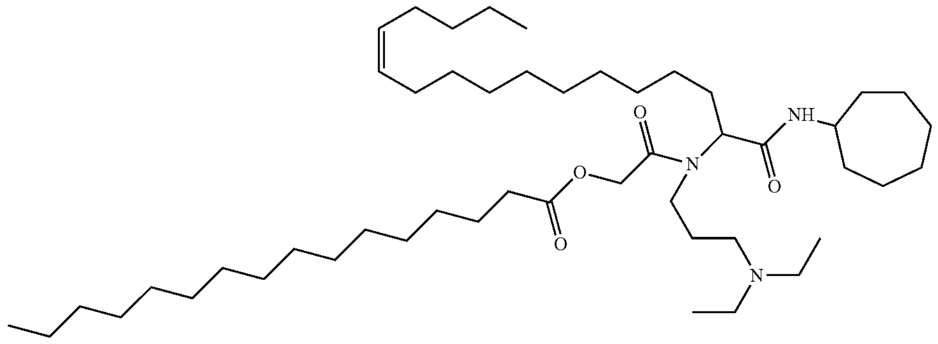
P462F12
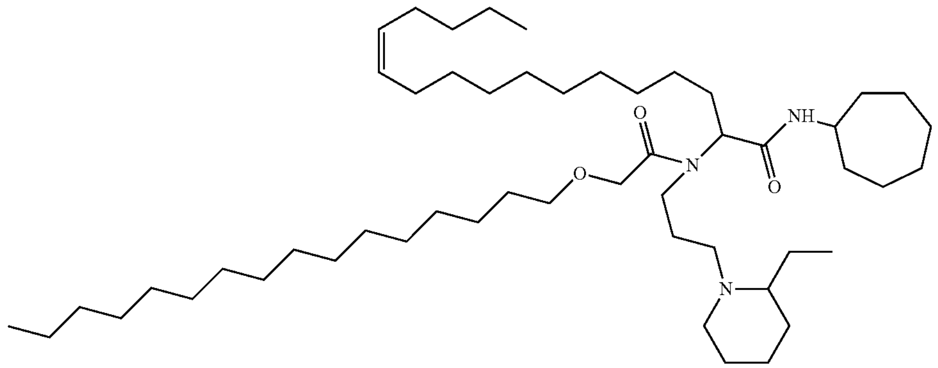

-continued
P462A8
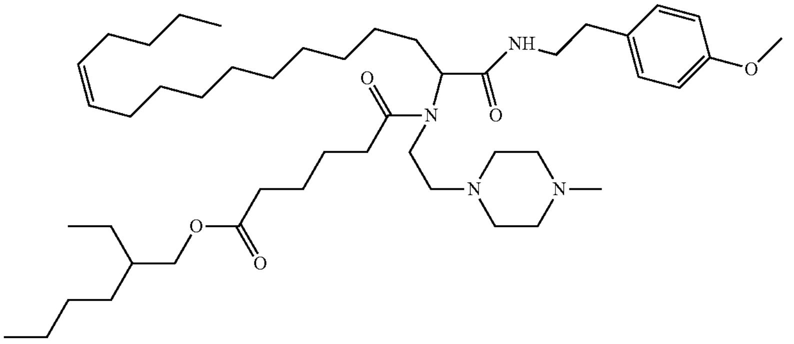
P463A9
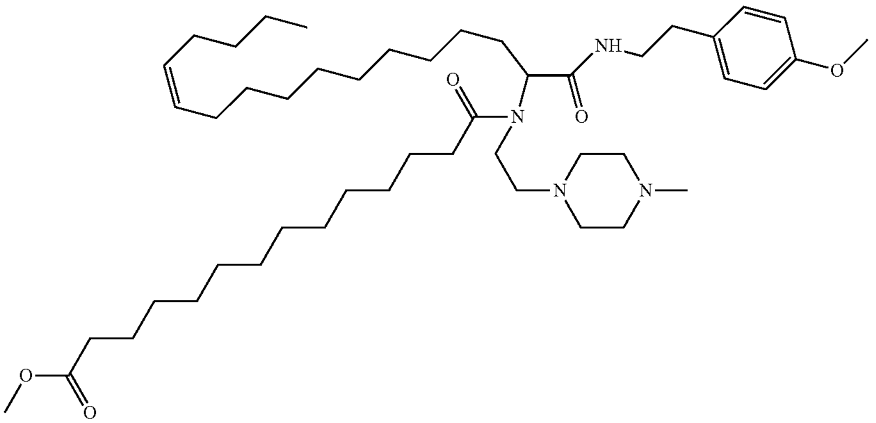
P463A10
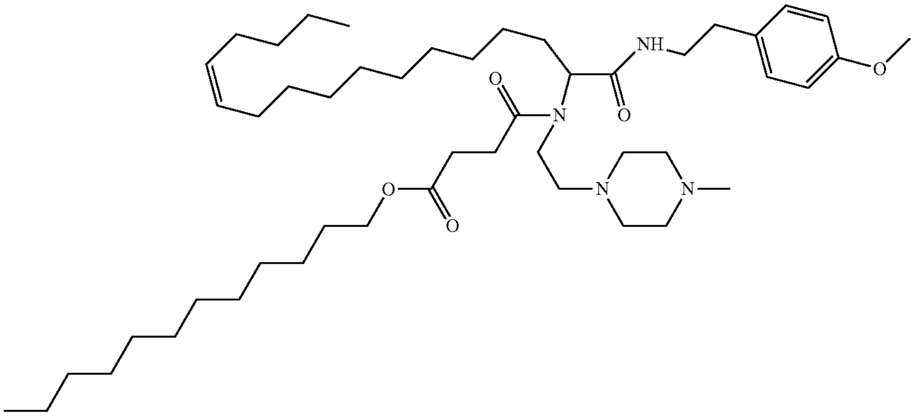
P463A11
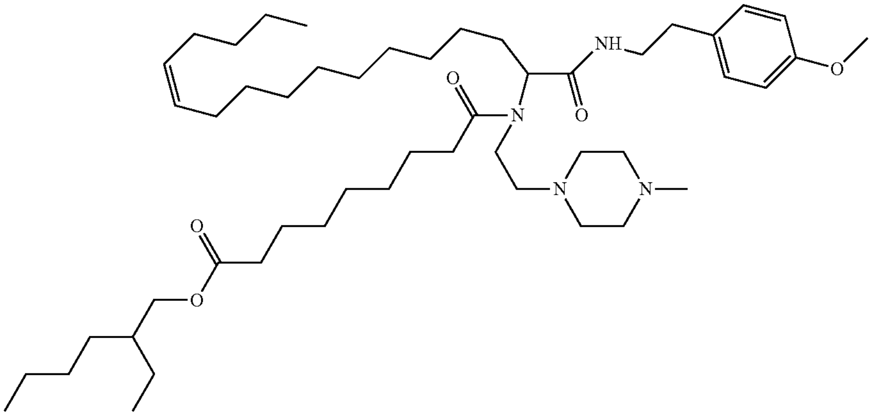

-continued
P463A12
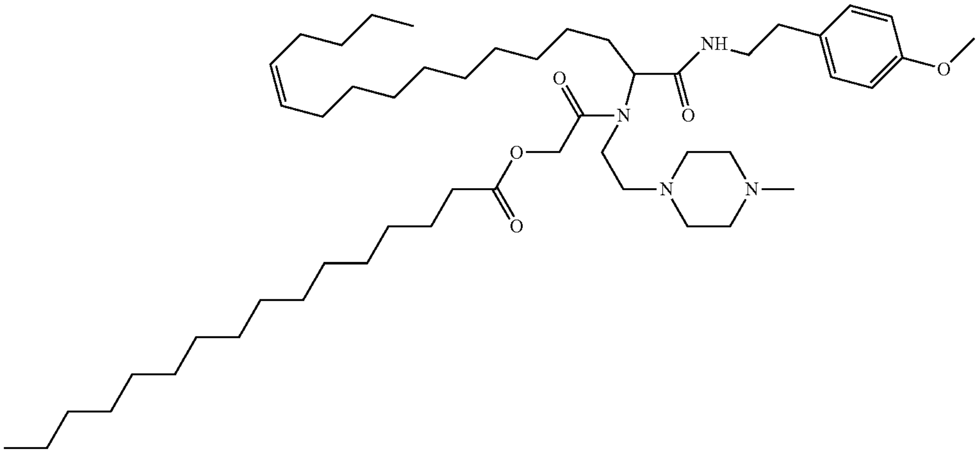
P463B10
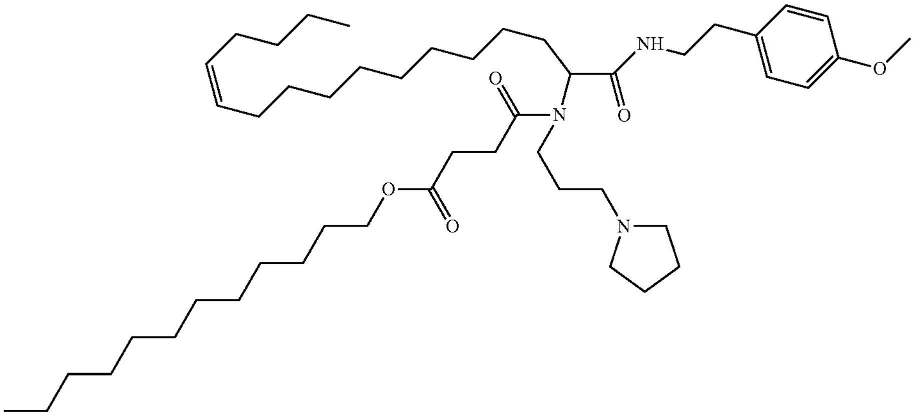
P463D8
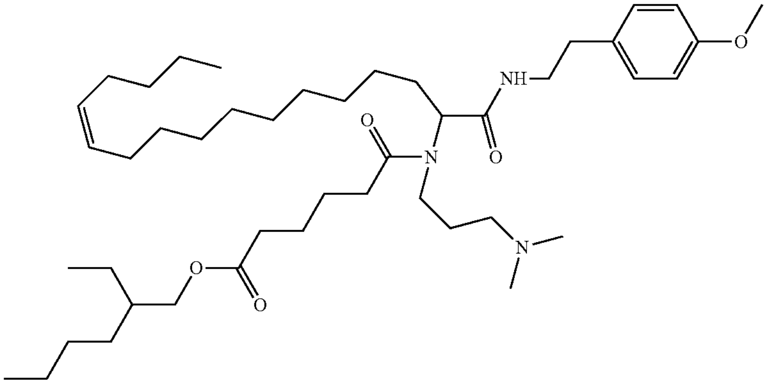

-continued
P463D10
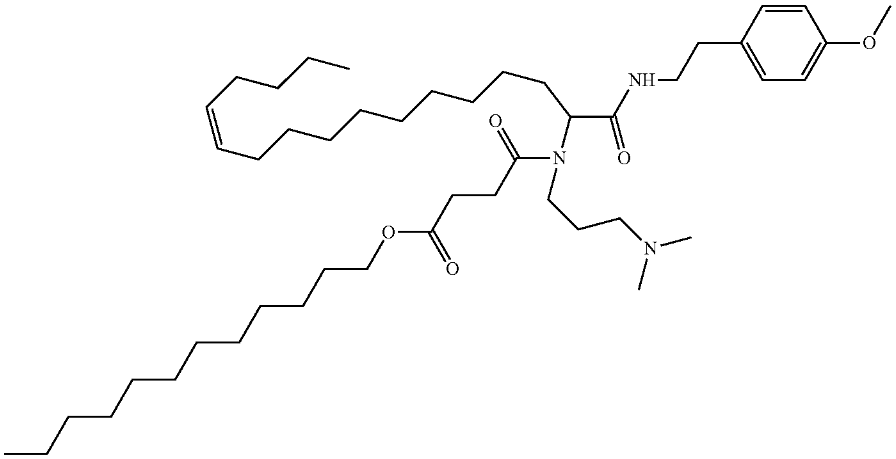
P463D12
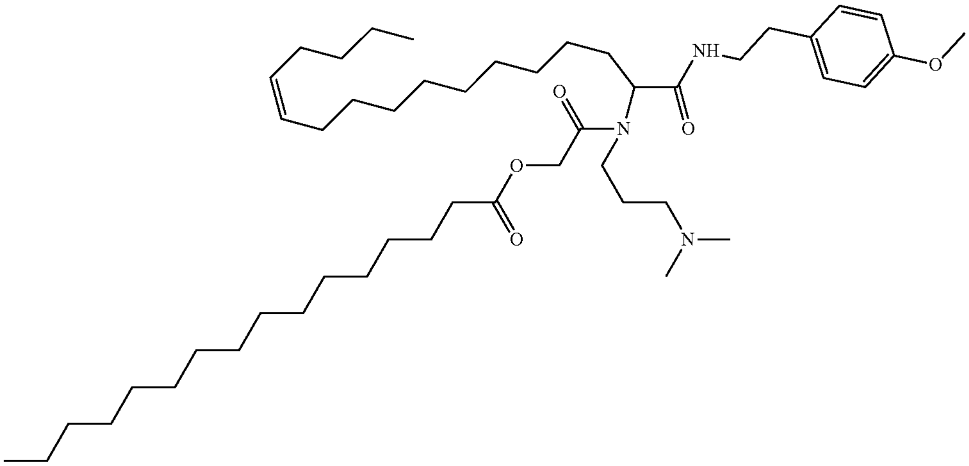
P464A4
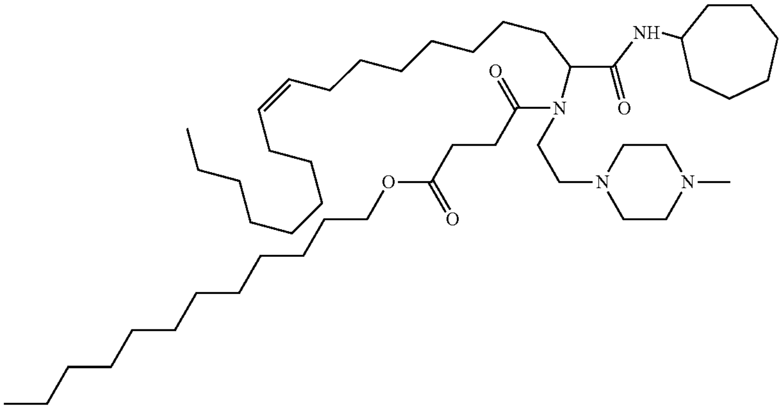

-continued
P464A5
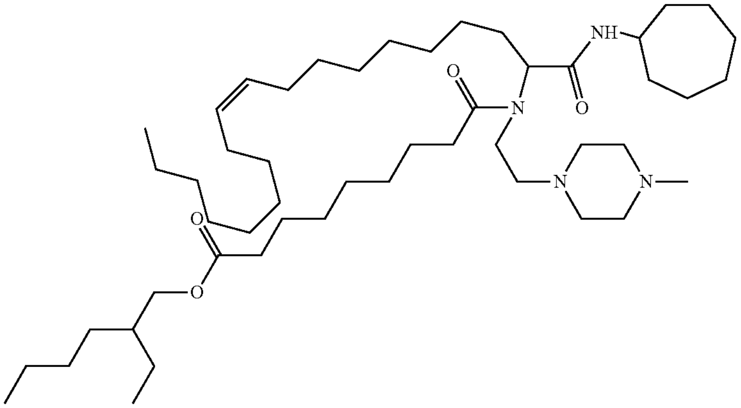
P464B6
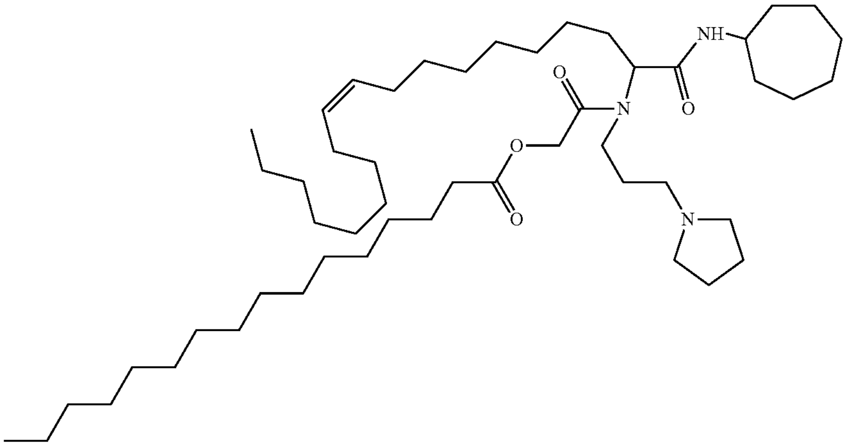
P464D6
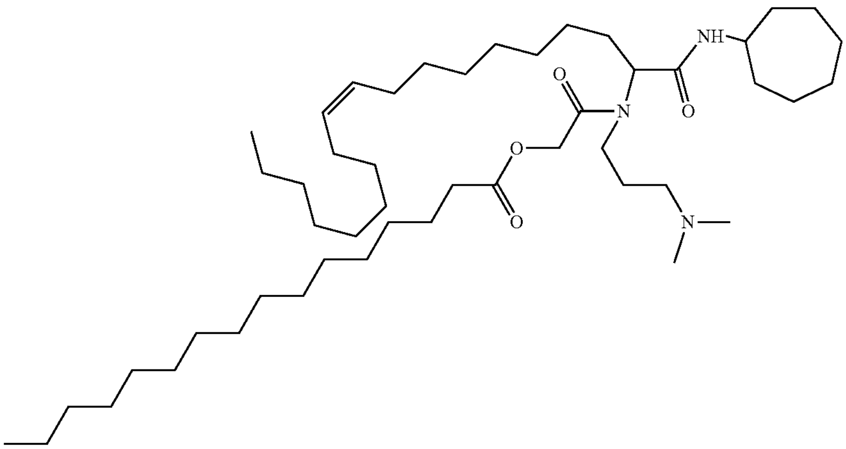

-continued
P464E6
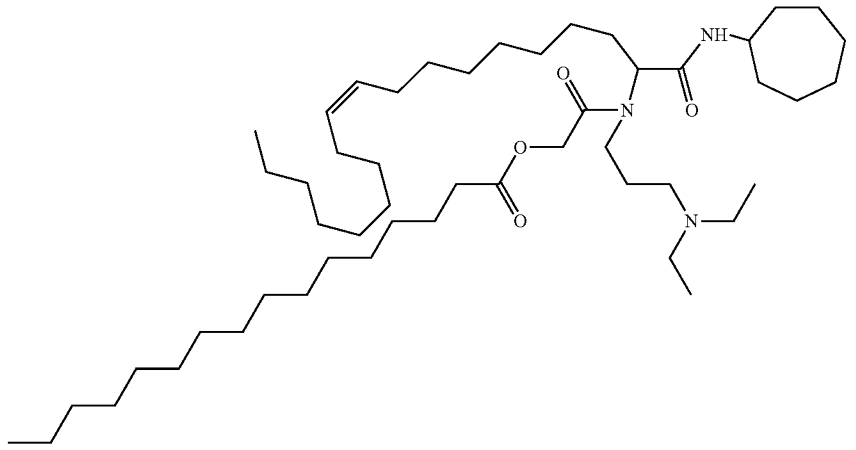
P465A2
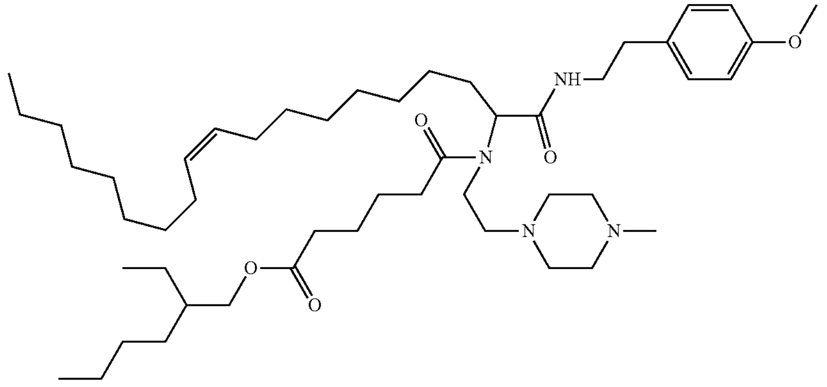
P465A5
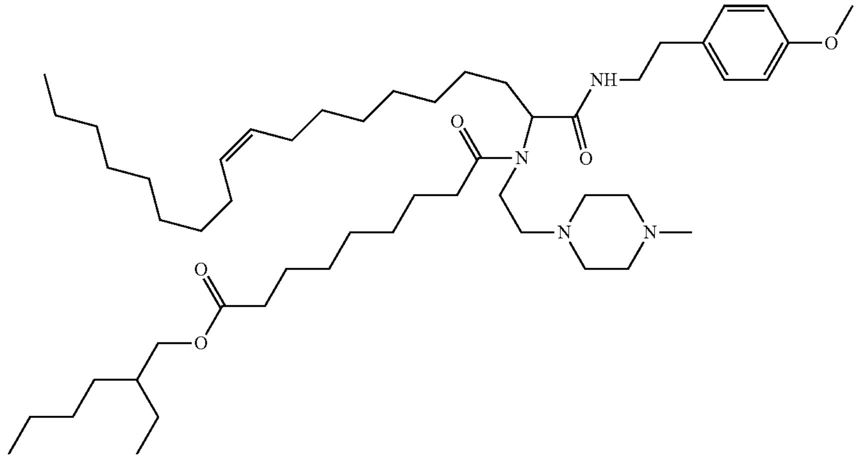

-continued
P465A6
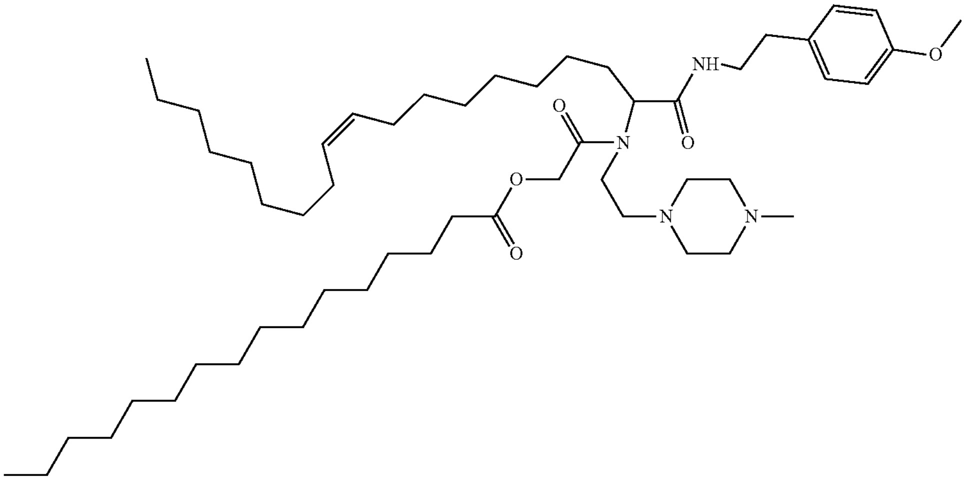
P465B4
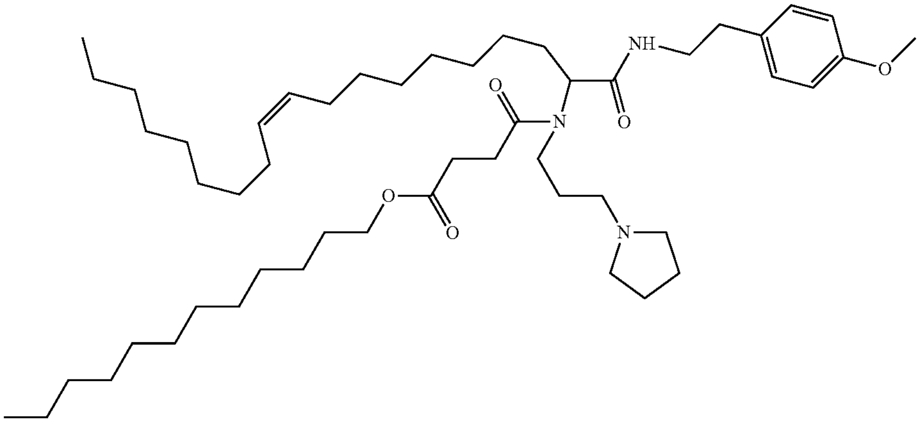
P465B10
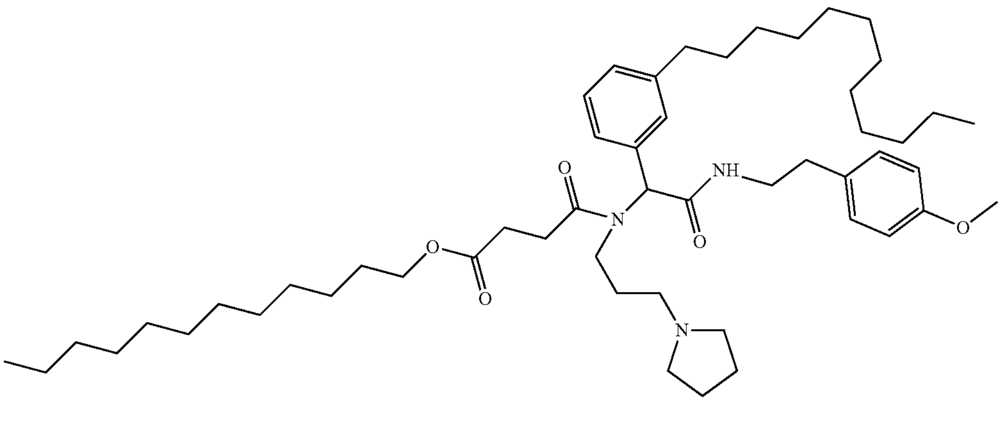

-continued
P465B12
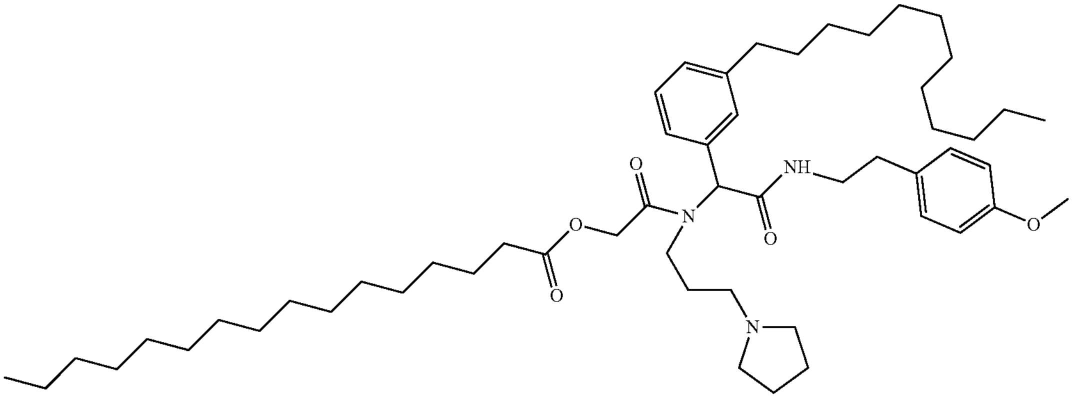
P465D10
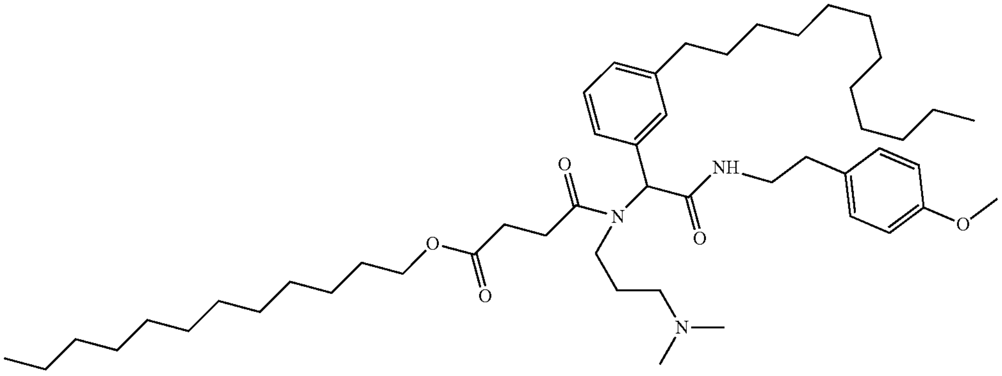
P470D7
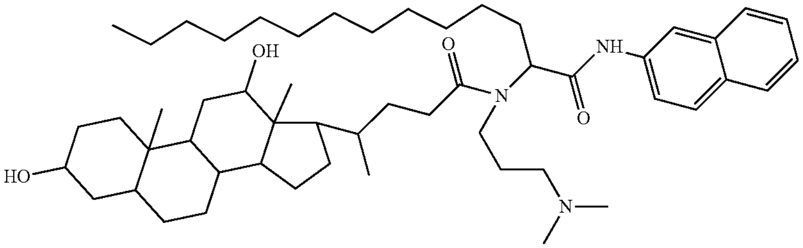
P500D6
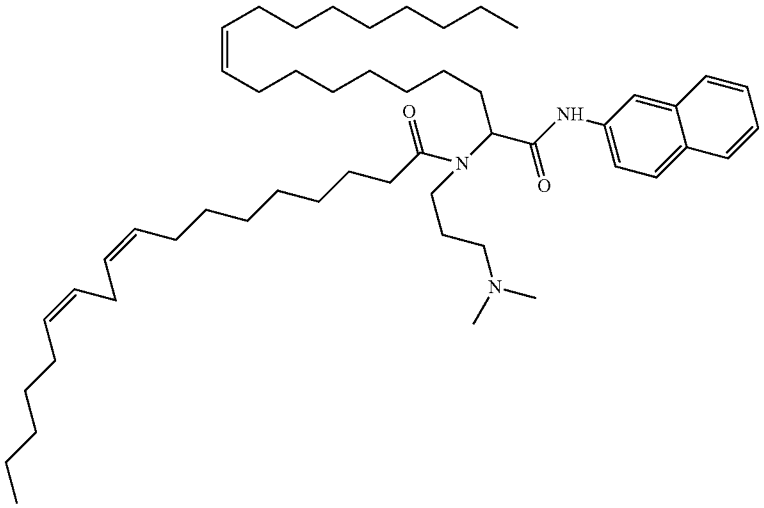

-continued
P56A7
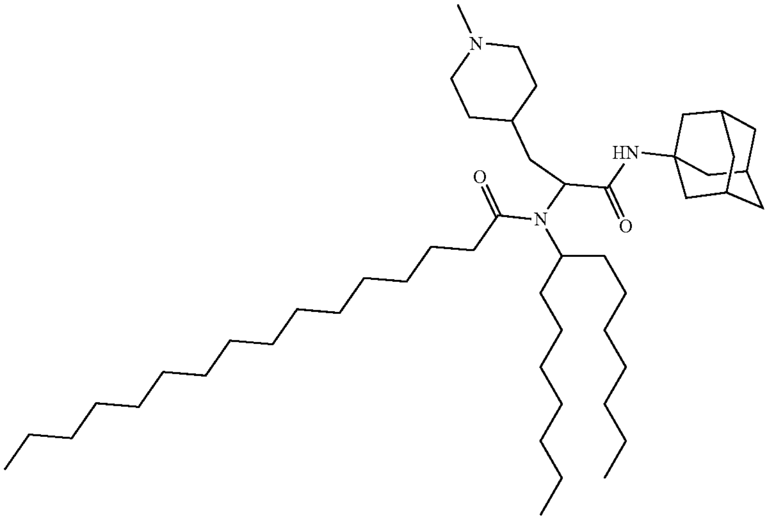
P319C8
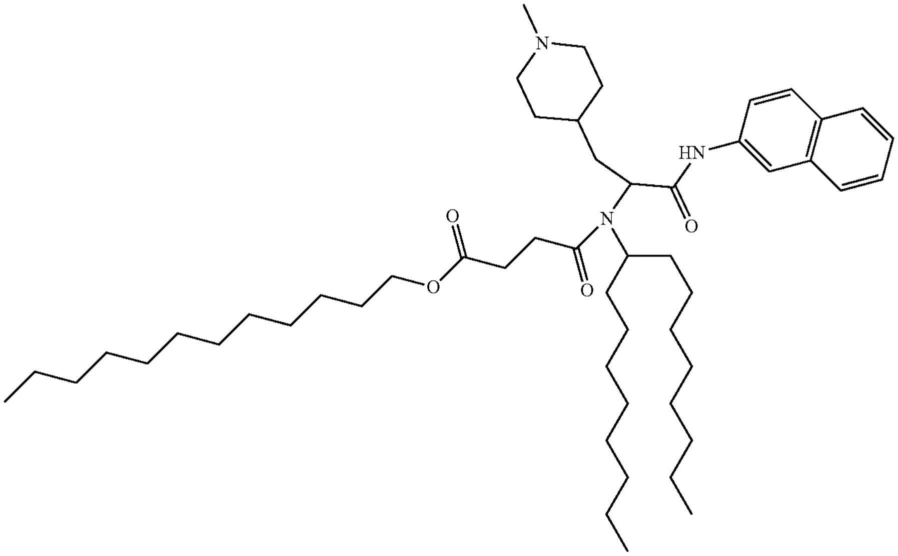
P363E8
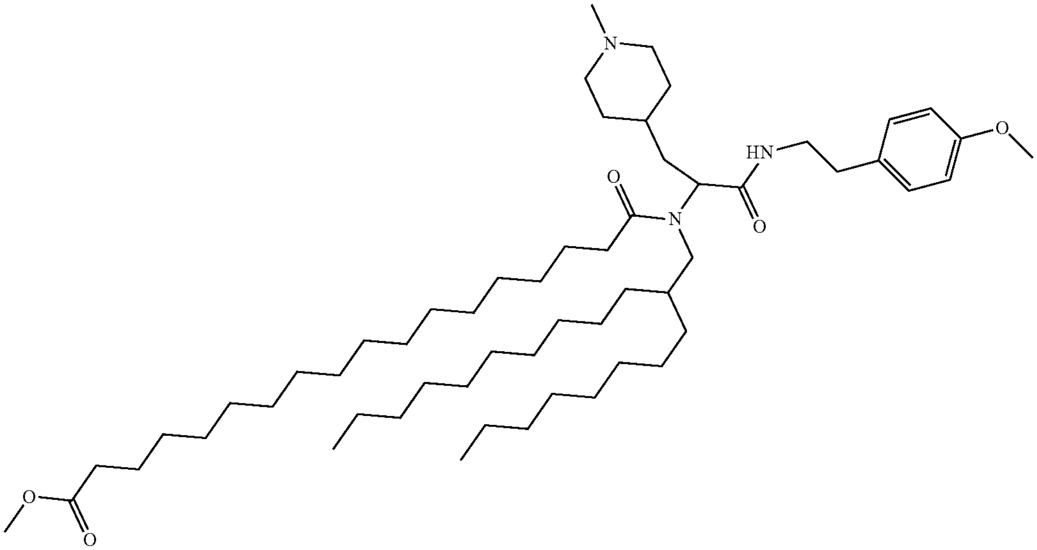

-continued
P56B9
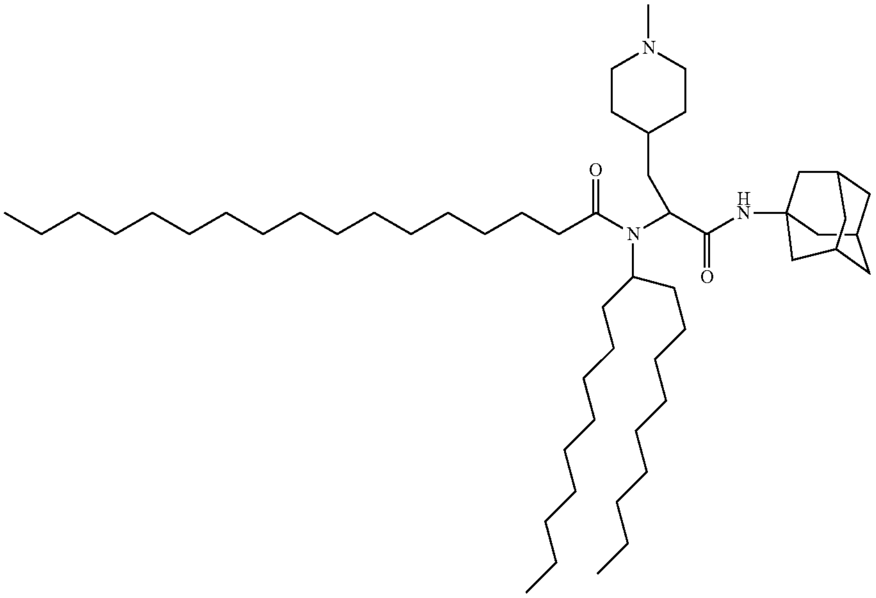
P313B7
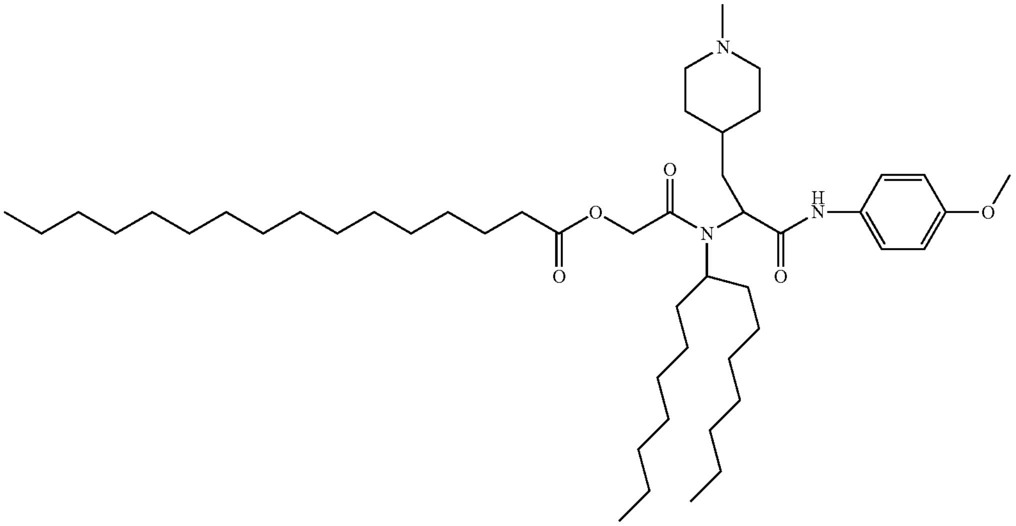
P287A12
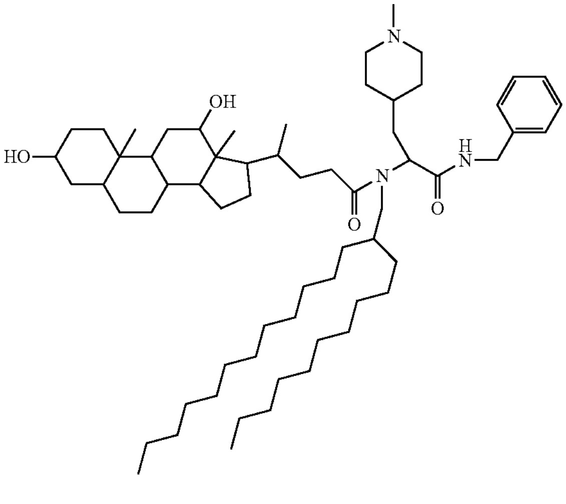
P287C12
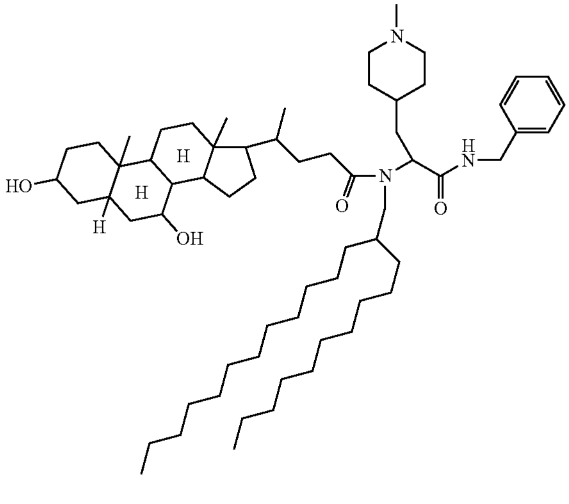

-continued
P161F12
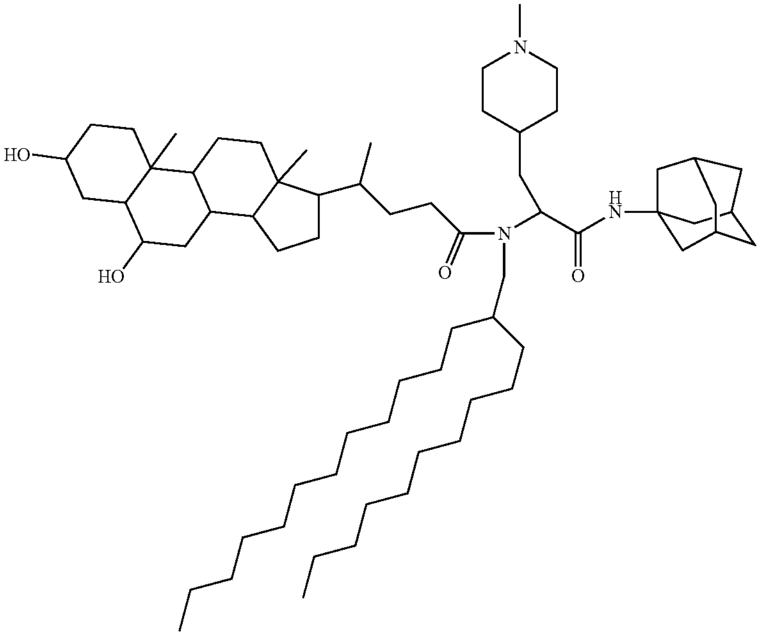
P331E4
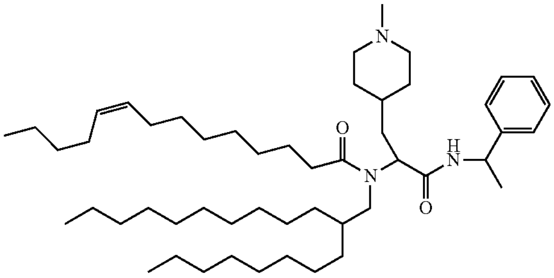
P149A1
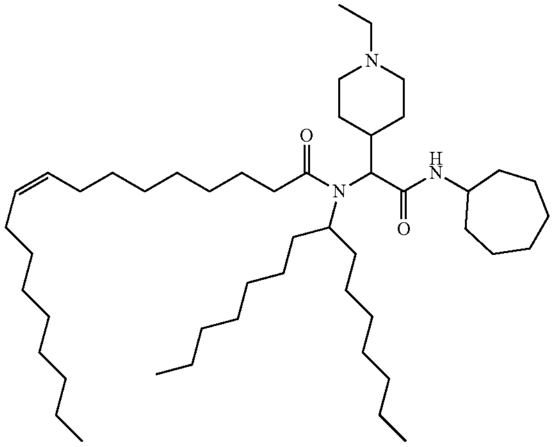
P149A3
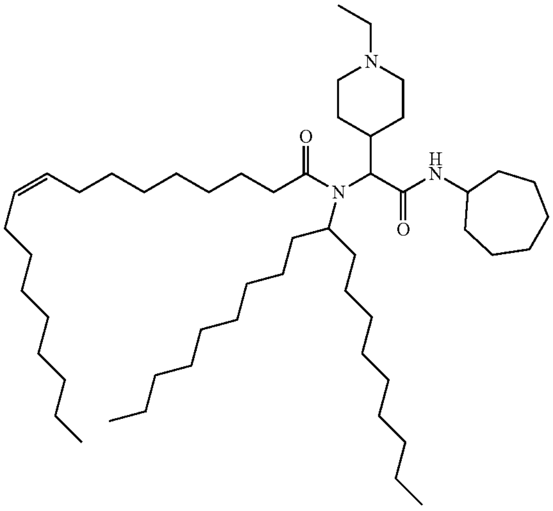
P149C1
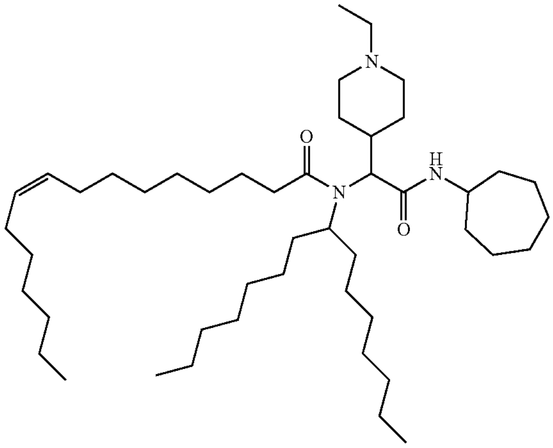

-continued
P149C2
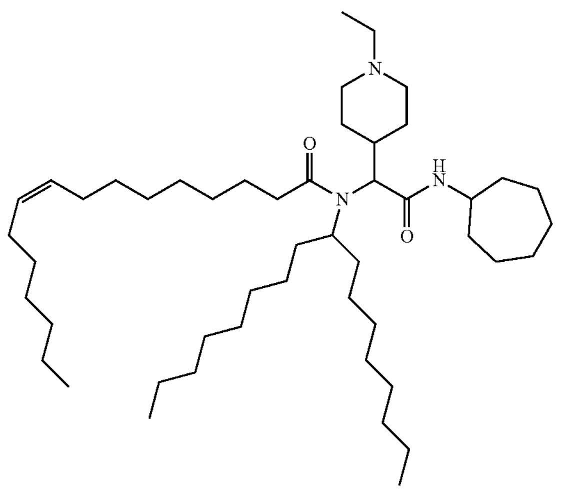
P149C3
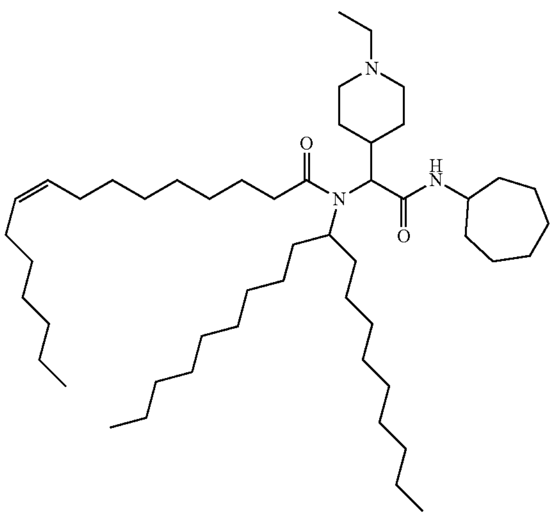
P313B6
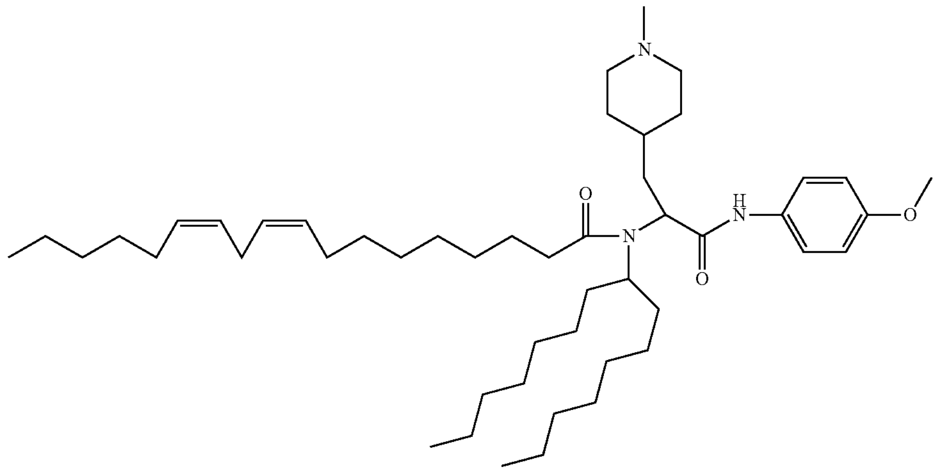
P319B6
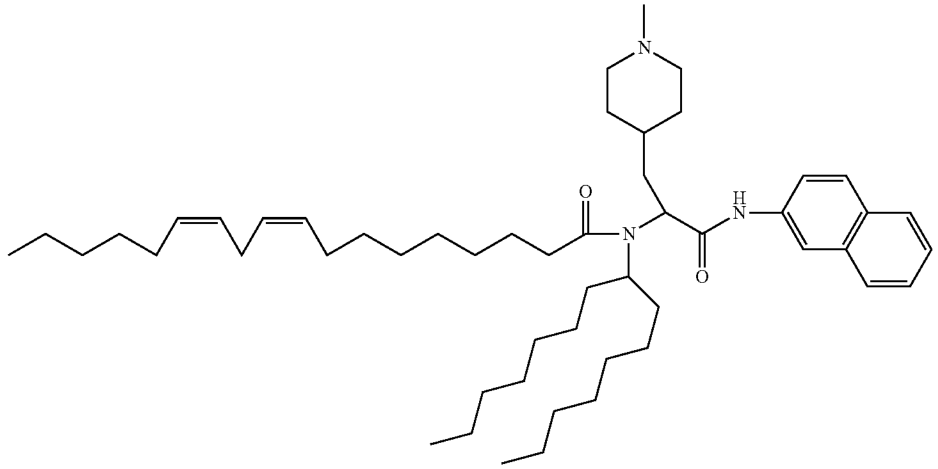

-continued
P343E5
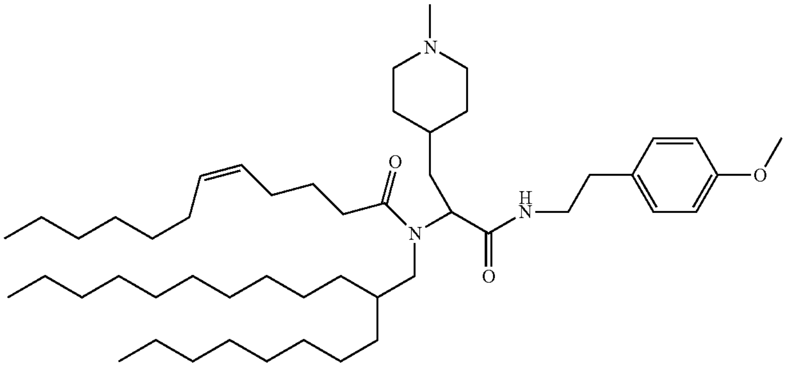
P343B1
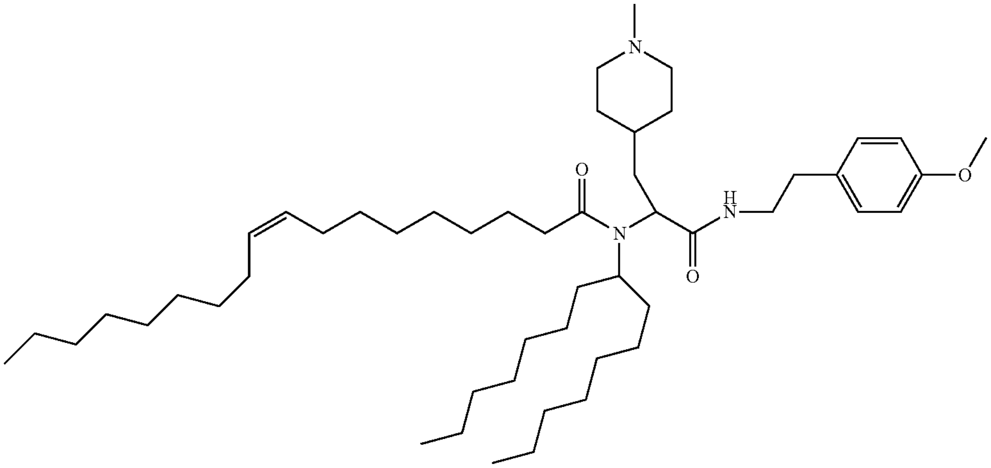
P363E10
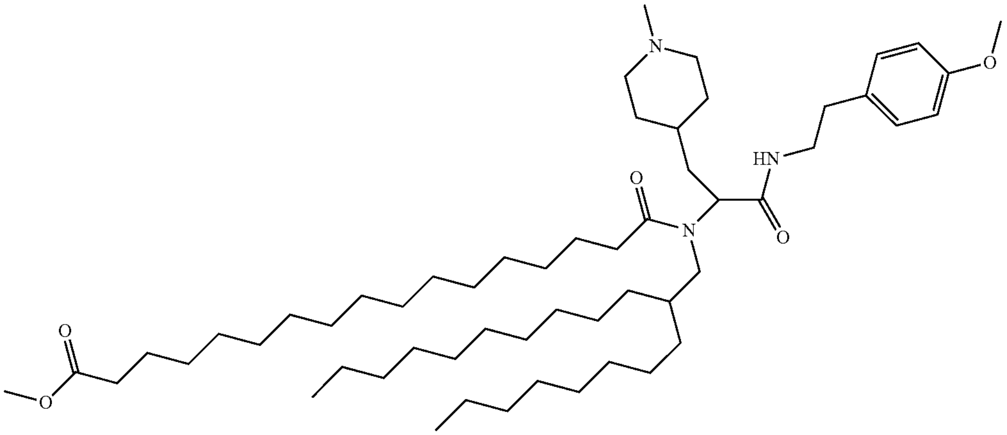

-continued
P341A10
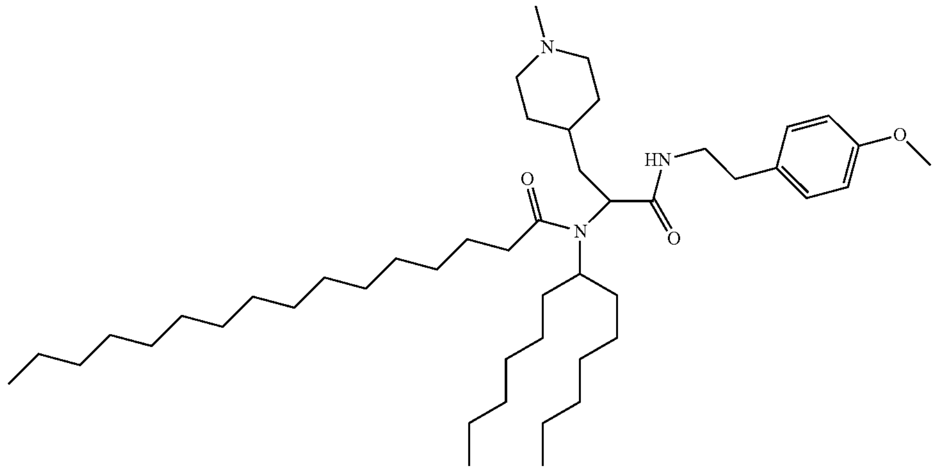
P363B8
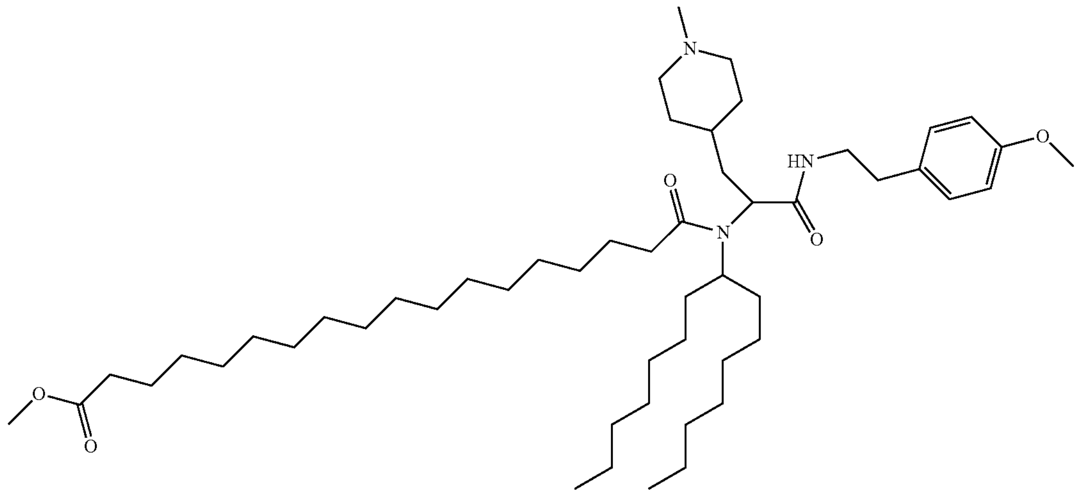
P343B6
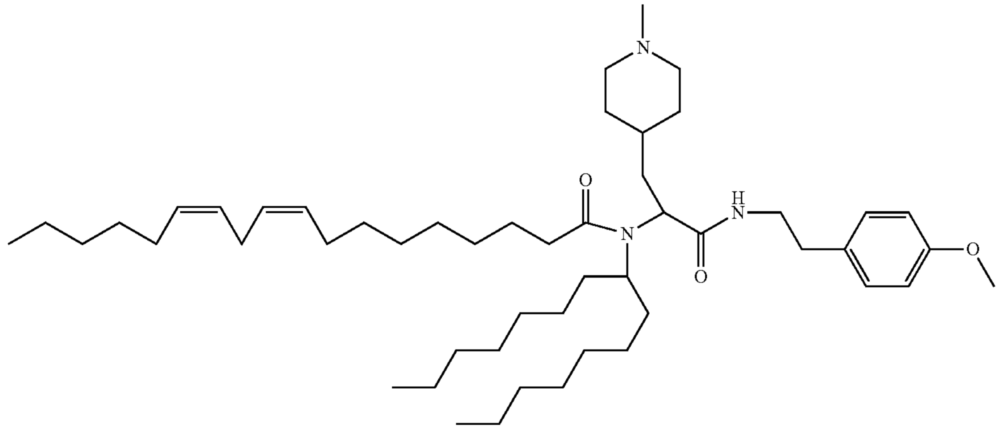

-continued
P343B8
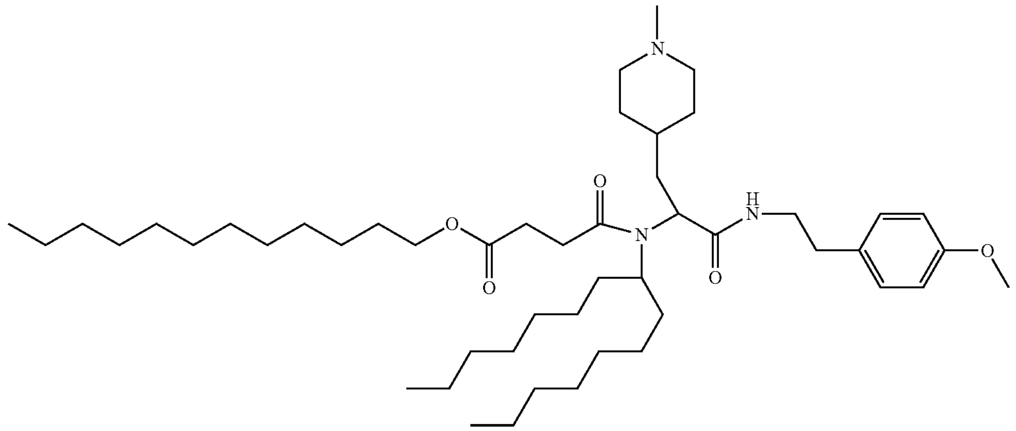
P153C1
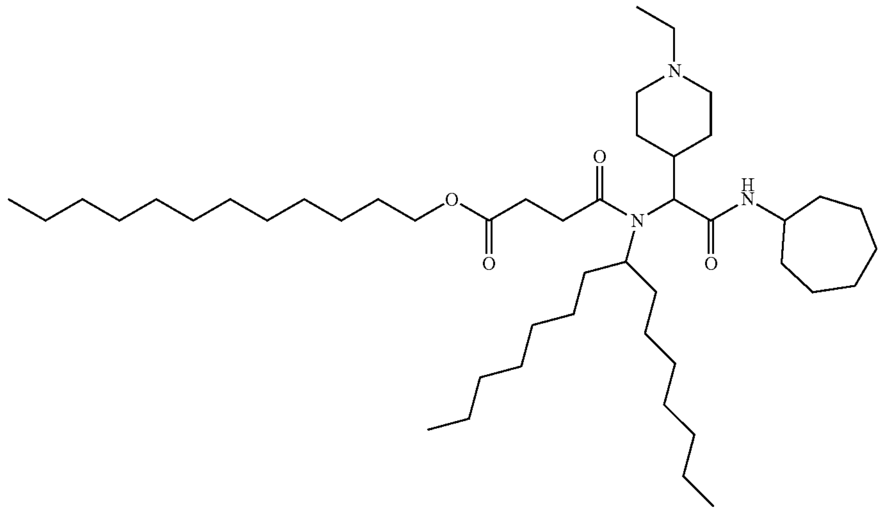
P153C2
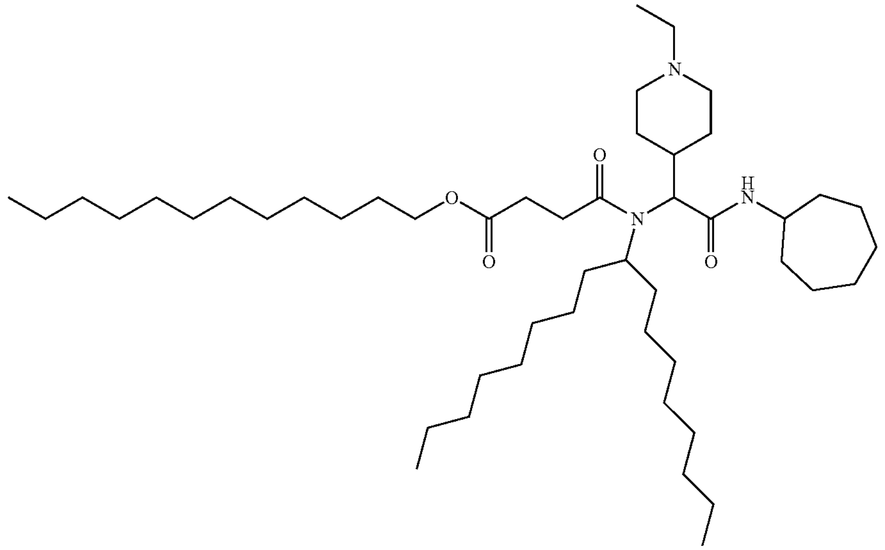

-continued
P153C3
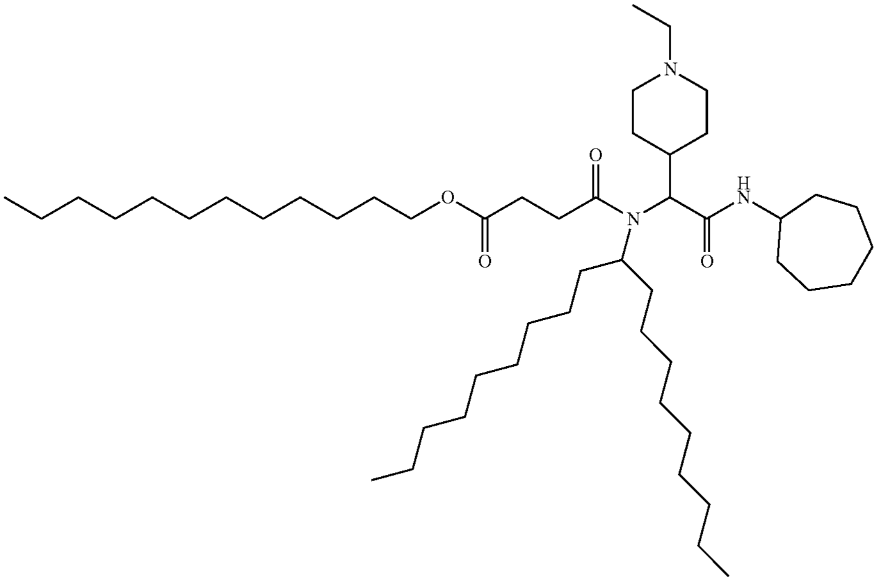
P153C5
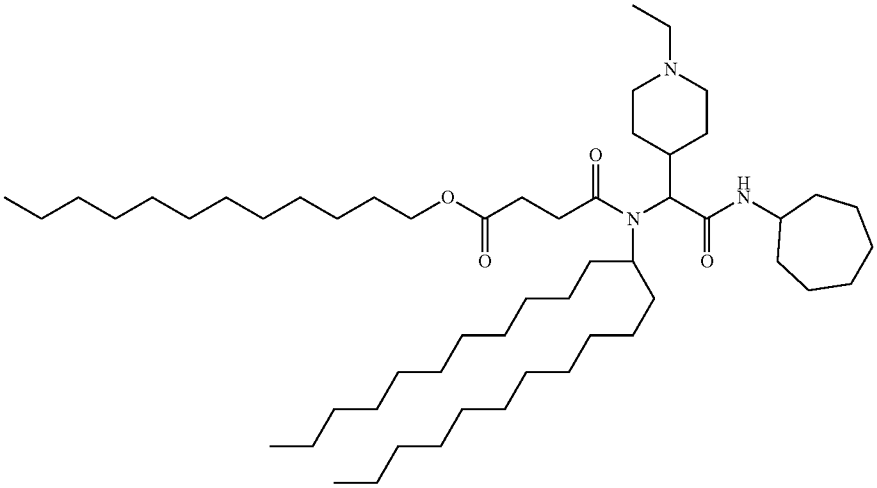
P56B2
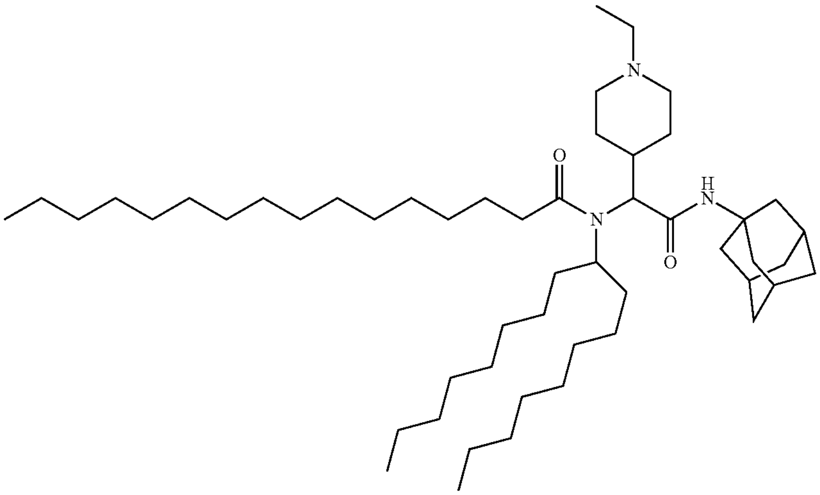

-continued
P56A3
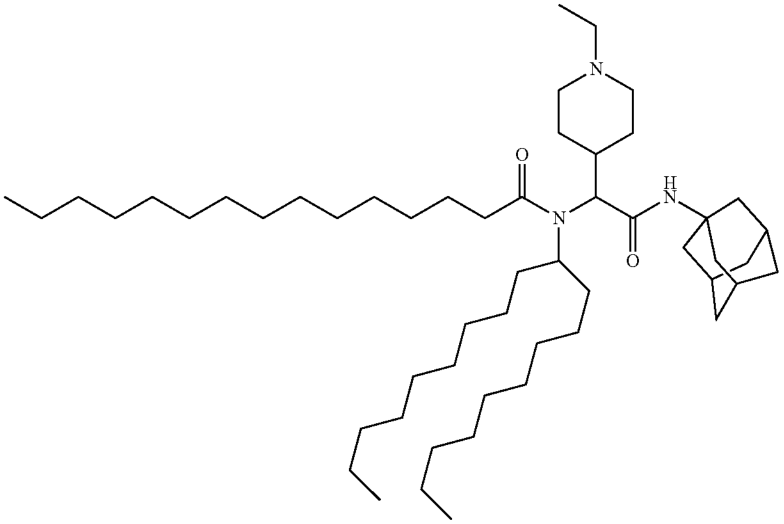
P56B3
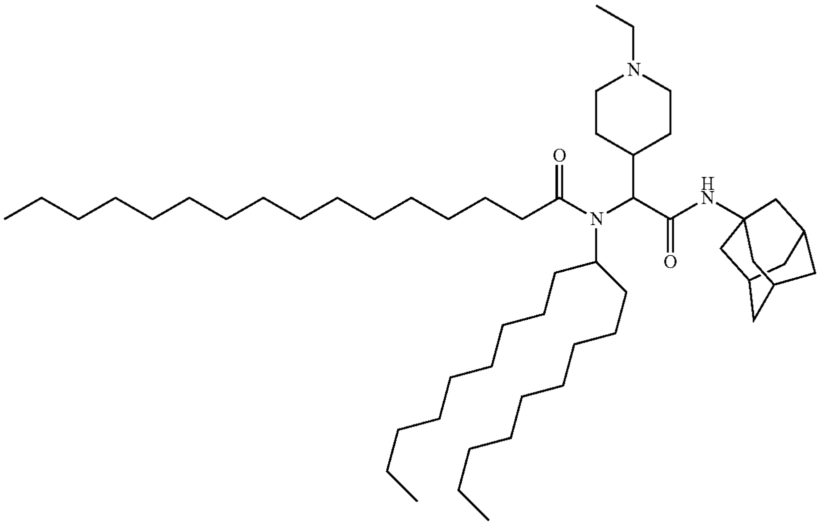
P56B7
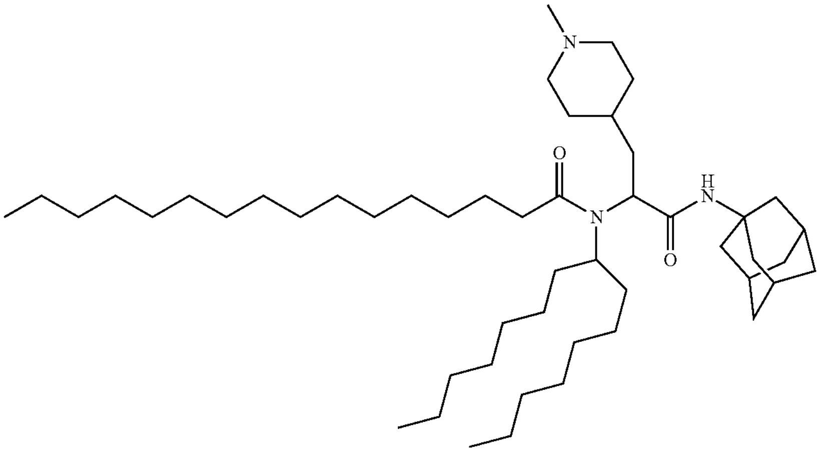

-continued
P56A8
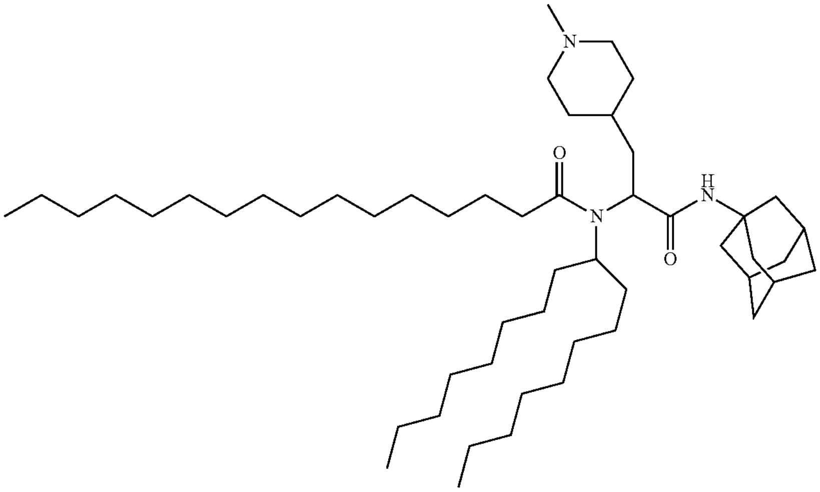
P56B6
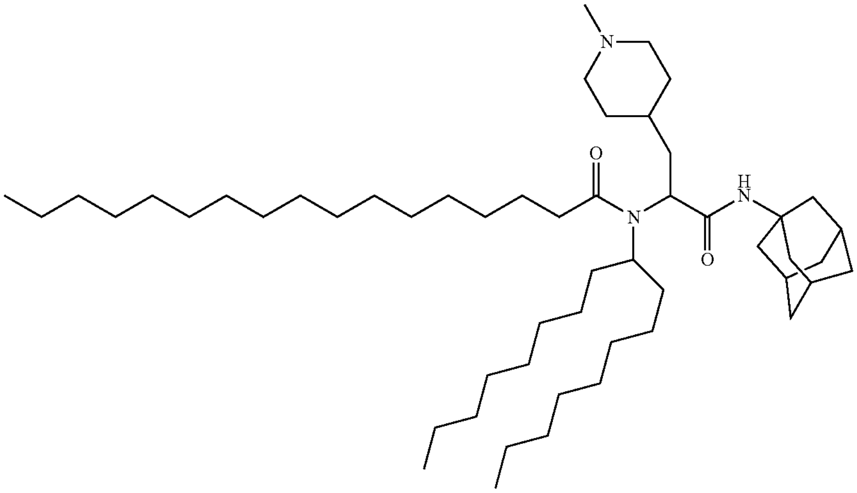
P56A9
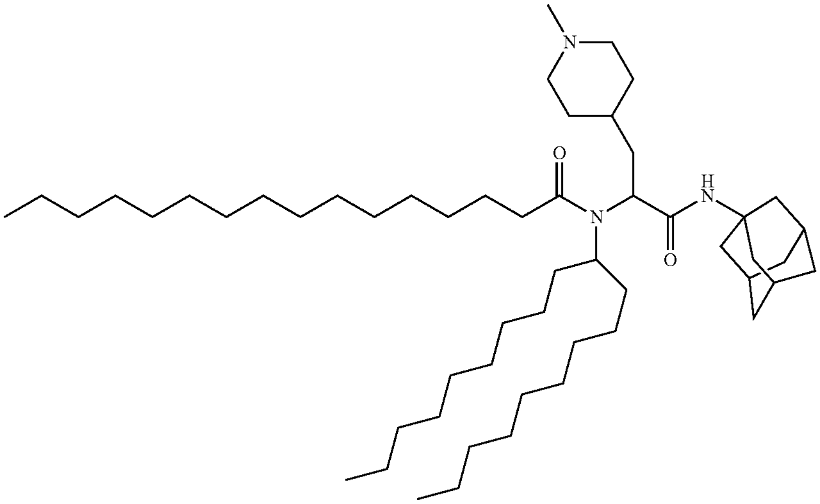

-continued
P55A6
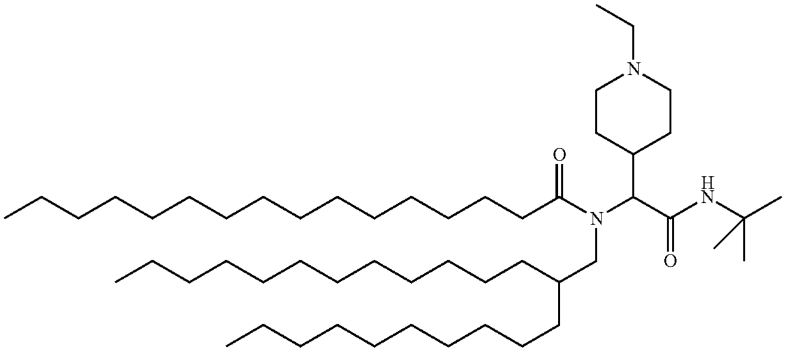
P55C12
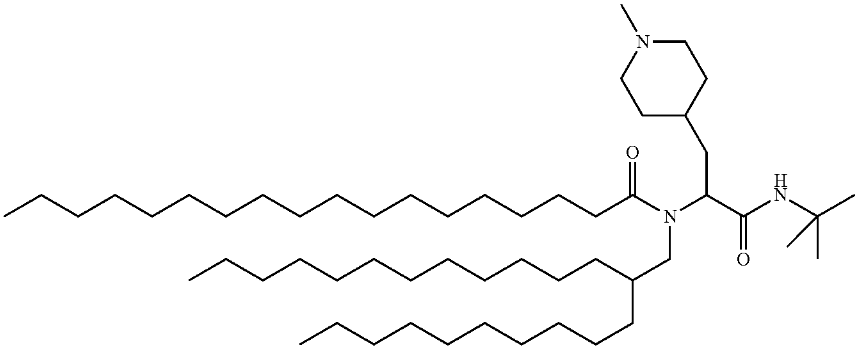
P343B6
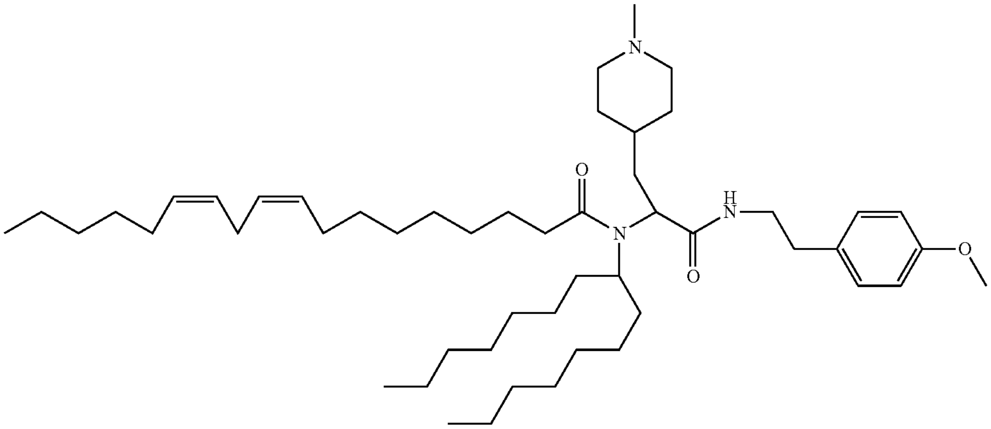
P343B8
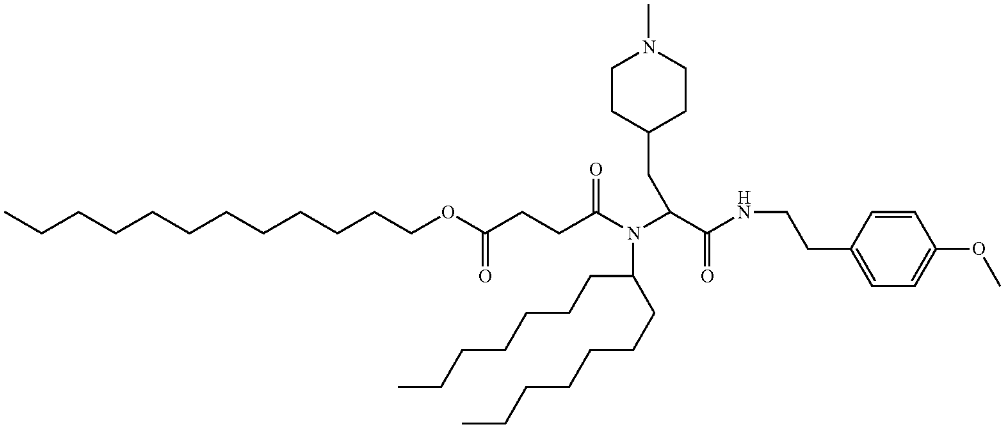

-continued
P153C1
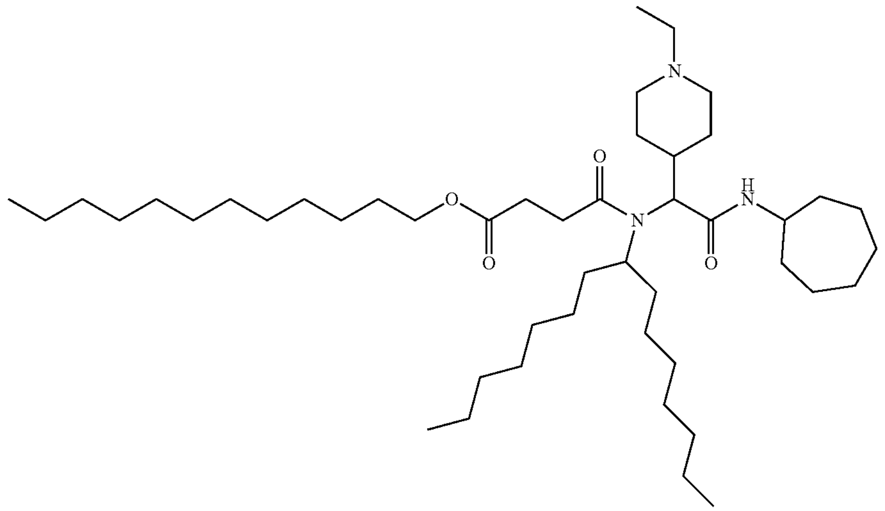
P153C2
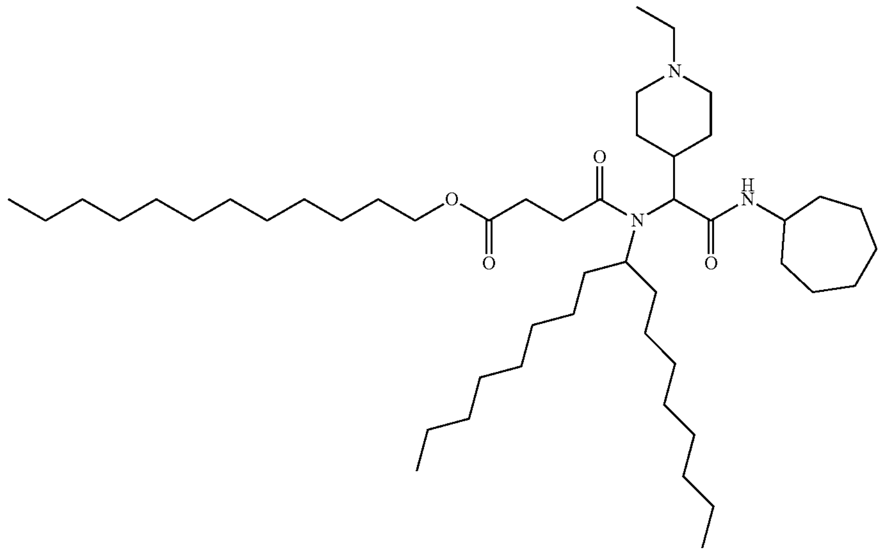
P153C3
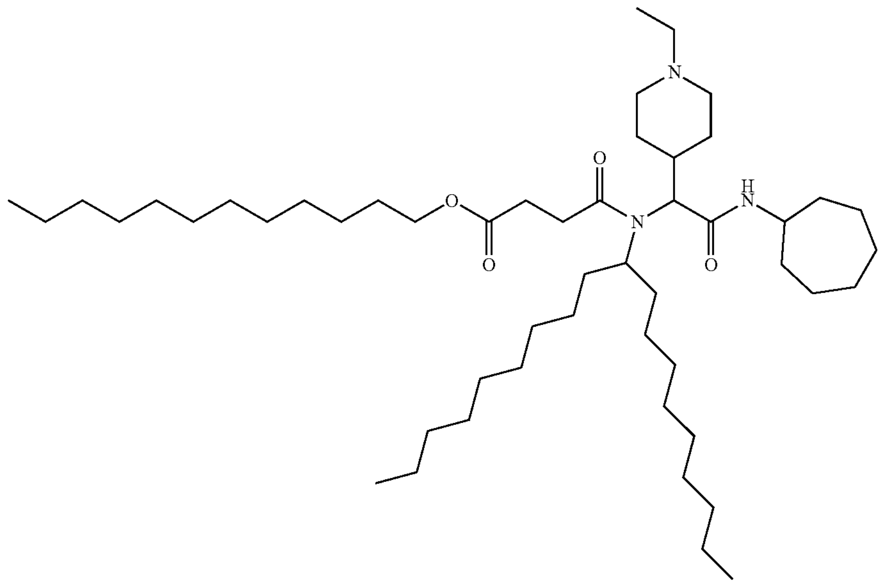

-continued
P153C5
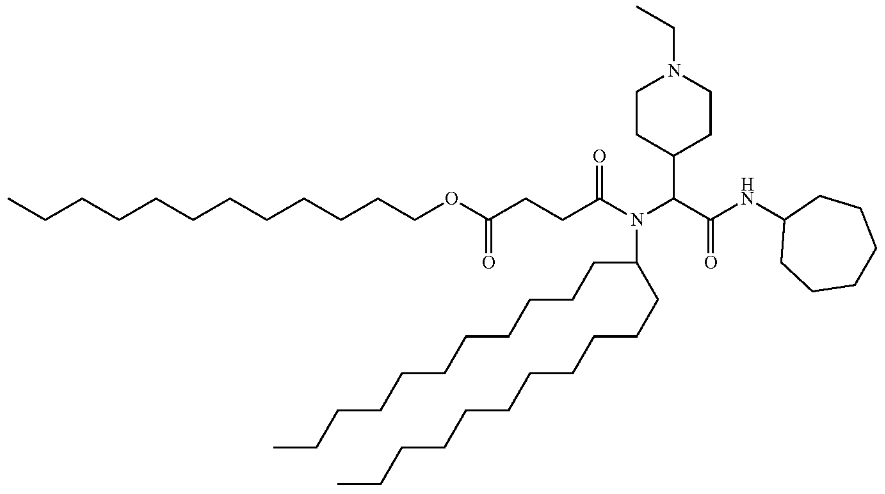
P56B2
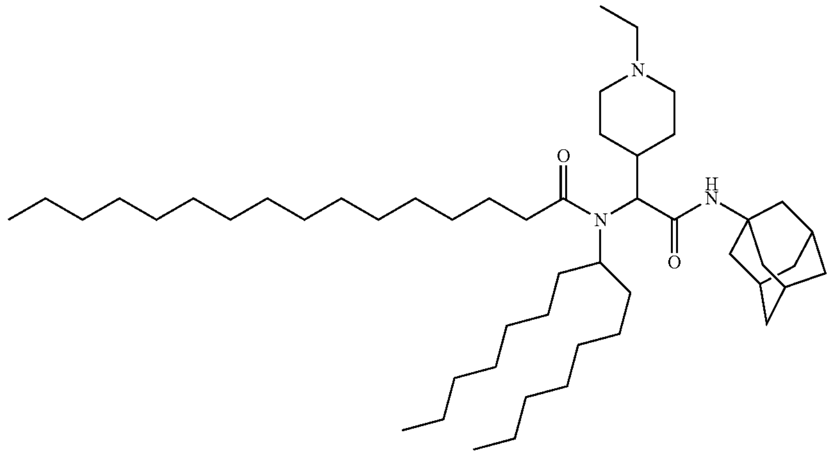
P56A3
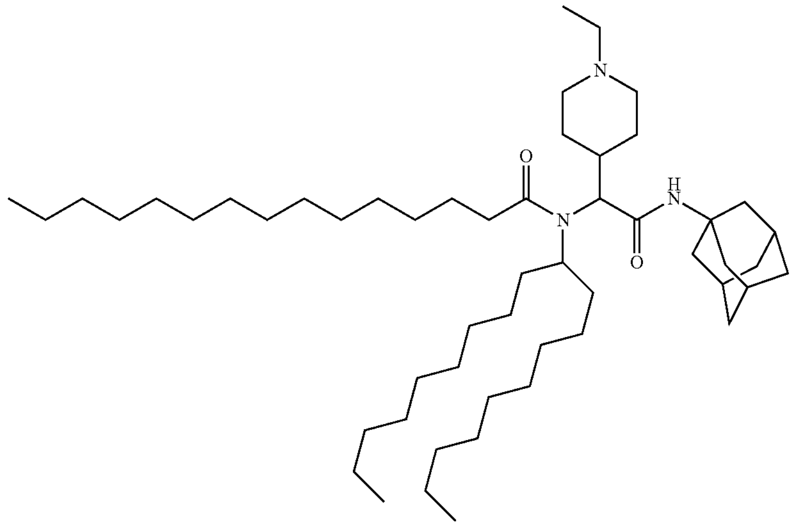

-continued
P56B3
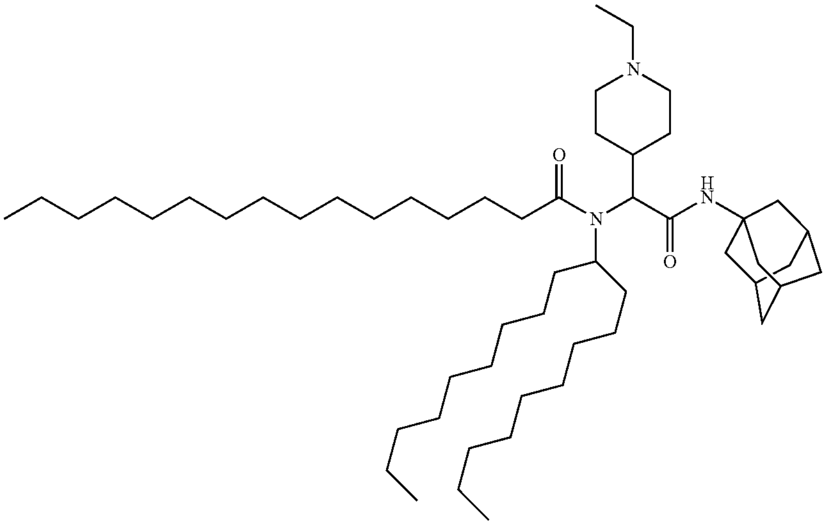
P56B7
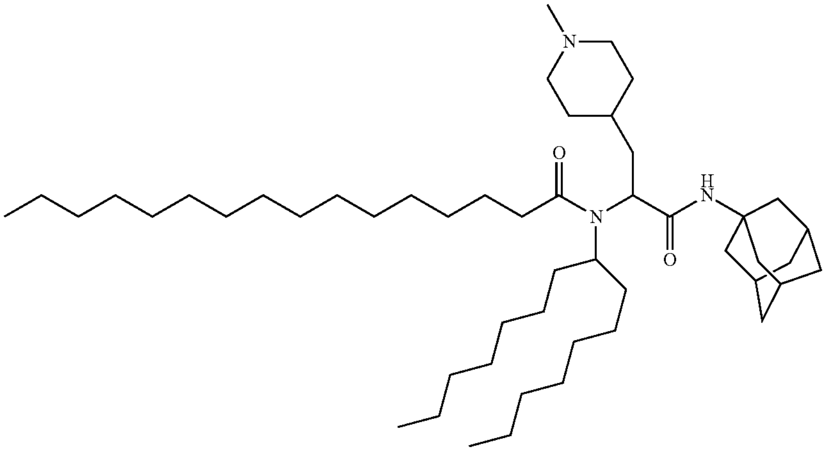
P56A8
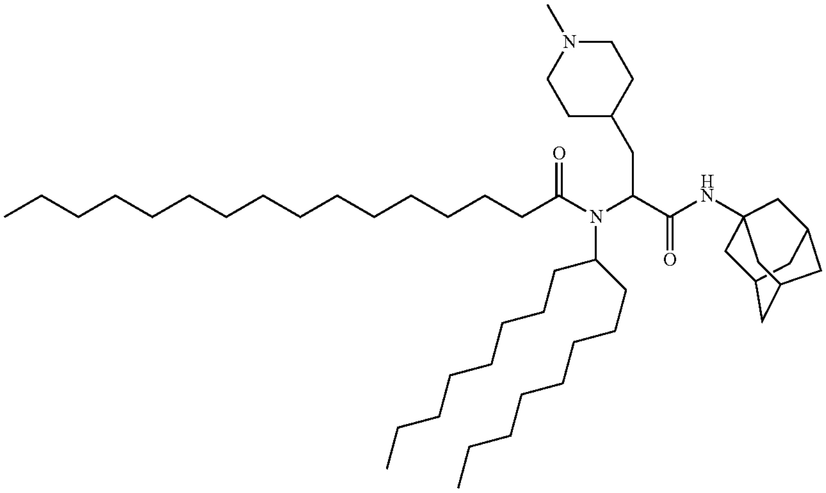

-continued
P56B8
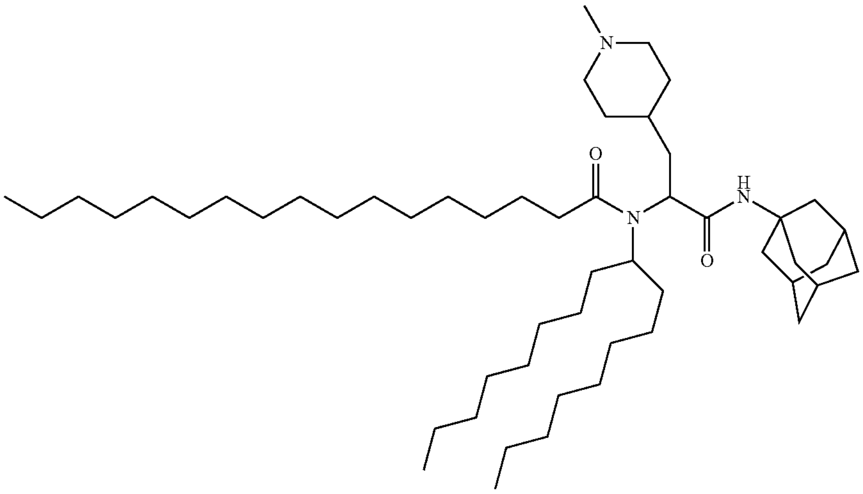
P56A9
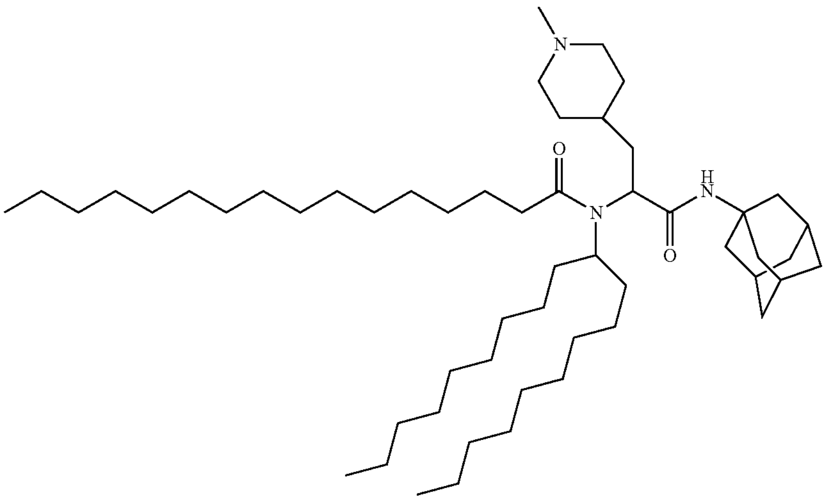
P55A6
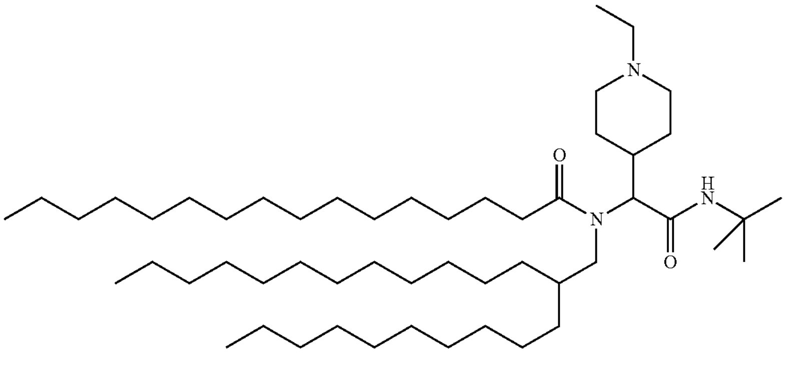

-continued
P55C12
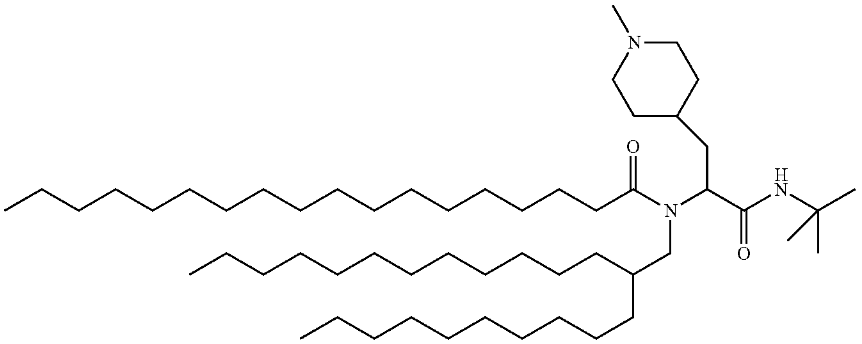
P54B6
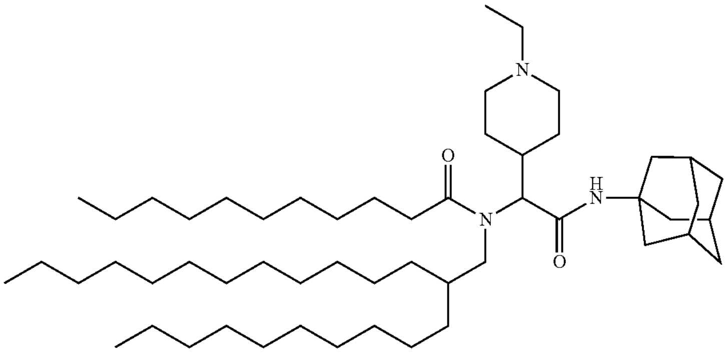
P54D6
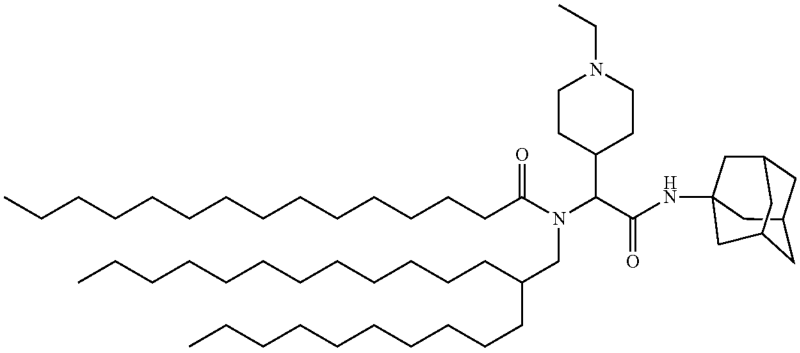
P54A10
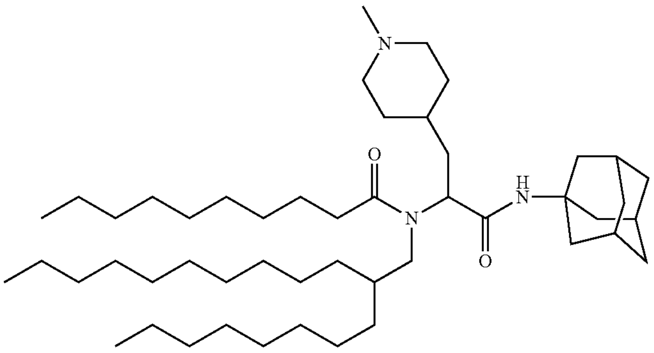

-continued
P54A12
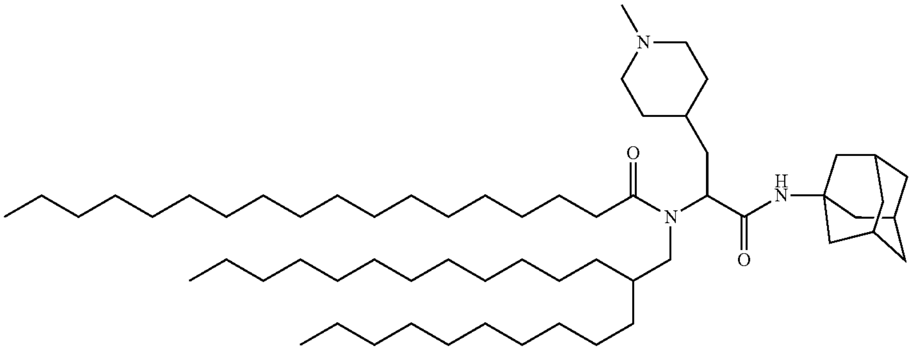
P53A5
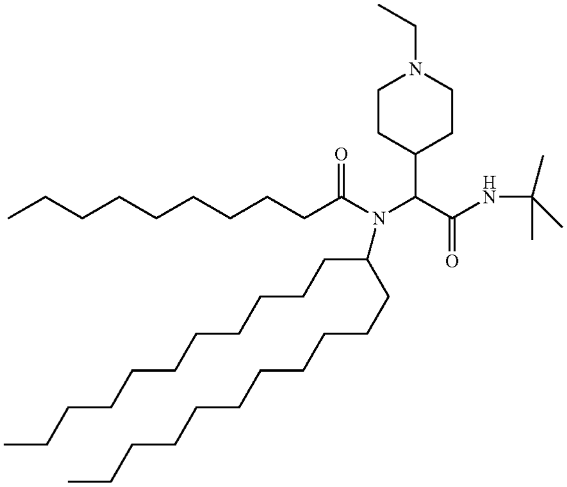
P53G11
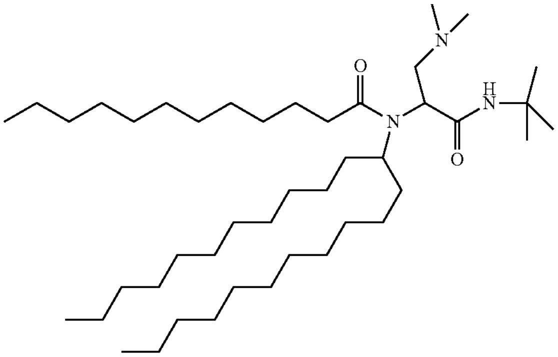
P53A12
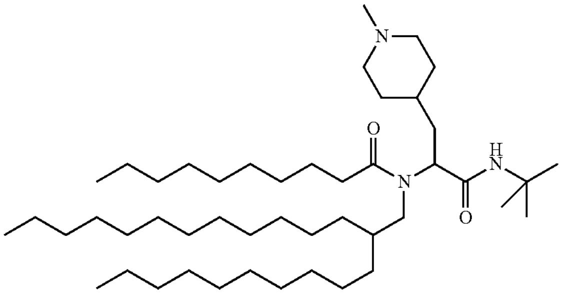
P53E12
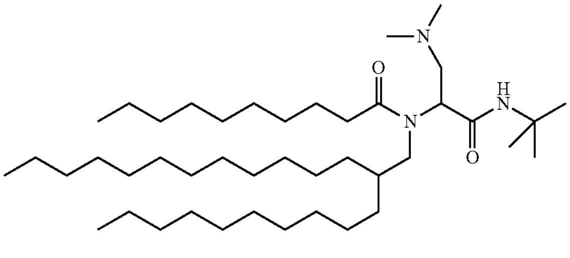
P52B5
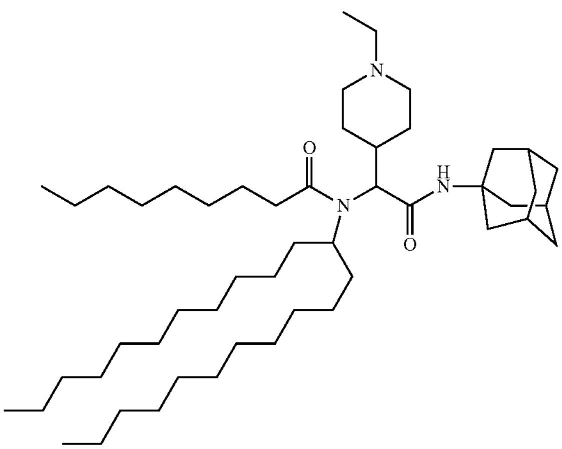
P52B6
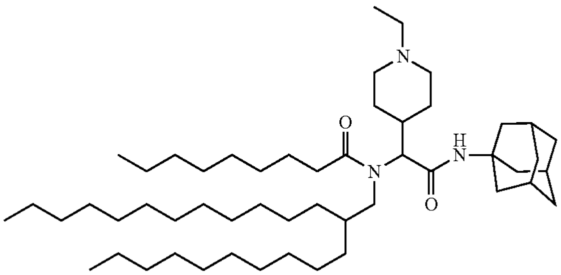

-continued
P52C6
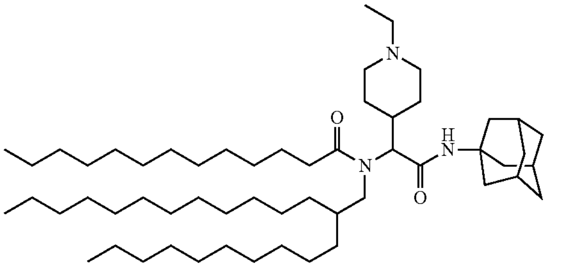
P52D6
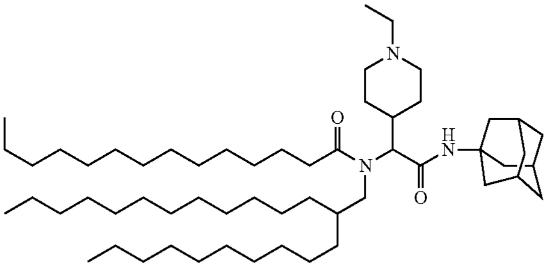
P52C12
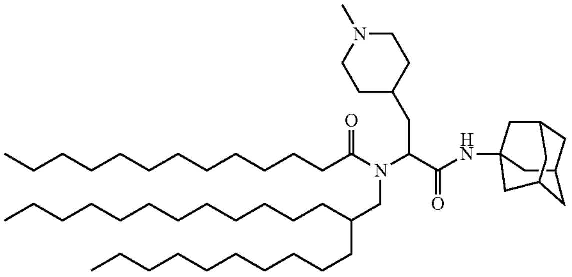
P51A12
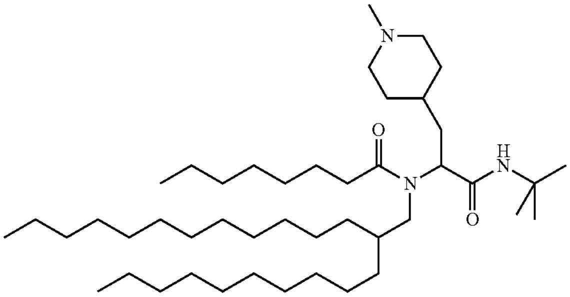
P51B12
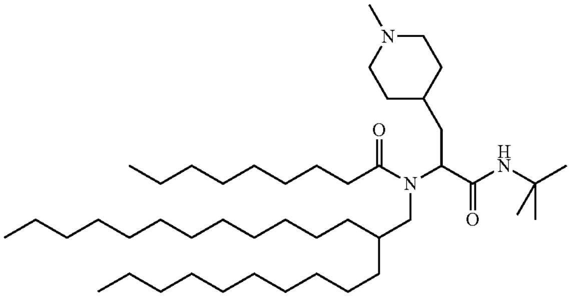
P51C12
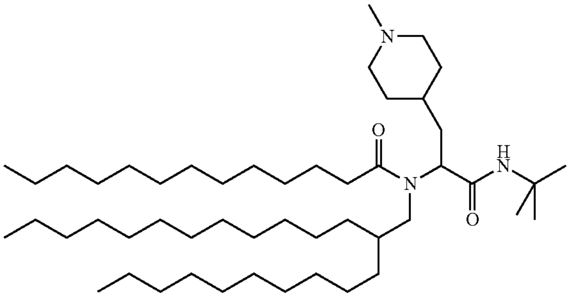
P51E12
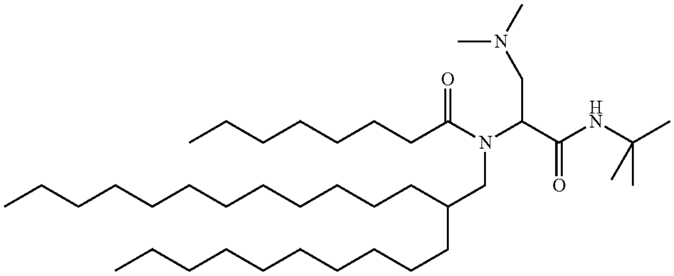
P42A4
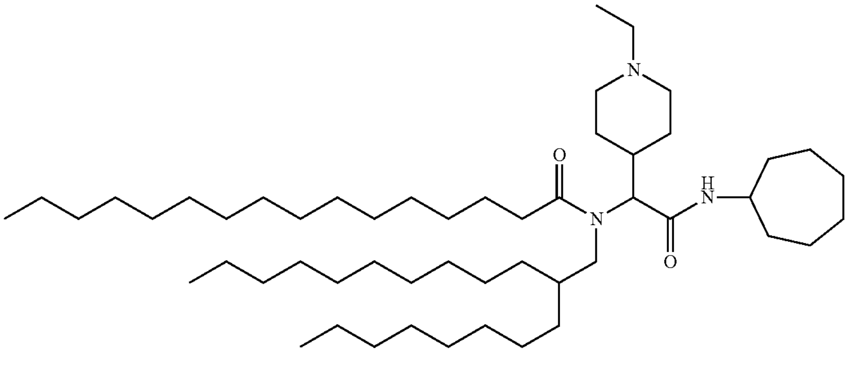

-continued
P42B4
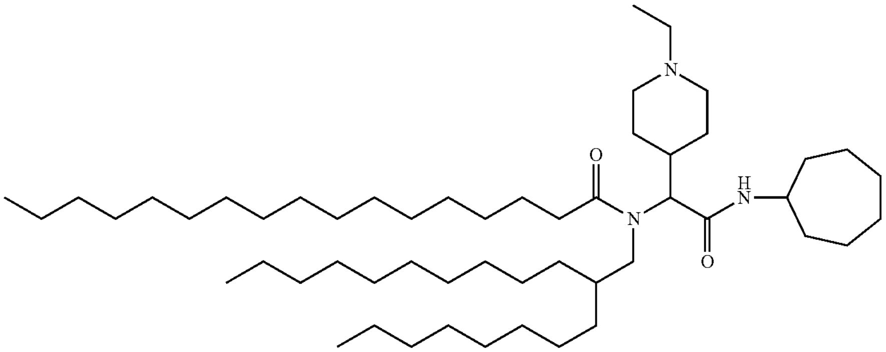
P40A10
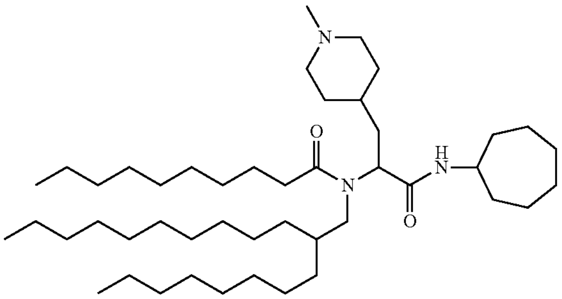
P40C12
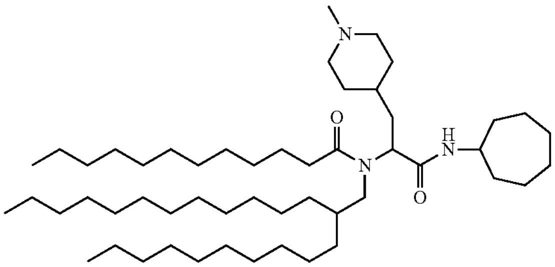
P40B2
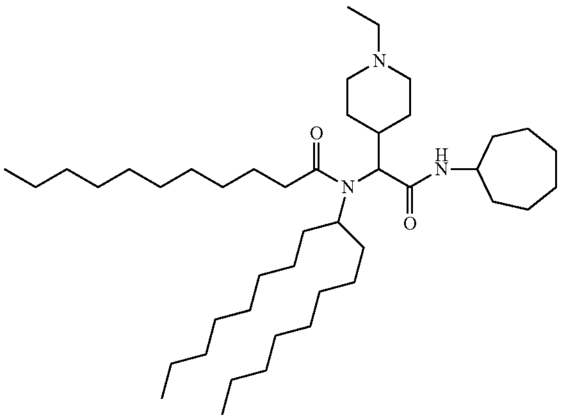
P40C2
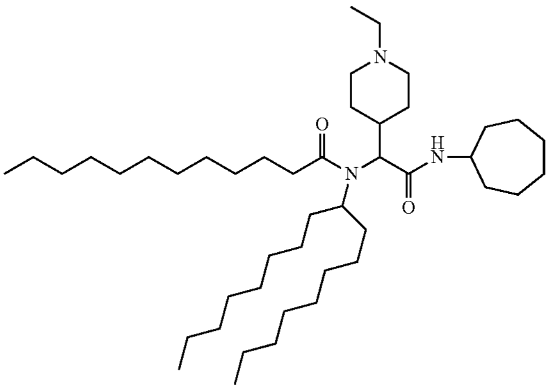
P40C4
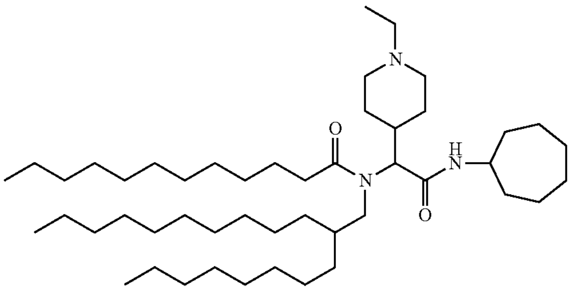
P40C4
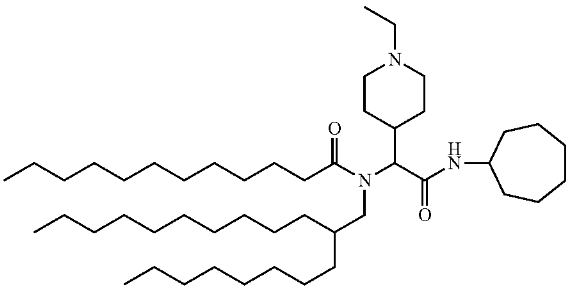

-continued
P38C3
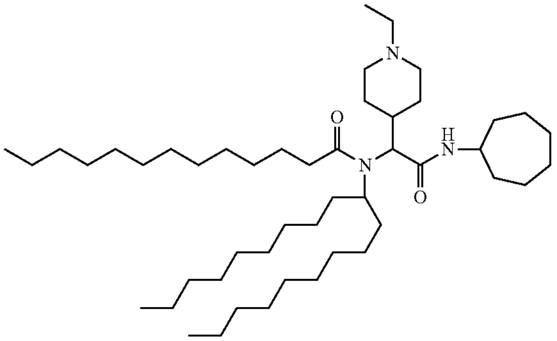
P38C4
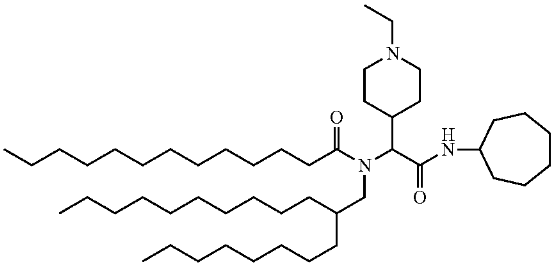
P38A6
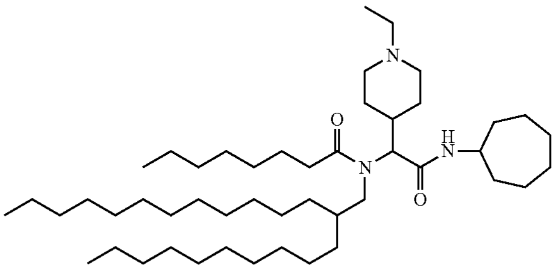
P38C7
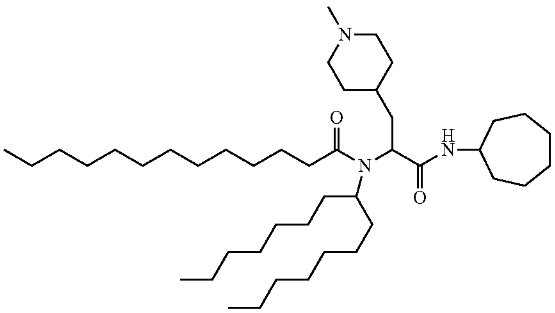
P38C8
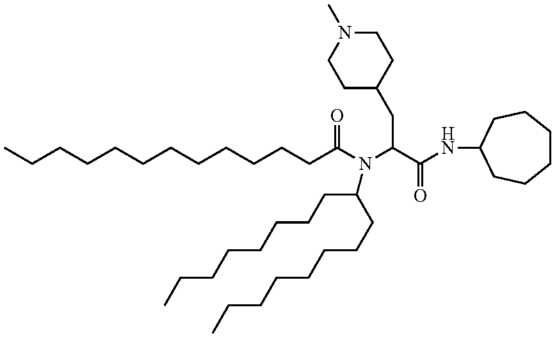
P36A9
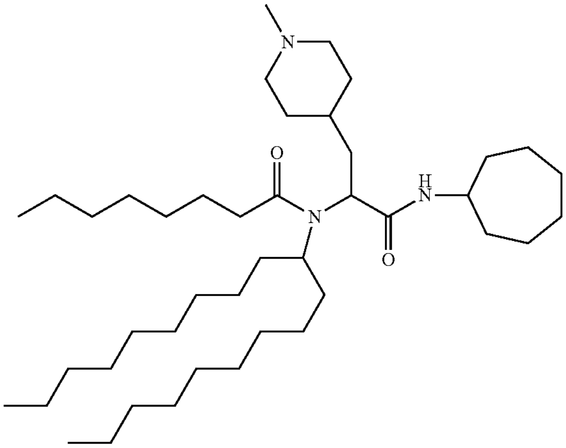
P38A10
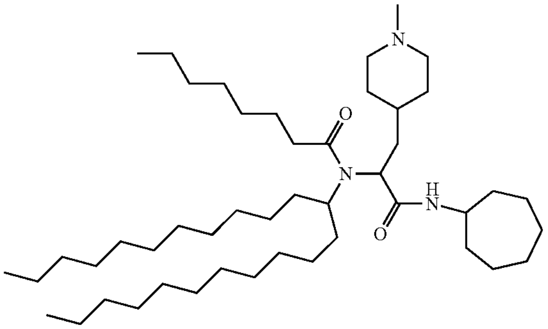
P38B10
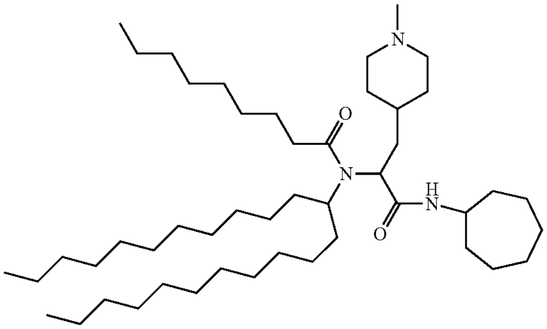

-continued
P38C10
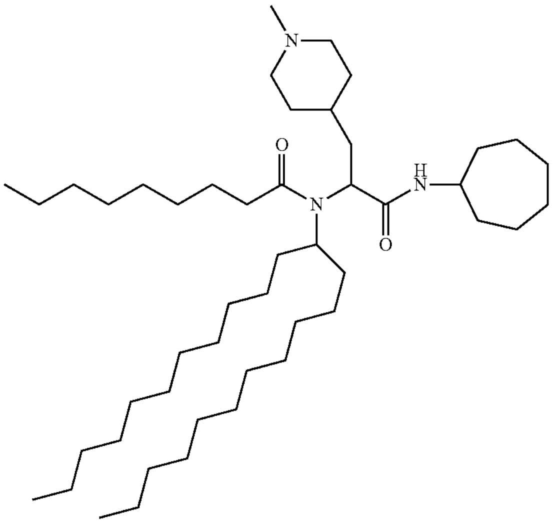
P38C1
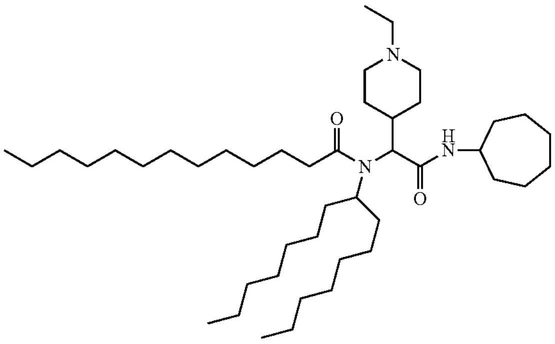
P38B2
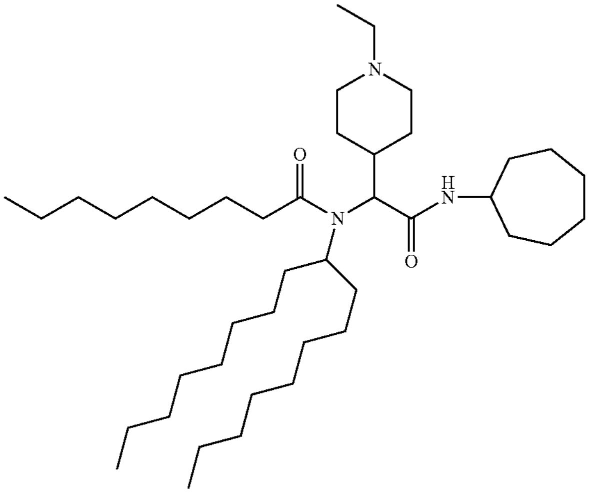
P28D10
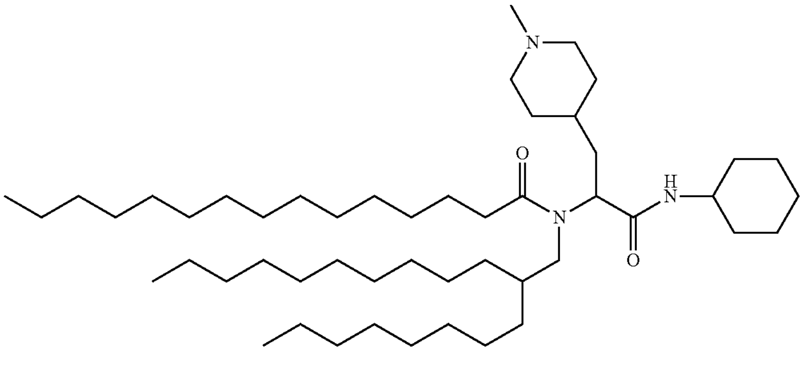

-continued
P30C4
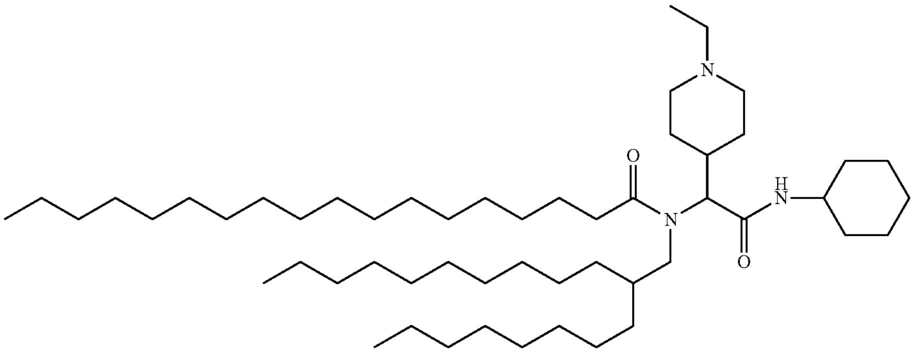
P30C1
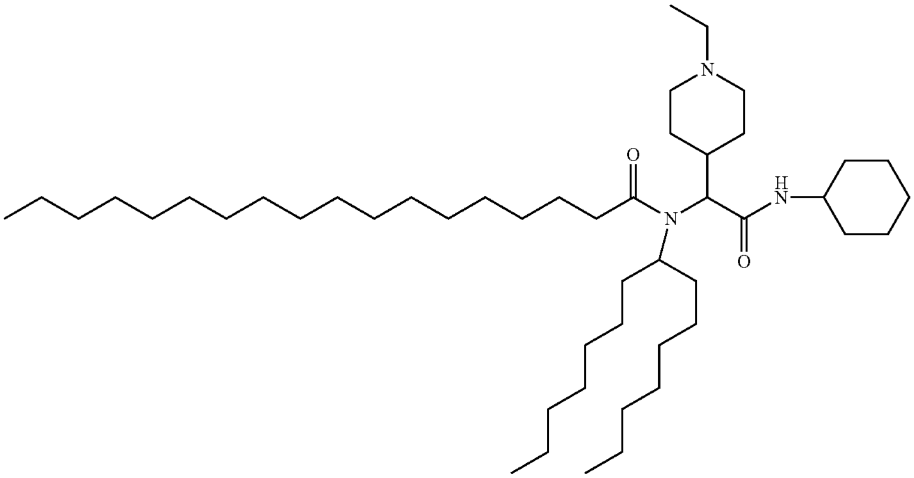
P30B1
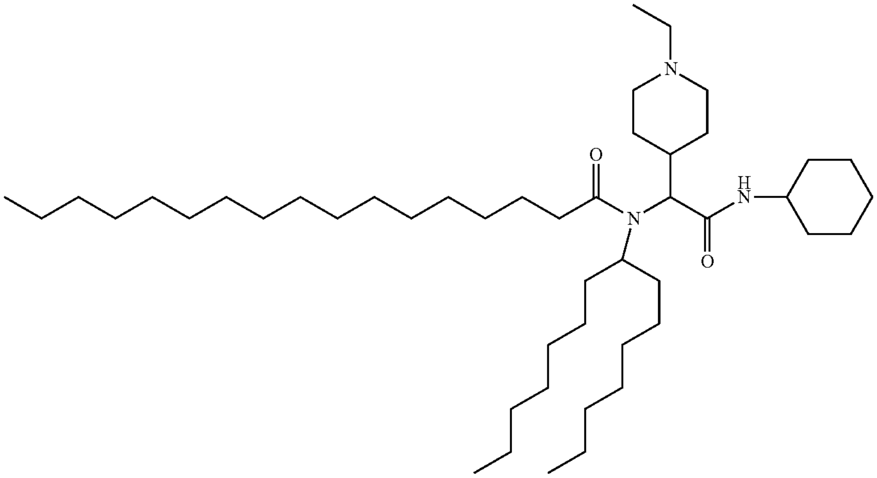

-continued
P26D4
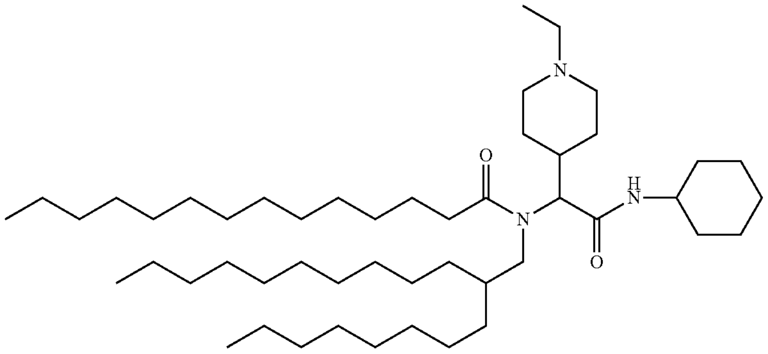
P1C4
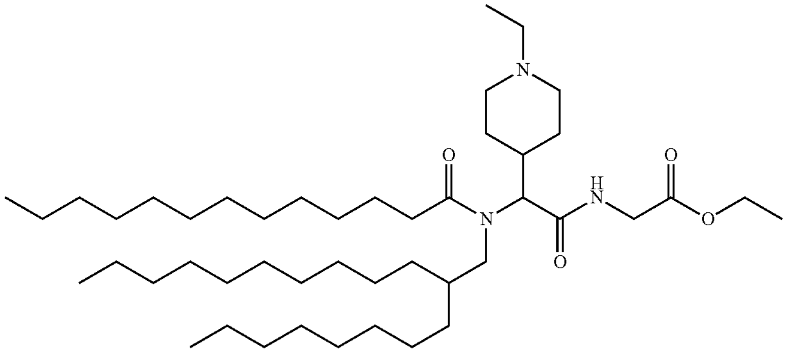
P43C10
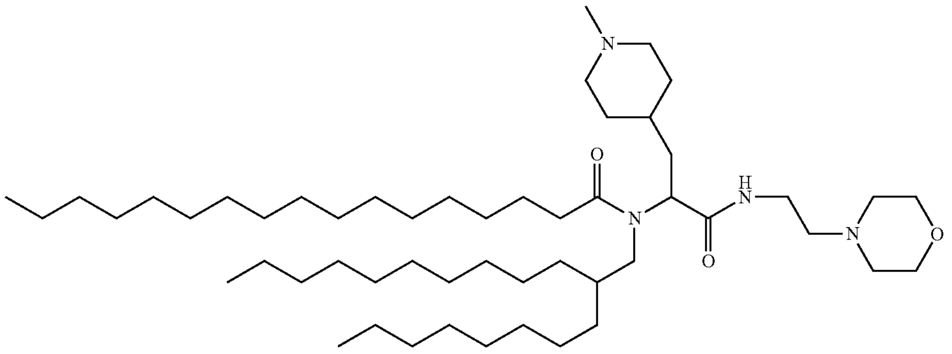
P43A12
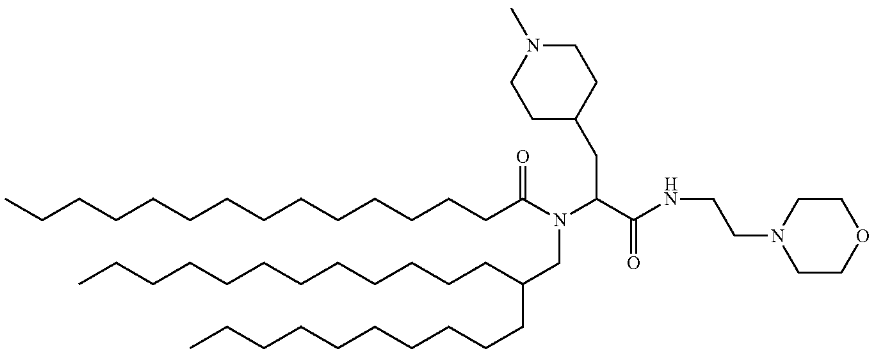

-continued
P43C12
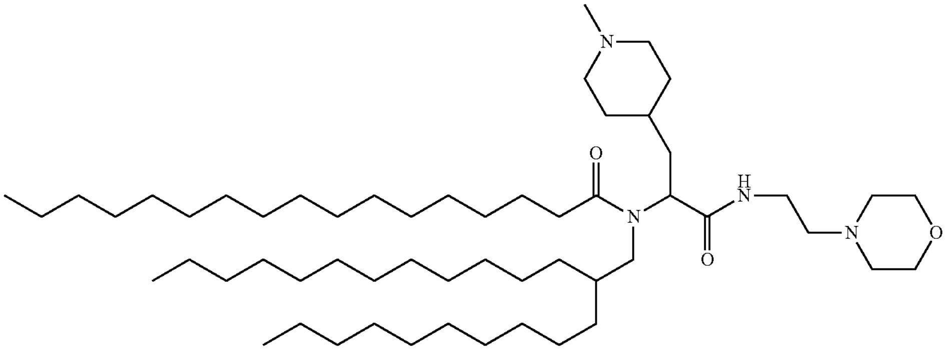
P41B4
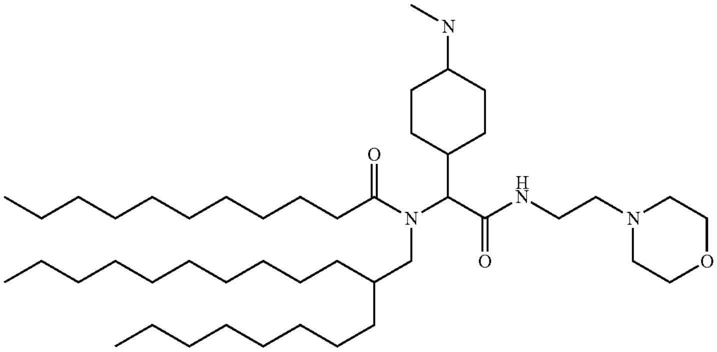
P41D4
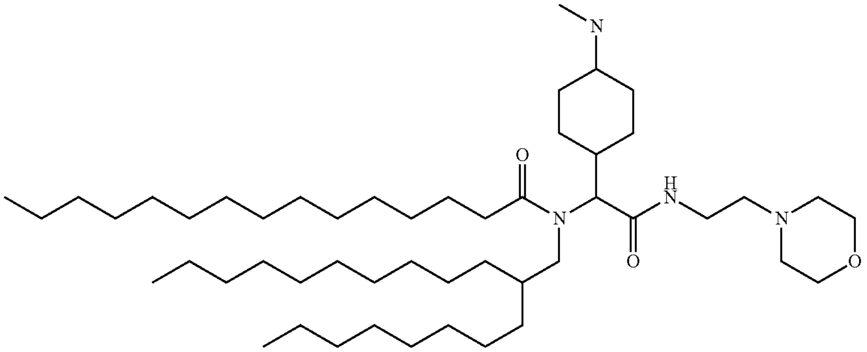
P41C6
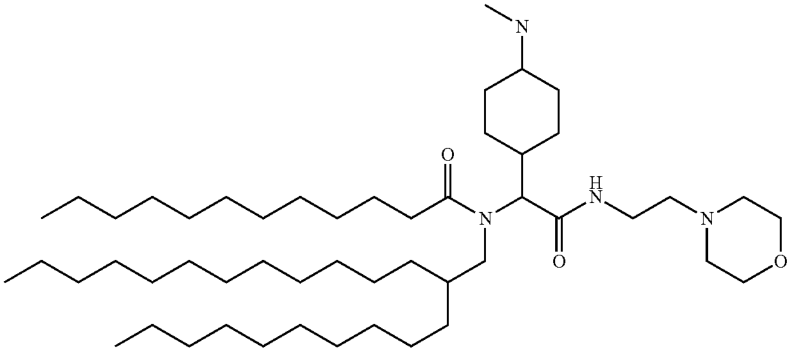

-continued
P41B10
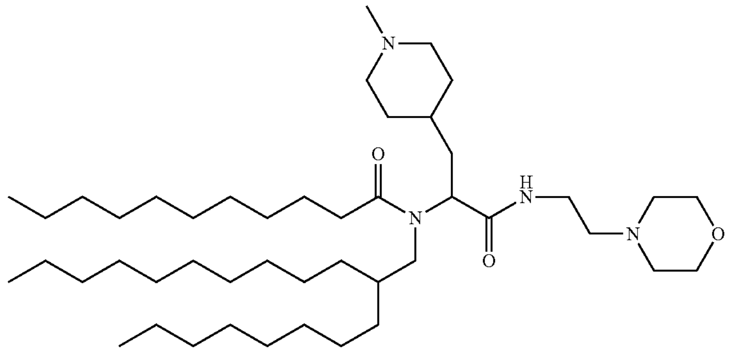
P41C10
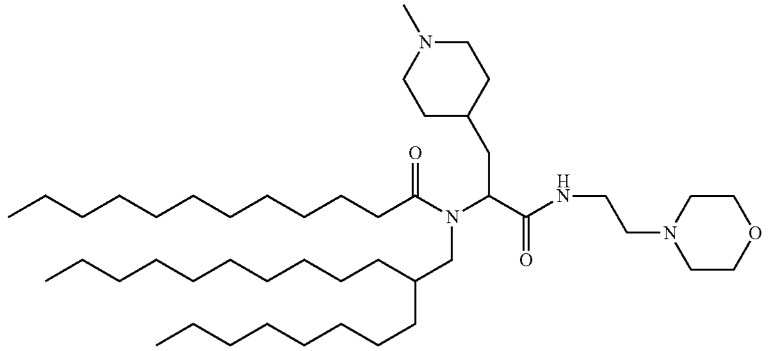
P41D10
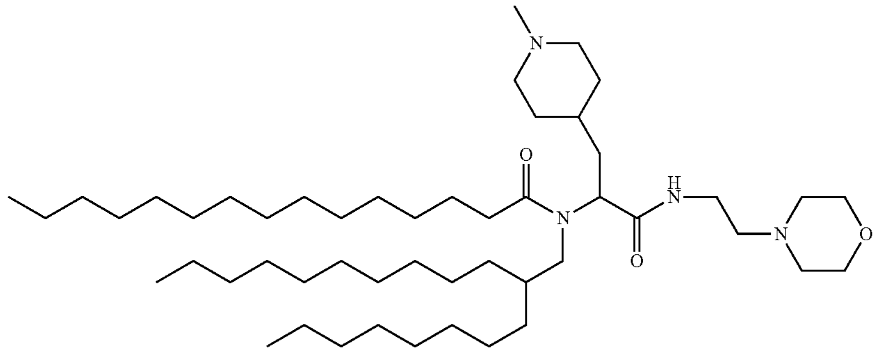
P41B12
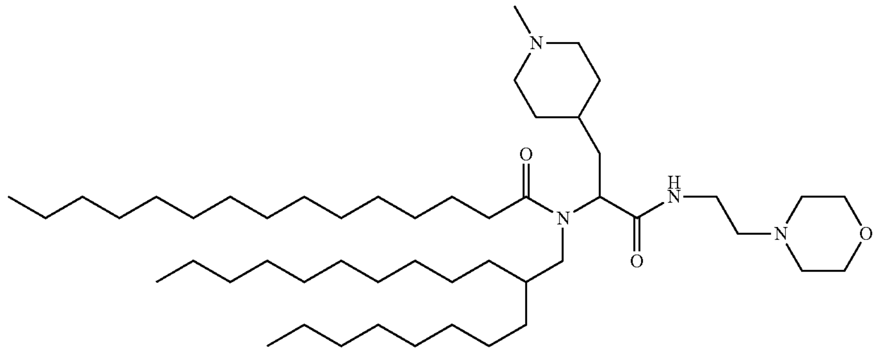

-continued
P39C10
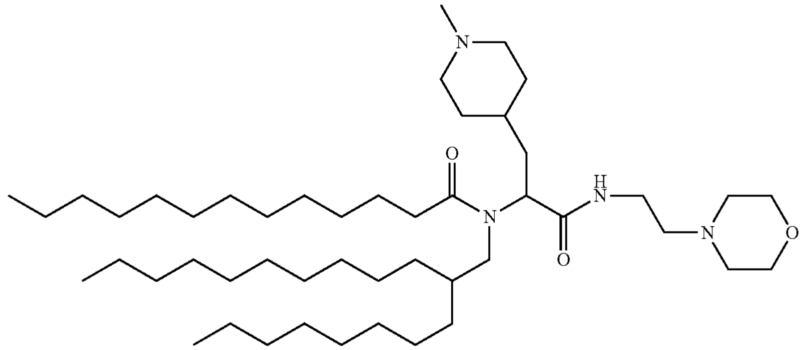
P39D10
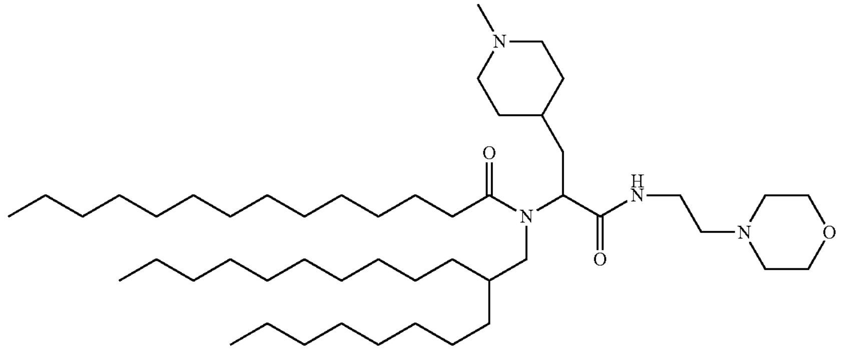
P39A12
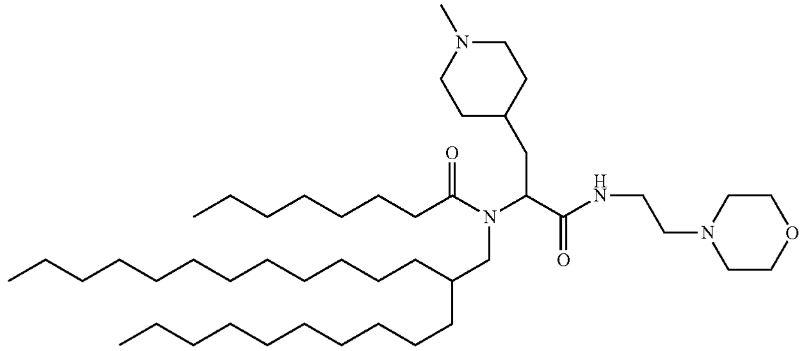
P39F12
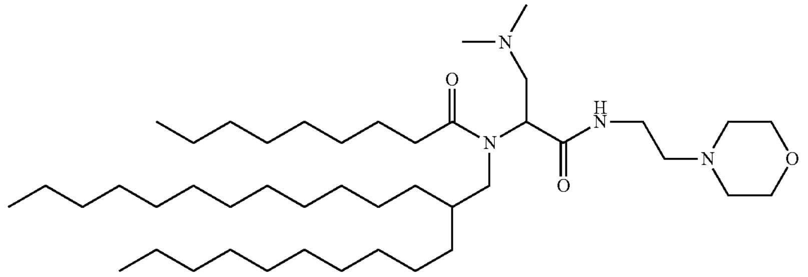
P39G12
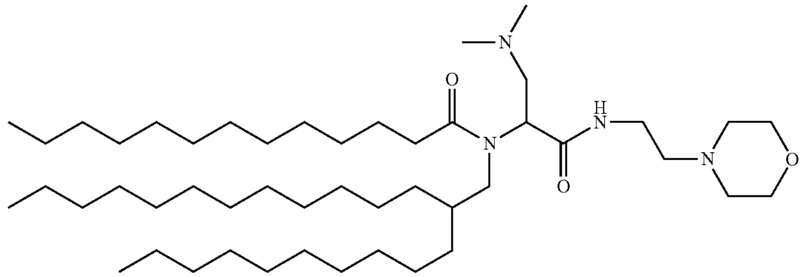

-continued
P39B12
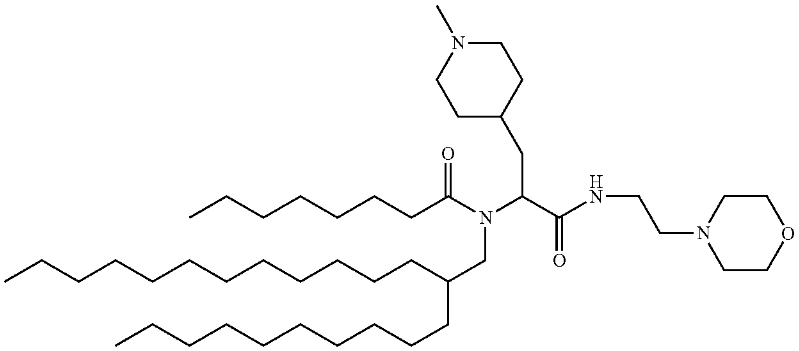
P39C12
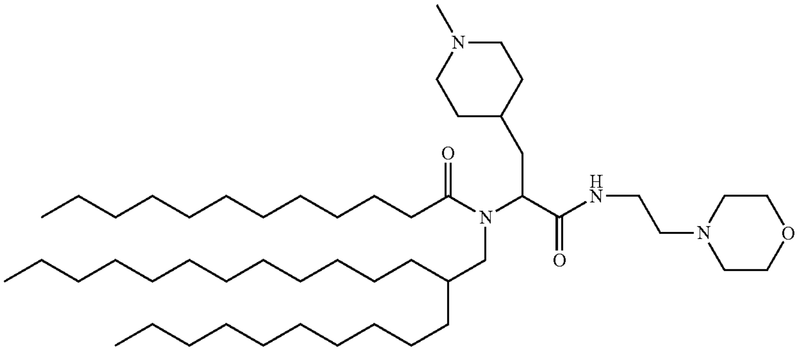
P39D4
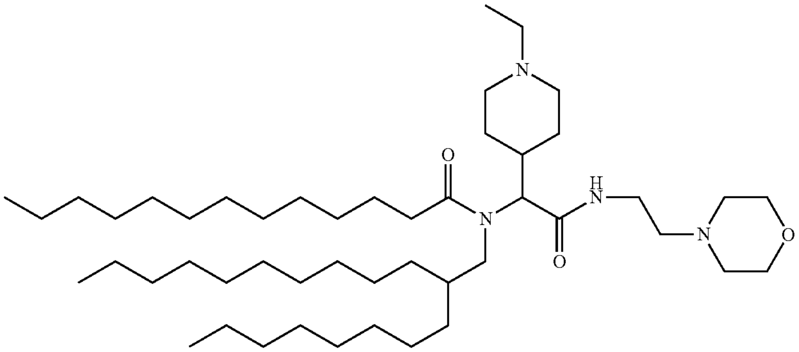
P39A6
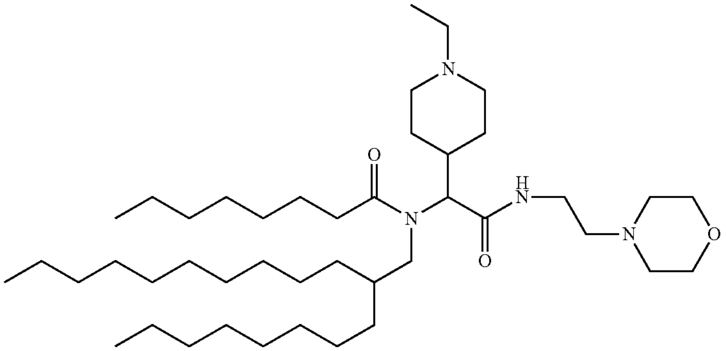

-continued
P38B12
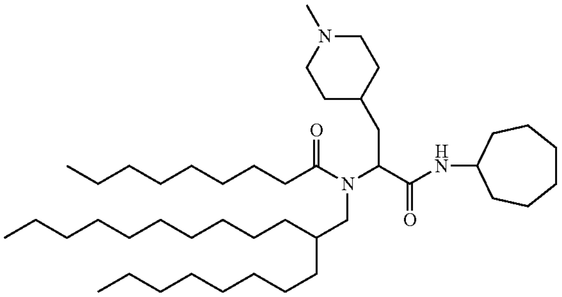
P38C12
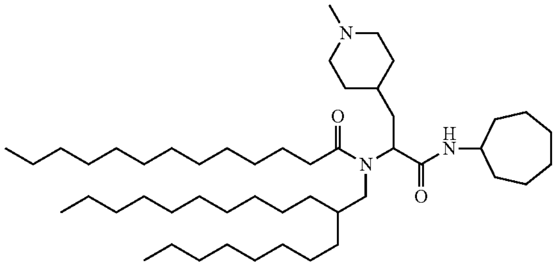
P143A7
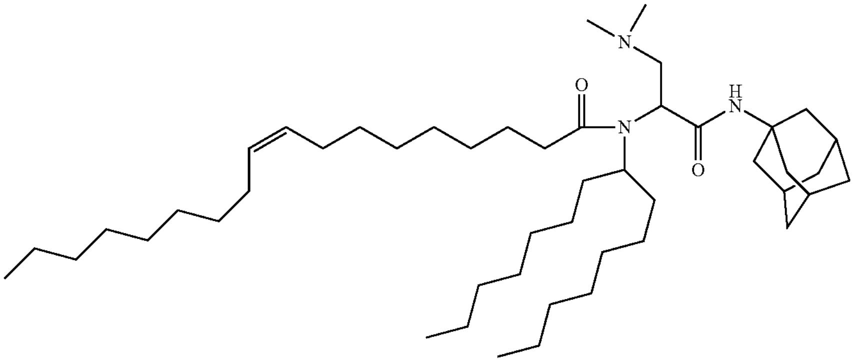
P143A9
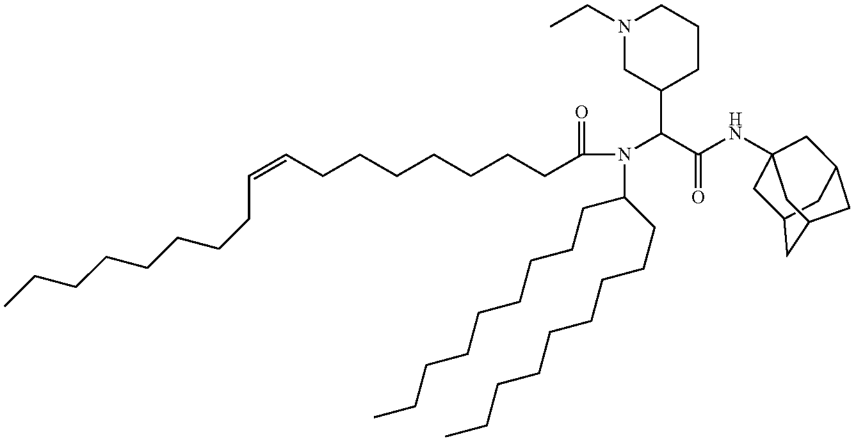
P143C7
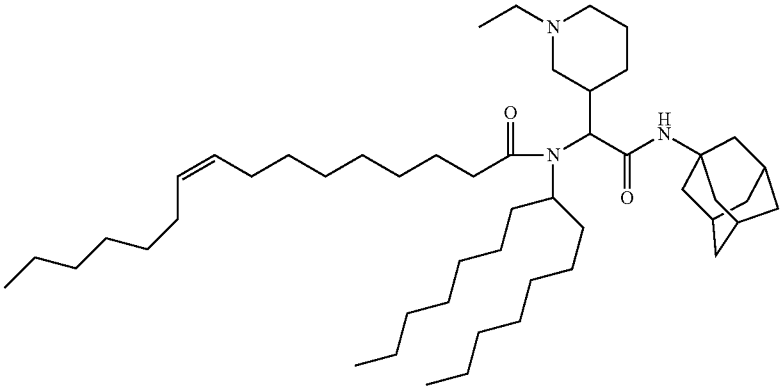

-continued
P143C9
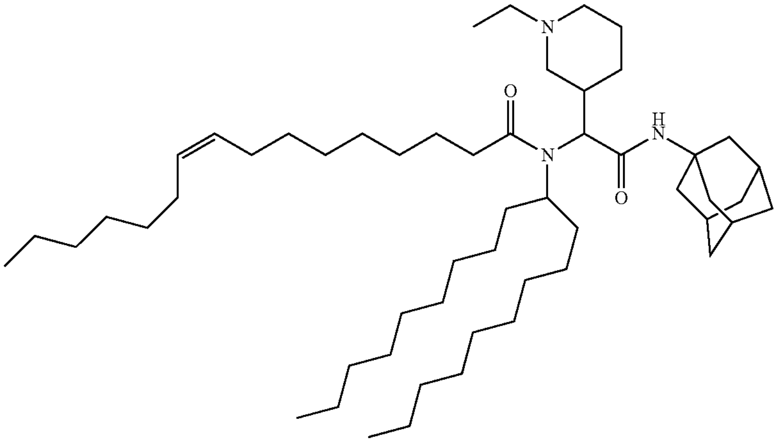
P143C10
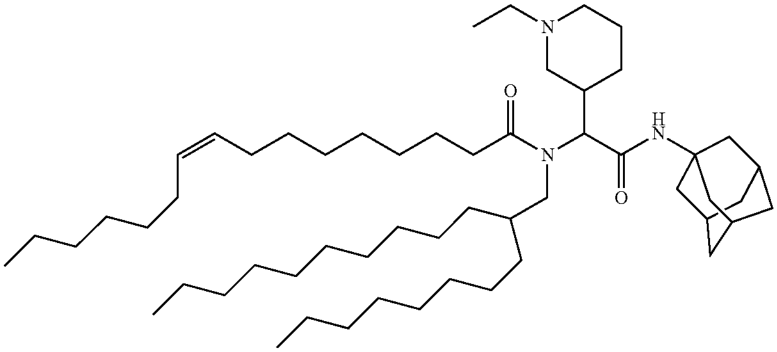
P143D10
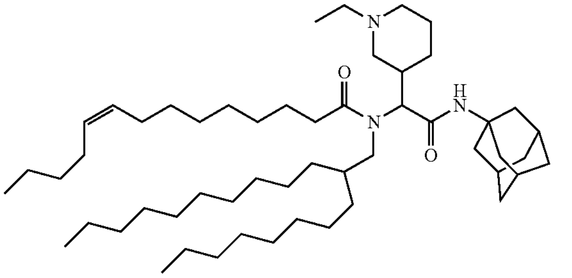
P147B10
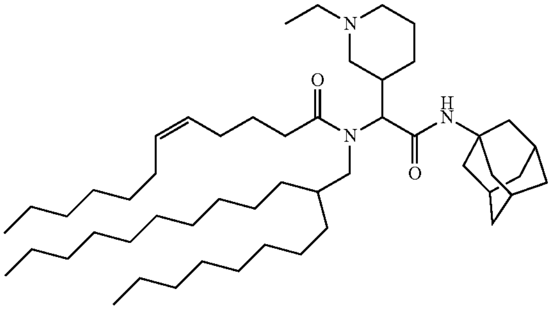
P147C7
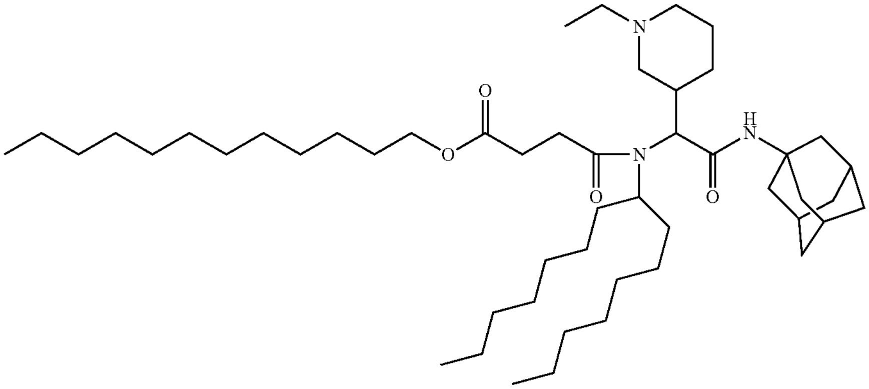

-continued
P147C8
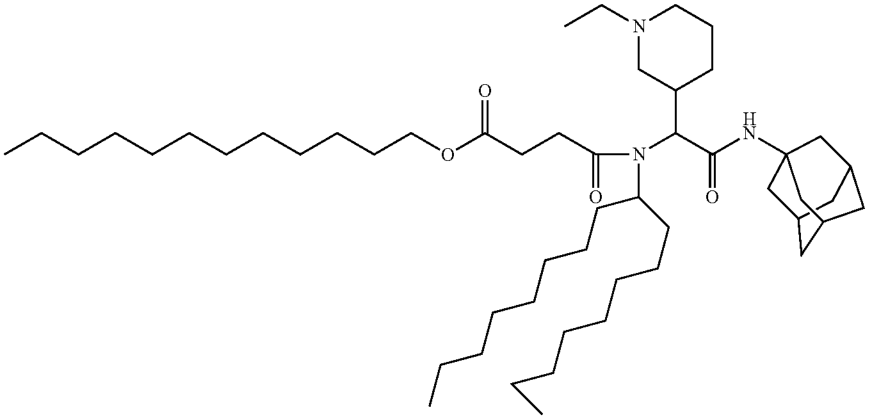
P147C9
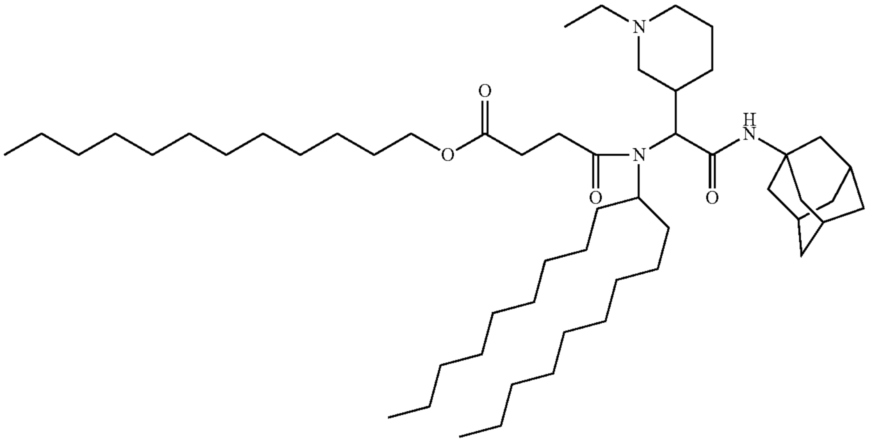
P147C10
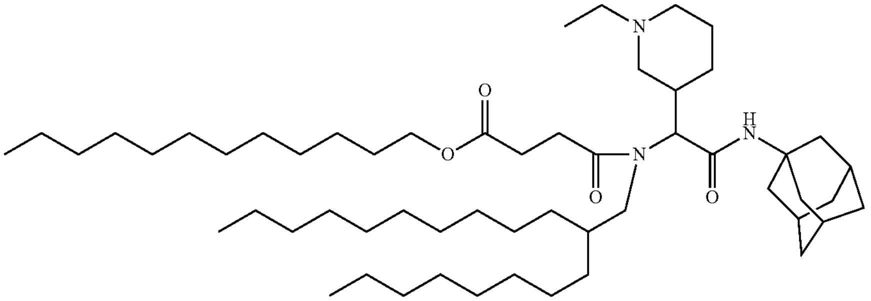
P147C12
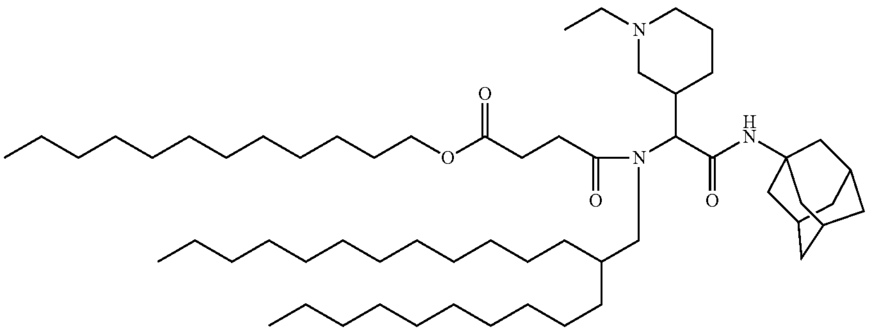

-continued
P147D10
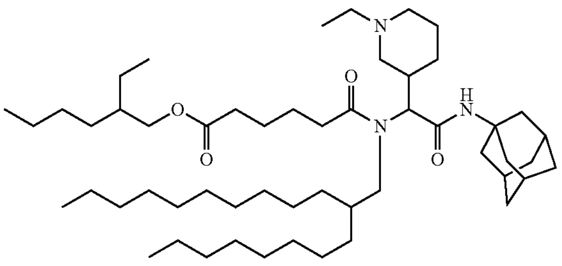
P147D12
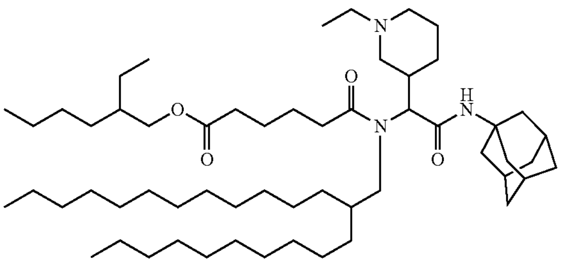
P150C2
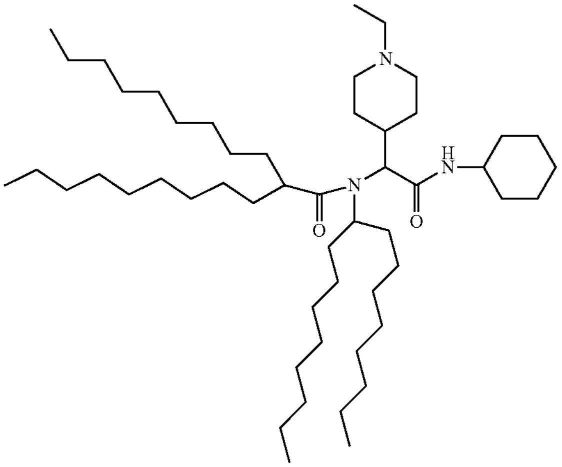
P147A4
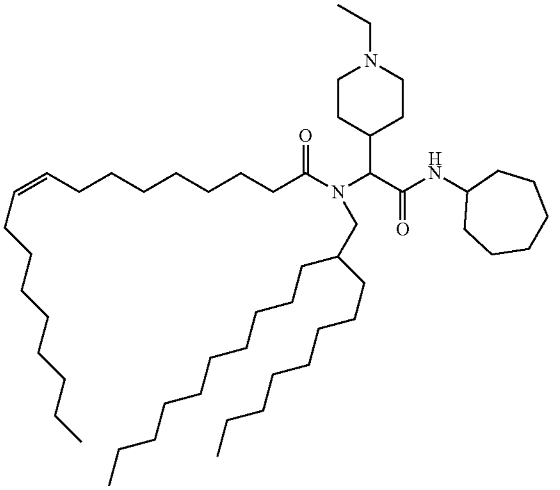
P149A7
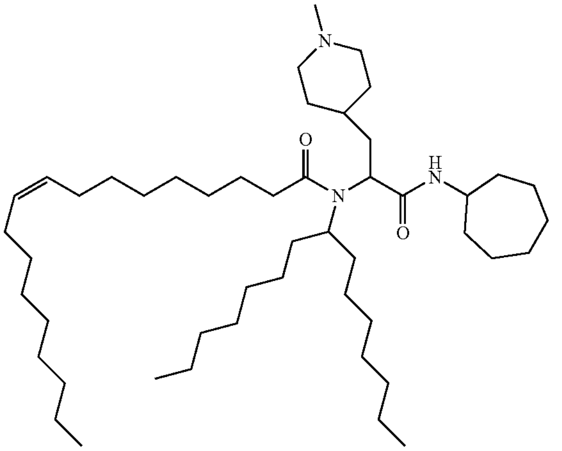
P149A9
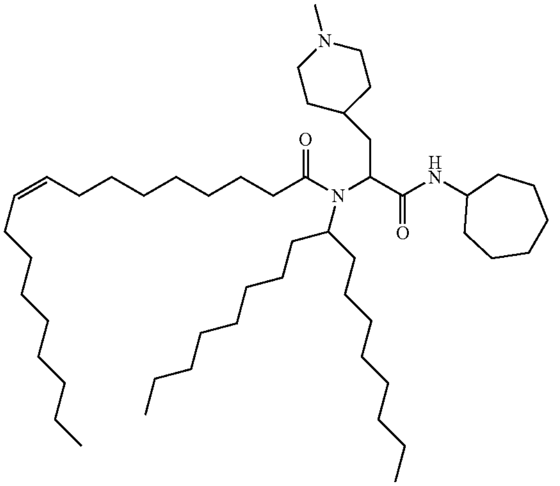

-continued
P148A1
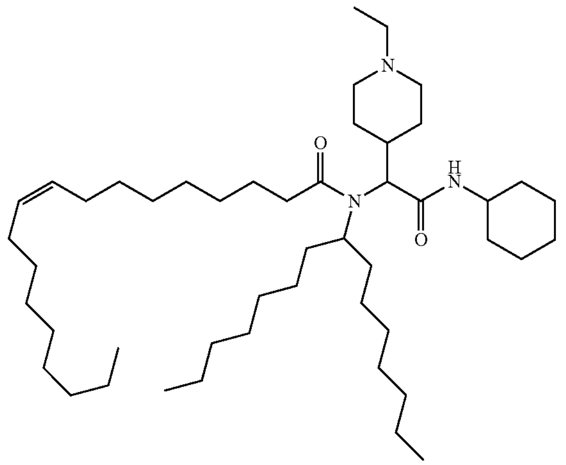
P148A2
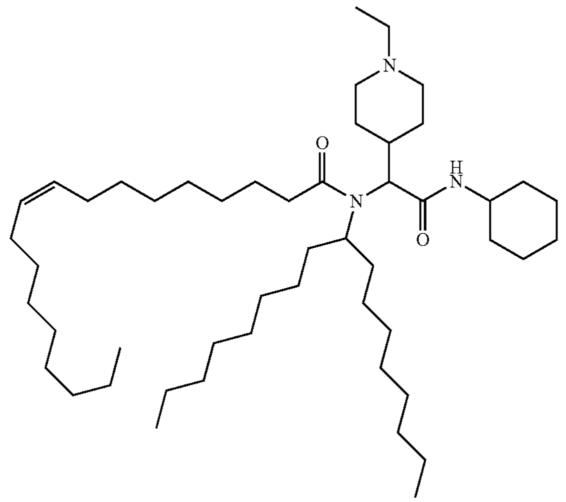
P148A3
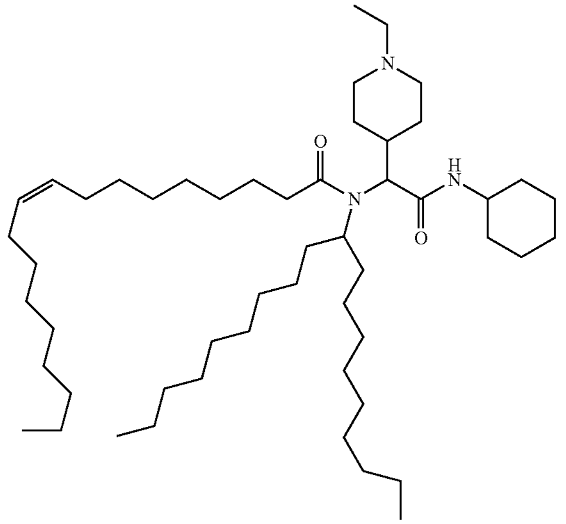
P148C1
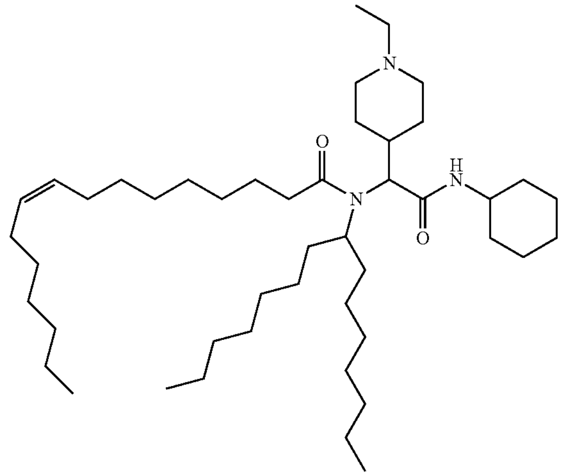
P148C2
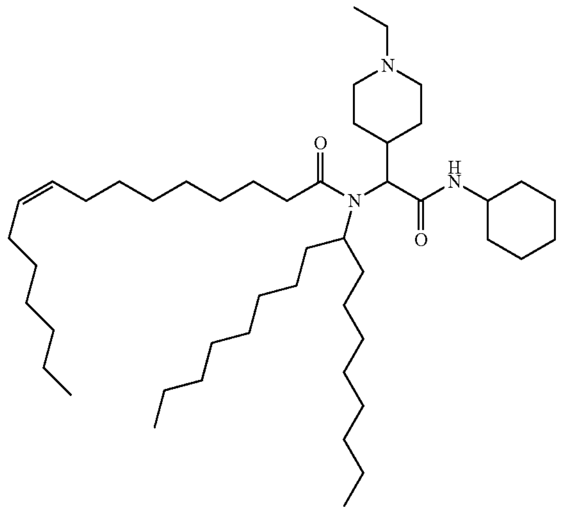
P148C3
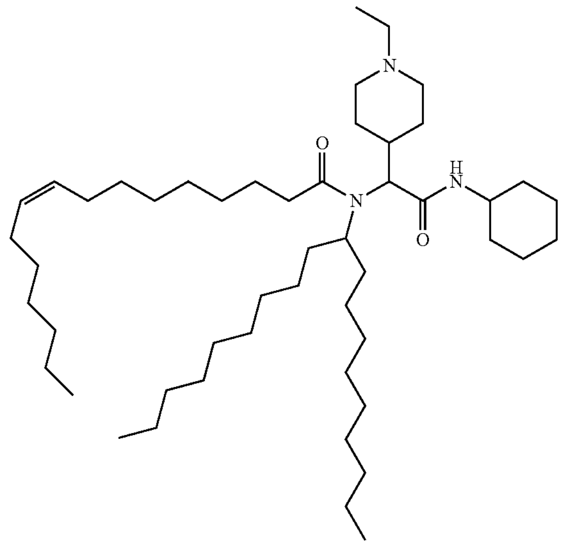

-continued
P153C4
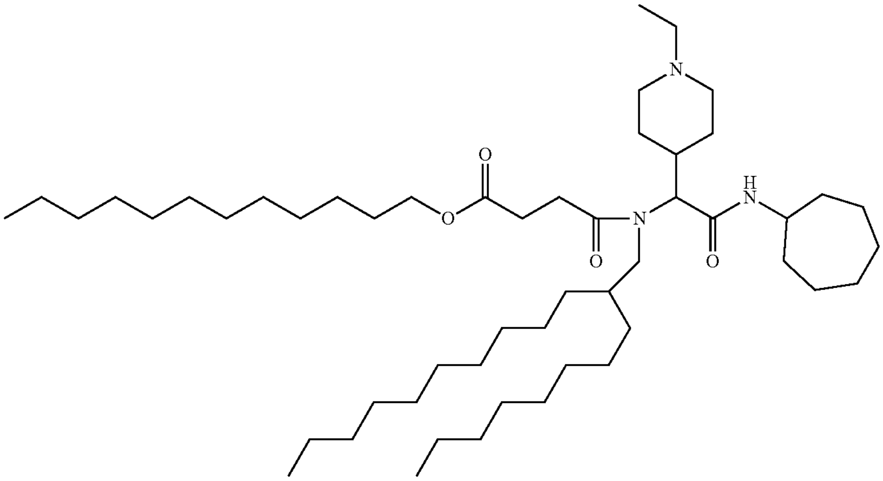
P153C5
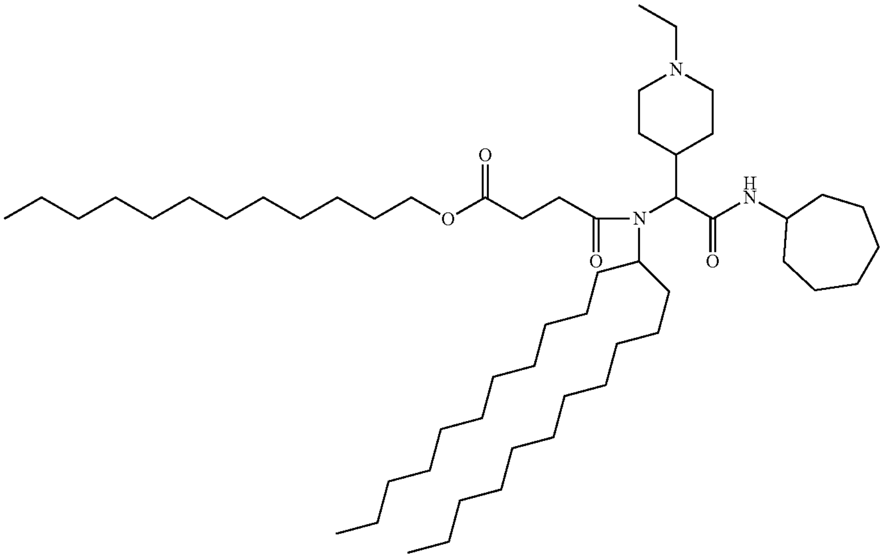
P153D10
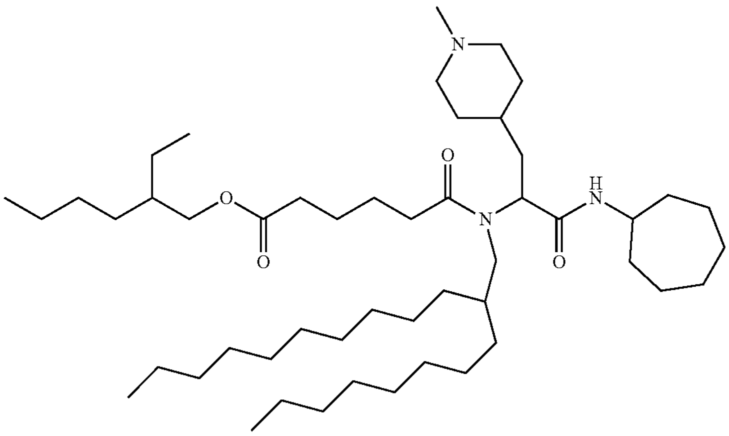

-continued
P153A1
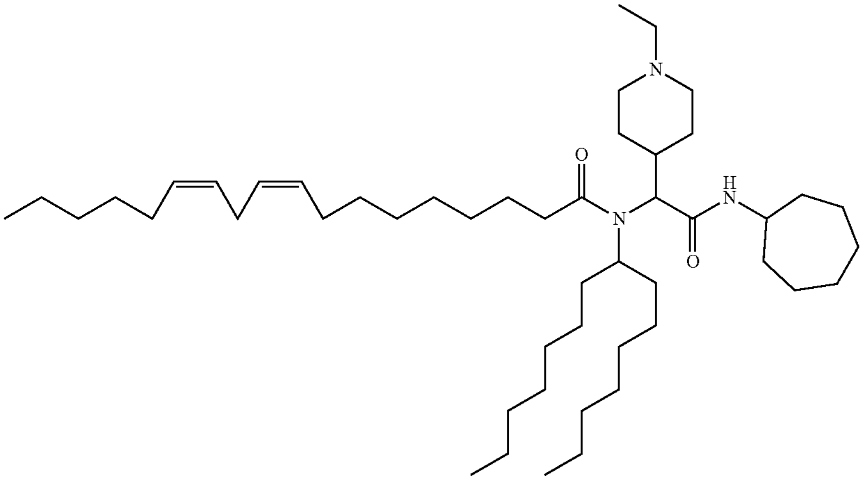
P153A2
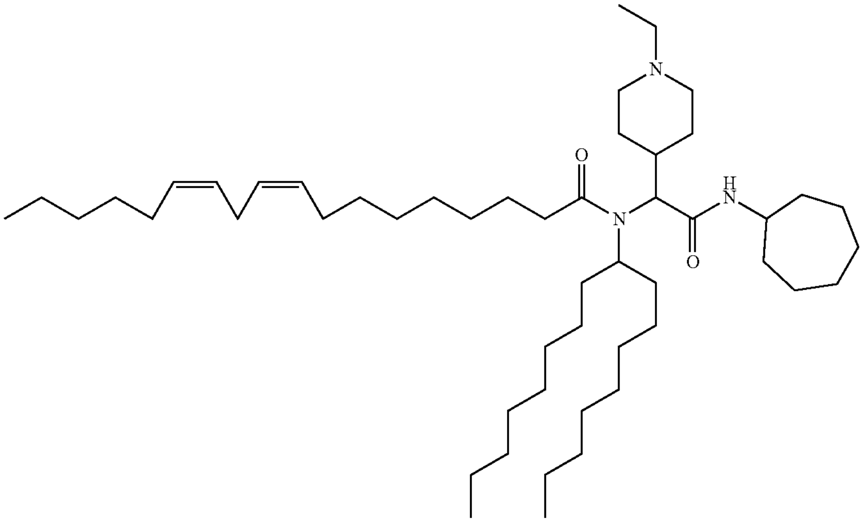
P153A3
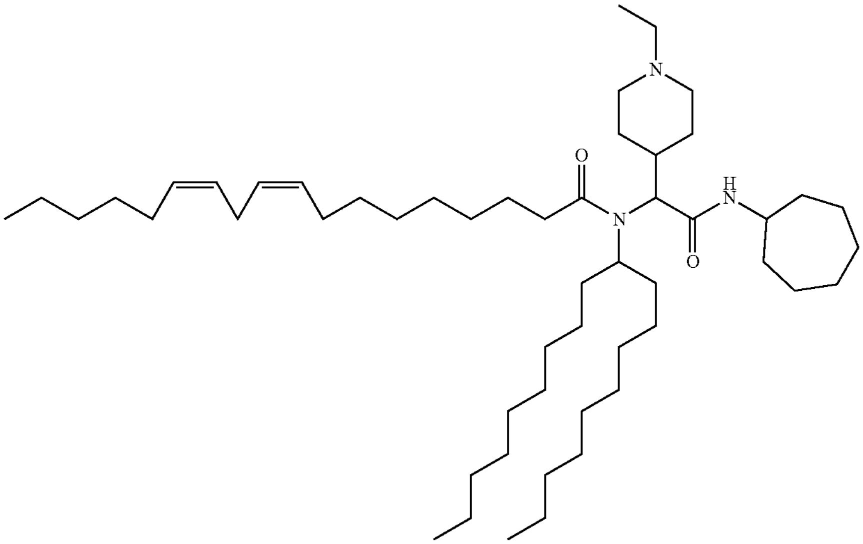

-continued
P153B10
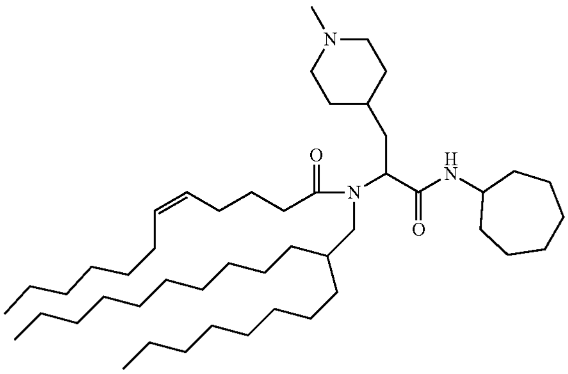
P152D10
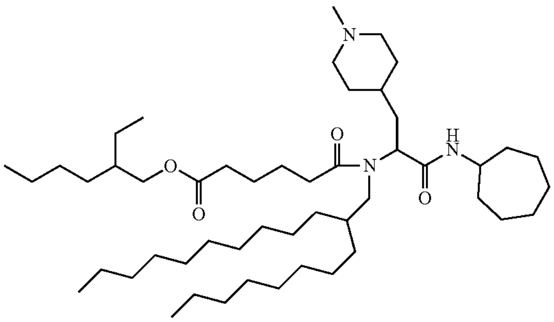
P152C1
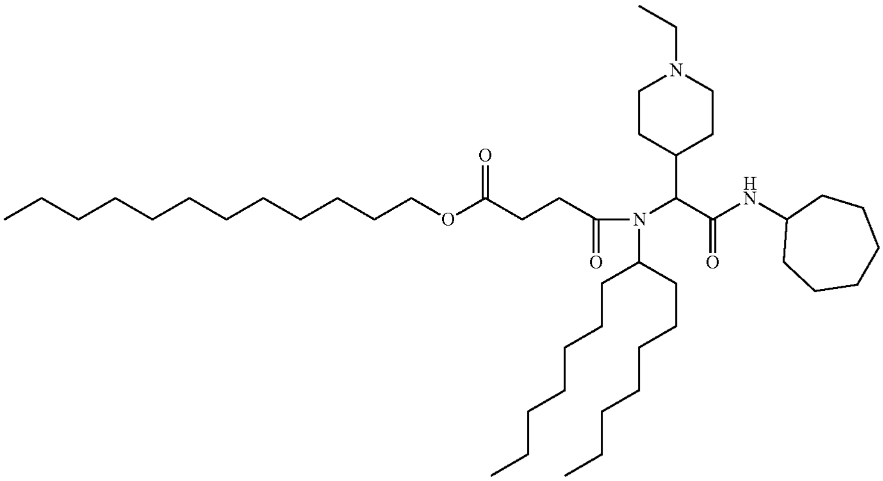
P152C2
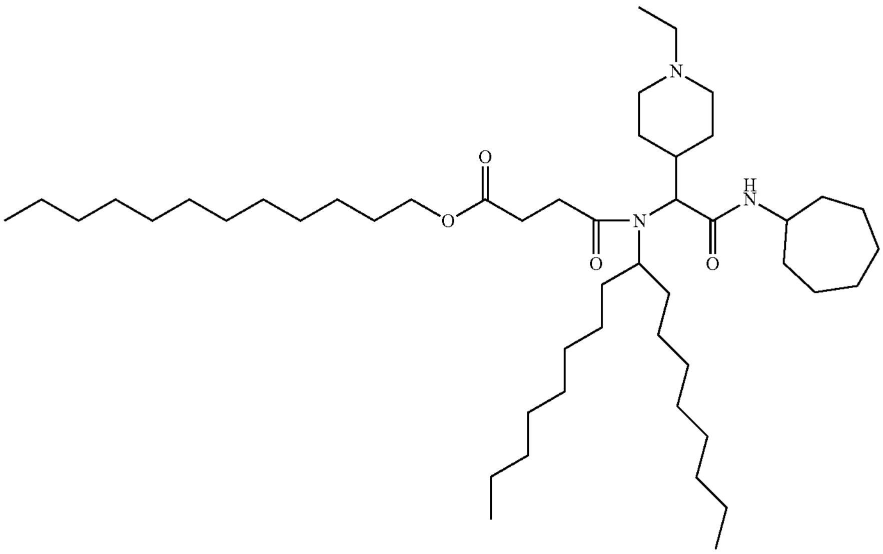

-continued
P151B3
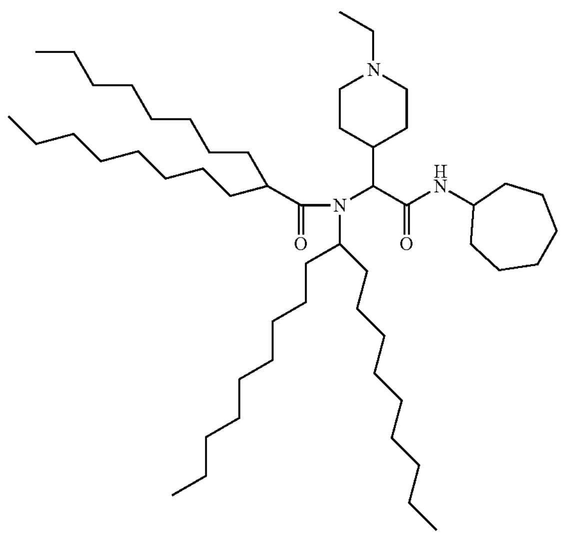
P151C2
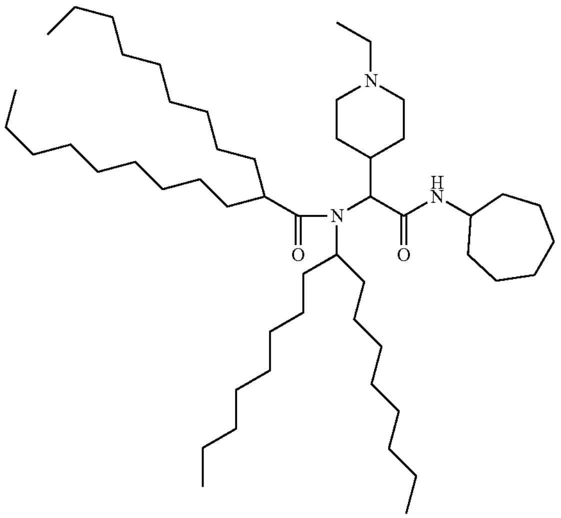
P154A10
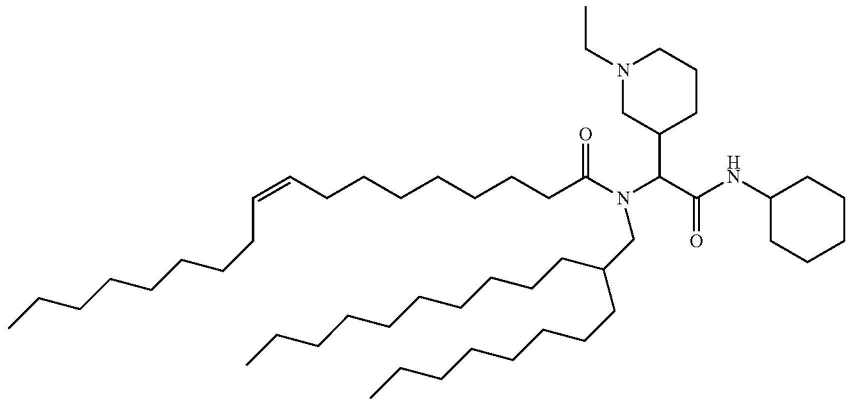
P154D10
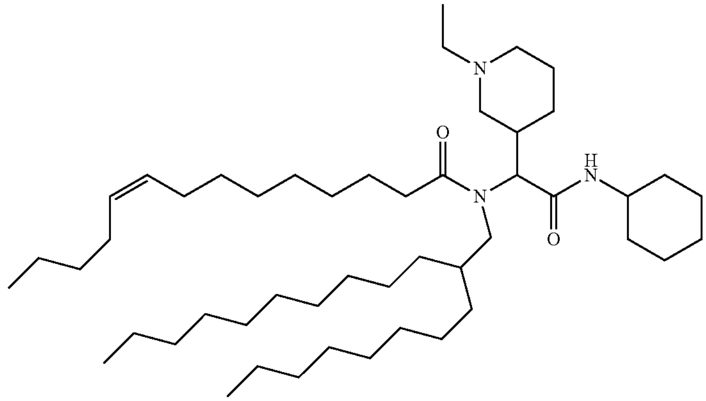

-continued
P160B4
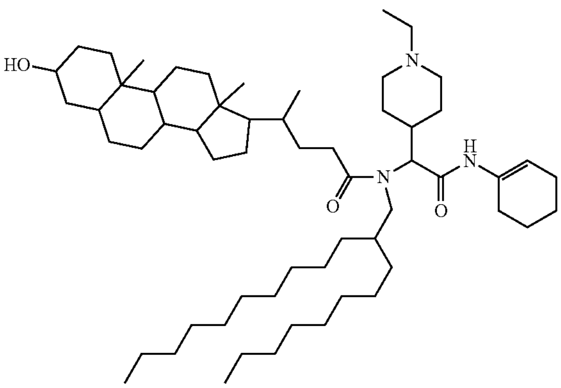
P160E6
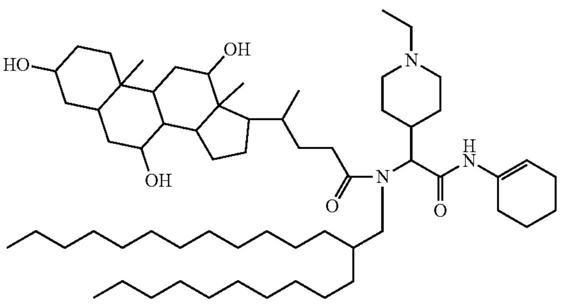
P158C10
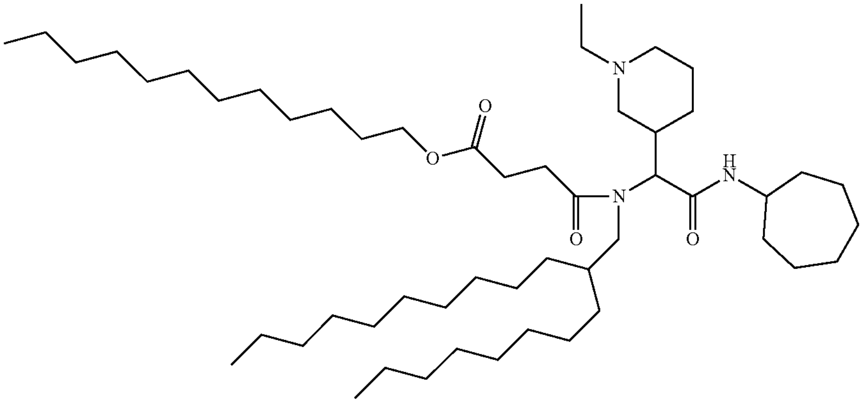
P161C4
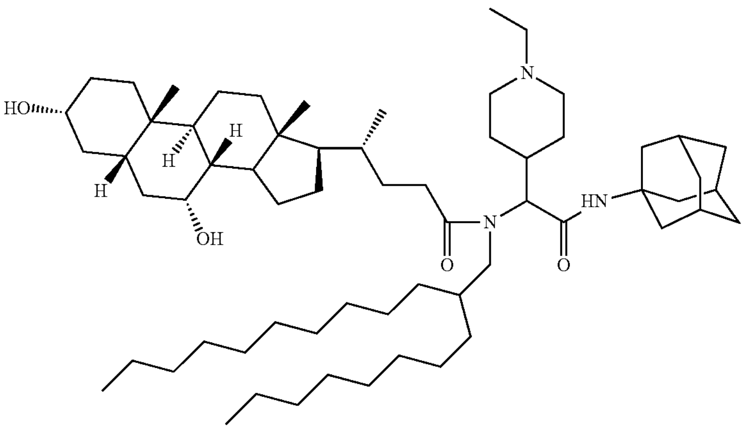

P161E4
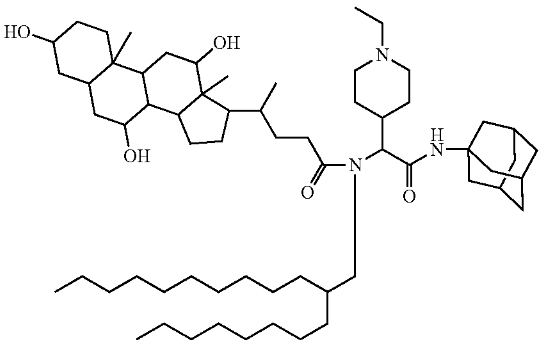
P161E6
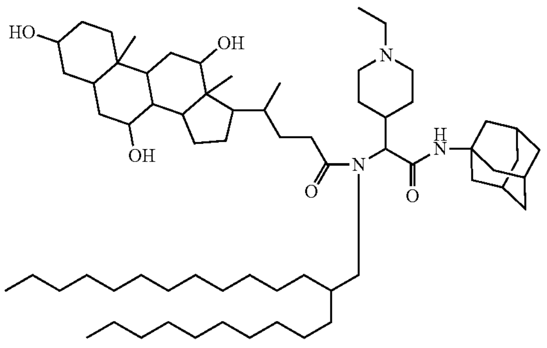
P161F4
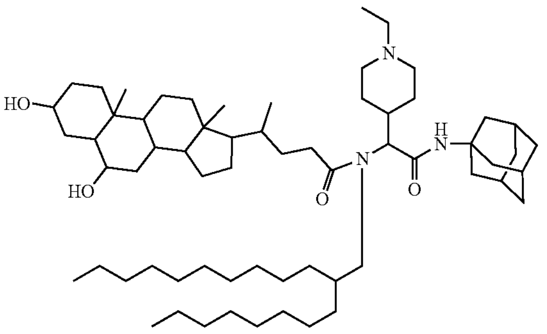
P161F5
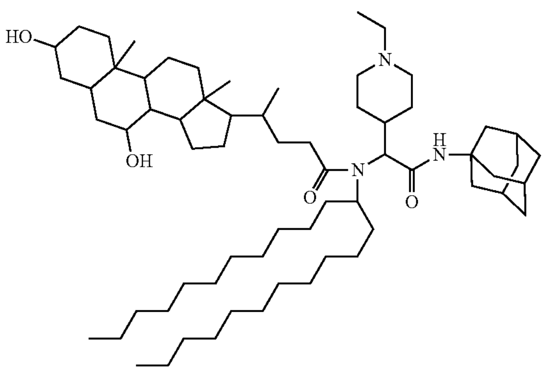
P161F6
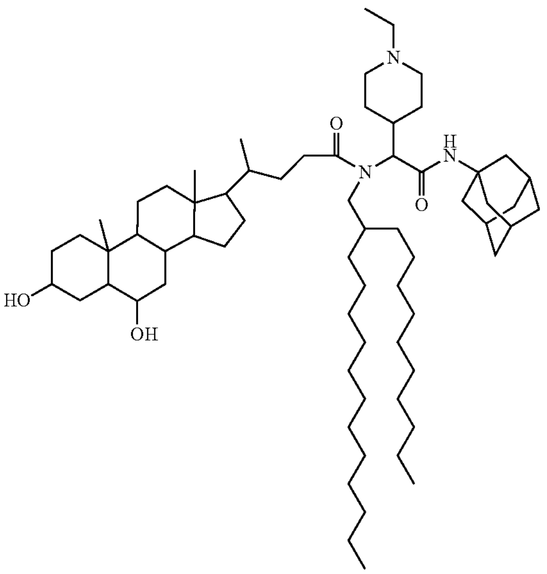
P165A10
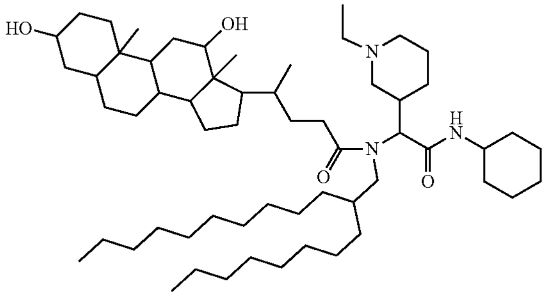

-continued
P165D10
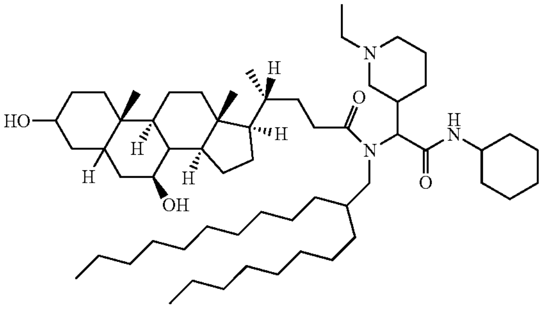
P165F10
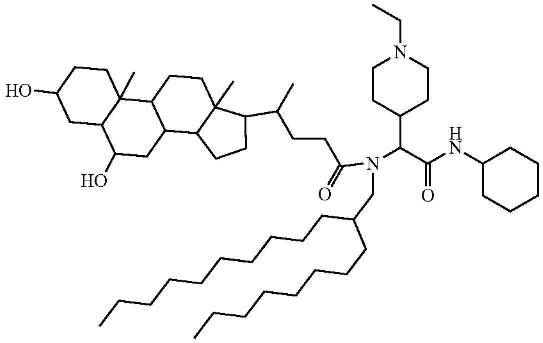
P165E12
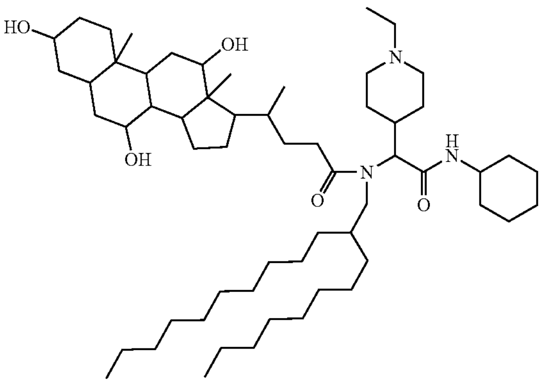
P169A2
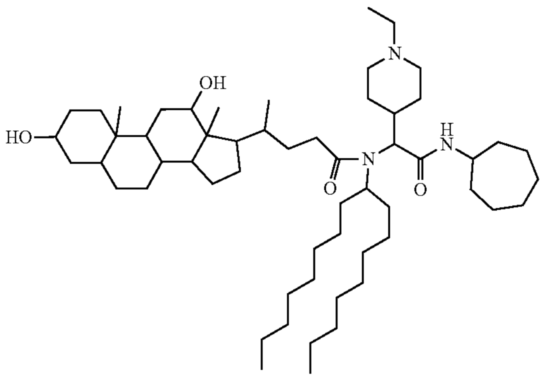
P169A8
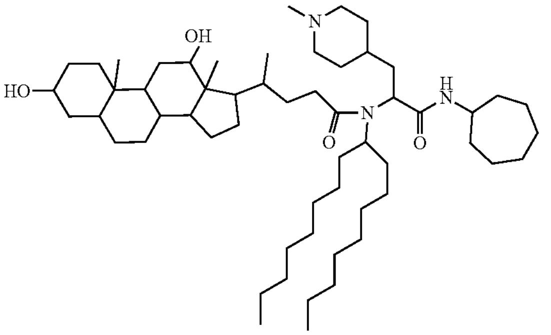
P169F10
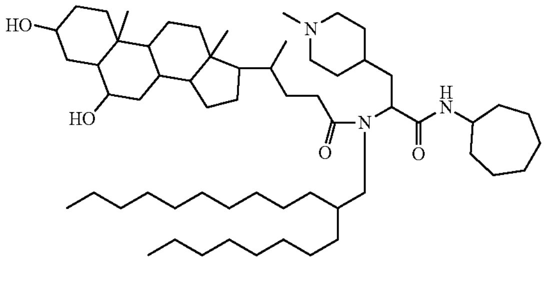
P169C10
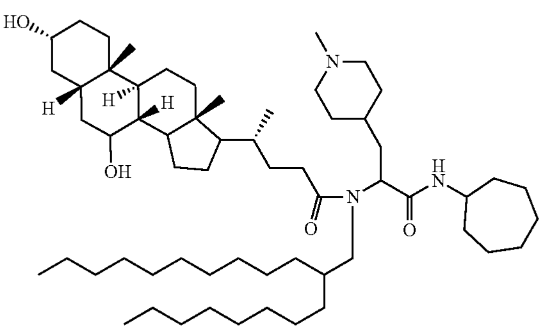
P169C12
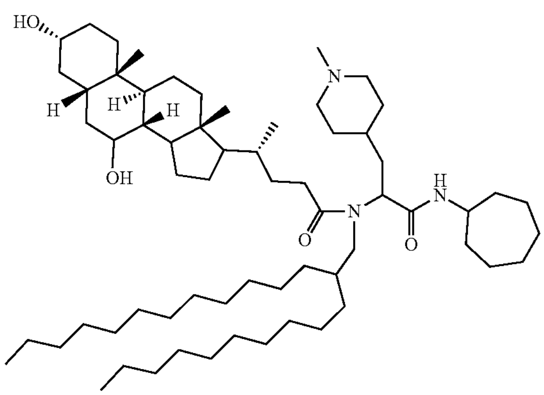

-continued
P170D12
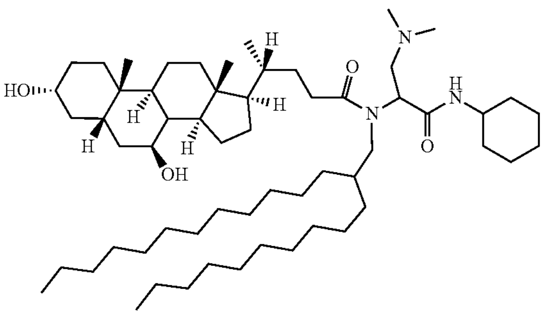
P171D12
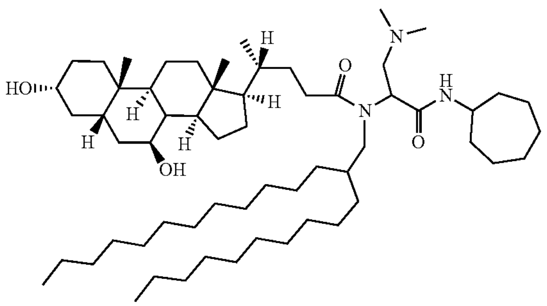
P173F10
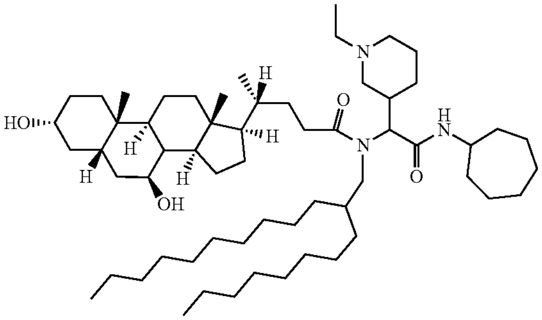
P177F6
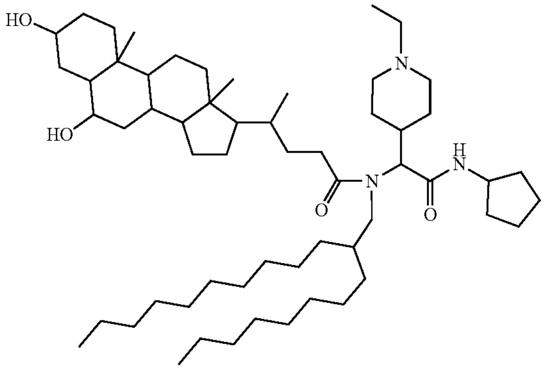
P235F9
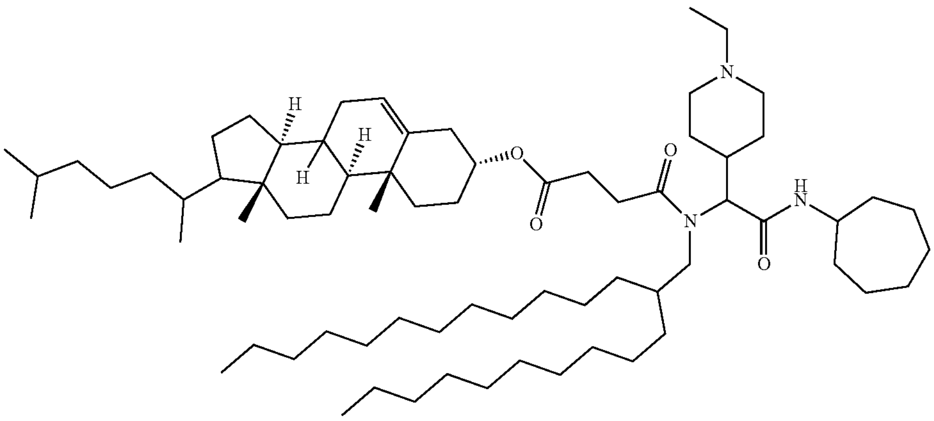
P235F11
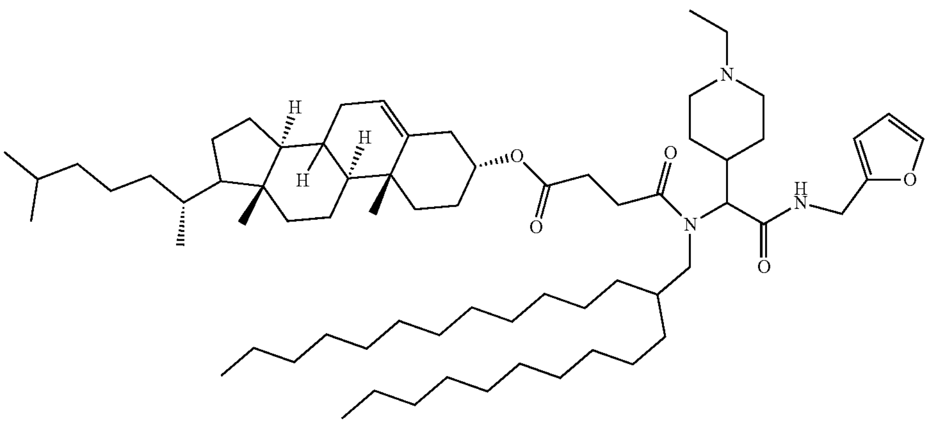

-continued
P235G10
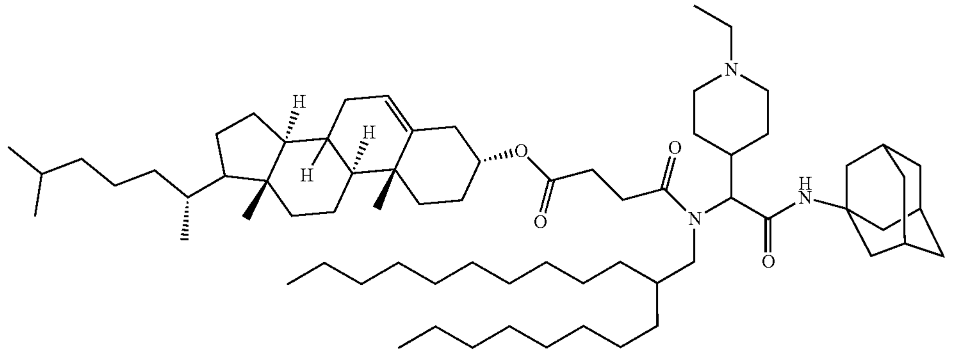
P235G11
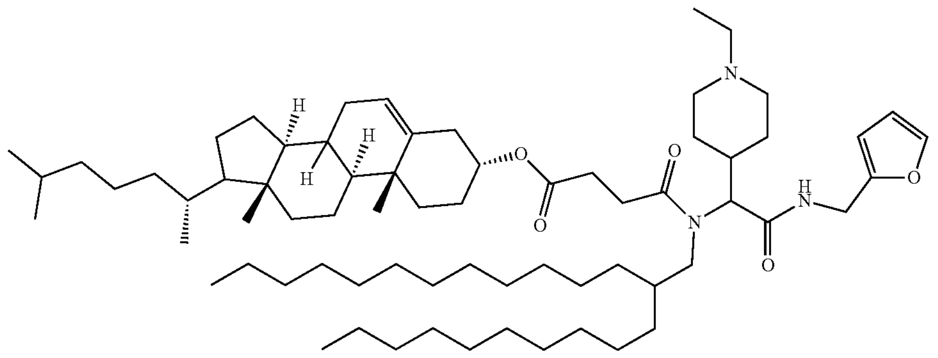
P235F7
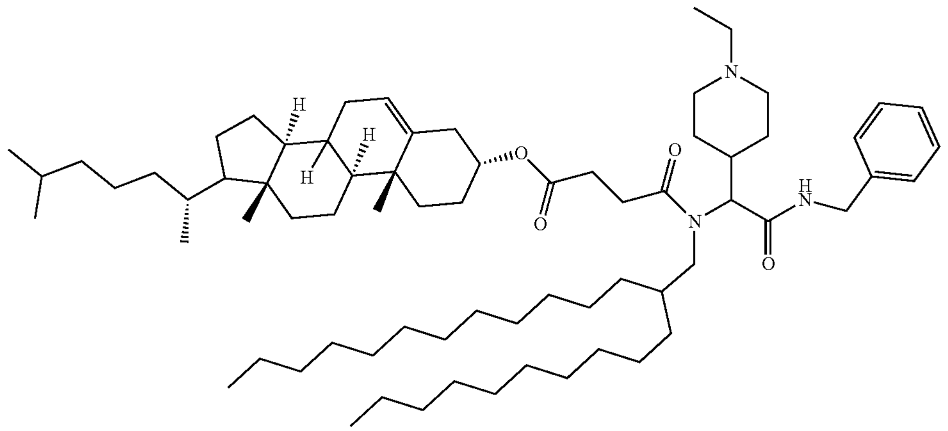

-continued
P245G8
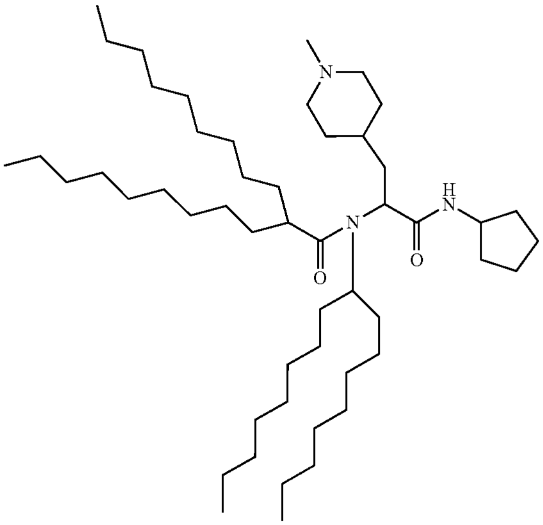
P245A4
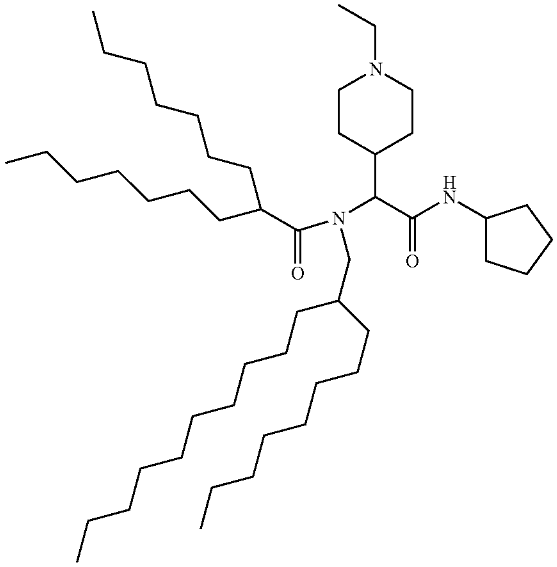
P247C4
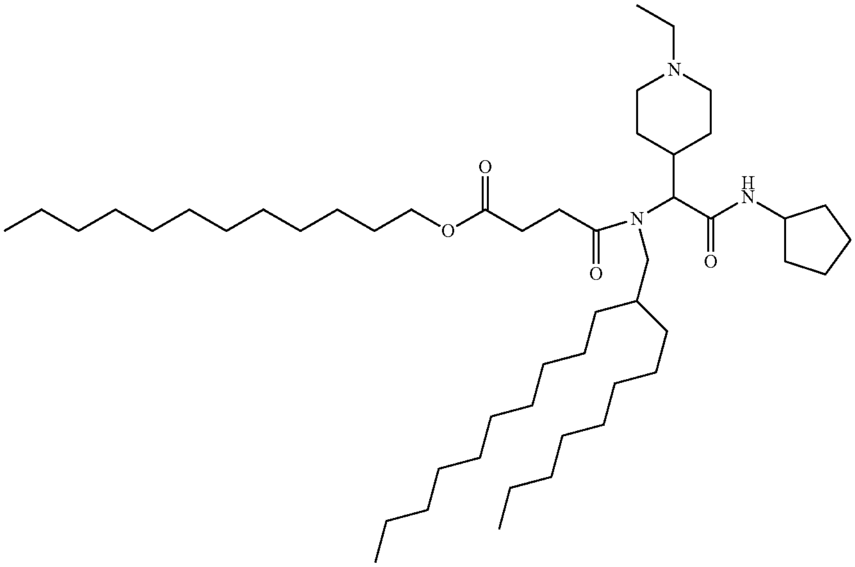
P247C6
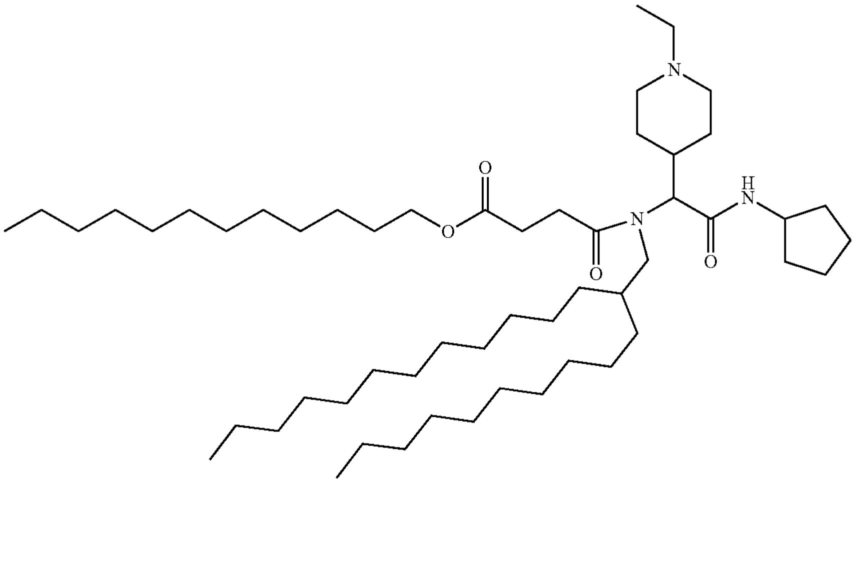

-continued
P247G12
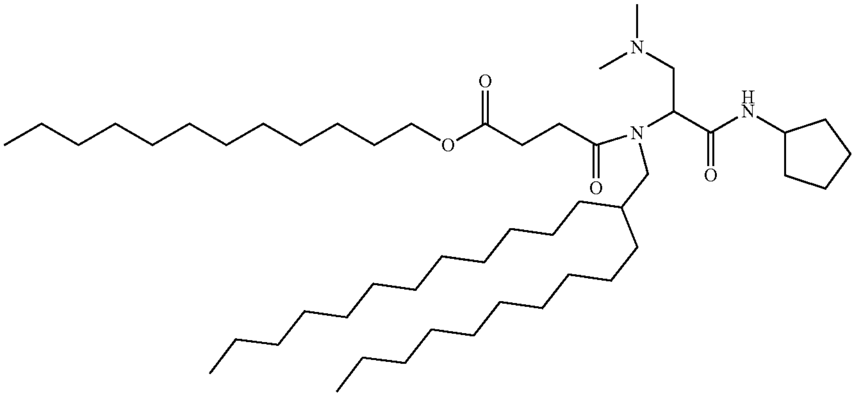
P254B10
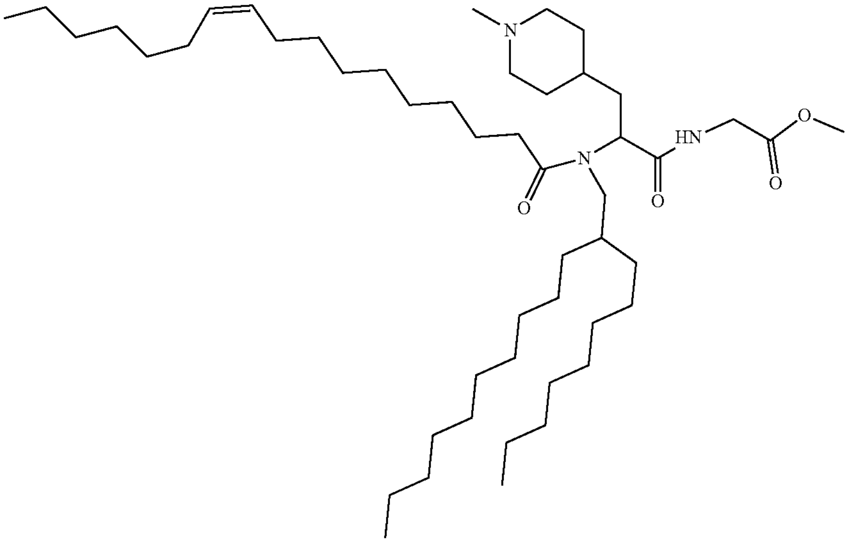
P255C6
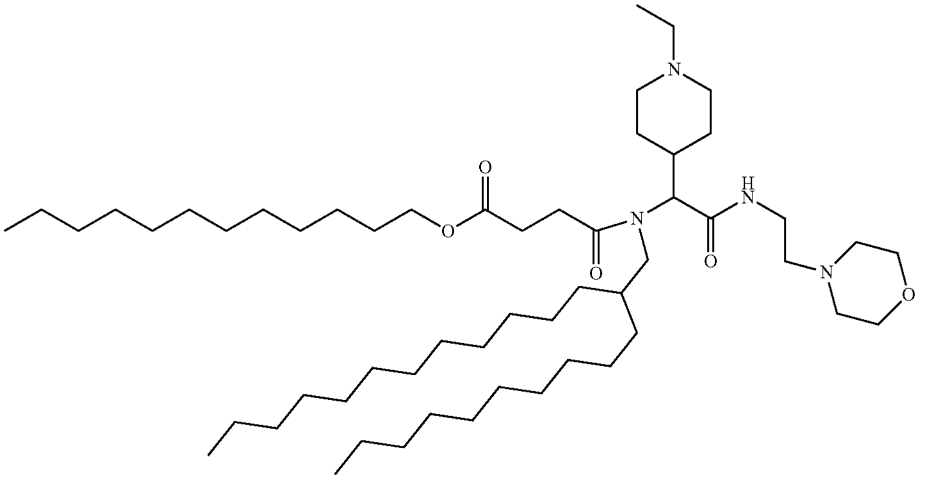

-continued
P255D6
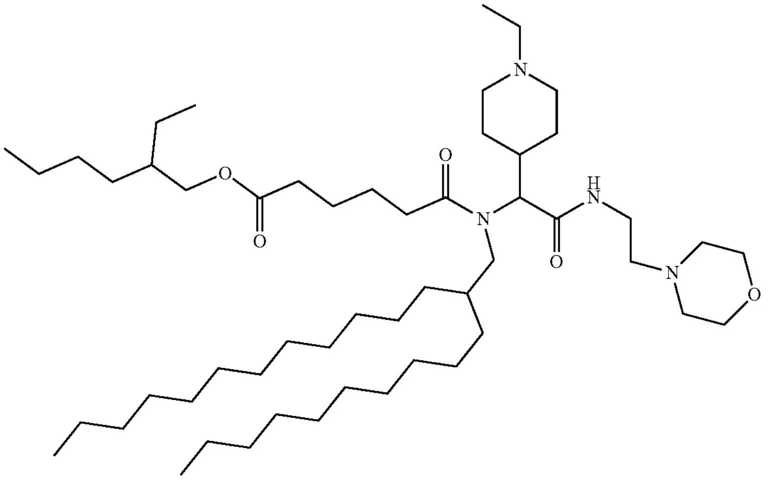
P25GB4
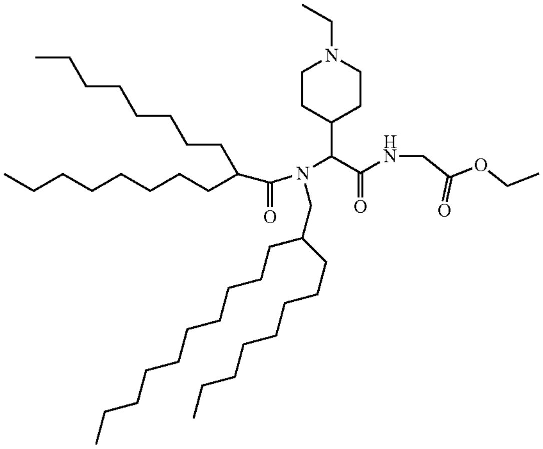
P256C4
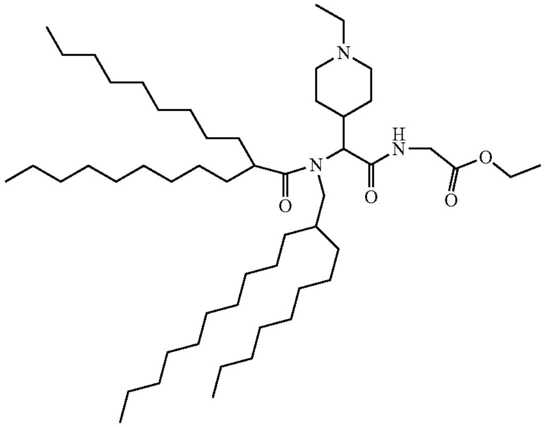
P256C6
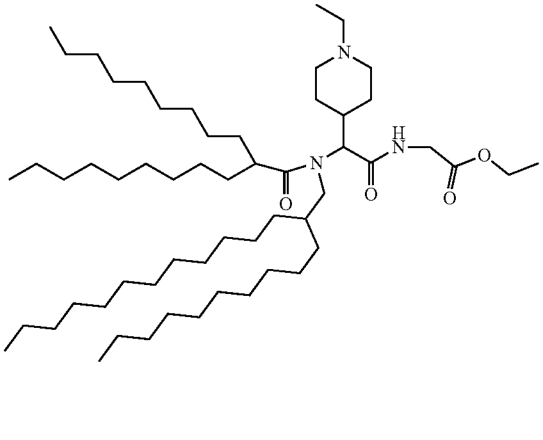
P257A6
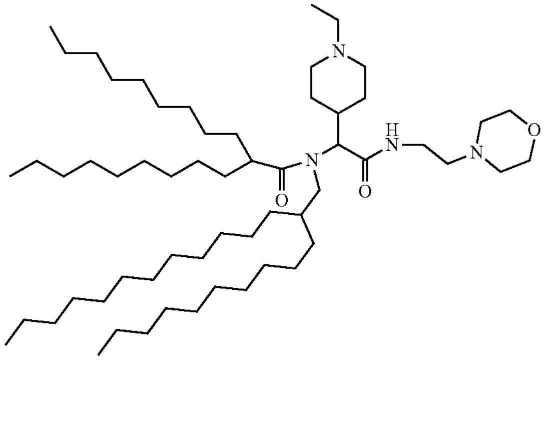

-continued
P258D6
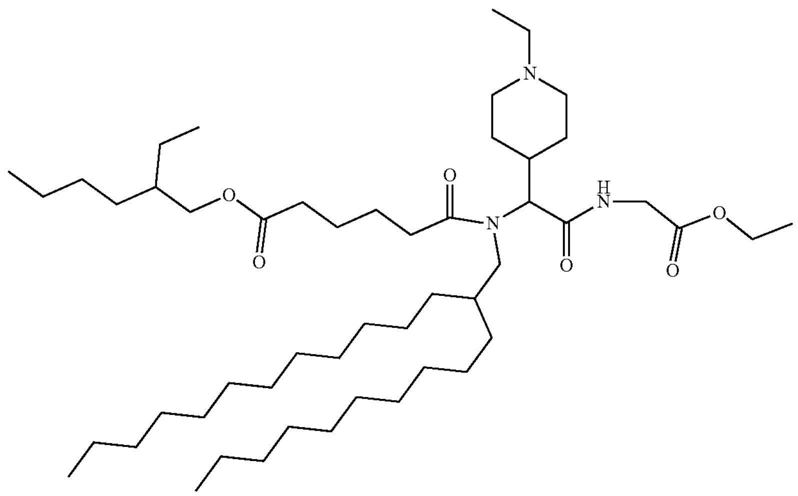
P258D10
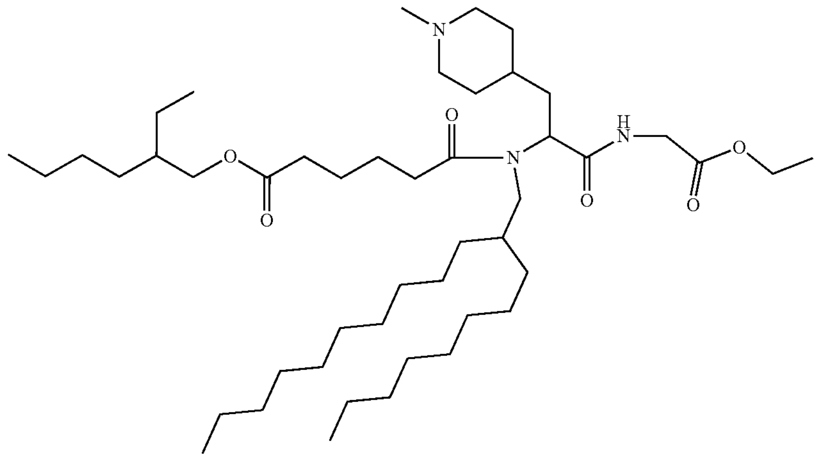
P258C12
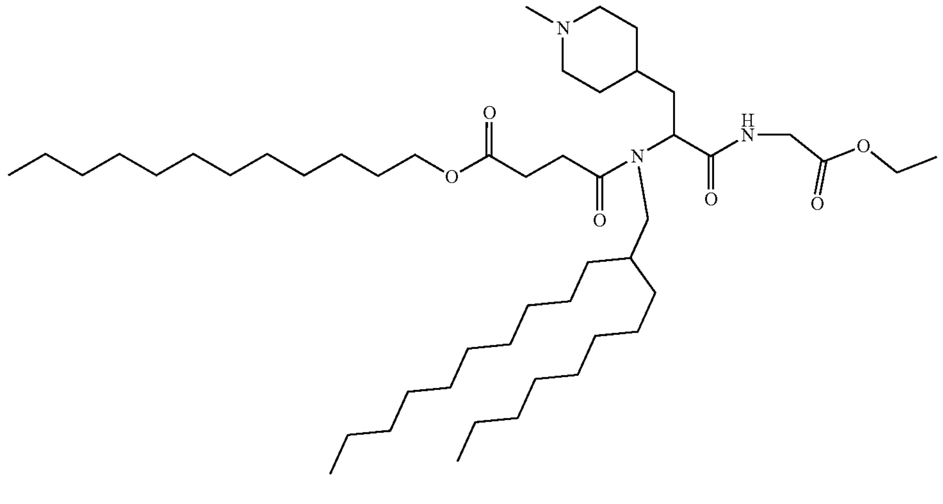

-continued
P259C4
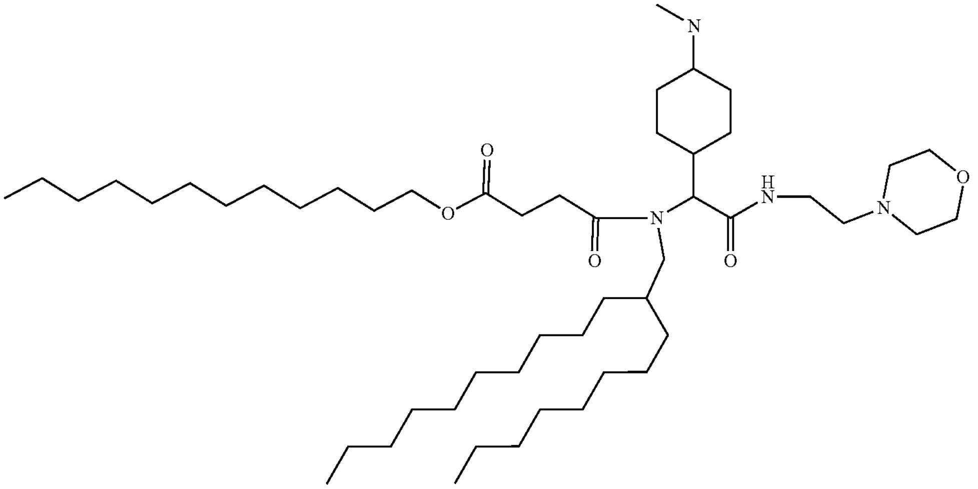
P259C6
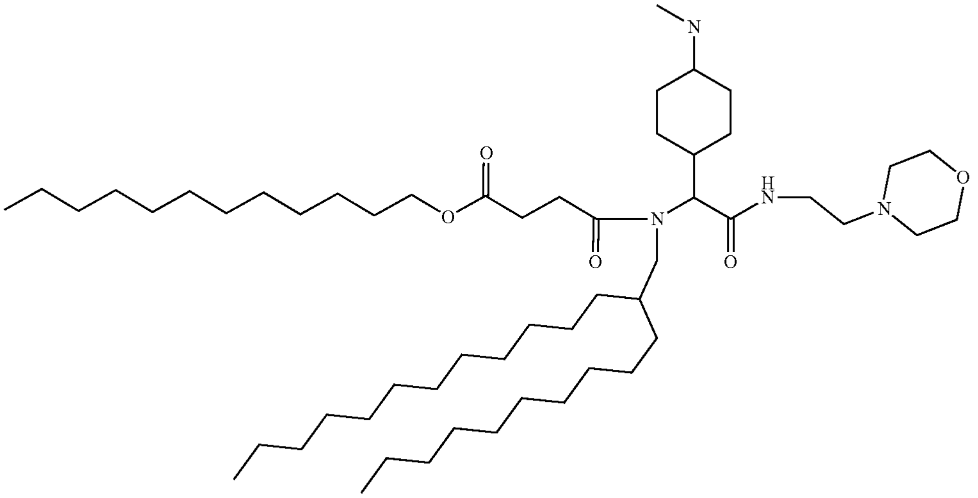
P259D6
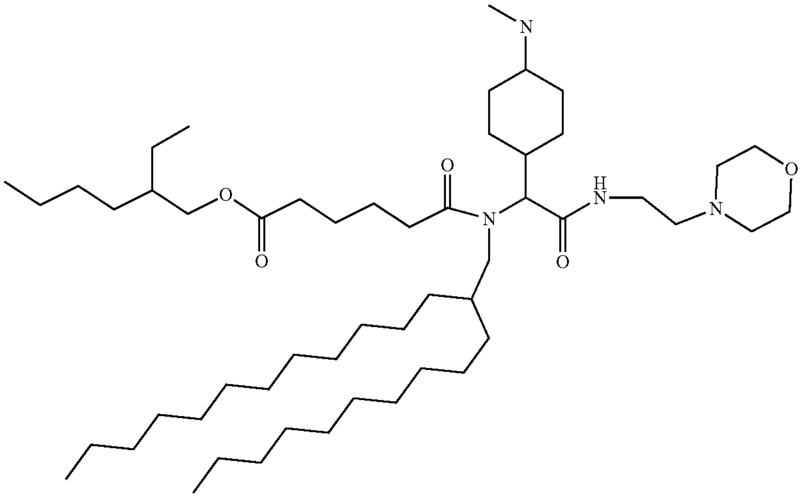

-continued
P259C12
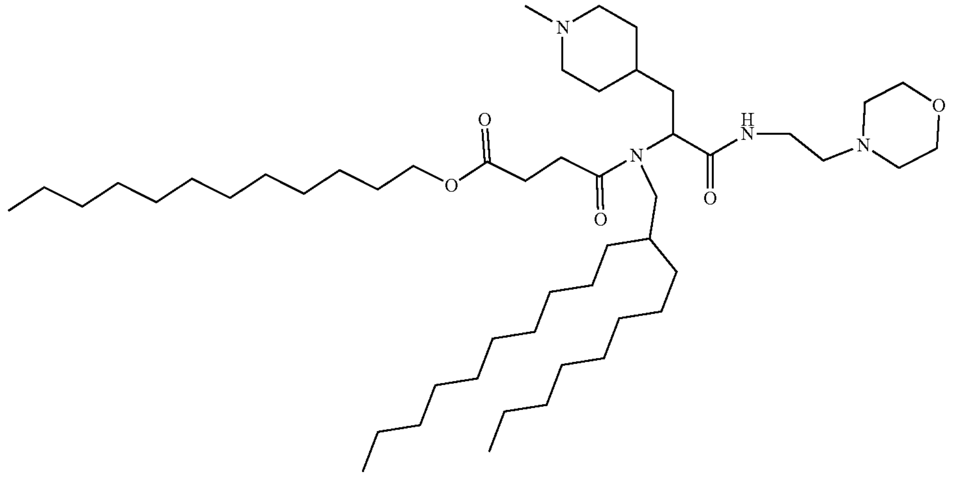
P265E6
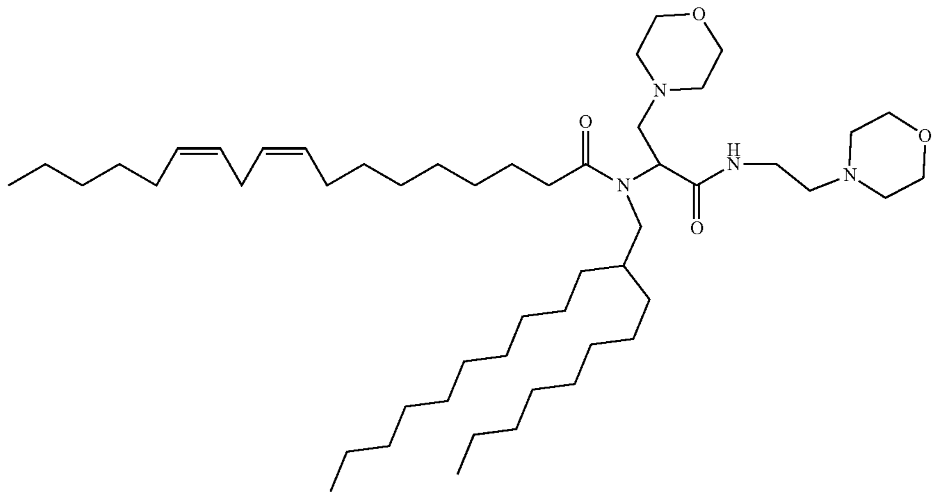
P266A1
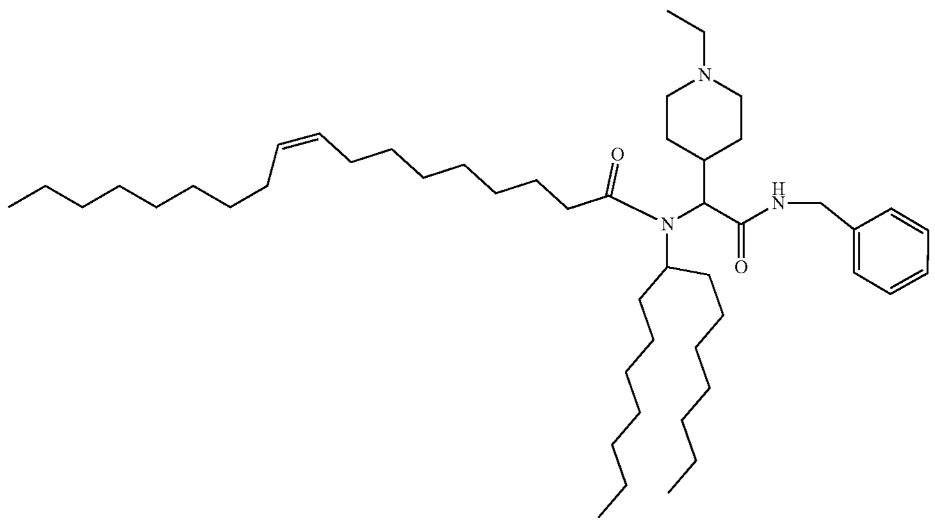

-continued
P266A2
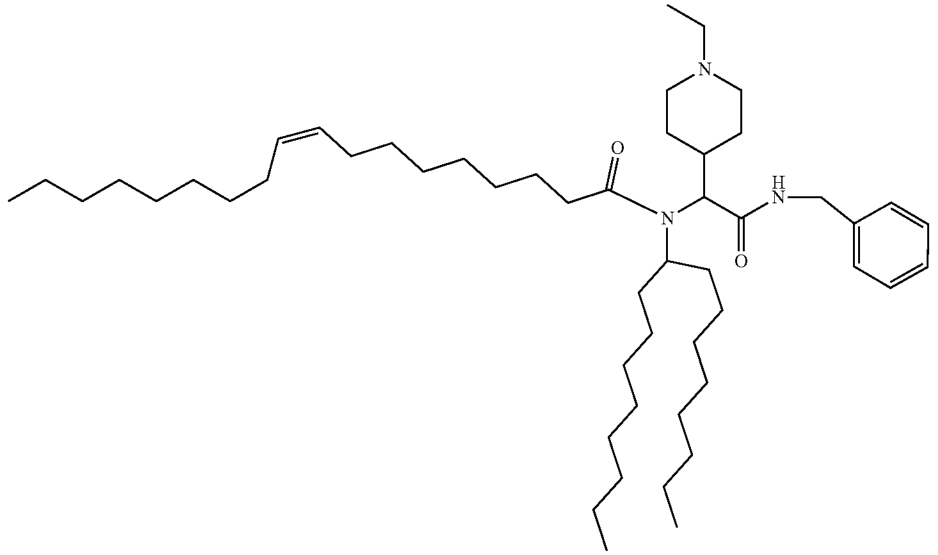
P266A3
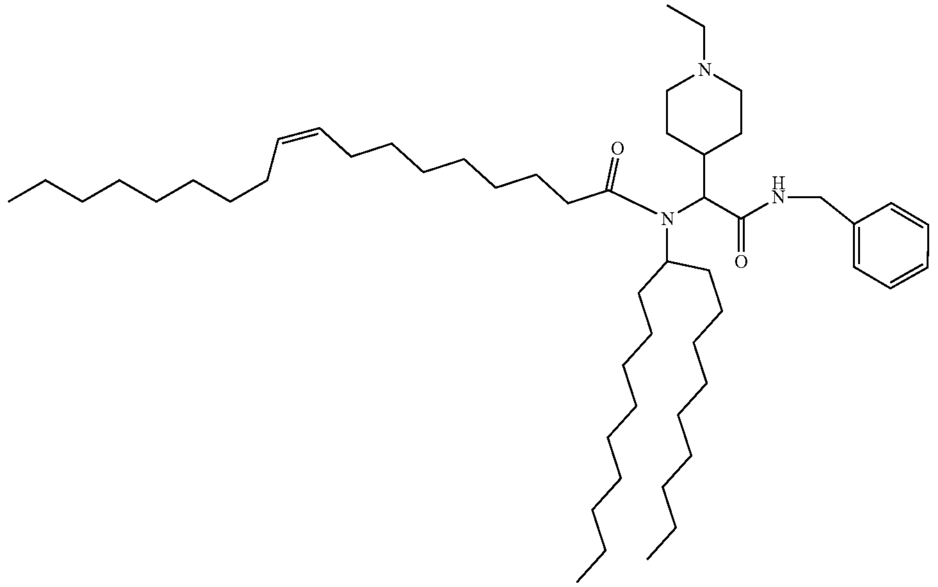

-continued
P266B2
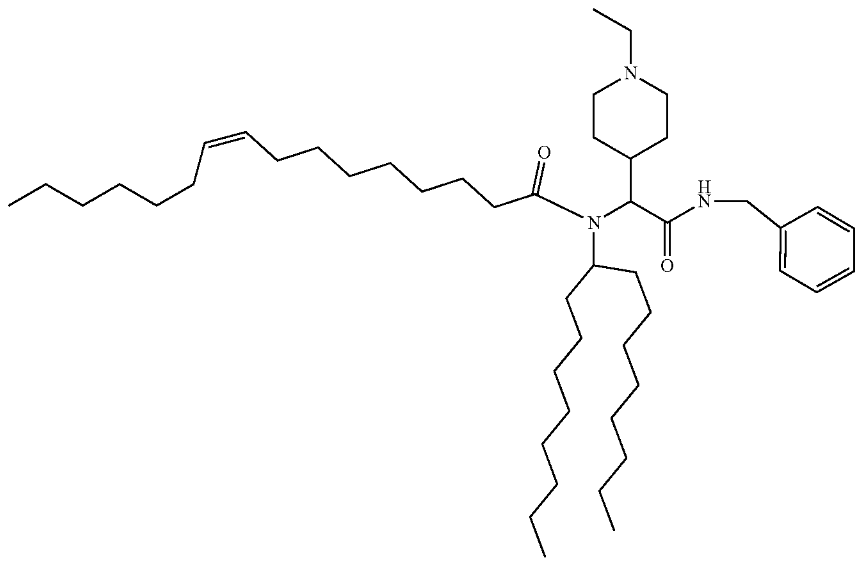
P266F1
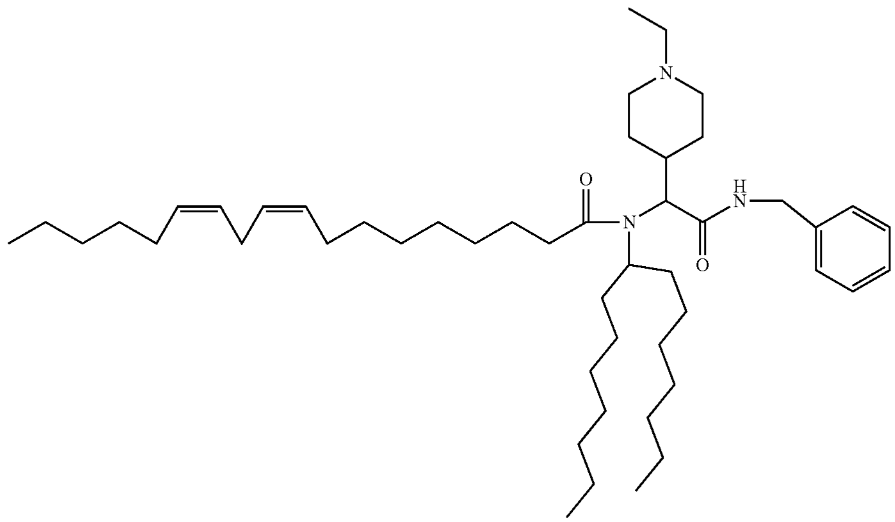
P266F2
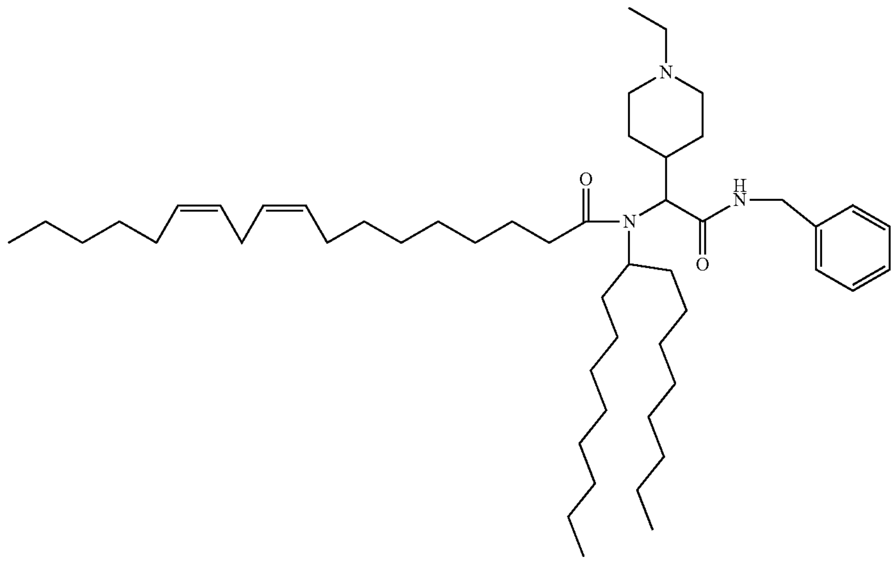

-continued
P266F3
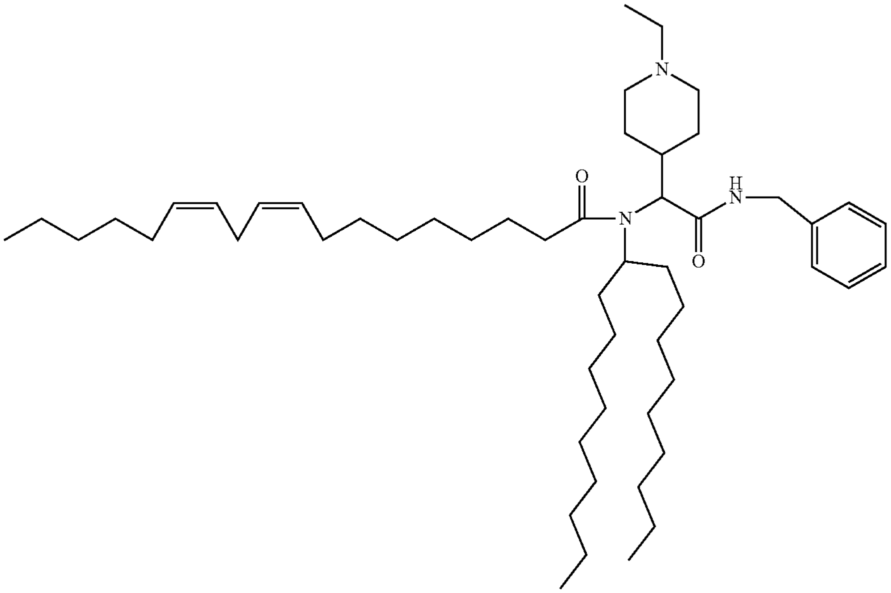
P266G1
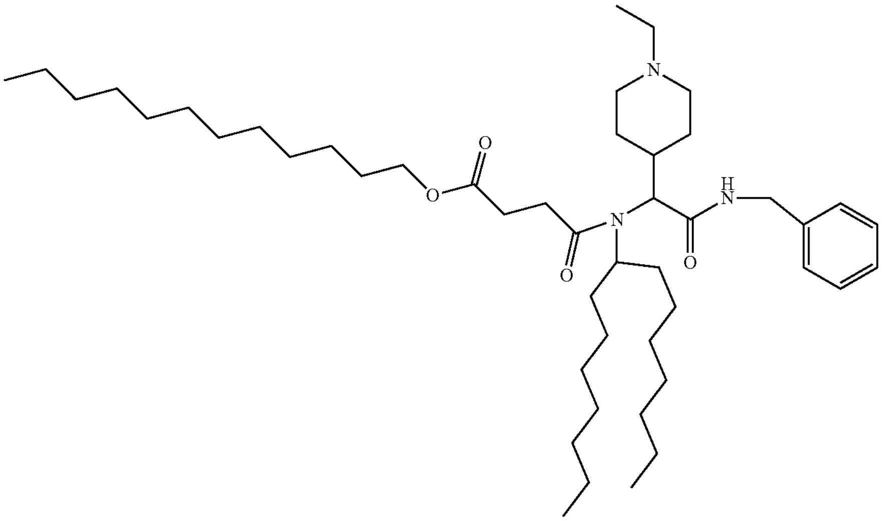

-continued
P266G2
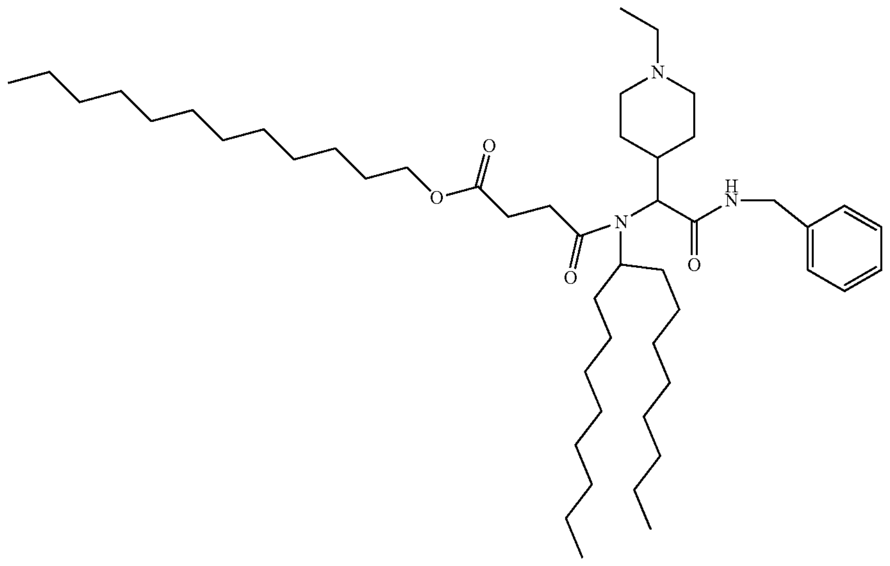
P266G3
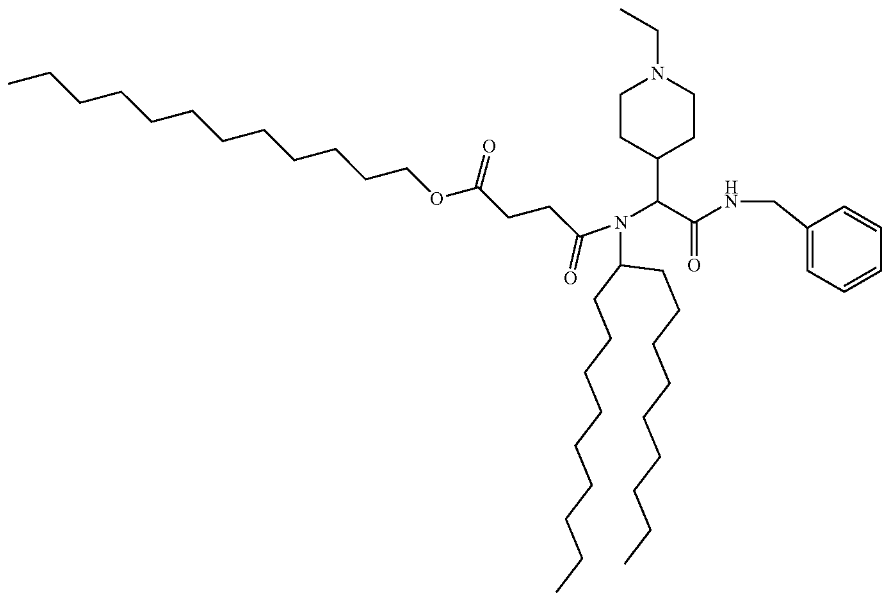

-continued
P266G5
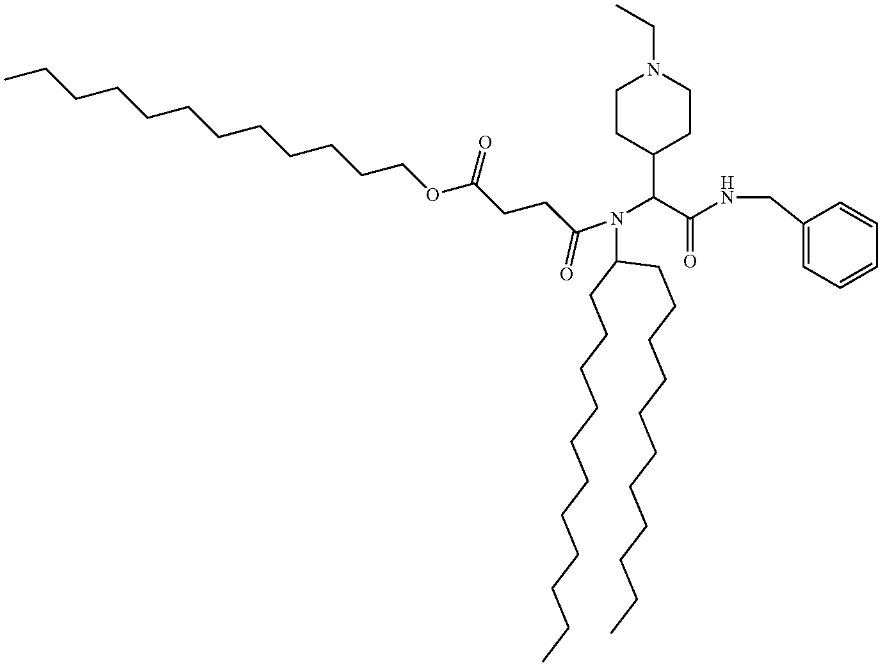
P267G2
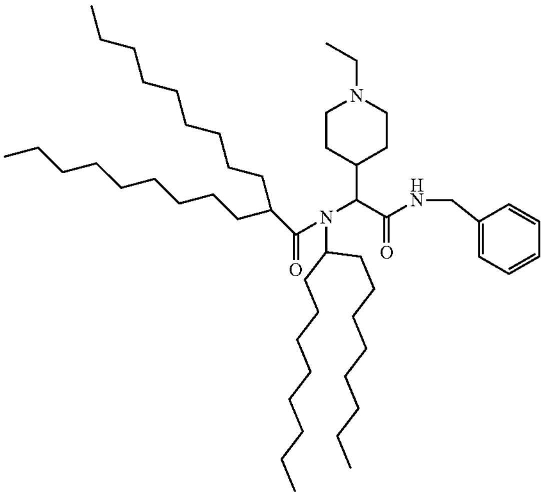
P268B2
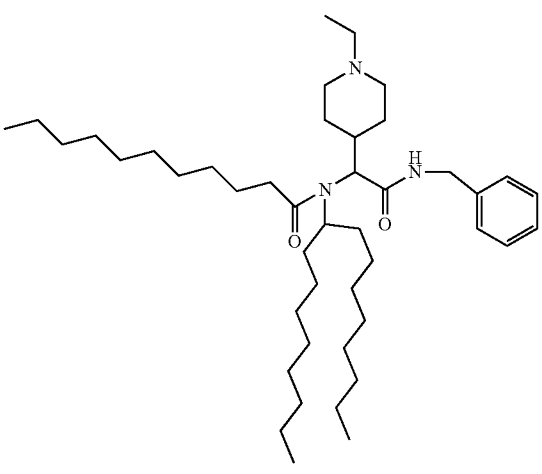

-continued
P269F1
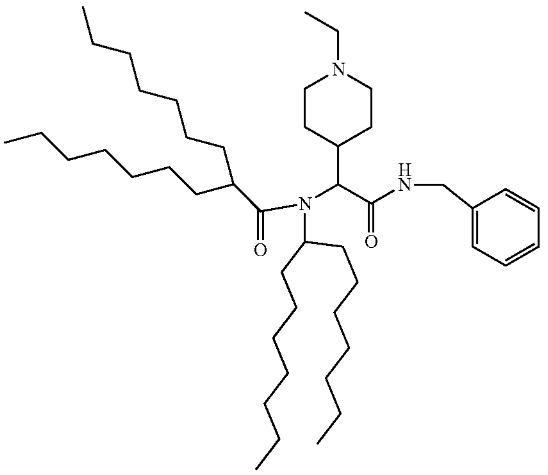
P287AG
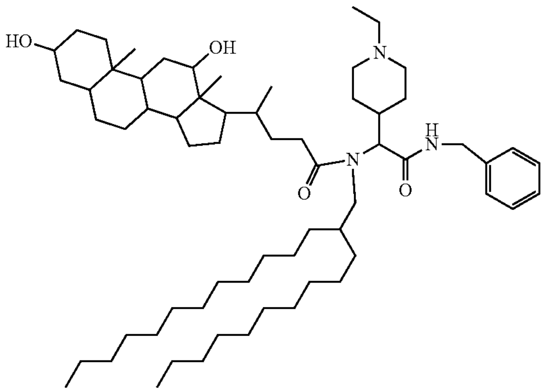
P287A10
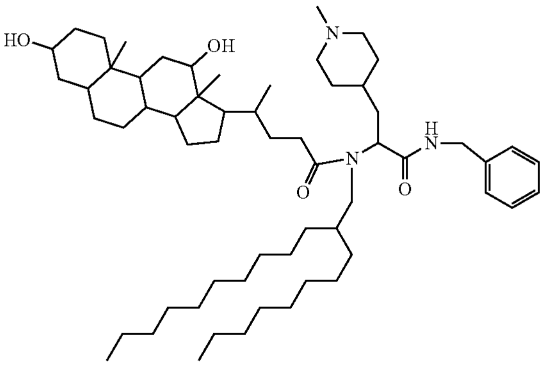
P287B10
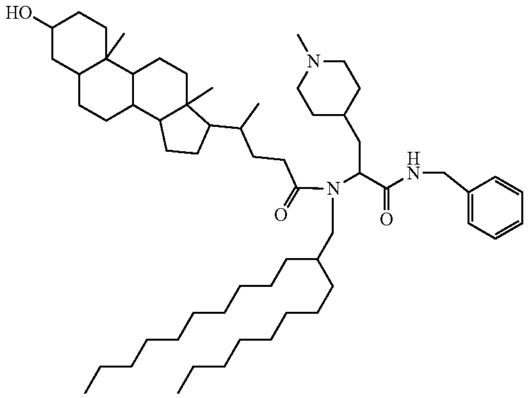
P287B12
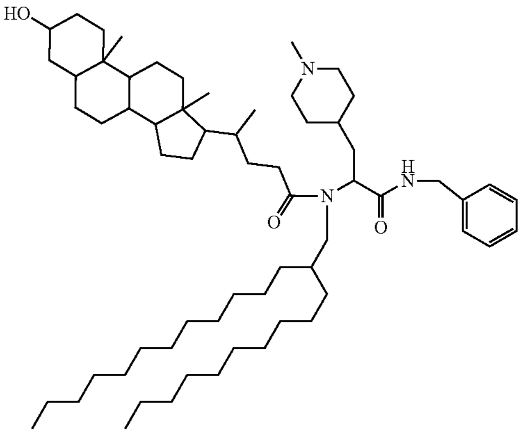
P287C4
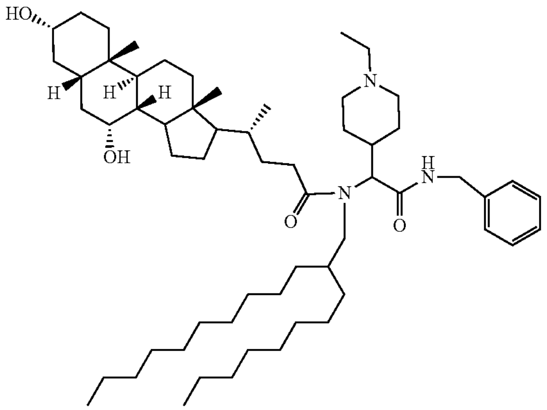

-continued
P287C6
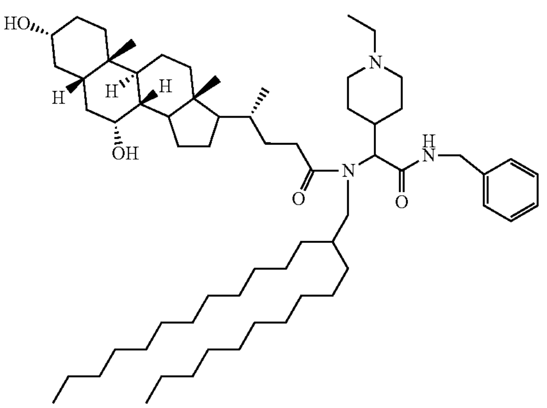
P287C10
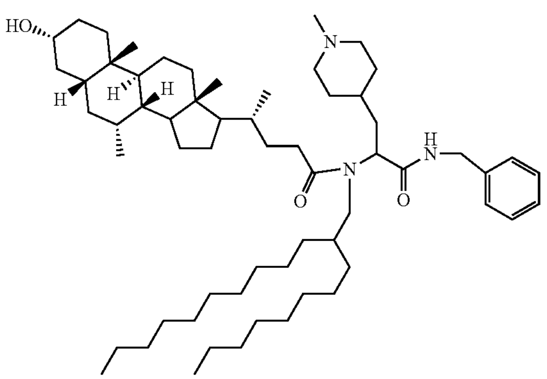
P287D10
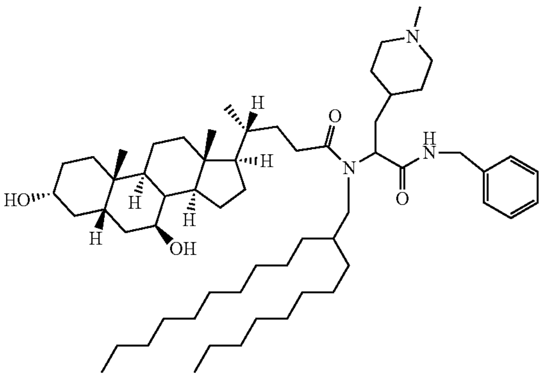
P287F4
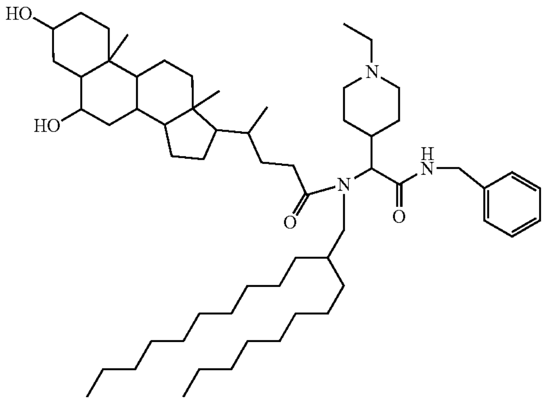
P287F6
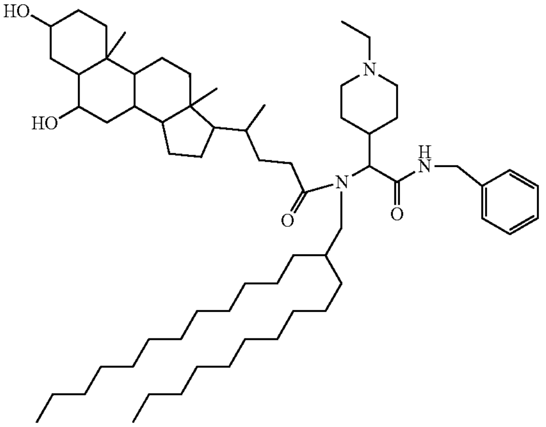
P287F10
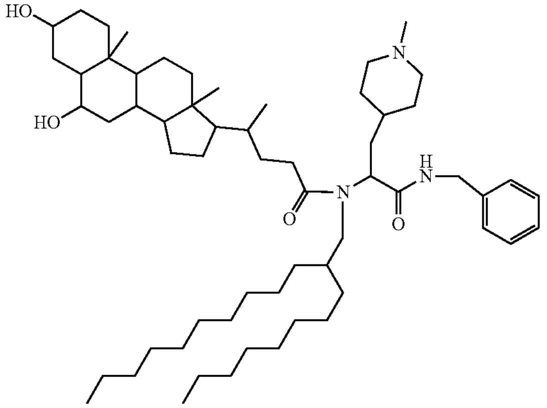

-continued
P287F12
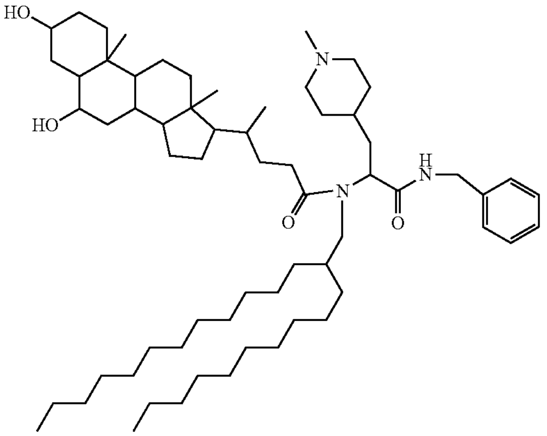
P294A6
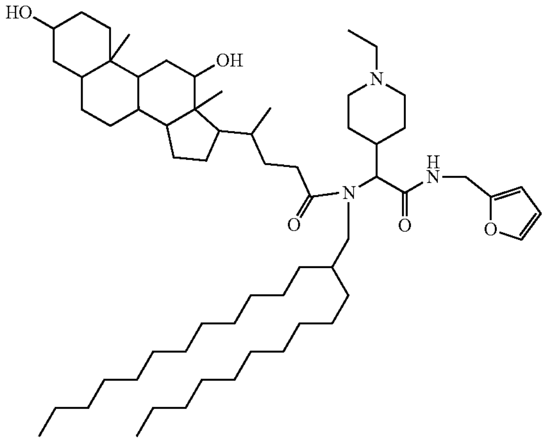
P310B10
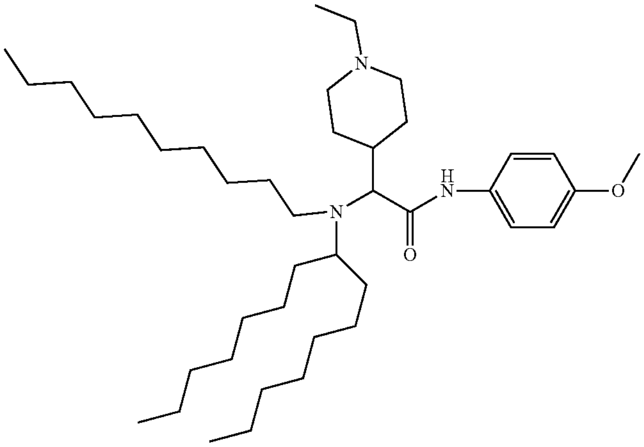
P310E12
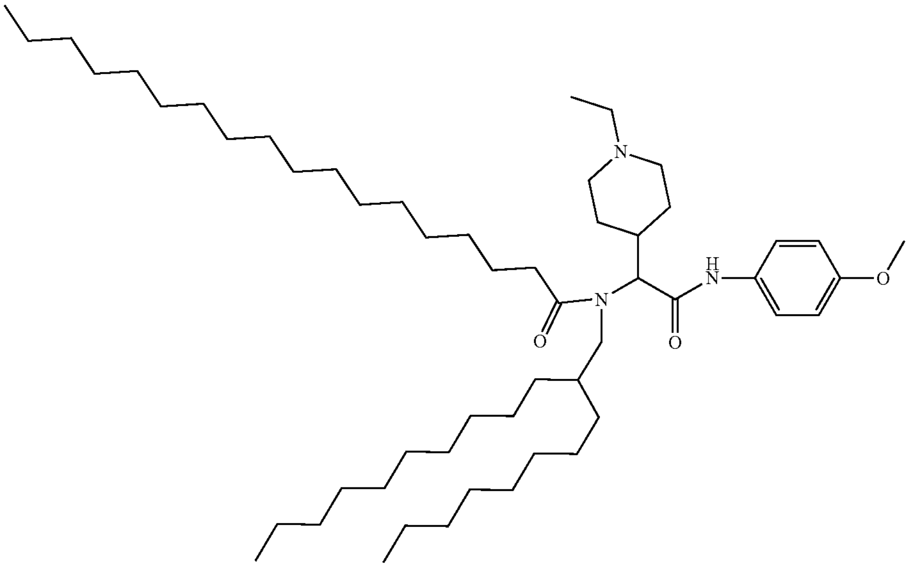

-continued
P312A1
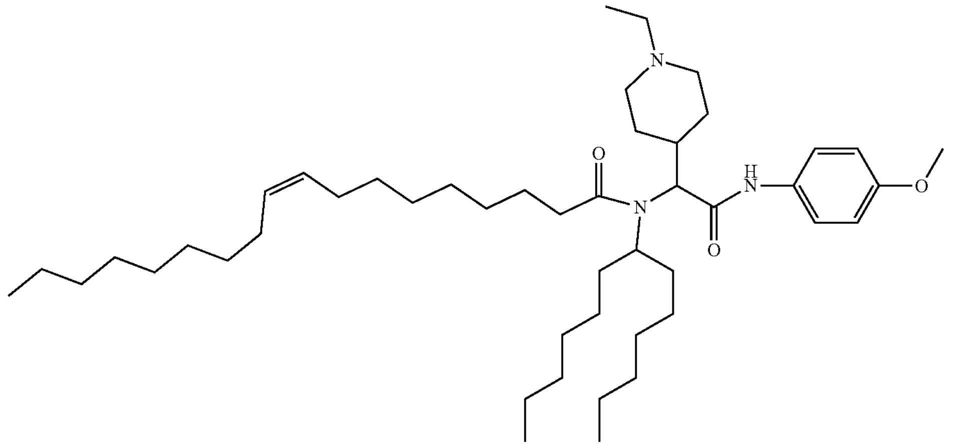
P312B1
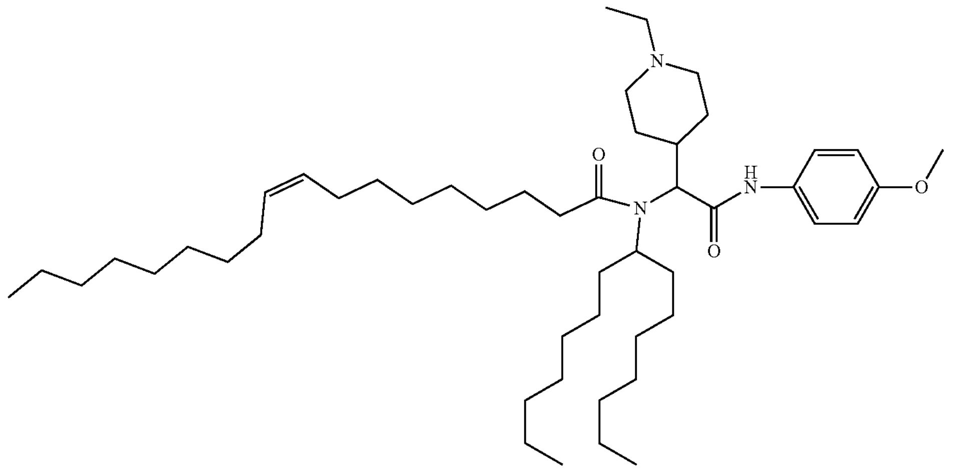
P312C1
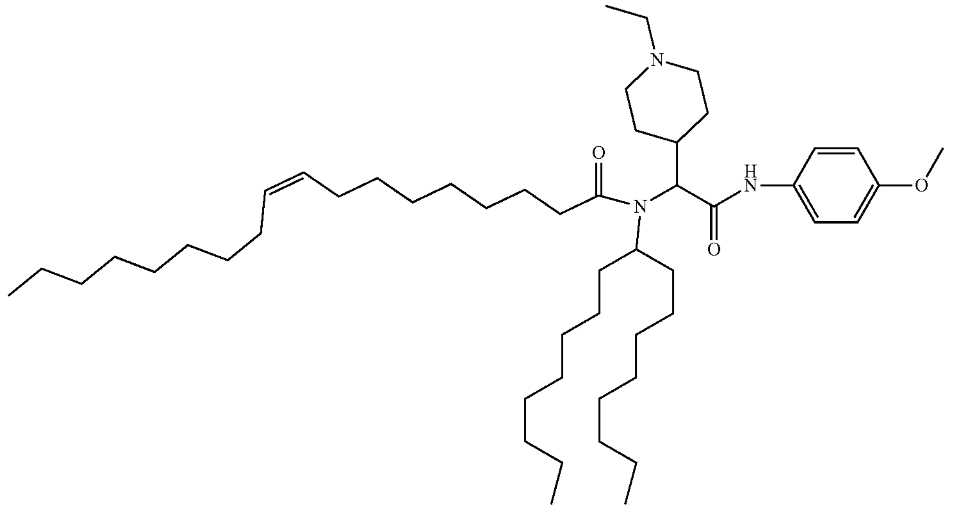

-continued
P312D1
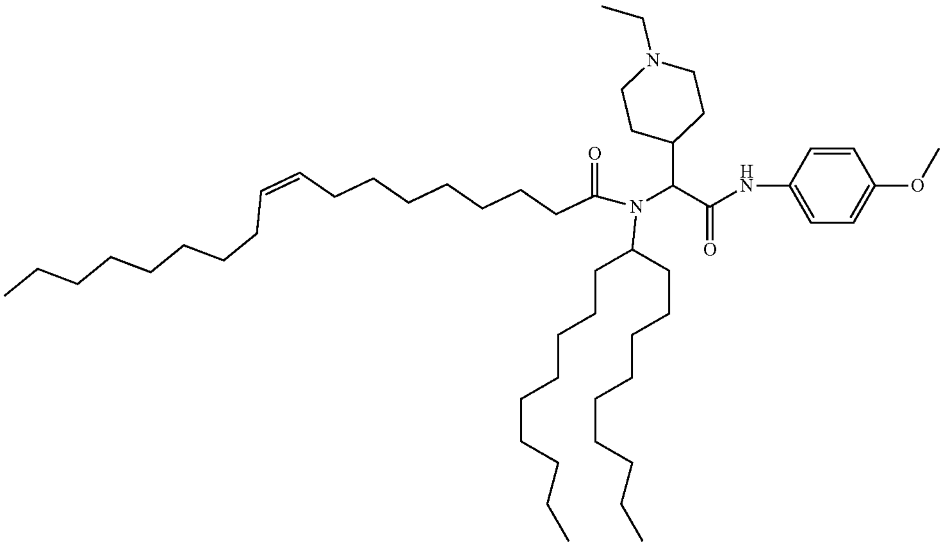
P312E1
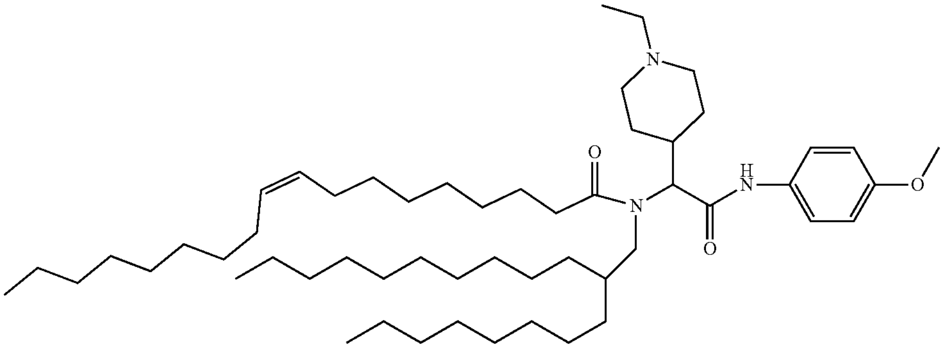
P312B3
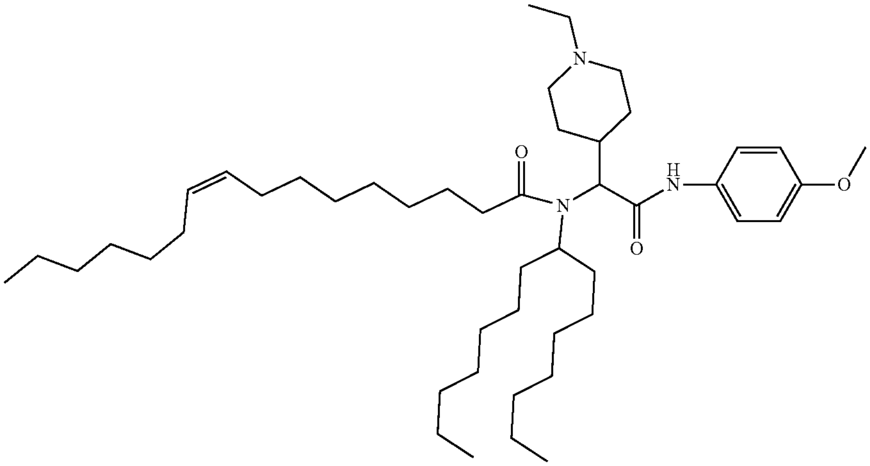

-continued
P312C3
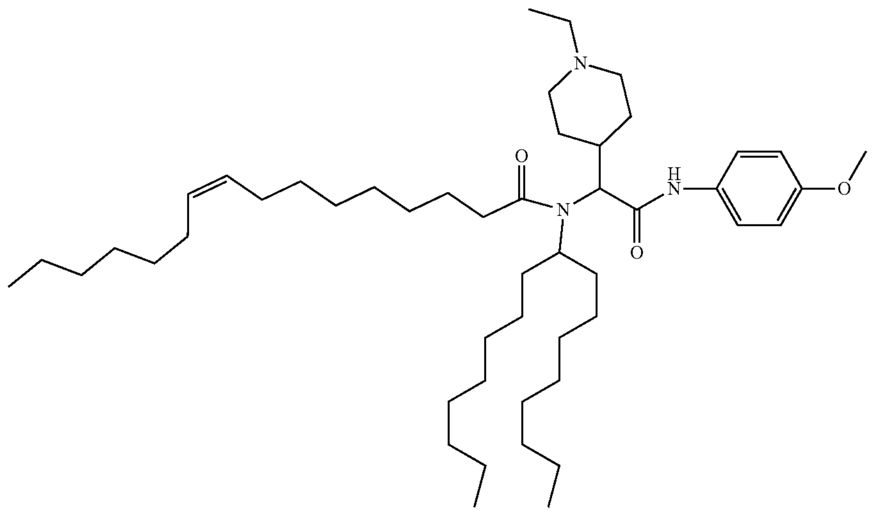
P312E3
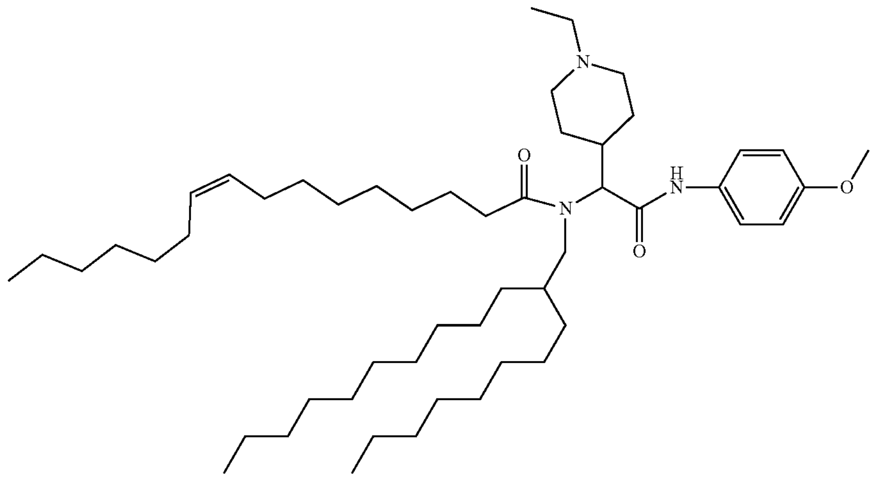
P312B6
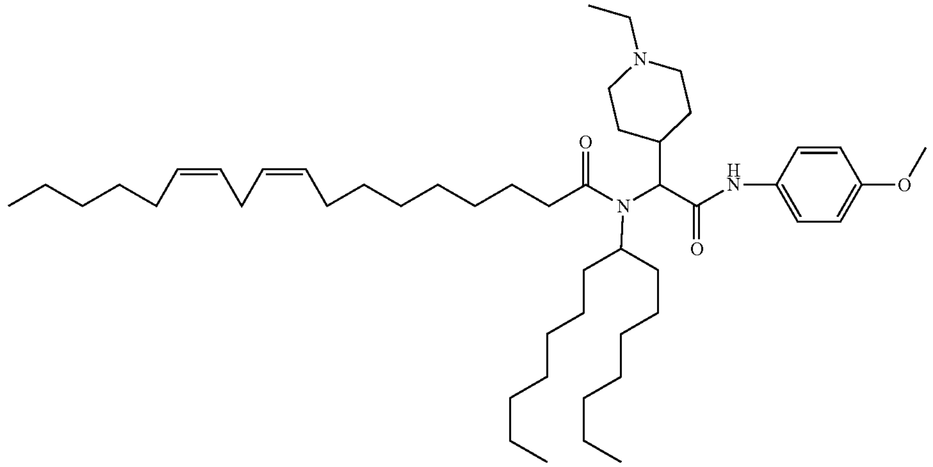

-continued
P312C6
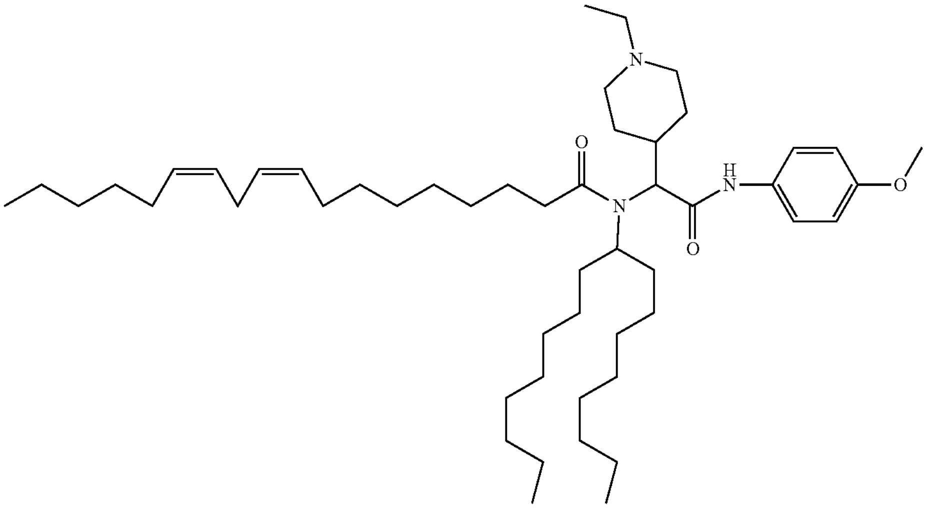
P312B7
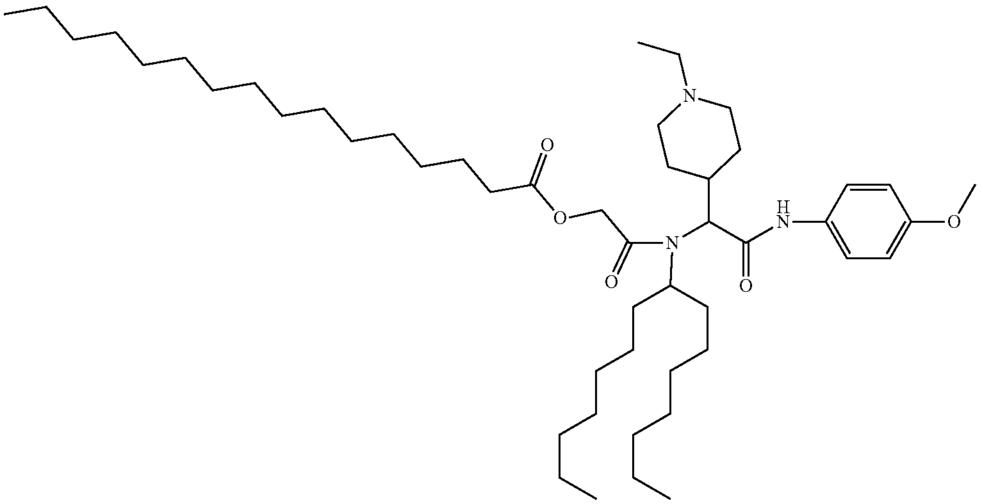
P312C7
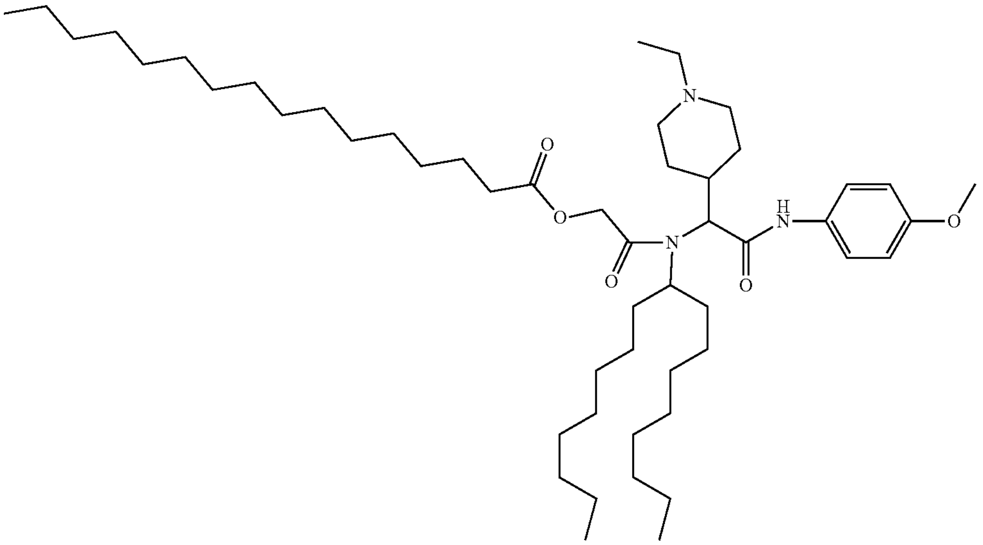

-continued
P312E7
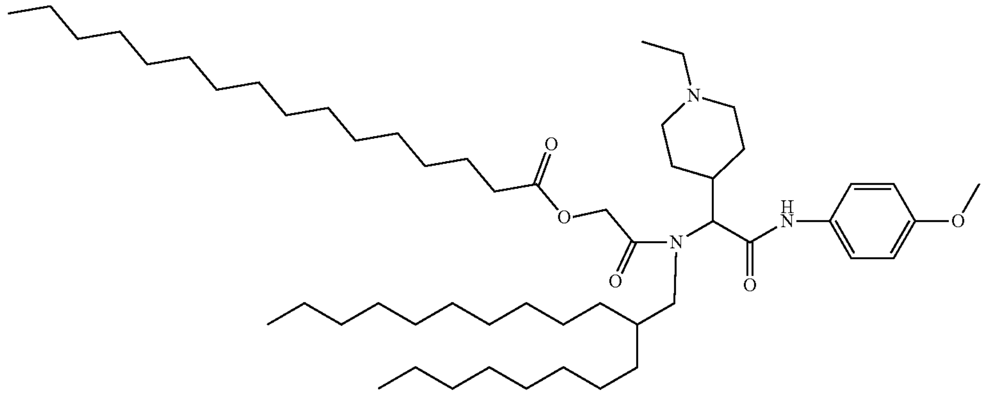
P313B1
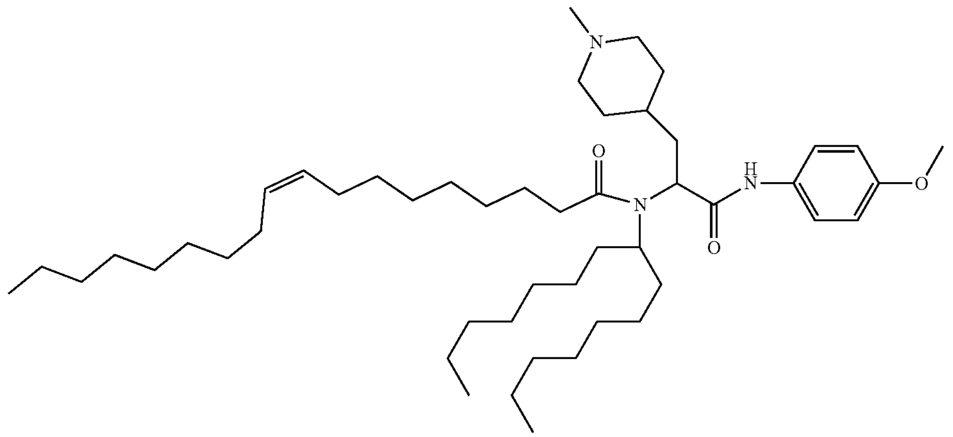
P313C1
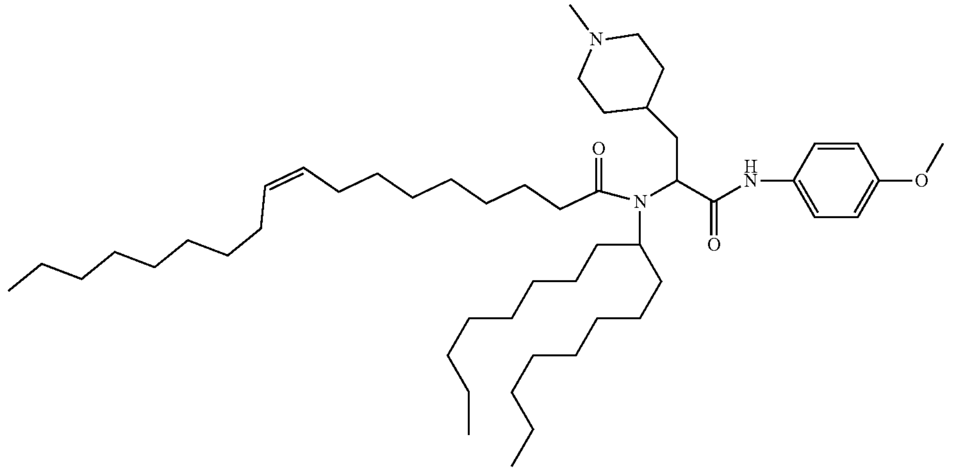

-continued
P313C6
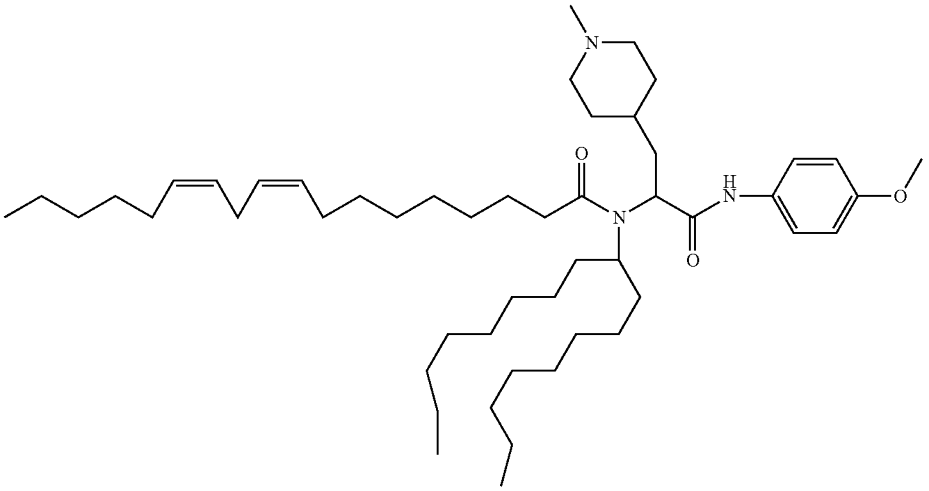
P313C7
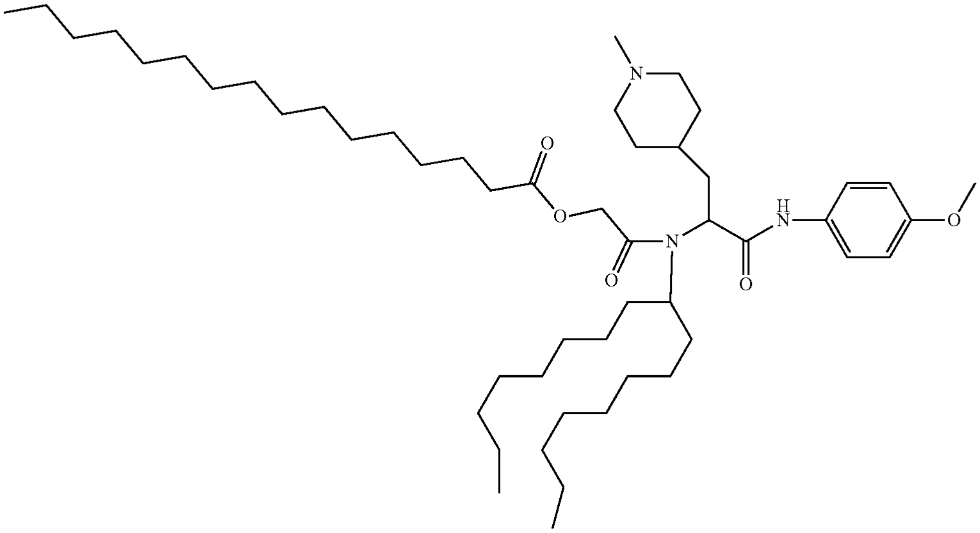
P313C8
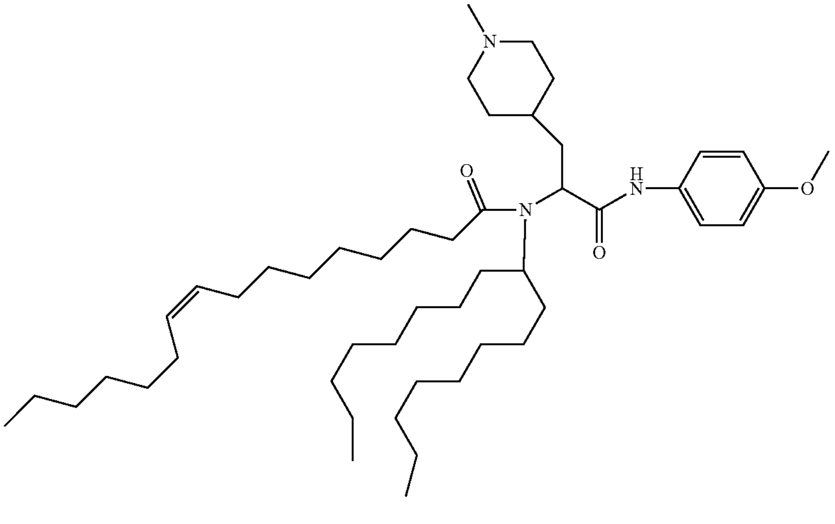

-continued
P314E1
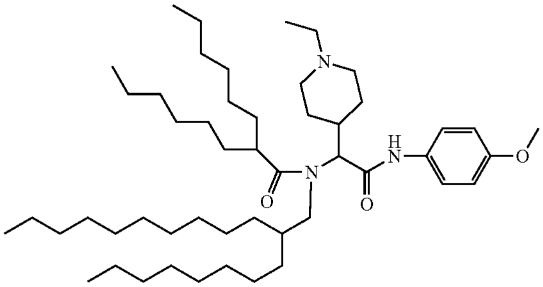
P314E3
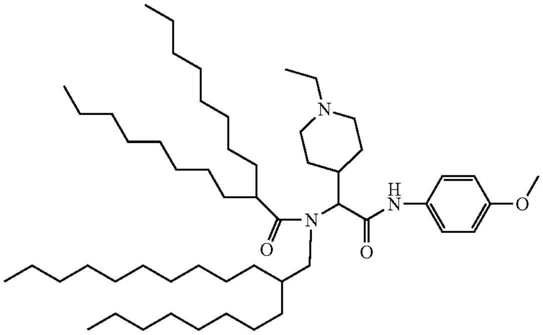
P314F1
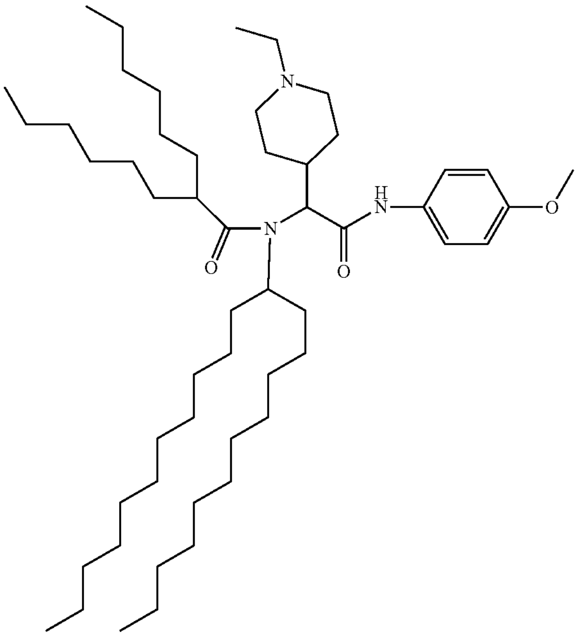
P314G1
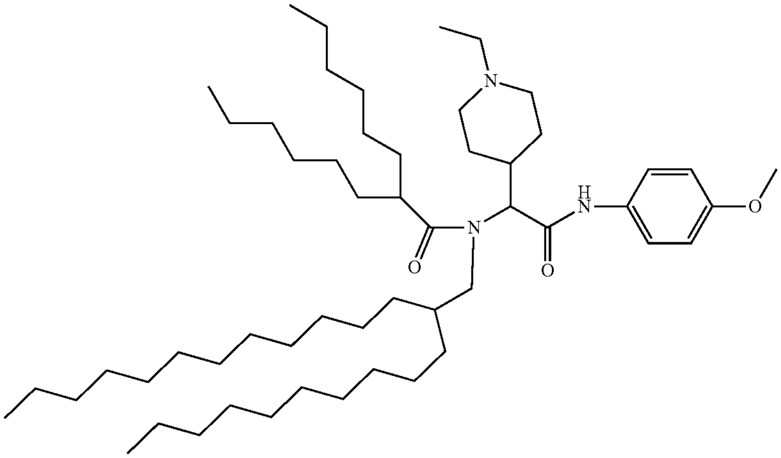

-continued
P316B6
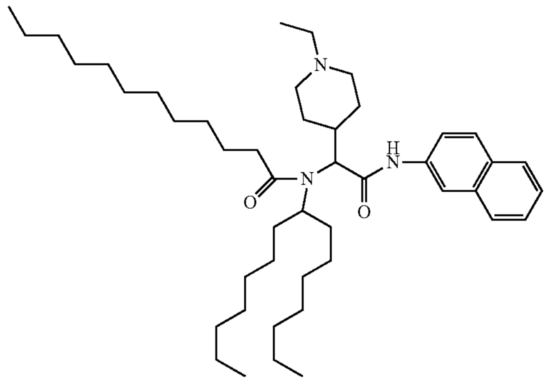
P316B7
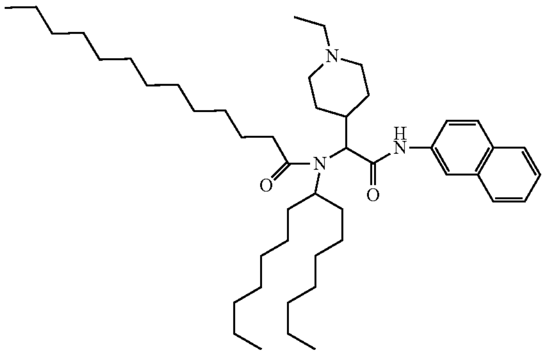
9316B8
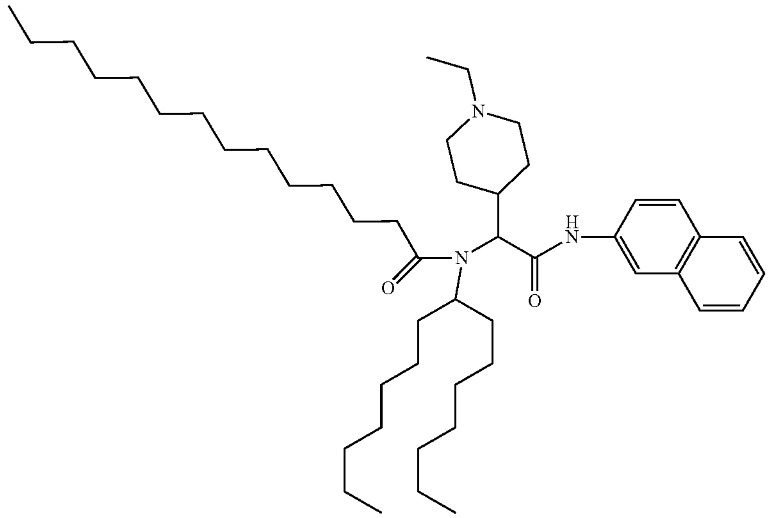
P316B10
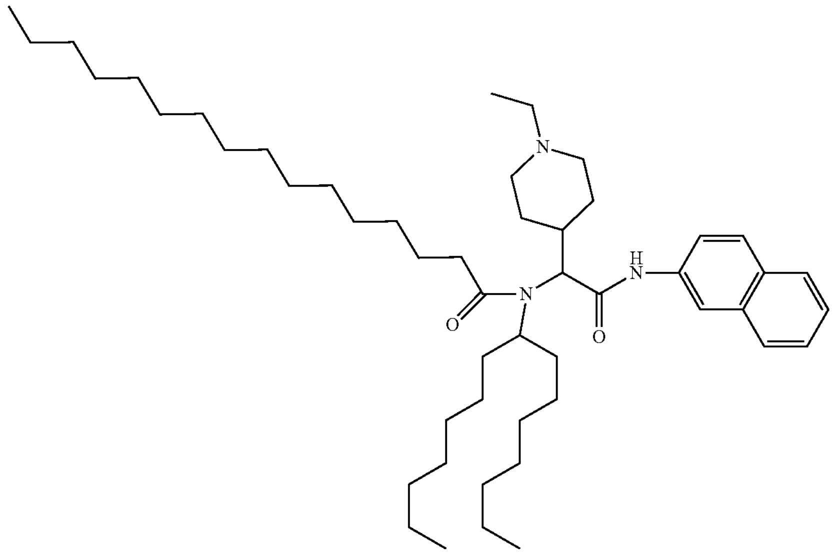

-continued
P316B11
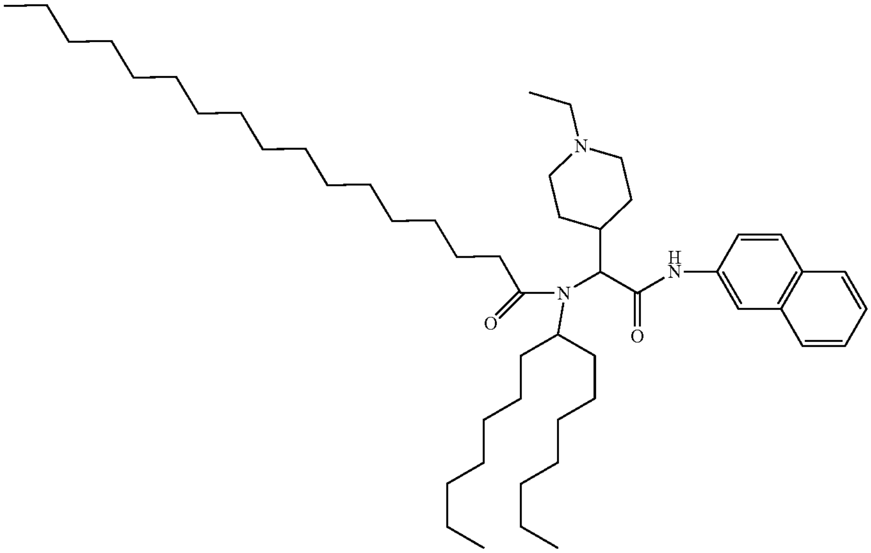
P316C8
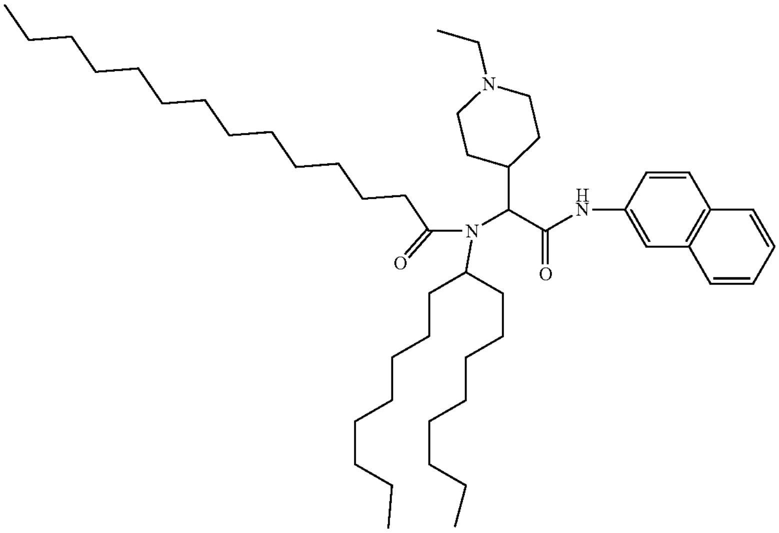
P316C11
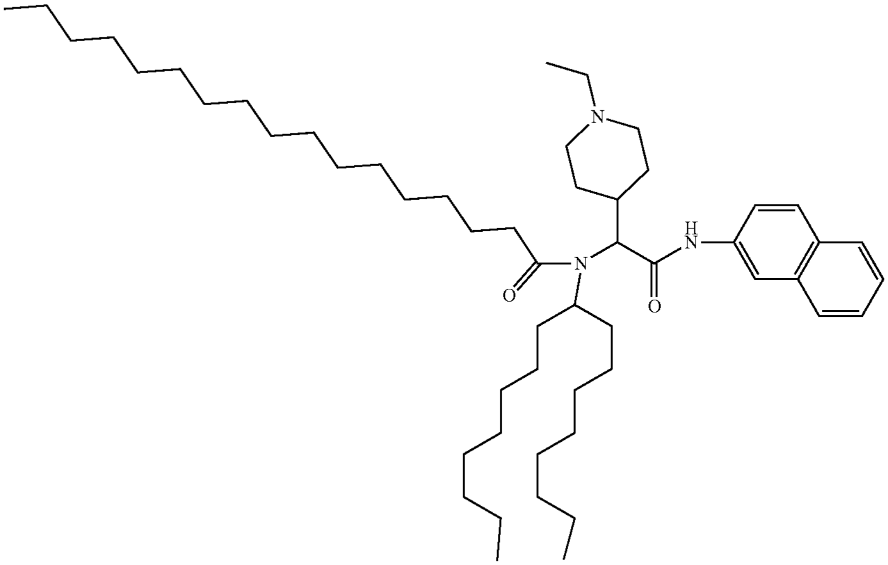

-continued
P316E1
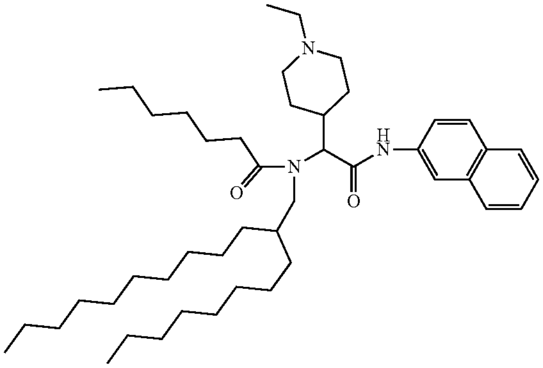
P316E5
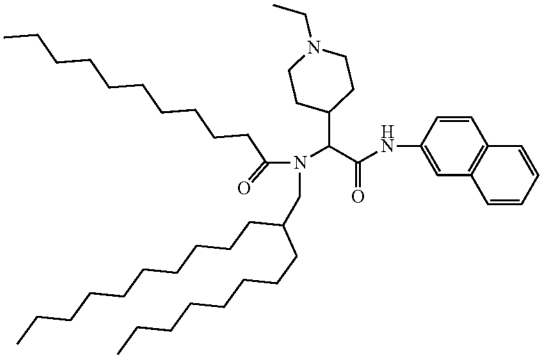
P316E6
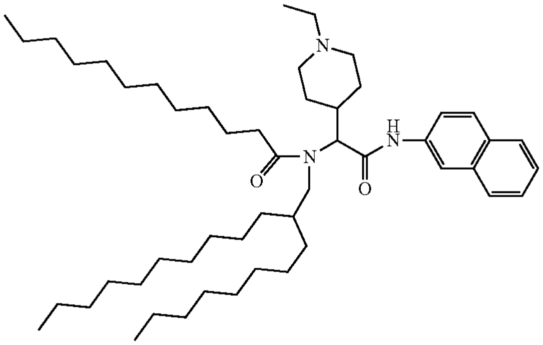
P316E7
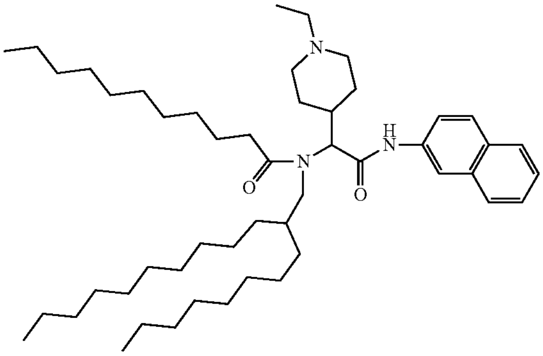
P316E8
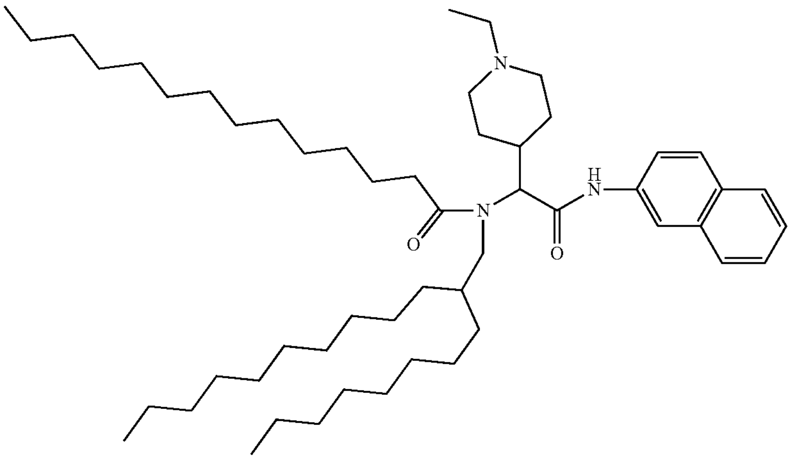

-continued
P316E10
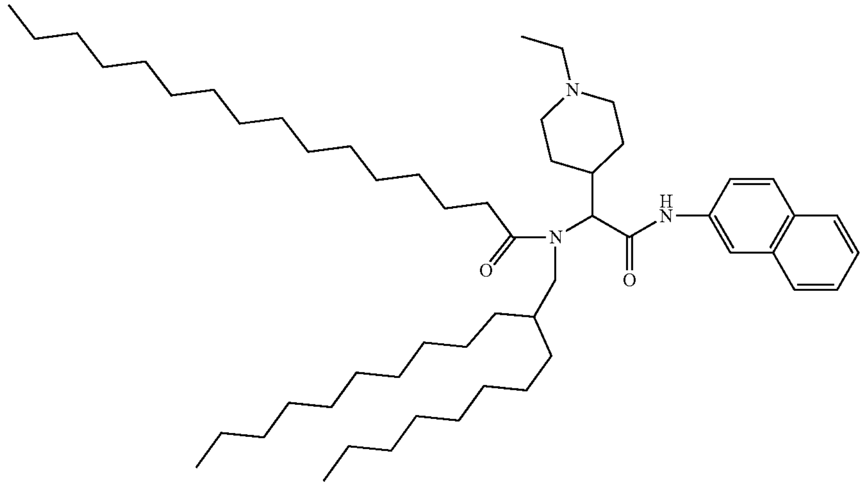
P316E11
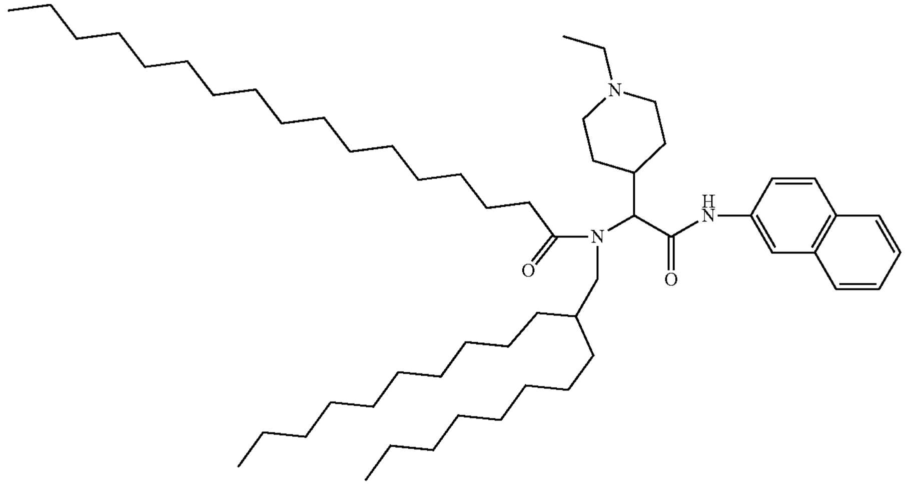
P316E12
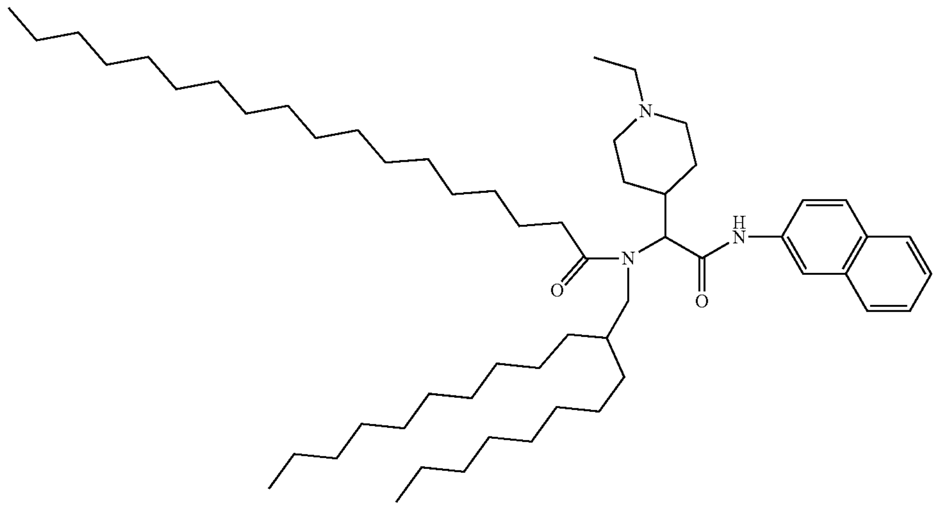

-continued
P318B1
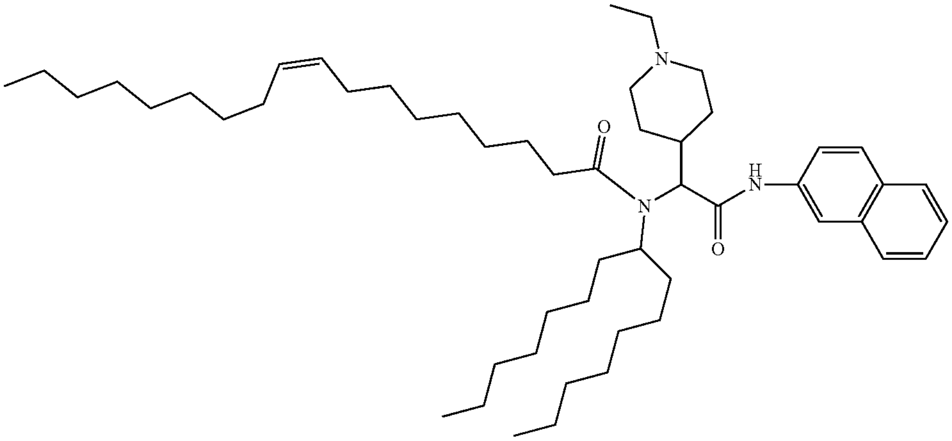
P318C1
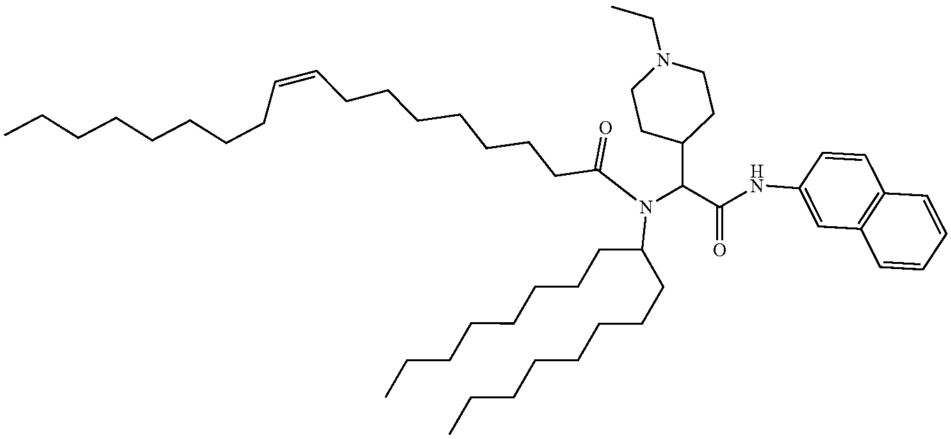
P318E1
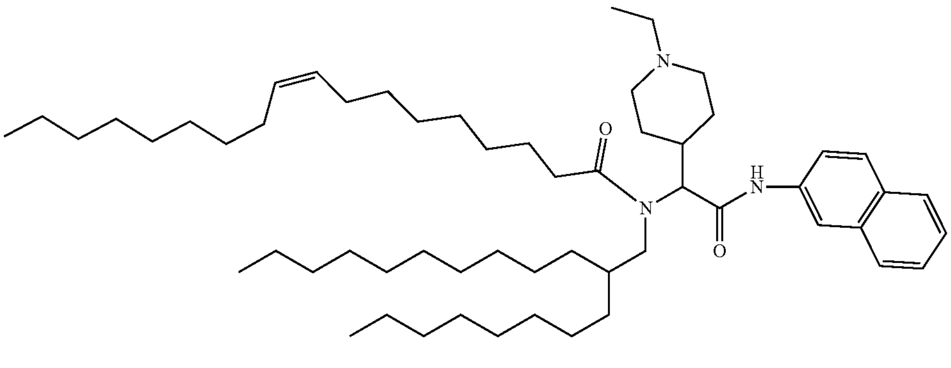

-continued
P318F1
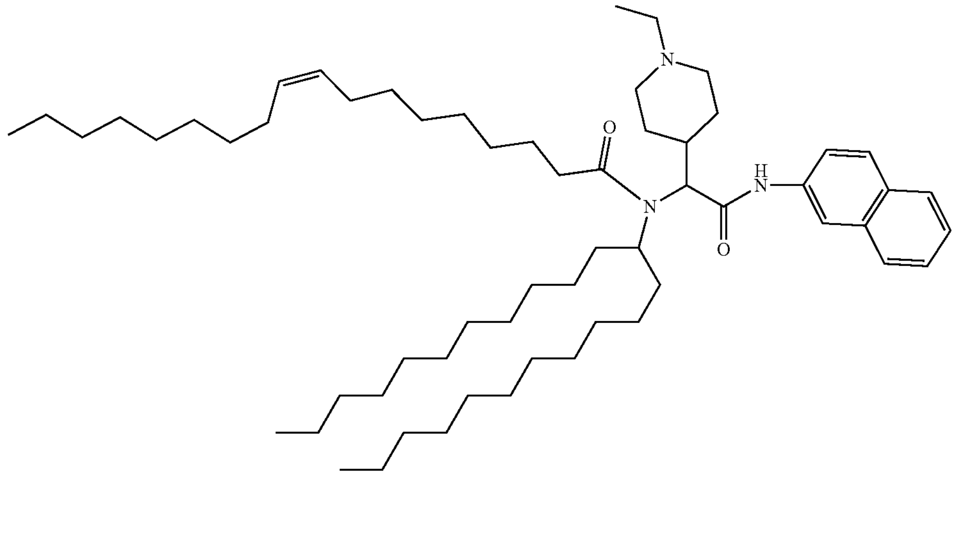
P318G1
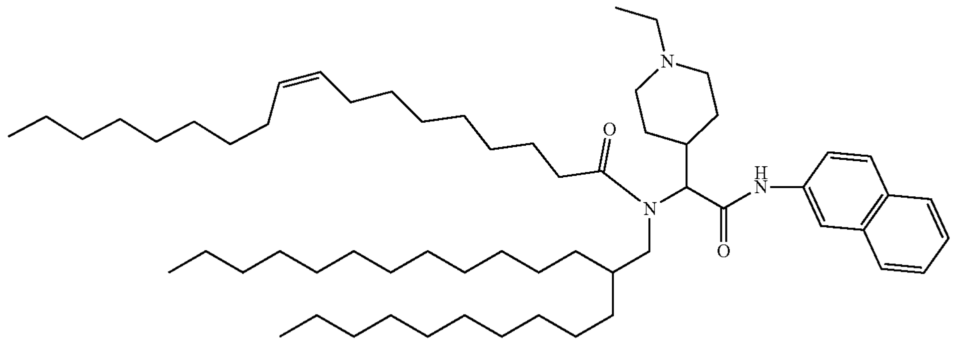
P318B3
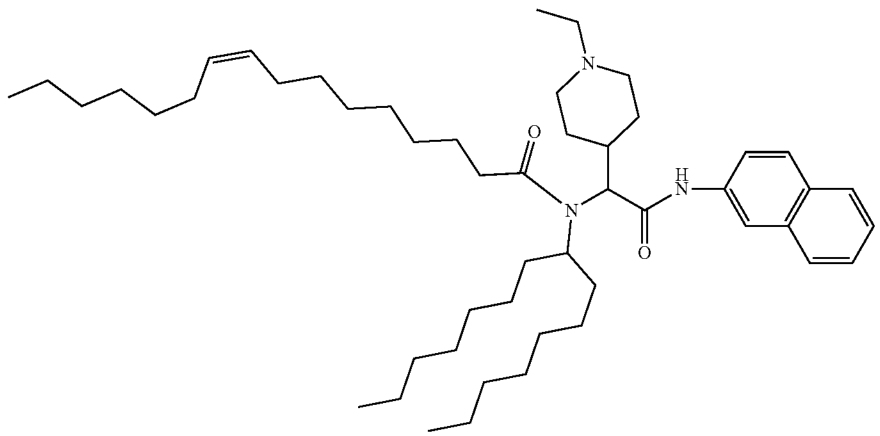

-continued
P18B6
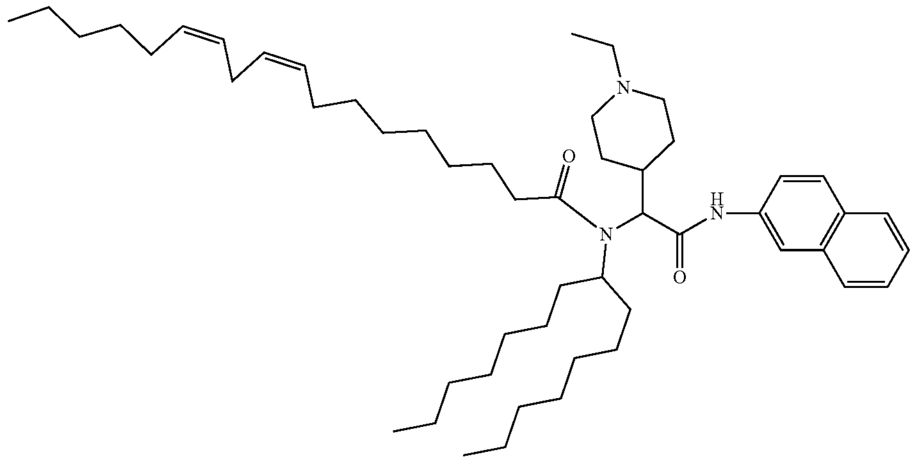
P318E6
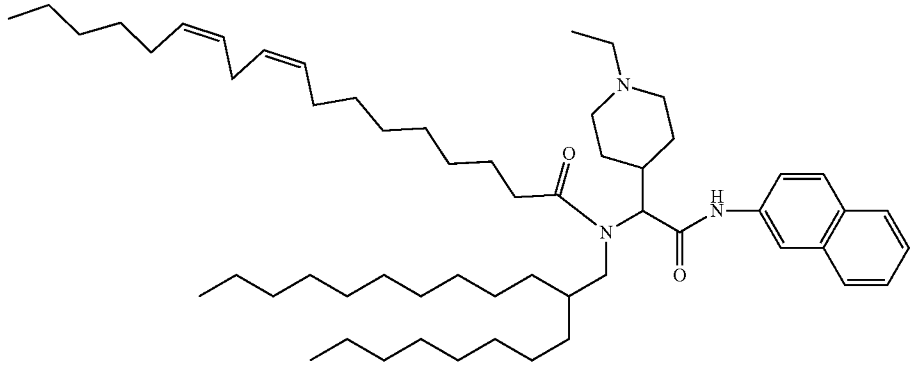
P318B7
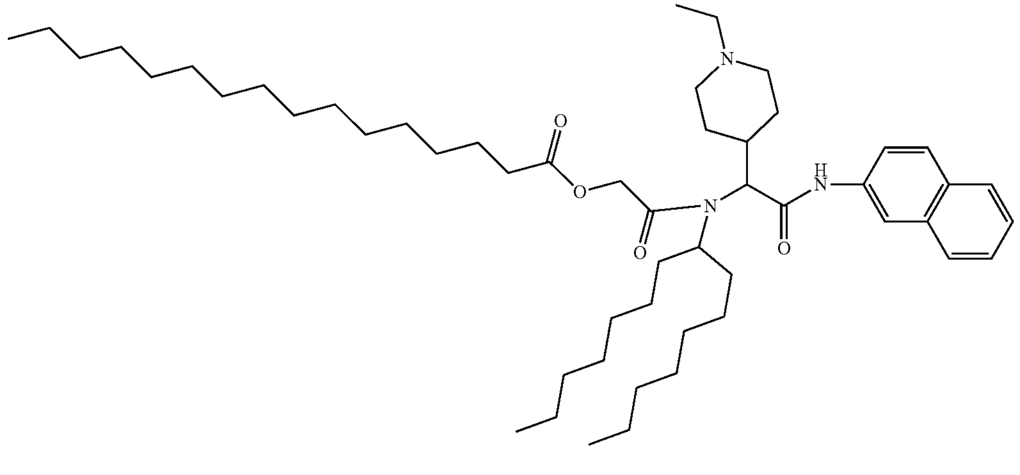

-continued
P318C7
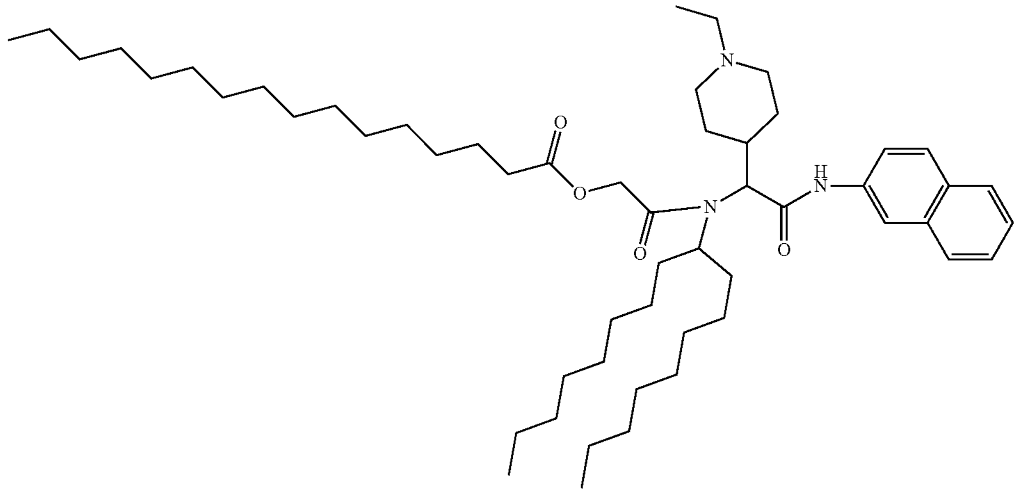
P318D7
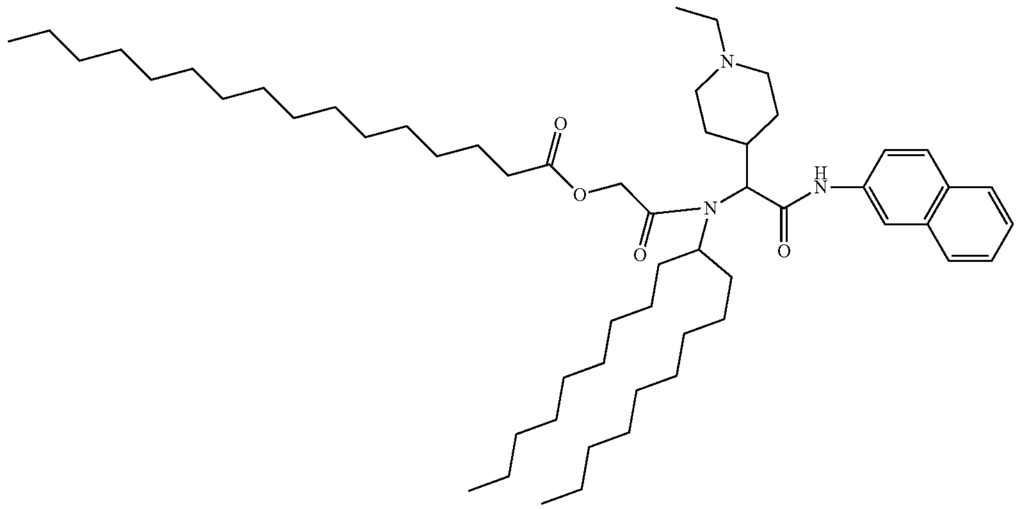
P318E7
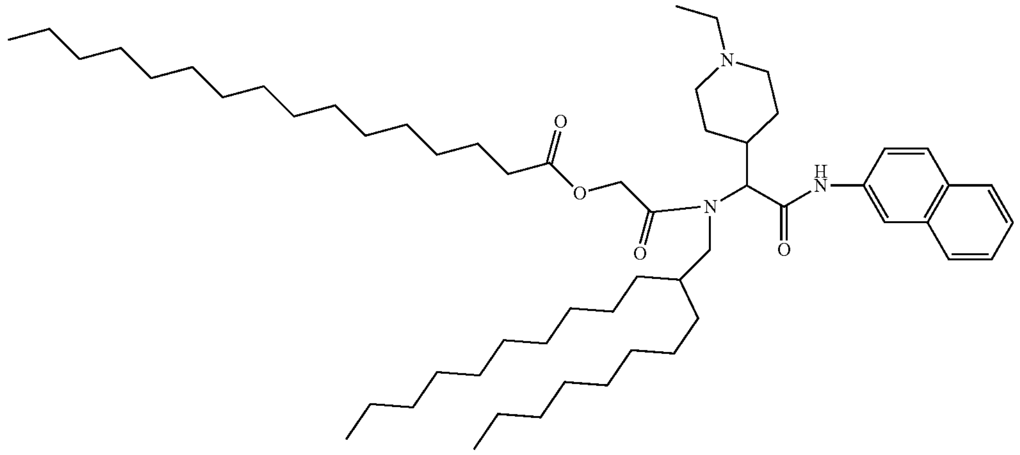

-continued
P318E10
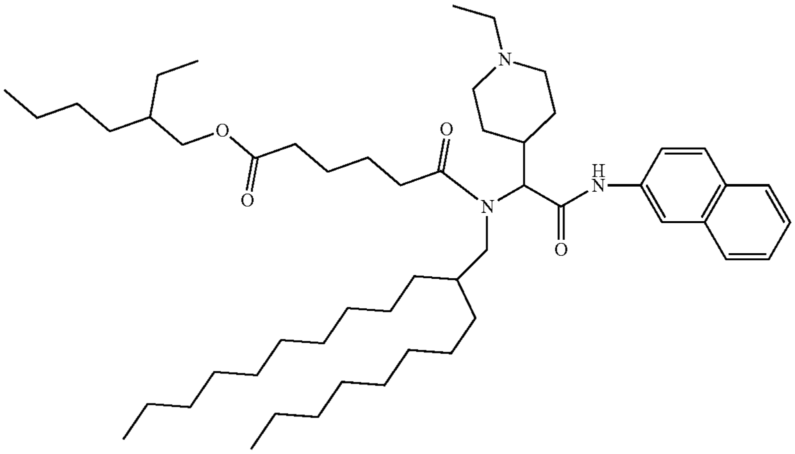
P318G10
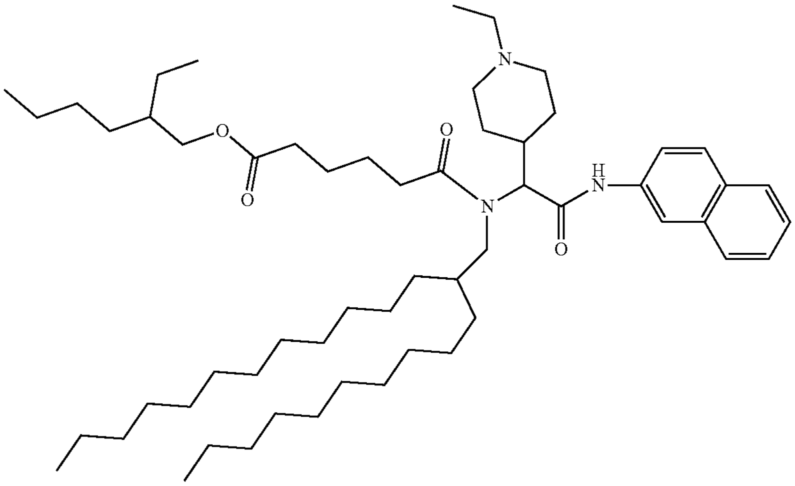
P318E12
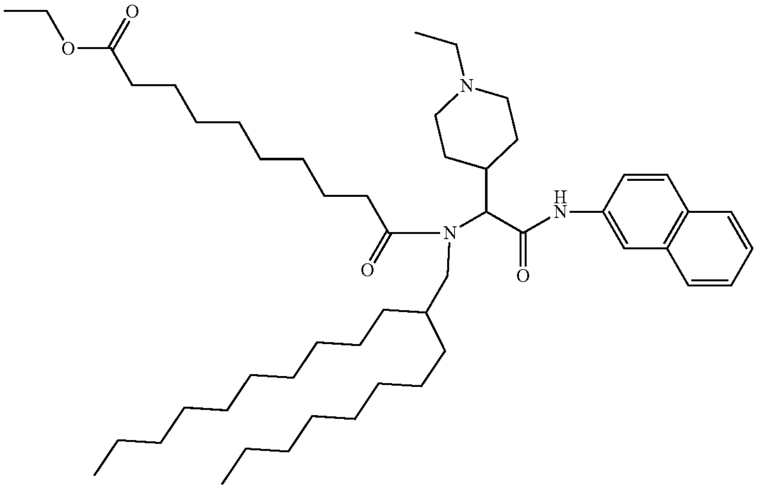

-continued
P319B7
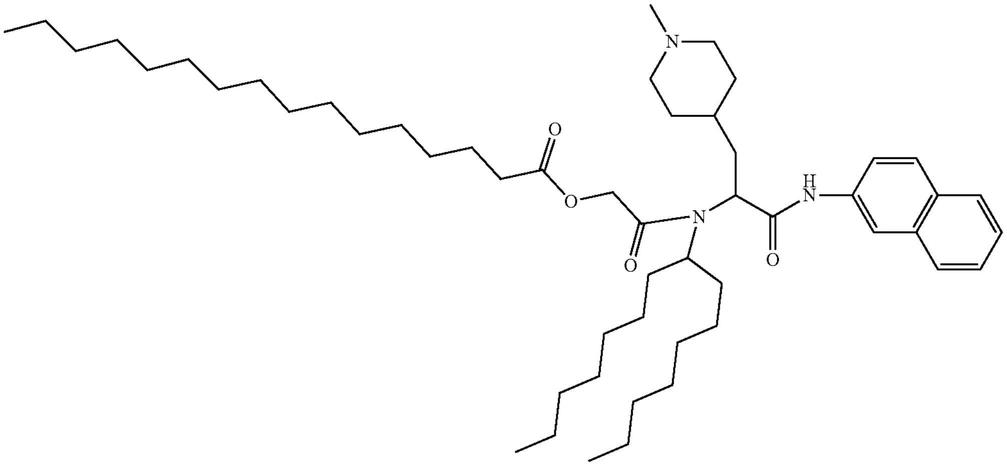
P319C1
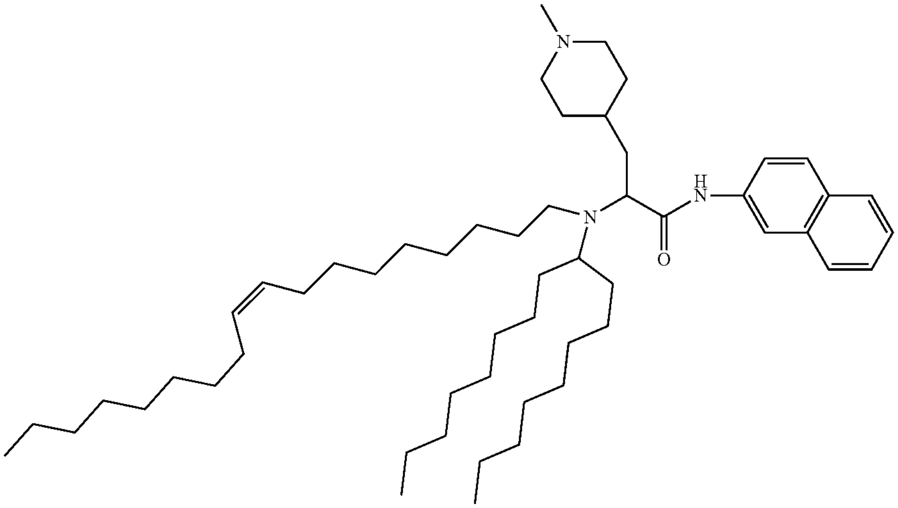
P320E1
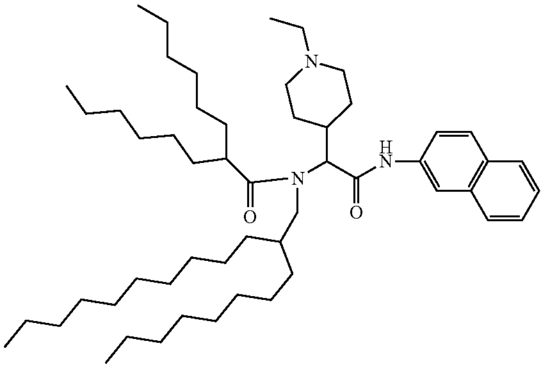
P320G1
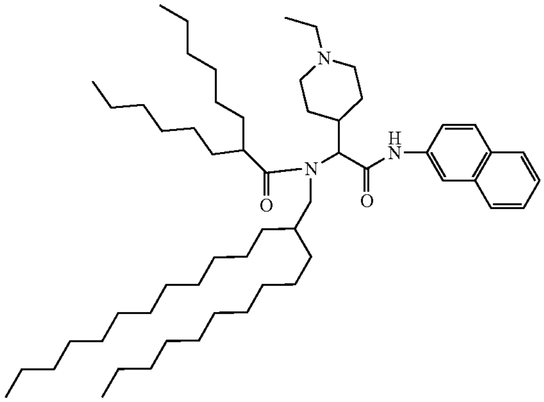

-continued
P320E2
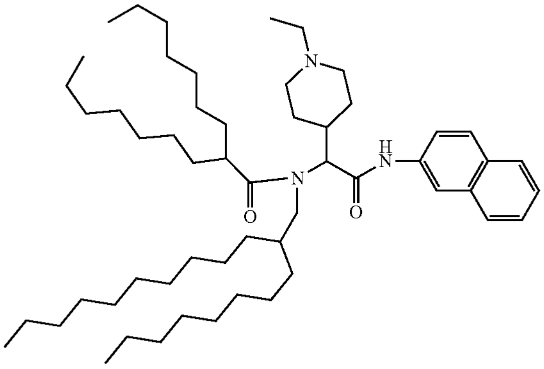
P320E3
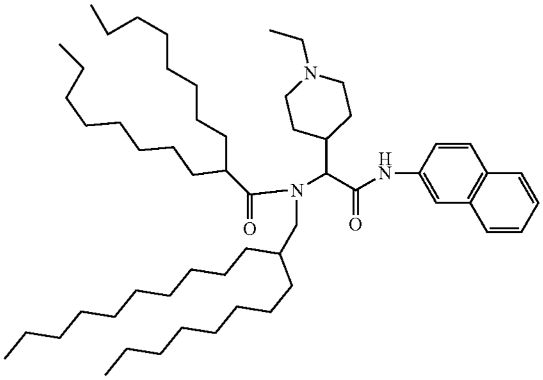
P320E7
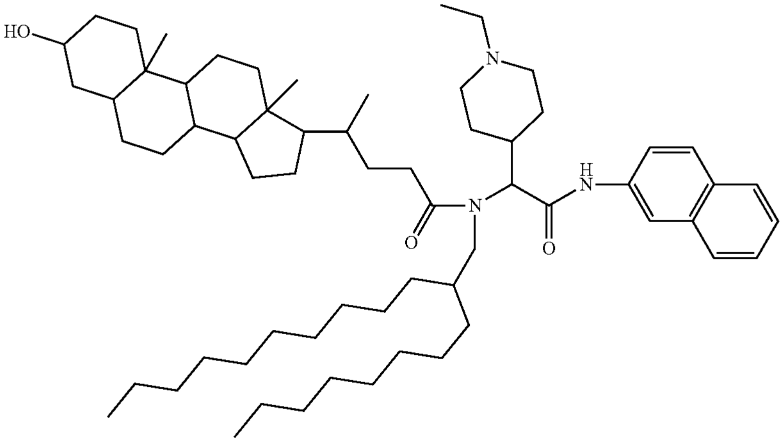
P321E1
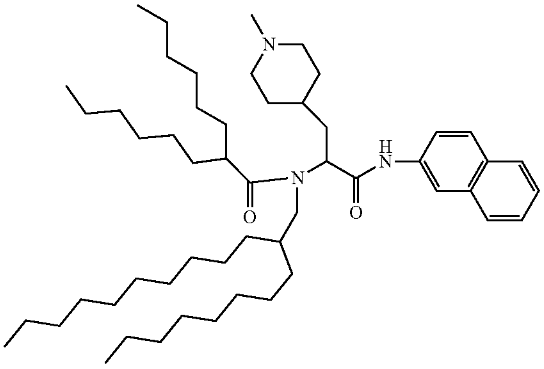
P321G1
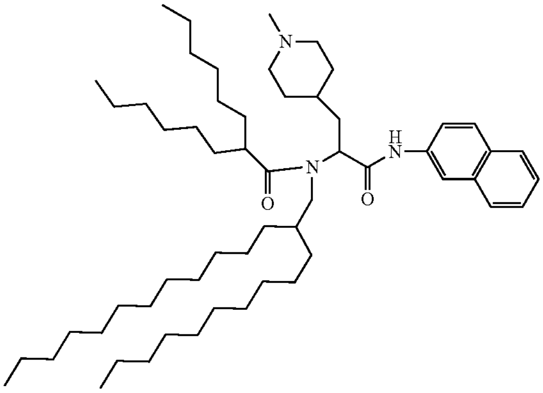

-continued
P328A10
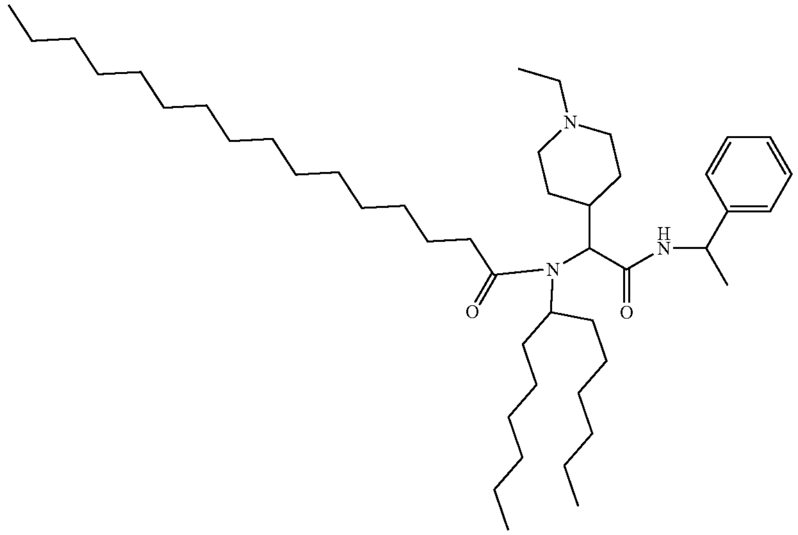
P328A11
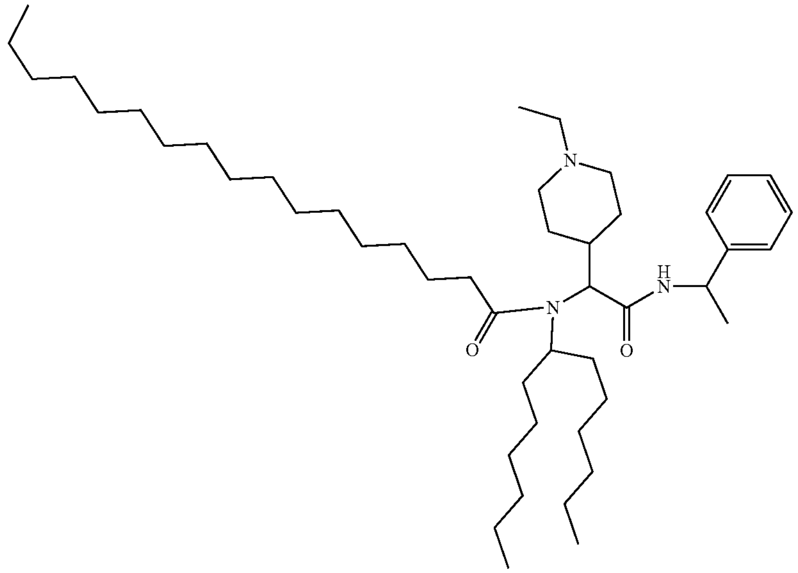
P329E7
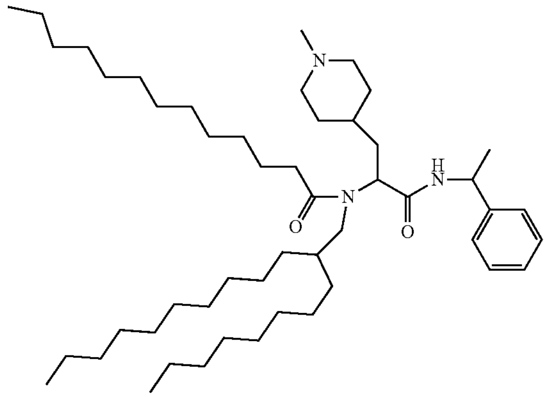
P329E8
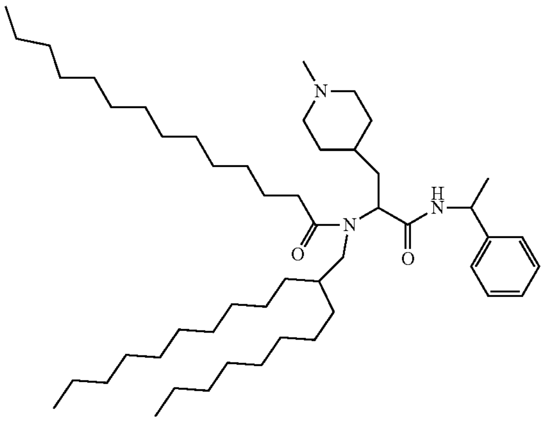

-continued
P329E10
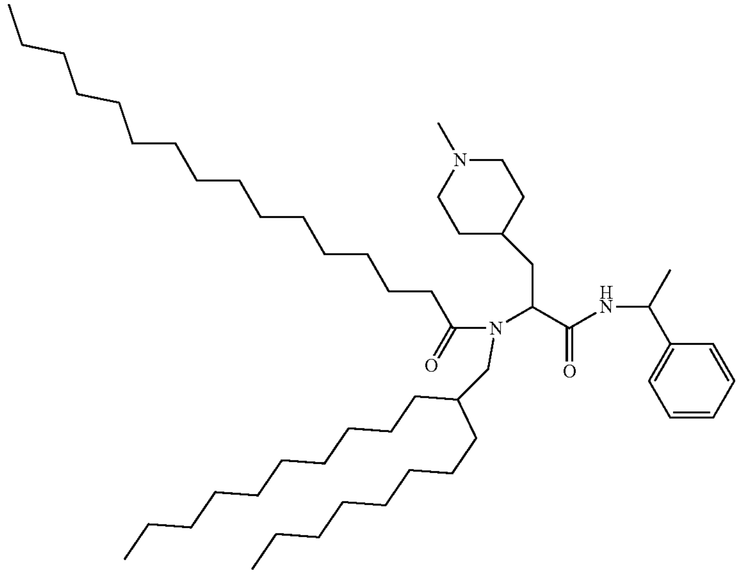
P329E11
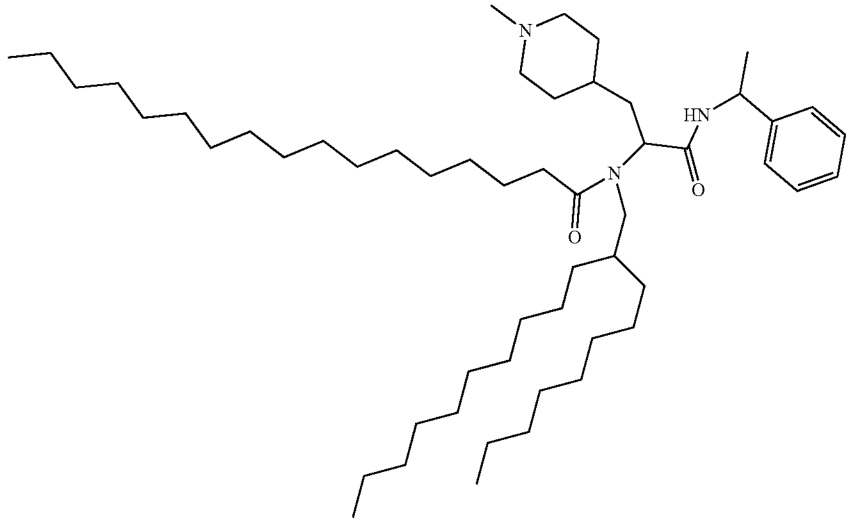
P329E12
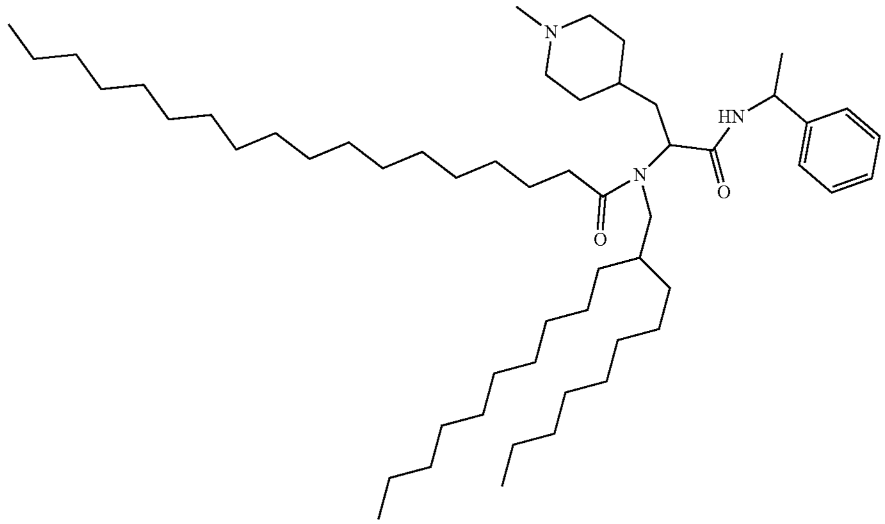

-continued
P330A1
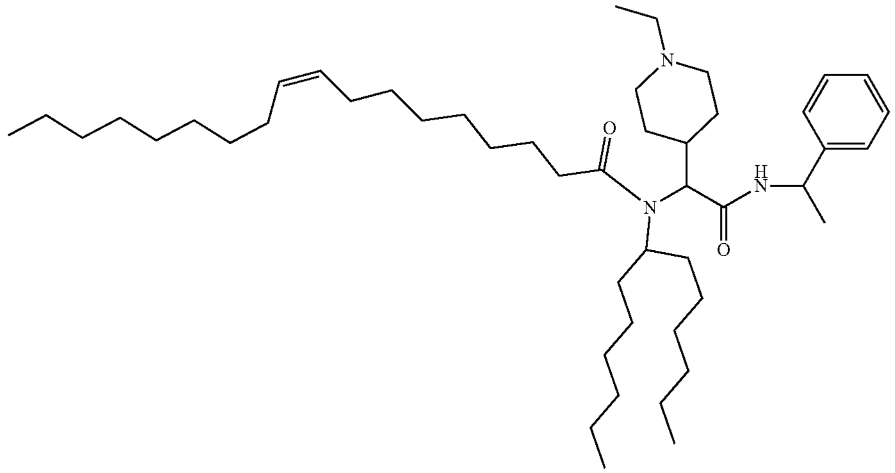
P330A7
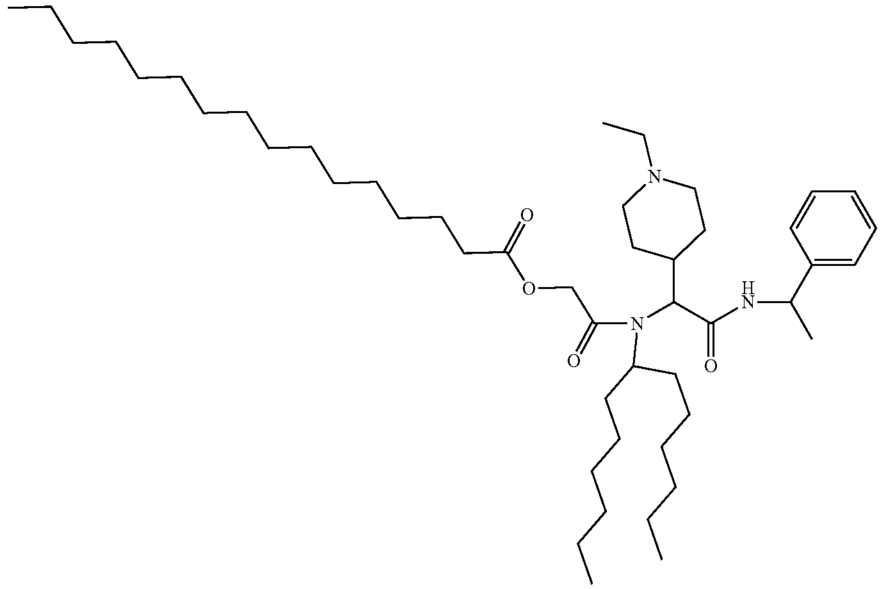
P330B1
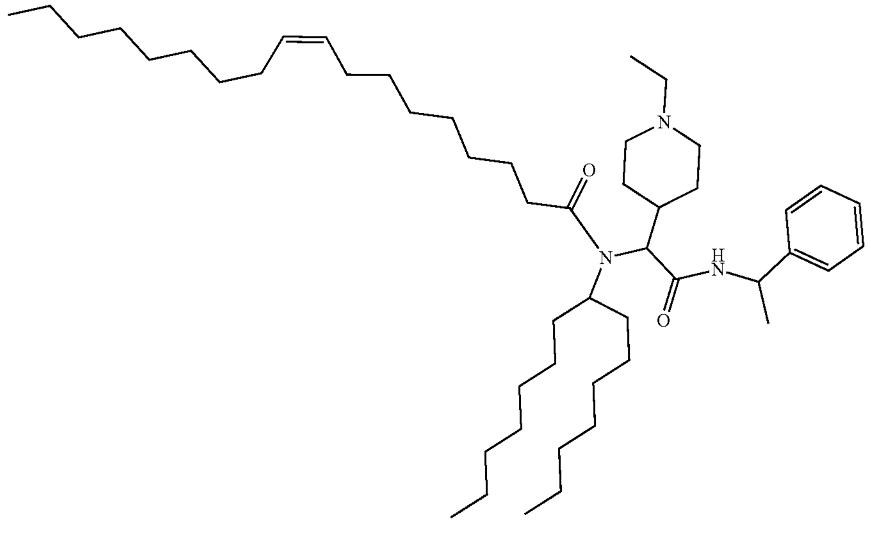

-continued
P330C1
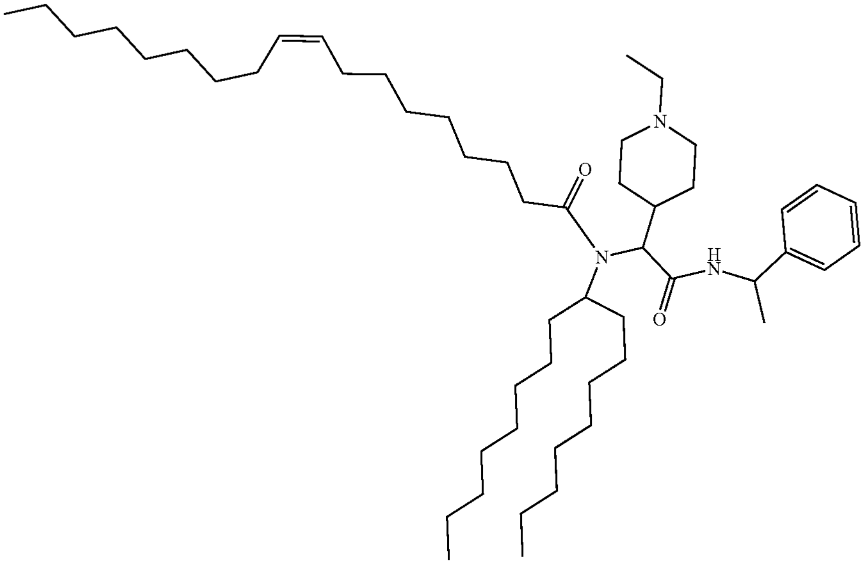
P330E1
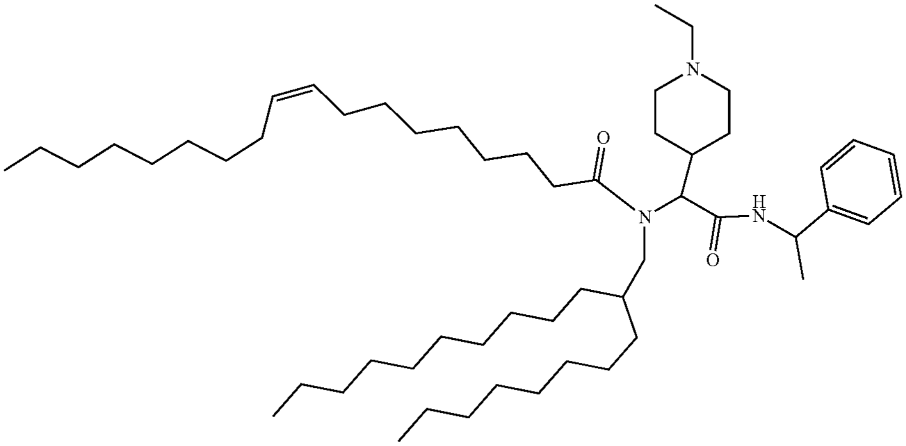
P330E6
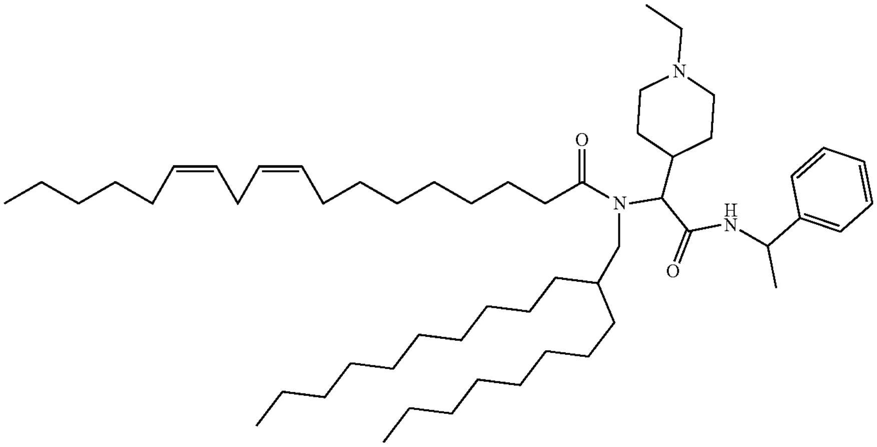

-continued
P330E8
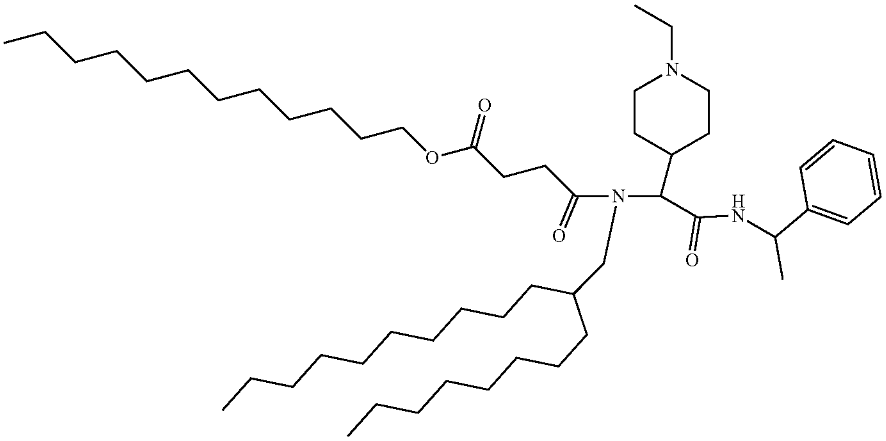
P331A1
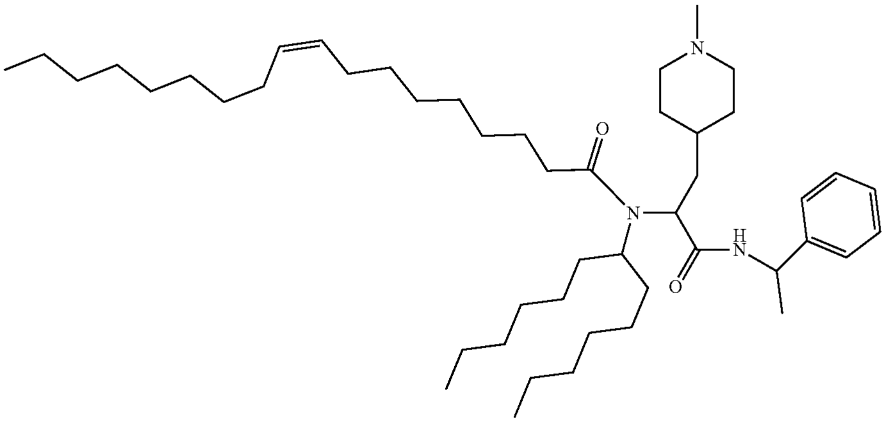
P331B1
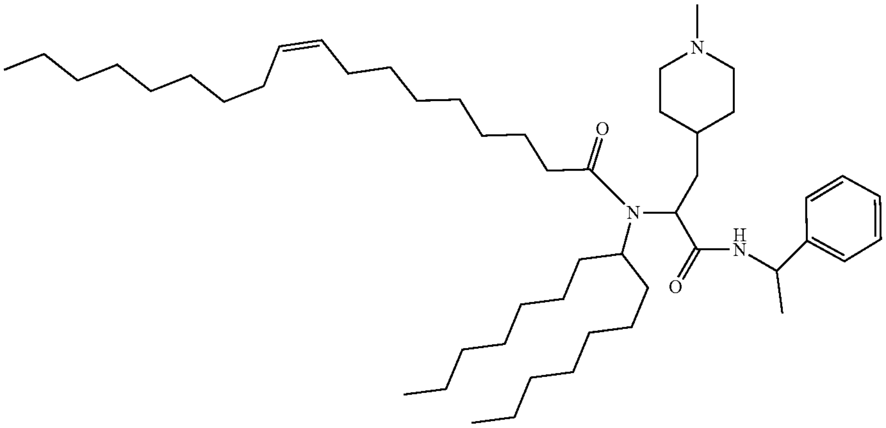

-continued
P331B3
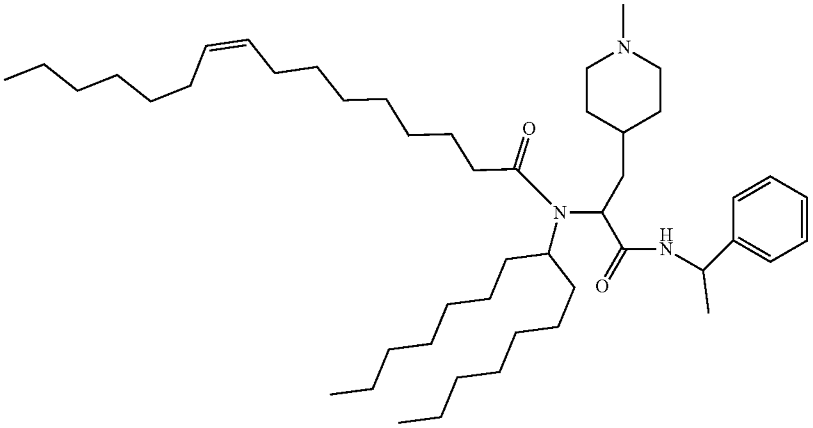
P331B6
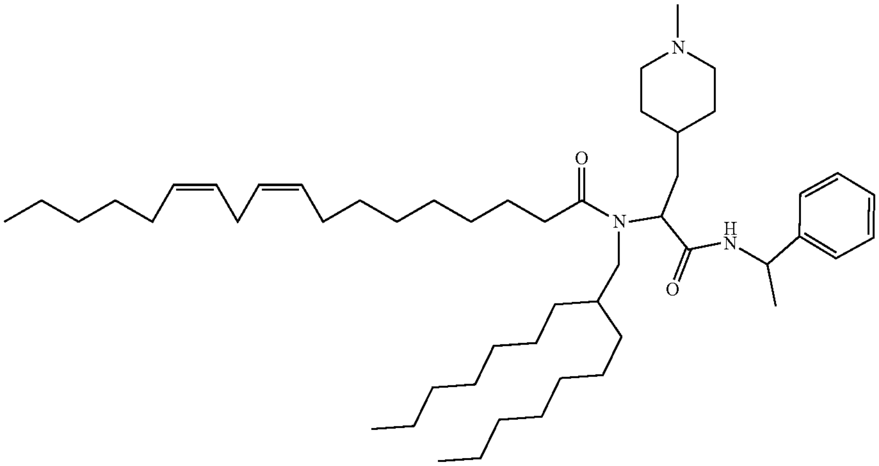
P331B8
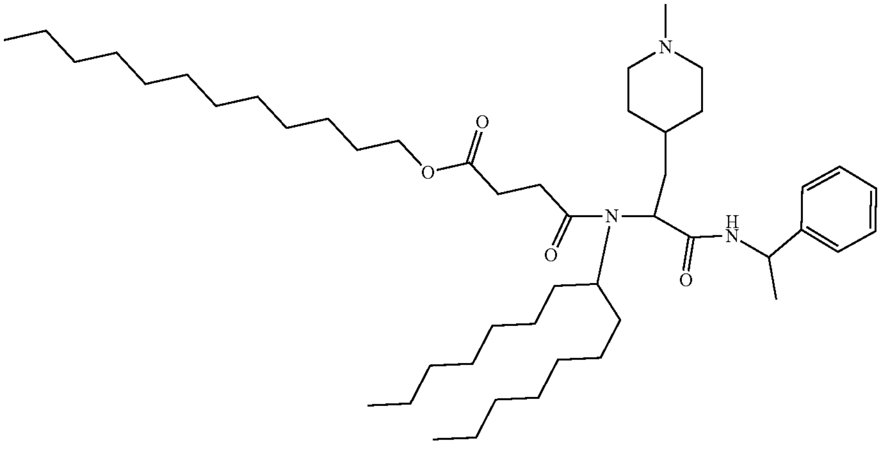

-continued
P331C1
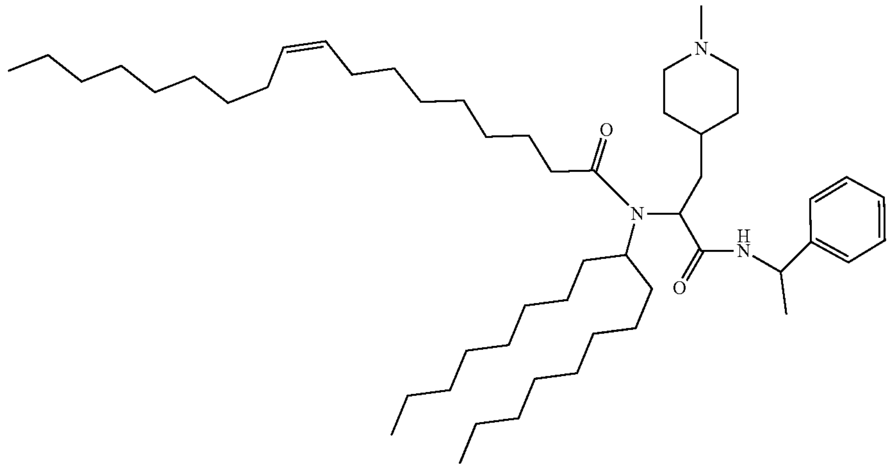
P331C4
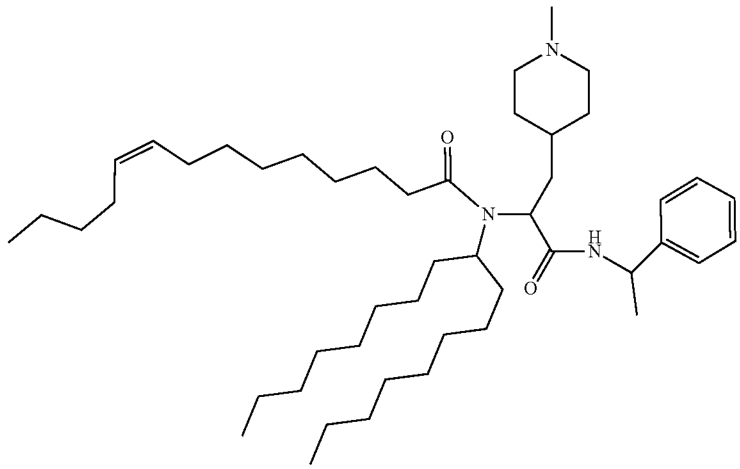
P331D1
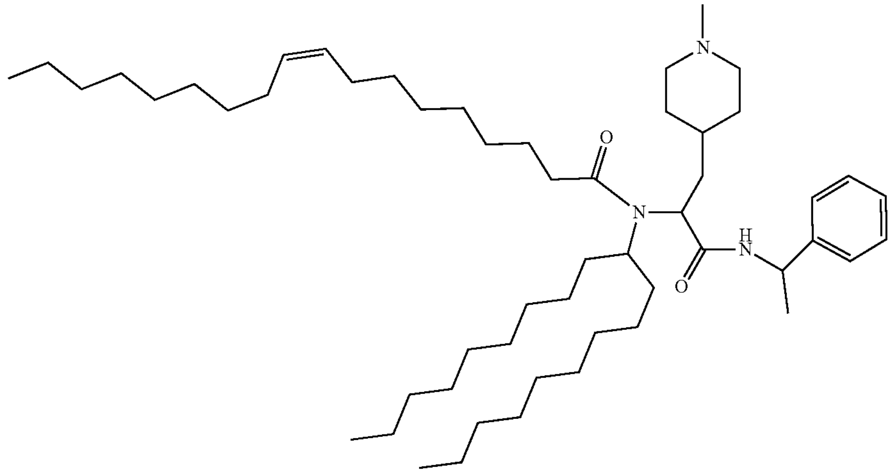

-continued
P331E1
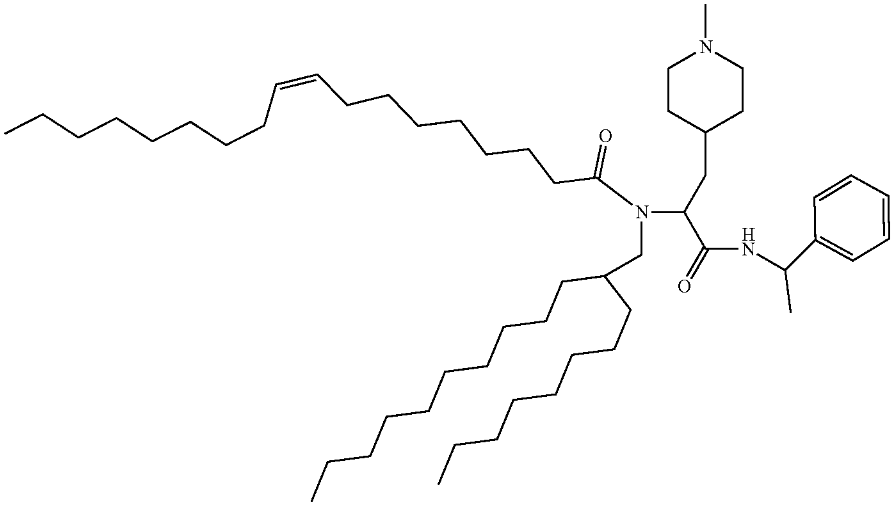
P331E6
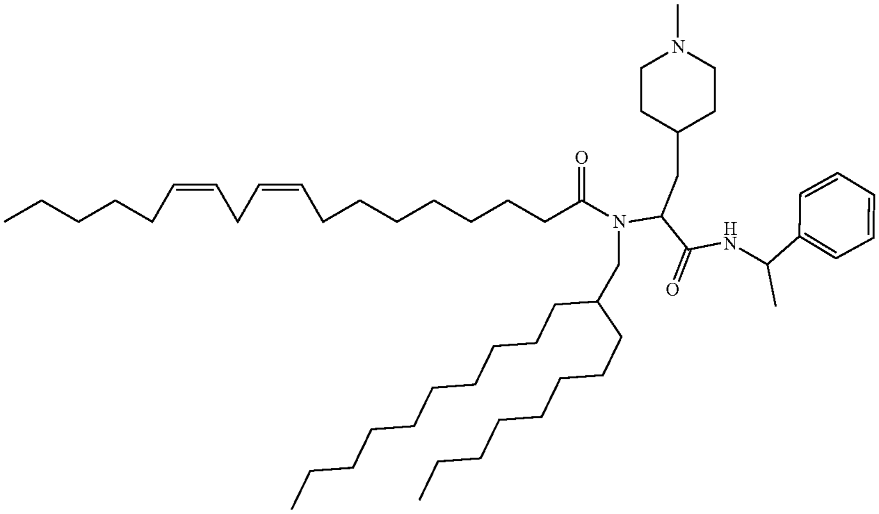
P332G1
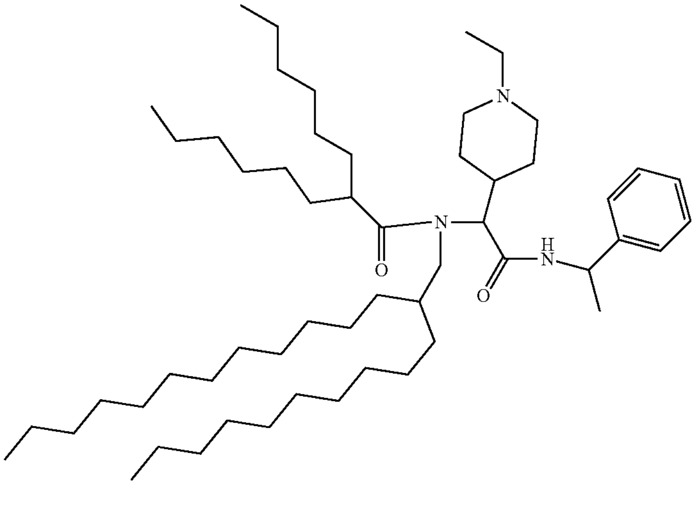

-continued
P341A9
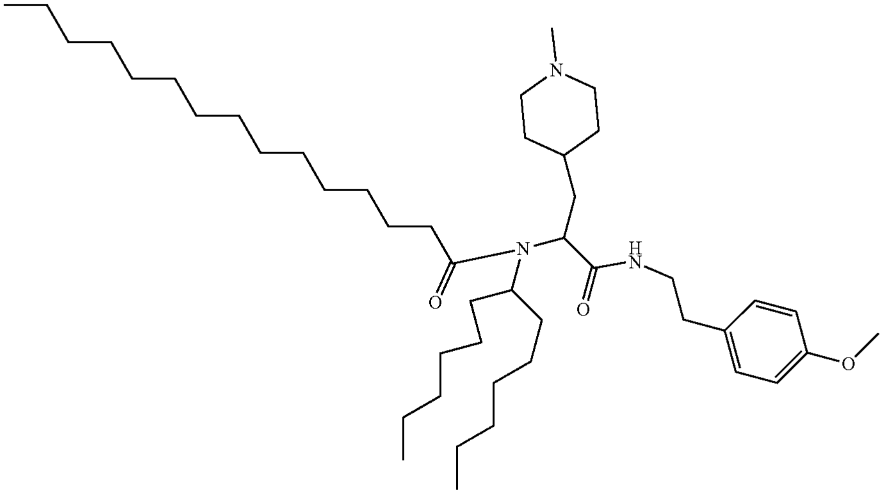
P34A11
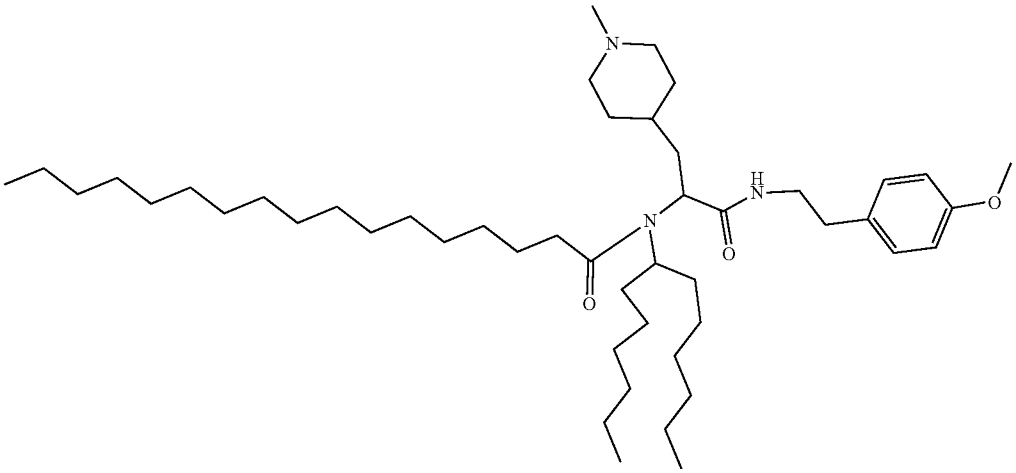
P341C9
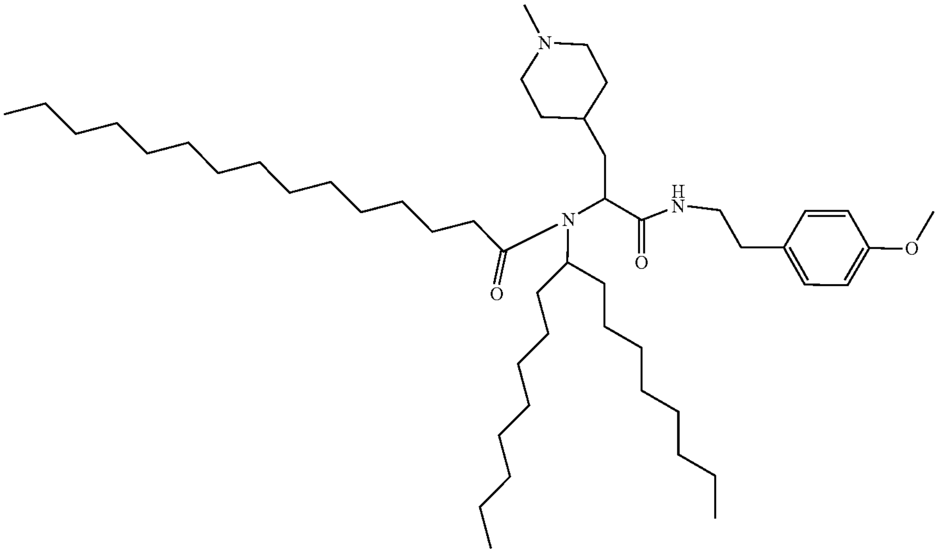

-continued
P341C11
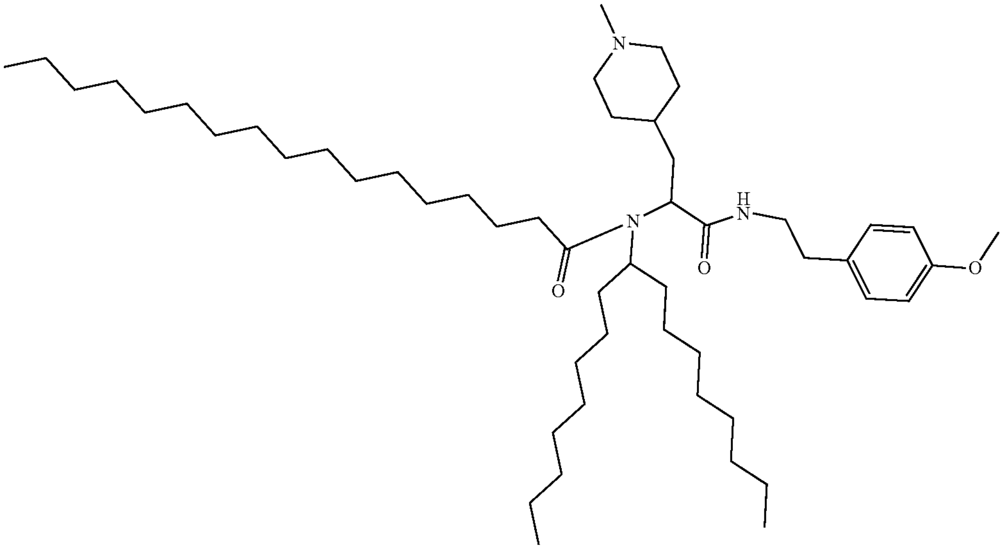
P341C12
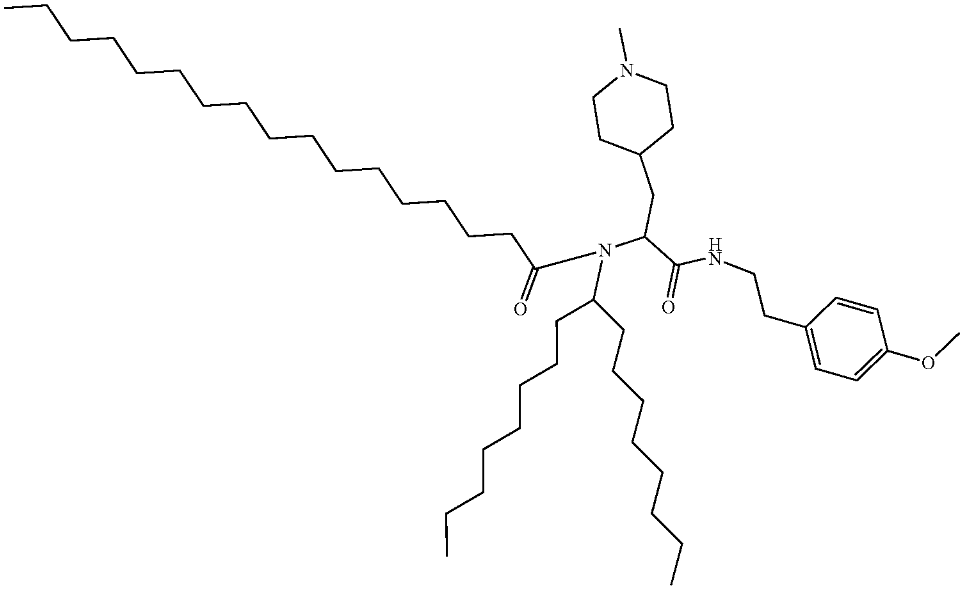

-continued
P341D11
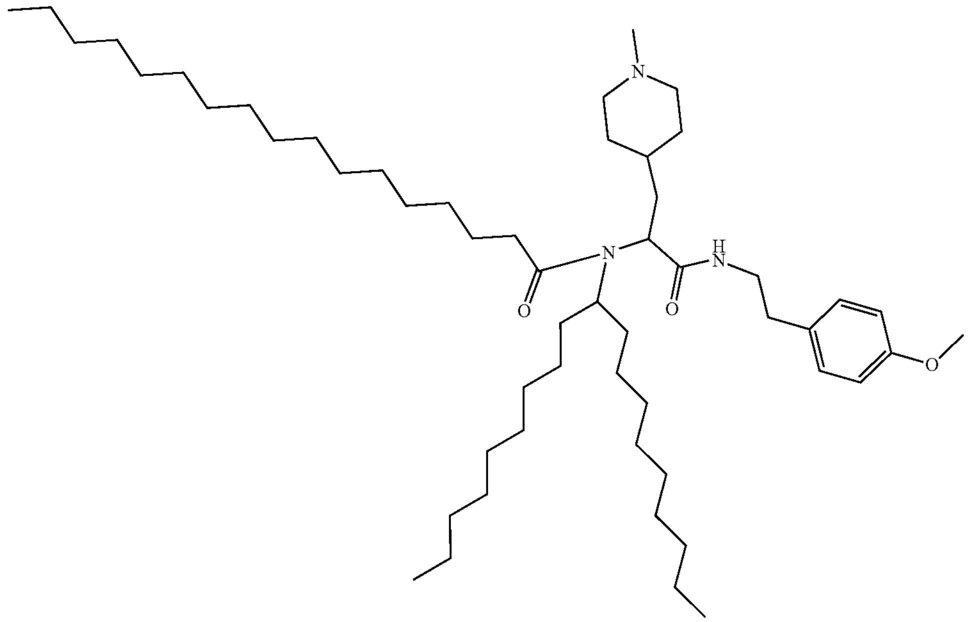
P341E1
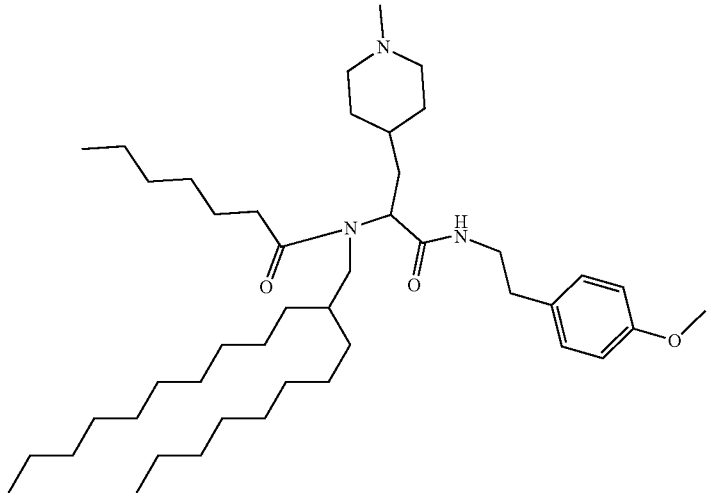

-continued
P341G11
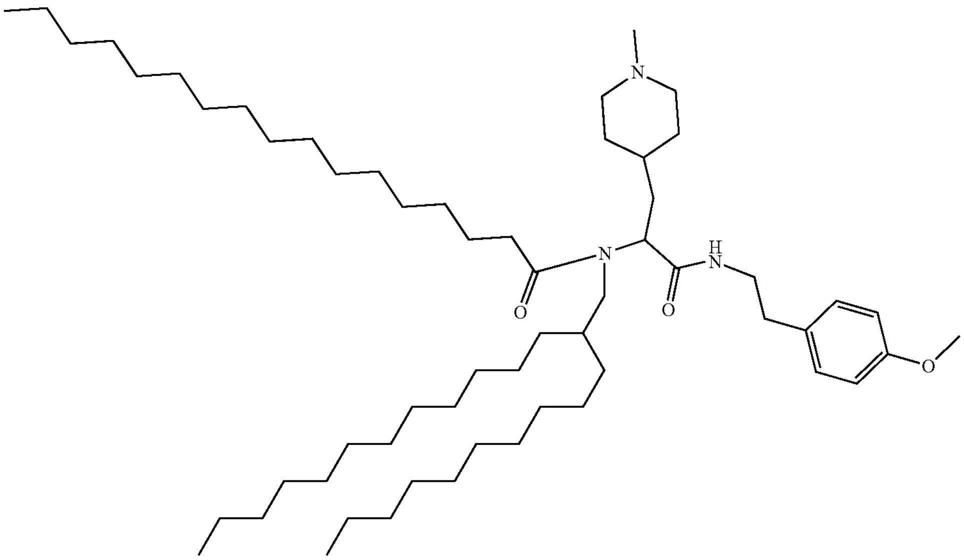
P342B1
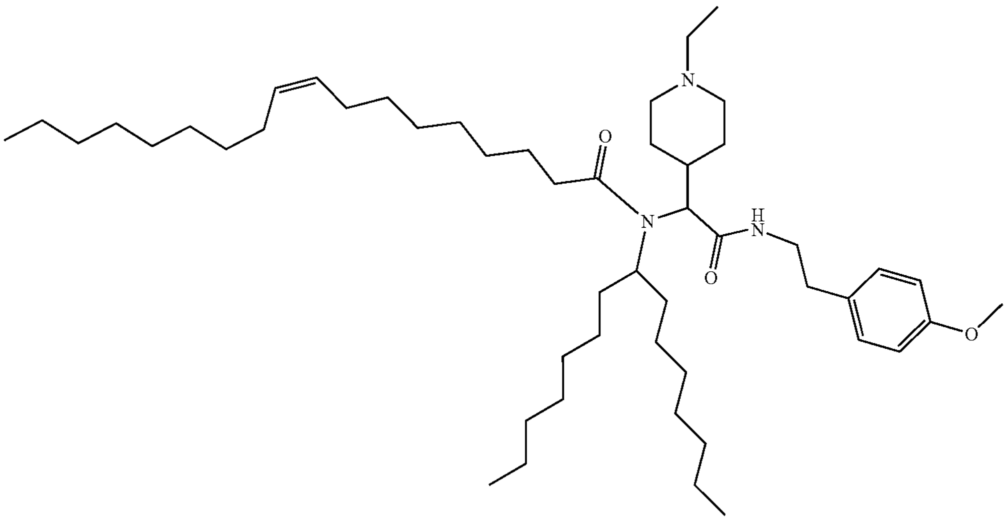

-continued
P342F1
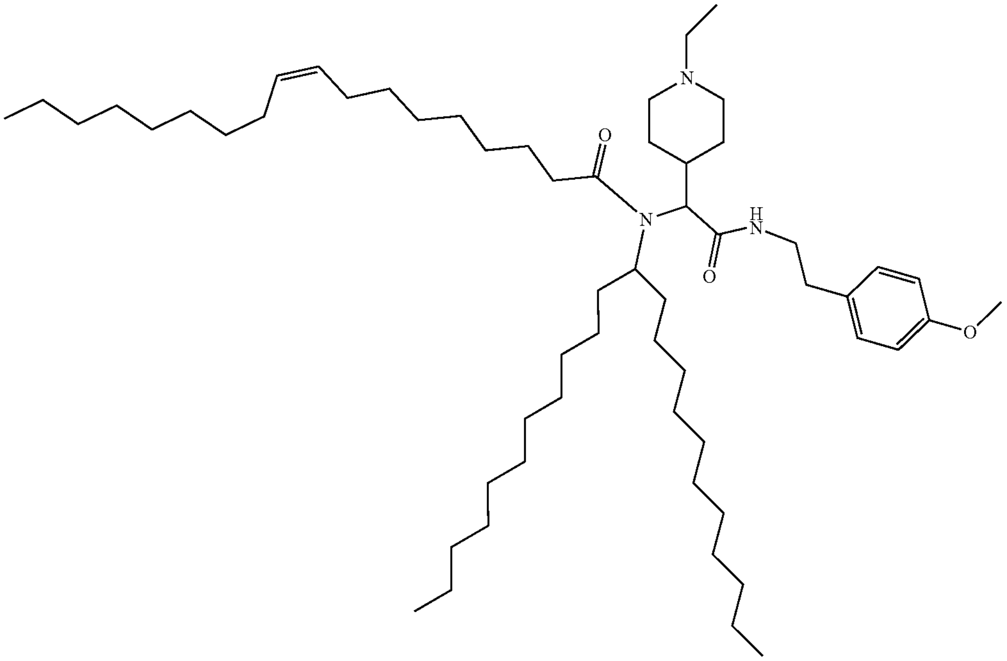
P342F8
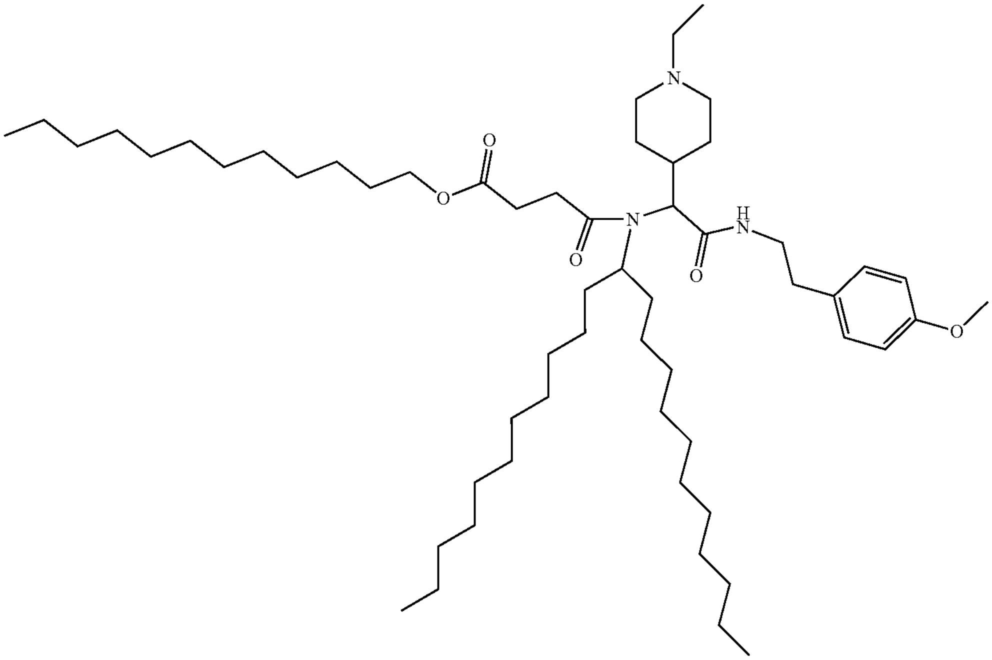

-continued
P342F12
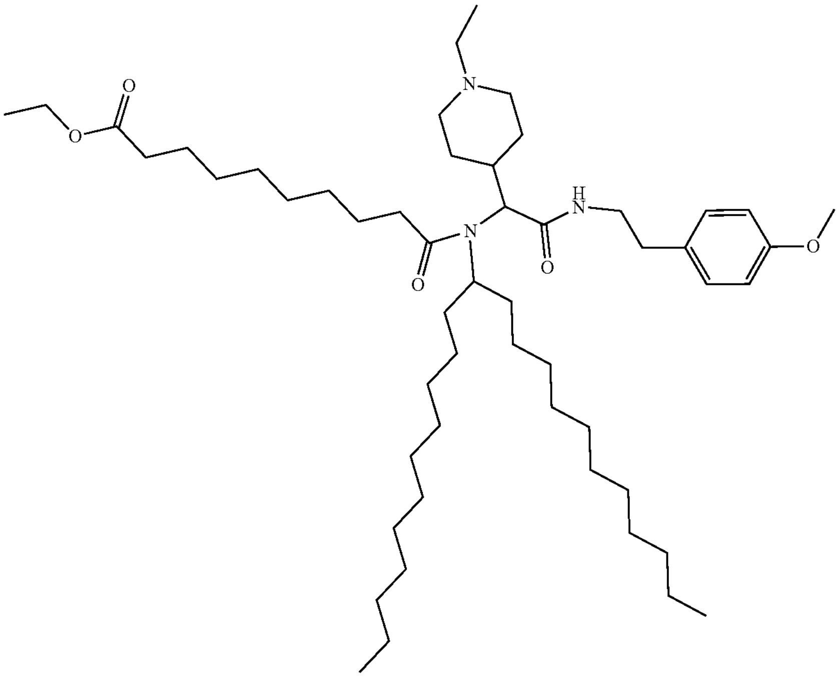
P343A1
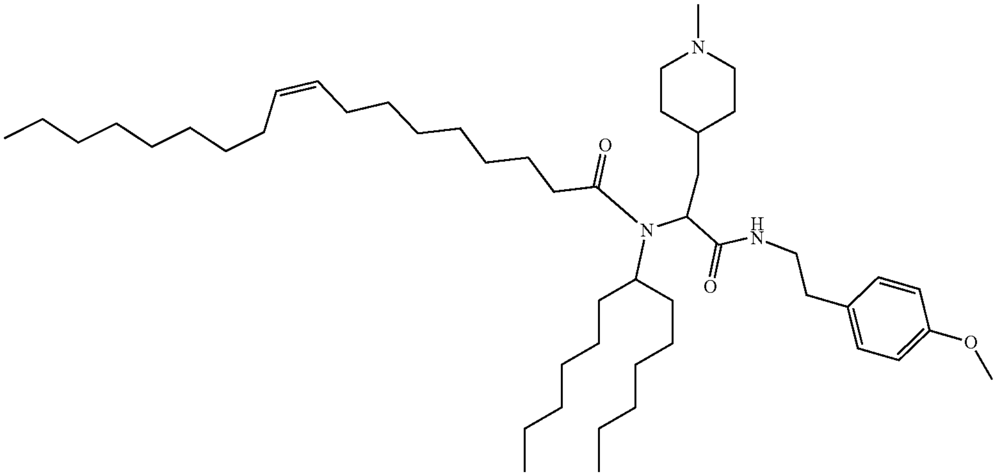
P343B3
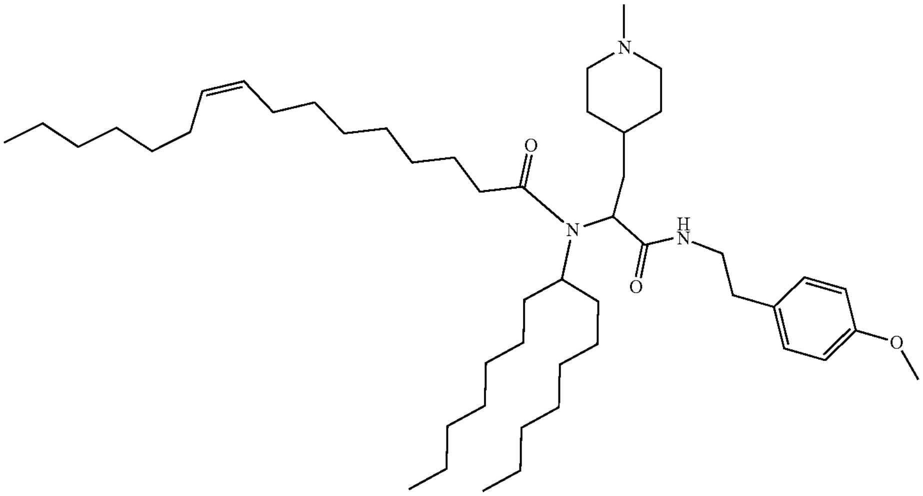

-continued
P343C1
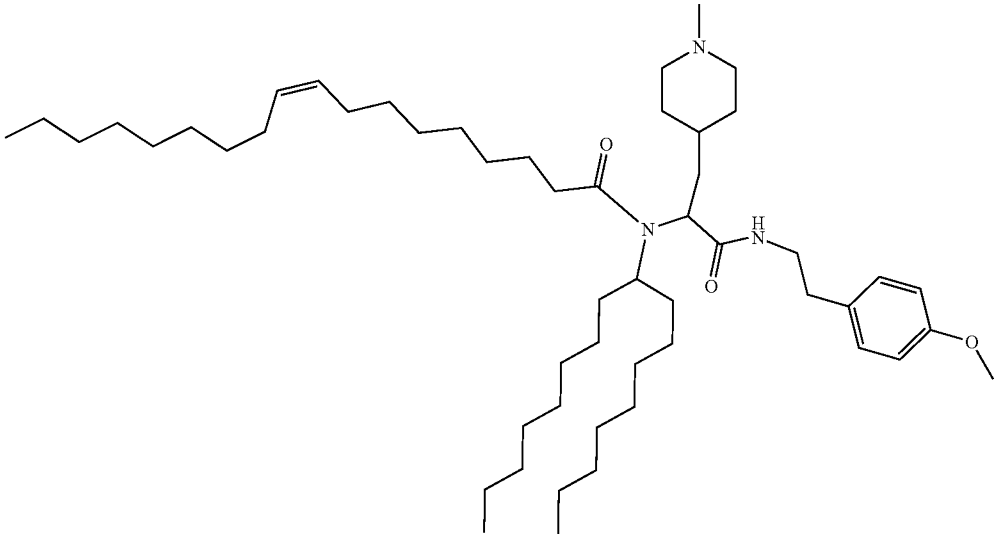
P343C3
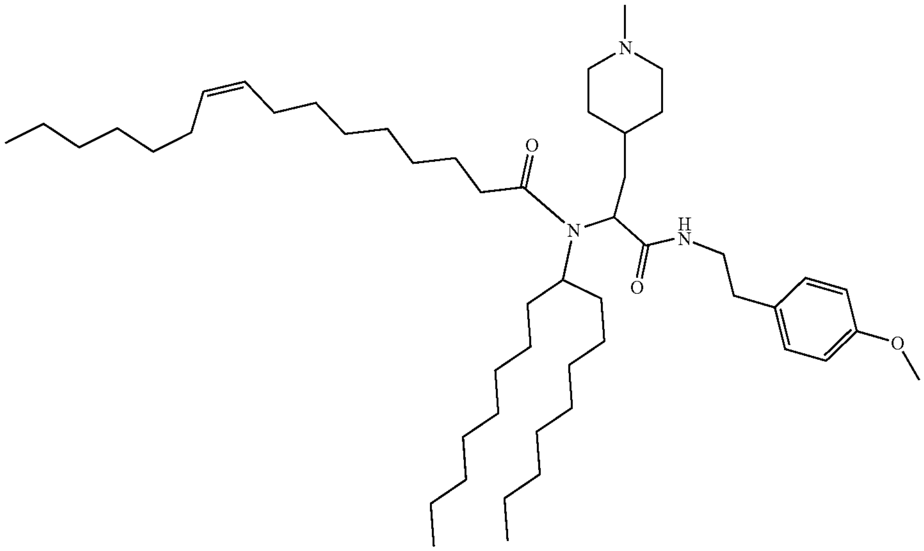
P343C6
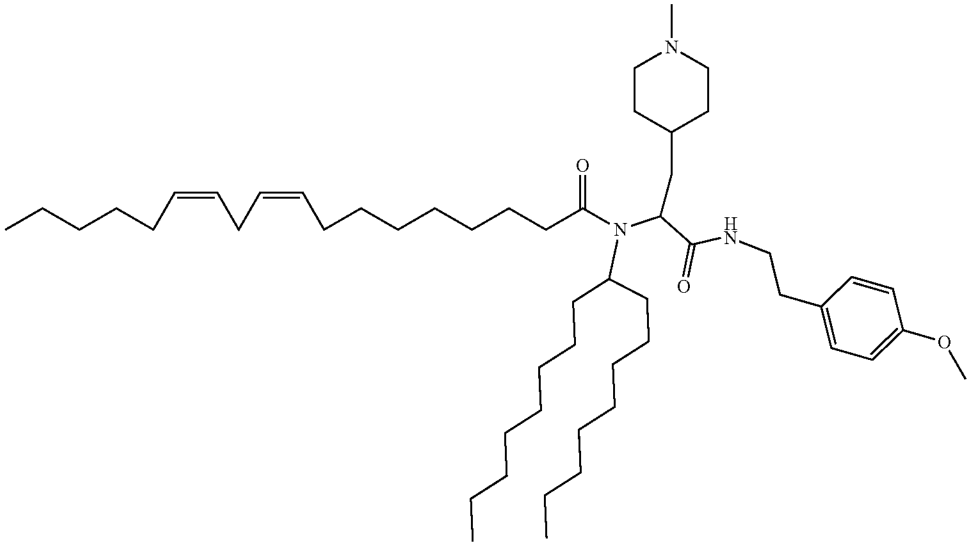

-continued
P343C8
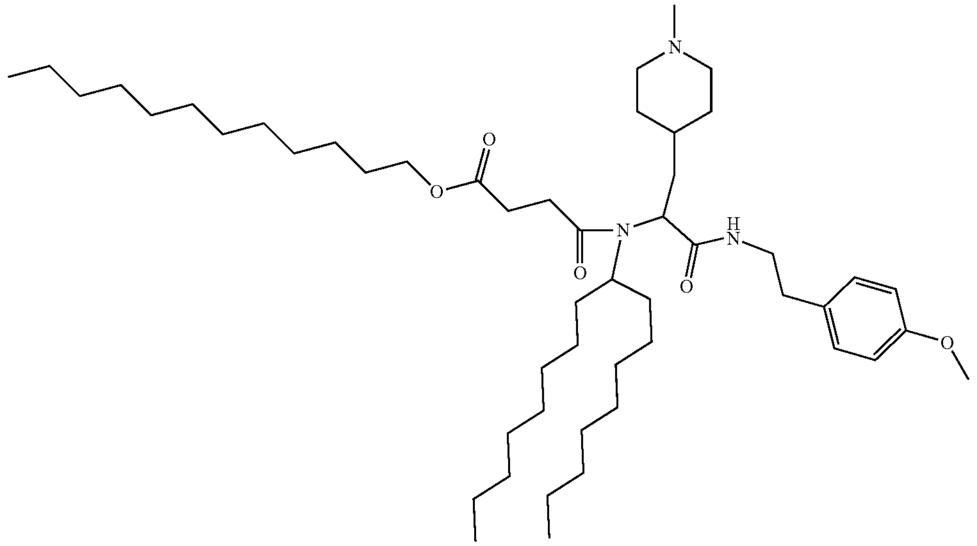
P343D1
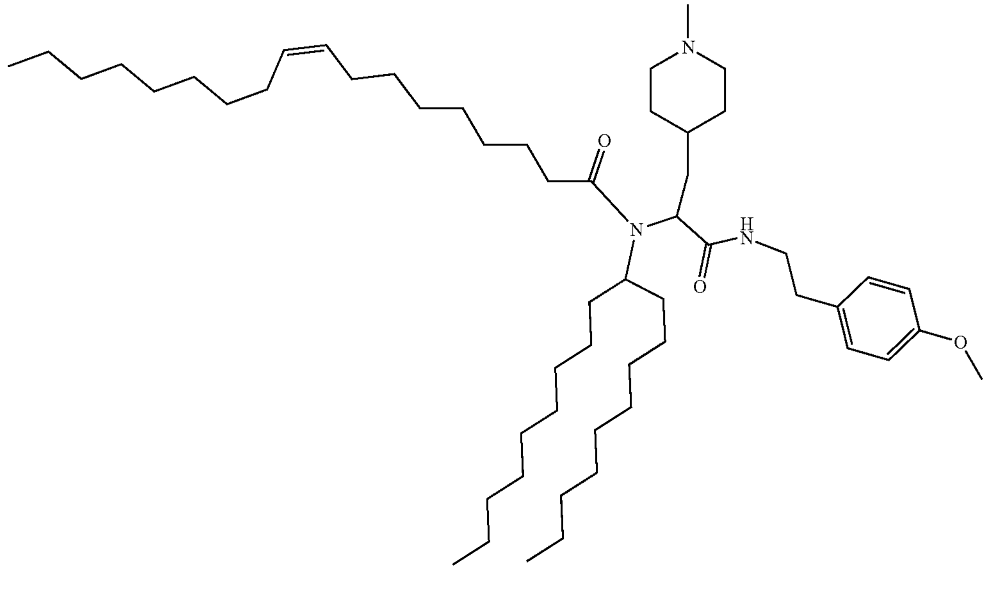

-continued
P343D3
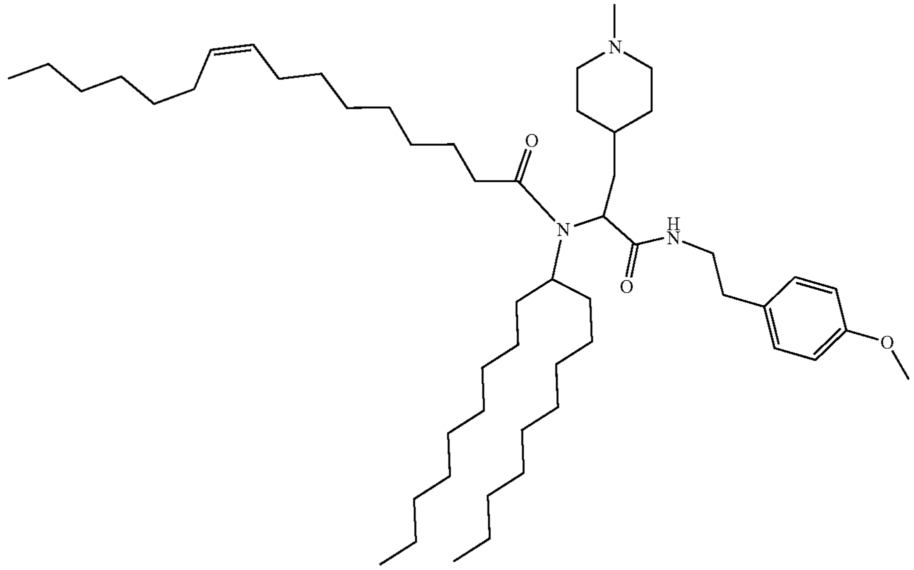
P343D7
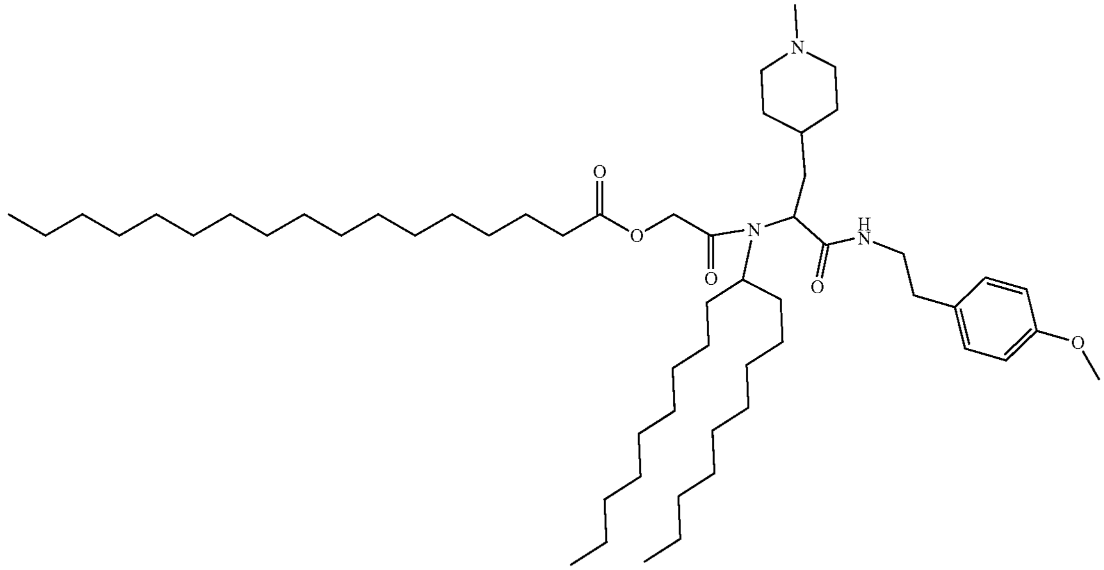
P343E1
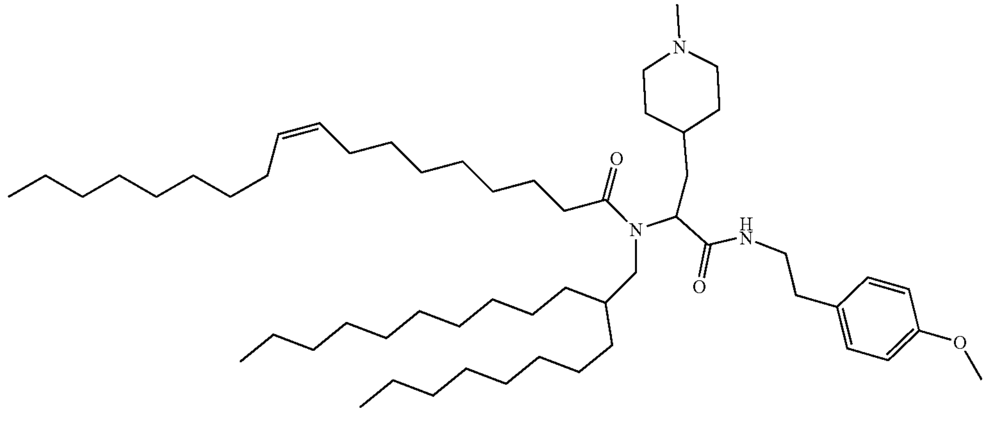

-continued
P344A3
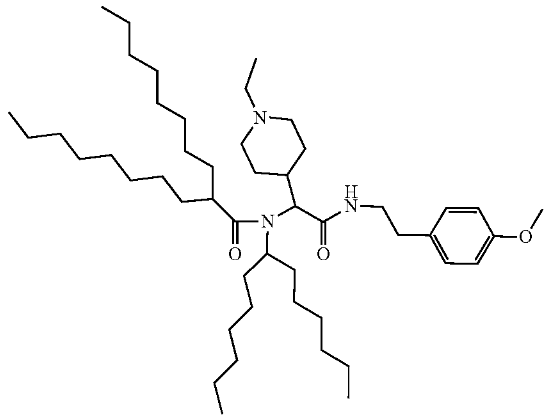
P344B5
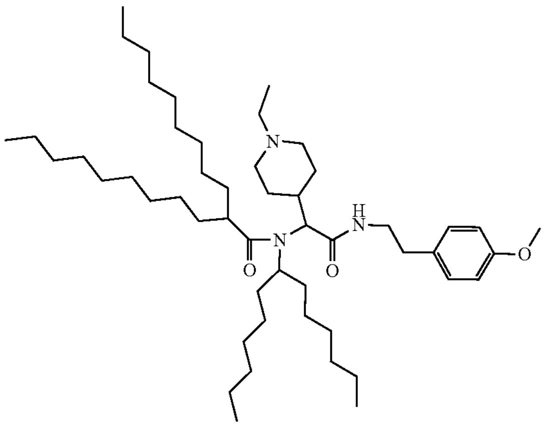
P344A4
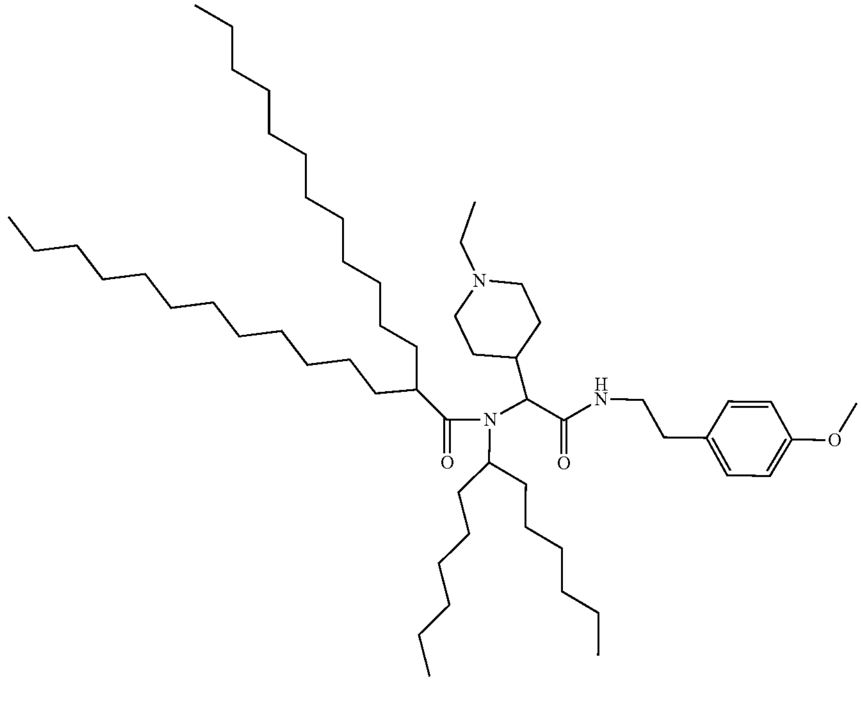

-continued
P344D3
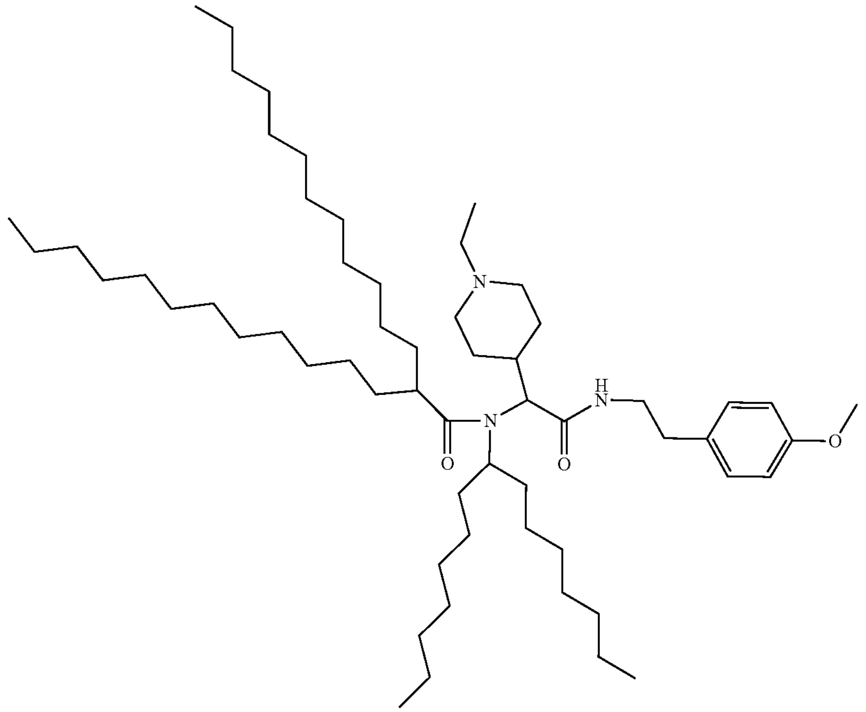
P344E2
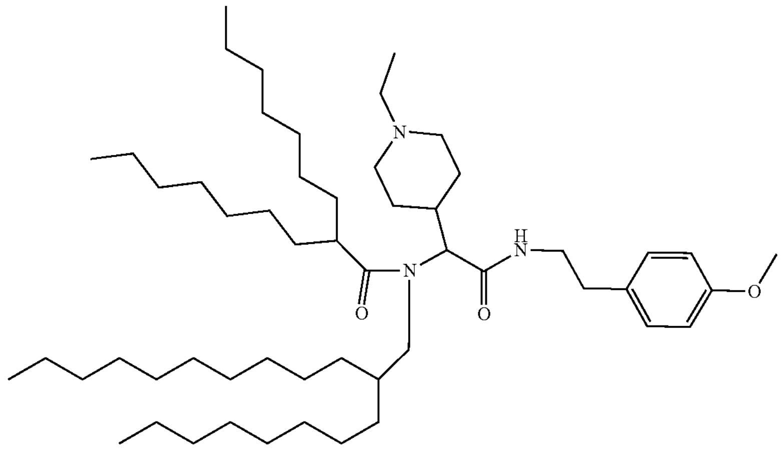

-continued
P345B2
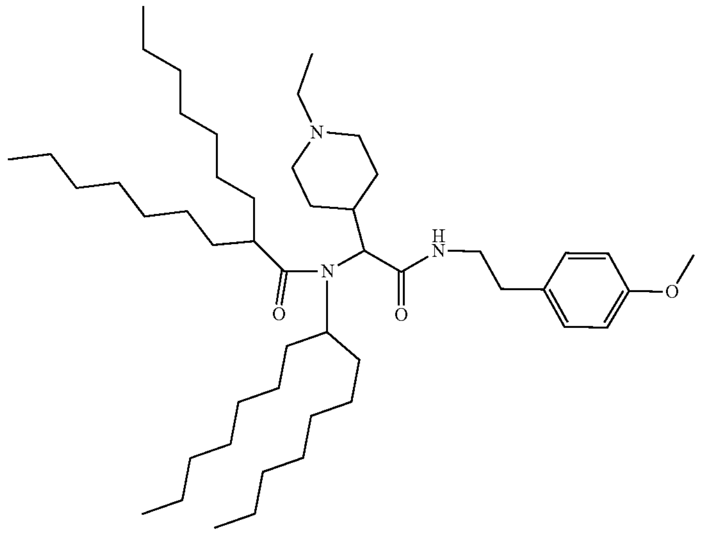
P345E1
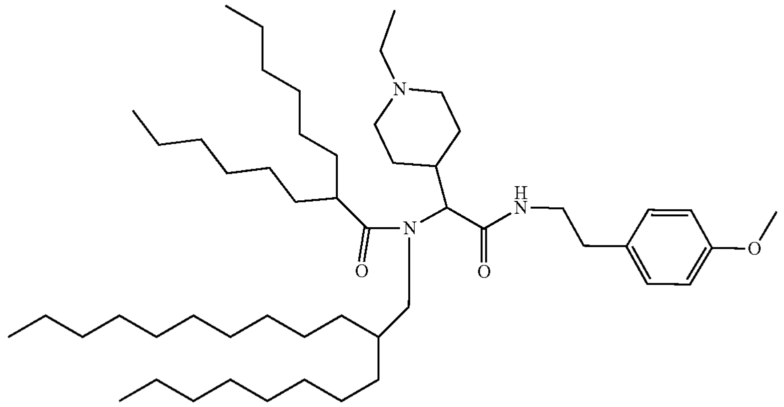
P345E7
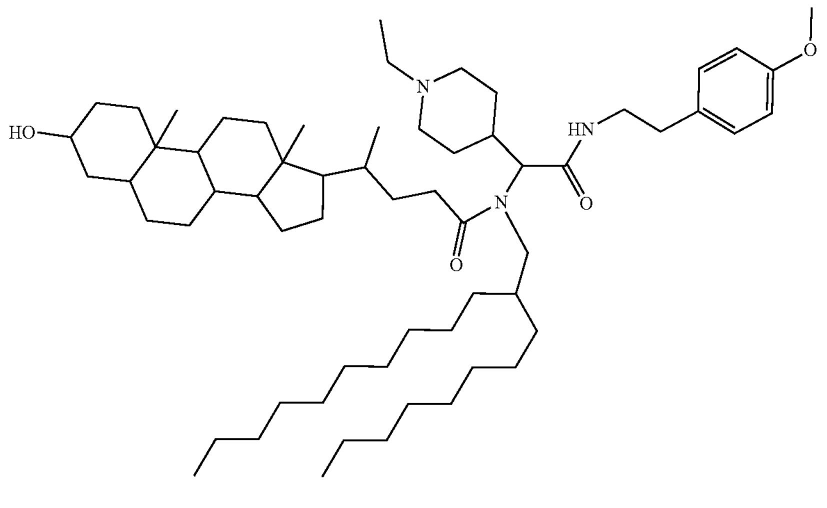

-continued
P345G7
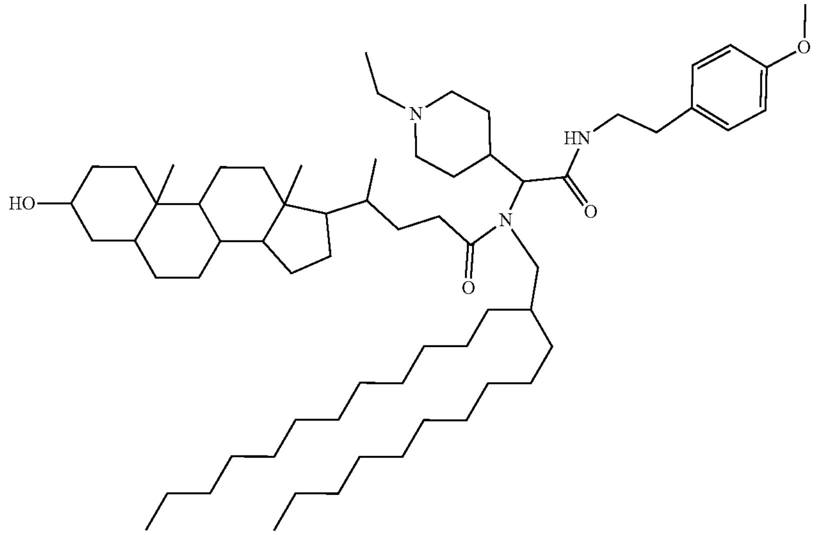
P359B2
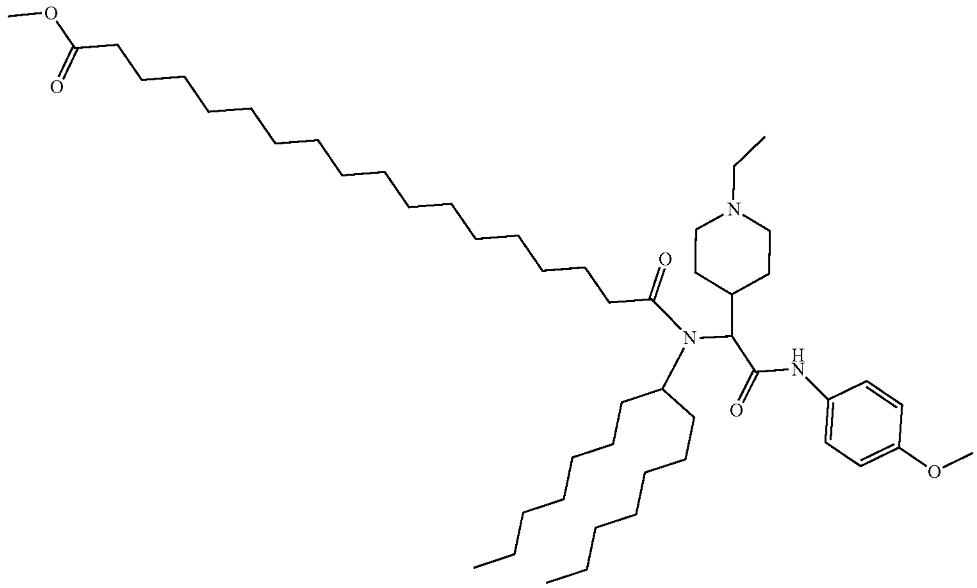
P359B4
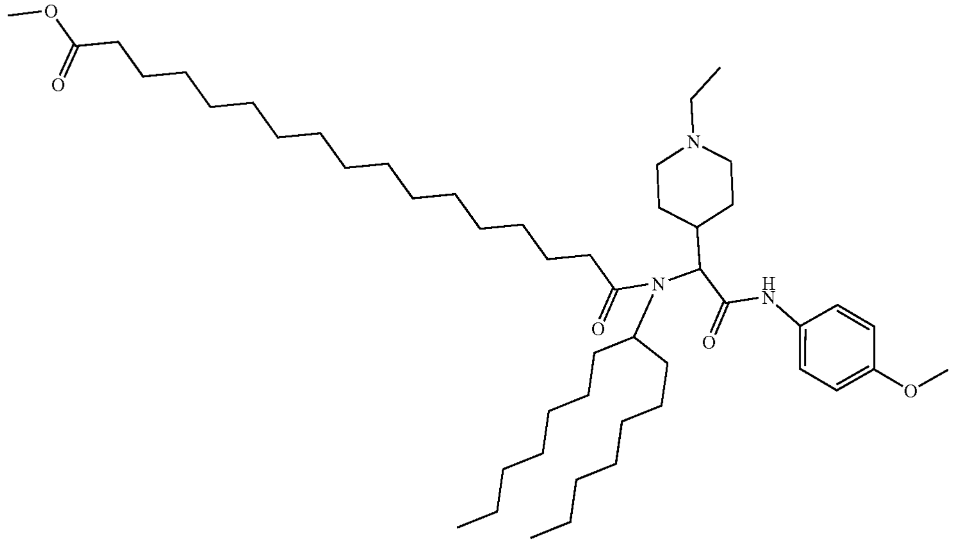

-continued
P359E4
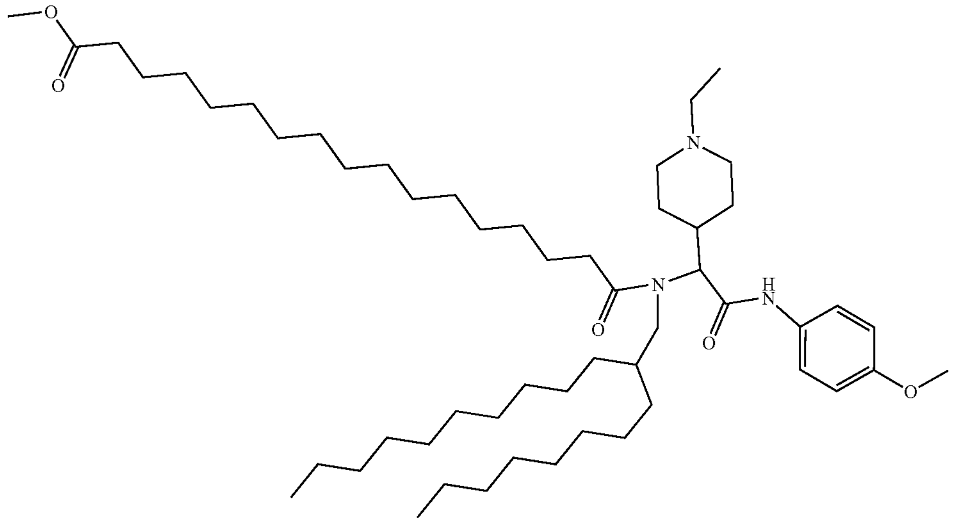
P360A4
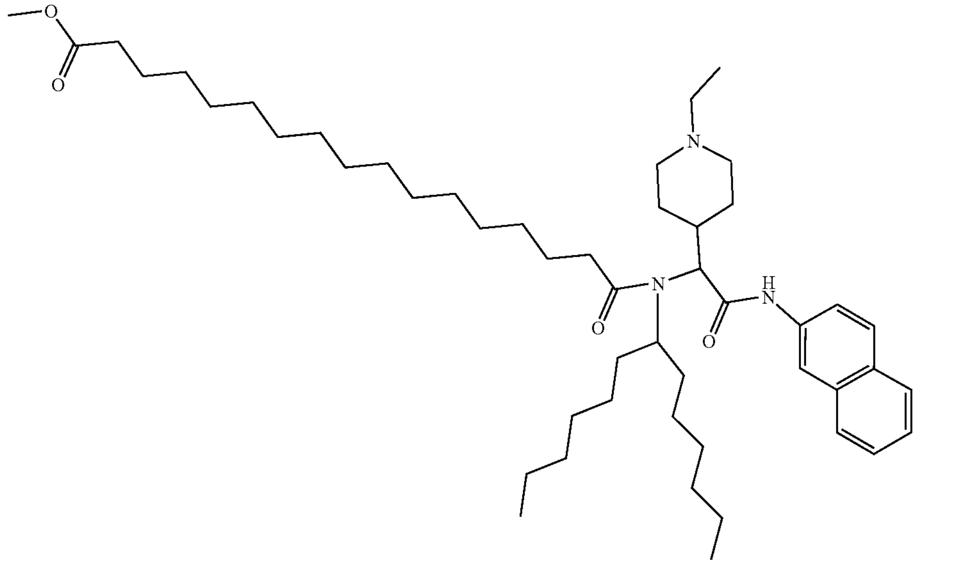

-continued
P360B2
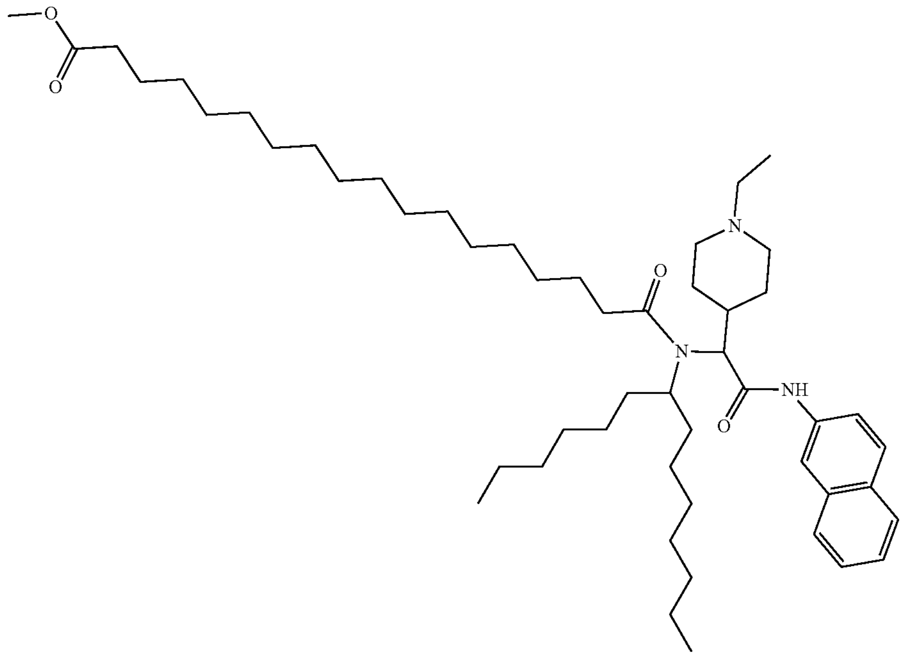
P360B9
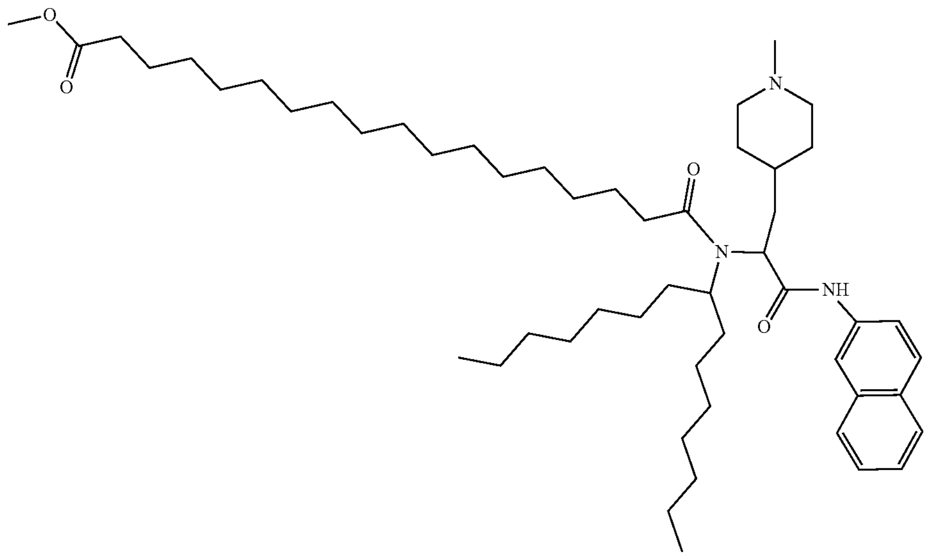
P360E3
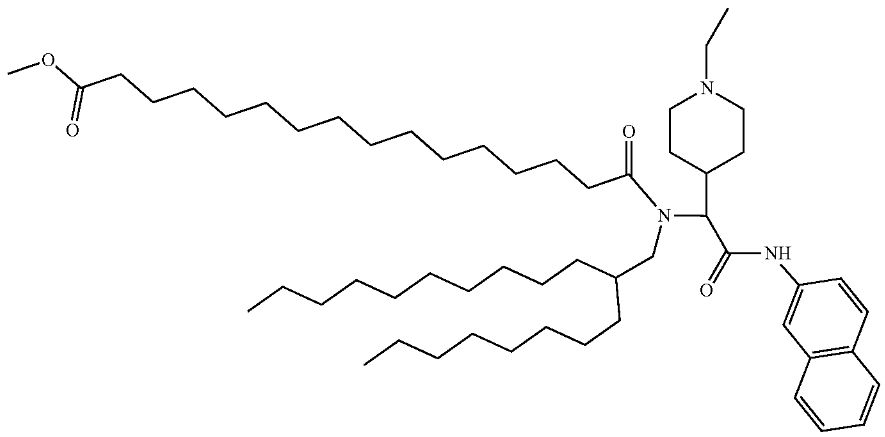

-continued
P362B2
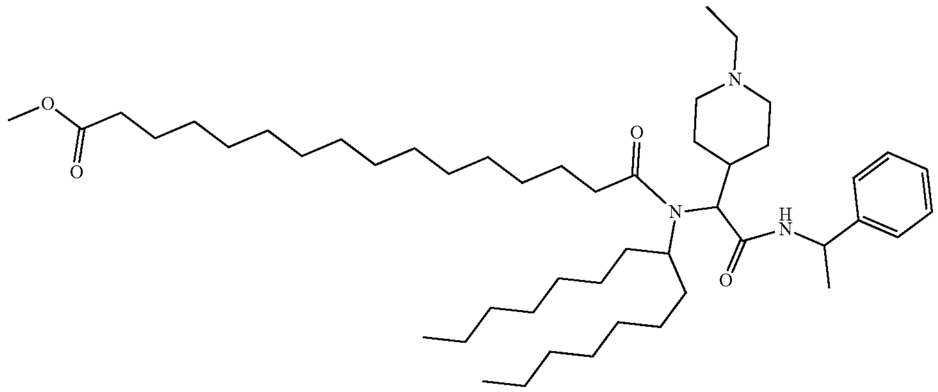
P362B3
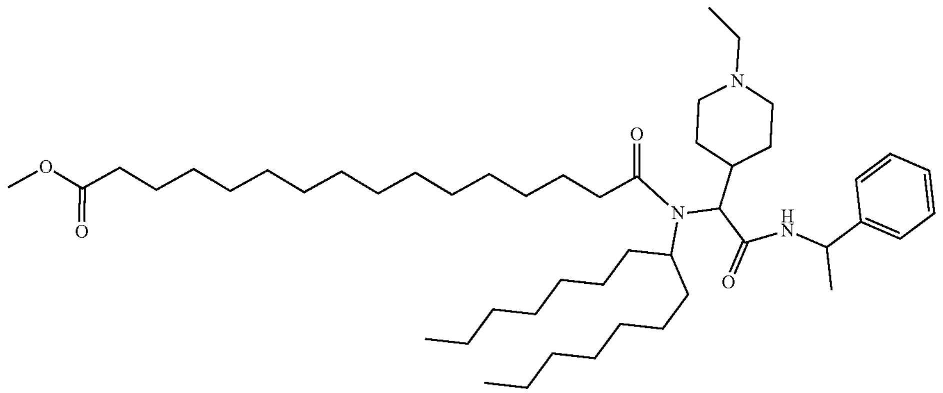
P362C3
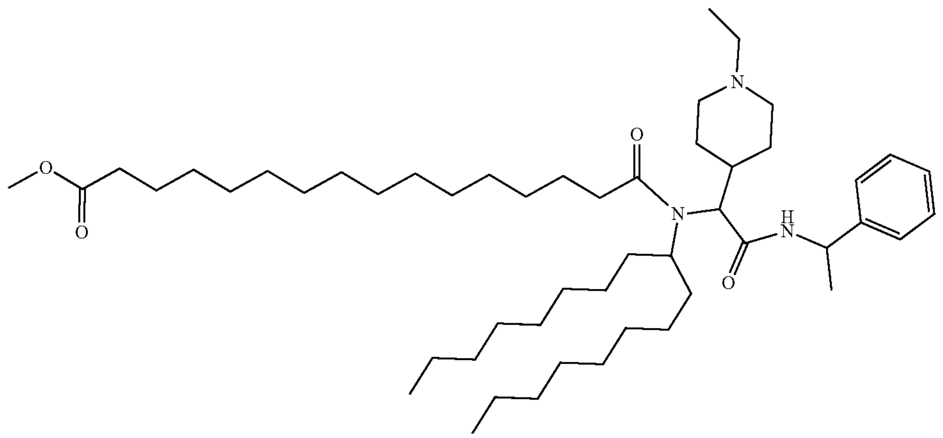

-continued
P362C4
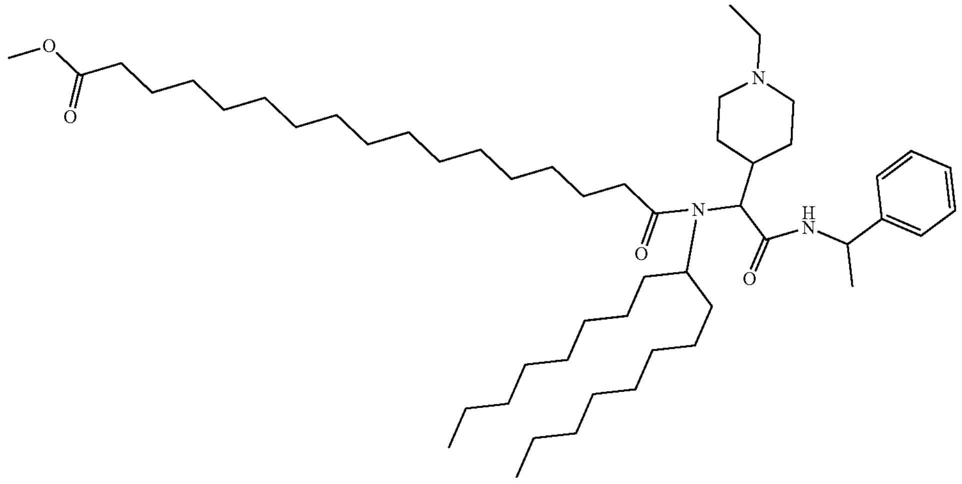
P362E3
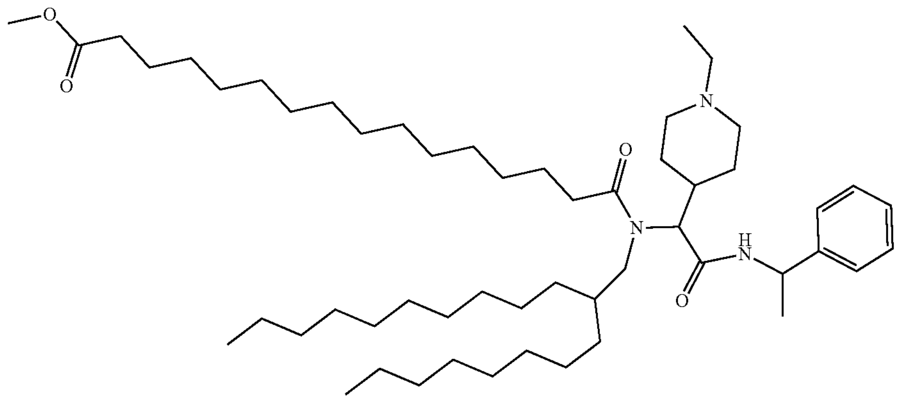
P363A2
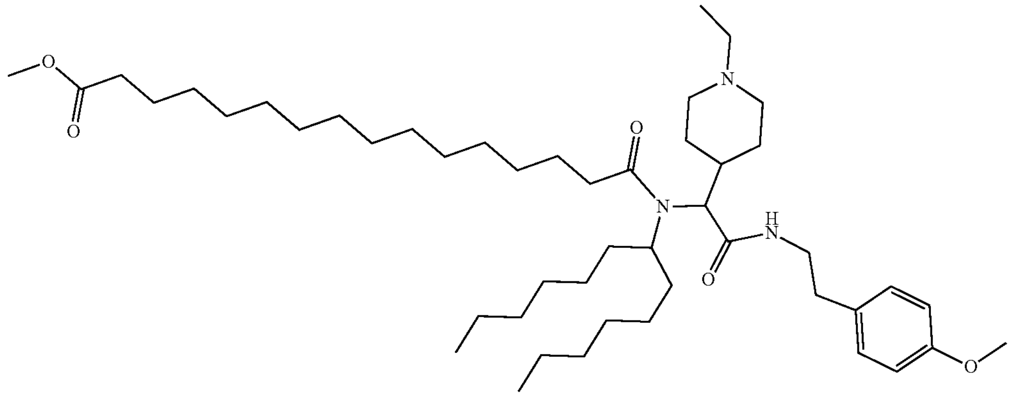

-continued
P363B2
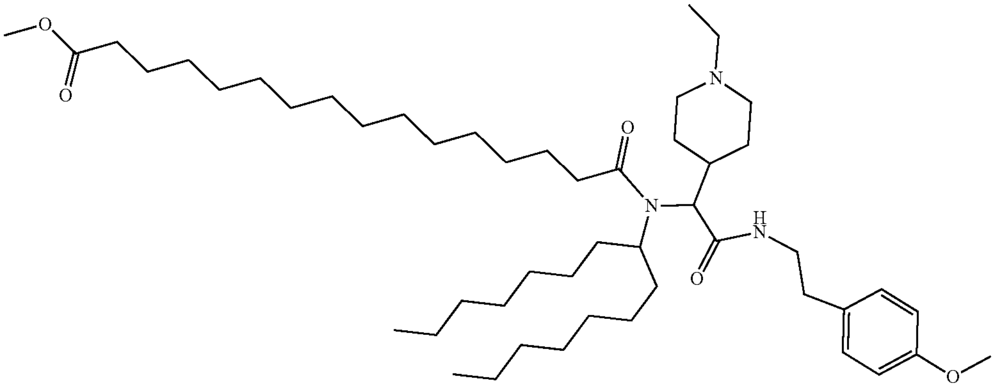
P363C3
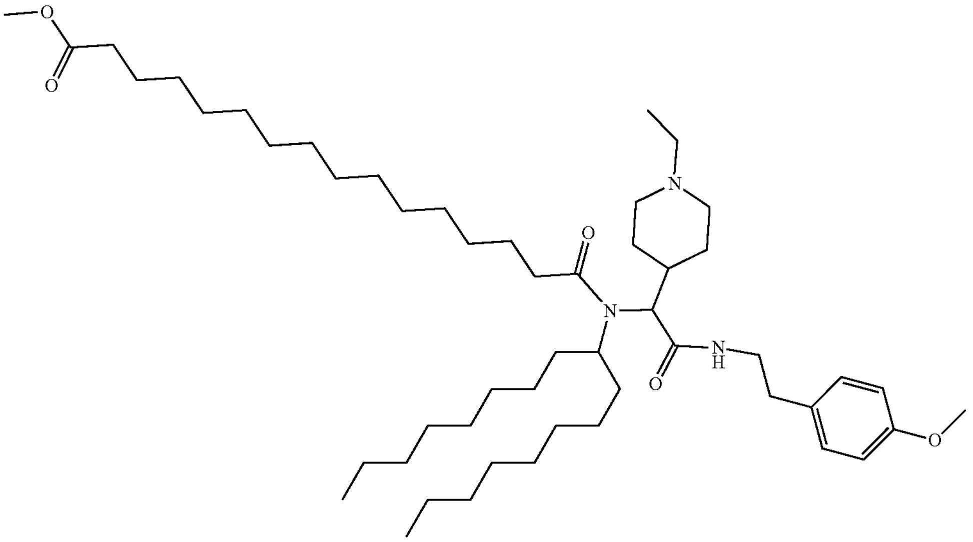
P363C10
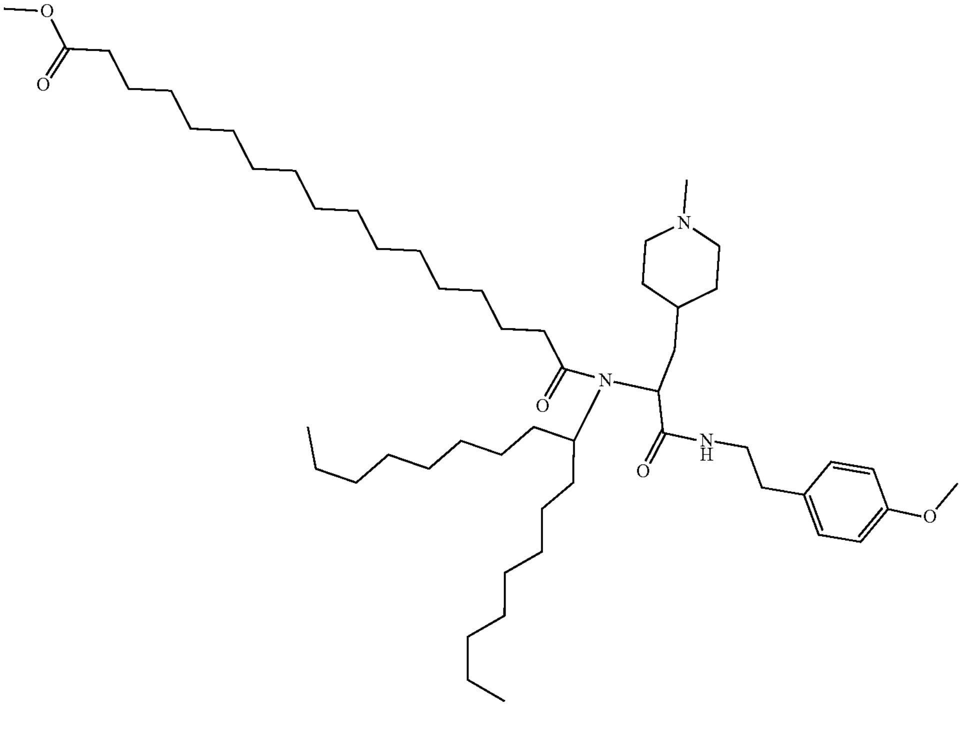

-continued
P363D9
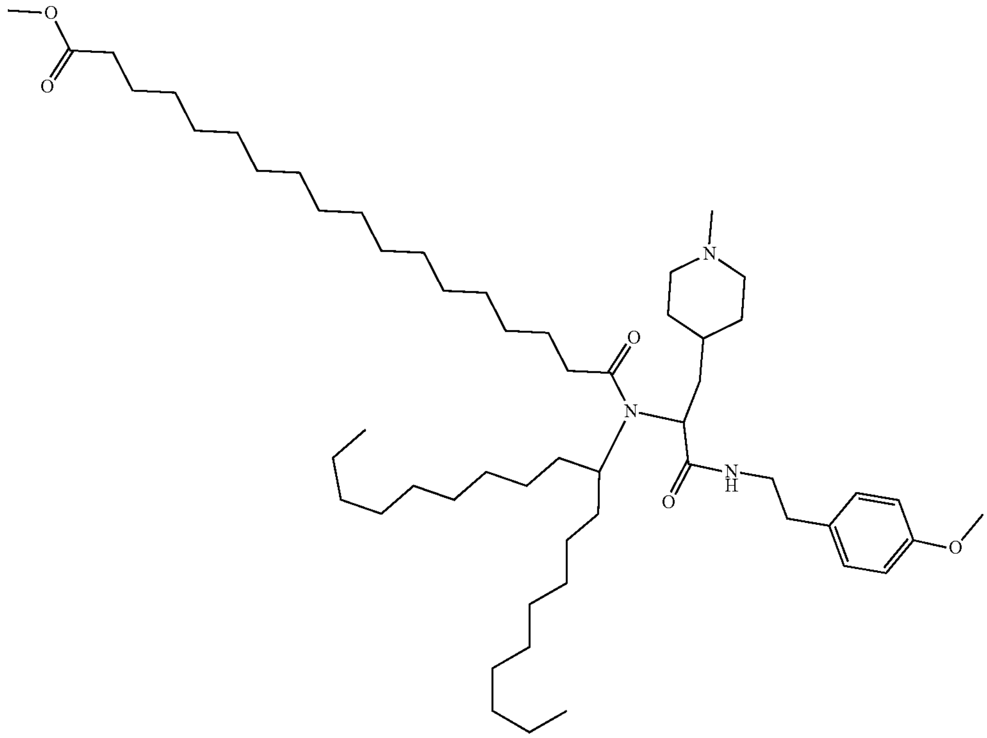
P363E2
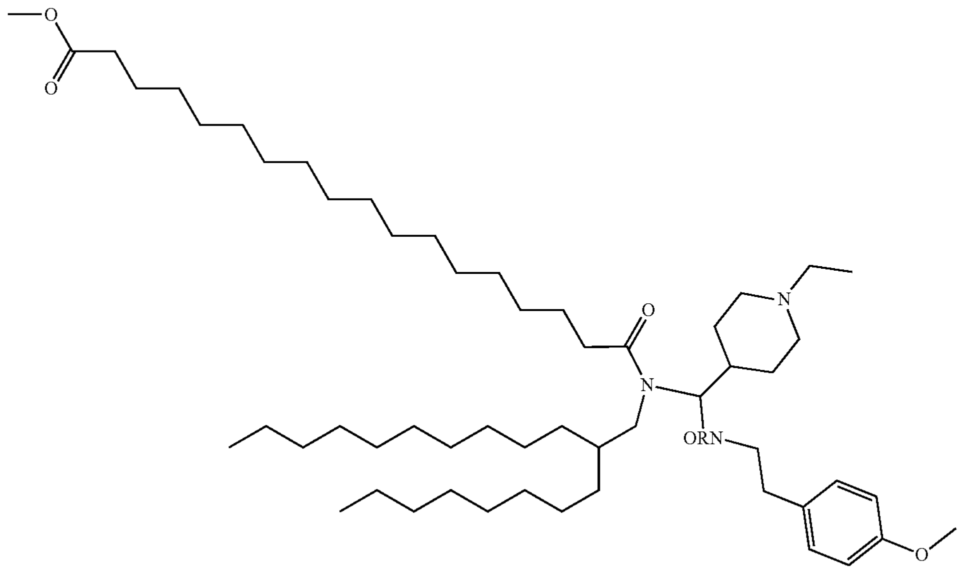

-continued
P363E3
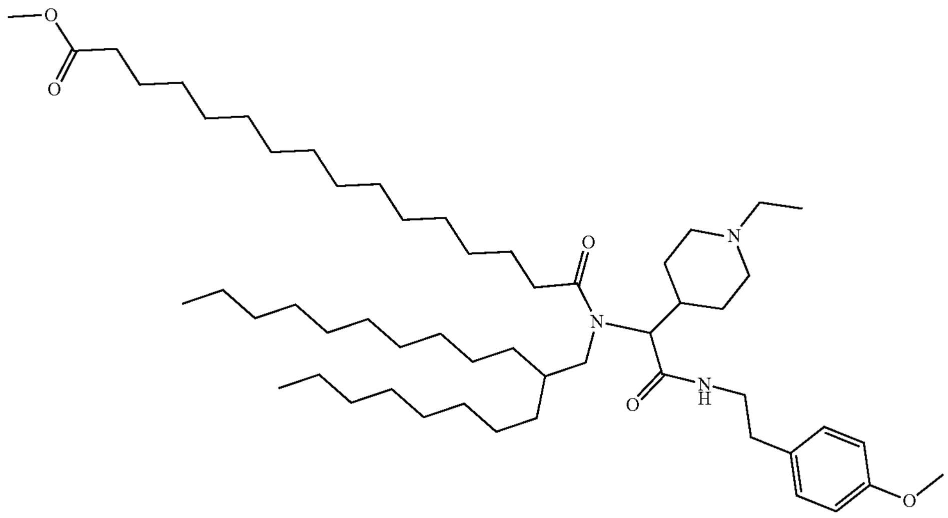
P363E4
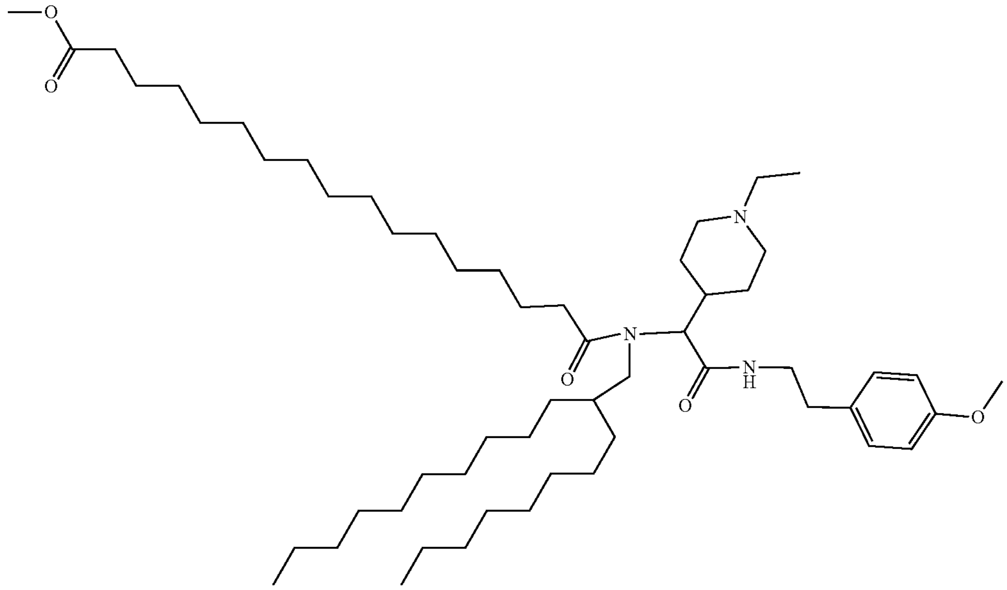
P363E12
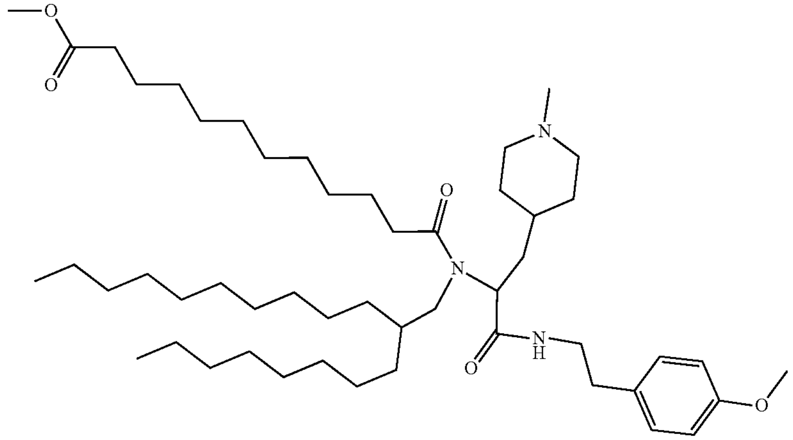

-continued

P363G10

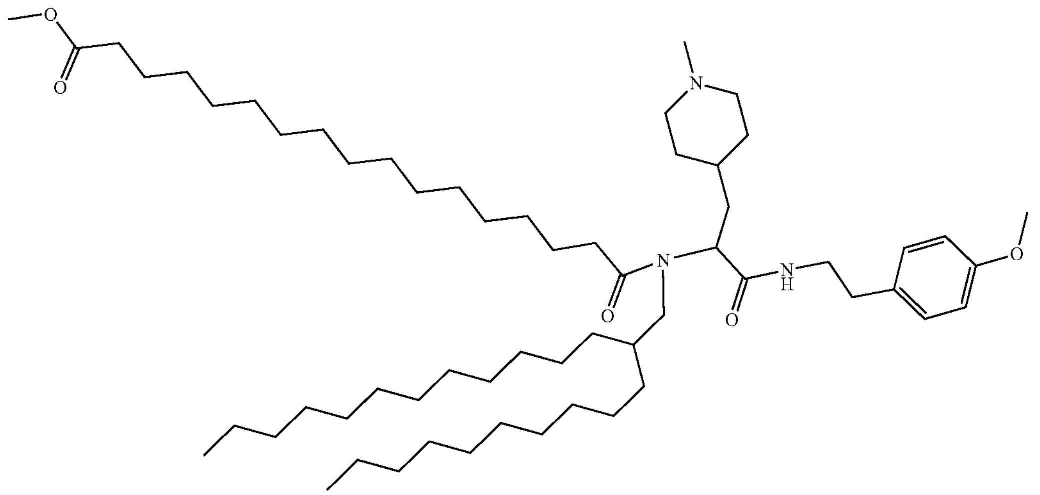

In some aspects, the nanoparticle compositions of the present invention are employed with another therapeutic compound separate from the nanoparticle for treatment of the same indication in the subject. In particular cases, the LNPs and the therapeutic agent are delivered separately or together. When delivered together, they may or may not be in the same formulation, and they may or may not be delivered by the same route.

In another aspect, the present disclosure provides methods of making a nanoparticle composition including lipid components comprising compounds of Formulae (I), (II), (III), and/or (IV).

DETAILED DESCRIPTION

Figure 1:
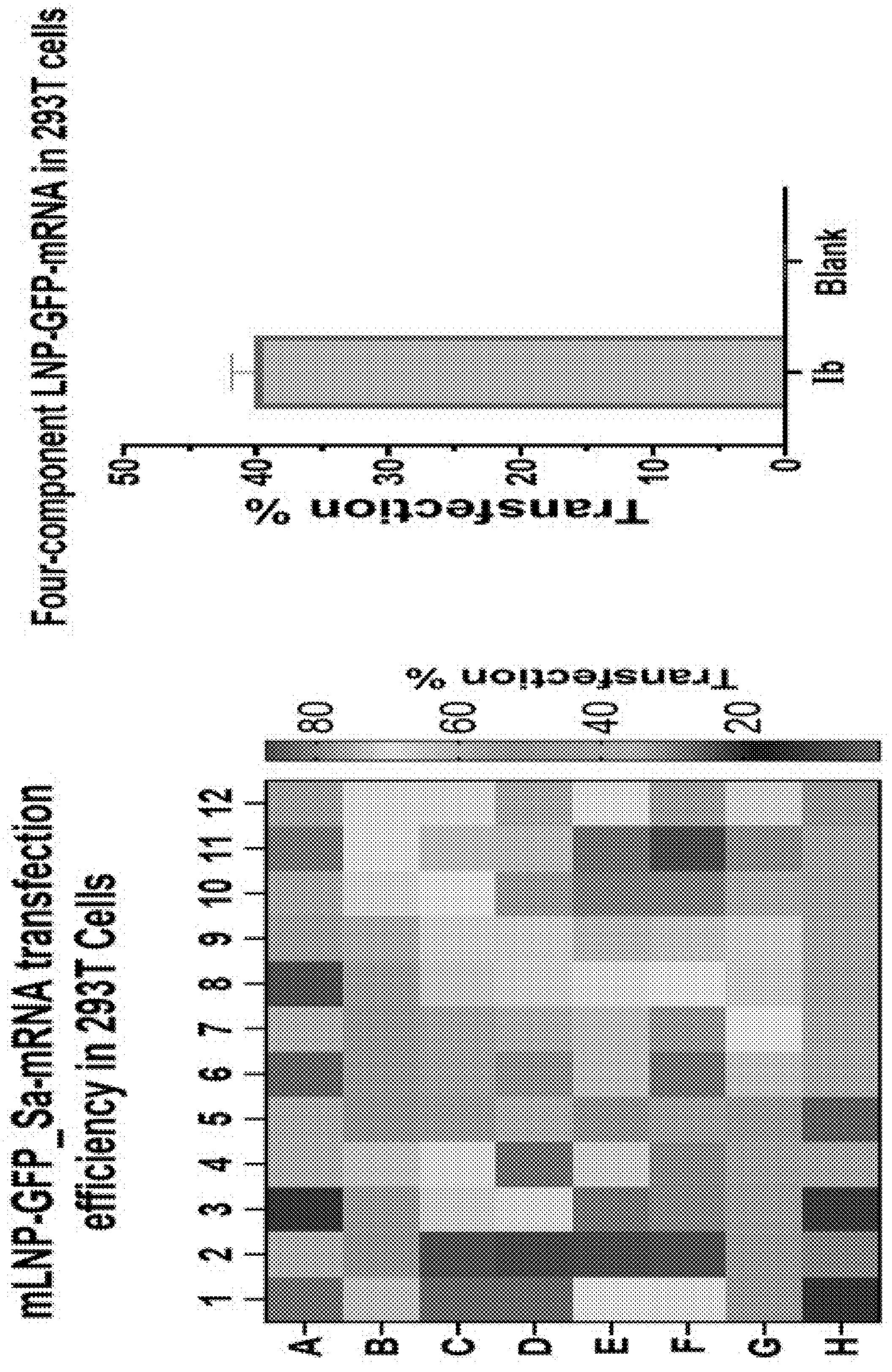
FIG. 1 shows a heat map of high-throughput screening of percent transfection of GFP-self-amplifying mRNA (GFP-saRNA) in to 293T cells in a 96-well plate, wherein the GFP-saRNA was delivered using mLNPs formulated with saccharide lipids and the ionizable lipid of Formula (Ib); compared to the percent transfection of GFP-saRNA delivered using 4 component LNPs comprising the ionizable lipid of Formula (Ib), a modular lipid, a phospholipid, and a PEG-lipid. The saccharide lipids of Formula (III)(a) corresponds to position E2 of the 96-well plate, the saccharide lipid of Formula (III)(b) corresponds to position F11, and the saccharide lipid of Formula (III)(c) corresponds to position C6.

The disclosure relates to novel lipids and lipid nanoparticle compositions including at least one novel lipid of the present disclosure. The disclosure also provides methods of delivering a biologically active agent to a cell, specifically delivering a biologically active agent to an organ and treating a disease or disorder in a mammal in need thereof. For example, a method of producing a polypeptide of interest in a cell involves contacting a nanoparticle composition comprising an mRNA with a cell, whereby the mRNA may be translated to produce the polypeptide of interest. A method of delivering a biologically active agent to a cell or organ may involve administration of a nanoparticle composition including the biologically active agent to a subject, in which the administration involves contacting the cell or organ with the composition, whereby the biologically active agent is delivered to the cell or organ.

The present disclosure provides novel saccharide lipids. Viral particles have a lipid envelop, which modifies envelop proteins or lipids with saccharides. Disaccharides have been shown to impact the lateral organization of lipid membranes, as discussed in J. Am. Chem. Soc. 2014, 136, 46, 16167-16175, which is incorporated herein by reference in its entirety. Novel saccharide lipids mimic the characteristics of viral particles, which improve transfection efficiency compared to 4 component LNPs.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

As used herein, the term "alkyl" or "alkyl group" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms), which is optionally substituted. The notation "$C_{1-14}$ alkyl" means an optionally substituted linear or branched, saturated hydrocarbon including 1-14 carbon atoms. Unless otherwise specified, an alkyl group described herein refers to both unsubstituted and substituted alkyl groups.

As used herein, the term "alkenyl" or "alkenyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond, which is optionally substituted. The notation "$C_{2-14}$ alkenyl" means an optionally substituted linear or branched hydrocarbon including 2-14 carbon atoms and at least one carbon-carbon double bond. An alkenyl group may include one, two, three, four, or more carbon-carbon double bonds. For example, $C_{18}$ alkenyl may include one or more double bonds. A $C_{18}$ alkenyl group including two double bonds may be a linoleyl group. Unless otherwise specified, an alkenyl group described herein refers to both unsubstituted and substituted alkenyl groups.

As used herein, the term "alkynyl" or "alkynyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one carbon-carbon triple bond, which is optionally substituted. The notation "$C_{2-14}$ alkynyl" means an optionally substituted linear or branched hydrocarbon including 2-14 carbon atoms and at least one carbon-carbon triple bond. An alkynyl group may include one, two, three, four, or more carbon-carbon triple bonds. For example, $C_{18}$ alkynyl may include one or more carbon-carbon triple bonds. Unless otherwise specified, an alkynyl group described herein refers to both unsubstituted and substituted alkynyl groups.

Alkyl, alkenyl, and cyclyl (e.g., carbocyclyl and heterocyclyl) groups may be optionally substituted unless otherwise specified.

About, Approximately: As used herein, the terms "approximately" and "about," as applied to one or more values of interest, refer to a value that is similar to a stated reference value. In certain aspects, the term "approximately" or "about" refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). For example, when used in the context of an amount of a given compound in a lipid component of a nanoparticle composition, "about" may mean+/−10% of the recited value.

As used herein, the term "compound," is meant to include all isomers and isotopes of the structure depicted. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

As used herein, the term "contacting" means establishing a physical connection between two or more entities. For example, contacting a cell with a nanoparticle composition means that the cell and a nanoparticle are made to share a physical connection. Methods of contacting cells with external entities both in vivo and ex vivo are well known in the biological arts. For example, contacting a nanoparticle composition and a cell disposed within a mammal may be performed by varied routes of administration (e.g., intravenous, intranasal, intratracheal, intraperitoneal, intramuscular, intradermal, and subcutaneous) and may involve varied amounts of nanoparticle compositions. Moreover, more than one cell may be contacted by a nanoparticle composition.

As used herein, the term "delivering" means providing an entity to a destination. For example, delivering a biologically active agent to a subject may involve administering a nanoparticle composition including the biologically active agent to the subject (e.g., by an intravenous, intranasal, intratracheal, intraperitoneal, intramuscular, intradermal, or subcutaneous route). Administration of a nanoparticle composition to a mammal or cell may involve contacting one or more cells with the nanoparticle composition.

As used herein, "encapsulation efficiency" refers to the amount of a biologically active agent that becomes part of a nanoparticle composition, relative to the initial total amount of biologically active agent used in the preparation of a nanoparticle composition. For example, if 97 mg of biologically active agent are encapsulated in a nanoparticle composition out of a total 100 mg of biologically active agent initially provided to the composition, the encapsulation efficiency may be given as 97%. As used herein, "encapsulation" may refer to complete, substantial, or partial enclosure, confinement, surrounding, or encasement.

As used herein, "expression" of a nucleic acid sequence refers to translation of an mRNA into a polypeptide or protein and/or post-translational modification of a polypeptide or protein.

As used herein, the term "isomer" means any geometric isomer, tautomer, zwitterion, stereoisomer, enantiomer, or diastereomer of a compound. Compounds may include one or more chiral centers and/or double bonds and may thus exist as stereoisomers, such as double-bond isomers (i.e., geometric E/Z isomers) or diastereomers (e.g., enantiomers (i.e., (+) or (−)) or cis/trans isomers). The present disclosure encompasses any and all isomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereomeric mixtures of compounds and means of resolving them into their component enantiomers or stereoisomers are well-known.

A person of ordinary skill in the art will recognize that the reactions can be optimized to give one isomer preferentially, new schemes may be devised to produce a single isomer, or isomeric mixtures containing any of a variety of isomer ratios may be utilized. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures. If one isomer is preferred, techniques such as preparative thin layer chromatography, preparative HPLC, preparative chiral HPLC, or preparative SFC may be used to separate the isomers.

As used herein, a "lipid component" is that component of a nanoparticle composition that includes one or more lipids. For example, the lipid component may include one or more cationic/ionizable, PEGylated, structural, or other lipids, such as phospholipids.

As used herein, a "stabilizer lipid" or "stabilizer" refers to a lipid component that functions to prevent particle aggregation; improve particle stability during preparation and storage; and modulates immune response against the nanoparticle. Stabilizers include saccharide lipids of the disclosure and PEGlyated lipids. In some aspects, modular lipids of the disclosure may be a stabilizer lipid if it contains a PEG and/or saccharide group.

As used herein, "methods of administration" may include intravenous, intramuscular, intradermal, subcutaneous, or other methods of delivering a composition to a subject. A method of administration may be selected to target delivery (e.g., to specifically deliver) to a specific region or system of a body.

As used herein, "modified" means non-natural. For example, an RNA may be a modified RNA. That is, an RNA may include one or more nucleobases, nucleosides, nucleotides, or linkers that are non-naturally occurring. A "modified" species may also be referred to herein as an "altered" species. Species may be modified or altered chemically, structurally, or functionally. For example, a modified nucleobase species may include one or more substitutions that are not naturally occurring.

As used herein, "naturally occurring" means existing in nature without artificial aid.

As used herein, "patient" refers to a subject who may seek or be in need of treatment, requires treatment, is receiving treatment, will receive treatment, or a subject who is under care by a trained professional for a particular disease or condition.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient," as used herein, refers to any ingredient other than the compounds described herein (for example, a vehicle capable of suspending, complexing, or dissolving the active compound) and having the properties of being substantially nontoxic and non-inflammatory in a patient. Excipients may include, for example: anti-adherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E (alpha-tocopherol), vitamin C, xylitol, and other species disclosed herein.

Compositions may also include salts of one or more compounds. Salts may be pharmaceutically acceptable salts. As used herein, "pharmaceutically acceptable salts" refers to derivatives of the disclosed compounds wherein the parent compound is altered by converting an existing acid or base moiety to its salt form (e.g., by reacting a free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, $17^{th}$ ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), each of which is incorporated herein by reference in its entirety.

As used herein, the term "polypeptide" or "polypeptide of interest" refers to a polymer of amino acid residues typically joined by peptide bonds that can be produced naturally (e.g., isolated or purified) or synthetically.

As used herein, an "RNA" refers to a ribonucleic acid that may be naturally or non-naturally occurring. For example, an RNA may include modified and/or non-naturally occurring components such as one or more nucleobases, nucleosides, nucleotides, or linkers. An RNA may include a cap structure, a chain terminating nucleoside, a stem loop, a polyA sequence, and/or a polyadenylation signal. An RNA may have a nucleotide sequence encoding a polypeptide of interest. For example, an RNA may be a messenger RNA (mRNA). Translation of an mRNA encoding a particular polypeptide, for example, in vivo translation of an mRNA inside a cell, may produce the encoded polypeptide. RNAs may be selected from the non-liming group consisting of small interfering RNA (siRNA), asymmetrical interfering RNA (aiRNA), microRNA (miRNA), Dicer-substrate RNA (dsRNA), small hairpin RNA (shRNA), mRNA, and mixtures thereof.

As used herein, the terms "PEG lipids" or "PEG-modified lipids" or "PEGylated lipids" refer to a lipid modified with polyethylene glycol. A PEG lipid may be selected from the non-limiting group consisting of PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

As used herein, the term "structural lipids" are steroids, structural lipids suitable for 4 component LNPs include, cholesterol, fecosterol, sitosterol, ergosterol, campesterol, stigmasterol, brassicasterol, tomatidine, tomatine, ursolic acid, alpha-tocopherol, and mixtures thereof. In some aspects, a two-component or three-component mLNP of the present disclosure is free of structural lipids. For example, a two-component or three-component mLNP of the present disclosure may be free of steroids/structural lipids such as cholesterol, fecosterol, sitosterol, ergosterol, campesterol, stigmasterol, brassicasterol, tomatidine, tomatine, ursolic acid, alpha-tocopherol, and mixtures thereof.

As used herein, "size" or "mean size" in the context of nanoparticle compositions refers to the mean diameter of a nanoparticle composition.

As used herein, the term "subject" or "patient" refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants.

The term "biologically active agent" refers to any agent that, when administered to a subject, has a therapeutic, diagnostic, and/or prophylactic effect and/or elicits a desired biological and/or pharmacological effect. Such agents include, but are not limited to, cytotoxins, radioactive ions, chemotherapeutic agents, small molecule drugs, proteins, and nucleic acids.

As used herein, the terms "therapeutically effective amount" or "effective amount" means an amount of an agent to be delivered (e.g., nucleic acid, drug, composition, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Nanoparticle Compositions

The present disclosure provides novel nanoparticle compositions. As used herein, a "nanoparticle composition" is a composition comprising one or more lipids. Nanoparticle compositions are typically sized on the order of micrometers or smaller and may include a lipid bilayer. Nanoparticle compositions encompass lipid nanoparticles (LNPs), liposomes (e.g., lipid vesicles), and lipoplexes. Nanoparticle compositions comprising a lipid component comprising at least one compound according to Formulae (I), (II), (III) or (IV) are described herein. In some aspects, LNPs of the present disclosure exclude lipid compositions that have a core-shell structure.

In one aspect, the present disclosure provides compounds of Formula (I) or a salt or isomer thereof:

(I)

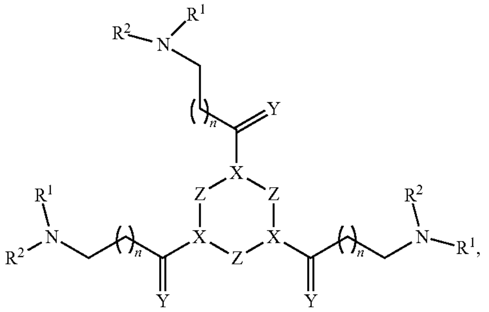

wherein each n is independently an integer from 0-10, e.g., 0, 1, 2, 3, 4, 5, 6, 7, 8, 9, or 10, or any subrange selected from within the range of 0-10, e.g., 2-9, 3-8, 4-7, 1-5, 1-4, 5-9, etc.; each of $R^1$ and $R^2$ is independently selected from H, C1-C24 alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

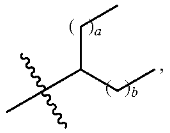

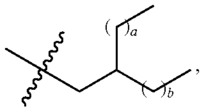

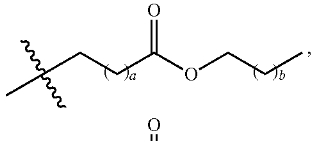

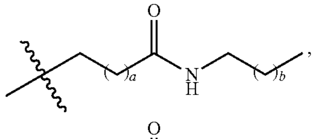

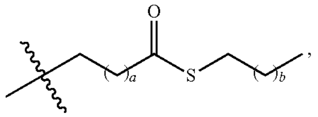

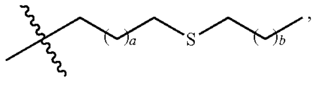

-continued
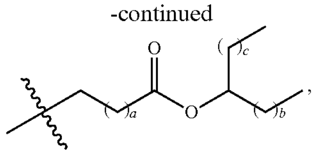
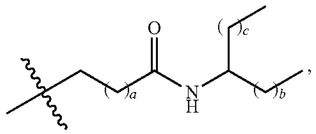
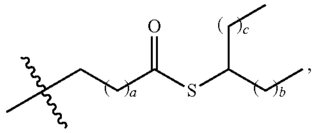
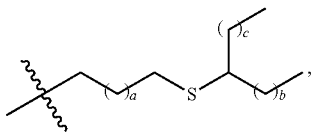
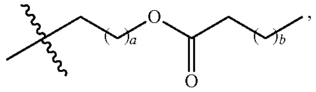
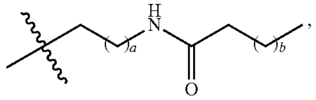
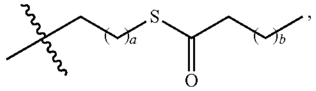
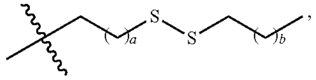
-continued
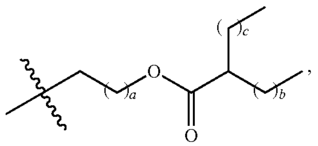
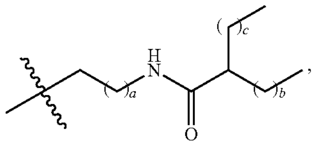
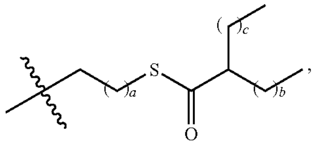
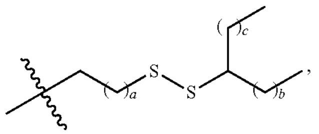
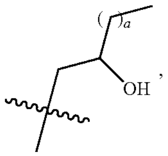
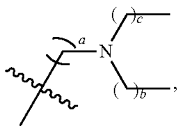
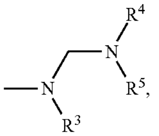
a, b and c are each independently an integer from 1-24;
each X is independently selected from CH, or N;
each Y is independently selected from $CH_2$, NH, O, or S; and
each Z is independently selected from $CH_2$, NH, O, or S.
(Ia)
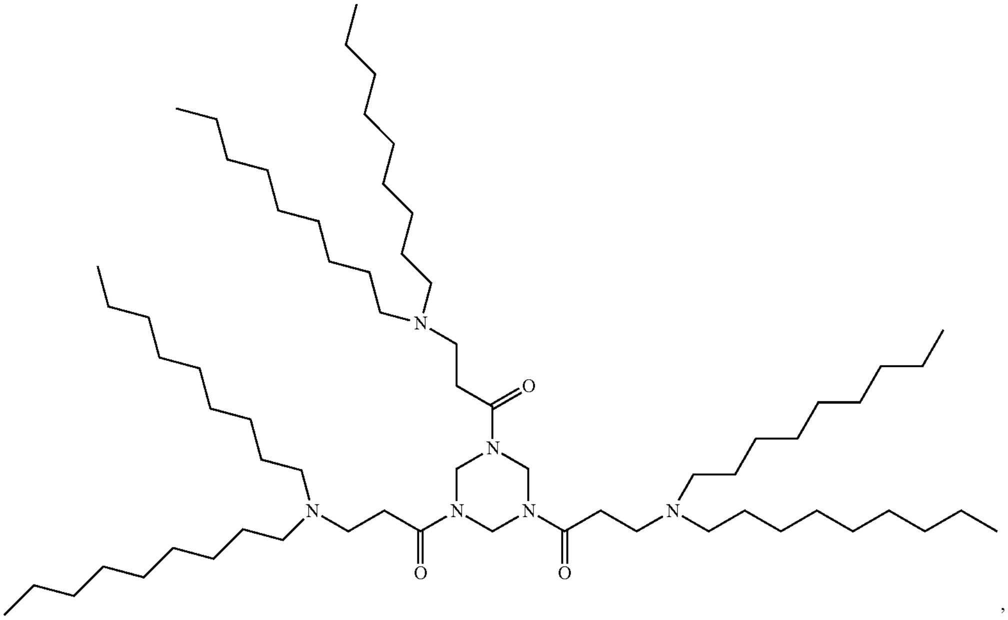
, -continued (Ib)

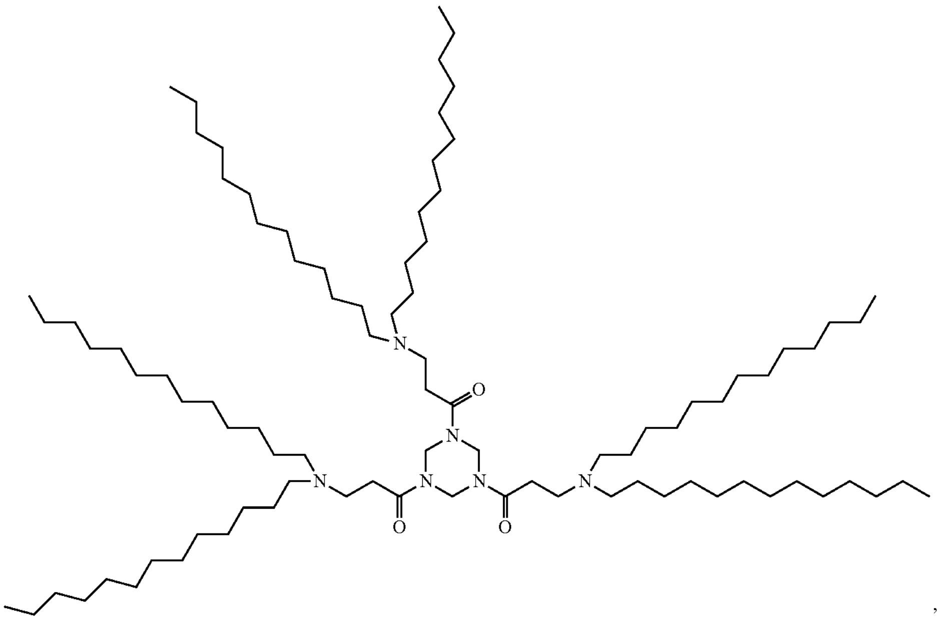

, or a salt or isomer thereof.

Synthesis Scheme 1.

In one aspect, the present disclosure provides the general synthesis routes for the synthesis of the compound of Formula I.

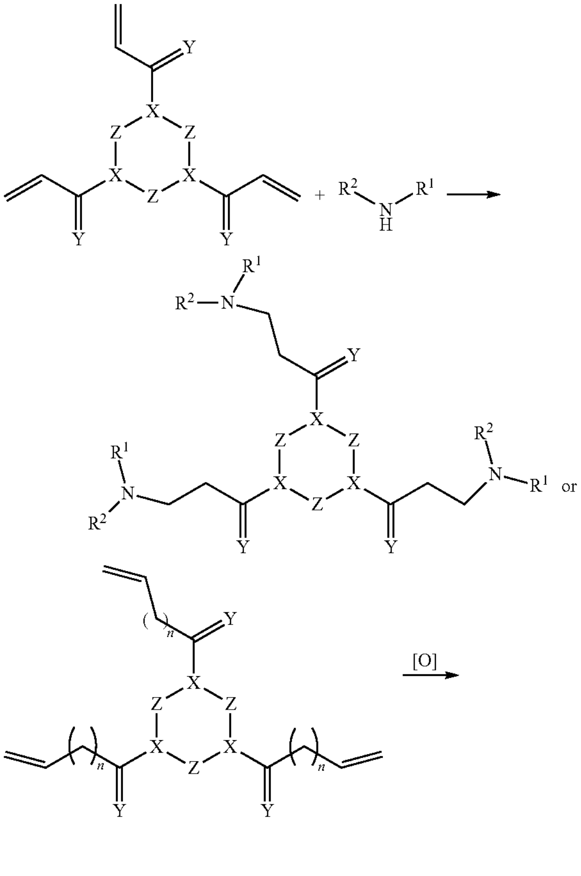

-continued

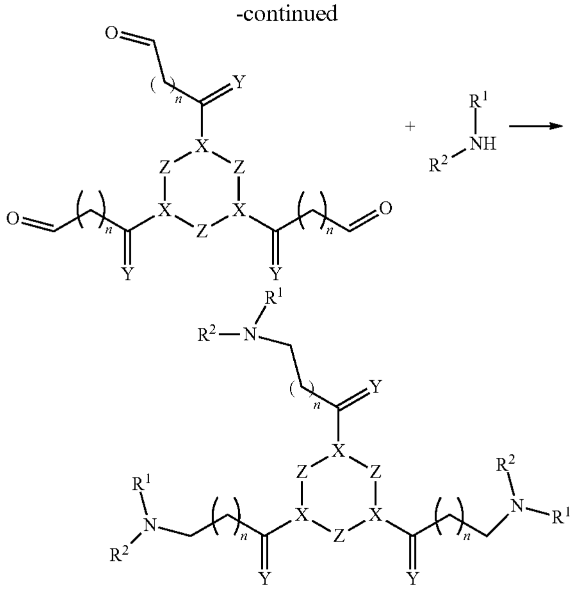

In one aspect, the present disclosure provides compounds of Formula (II):

(II)

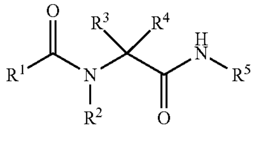

or a salt or isomer thereof, wherein each of $R^1$, $R^4$ and $R^5$ is independently selected from $C_2$-$C_{24}$ alkyl, $C_2$-$C_{24}$ alkenyl, $C_2$-$C_{24}$ alkynyl, substituted $C_2$-$C_{24}$ alkyl, substituted alkenyl, substituted alkynyl, substituted acyl, substituted carbocyclyl, substituted heterocyclyl, substituted aryl, substituted heteroaryl, poly(ethylene glycol) (PEG),
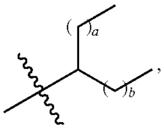,
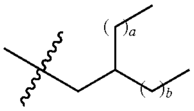,
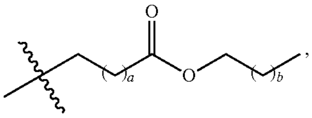,
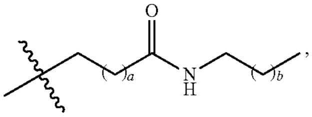,
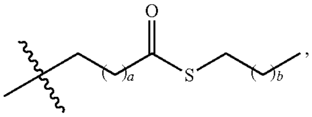,
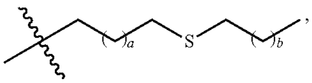,
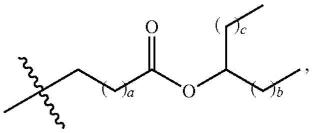,
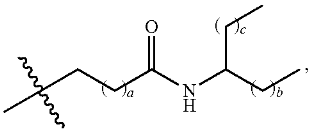,
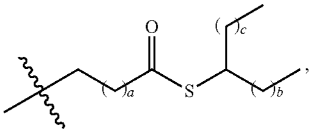,
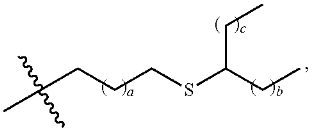,
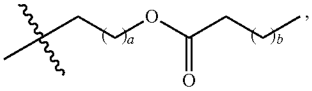,
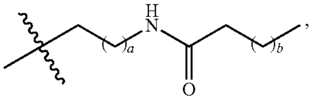,
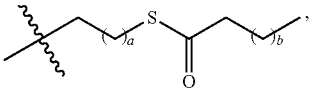,
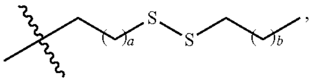,
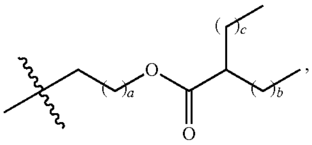,
-continued
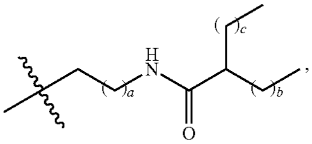,
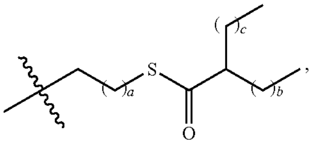,
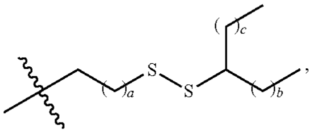,
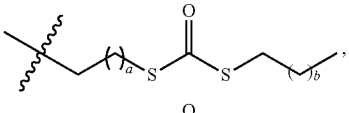,
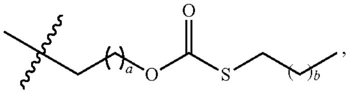,
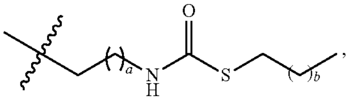,
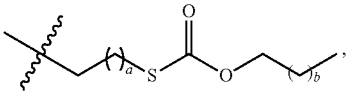,
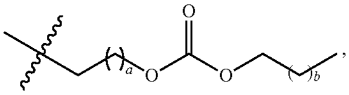,
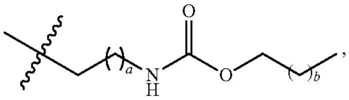,
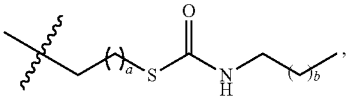,
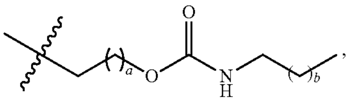,
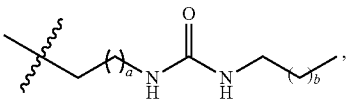,
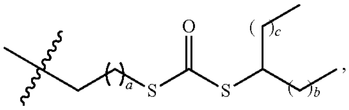,
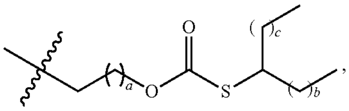,
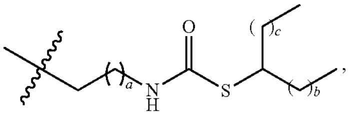, -continued
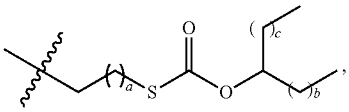,
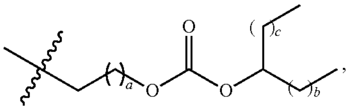,
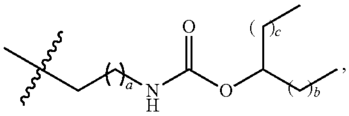,
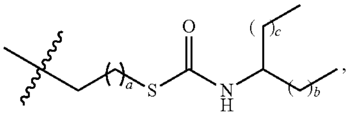,
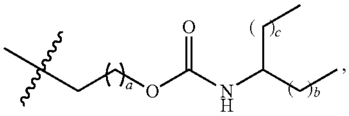,
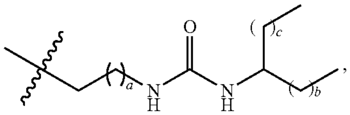, 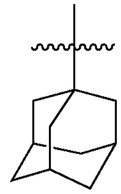,
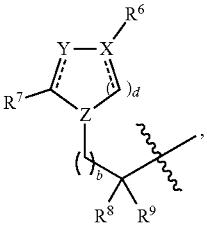, 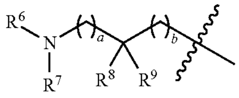,
each of $R^2$ and $R^3$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl, poly(ethylene glycol) (PEG),
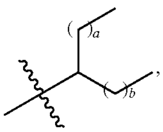, 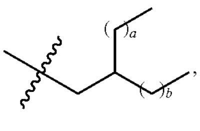,
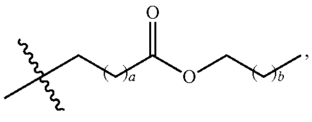,
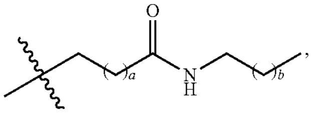,
-continued
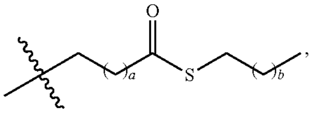,
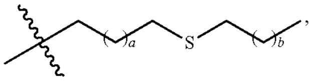,
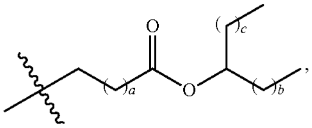,
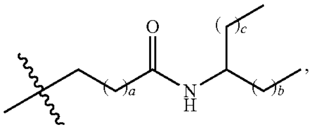,
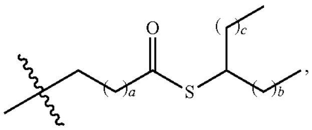,
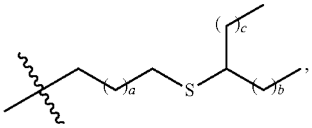,
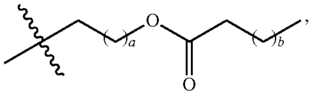,
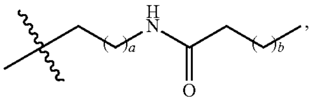,
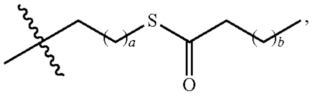,
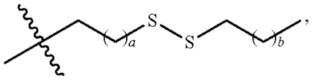,
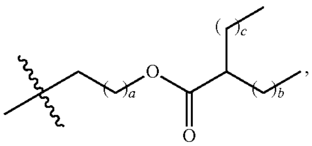,
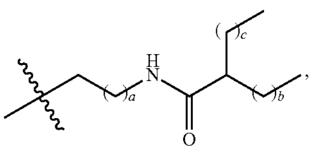,
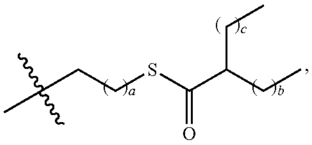, -continued
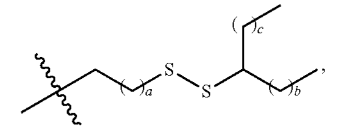
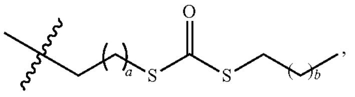
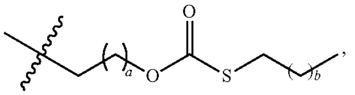
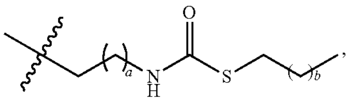
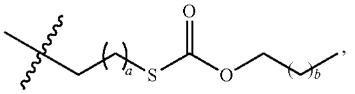
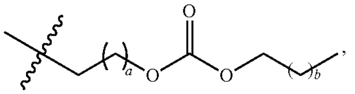
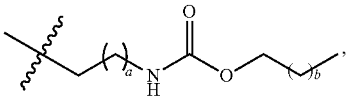
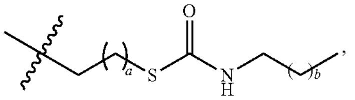
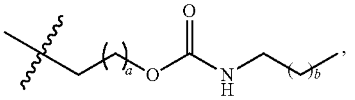
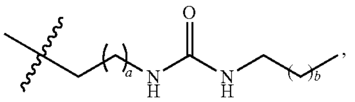
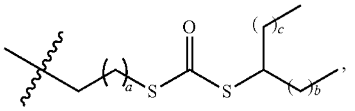
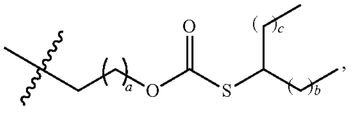
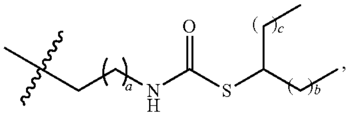
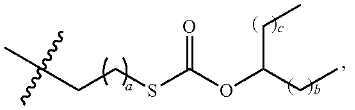
-continued
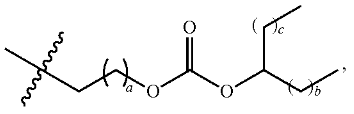
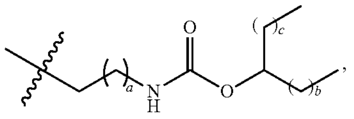
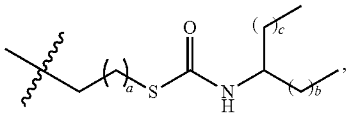
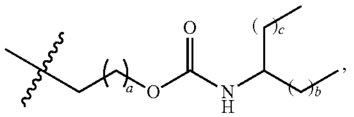
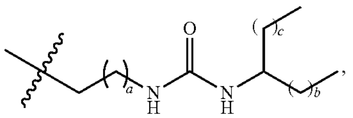
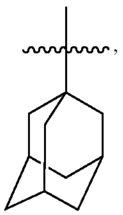
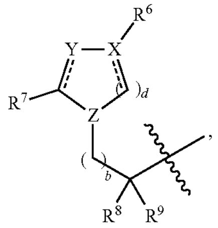
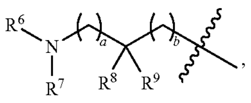
a, b and c are each independently an integer from 0-24;
each of $R^6$, $R^7$, $R^8$, $R^9$ is independently selected from H, C1-C24 alkyl, C1-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl,
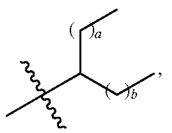
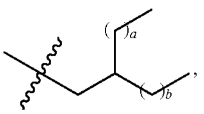
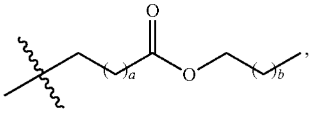
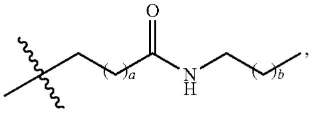

-continued
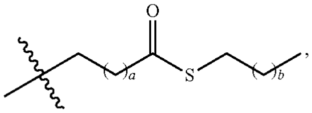
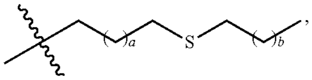
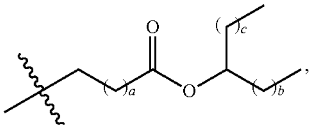
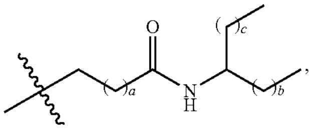
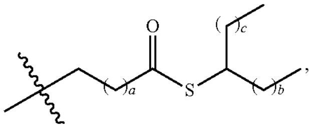
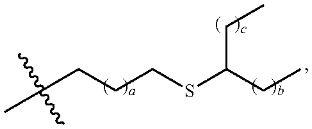
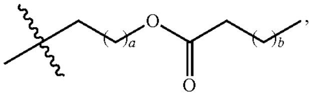
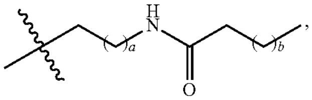
-continued
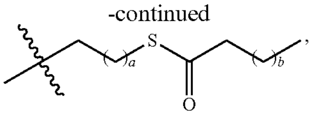
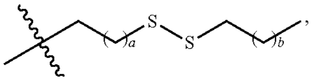
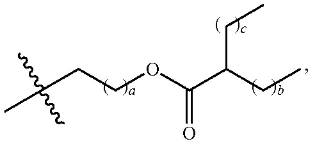
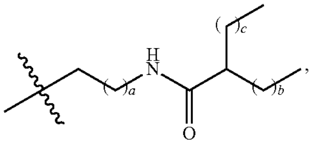
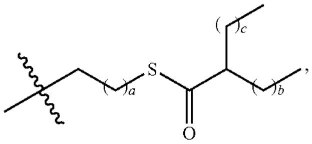
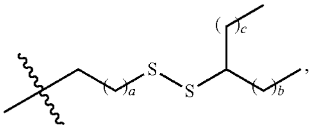
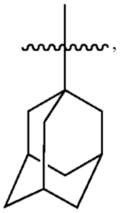
a, b and c are each independently an integer from 0-24;
each X is independently selected from CH or N;
each Y is independently selected from $CH_2$, NH, O, or S;
each Z is independently selected from CH or N;
In certain aspects, compounds of Formula II may include, for example, the following compounds:
Synthesis Scheme 2.
(IIa)
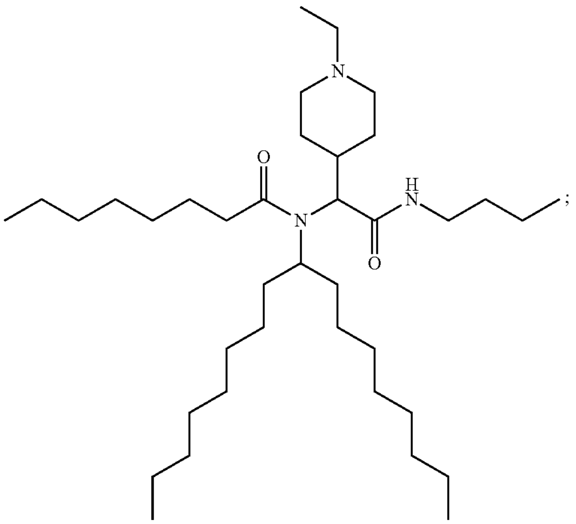
or -continued
(IIb)
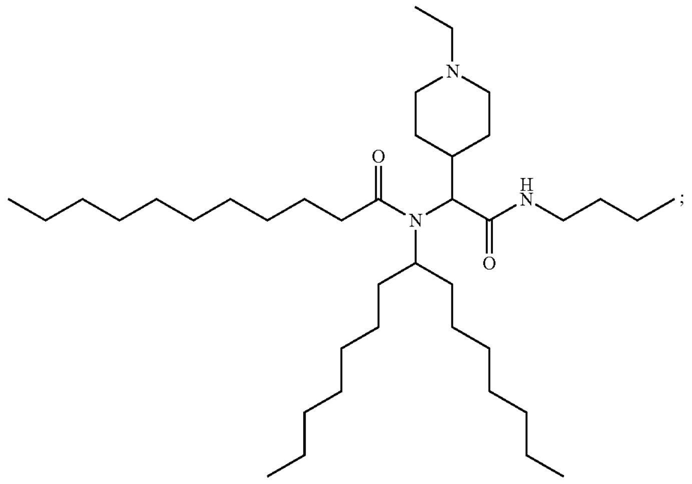
(IIc)
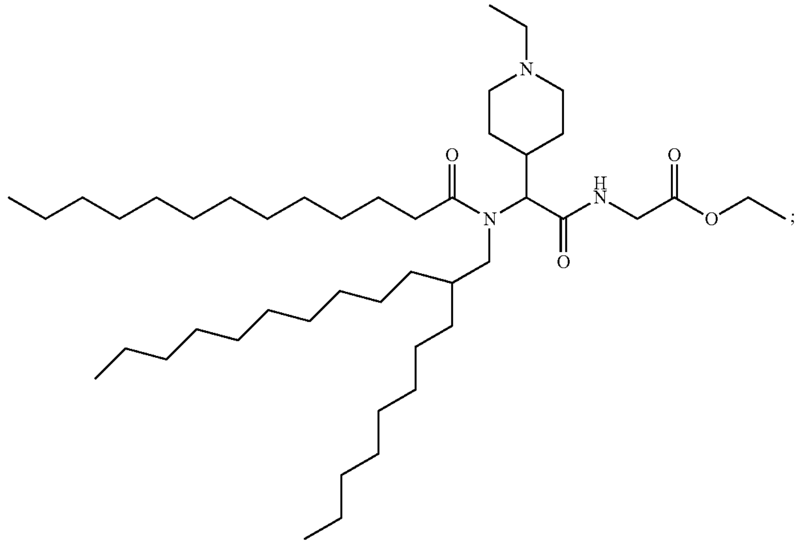
(IId)
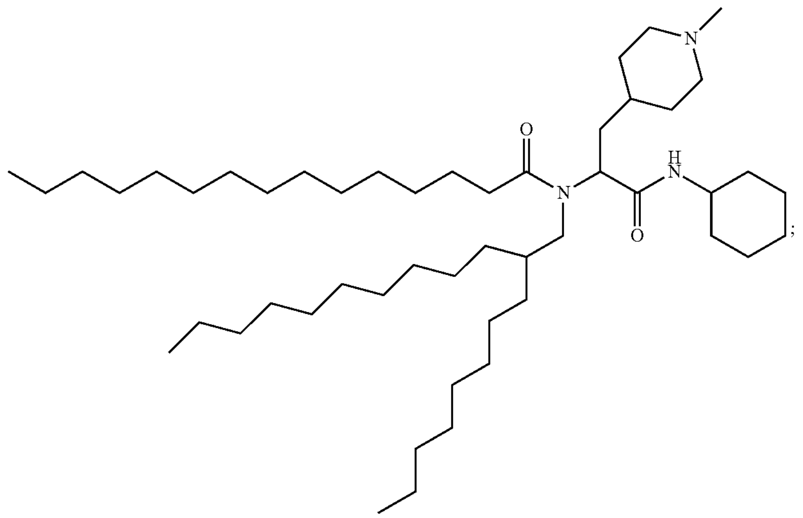

-continued (IIe)

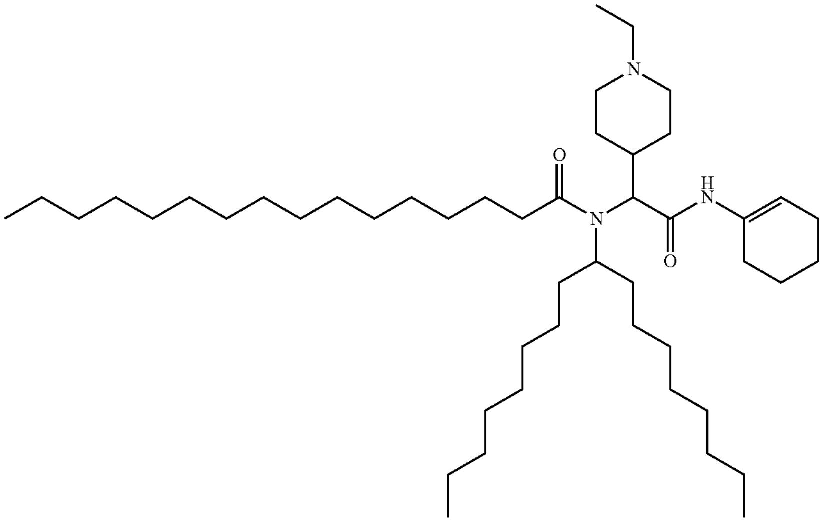

General synthetic route for the synthesis of compounds of Formula II.

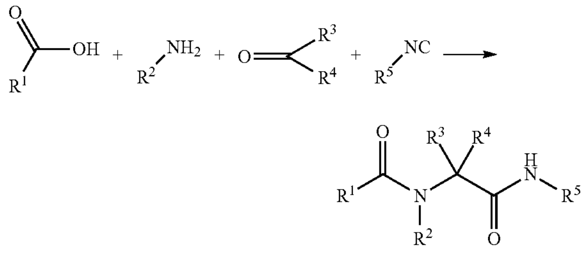

In one aspect, the present disclosure provides compounds of Formula (III):

(III)

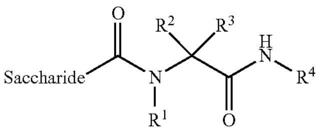

or a salt or isomer thereof, wherein each of $R^1$, $R^2$, $R^3$ and $R^4$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl, poly(ethylene glycol) (PEG),

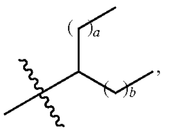

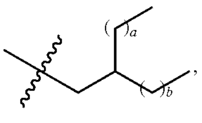

-continued

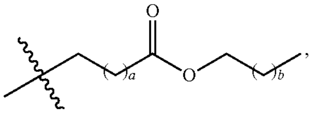

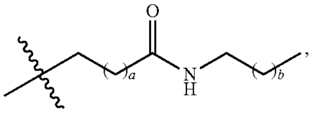

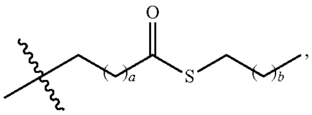

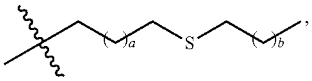

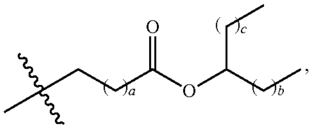

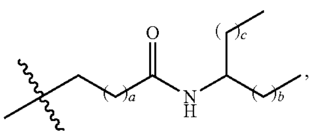

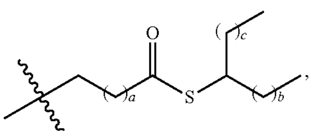

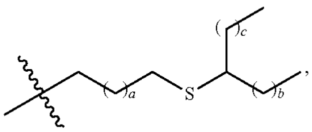

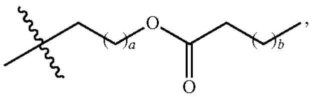

-continued
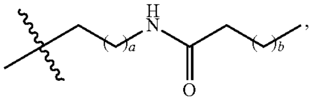
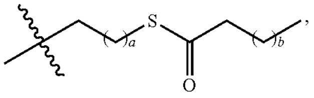
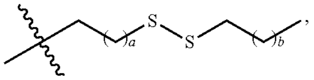
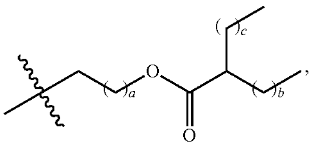
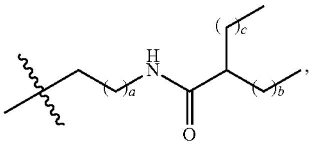
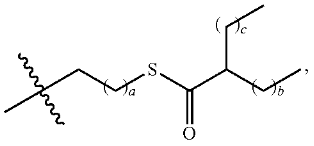
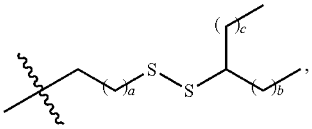
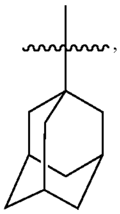
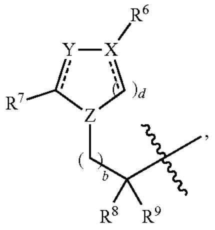
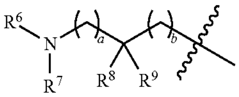
a, b and c are each independently an integer from 0-24; $R^6$, $R^7$, $R^8$ and $R^9$ are each independently selected from H, C1-C24 alkyl, C1-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl,
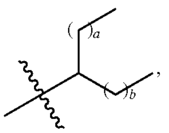
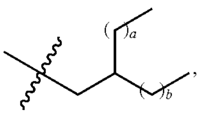
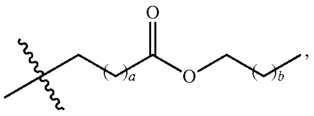
-continued
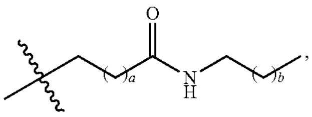
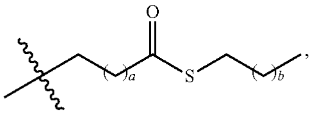
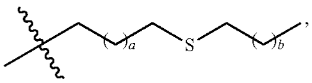
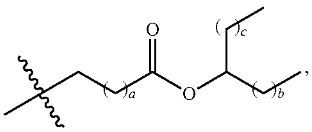
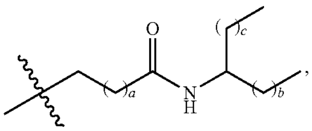
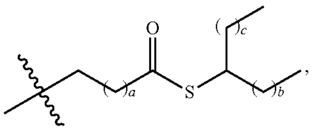
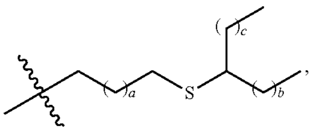
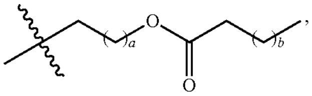
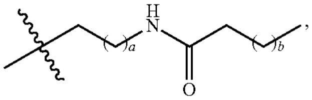
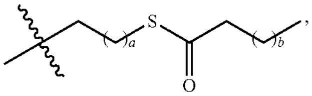
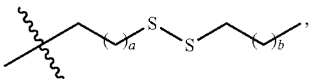
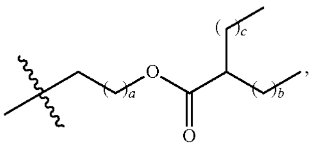
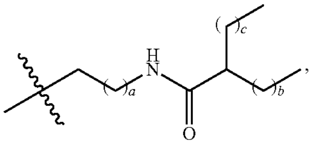
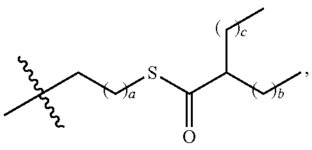

-continued

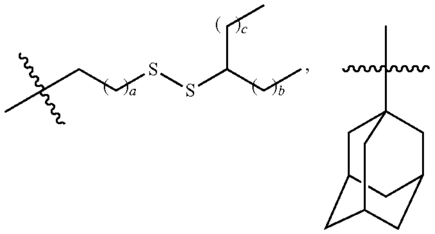

a, b and c are each independently an integer from 0-24;

each X is independently selected from CH or N;

each Y is independently selected from $CH_2$, NH, O, or S;

each Z is independently selected from CH or N;

and wherein the saccharide is selected from monosaccharides, disaccharides, oligosaccharides, and polysaccharides.

In certain aspects, compounds of Formula III may include, for example, the following compounds:

Synthesis Scheme 3.

(III)(a)

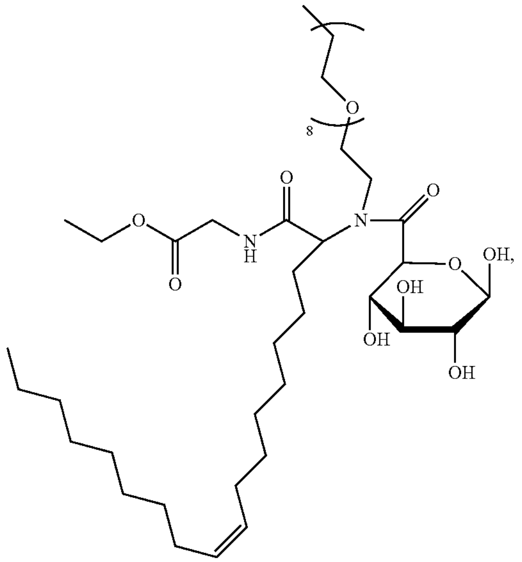

P1_E2

-continued (III)(b)

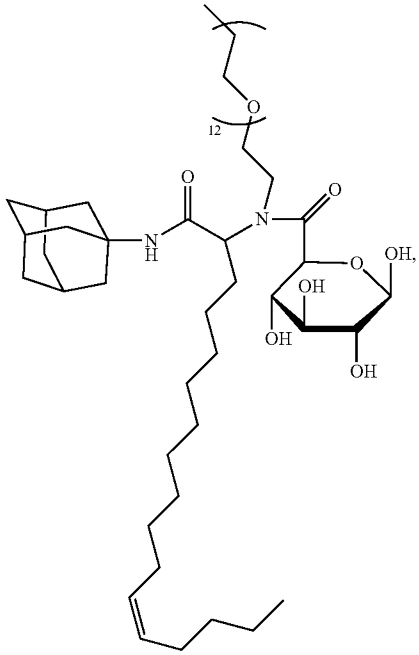

P1_F11

(III)(c)

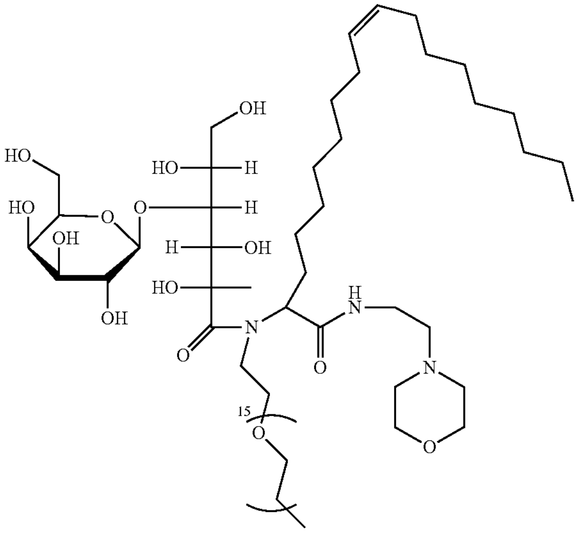

P1_C6

-continued
(III)(d)
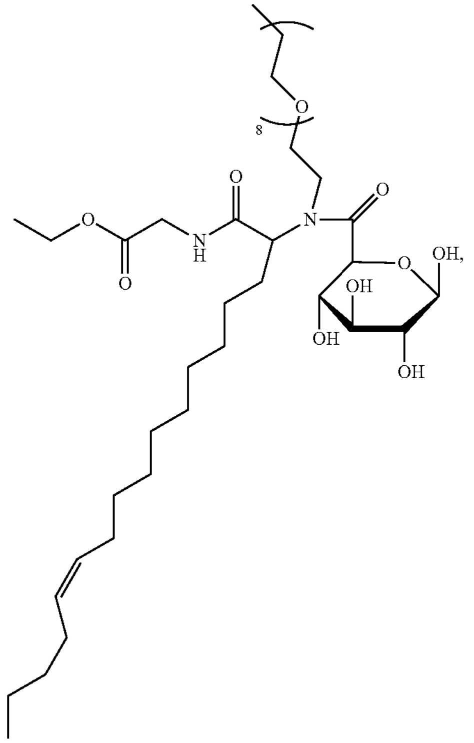
P1_E8
(III)(e)
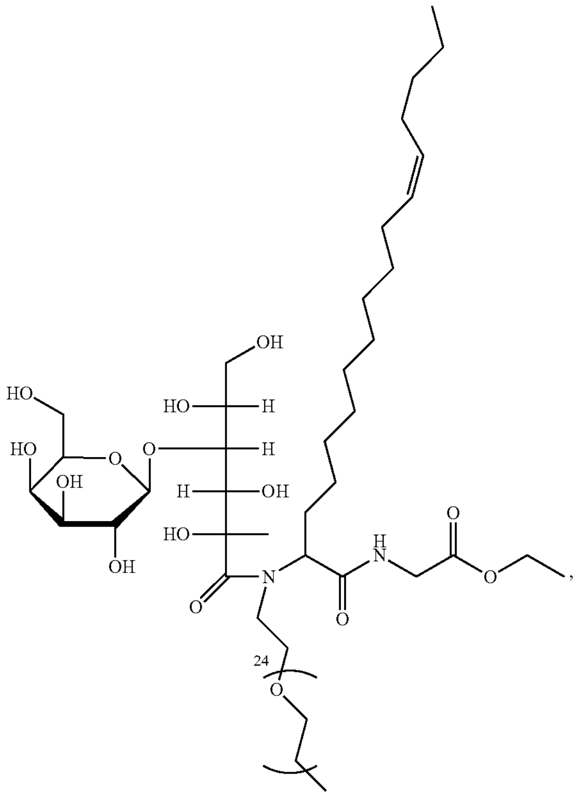
P1_D8
-continued
(III)(f)
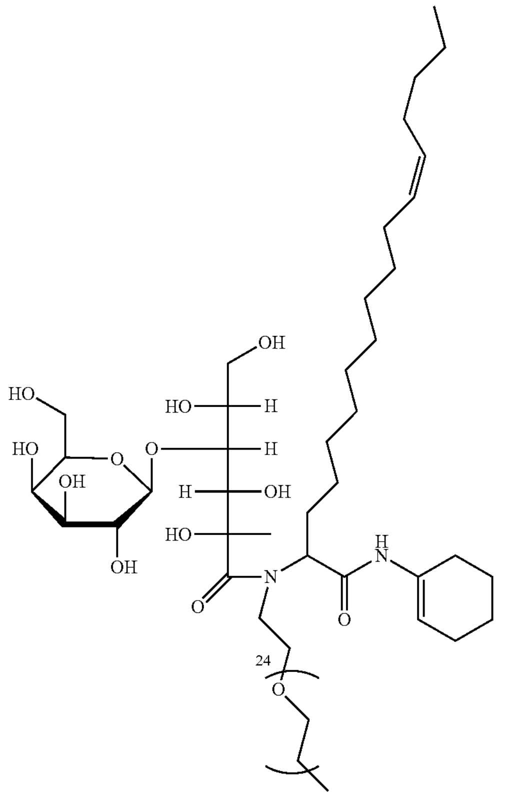
P1_D9
In one aspect, the present disclosure provides the general synthesis route for the synthesis of compounds of Formula III.
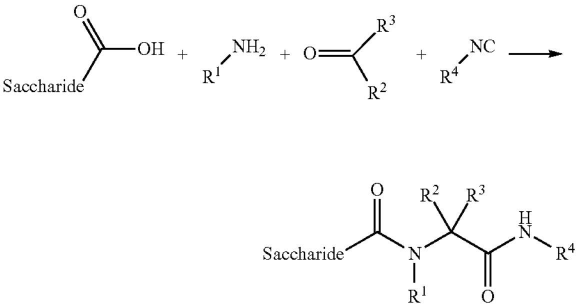
In one aspect, the
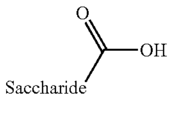

is one of
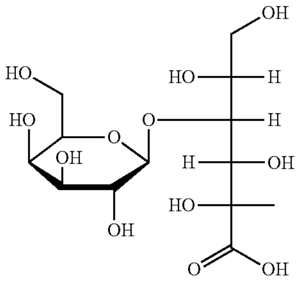
S-Ac-1
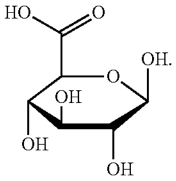
S-Ac-2
In one aspect, the
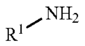
is one of
A1
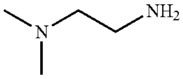
A2
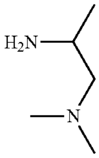
A3
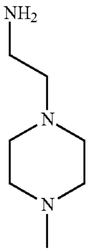
A4
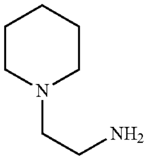
-continued
A5
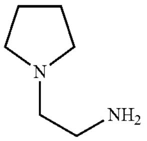
A6
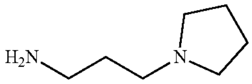
A7
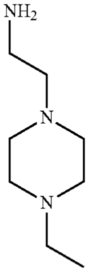
A8
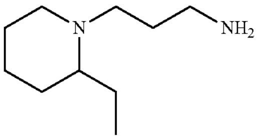
A9
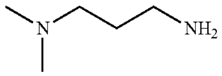
A10
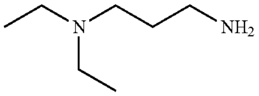
A11
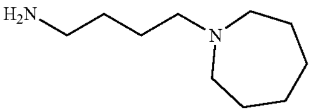
A12
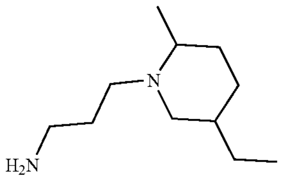
A13
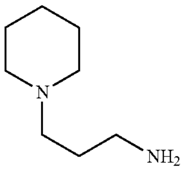
A14
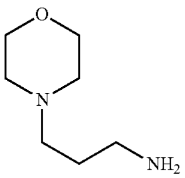

-continued
A15
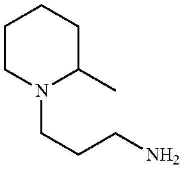
A16
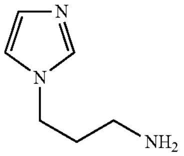
A17
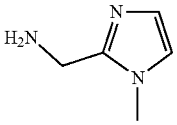
A18
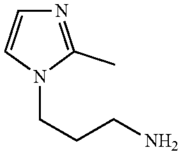
A19
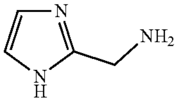
A20
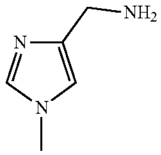
DA13p
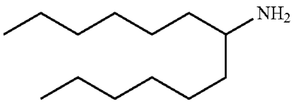
DA15p
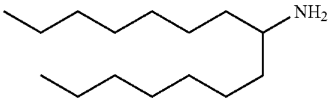
DA16p
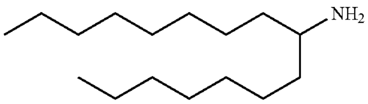
DA17p
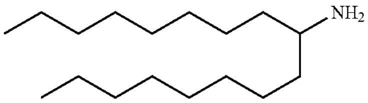
DA19p
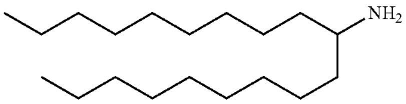
DA23p
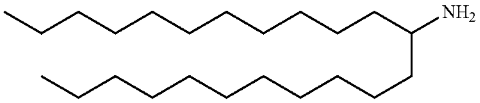
-continued
DA24mp
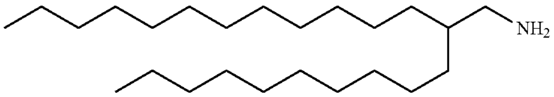
DA20mp
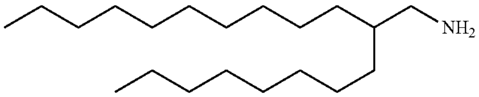
Am-PEG$_8$
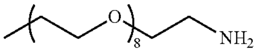
Am-PEG$_{12}$
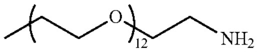
Am-PEG$_{15}$
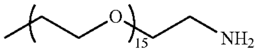
Am-PEG$_{24}$
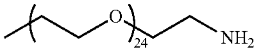
Am-PEG$_{48}$
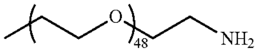
SA6
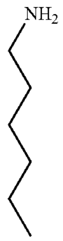
SA7
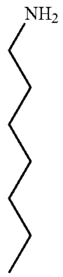
SA8
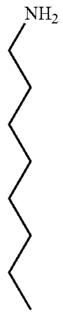

-continued
SA9
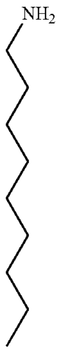
SA10
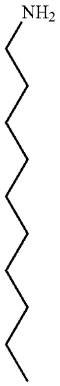
SA11
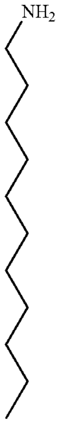
SA12
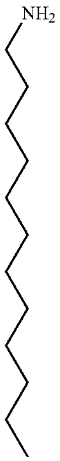
-continued
SA13
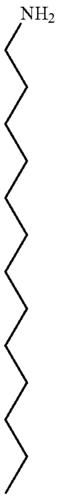
SA14
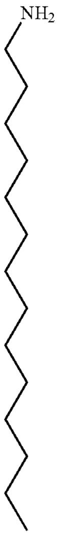
SA15
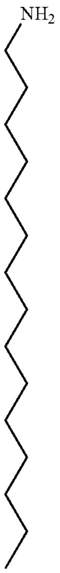

-continued
SA16
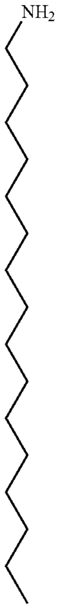
SA17
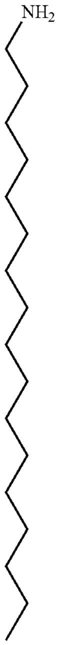
-continued
SA18
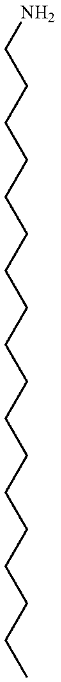
SA13
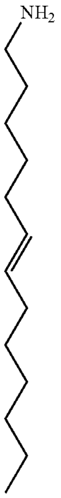

-continued
SA14
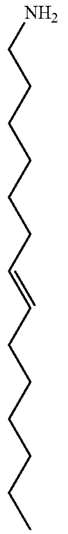
SA15
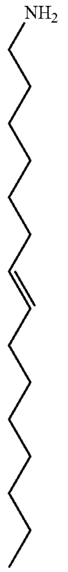
-continued
SA16
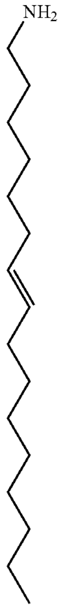
SA17
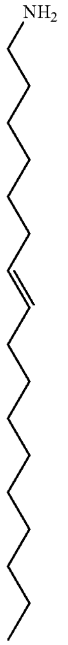

-continued
SA18
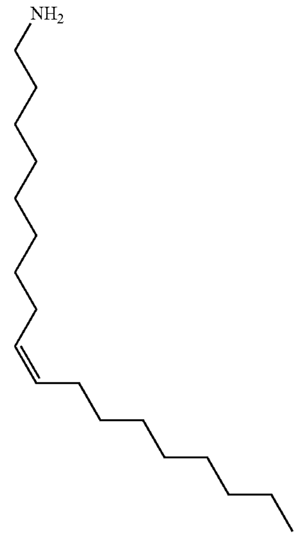
In one aspect, the
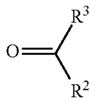
is one of
ALA1
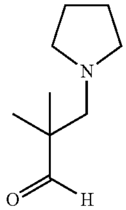
ALA2
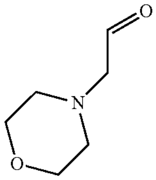
ALA3
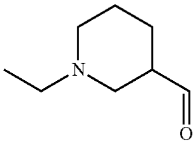
ALA4
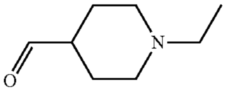
ALA5
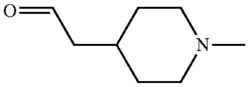
-continued
ALA6
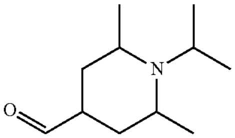
ALA7
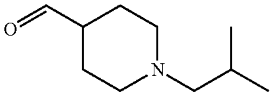
ALA8
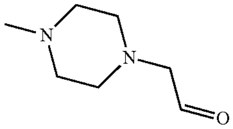
ALA9
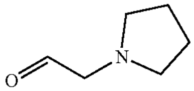
ALA10
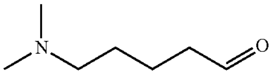
ALA11
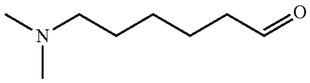
ALA12
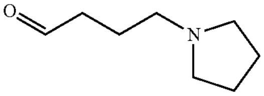
ALA13
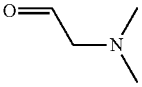
ALA14
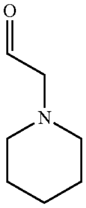
ALA15
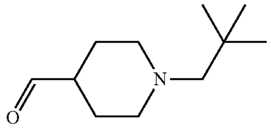
ALA16
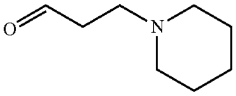
ALA17
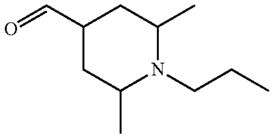
AL8
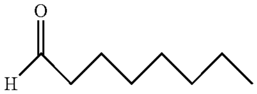

-continued
AL9
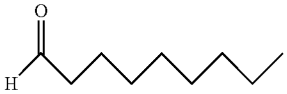
AL10
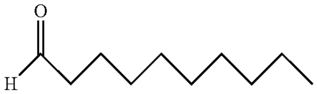
AL11
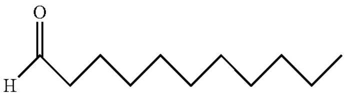
AL12
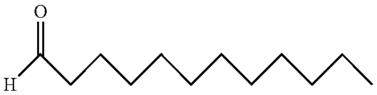
AL13
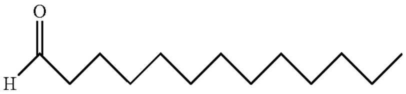
AL15
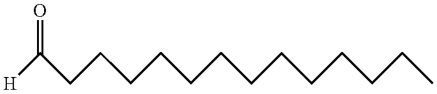
AL16
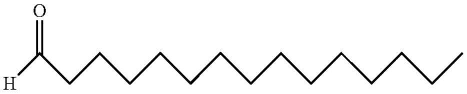
AL16e
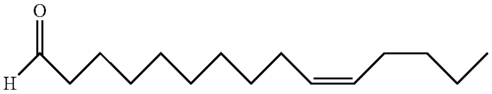
AL10P
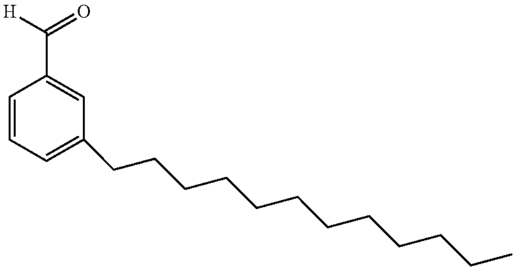
K9
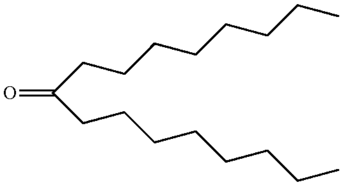
K10
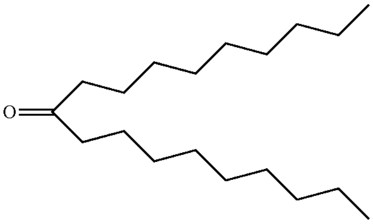
-continued
K11
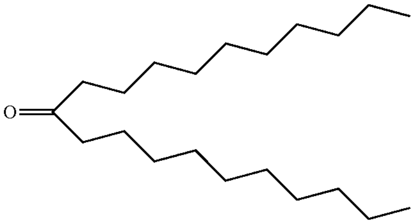
K12
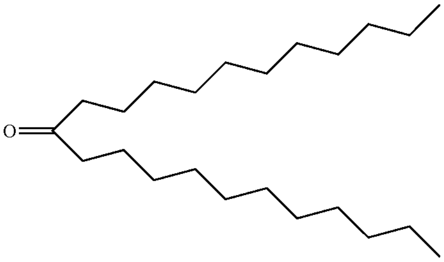
K14
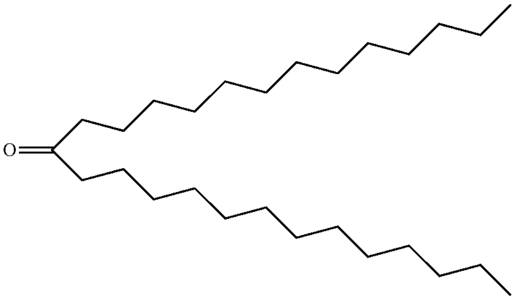
K16
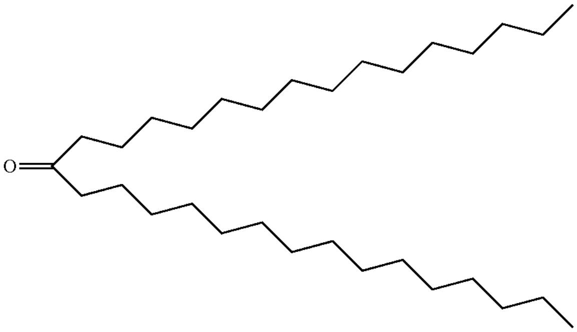
K18e
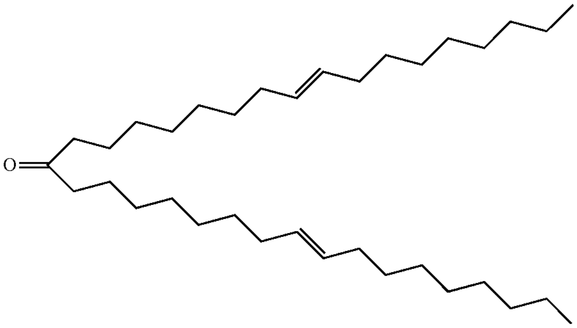
AL-PEG$_8$
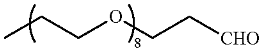

-continued

AL-PEG12

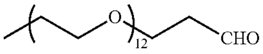

AL-PEG15

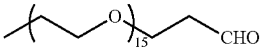

AL-PEG24

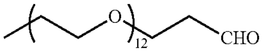

AL-PEG48

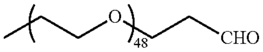

In one aspect, the

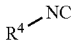

is one of:

Iso1

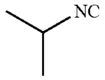

Iso2

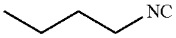

Iso3

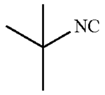

Iso4

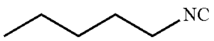

Iso5

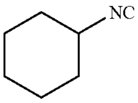

Iso6

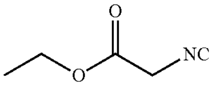

Iso7

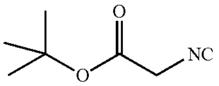

Iso8

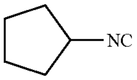

Iso9

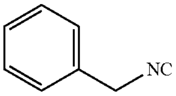

Iso10

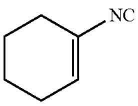

Iso11

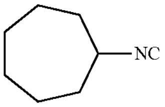

-continued

Iso12

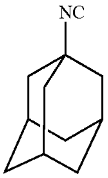

Iso13

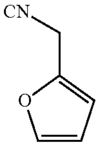

Iso 14

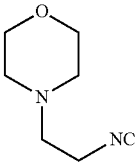

Iso15

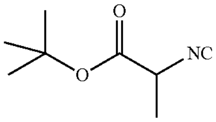

In one aspect, the present disclosure provides compounds of Formula (IV):

(IV)

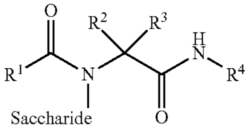

or a salt or isomer thereof, wherein each of $R^1$, $R^2$, $R^3$ and $R^4$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl, poly(ethylene glycol) (PEG),

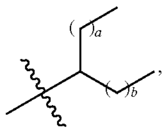,
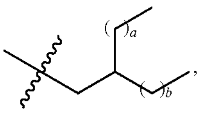,
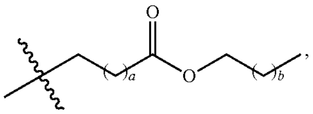,
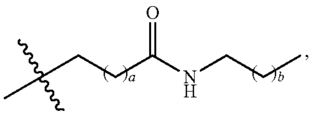,

-continued
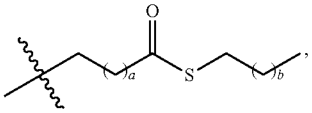
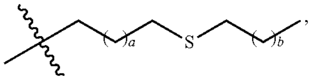
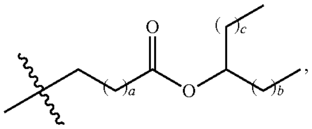
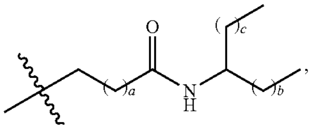
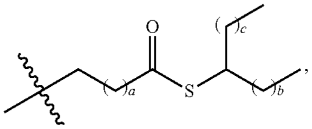
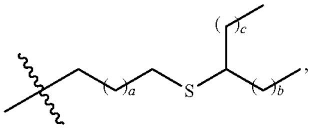
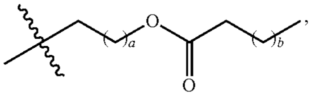
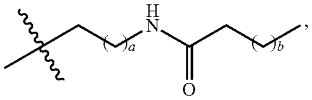
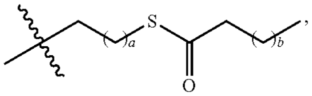
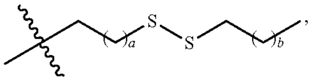
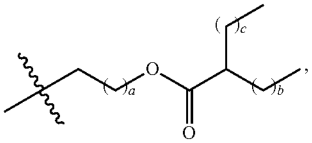
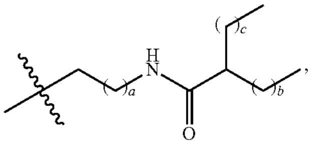
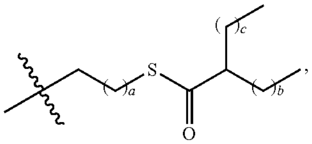
-continued
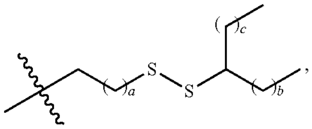
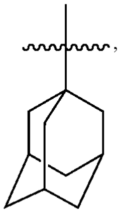
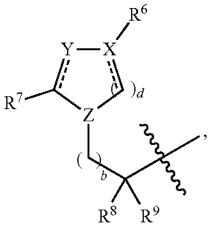
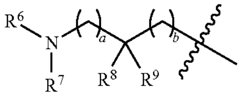
a, b and c are each independently an integer from 0-24;
each of $R^6$, $R^7$, $R^8$ and $R^9$ is independently selected from H, C1-C24 alkyl, C1-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl,
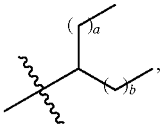
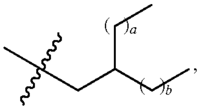
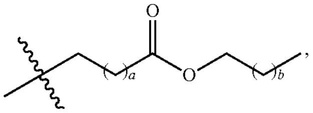
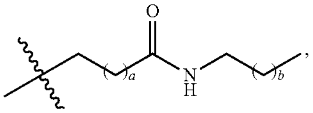
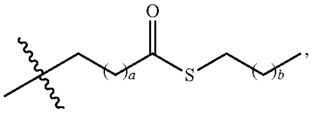
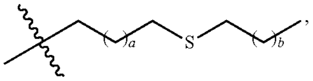
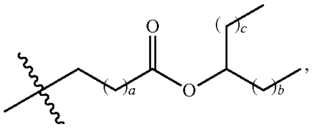
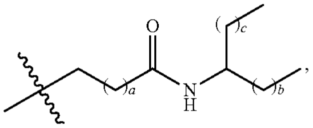
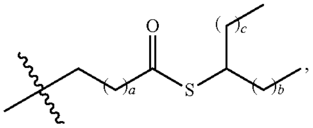

-continued

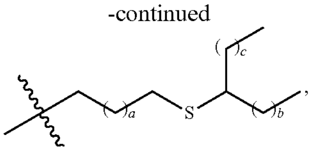

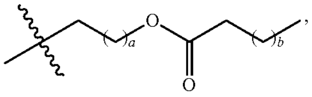

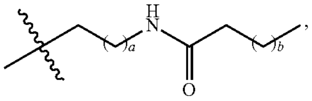

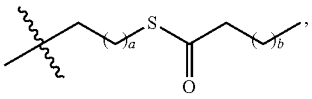

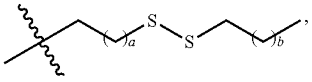

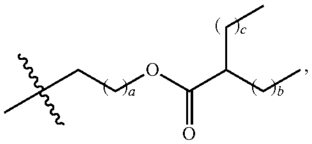

-continued

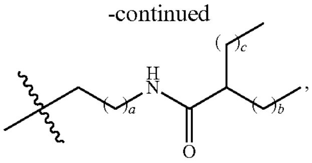

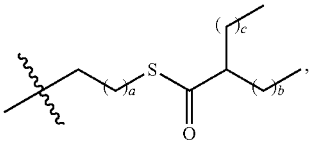

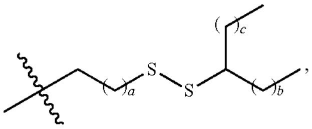

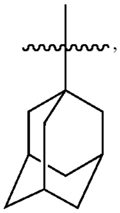

a, b and c are each independently an integer from 0-24;

each X is independently selected from CH or N;

each Y is independently selected from $CH_2$, NH, O, or S;

each Z is independently selected from CH or N;

each saccharide is independently selected from monosaccharides, disaccharides, oligosaccharides, and polysaccharides.

In certain aspects, compounds of Formula IV may include, for example, the following compound:

Synthesis Scheme 4.

(IV)(a)

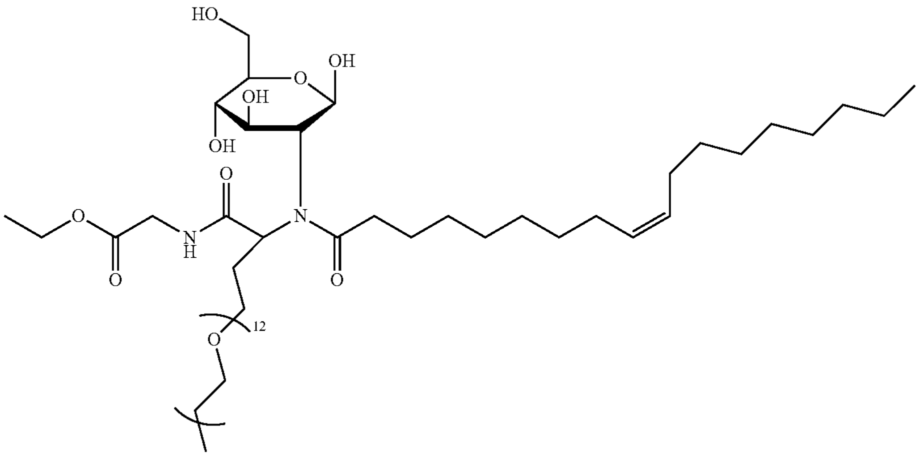

-continued
(IV)(b)
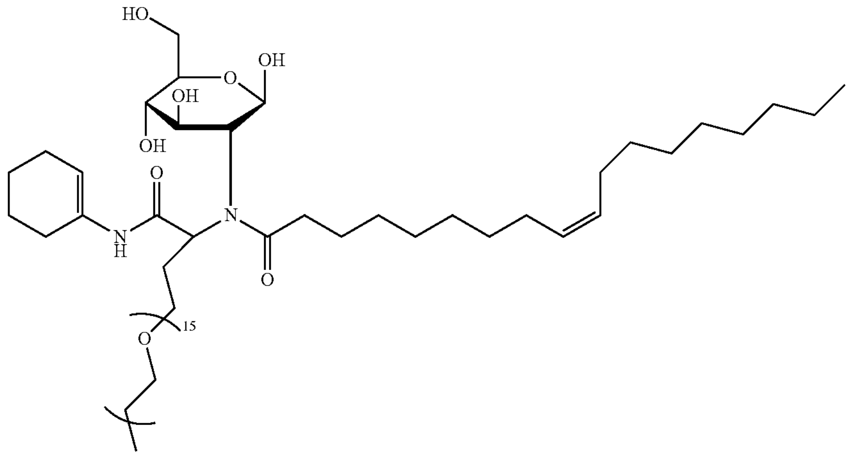
(IV)(c)
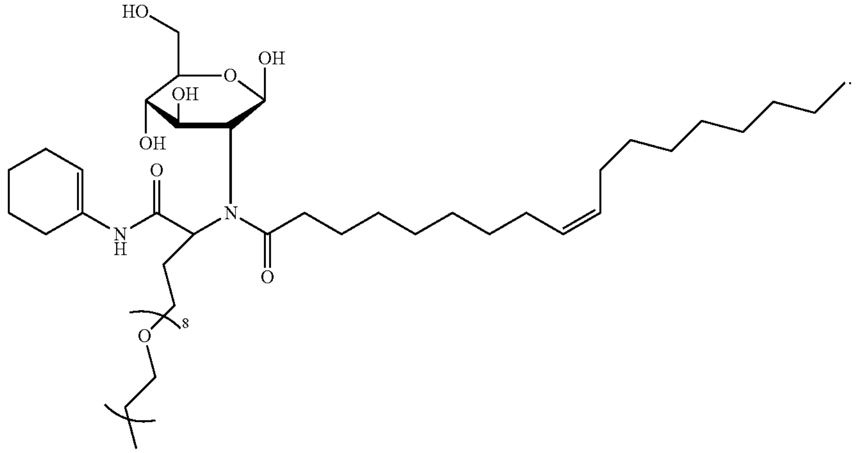
In one aspect, the present disclosure provides the general synthesis route for the synthesis of compounds of Formula IV.
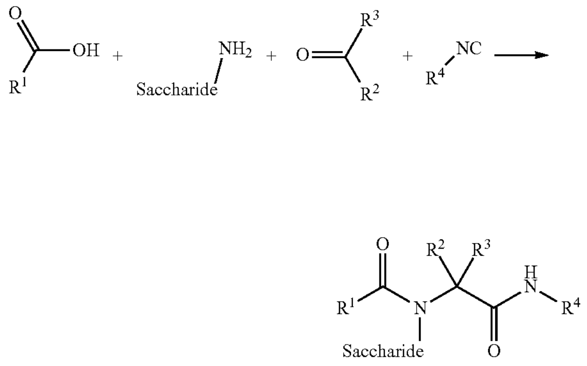
In one aspect, the
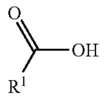
is one or
AAC1
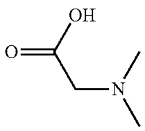
AAC2
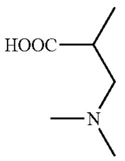
AAC3
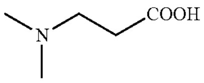
AAC4
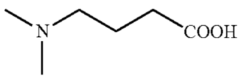

-continued
AAC5
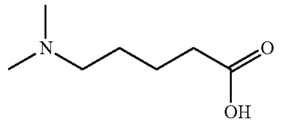
AAC6
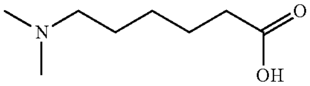
AAC7
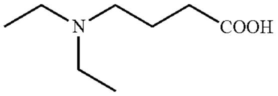
AAC8
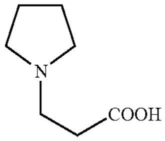
AAC9
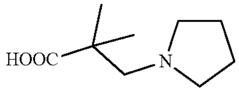
AAC10
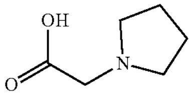
AAC11
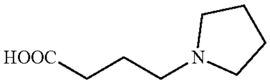
AAC12
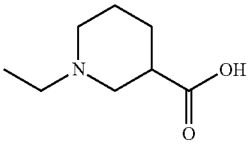
AAC13
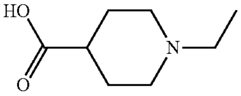
AAC14
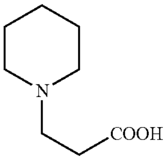
AAC15
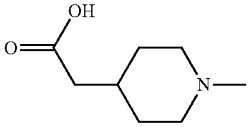
AAC16
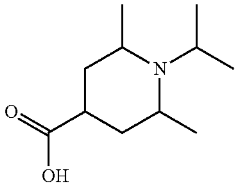
-continued
AAC17
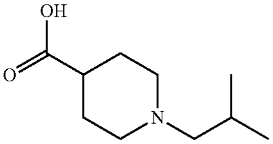
AAC18
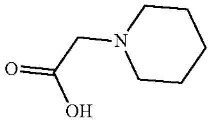
AAC19
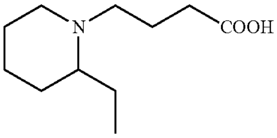
AAC20
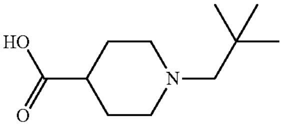
AAC21
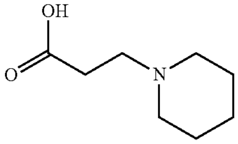
AAC22
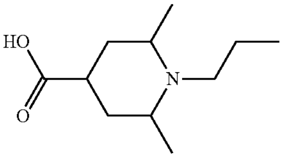
AAC23
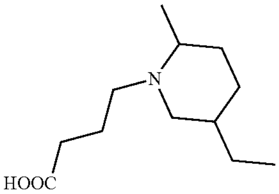
AAC24
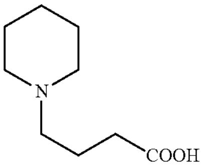
AAC25
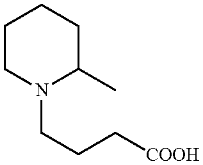
AAC26
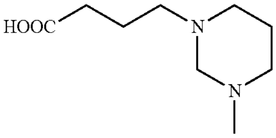

-continued
AAC27
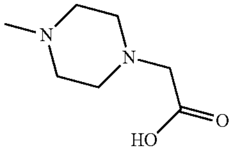
AAC28
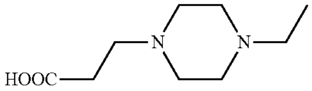
AAC29
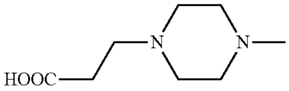
AAC30
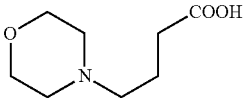
AAC31
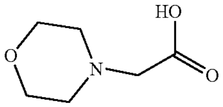
AAC32
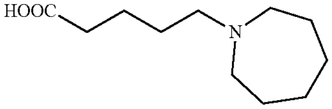
AAC33
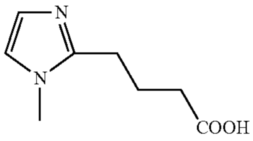
AAC34
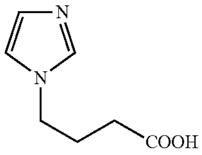
AAC35
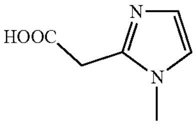
AC6
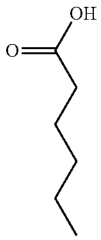
-continued
AC7
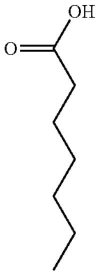
AC8
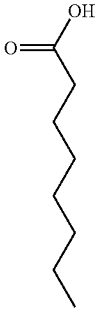
AC9
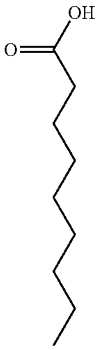
AC10
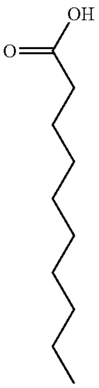

-continued
AC11
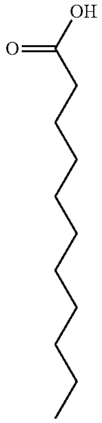
AC12
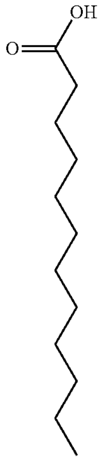
AC13
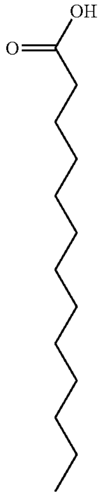
-continued
AC14
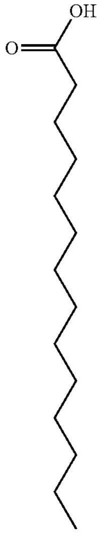
AC15
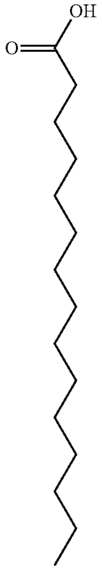

-continued
AC16
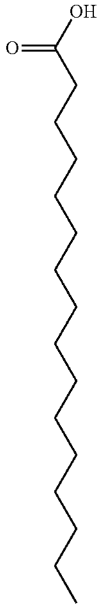
AC17
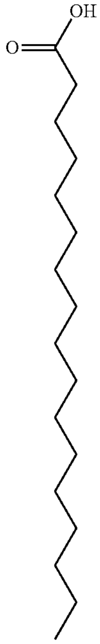
AC18
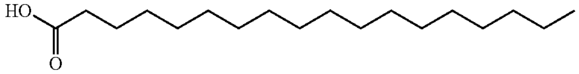
ACes18
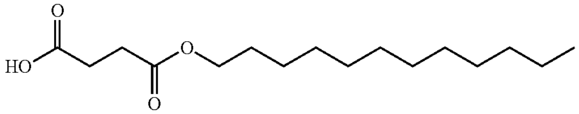
-continued
ACd11
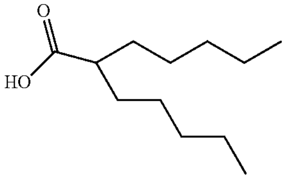
ACd13
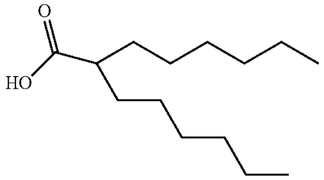
ACd15
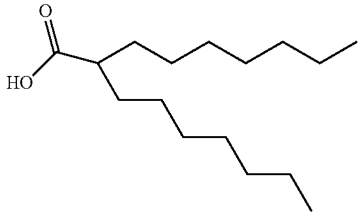
ACd17
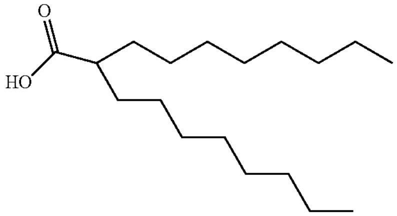
ACd19
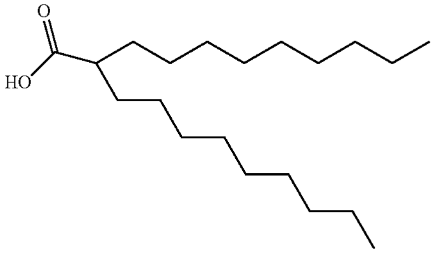
ACd21
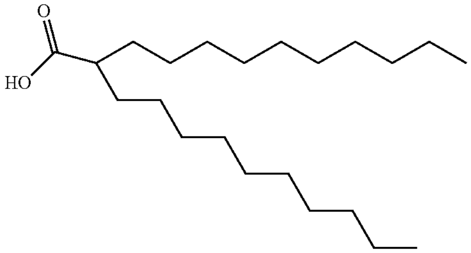

-continued
ACd25
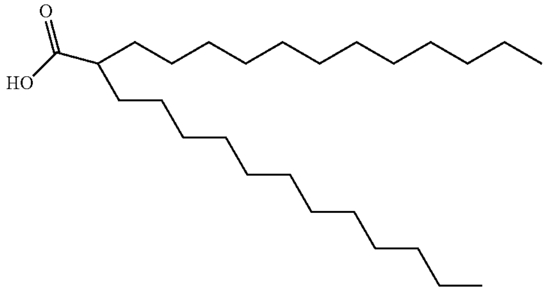
ACe18
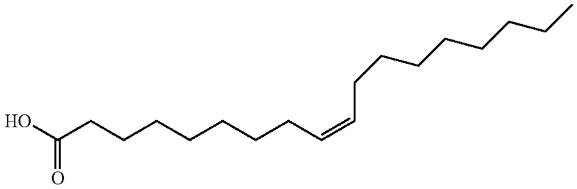
ACe17
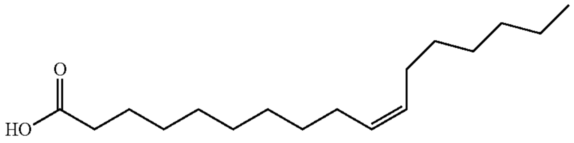
ACe16
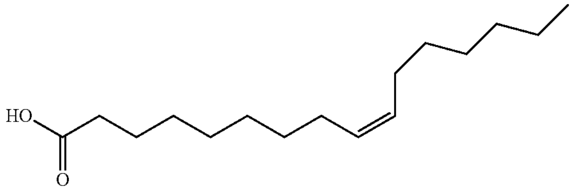
ACe15
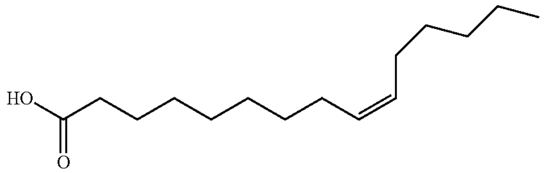
ACe14
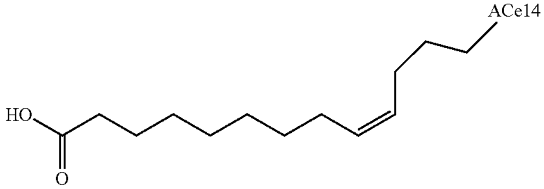
ACe13
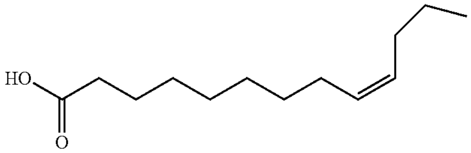
ACe12
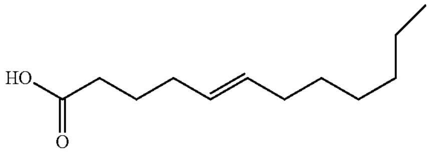
-continued
ACes14
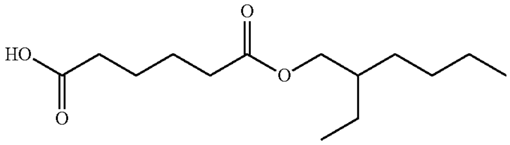
In one aspect, the
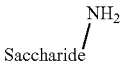
is one of
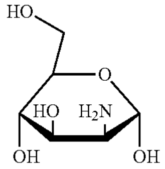
G-Am-1
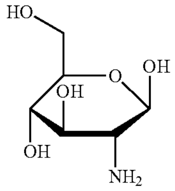
G-Am-2
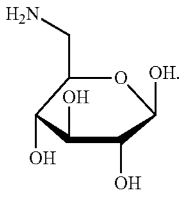
G-Am-3
In one aspect, the
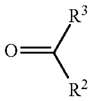
is one of
ALA1
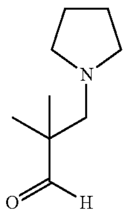

-continued
ALA2
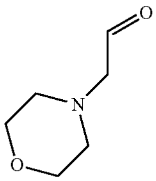
ALA3
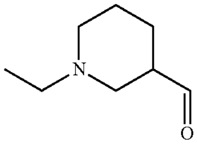
ALA4
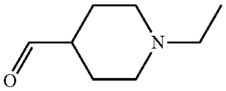
ALA5
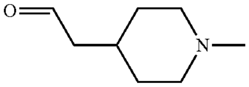
ALA6
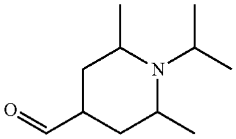
ALA7
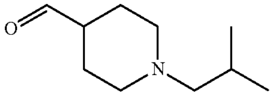
ALA8
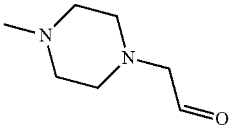
ALA9
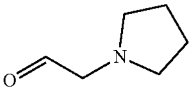
ALA10
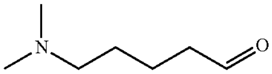
ALA11
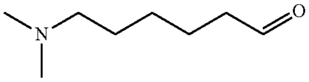
ALA12
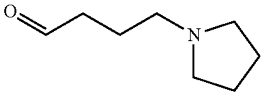
ALA13
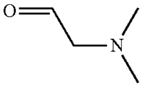
-continued
ALA14
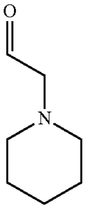
ALA15
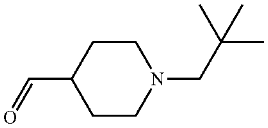
ALA16
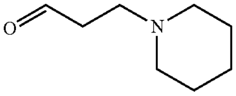
ALA17
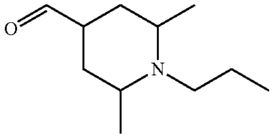
AL8
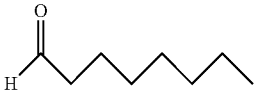
AL9
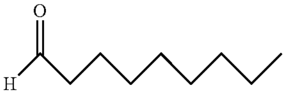
AL10
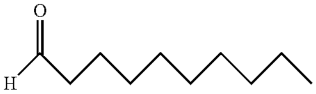
AL11
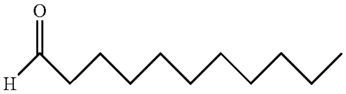
AL12
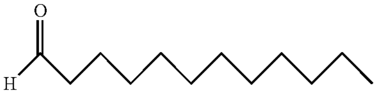
AL13
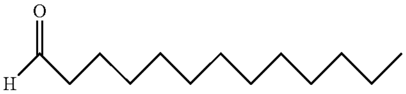
AL15
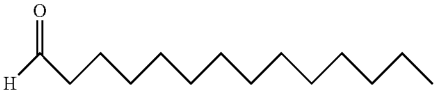
AL16
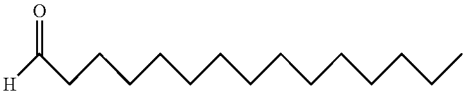
AL16e
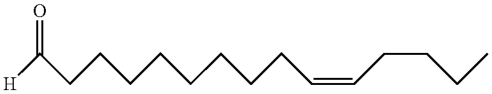

-continued
AL10P
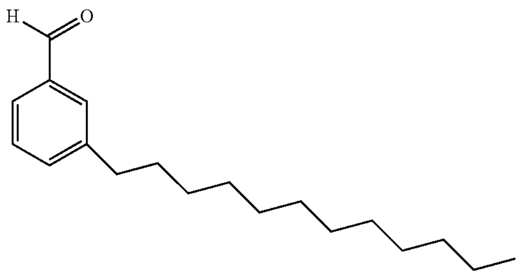
K9
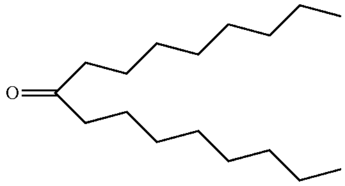
K10
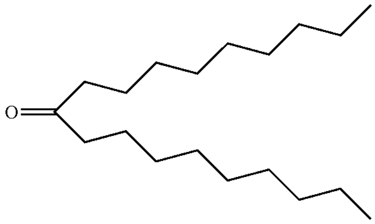
K11
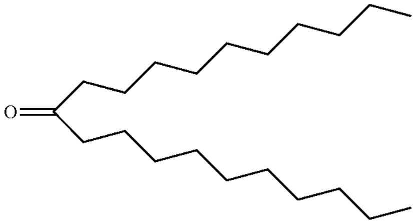
K12
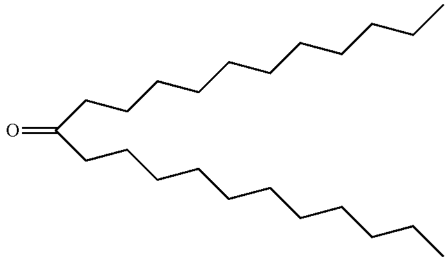
K14
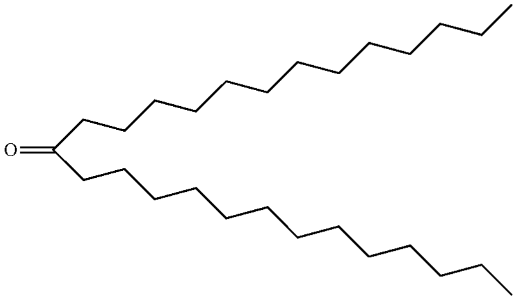
-continued
K16
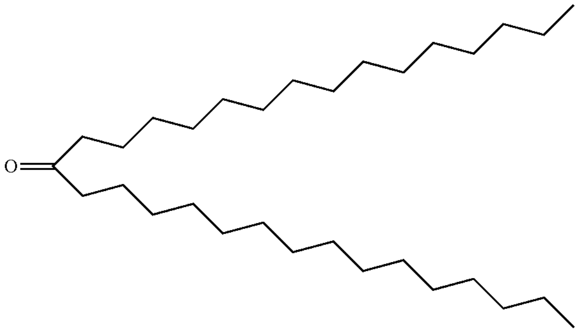
K18e
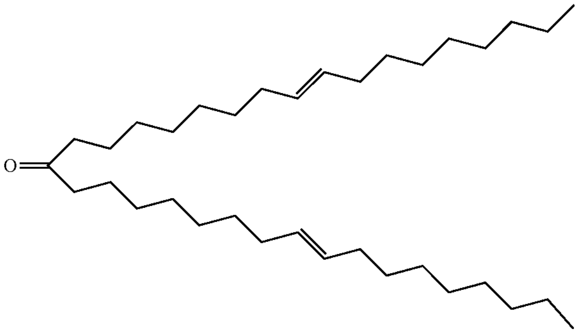
AL-PEG$_8$
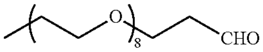
AL-PEG$_{12}$
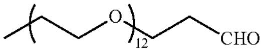
AL-PEG$_{15}$
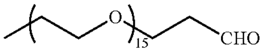
AL-PEG$_{24}$
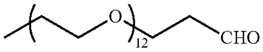
AL-PEG$_{48}$
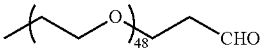
In one aspect, the
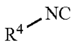
is one of:
Iso1
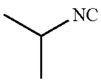
Iso2
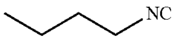
Iso3
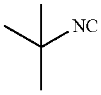

-continued

Iso4

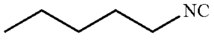

Iso5

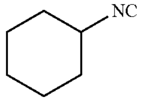

Iso6

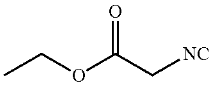

Iso7

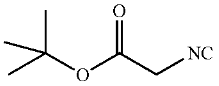

Iso8

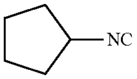

Iso9

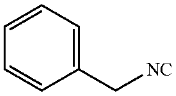

Iso10

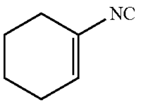

Iso11

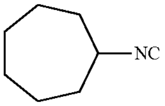

Iso12

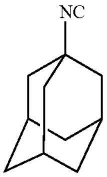

Iso13

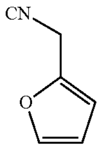

Iso 14

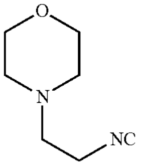

Iso15

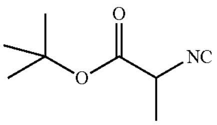

Lipid Nanoparticle

In some aspects, the dimension of a nanoparticle composition is 1 μm or shorter (e.g., 1 μm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter), e.g., when measured by dynamic light scattering (DLS), transmission electron microscopy, scanning electron microscopy, or another method. Nanoparticle compositions include, for example, lipid nanoparticles (LNPs), liposomes, lipid vesicles, and lipoplexes. In some aspects, nanoparticle compositions are vesicles including one or more lipid bilayers. In certain aspects, a nanoparticle composition includes two or more concentric bilayers separated by aqueous compartments. Lipid bilayers may be functionalized and/or cross-linked to one another. Lipid bilayers may include one or more ligands, proteins, or channels.

Nanoparticle compositions comprise a lipid component including at least one compound according to Formulae (I), (II), (III) and (IV). For example, the lipid component of a nanoparticle composition may include one or more of Formulae (I)-(IV). Nanoparticle compositions may also include a variety of other components. For example, the lipid component of a nanoparticle composition may include one or more other lipids in addition to a lipid according to Formulae (I), (II), (III) and (IV).

Typically the LNPs used as the delivery system in the research and development of new drugs, including FDA approved mRNA vaccines such as the mRNA COVID vaccines, and FDA approved siRNA therapies, such as the siRNA therapy for the treatment of polyneuropathy in people with hereditary transthyretin-mediated amyloidosis, use a 4 component LNP delivery system. In a four component LNP delivery system, phospholipids function to increase transfection efficacy of nucleic acids; cationic/ionizable lipids function to stabilize nucleic acids within the lipid nanoparticle; stabilizing lipids serve as the "lipid raft," which stabilizes the integrity of the LNP; and PEG-lipids inhibit aggregation and prevent clearance by macrophages, monocytes, or other phagocytic cells in vivo. The LNPs of the present disclosure is a 2-3 component LNP. The 2 component LNP comprises an ionizable lipid and a saccharide lipid. The 3 component LNP comprise an ionizable lipid, a phospholipid and a saccharide lipid.

In one aspect, the present disclosure provides a nanoparticle composition comprising a modular lipid component, a stabilizer lipid component, and/or a phospholipid component, optionally wherein the nanoparticle composition is a two-component composition or a three-component composition. In some aspects, the nanoparticle composition comprises a modular lipid component, a phospholipid component, and a saccharide lipid component. In some aspects, the modular lipid component comprises a linker, a cationic ionizable group and a lipid raft group. In some aspects, the phospholipid component comprise 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanol amine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2- didocosahexaenoyl-sn-glycero-3-phosphoethanolamine, 1,2-dioleoyl-sn-glycero-3-phospho-rac-(1-glycerol) sodium salt (DOPG), sphingomyelin, or a mixture thereof. In some aspects, the nanoparticle composition of the disclosure further comprising a biologically active agent.

Cationic/Ionizable Lipids

As used herein, the terms "ionizable lipid" or "cationic lipid" refers to a lipid that may have a positive or partial positive charge at physiological pH. A nanoparticle composition may include one or more ionizable lipids in addition to a lipid according to Formula (I)-(X).

Phospholipids

The lipid component of a nanoparticle composition may include one or more phospholipids, such as one or more (poly) unsaturated lipids. Phospholipids may assemble into one or more lipid bilayers. In general, phospholipids may include a phospholipid moiety and one or more fatty acid moieties.

Phospholipids useful in the compositions and methods of the disclosure may be selected from the non-limiting group consisting of 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin. In some aspects, a nanoparticle composition includes DSPC. In certain aspects, a nanoparticle composition includes DOPE. In some aspects, a nanoparticle composition includes both DSPC and DOPE.

Modular Lipids

In one aspect, the present disclosure provides a modular lipid comprising two or more functional groups and at least one linker between at least two functional groups. In some aspects, one of the two or more functional groups is a lipid group, a lipid raft group, a cationic ionizable group, a steric group, a sterol group, a saccharide group, a folate group, a GalNAc group, a oligo peptide group, or a oligo nucleotide group. In some aspects, the linker is covalently linked to two or more functional groups. In some aspects, the two or more functional groups comprise a lipid raft group and a cationic ionizable group. In one aspect, the two or more functional groups comprise a sterol group and a cationic ionizable group. In one aspect, the two or more functional groups comprise a saccharide group and at least one of a sterol group and a PEG group.

In one aspect, the present disclosure provides a method for synthesizing a modular lipid comprising a cationic ionizable group and a sterol group, the method comprising performing four component reaction of an acid compound, an amine compound, a ketone compound, and an isocyanide compound as follows:

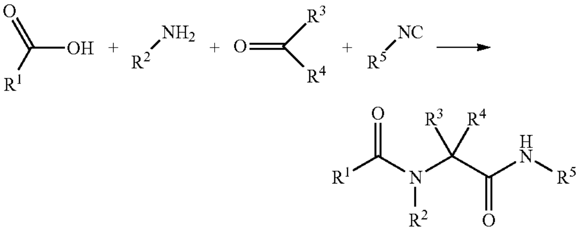

wherein each $R^1$, $R^4$ and $R^5$ is independently selected from $C_2$-$C_{24}$ alkyl, $C_2$-$C_{24}$ alkenyl, $C_2$-$C_{24}$ alkynyl, substituted $C_2$-$C_{24}$ alkyl, substituted alkenyl, substituted alkynyl, substituted acyl, substituted carbocyclyl, substituted heterocyclyl, substituted aryl, substituted heteroaryl, poly(ethylene glycol) (PEG),

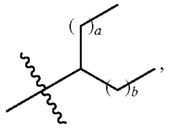,
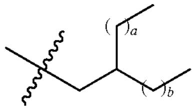,
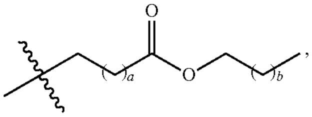,
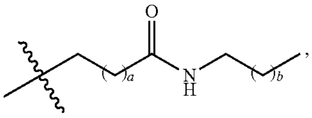,
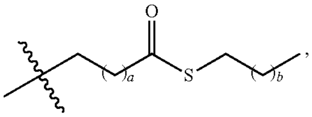,
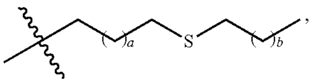,
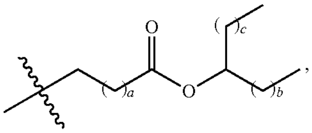,
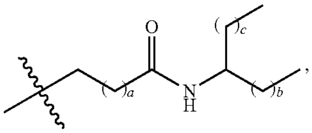,
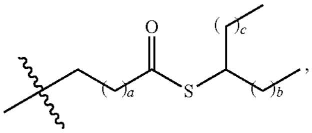,
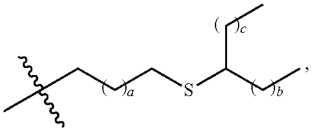, -continued
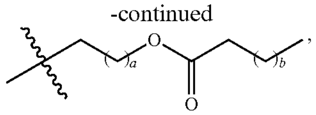
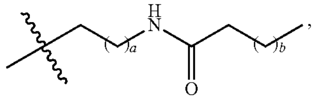
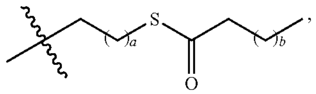
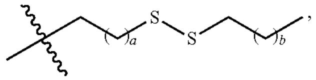
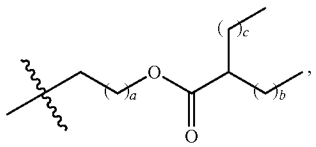
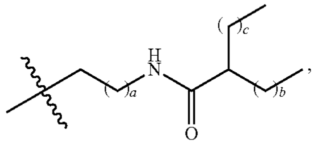
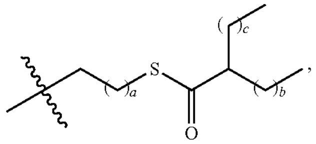
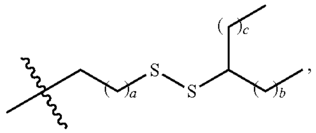
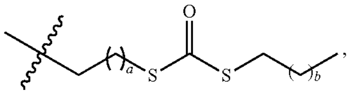
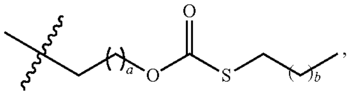
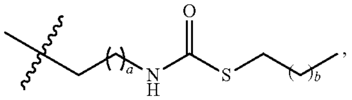
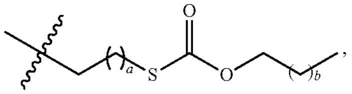
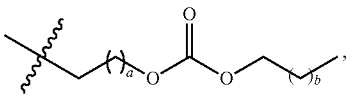
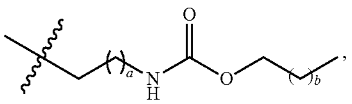
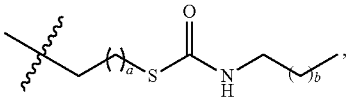
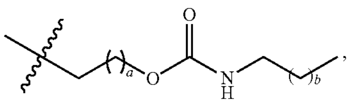
-continued
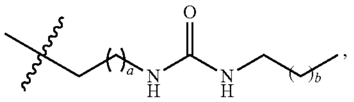
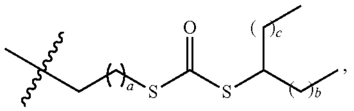
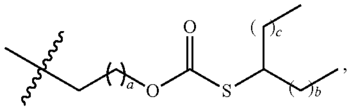
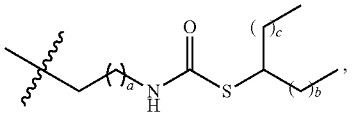
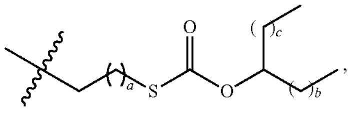
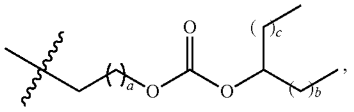
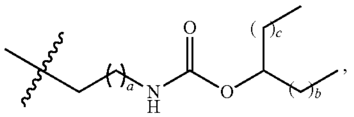
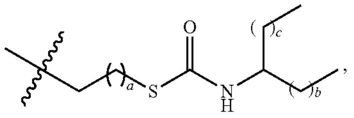
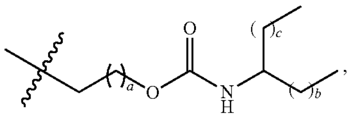
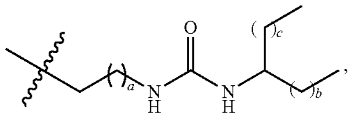
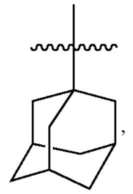
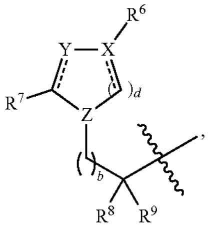
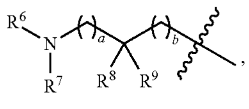
wherein each $R^2$ and $R^3$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl, poly(ethylene glycol) (PEG) and -continued
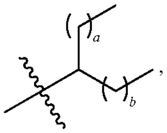, 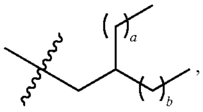,
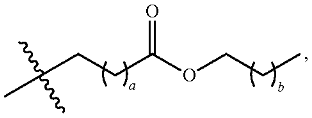,
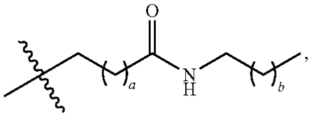,
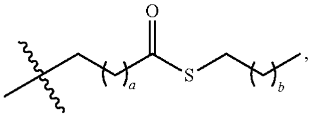,
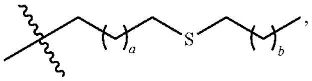,
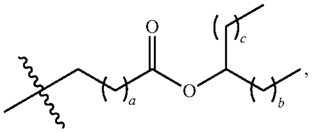,
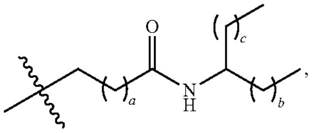,
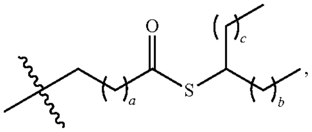,
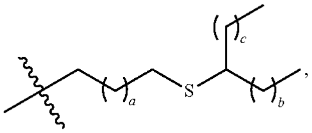,
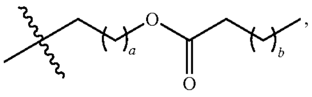,
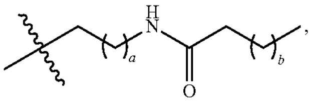,
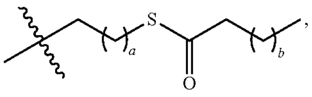,
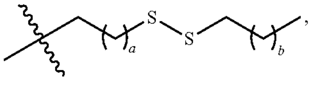,
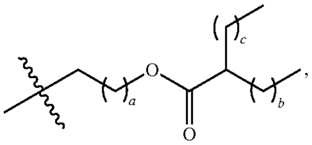,
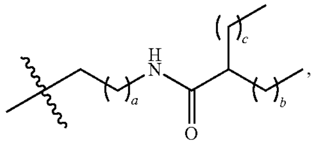,
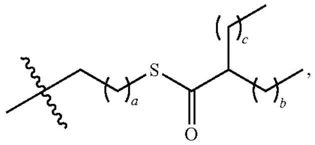,
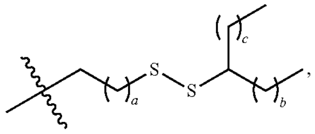,
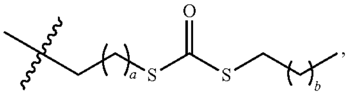,
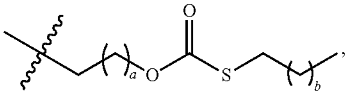,
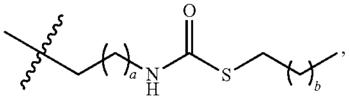,
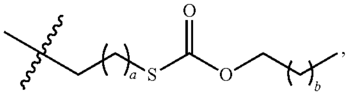,
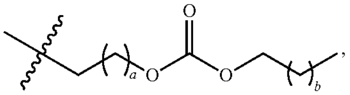,
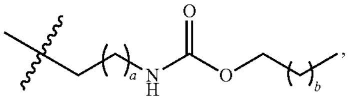,
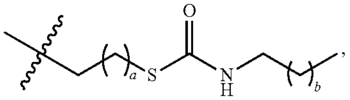,
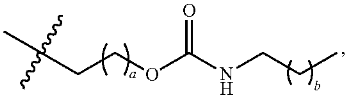,
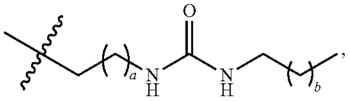,
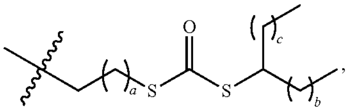,
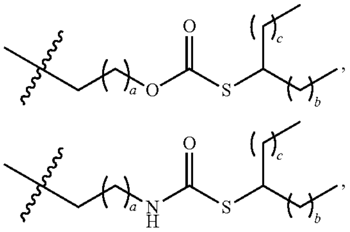, -continued

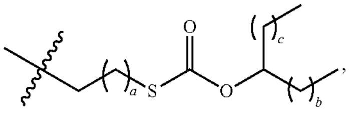

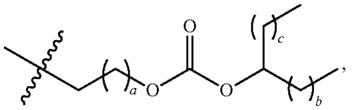

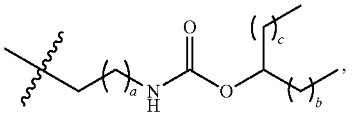

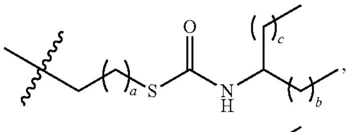

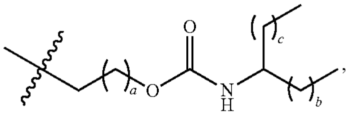

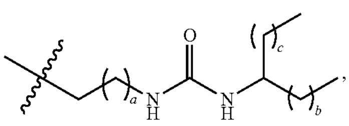

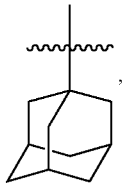

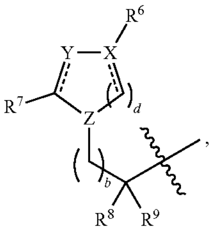

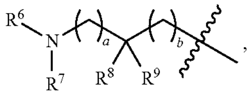

wherein each $R^6$, $R^7$, $R^8$ and $R^9$ is independently selected from H, C1-C24 alkyl, C1-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl,

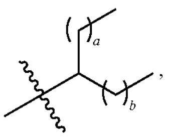

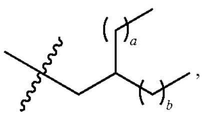

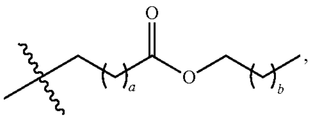

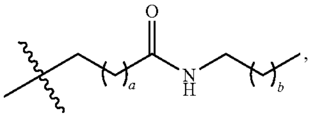

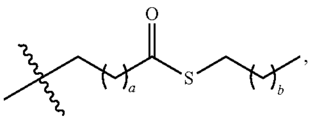

-continued

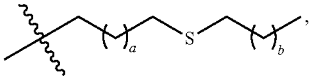

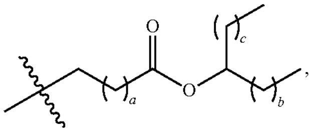

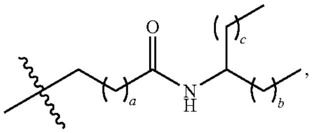

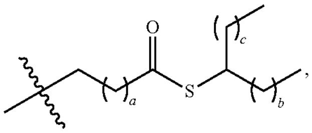

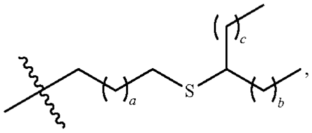

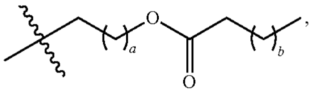

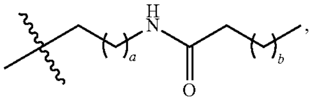

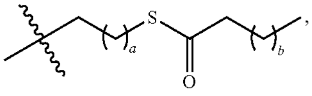

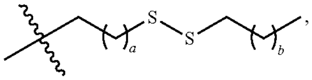

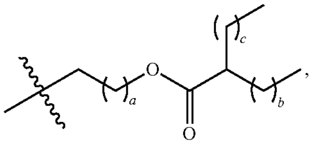

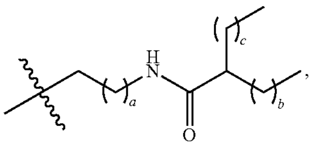

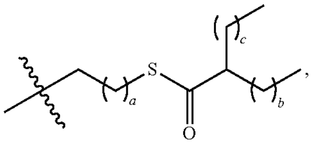

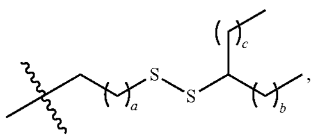

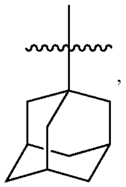

a, b, c and dare each independently an integer from 0-24;
each B is independently selected from $CH_2$; NH, O, or S;
each X is independently selected from CH or N;
each Y is independently selected from $CH_2$, NH, O, or S; and
each Z is independently selected from CH or N.

In some aspects, the acid is:
AAC1
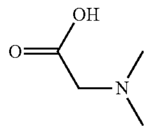
AAC2
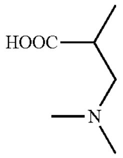
AAC3
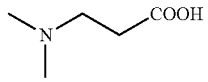
AAC4
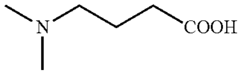
AAC5
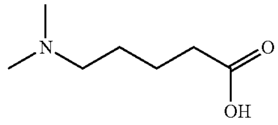
AAC6
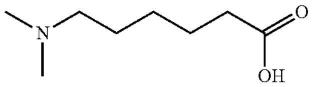
AAC7
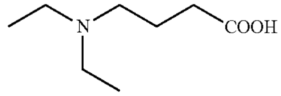
AAC8
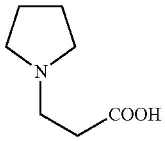
AAC9
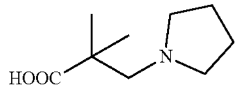
AAC10
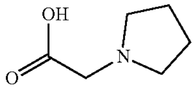
AAC11
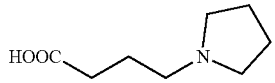
AAC12
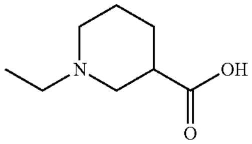
AAC13
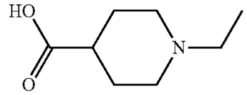
AAC14
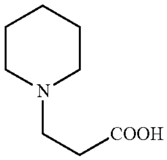
AAC15
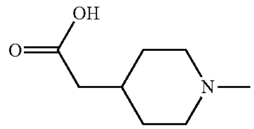
AAC16
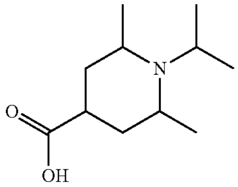
AAC17
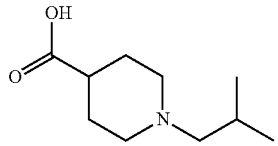
AAC18
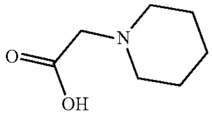
AAC19
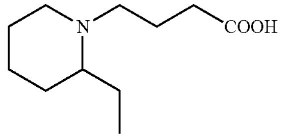
AAC20
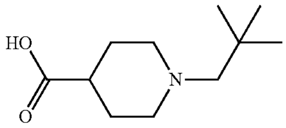

-continued
AAC21
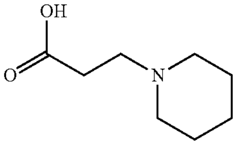
AAC22
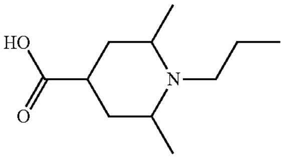
AAC23
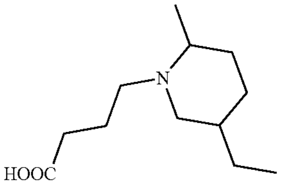
AAC24
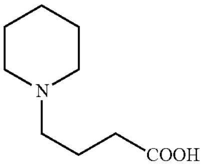
AAC25
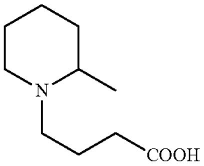
AAC26
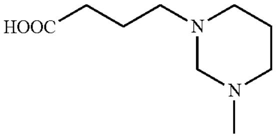
AAC27
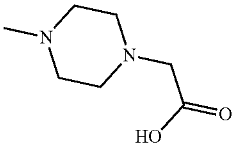
AAC28
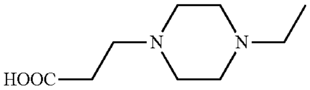
AAC29
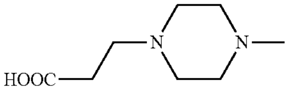
AAC30
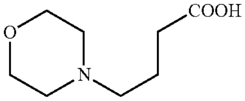
AAC31
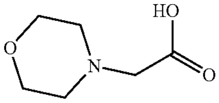
AAC32
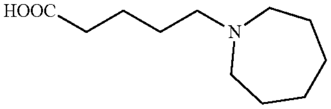
AAC33
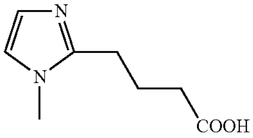
AAC34
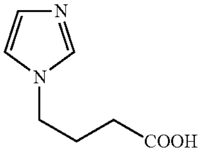
AAC35
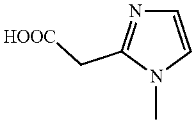
AAC36
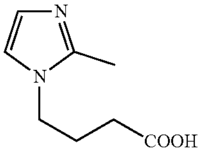
AAC37
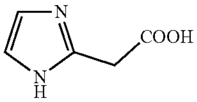
AAC38
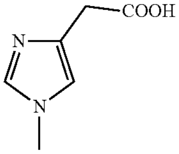
AC7
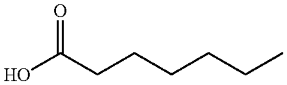
AC8
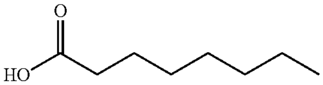
AC9
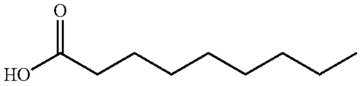
AC10
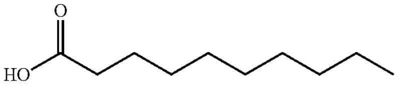

-continued
AC11
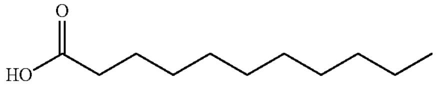
AC12
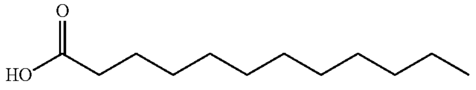
AC13
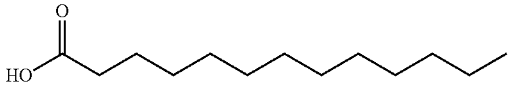
AC14
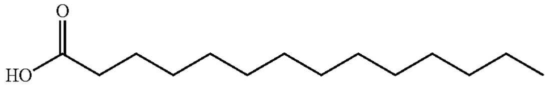
AC15
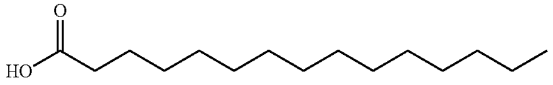
AC16
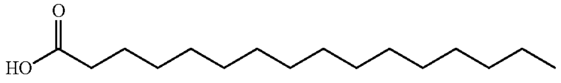
AC17
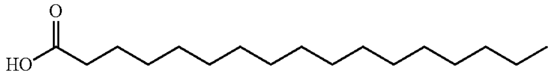
AC18
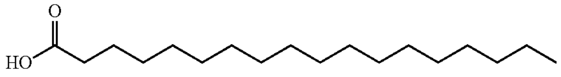
ACe18
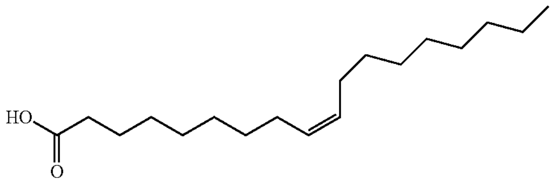
ACe17
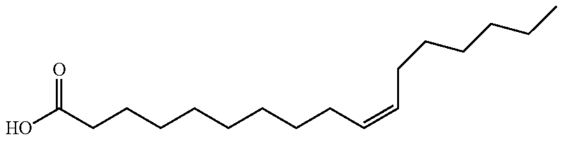
ACe16
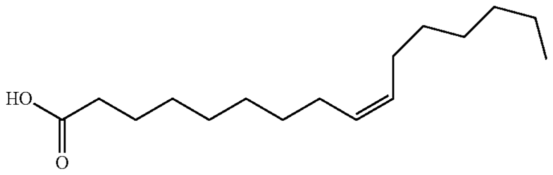
ACe14
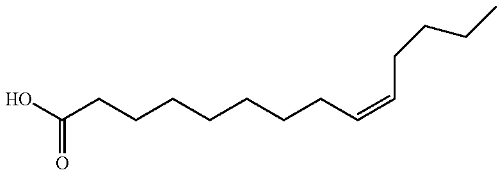
ACe12
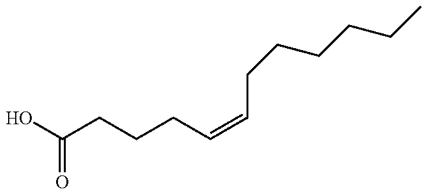
AC18e2
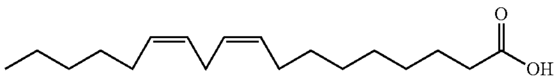
ACes16
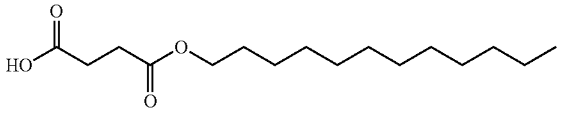
ACes14
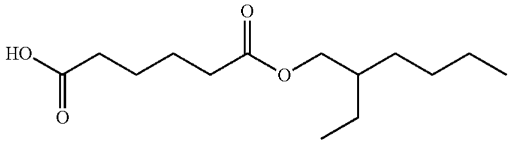
ACes13
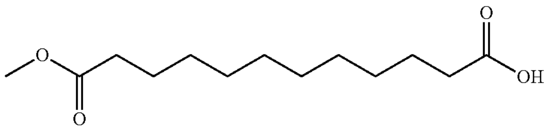
ACd13
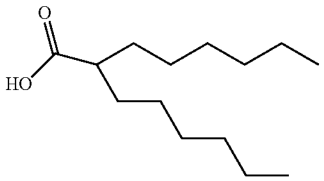

-continued
ACd15
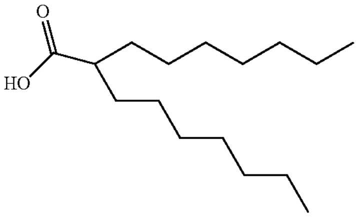
ACes14-2
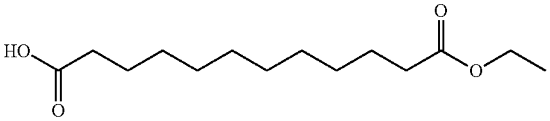
ACd25
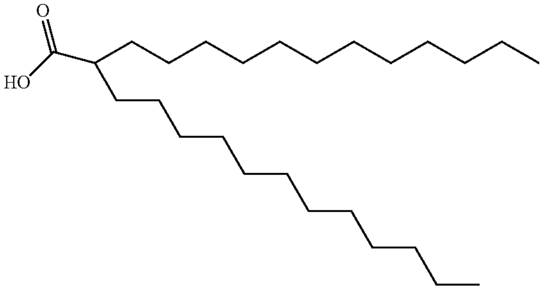
ACes17
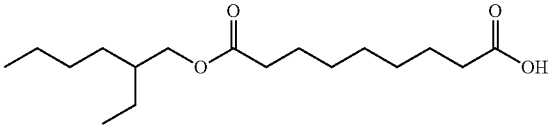
ACes18
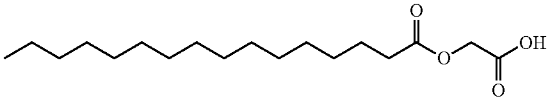
ACes18-2
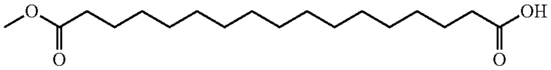
ACe20
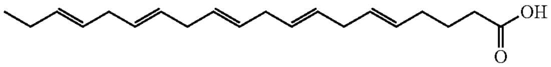
ACd17
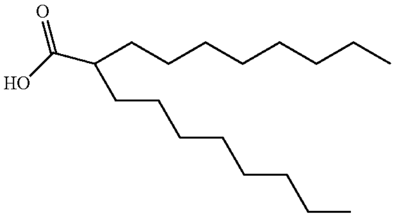
ACd19
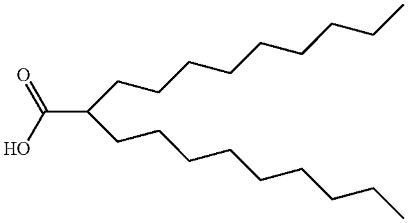
ACes19
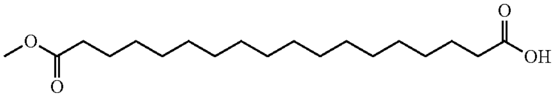
ACes12
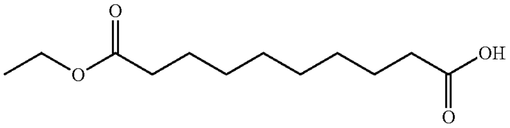
ACes17-2
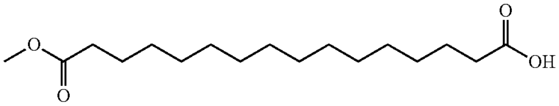
ACes12-2
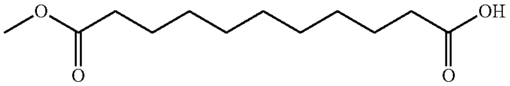
ACes15
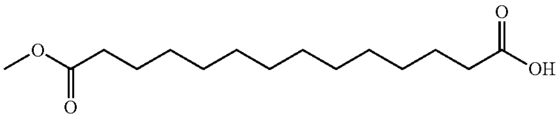

-continued
AmAc-21e
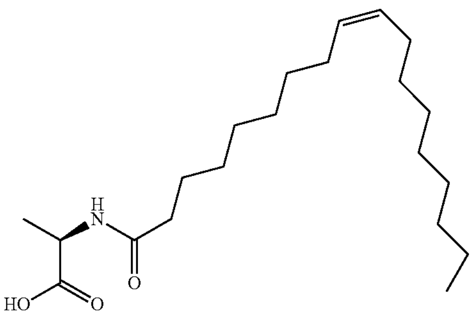
AmAc-13
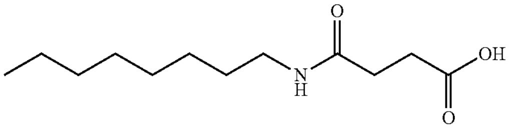
AmAc-21
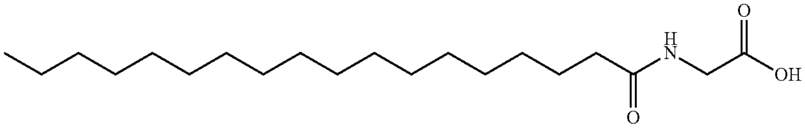
AmAc-15
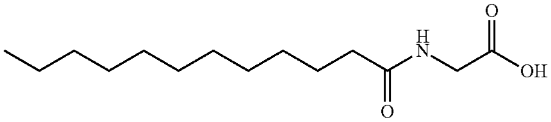
AmAc-17
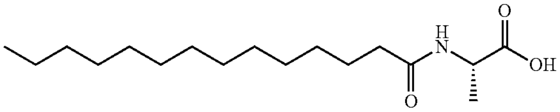
AmAc-19
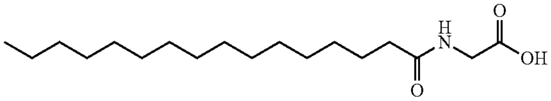
AmAc-15-3
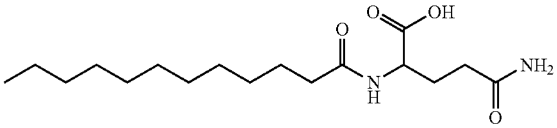
AmAc-17-OH
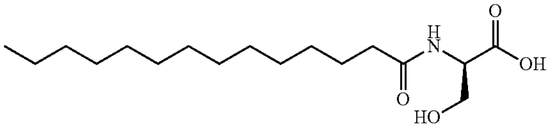
AmAc-15-2
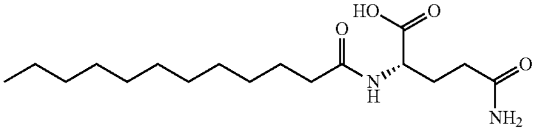
AmAc-32
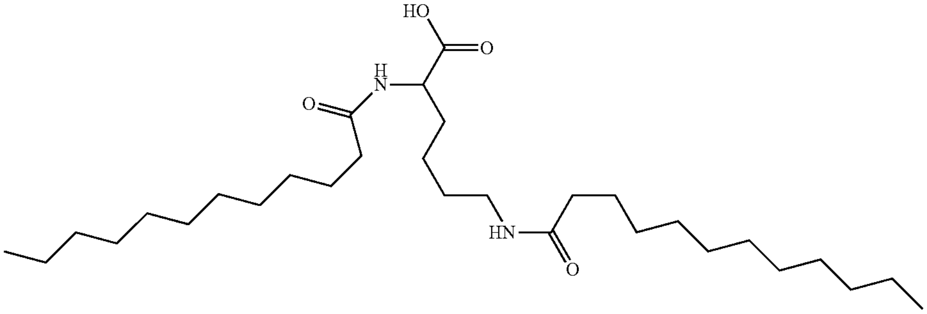
ACh1
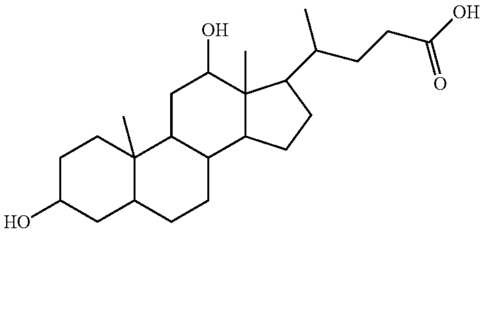
ACh2
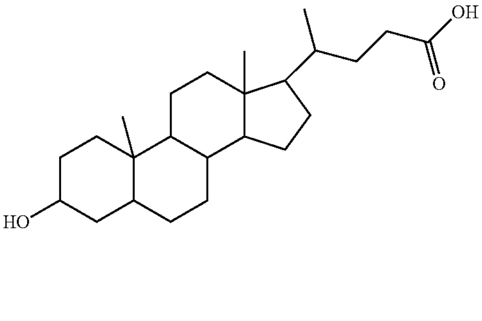

-continued
ACh3′
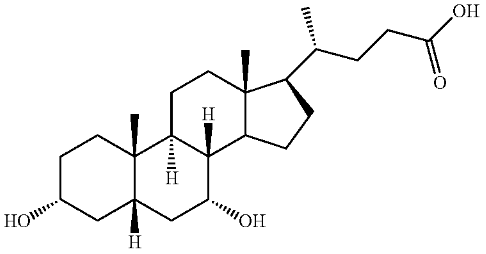
ACh3
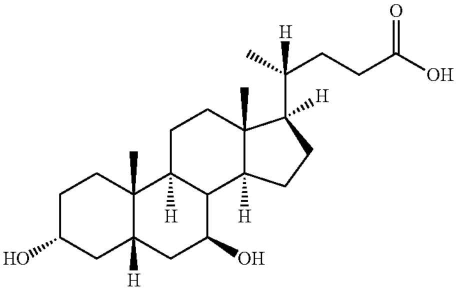
ACh4
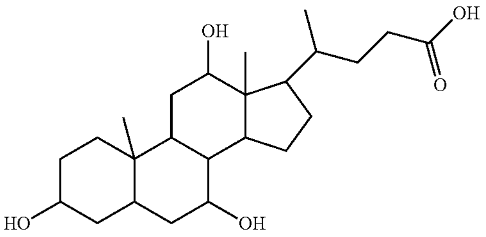
ACh5
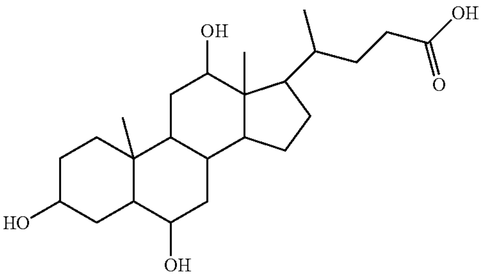
ACh6
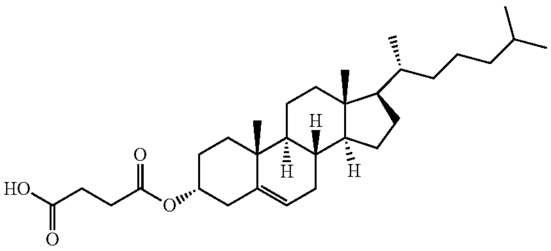
VAC1
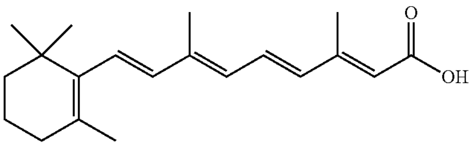
VAC2
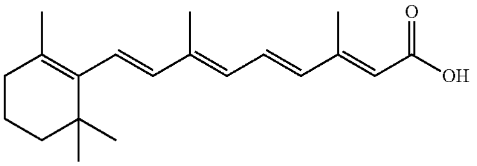
S1-Ac
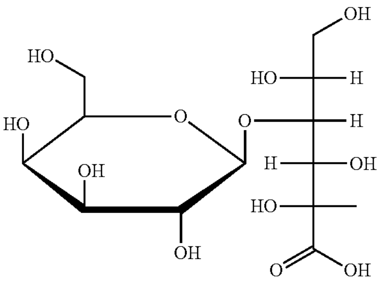
SAc-2
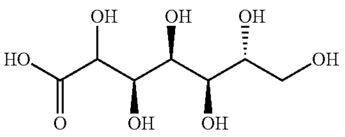
SAc-3
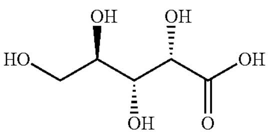
SAc-4
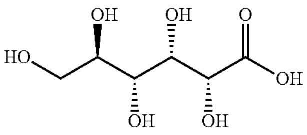
G-Ac
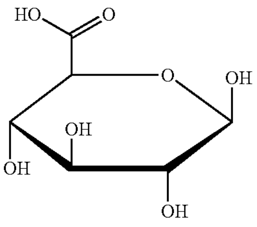
COOH-PEG1
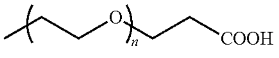
COOH-PEG$_{2000}$
COOH-PEG2
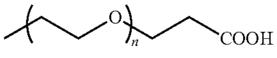
COOH-PEG$_{1000}$ -continued
COOH-PEG3
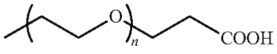
COOH-$PEG_{750}$
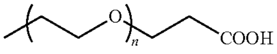
COOH-$PEG_{550}$
COOH-PEG4
COOH-PEG5
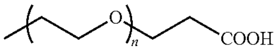
COOH-$PEG_{350}$
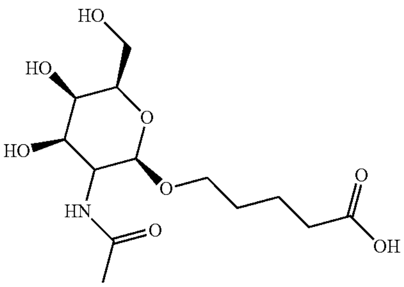
GalNAc COOH
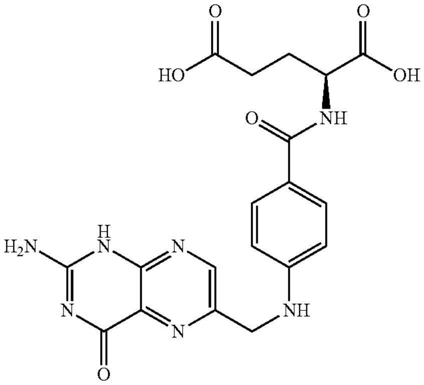
Folic acid -continued
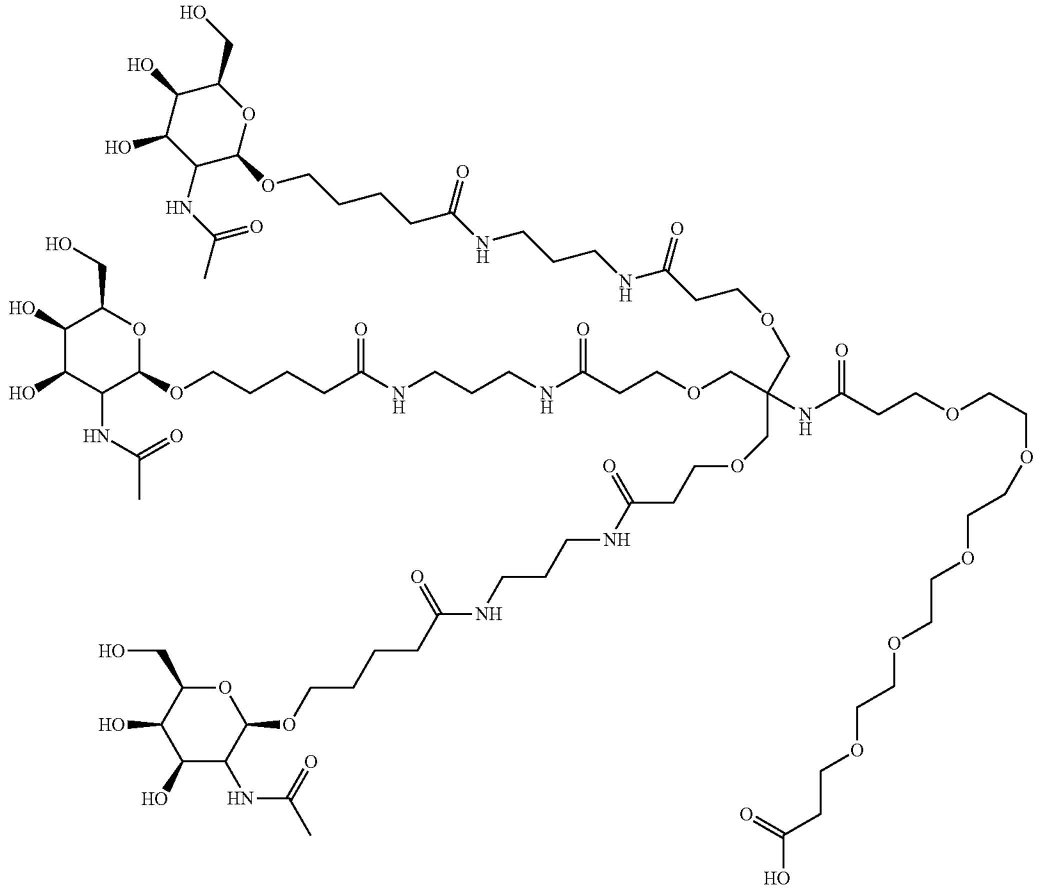
Tri-GalNAc COOH
DAC1
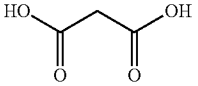
DAC2
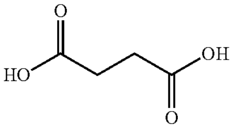
DAC3
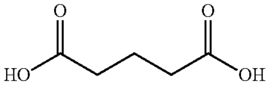
DAC4
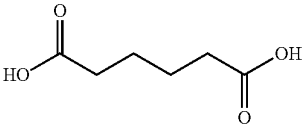
DAC5
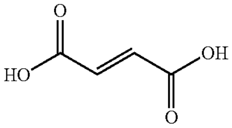
DAC6
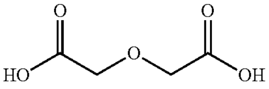
DAC7
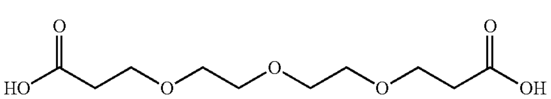
DAC8
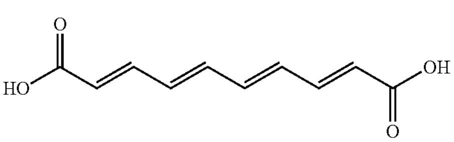
DAC9
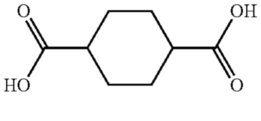
DAC10
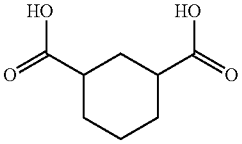

-continued
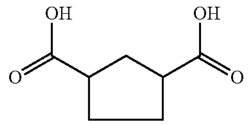
DAC11
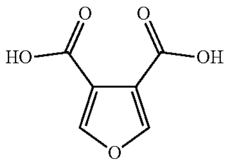
DAC12
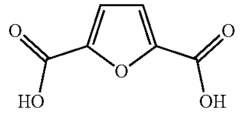
DAC13
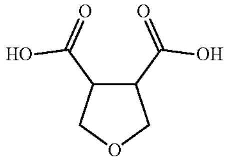
DAC14
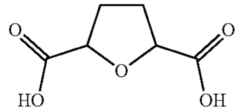
DAC15
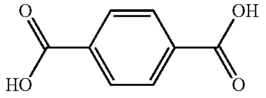
DAC16
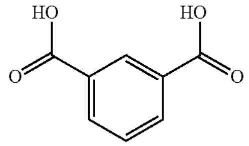
DAC17
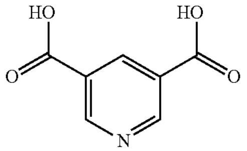
DAC18
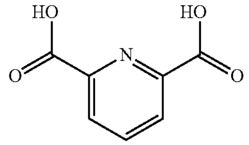
DAC19
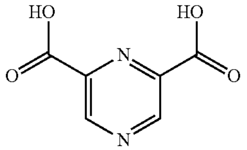
DAC20
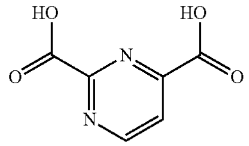
DAC21
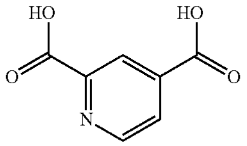
DAC22
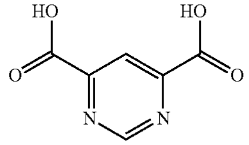
DAC23
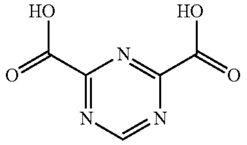
DAC24
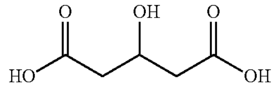
DAC-OH-1
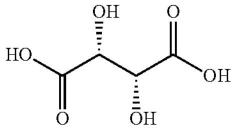
DAC-OH-2
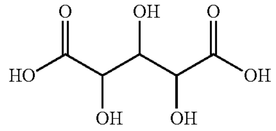
DAC-OH-3
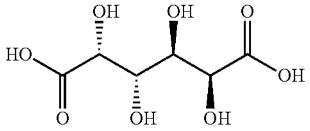
DAC-OH-4
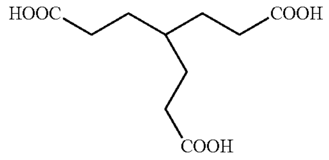
TAC1
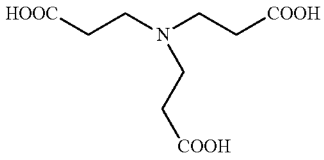
TAC2

-continued
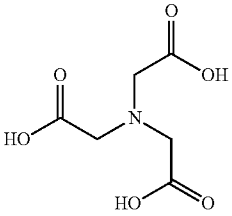
TAC3
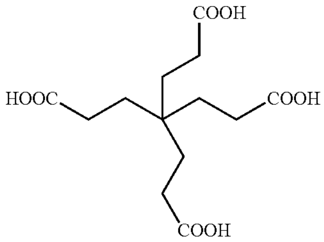
TAC4
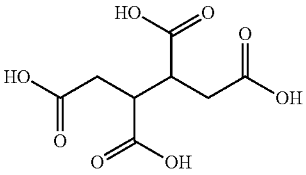
TAC5
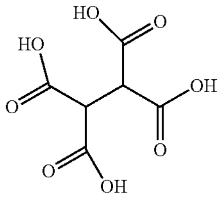
TAC6
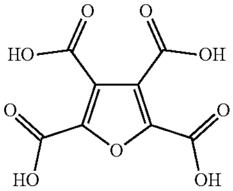
TAC7
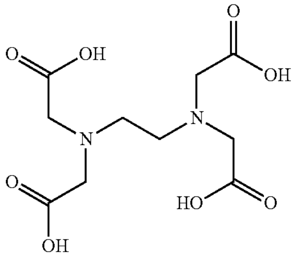
TAC8
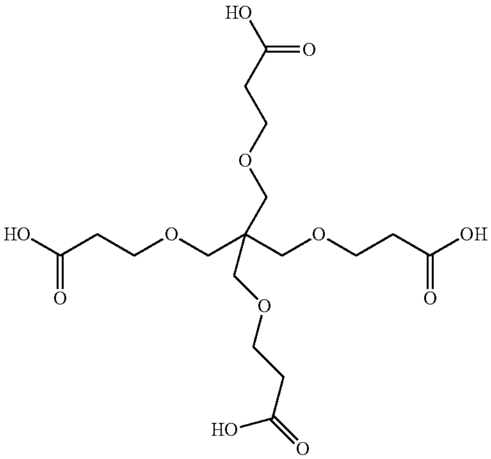
TAC9
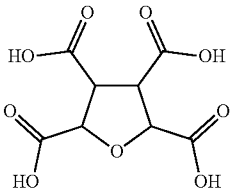
TAC10
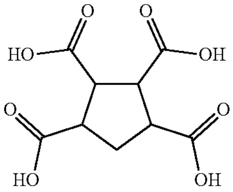
TAC11
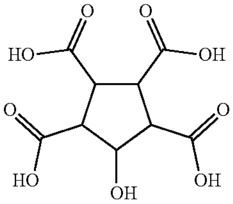
TAC12

In some aspects, the amine is:
A1
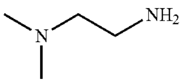
A3
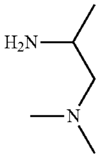
A2
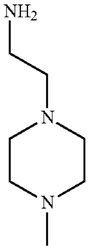
A4
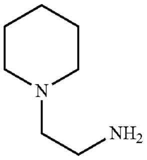
A5
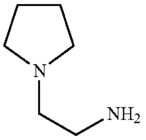
A6
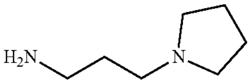
A7
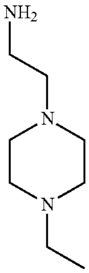
A8
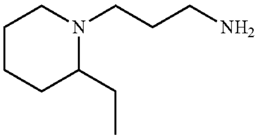
A9
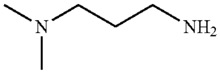
A10
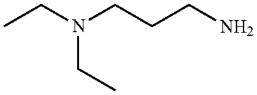
-continued
A11
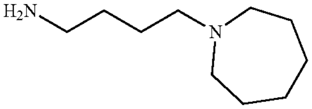
A12
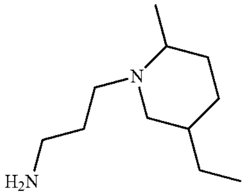
A13
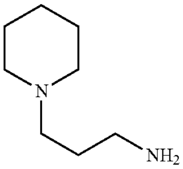
A14
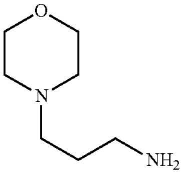
A15
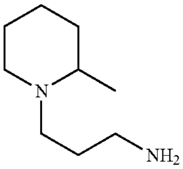
A16
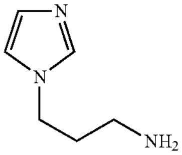
A17
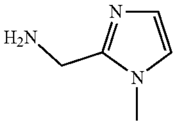
A18
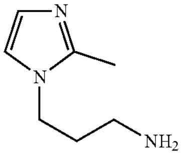
A19
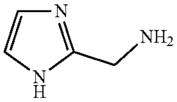
A20
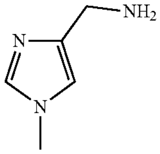

-continued
AP1
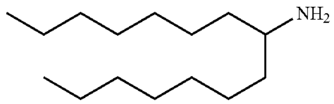
AP2
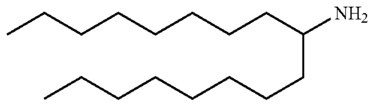
AP3
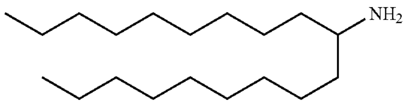
AP4
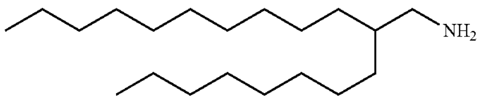
AP5
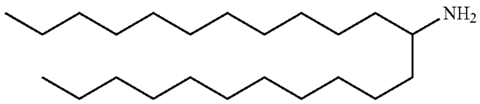
AP6
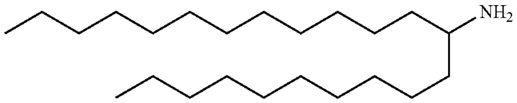
AP7
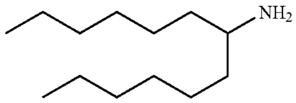
AP8
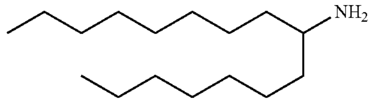
SA6
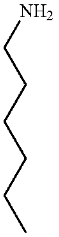
SA7
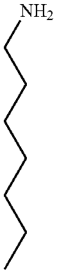
-continued
SA8
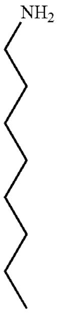
SA9
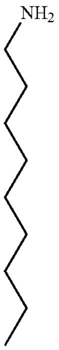
SA10
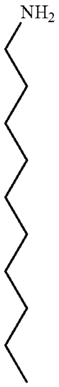
SA11
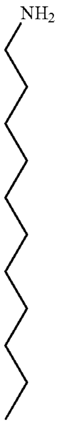

-continued
SA12
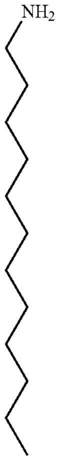
SA13
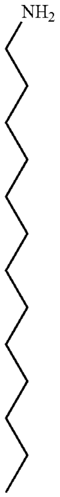
SA14
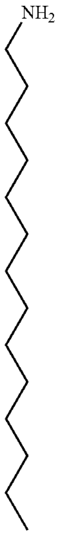
-continued
SA15
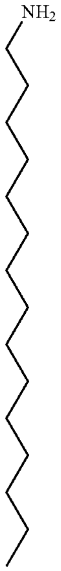
SA16
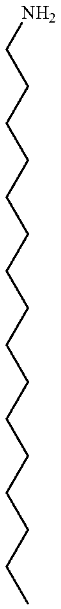

SA17
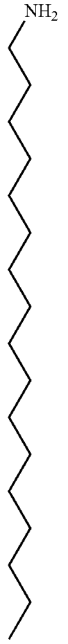
SA18
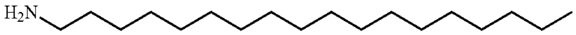
SAm-2
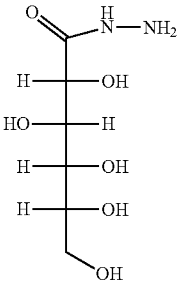
SAm-3
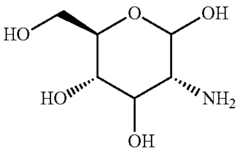
SAm-4
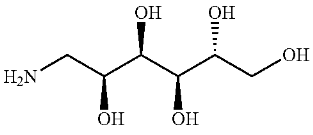
SAm-5
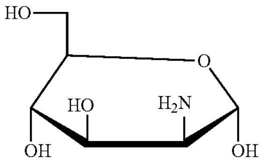
SAm-6
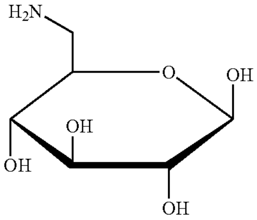
ChAm-1
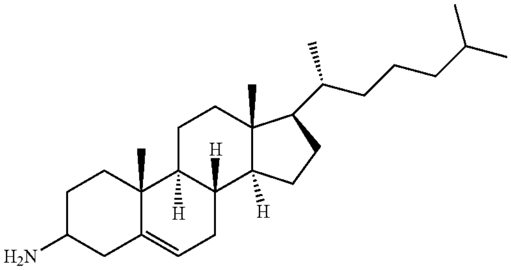
A21
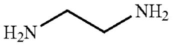
A22
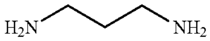
A23
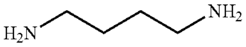
A24
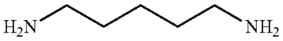
A25
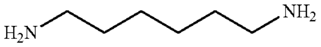
A26
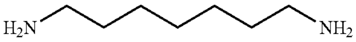
A27
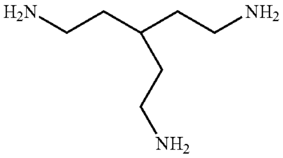
A28
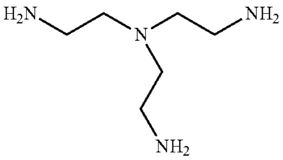
NH2-PEG1
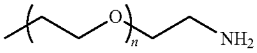
NH2-PEG$_{2000}$
NH2-PEG2
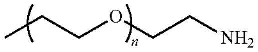
NH2-PEG$_{1000}$
NH2-PEG3
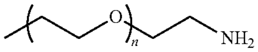
NH2-PEG$_{750}$ NH2-PEG4
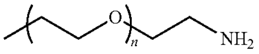
NH2-PEG550
NH2-PEG5
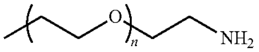
NH2-PEG350
In some aspects, the aldehyde or ketone is:
ALA1
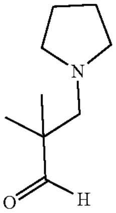
ALA2
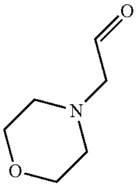
ALA3
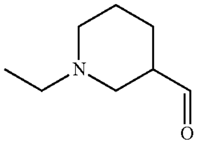
ALA4
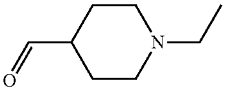
ALA5
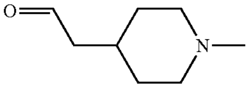
ALA6
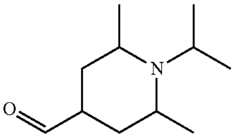
ALA7
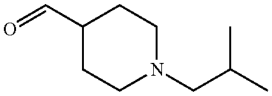
ALA8
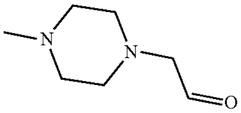
ALA9
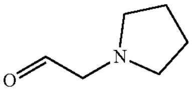
ALA10
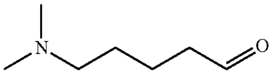
ALA11
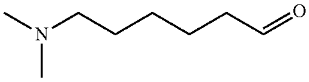
ALA12
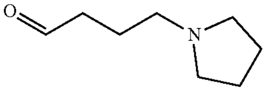
ALA13
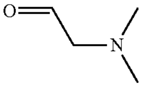
ALA14
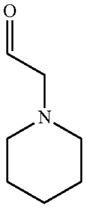
ALA15
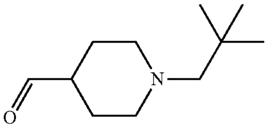
ALA16
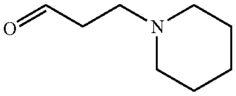
ALA17
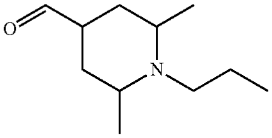
ALd1
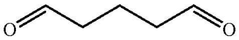
ALd2
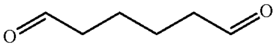
ALd3
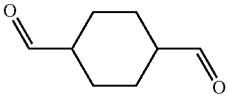
ALd4
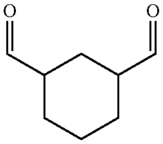
ALd5
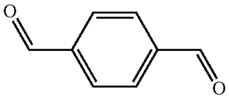
ALd6
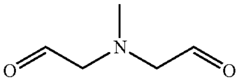

-continued
ALd7
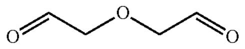
ALd8
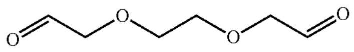
ALd9
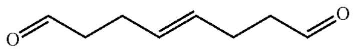
ALt1
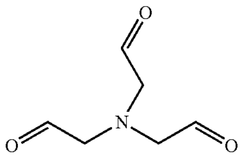
ALt2
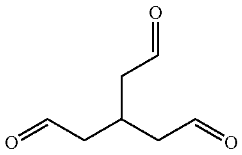
ALt3
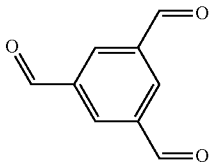
ALt4
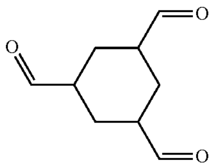
ALt5
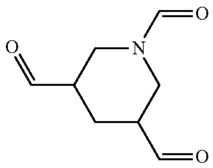
ALt6
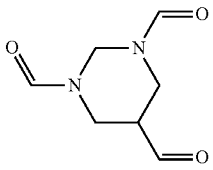
ALt7
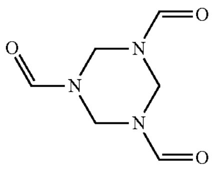
ALt8
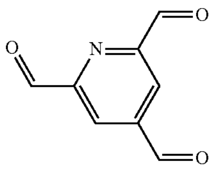
-continued
ALt9
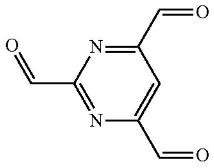
ALt10
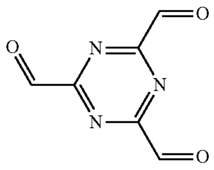
ALt11
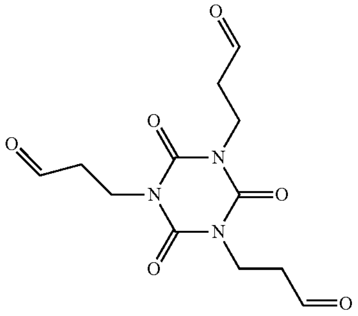
ALt12
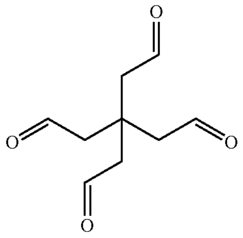
ALt13
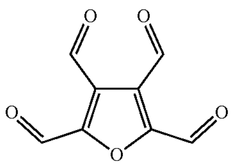
ALt14
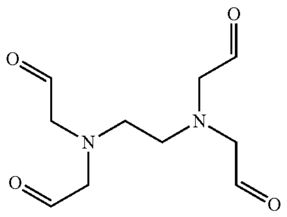

-continued
ALt15
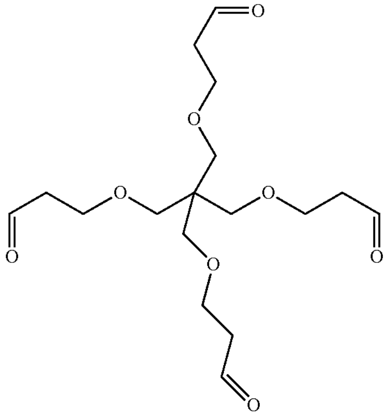
AL8
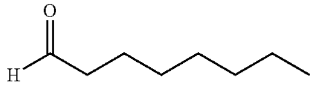
AL9
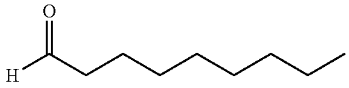
AL10
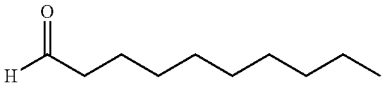
AL11
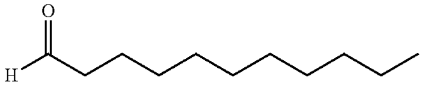
AL12
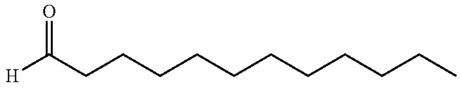
AL13
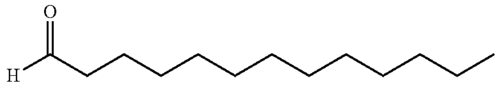
AL15
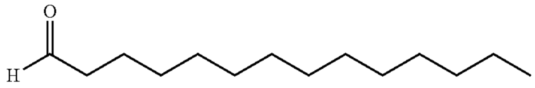
AL16
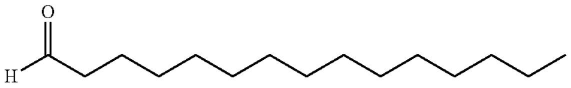
AL16e
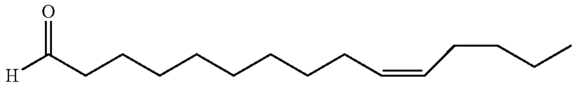
-continued
AL10P
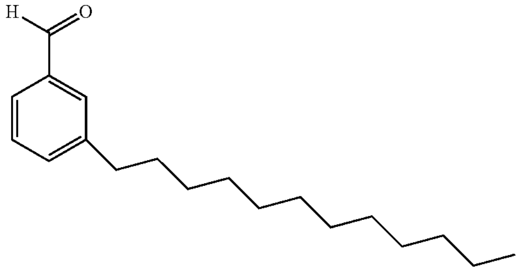
AL14e
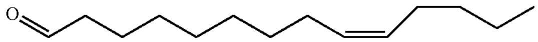
AL18e
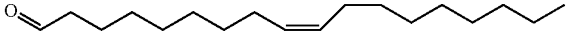
K9
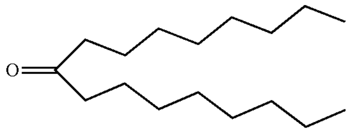
K10
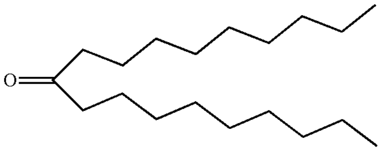
K11
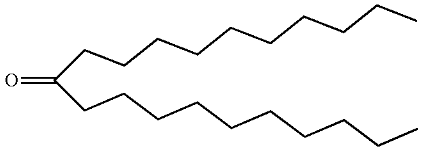
K12
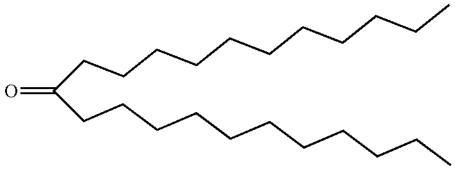
K14
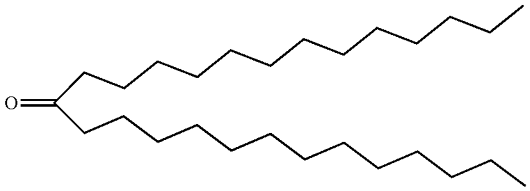
K16
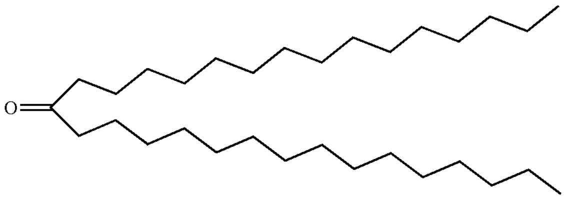

-continued
K18e
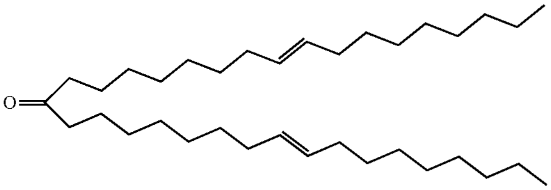
SAL-2
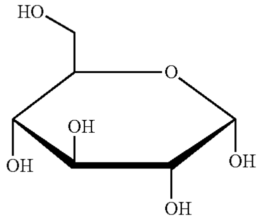
SAL-3
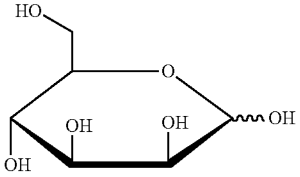
SAL-4
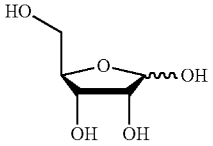
SAL-1
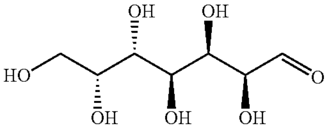
CHO-PEG1
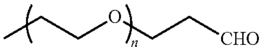
CHO-PEG$_{2000}$
CHO-PEG2
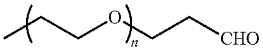
CHO-PEG$_{1000}$
CHO-PEG3
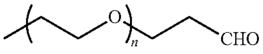
CHO-PEG$_{750}$
CHO-PEG4
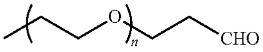
CHO-PEG$_{550}$
CHO-PEG5
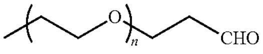
CHO-PEG$_{350}$
In some aspects, the isocyanide is:
Iso1
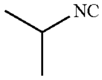
Iso2
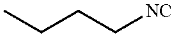
Iso3
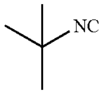
Iso4
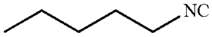
Iso5
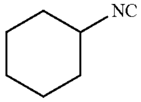
Iso6
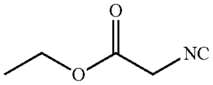
Iso7
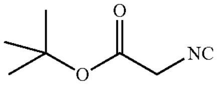
Iso8
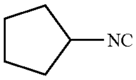
Iso9
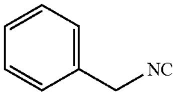
Iso10
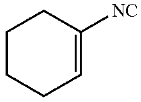
Iso11
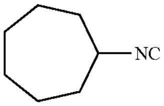
Iso12
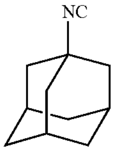
Iso13
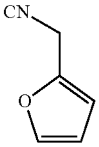
Iso 14
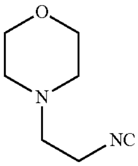

-continued
Iso 15
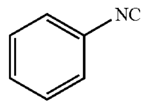
Iso16
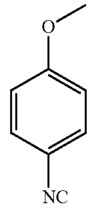
Iso17
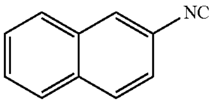
Iso 18
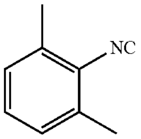
Iso 19
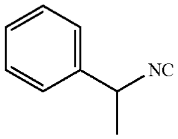
Iso 19'
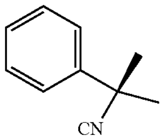
Iso 20
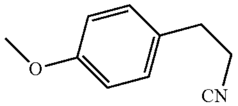
Iso21
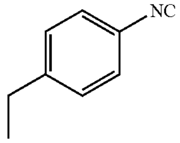
Iso 22
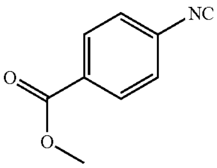
Iso 23
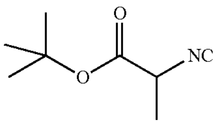
Iso24
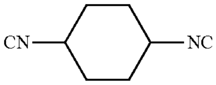
-continued
Iso25
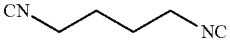
Iso26
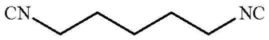
Iso27
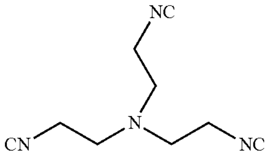
Iso28
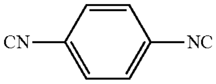
Iso29
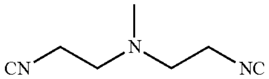
In one aspect, the present disclosure provides a modular lipid of Formula V, VI, VII, VIII, IX, or X:
V
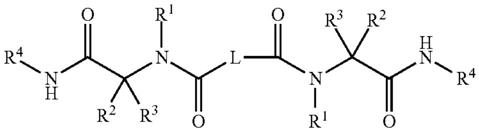
VI
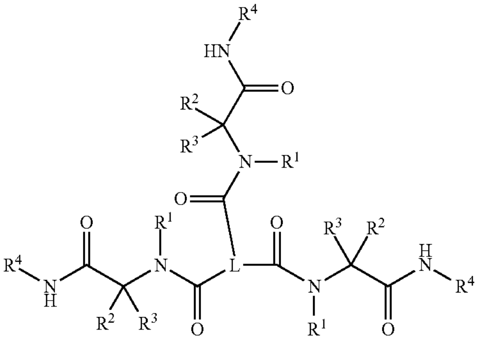
VII
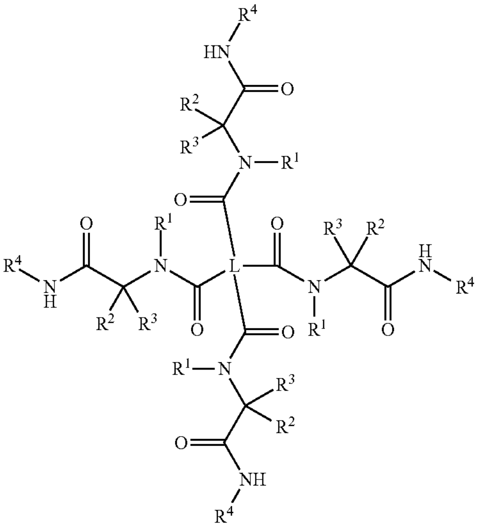

-continued

VIII

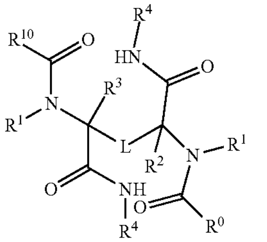

IX

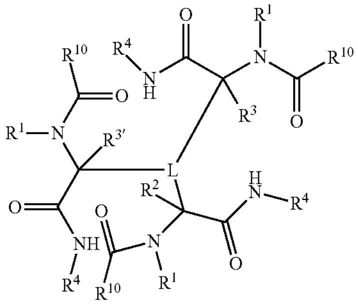

X

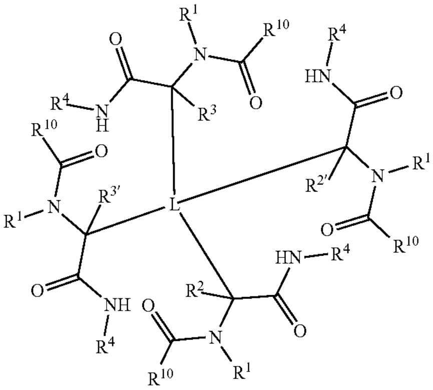

or a salt or isomer thereof, wherein each $R^1$, $R^4$, and $R^{10}$, is independently selected from $C_2$-$C_{24}$ alkyl, $C_2$-$C_{24}$ alkenyl, $C_2$-$C_{24}$ alkynyl, substituted $C_2$-$C_{24}$ alkyl, substituted alkenyl, substituted alkynyl, substituted acyl, substituted carbocyclyl, substituted heterocyclyl, substituted aryl, substituted heteroaryl, poly(ethylene glycol) (PEG),

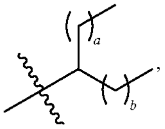

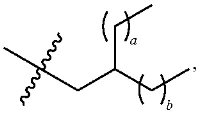

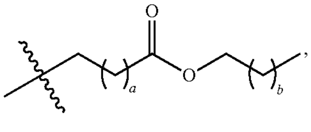

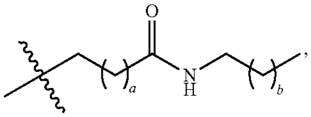

-continued

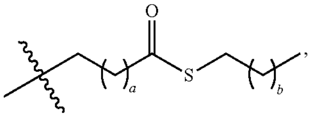

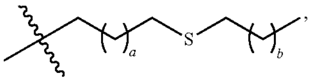

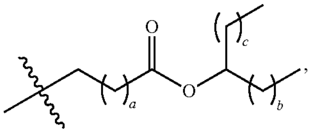

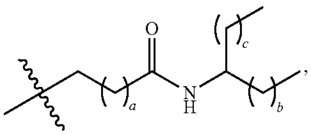

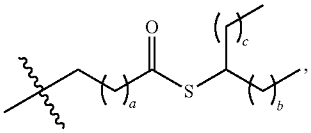

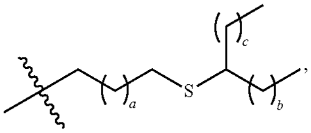

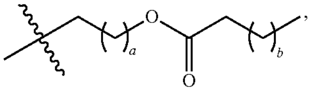

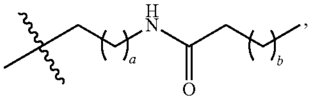

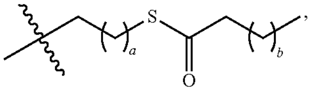

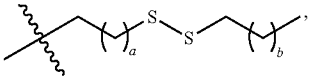

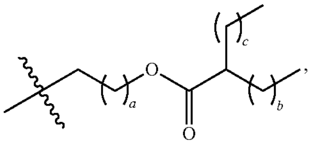

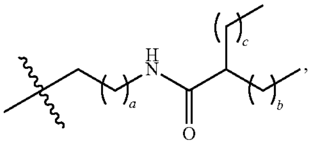

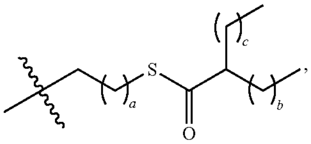

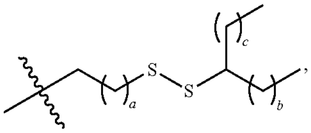

-continued
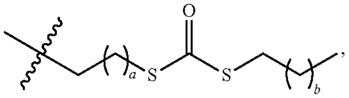
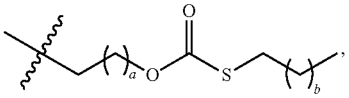
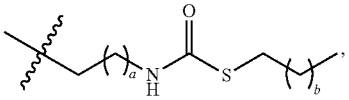
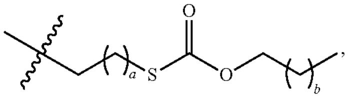
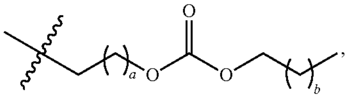
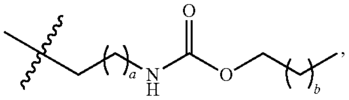
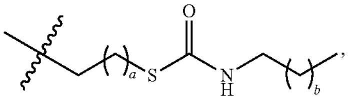
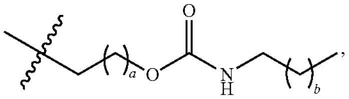
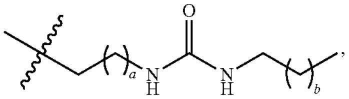
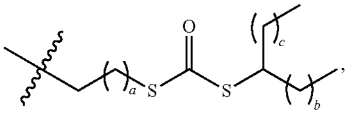
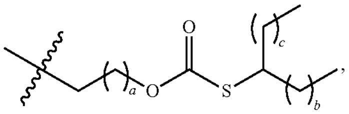
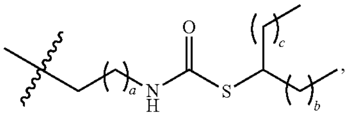
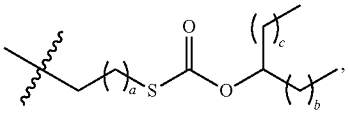
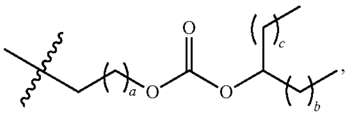
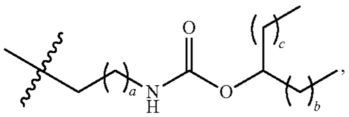
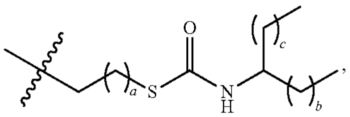
-continued
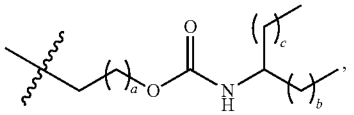
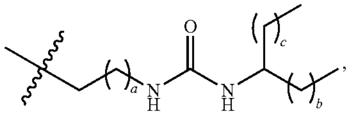
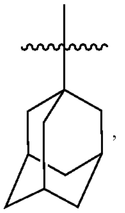
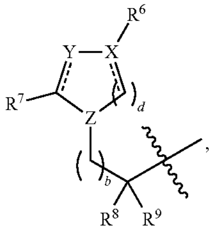
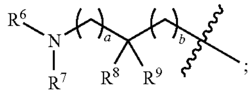
;
each $R^2$, $R^{2'}$, $R^3$ and $R^{3'}$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl, poly(ethylene glycol) (PEG) and
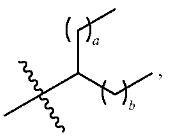
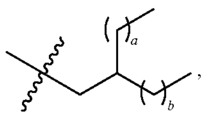
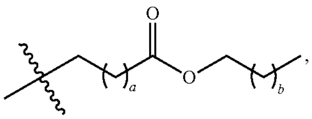
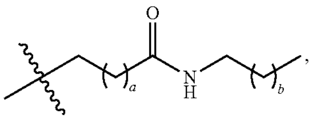
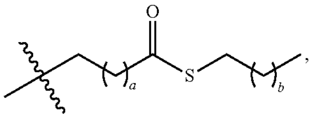
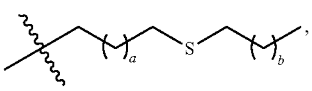
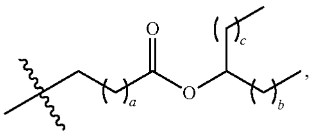
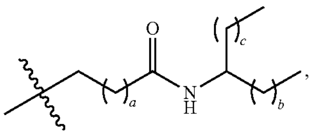

-continued
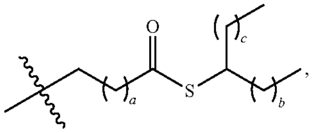
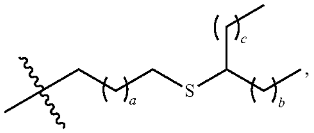
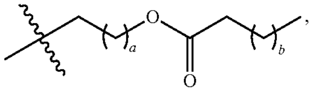
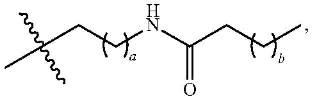
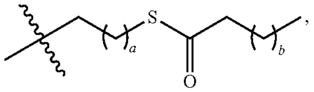
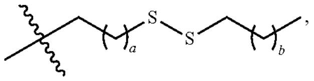
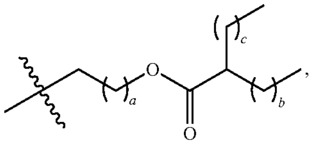
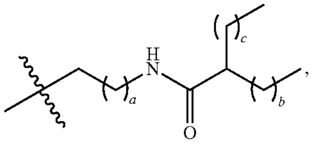
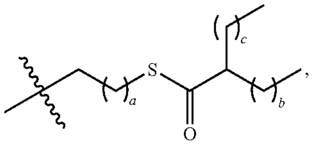
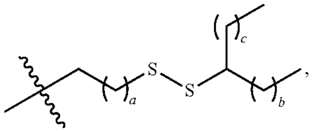
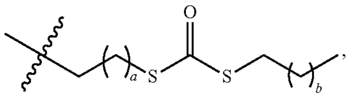
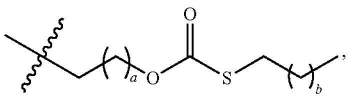
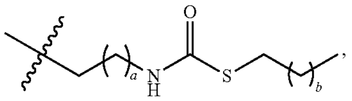
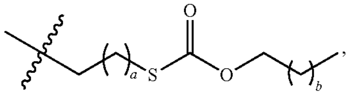
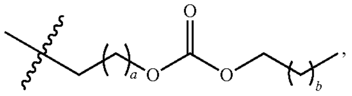
-continued
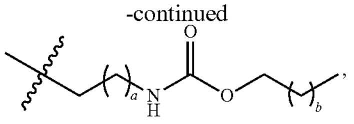
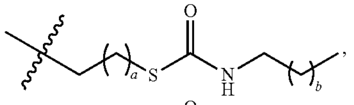
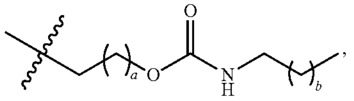
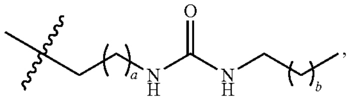
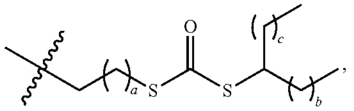
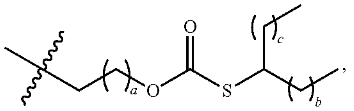
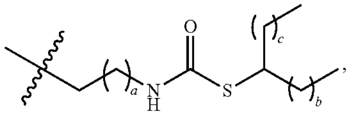
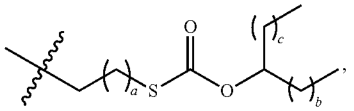
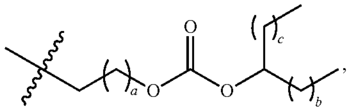
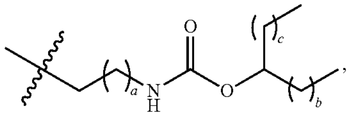
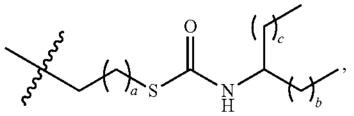
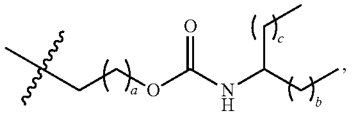
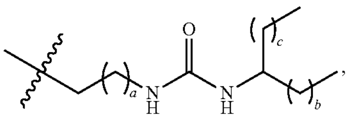
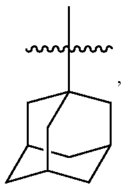
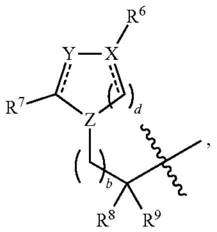
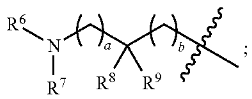

each L is independently selected from alkyl, alkenyl, alkynyl, substituted alkyl, substituted alkenyl, substituted alkynyl, substituted acyl, substituted carbocyclyl, substituted heterocyclyl, substituted aryl, substituted heteroaryl, poly (ethylene glycol) (PEG) and

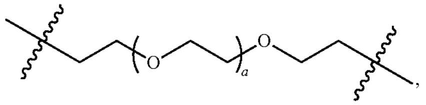
,
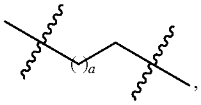
,
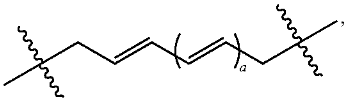
,
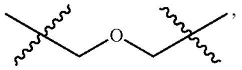
,
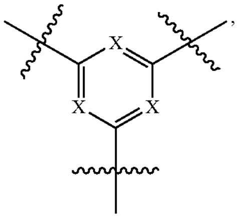
,
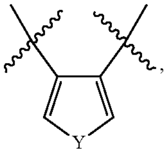
,
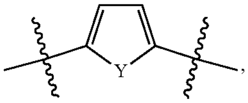
,
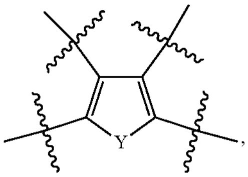
,
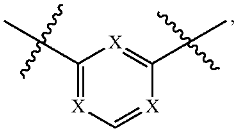
,
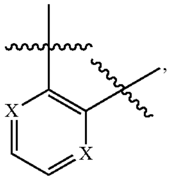
,
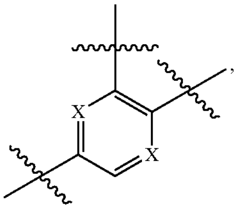
,
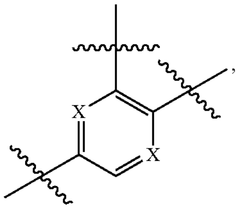
,
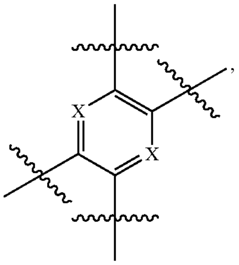
,
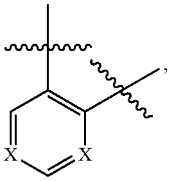
, -continued

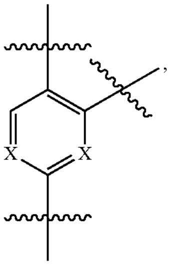
,
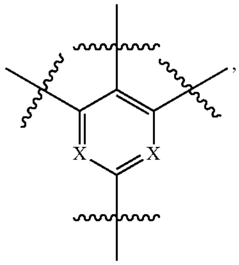
,
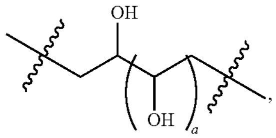
,
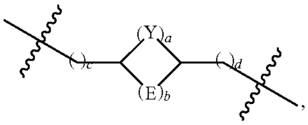
,
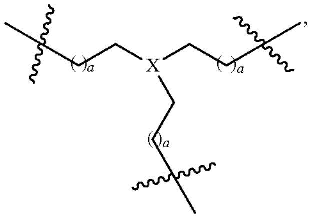
,
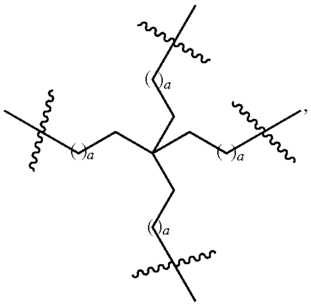
,
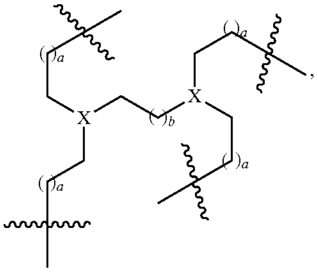
,
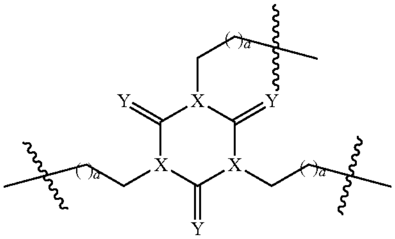

$R^6$, $R^7$, $R^8$ and $R^9$ are each independently selected from H, C1-C24 alkyl, C1-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl,

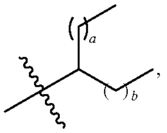, 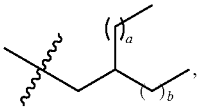,

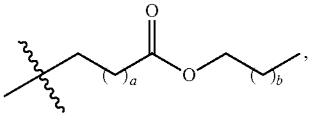,

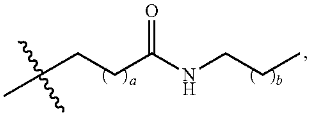,

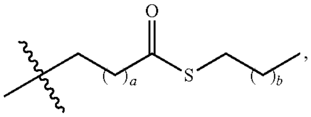,

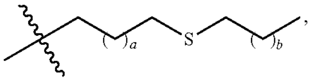,

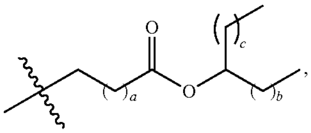,

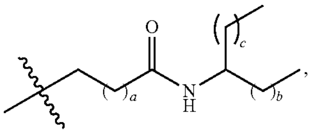,

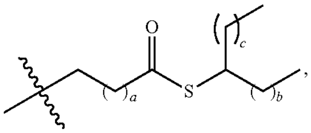,

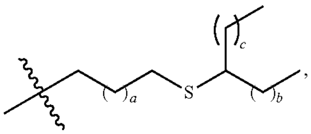,

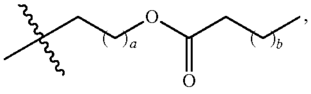,

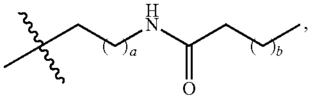,

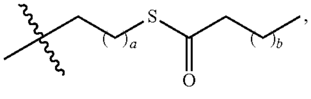,

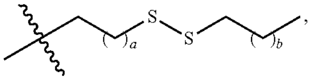,

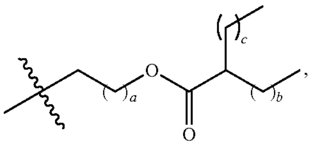,

-continued

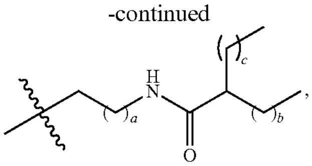,

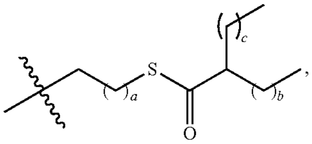,

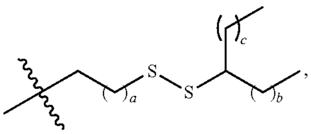, 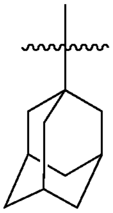, a, b, c and d are each independently an integer from 0-24; each E is independently selected from $CH_2$, NH, O, or S; each X is independently selected from CH, N; each Y is independently selected from $CH_2$, NH, O, or S; each Z is independently selected from CH or N.

In one aspect, the present disclosure provides methods for synthesizing a modular lipid of Formula V, VI and VII comprising performing the following four component reaction:

V

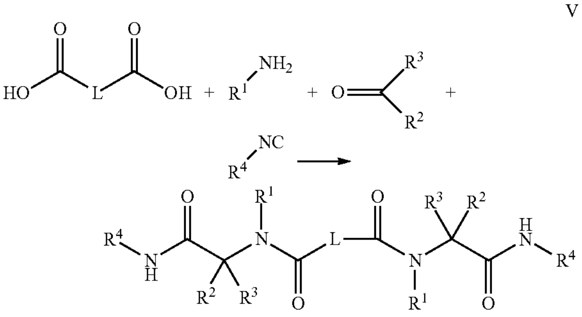

VI

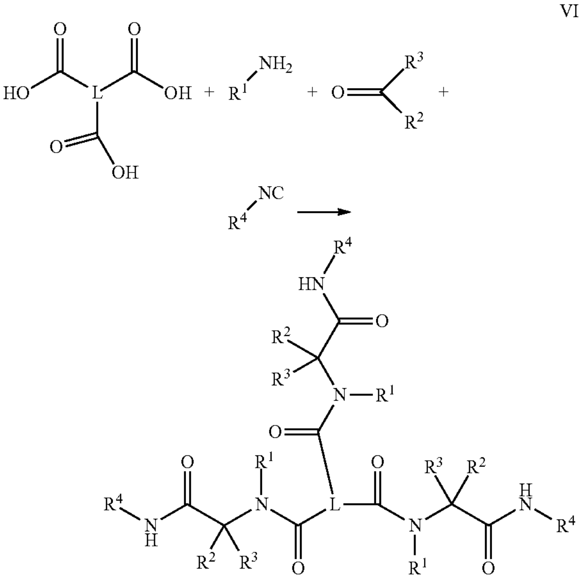

-continued

VII

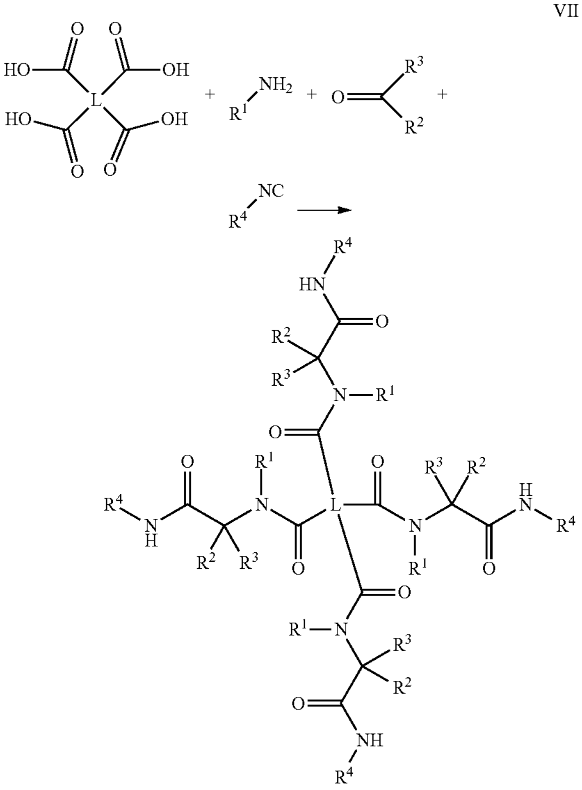

or a salt or isomer thereof, wherein each $R^1$ and $R^4$ is independently selected from $C_2$-$C_{24}$ alkyl, $C_2$-$C_{24}$ alkenyl, $C_2$-$C_{24}$ alkynyl, substituted $C_2$-$C_{24}$ alkyl, substituted alkenyl, substituted alkynyl, substituted acyl, substituted carbocyclyl, substituted heterocyclyl, substituted aryl, substituted heteroaryl, poly(ethylene glycol) (PEG),

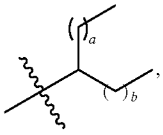

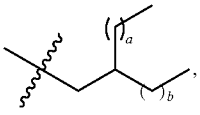

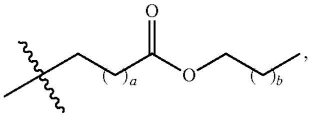

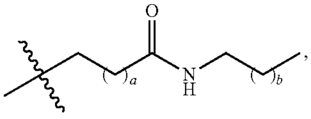

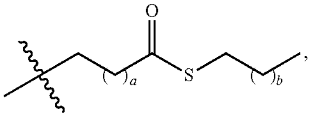

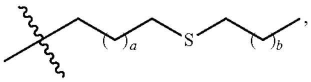

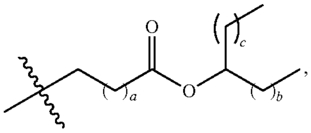

-continued

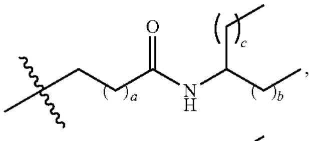

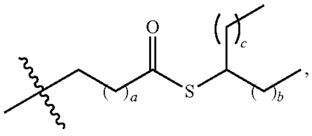

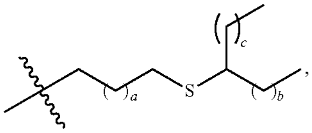

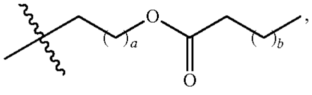

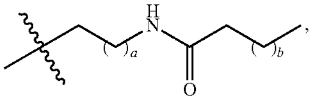

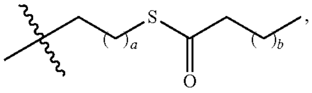

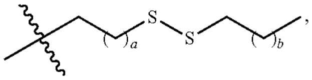

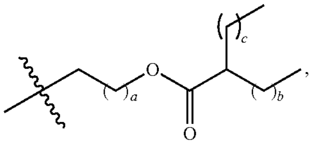

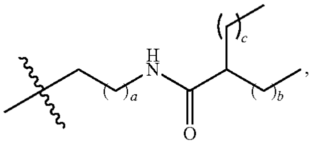

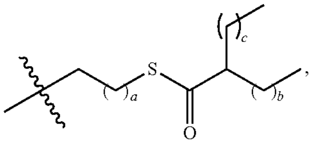

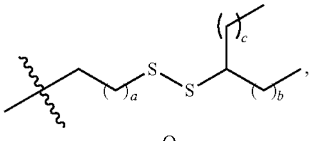

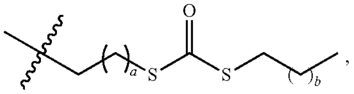

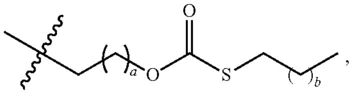

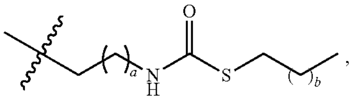

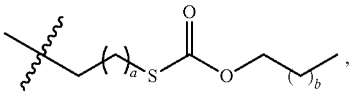

-continued
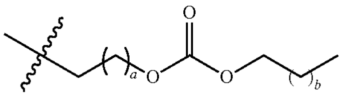,
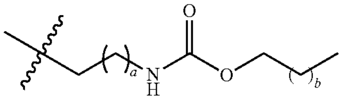,
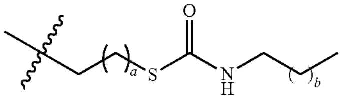,
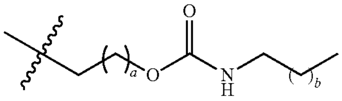,
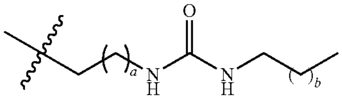,
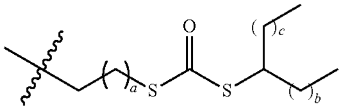,
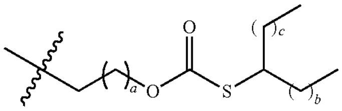,
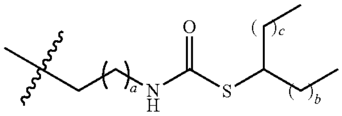,
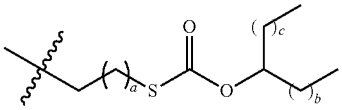,
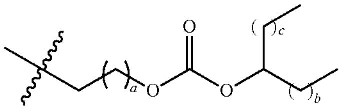,
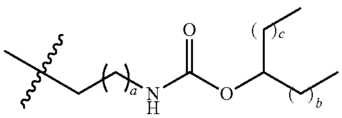,
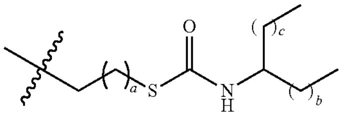,
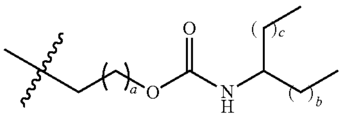,
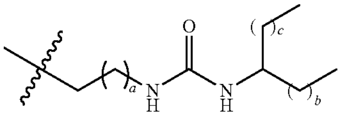, 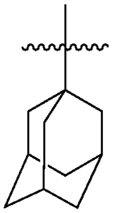,
-continued
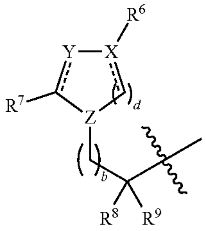, 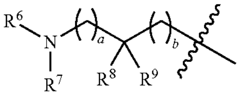
each $R^2$ and $R^3$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl, poly(ethylene glycol) (PBG) and
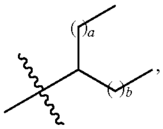, 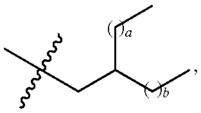,
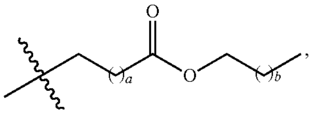,
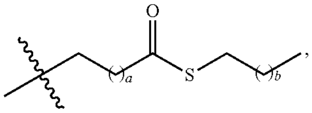,
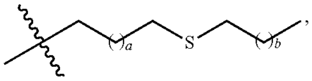,
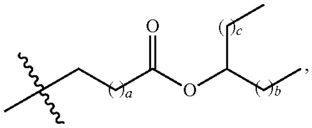,
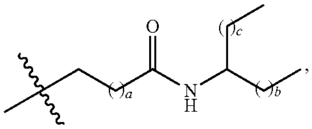,
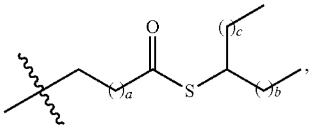,
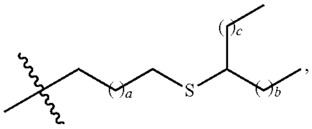,
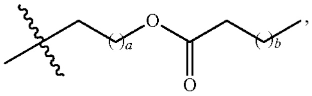,
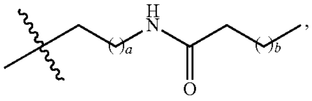,
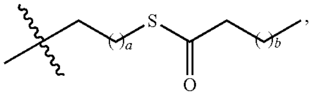, -continued
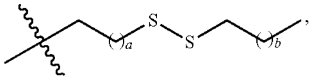
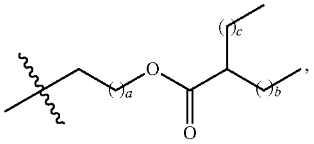
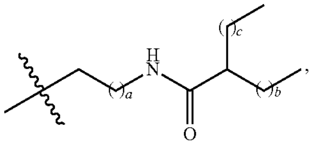
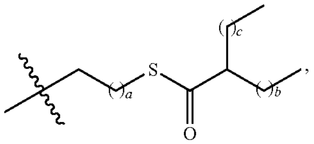
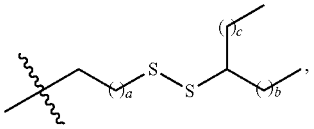
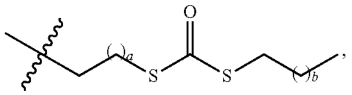
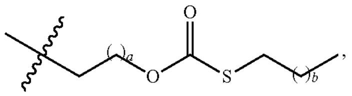
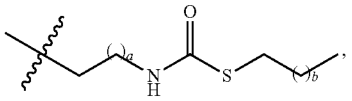
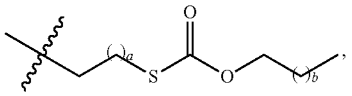
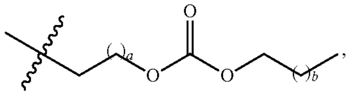
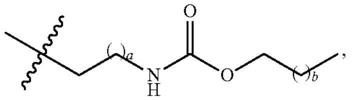
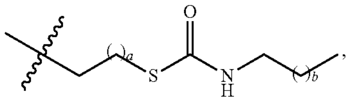
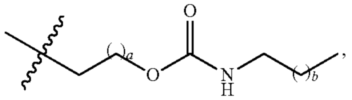
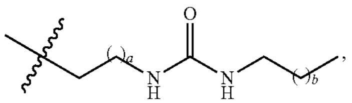
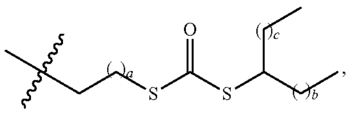
-continued
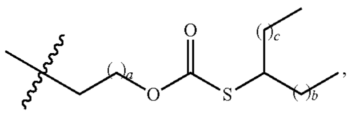
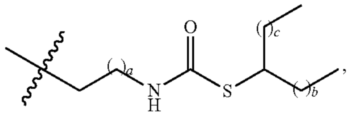
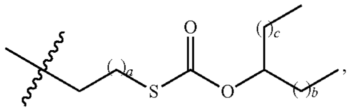
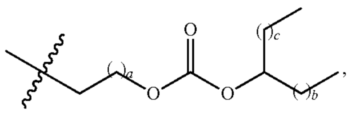
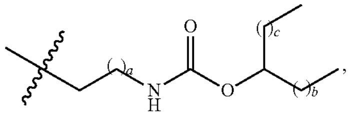
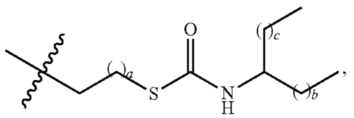
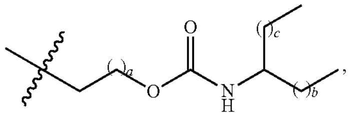
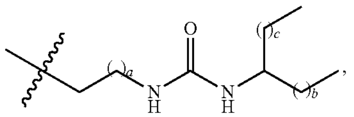
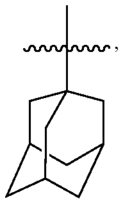
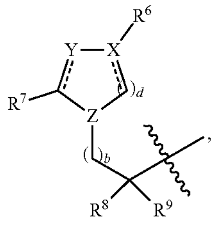
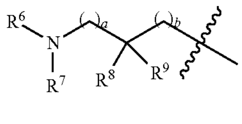
each L is independently selected from alkyl, alkenyl, alkynyl, substituted alkyl, substituted alkenyl, substituted alkynyl, substituted acyl, substituted carbocyclyl, substituted heterocyclyl, substituted aryl, substituted heteroaryl, poly (ethylene glycol) (PEG) and
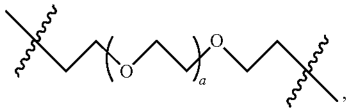

-continued
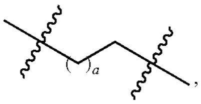,
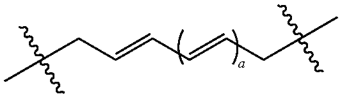,
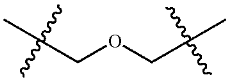,
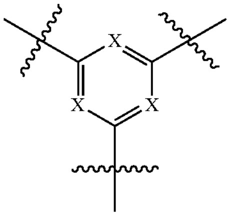,
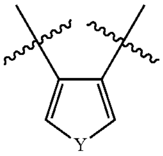,
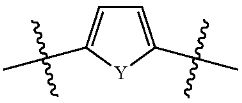,
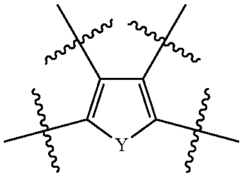,
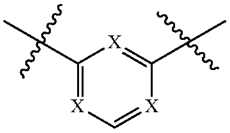,
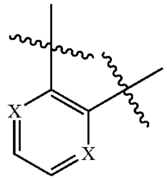,
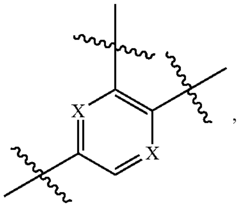,
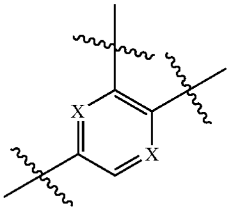,
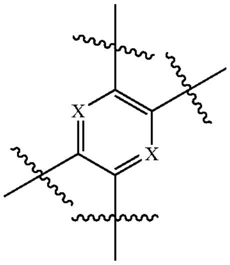,
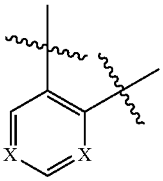,
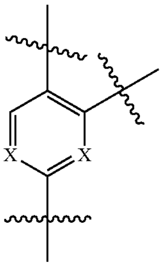,
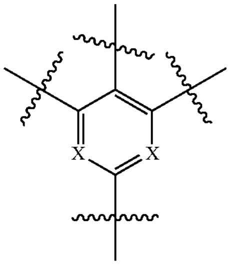,
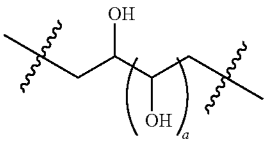,
-continued
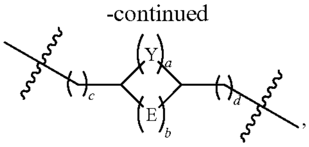,
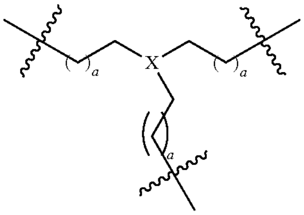,
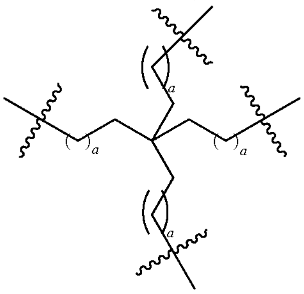,
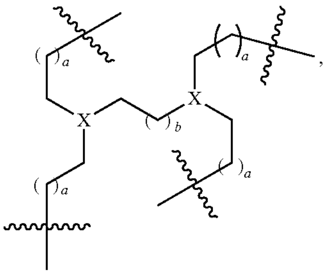,
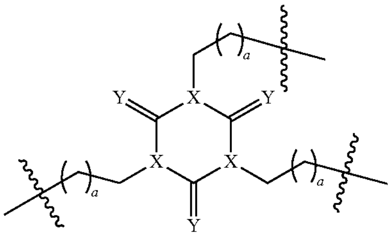
$R^6$, $R^7$, $R^8$ and $R^9$ are each independently selected from H, C1-C24 alkyl, $C_1$-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl,
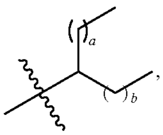,
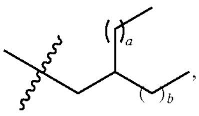,
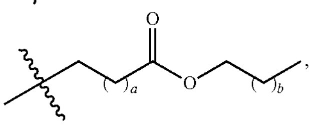,
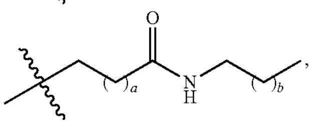, -continued

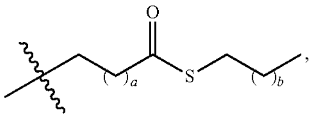,

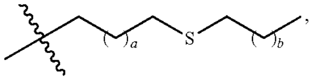,

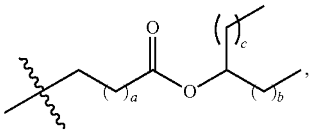,

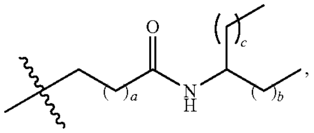,

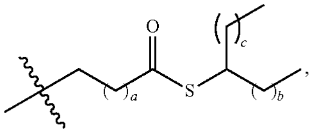,

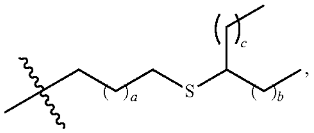,

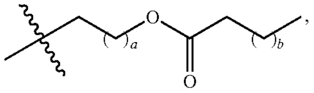,

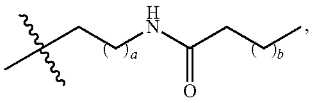,

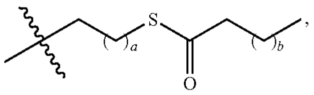,

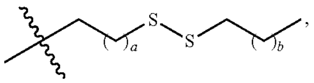,

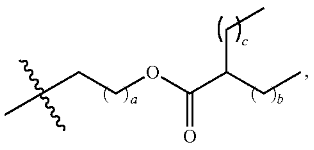,

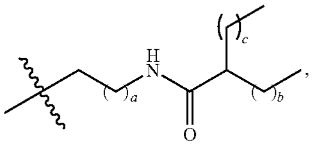,

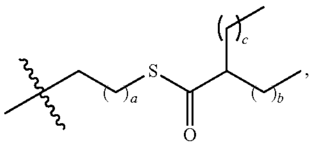,

-continued

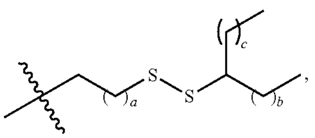, 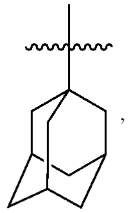, a, b, c and d are each independently an integer from 0-24;
each E is independently selected from $CH_2$, NH, O, or S;
each X is independently selected from CH, N;
each Y is independently selected from $CH_2$, NH, O, or S;
each Z is independently selected from CH or N.

In one aspect, the present disclosure provides methods for synthesizing a modular lipid of Formula VIII, IX and X comprising performing the following four component reaction:

VIII

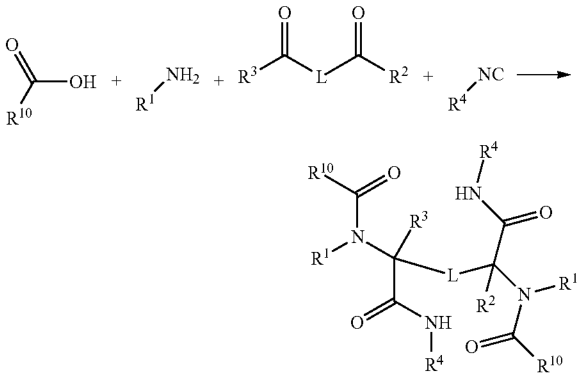

IX

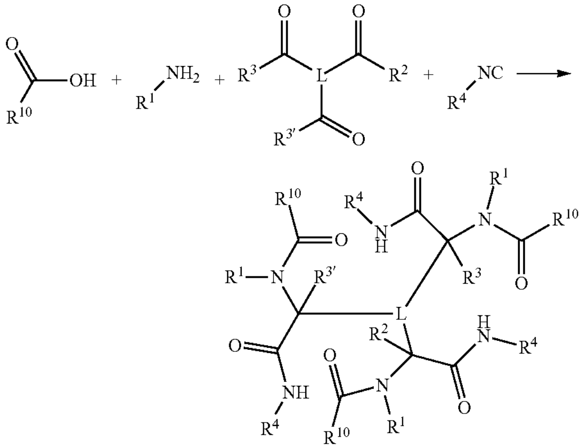

X

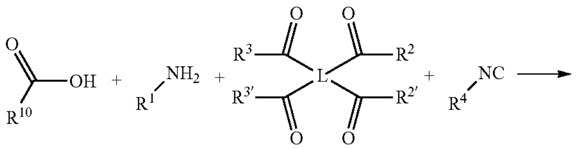

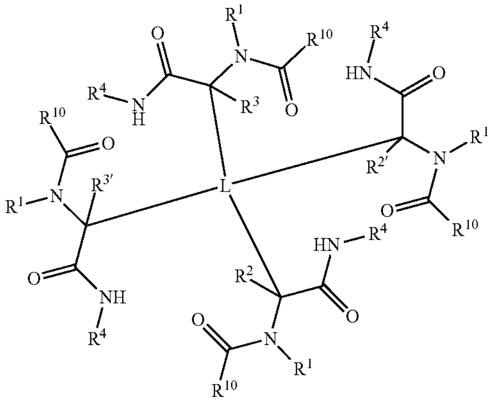
or a salt or isomer thereof, wherein
each $R^1$, $R^4$, and $R^{10}$ is independently selected from $C_2$-$C_{24}$ alkyl, $C_2$-$C_{24}$ alkenyl, $C_2$-$C_{24}$ alkynyl, substituted $C_2$-$C_{24}$ alkyl, substituted alkenyl, substituted alkynyl, substituted acyl, substituted carbocyclyl, substituted heterocyclyl, substituted aryl, substituted heteroaryl, poly(ethylene glycol) (PEG),
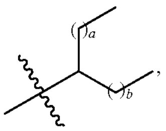
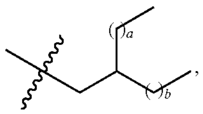
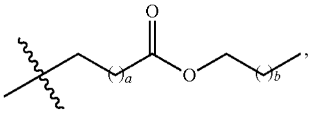
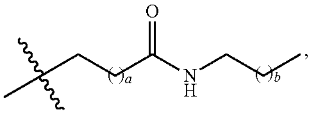
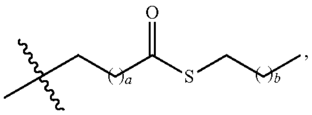
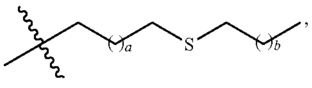
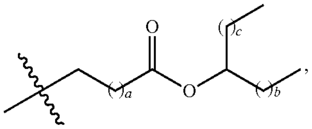
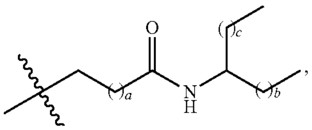
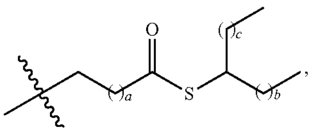
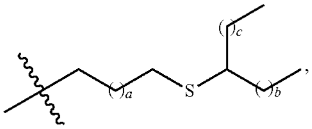
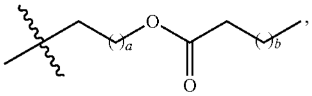
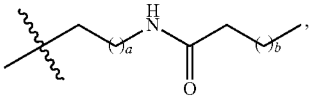
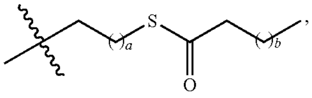
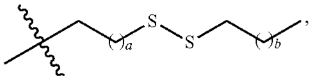
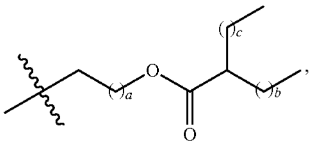
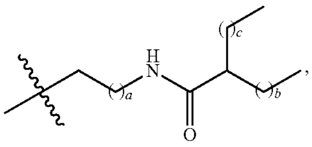
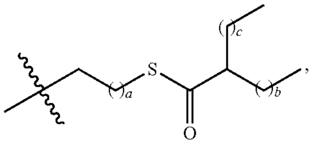
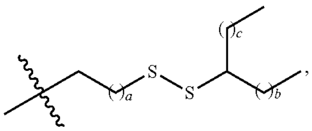
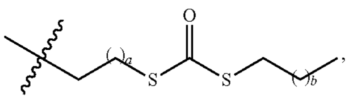
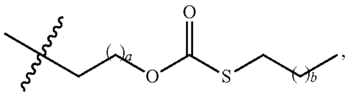
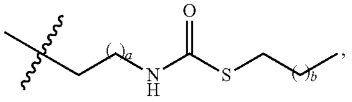
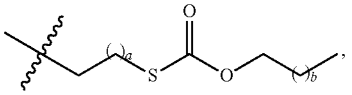
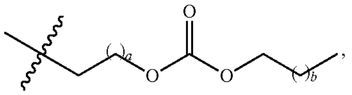
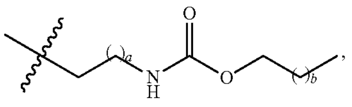

-continued
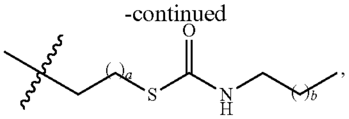
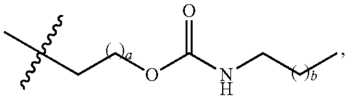
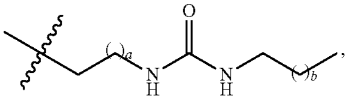
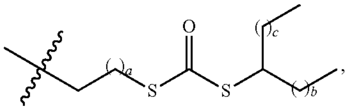
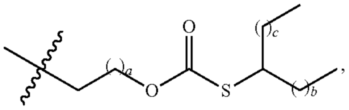
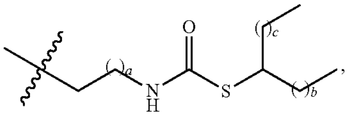
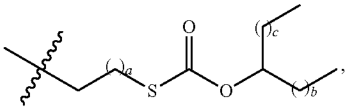
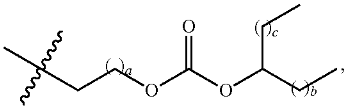
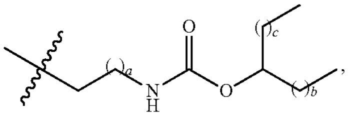
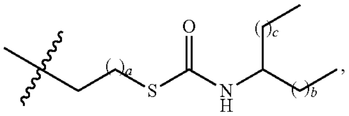
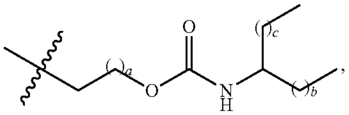
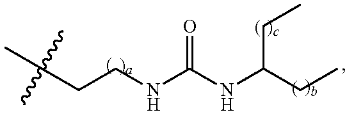
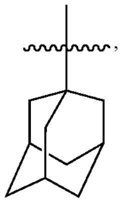
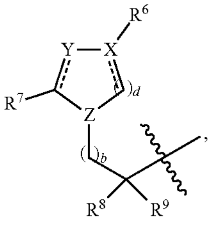
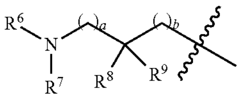
each $R^2$, $R^{2'}$, $R^3$ and $R^{3'}$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl, poly(ethylene glycol) (PEG) and
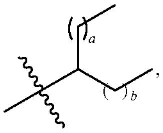
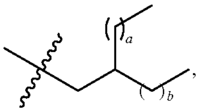
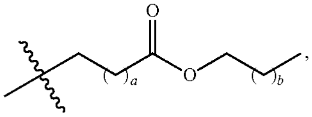
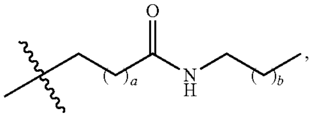
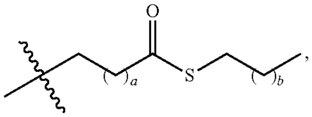
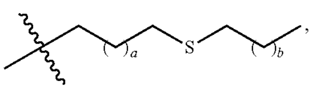
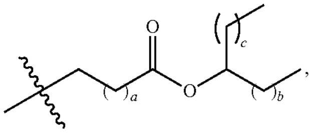
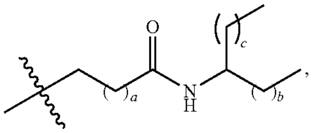
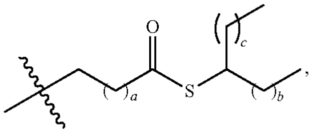
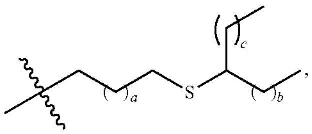
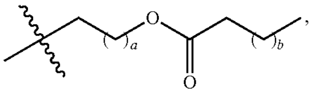
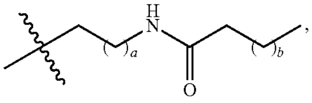
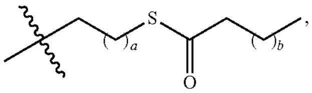
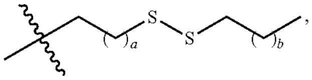

-continued
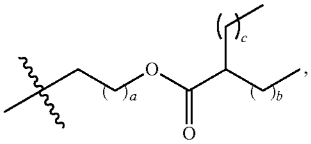,
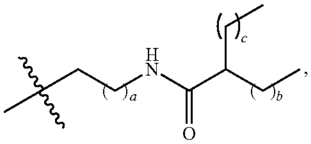,
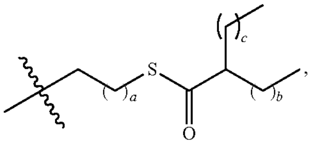,
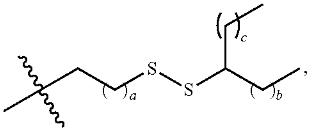,
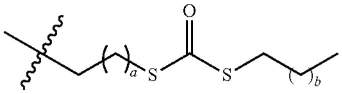,
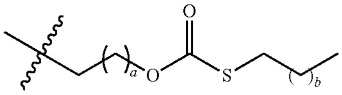,
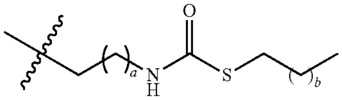,
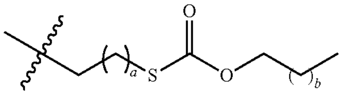,
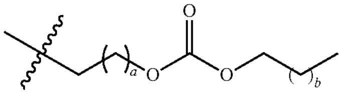,
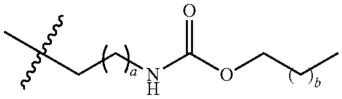,
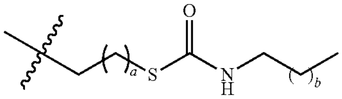,
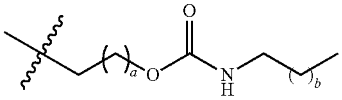,
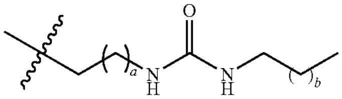,
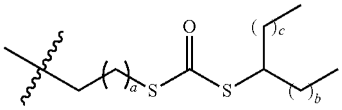,
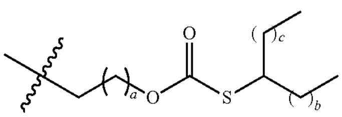,
-continued
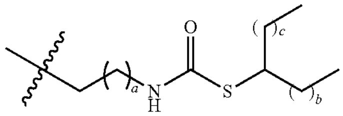,
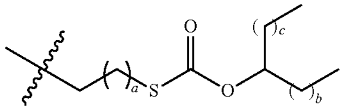,
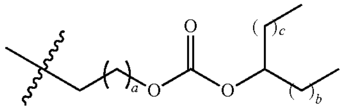,
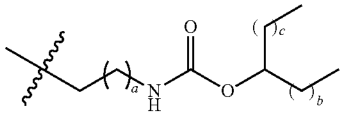,
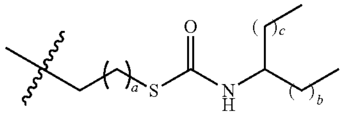,
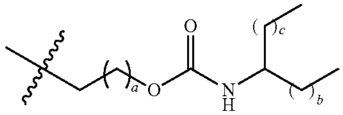,
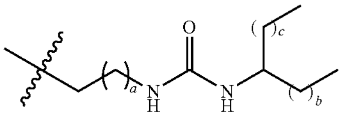, 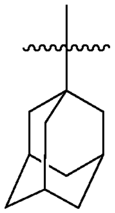,
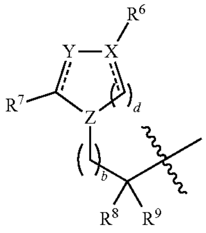, 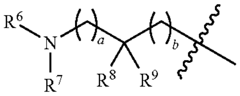
each L is independently selected from alkyl, alkenyl, alkynyl, substituted alkyl, substituted alkenyl, substituted alkynyl, substituted acyl, substituted carbocyclyl, substituted heterocyclyl, substituted aryl, substituted heteroaryl, poly (ethylene glycol) (PEG) and
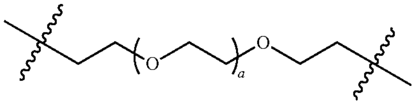,
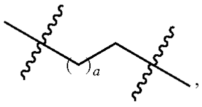, 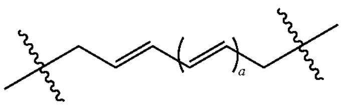, -continued
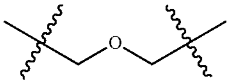
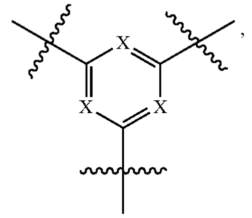
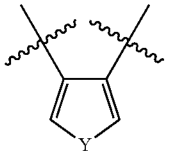
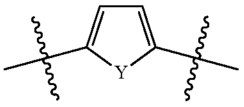
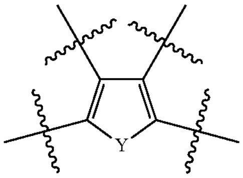
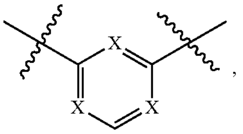
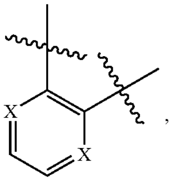
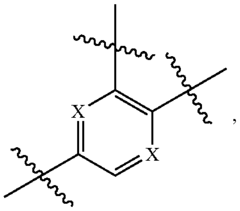
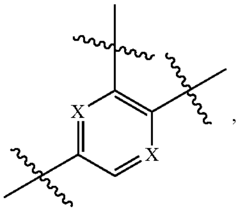
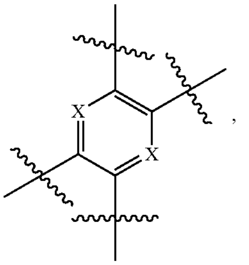
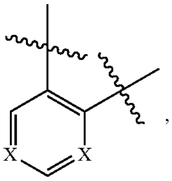
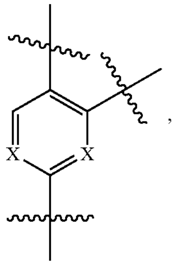
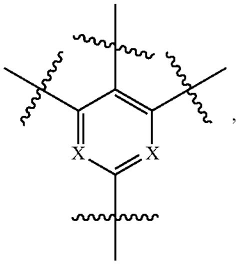
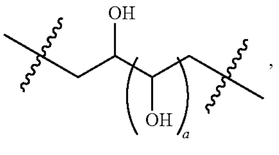
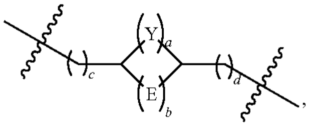
-continued
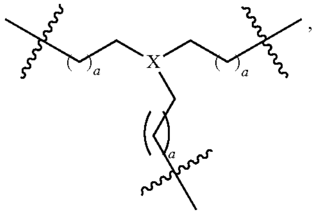
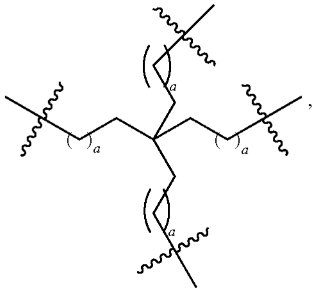
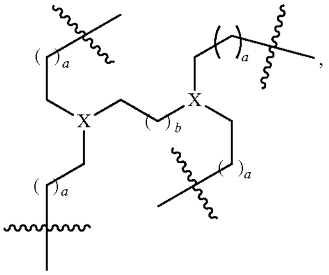
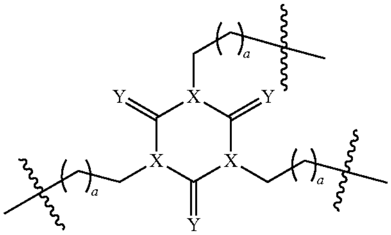
$R^6$, $R^7$, $R^8$ and $R^9$ are each independently selected from H, C1-C24 alkyl, C1-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl,
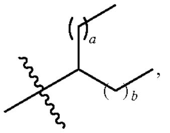
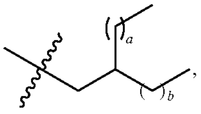
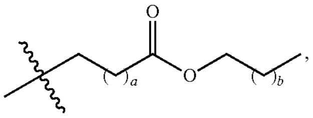
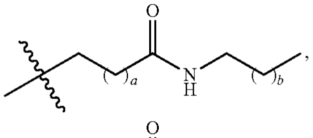
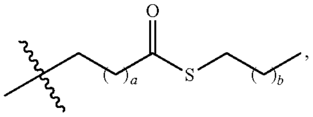

-continued
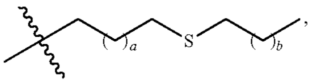,
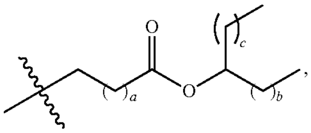,
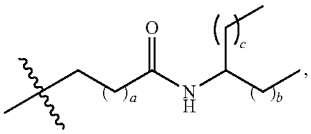,
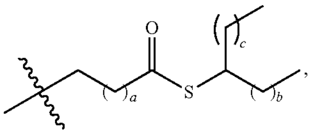,
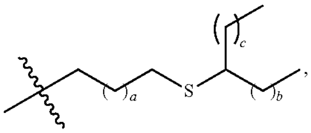,
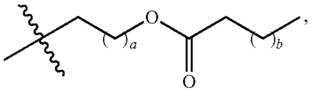,
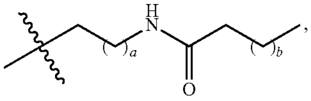,
-continued
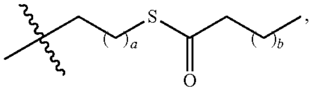,
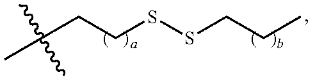,
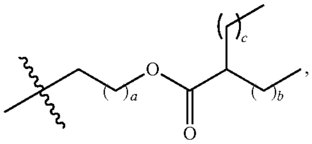,
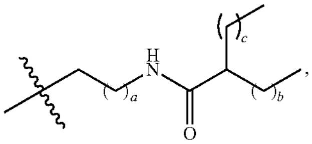,
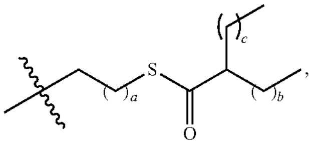,
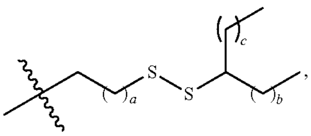, 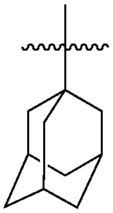,
a, b, c and d are each independently an integer from 0-24;
each E is independently selected from $CH_2$, NH, O, or S;
each X is independently selected from CH, N;
each Y is independently selected from $CH_2$, NH, O, or S;
each Z is independently selected from CH or N.
In one aspect, the present disclosure provides a modular lipid, wherein the lipid is:
P161F6
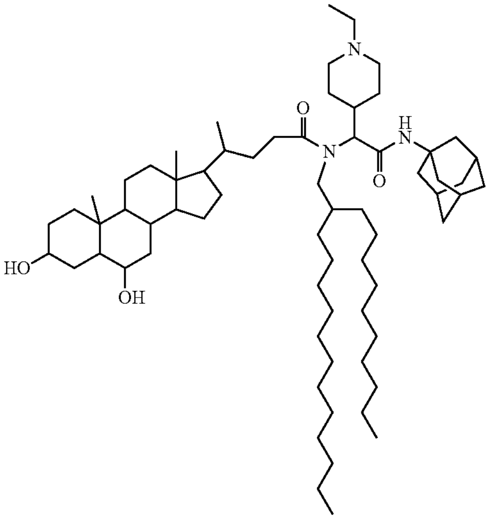
P161F5
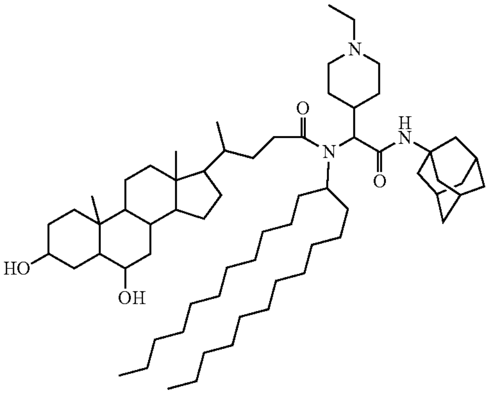

-continued
P161F12
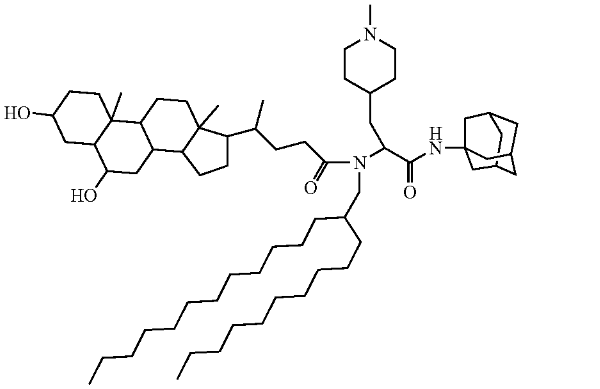
P161F10
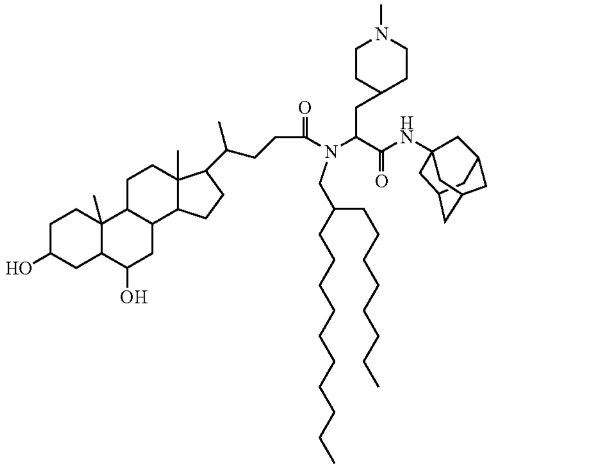
P287A12
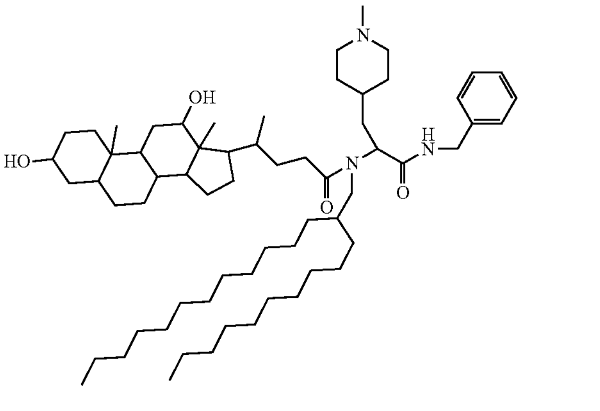
P287C12
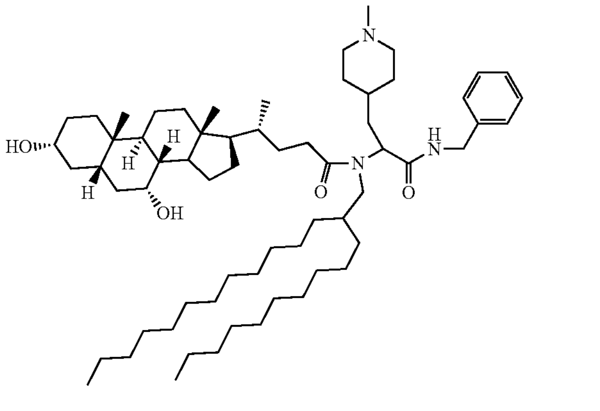

-continued
HP3G5
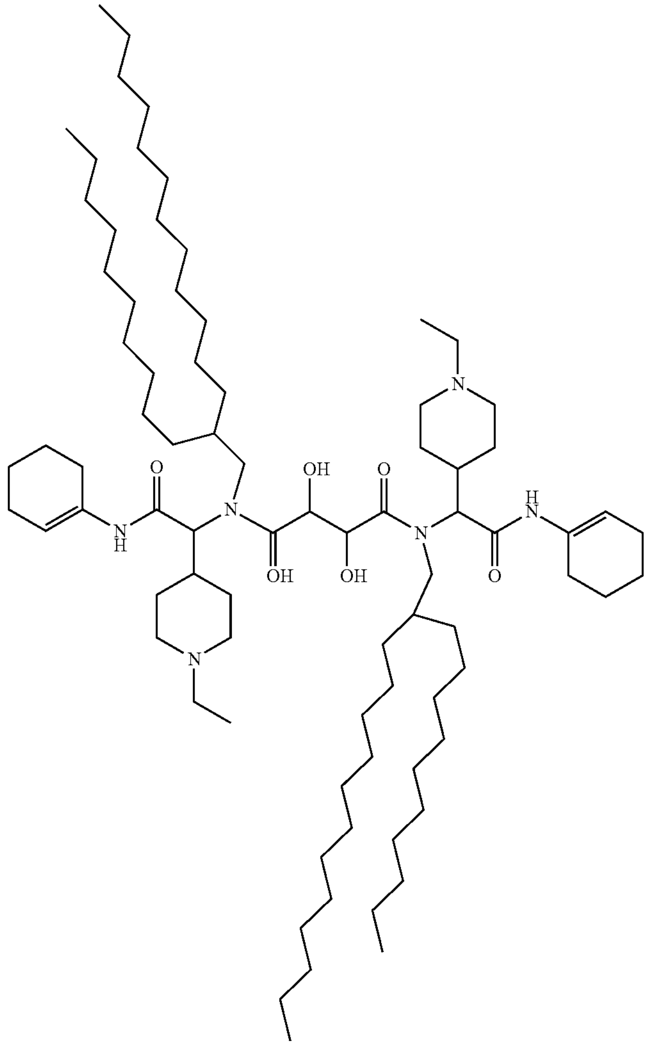
HP3H5
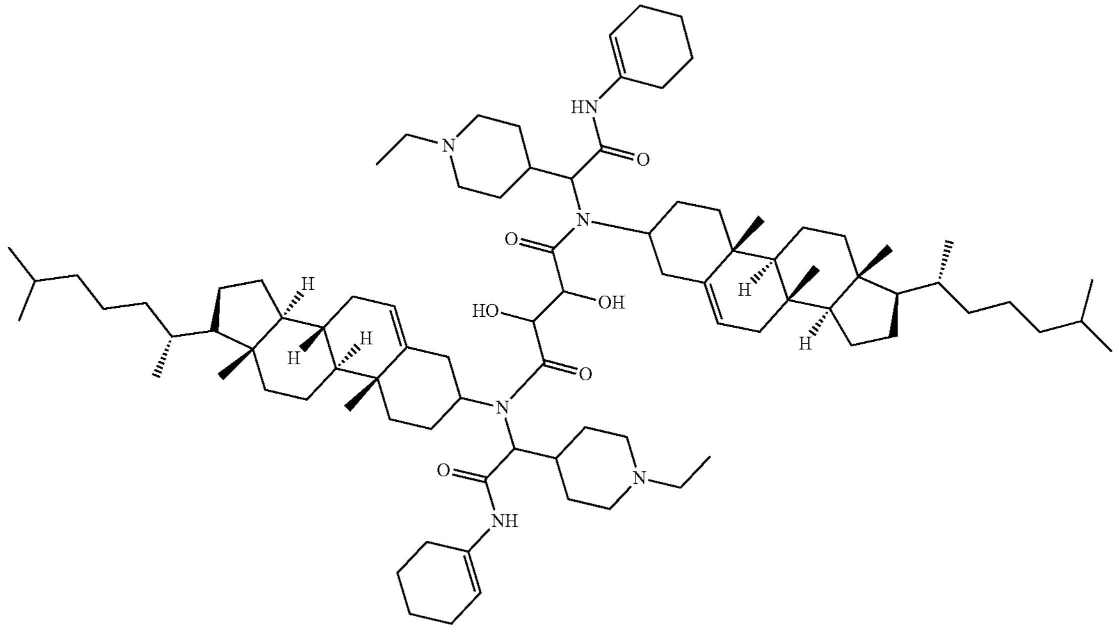

-continued
SP1E2
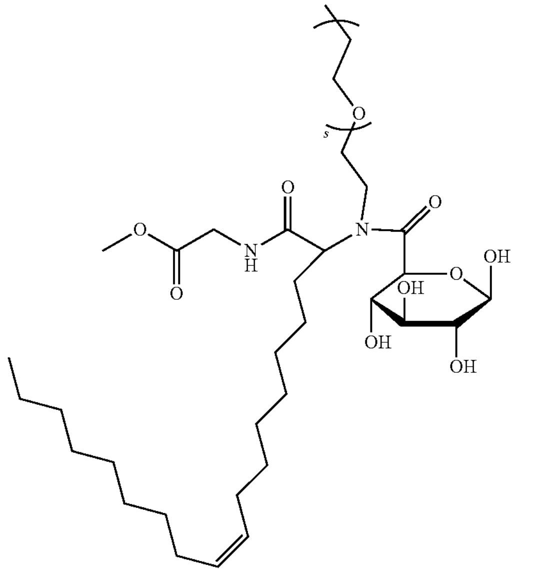
SP1F2
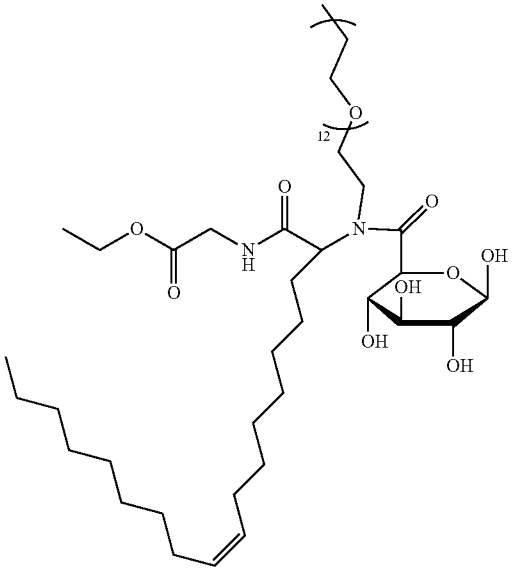
SP1F11
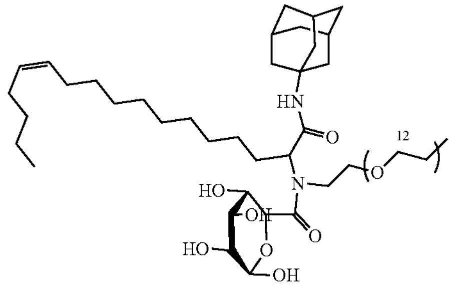
SP1E8
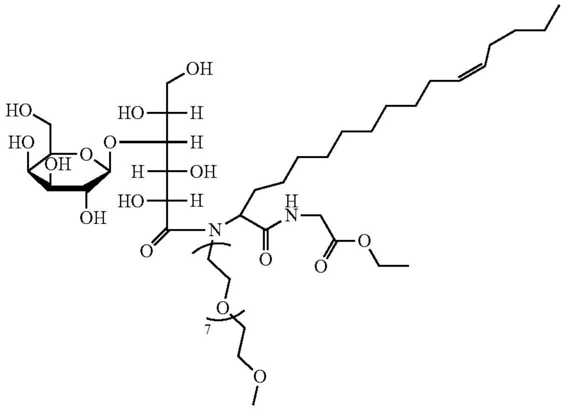
SP1E2K
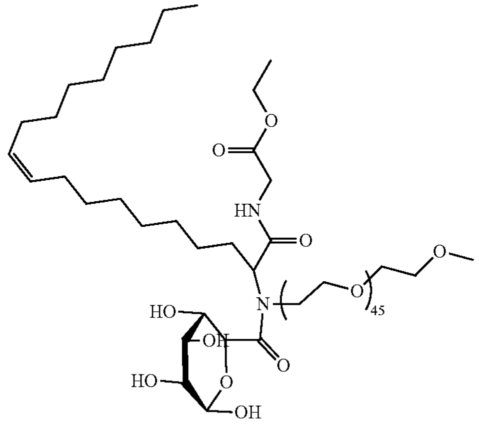
SP1E2KI
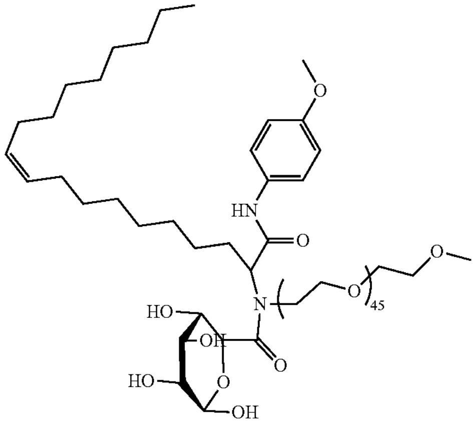

-continued
SP2B12
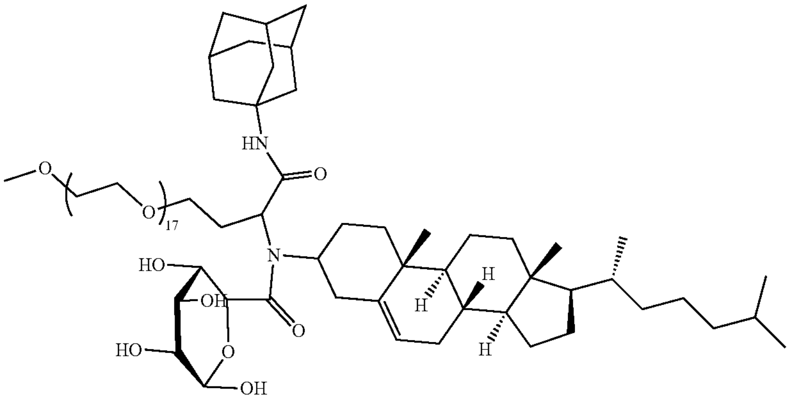
SP2A3
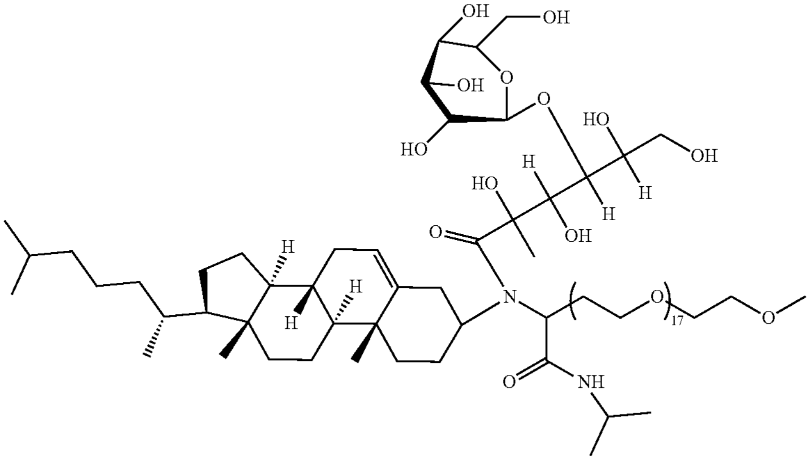
SP4A7
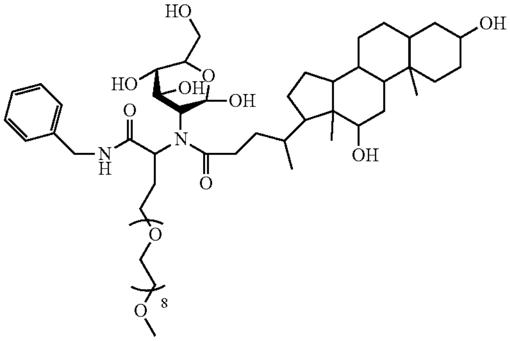
SP6A1
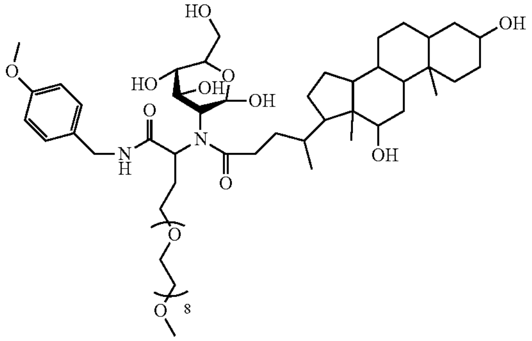
SP11A6
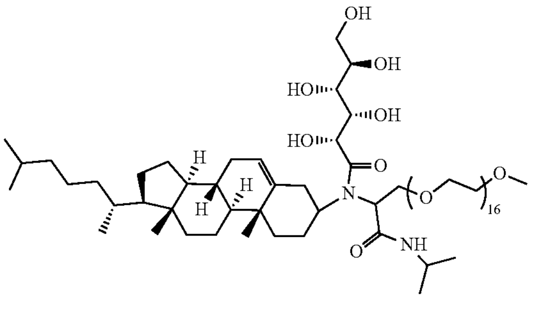
SP11H6
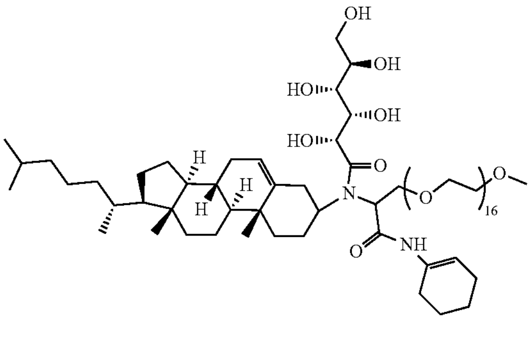

-continued

SP11H3

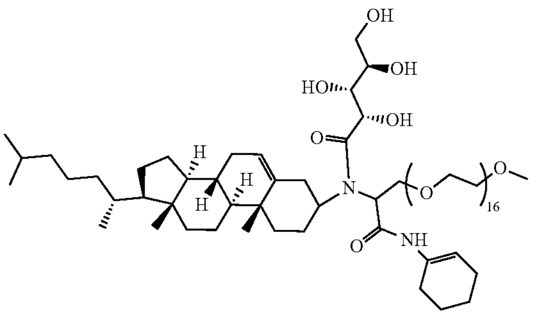

SP11A12

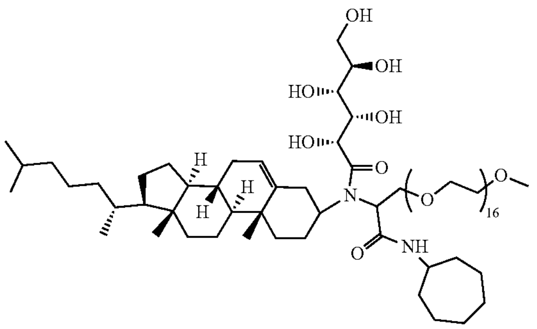

SP1E2-PEG3

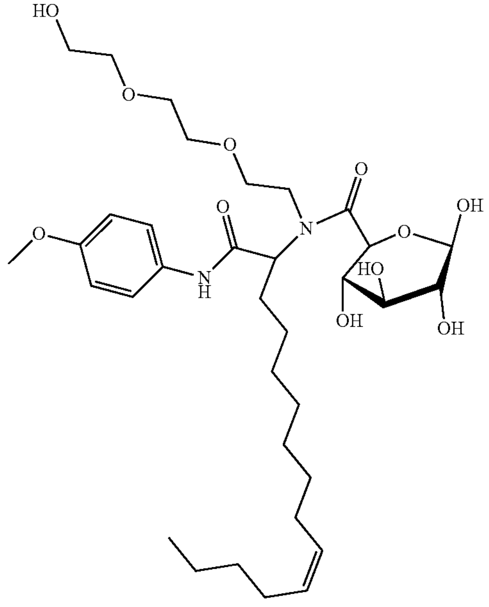

Saccharide Lipids

As used herein, the term "saccharide lipid" or "saccharide stabilizer lipid" refer to the novel lipids of the present disclosure, which mimics the lipids of the lipid envelopes of certain viral particles. Saccharide lipids are viral envelope lipids with saccharide modifications. Saccharide lipids are useful in the composition and methods of the disclosure include the compounds of Formulae (III) and (IV). Other saccharide lipids with similar structures to the compounds of Formulae (III) and (IV), e.g., the saccharide lipids used to form the LNPs of FIG. 1, FIG. 2, FIG. 3, and FIG. 4, are also contemplated. In one aspect, a saccharide lipid is a modular lipid. In one aspect, a saccharide lipid is a bipolar lipid.

Monosaccharides useful in the composition of the disclosure include trioses (ketotriose, aldotriose), tetroses (ketotetrose, aldotetroses), pentoses (ribulose, xylulose, ribose, arabinose, xylose, lyxose, deoxyribose), hexoses (psicose, fructose, sorbose, tagatose, allose, altrose, glucose, mannose, fucose, fuculose, rhamnose, heptose, octose, nonose, gulose, idose, galactose, talose), sedoheptulose.

Disaccharides useful in the composition of the disclosure include sucrose, lactose, maltose, trehalose, turanose, cellobiose.

Oligosaccharides useful in the composition of the disclosure include raffinose, melezitose, maltotriose, acarbose, stachyose, fructooligosaccharide, galactooligosaccharides, mannanoligosaccharides.

Polysaccharides useful in the composition of the disclosure include ploygIycitol, n-acetylglucosamine, chitin.

Adjuvants

In some aspects, a nanoparticle composition that includes one or more lipids described herein may further include one or more adjuvants, e.g., Glucopyranosyl Lipid Adjuvant (GLA), CpG oligodeoxynucleotides (e.g., Class A or B), poly(I:C), aluminum hydroxide, and Pam3CSK4.

Biologically Active Agents

Nanoparticle compositions may include a payload. The payload may comprise one or more biologically active agents. The disclosure features methods of delivering a biologically active agent to a cell or organ and treating a disease or disorder in a subject in need thereof comprising administering to a subject and/or contacting a cell with a nanoparticle composition including a biologically active agent.

A biologically active agent may be a substance that, once delivered to a cell or organ, brings about a desirable change in the cell, organ, or other bodily tissue or system. Such species may be useful in the treatment of one or more diseases, disorders, or conditions. In some aspects, a biologically active agent is a small molecule drug useful in the treatment of a particular disease, disorder, or condition.

Examples of drugs useful in the nanoparticle compositions include, but are not limited to, antineoplastic agents (e.g., vincristine, doxorubicin, mitoxantrone, camptothecin, cisplatin, bleomycin, cyclophosphamide, methotrexate, and streptozotocin), antitumor agents (e.g., actinomycin D, vincristine, vinblastine, cystine arabinoside, anthracyclines, alkylative agents, platinum compounds, antimetabolites, and nucleoside analogs, such as methotrexate and purine and pyrimidine analogs), anti-infective agents, local anesthetics (e.g., dibucaine and chlorpromazine), beta-adrenergic blockers (e.g., propranolol, timolol, and labetolol), antihypertensive agents (e.g., clonidine and hydralazine), anti-depressants (e.g., imipramine, amitriptyline, and doxepim), anti-conversants (e.g., phenytoin), antihistamines (e.g., diphenhydramine, chlorphenirimine, and promethazine), antibiotic/antibacterial agents (e.g., gentamycin, ciprofloxacin, and cefoxitin), antifungal agents (e.g., miconazole, terconazole, econazole, isoconazole, butaconazole, clotrimazole, itraconazole, nystatin, naftifine, and amphotericin B), antiparasitic agents, hormones, hormone antagonists, immunomodulators, neurotransmitter antagonists, antiglaucoma agents, vitamins, narcotics, and imaging agents.

Polynucleotides and Nucleic Acids

In some aspects, the biologically active agent delivered in a LNP of the disclosure is a polynucleotide or nucleic acid (e.g., ribonucleic acid or deoxyribonucleic acid). The term "polynucleotide," in its broadest sense, includes any compound and/or substance that is or can be incorporated into an oligonucleotide chain. Exemplary polynucleotides for use in accordance with the present disclosure include, but are not limited to, one or more of deoxyribonucleic acid (DNA), ribonucleic acid (RNA) including messenger mRNA (mRNA), hybrids thereof, RNAi-inducing agents, RNAi agents, siRNAs, shRNAs, miRNAs, antisense RNAs, ribozymes, catalytic DNA, RNAs that induce triple helix formation, aptamers, vectors, etc. In some aspects, a biologically active agentis an RNA. RNAs useful in the compositions and methods described herein can be selected from the group consisting of, but are not limited to, shortmers, antagomirs, antisense, ribozymes, small interfering RNA (siRNA), asymmetrical interfering RNA (aiRNA), microRNA (miRNA), Dicer-substrate RNA (dsRNA), small hairpin RNA (shRNA), transfer RNA (tRNA), messenger RNA (mRNA), and mixtures thereof. In certain aspects, the RNA is an mRNA.

In certain aspects, a biologically active agent is an mRNA. An mRNA may encode any polypeptide of interest, including any naturally or non-naturally occurring or otherwise modified polypeptide. A polypeptide encoded by an mRNA may be of any size and may have any secondary structure or activity. In some aspects, a polypeptide encoded by an mRNA may have a therapeutic effect when expressed in a cell.

In other aspects, a biologically active agent is a siRNA. A siRNA may be capable of selectively modulating the expression of a gene of interest. For example, a siRNA could be selected to knock down or down regulate a gene associated with a particular disease, disorder, or condition upon administration to a subject in need thereof. A siRNA may comprise a sequence that is complementary to an mRNA sequence that encodes a protein of interest. In some aspects, the siRNA may be an immunomodulatory siRNA.

In some aspects, a biologically active agent is a shRNA or a vector or plasmid encoding the same. A shRNA may be produced inside a target cell upon delivery of an appropriate construct to the nucleus. Constructs and mechanisms relating to shRNA are well known in the relevant arts.

Nucleic acids and polynucleotides useful in the disclosure typically include a first region of linked nucleosides encoding a polypeptide of interest (e.g., a coding region), a first flanking region located at the 5'-terminus of the first region (e.g., a 5'-UTR), a second flanking region located at the 3'-terminus of the first region (e.g., a 3'-UTR), at least one 5'-cap region, and a 3'-stabilizing region. In some aspects, a nucleic acid or polynucleotide further includes a poly-A region or a Kozak sequence (e.g., in the 5'-UTR). In some cases, polynucleotides may contain one or more intronic nucleotide sequences capable of being excised from the polynucleotide. In some aspects, a polynucleotide or nucleic acid (e.g., an mRNA) may include a 5' cap structure, a chain terminating nucleotide, a stem loop, a polyA sequence, and/or a polyadenylation signal. Any one of the regions of a nucleic acid may include one or more alternative components (e.g., an alternative nucleoside). For example, the 3'-stabilizing region may contain an alternative nucleoside such as an L-nucleoside, an inverted thymidine, or a 2'-O-methyl nucleoside and/or the coding region, 5'-UTR, 3'-UTR, or cap region may include an alternative nucleoside such as a 5-substituted uridine (e.g., 5-methoxyuridine), a 1-substituted pseudouridine (e.g., 1-methyl-pseudouridine or 1-ethyl-pseudouridine), and/or a 5-substituted cytidine (e.g., 5-methyl-cytidine).

Formulations

Nanoparticle compositions may include a lipid component and one or more additional components, such as a biologically active agent. A nanoparticle composition may be designed for one or more specific applications or targets. The elements of a nanoparticle composition may be selected based on a particular application or target, and/or based on the efficacy, toxicity, expense, ease of use, availability, or other feature of one or more elements. Similarly, the particular formulation of a nanoparticle composition may be selected for a particular application or target according to, for example, the efficacy and toxicity of particular combinations of elements.

The lipid component of a nanoparticle composition may include, for example, an ionizable lipid according to Formula (I) or (II), a saccharide lipid according to Formulae (III) or (IV), and optionally a phospholipid (such as an unsaturated lipid, e.g., DOPE or DSPC). The elements of the lipid component may be provided in specific fractions.

The amount of a biologically active agent in a nanoparticle composition may depend on the size, composition, desired target and/or application, or other properties of the nanoparticle composition as well as on the properties of the biologically active agent. For example, the amount of a nucleic acid useful in a nanoparticle composition may depend on the size, sequence, and other characteristics of the nucleic acid. The relative amounts of a biologically active agent and other elements (e.g., lipids) in a nanoparticle composition may also vary. In some aspects, the wt/wt ratio of the lipid component to a biologically active agent in a nanoparticle composition may be from about 1:1 to about 60:1, such as 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, and 60:1. For example, the wt/wt ratio of the lipid component to a biologically active agent may be from about 1:1 to about 4:1. In certain aspects, the wt/wt ratio is about 20:1. In certain aspects, the wt/wt ratio is about 60:1. The amount of a biologically active agent in a nanoparticle composition may, for example, be measured using absorption spectroscopy (e.g., ultraviolet-visible spectroscopy).

In one aspect, the present disclosure provides a method of formulating the nanoparticles of the disclosure, wherein the nucleic acid is dissolved in a first solution comprising an acidic buffer or neutral buffer and the lipid components are dissolved in a second solution comprising ethanol whereby the nanoparticle is formed by mixing said first solution with said second solution. In some aspects, the acidic buffer is a citrate buffer. In some aspects, the acidic buffer has a pH of 3-6. In some aspects, the acidic buffer has a pH of 4.5. In some aspects, the neutral buffer is a PBS. In some aspects, the neutral buffer has a pH of 7-8. In some aspects, the neutral buffer has a pH of 7.4.

Pharmaceutical Compositions

Nanoparticle compositions may be formulated in whole or in part as pharmaceutical compositions. Pharmaceutical compositions may include one or more nanoparticle compositions. For example, a pharmaceutical composition may include one or more nanoparticle compositions including one or more different biologically active agents. Pharmaceutical compositions may further include one or more pharmaceutically acceptable excipients or accessory ingredients such as those described herein. General guidelines for the formulation and manufacture of pharmaceutical compositions and agents are available, for example, in Remington's *The Science and Practice of Pharmacy*, $21^{st}$ Edition, A. R. Gennaro; Lippincott, Williams & Wilkins, Baltimore, Md., 2006. Conventional excipients and accessory ingredients may be used in any pharmaceutical composition, except insofar as any conventional excipient or accessory ingredient may be incompatible with one or more components of a nanoparticle composition. An excipient or accessory ingredient may be incompatible with a component of a nanoparticle composition if its combination with the component may result in any undesirable biological effect or otherwise deleterious effect.

In some aspects, one or more excipients or accessory ingredients may make up greater than 50% of the total mass or volume of a pharmaceutical composition including a nanoparticle composition. For example, the one or more excipients or accessory ingredients may make up 50%, 60%, 70%, 80%, 90%, or more of a pharmaceutical convention. In some aspects, a pharmaceutically acceptable excipient is at least 95%, at least 96%, at least 97%, at least 98%, at least 99%, or 100% pure. In some aspects, an excipient is approved for use in humans and for veterinary use. In some aspects, an excipient is approved by United States Food and Drug Administration. In some aspects, an excipient is pharmaceutical grade. In some aspects, an excipient meets the standards of the United States Pharmacopoeia (USP), the European Pharmacopoeia (EP), the British Pharmacopoeia, and/or the International Pharmacopoeia.

Relative amounts of the one or more nanoparticle compositions, the one or more pharmaceutically acceptable excipients, and/or any additional ingredients in a pharmaceutical composition in accordance with the present disclosure will vary, depending upon the identity, size, and/or condition of the subject treated and further depending upon the route by which the composition is to be administered.

In certain aspects, the nanoparticle compositions and/or pharmaceutical compositions of the disclosure are refrigerated or frozen for storage and/or shipment (e.g., being stored at a temperature of 4° C. or lower, such as a temperature between about −150° C. and about 0° C. or between about −80° C. and about −20° C. For example, the pharmaceutical composition comprising a compound of any of Formula (I), (II), (III) and/or (IV) is a solution that is refrigerated for storage and/or shipment at, for example, about −20° C., −30° C., −40° C., −50° C., −60° C., −70° C., or −80° C. In certain aspects, the disclosure also relates to a method of increasing stability of the nanoparticle compositions and/or pharmaceutical compositions comprising a compound of any of Formulae (I), (II), (III) and/or (IV) by storing the nanoparticle compositions and/or pharmaceutical compositions at a temperature of 4° C. or lower, such as a temperature between about −150° C. and about 0° C. or between about −80° C. and about −20° C., e.g., about −5° C., −10° C., −15° C., −20° C., −25° C., −30° C., −40° C., −50° C., −60° C., −70° C., −80° C., −90° C., −130° C. or −150° C.). For example, the nanoparticle compositions and/or pharmaceutical compositions disclosed herein are stable for about at least 1 week, at least 2 weeks, at least 3 weeks, at least 4 weeks, at least 5 weeks, at least 6 weeks, at least 1 month, at least 2 months, at least 4 months, at least 6 months, at least 8 months, at least 10 months, at least 12 months, at least 14 months, at least 16 months, at least 18 months, at least 20 months, at least 22 months, or at least 24 months, e.g., at a temperature of 4° C. or lower (e.g., between about 4° C. and −20° C.). In one embodiment, the formulation is stabilized for at least 4 weeks at about 4° C. In certain aspects, the pharmaceutical composition of the disclosure comprises a nanoparticle composition disclosed herein and a pharmaceutically acceptable carrier selected from one or more of Tris, an acetate (e.g., sodium acetate), an citrate (e.g., sodium citrate), saline, PBS, and sucrose. In certain embodiments, the carrier may be at a concentration of 1-100 mM (e.g., including but not limited to any numerical value or range within the range of 1-100 mM such as 1, 2, 3, 4, . . . 97, 98, 99, 100, 10-90 mM, 20-80 mM, 30-70 mM and so on).

In certain aspects, the pharmaceutical composition of the disclosure has a pH value between about 5 and 8 (e.g., 5, 5.5, 6. 6.5, 6.8 6.9, 7.0, 7.1, 7.2, 7.3, 7.4, 7.5, 7.6, 7.7, 7.8, 7.9 or 8.0, or between 7.5 and 8 or between 7 and 7.8). For example, a pharmaceutical composition of the disclosure comprises a nanoparticle composition disclosed herein, Tris, saline and sucrose, and has a pH of about 7.5-8, which is suitable for storage and/or shipment at, for example, about −20° C. For example, a pharmaceutical composition of the disclosure comprises a nanoparticle composition disclosed herein and PBS and has a pH of about 7-7.8, suitable for storage and/or shipment at, for example, about 4° C. or lower. “Stability,” “stabilized,” and “stable” in the context of the present disclosure refers to the resistance of nanoparticle compositions and/or pharmaceutical compositions disclosed herein to chemical or physical changes (e.g., degradation, particle size change, aggregation, change in encapsulation, etc.) under given manufacturing, preparation, transportation, storage and/or in-use conditions, e.g., when stress is applied such as shear force, freeze/thaw stress, etc.

In certain embodiments, the pharmaceutical composition of the disclosure contain the therapeutic or prophylactic agent at a ratio of 0.05 to 25 mg/ml, 0.1 to 20 mg/ml, 0.2 to 18 mg/ml, 0.5 to 15 mg/ml, 0.7 to 12 mg/ml, 0.9 to 10 mg/ml, 1 to 8 mg/ml, 1.5 to 6 mg/ml, 2 to 5 mg/ml, 2.5 to 4 mg/ml, 0.5 to 3.0 mg/ml, 0.2 to 4.0 mg/ml, 0.4 to 2.0 mg/ml, and any numerical value or range within the range of 0.05 to 25 mg/ml.

Nanoparticle compositions and/or pharmaceutical compositions including one or more nanoparticle compositions may be administered to any patient or subject, including those patients or subjects that may benefit from a therapeutic effect provided by the delivery of a biologically active agent to one or more particular cells, tissues, organs, or systems or groups thereof, such as the renal system. Although the descriptions provided herein of nanoparticle compositions and pharmaceutical compositions including nanoparticle compositions are principally directed to compositions which are suitable for administration to humans, it will be understood by the skilled artisan that such compositions are generally suitable for administration to any other mammal. Modification of compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the compositions is contemplated include, but are not limited to, humans, other primates, and other mammals, including commercially relevant mammals such as cattle, pigs, hoses, sheep, cats, dogs, mice, and/or rats.

A pharmaceutical composition including one or more nanoparticle compositions may be prepared by any method known or hereafter developed in the art of pharmacology. In general, such preparatory methods include bringing the active ingredient into association with an excipient and/or one or more other accessory ingredients, and then, if desirable or necessary, dividing, shaping, and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient (e.g., nanoparticle composition).

The amount of the active ingredient is generally equal to the dosage of the active ingredient which would be administered to a subject and/or a convenient fraction of such a dosage such as, for example, one-half or one-third of such a dosage.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

Methods of Producing Polypeptides in Cells

The present disclosure provides methods of producing a polypeptide of interest in a cell. Methods of producing polypeptides involve contacting a cell with a nanoparticle composition including an mRNA, including a self-amplifying mRNA, encoding the polypeptide of interest. Upon contacting the cell with the nanoparticle composition, the mRNA may be taken up and translated in the cell to produce the polypeptide of interest.

In general, the step of contacting a cell with a nanoparticle composition including an mRNA encoding a polypeptide of interest may be performed in vivo, ex vivo, in culture, or in vitro. The amount of nanoparticle composition contacted with a cell, and/or the amount of mRNA therein, may depend on the type of cell or tissue being contacted, the means of administration, the physiochemical characteristics of the nanoparticle composition and the mRNA (e.g., size, charge, and chemical composition) therein, and other factors. In general, an effective amount of the nanoparticle composition will allow for efficient polypeptide production in the cell. Metrics for efficiency may include polypeptide translation (indicated by polypeptide expression), level of mRNA degradation, and immune response indicators.

The step of contacting a nanoparticle composition including an mRNA with a cell may involve or cause transfection. A phospholipid included in the lipid component of a nanoparticle composition may facilitate transfection and/or increase transfection efficiency, for example, by interacting and/or fusing with a cellular or intracellular membrane. Transfection may allow for the translation of the mRNA within the cell.

Methods of Delivering Therapeutic Agents to Cells and Organs

The present disclosure provides methods of delivering a biologically active agent to a cell or organ. Delivery of a biologically active agent to a cell involves administering a nanoparticle composition including the biologically active agent to a subject, where administration of the composition involves contacting the cell with the composition. For example, a protein, cytotoxic agent, radioactive ion, chemotherapeutic agent, or nucleic acid (such as an RNA, e.g., mRNA) may be delivered to a cell or organ. In the instance that a biologically active agent is an mRNA, upon contacting a cell with the nanoparticle composition, a translatable mRNA may be translated in the cell to produce a polypeptide of interest. However, mRNAs that are substantially not translatable may also be delivered to cells. Substantially non-translatable mRNAs may be useful as vaccines and/or may sequester translational components of a cell to reduce expression of other species in the cell.

In some aspects, a nanoparticle composition may target a particular type or class of cells (e.g., cells of a particular organ or system thereof). For example, a nanoparticle composition including a biologically active agent of interest may be specifically delivered to a liver, kidney, spleen, femur, or lung. Specific delivery to a particular class of cells, an organ, or a system or group thereof implies that a higher proportion of nanoparticle compositions including a biologically active agent are delivered to the destination (e.g., tissue) of interest relative to other destinations, e.g., upon administration of a nanoparticle composition to a mammal. In some aspects, specific delivery may result in a greater than 2 fold, 5 fold, 10 fold, 15 fold, or 20 fold increase in the amount of biologically active agent per 1 g of tissue of the targeted destination (e.g., tissue of interest, such as a liver) as compared to another destination (e.g., the spleen). In some aspects, the tissue of interest is selected from the group consisting of a liver, kidney, a lung, a spleen, a femur, an ocular tissue (e.g., via intraocular, subretinal, or intravitreal injection), vascular endothelium in vessels (e.g., intra-coronary or intra-femoral) or kidney, and tumor tissue (e.g., via intratumoral injection).

As another example of targeted or specific delivery, an mRNA that encodes a protein-binding partner (e.g., an antibody or functional fragment thereof, a scaffold protein, or a peptide) or a receptor on a cell surface may be included in a nanoparticle composition. An mRNA may additionally or instead be used to direct the synthesis and extracellular localization of lipids, carbohydrates, or other biological moieties. Alternatively, other biologically active agents or elements (e.g., lipids or ligands) of a nanoparticle composition may be selected based on their affinity for particular receptors (e.g., low density lipoprotein receptors) such that a nanoparticle composition may more readily interact with a target cell population including the receptors. For example, ligands may include, but are not limited to, members of a specific binding pair, antibodies, monoclonal antibodies, Fv fragments, single chain Fv (scFv) fragments, Fab' fragments, $F(ab')_2$ fragments, single domain antibodies, camelized antibodies and fragments thereof, humanized antibodies and fragments thereof, and multivalent versions thereof; multivalent binding reagents including mono- or bi-specific antibodies such as disulfide stabilized Fv fragments, scFv tandems, diabodies, tribodies, or tetrabodies; and aptamers, receptors, and fusion proteins.

In some aspects, a ligand may be a surface-bound antibody, which can permit tuning of cell targeting specificity. This is especially useful since highly specific antibodies can be raised against an epitope of interest for the desired targeting site. In one embodiment, multiple antibodies are expressed on the surface of a cell, and each antibody can have a different specificity for a desired target. Such approaches can increase the avidity and specificity of targeting interactions.

In certain aspects, compositions in accordance with the present disclosure may be administered at dosage levels sufficient to deliver from about 0.0001 mg/kg to about 10 mg/kg, from about 0.001 mg/kg to about 10 mg/kg, from about 0.005 mg/kg to about 10 mg/kg, from about 0.01 mg/kg to about 10 mg/kg, from about 0.05 mg/kg to about 10 mg/kg, from about 0.1 mg/kg to about 10 mg/kg, from about 1 mg/kg to about 10 mg/kg, from about 2 mg/kg to about 10 mg/kg, from about 5 mg/kg to about 10 mg/kg, from about 0.0001 mg/kg to about 5 mg/kg, from about 0.001 mg/kg to about 5 mg/kg, from about 0.005 mg/kg to about 5 mg/kg, from about 0.01 mg/kg to about 5 mg/kg, from about 0.05 mg/kg to about 5 mg/kg, from about 0.1 mg/kg to about 5 mg/kg, from about 1 mg/kg to about 5 mg/kg, from about 2 mg/kg to about 5 mg/kg, from about 0.0001 mg/kg to about 2.5 mg/kg, from about 0.001 mg/kg to about 2.5 mg/kg, from about 0.005 mg/kg to about 2.5 mg/kg, from about 0.01 mg/kg to about 2.5 mg/kg, from about 0.05 mg/kg to about 2.5 mg/kg, from about 0.1 mg/kg to about 2.5 mg/kg, from about 1 mg/kg to about 2.5 mg/kg, from about 2 mg/kg to about 2.5 mg/kg, from about 0.0001 mg/kg to about 1 mg/kg, from about 0.001 mg/kg to about 1 mg/kg, from about 0.005 mg/kg to about 1 mg/kg, from about 0.01 mg/kg to about 1 mg/kg, from about 0.05 mg/kg to about 1 mg/kg, from about 0.1 mg/kg to about 1 mg/kg, from about 0.0001 mg/kg to about 0.25 mg/kg, from about 0.001 mg/kg to about 0.25 mg/kg, from about 0.005 mg/kg to about 0.25 mg/kg, from about 0.01 mg/kg to about 0.25 mg/kg, from about 0.05 mg/kg to about 0.25 mg/kg, or from about 0.1 mg/kg to about 0.25 mg/kg of a biologically active agent (e.g., an mRNA) in a given dose, where a dose of 1 mg/kg (mpk) provides 1 mg of a biologically active agent per 1 kg of subject body weight. In some aspects, a dose of about 0.001 mg/kg to about 10 mg/kg of a biologically active agent (e.g., mRNA) of a nanoparticle composition may be administered. In other aspects, a dose of about 0.005 mg/kg to about 2.5 mg/kg of a biologically active agent may be administered. In certain aspects, a dose of about 0.1 mg/kg to about 1 mg/kg may be administered. In other aspects, a dose of about 0.05 mg/kg to about 0.25 mg/kg may be administered. A dose may be administered one or more times per day, in the same or a different amount, to obtain a desired level of mRNA expression and/or therapeutic, diagnostic, prophylactic, or imaging effect.

The desired dosage may be delivered, for example, three times a day, two times a day, once a day, every other day, every third day, every week, every two weeks, every three weeks, or every four weeks. In certain aspects, the desired dosage may be delivered using multiple administrations (e.g., two, three, four, five, six, seven, eight, nine, ten, eleven, twelve, thirteen, fourteen, or more administrations). In some aspects, a single dose may be administered, for example, prior to or after a surgical procedure or in the instance of an acute disease, disorder, or condition.

Nanoparticle compositions including one or more biologically active agents may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. For example, one or more nanoparticle compositions including one or more different biologically active agents may be administered in combination. Compositions can be administered concurrently with, prior to, or subsequent to, one or more other desired therapeutics or medical procedures. In general, each agent will be administered at a dose and/or on a time schedule determined for that agent. In some aspects, the present disclosure encompasses the delivery of compositions, or imaging, diagnostic, or prophylactic compositions thereof in combination with agents that improve their bioavailability, reduce and/or modify their metabolism, inhibit their excretion, and/or modify their distribution within the body.

It will further be appreciated that biologically active, or imaging active agents utilized in combination may be administered together in a single composition or administered separately in different compositions. In general, it is expected that agents utilized in combination will be utilized at levels that do not exceed the levels at which they are utilized individually. In some aspects, the levels utilized in combination may be lower than those utilized individually.

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a composition useful for treating cancer may be administered concurrently with a chemotherapeutic agent), or they may achieve different effects (e.g., control of any adverse effects, such as infusion related reactions).

This disclosure includes the following non-limiting items:

1. A nanoparticle composition comprising an ionizable lipid component and a saccharide lipid component.
2. A nanoparticle composition having two lipid components, wherein the two lipid components are an modular lipid component and a stabilizer lipid component, wherein the stabilizer lipid component is a saccharide lipid compound or a PEG lipid, wherein the modular lipid component comprises from about 0.5 mol % to about 99.5 mol % of total lipid components present in the nanoparticle, and wherein the stabilizer lipid component comprises from about 0.5 mol % to about 99.5 mol % of the total lipid components present in the nanoparticle.
3. A nanoparticle composition having three lipid components, and a phospholipid component, wherein the stabilizer lipid component is a saccharide lipid compound or a PEG lipid, wherein the phospholipid component comprises from about 5 to 60 mol % of total lipid components present in the nanoparticle, wherein the stabilizer lipid component comprises from about 0.2 to 80 mol % of the total lipid present in the nanoparticle, wherein the modular lipid or ionizable lipid component comprises from about 5 to 80 mol % of the total lipid components present in the nanoparticle.

4. A nanoparticle composition having three lipid components, wherein the three lipid components are a modular lipid component, a ionizable lipid component, and a phospholipid component, wherein the stabilizer lipid component is a saccharide lipid compound or a PEG lipid, wherein the phospholipid component comprises from about 15 mol % to about 55 mol % of total lipid components present in the nanoparticle, wherein the modular lipid component comprises from about 3 mol % to about 25 mol % of total lipid components present in the nanoparticle, wherein the ionizable lipid component comprises from about 30 mol % to about 80 mol % of the total lipid components present in the nanoparticle.

5. The nanoparticle composition of any one of items 1-4, wherein the stabilizer lipid component is a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

6. The nanoparticle composition of any one of items 1-5, further comprising a biologically active agent.

7. The nanoparticle composition of any one of items 3-4, wherein the phospholipid component comprises 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanol amine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, or a mixture thereof.

8. A compound of Formula III (III)

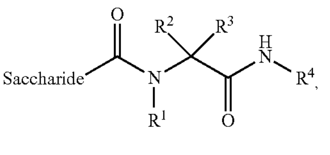

or a salt or isomer thereof, wherein each of $R^1$, $R^2$, $R^3$ and $R^4$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl, poly(ethylene glycol) (PEG),

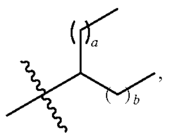,
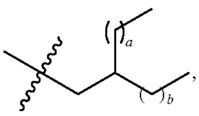,
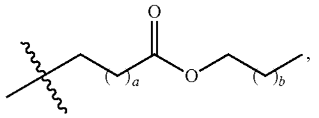,
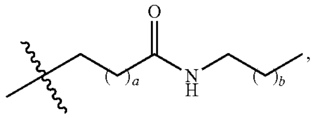,
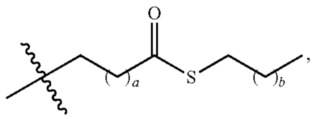,
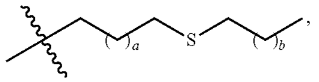,
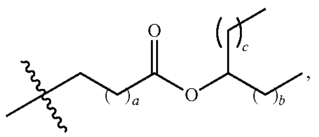,
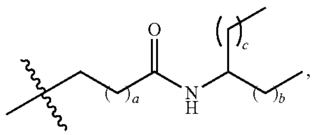,
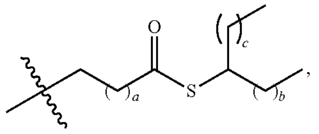,
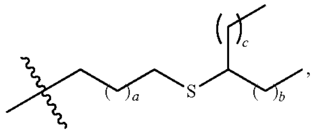,
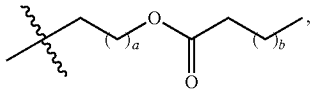,
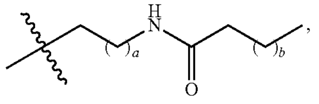,
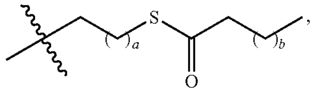,
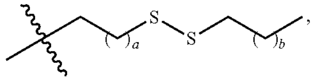, -continued

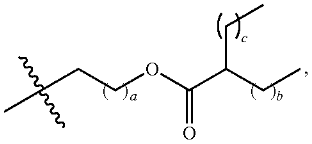

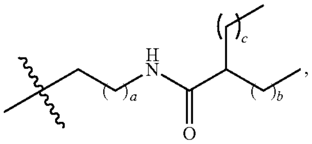

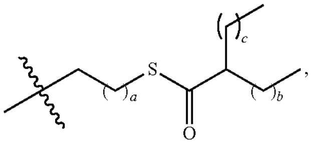

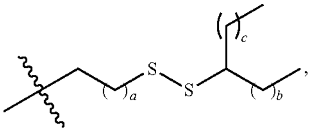 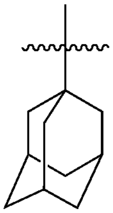 ,

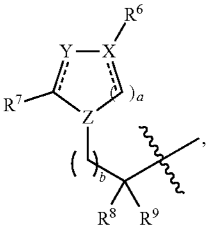 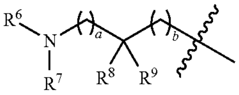 ;

each of $R^6$, $R^7$, $R^8$ and $R^9$ is independently selected from H, C1-C24 alkyl, C1-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl,

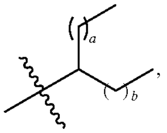 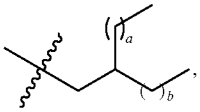

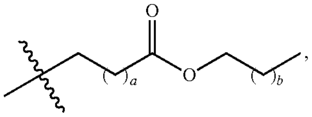

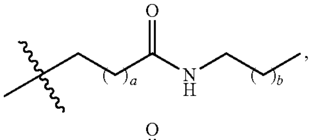

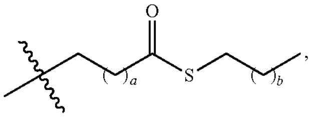

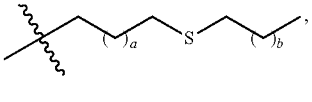

-continued

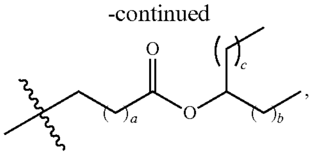

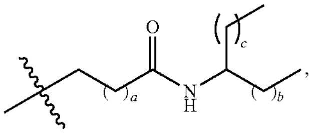

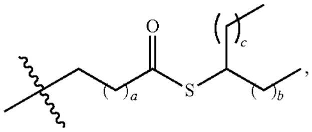

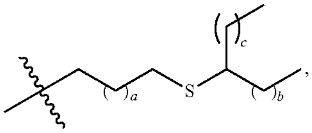

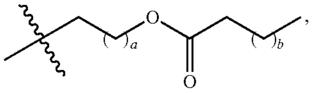

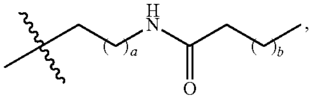

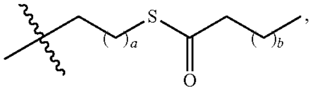

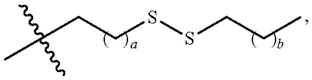

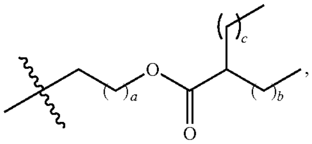

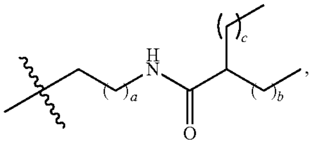

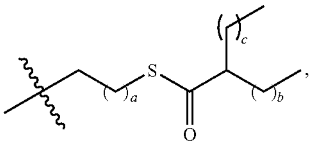

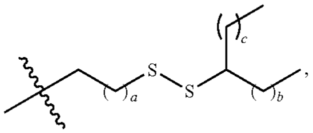 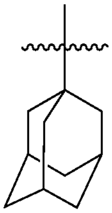 ;

a, b and c are each independently an integer from 0-24;

each X is independently selected from CH, N;

each Y is independently selected from $CH_2$, NH, O, or S;

each Z is independently selected from CH or N; and each saccharide is independently selected from monosaccharides, disaccharides, oligosaccharides, and polysaccharides.

9. The compound of item 8, wherein the saccharide is a monosaccharide.

10. The compound of item 9, wherein the monosaccharide is independently selected from ketotriose, aldotriose, ketotetrose, aldotetroses, ribulose, xylulose, ribose, arabinose, xylose, lyxose, deoxyribose, psicose, fructose, sorbose, tagatose, allose, altrose, glucose, mannose, fucose, fuculose, rhamnose, heptose, octose, nonose, gulose, idose, galactose, talose, sedoheptulose, or a combination thereof.

11. The compound of item 8, wherein the saccharide is a disaccharide.

12. The compound of item 11, wherein the disaccharide is independently selected from sucrose, lactose, maltose, trehalose, turanose, cellobiose, or a combination thereof.

13. The compound of item 8, wherein the saccharide is an oligosaccharide.

14. The compound of item 13, wherein the oligosaccharide is independently selected from raffinose, melezitose, maltotriose, acarbose, stachyose, fructooligosaccharide, galactooligosaccharides, mannanoligosaccharides, or a combination thereof.

15. The compound of item 8, wherein the saccharide is a polysaccharide.

16. The compound of item 15, wherein the polysaccharide is independently selected from ploygiycitol, n-acetyl-glucosamine, chitin.

17. The compound of item 8, wherein the compound is:

(III)(a)

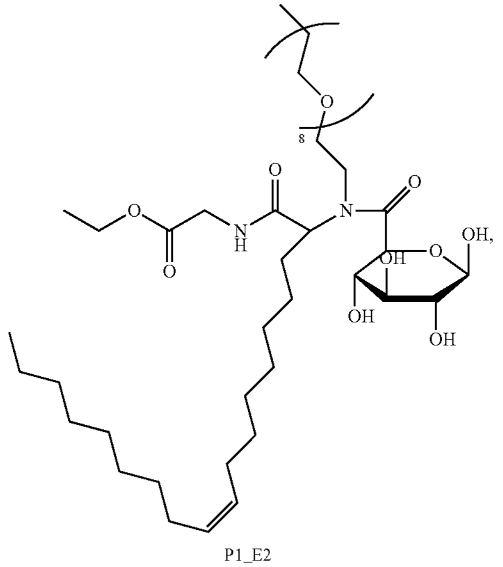

P1_E2

-continued (III)(b)

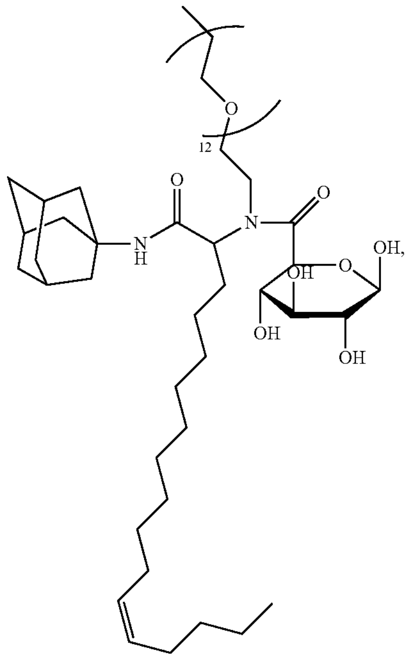

P1_F11

(III)(c)

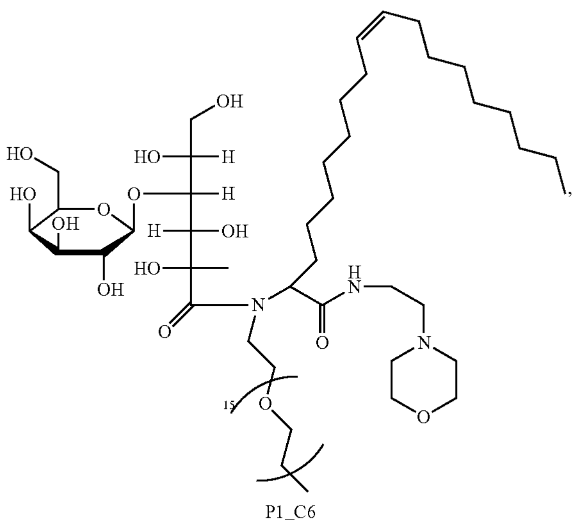

P1_C6

-continued
(III)(d)
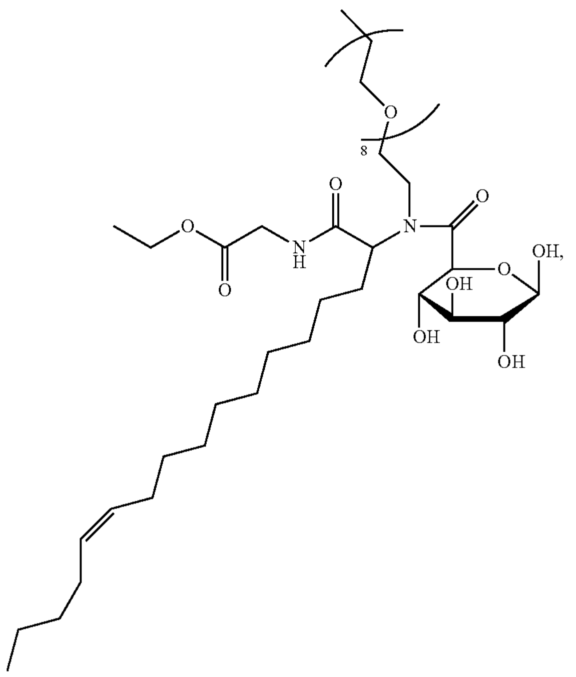
P1_E8
(III)(e)
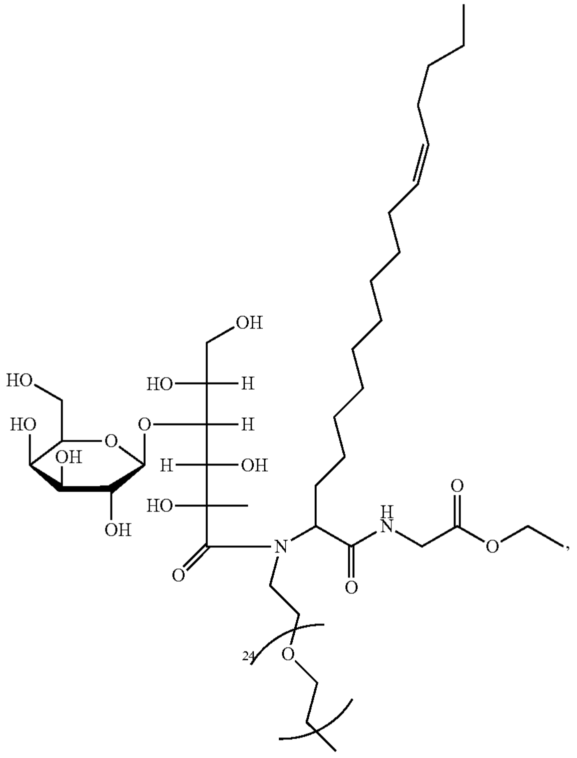
P1_D8
-continued
(III)(f)
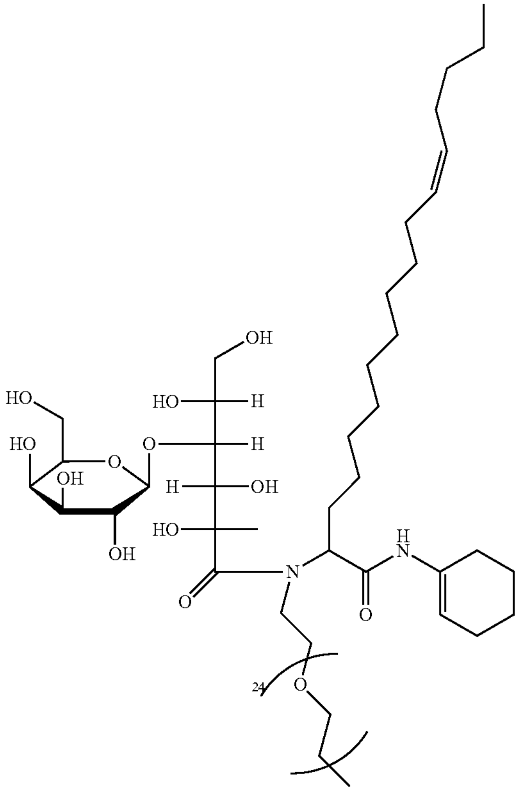
P1_D9
or a salt or isomer thereof.
18. A method for synthesizing the compound of any one of items 8-17 comprising performing the following four component reaction:
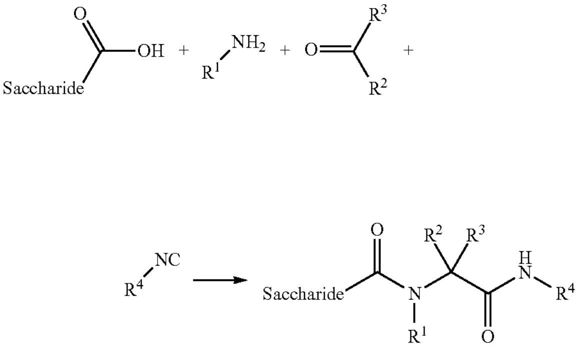
19. The method of item 18, wherein the
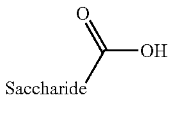
is S-Ac-1
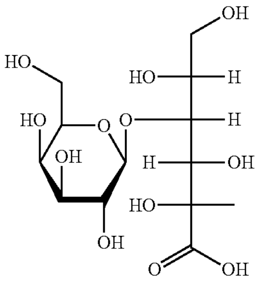
S-Ac-2
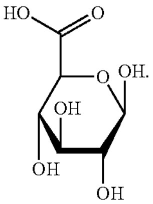
20. The method of any one of items 18-19, wherein the
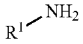
is
A1
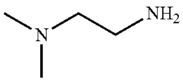
A3
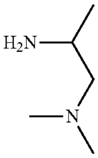
A2
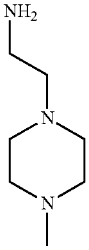
A4
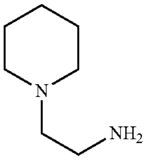
A5
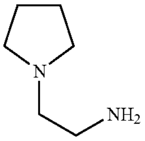
-continued
A6
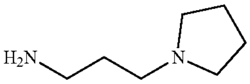
A7
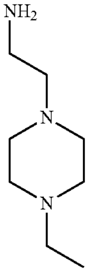
A8
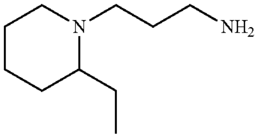
A9
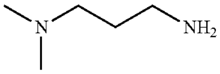
A10
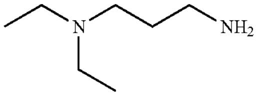
A11
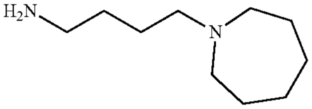
A12
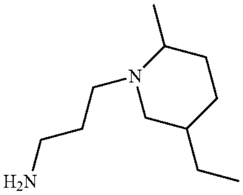
A13
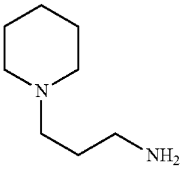
A14
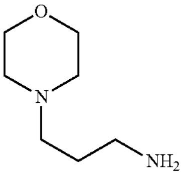
A15
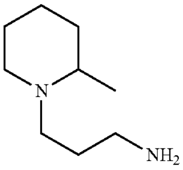

-continued
A16
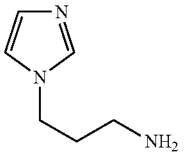
A17
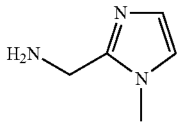
A18
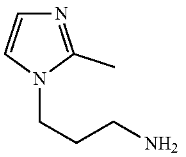
A19
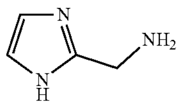
A20
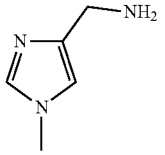
DA13p
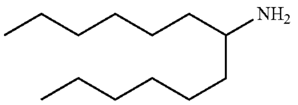
DA15p
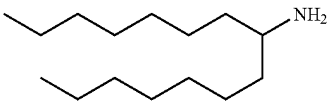
DA16p
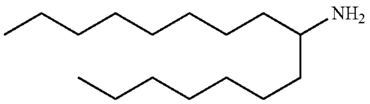
DA17p
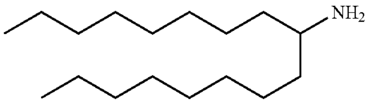
DA19p
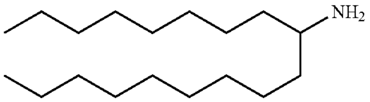
DA23p
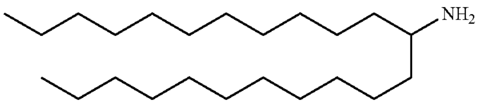
DA24mp
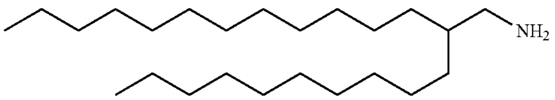
-continued
DA20mp
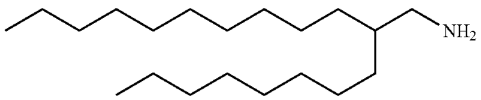
Am-PEG$_8$
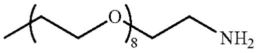
Am-PEG$_{12}$
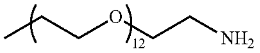
Am-PEG$_{15}$
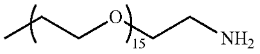
Am-PEG$_{24}$
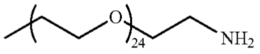
Am-PEG$_{48}$
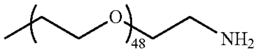
SA6
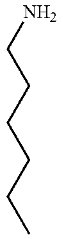
SA7
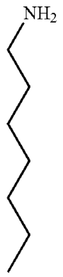
SA8
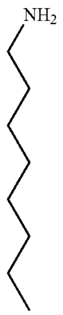

-continued
SA9
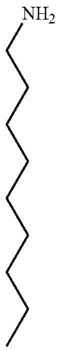
SA10
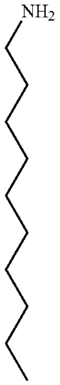
SA11
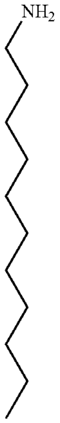
SA12
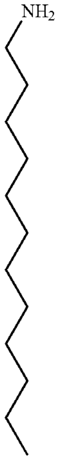
-continued
SA13
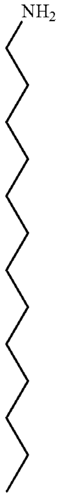
SA14
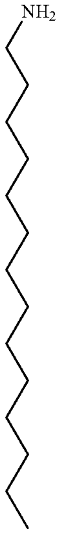
SA15
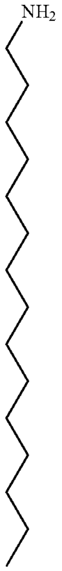

-continued
SA16
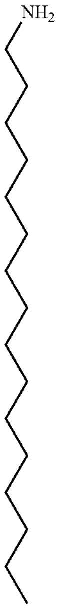
SA17
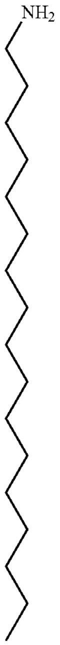
-continued
SA18
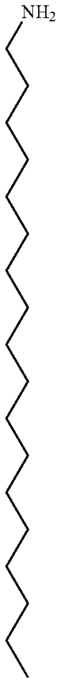
SA13
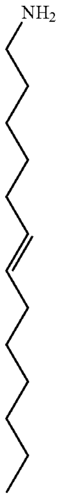

SA14
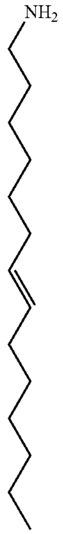
SA15
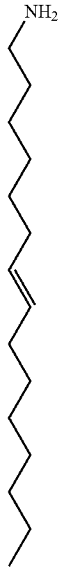
SA16
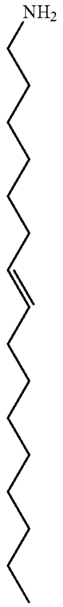
SA17
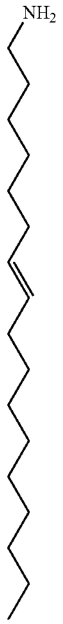

-continued
SA18
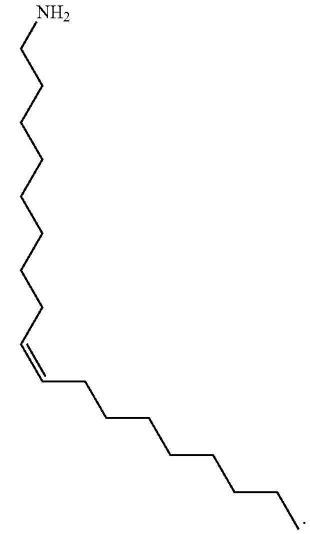
21. The method of any one of items 18-20, wherein the
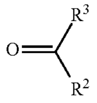
is
ALA1
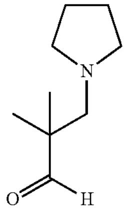
ALA2
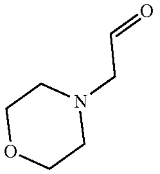
ALA3
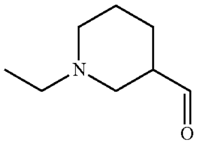
ALA4
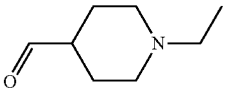
ALA5
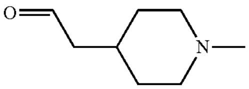
-continued
ALA6
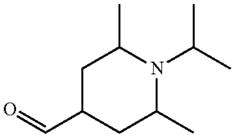
ALA7
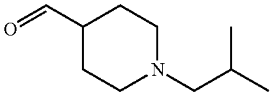
ALA8
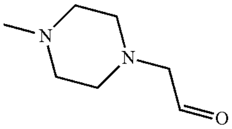
ALA9
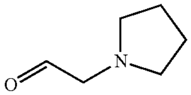
ALA10
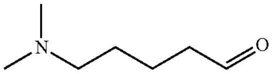
ALA11
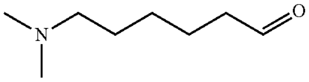
ALA12
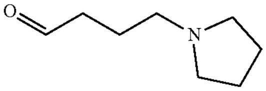
ALA13
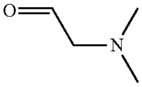
ALA14
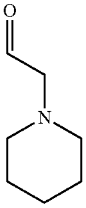
ALA15
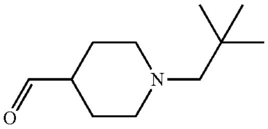
ALA16
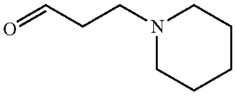
ALA17
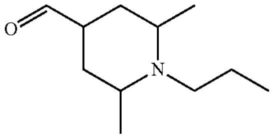
AL8
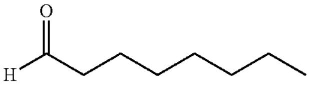

AL9
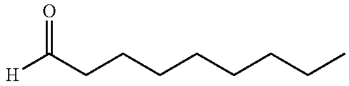
AL10
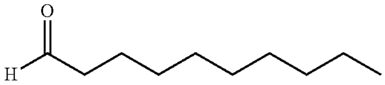
AL11
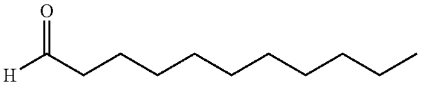
AL12
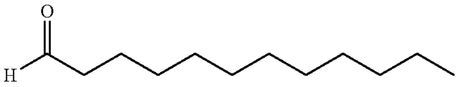
AL13
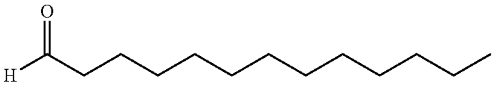
AL15
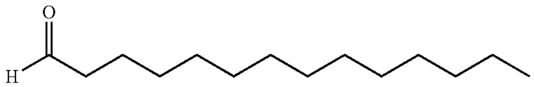
AL16
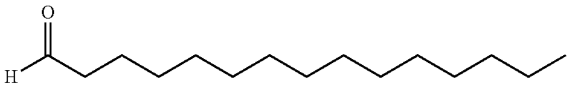
AL16e
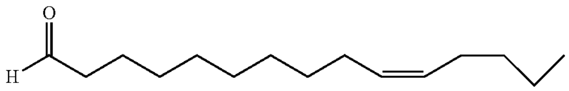
AL10P
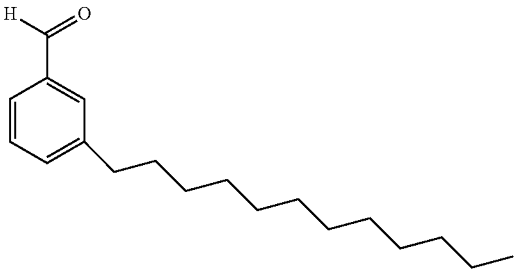
K9
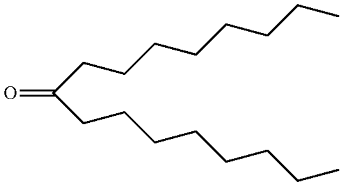
K10
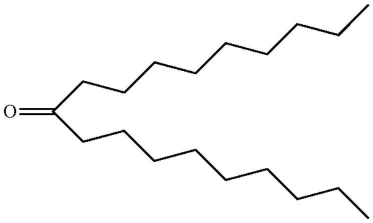
K11
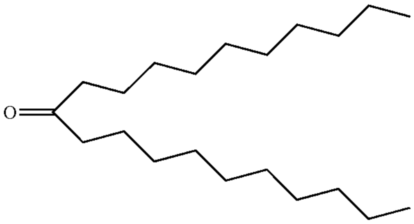
K12
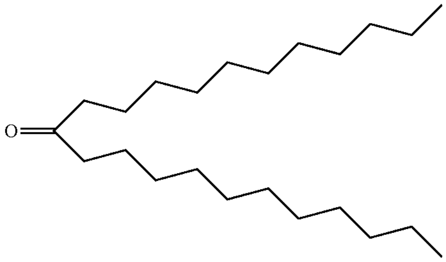
K14
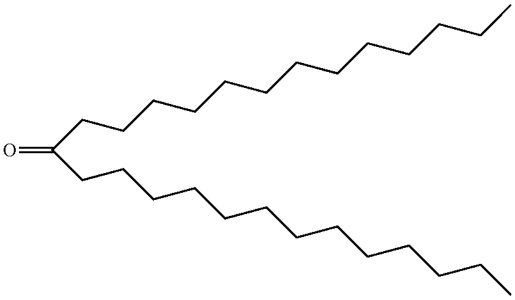
K16
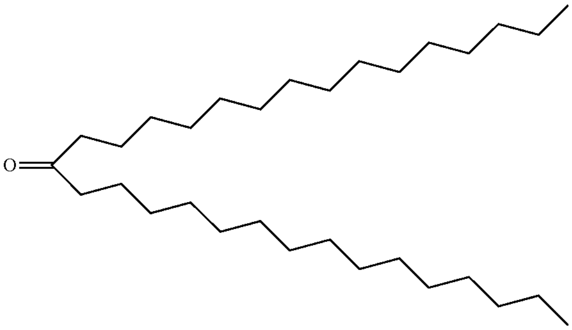
K18e
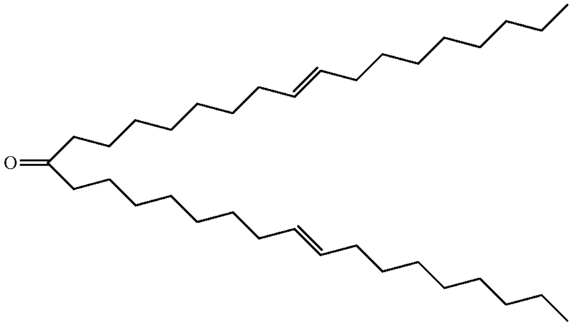
K18e
AL-PEG$_8$
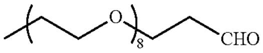

-continued

AL-PEG12

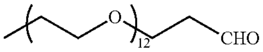

AL-PEG15

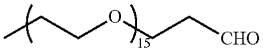

AL-PEG26

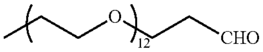

AL-PEG48

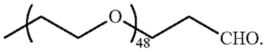

22. The method of any one of items 18-21, wherein the

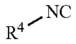

is

Iso1

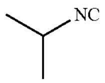

Iso2

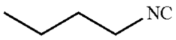

Iso3

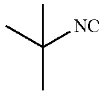

Iso4

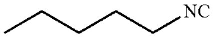

Iso5

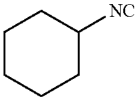

Iso6

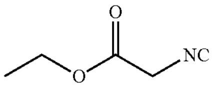

Iso7

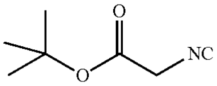

Iso8

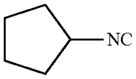

Iso9

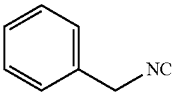

Iso10

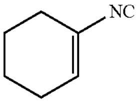

Iso11

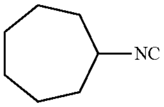

-continued

Iso12

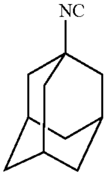

Iso13

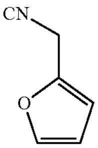

Iso14

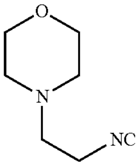

Iso15

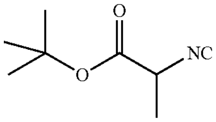

23. A compound of Formula IV (IV)

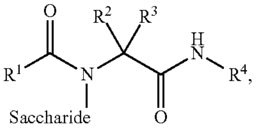

or a salt or isomer thereof, wherein each of $R^1$, $R^2$, $R^3$ and $R^4$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl, poly(ethylene glycol) (PEG),

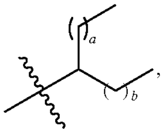

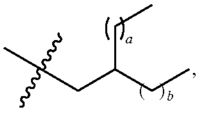

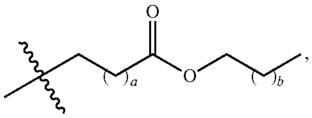

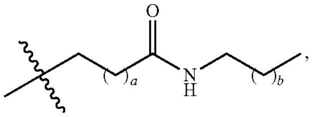

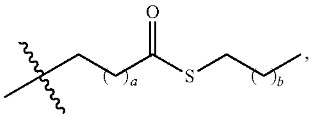

-continued
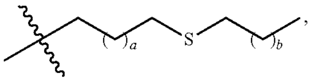,
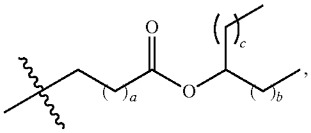,
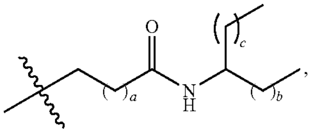,
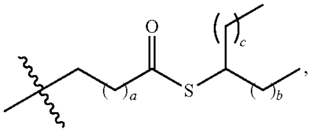,
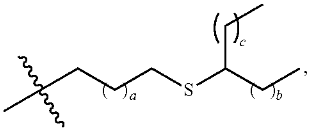,
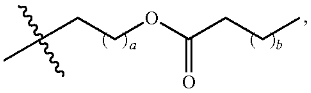,
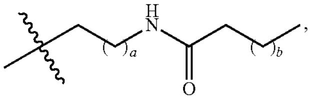,
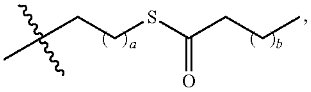,
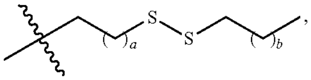,
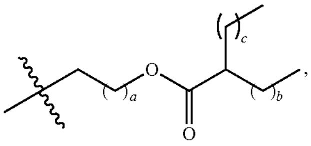,
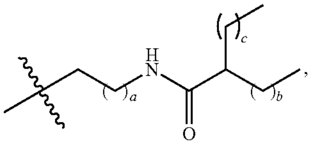,
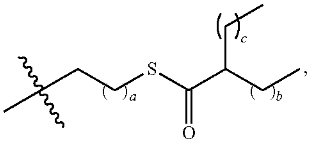,
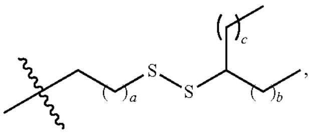, 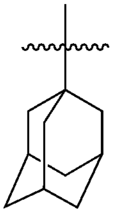,
-continued
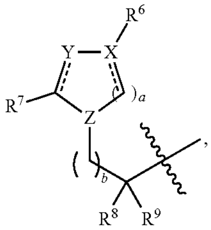, 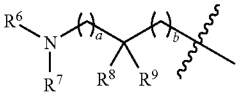;
a, b and c are each independently an integer from 0-24; each of $R^6$, $R^7$, $R^8$ and $R^9$ is independently selected from H, C1-C24 alkyl, C1-C24 alkenyl, C1-C24 alkynyl, substituted alkyl; substituted alkenyl, substituted alkynyl, substituted acyl, substituted carbocyclyl, substituted heterocyclyl, substituted aryl, substituted heteroaryl,
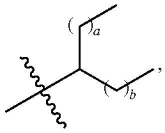, 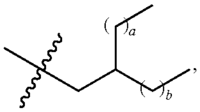,
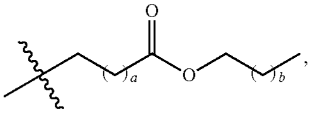,
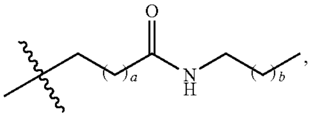,
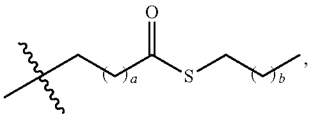,
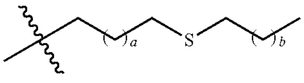,
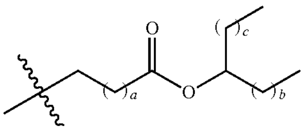,
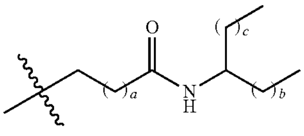,
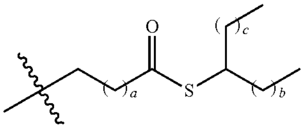,
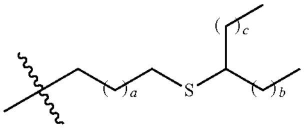,
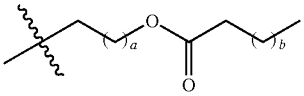, -continued

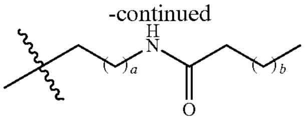

,

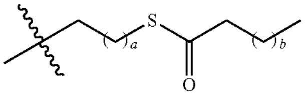

,

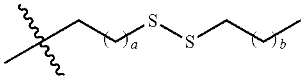

,

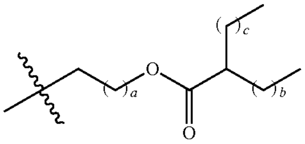

,

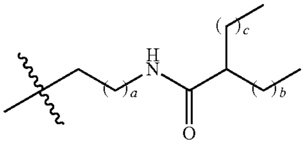

,

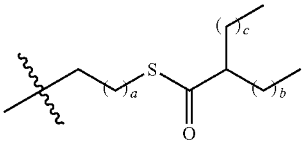

,

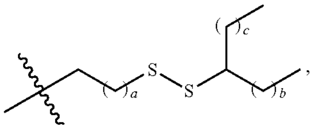

,

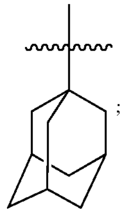

;

a, b and c are each independently an integer from 0-24;

each X is independently selected from CH or N;

each Y is independently selected from $CH_2$, NH, O, or S;

each Z is independently selected from CH or N;

each saccharide is independently selected from monosaccharides, disaccharides, oligosaccharides, and polysaccharides.

24. The compound of item 23, wherein the saccharide is a monosaccharide.

25. The compound of item 24, wherein the monosaccharide is independently selected from ketotriose, aldotriose, ketotetrose, aldotetroses, ribulose, xylulose, ribose, arabinose, xylose, lyxose, deoxyribose, psicose, fructose, sorbose, tagatose, allose, altrose, glucose, mannose, fucose, fuculose, rhamnose, heptose, octose, nonose, gulose, idose, galactose, talose, and sedoheptulose.

26. The compound of item 23, wherein the saccharide is a disaccharide.

27. The compound of item 26, wherein the disaccharide is independently selected from sucrose, lactose, maltose, trehalose, turanose, cellobiose.

28. The compound of item 23, wherein the saccharide is an oligosaccharide.

29. The compound of item 28, wherein the oligosaccharide is independently selected from raffinose, melezitose, maltotriose, acarbose, stachyose, fructooligosaccharide, galactooligosaccharides, and mannanoligosaccharides.

30. The compound of item 23, wherein the saccharide is a polysaccharide.

31. The compound of item 30, wherein the polysaccharide is independently selected from ploygylcitol, n-acetylglucosamine, and chitin.

32. The compound of item 23, wherein the compound is:

(IV)(a)

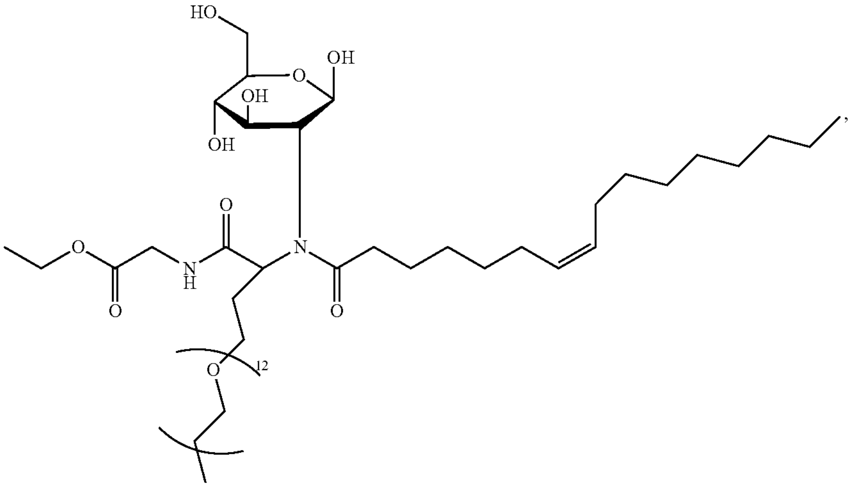

,

-continued
(IV)(b)
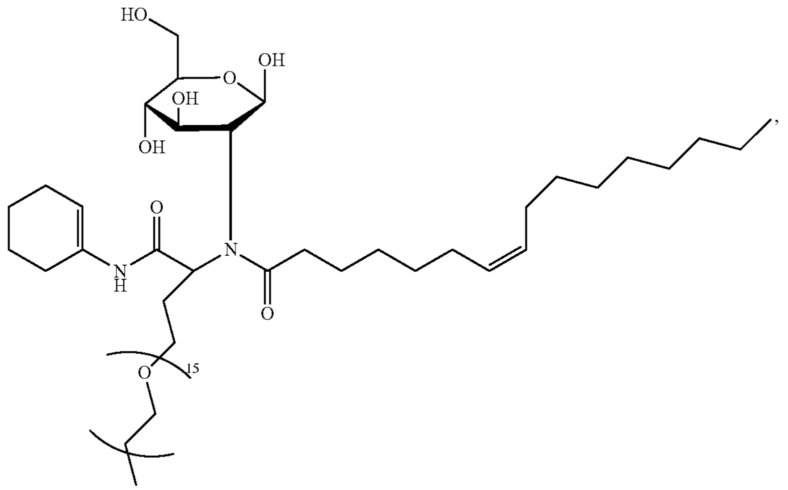
(IV)(c)
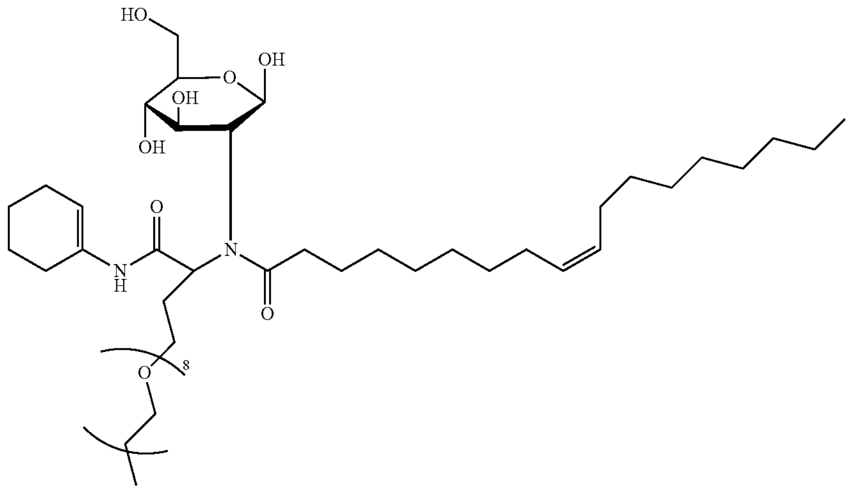
or a salt or isomer thereof.
33. An compound selected from:
P83B4
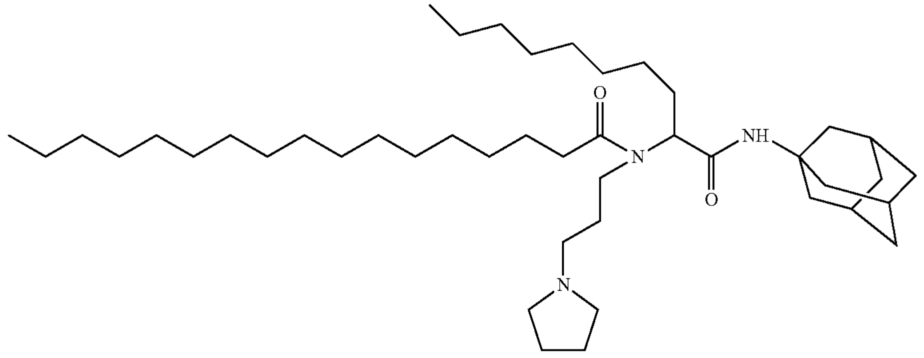

-continued
P83C4
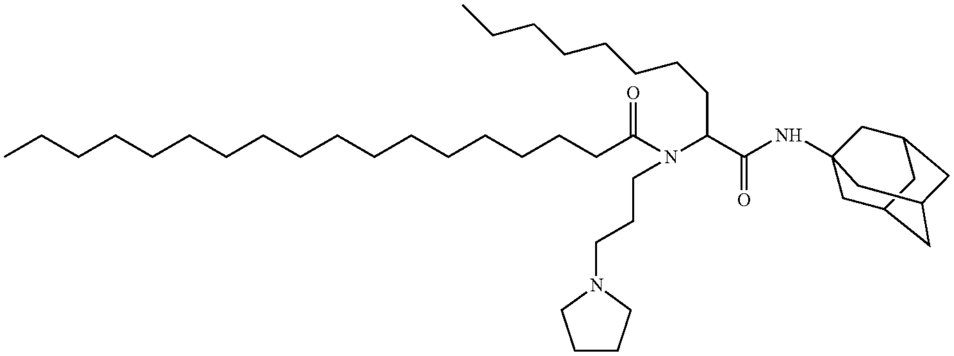
P83A4
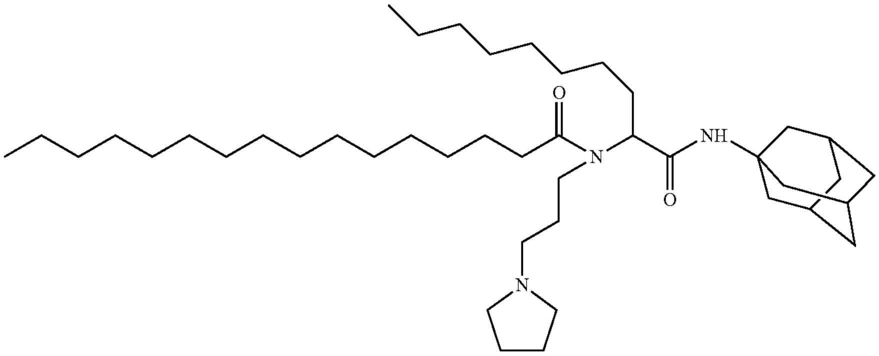
P94B4
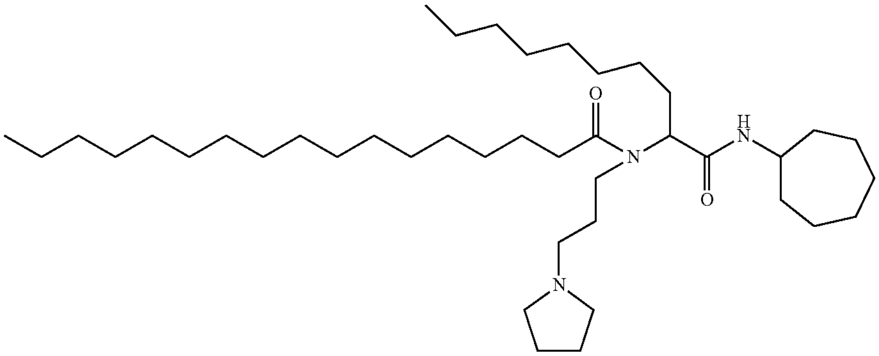
P94C4
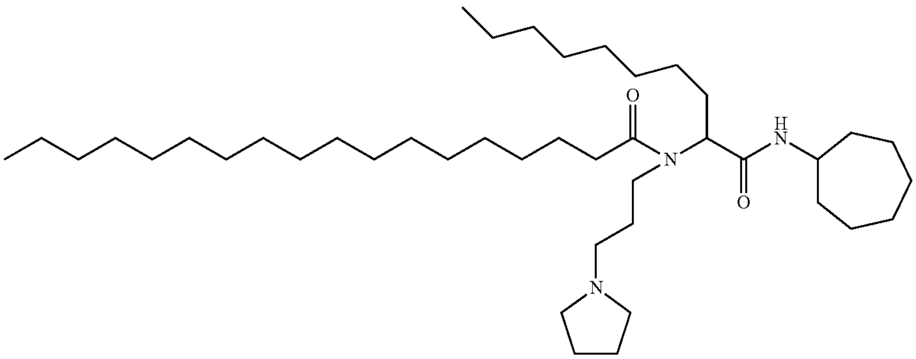

-continued
P95G12
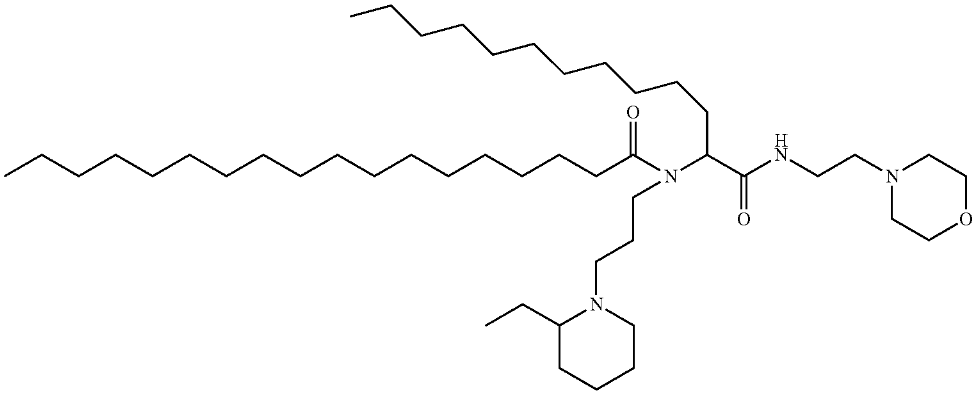
P110C10
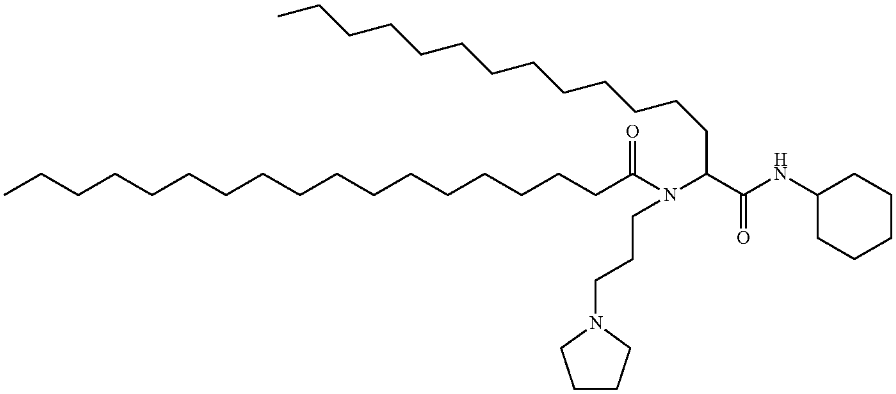
P366B5
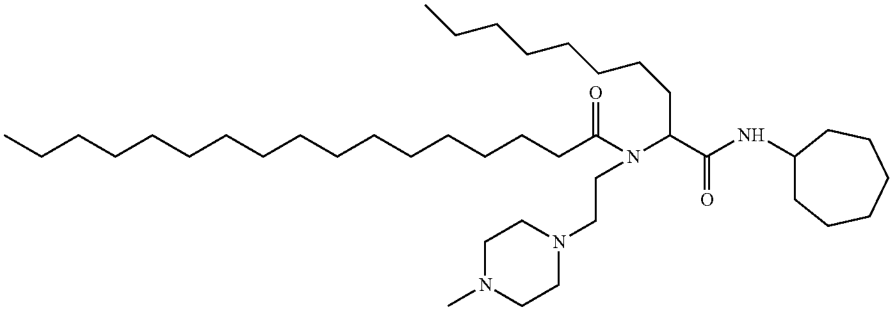
P366B6
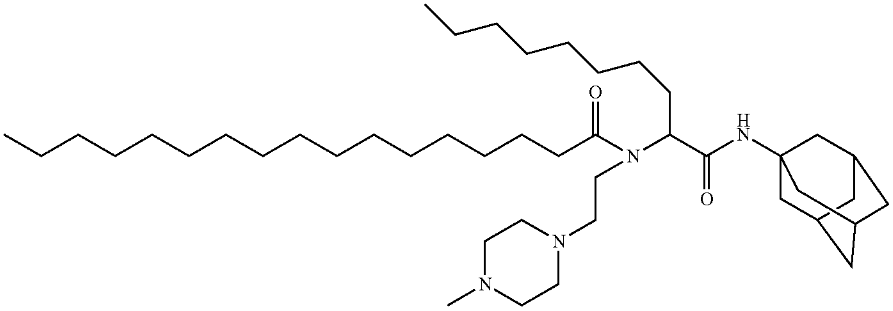

-continued
P366B12
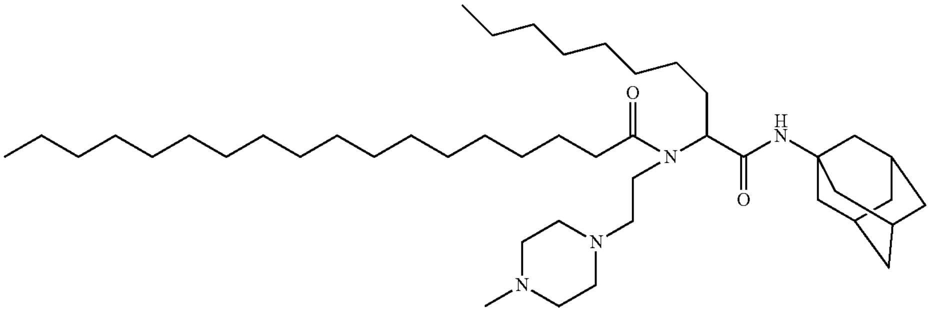
P366C1
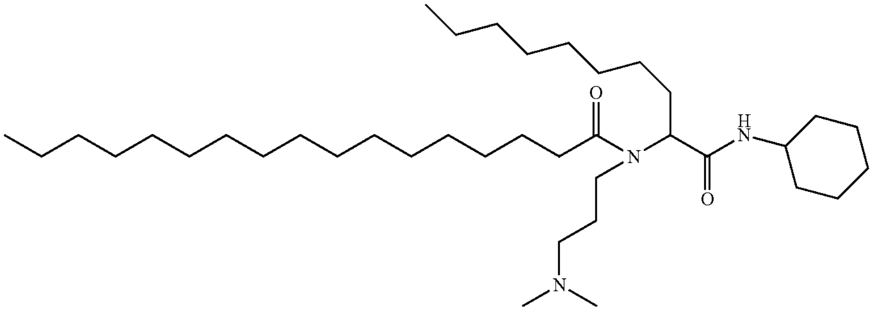
P366C4
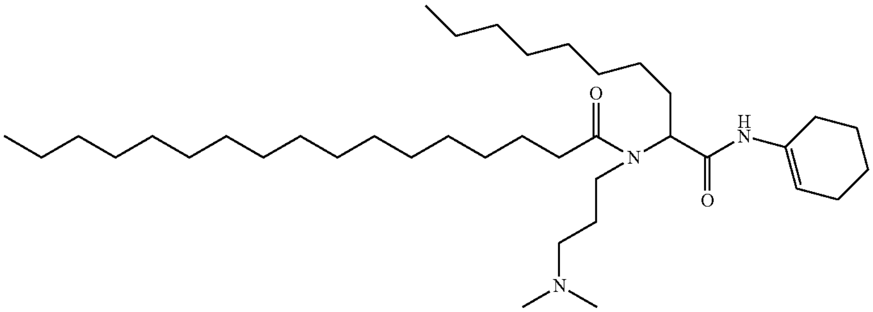
P366C6
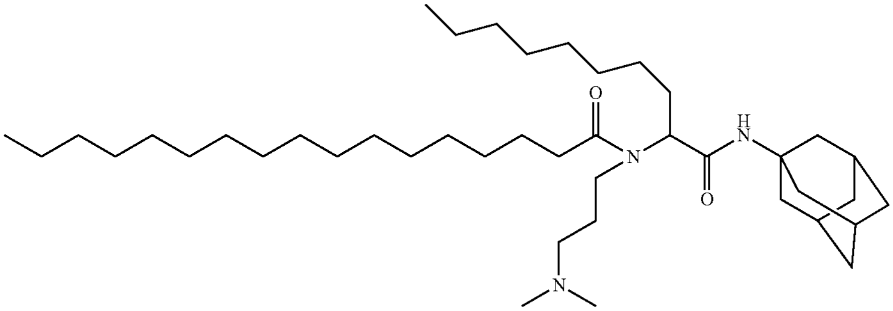
P366C7
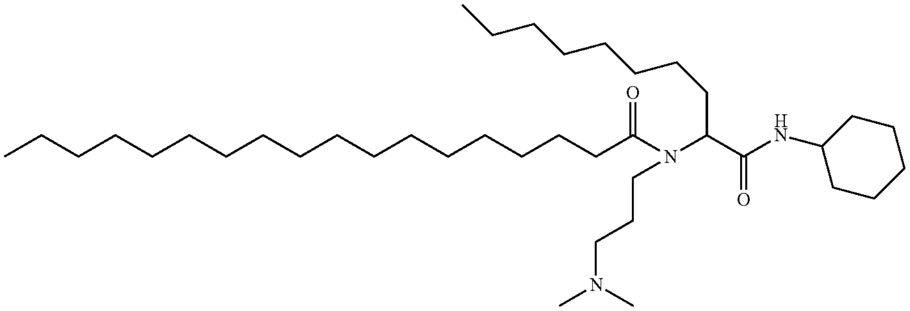

-continued
P366C11
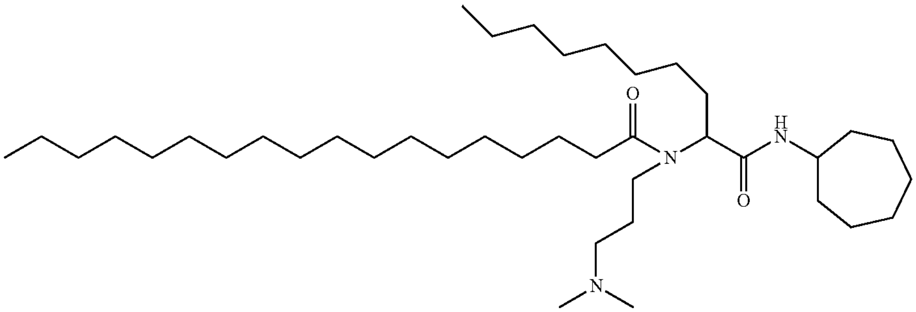
P366C12
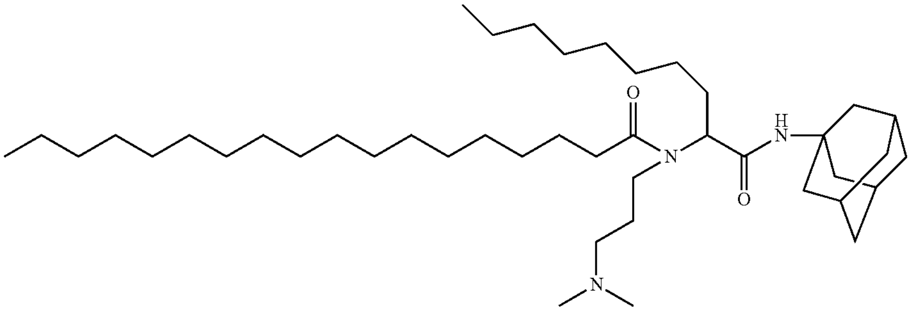
P366D11
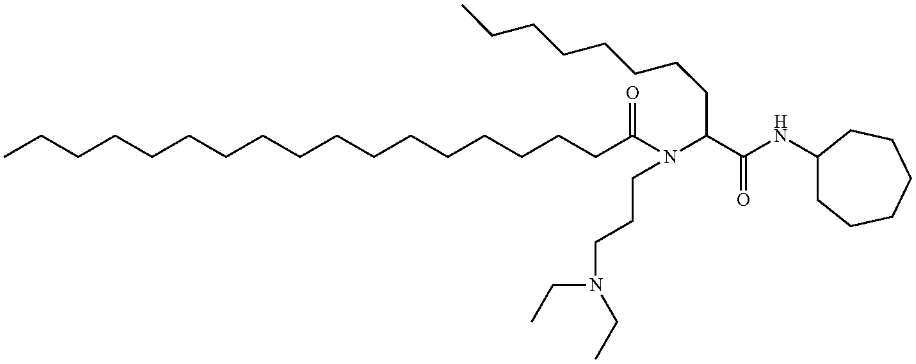
P366D12
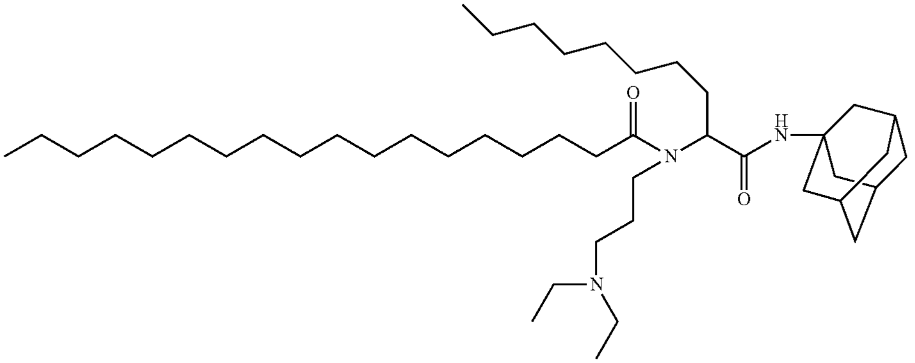

-continued
P368C5
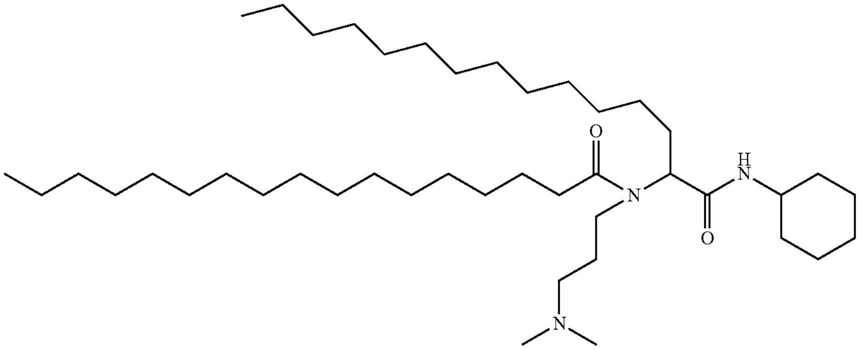
P368C12
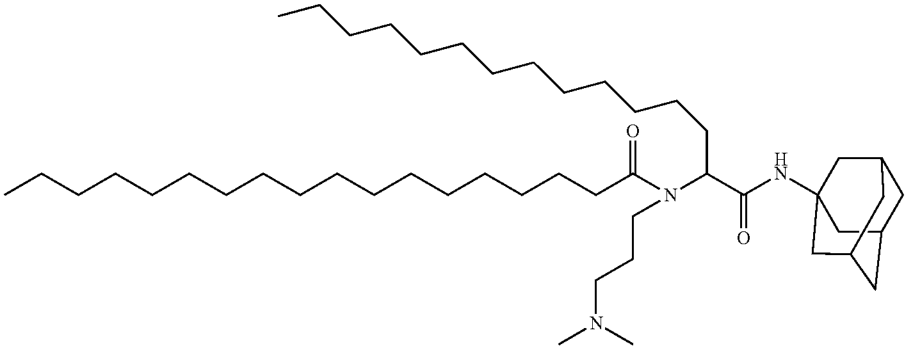
P368D12
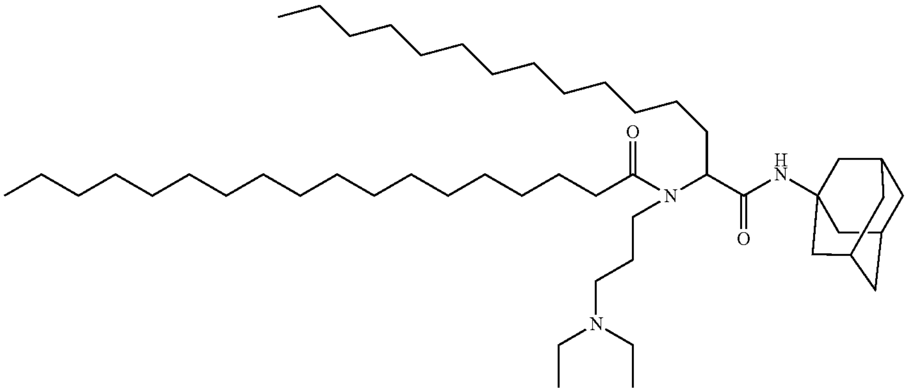
P370D6
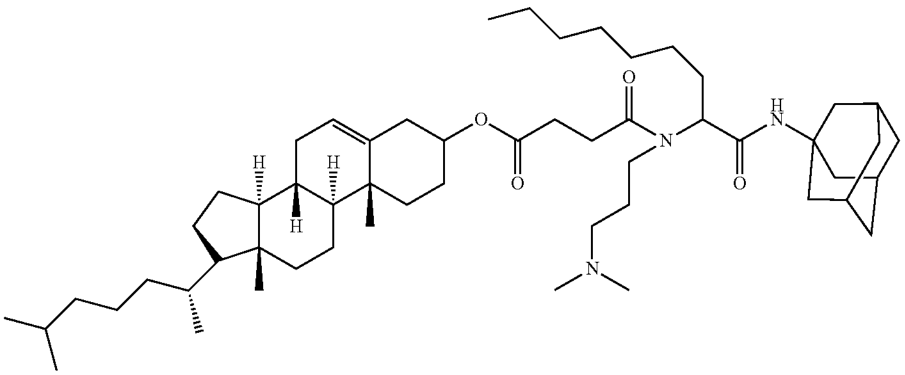

-continued
P371A6
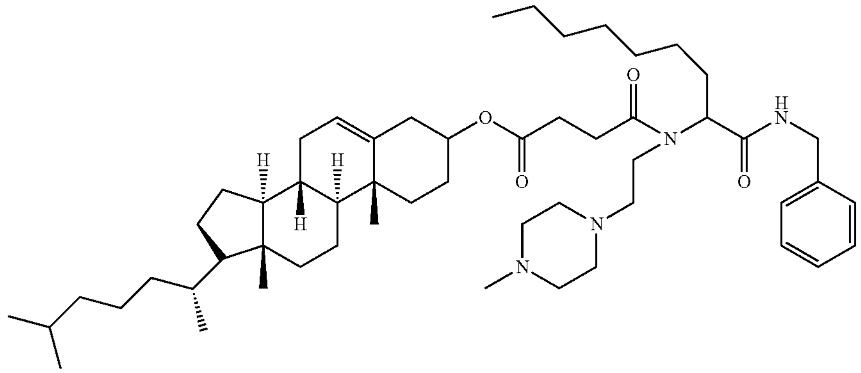
P371D6
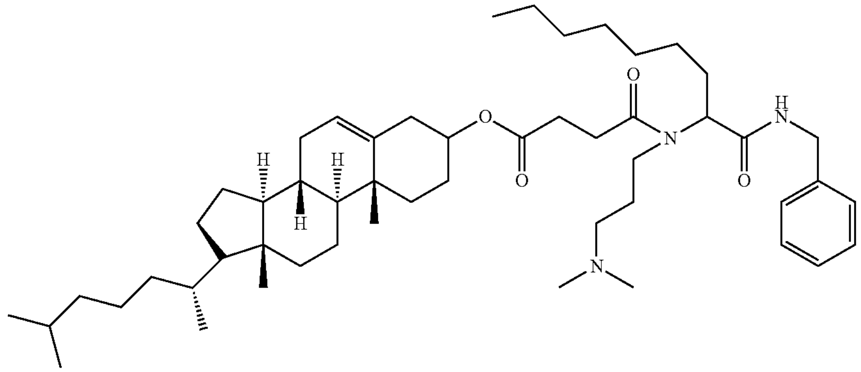
P374F7
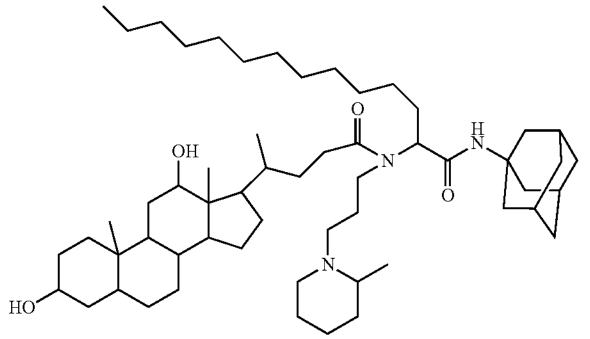
P376F1
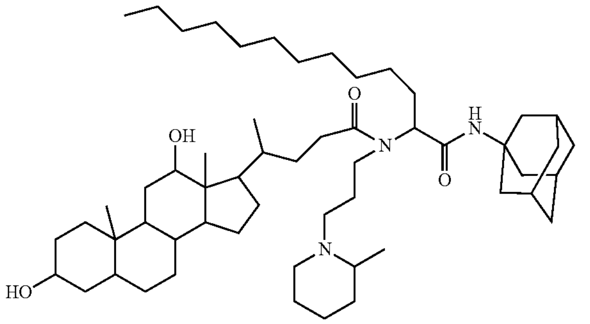
P380D1
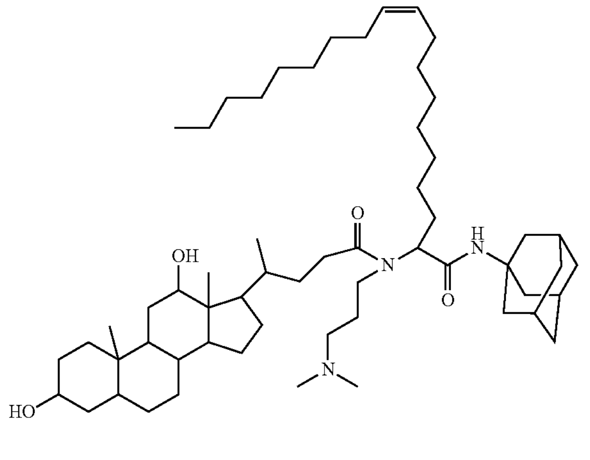
P380E1
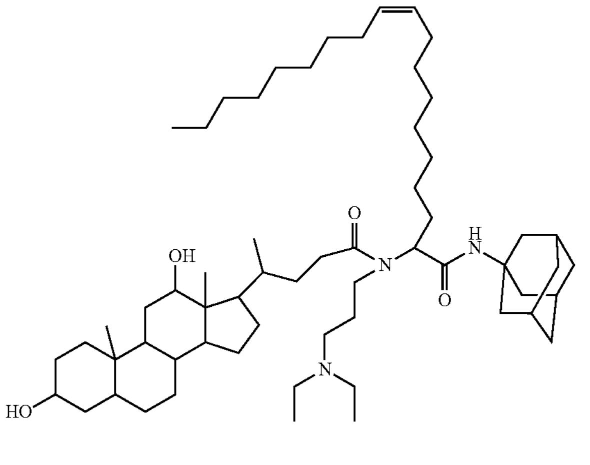

-continued
P380F1
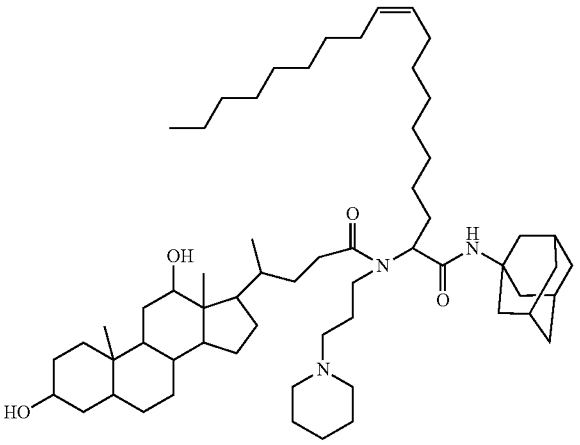
P380F4
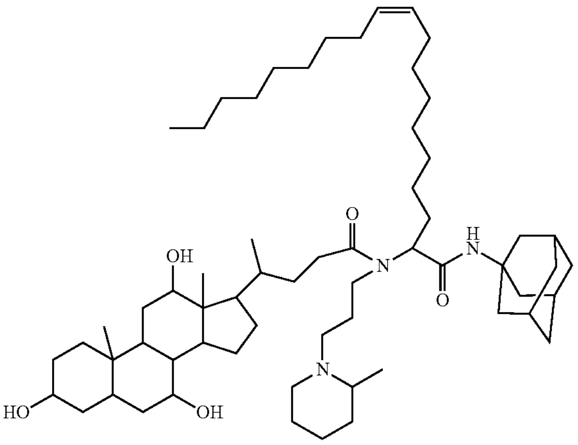
P381F1
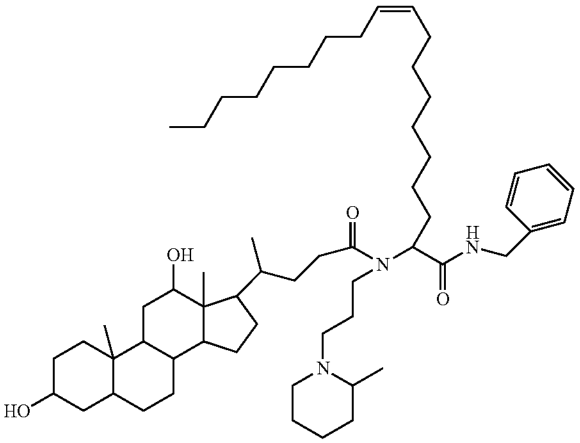
P383A9
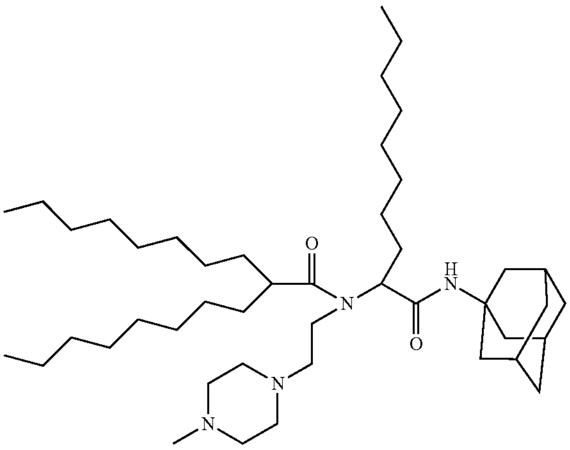
P383B10
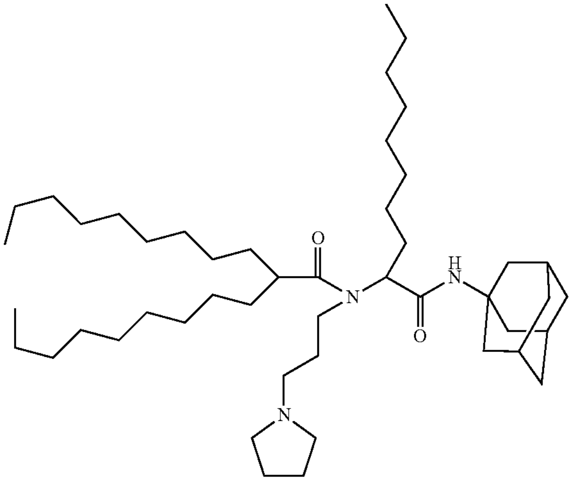
P386D12
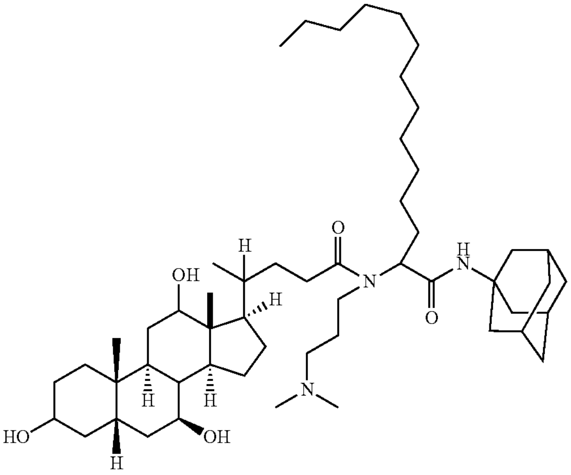

-continued
P387A4
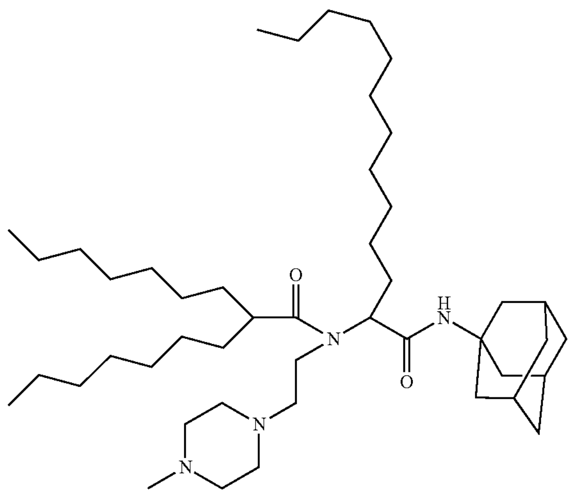
P390E12
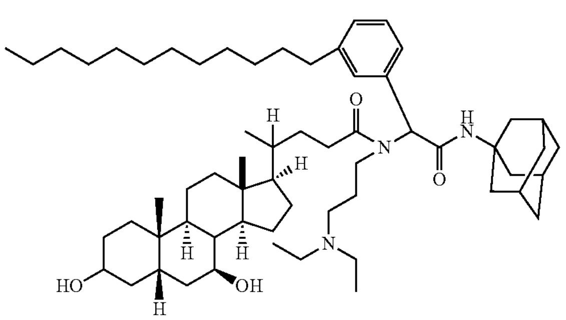
P394A7
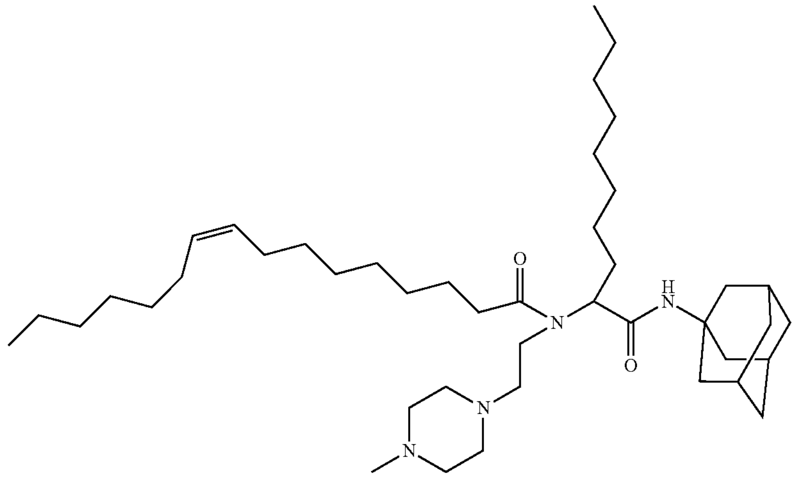
P394D7
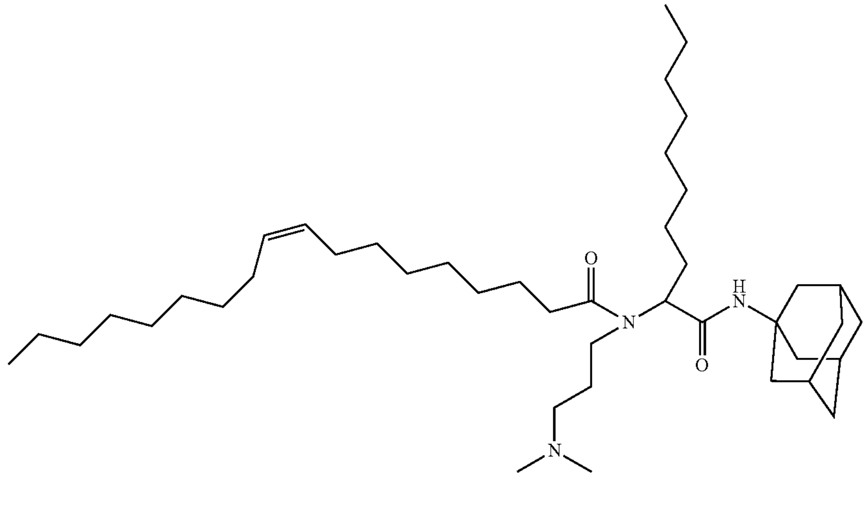

-continued
P394D12
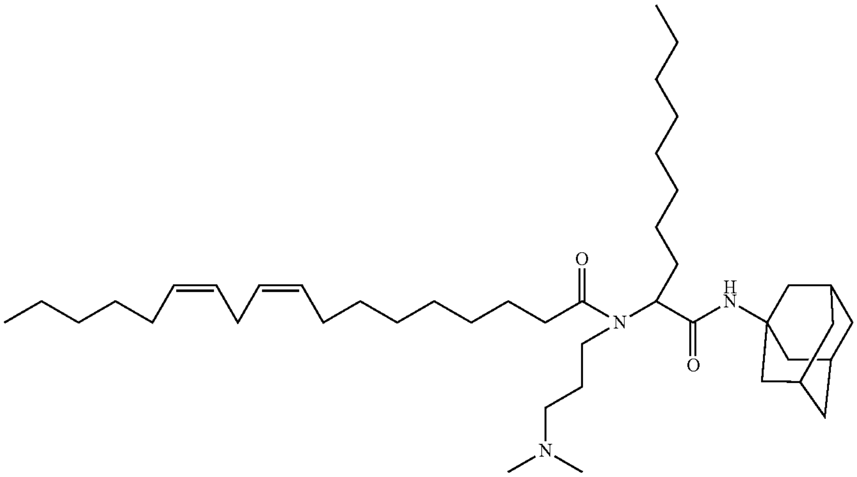
P394H8
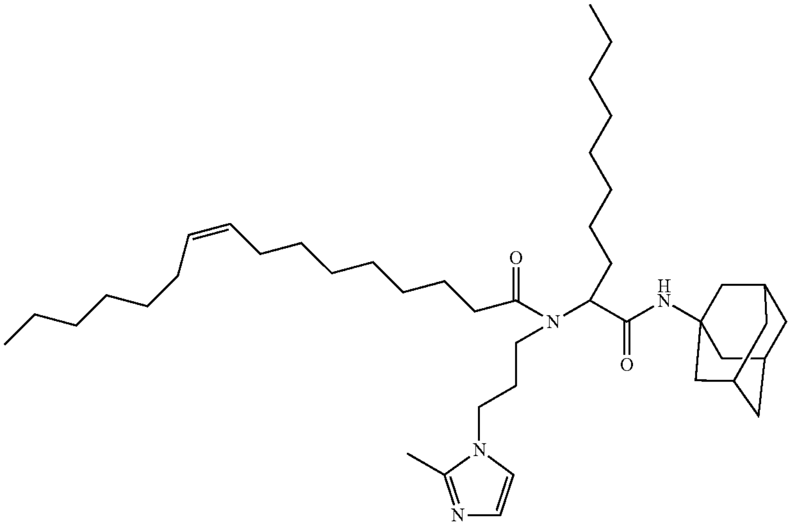
P394H9
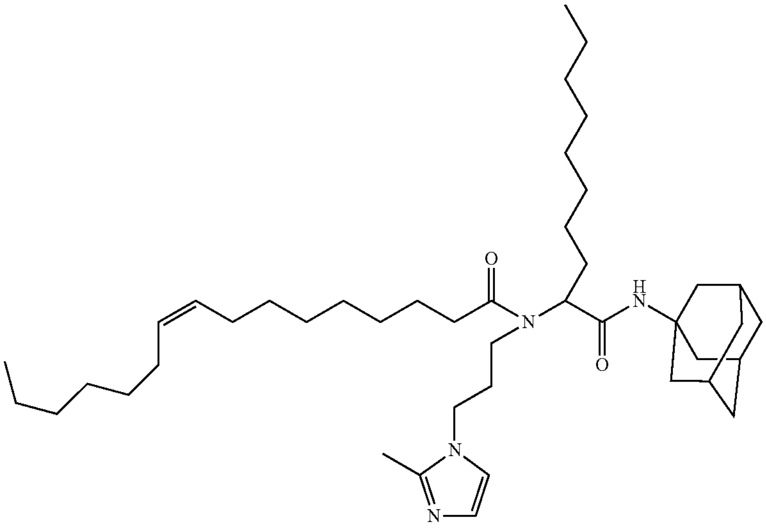

-continued
P398D1
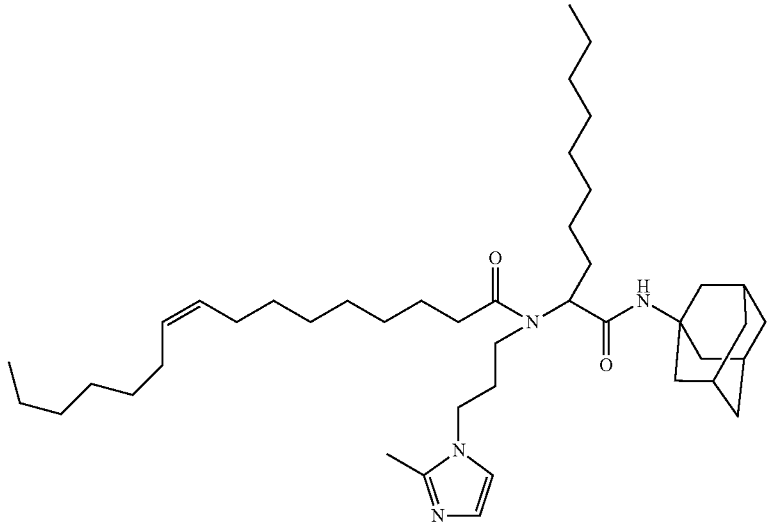
P398D6
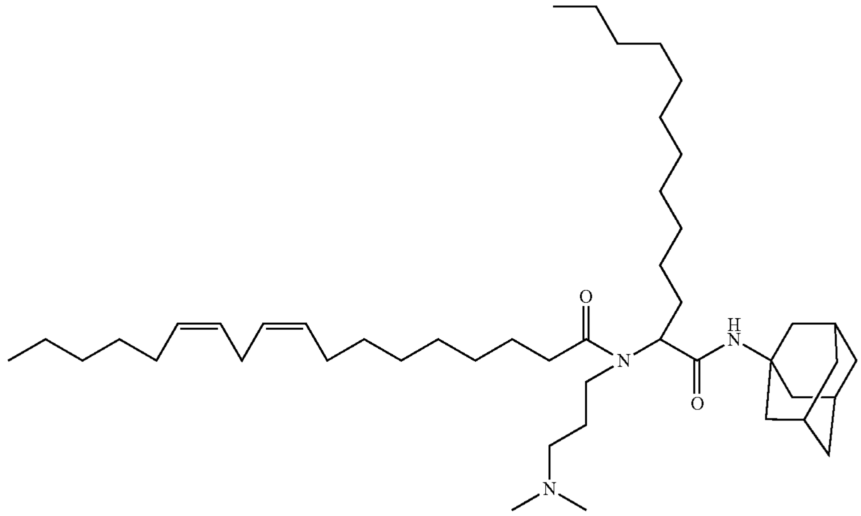
P398D7
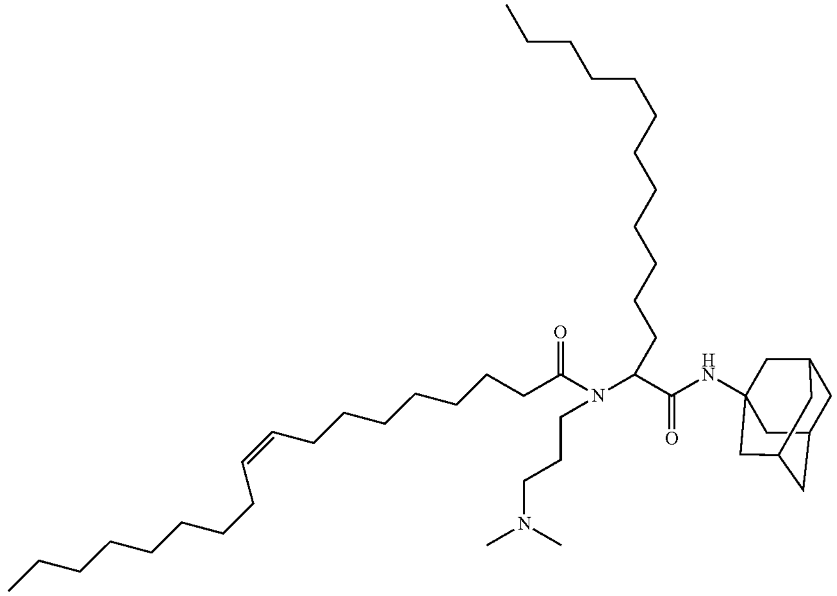

-continued
P398D8
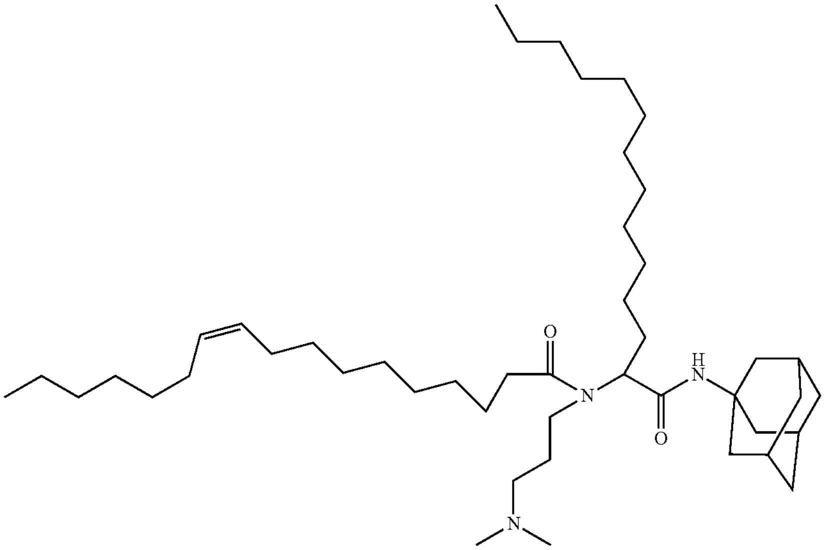
P398D9
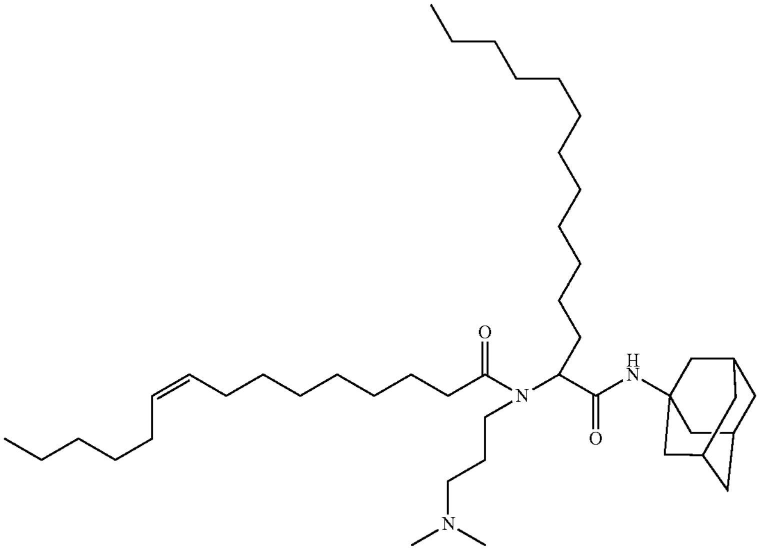
P398D12
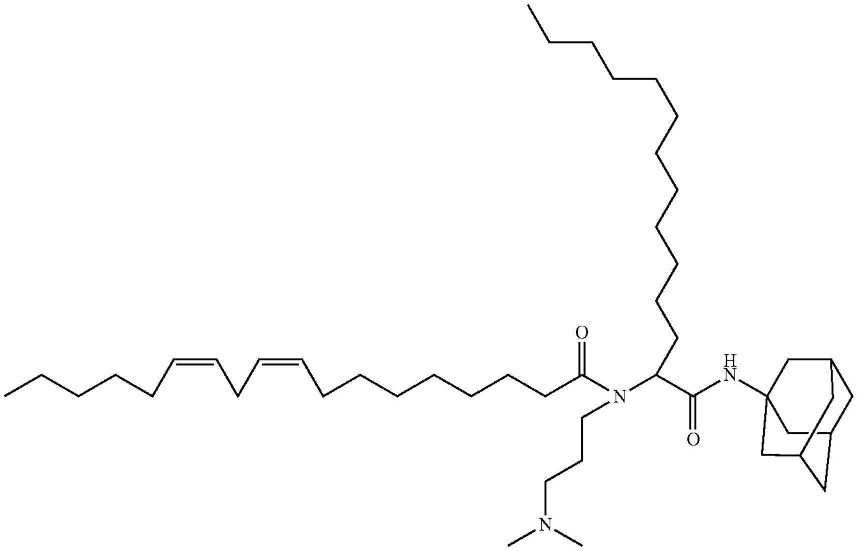

-continued
P398E1
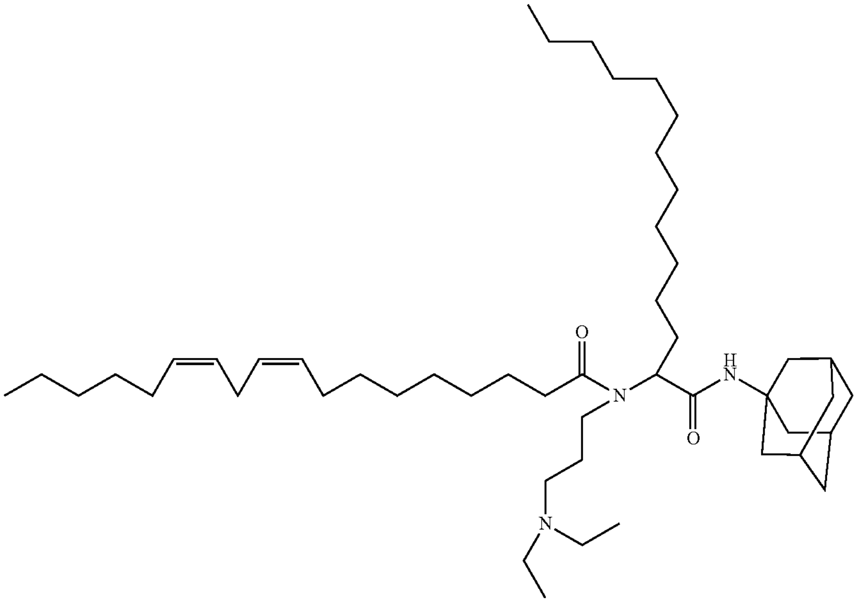
P399A1
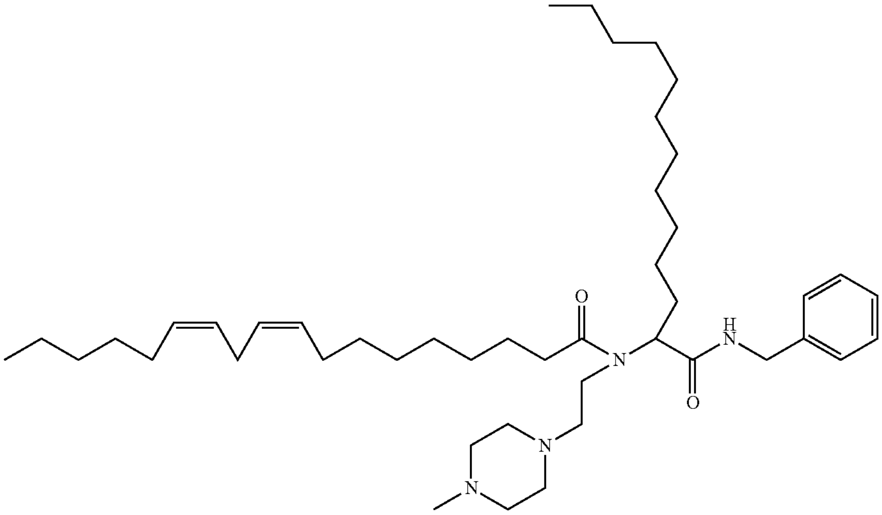
P399A9
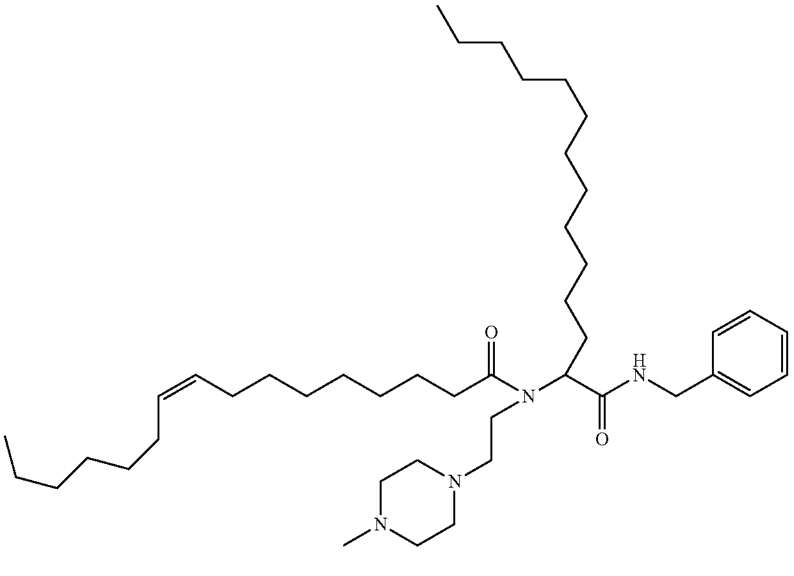

-continued
P399E1
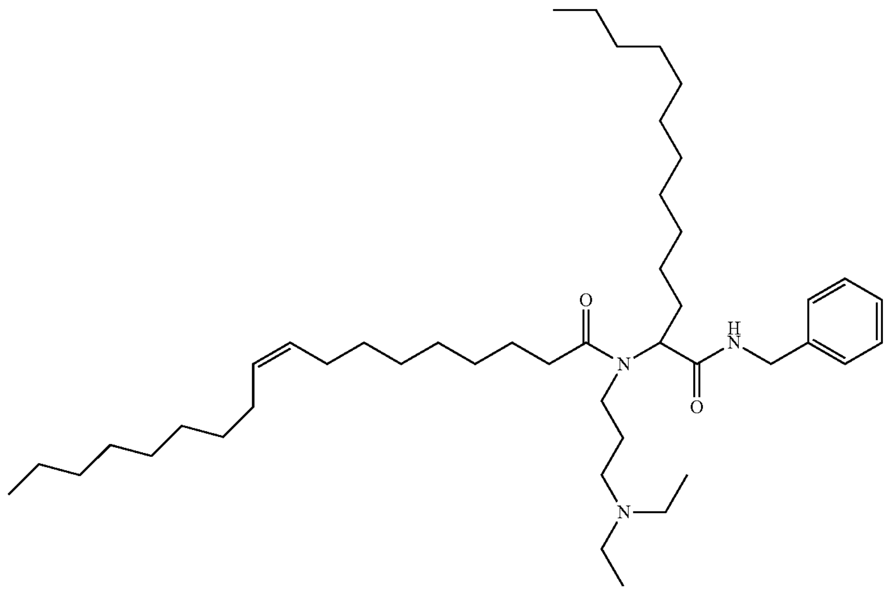
P399F1
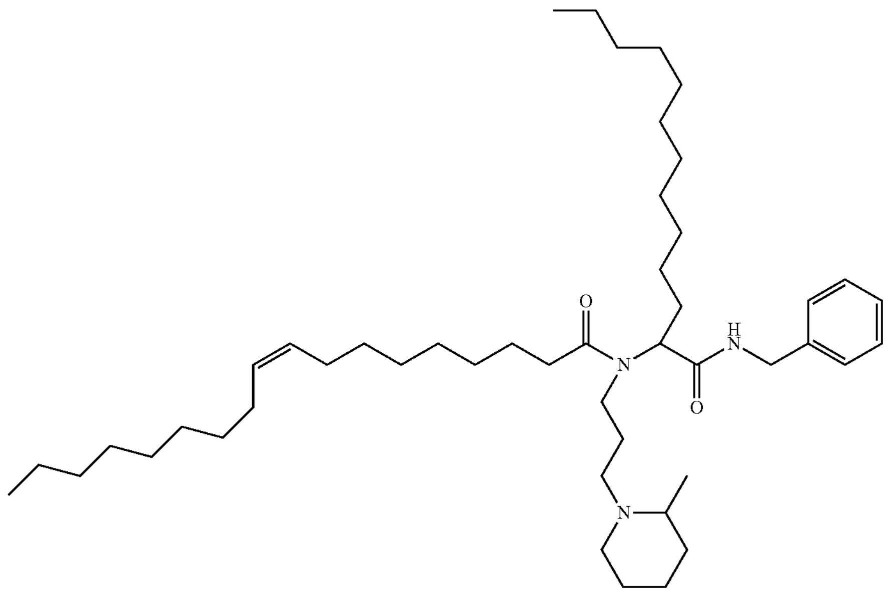

-continued
P399F12
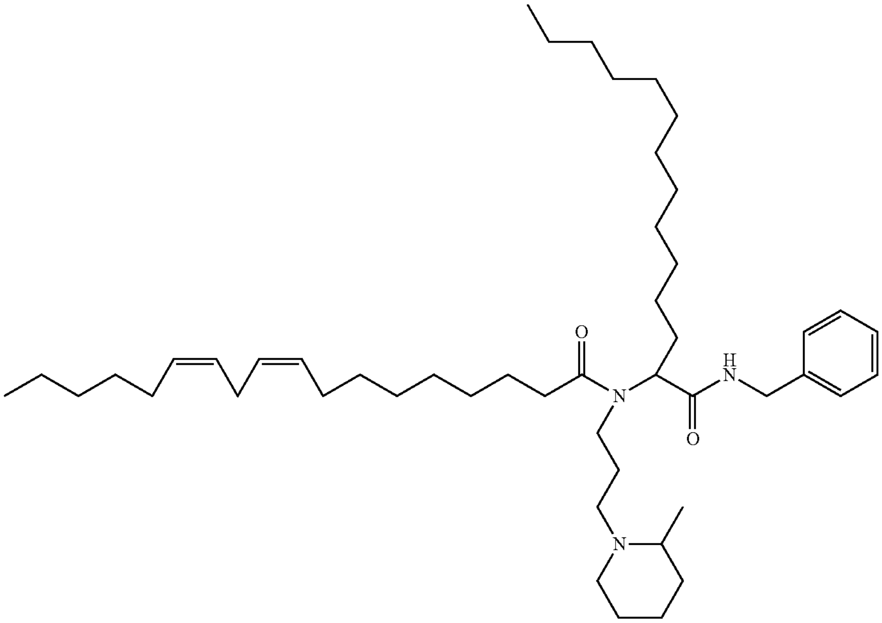
P399H1
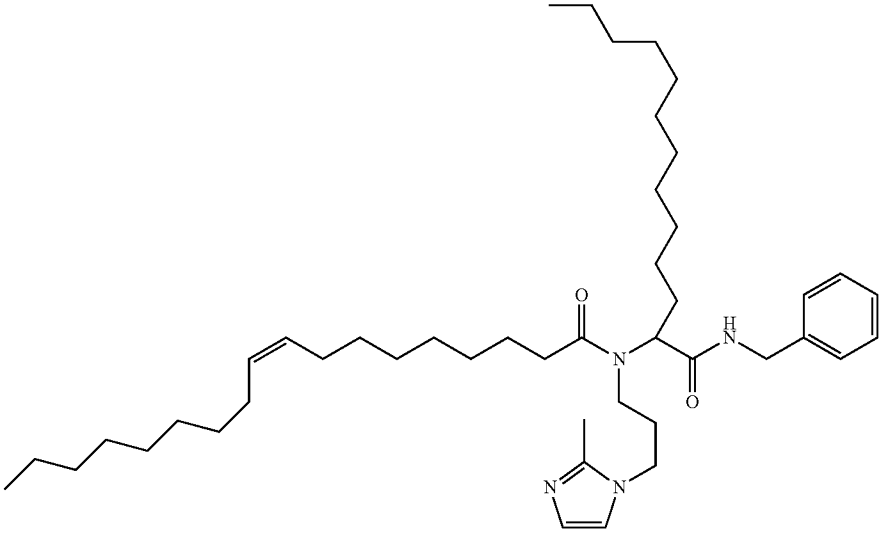

-continued
P399H3
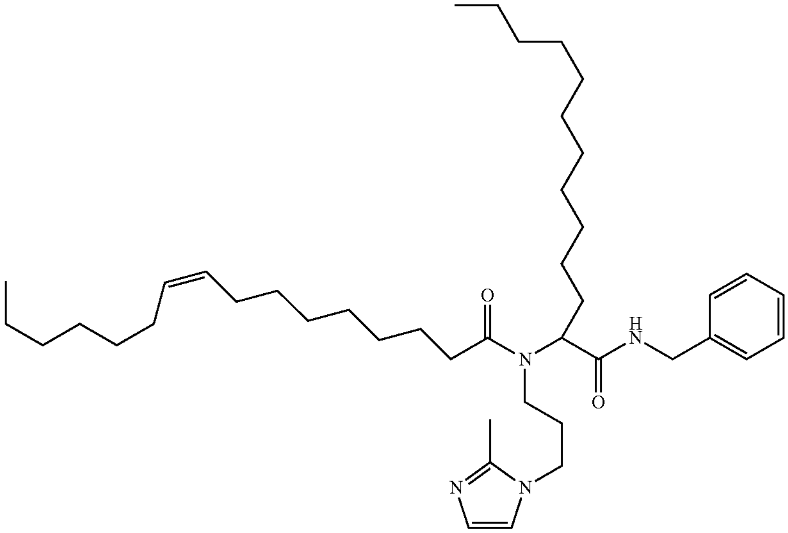
P400A3
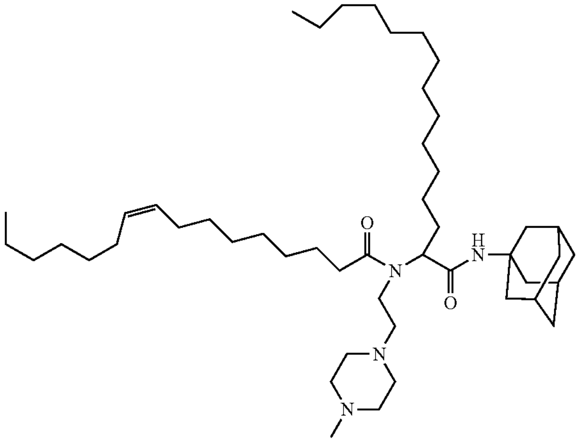
P400A4
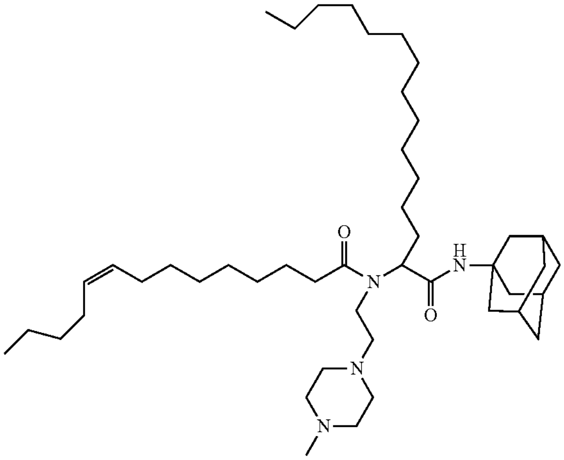
P400D12
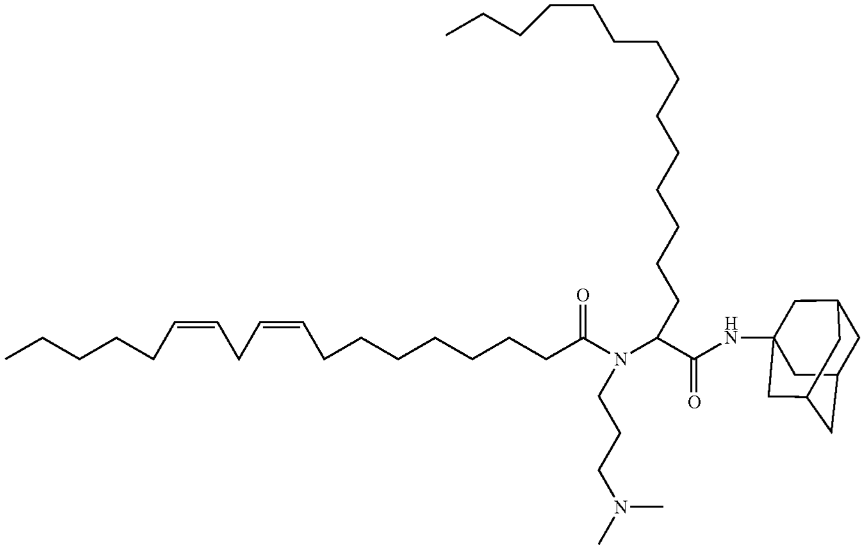

-continued
P401A3
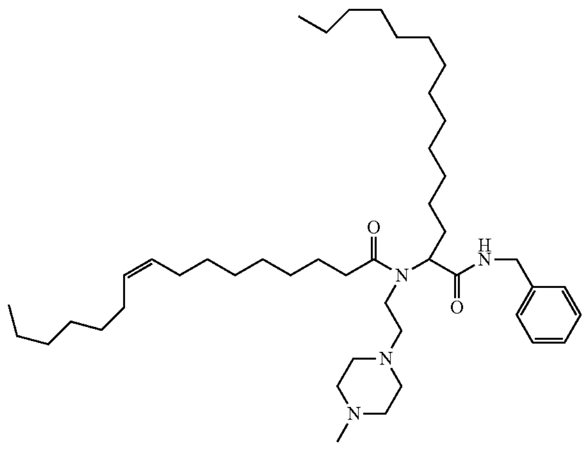
P401A4
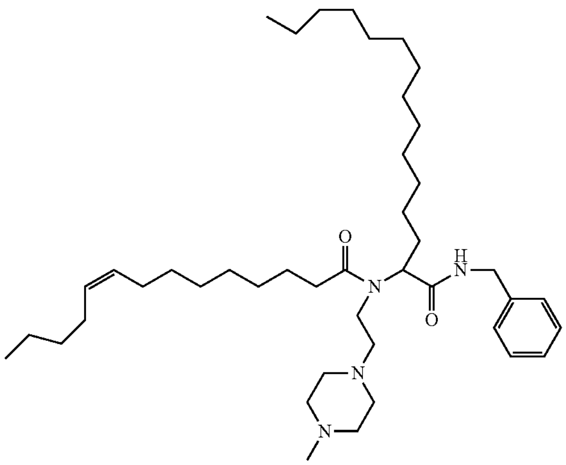
P401A6
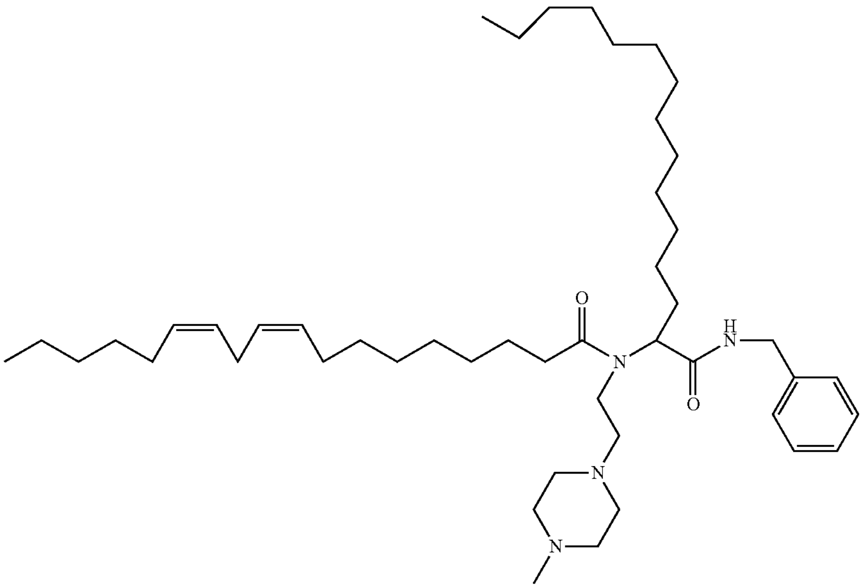
P401D1
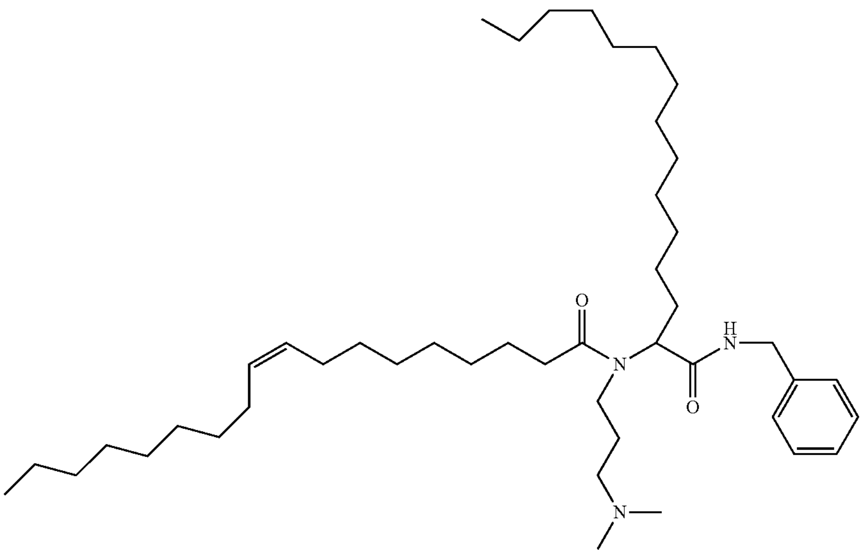

-continued
P401E1
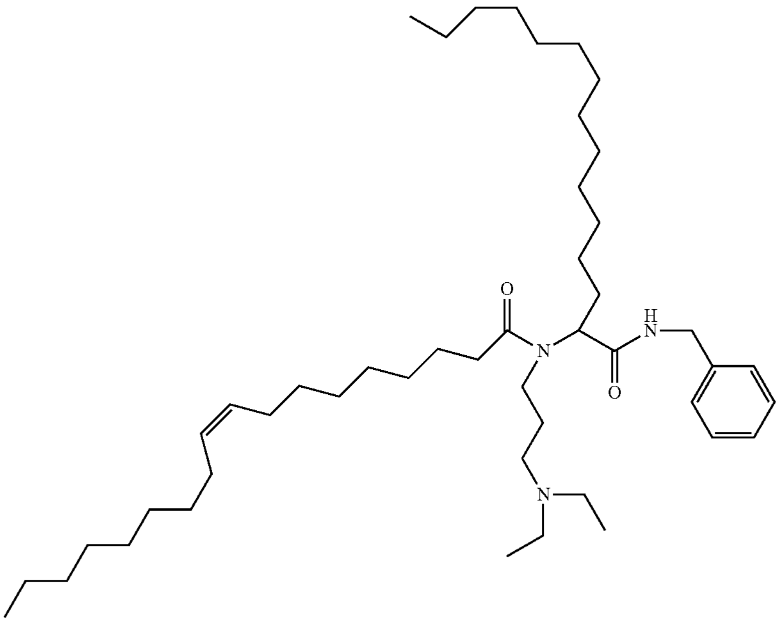
P401E9
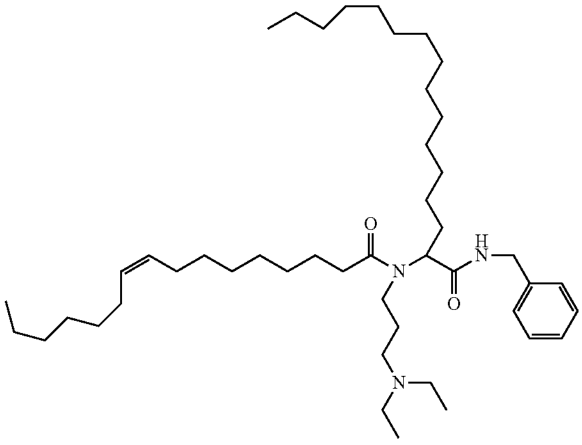
P401E10
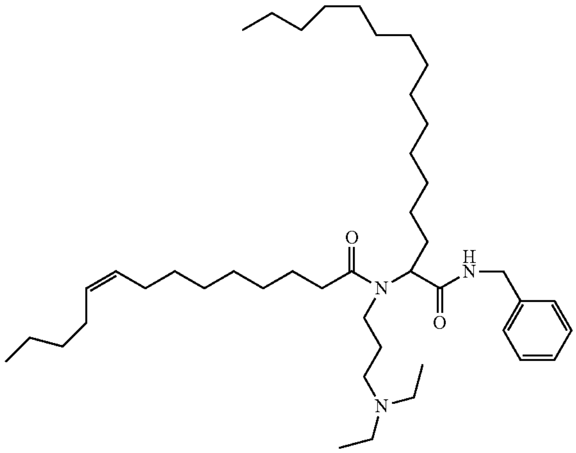

-continued
P401E12
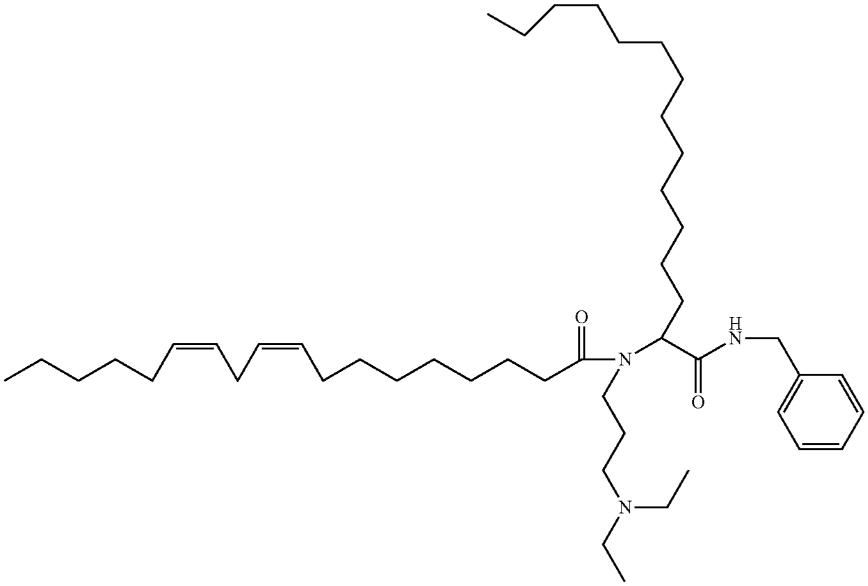
P401H12
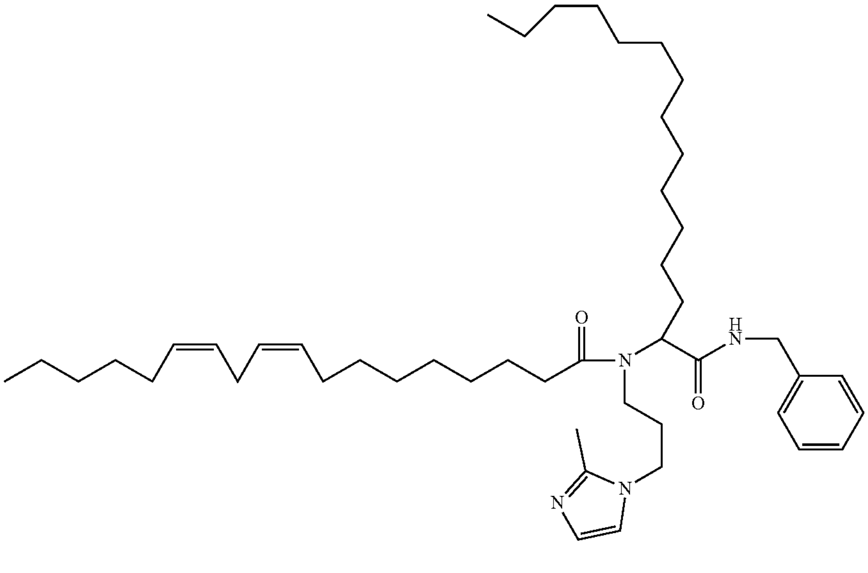
P402A7
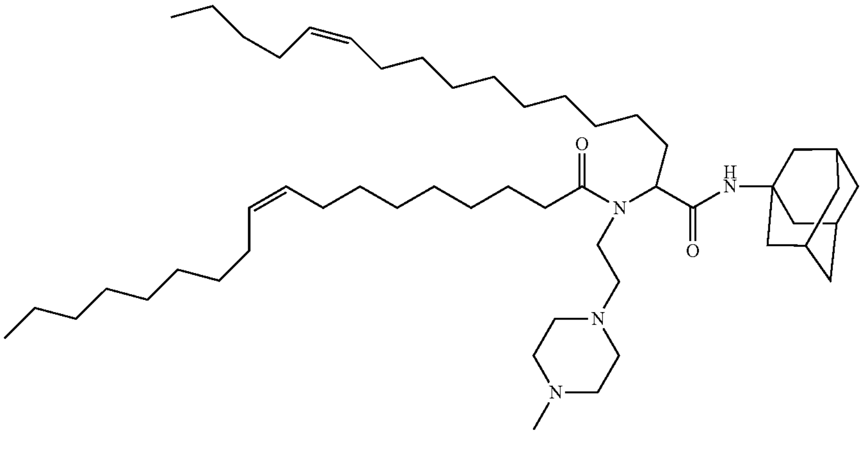

-continued
P402A9
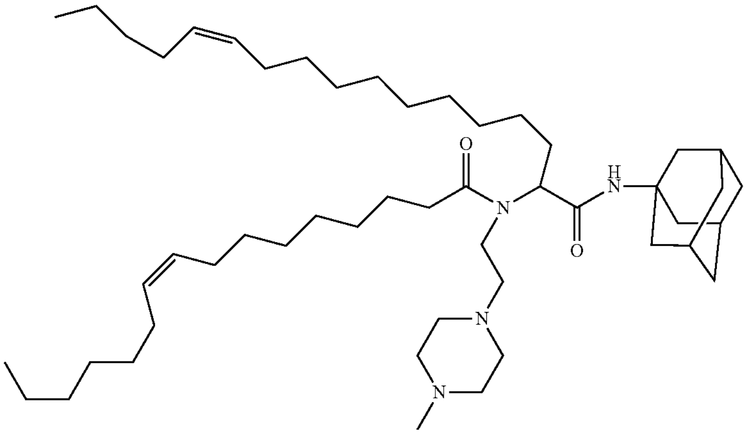
P402D7
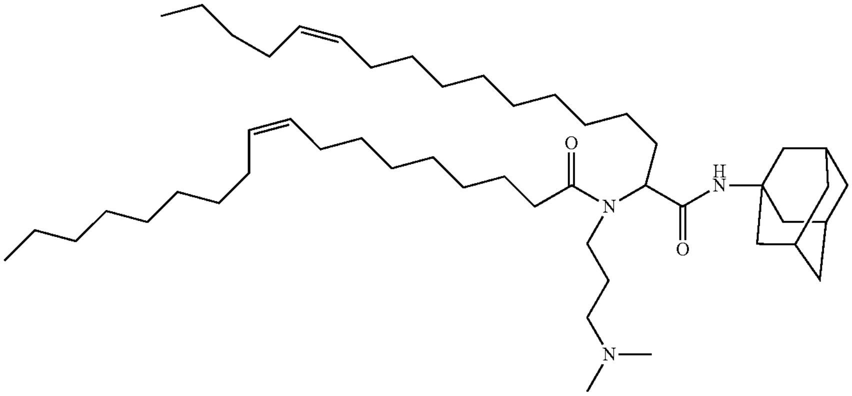
P402D9
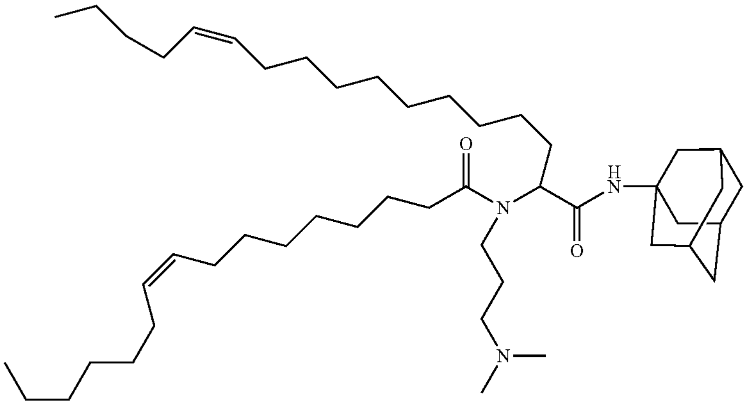
P402D12
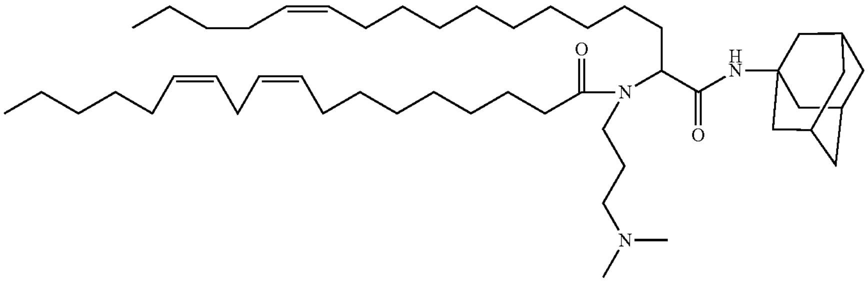

-continued
P402E12
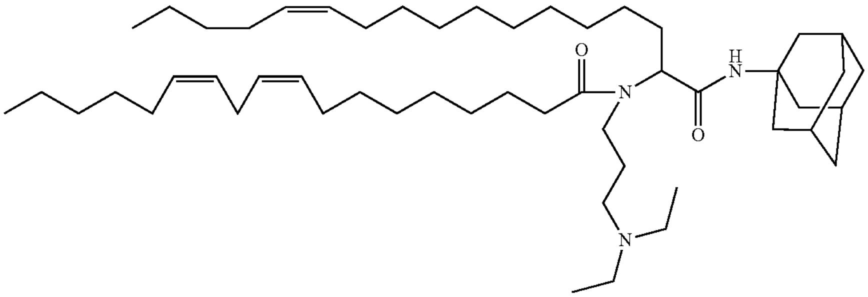
P403A7
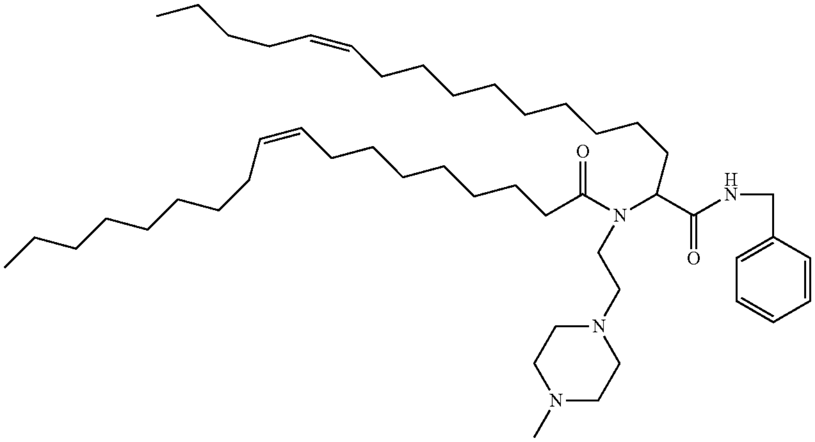
P403A9
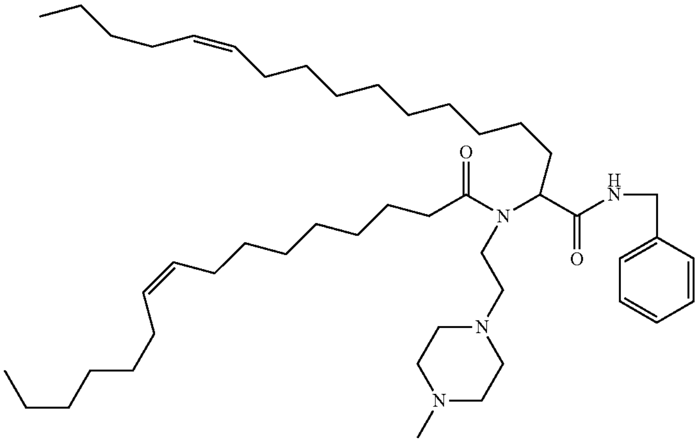
P403H7
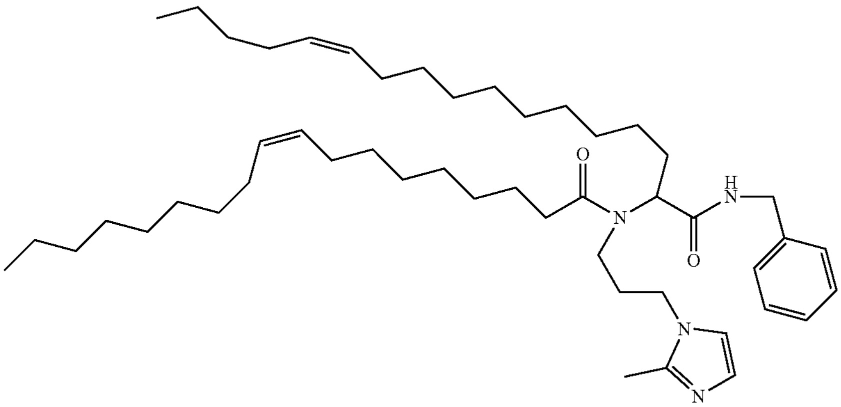

-continued
P403H10
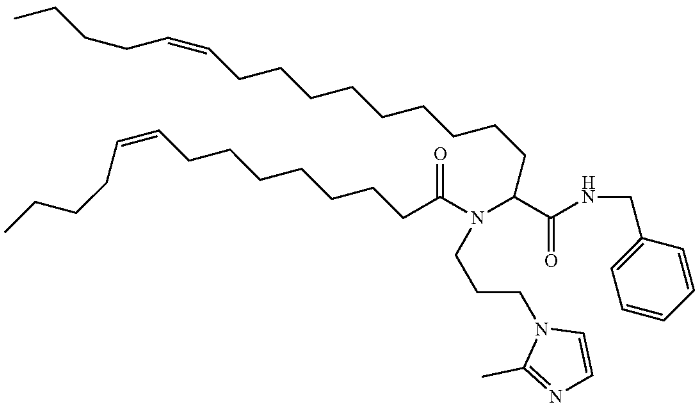
P404D1
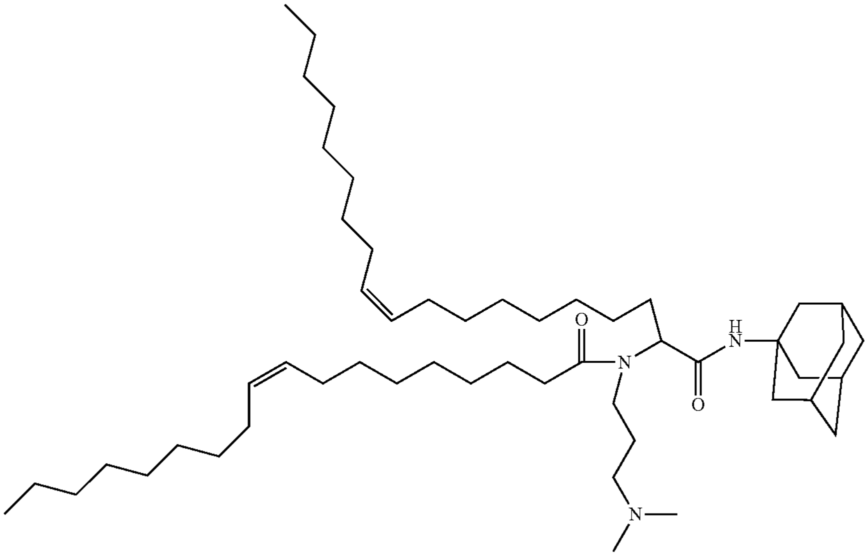
P404D3
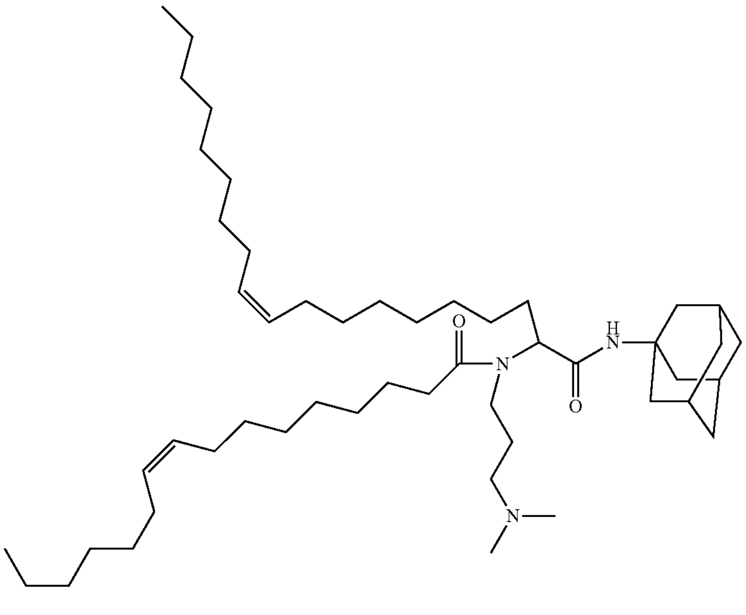

-continued
P404D6
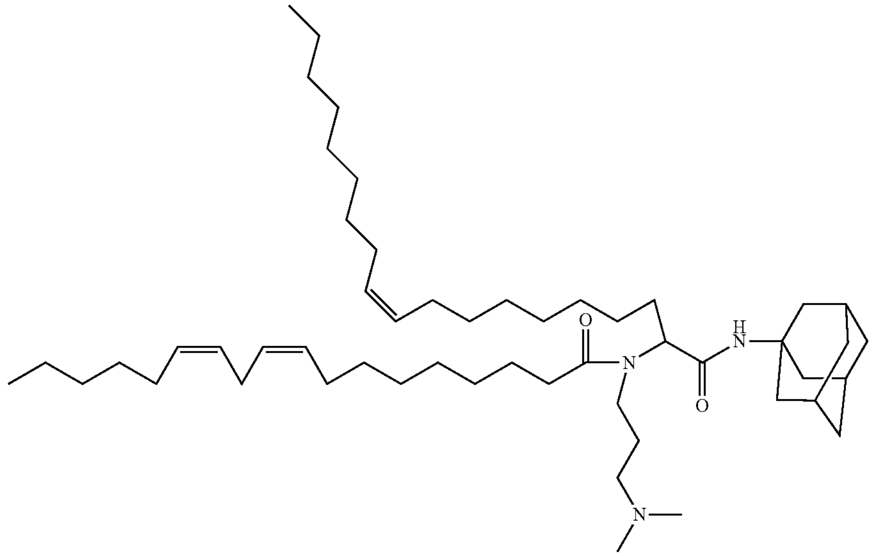
P404E1
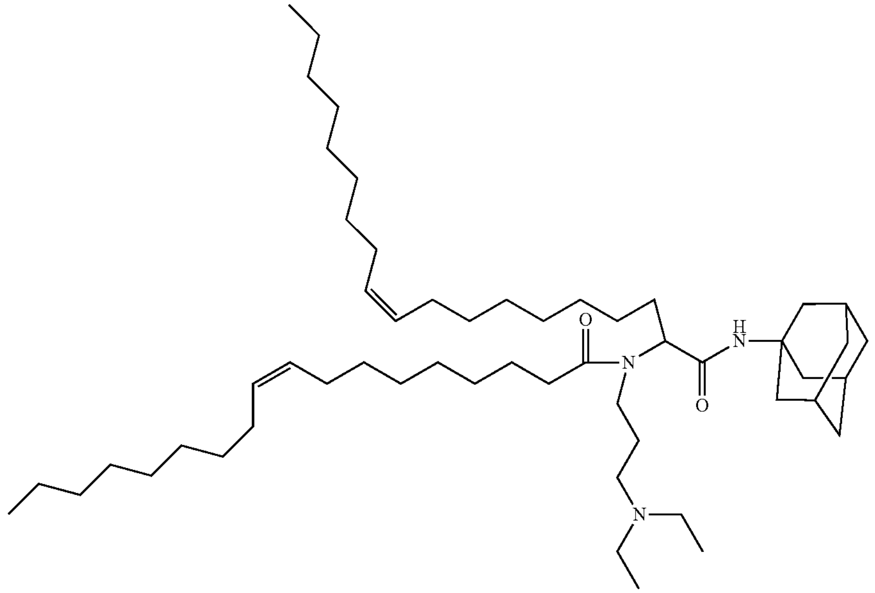

-continued
P405E3
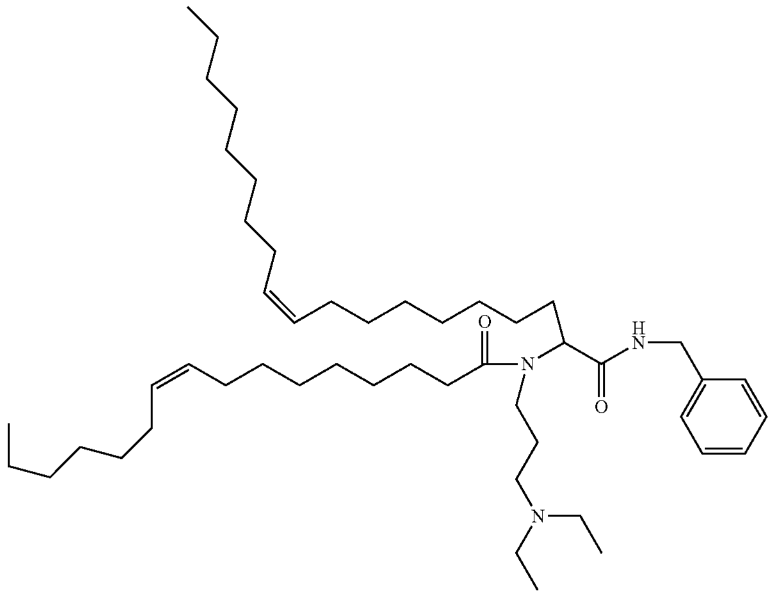
P406A6
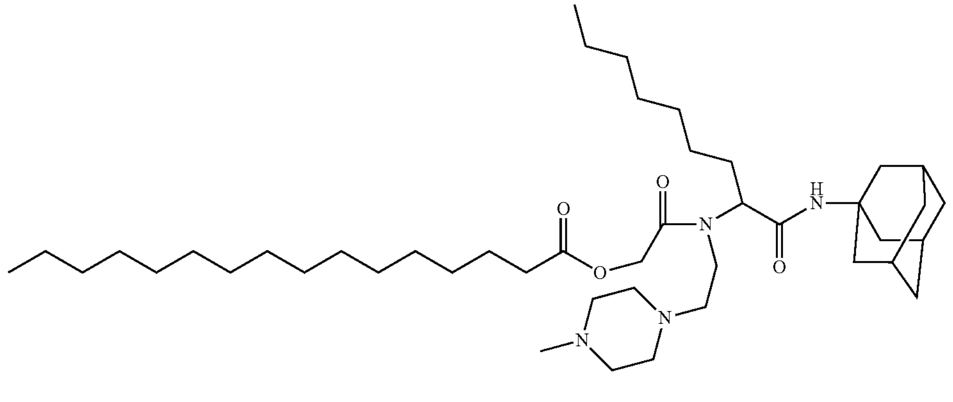
P406A12
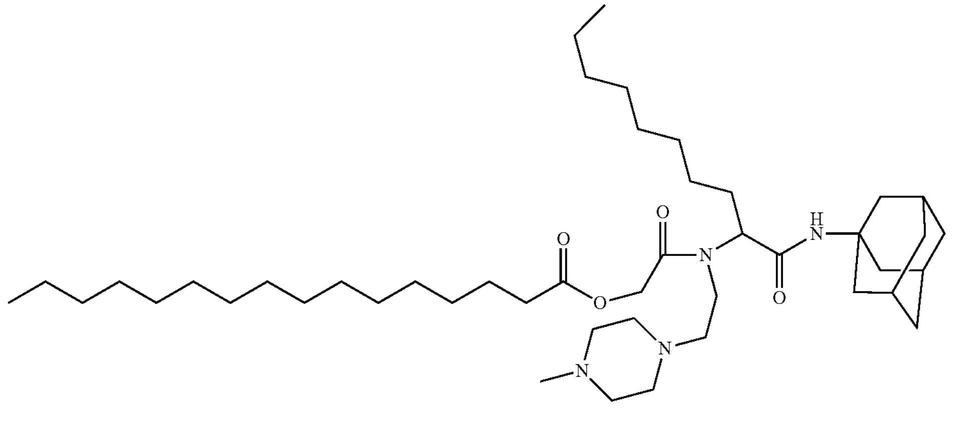

-continued
P406E12
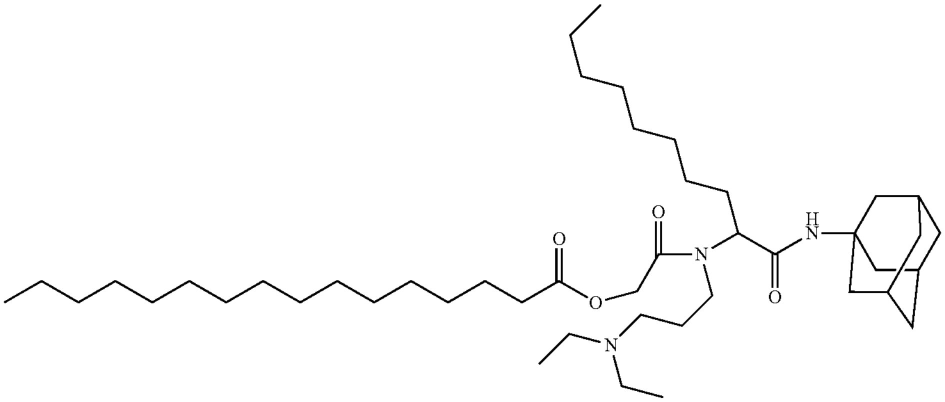
P406F12
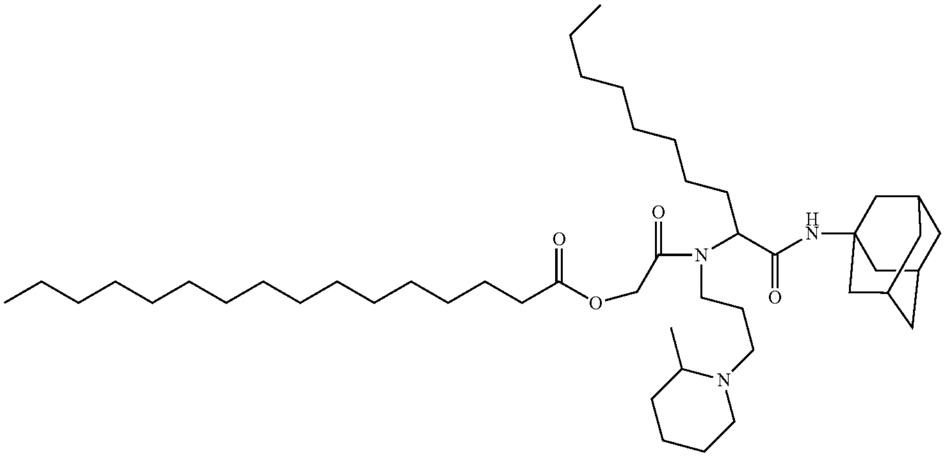
P406H6
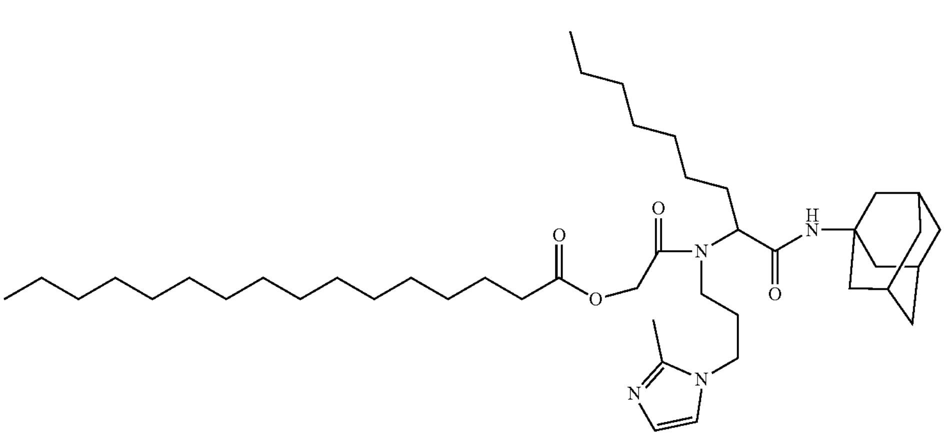

-continued
P406H10
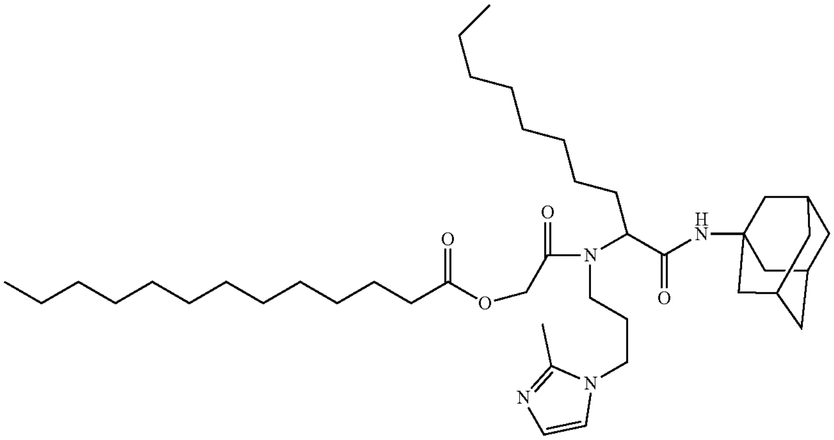
P406H12
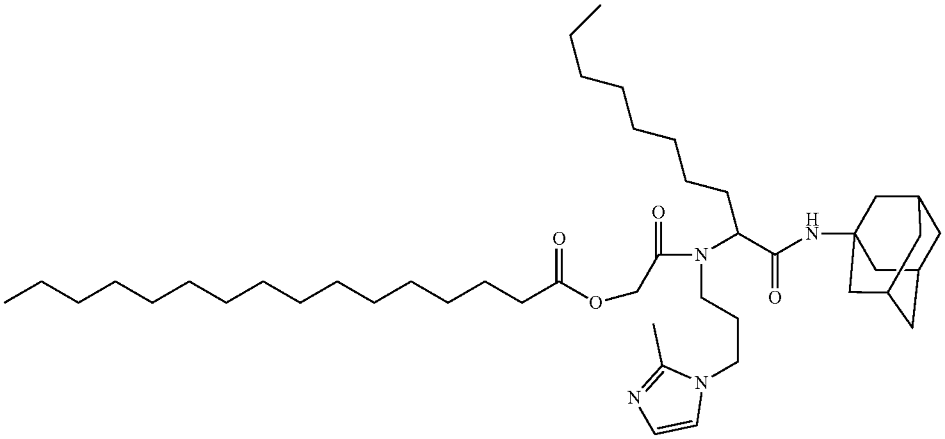
P407D12
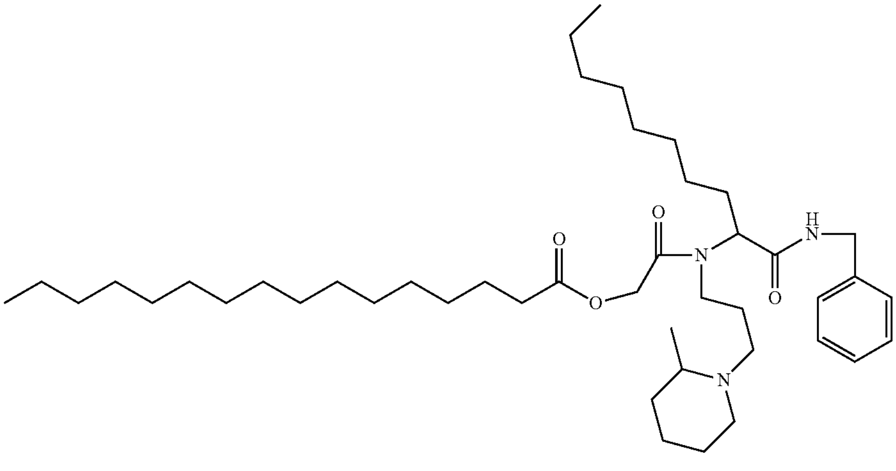

-continued
P407F12
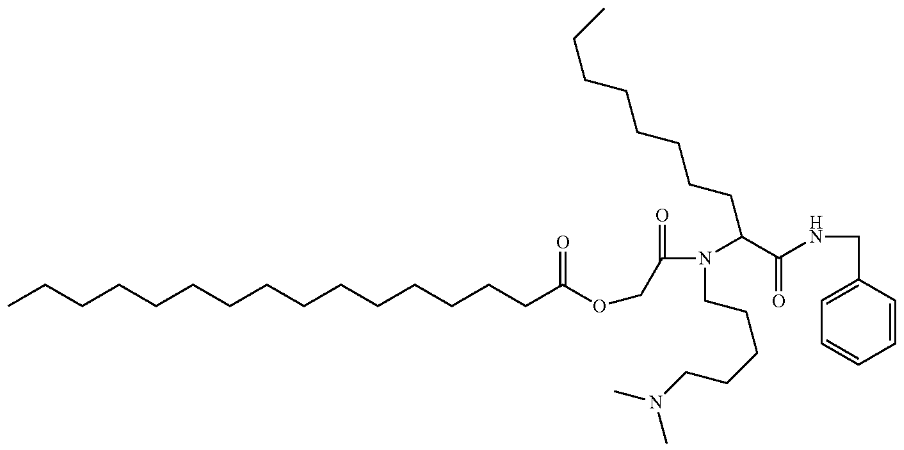
P408H4
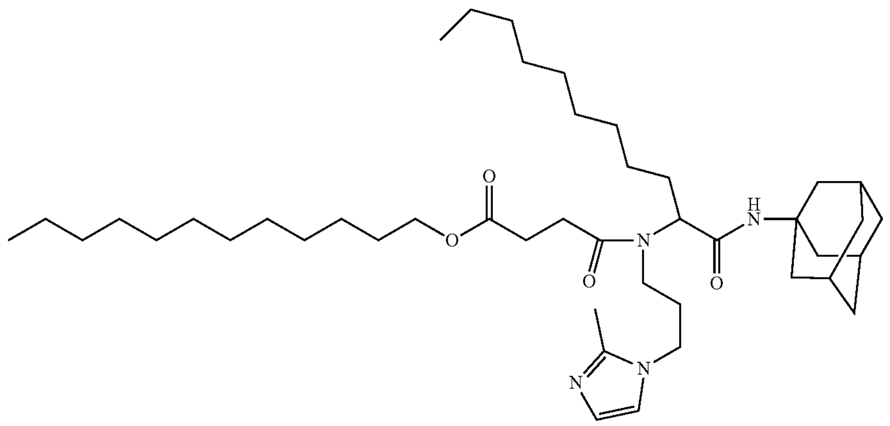
P410A6
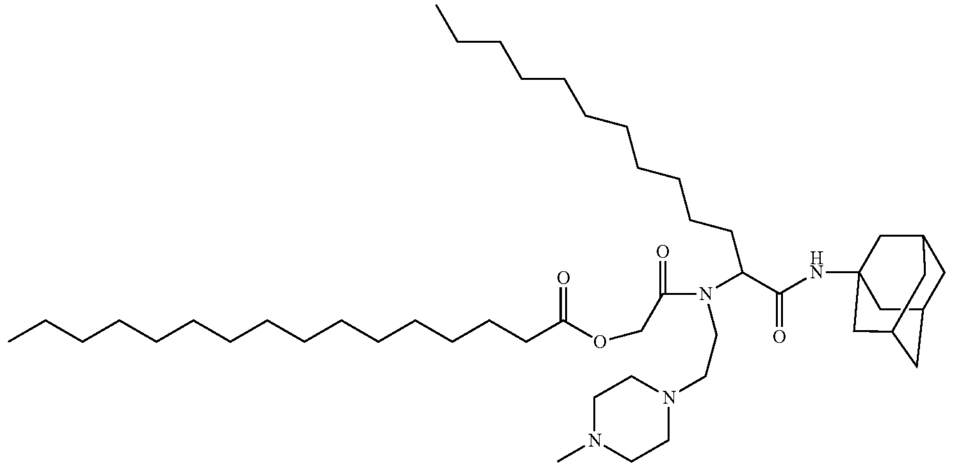

-continued
P410A10
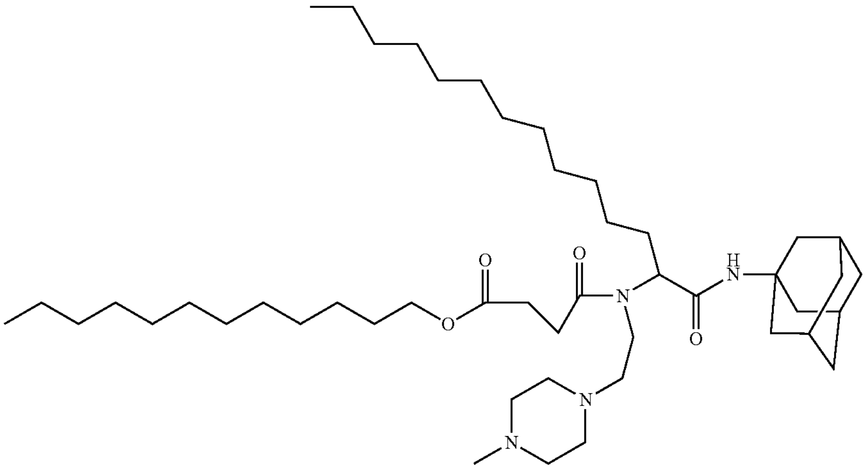
P410D4
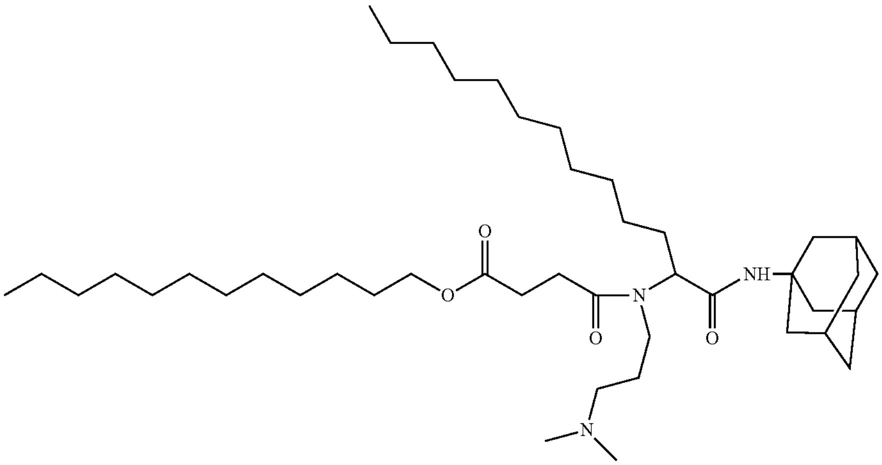
P410E12
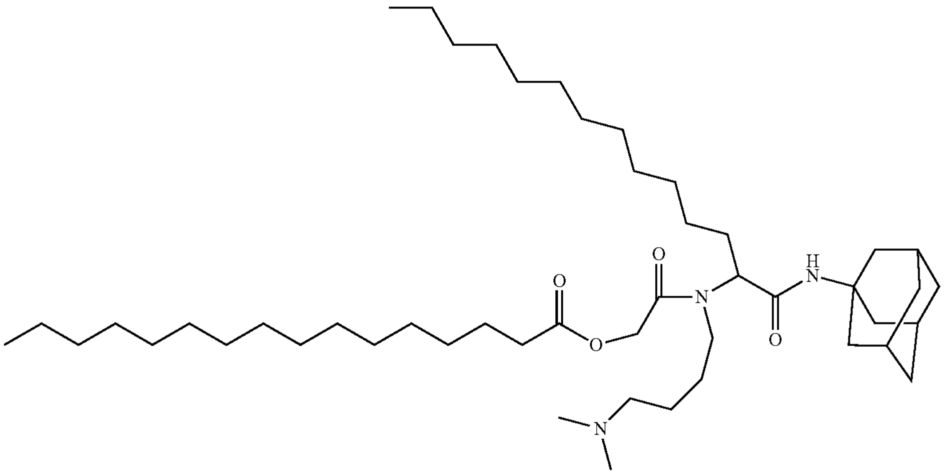

-continued
P410D12
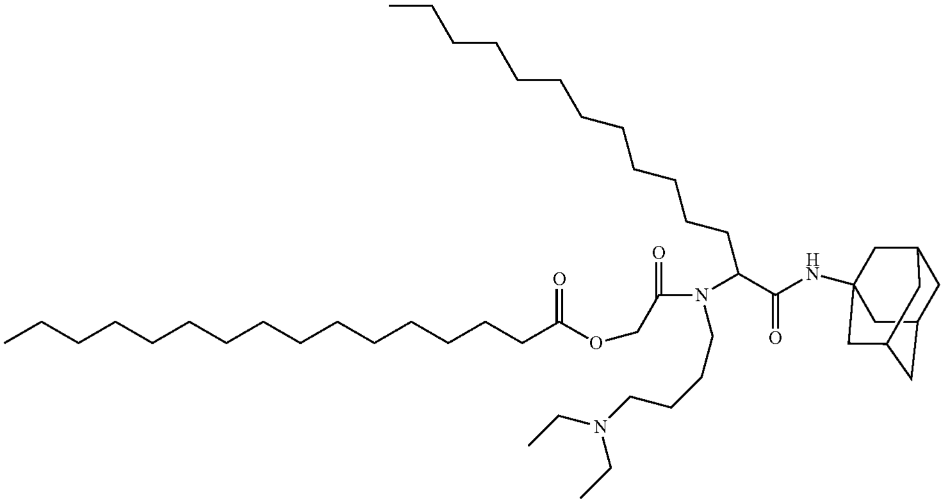
P410F12
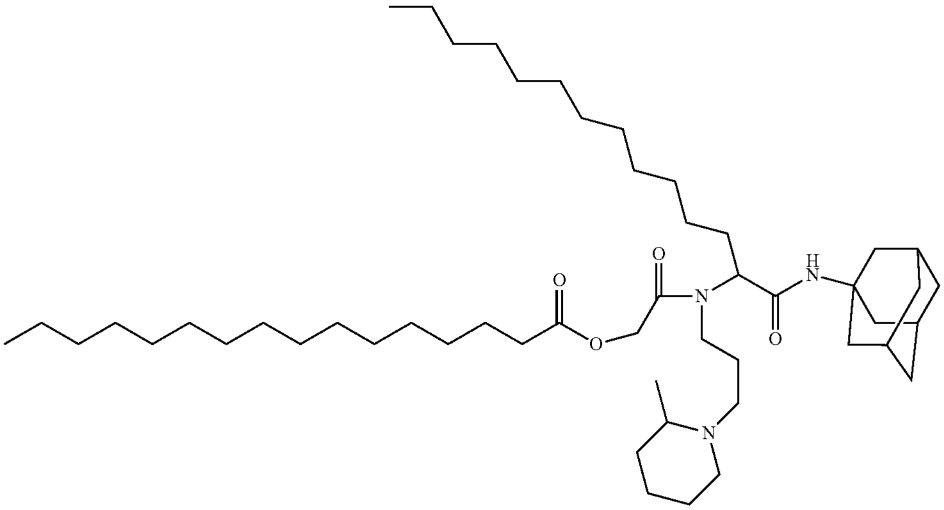
P410H4
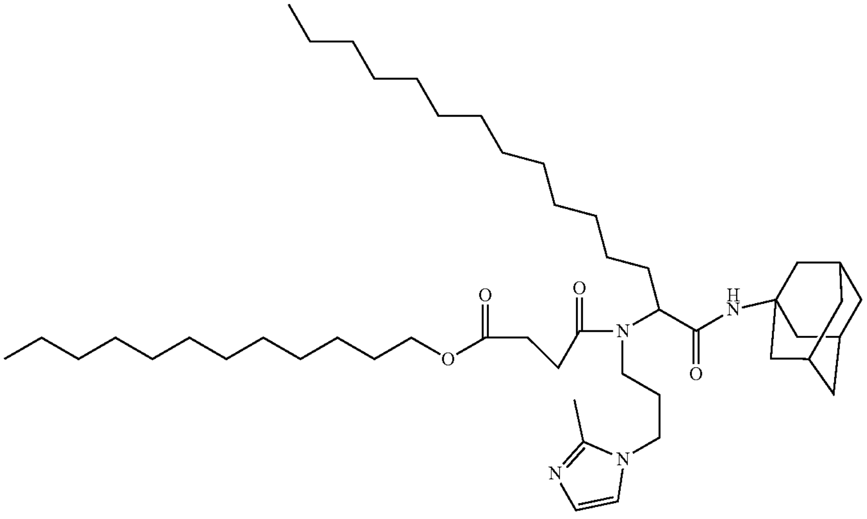

-continued
P410H6
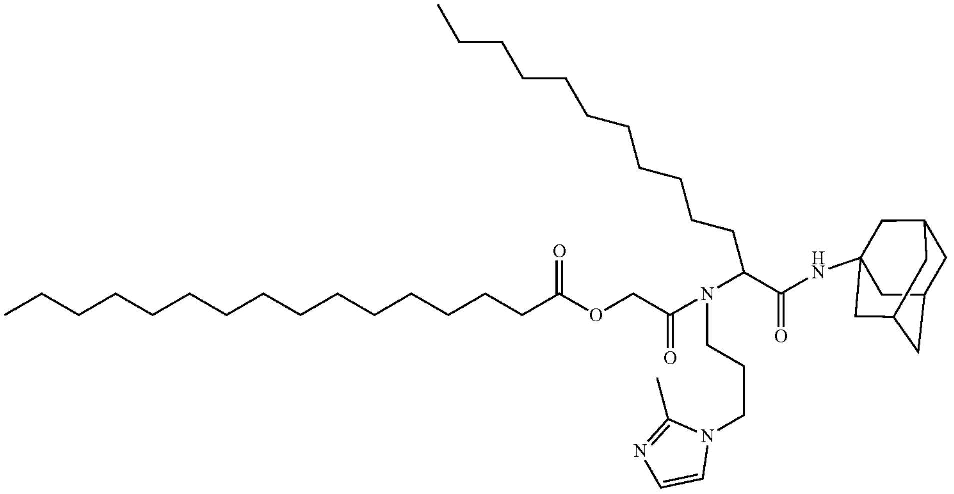
P410H8
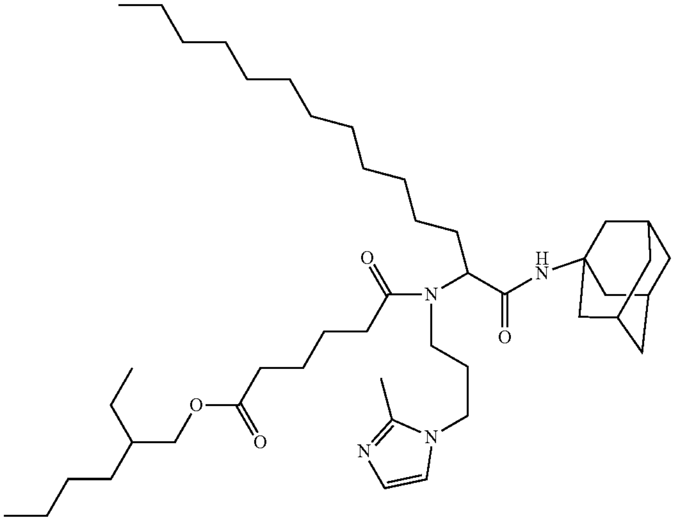
P410H10
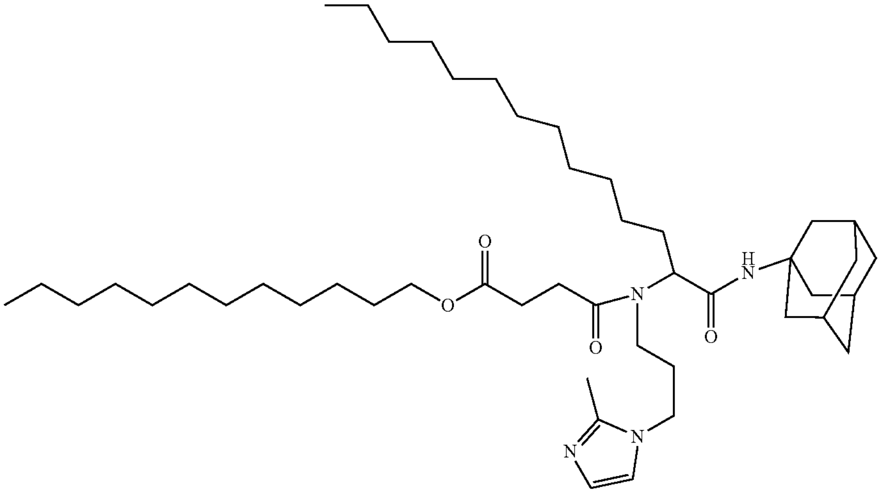

-continued
P411C6
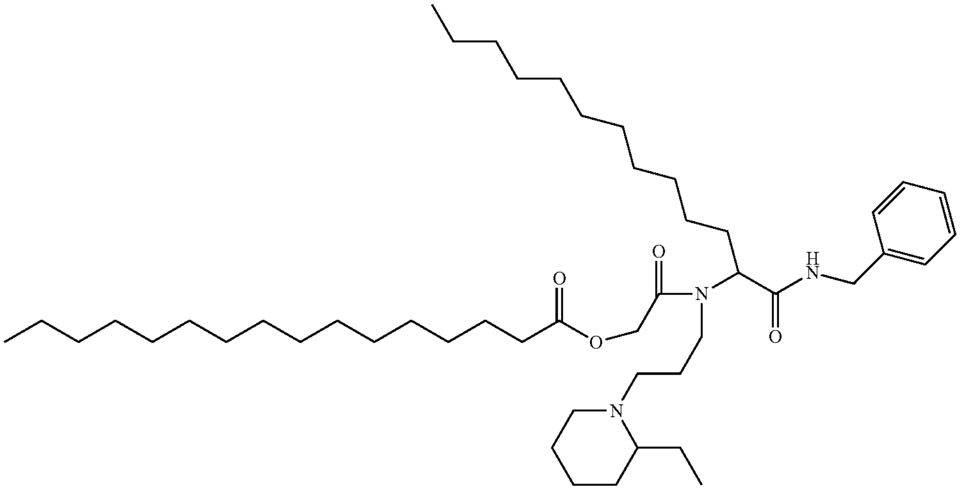
P411C12
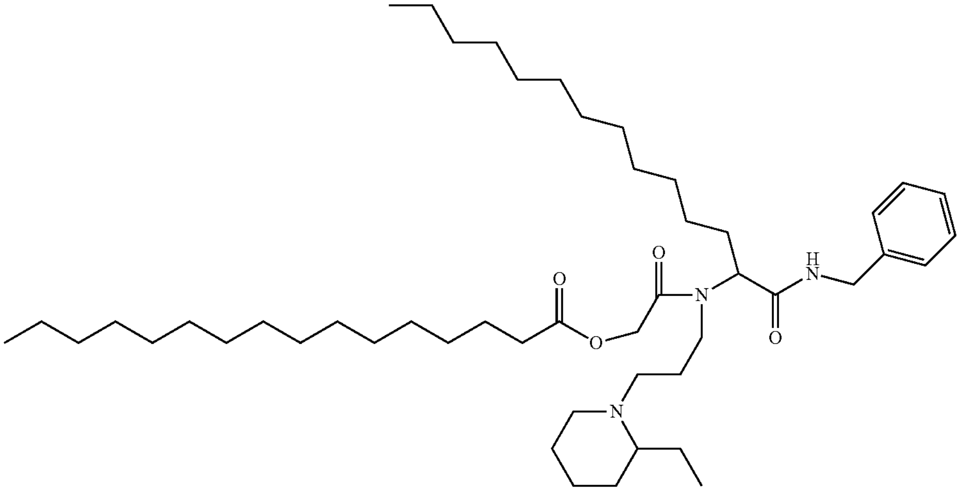
P411F12
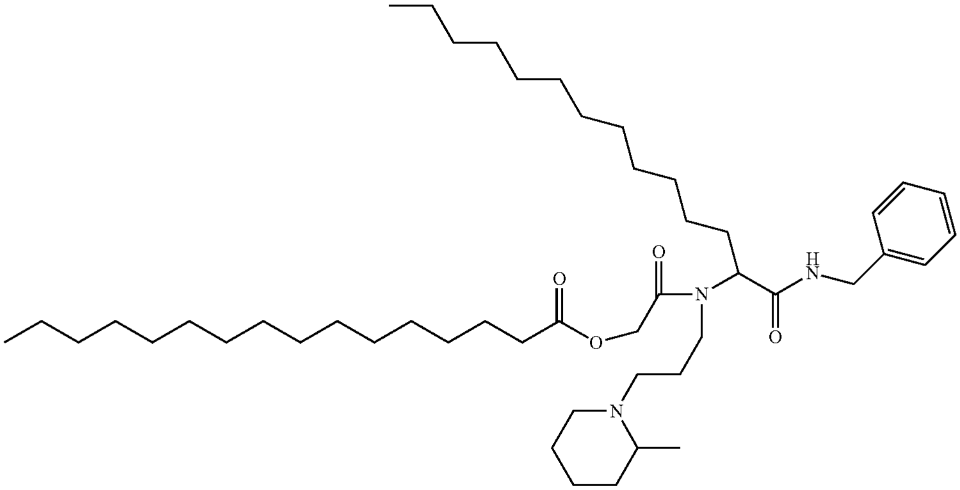

-continued
P411H6
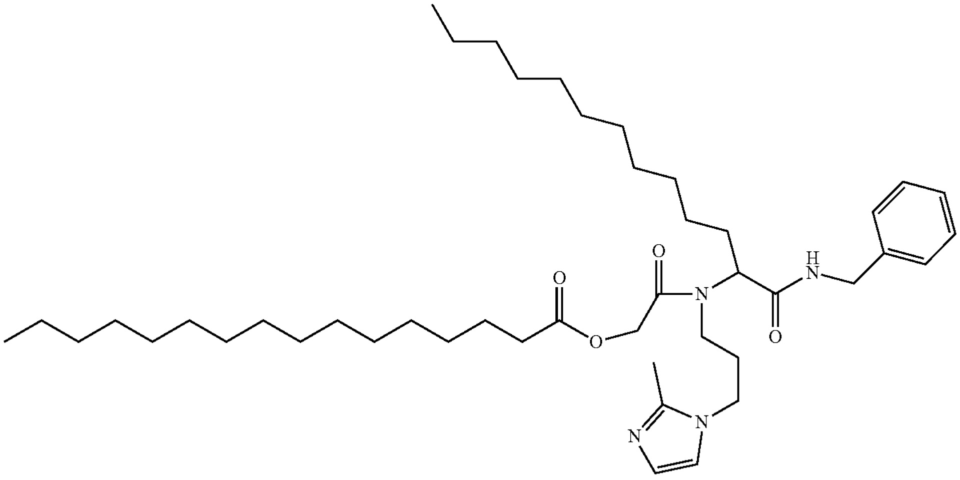
P411H10
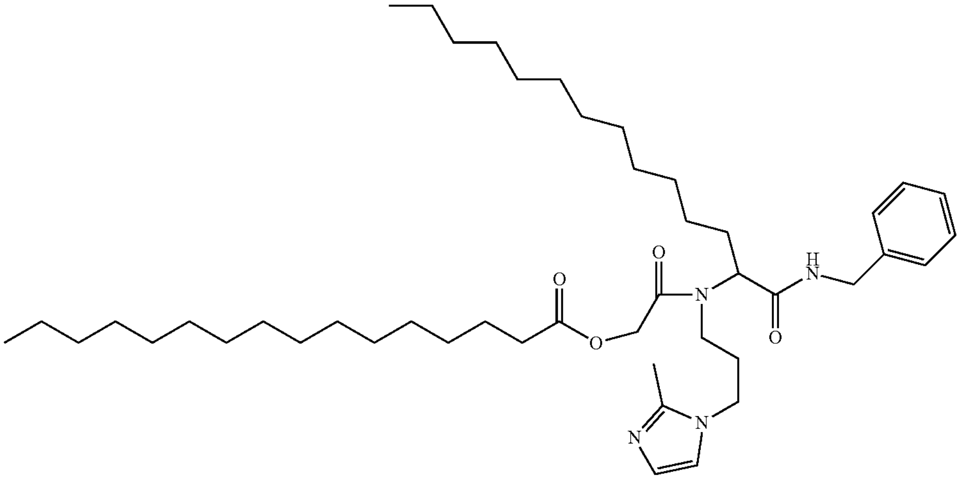
P411H12
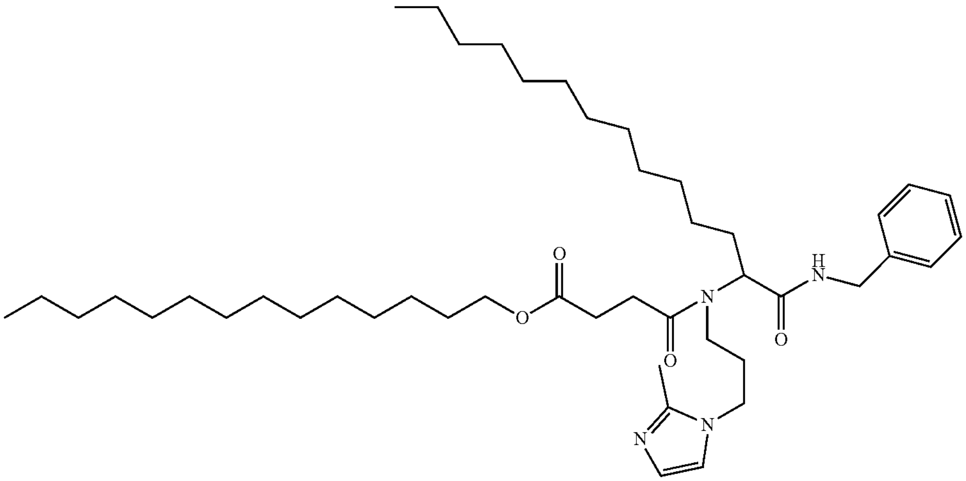

-continued
P412A6
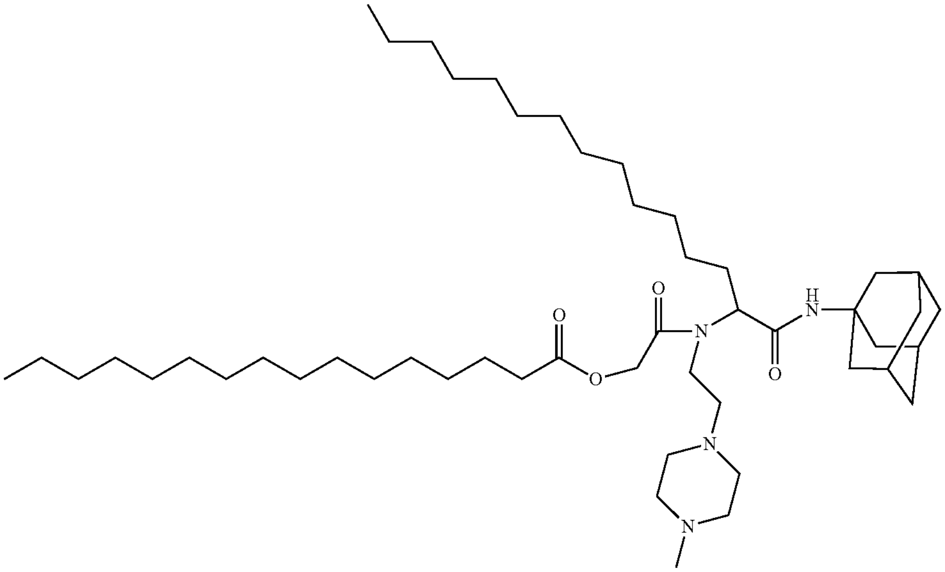
P412D6
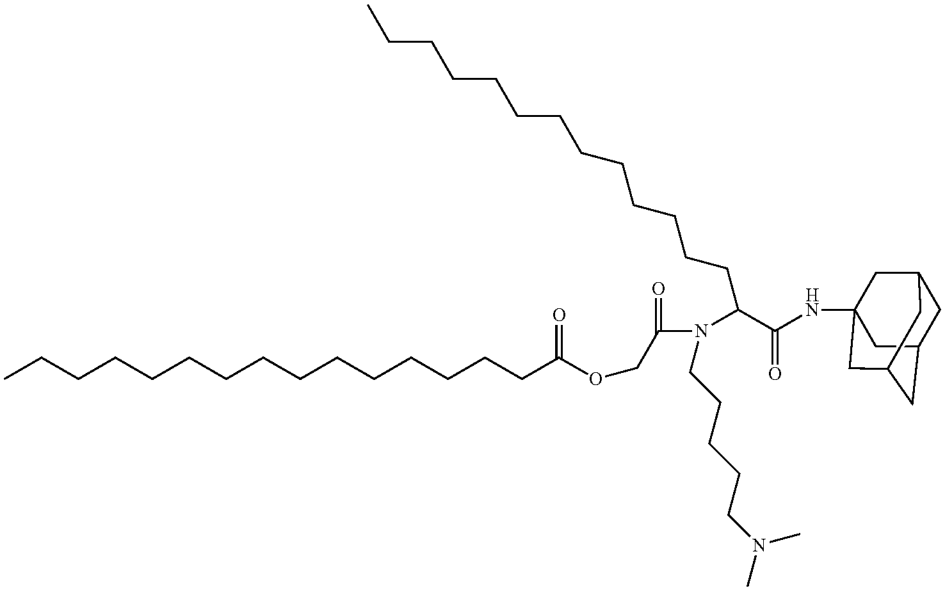

-continued
P412D10
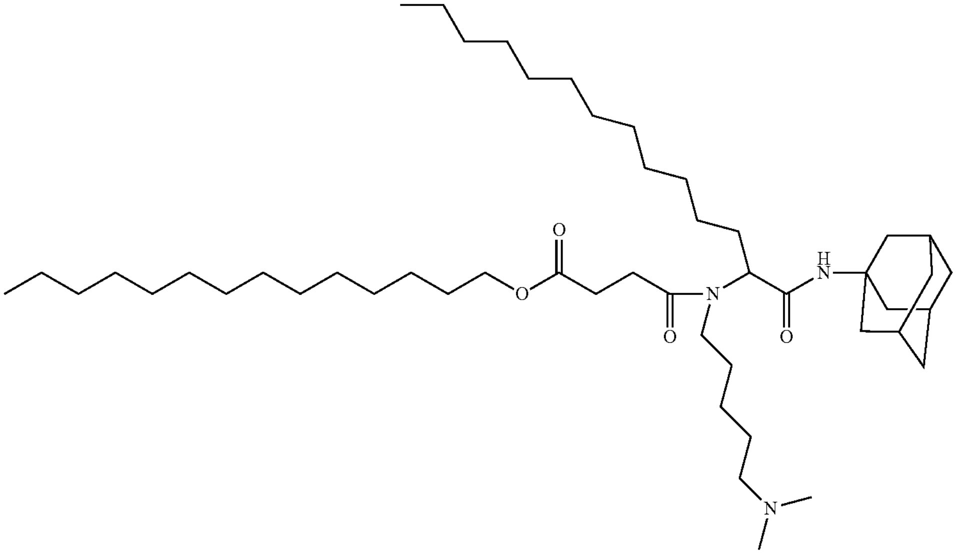
P412D12
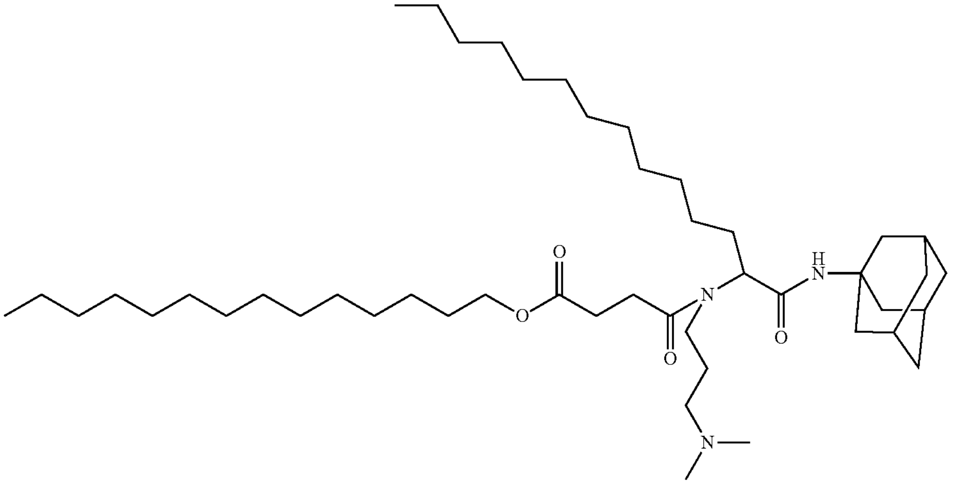
P412H2
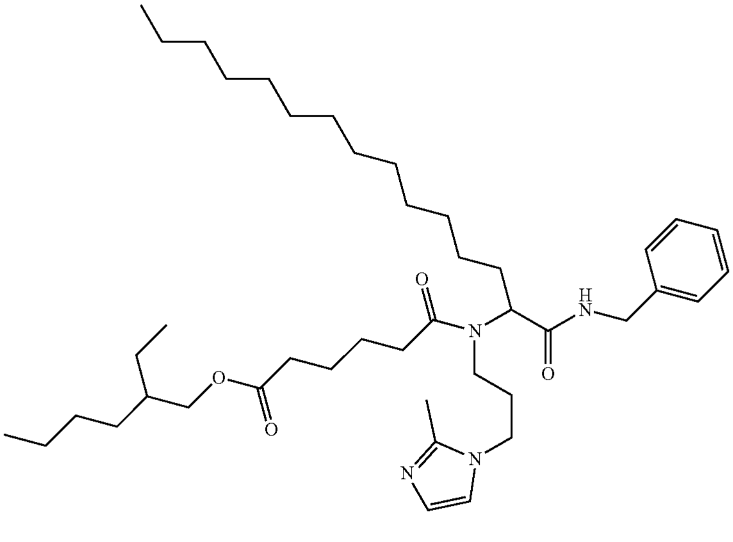

-continued
P412H4
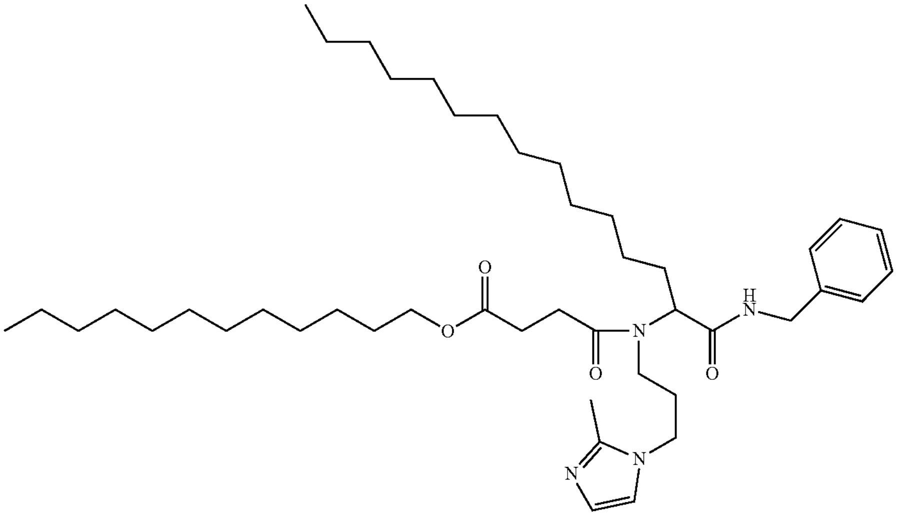
P412H6
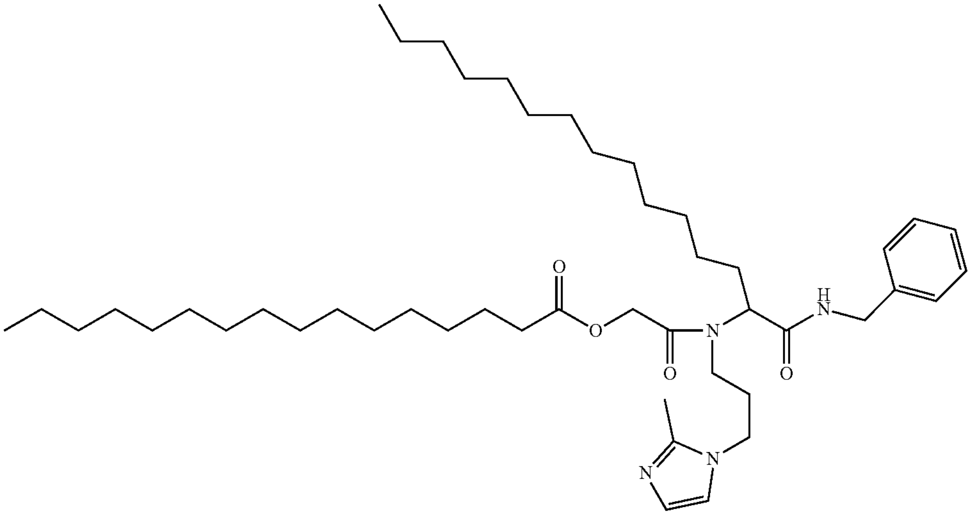
P412H10
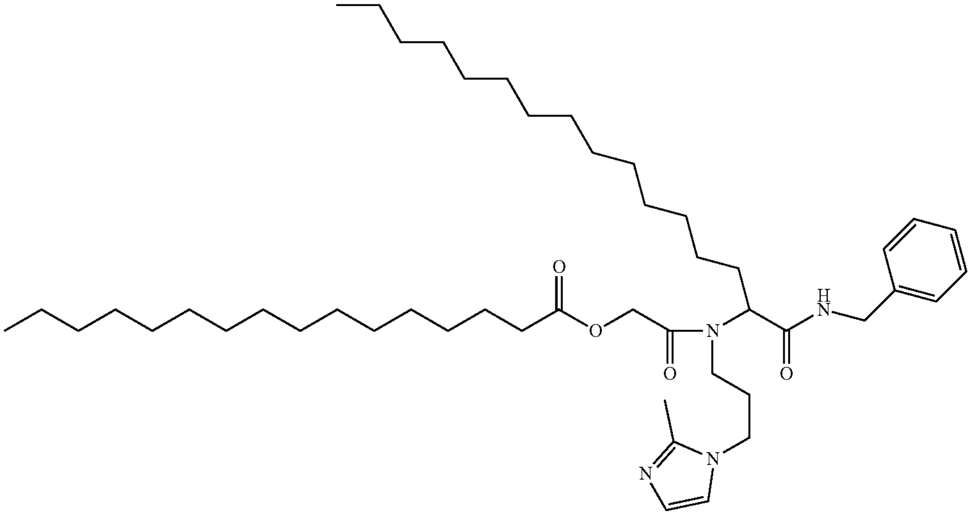

-continued
P414A10
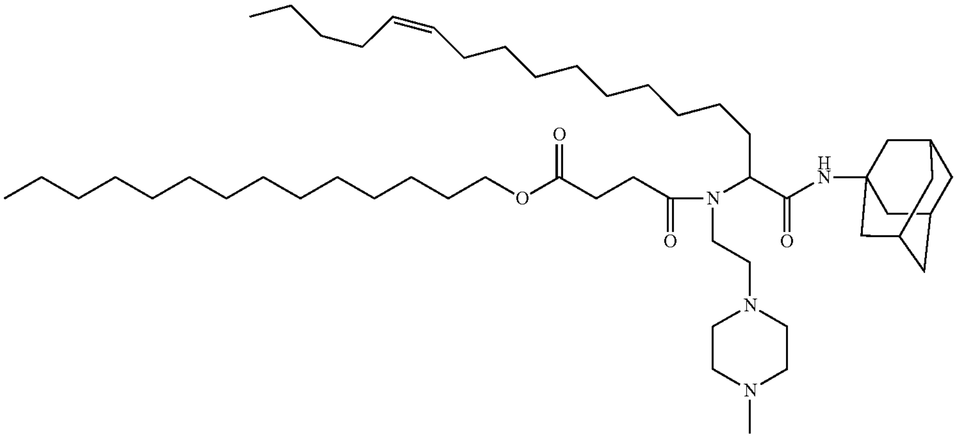
P414A11
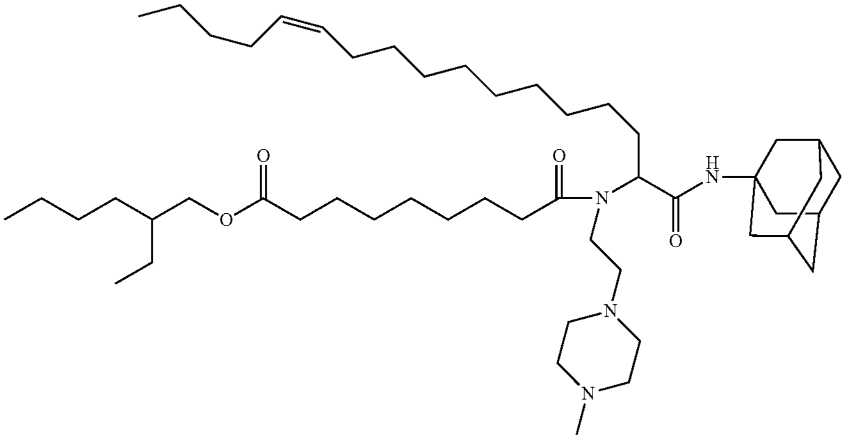
P414A12
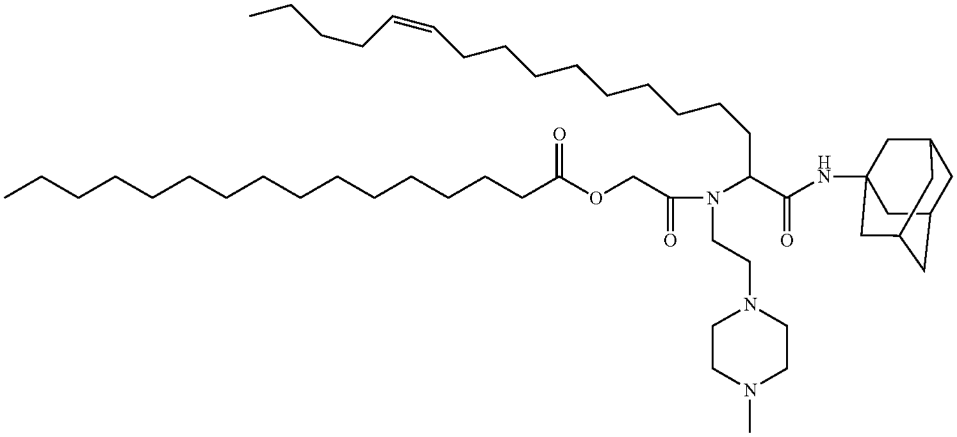

-continued
P414D12
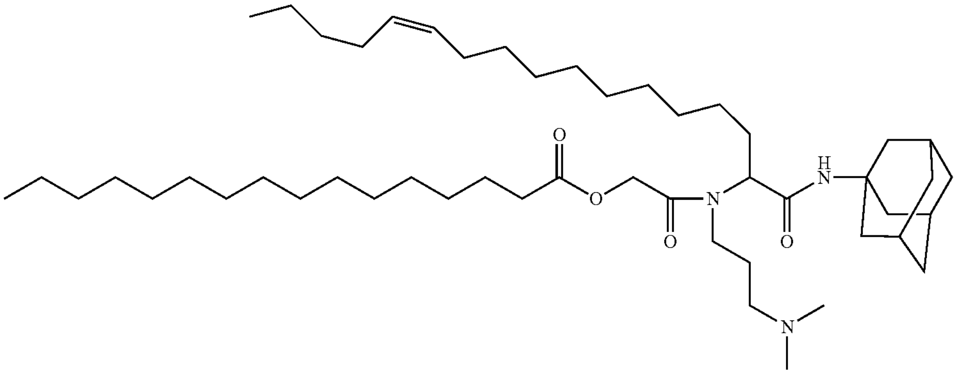
P414E12
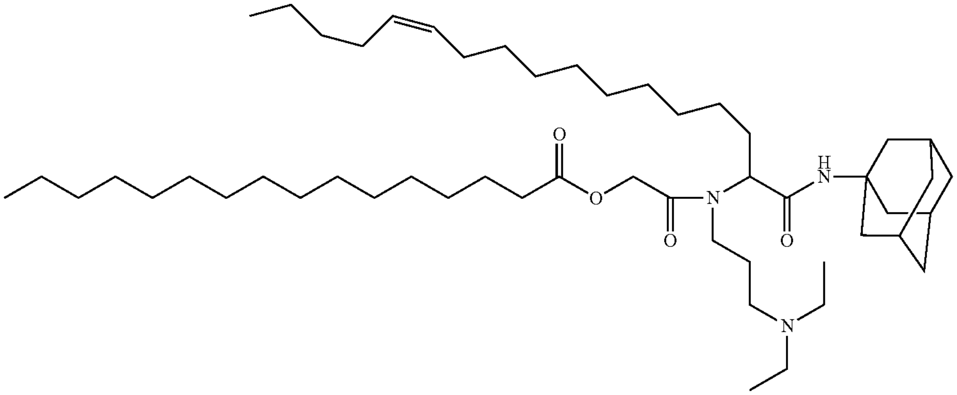
P415A12
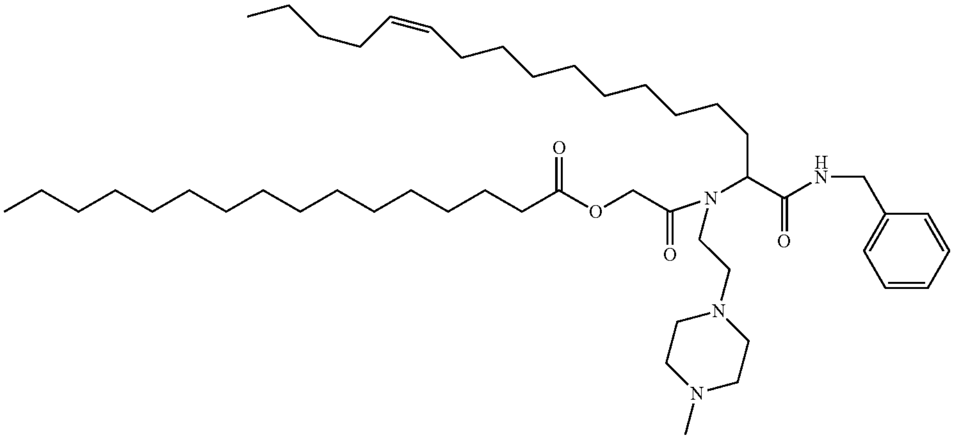
P415C12
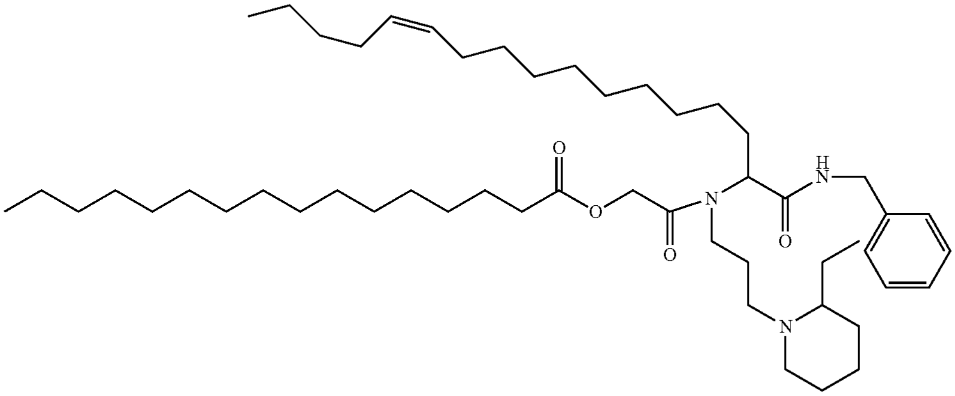

-continued
P415C12
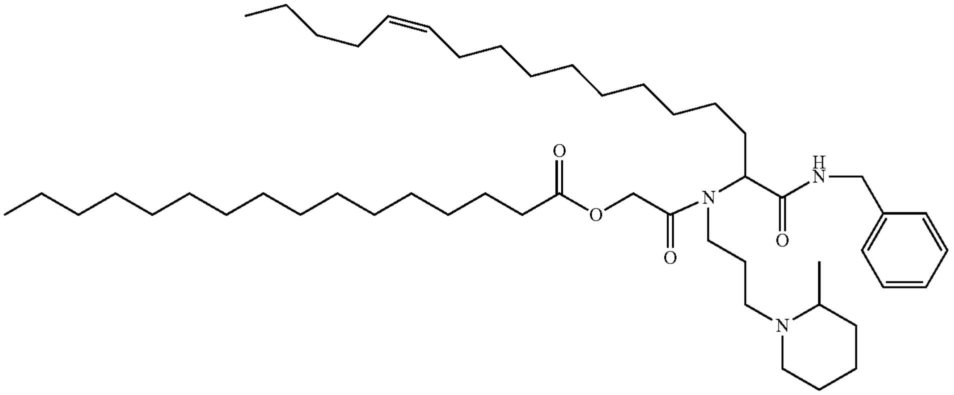
P416D4
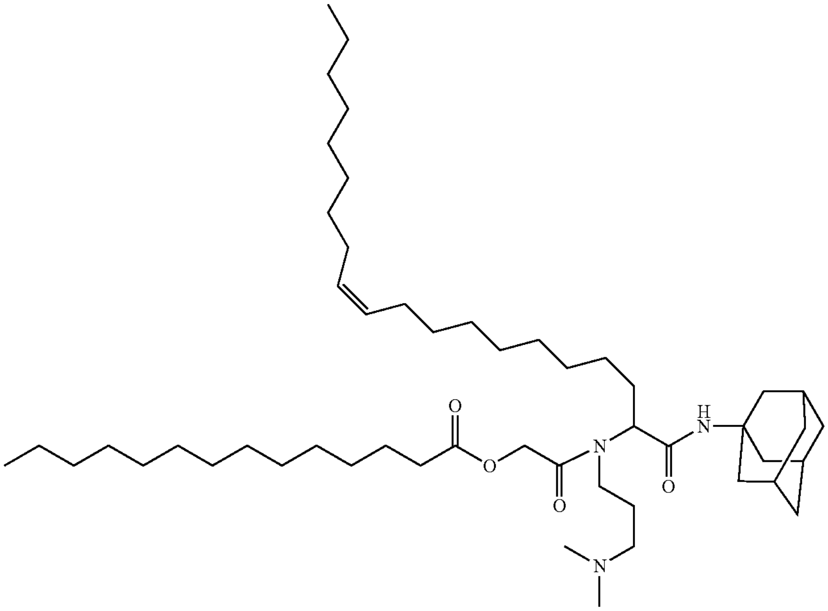
P416D6
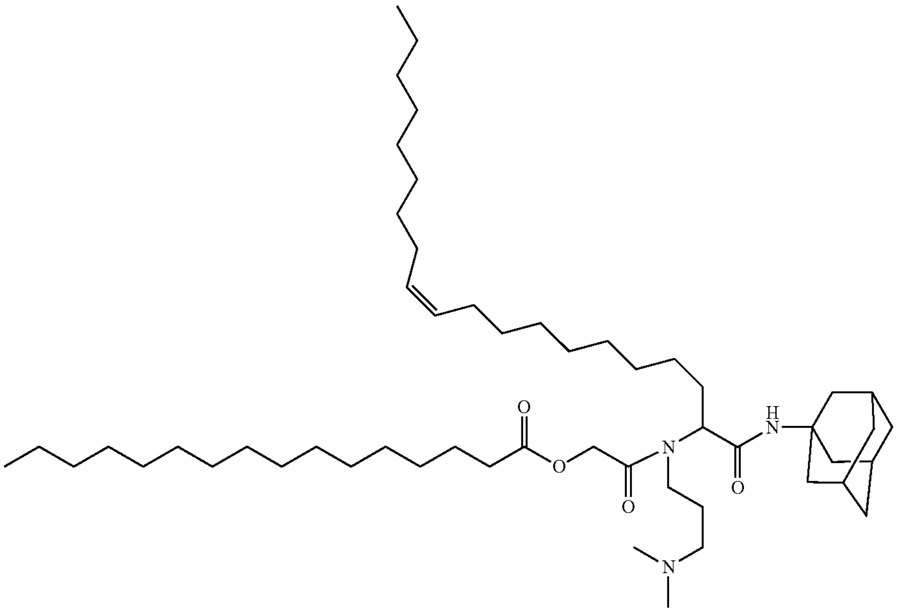

-continued
P416E4
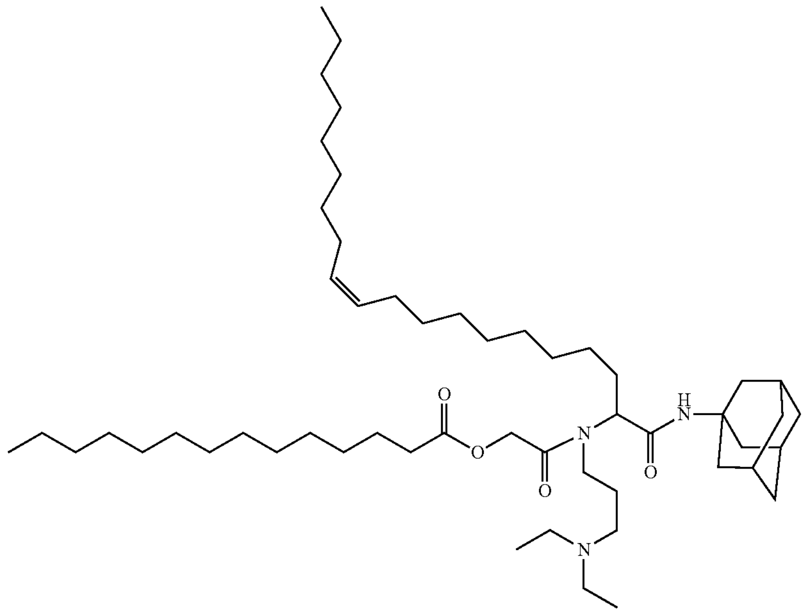
P416E6
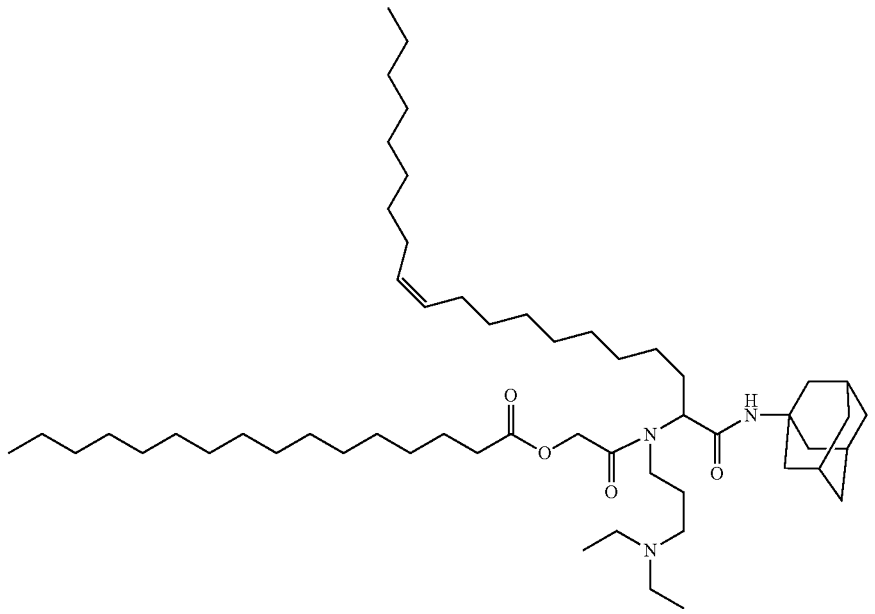

-continued
P417A4
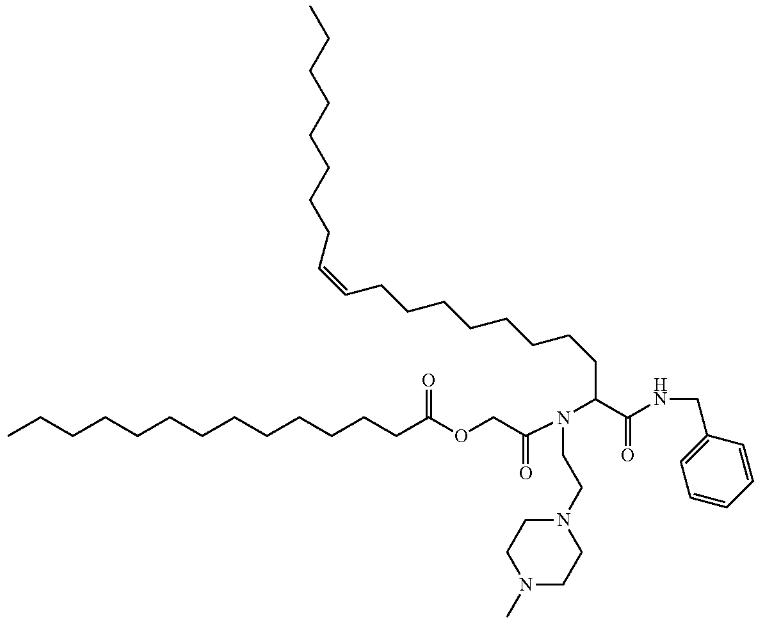
P417D6
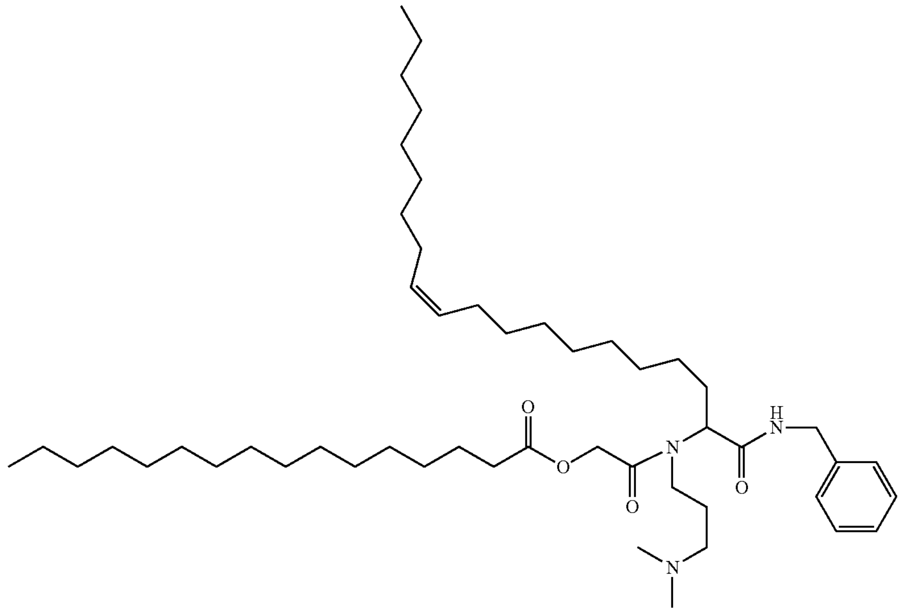

-continued
P417E6
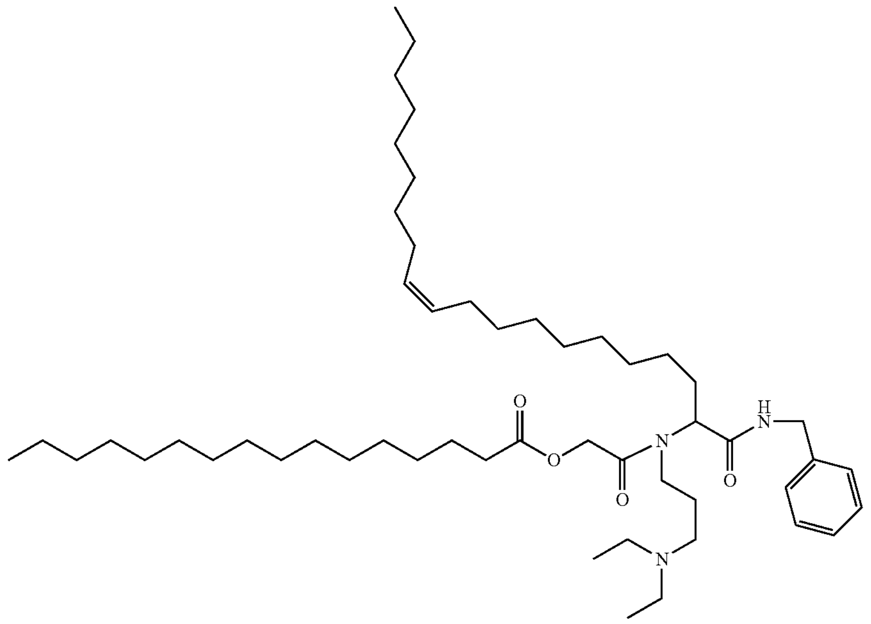
P417F4
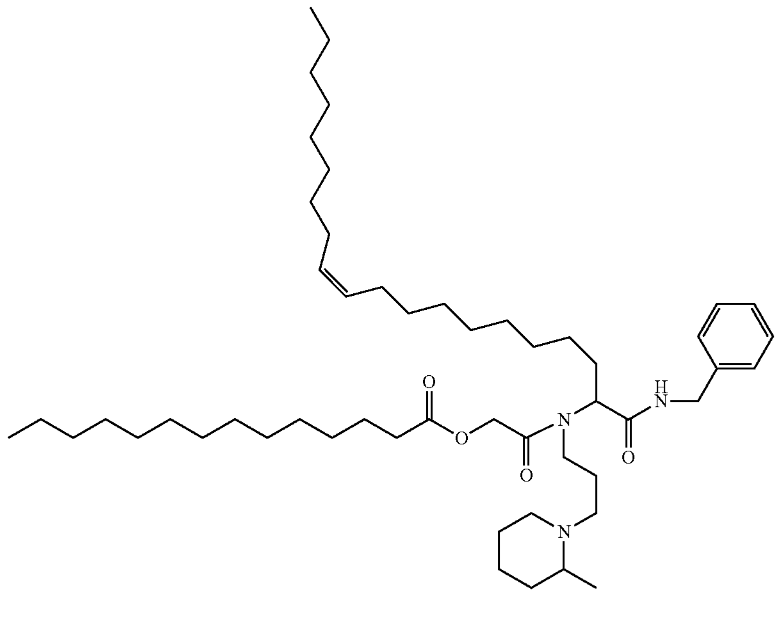

-continued
P417H2
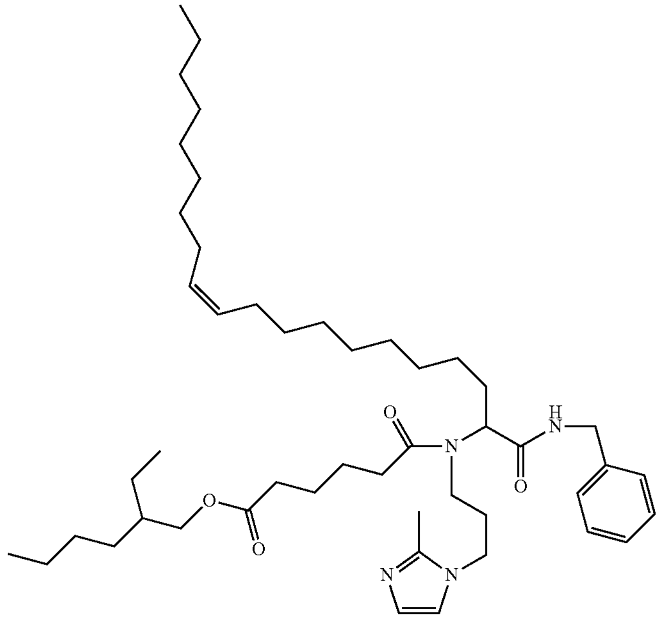
P417H4
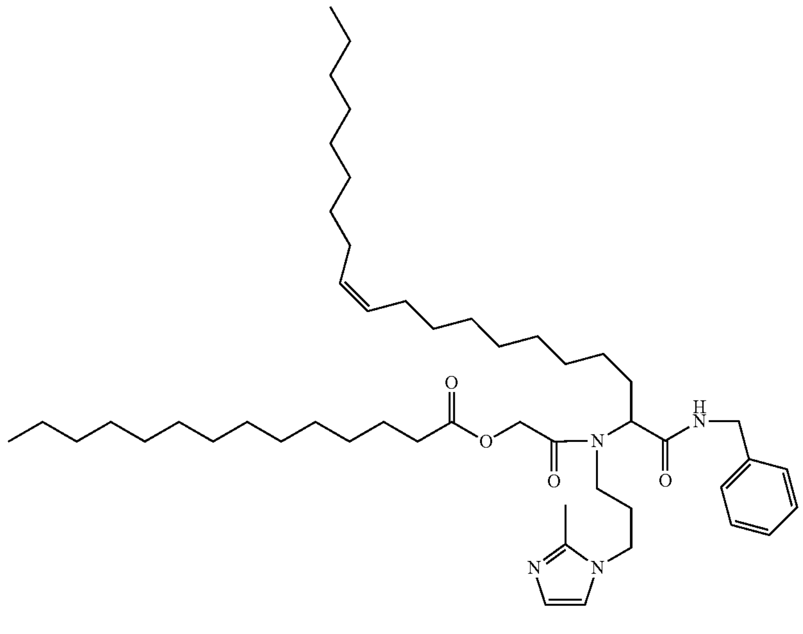

-continued
P417H6
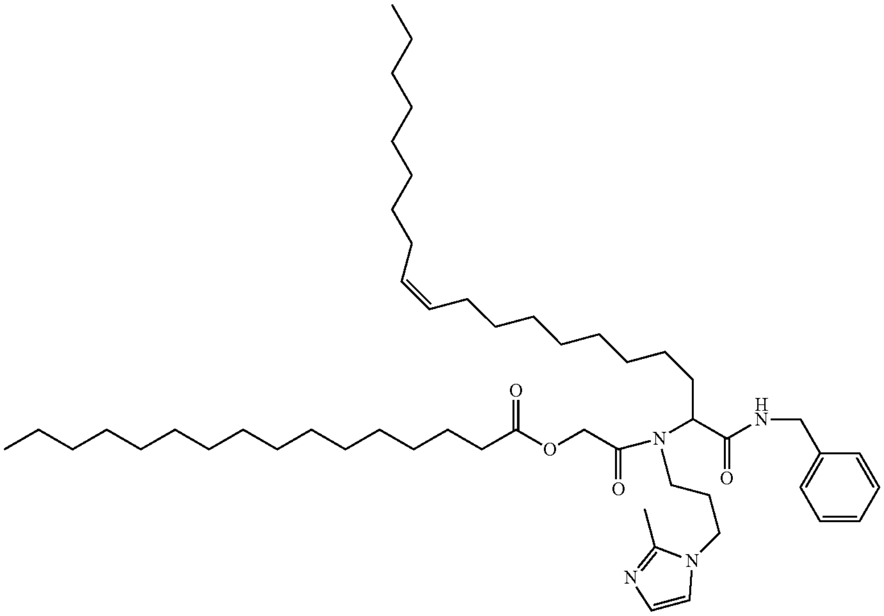
P432A2
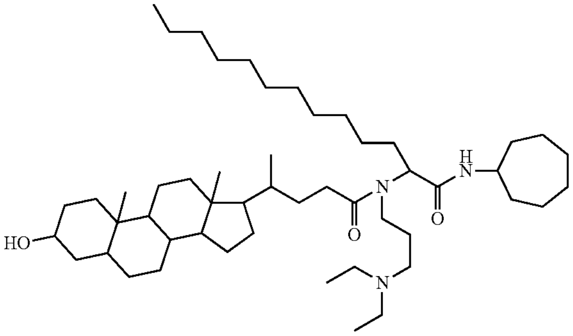
P423C7
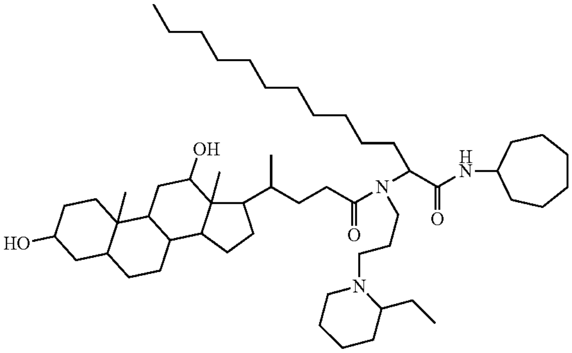
P429D1
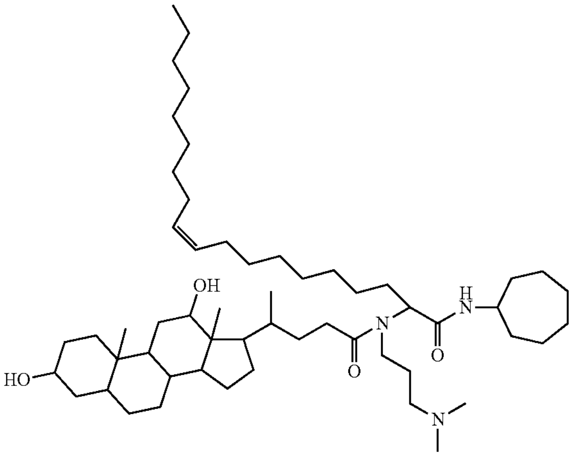
P441D1
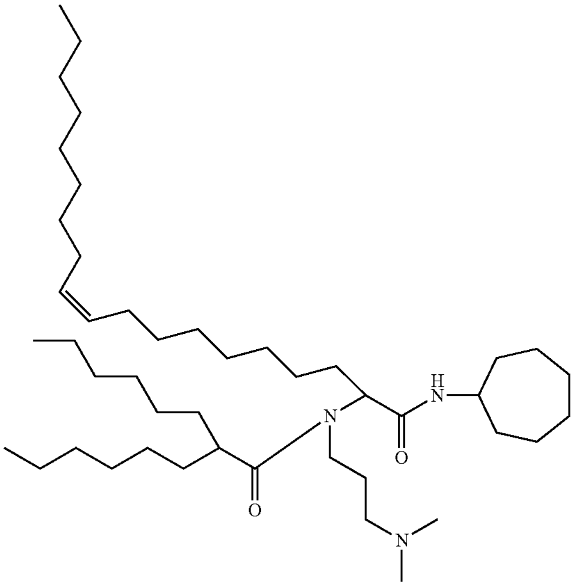

-continued
P442H1
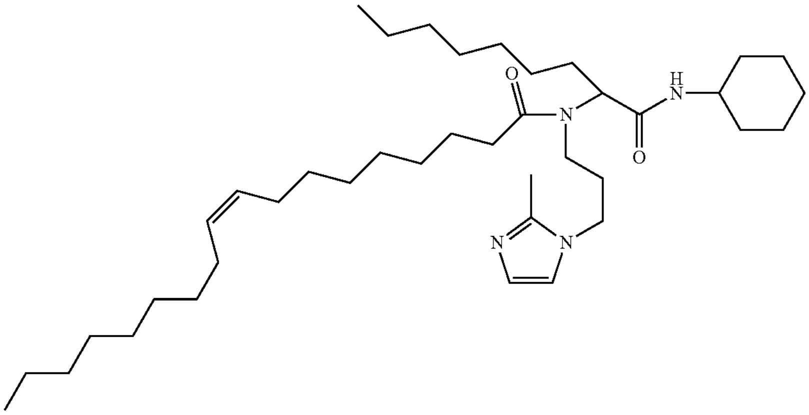
P442H7
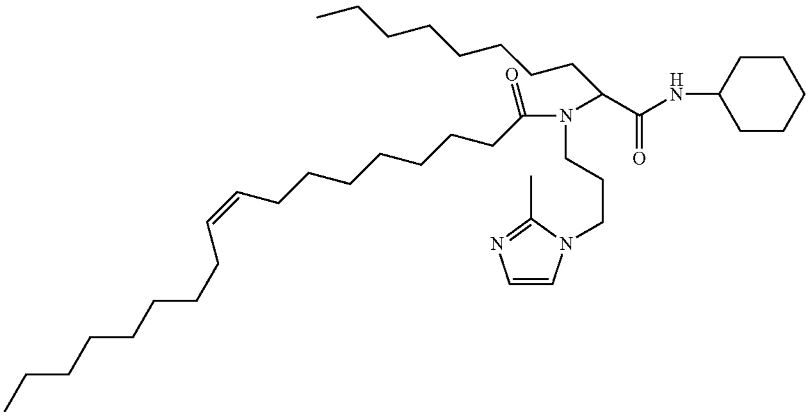
P443H1
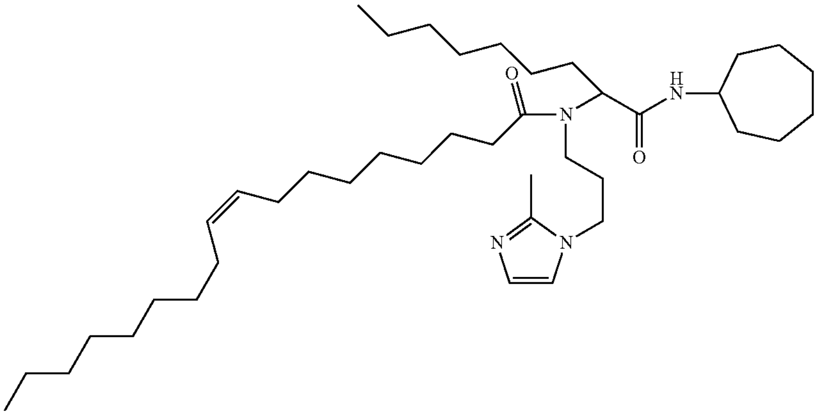

-continued
P443A1
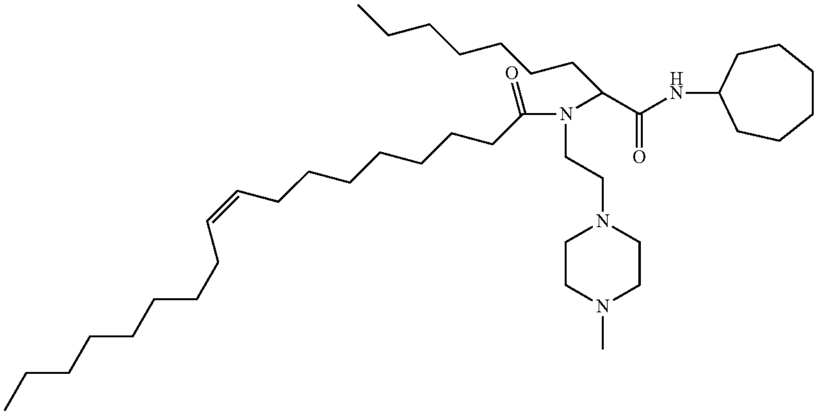
P443A7
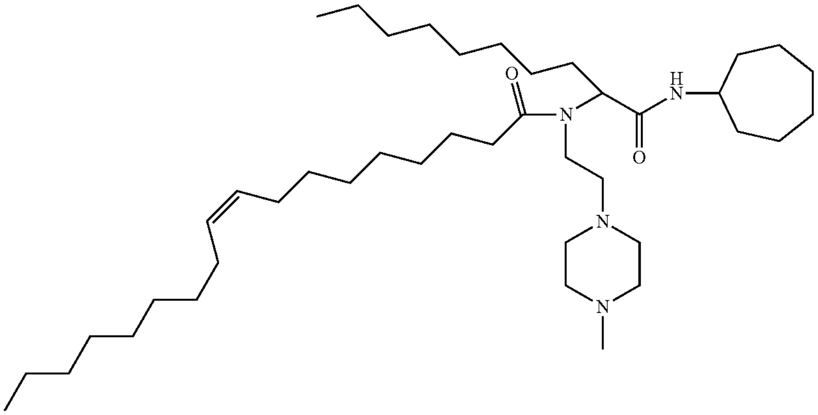
P446H7
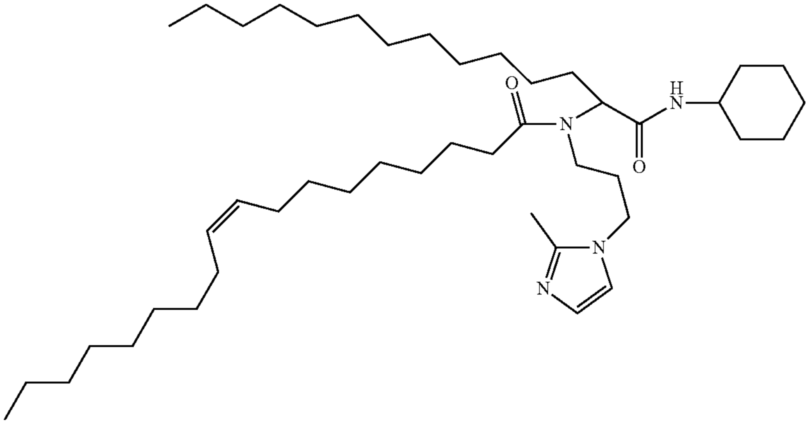

-continued
P446D7
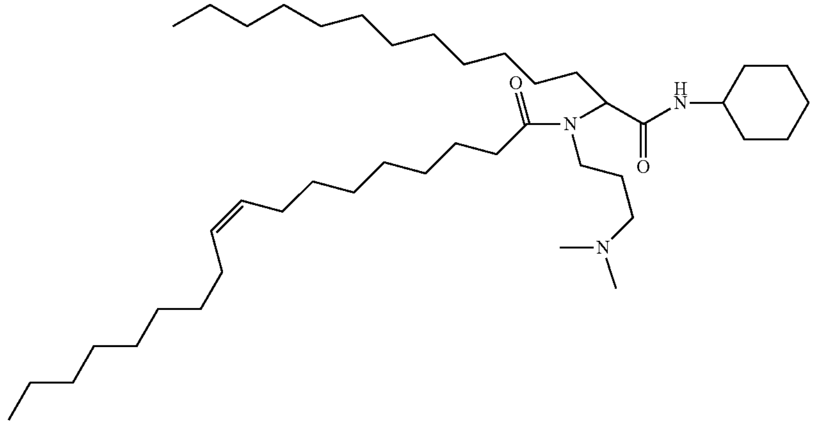
P446D12
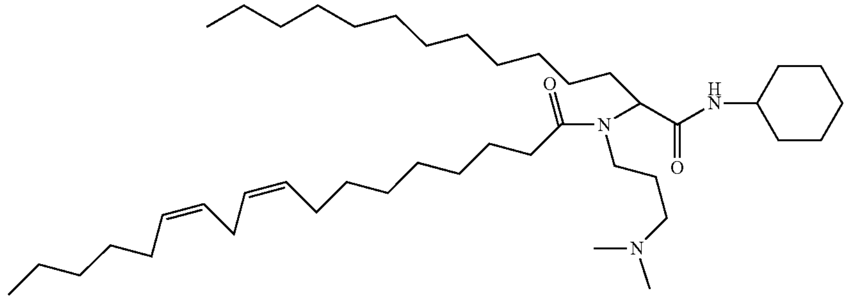
P447A1
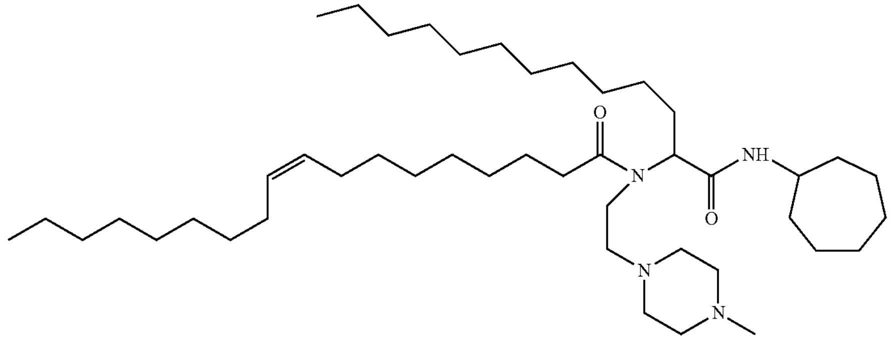
P447A6
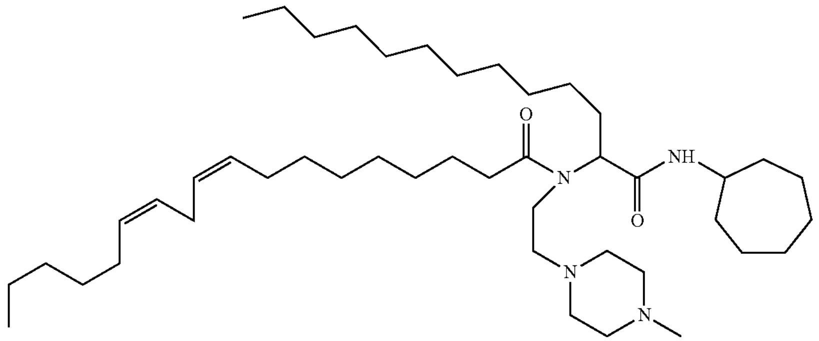

-continued
P447A7
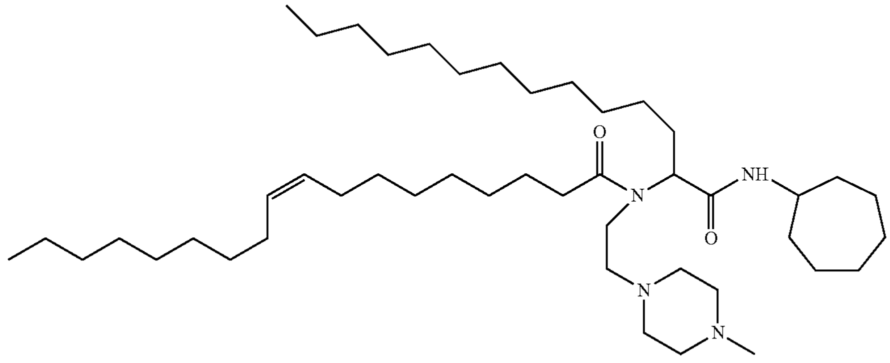
P447A9
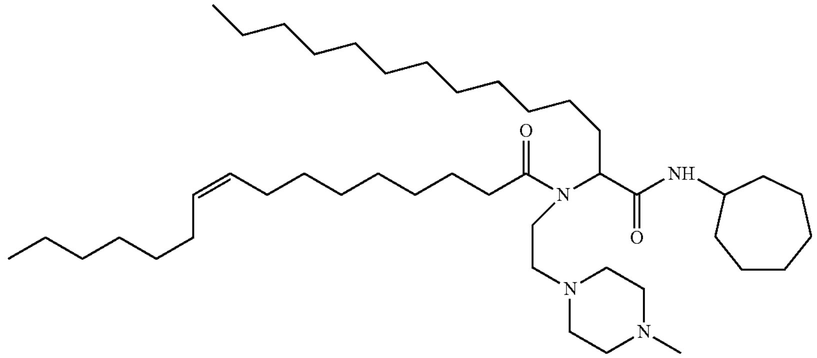
P447A12
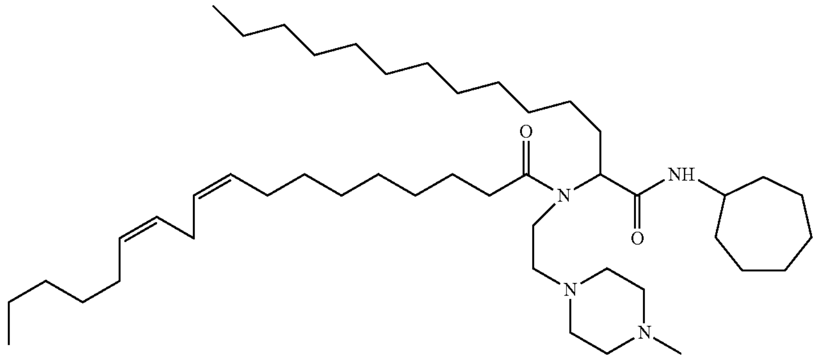
P447D1
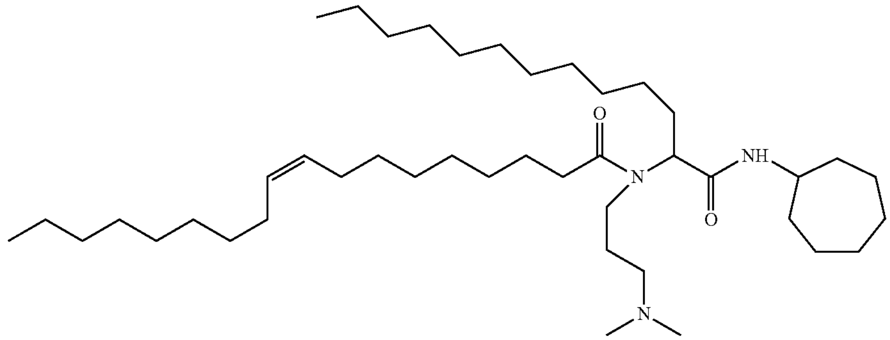

-continued
P447D6
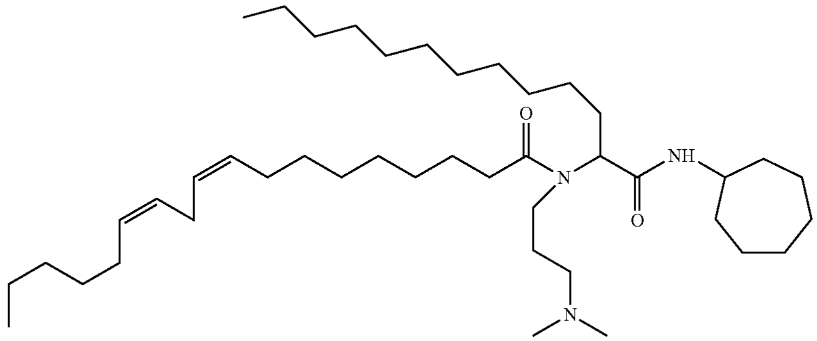
P447D7
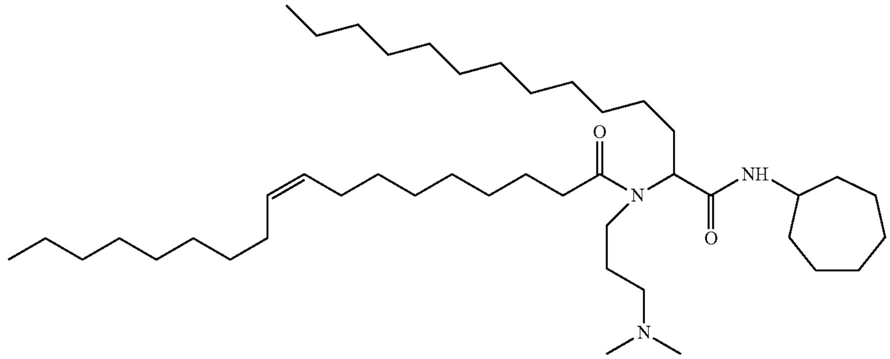
P447D12
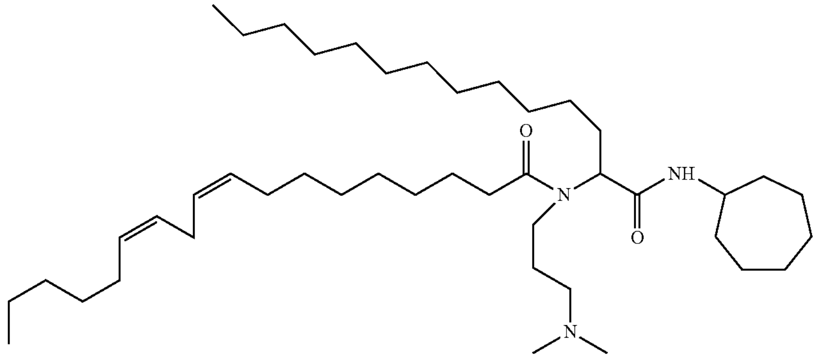
P447H1
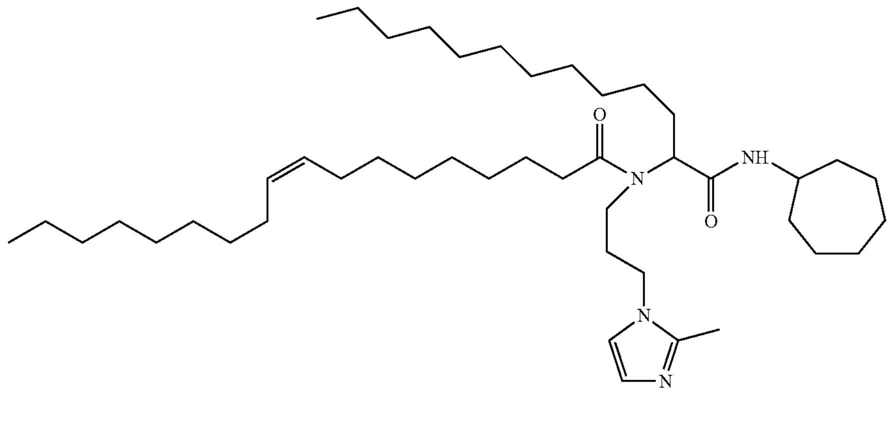

-continued
P447H3
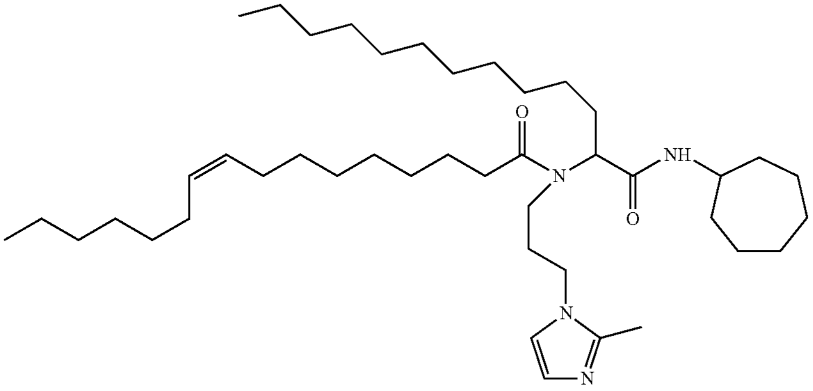
P447H7
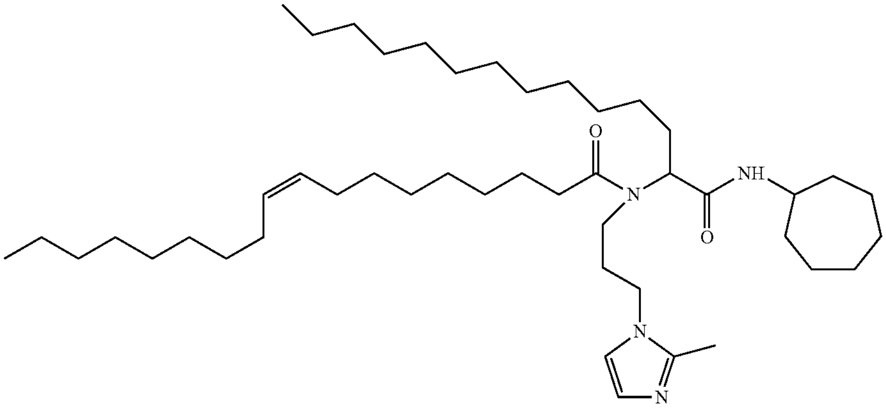
P447H9
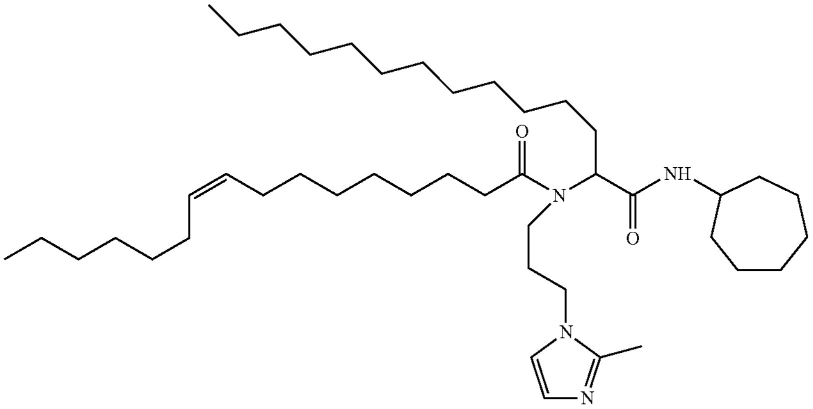
P447H10
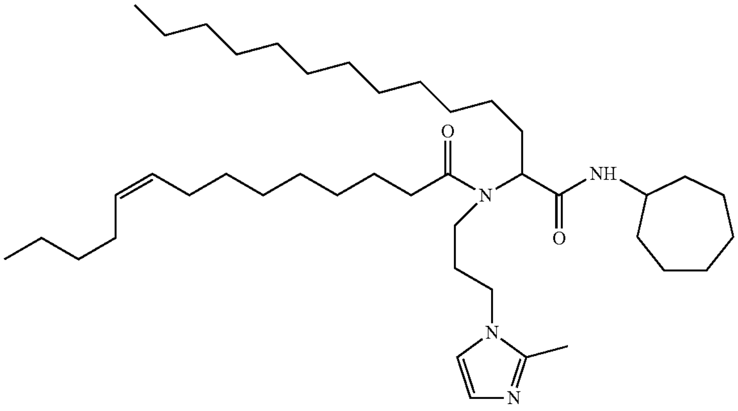

-continued
P447H12
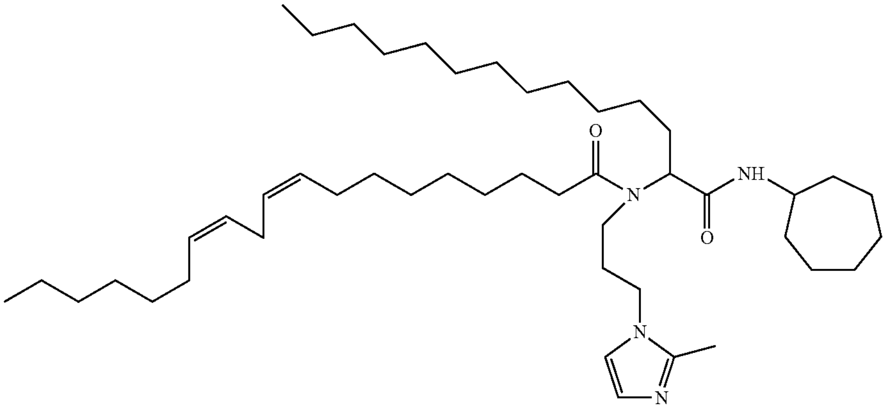
P448A1
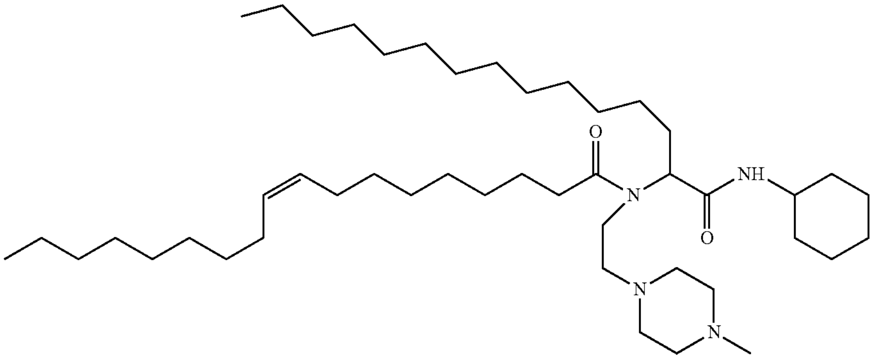
P448A6
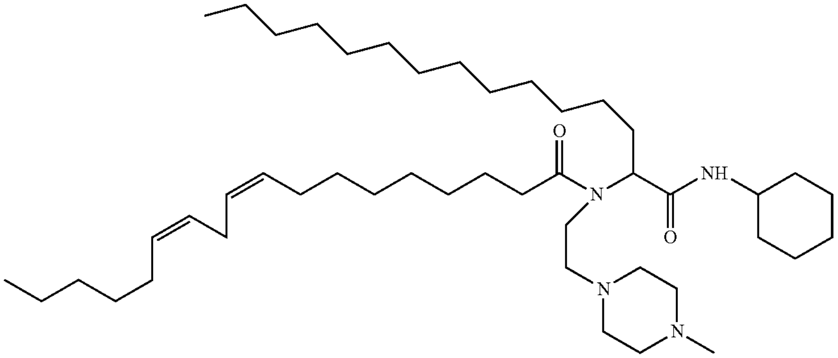
P448D7
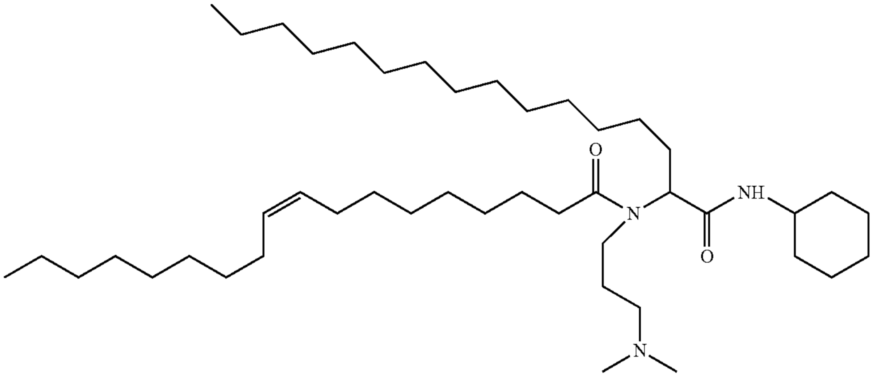

-continued
P448H7
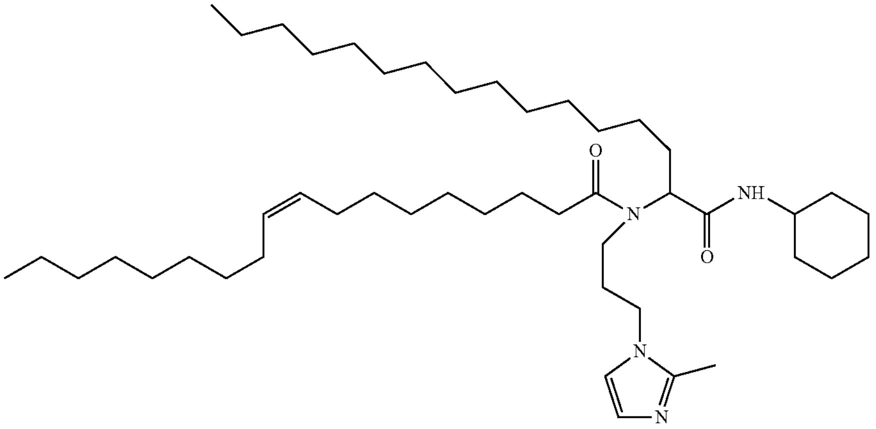
P448H9
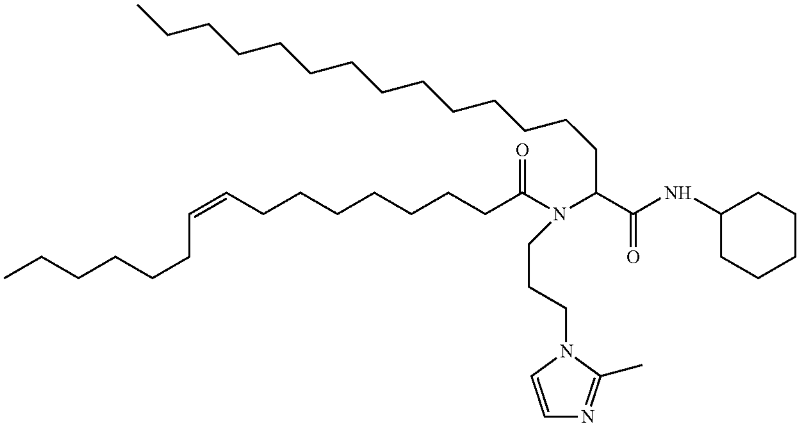
P449A3
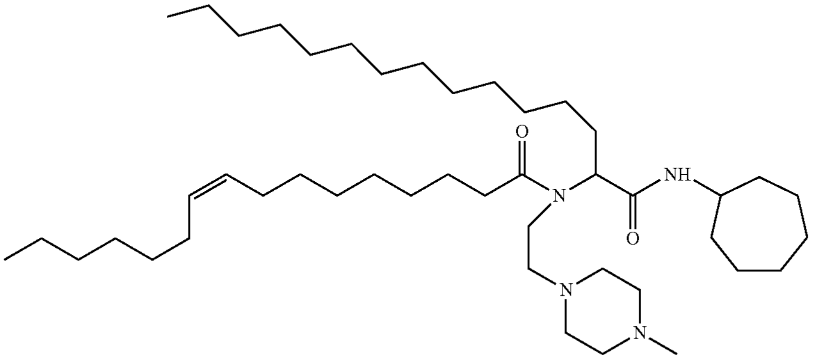
P449A6
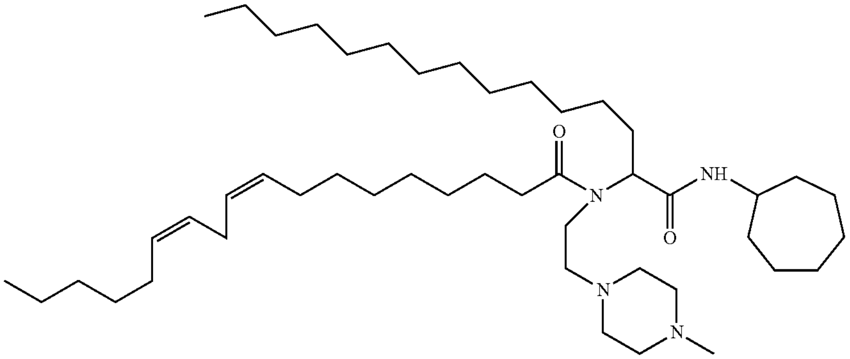

-continued
P449A12
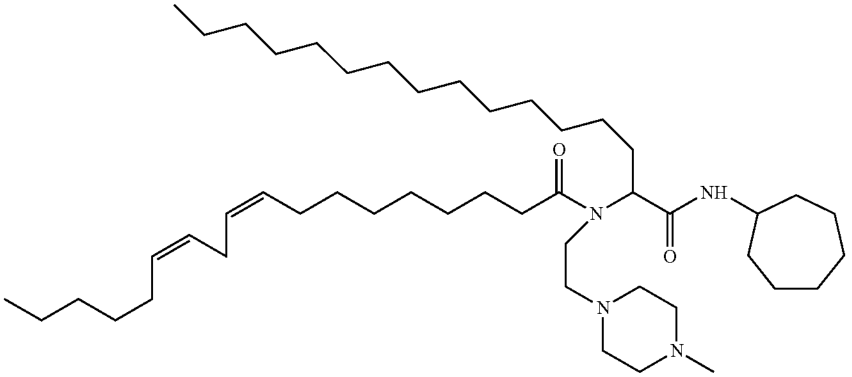
P449D1
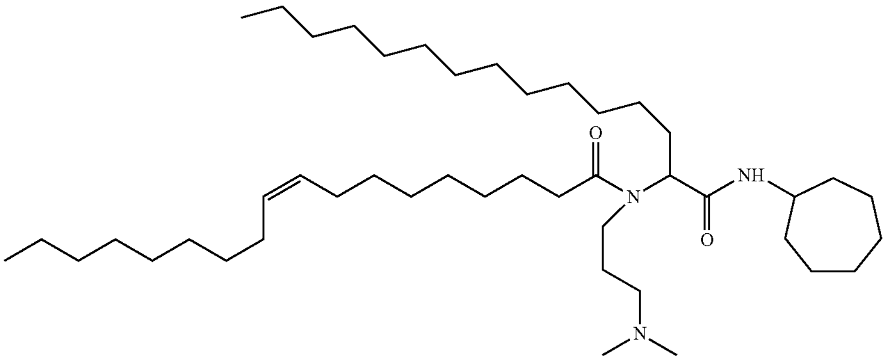
P448H7
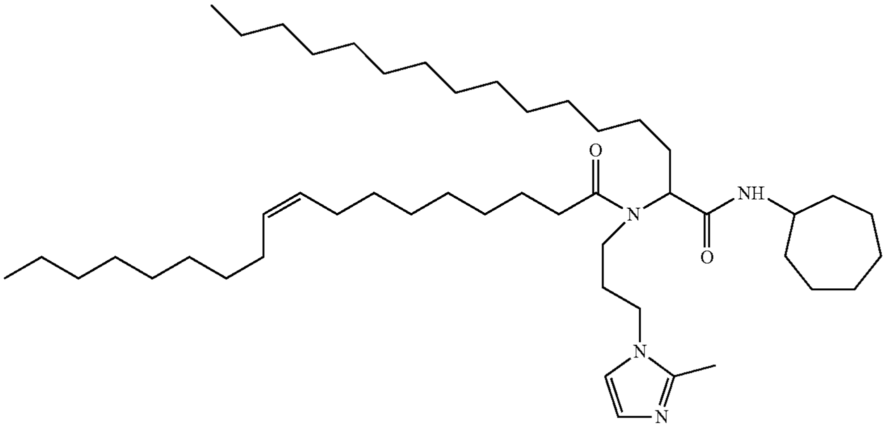
P451A7
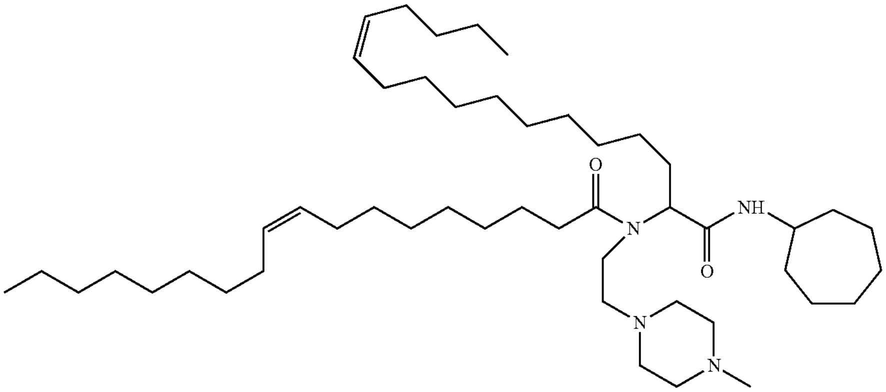

-continued
P451A9
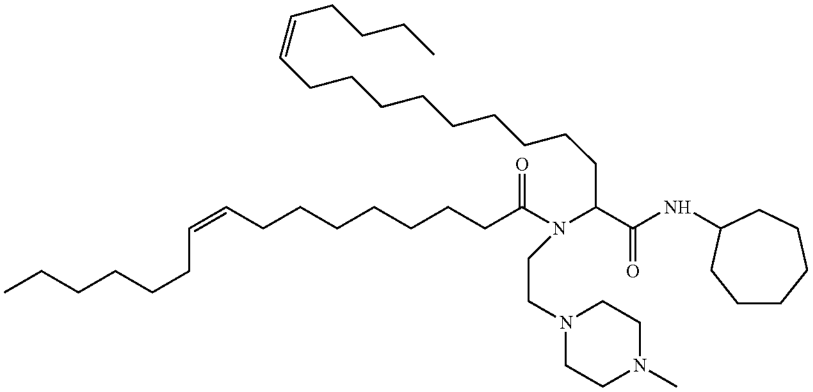
P451A10
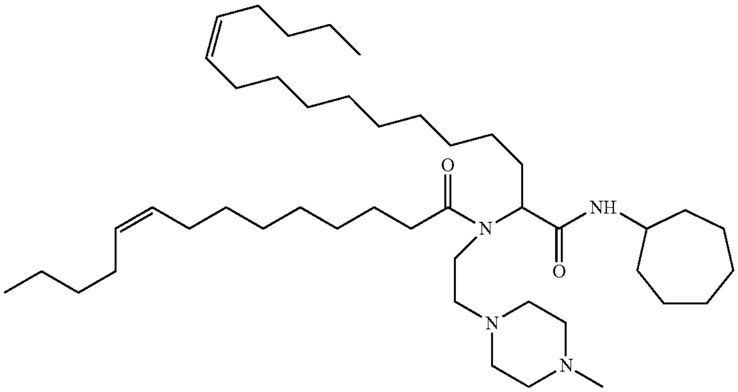
P451A12
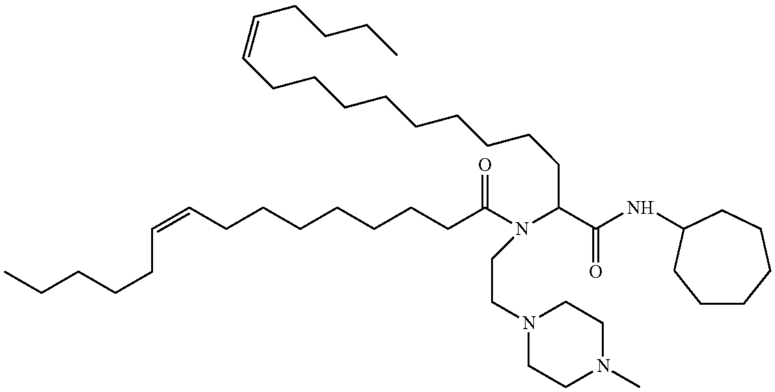

P451D12
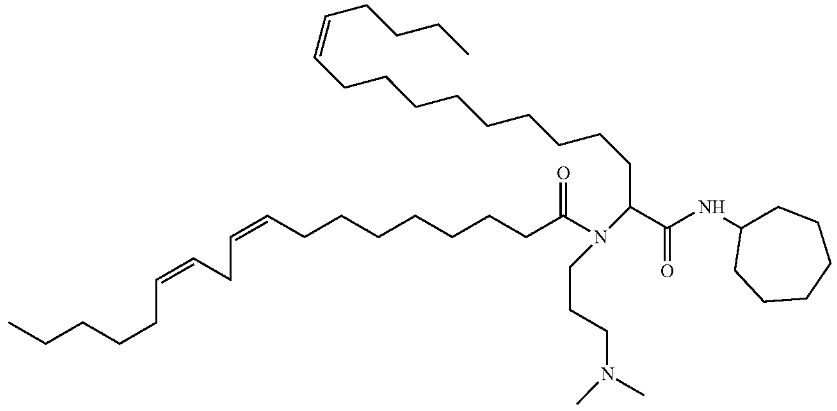
P451H7
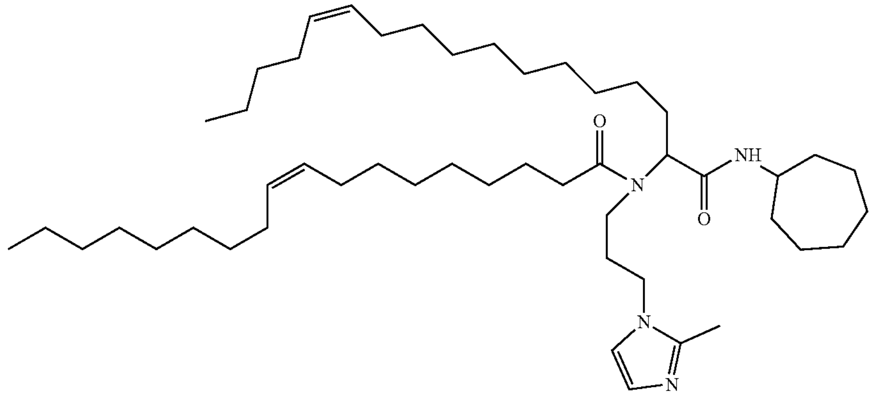
P451H9
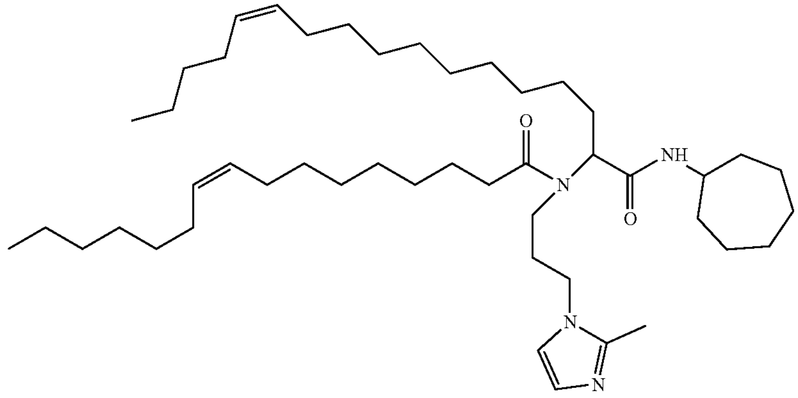

-continued
P453A4
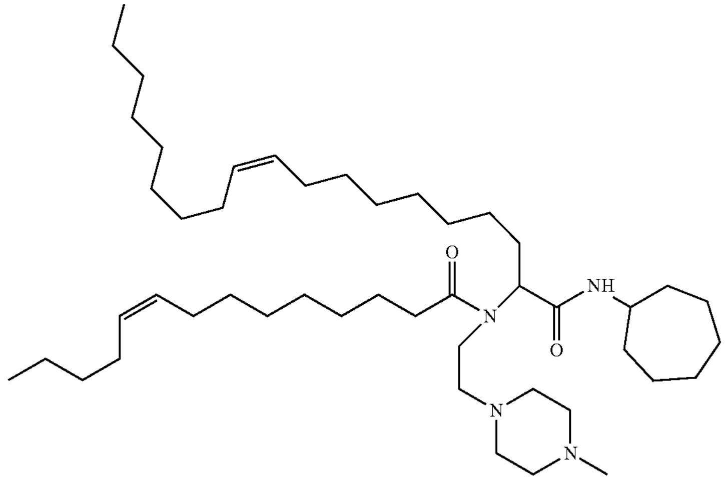
P453A6
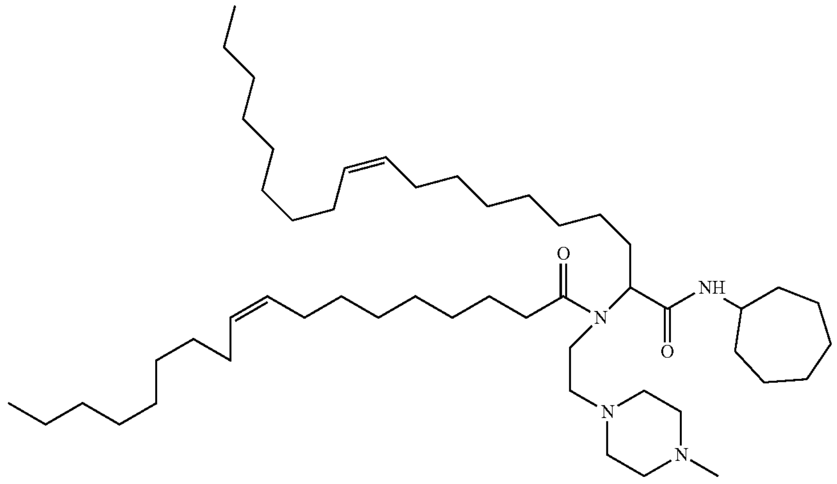
P453H1
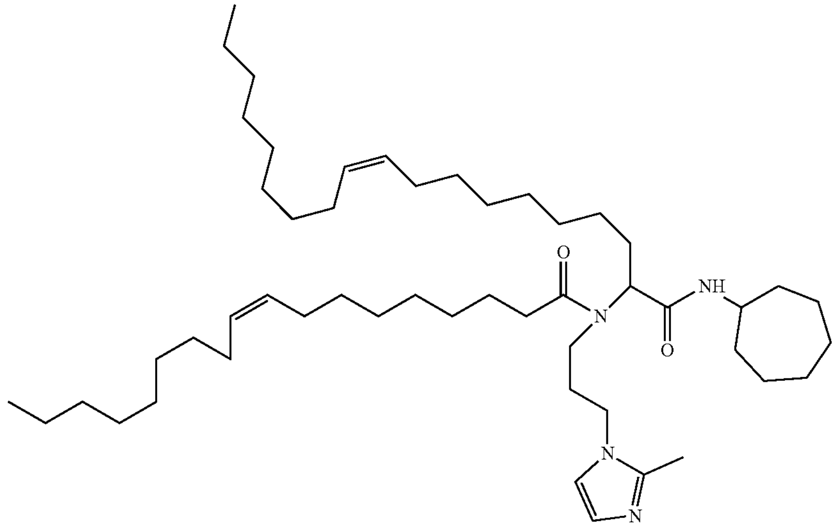

-continued
P453H3
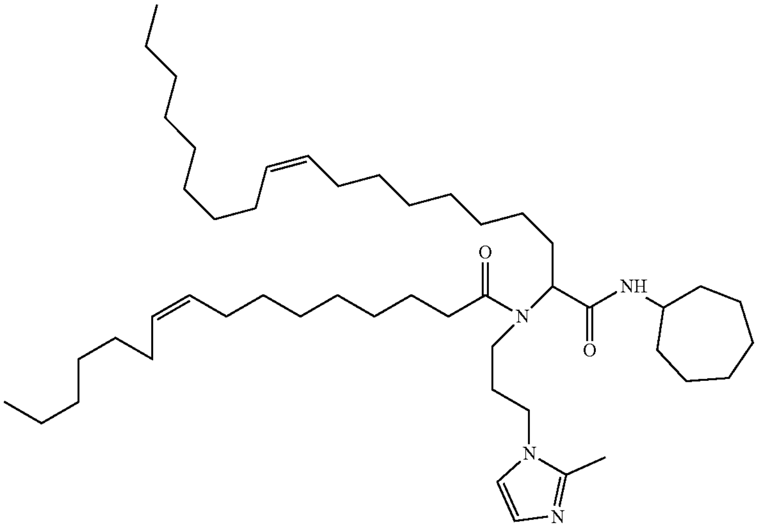
P454A6
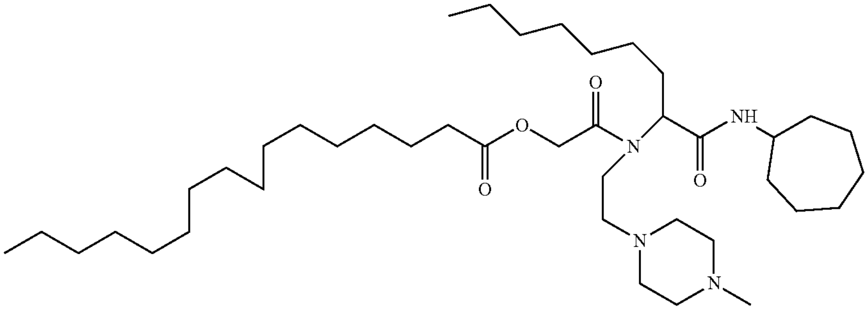
P454A12
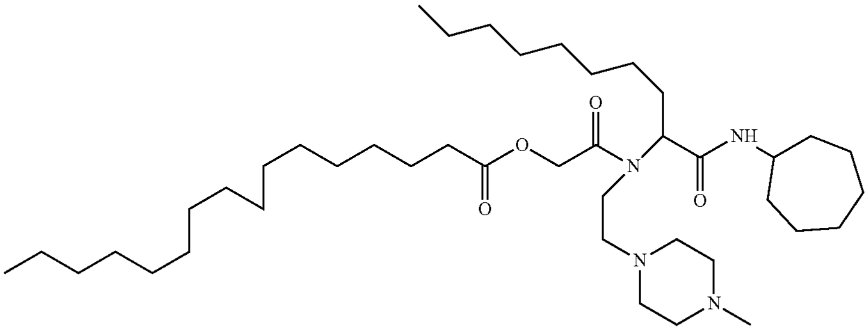
P454B12
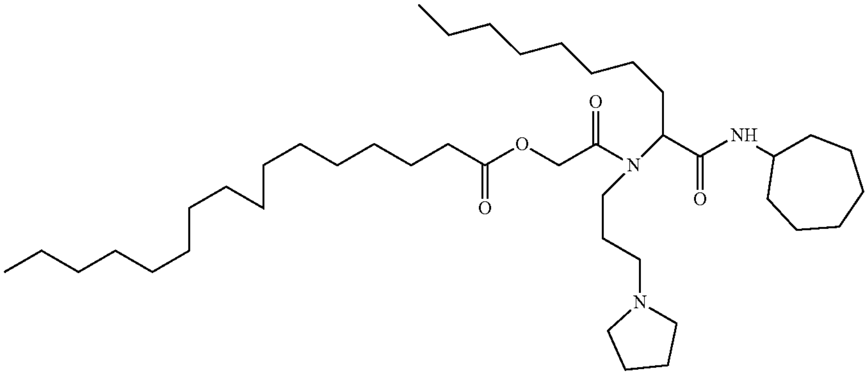

-continued
B454C12
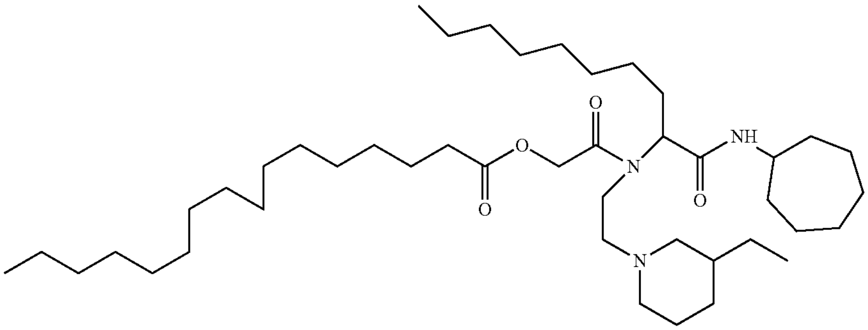
P454D12
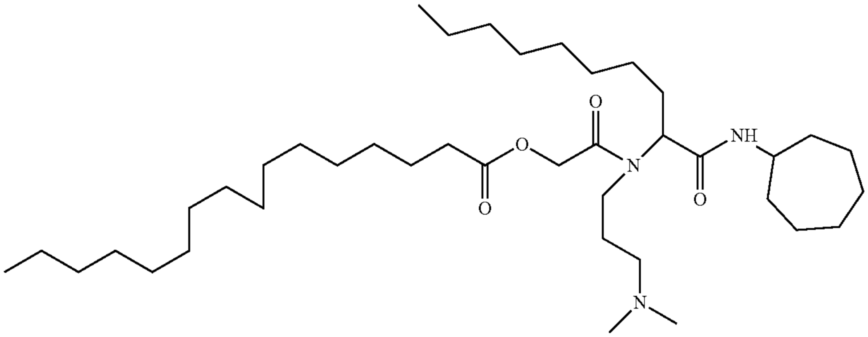
P454E12
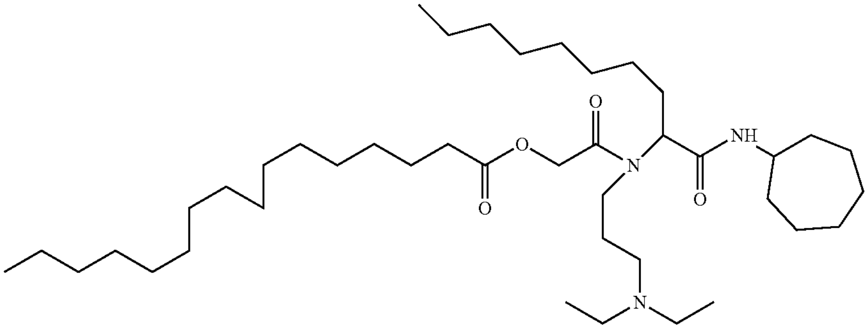
P454F12
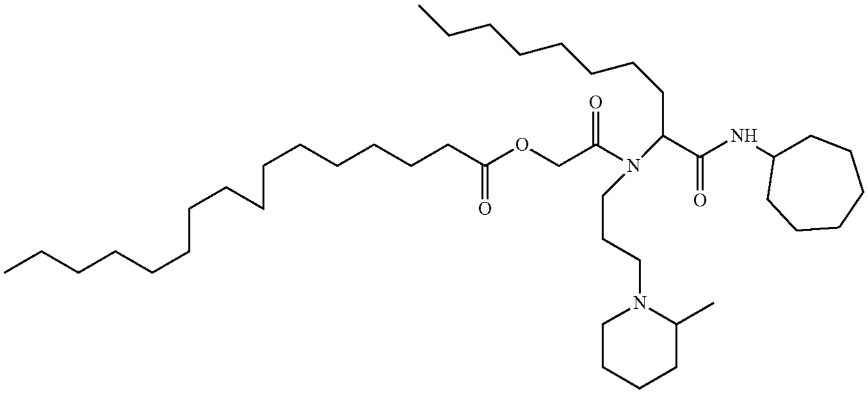

-continued
P454H6
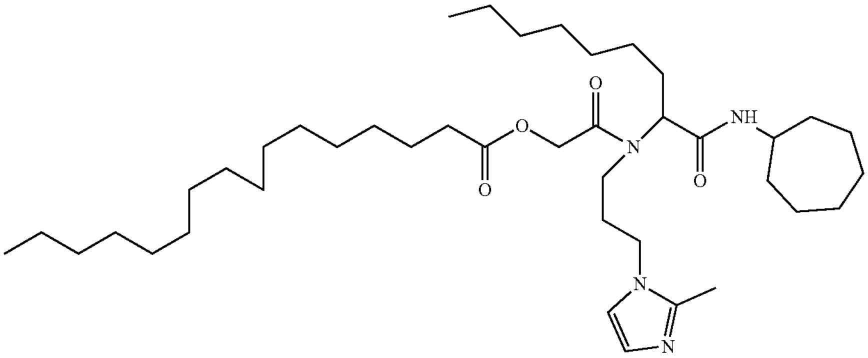
P455A6
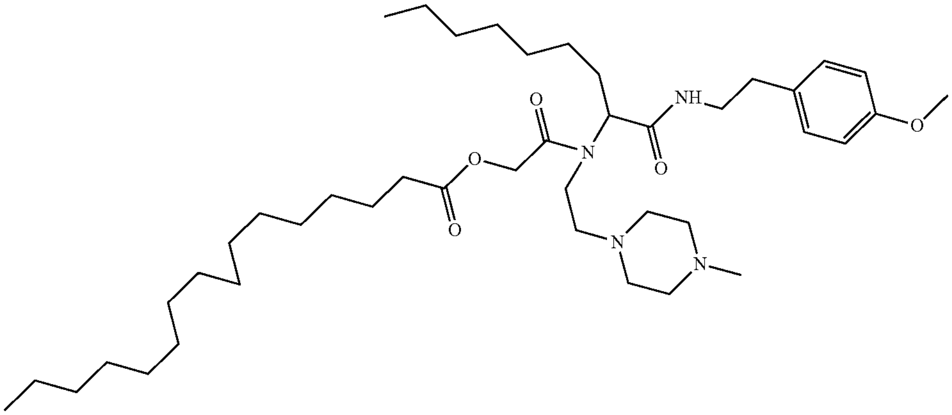
A455A12
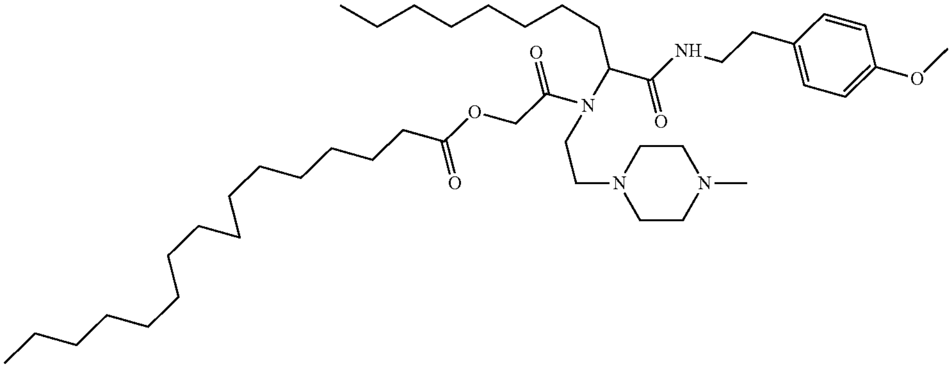
P455C12
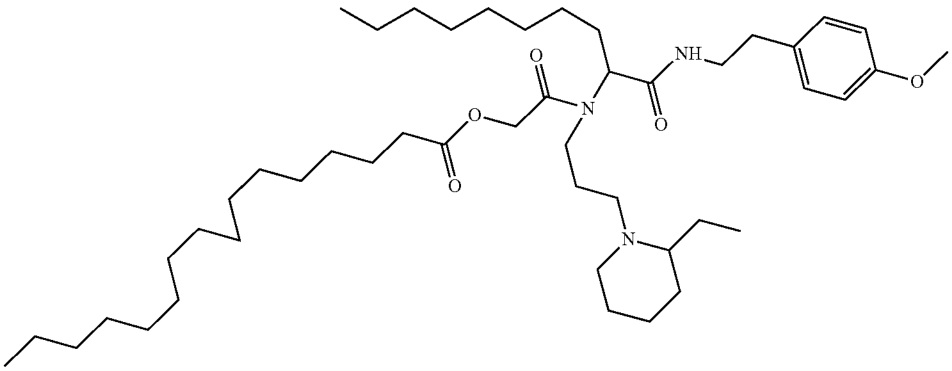

-continued
P455D12
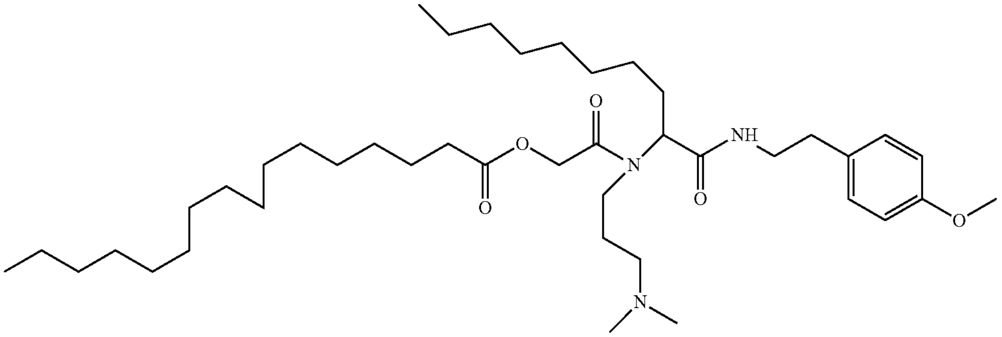
P455F12
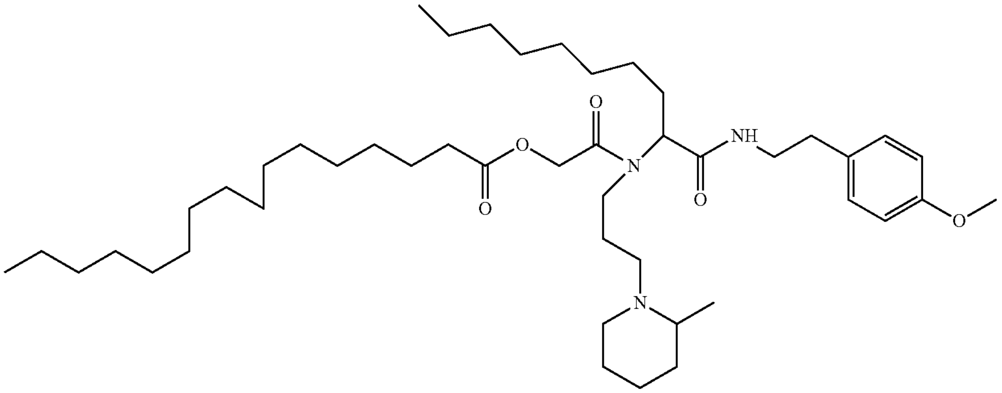
P458A10
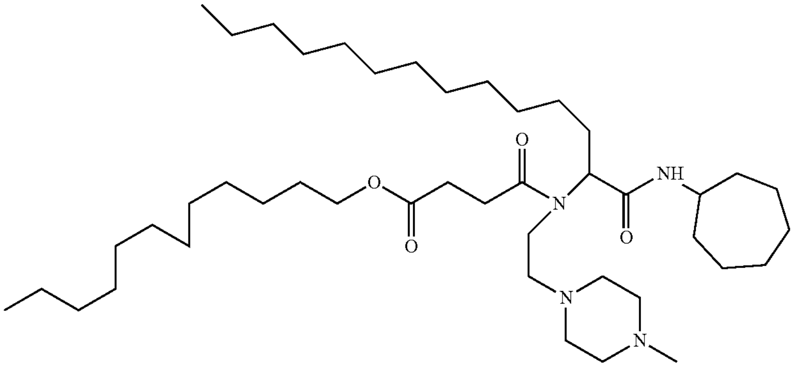
P460A11
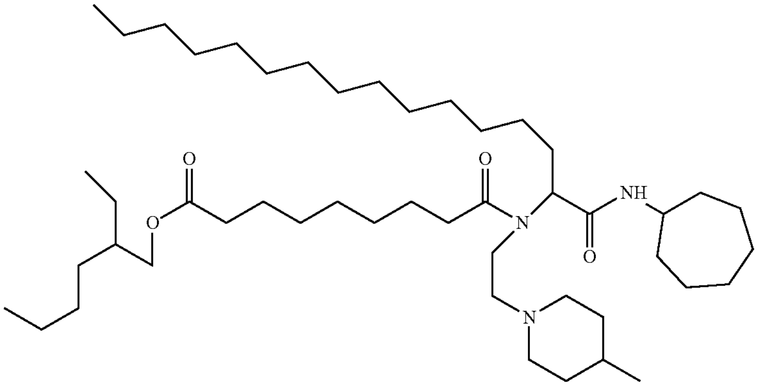

-continued
P461A2
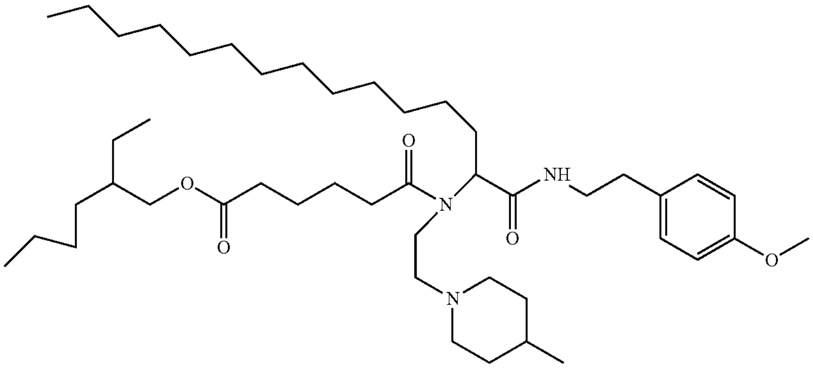
P461A5
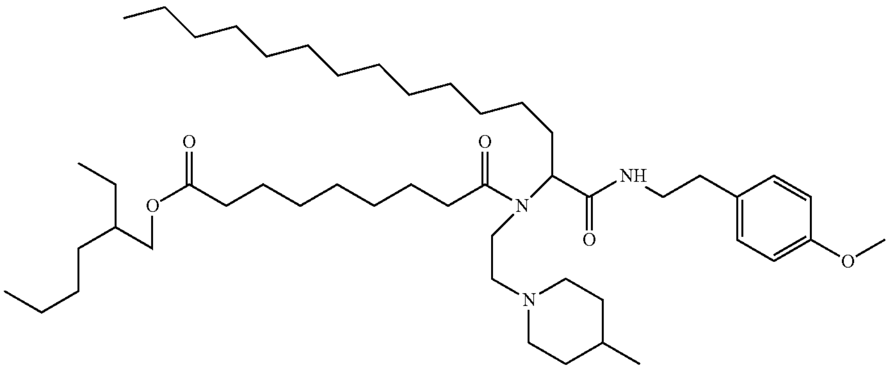
P458A11
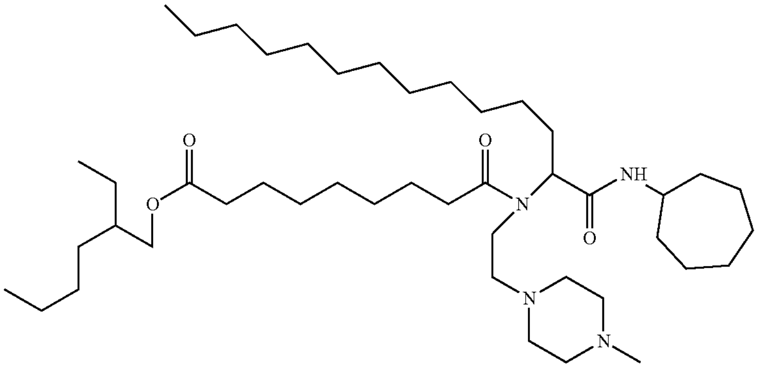
P458A12
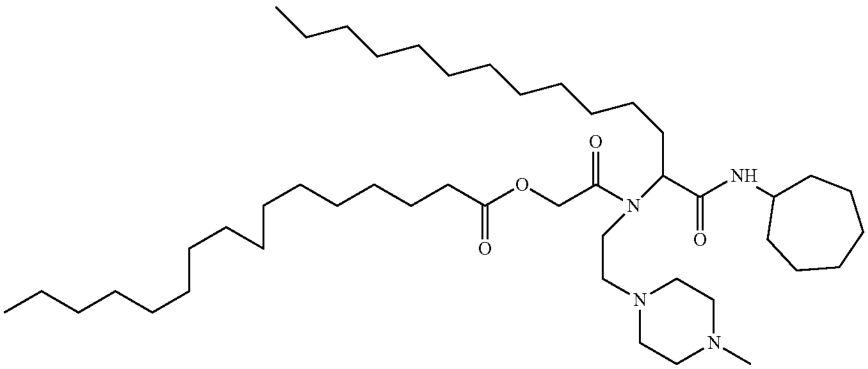

-continued
P458B12
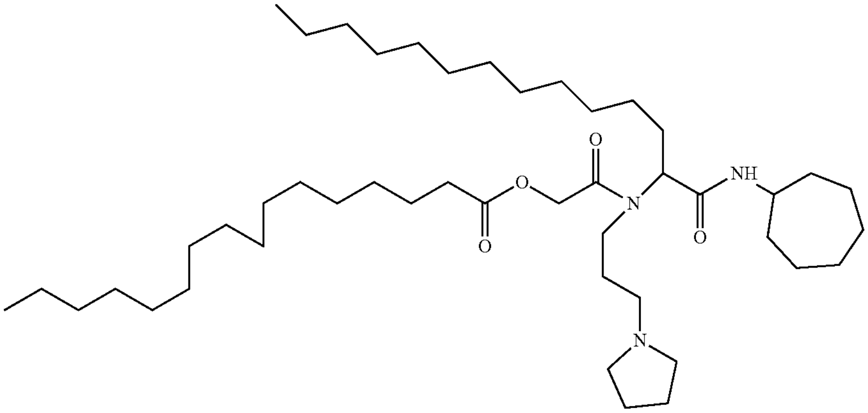
P458C12
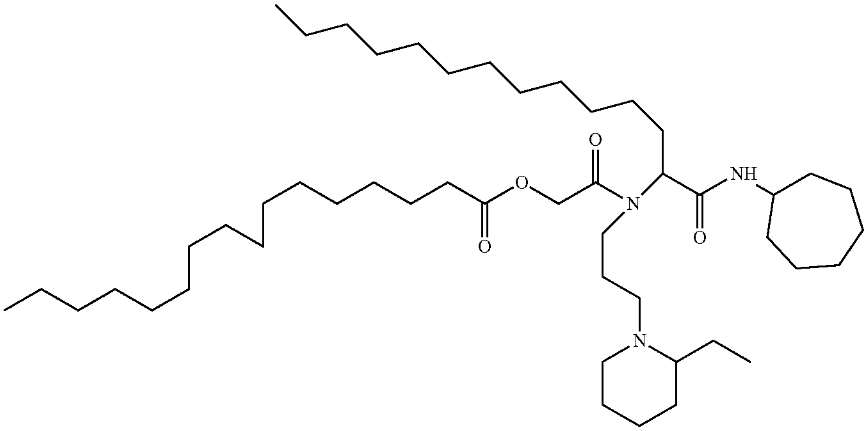
P458D12
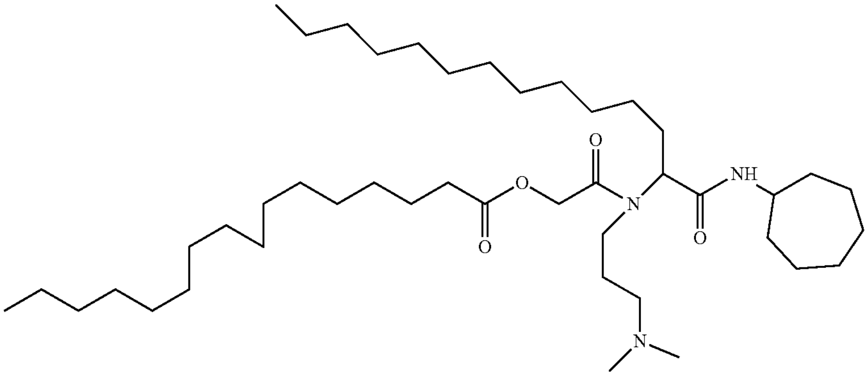
P458F12
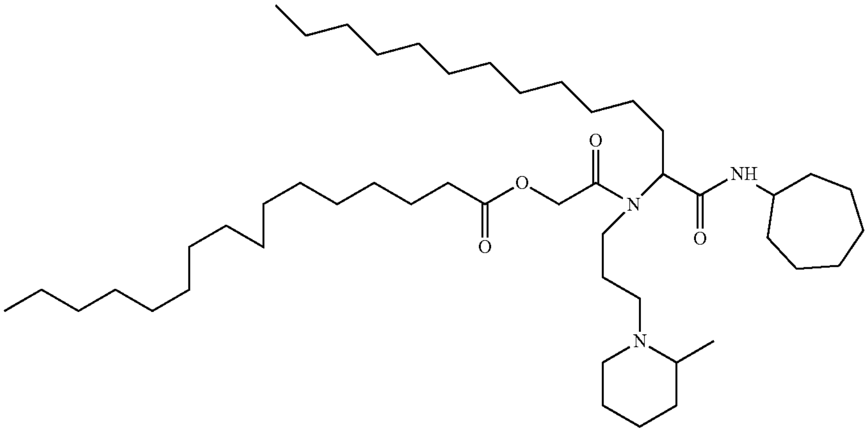

-continued
P459C6
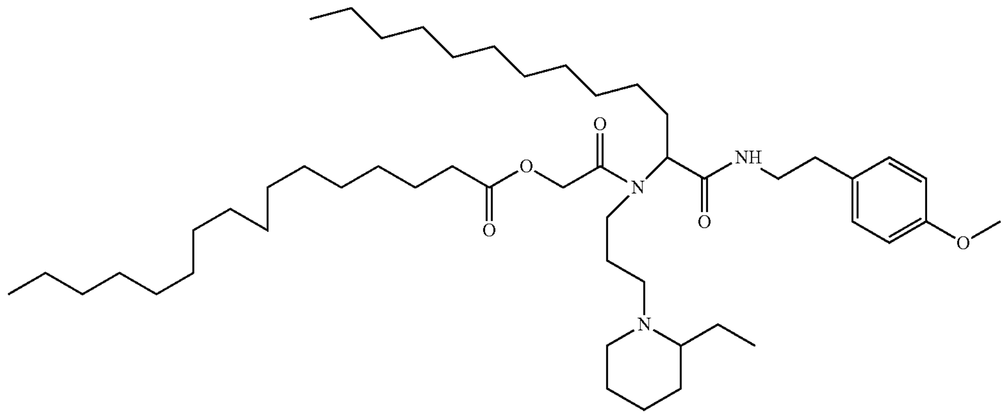
P459C12
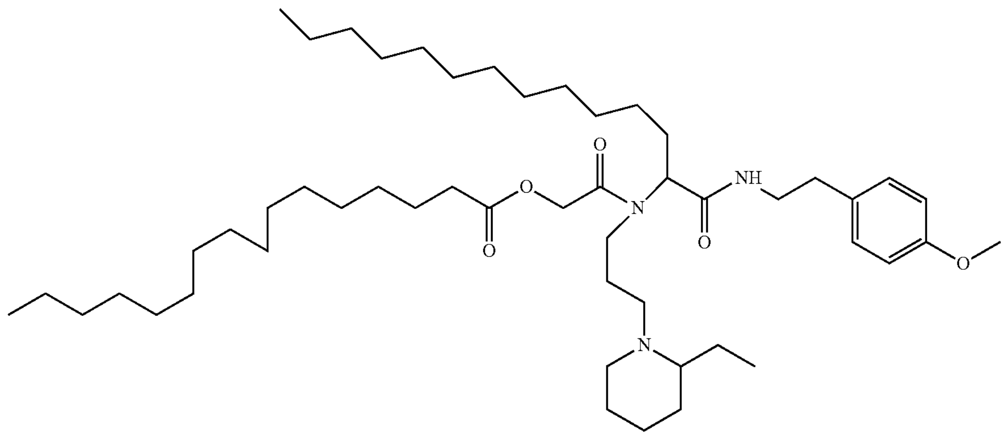
P459F4
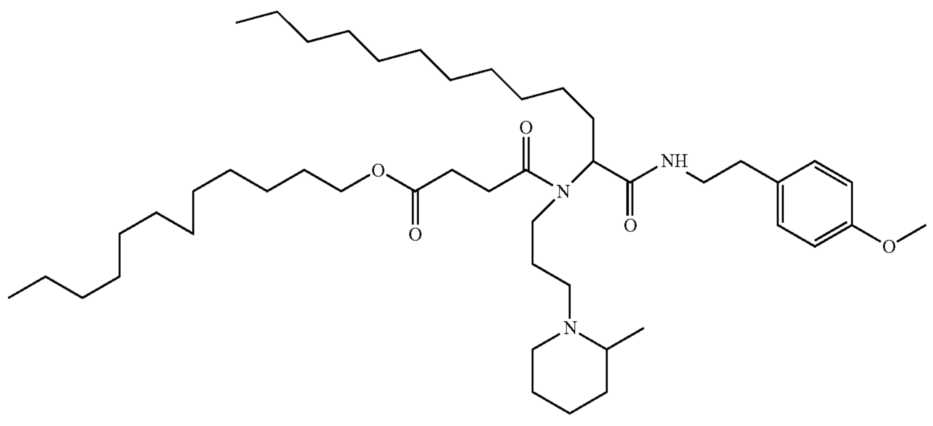

-continued
P459F6
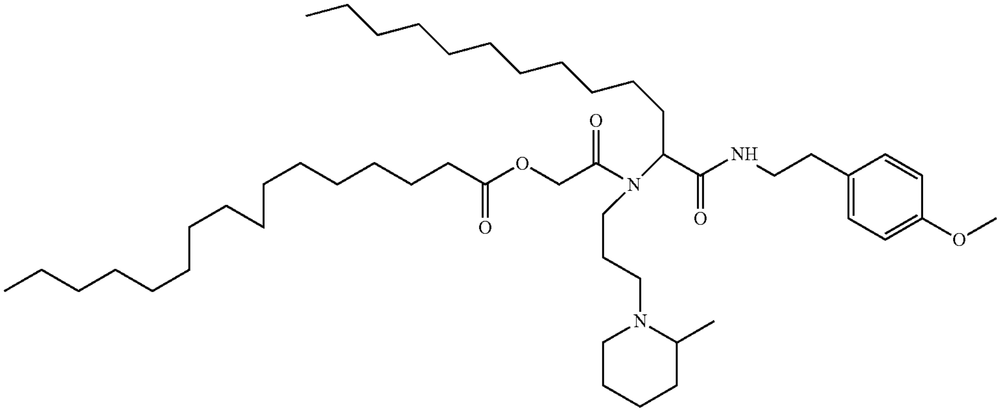
P460A5
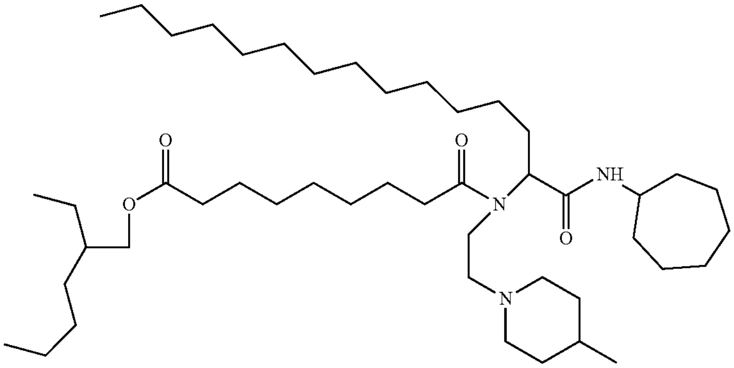
P460A6
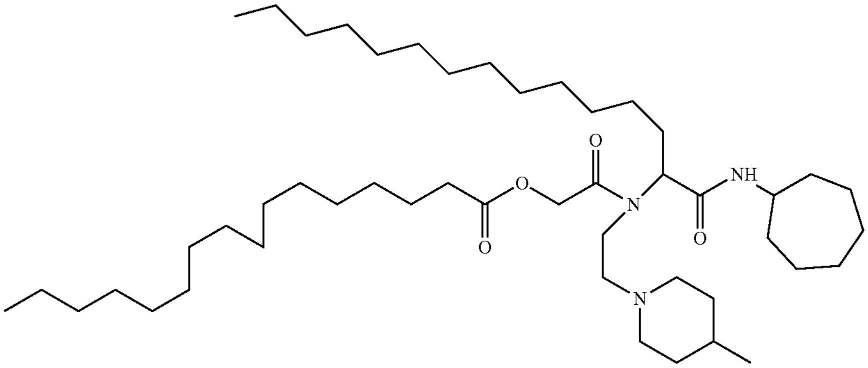
P460A11
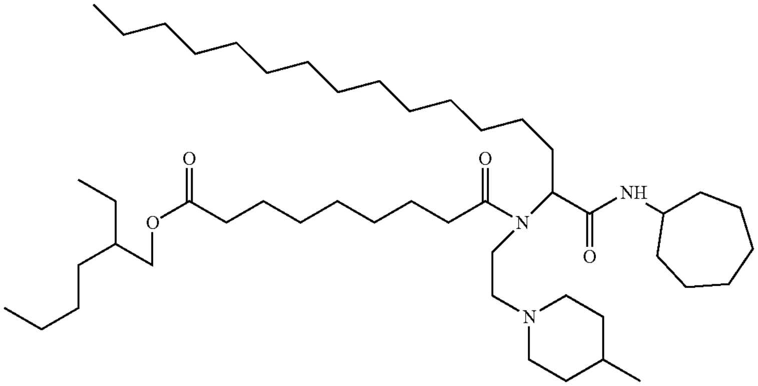

-continued
P461A2
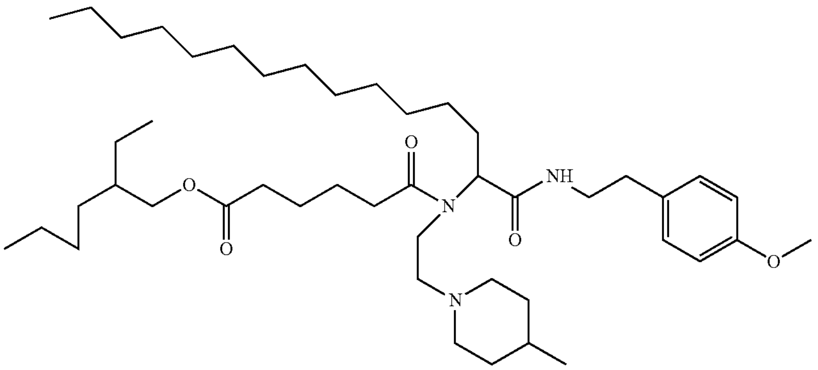
P461A5
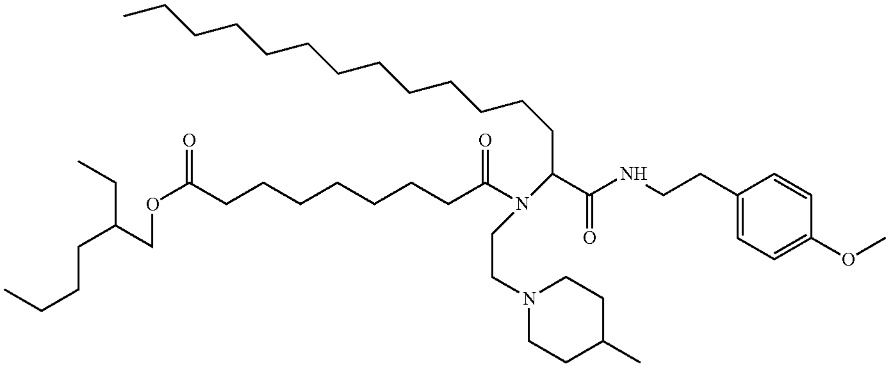
P461H6
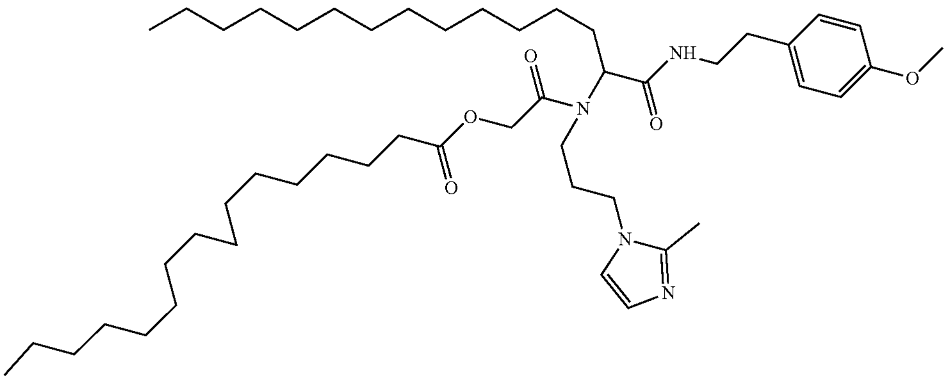
P461H12
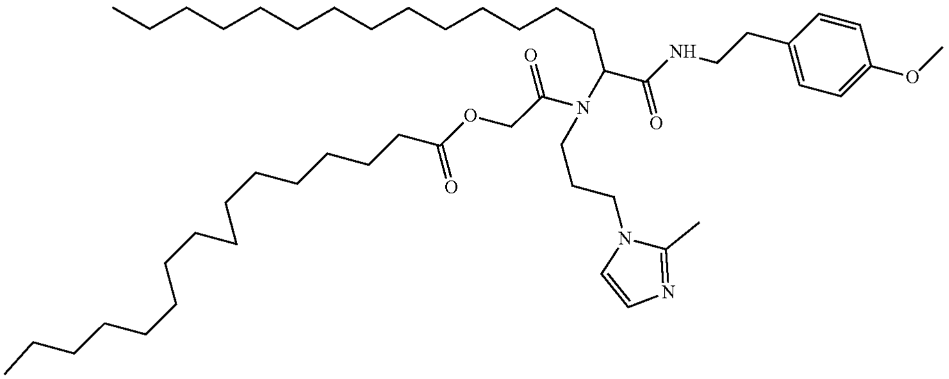

-continued
P462A10
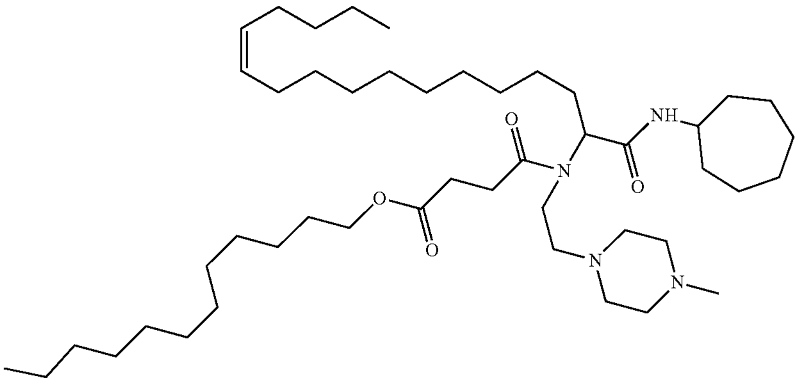
P462A11
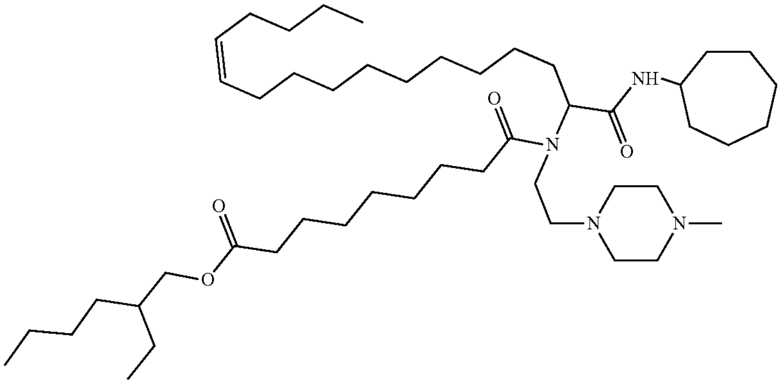
P462A12
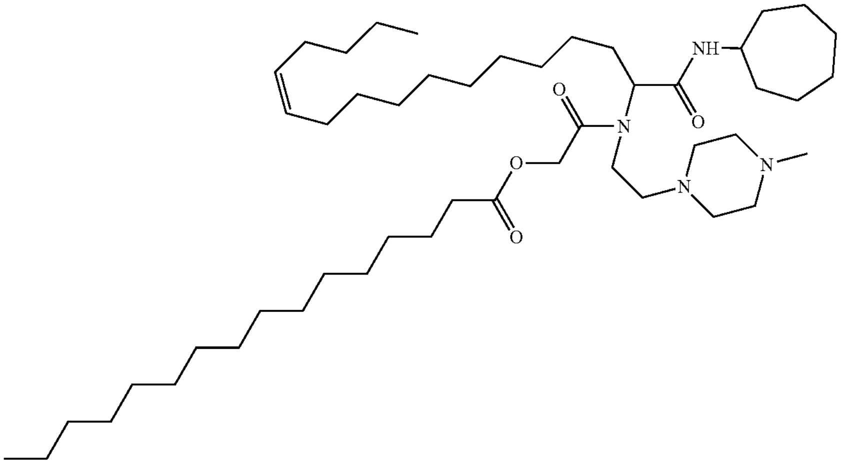
P462C12
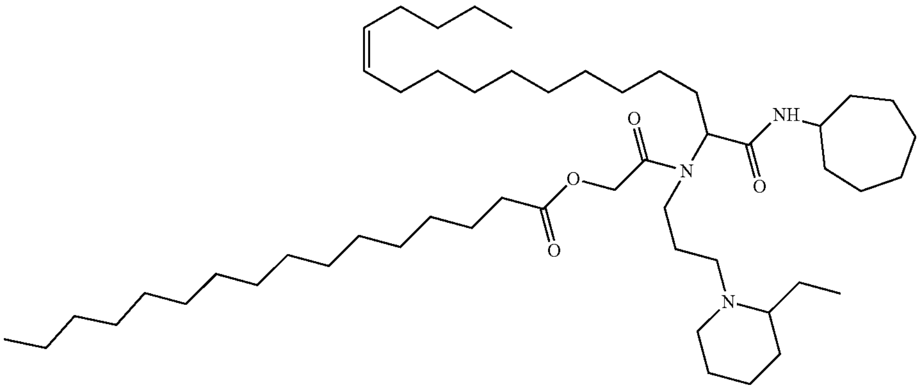

-continued
P462E10
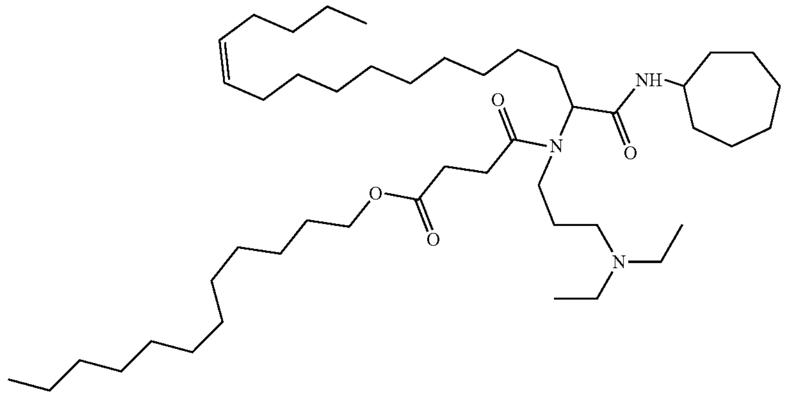
P462E11
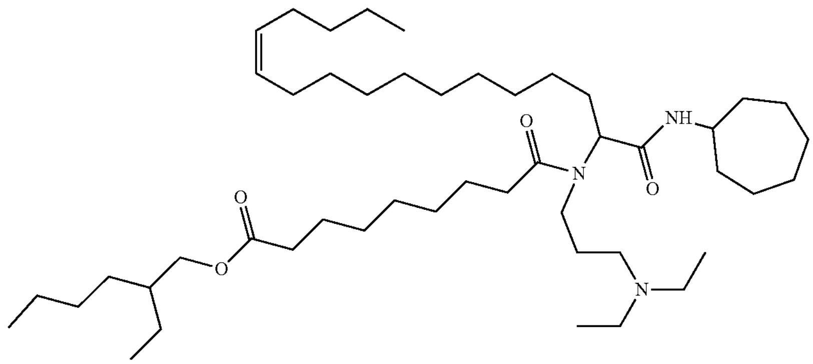
P462E12
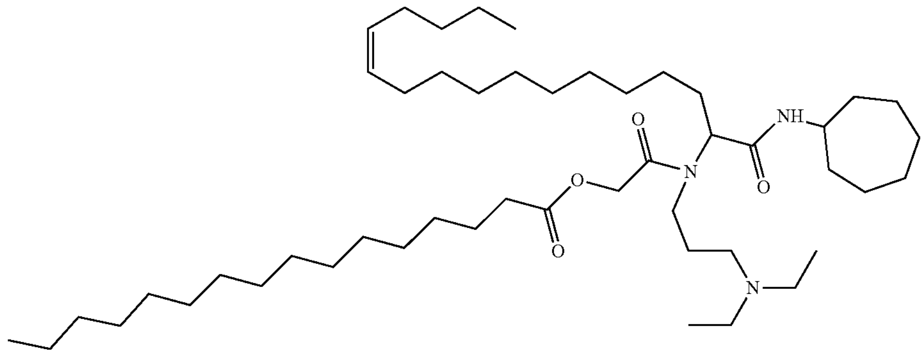
P462F12
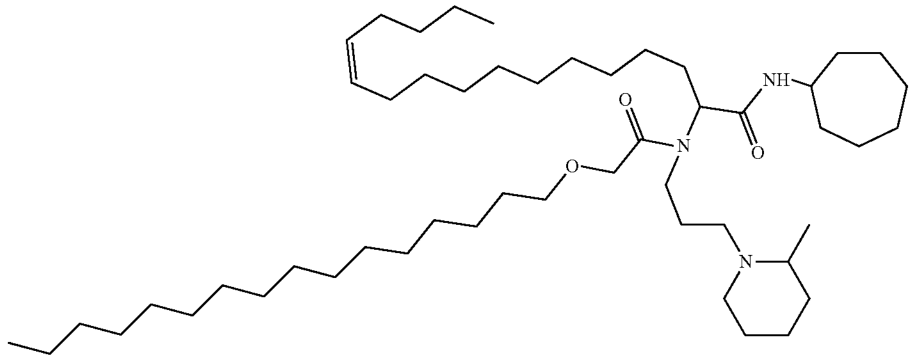

-continued
P463A8
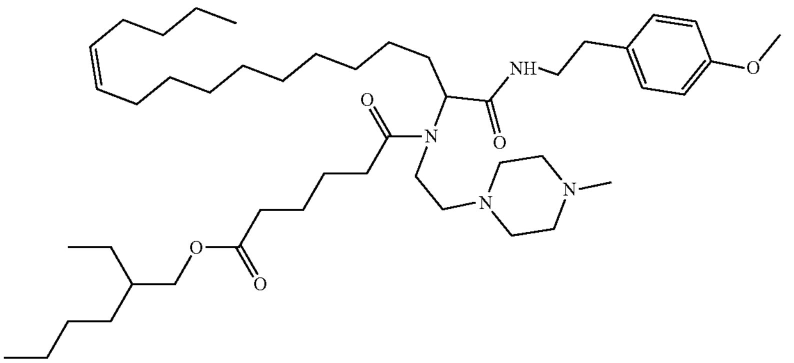
P463A9
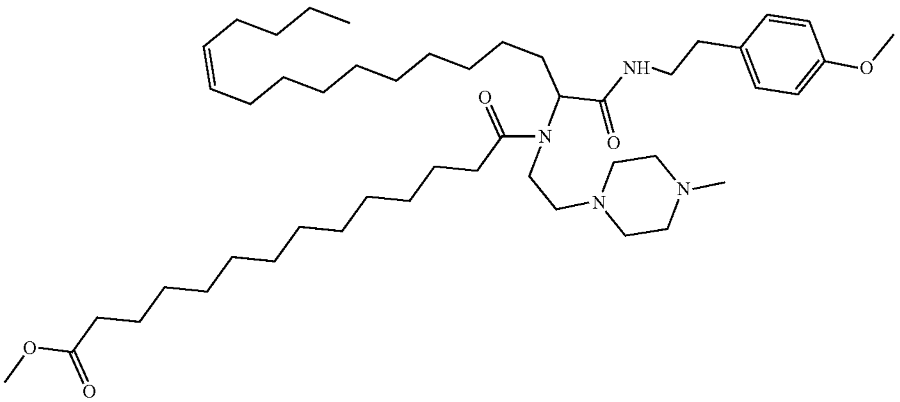
P463A10
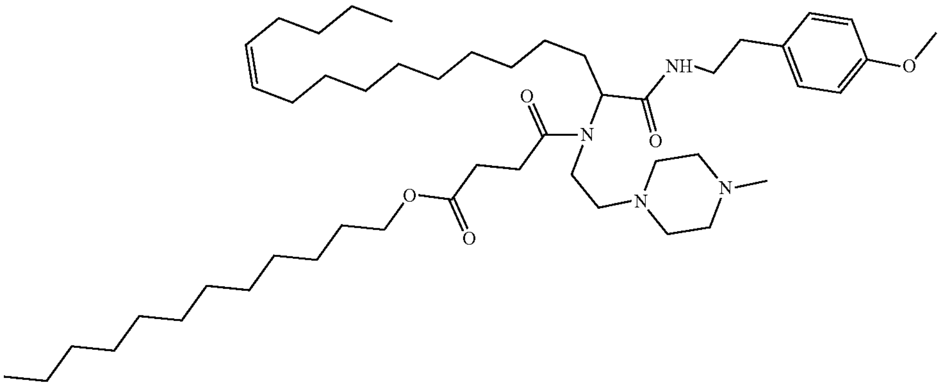
P463A11
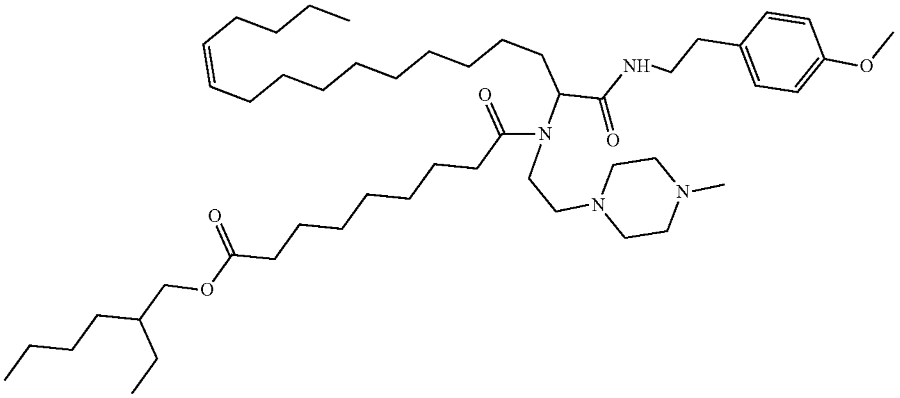

-continued
P463A12
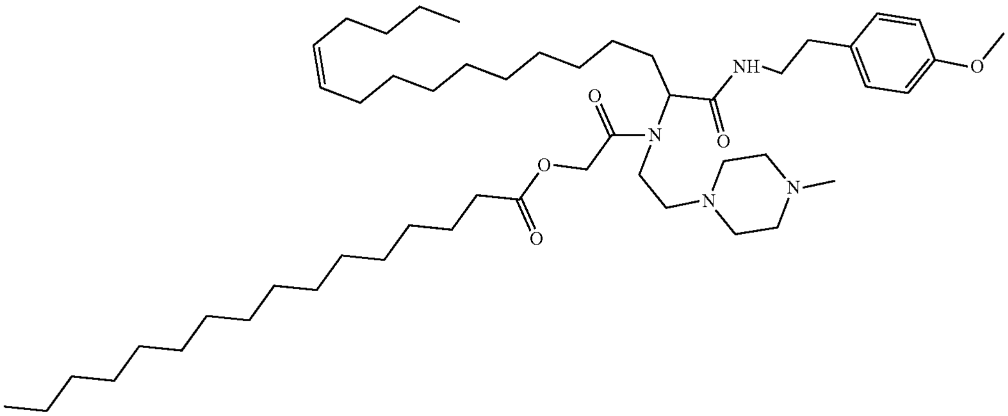
P463B10
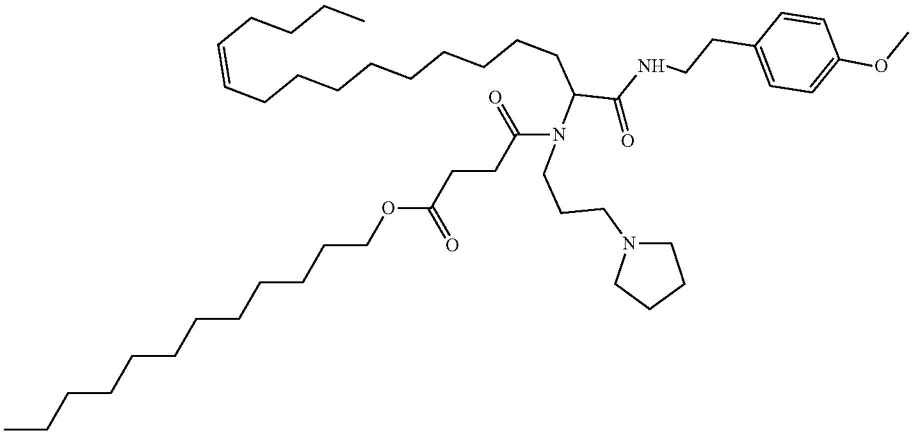
P463D8
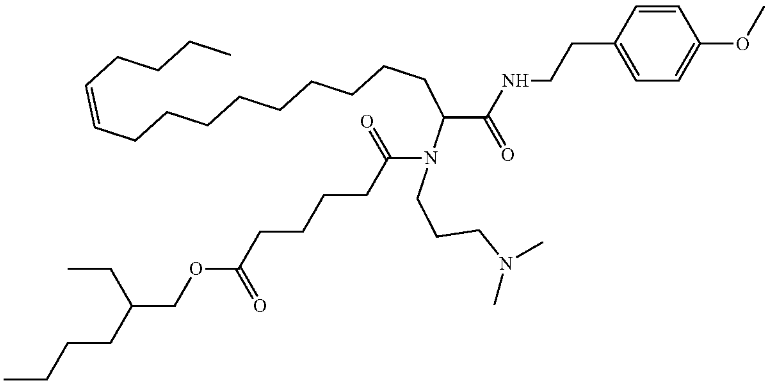

-continued
P463D10
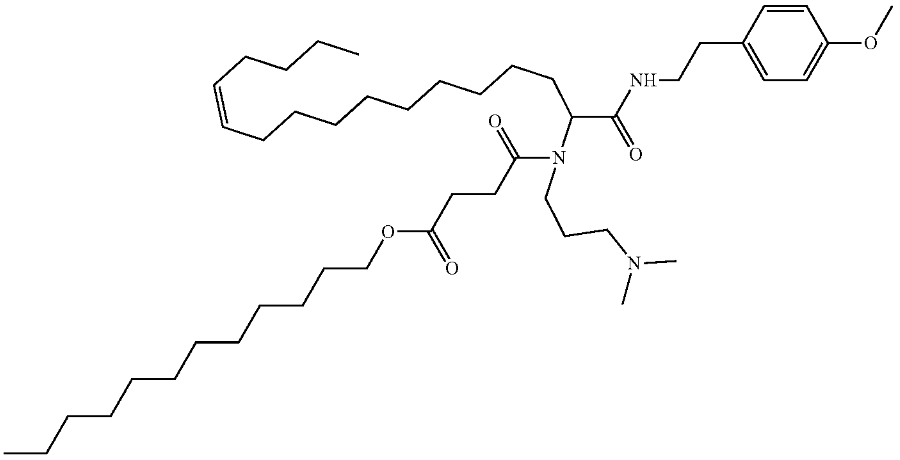
P463D12
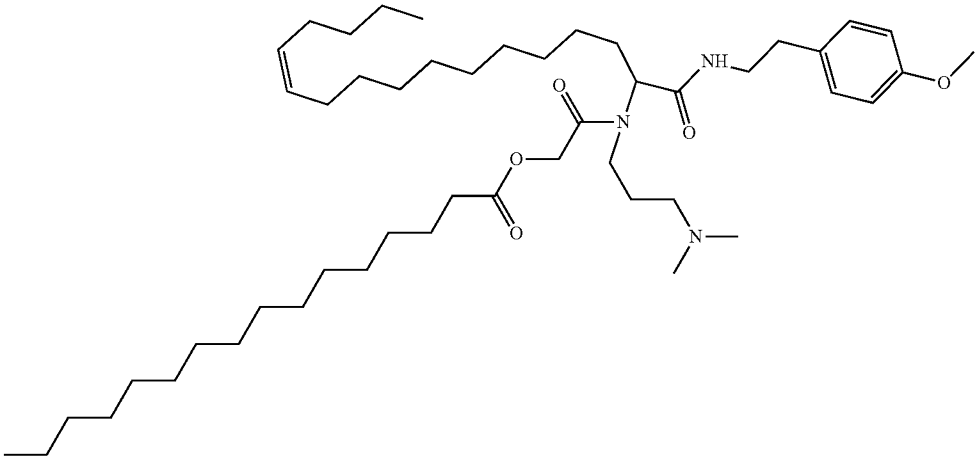
P464A4
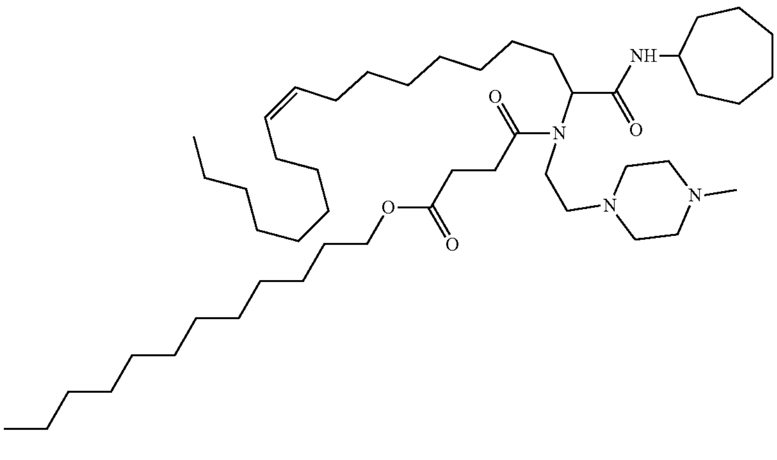

-continued
P464A5
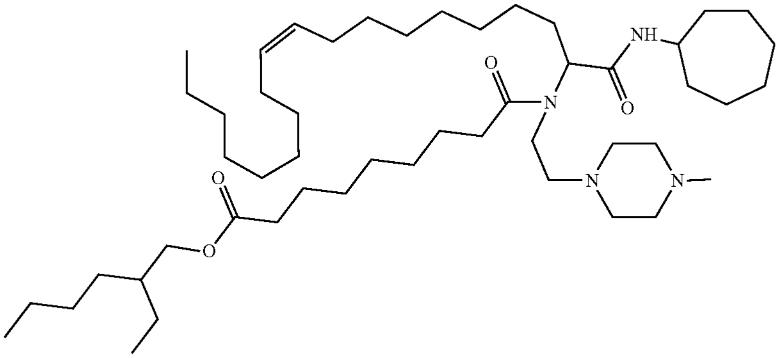
P464B6
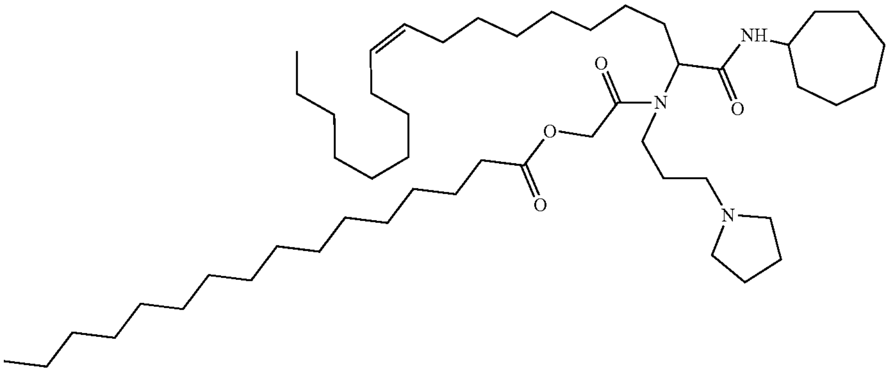
P464D6
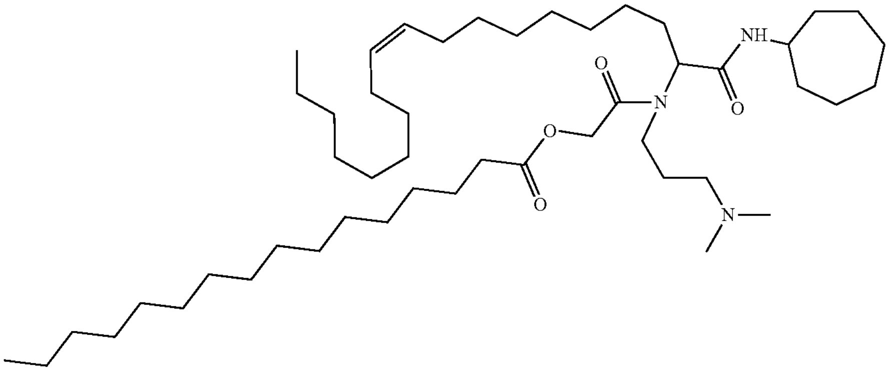
P464E6
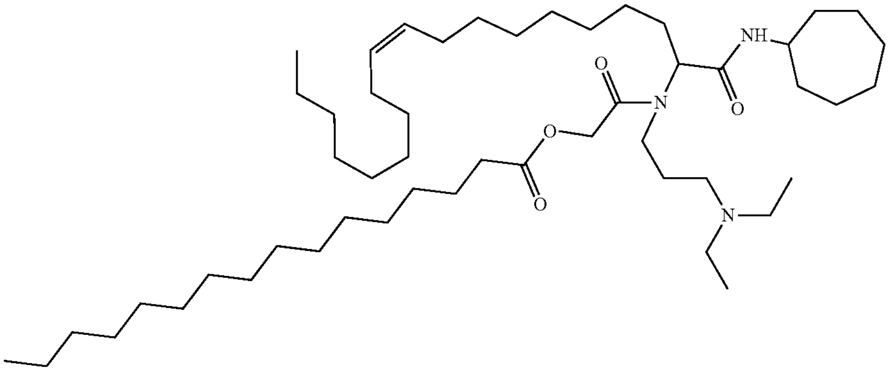

-continued
P465A2
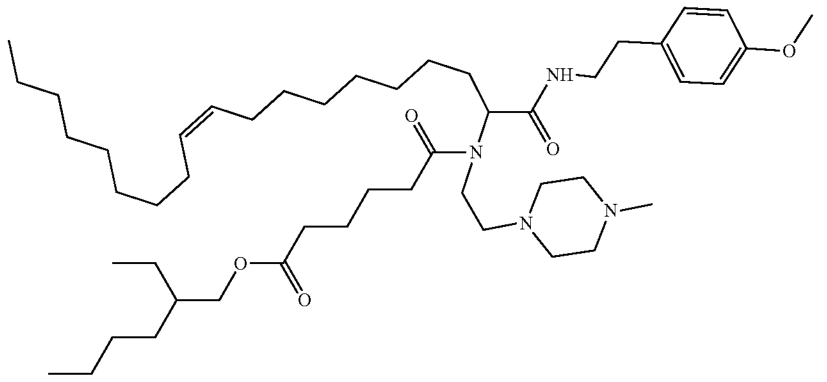
P465A5
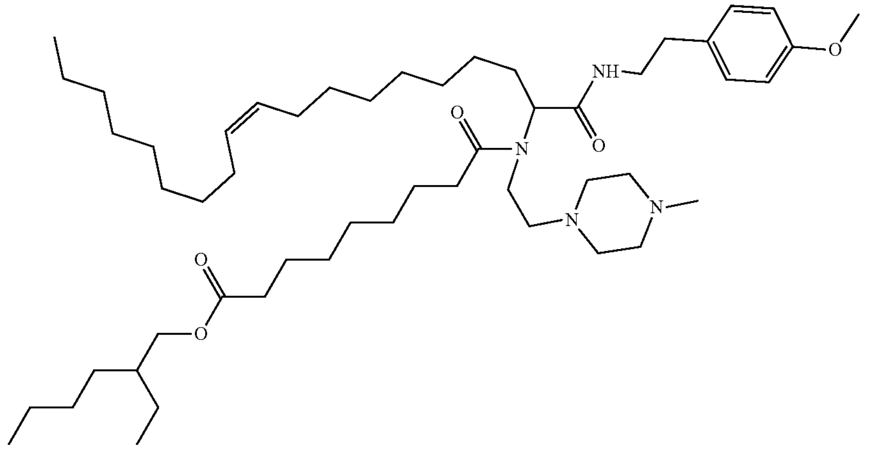
P465A6
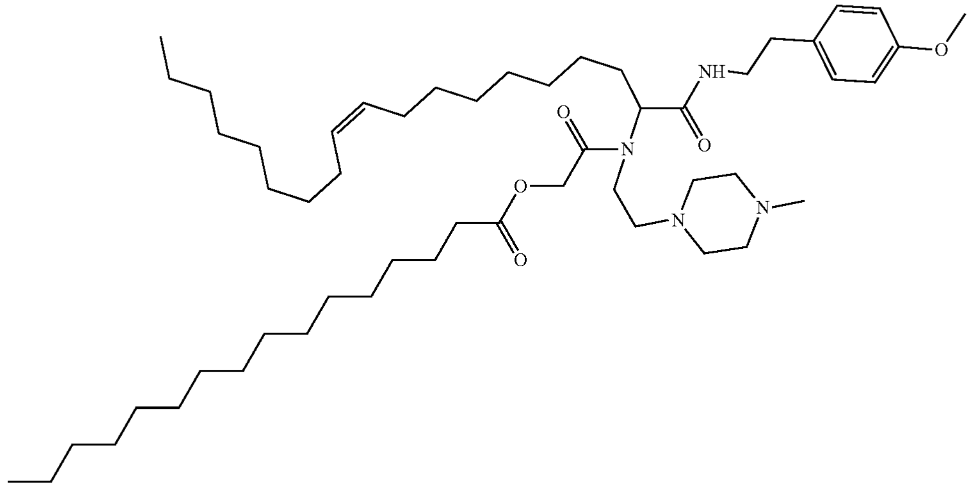

-continued
P465B4
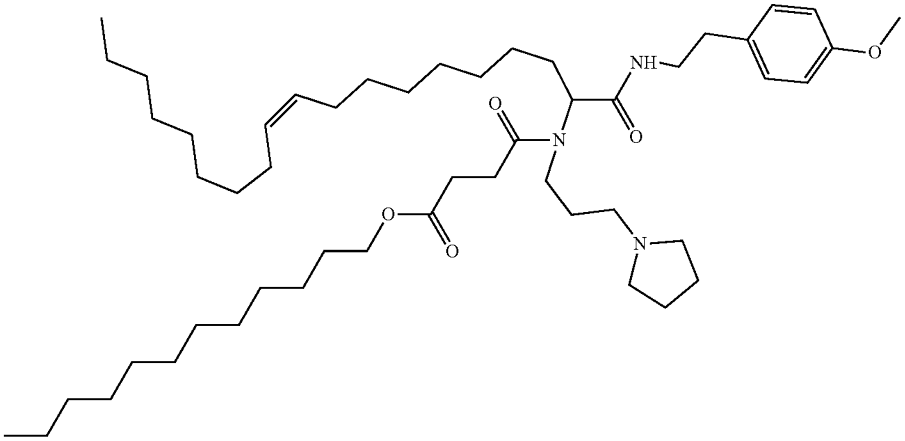
P465B10
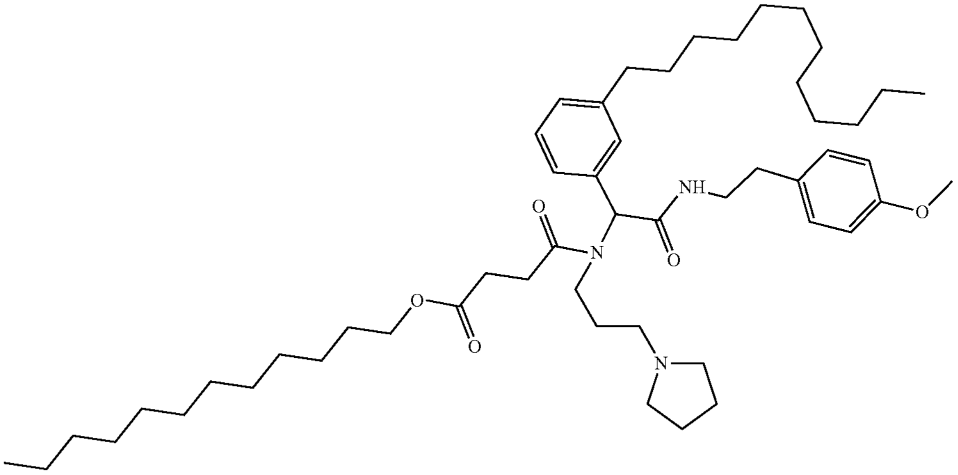
P465B12
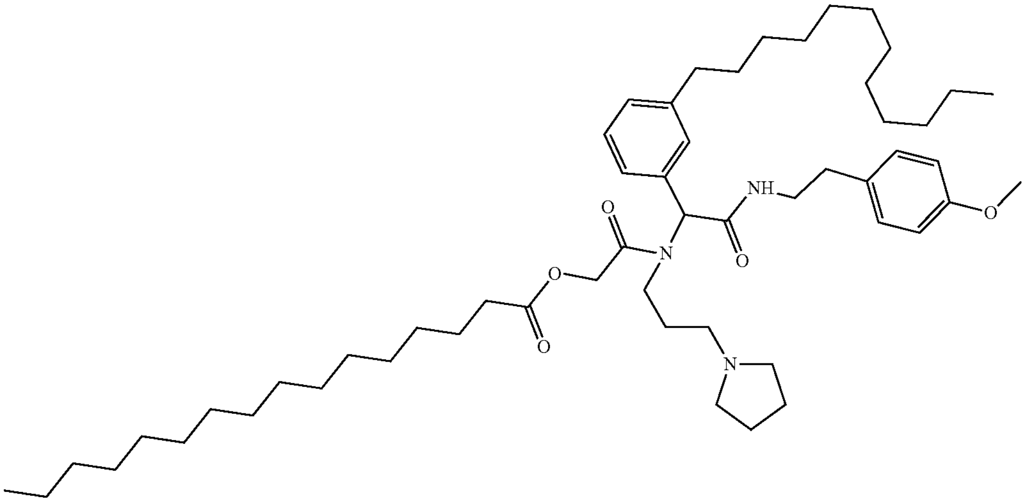

-continued
P465D10
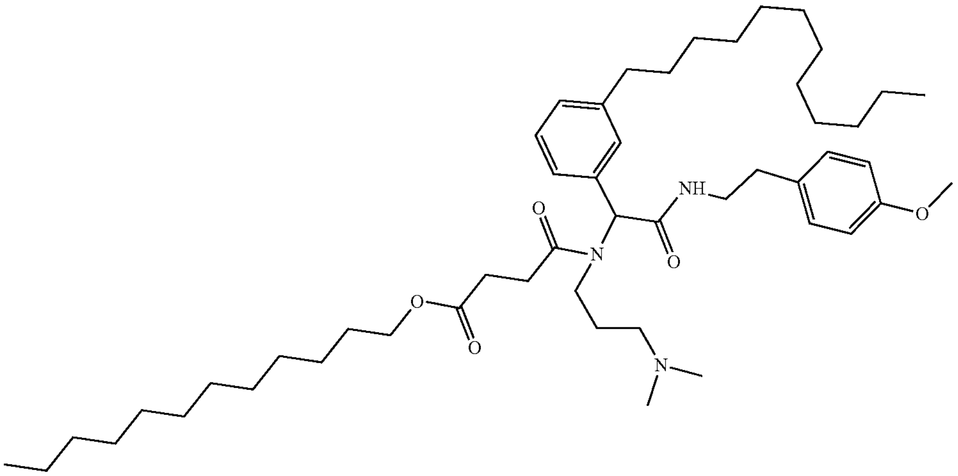
P470D7
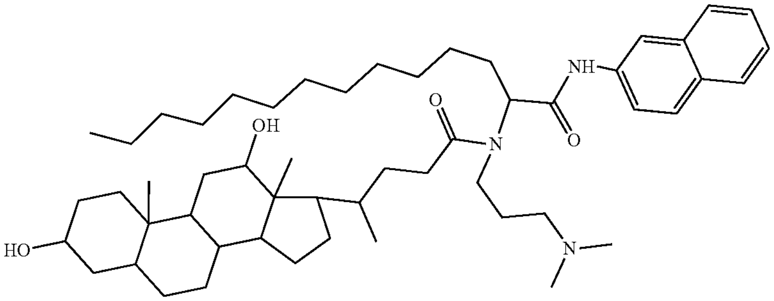
P500D6
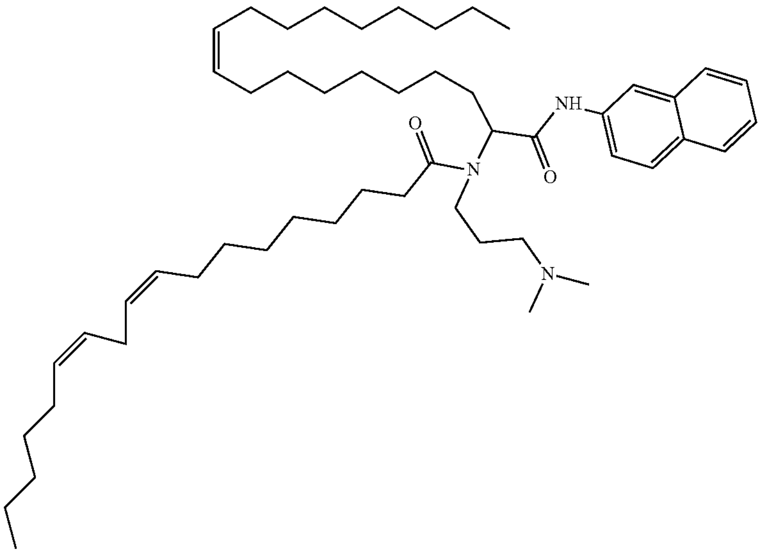

-continued
P56A7
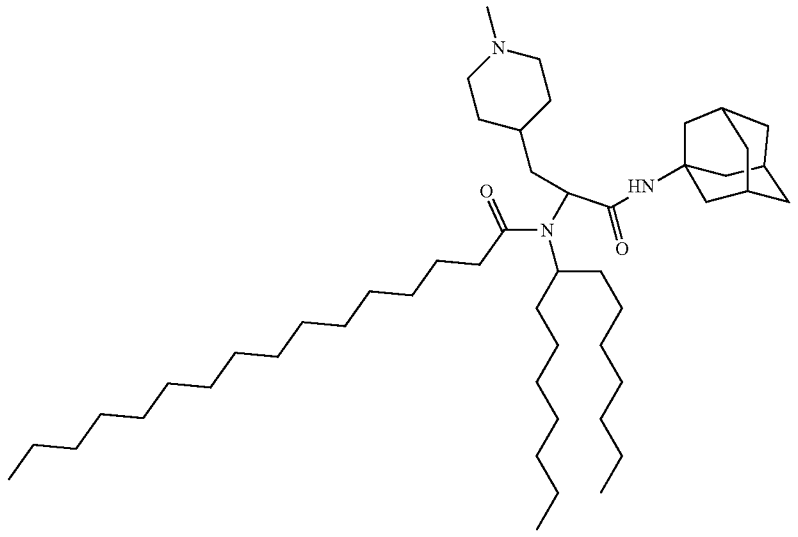
P319C8
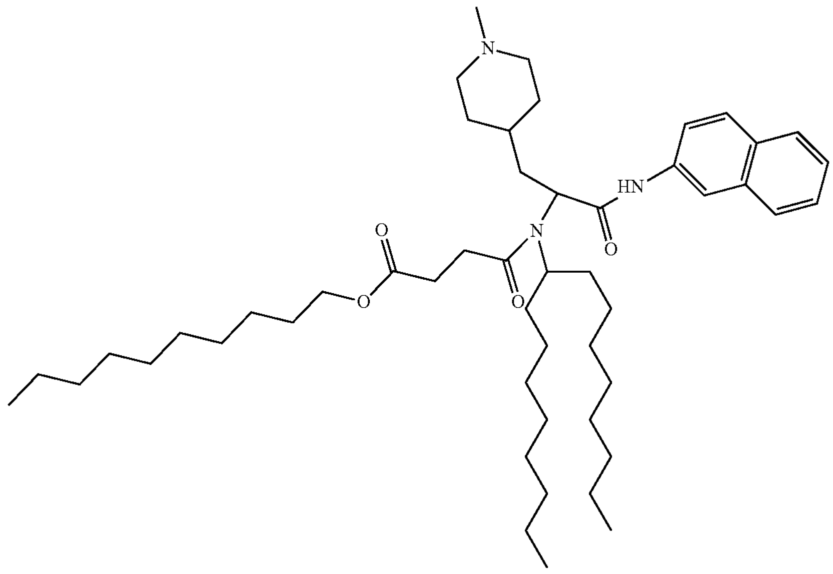
P363E8
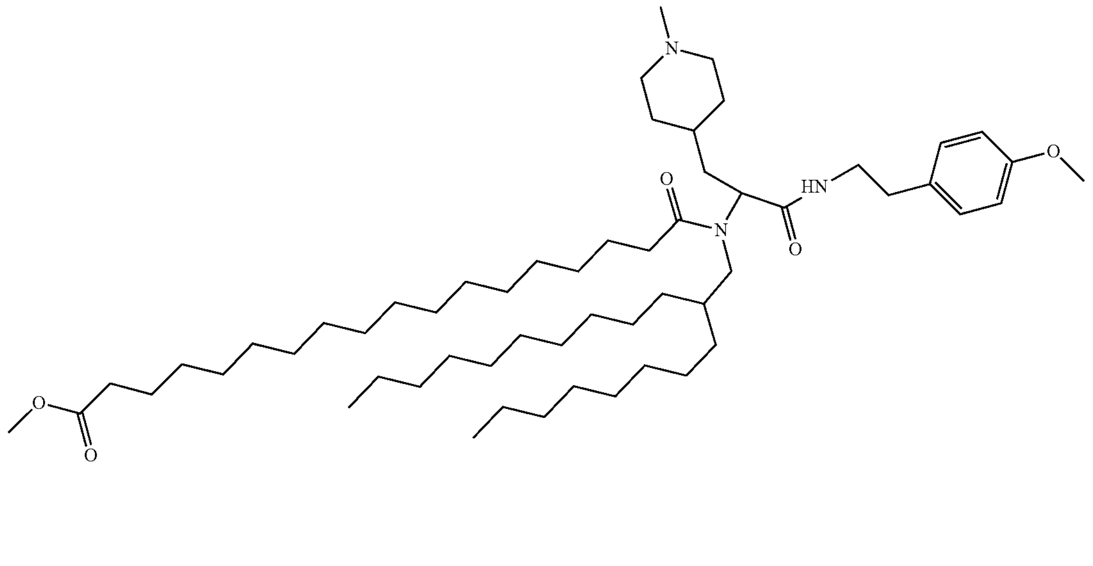

-continued
P56B9
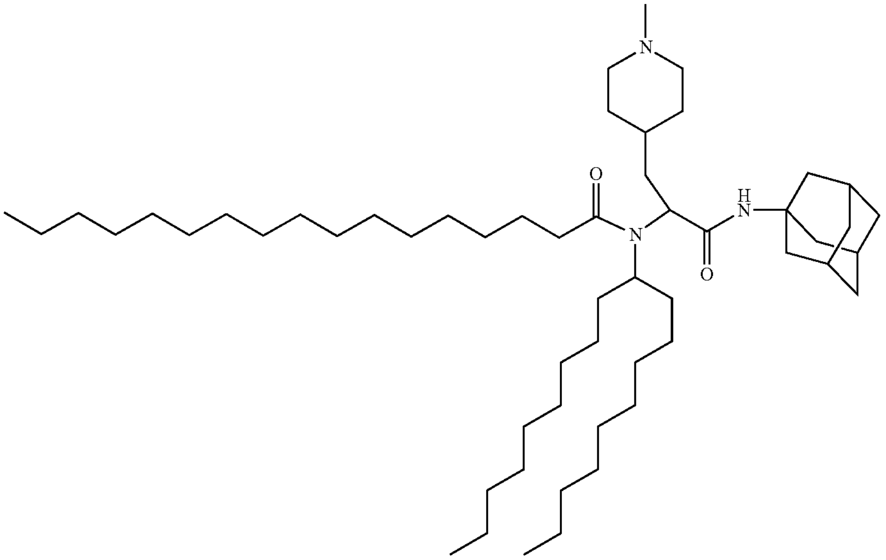
P313B7
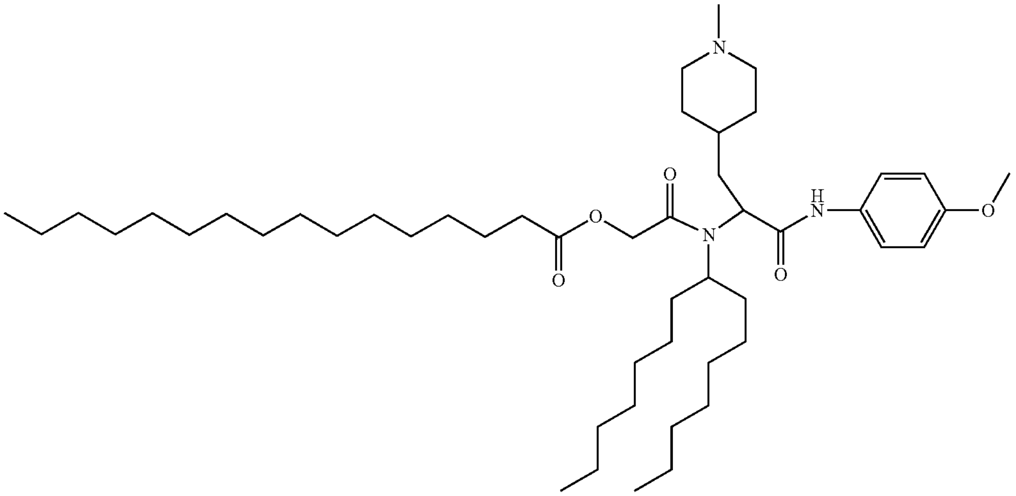
P287A12
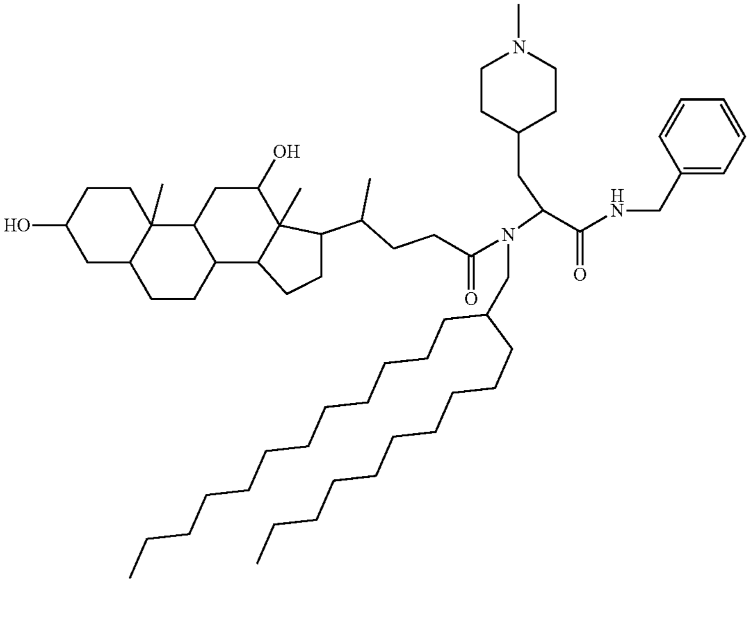

-continued
P287C12
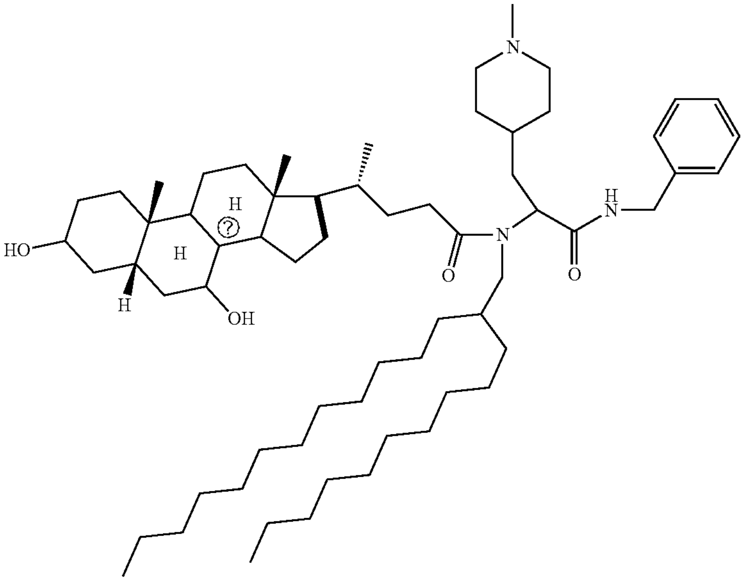
P161F12
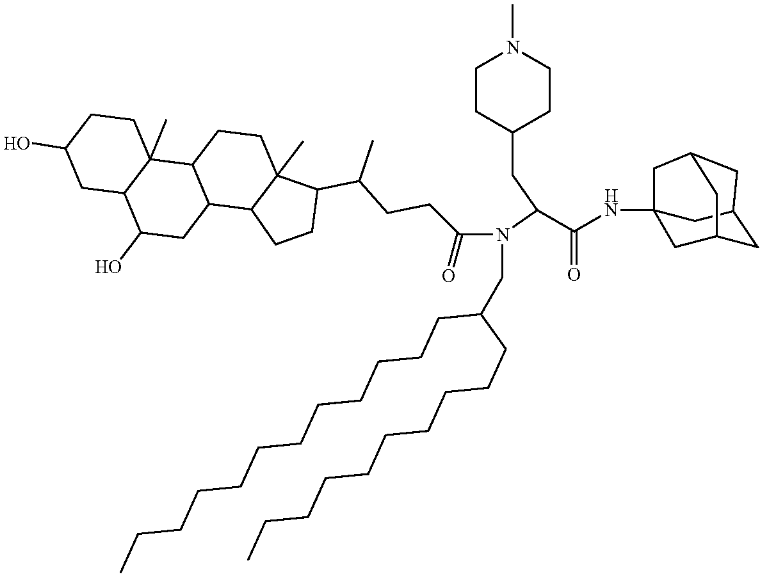
P331E4
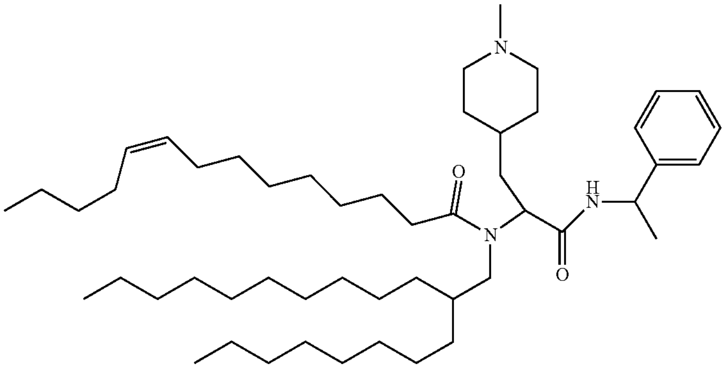

-continued
P149A1
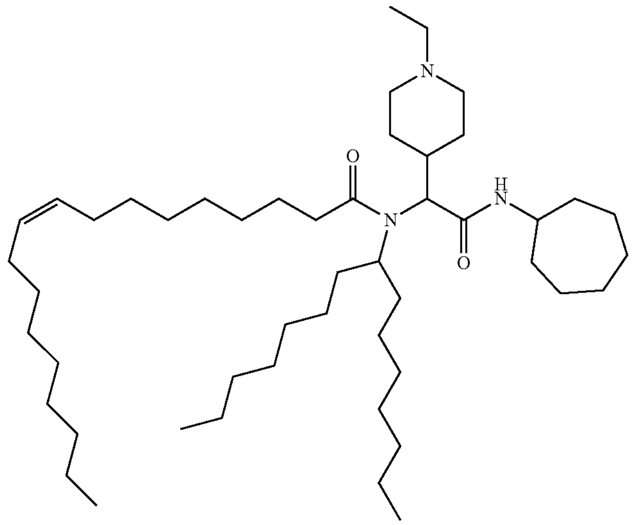
P149A3
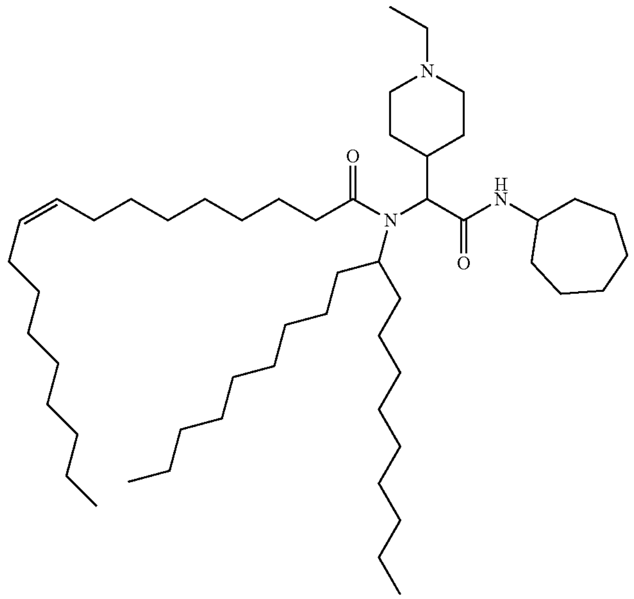
P149C1
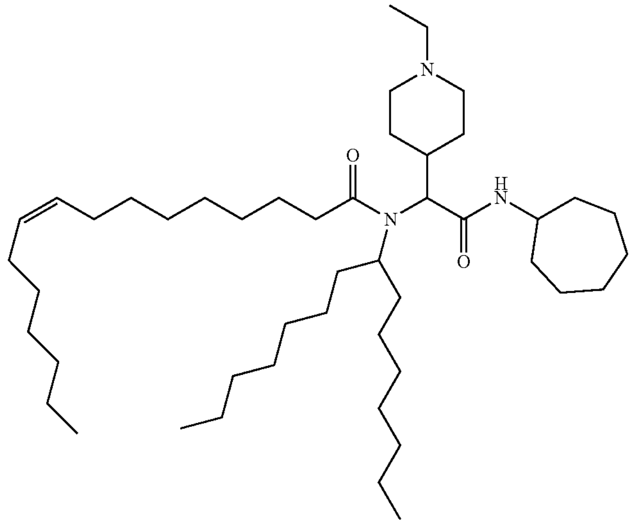

-continued
P149C2
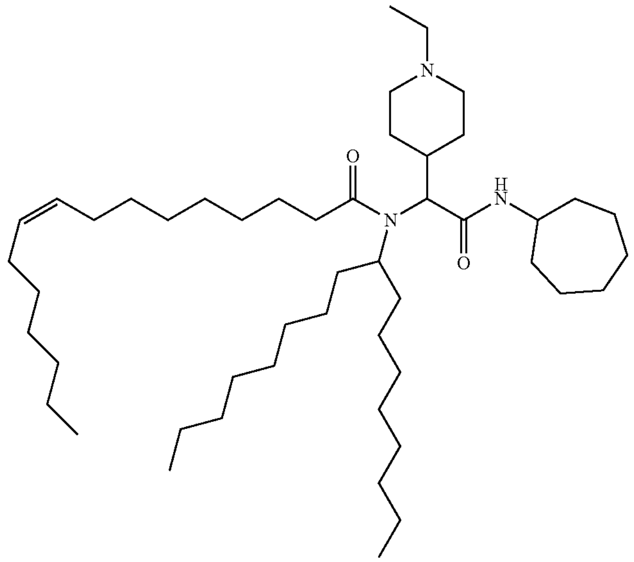
P149C3
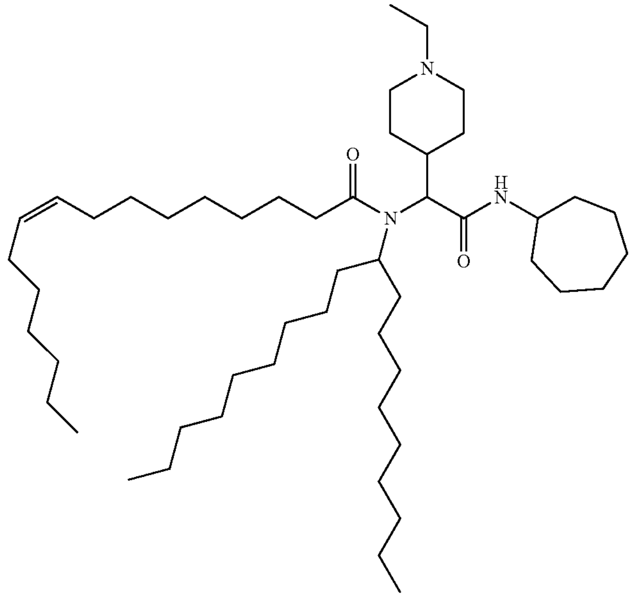
P313B6
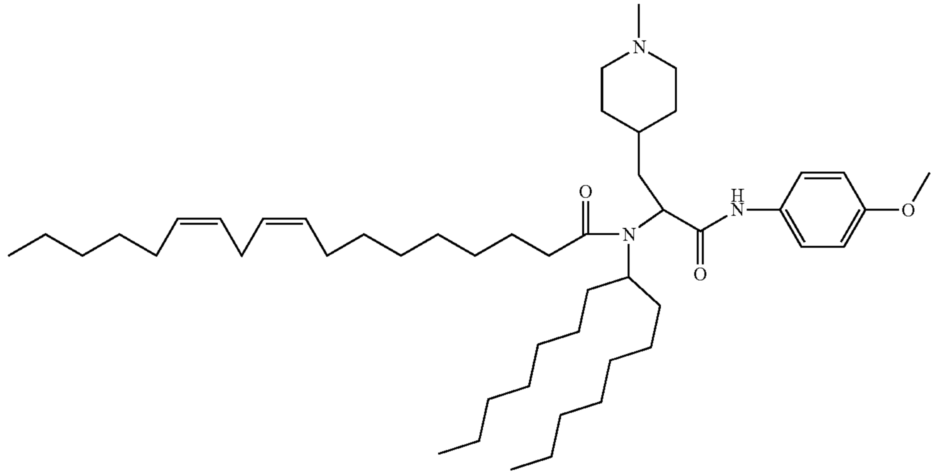

-continued
P319B6
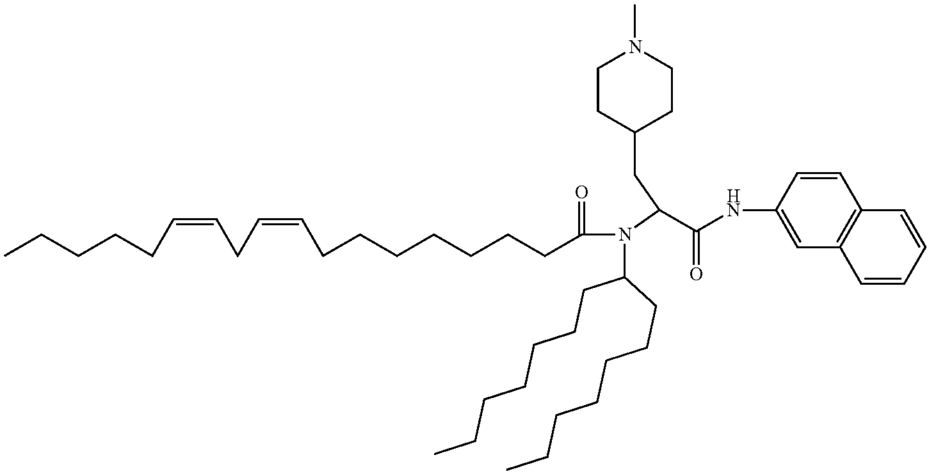
P343E5
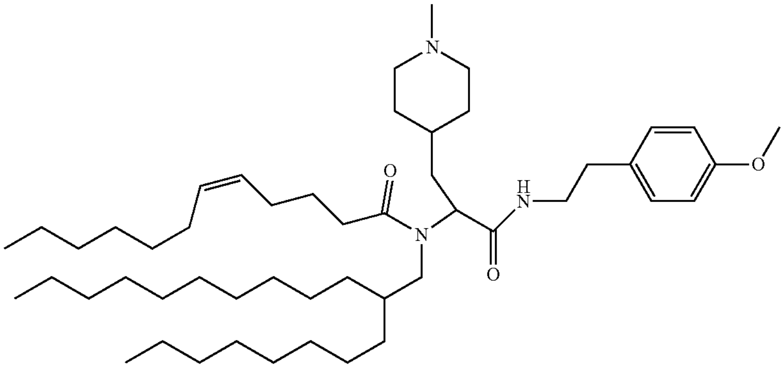
P343B1
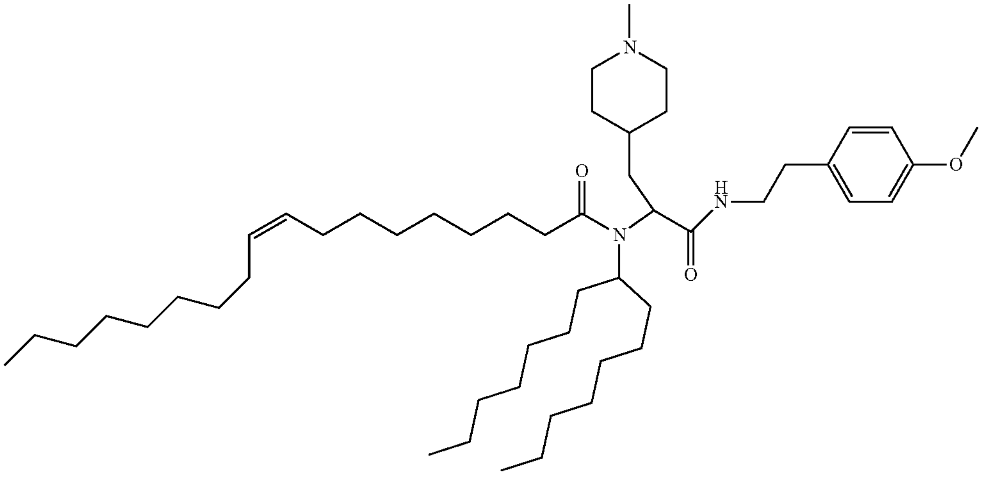

-continued
P363E10
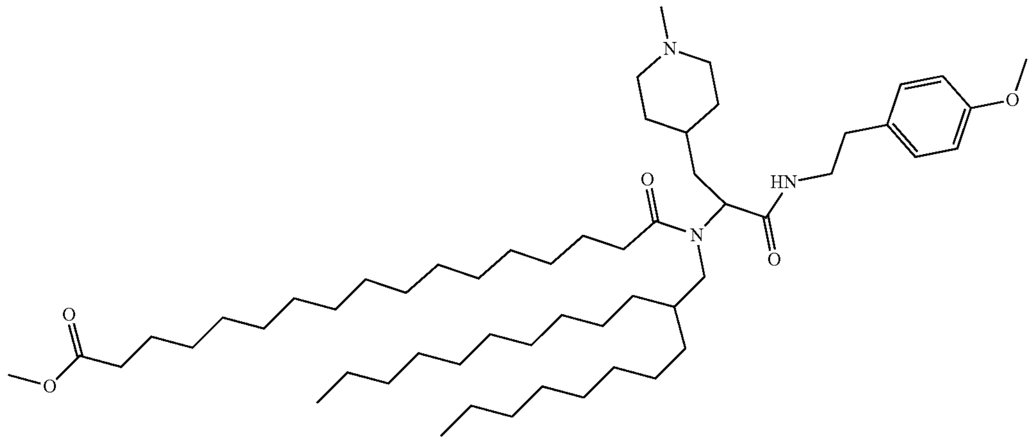
P341A10
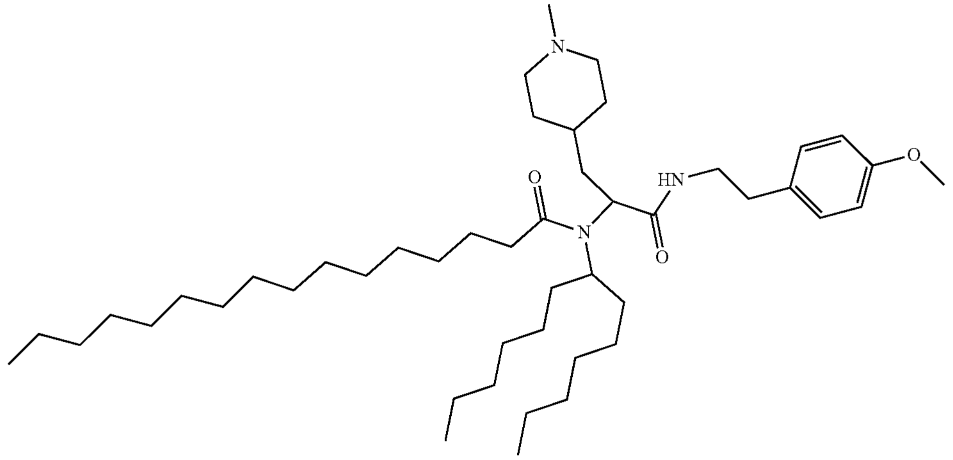
P363B8
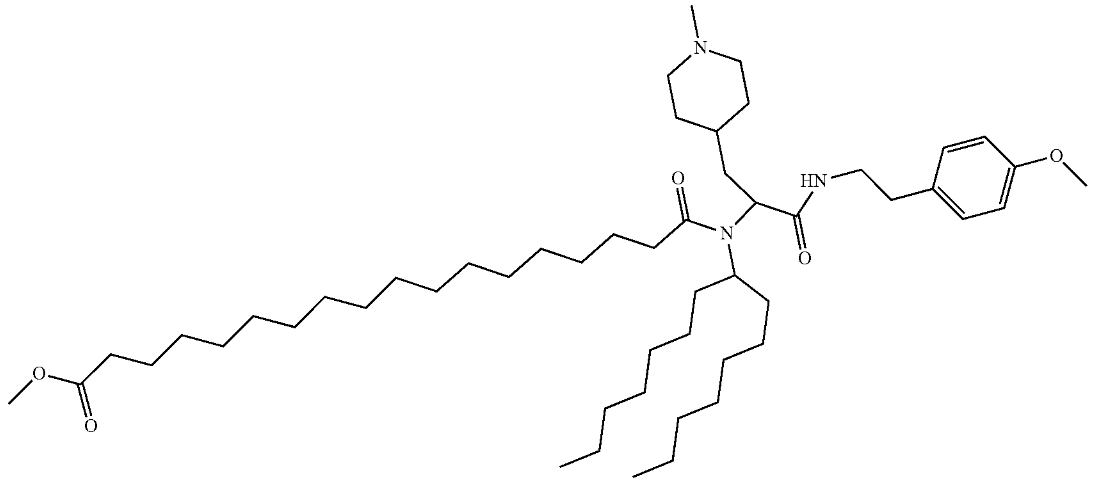

-continued
P343B6
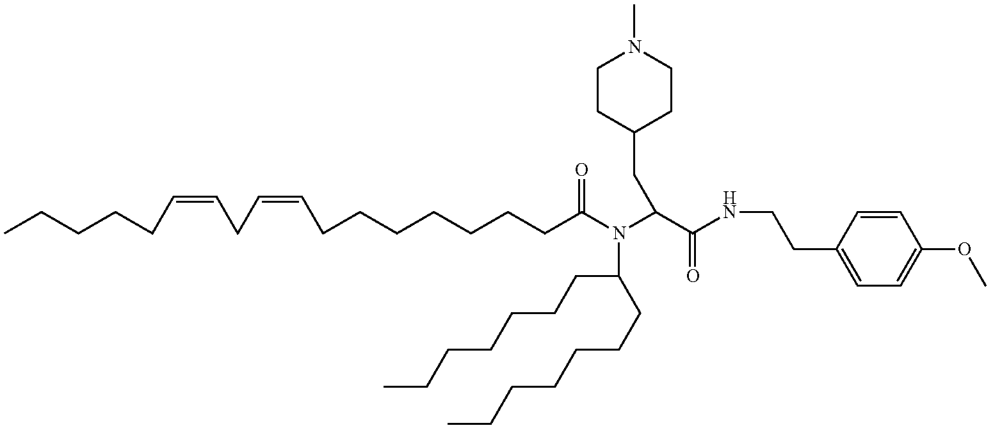
P343B8
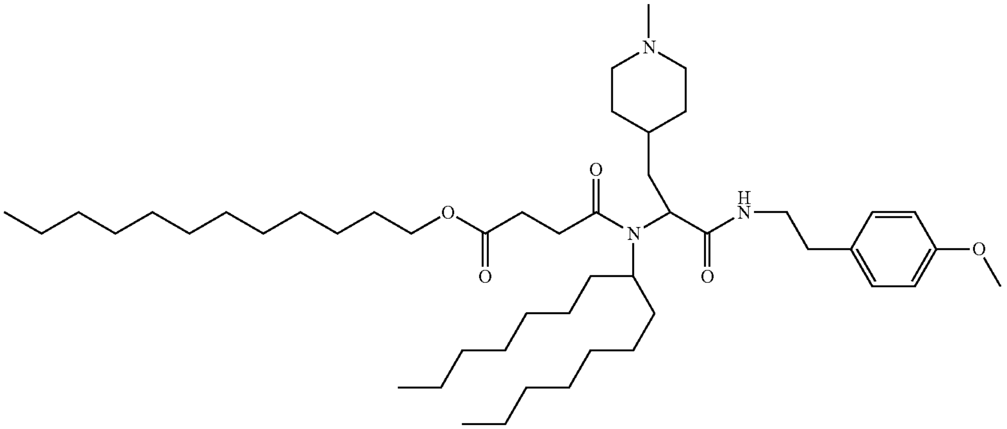
P153C1
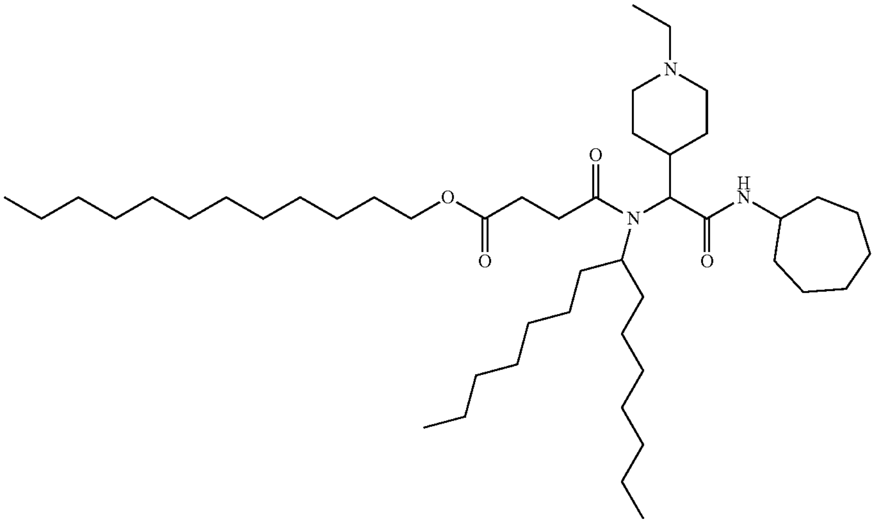

-continued
P153C2
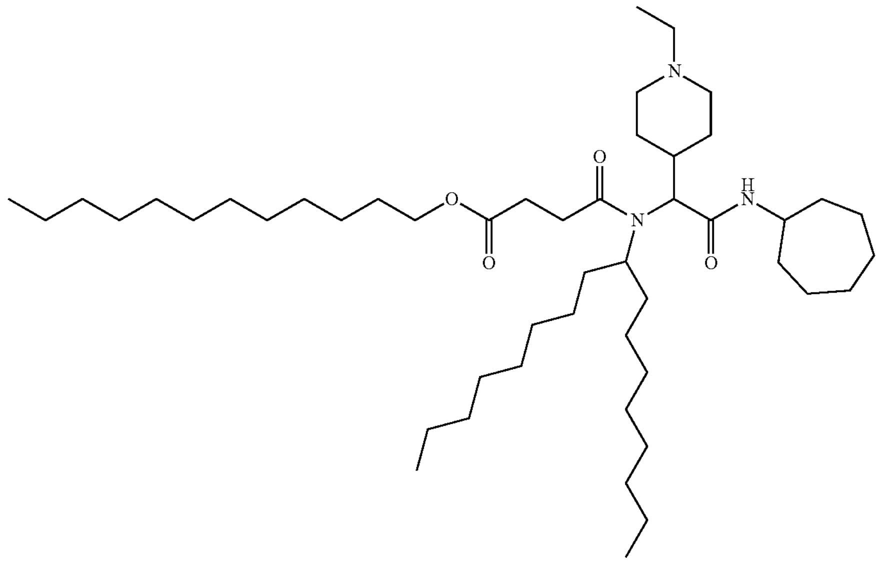
P153C3
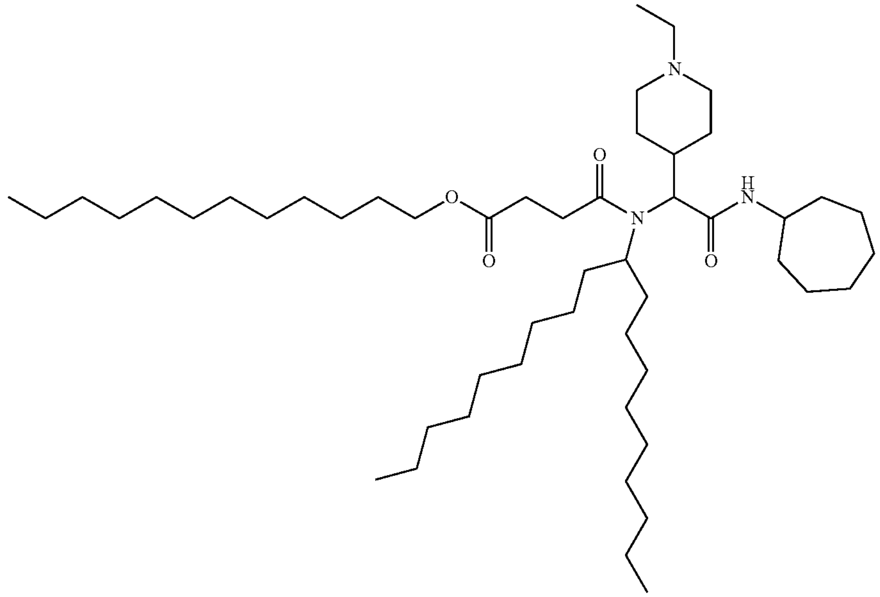
P153C5
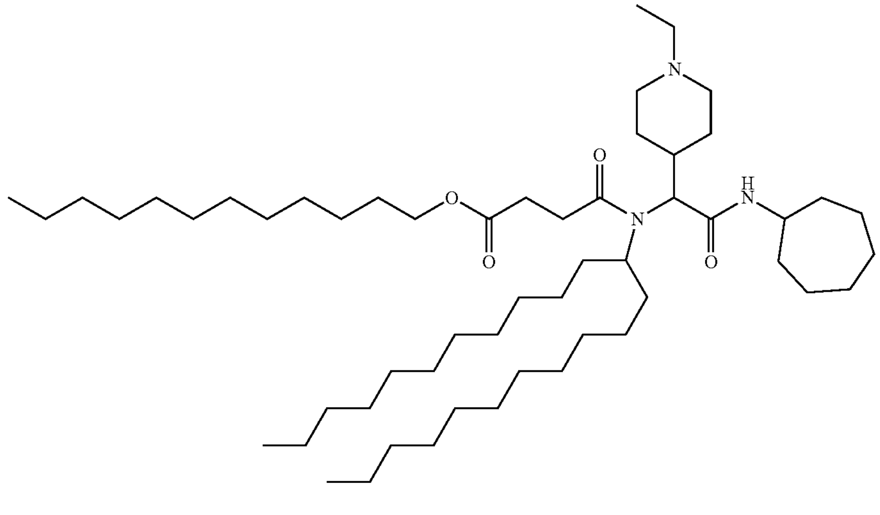

-continued
P56B2
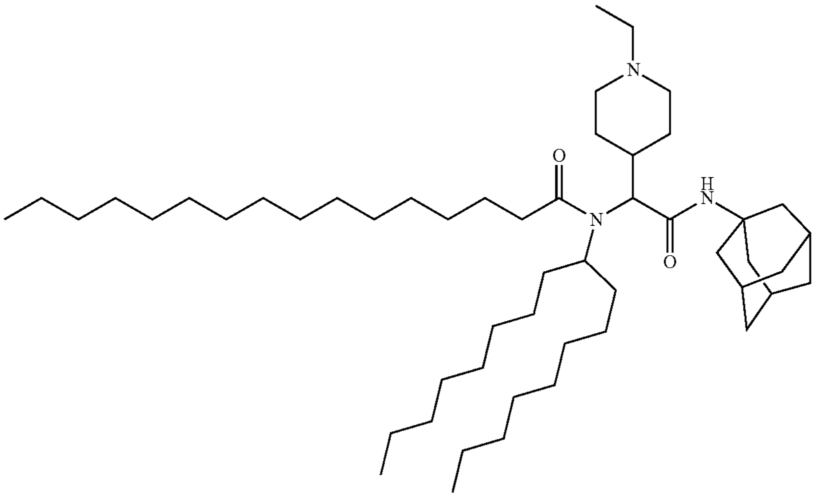
P56A3
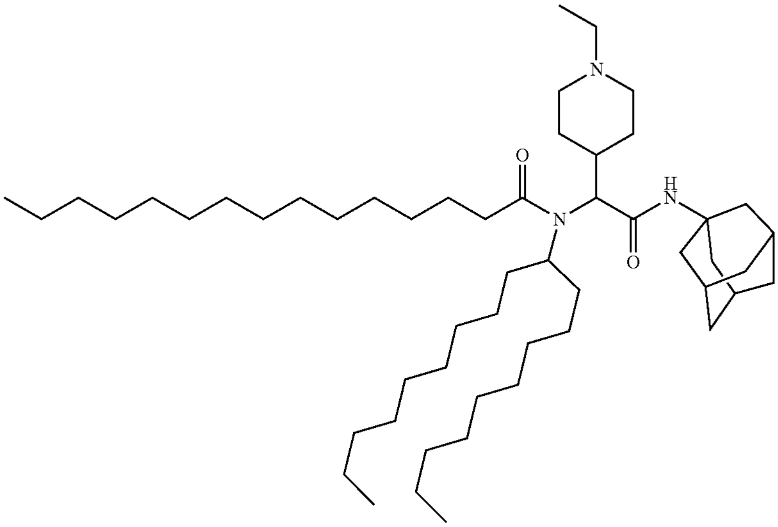
P56B3
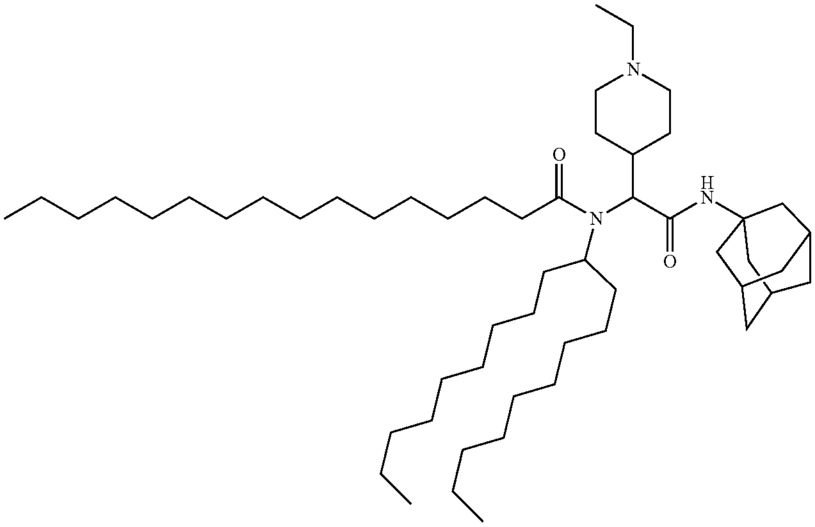

-continued
P56B7
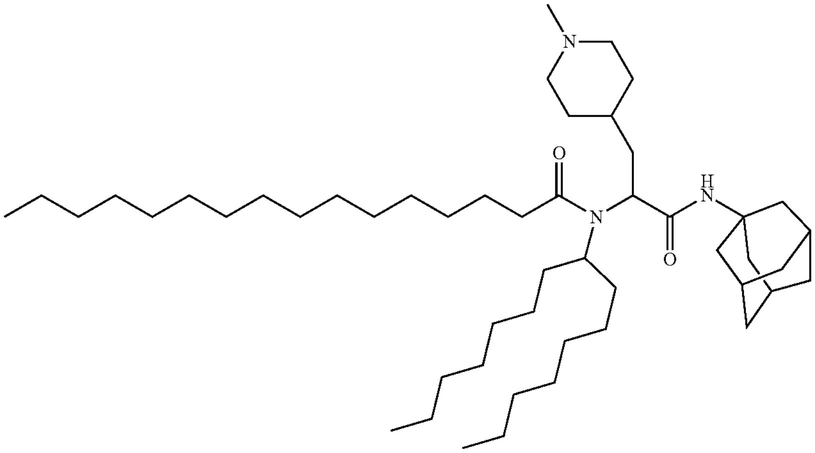
P56A8
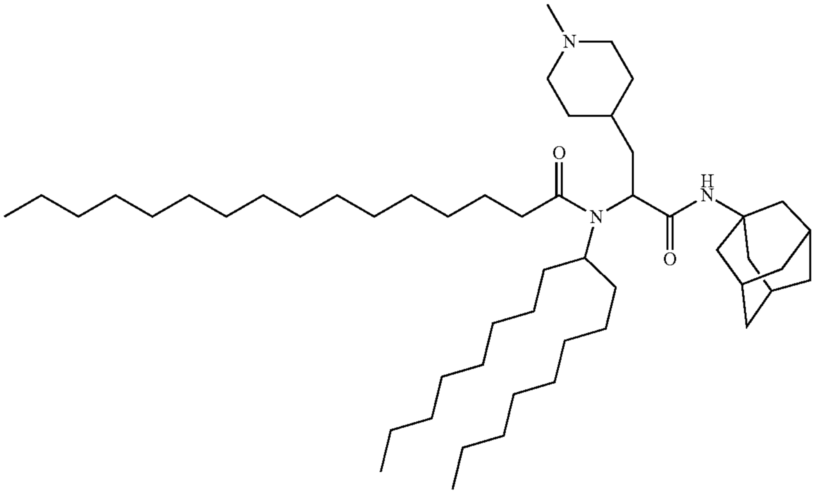
P56B8
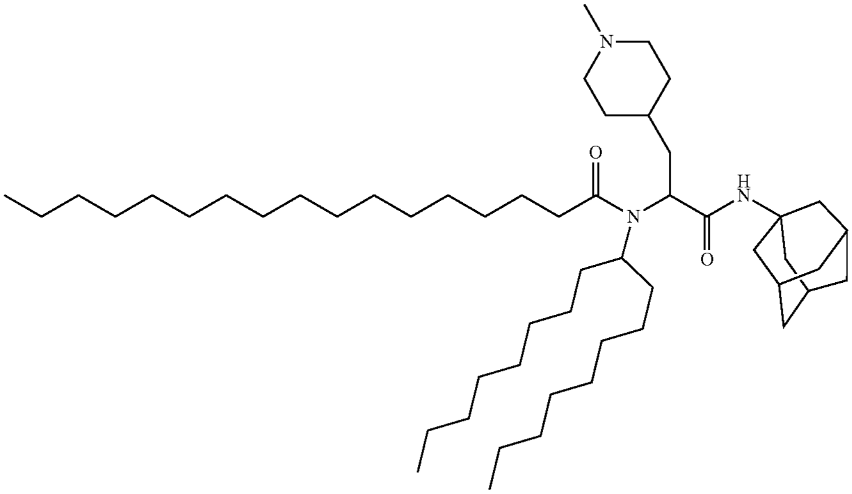

-continued
P56A9
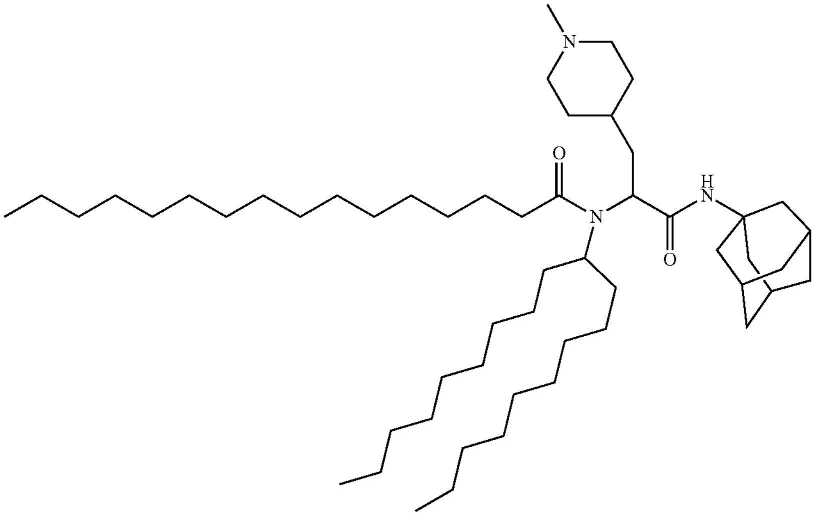
P55A6
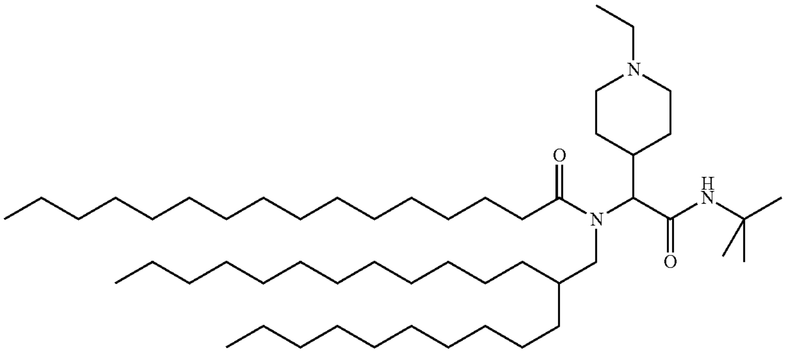
P55C12
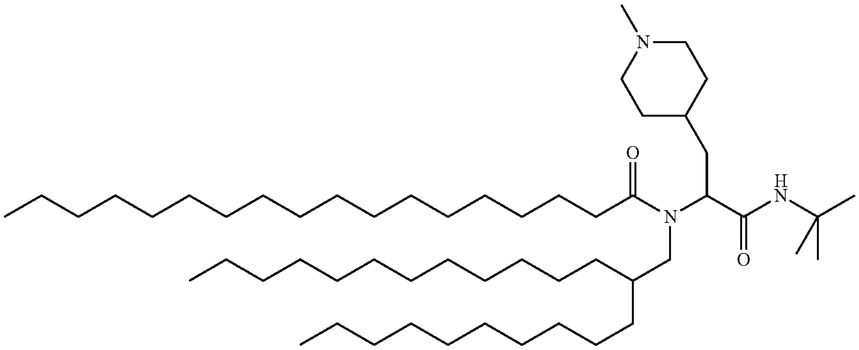
P343B6
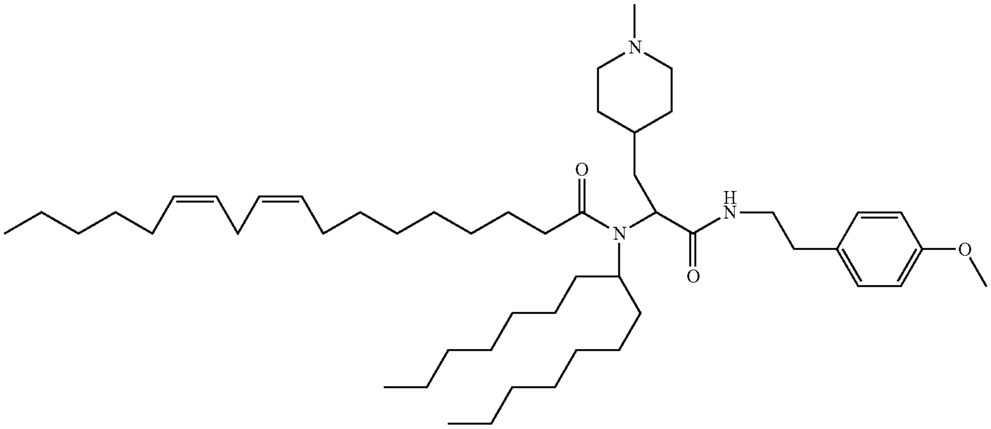

-continued
P343B8
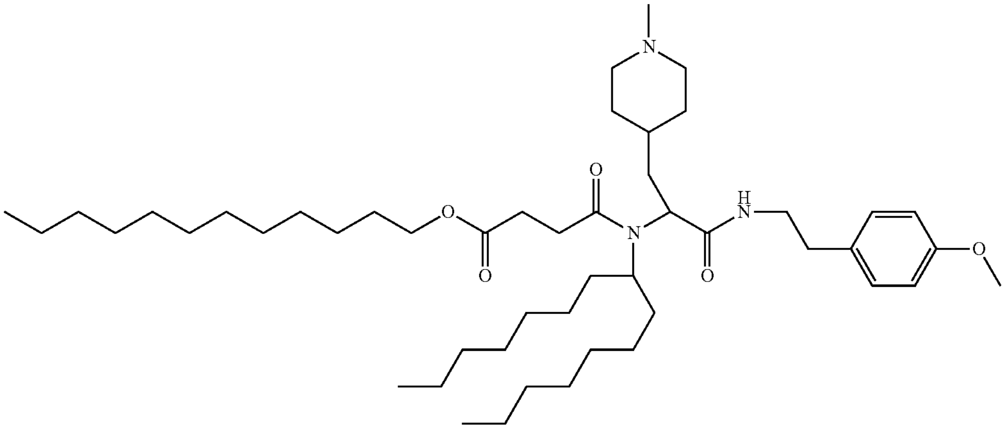
P153C1
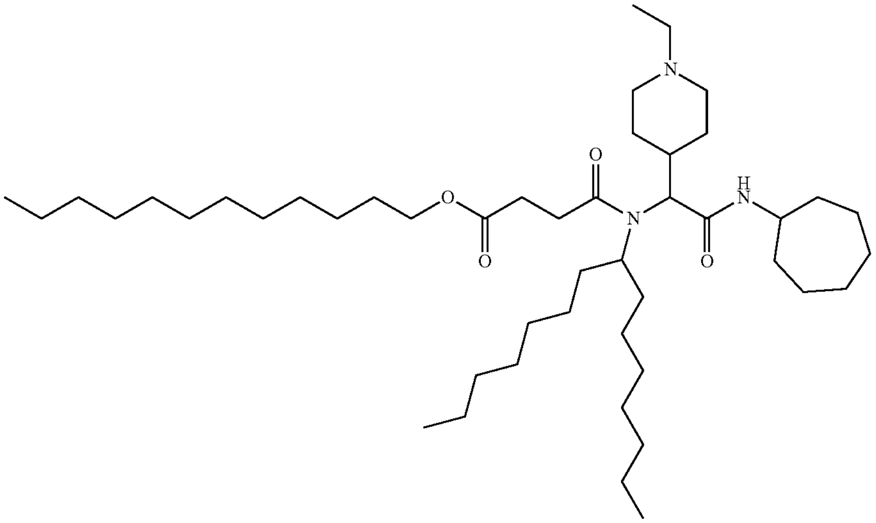
P153C2
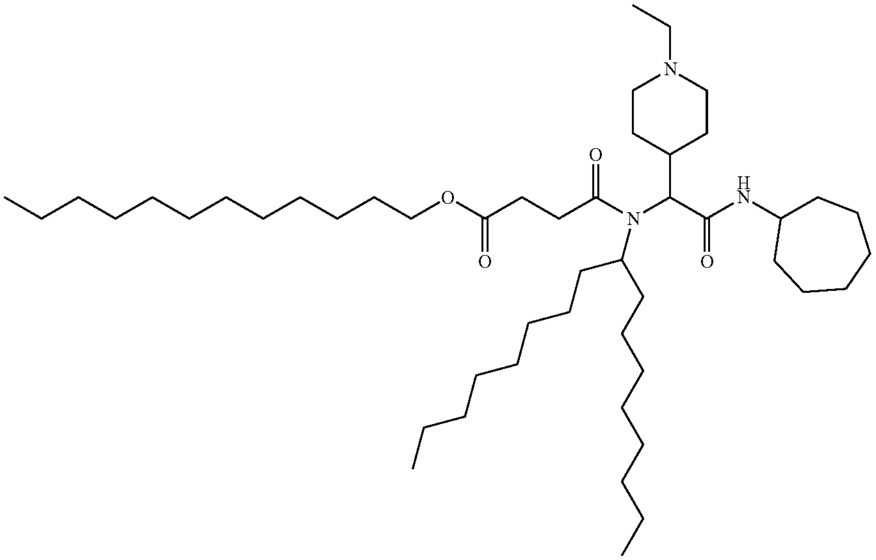

-continued
P153C3
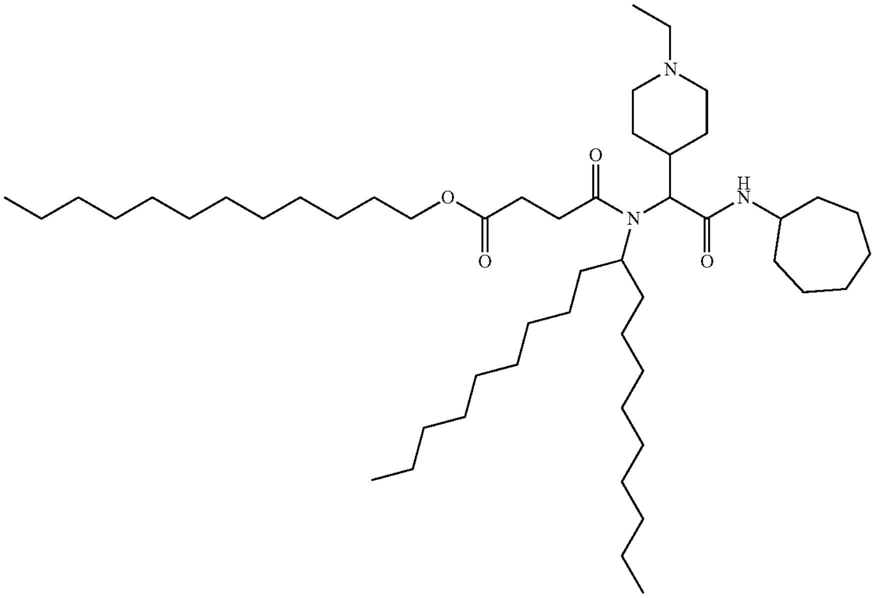
P153C5
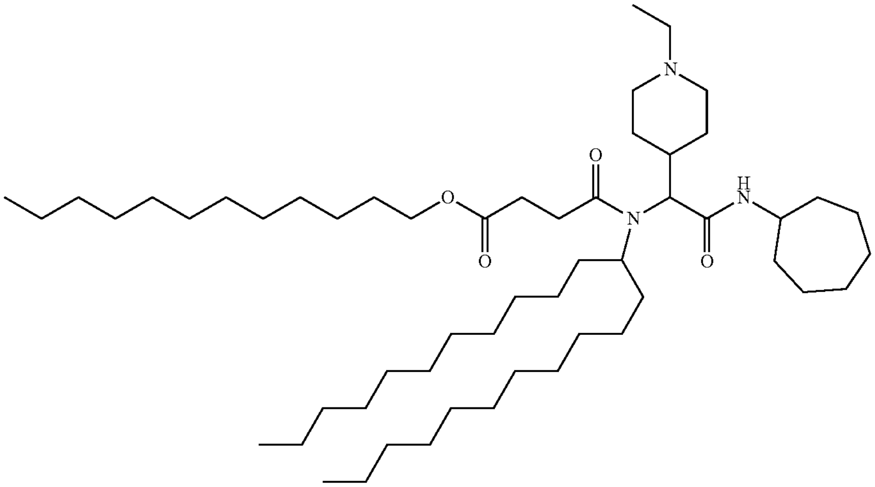
P56B2
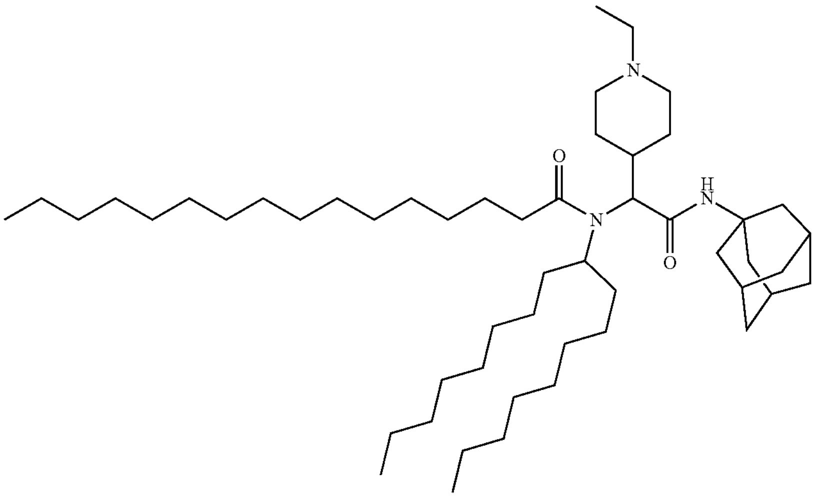

-continued
P56A3
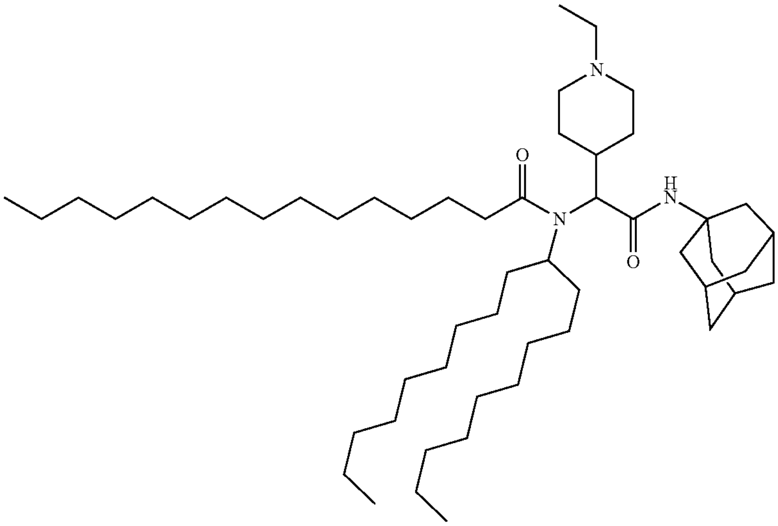
P56B3
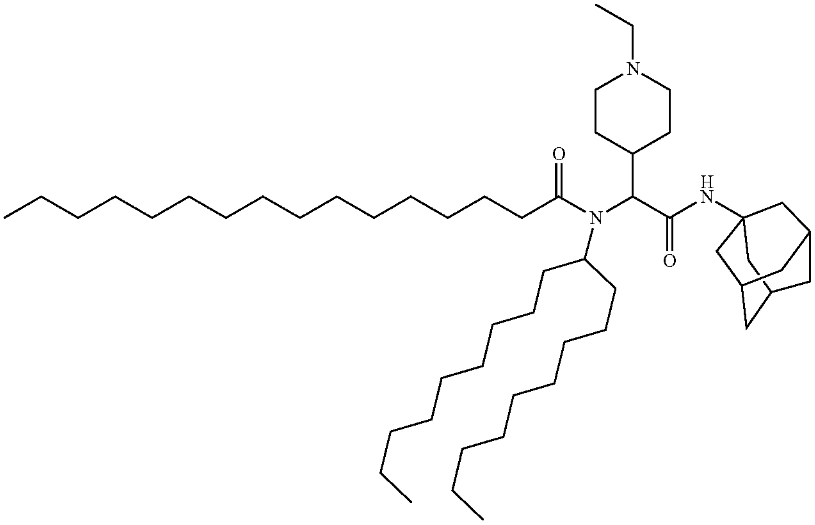
P56B7
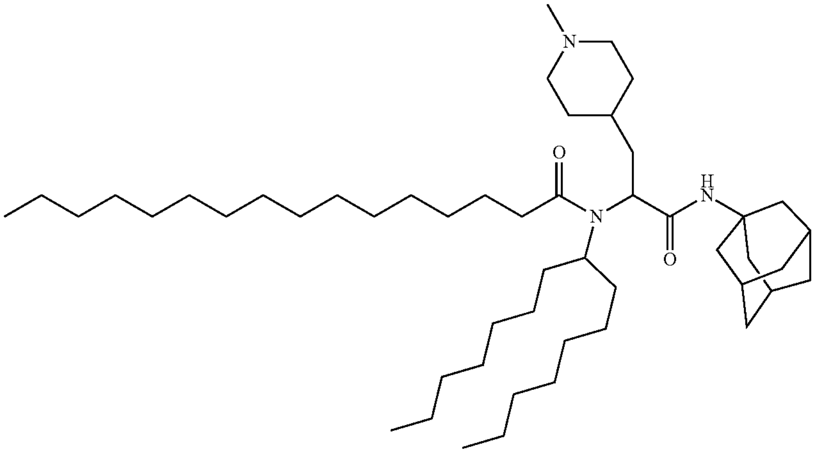

-continued
P56A8
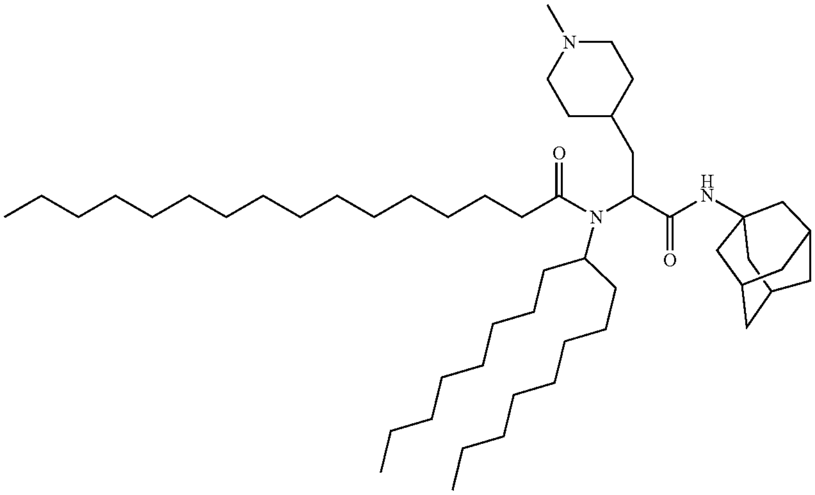
P56B8
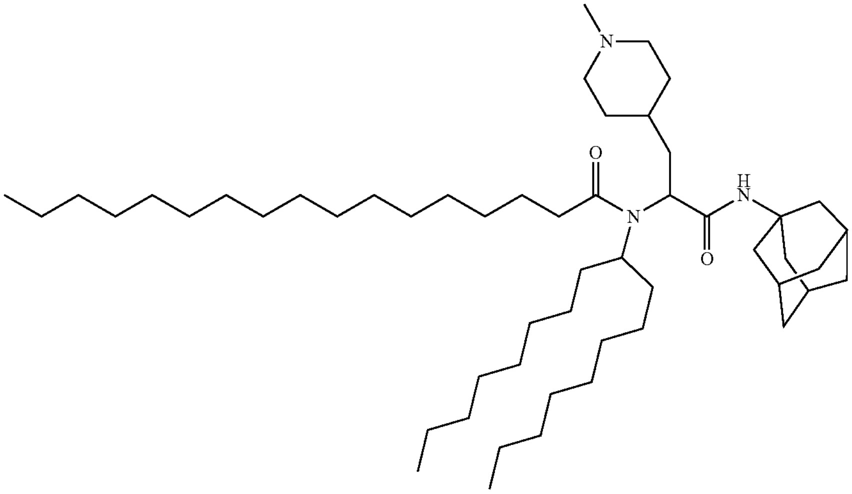
P56A9
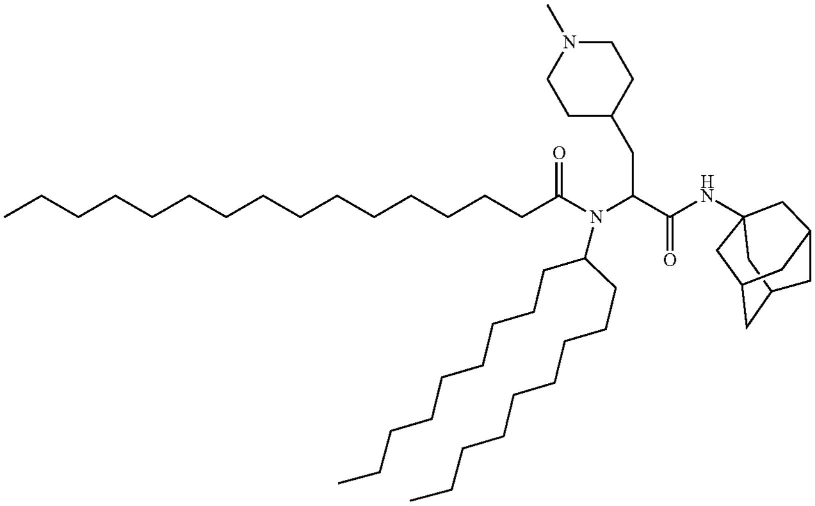

-continued
P55A6
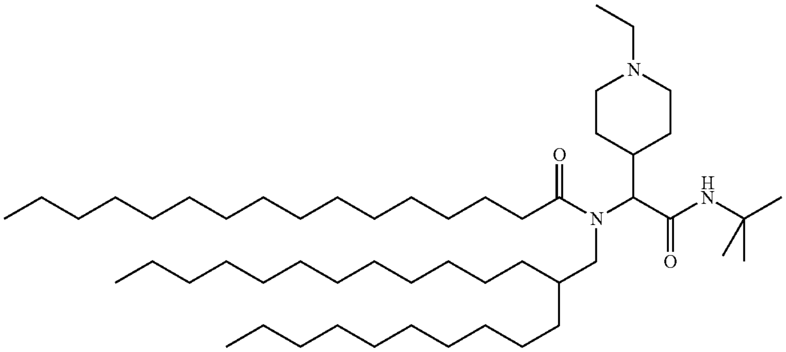
P55C12
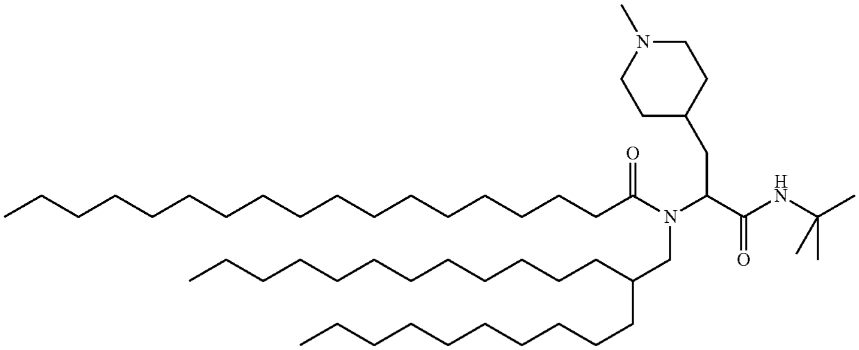
P54B6
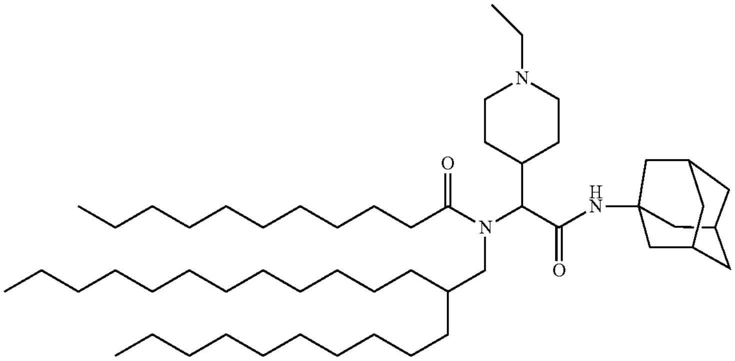
P54D6
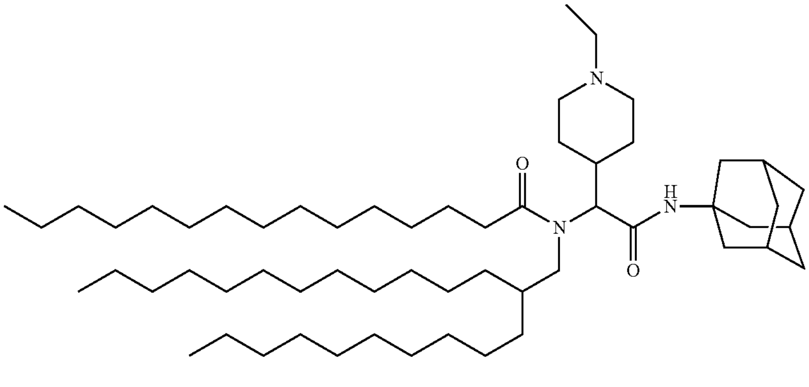

-continued
P54A10
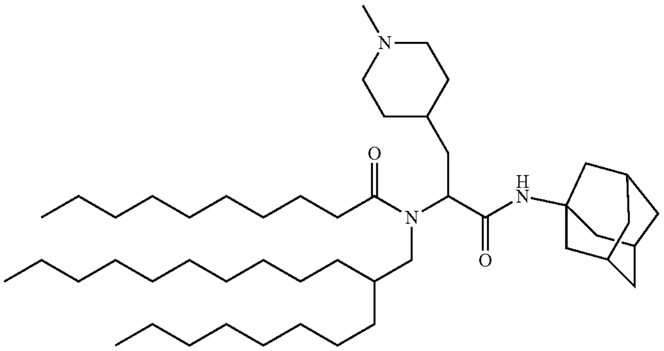
P54A12
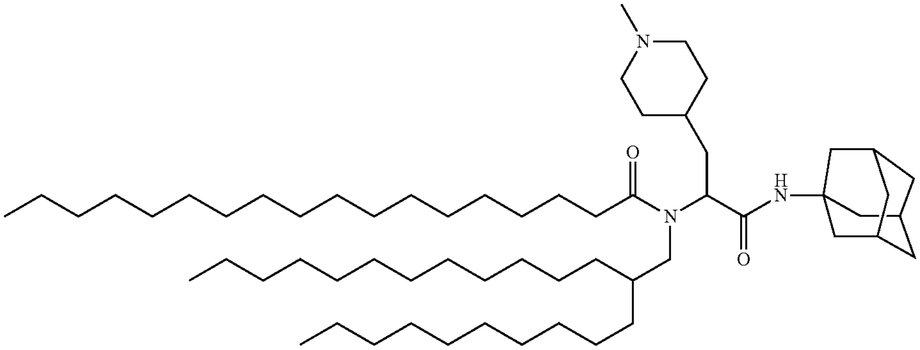
P53A5
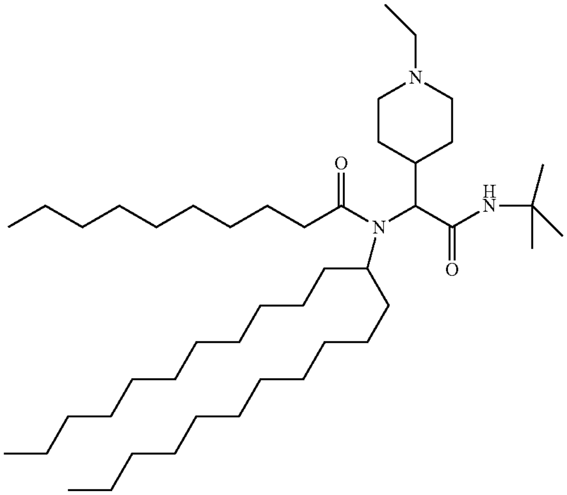
P53G11
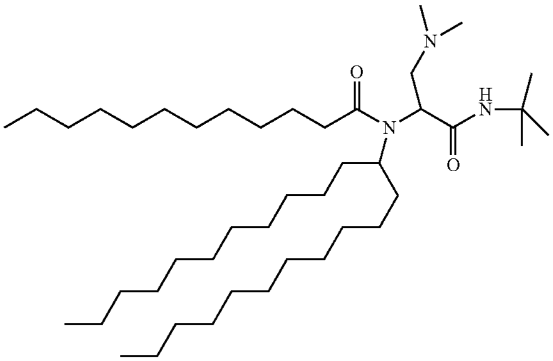
P53A12
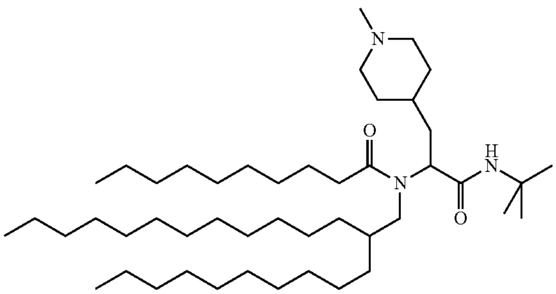
P53E12
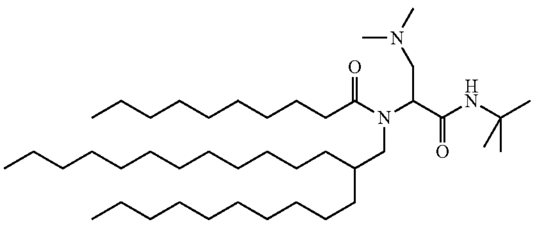

-continued
P52B5
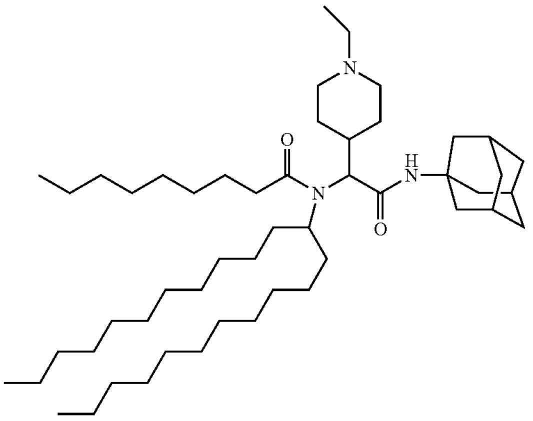
P52B6
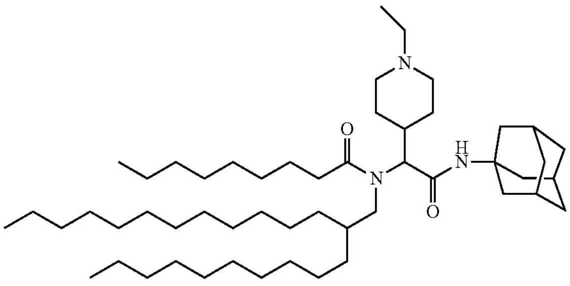
P52C6
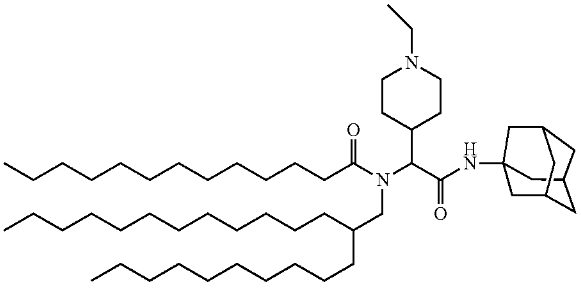
P52D6
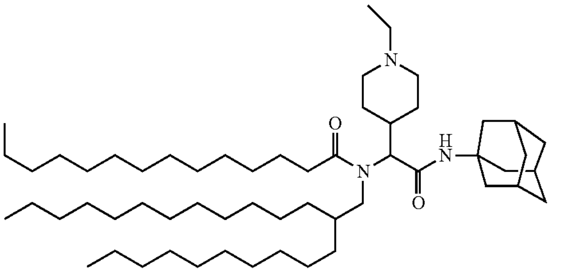
P52C12
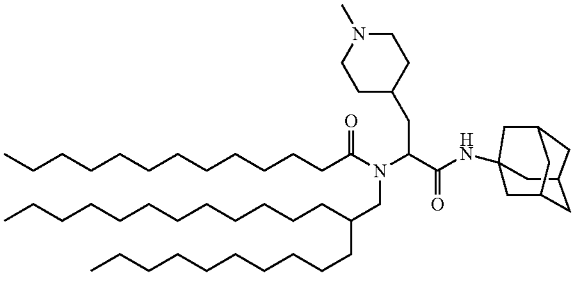
P51A12
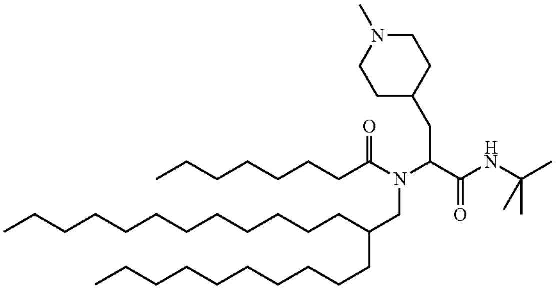
P51B12
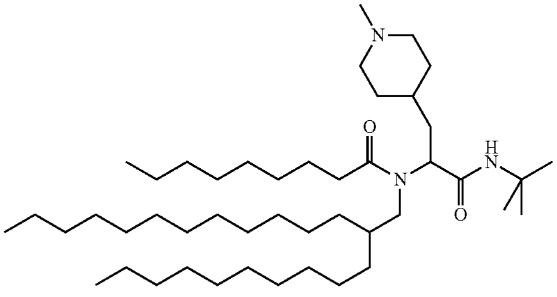
P51C12
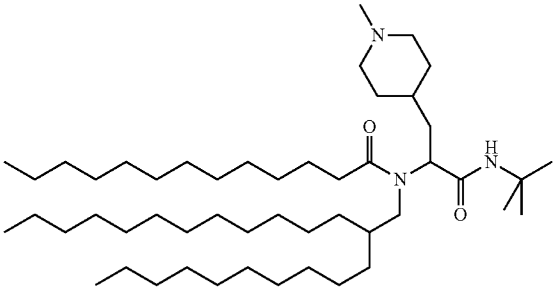
P51E12
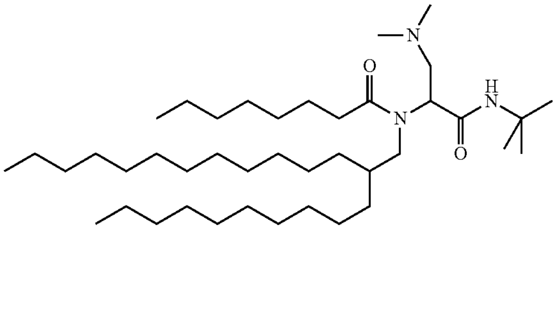

-continued
P42A4
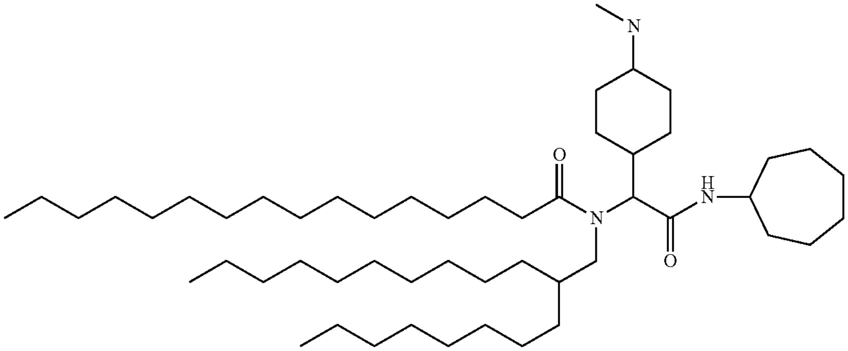
P42B4
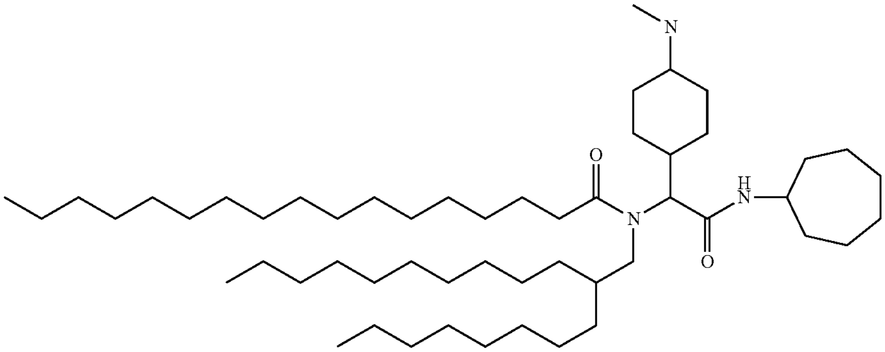
P40A10
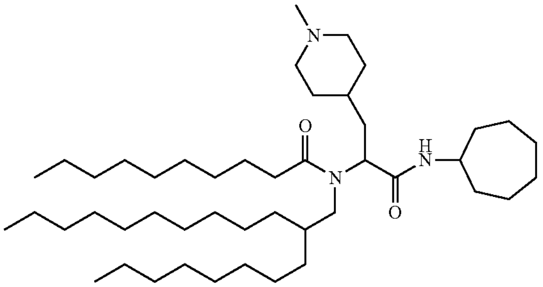
P40C12
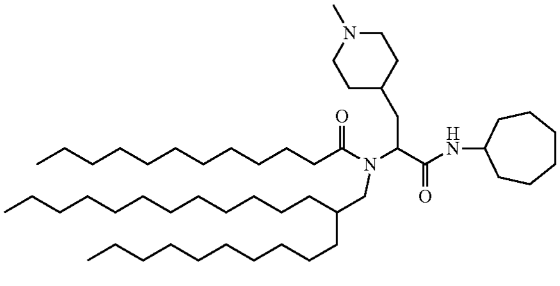
P40B2
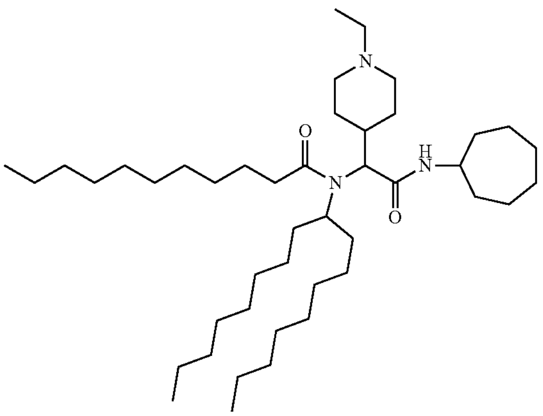
P40C2
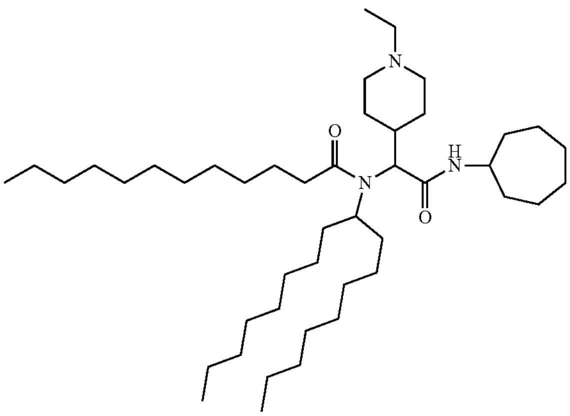

-continued
P40C4
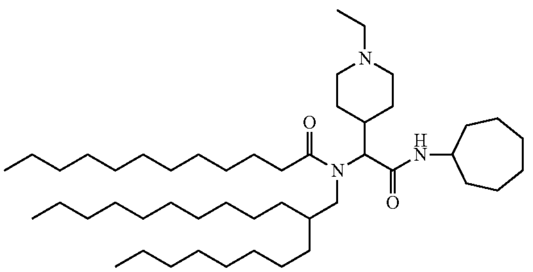
P40C4
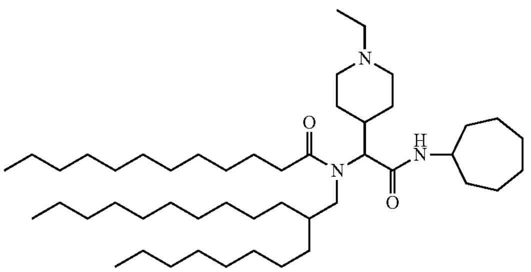
P38C3
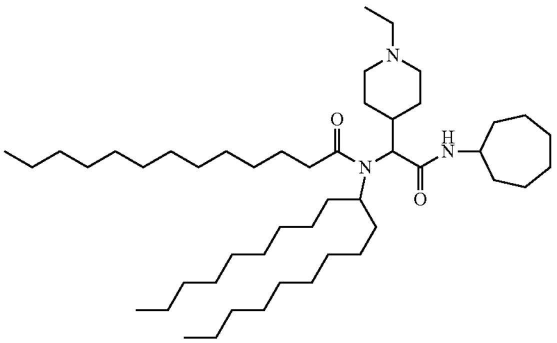
P38C4
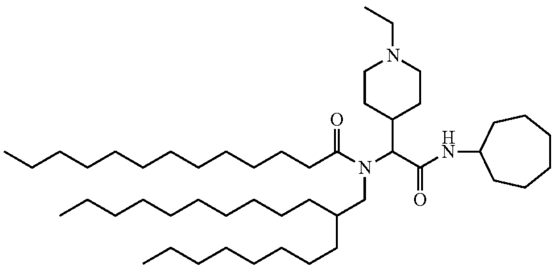
P38A6
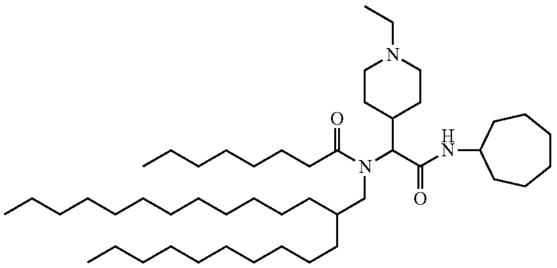
P38C7
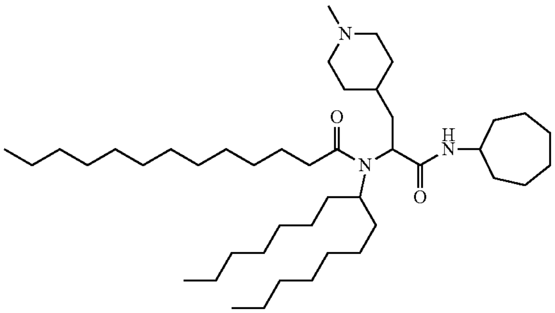
P38C8
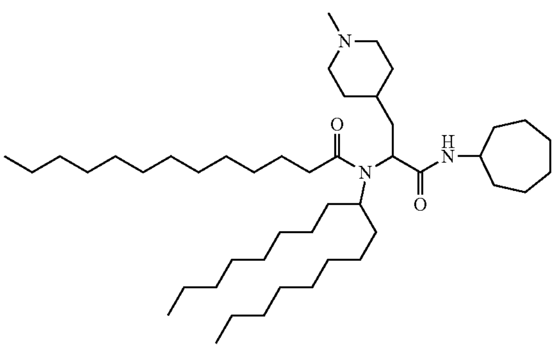
P38A9
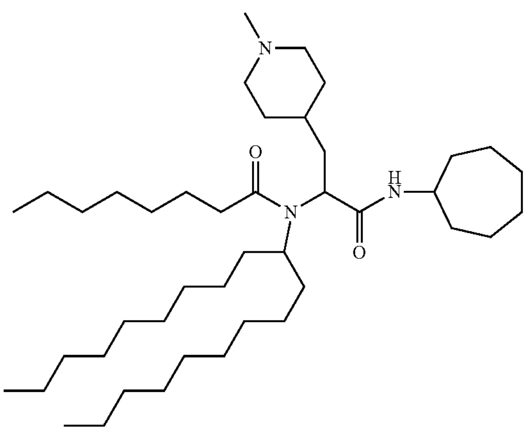

-continued
P38A10
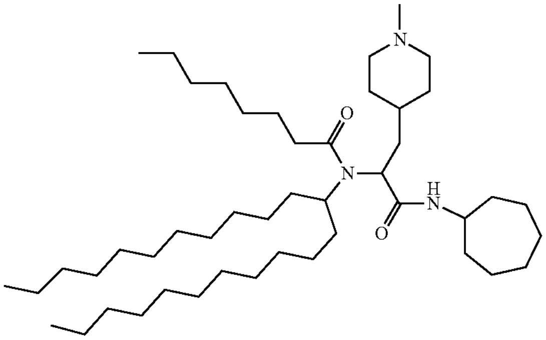
P38B10
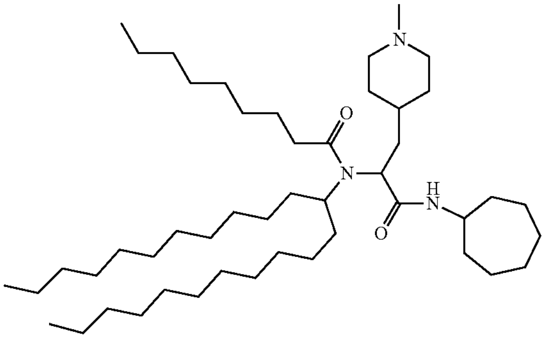
P38C10
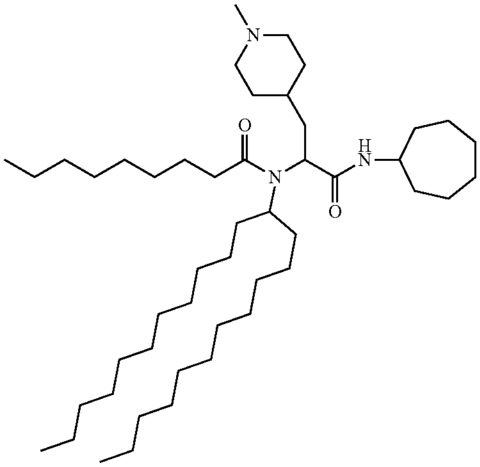
P38C1
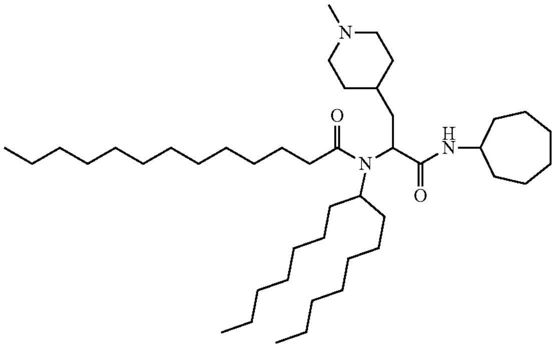
P38B2
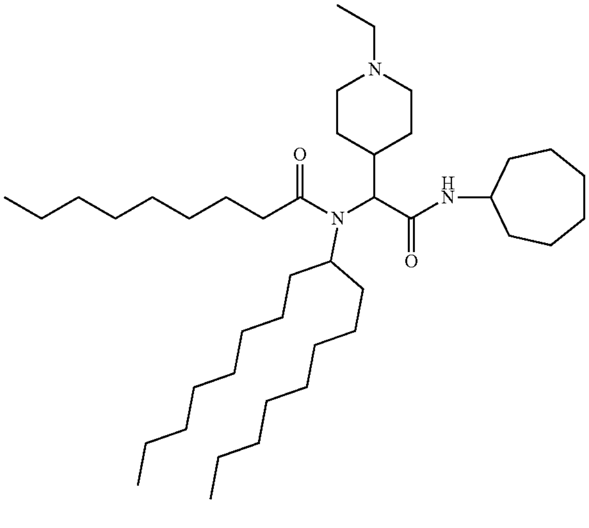

-continued
P28D10
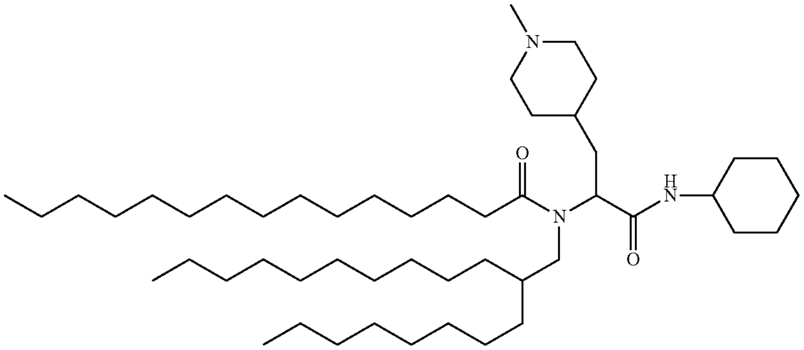
P30C4
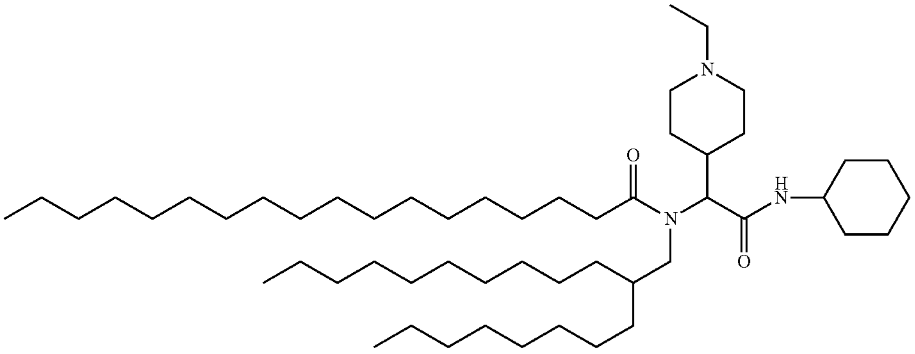
P30C1
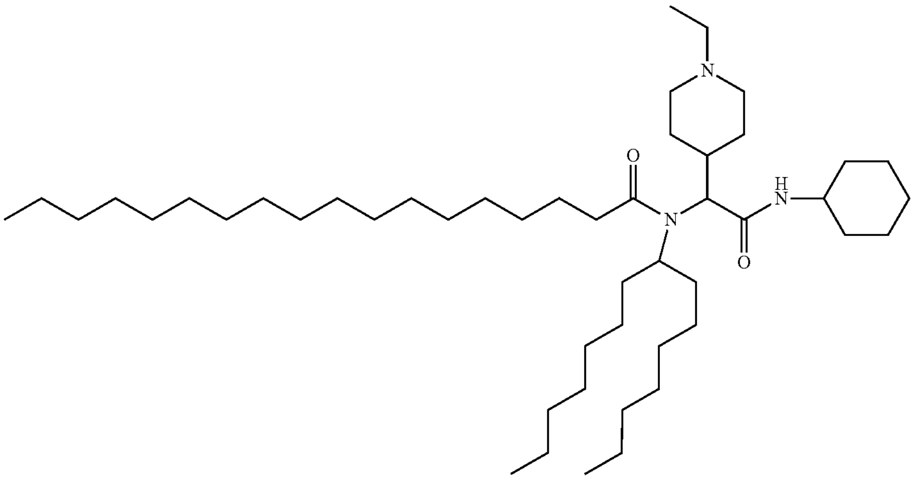

-continued
P30B1
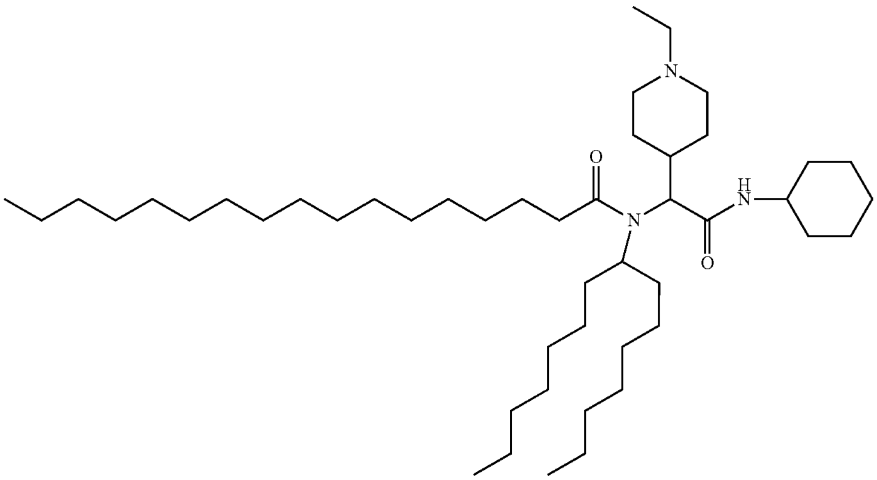
P26D4
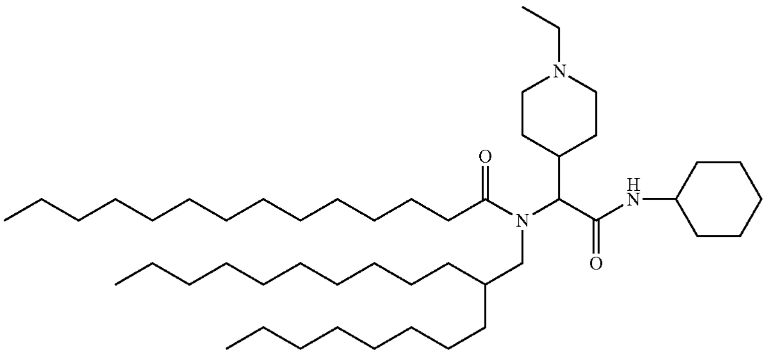
P1C4
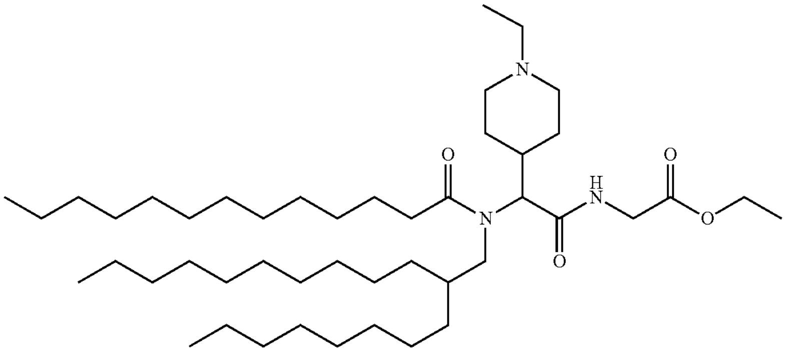
P43C10
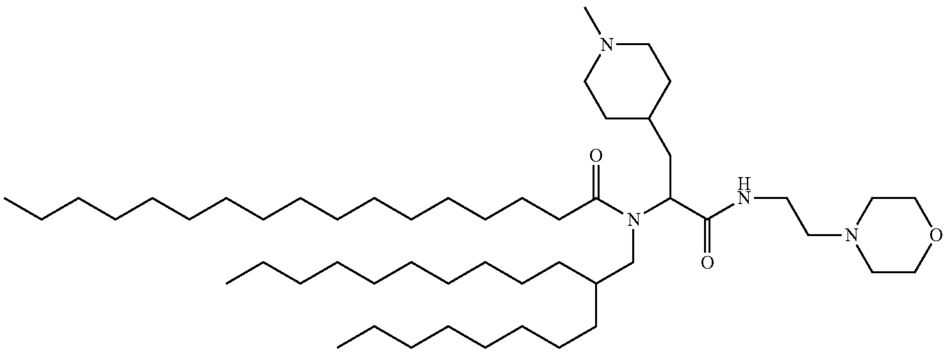

-continued
P43A12
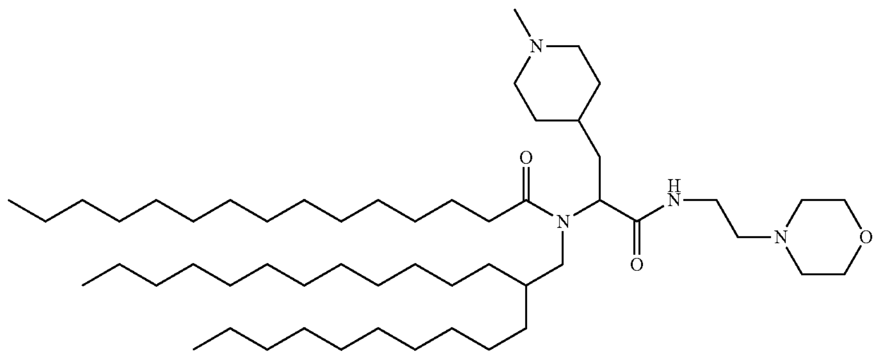
P43C12
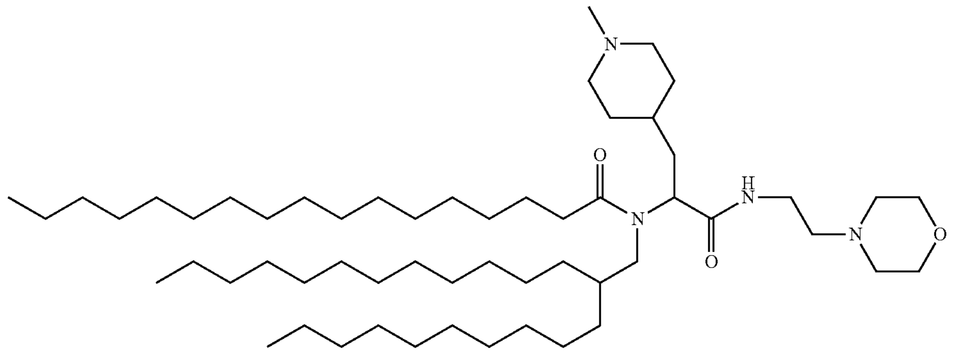
P41B4
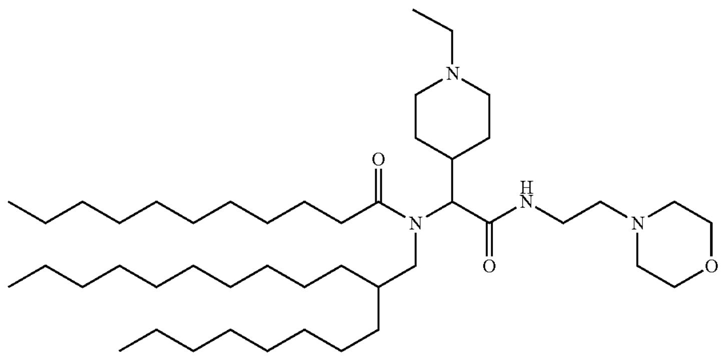
P41D4
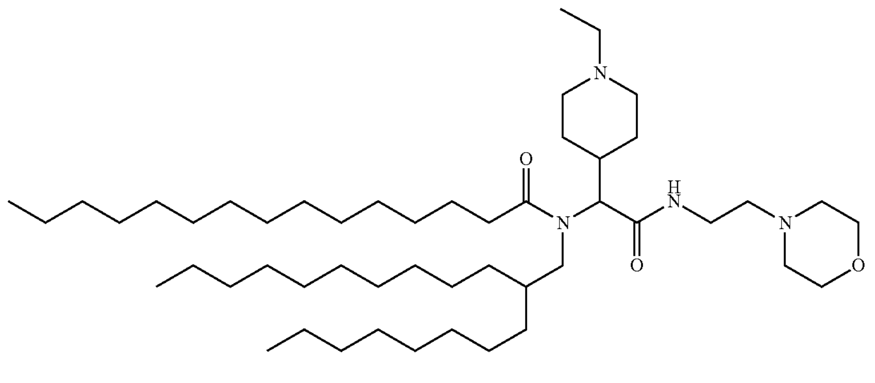

-continued
P41C6
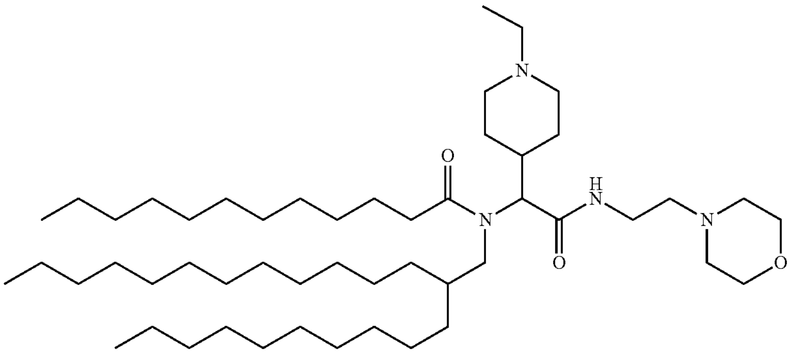
P41B10
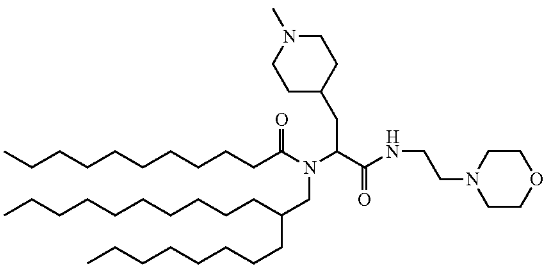
P41C10
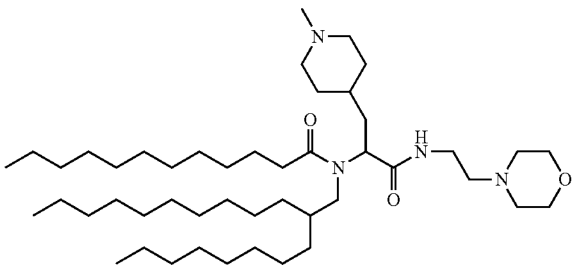
P41D10
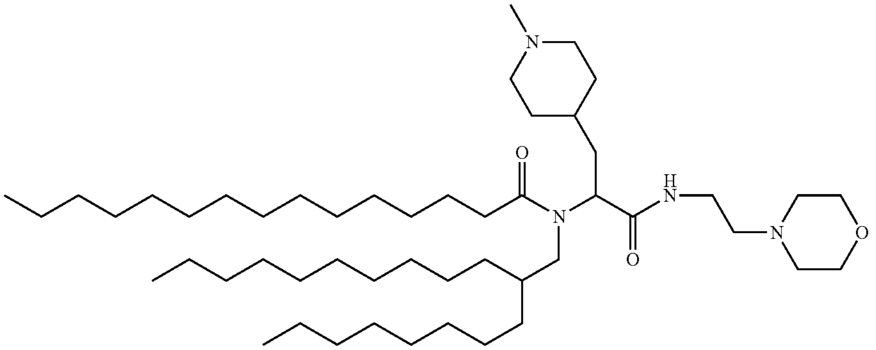
P41B12
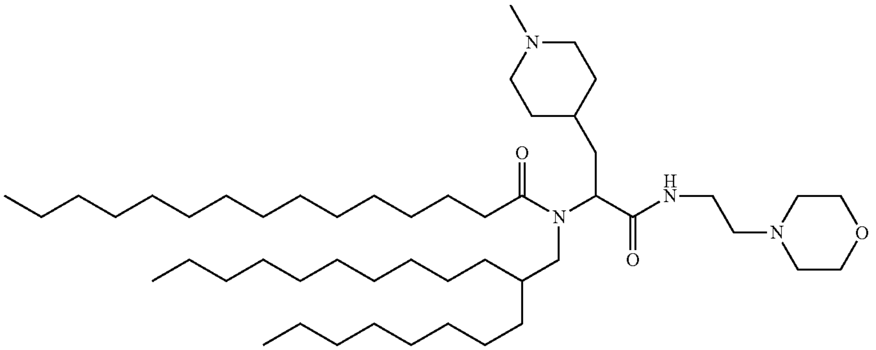

-continued
P39C10
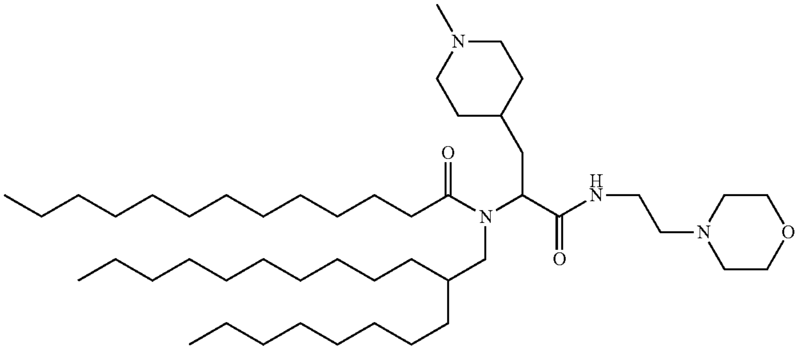
P39D10
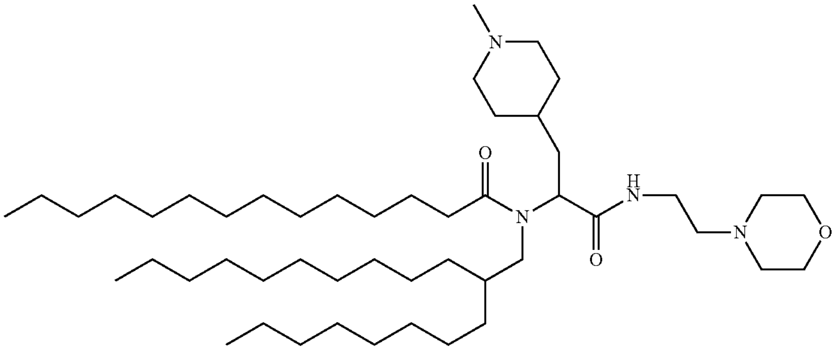
P39A12
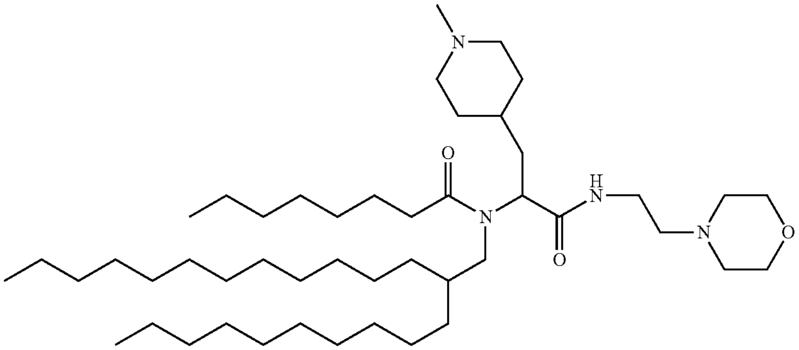
P39F12
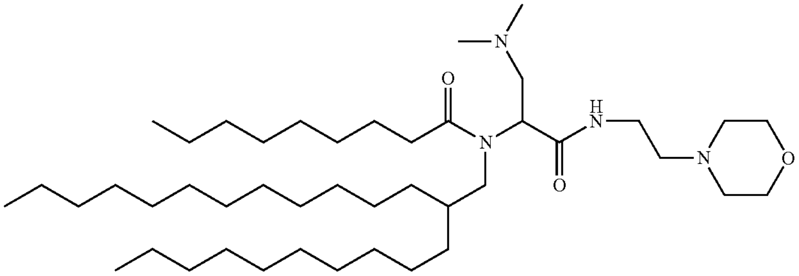
P39G12
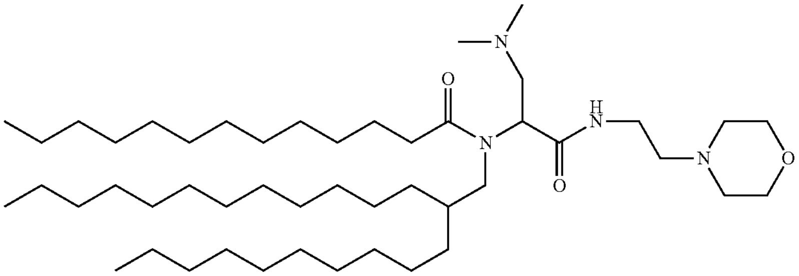

-continued
P39B12
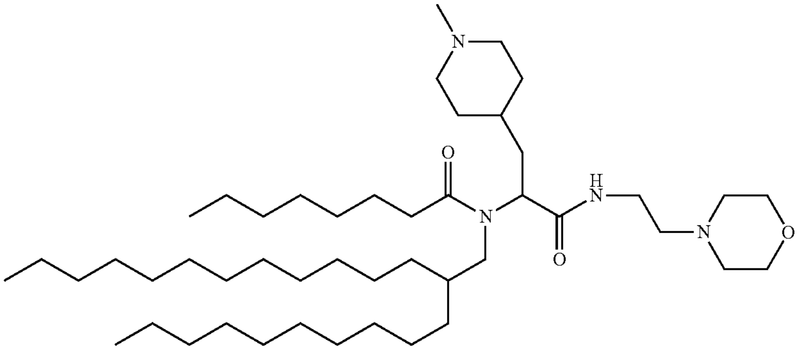
P39C12
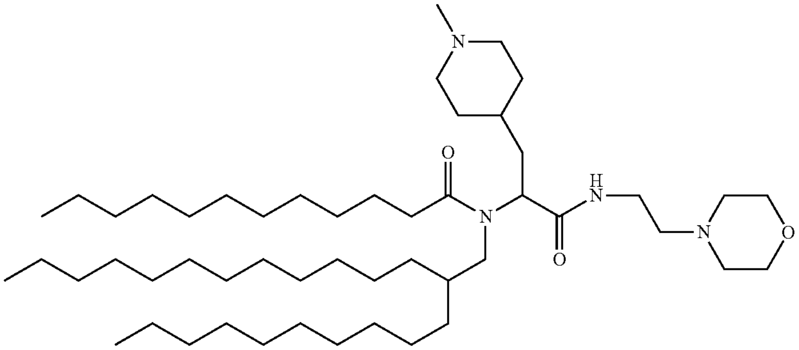
P39D4
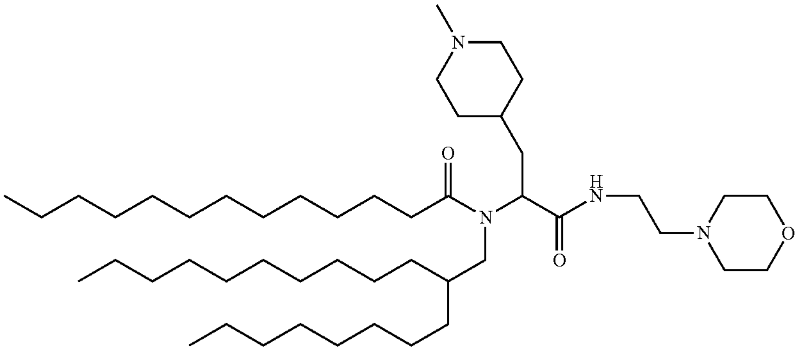
P39A6
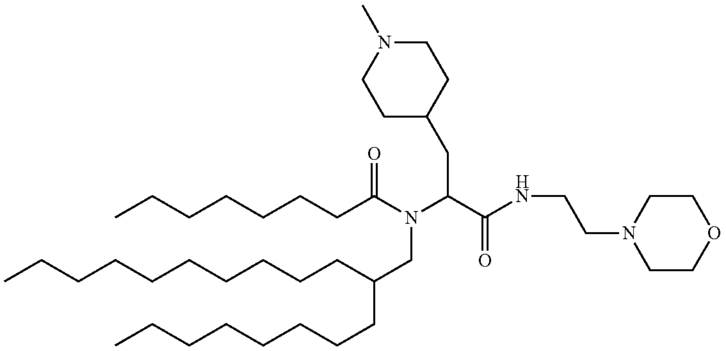

-continued
P38B12
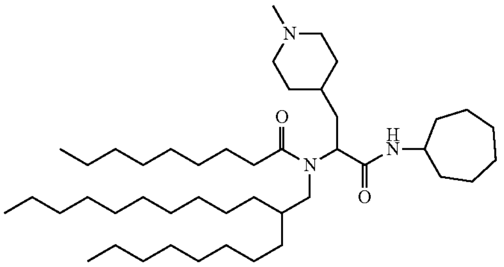
P38C12
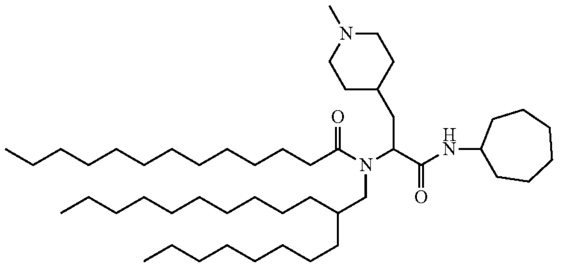
P143A7
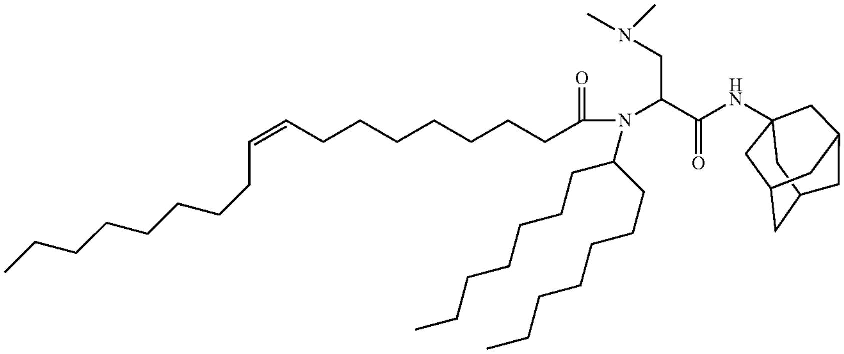
P143A9
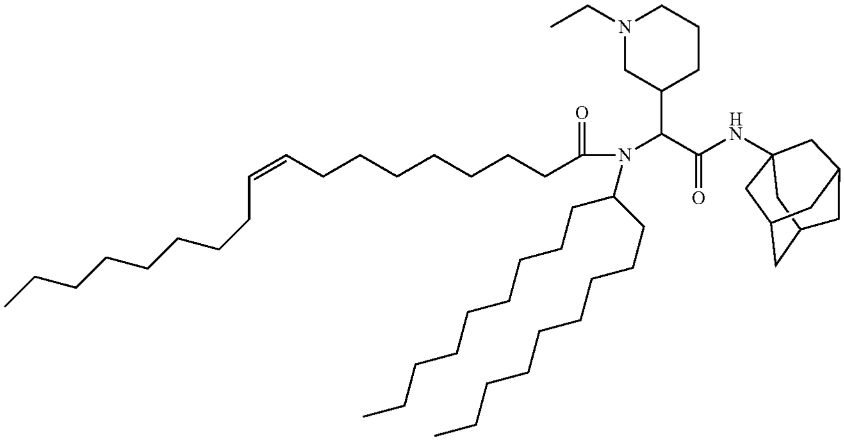
P143C7
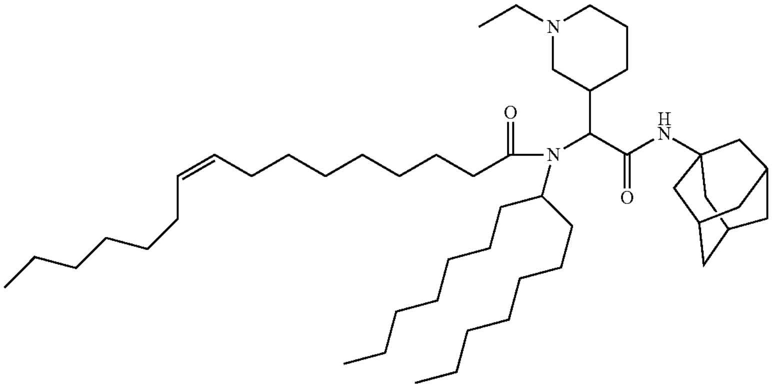

-continued
P143C9
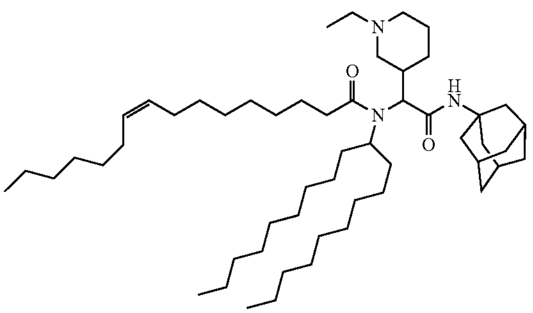
P143C10
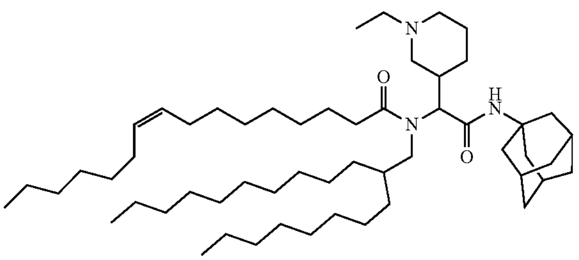
P143D10
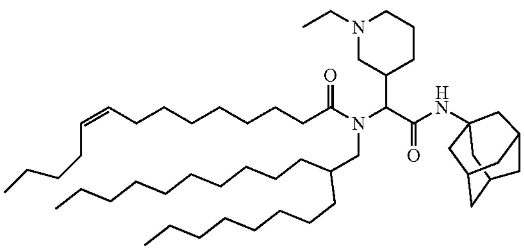
P147B10
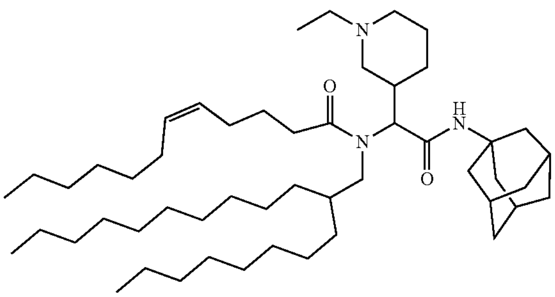
P147C7
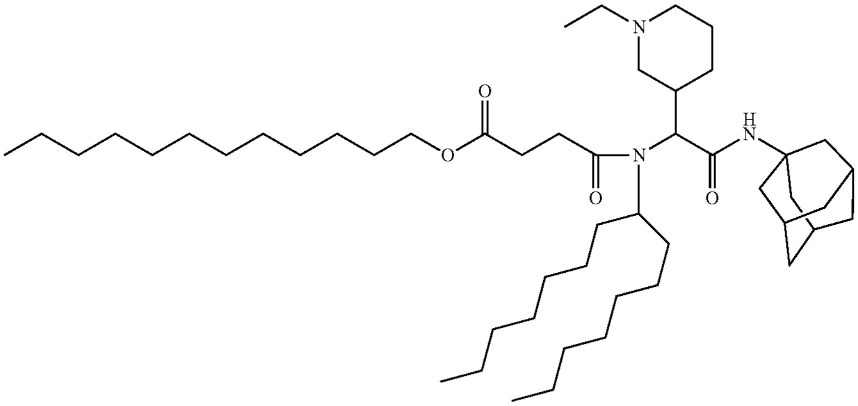
P147C8
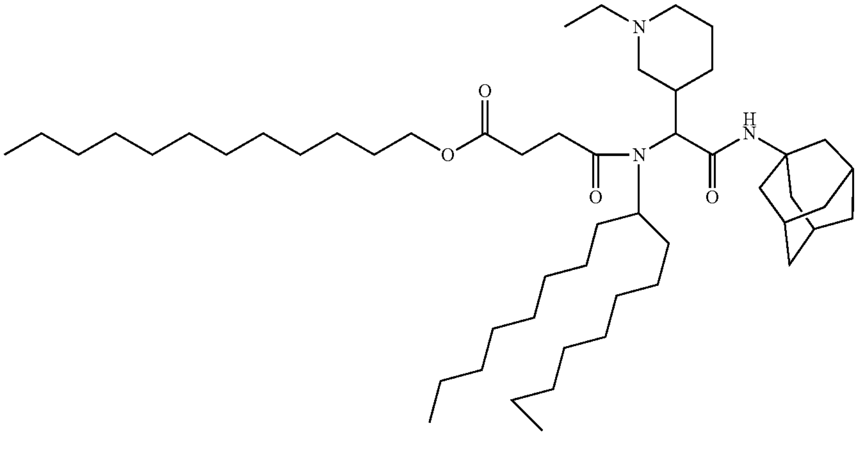

-continued
P147C9
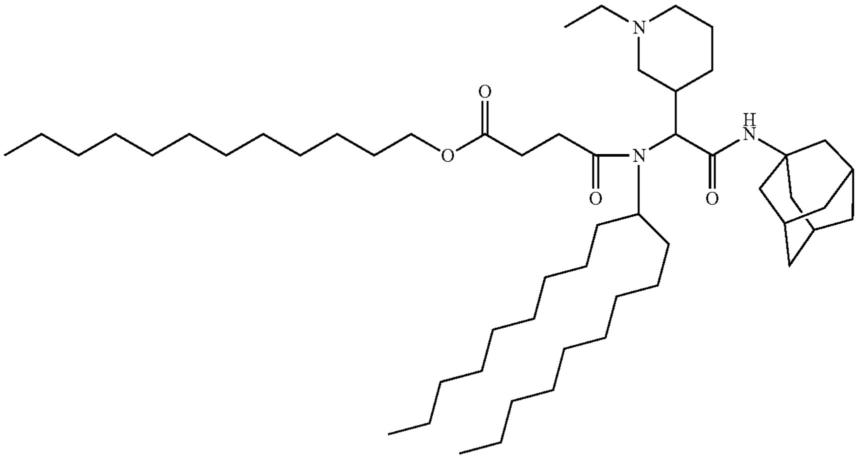
P147C10
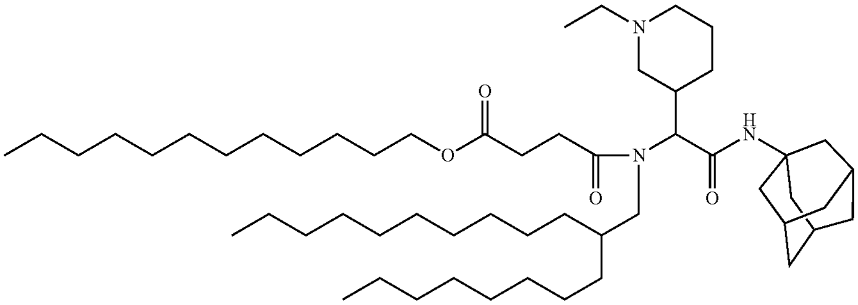
P147C12
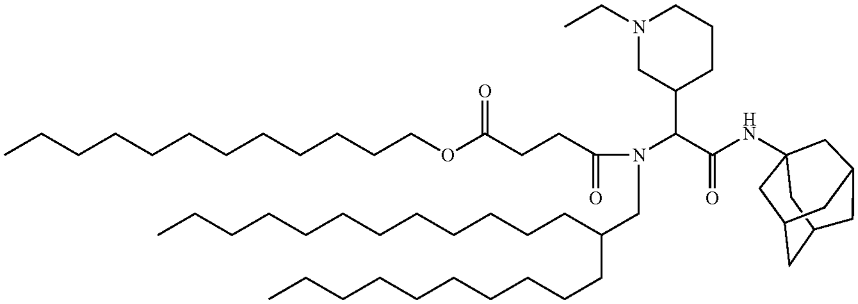
P147D10
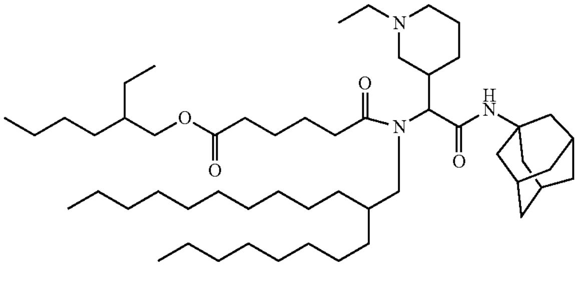
P147D12
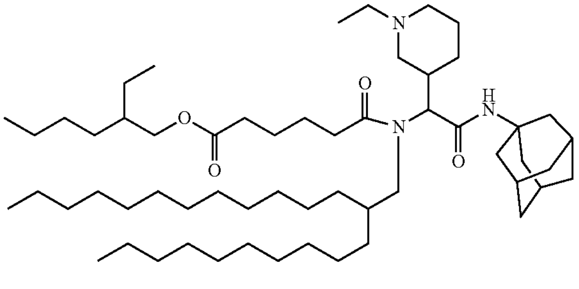

-continued
P150C2
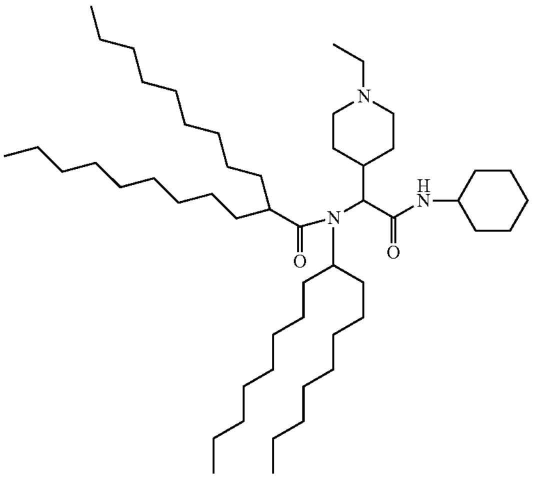
P149A4
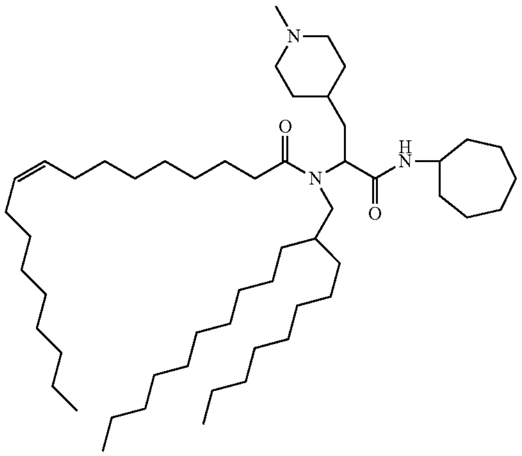
P149A7
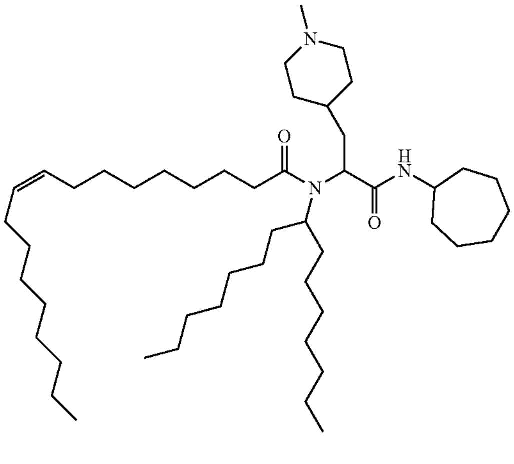
P149A8
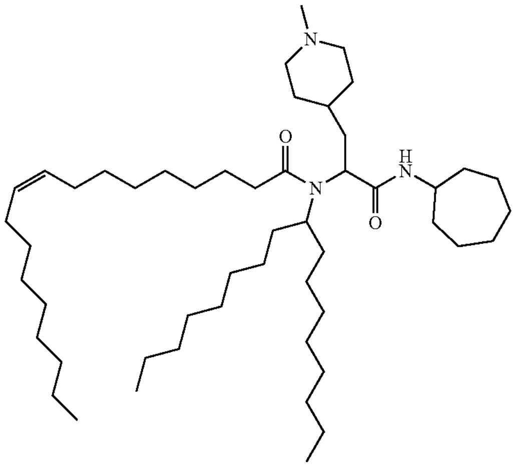

-continued
P148A1
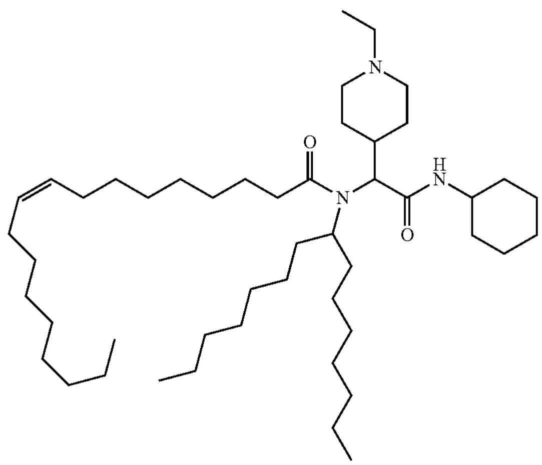
P148A2
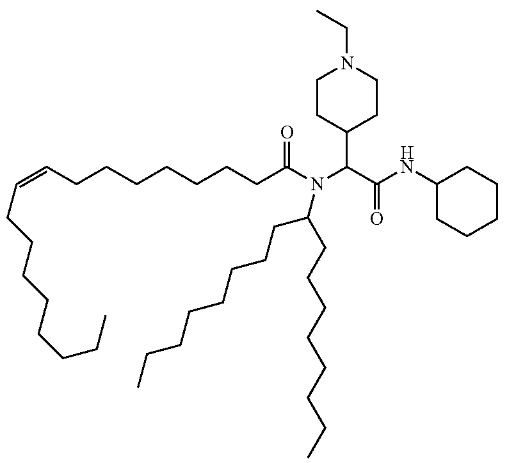
P148A3
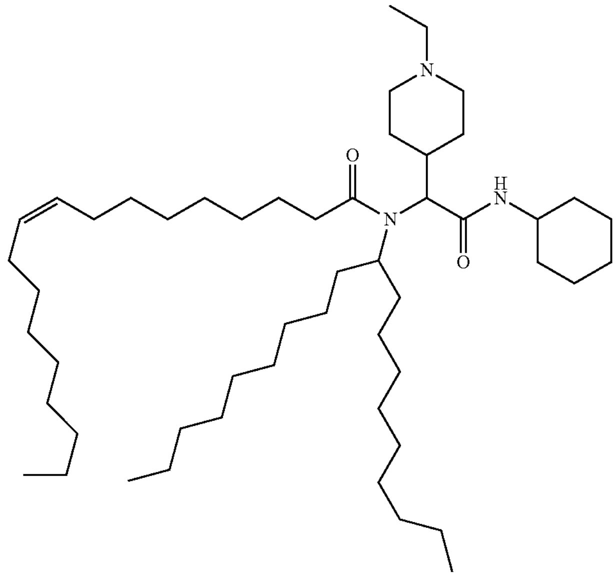

P148C1
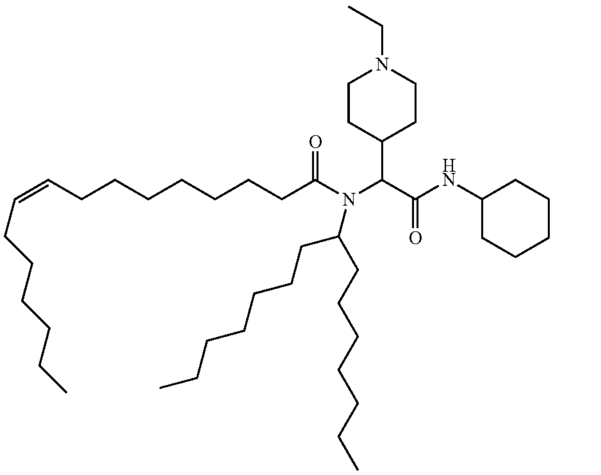
P148C2
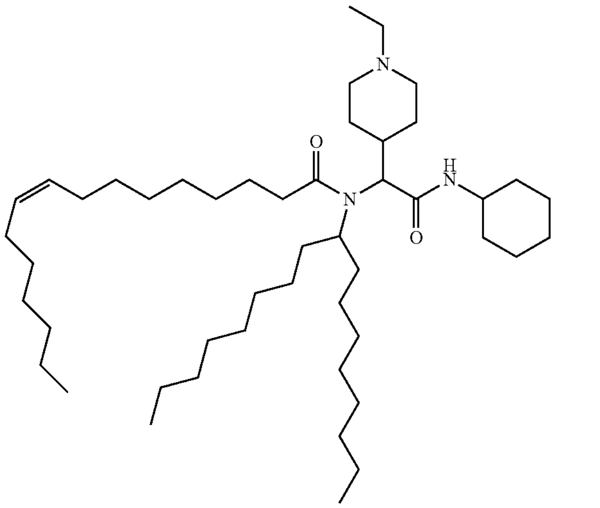
P148C3
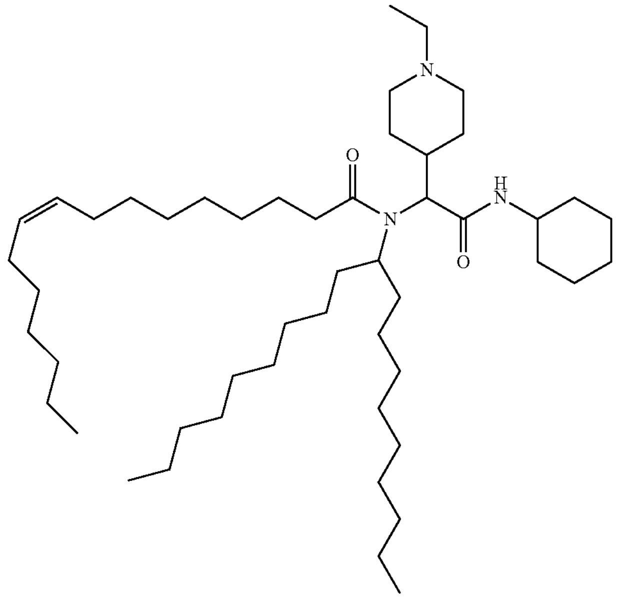
P153C4
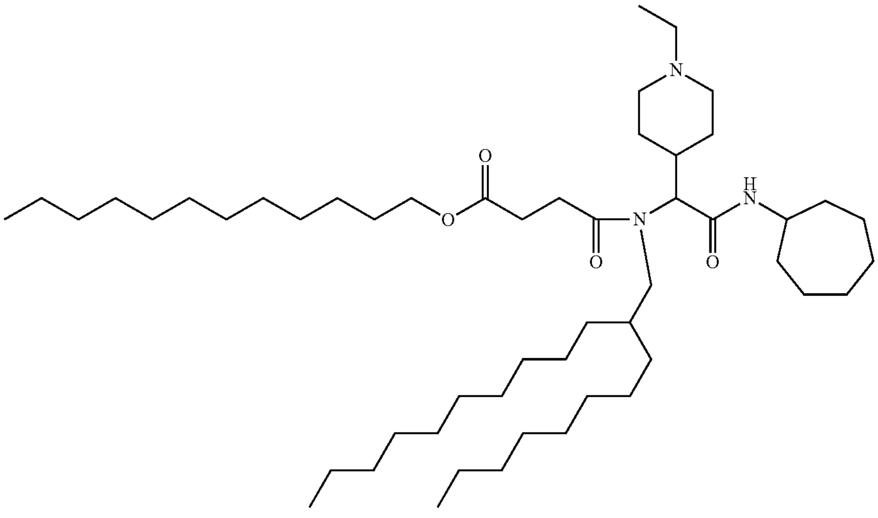

-continued
P153C5
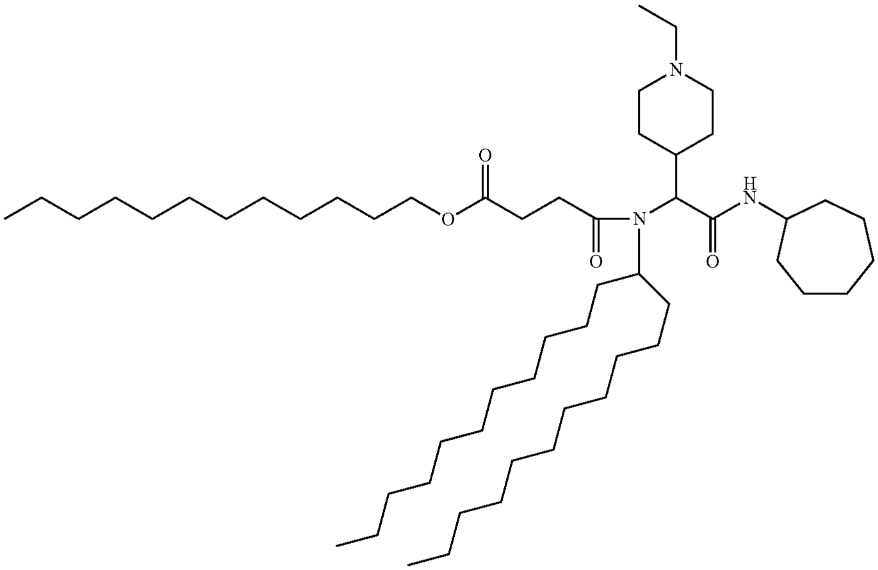
P153D10
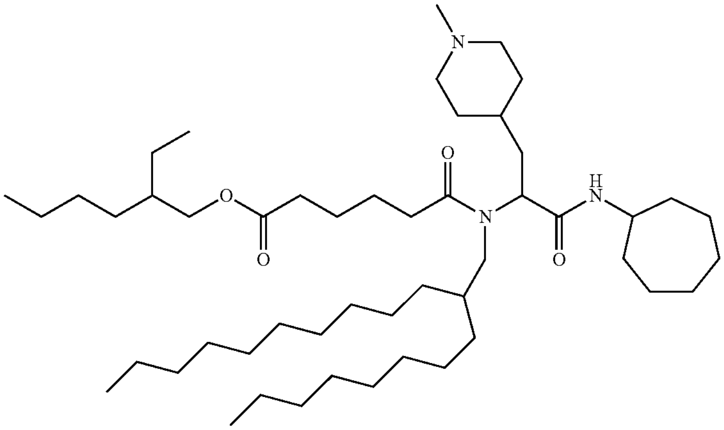
P153A1
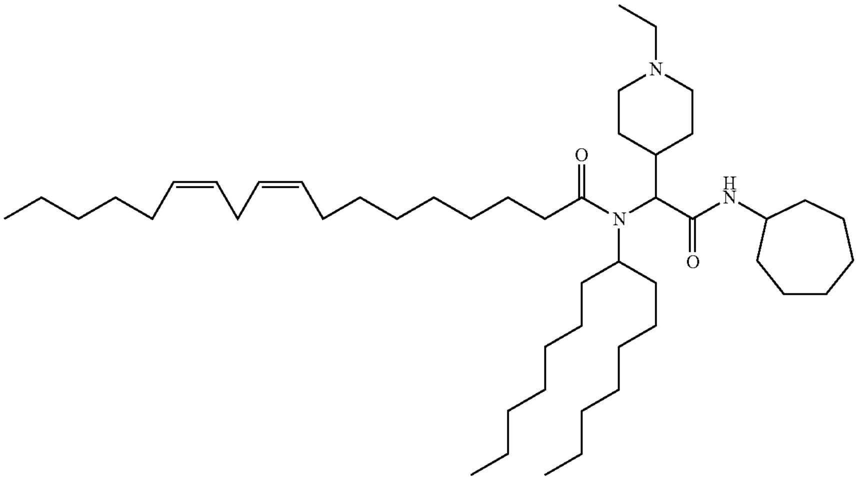

-continued
P153A2
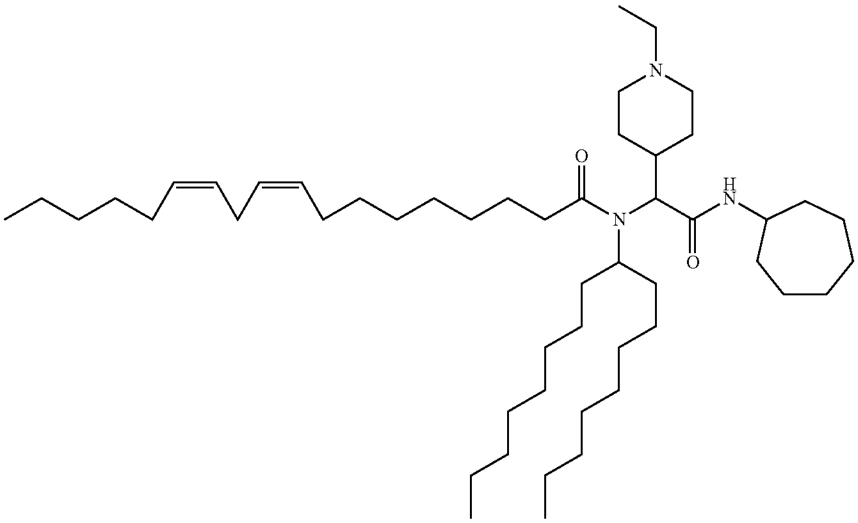
P153A3
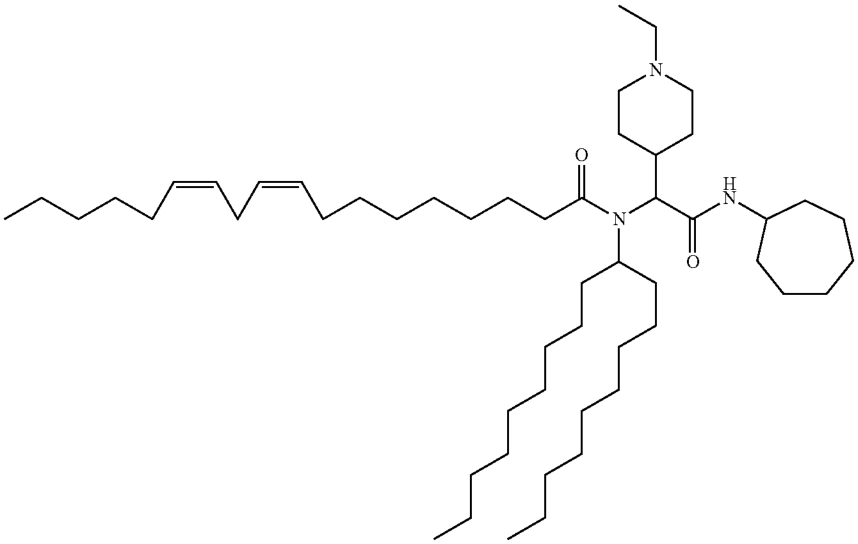
P153B10
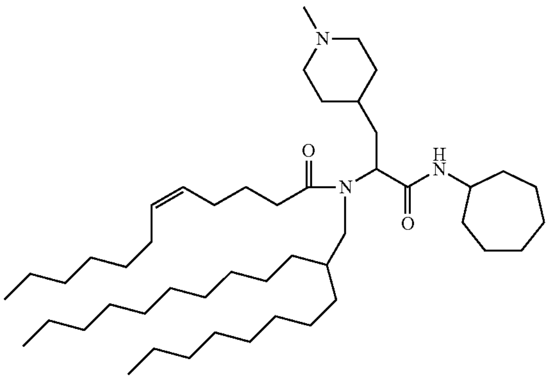
P152D10
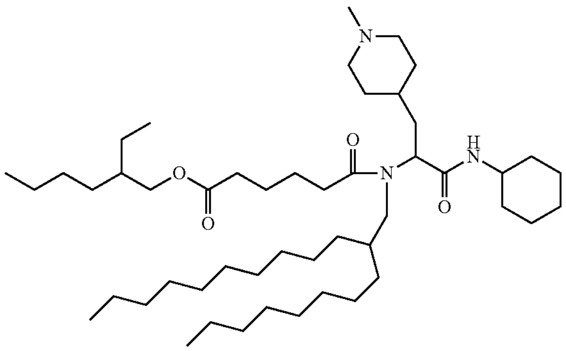

-continued
P152C1
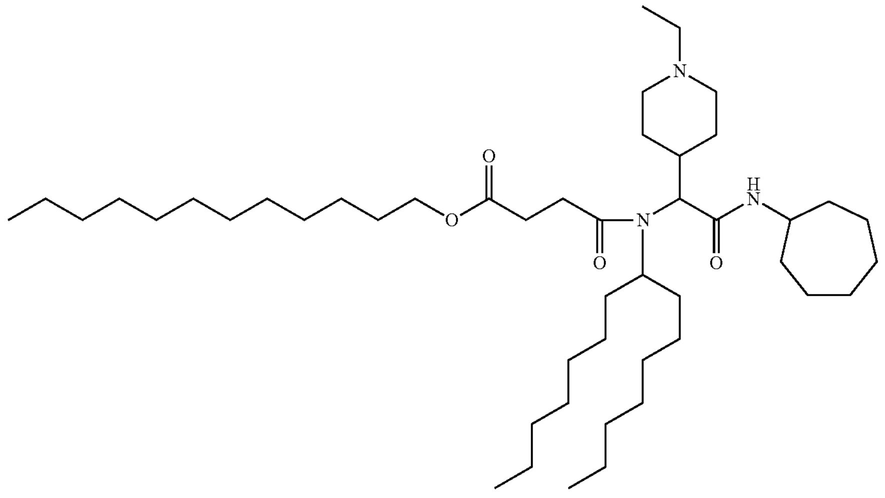
P152C2
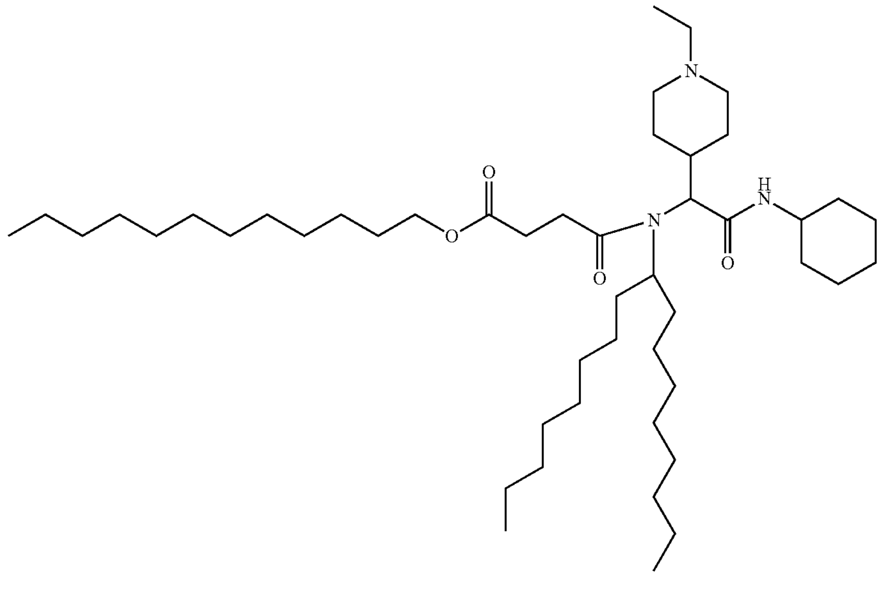

-continued
P151B3
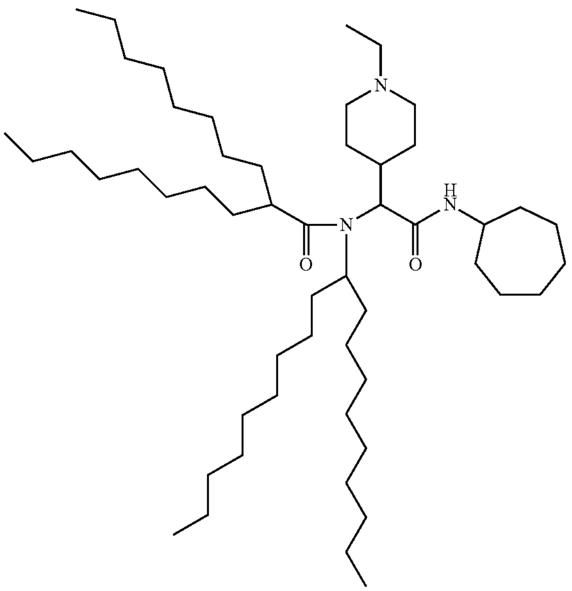
P151C2
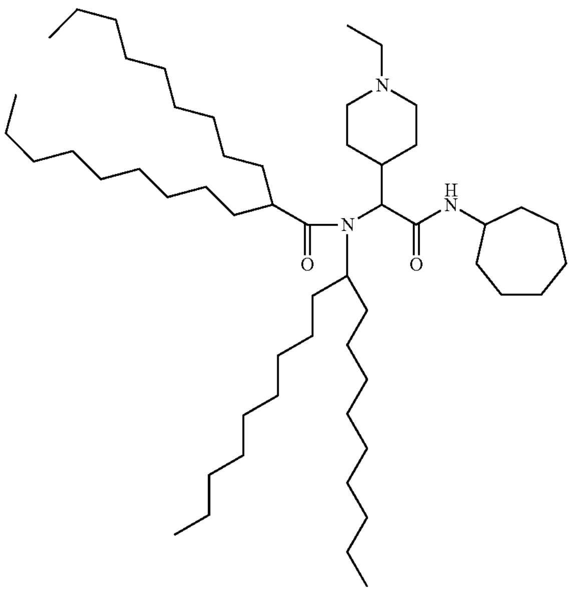
P154A10
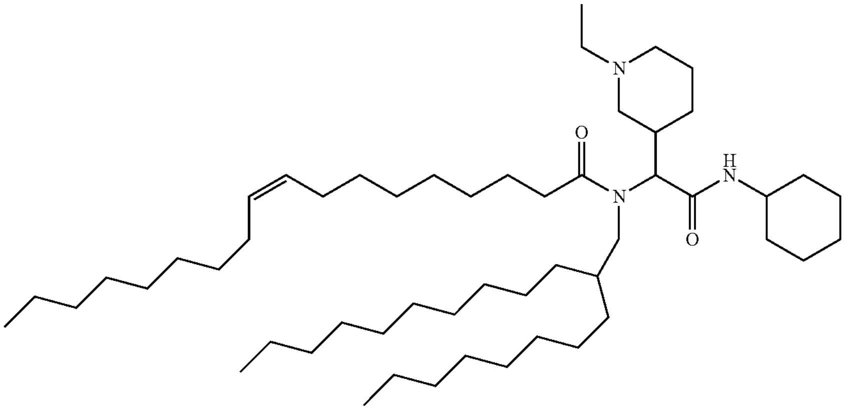
P154D10
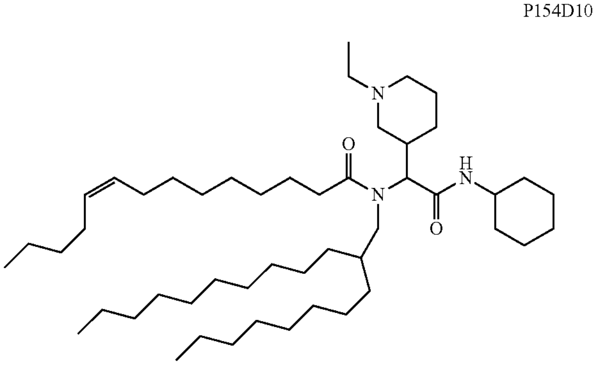
P160B4
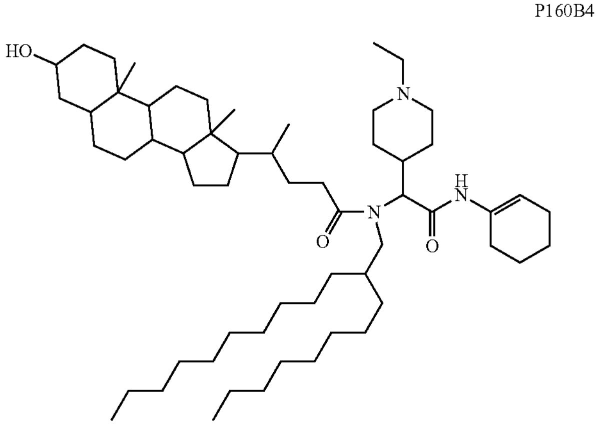

-continued
P160E6
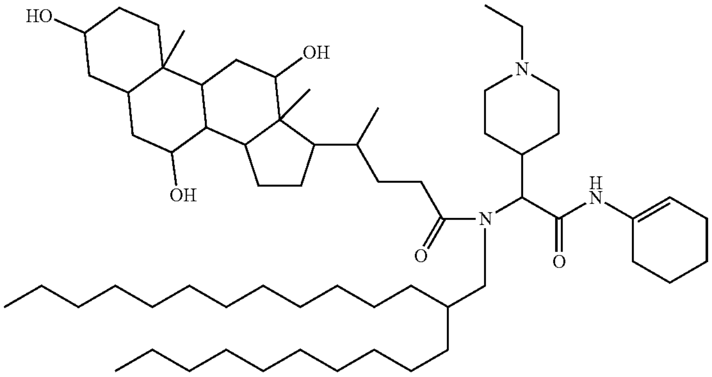
P158C10
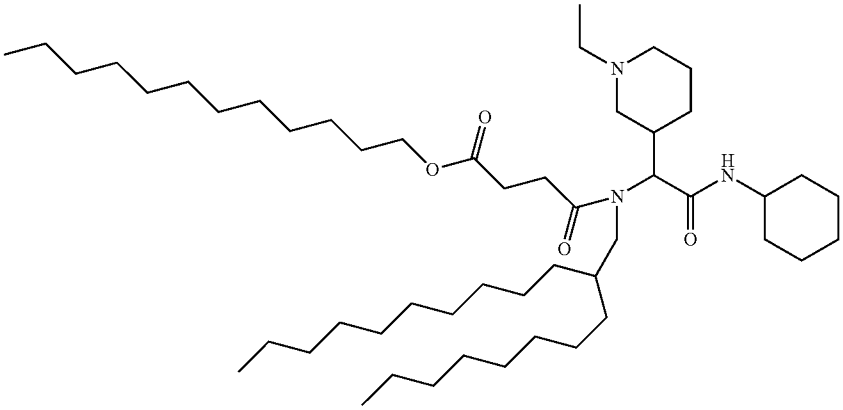
P161C4
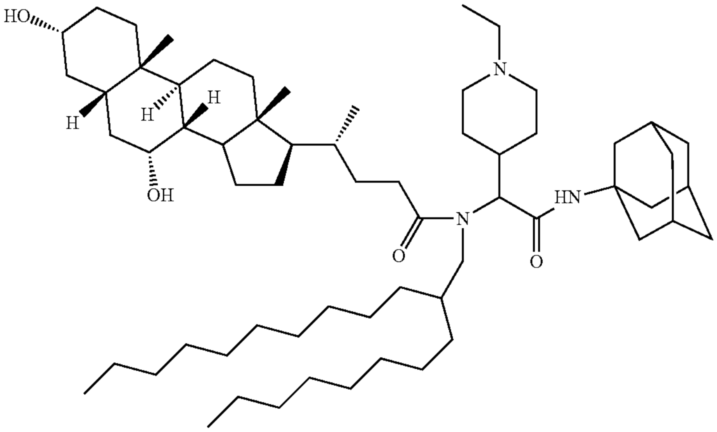
P161E4
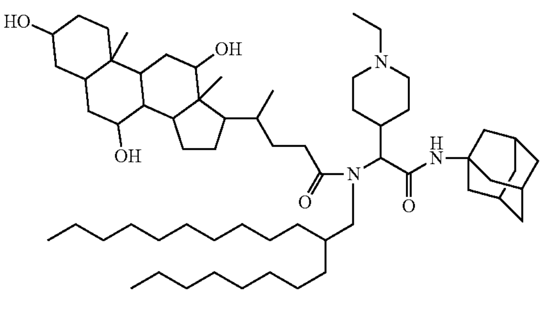
P161E6
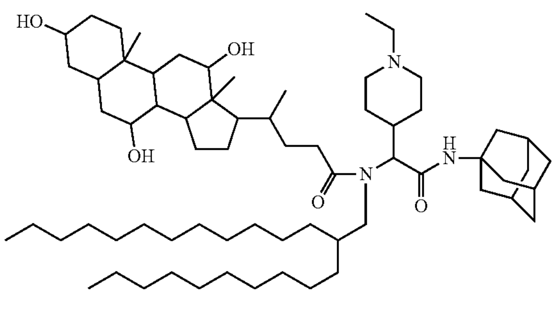

-continued
P161F4
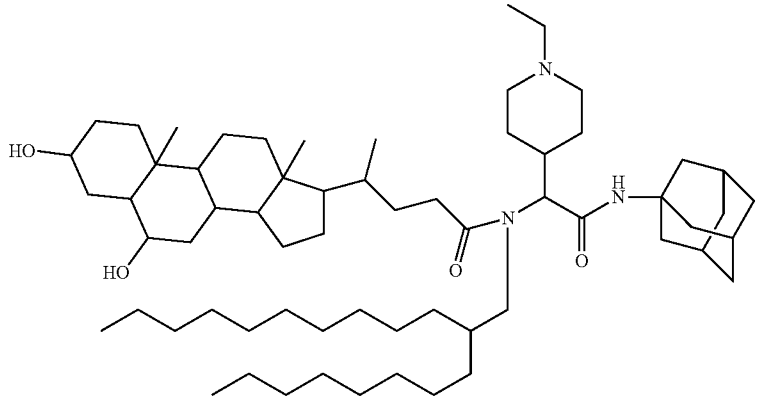
P161F5
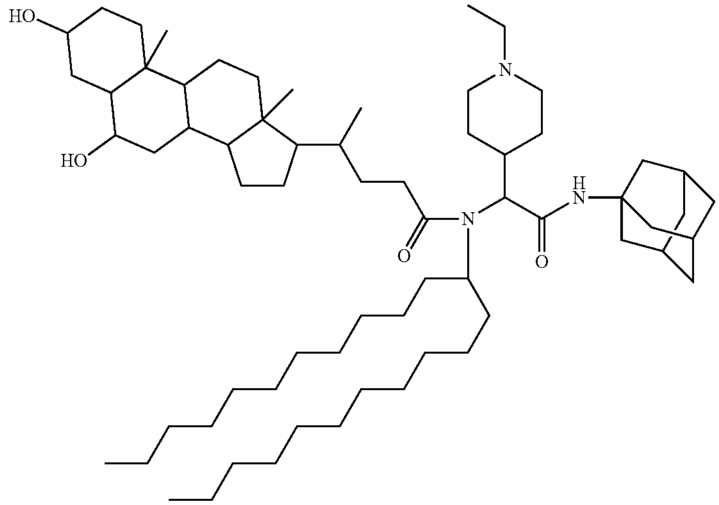
P161F6
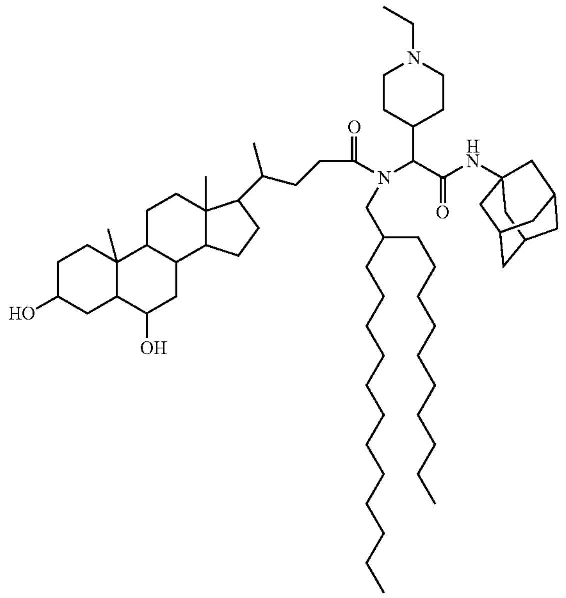
P165A10
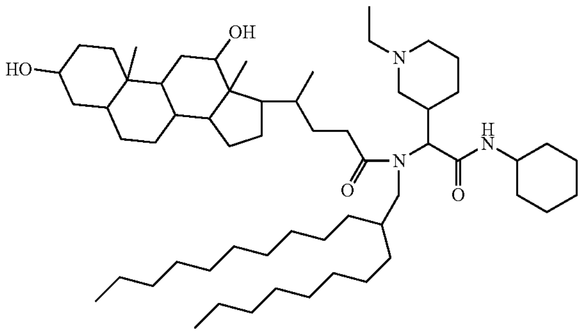

-continued
P165D10
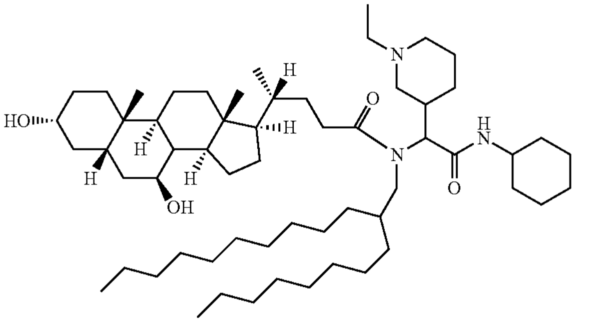
P165F10
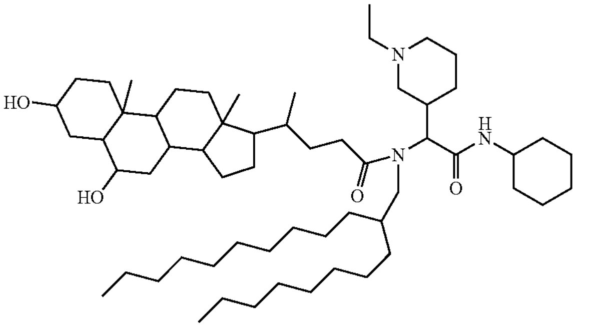
P165E12
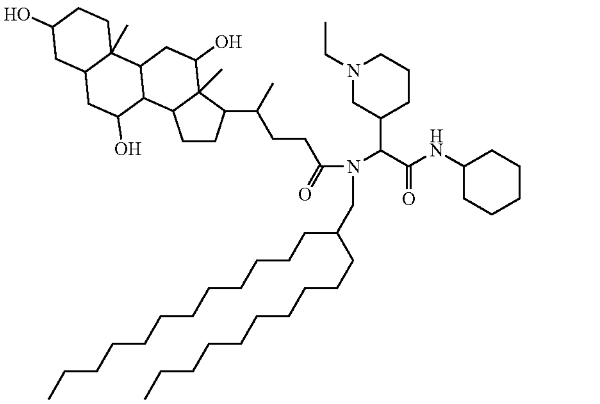
P169A2
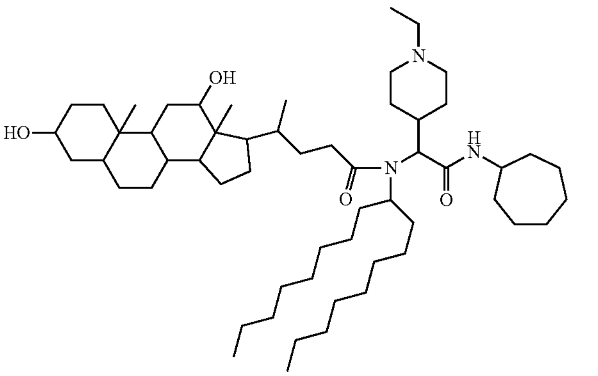
P169A8
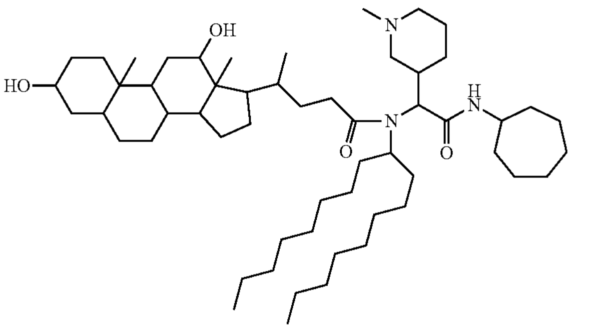
P169F10
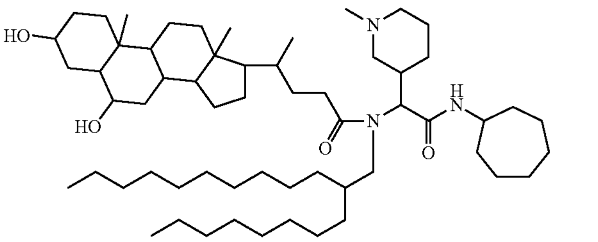
P169C10
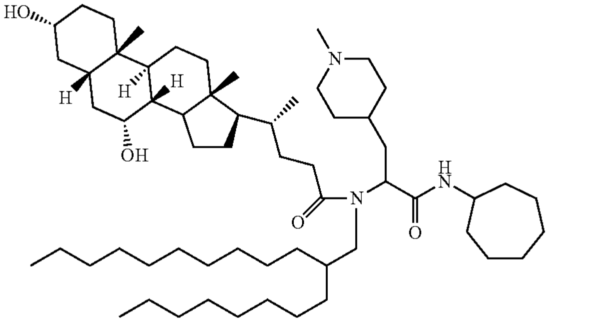
P169C12
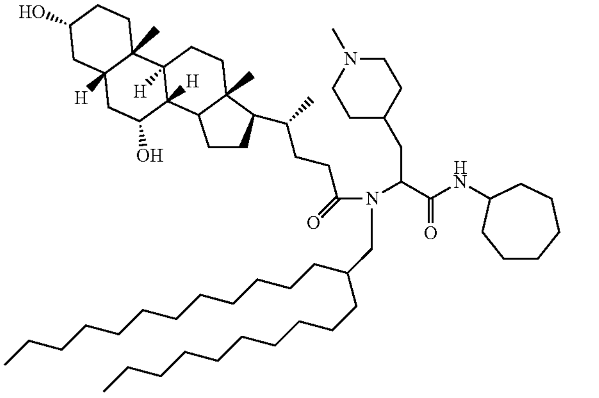

-continued
P170D12
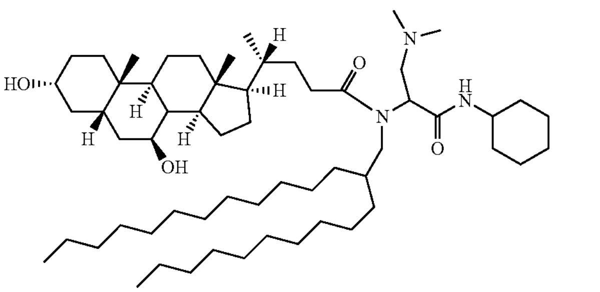
P171D12
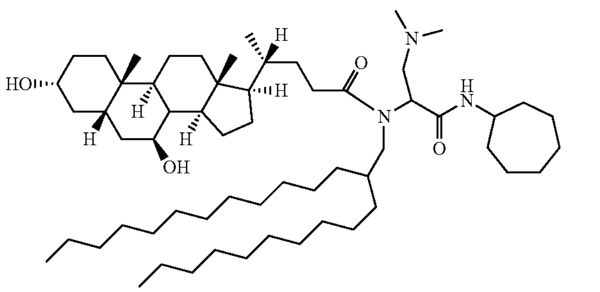
P173F10
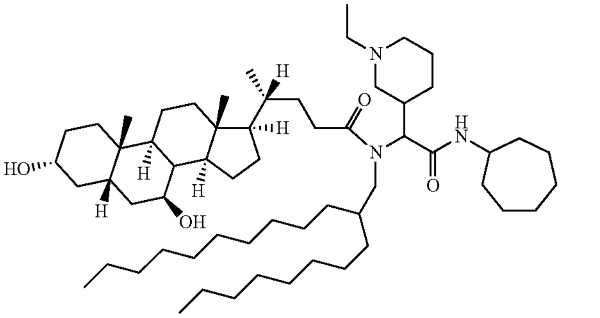
P177F6
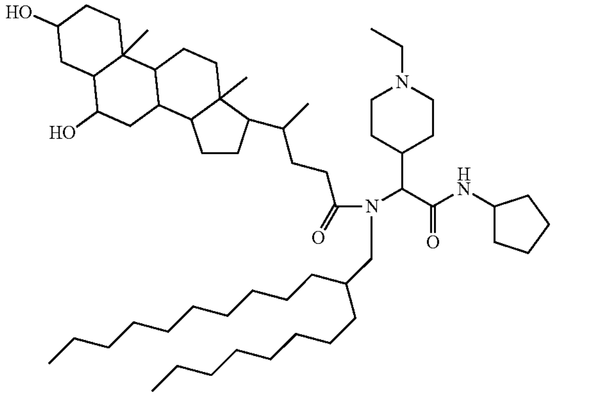
P235F9
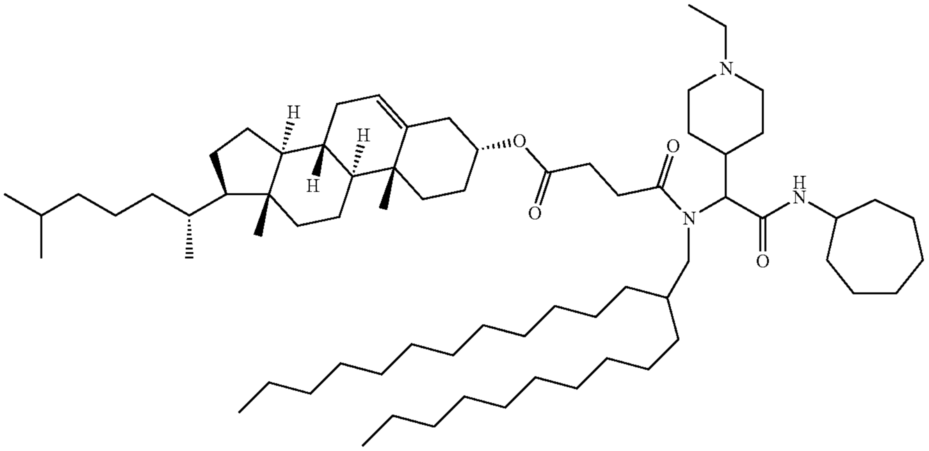
P235F11
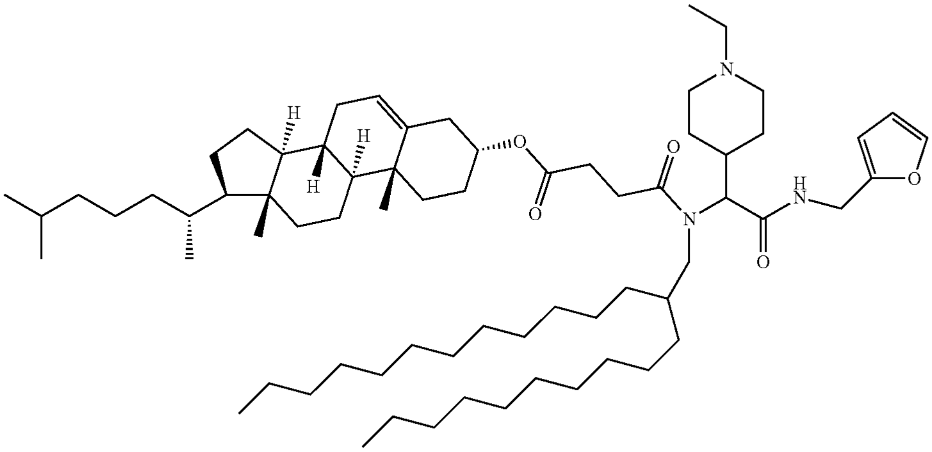

-continued
P235G10
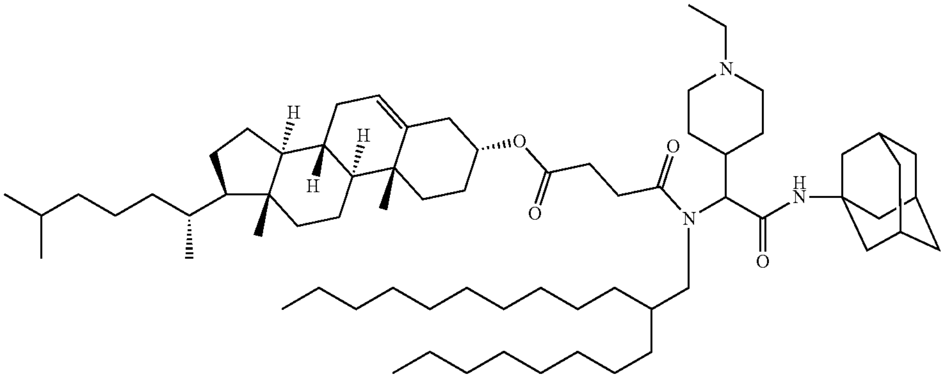
P235G11
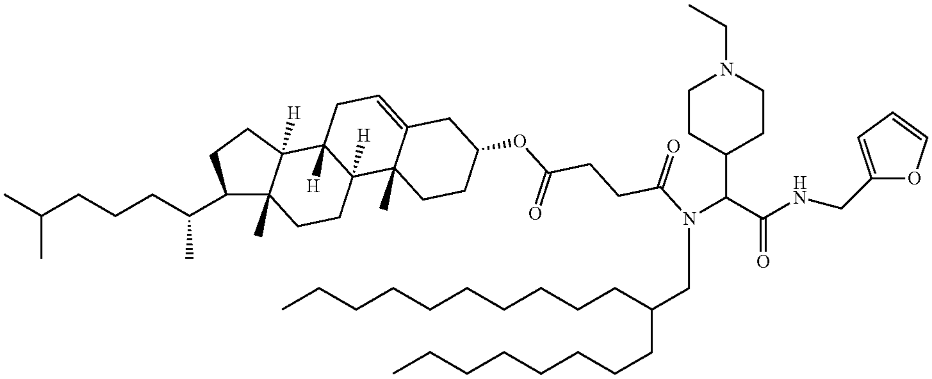
P235F7
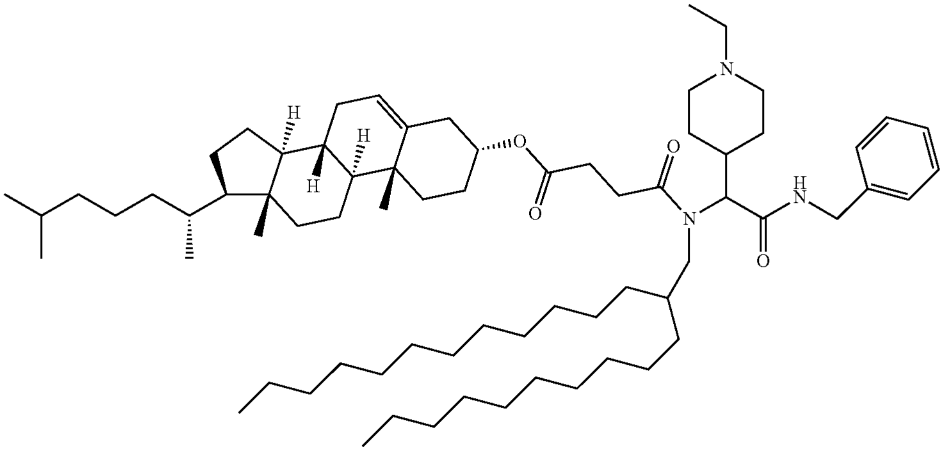

-continued
P245G8
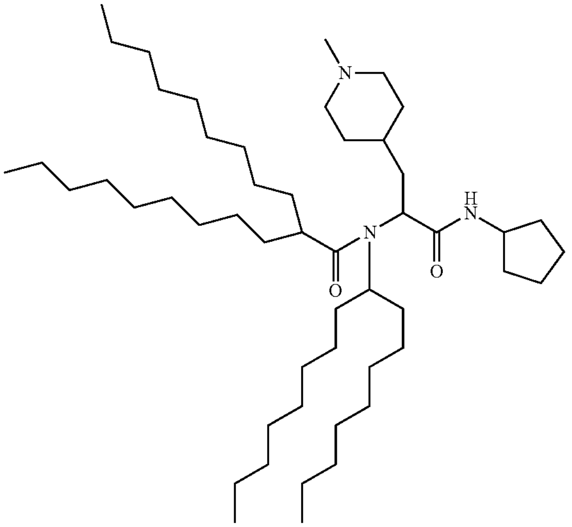
P245A4
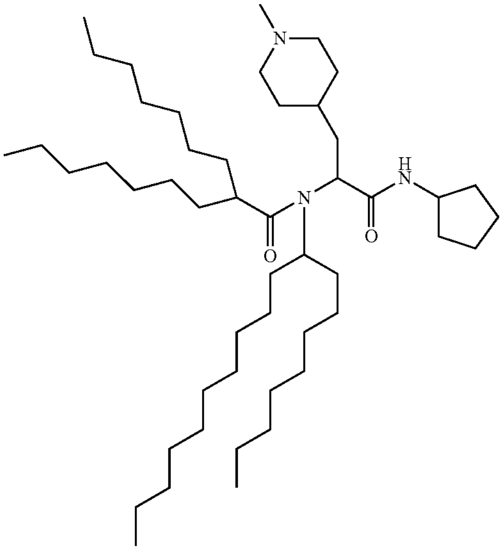
P247C4
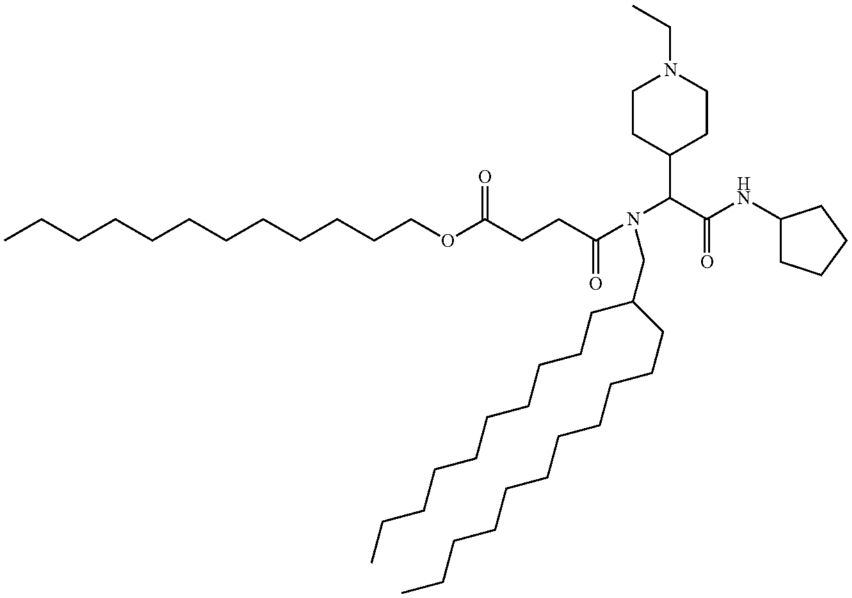
P247C6
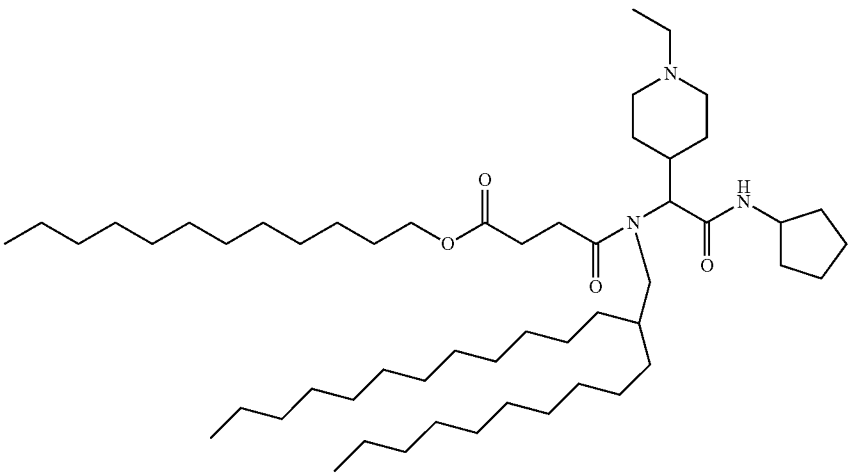

-continued
P247G12
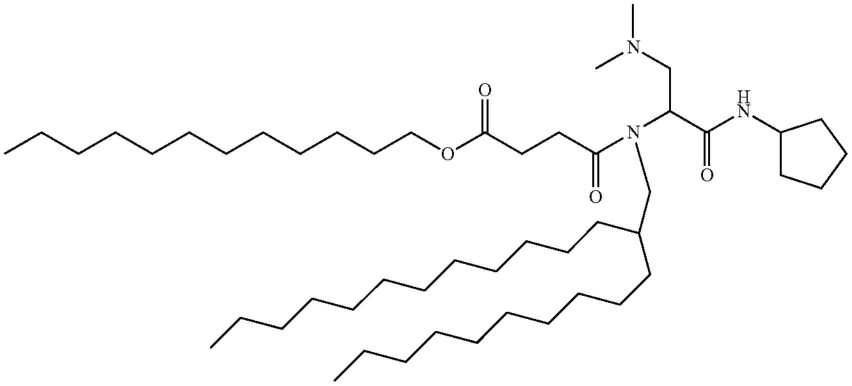
P254B10
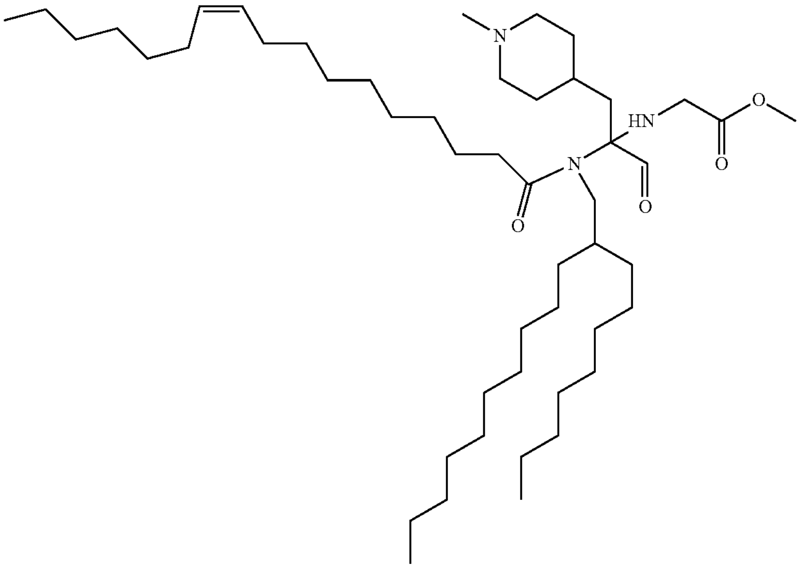
P255C6
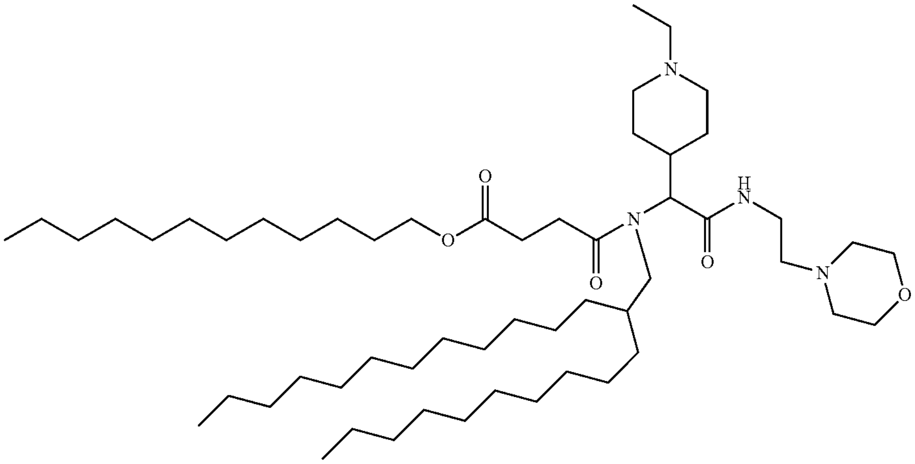

-continued
P255D6
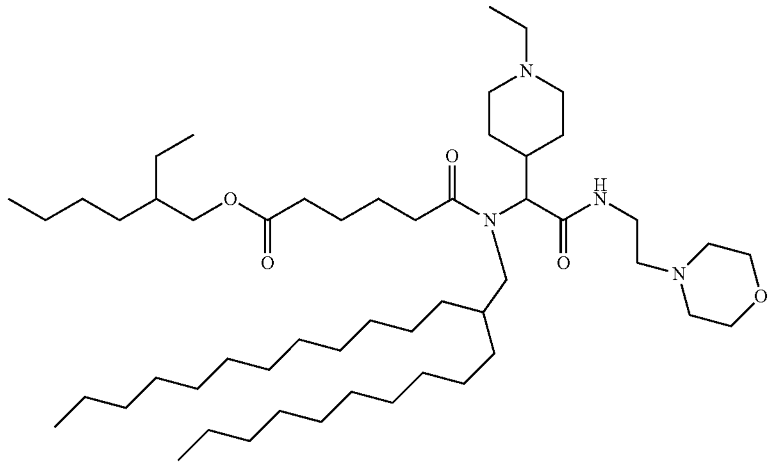
P256B4
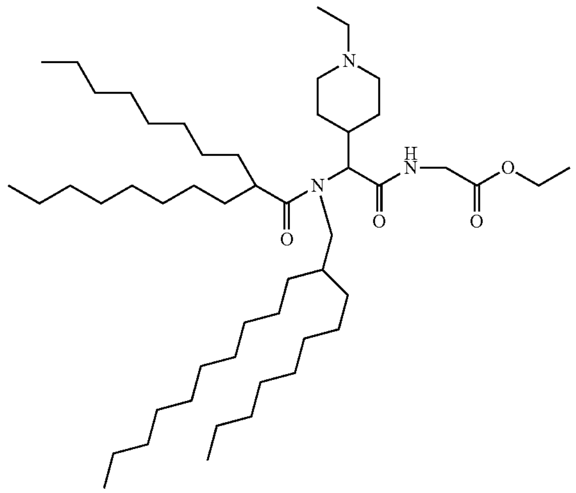
P256C4
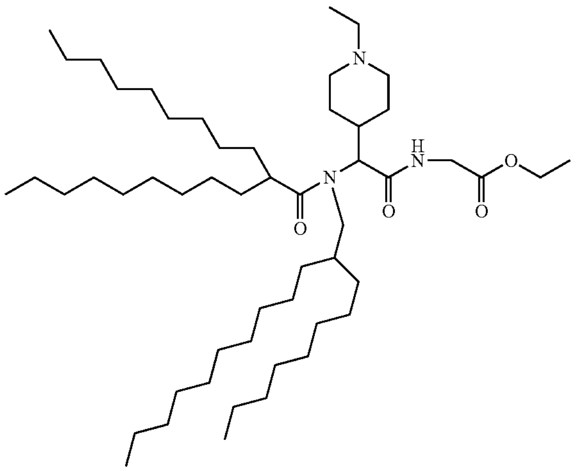
P256C6
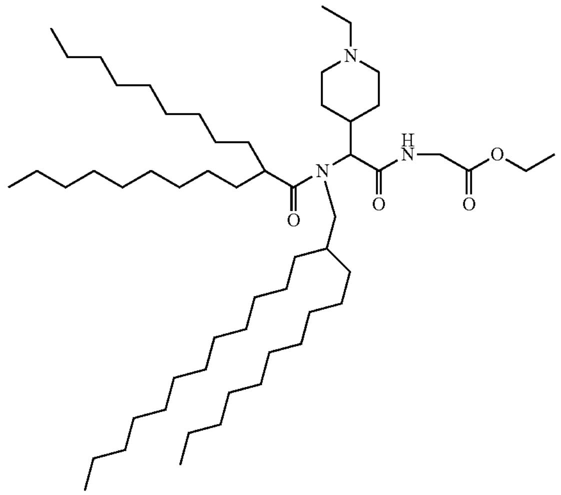
P257A6
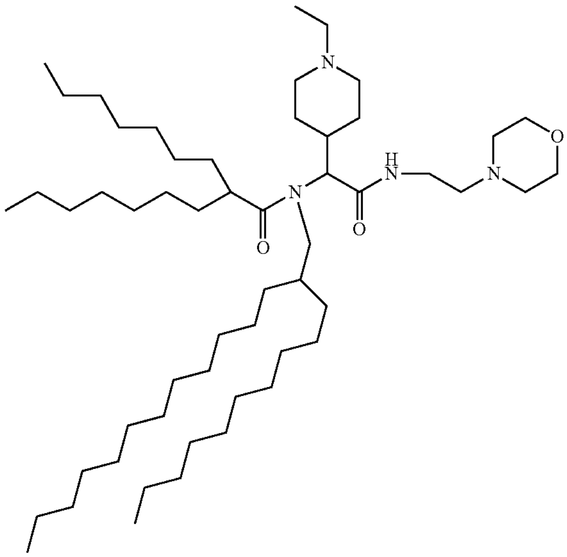

-continued
P258D6
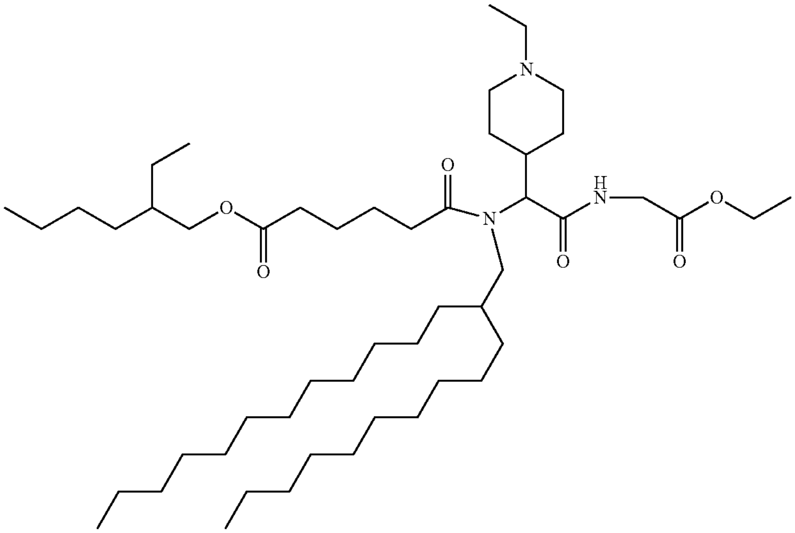
P258D10
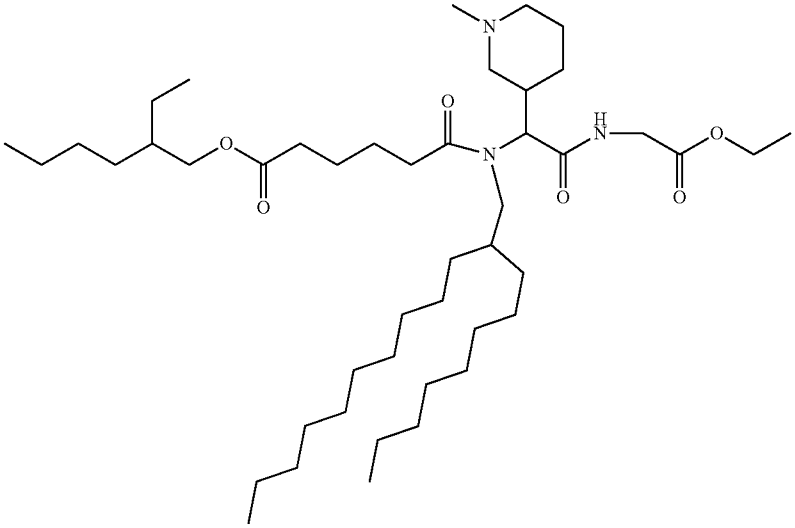
P258C12
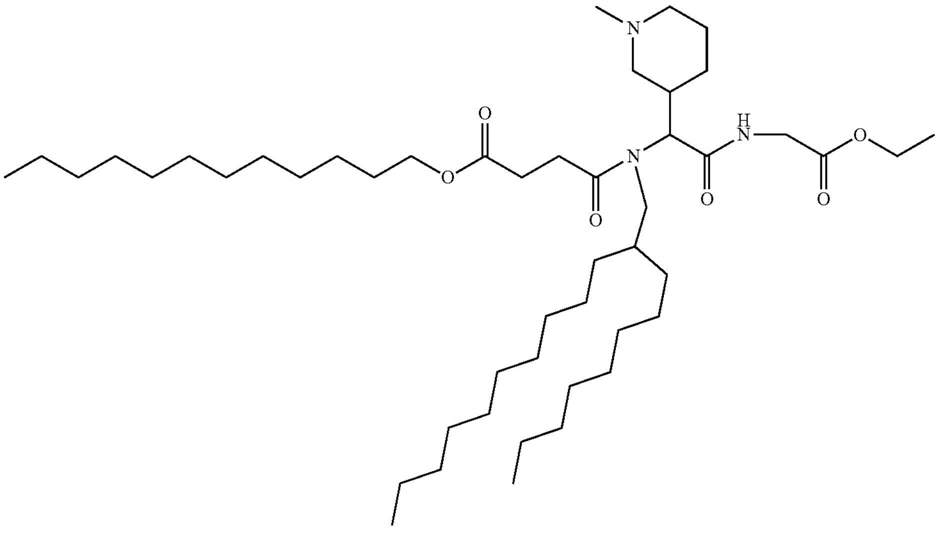

-continued
P259C4
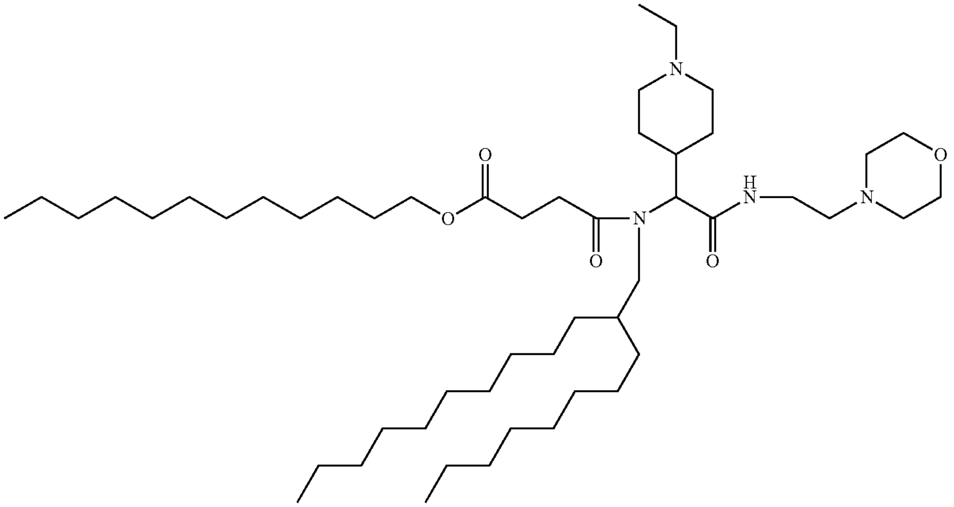
P259C6
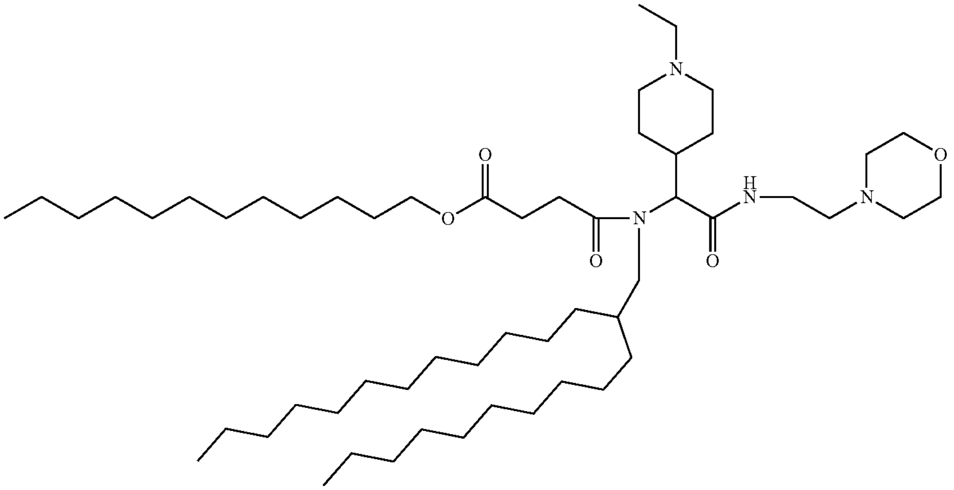
P259D6
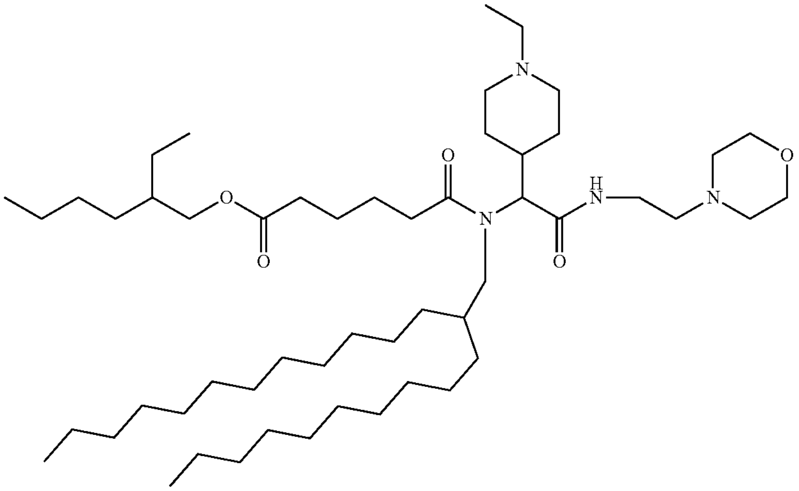

-continued
P259C12
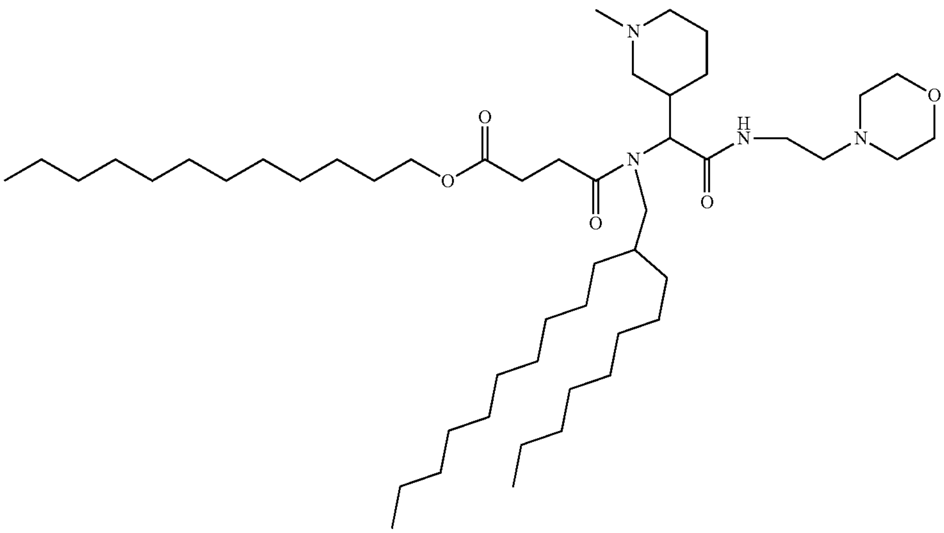
P265E6
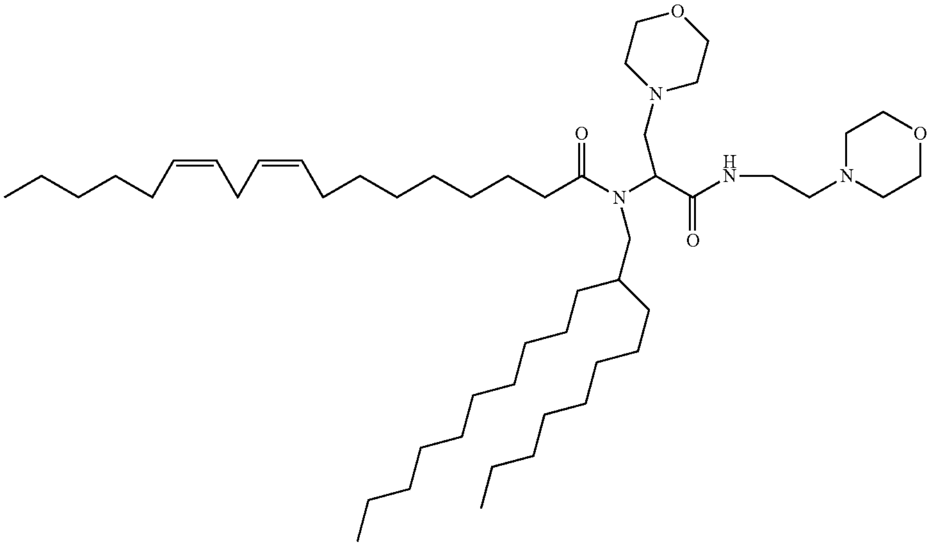
P266A1
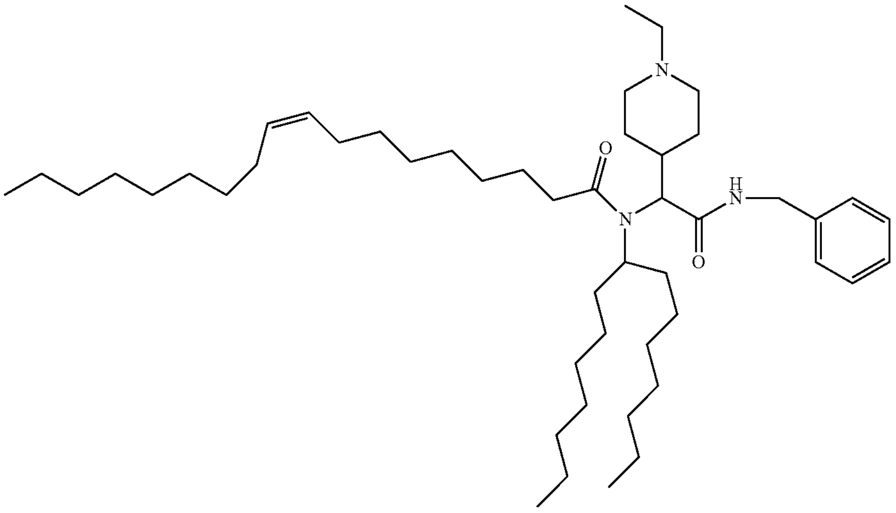

-continued
P266A2
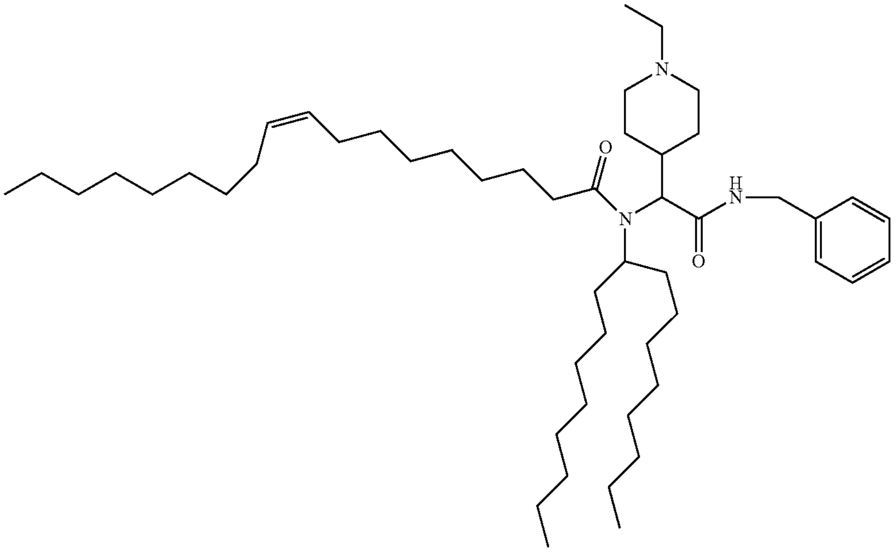
P266A3
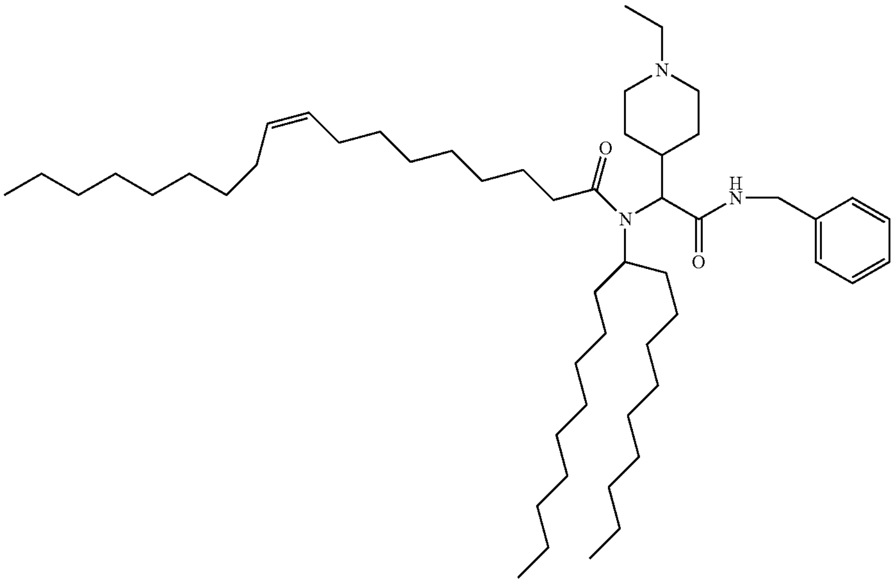

-continued
P266B2
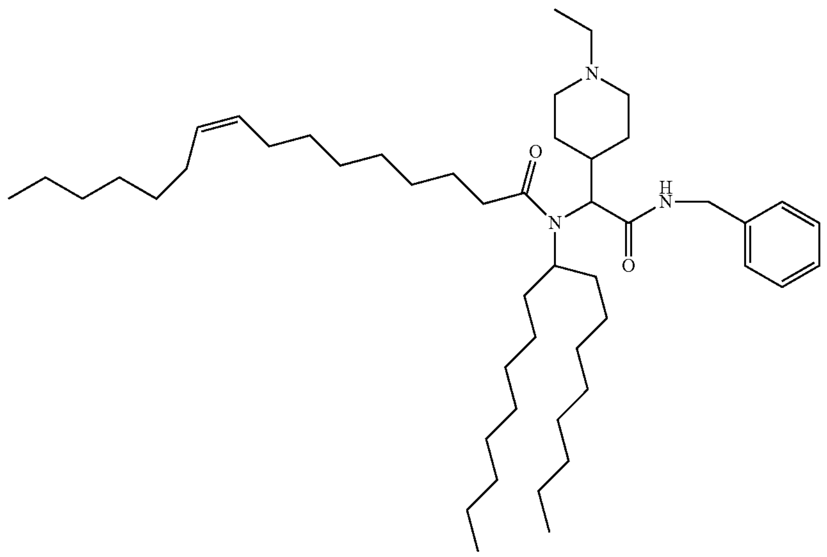
P266F1
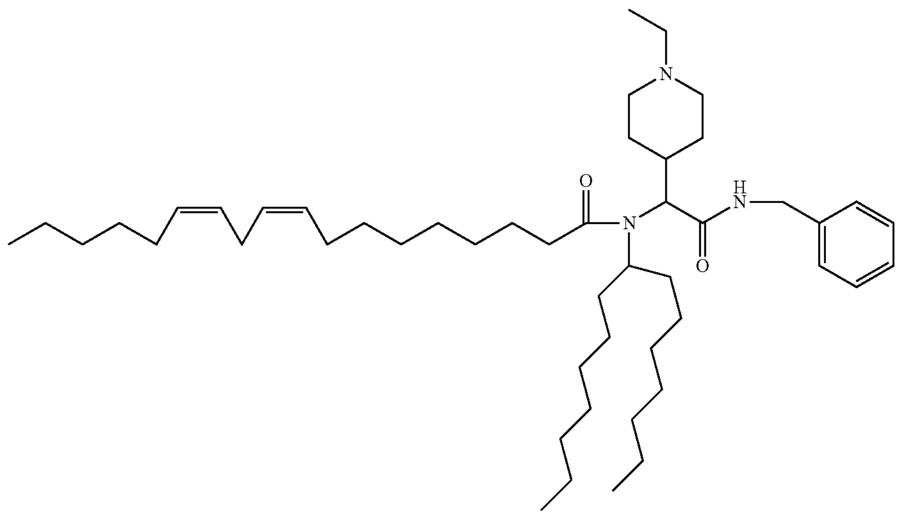
P266F2
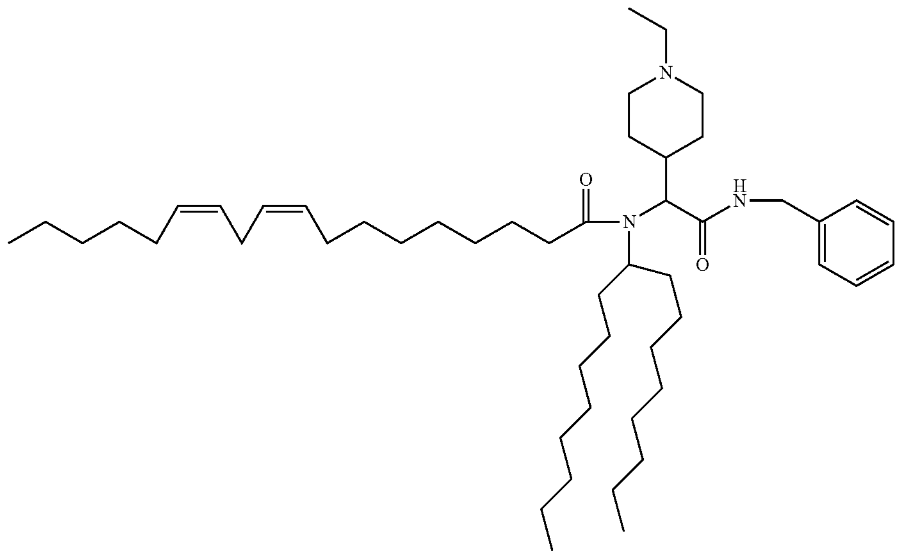

-continued
P266F3
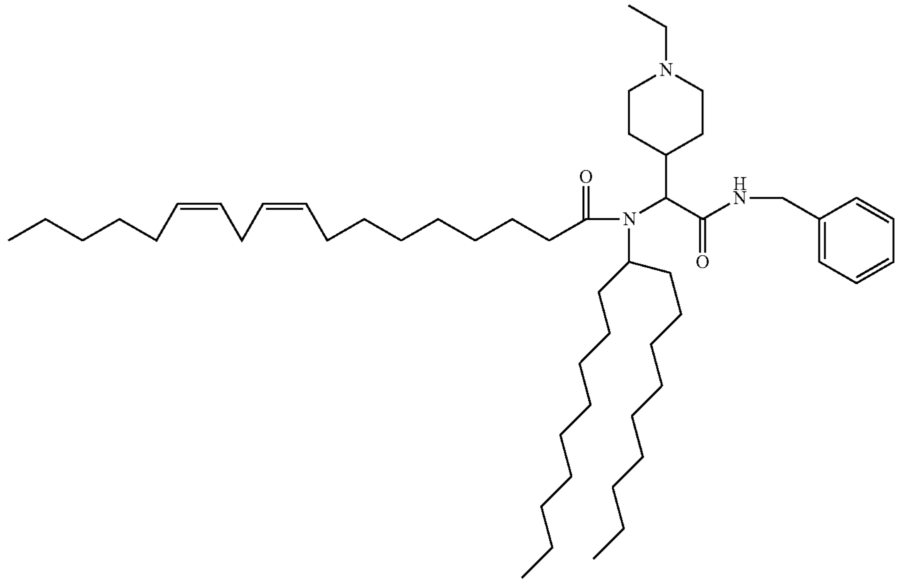
P266G1
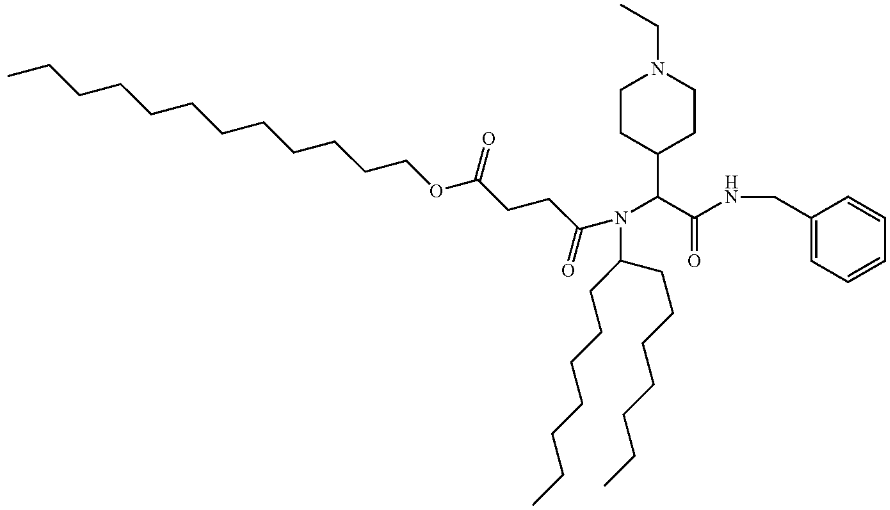
P266G2
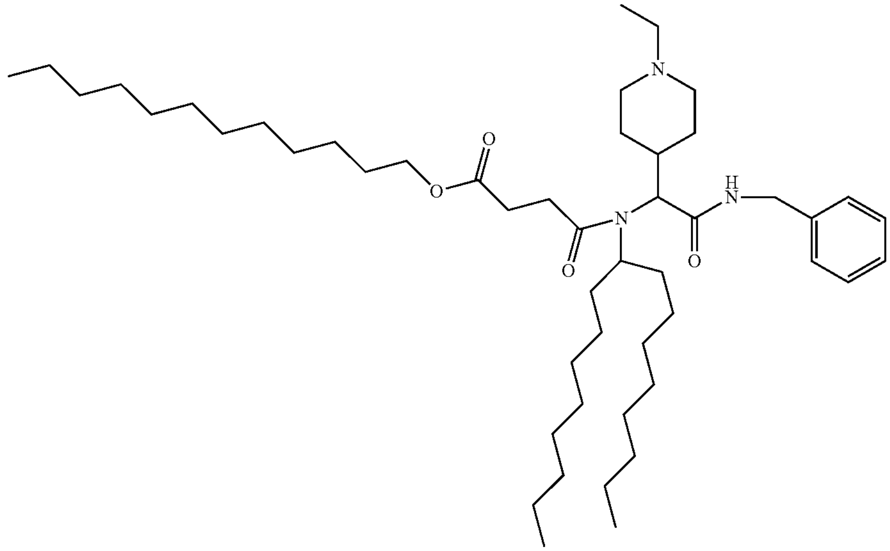

-continued
P266G3
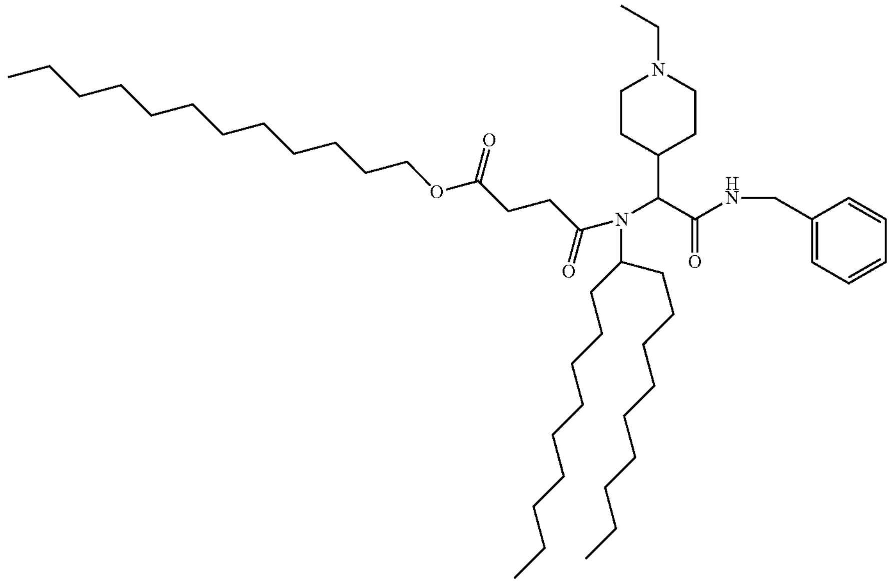
P266G5
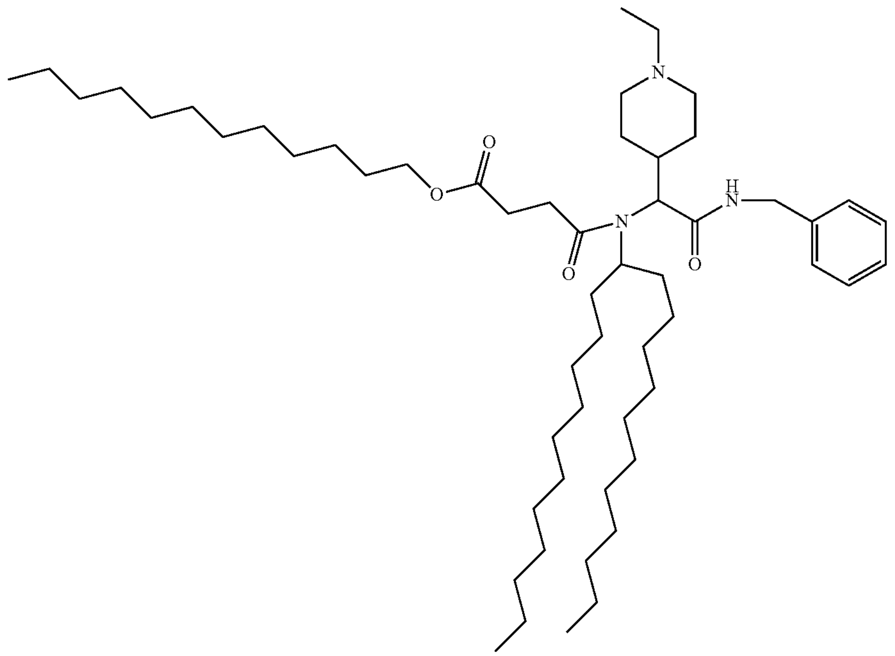

-continued
P267G2
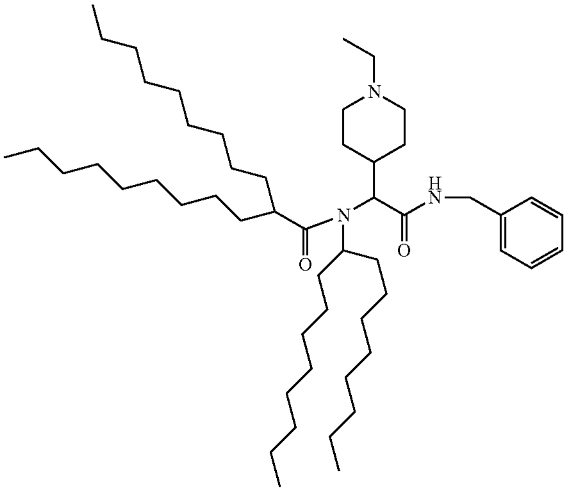
P268B2
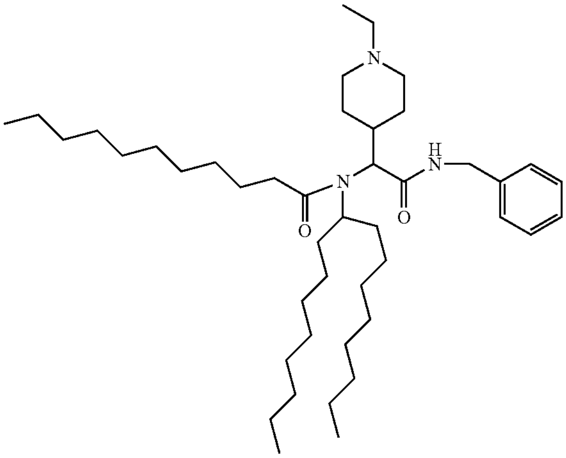
P269F1
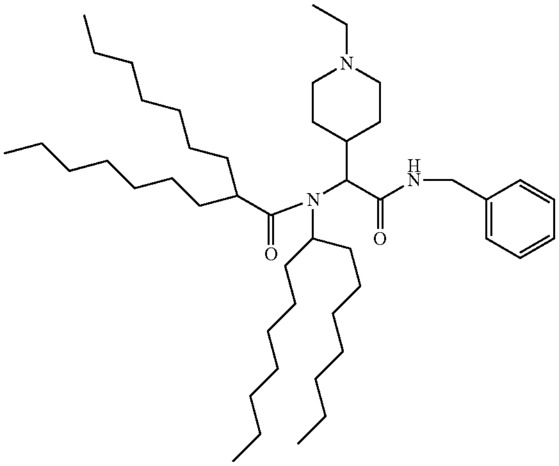
P287A6
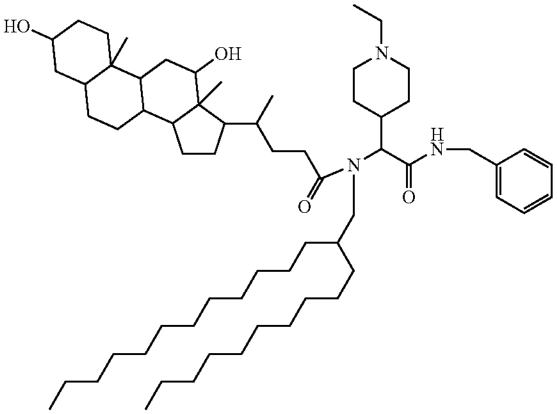
P287A10
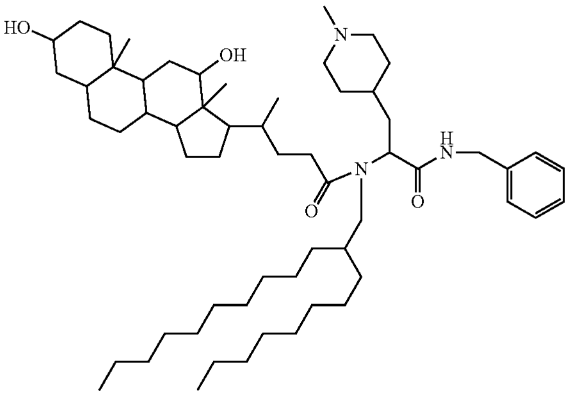
P287B10
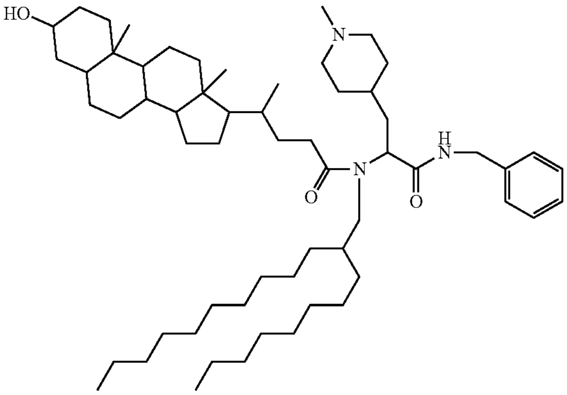

-continued
P287B12
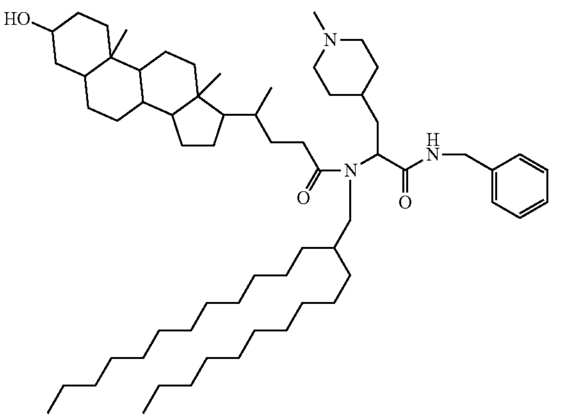
P287C4
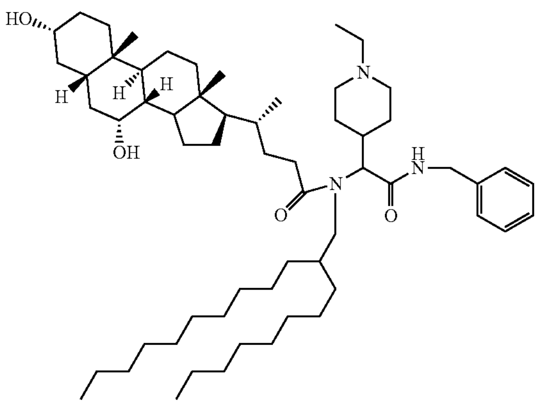
P287C6
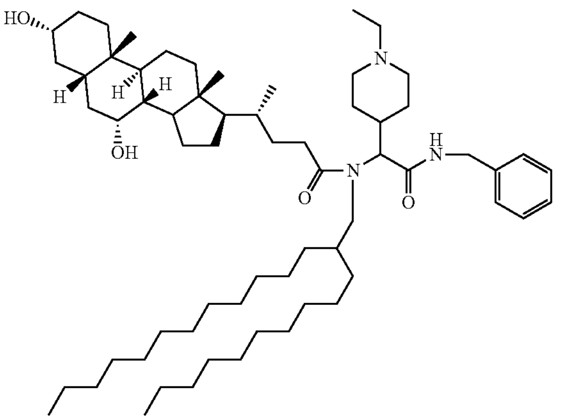
P287C10
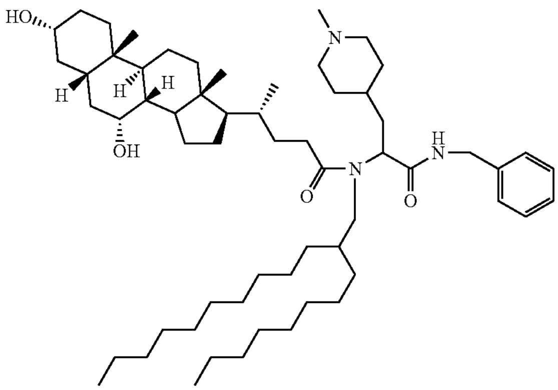
P287D10
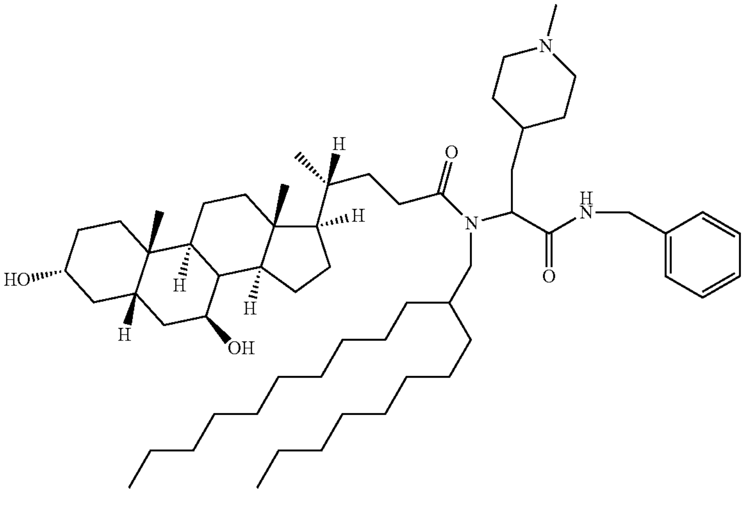

-continued
P287F4
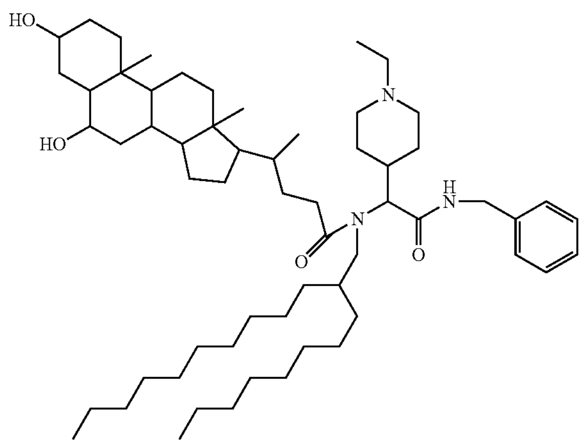
P287F6
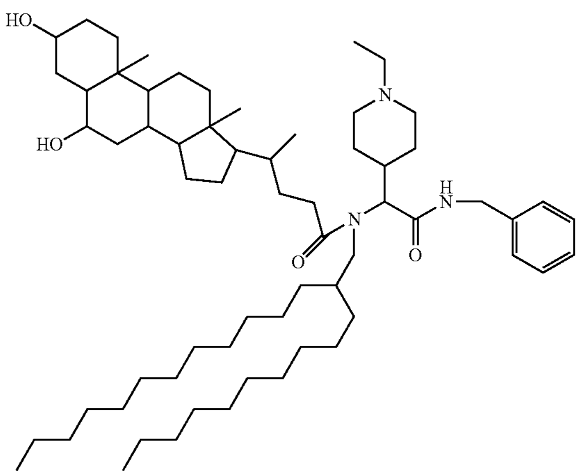
P287F10
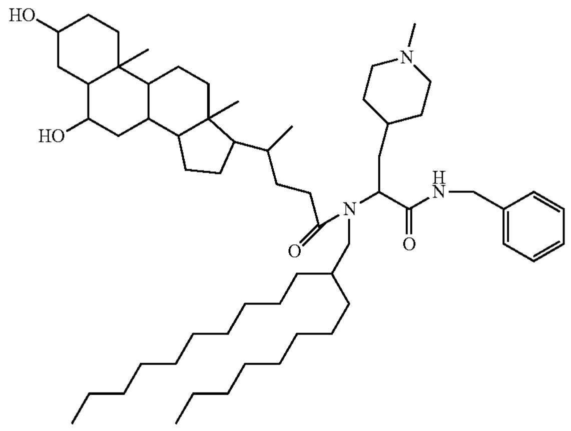
P287F12
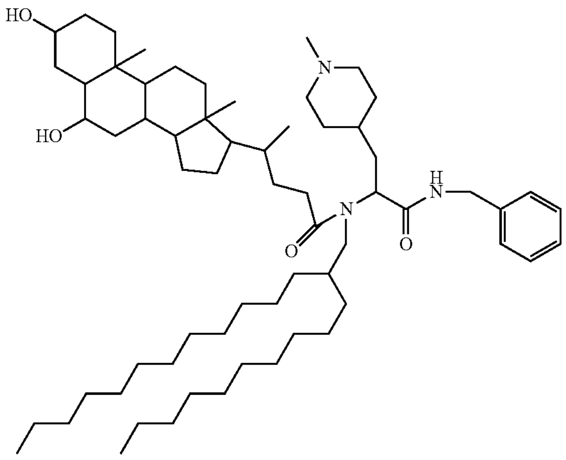
P294A6
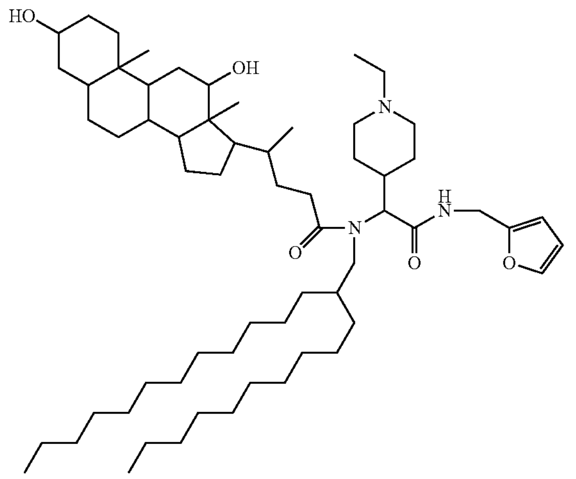
P310B10
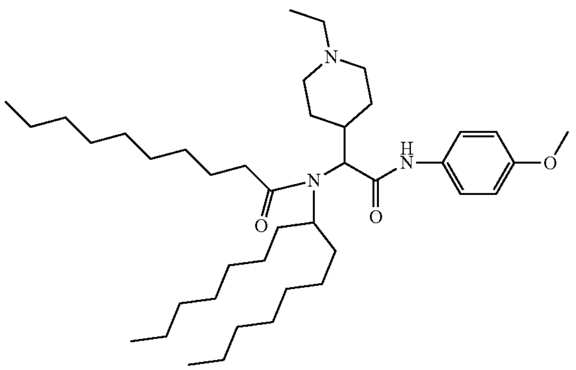

-continued
P310E12
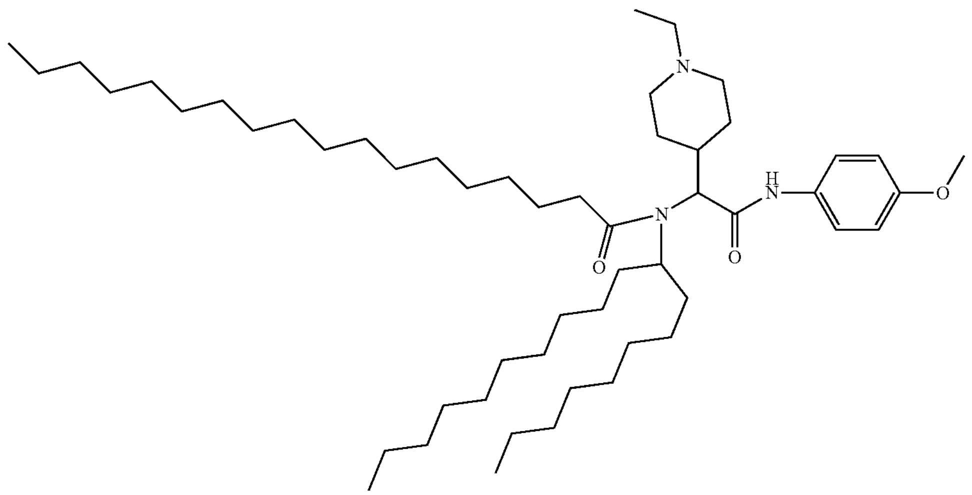
P312A1
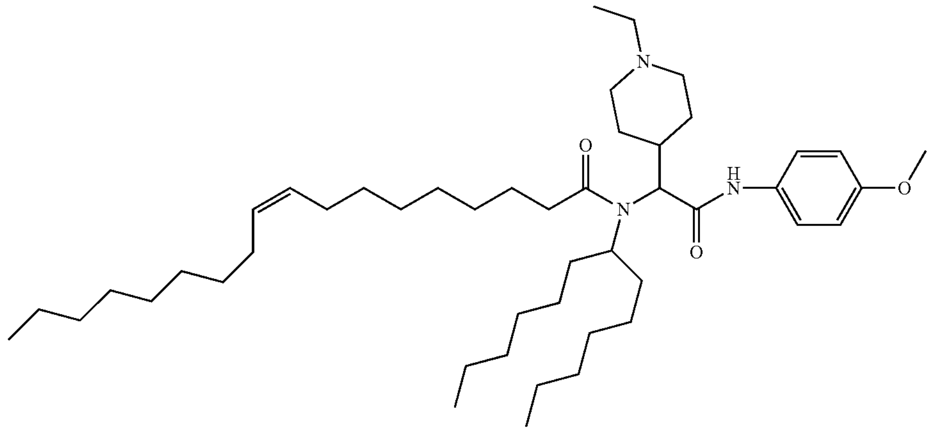
P312B1
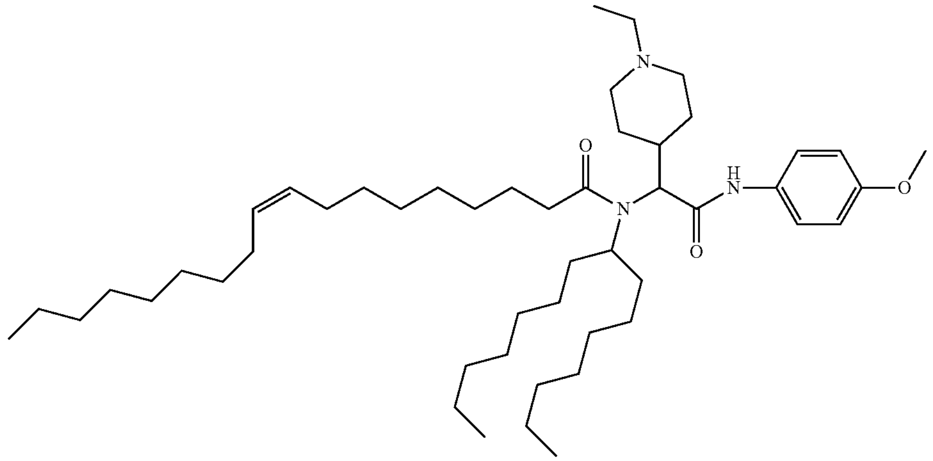

-continued
P312C1
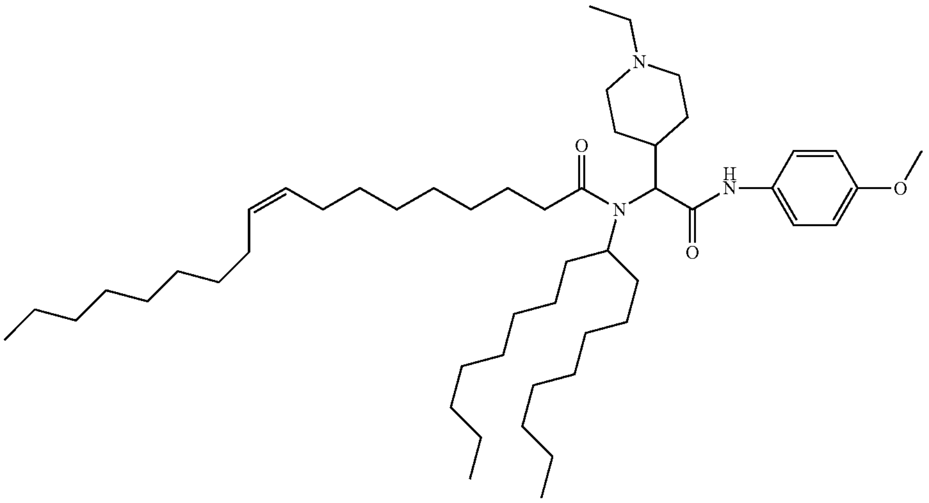
P312D1
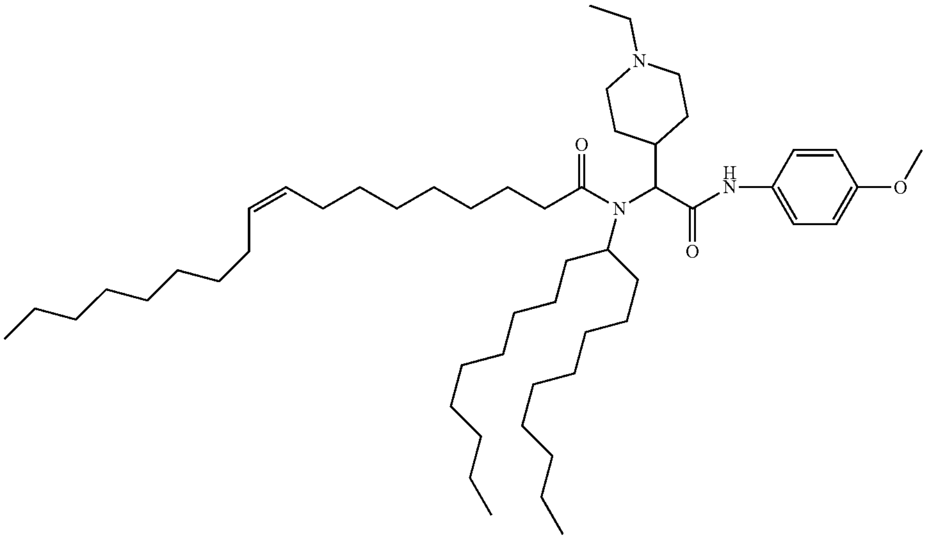
P312E1
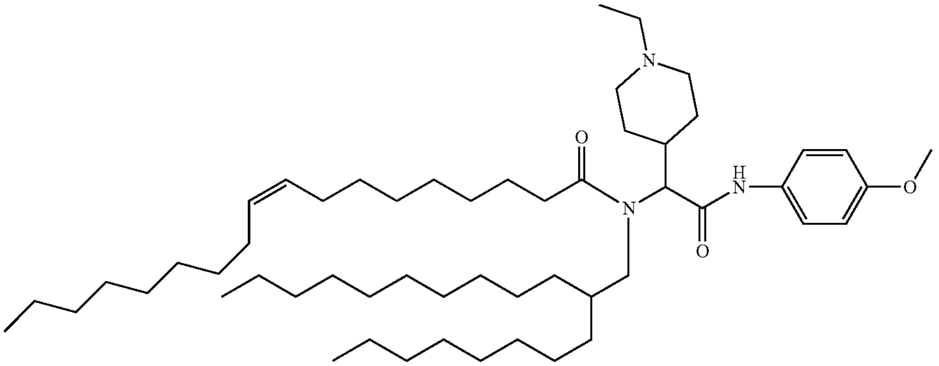

-continued
P312B3
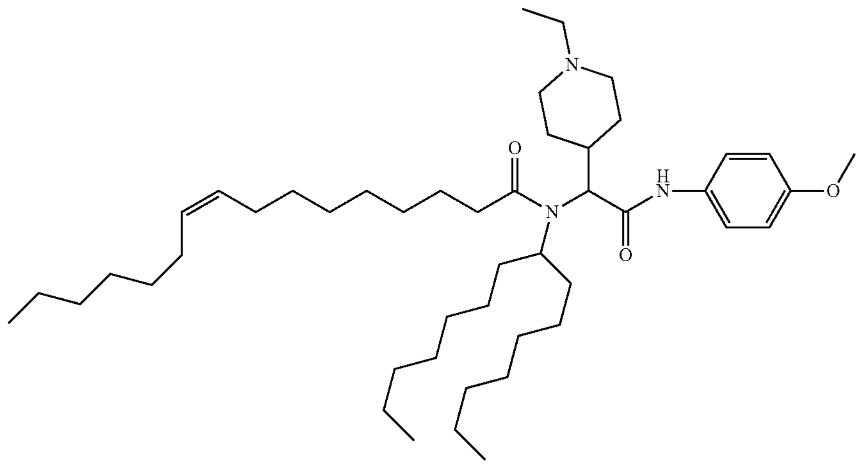
P312C3
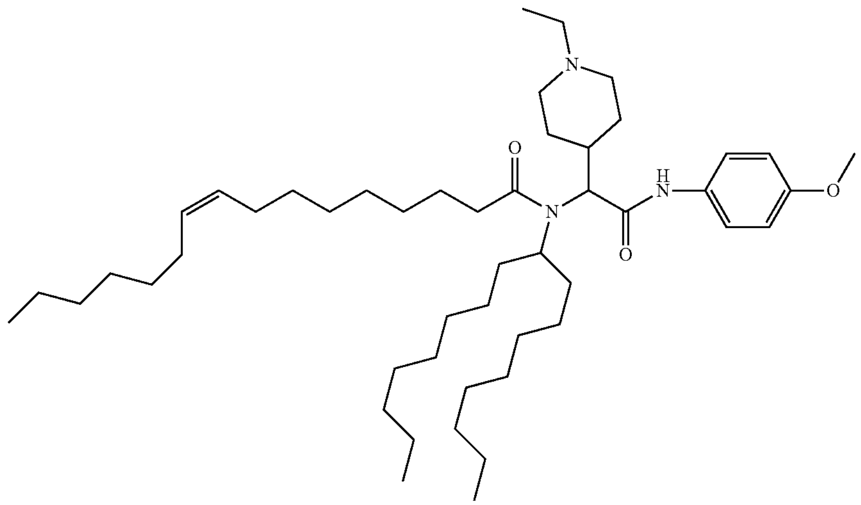
P312E3
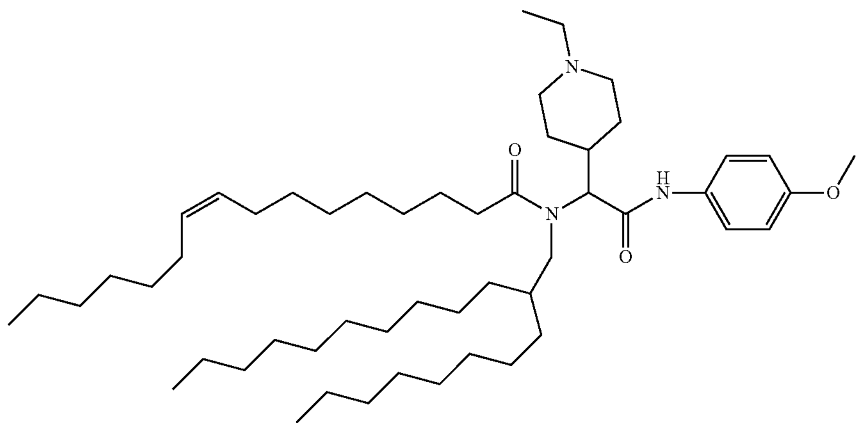

-continued
P312B6
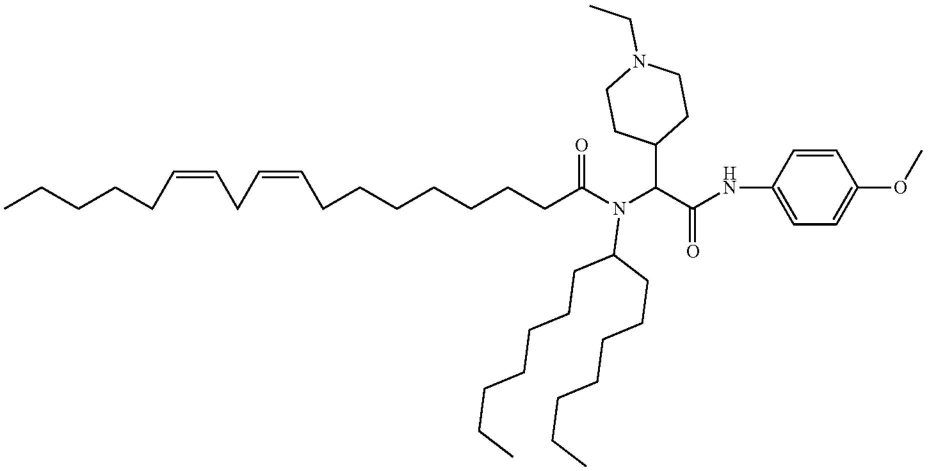
P312C6
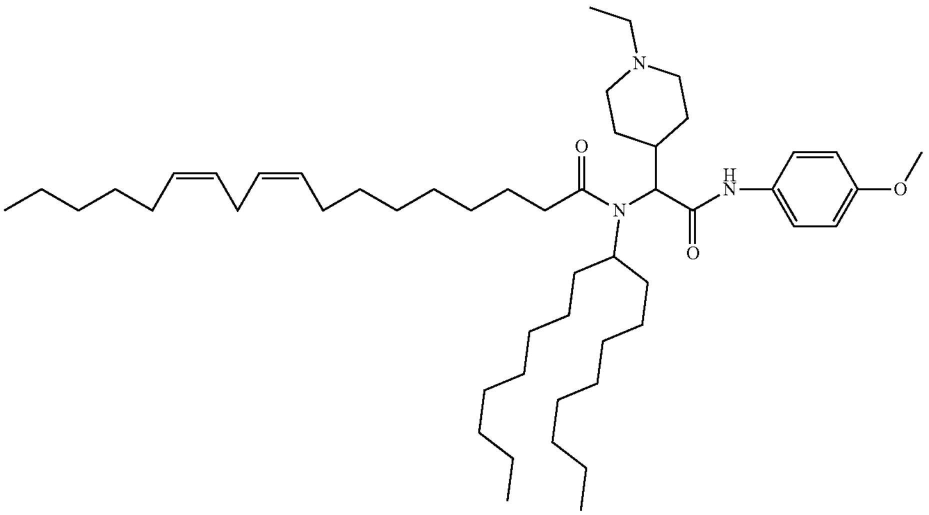
P312B7
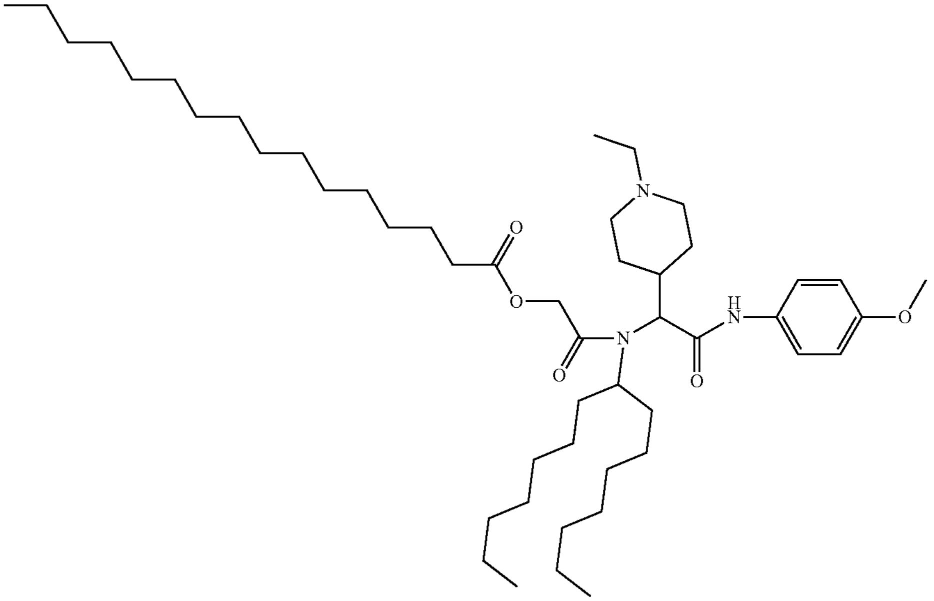

-continued
P312C7
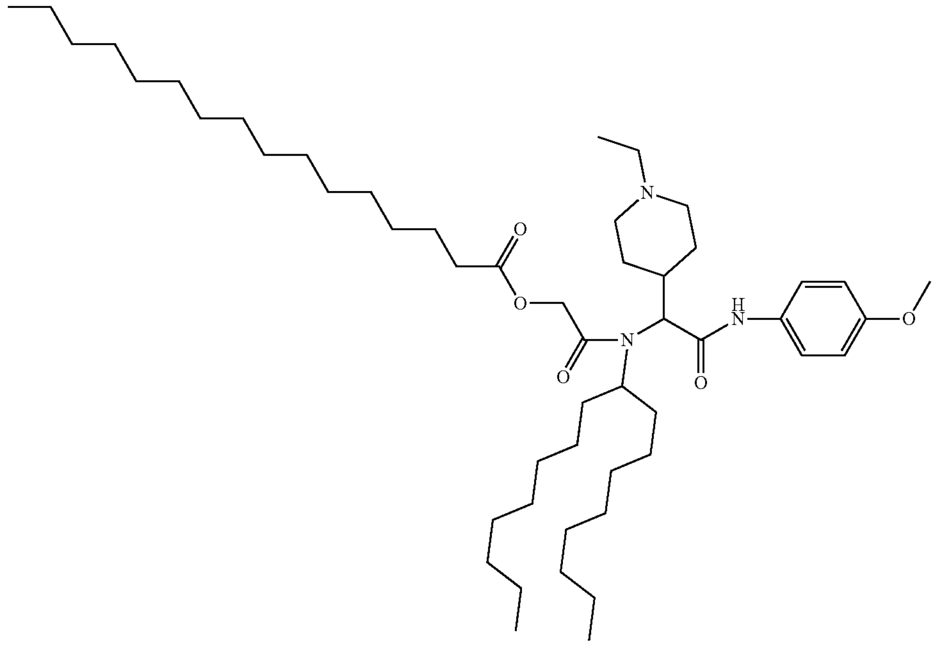
P312E7
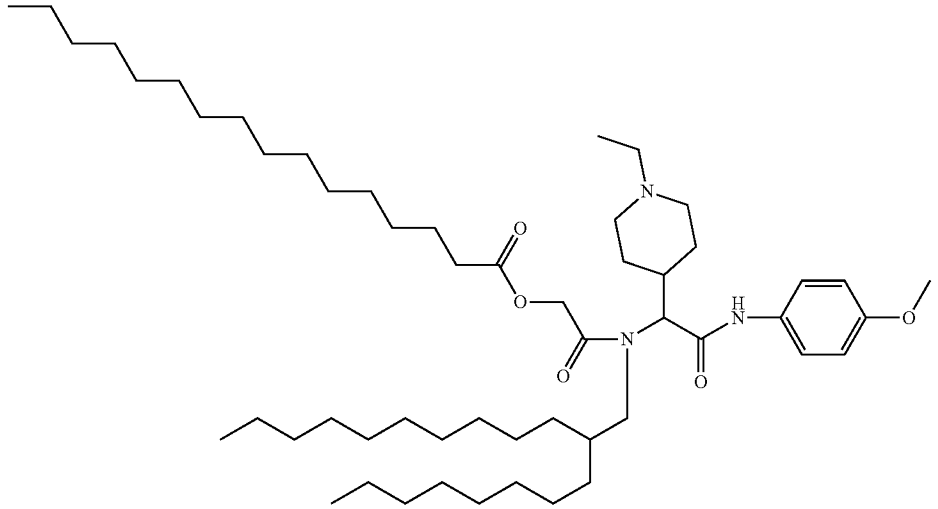
P313B1
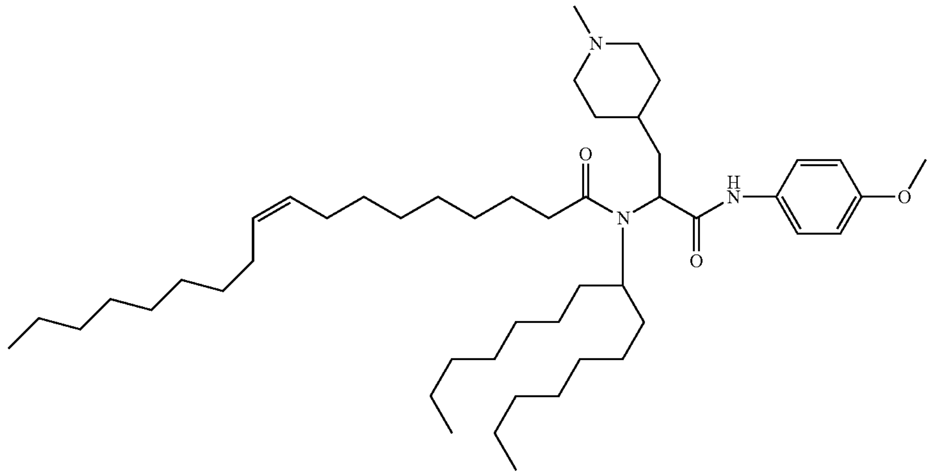

-continued
P313C1
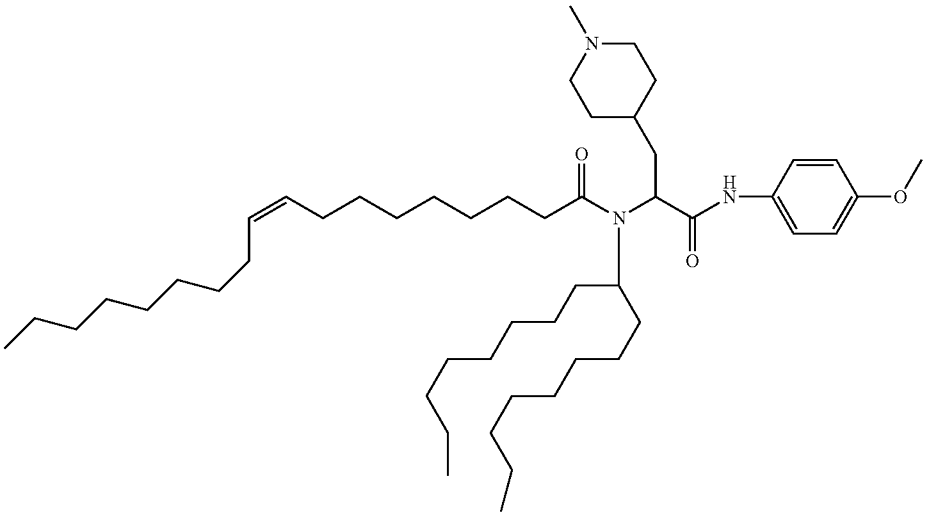
P313C6
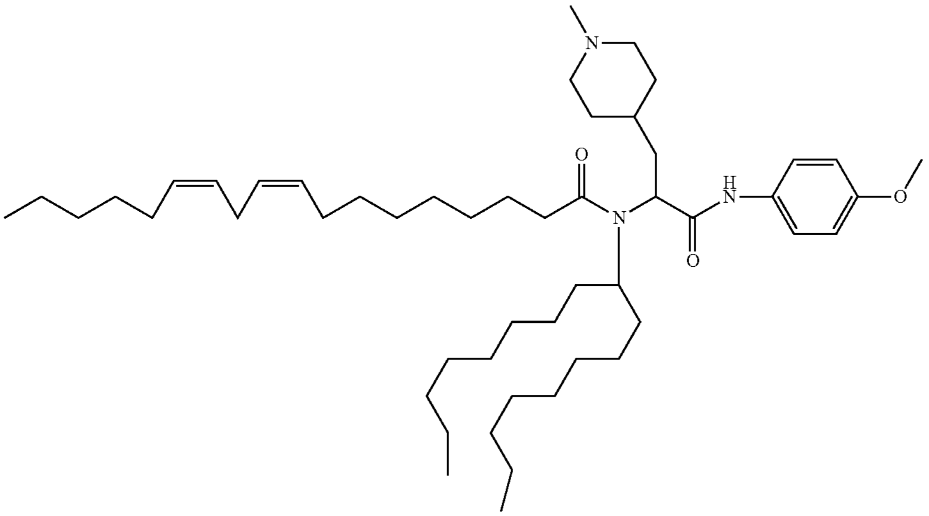
P313C7
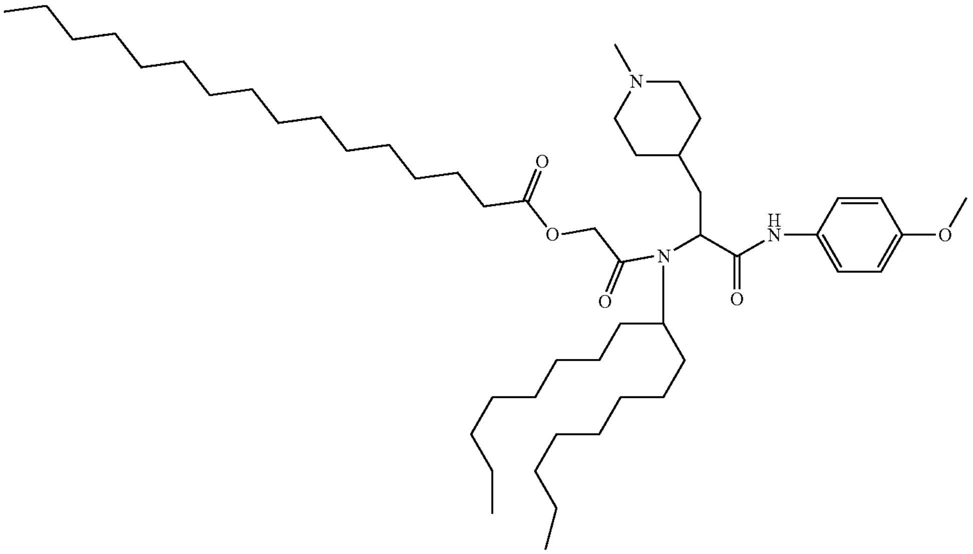

-continued
P313C8
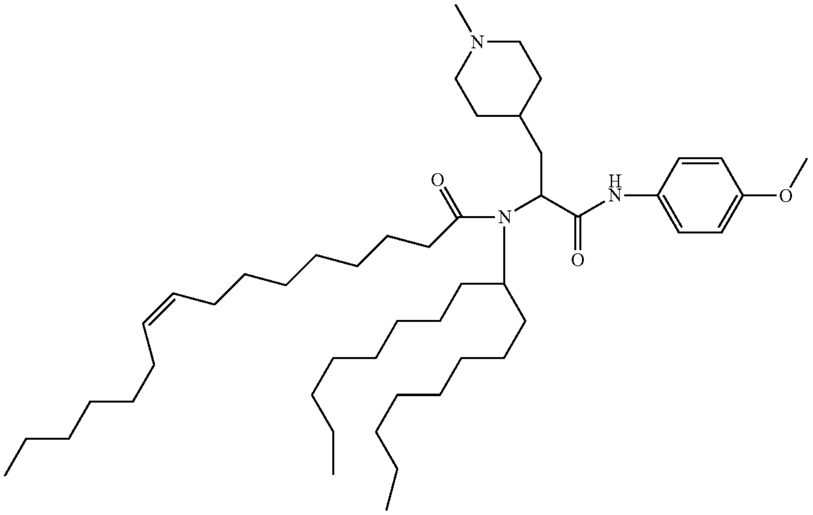
P314E1
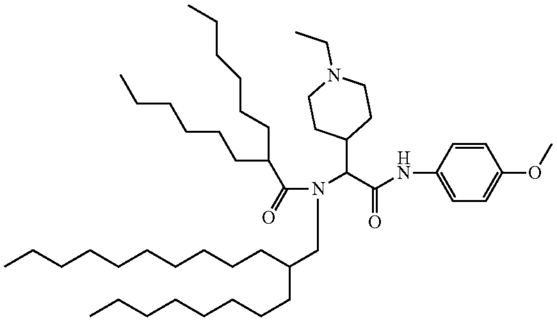
P314E3
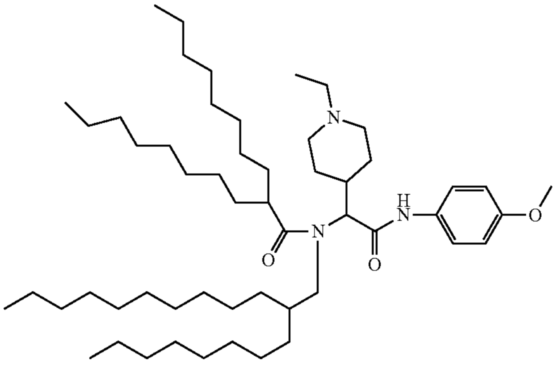
P314F1
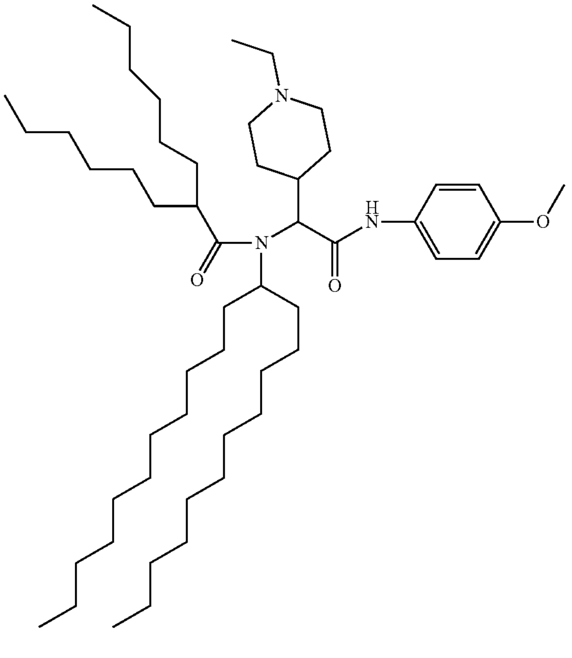
P314G1
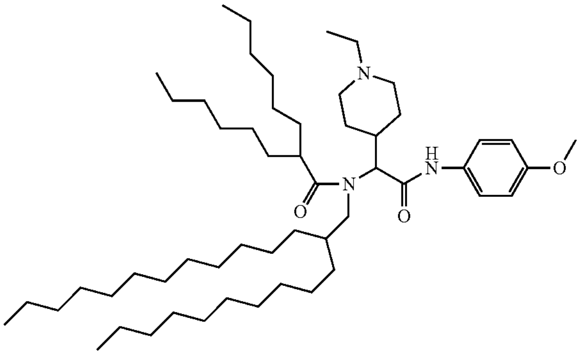

-continued
P316B6
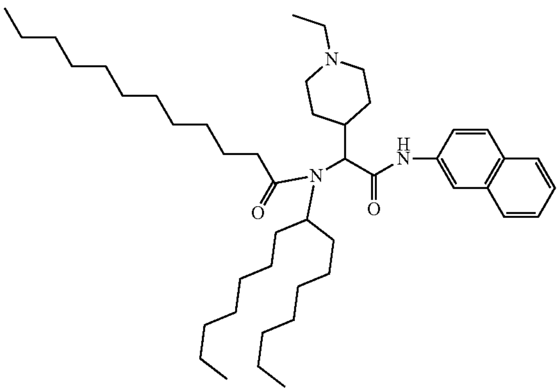
P316B7
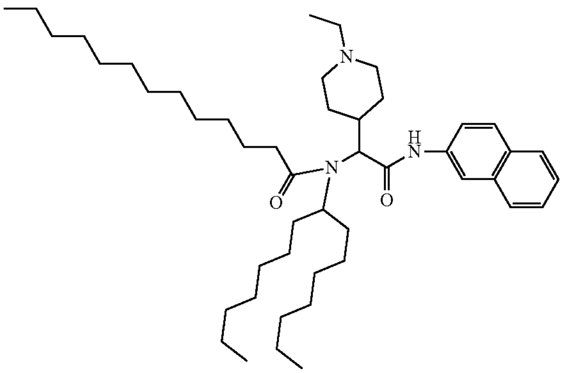
P316B8
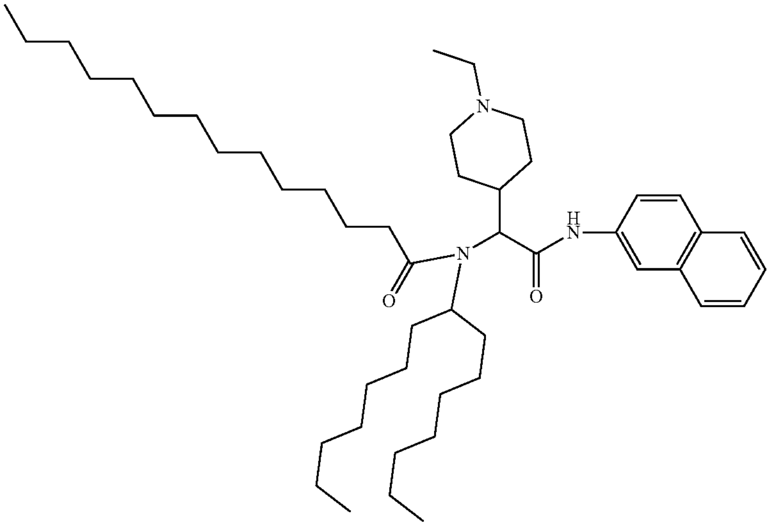
P316B10
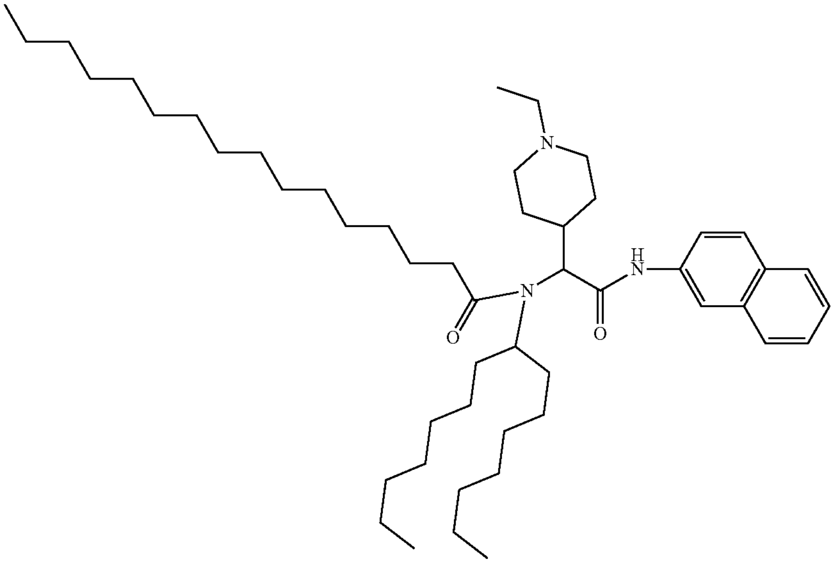

-continued
P316B11
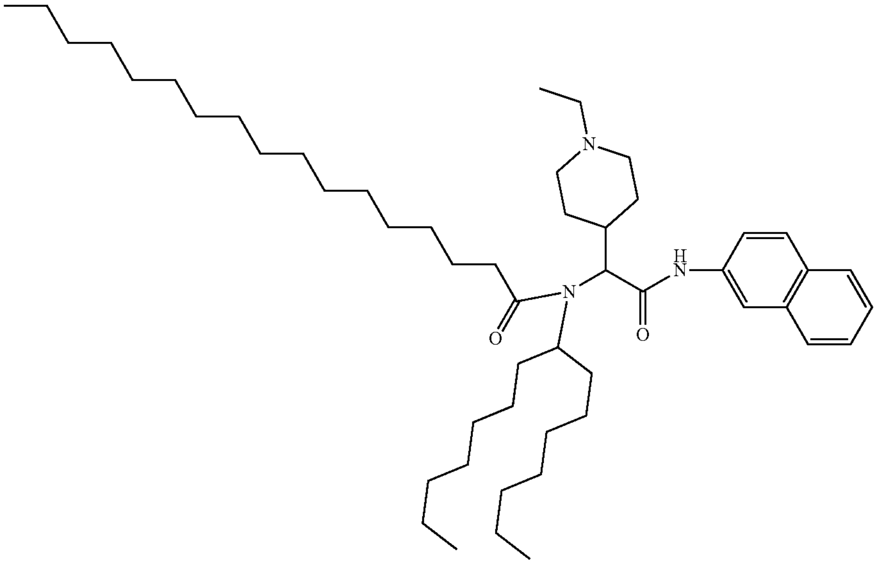
P316C8
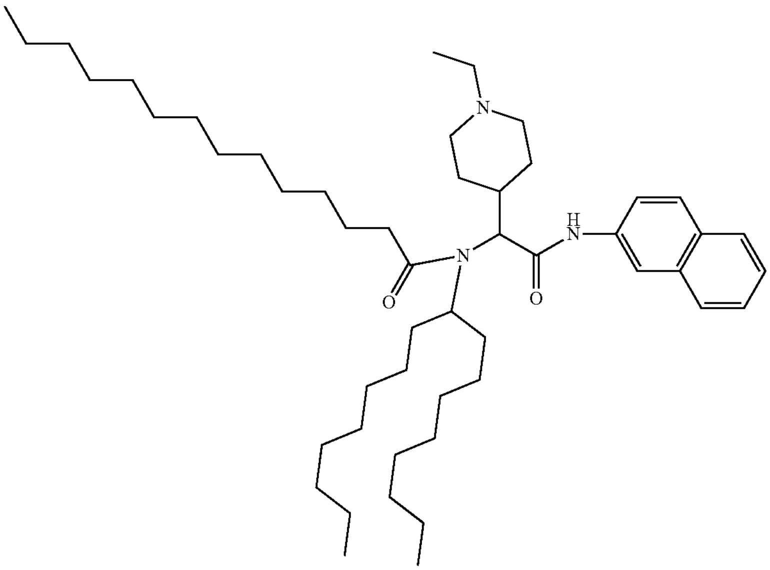

-continued
P316C11
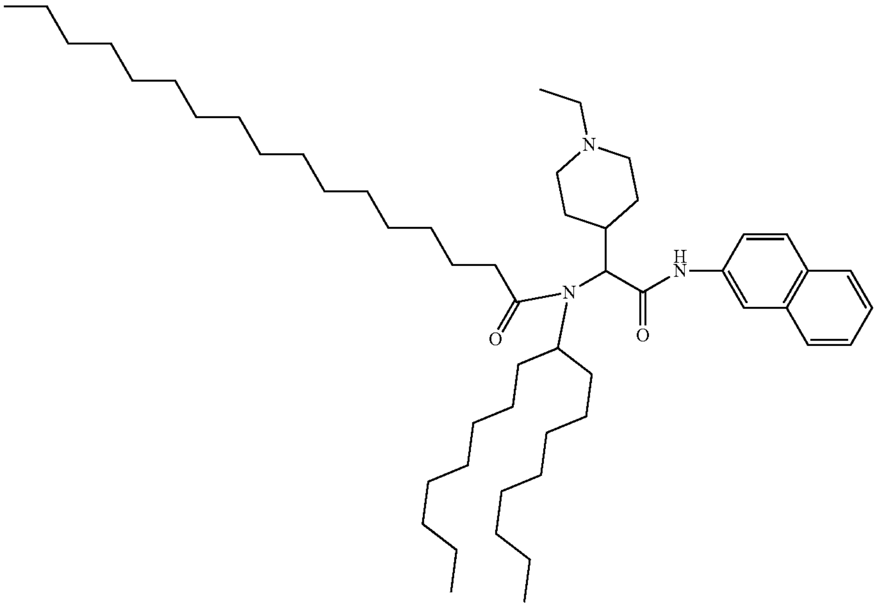
P316E1
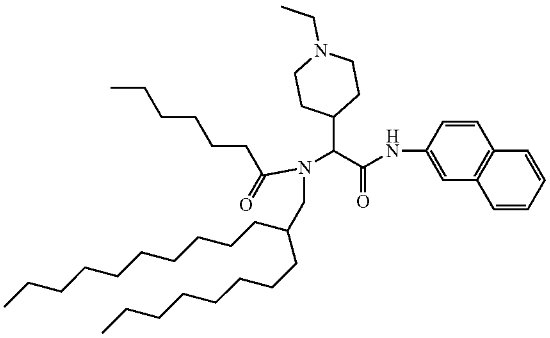
P316E5
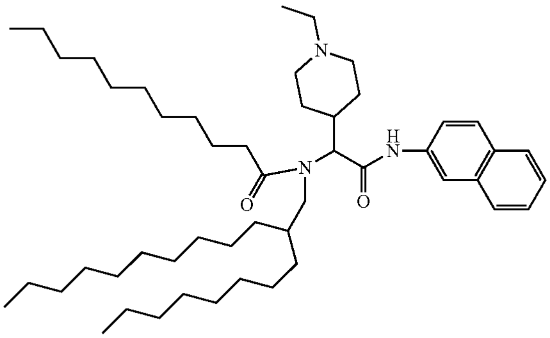
P316E6
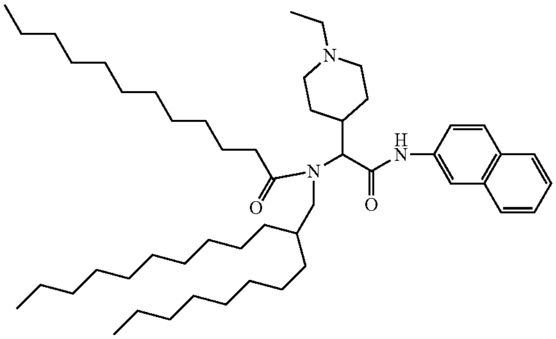
P316E7
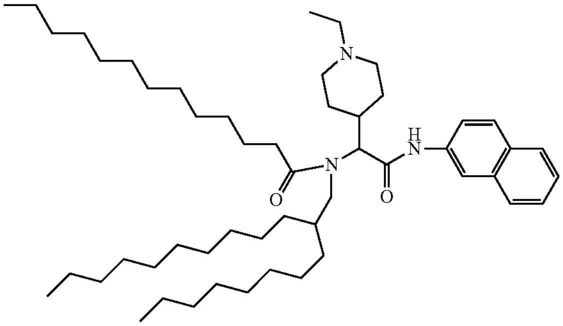

-continued
P316E8
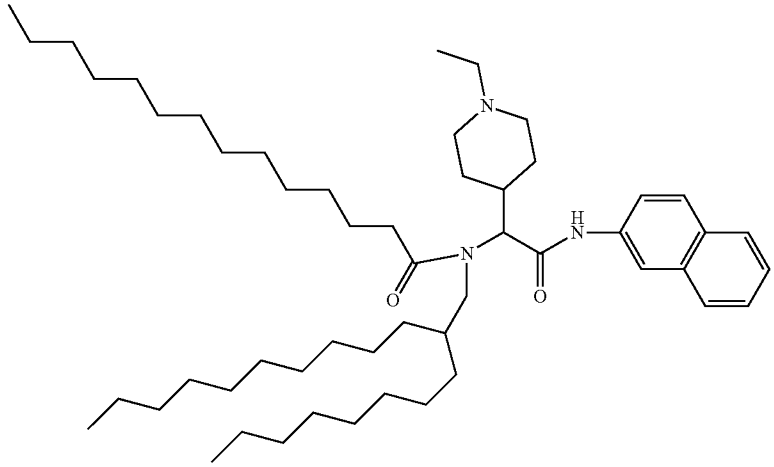
P316E10
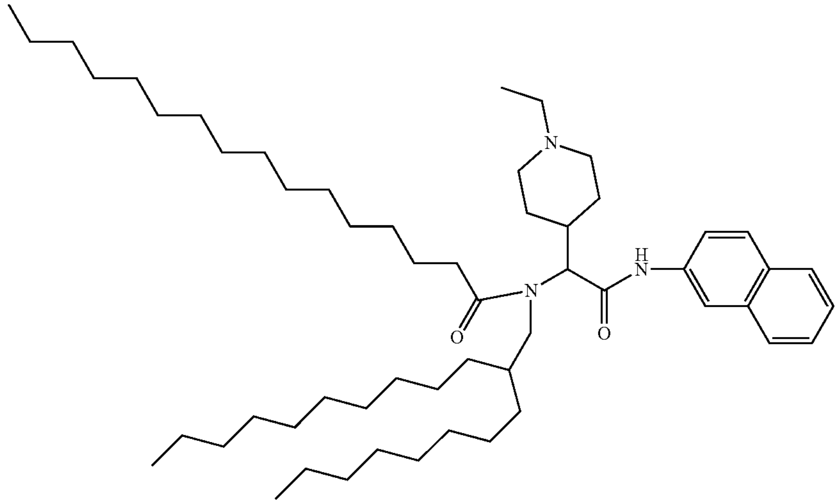
P316E11
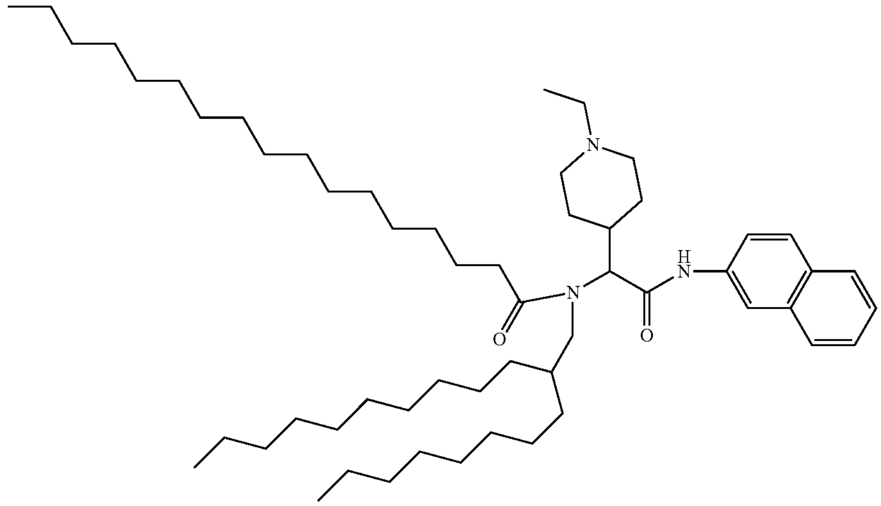

-continued
P316E12
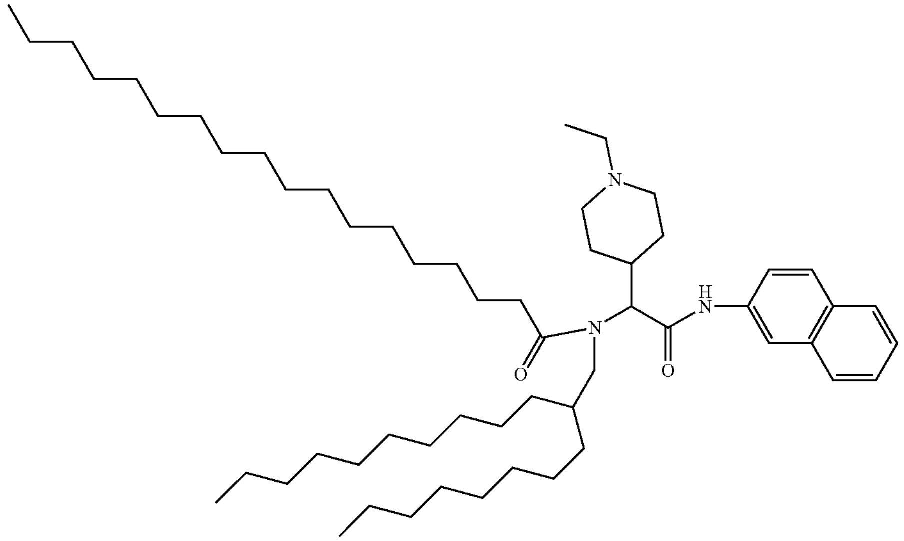
P318B1
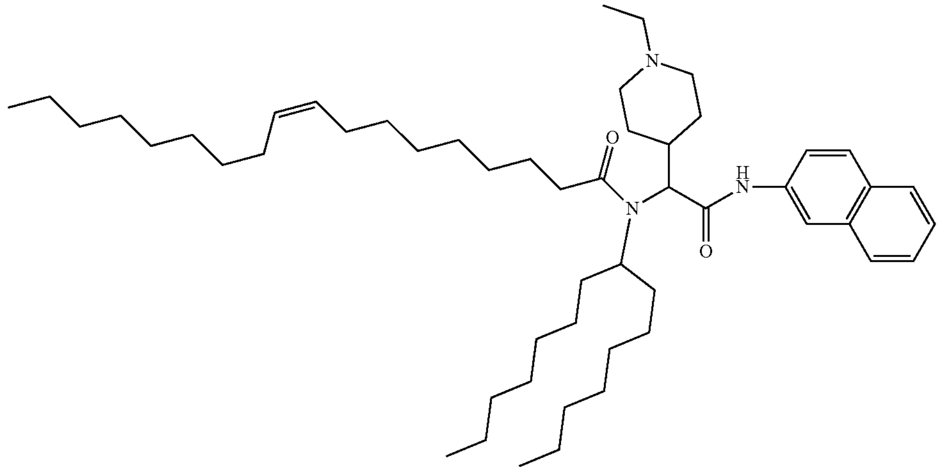
P318C1
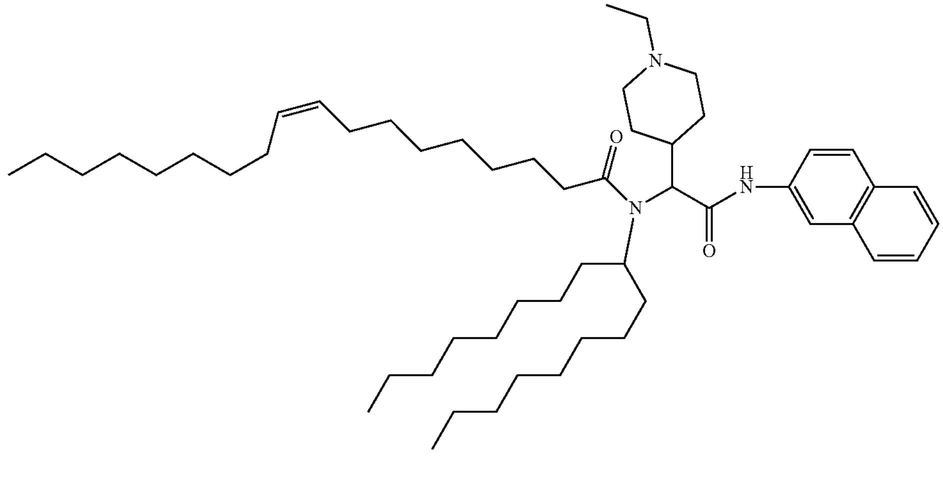

-continued
P318E1
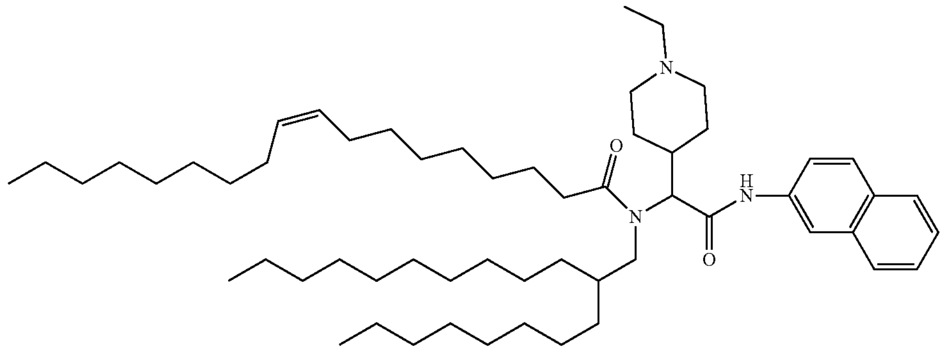
P318F1
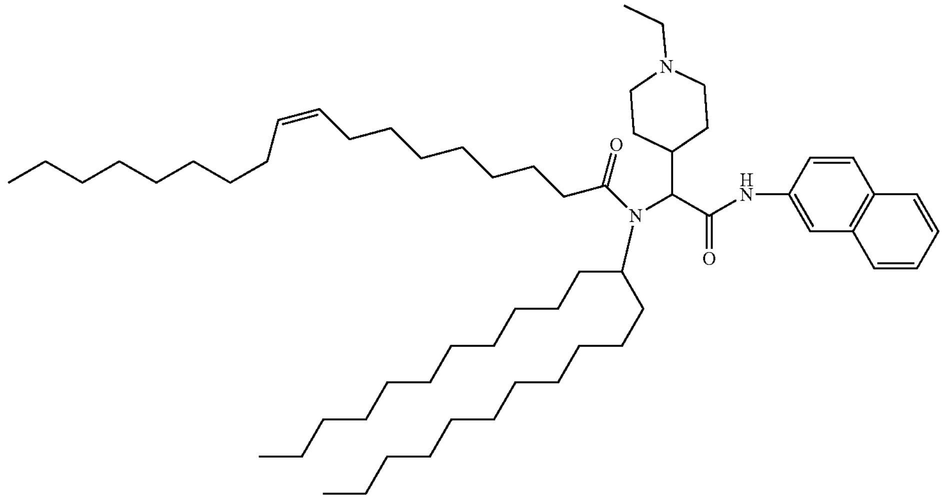
P318G1
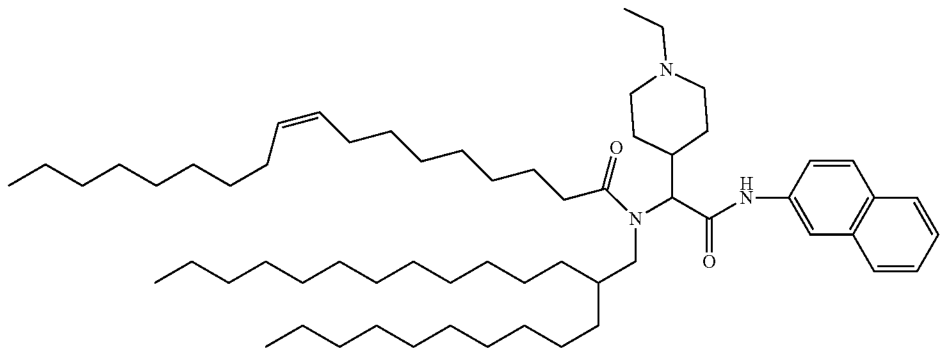
P318B3
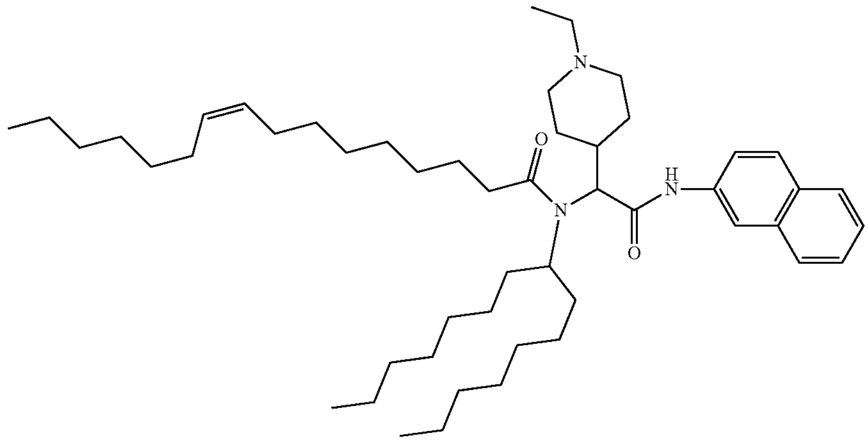

-continued
P318B6
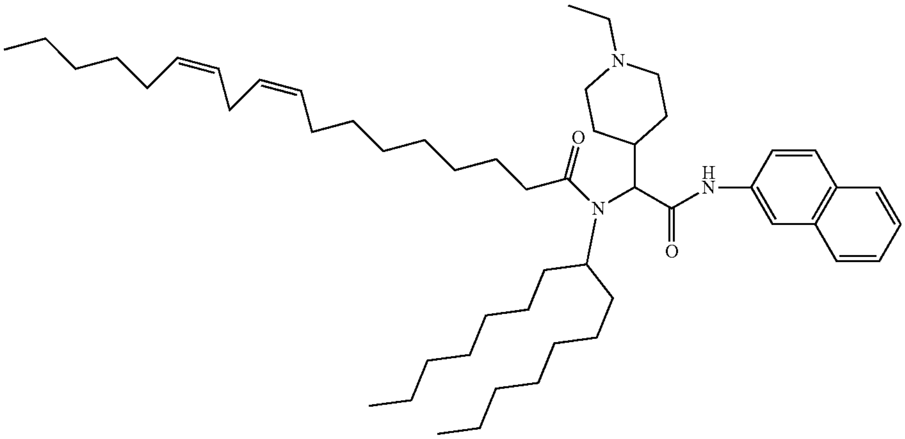
P318E6
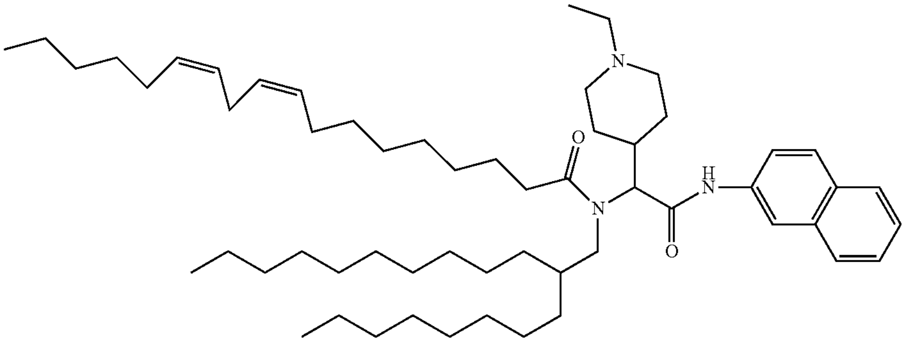
P318B7
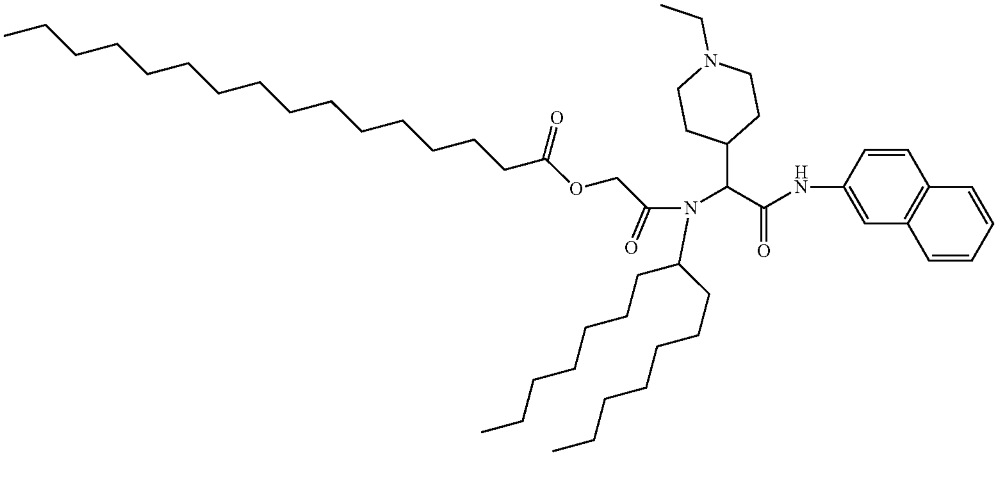

-continued
P318C7
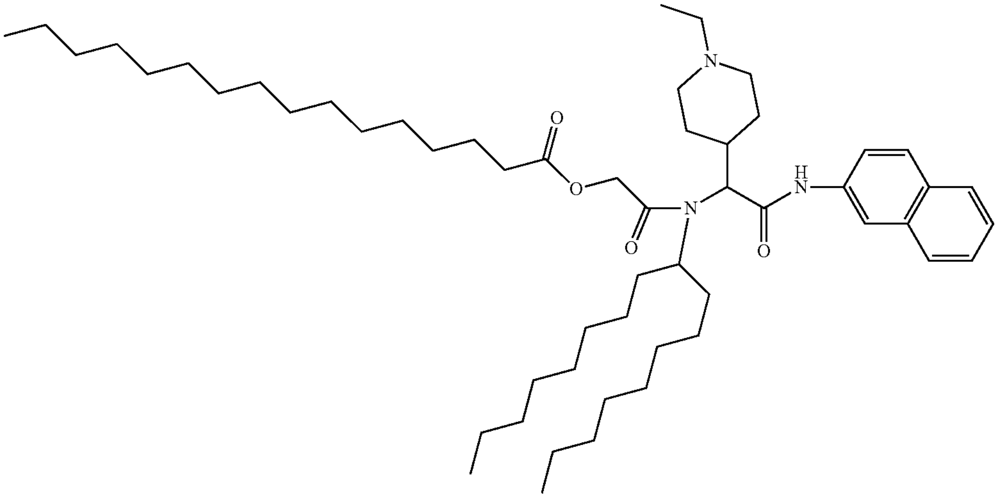
P318D7
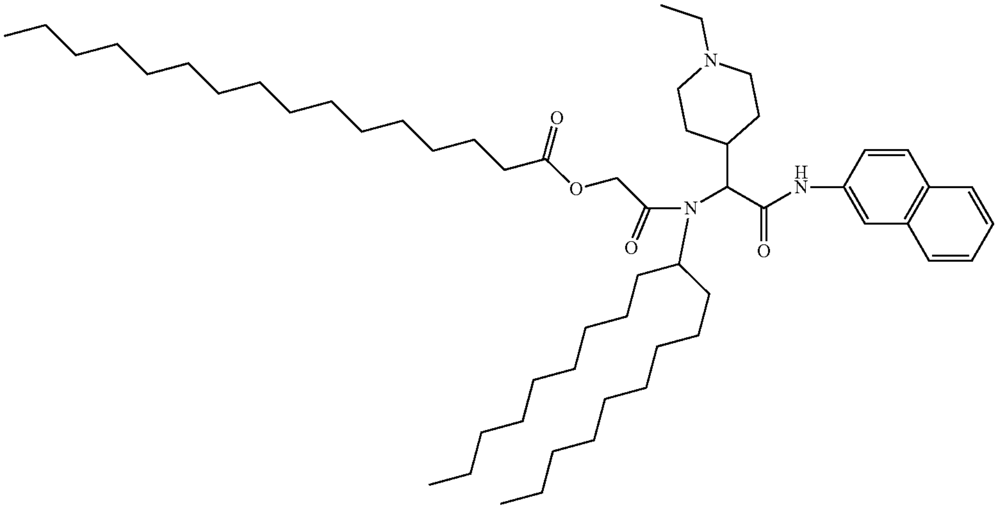
P318E7
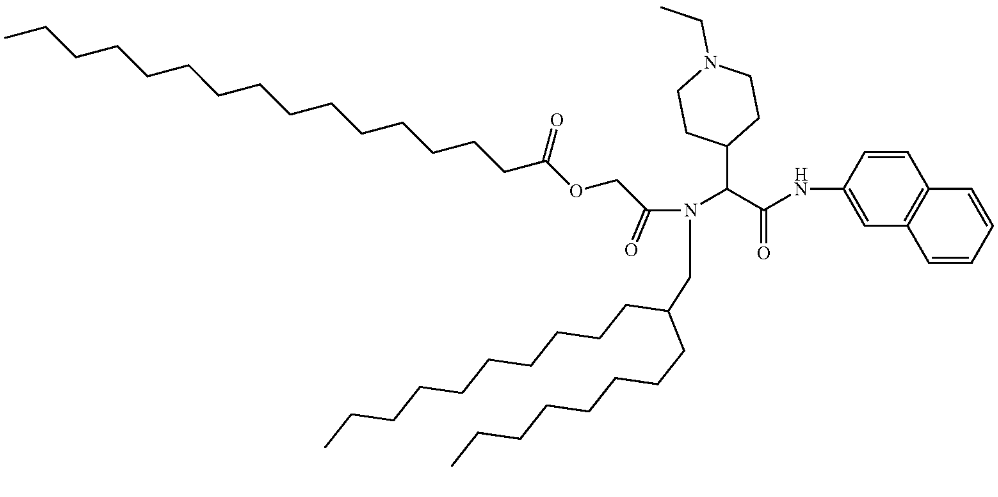

-continued
P318E10
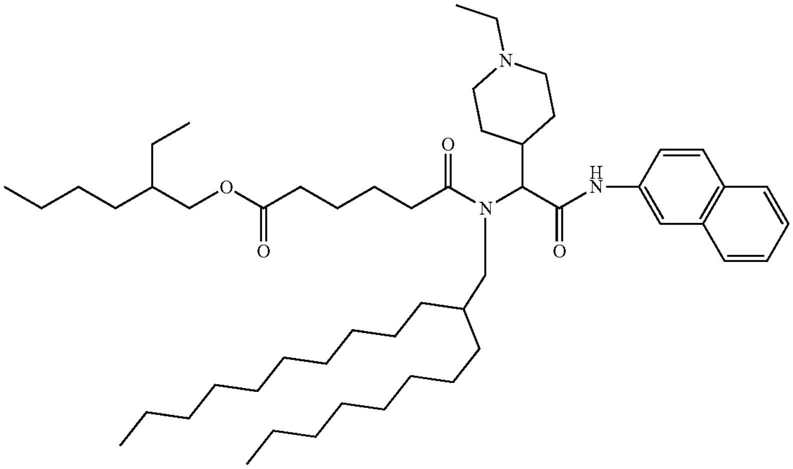
P318G10
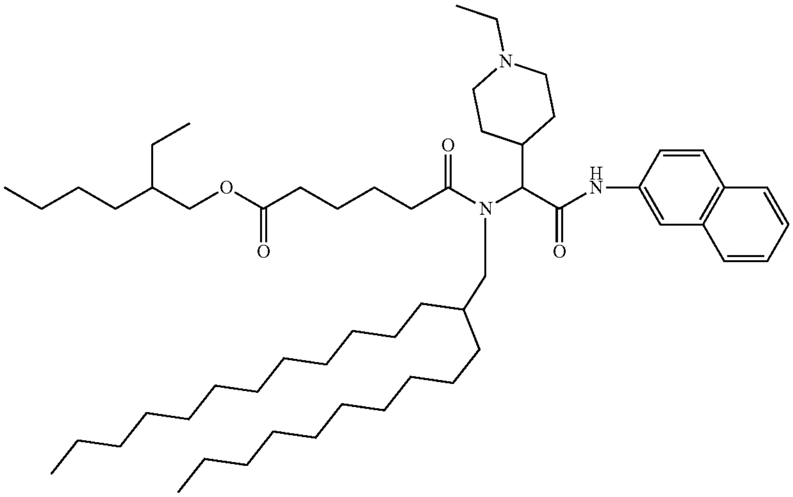
P318E12
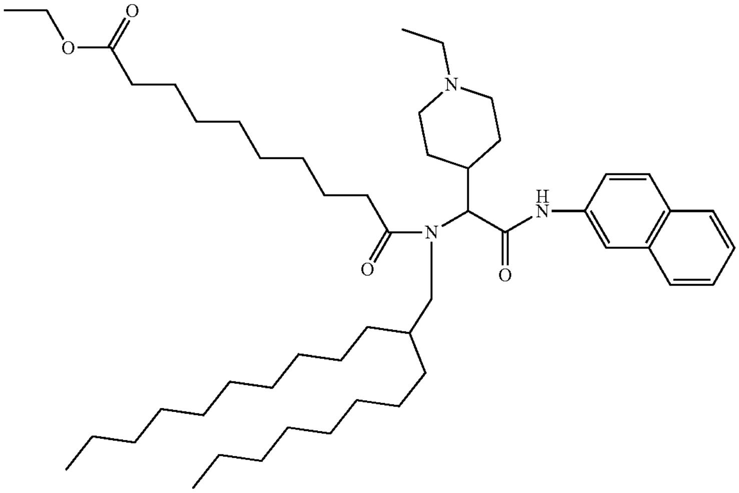

-continued
P319B7
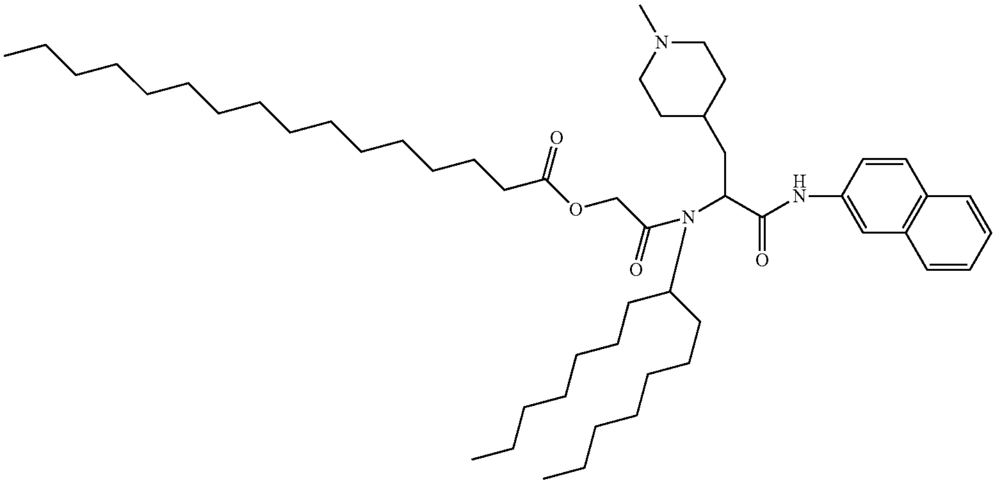
P319C1
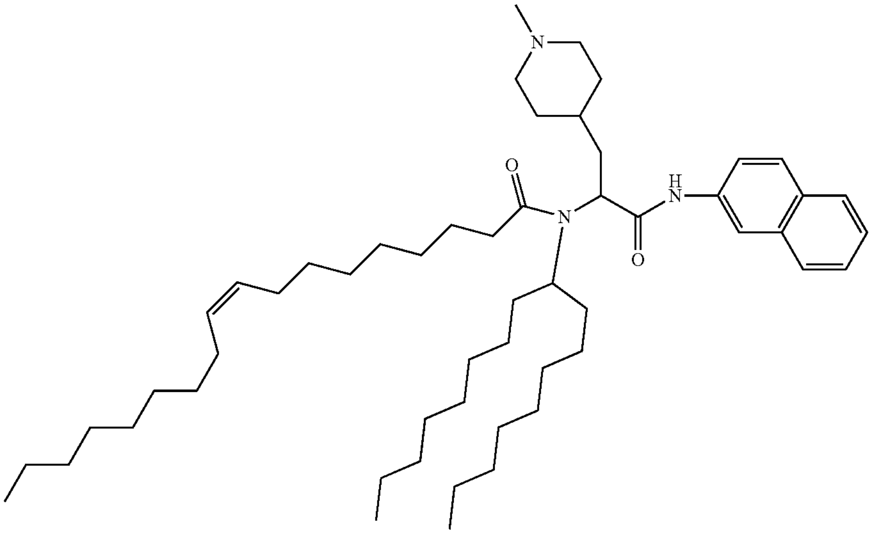
P320E1
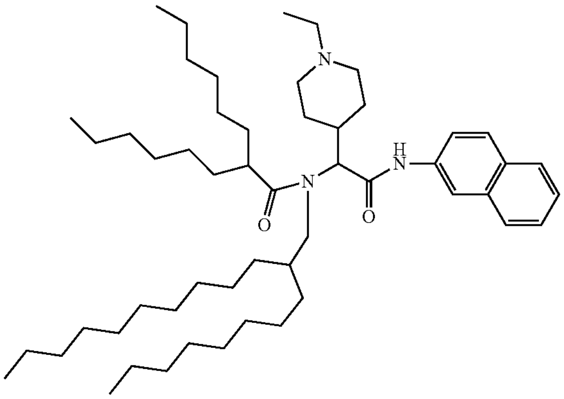
P320G1
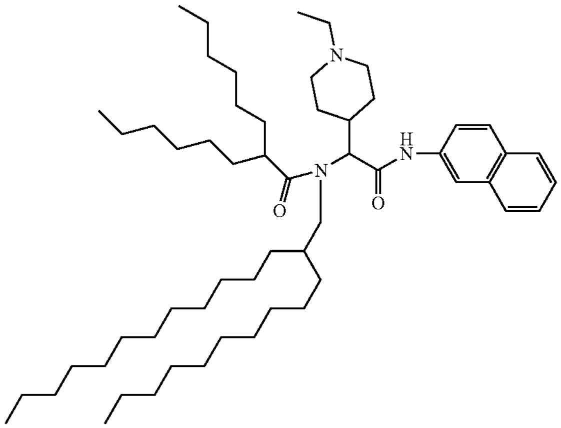

-continued
P320E2
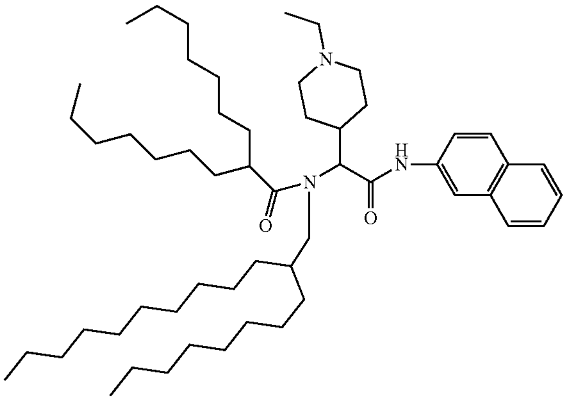
P320E3
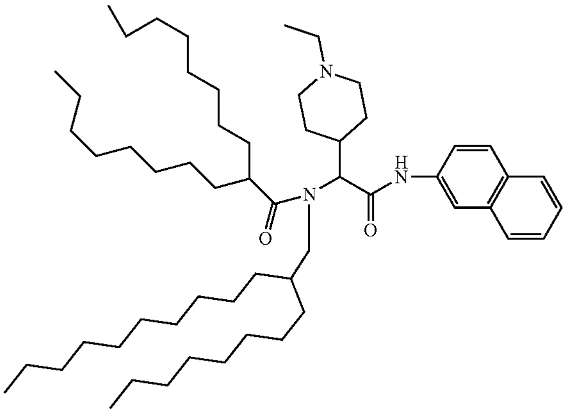
P320E7
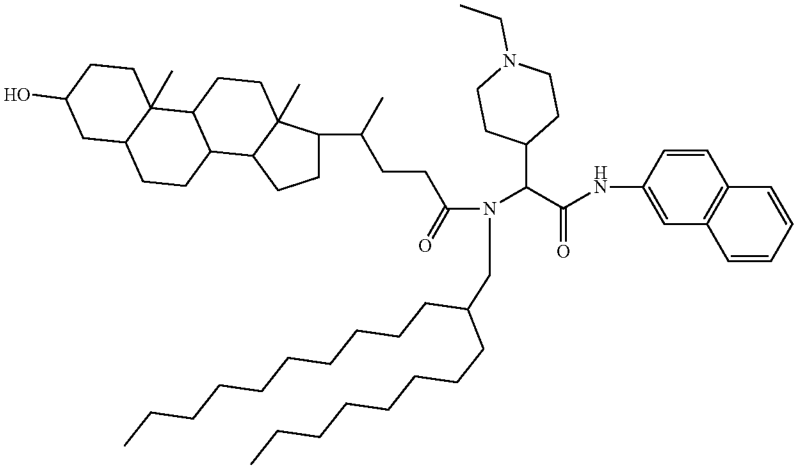
P321E1
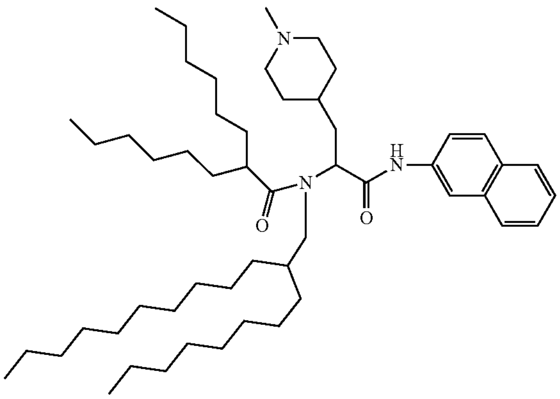
P321G1
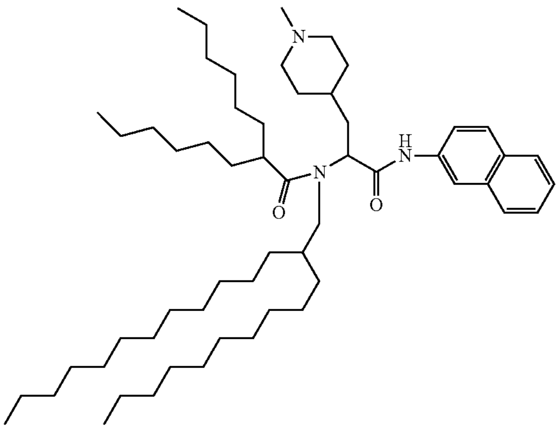

-continued
P328A10
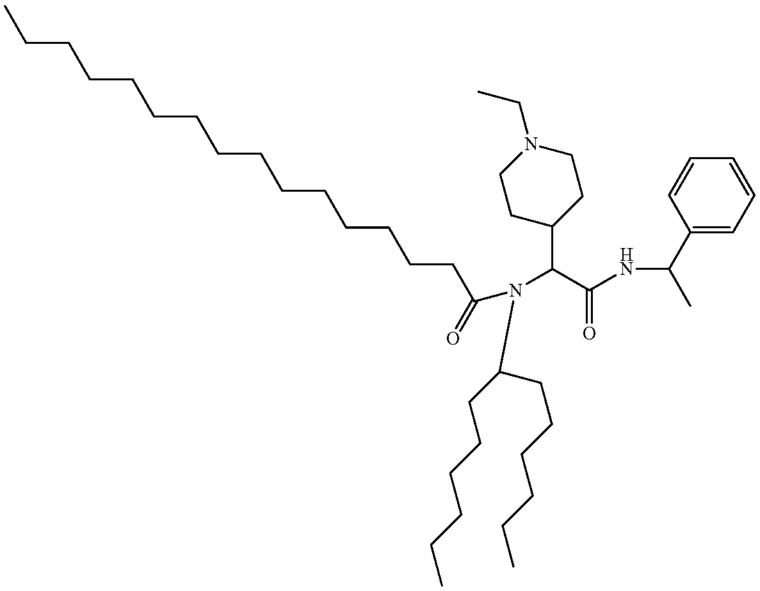
P328A11
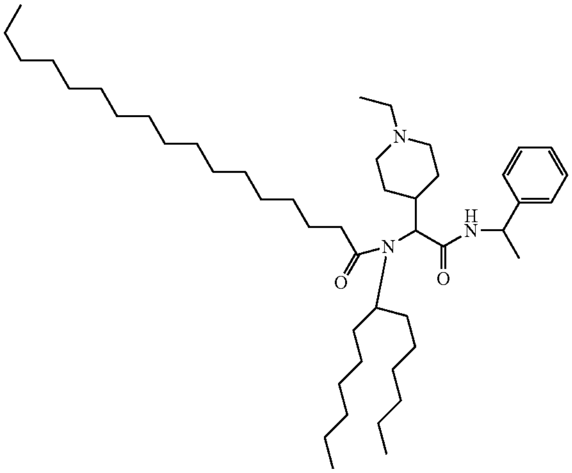
P329E7
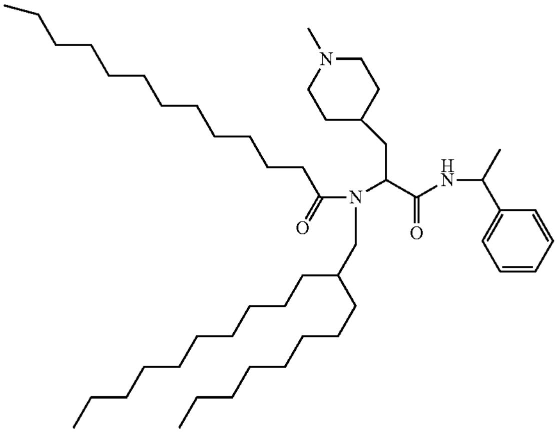
P329E8
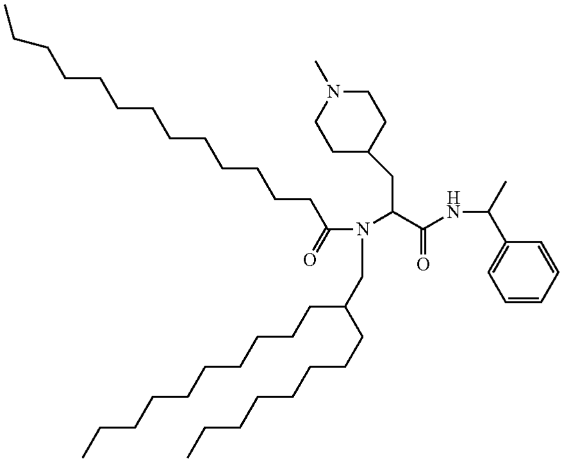
P329E10
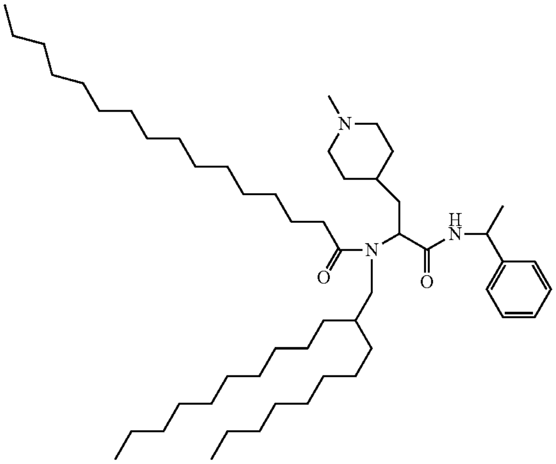

-continued
P329E11
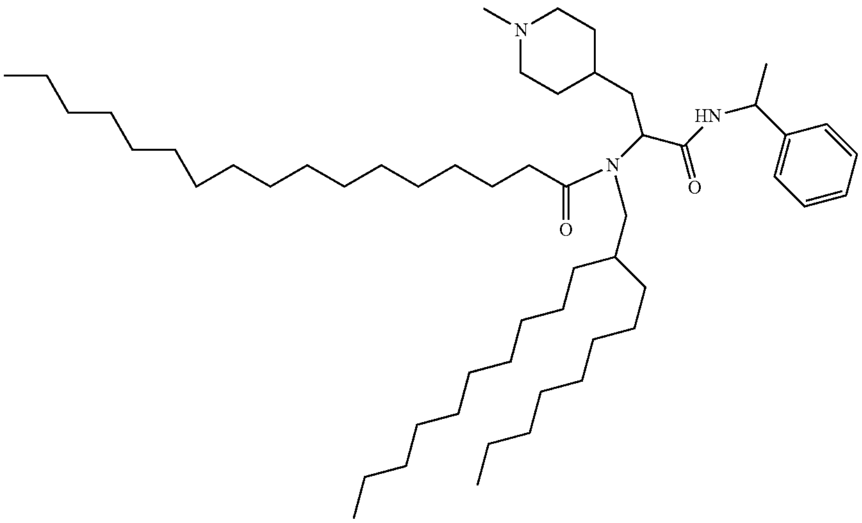
P329E12
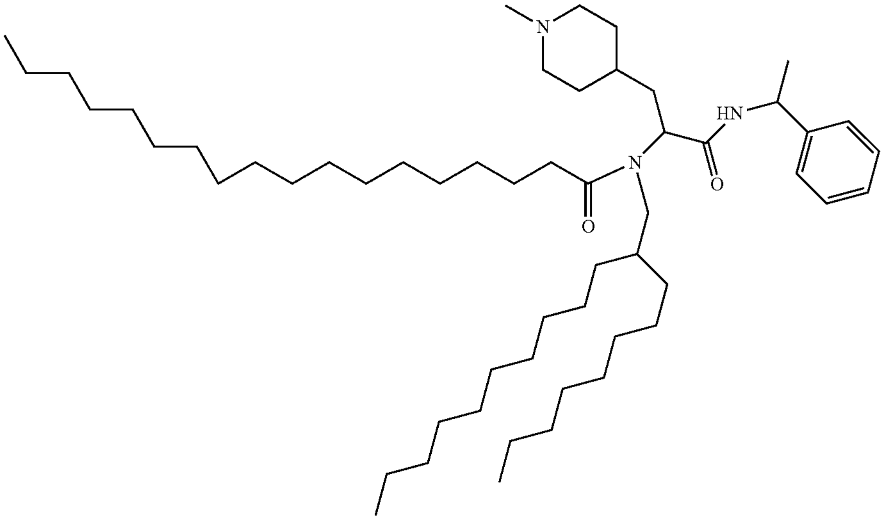
P330A1
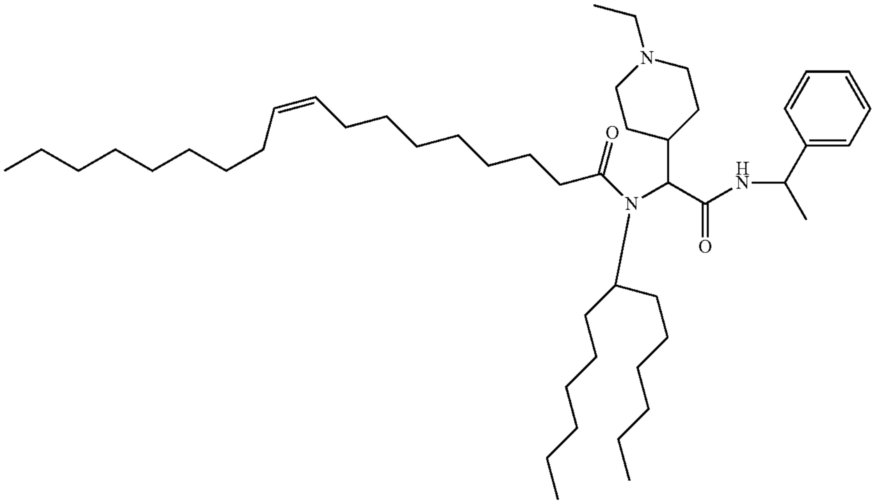

-continued
P330A7
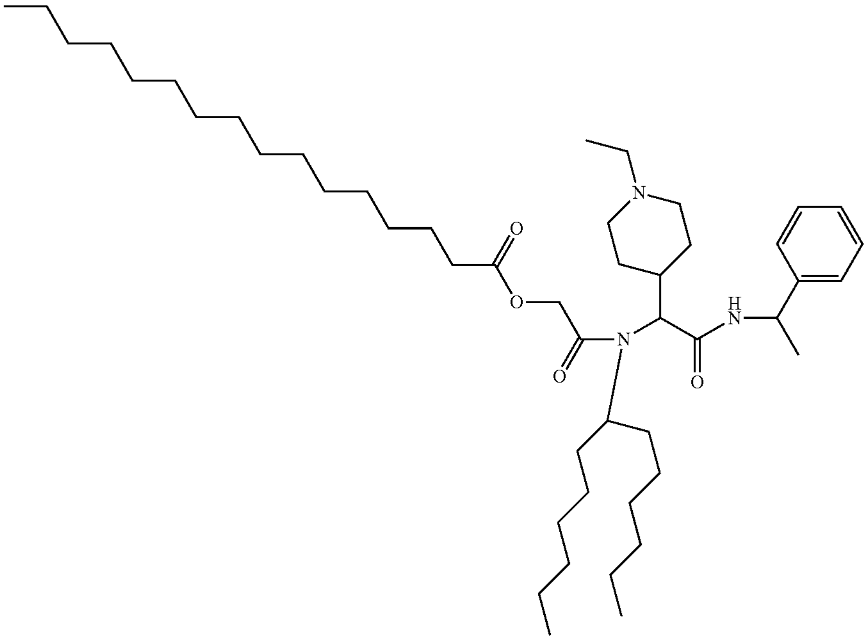
P330B1
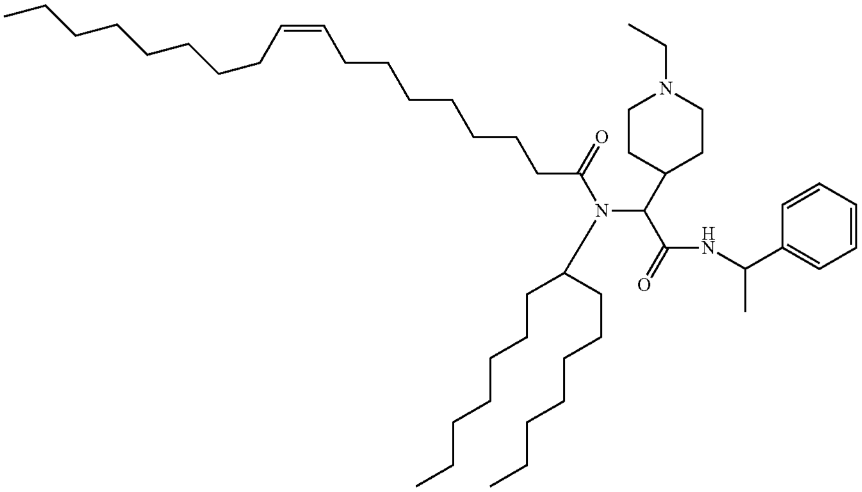
P330C1
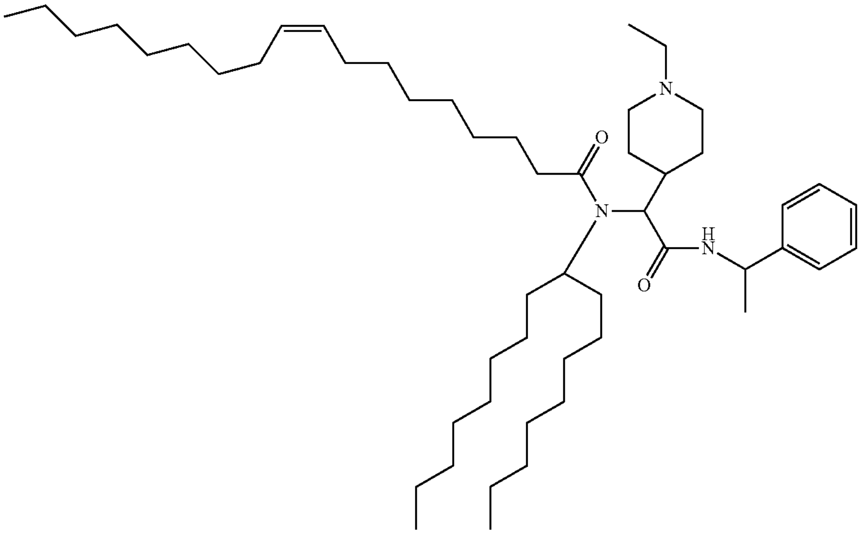

-continued
P330E1
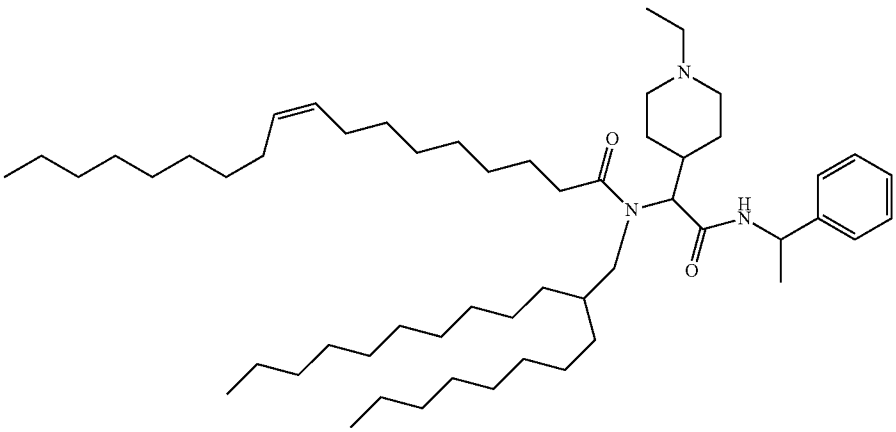
P330E6
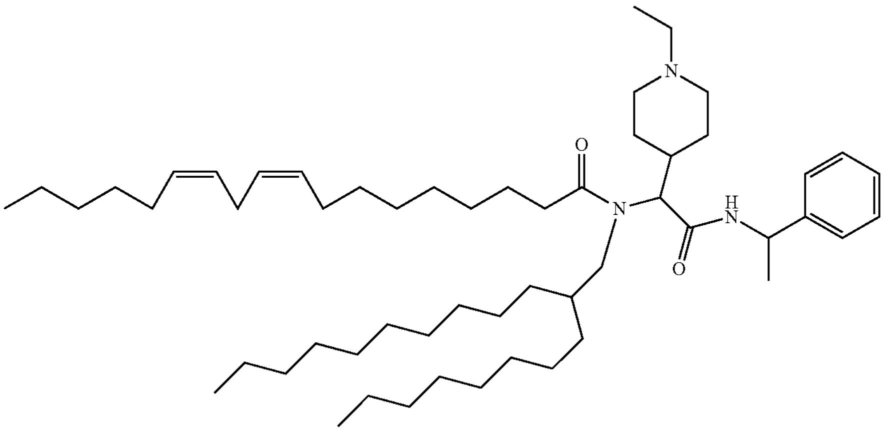
P330E8
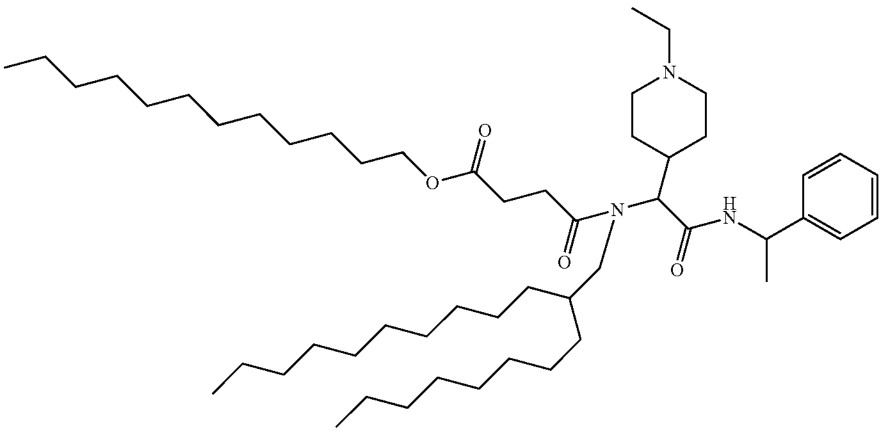

-continued
P331A1
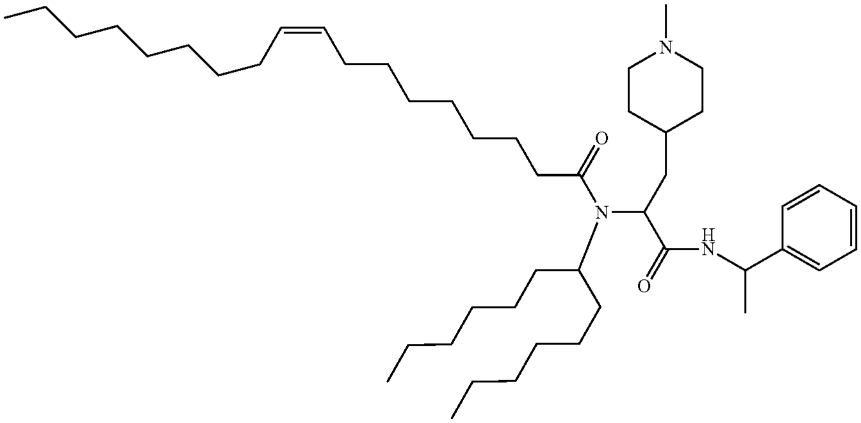
P331B1
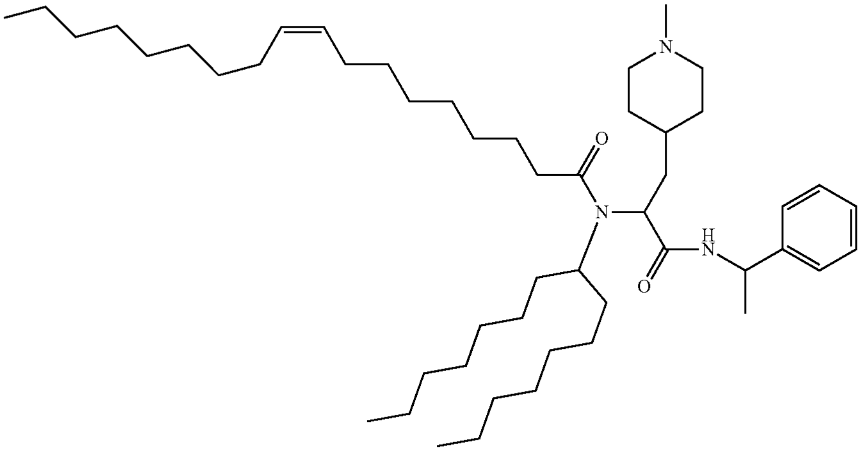
P331B3
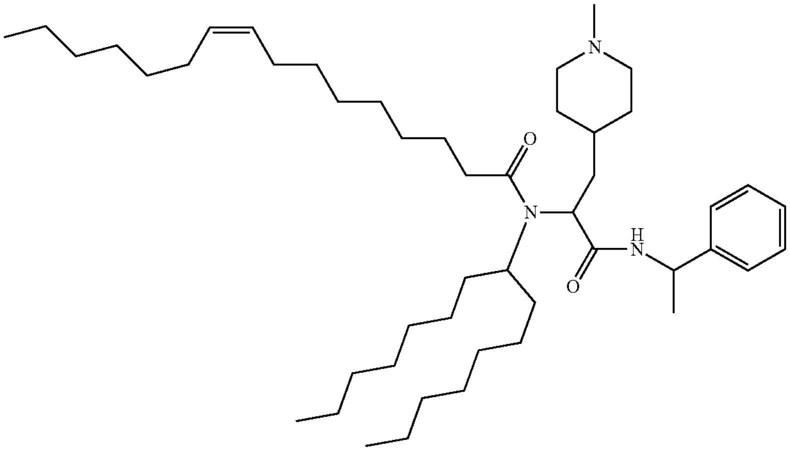

-continued
P331B6
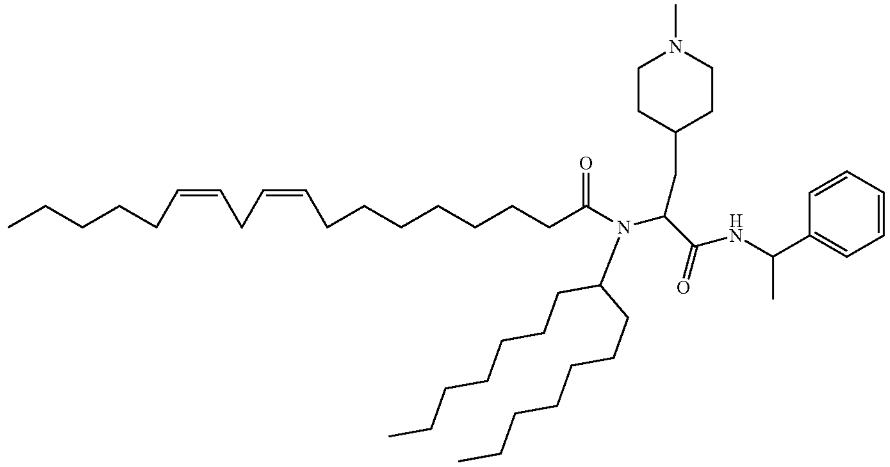
P331B8
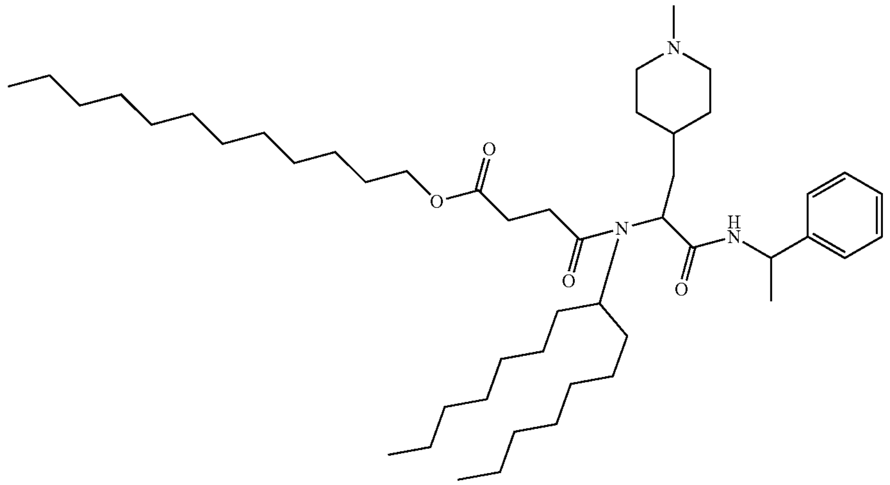
P331C1
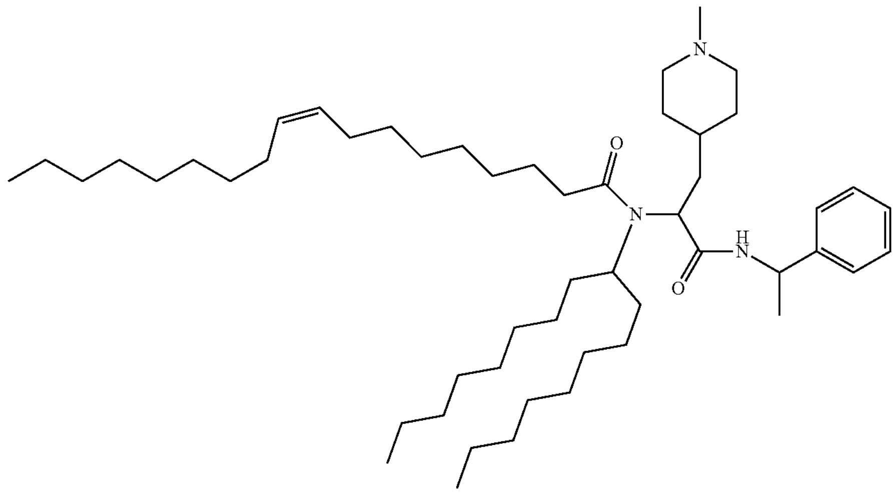

-continued
P331C4
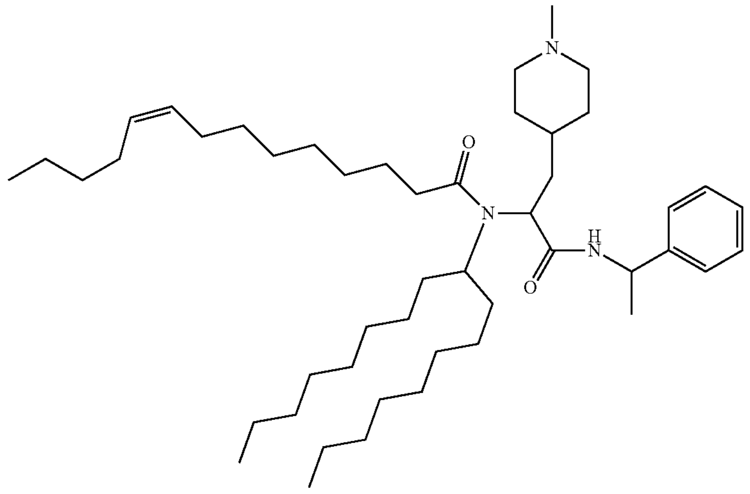
P331D1
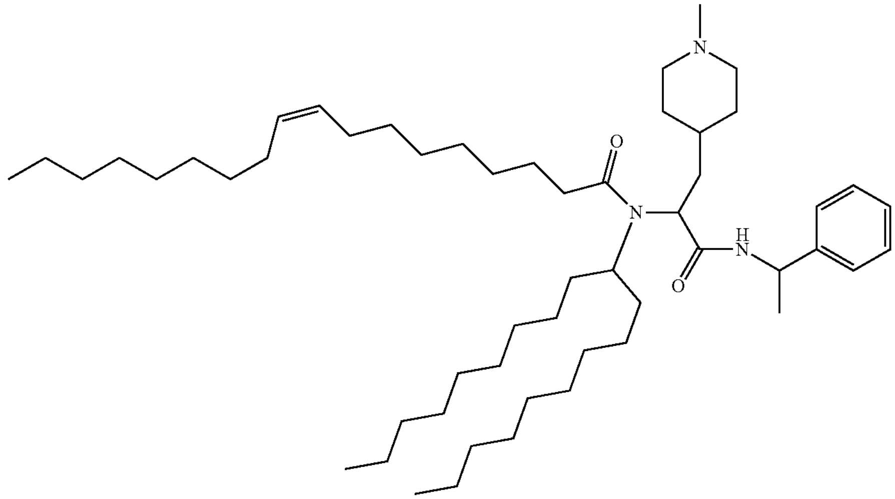
P331E1
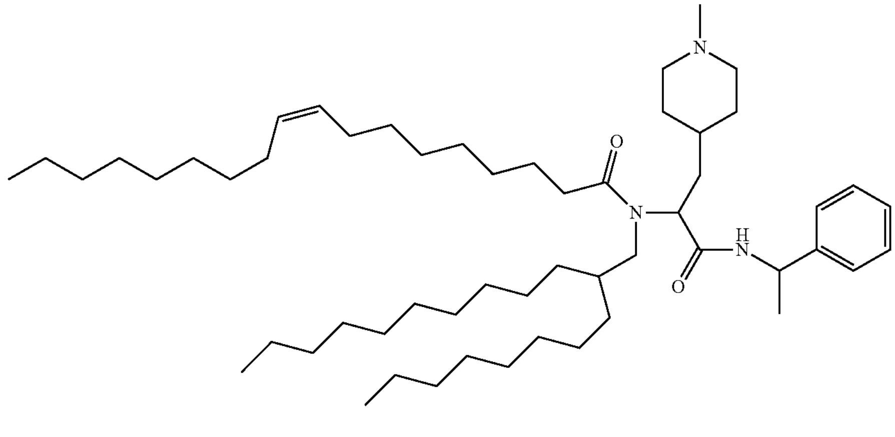

-continued
P331E6
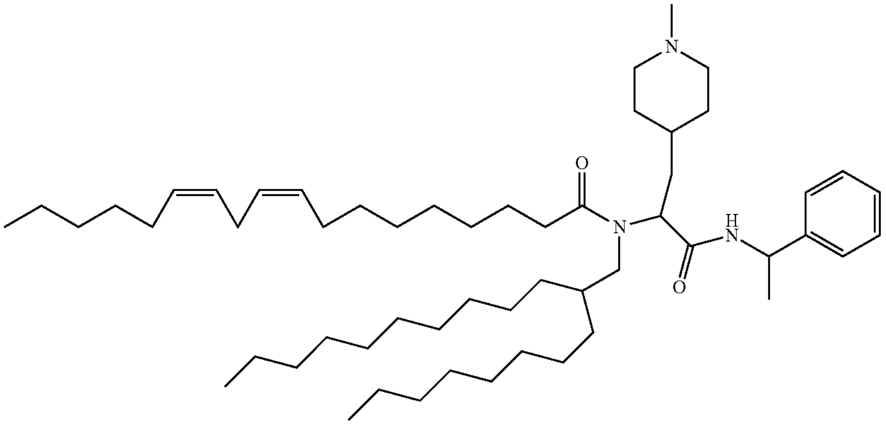
P332G1
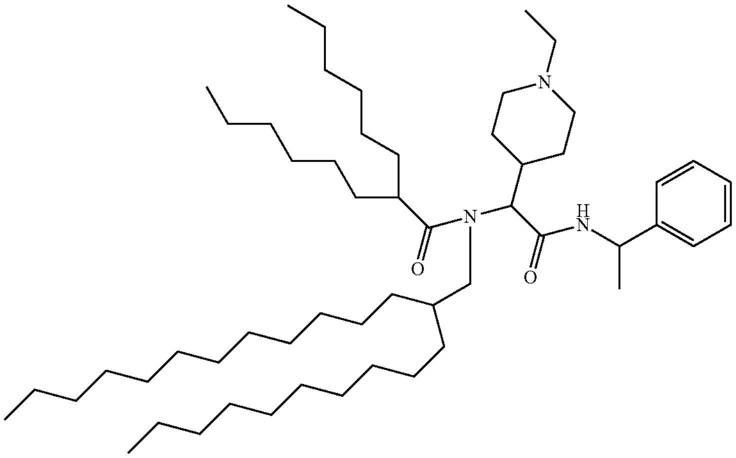
P341A9
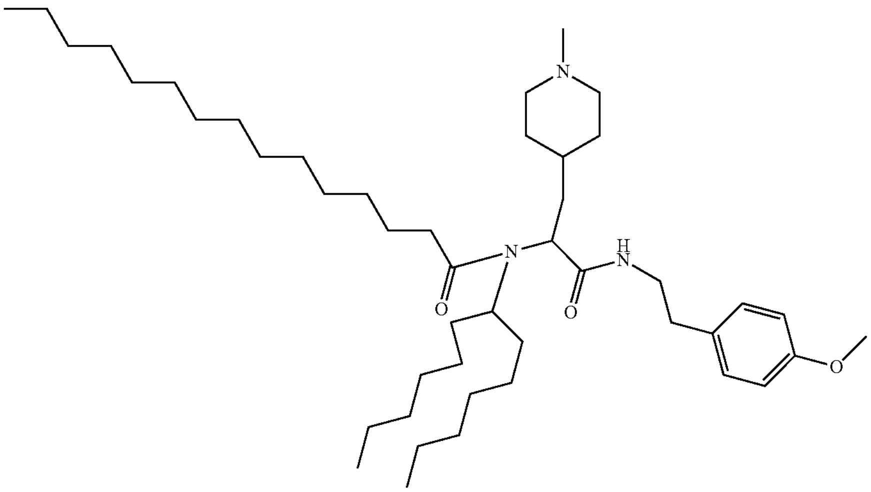

-continued
P341A11
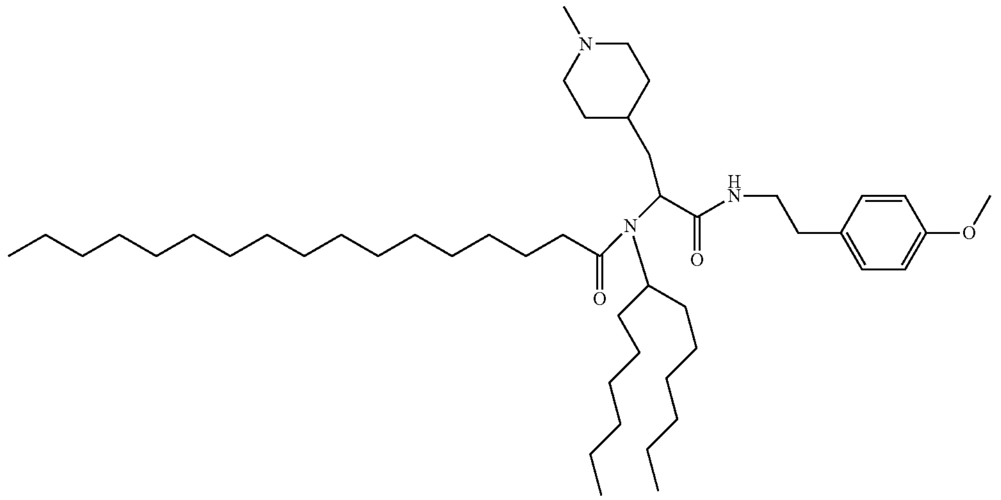
P341C9
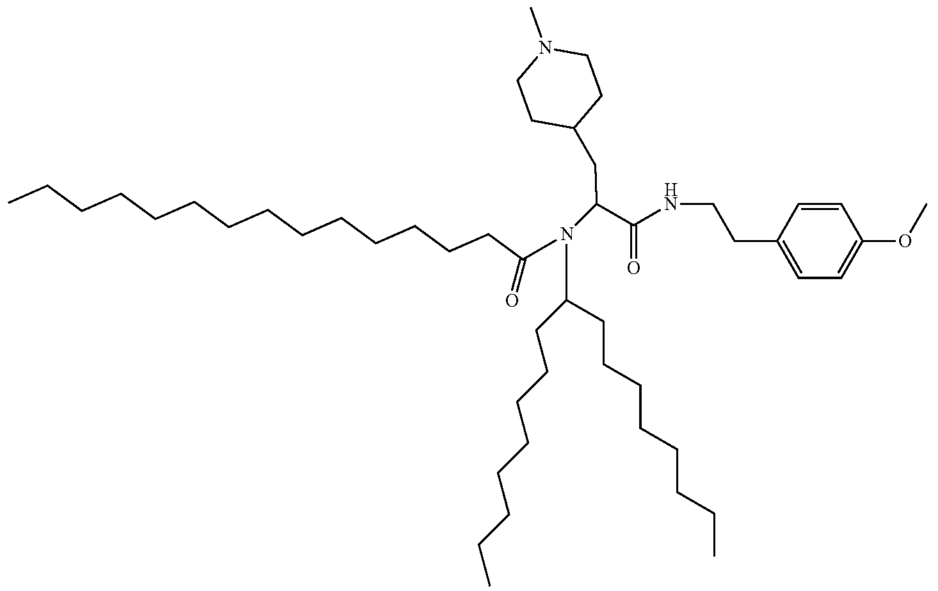

-continued
P341C11
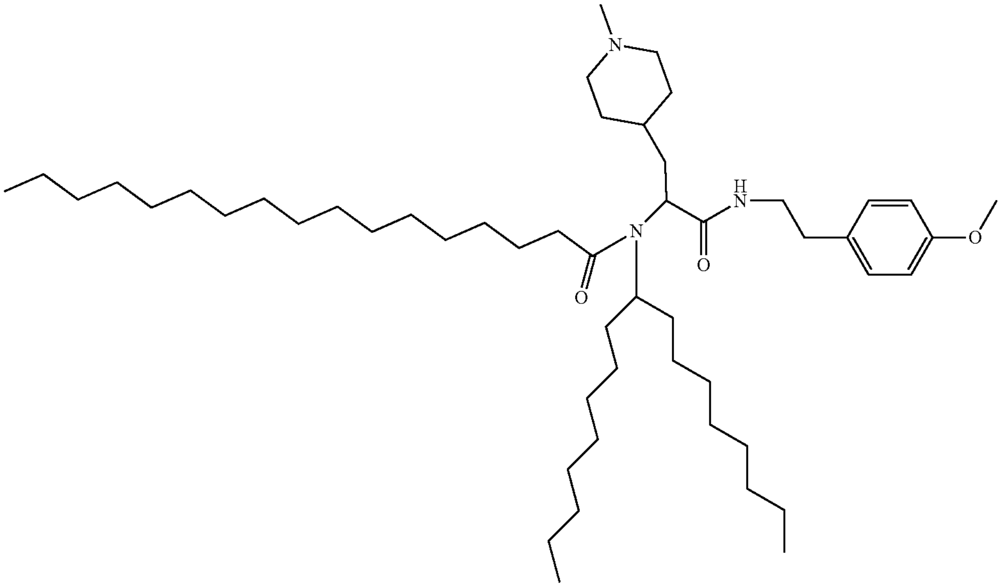
P341C12
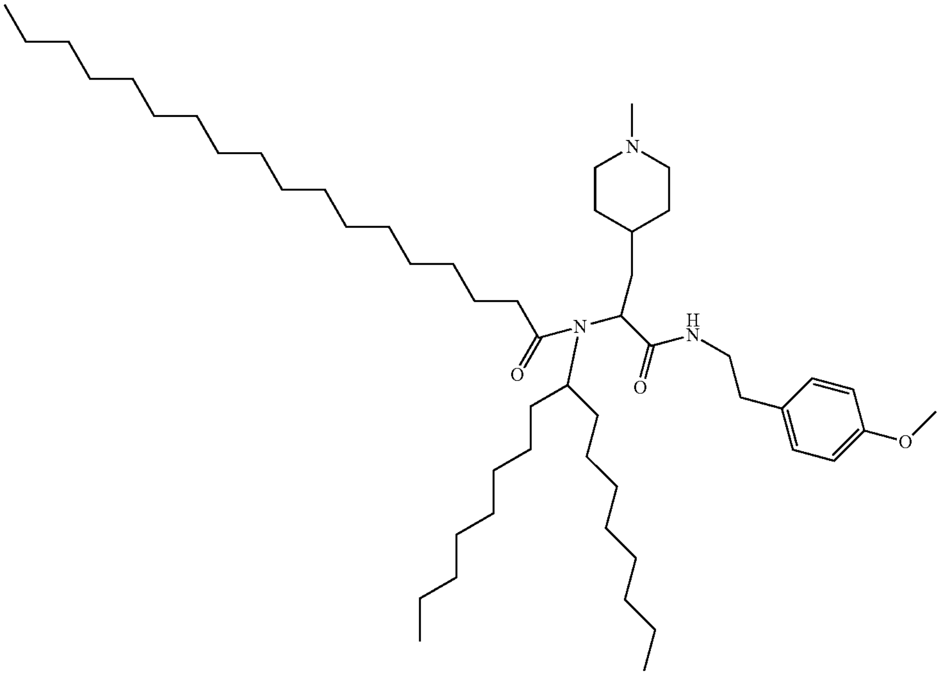

-continued
P341D11
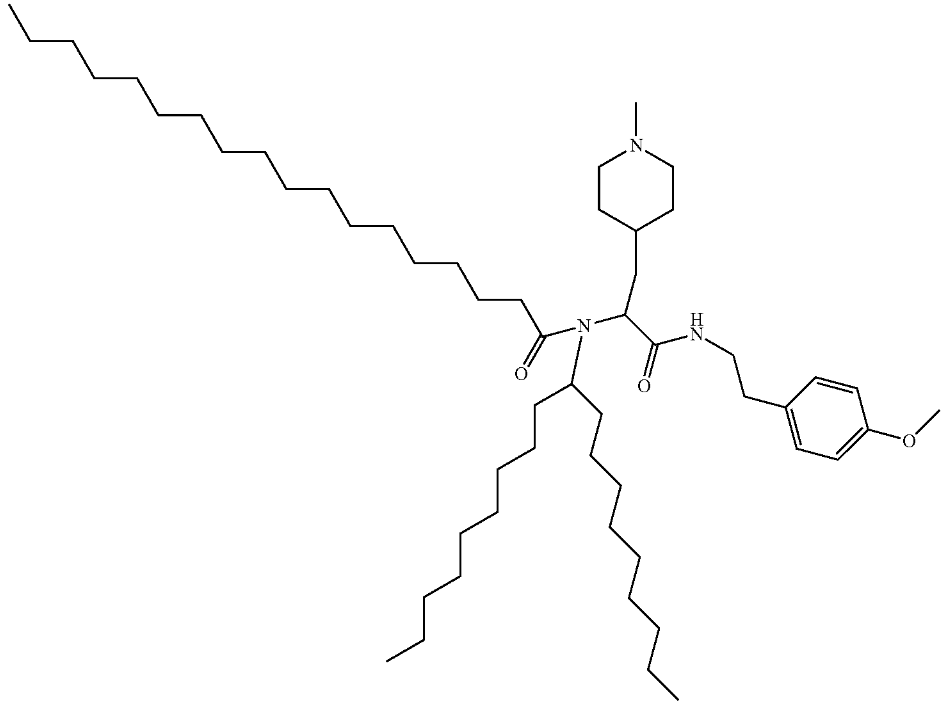
P341E1
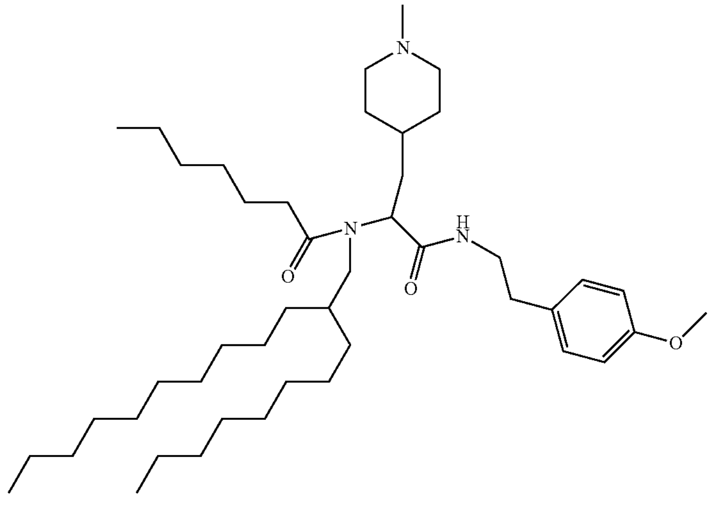

-continued
P341G11
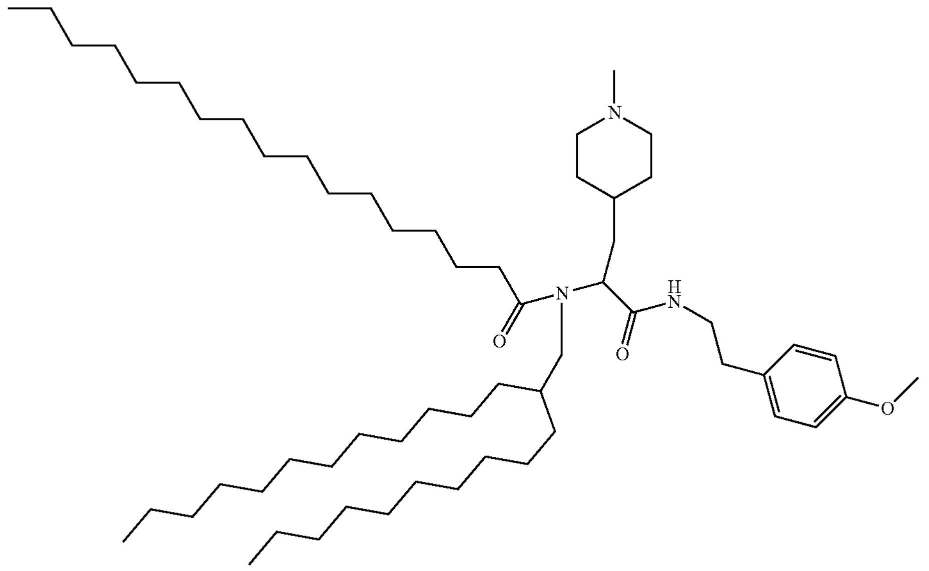
P342B1
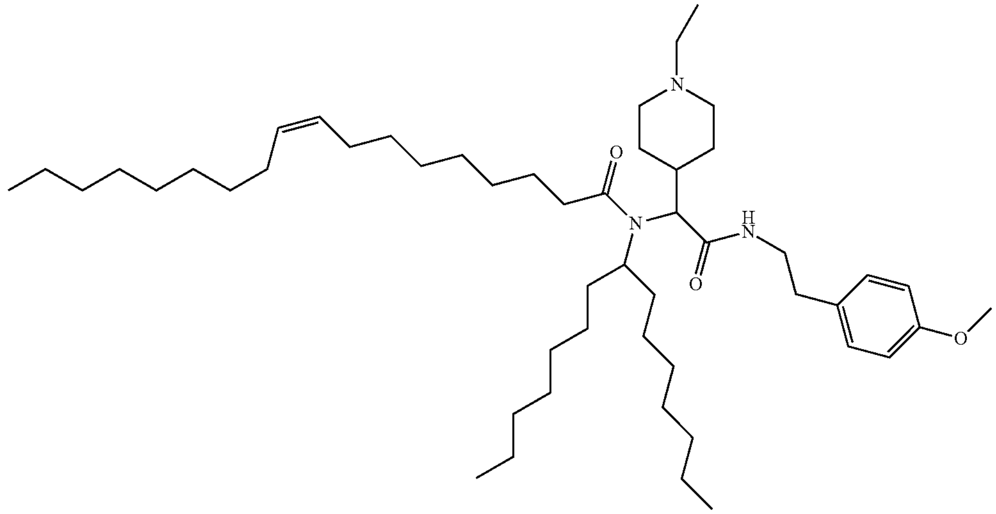

-continued
P342F1
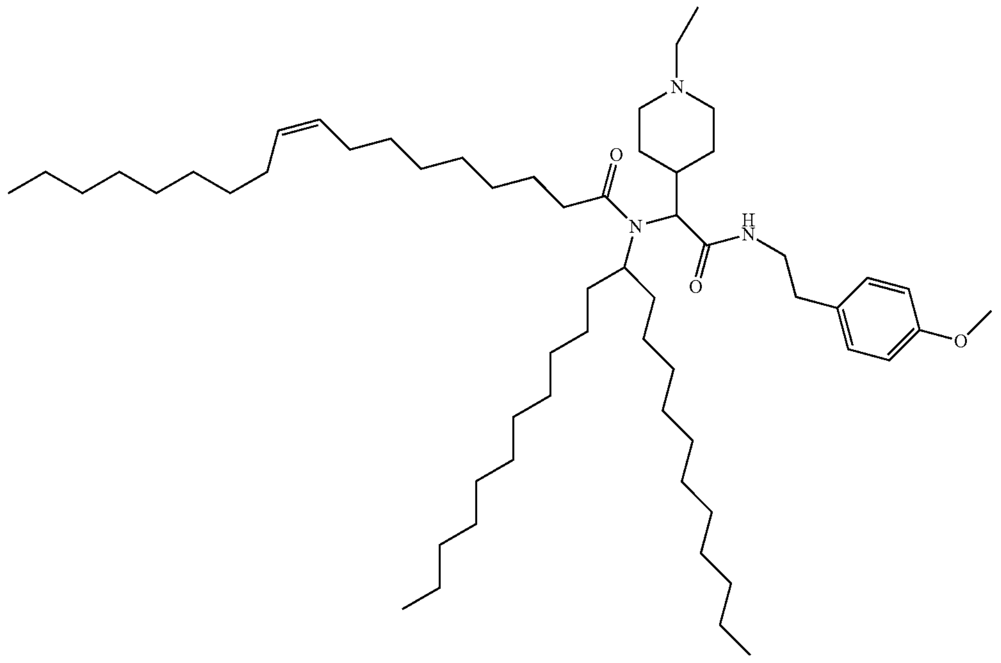
P342F8
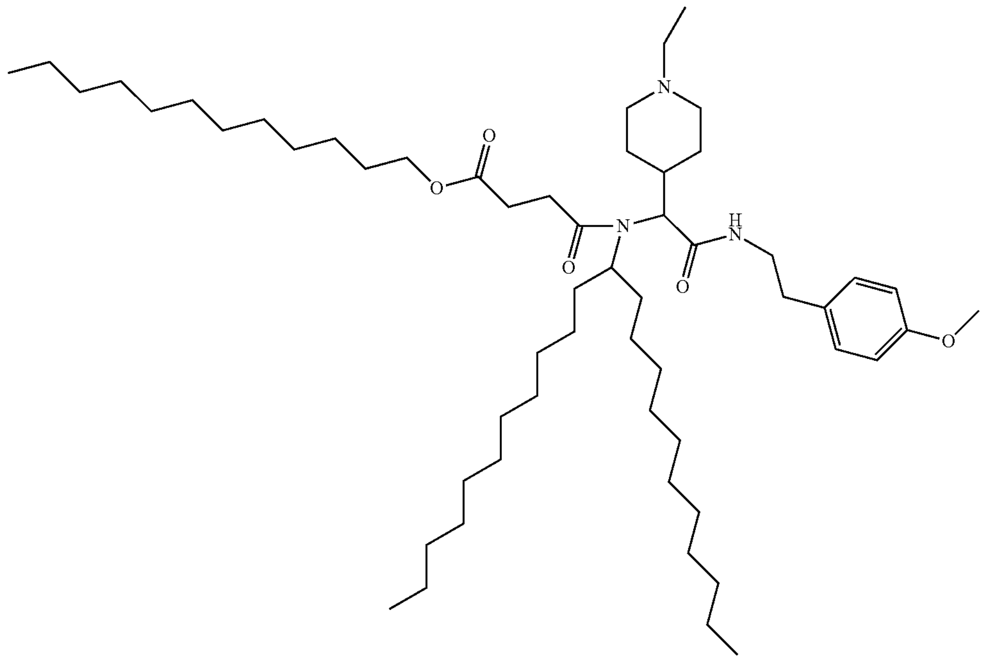

-continued
P342F12
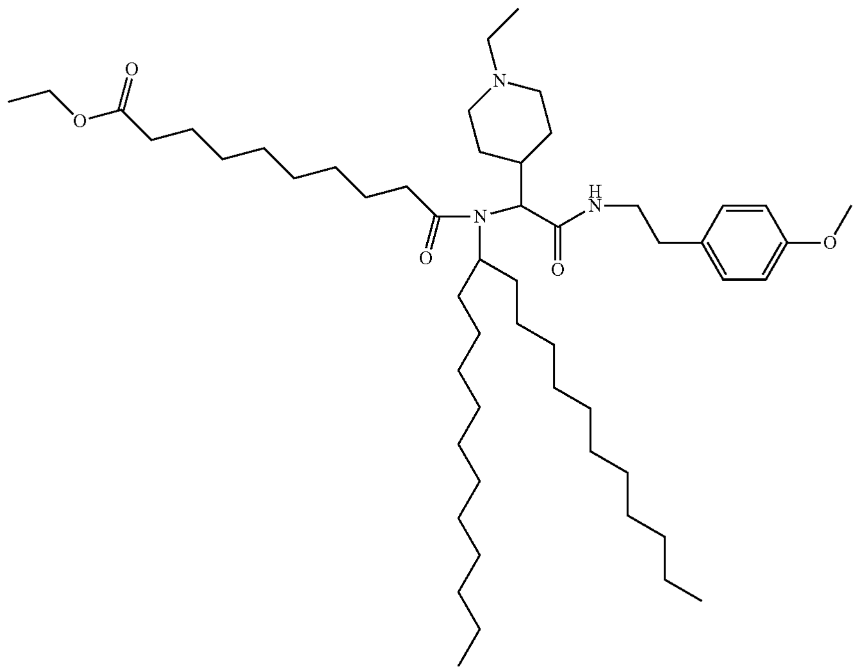
P343A1
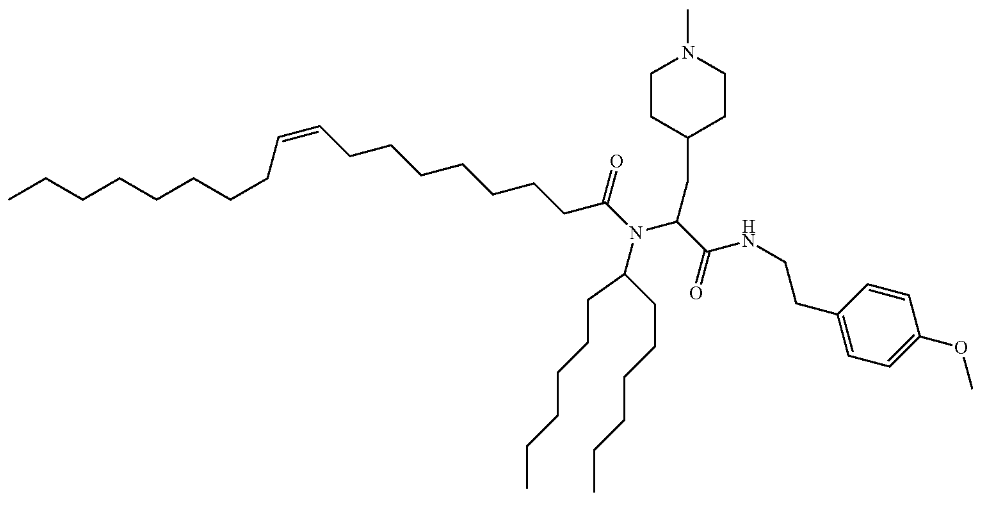

-continued
P343B3
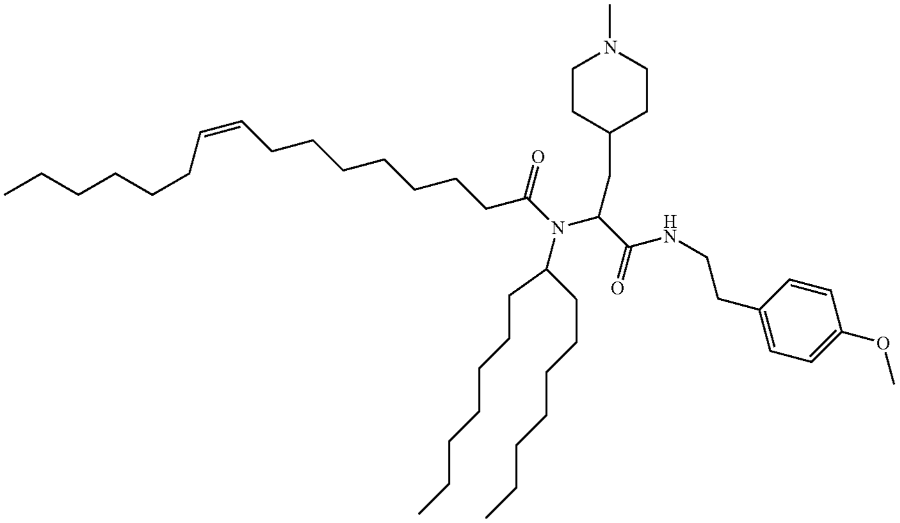
P343C1
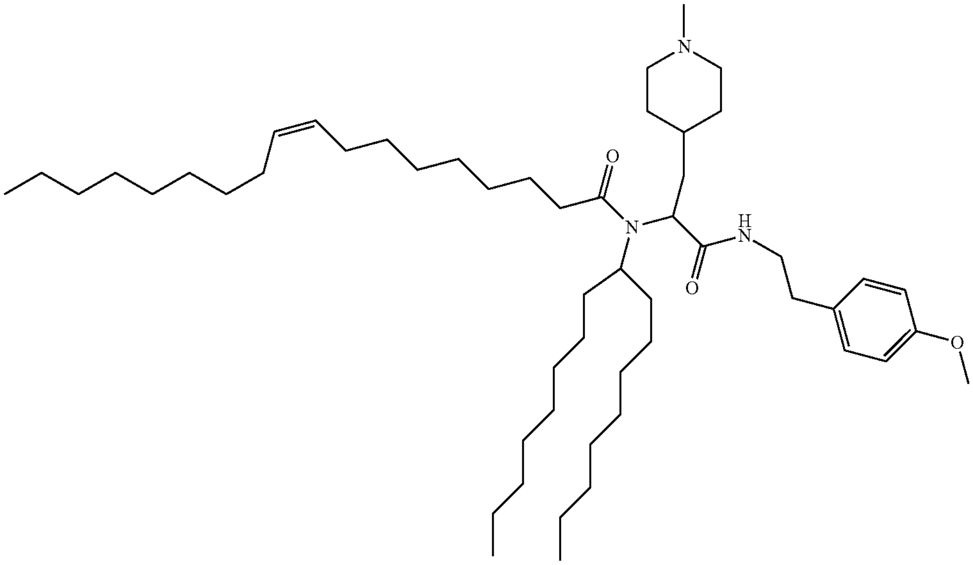
P343C3
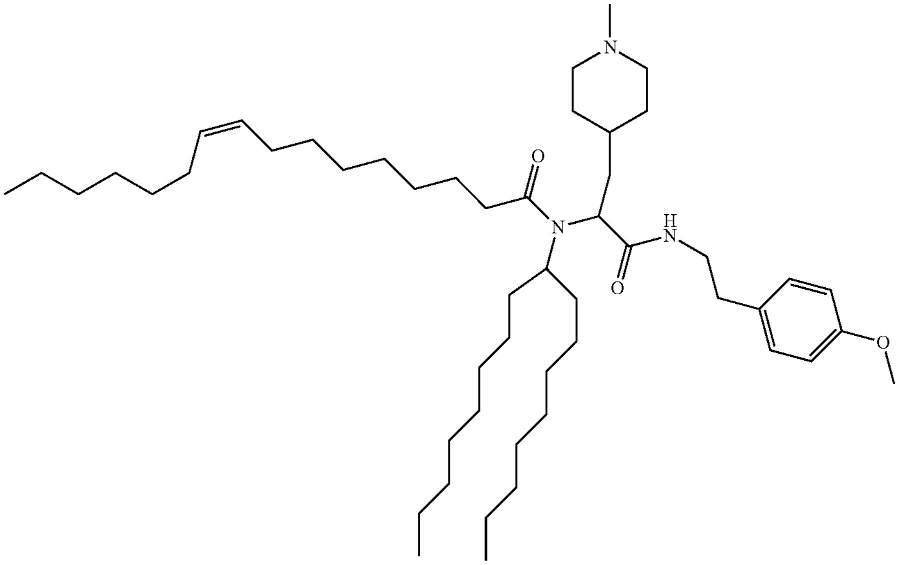

-continued
P343C6
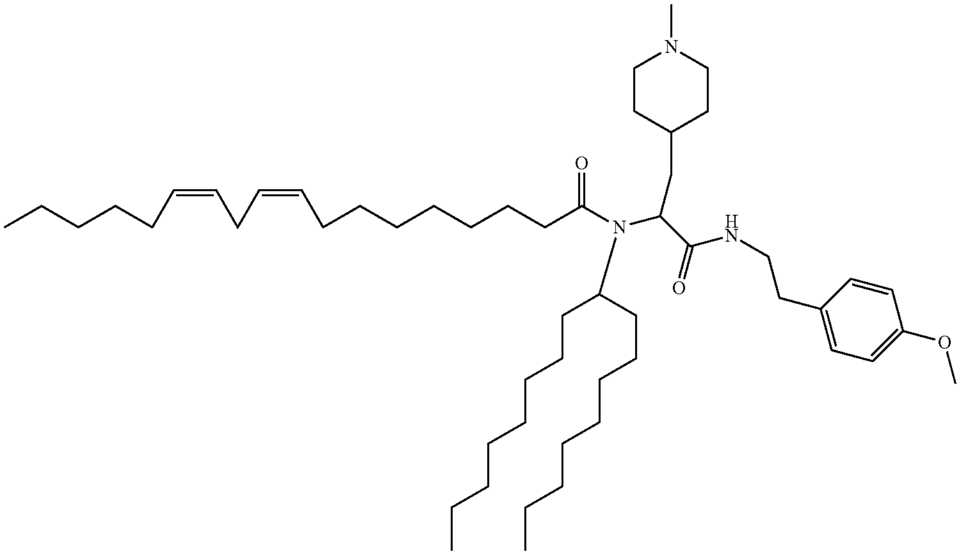
P343C8
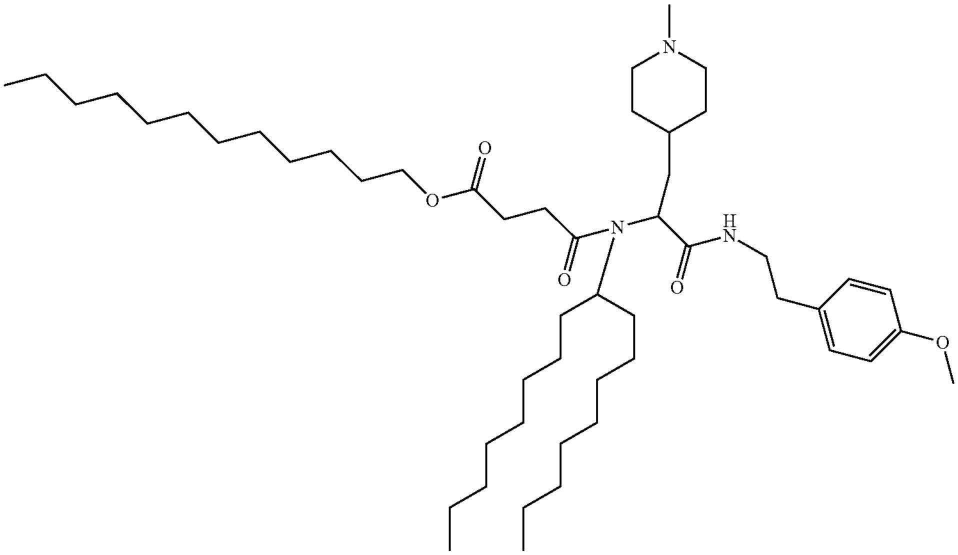

-continued
P343D1
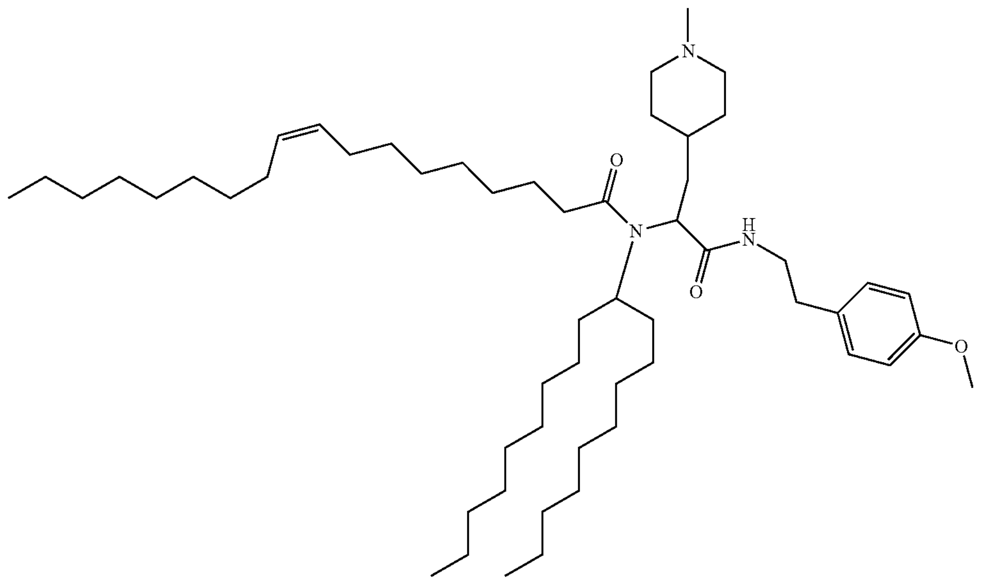
P343D3
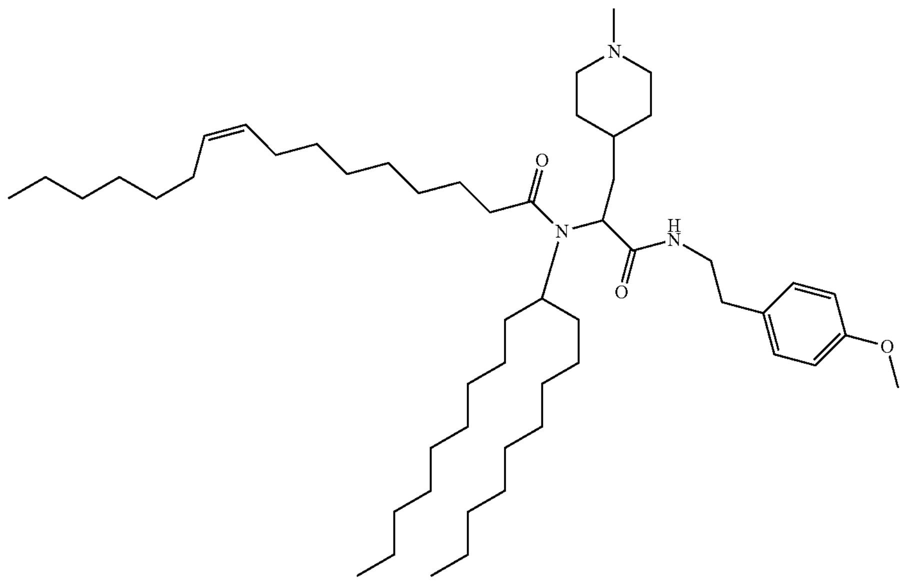

-continued
P343D7
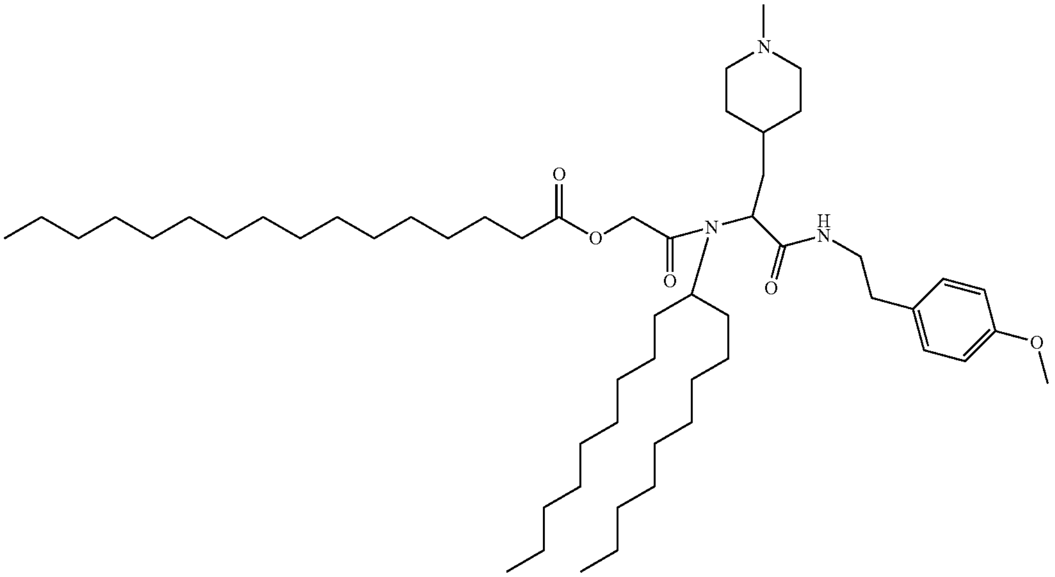
P343E1
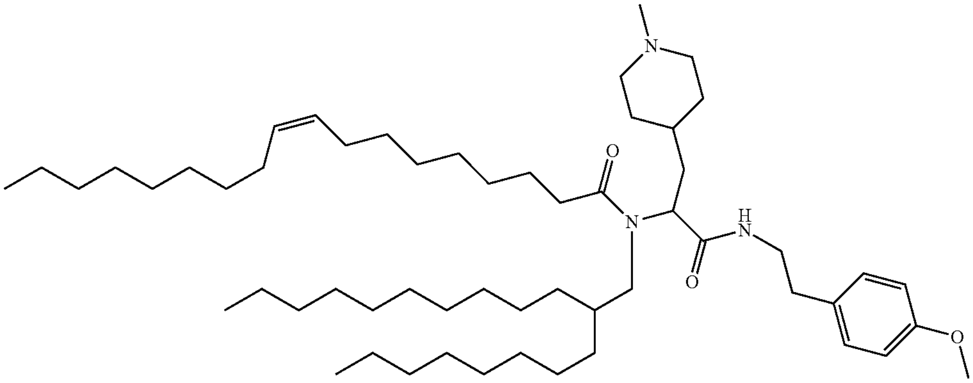
P344A3
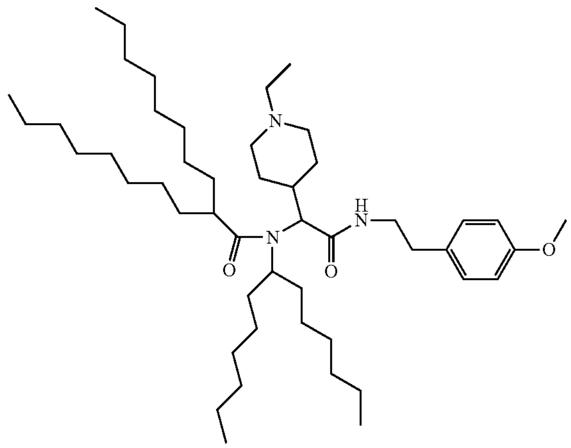
P344B5
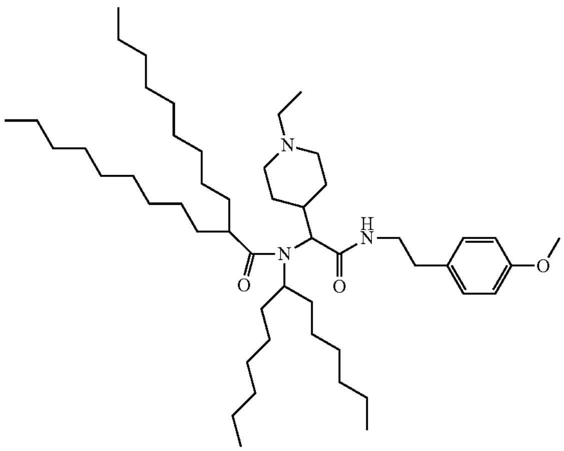

-continued
P344A4
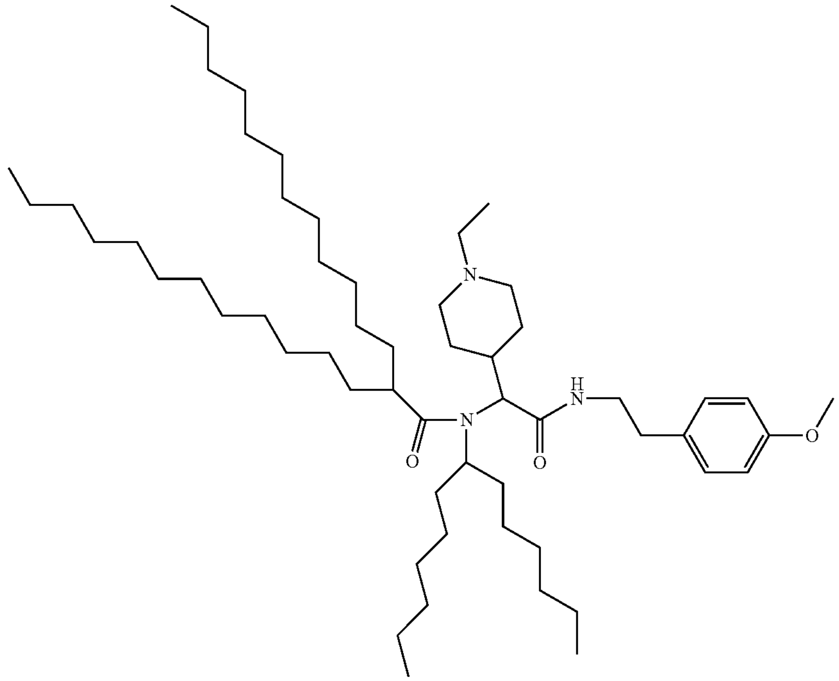
P344D3
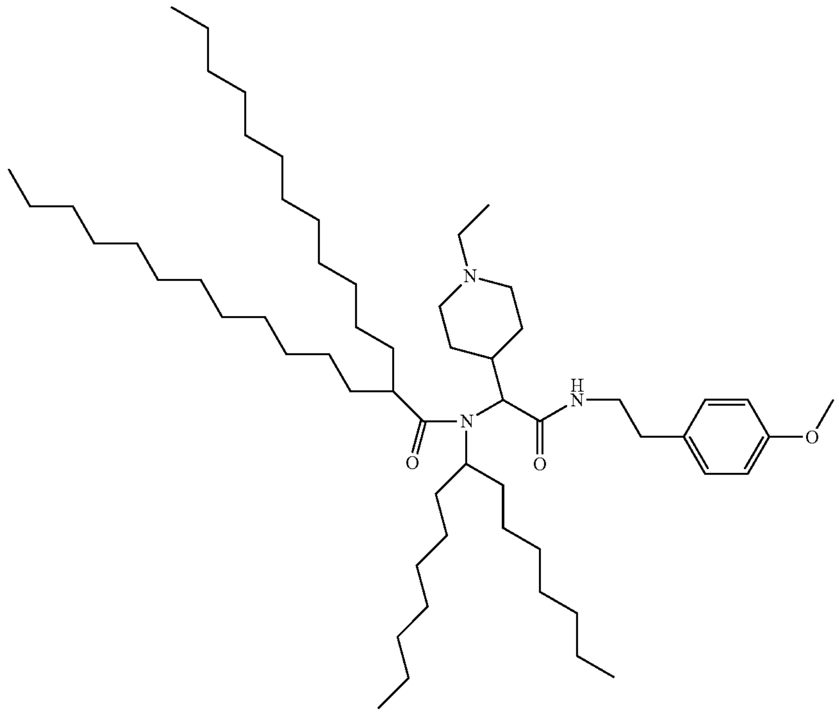

-continued
P344E2
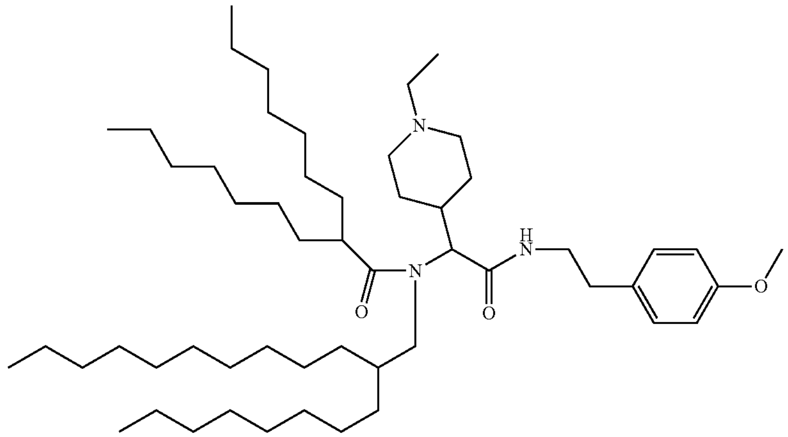
P345B2
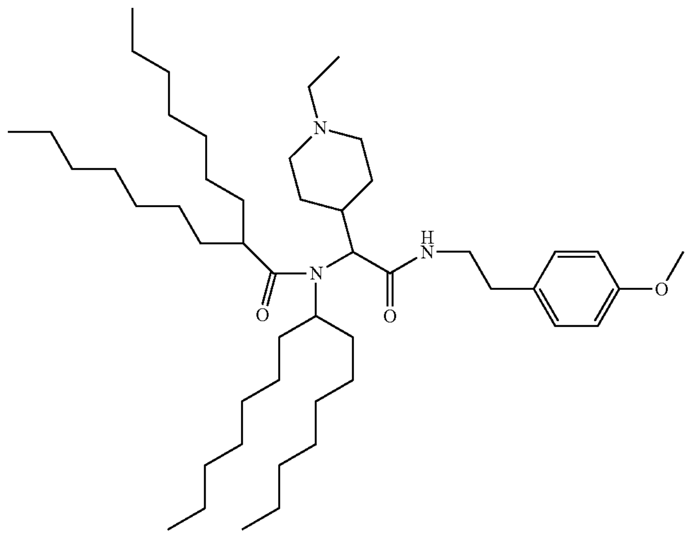
P345E1
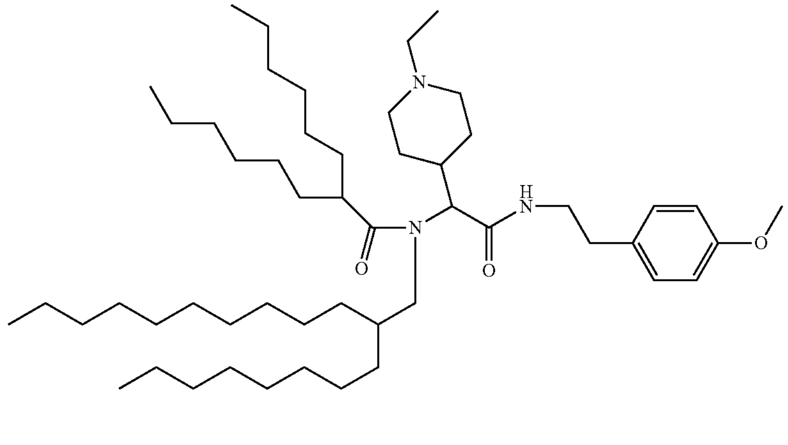

-continued
P345E7
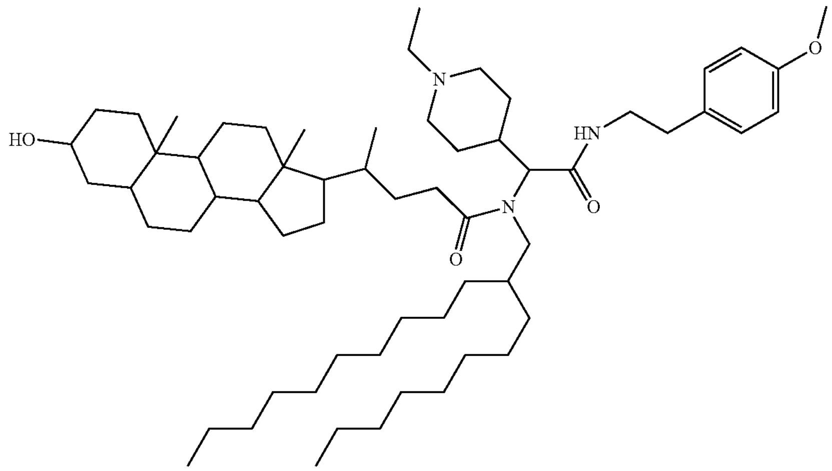
P345G7
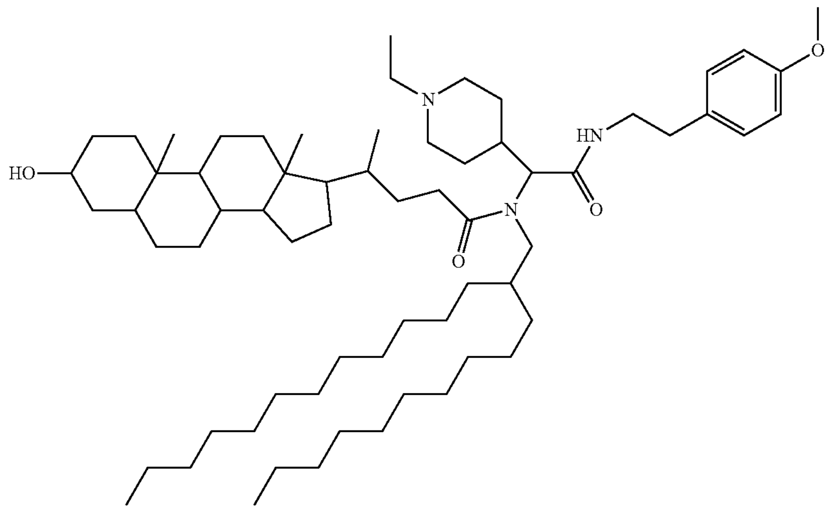
P359B2
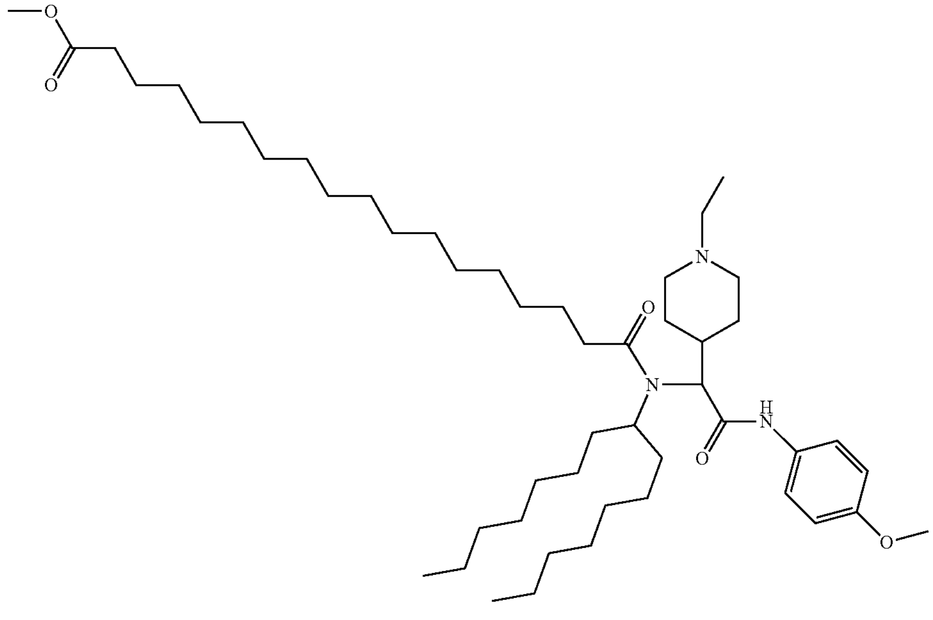

-continued
P359B4
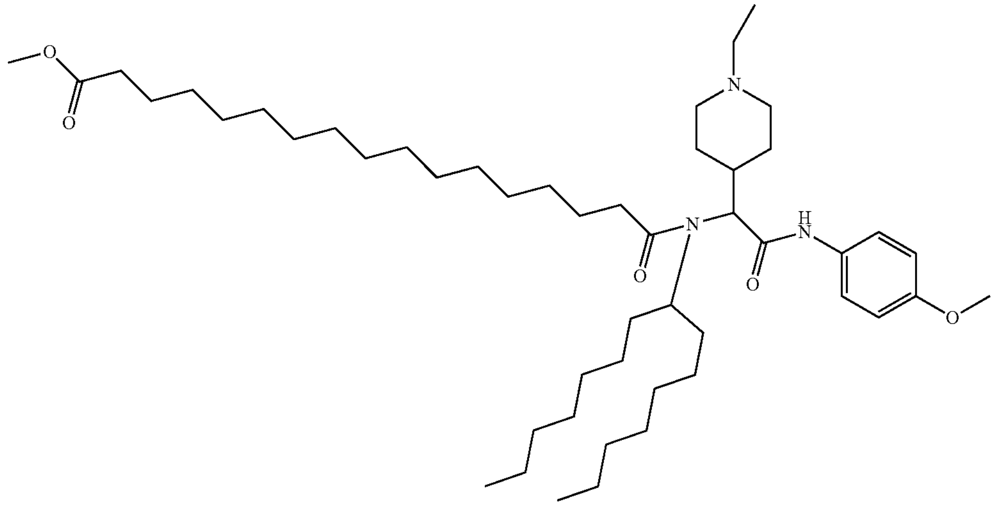
P359E4
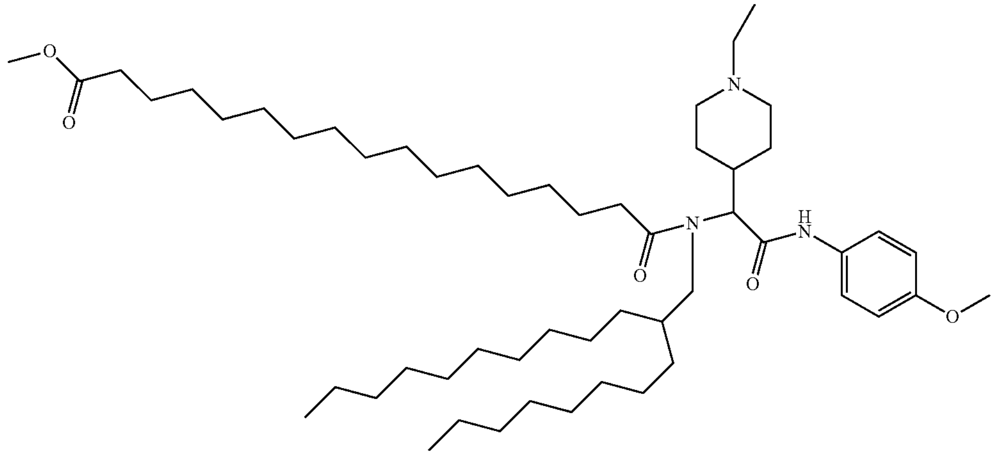
P360A4
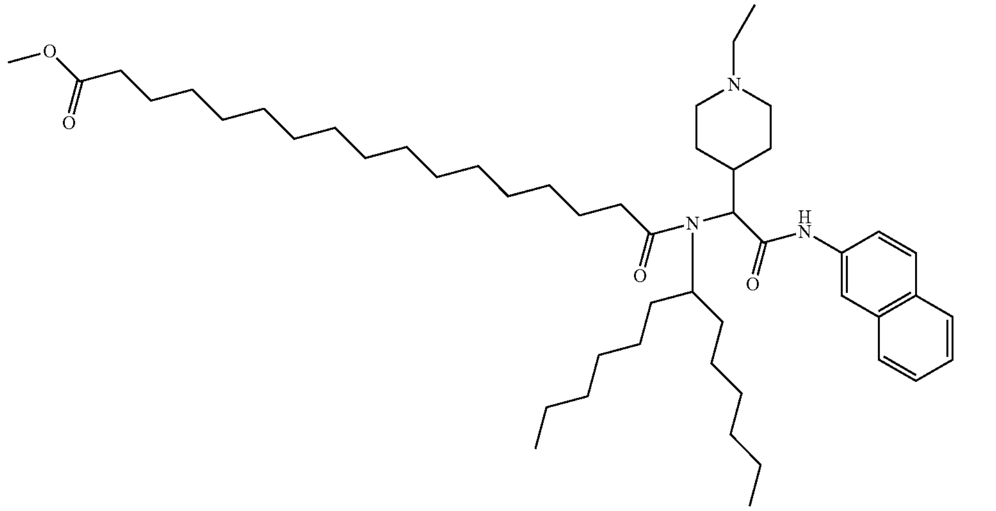

-continued
P360B2
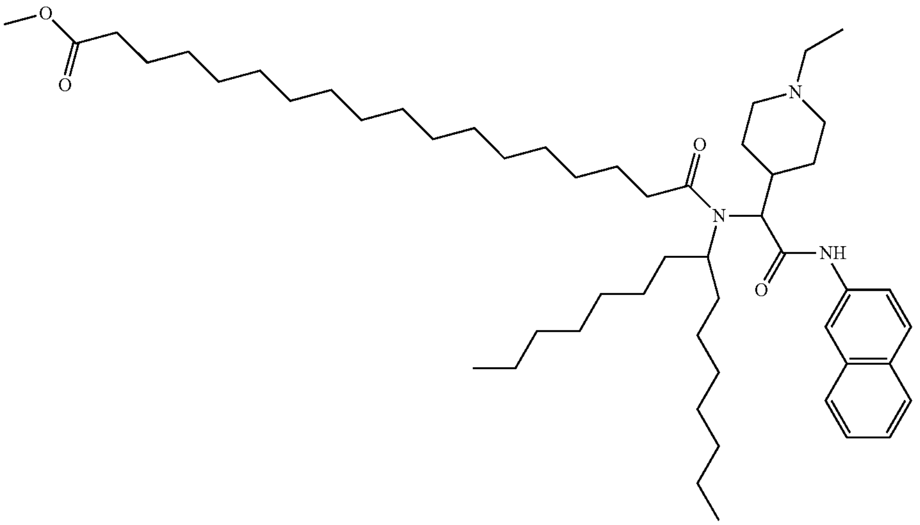
P360B9
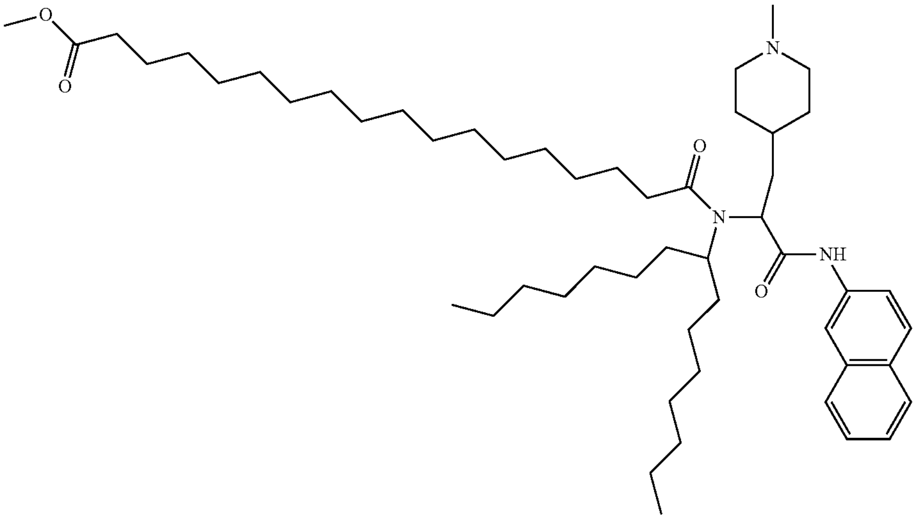
P360E3
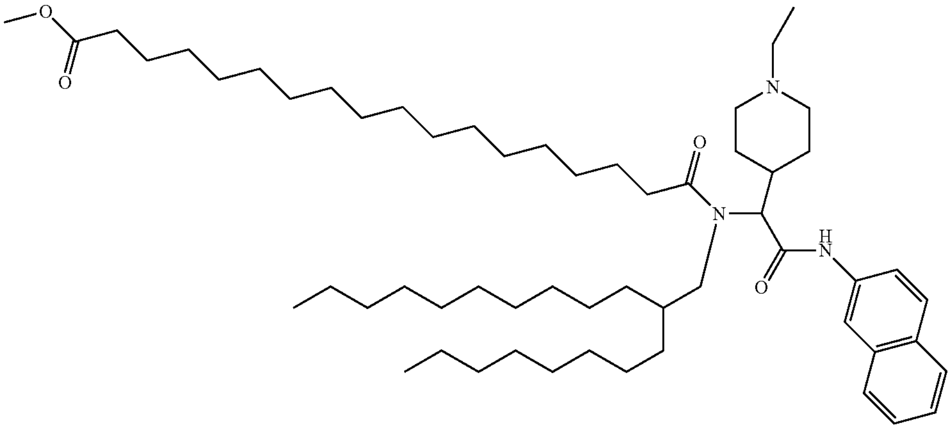

-continued
P362B2
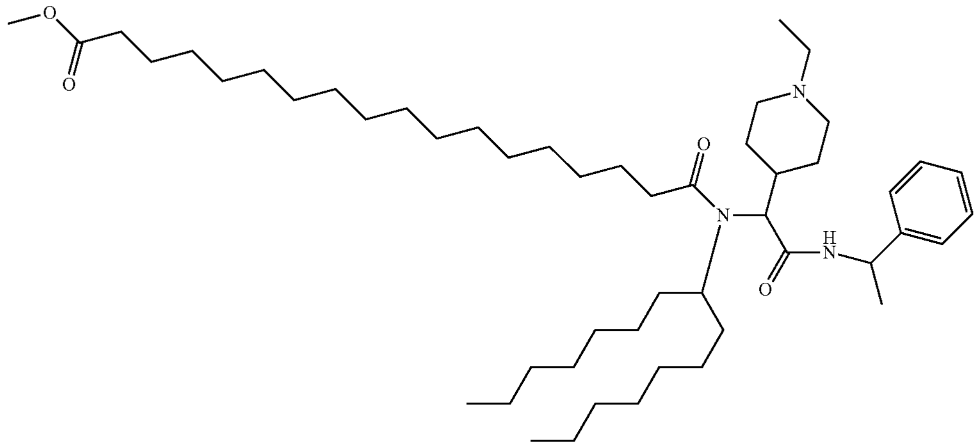
P362B3
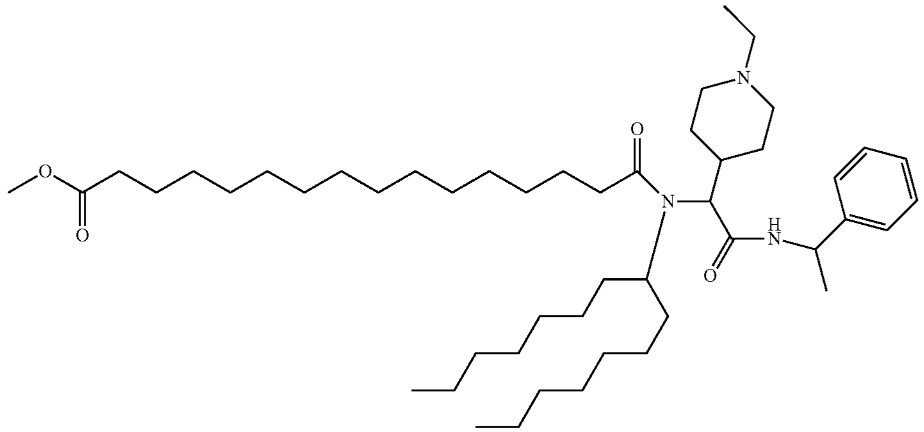
P362C3
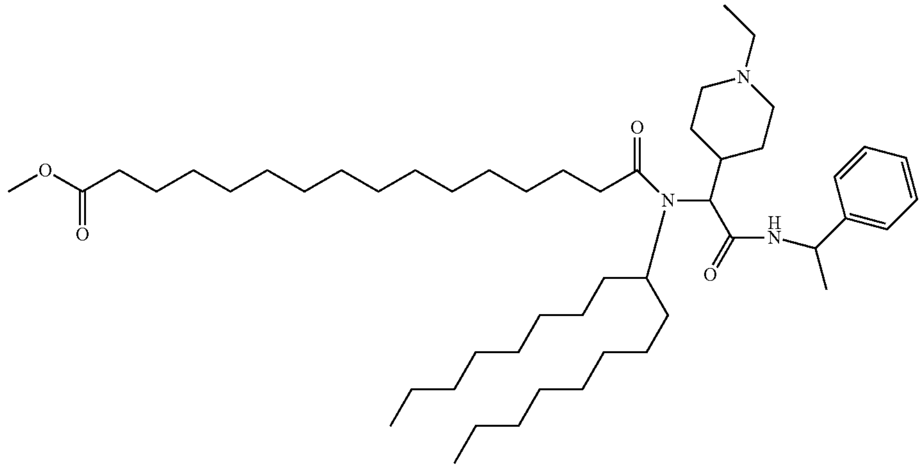

-continued
P362C4
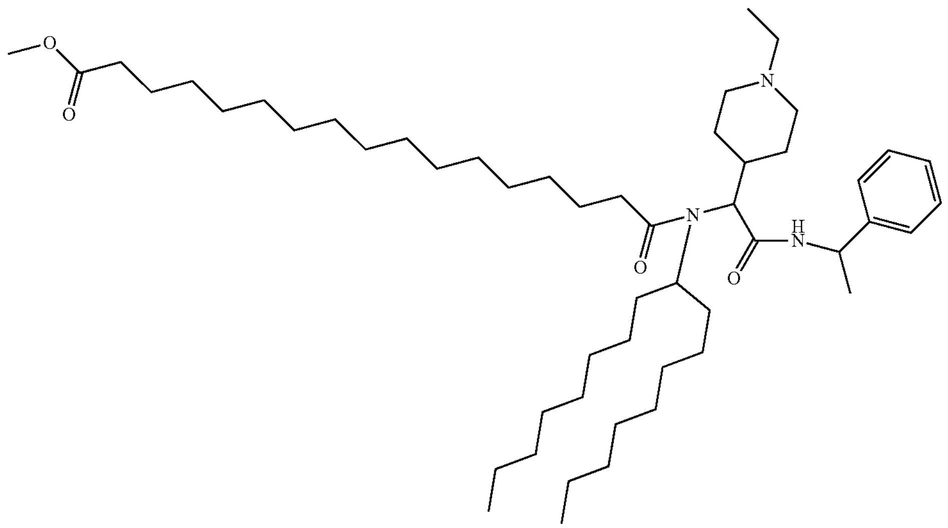
P362E3
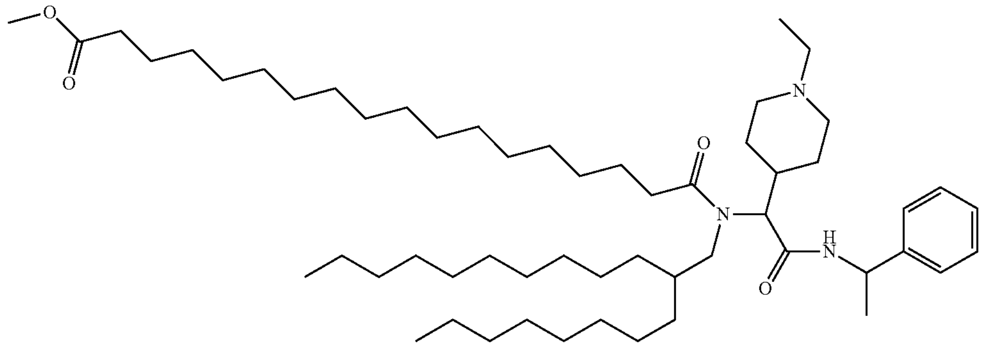
P363A2
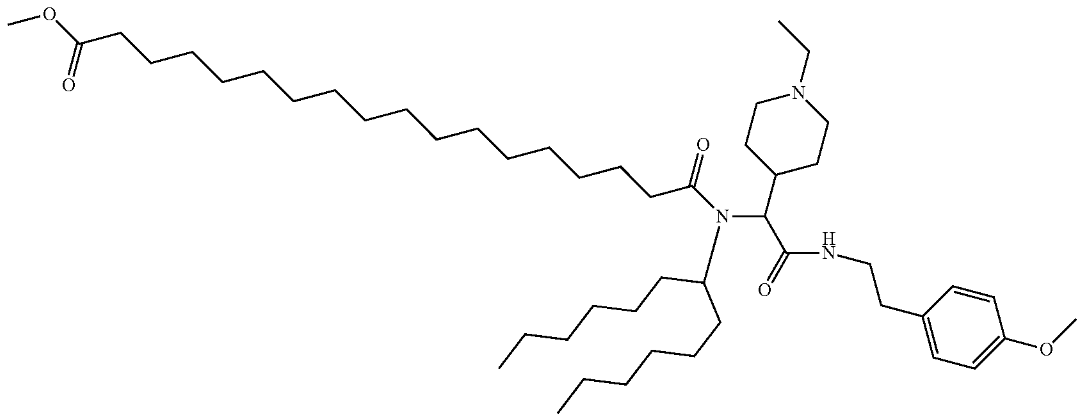

-continued
P363B2
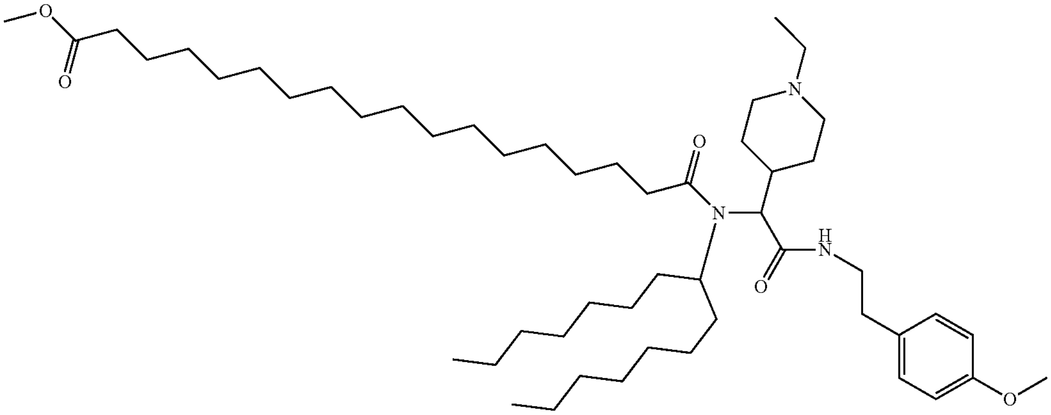
P363C3
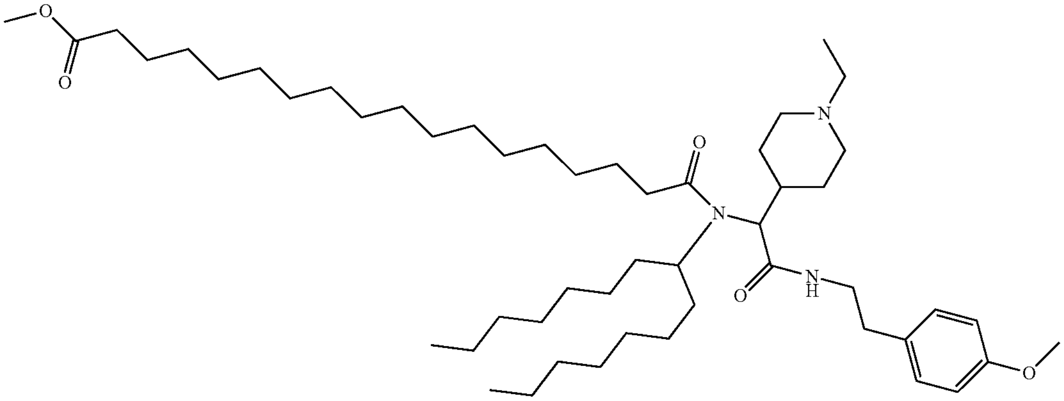
P363C10
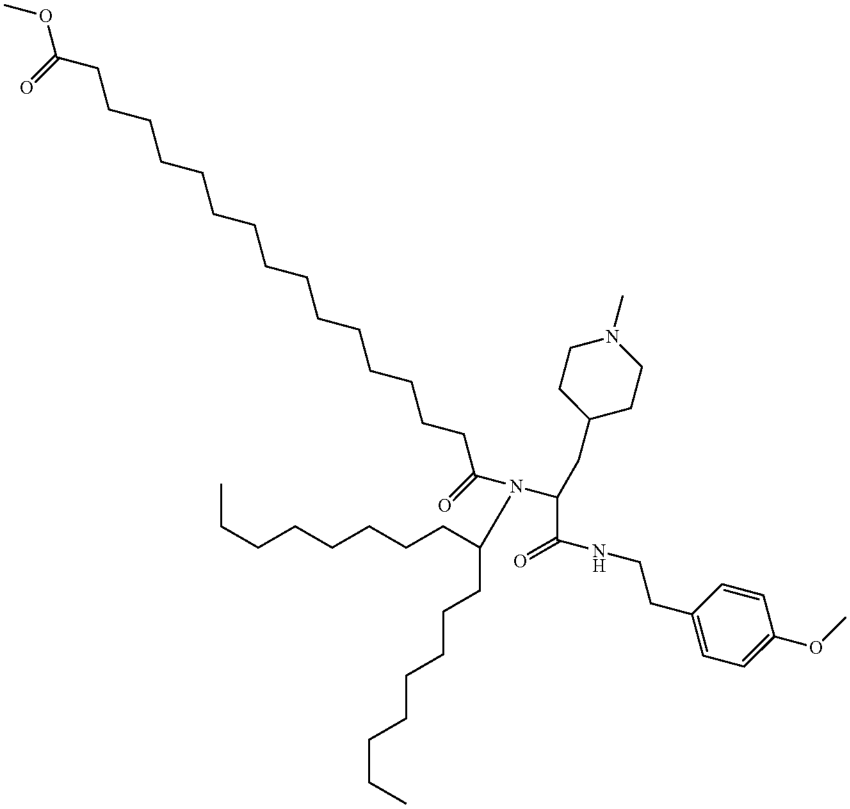

-continued
P363D9
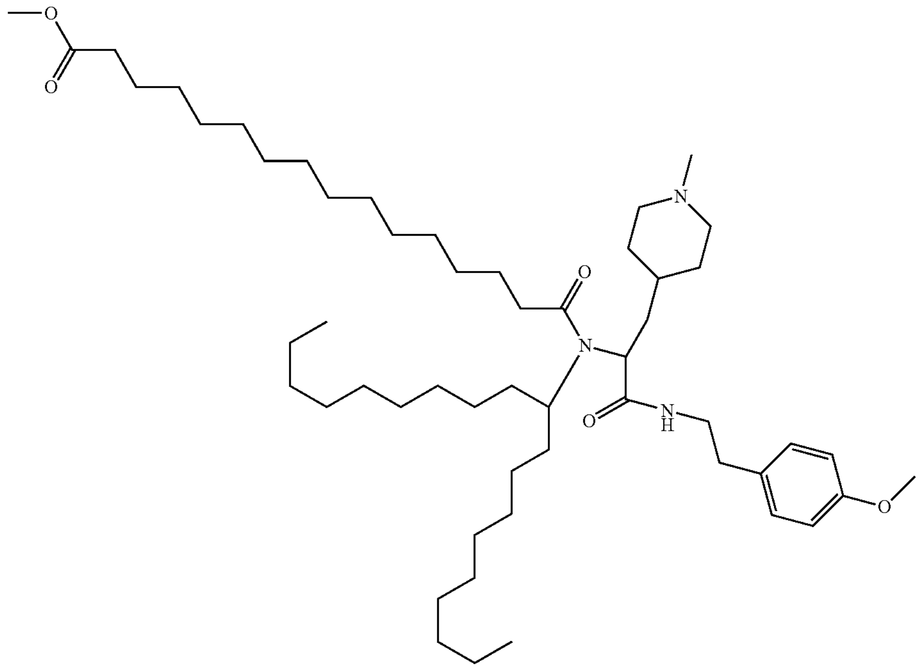
P363E2
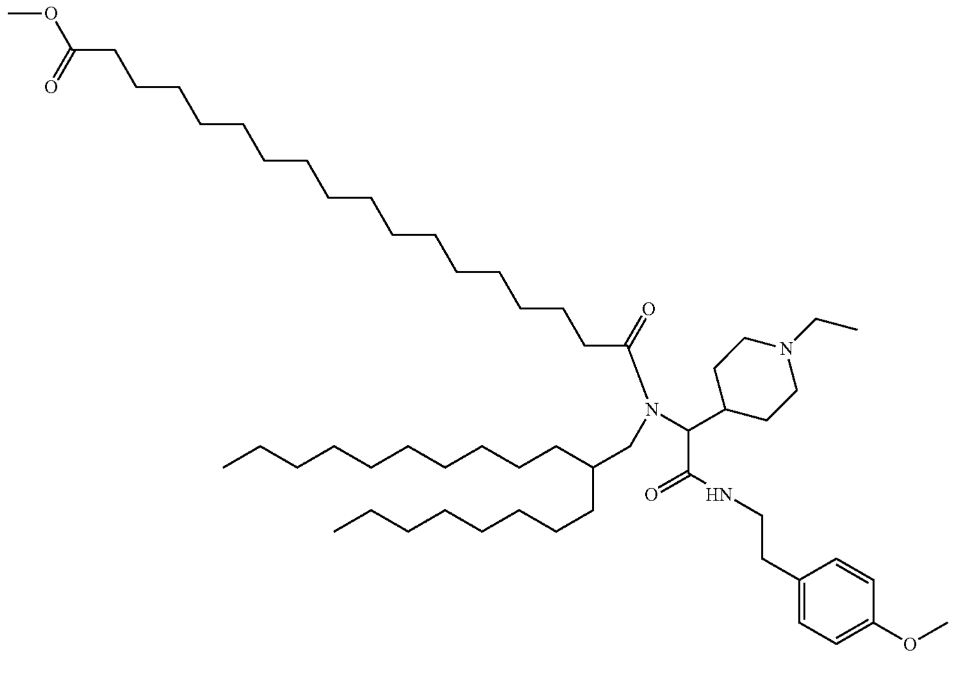

-continued
P363E3
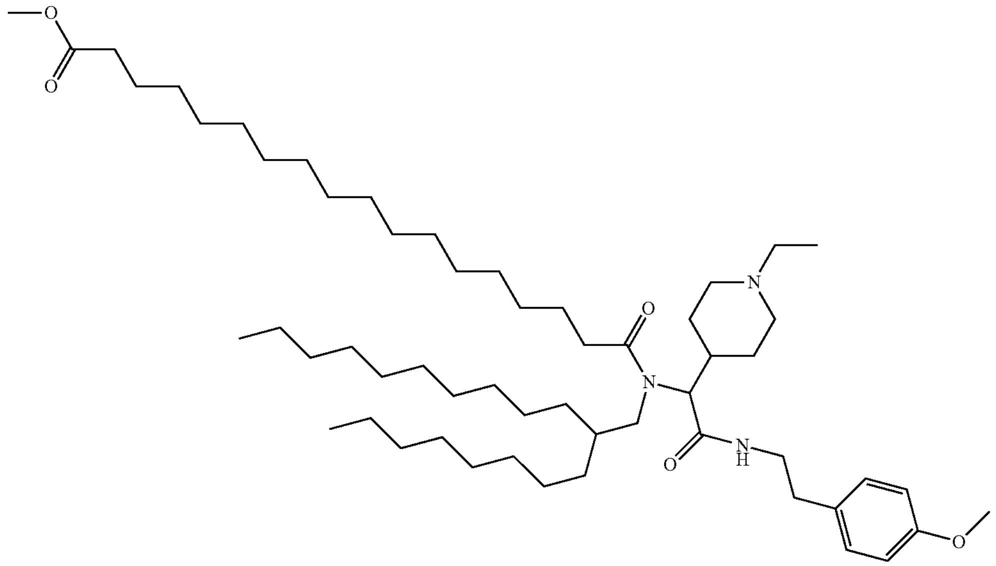
P363E4
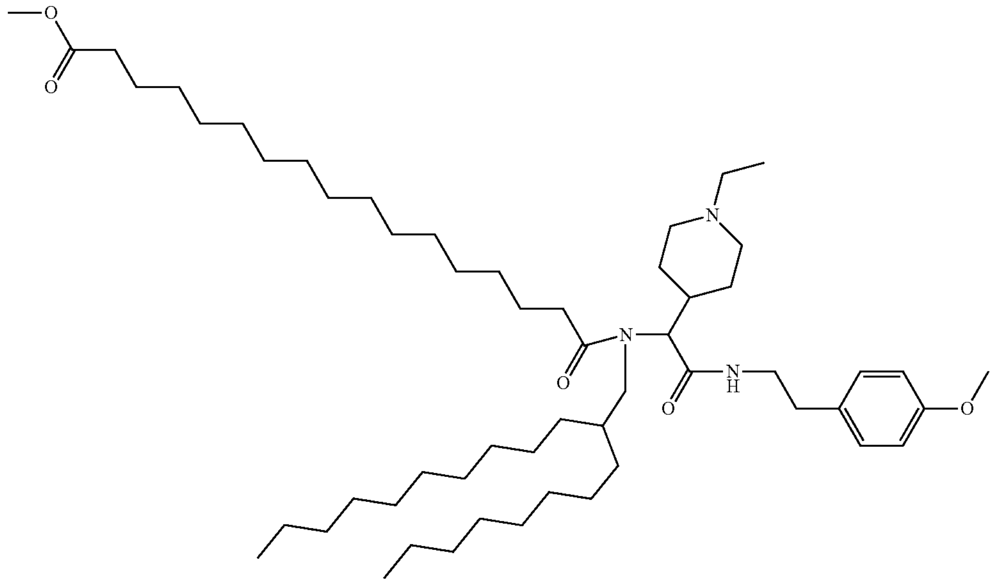
P363E12
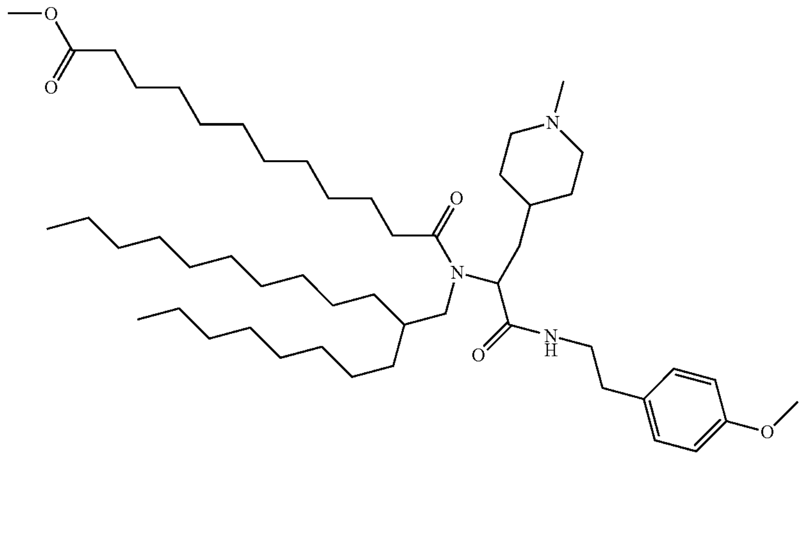

-continued
P363G10
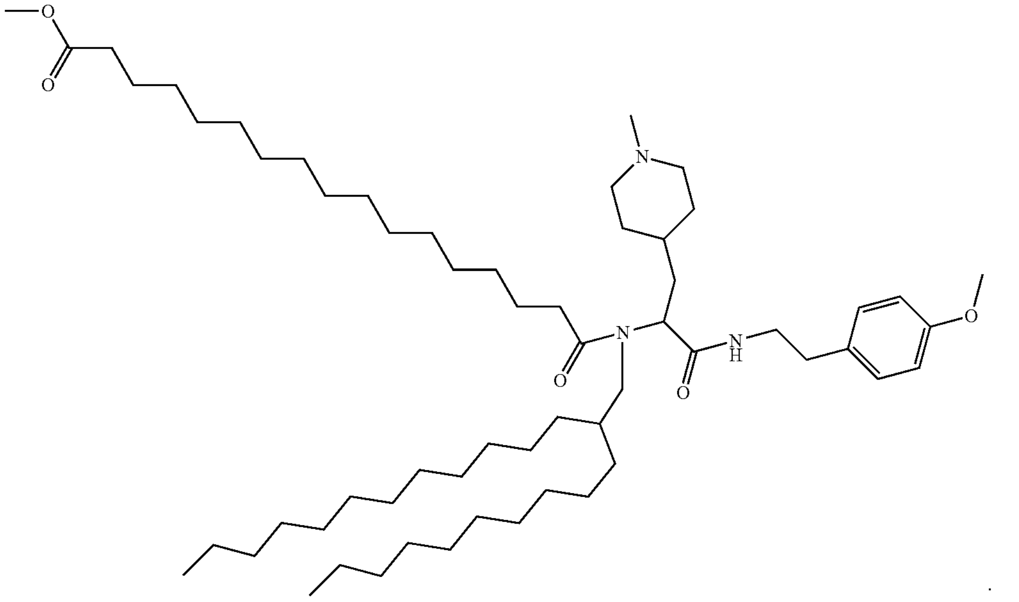
34. A method for synthesizing the compound of any one of items 23-32 comprising performing the following four component reaction:
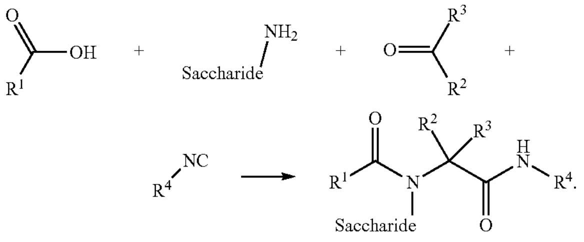
35. The method of item 34, wherein the
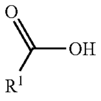
is
AAC1
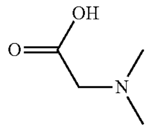
AAC2
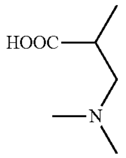
-continued
AAC3
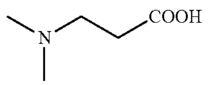
AAC4
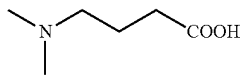
AAC5
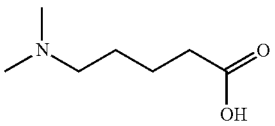
AAC6
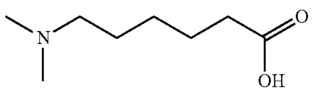
AAC7
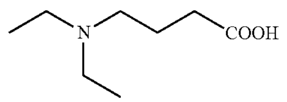
AAC8
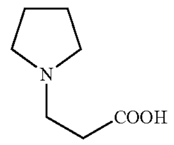
AAC9
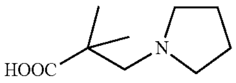
AAC10
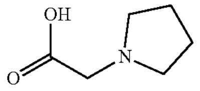

-continued
AAC11
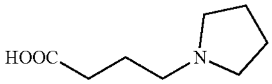
AAC12
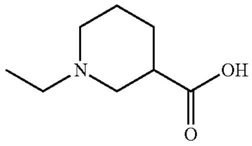
AAC13
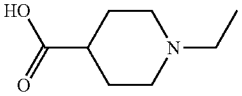
AAC14
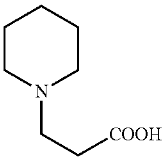
AAC15
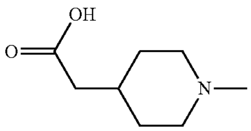
AAC16
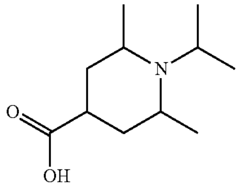
AAC17
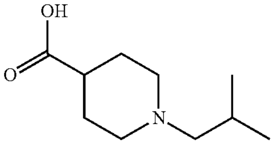
AAC18
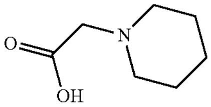
AAC19
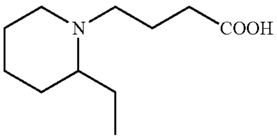
AAC20
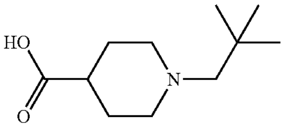
AAC21
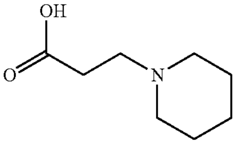
-continued
AAC22
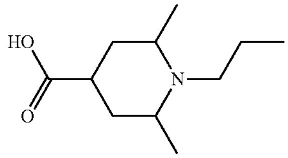
AAC23
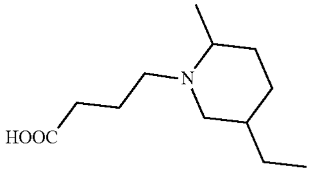
AAC24
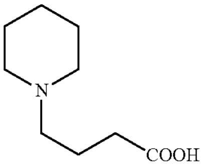
AAC25
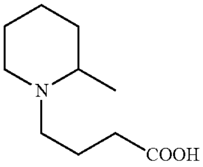
AAC26
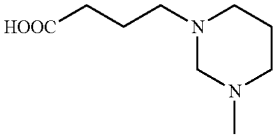
AAC27
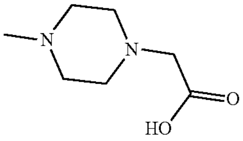
AAC28
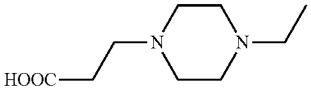
AAC29
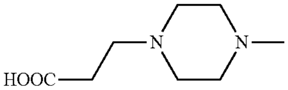
AAC30
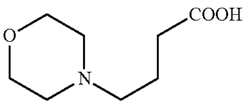
AAC31
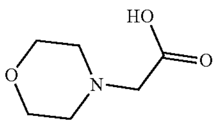
AAC32
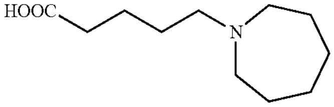

-continued
AAC33
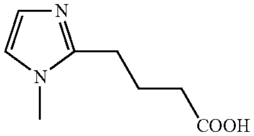
AAC34
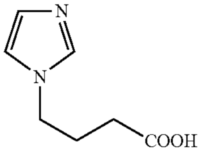
AAC35
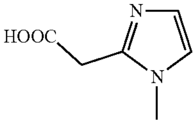
AC6
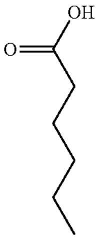
AC7
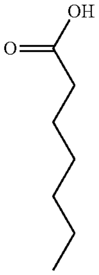
AC8
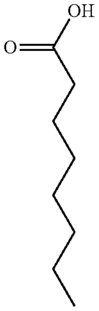
AC9
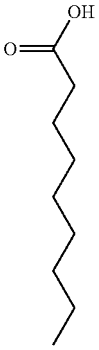
-continued
AC10
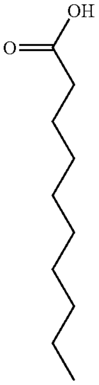
AC11
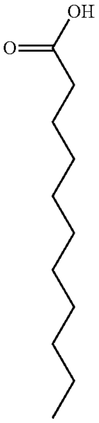
AC12
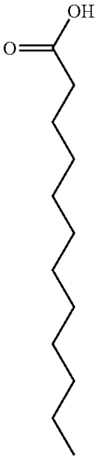

-continued
AC13
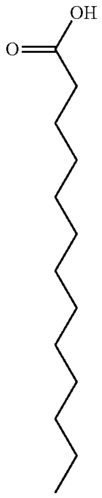
AC14
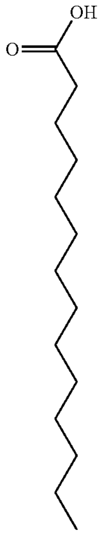
AC15
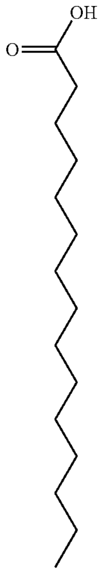
-continued
AC16
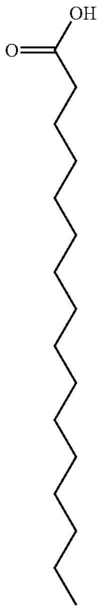
AC17
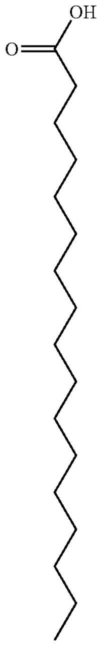
AC18
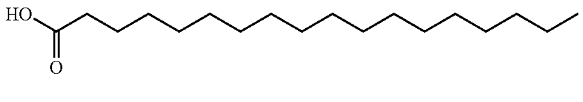
ACes16
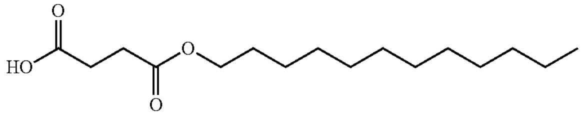

ACd11
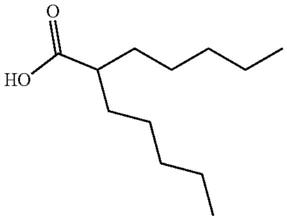
ACd13
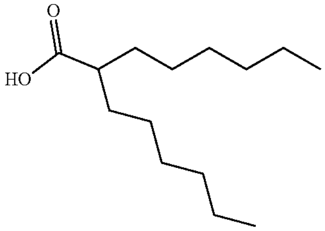
ACd15
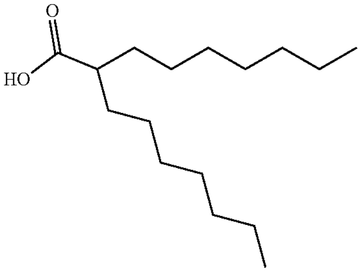
ACd17
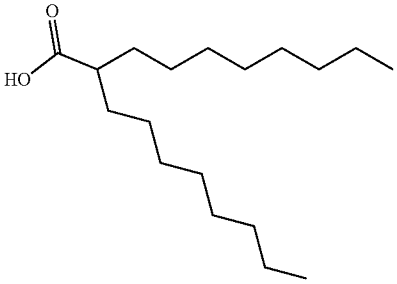
ACd19
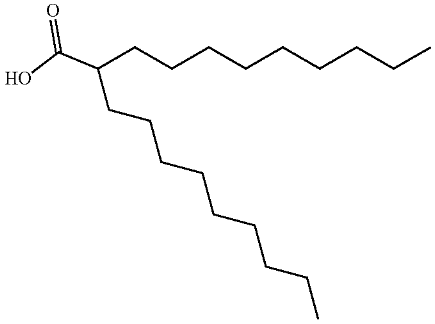
ACd21
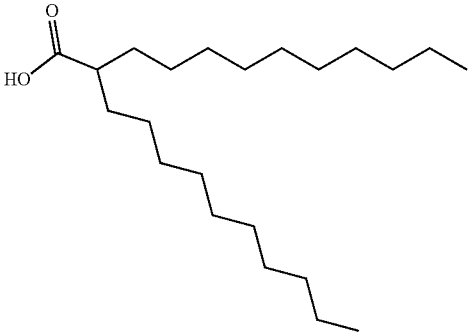
ACd25
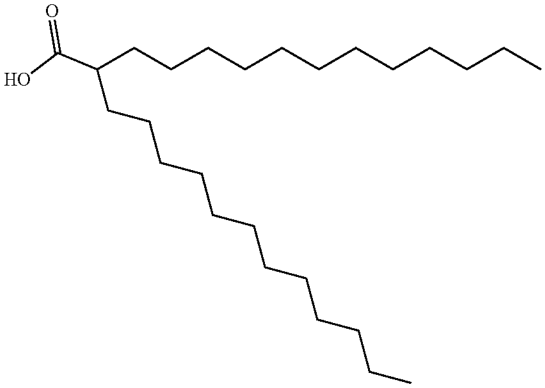
ACe18
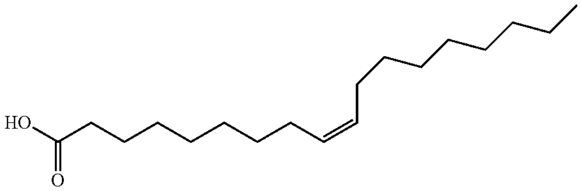
ACe17
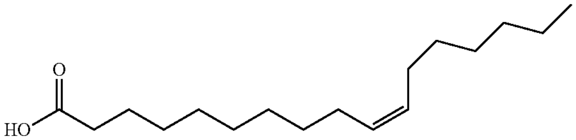
ACe16
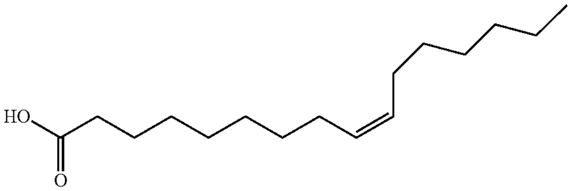
ACe15
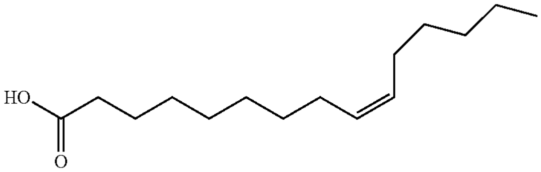

-continued
ACe14
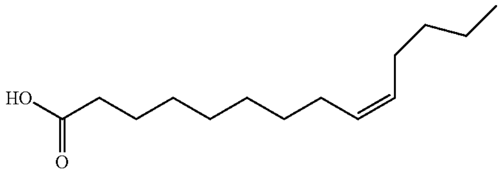
ACe13
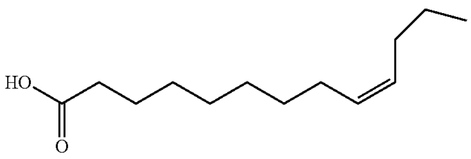
ACe12
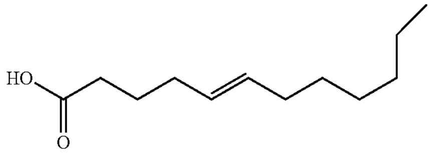
ACes14
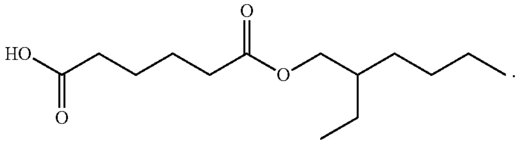
36. The method of any one of items 34-35, wherein the
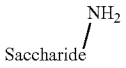
is
G-Am-1
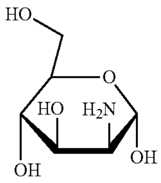
G-Am-2
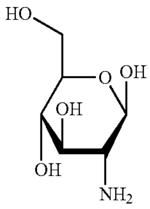
G-Am-3
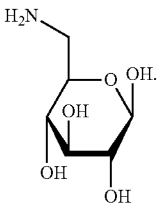
37. The method of any one of items 34-36, wherein the
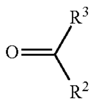
is
ALA1
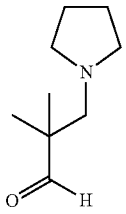
ALA2
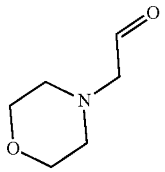
ALA3
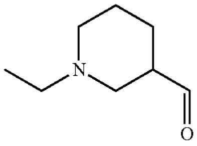
ALA4
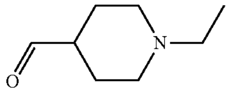
ALA5
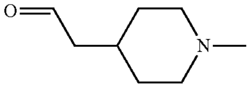
ALA6
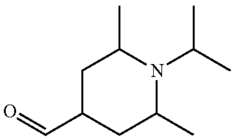
ALA7
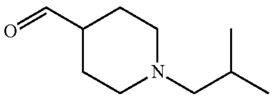
ALA8
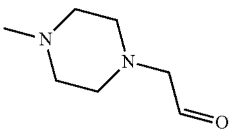
ALA9
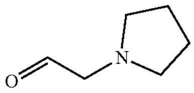
ALA10
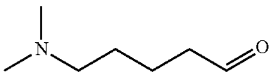

-continued
ALA11
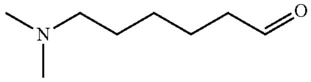
ALA12
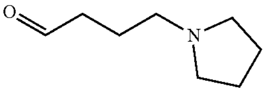
ALA13
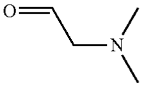
ALA14
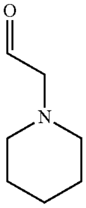
ALA15
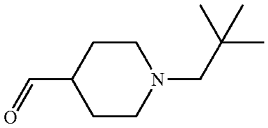
ALA16
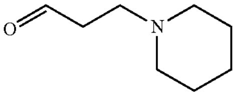
ALA17
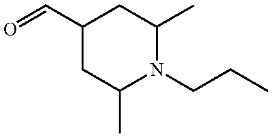
AL8
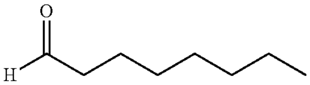
AL9
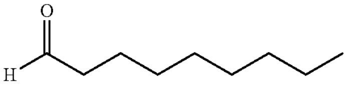
AL10
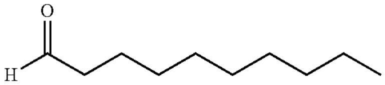
AL11
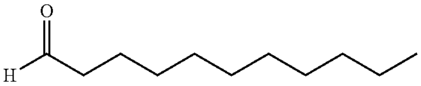
AL12
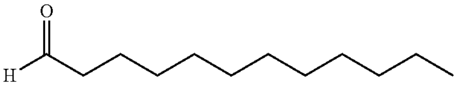
AL13
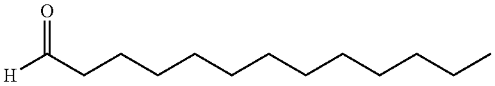
-continued
AL15
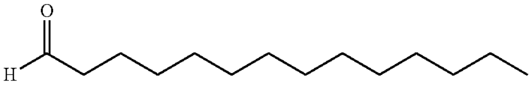
AL16
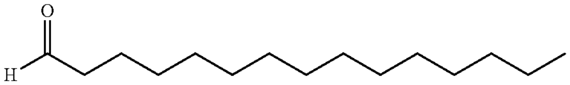
AL16e
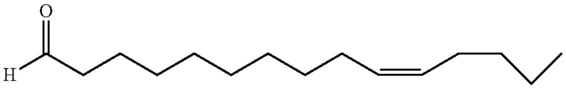
AL10P
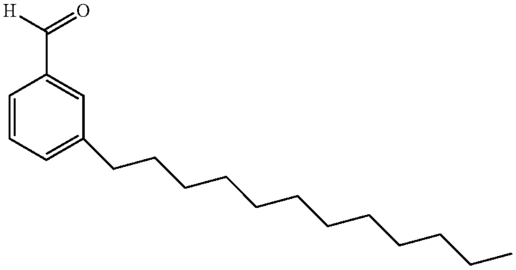
K9
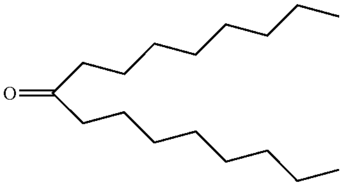
K10
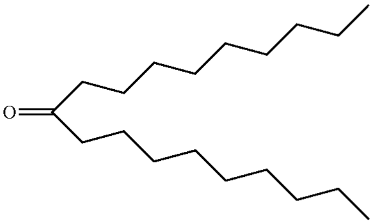
K11
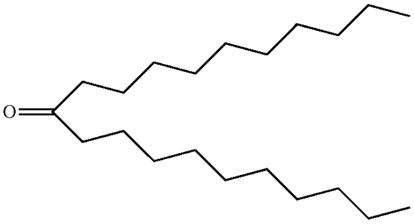
K12
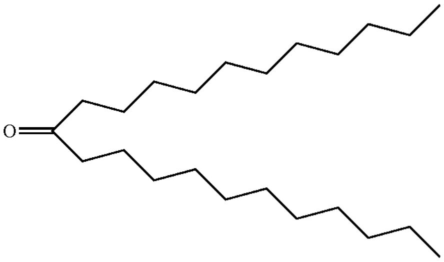

-continued
K14
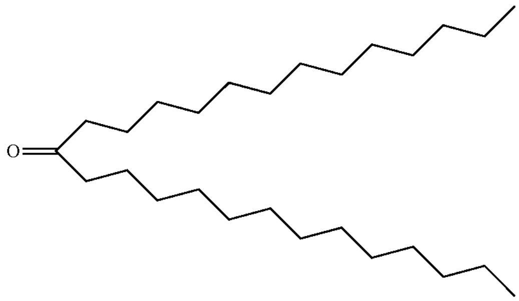
K16
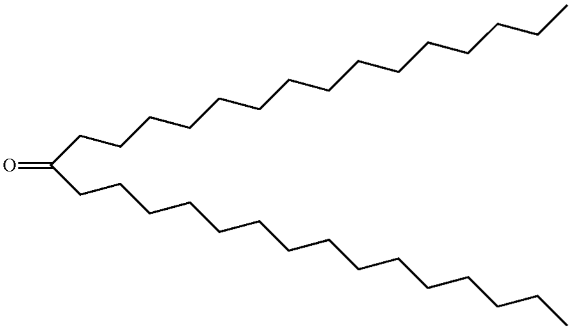
K18e
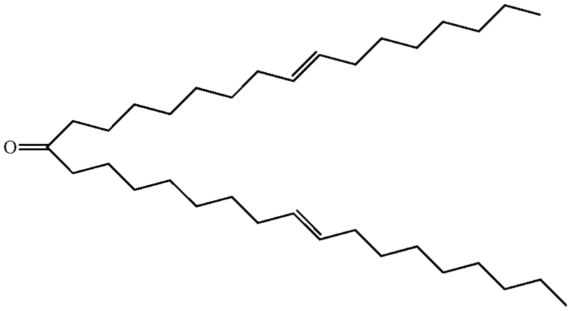
AL-PEG$_8$
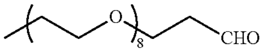
AL-PEG$_{12}$
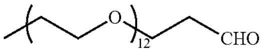
AL-PEG$_{15}$
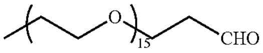
AL-PEG$_{24}$
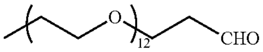
AL-PEG$_{48}$
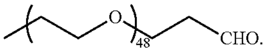
38. The method of any one of items 34-37, wherein the
is
Iso1
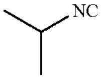
Iso2
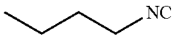
Iso3
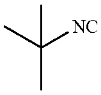
Iso4
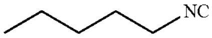
Iso5
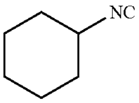
Iso6
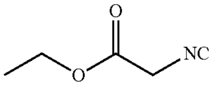
Iso7
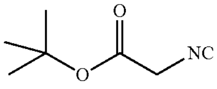
Iso8
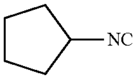
Iso9
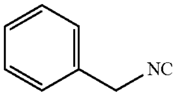
Iso10
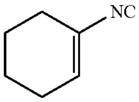
Iso11
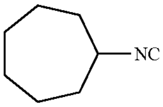
Iso12
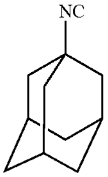
Iso13
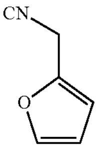
Iso14
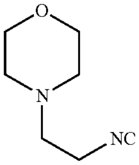

-continued

Iso15

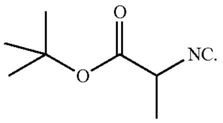

39. A method for synthesizing a modular lipid comprising a cationic ionizable group and/or a sterol derivative group, the method comprising performing four component reaction of an acid compound, an amine compound, an aldehyde or ketone compound, and an isocyanide compound as follows:

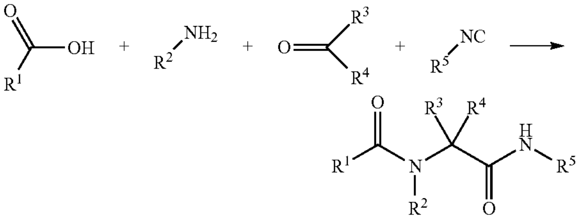

wherein each $R^1$, $R^4$ and $R^5$ is independently selected from $C_2$-$C_{24}$ alkyl, $C_2$-$C_{24}$ alkenyl, $C_2$-$C_{24}$ alkynyl, substituted $C_2$-$C_{24}$ alkyl, substituted alkenyl, substituted alkynyl, substituted acyl, substituted carbocyclyl, substituted heterocyclyl, substituted aryl, substituted heteroaryl, poly(ethylene glycol) (PEG),

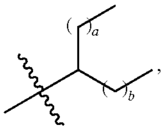,
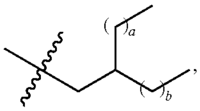,
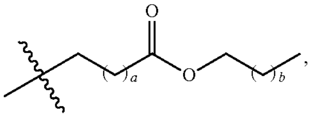,
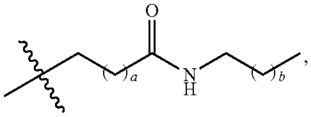,
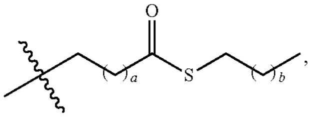,
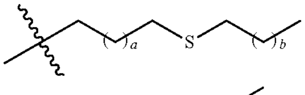,
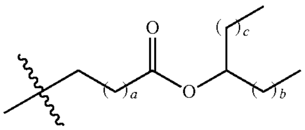,
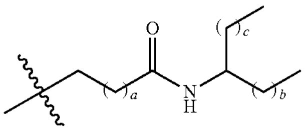, -continued

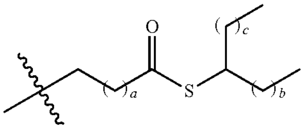,
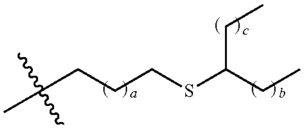,
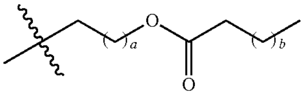,
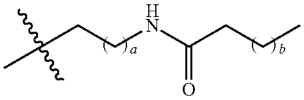,
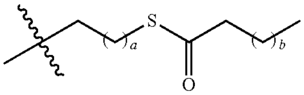,
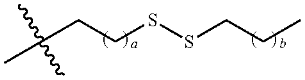,
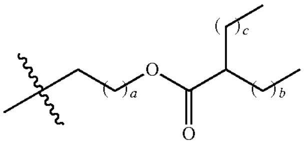,
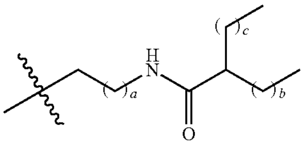,
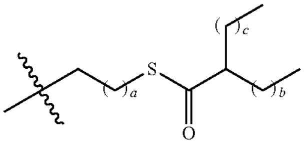,
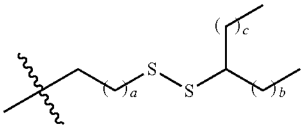,
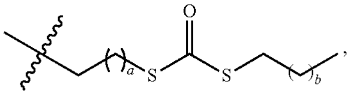,
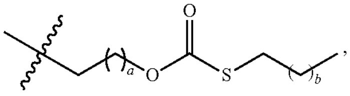,
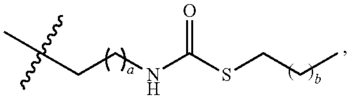,
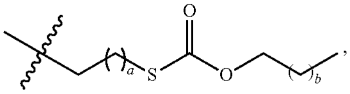,
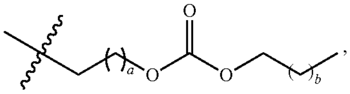, -continued
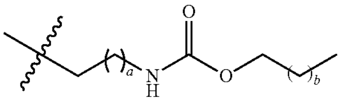
,
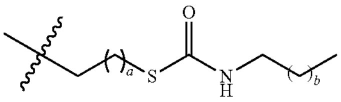
,
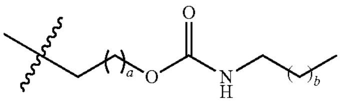
,
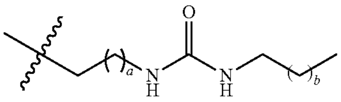
,
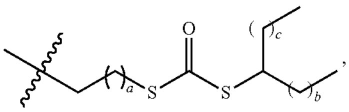
,
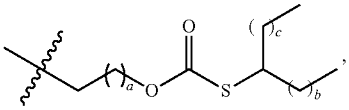
,
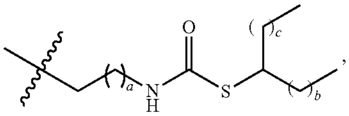
,
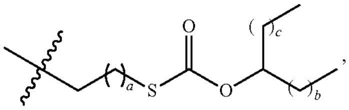
,
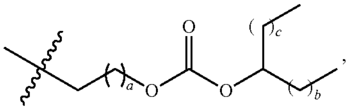
,
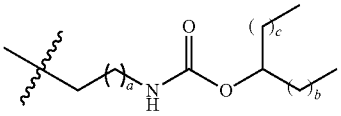
,
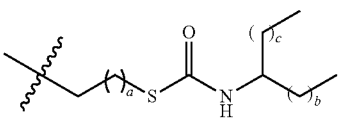
,
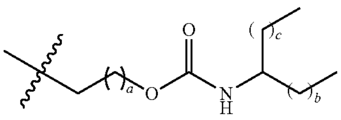
,
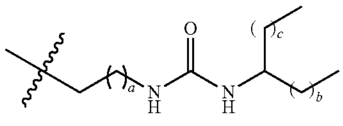
,
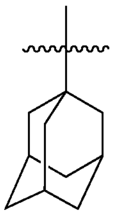
,
-continued
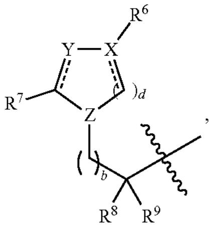
,
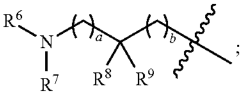
;
wherein each $R^2$ and $R^3$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl, poly(ethylene glycol) (PEG) and
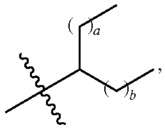
,
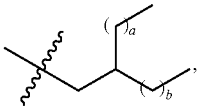
,
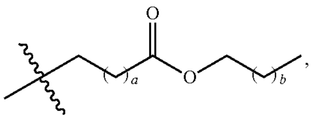
,
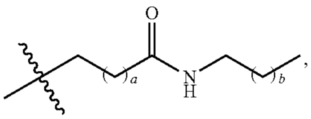
,
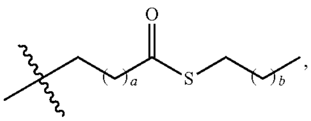
,
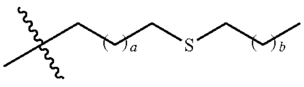
,
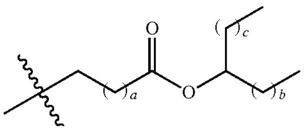
,
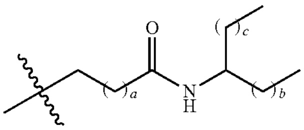
,
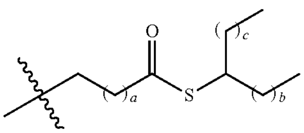
,
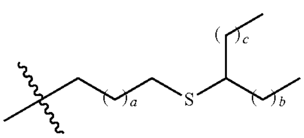
,
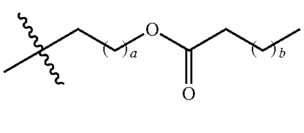
, -continued
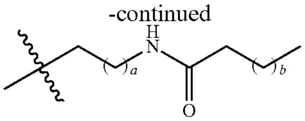,
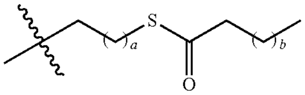,
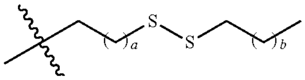,
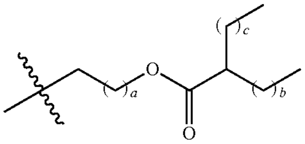,
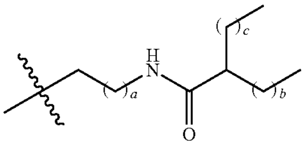,
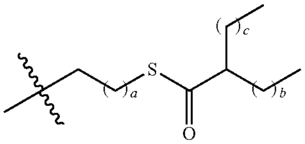,
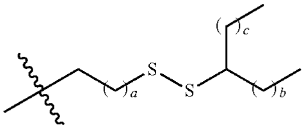,
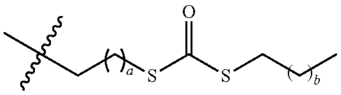,
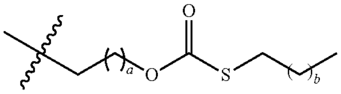,
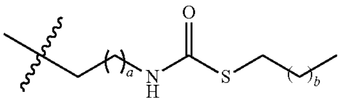,
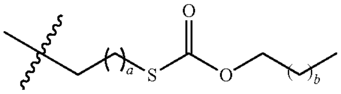,
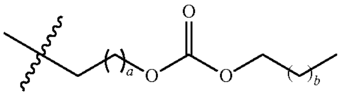,
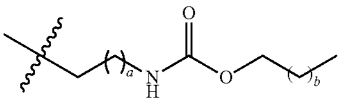,
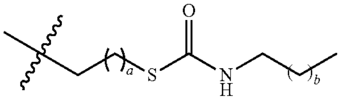,
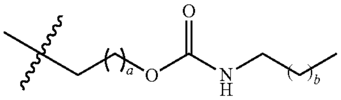,
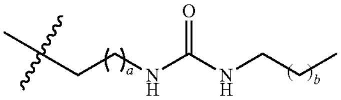,
-continued
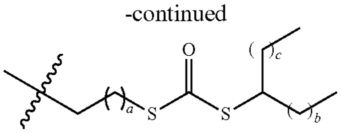,
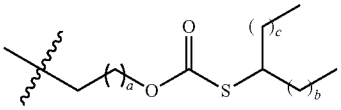,
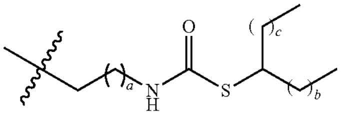,
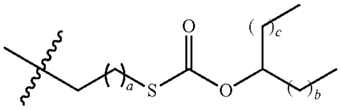,
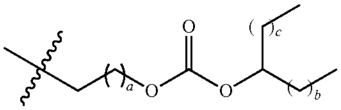,
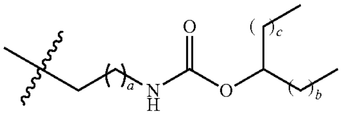,
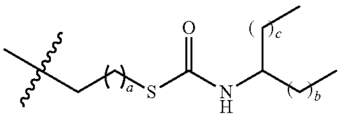,
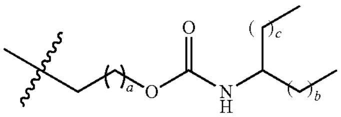,
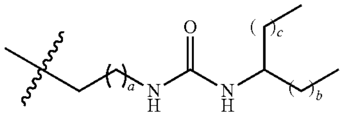, 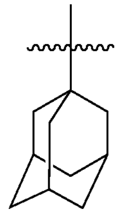,
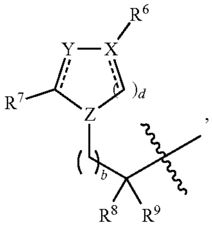, 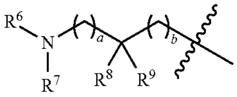
wherein each $R^6$, $R^7$, $R^8$ and $R^9$ is independently selected from H, C1-C24 alkyl, C1-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl,
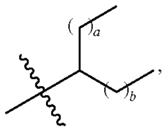, 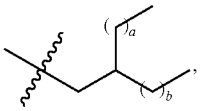, -continued
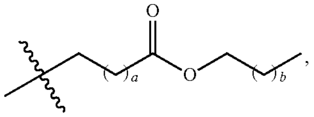
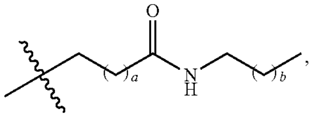
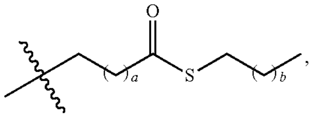
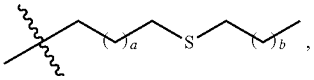
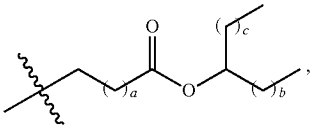
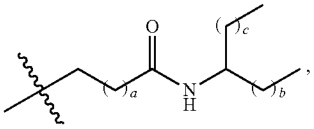
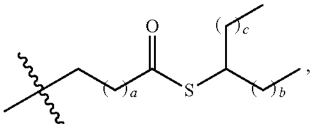
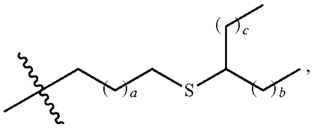
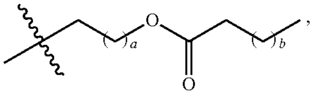
-continued
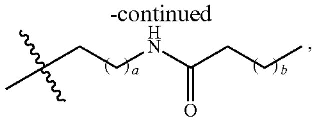
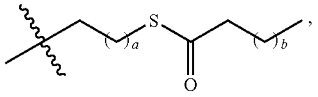
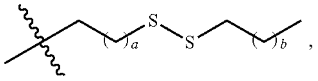
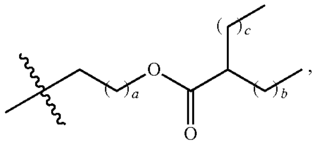
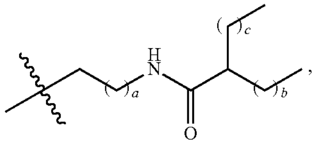
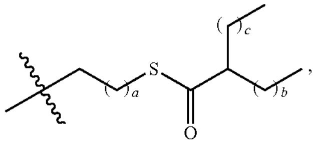
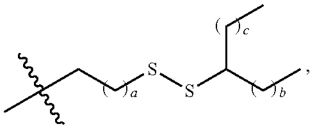
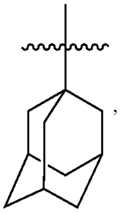
a, b, c and d are each independently an integer from 0-24; each X is independently selected from CH or N; each Y is independently selected from $CH_2$, NH, O, or S; and each Z is independently selected from CH or N.
40. The method of item 39, wherein the acid compound is:
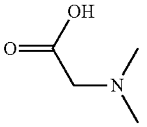
AAC1
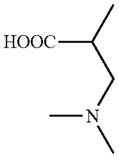
AAC2
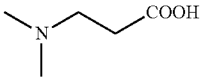
AAC3
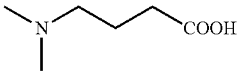
AAC4
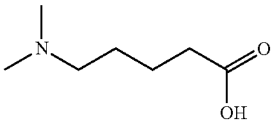
AAC5
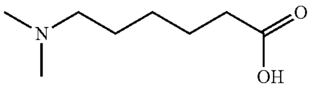
AAC6
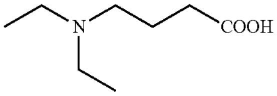
AAC7
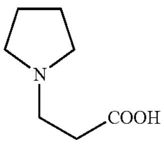
AAC8

-continued
AAC9
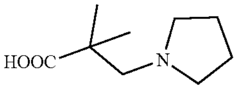
AAC10
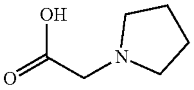
AAC11
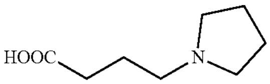
AAC12
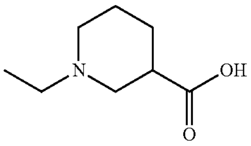
AAC13
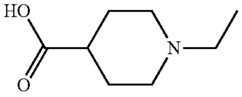
AAC14
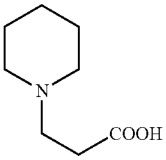
AAC15
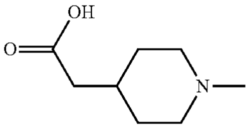
AAC16
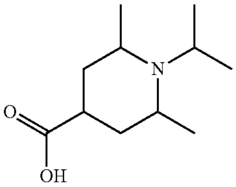
AAC17
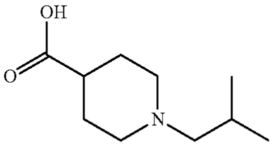
AAC18
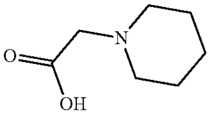
AAC19
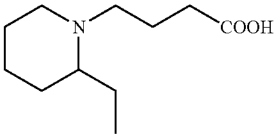
AAC20
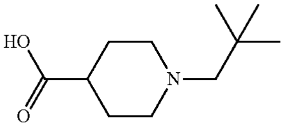
AAC21
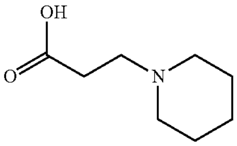
AAC22
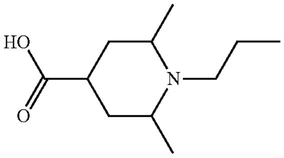
AAC23
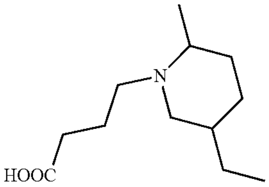
AAC24
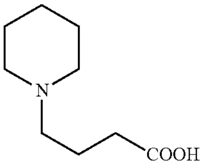
AAC25
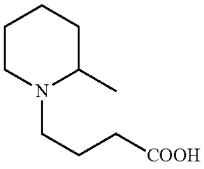
AAC26
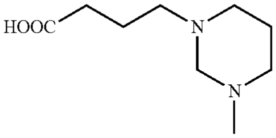

-continued
AAC27
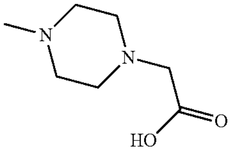
AAC28
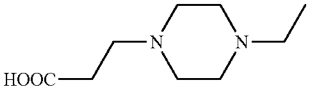
AAC29
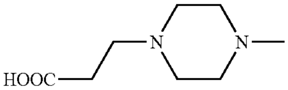
AAC30
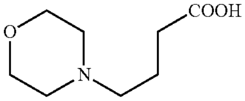
AAC31
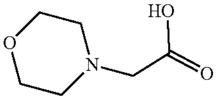
AAC32
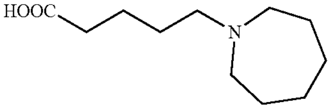
AAC33
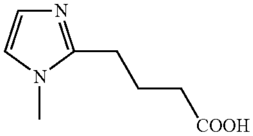
AAC34
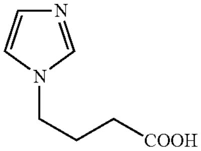
AAC35
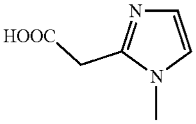
AAC36
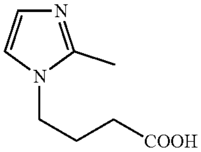
AAC37
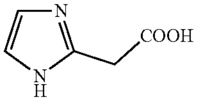
AAC38
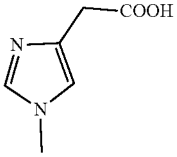
AC7
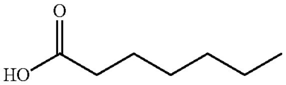
AC8
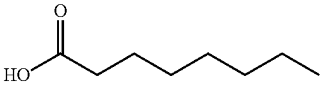
AC9
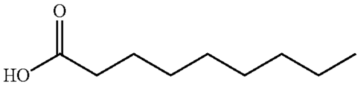
AC10
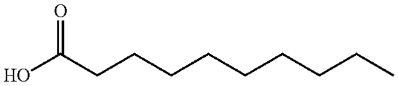
AC11
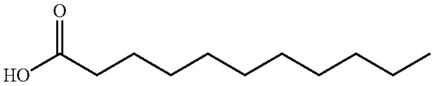
AC12
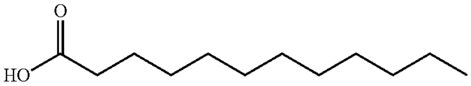
AC13
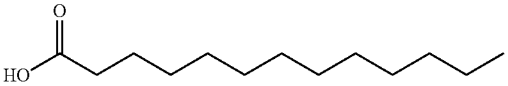
AC14
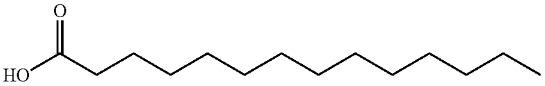
AC15
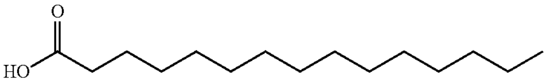
AC16
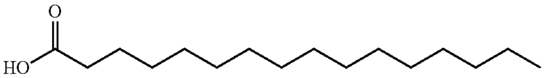
AC17
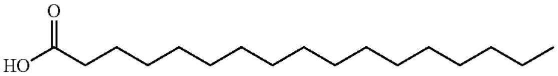
AC18
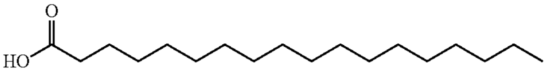

-continued
ACe18
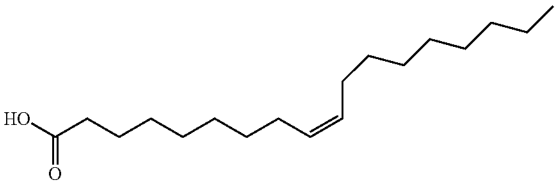
ACe17
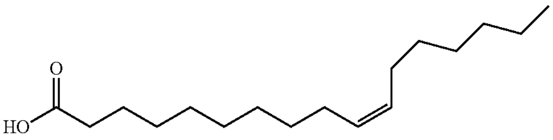
ACe16
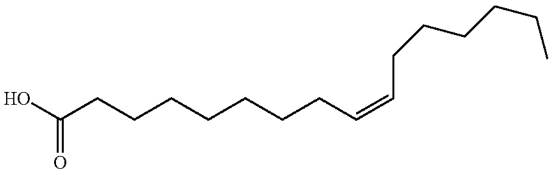
ACe14
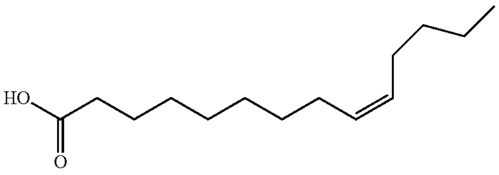
ACe12
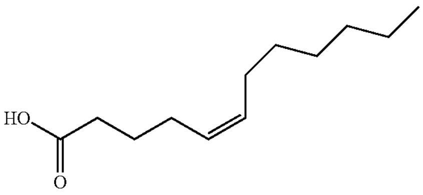
AC18e2
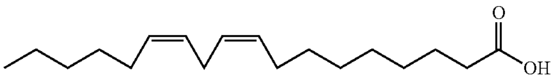
ACes16
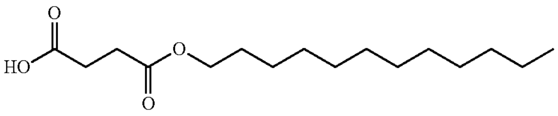
ACes14
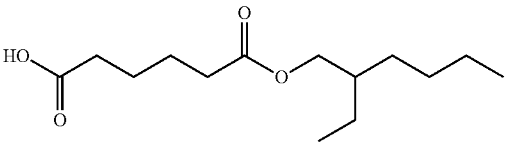
ACes13
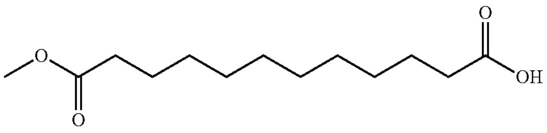
ACd13
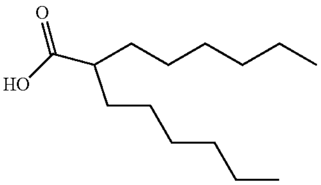
ACd15
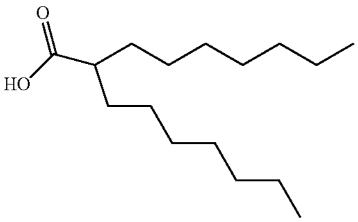
ACd17
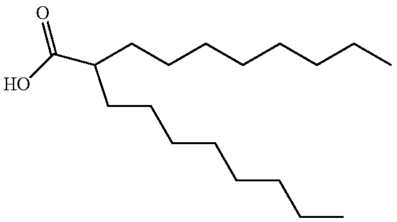
ACes14-2
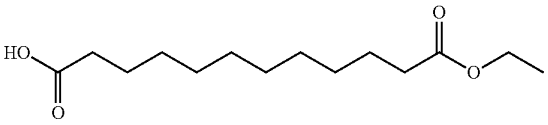
ACd19
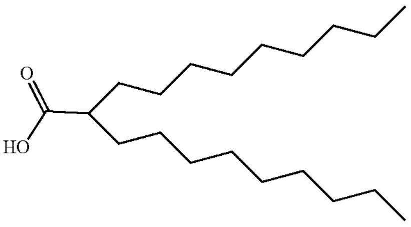

-continued
ACd25
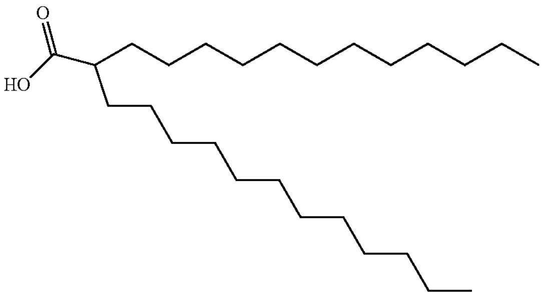
ACes19
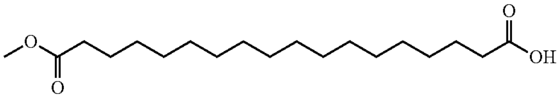
ACes17
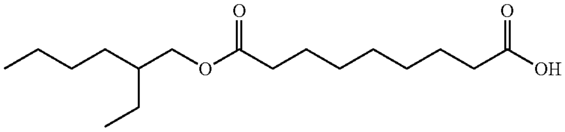
ACes12
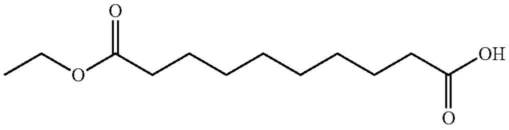
ACes18
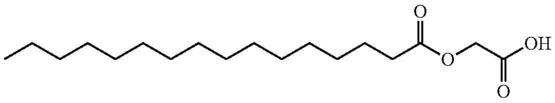
ACes17-2
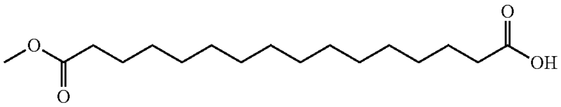
ACes18-2
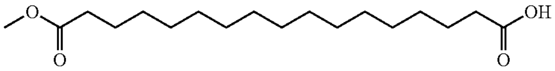
ACes12-2
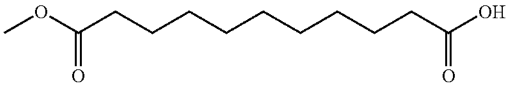
ACe20
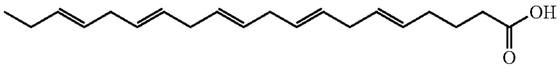
ACes15
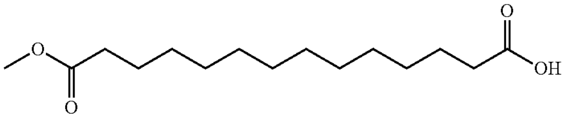
AmAc-21e
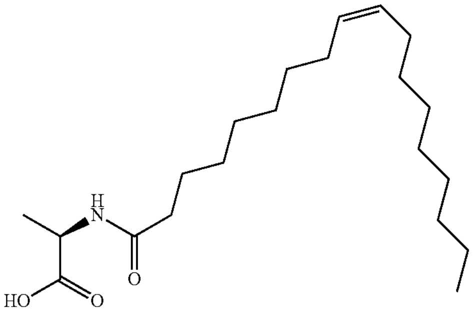
AmAc-13
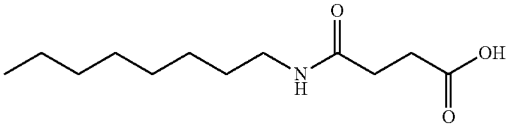
AmAc-21
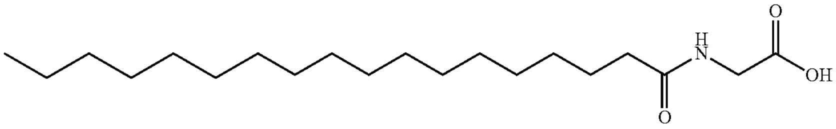
AmAc-15
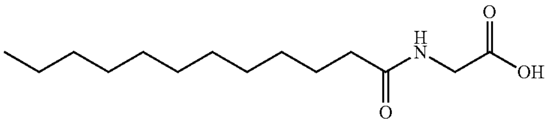
AmAc-17
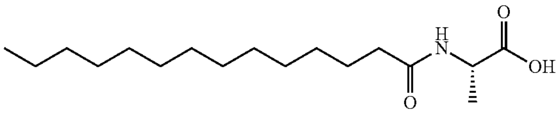

-continued
AmAc-19
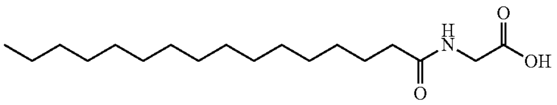
AmAc-15-3
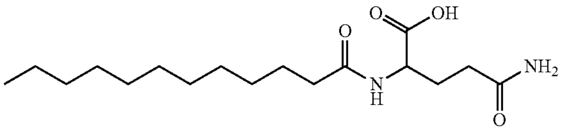
AmAc-17-OH
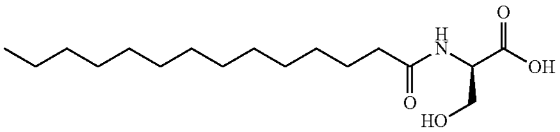
AmAc-15-2
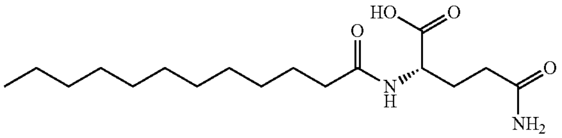
AmAc-32
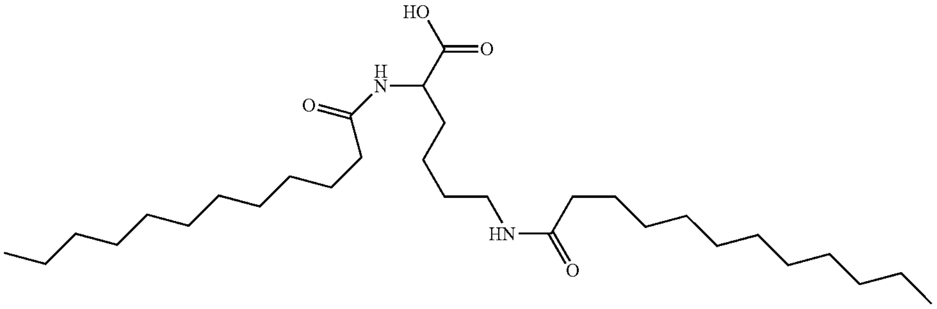
ACh1
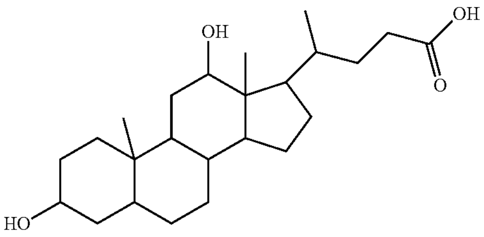
ACh2
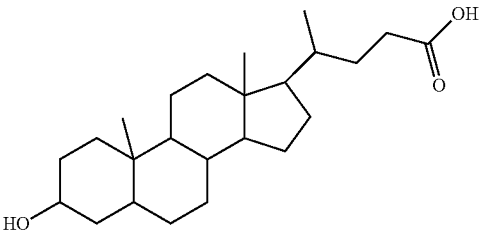
ACh3
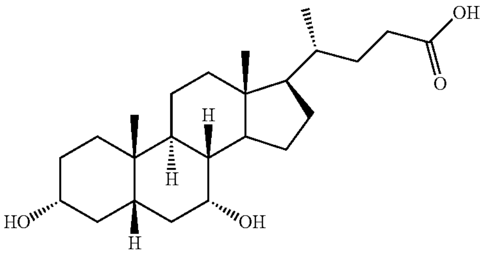
ACh3′
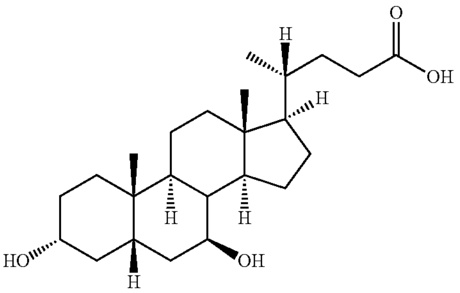
ACh4
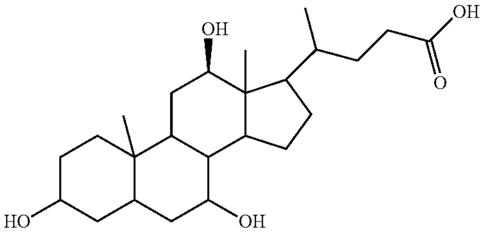
ACh5
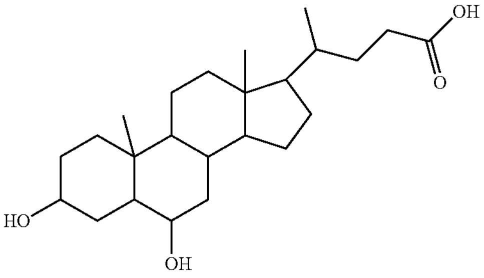

-continued
ACh6
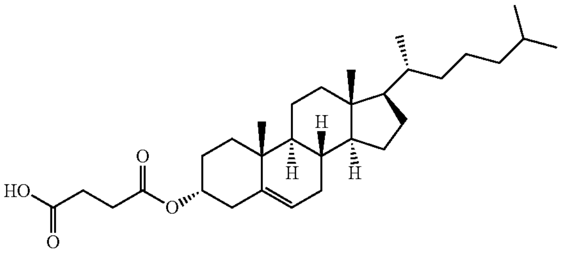
VAC1
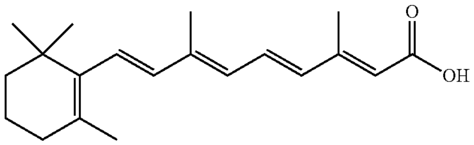
VAC2
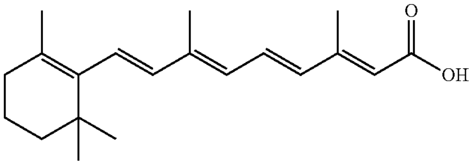
S1-Ac
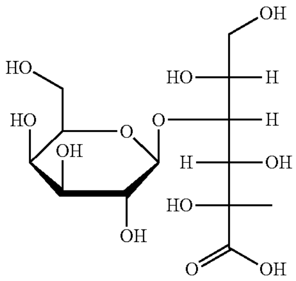
SAc-2
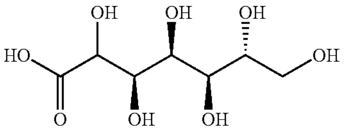
SAc-3
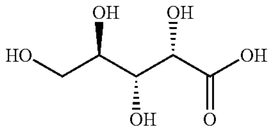
SAc-4
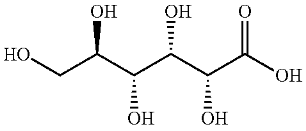
G-Ac
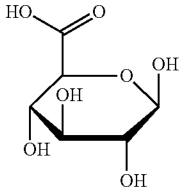
DAC1
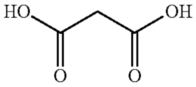
DAC2
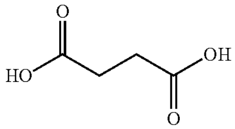
DAC3
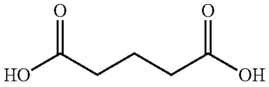
DAC4
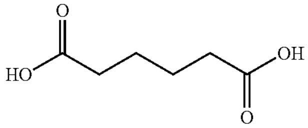
DAC5
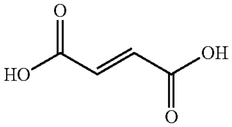
DAC6
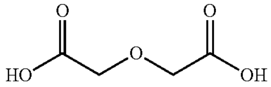
DAC7
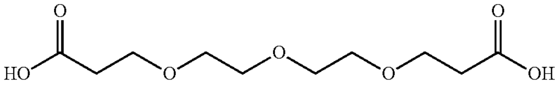
DAC8
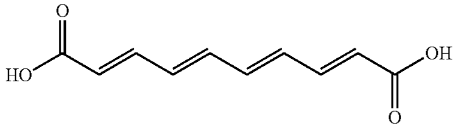

-continued
DAC9
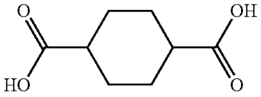
DAC10
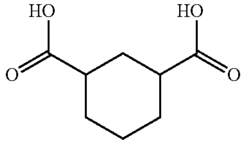
DAC11
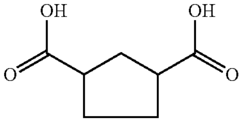
DAC12
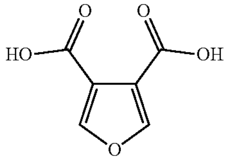
DAC13
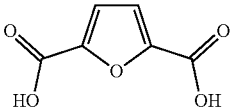
DAC14
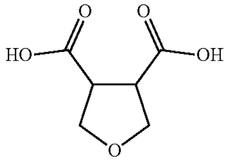
DAC15
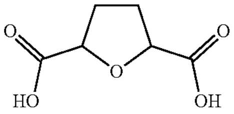
DAC16
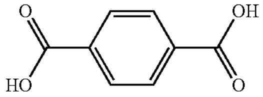
DAC17
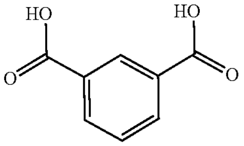
DAC18
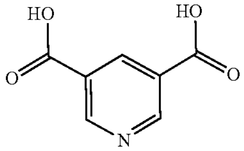
DAC19
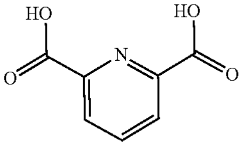
DAC20
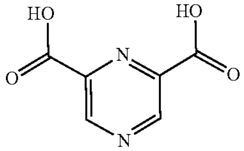
DAC21
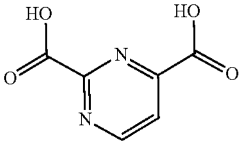
DAC22
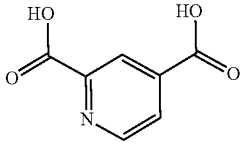
DAC23
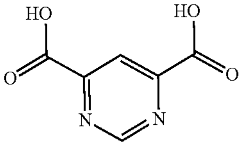
DAC24
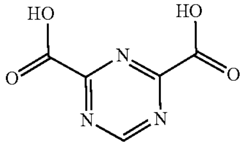
DAC-OH-1
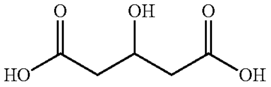
DAC-OH-2
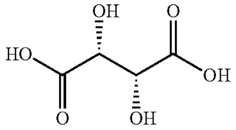
DAC-OH-3
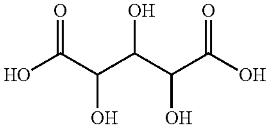
DAC-OH-4
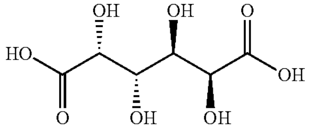

-continued
COOH-PEG1
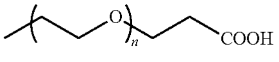
COOH-PEG2000
COOH-PEG2
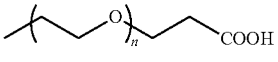
COOH-PEG1000
COOH-PEG3
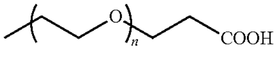
COOH-PEG750
COOH-PEG4
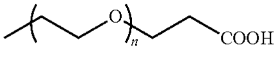
COOH-PEG550
COOH-PEG5
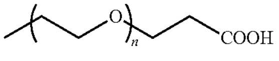
COOH-PEG350
GalNAc COOH
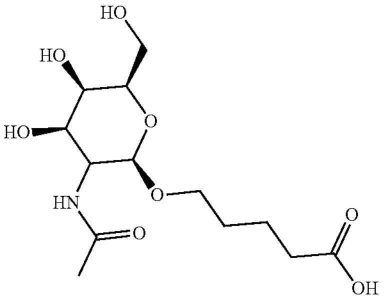
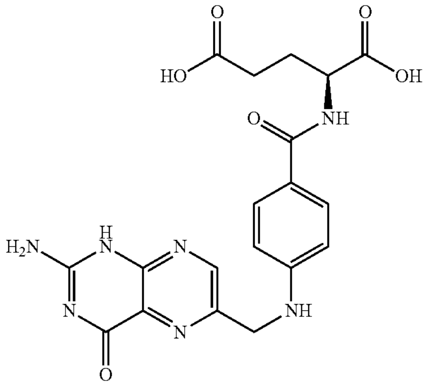
Folic acid
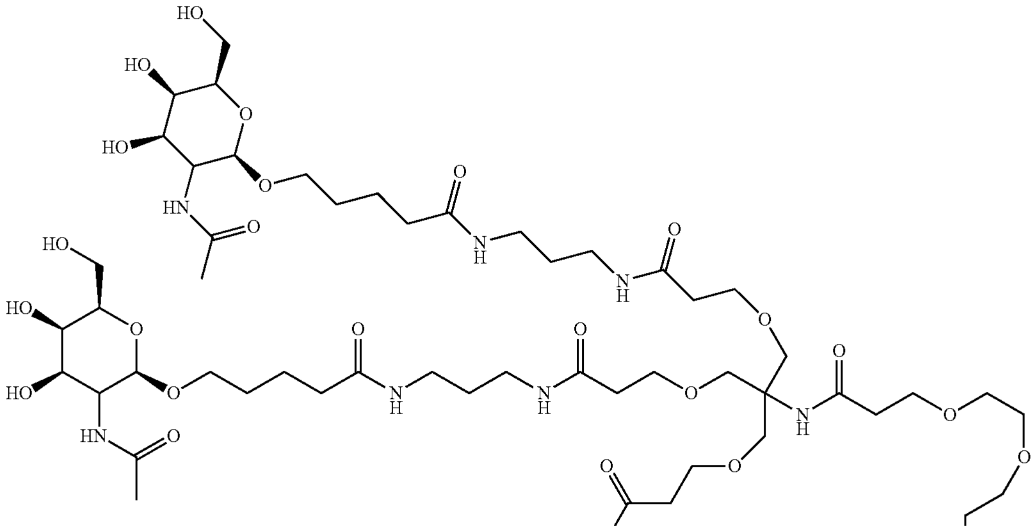

-continued
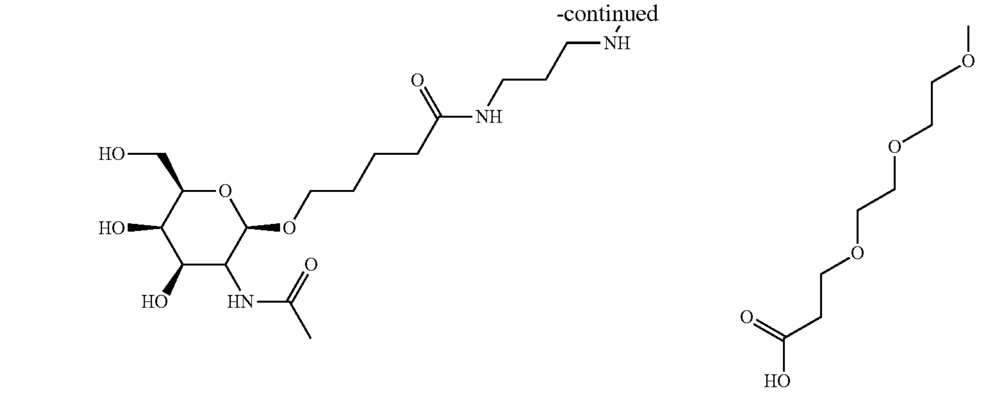
Tri-GalNAc COOH
TAC1
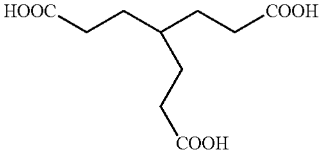
TAC2
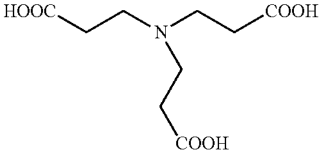
TAC3
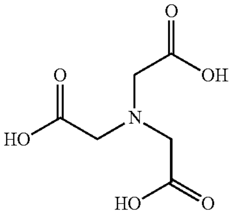
TAC4
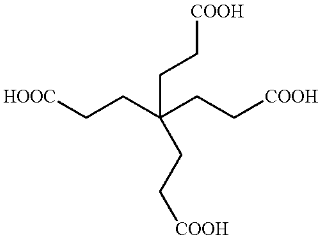
TAC5
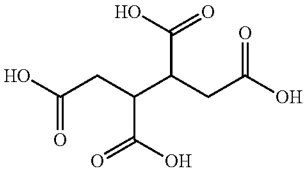
TAC6
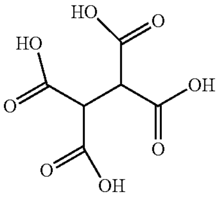
TAC7
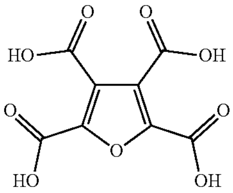
TAC8
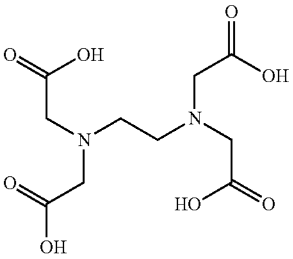

-continued
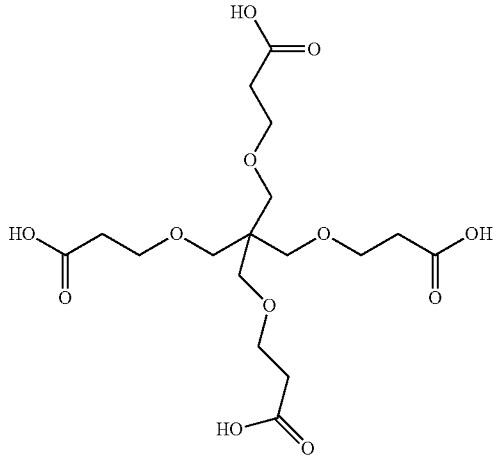
TAC9
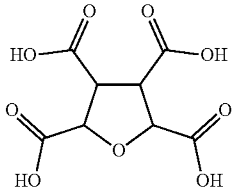
TAC10
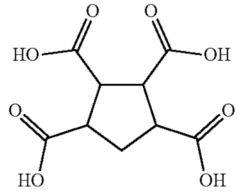
TAC11
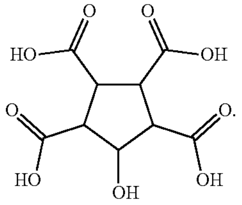
TAC12
41. The method of any one of items 39-40, wherein the amine compound is:
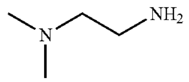
A1
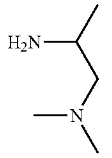
A3
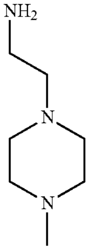
A2
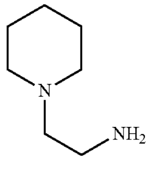
A4
-continued
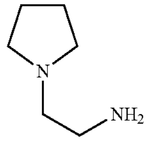
A5
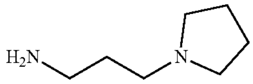
A6
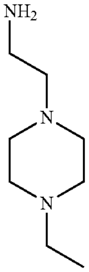
A7
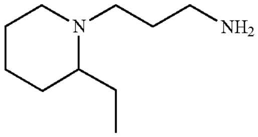
A8
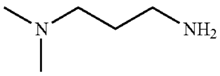
A9
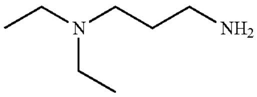
A10

-continued
A11
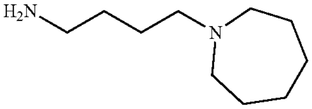
A12
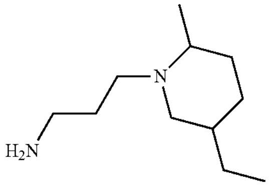
A13
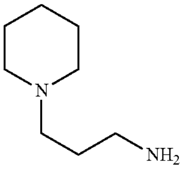
A14
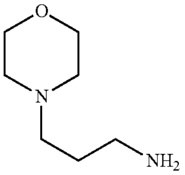
A15
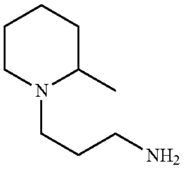
A16
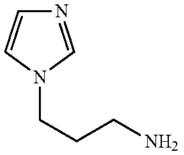
A17
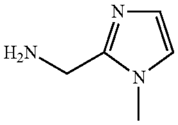
A18
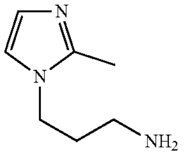
A19
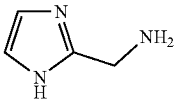
A20
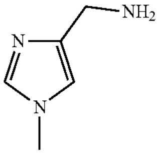
-continued
AP1
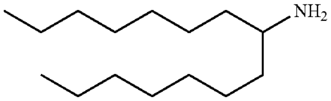
AP2
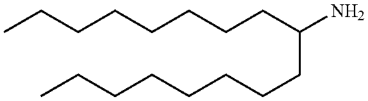
AP3
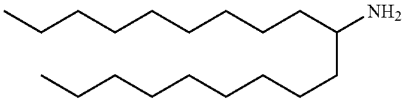
AP4
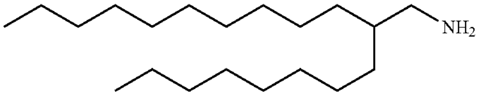
AP5
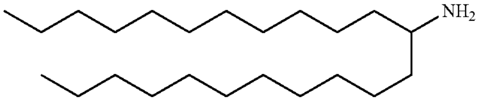
AP6
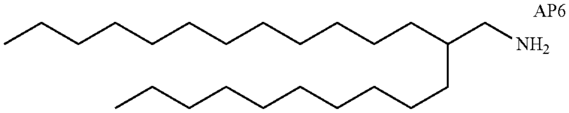
AP7
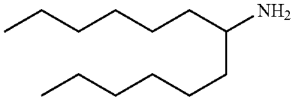
AP8
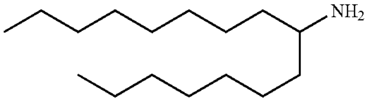
SA6
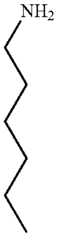
SA7
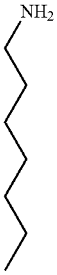

SA8
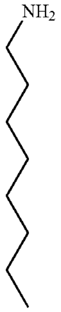
SA9
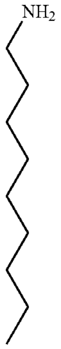
SA10
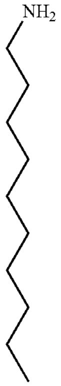
SA11
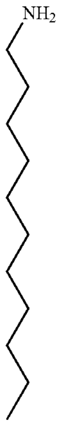
SA12
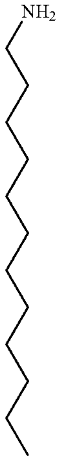
SA13
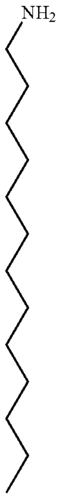
SA14
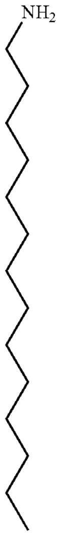

-continued
SA15
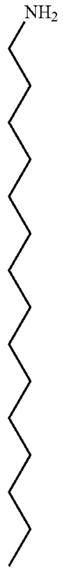
SA16
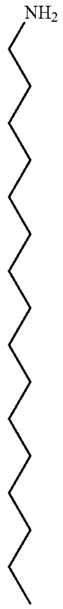
-continued
SA17
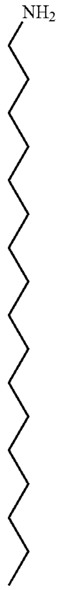
SA18
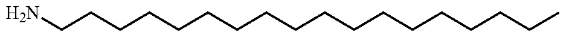
SAm-2
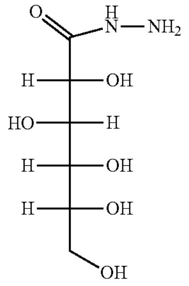
SAm-3
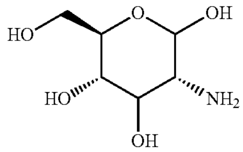
SAm-4
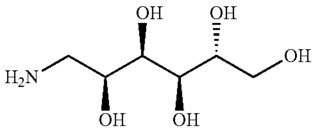
SAm-5
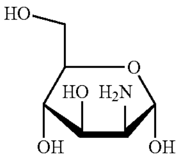
SAm-6
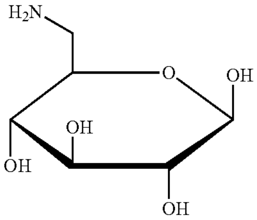

-continued
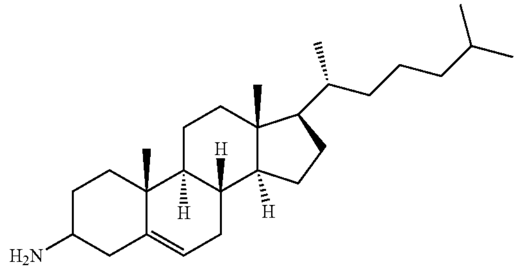
ChAm-1
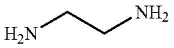
A21
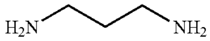
A22
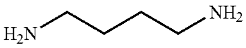
A23
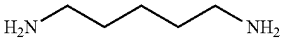
A24
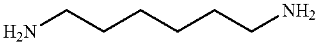
A25
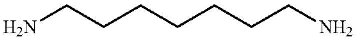
A26
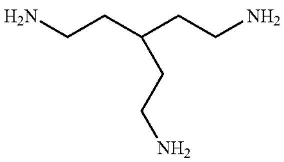
A27
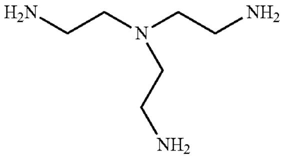
A28
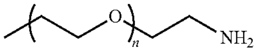
NH2-PEG1
$NH2-PEG_{2000}$
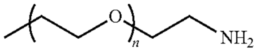
NH2-PEG2
$NH2-PEG_{1000}$
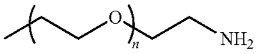
NH2-PEG3
$NH2-PEG_{750}$
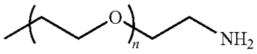
NH2-PEG4
$NH2-PEG_{550}$
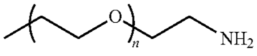
NH2-PEG5
$NH2-PEG_{350}$
42. The method of any one of items 39-41, wherein the aldehyde or ketone compound is:
ALA1
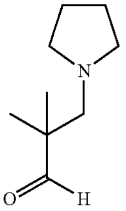
ALA2
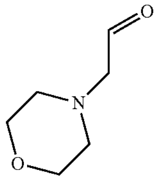
ALA3
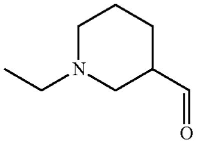
ALA4
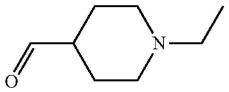
ALA5
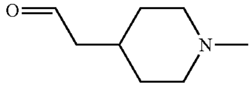
ALA6
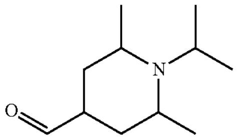
ALA7
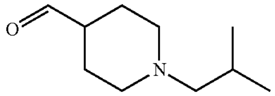
ALA8
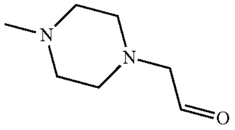
ALA9
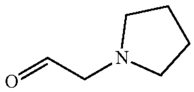
ALA10
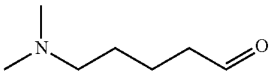
ALA11
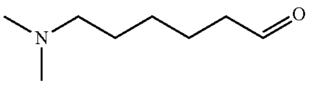
ALA12
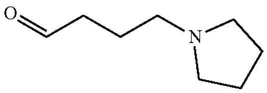

-continued
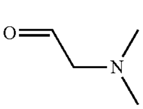
ALA13
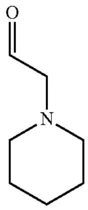
ALA14
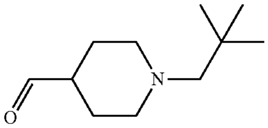
ALA15
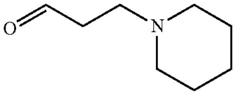
ALA16
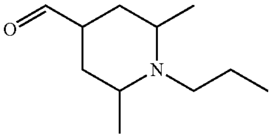
ALA17
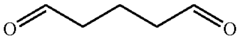
ALd1
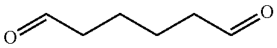
ALd2
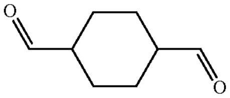
ALd3
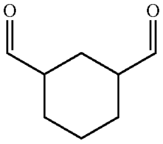
ALd4
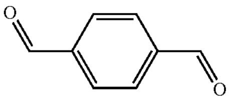
ALd5
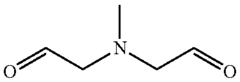
ALd6
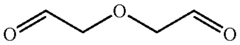
ALd7
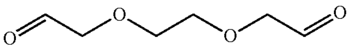
ALd8
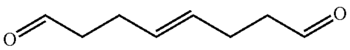
ALd9
-continued
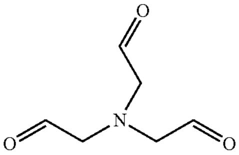
ALt1
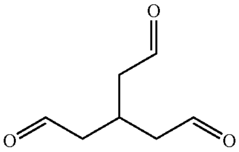
ALt2
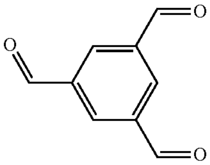
ALt3
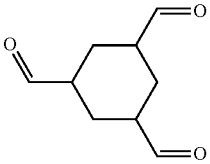
ALt4
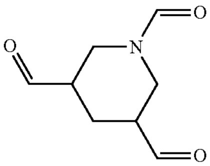
ALt5
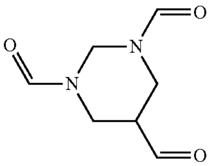
ALt6
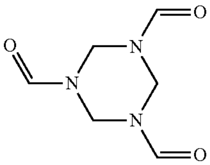
ALt7
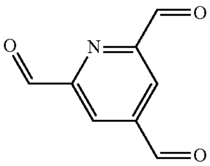
ALt8
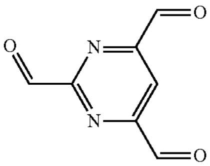
ALt9

-continued
ALt10
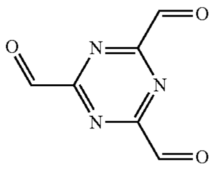
ALt11
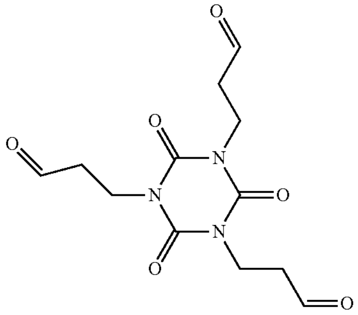
ALt12
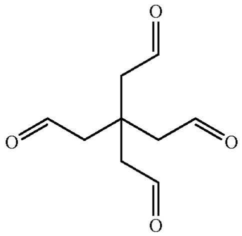
ALt13
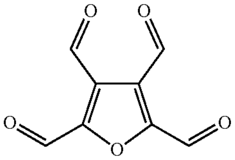
ALt14
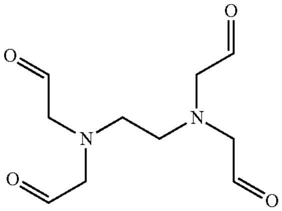
ALt15
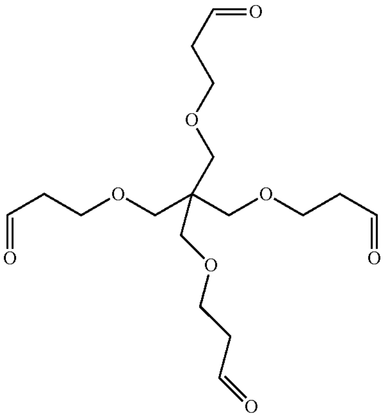
-continued
AL8
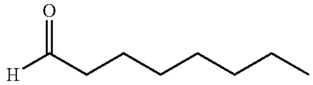
AL9
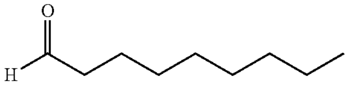
AL10
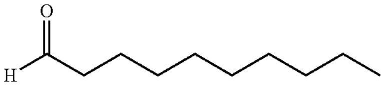
AL11
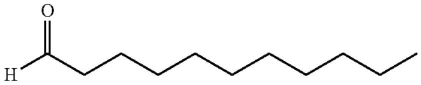
AL12
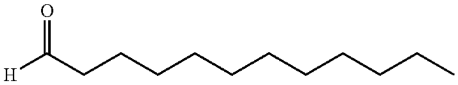
AL13
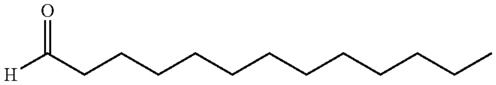
AL15
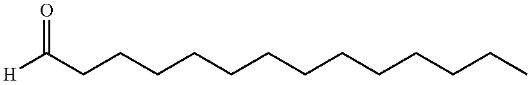
AL16
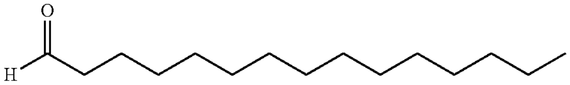
AL16e
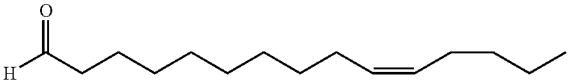
AL14e
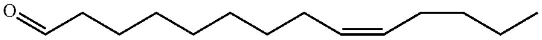
AL18e
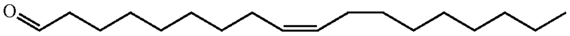
AL10P
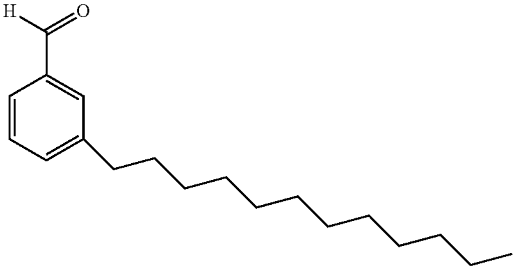
K9
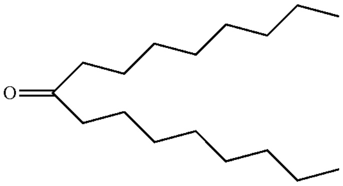

-continued
K10
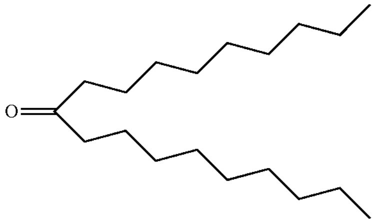
K11
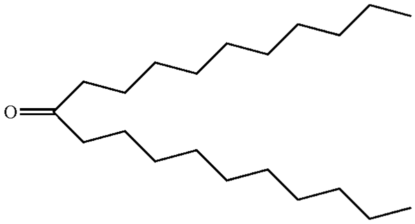
K12
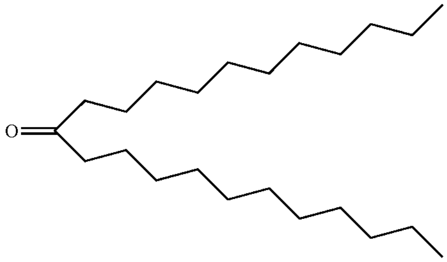
K14
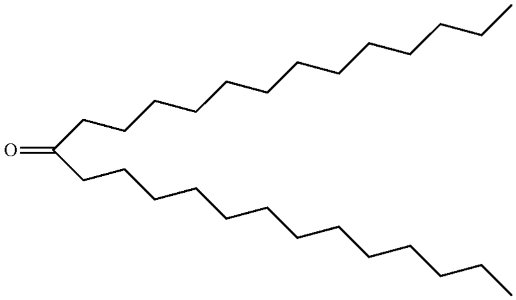
K16
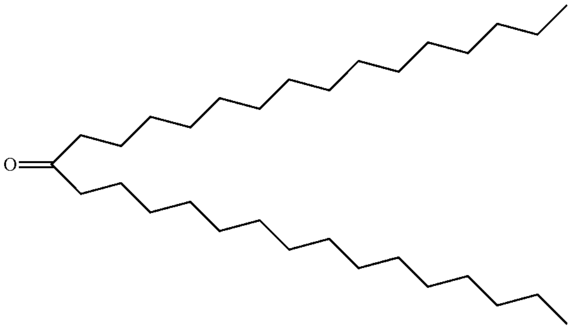
-continued
K18e
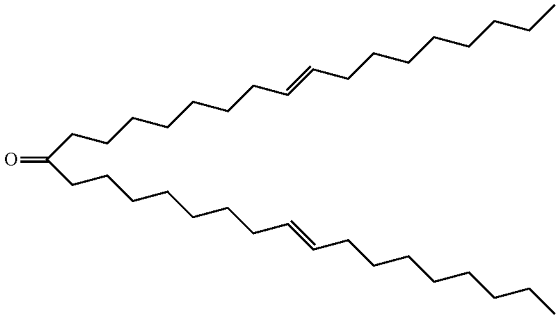
SAL-2
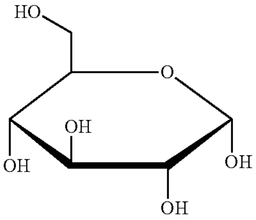
SAL-3
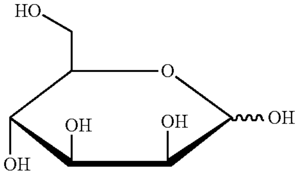
SAL-4
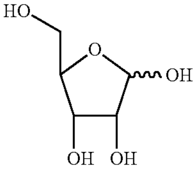
SAL-1
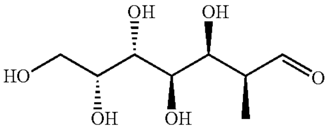
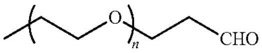
CHO-PEG1
CHO-$PEG_{2000}$
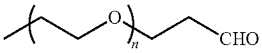
CHO-PEG2
CHO-$PEG_{1000}$
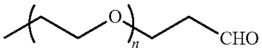
CHO-PEG3
CHO-$PEG_{750}$
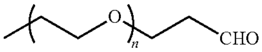
CHO-PEG4
CHO-$PEG_{550}$
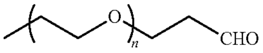
CHO-PEG5
CHO-$PEG_{350}$
43. The method of any one of items 39-42, wherein the isocyanide compound is:

Iso1
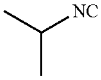
Iso2
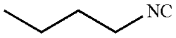
Iso3
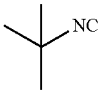
Iso4
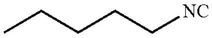
Iso5
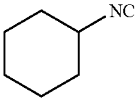
Iso6
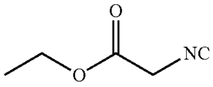
Iso7
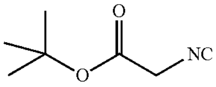
Iso8
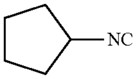
Iso9
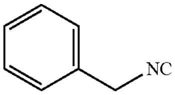
Iso10
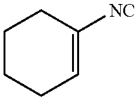
Iso11
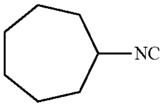
Iso12
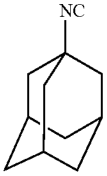
Iso13
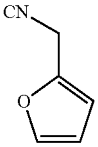
Iso14
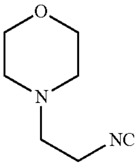
-continued
Iso15
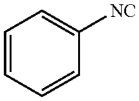
Iso16
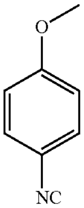
Iso17
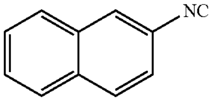
Iso18
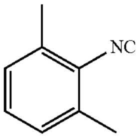
Iso19
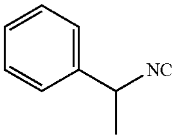
Iso19′
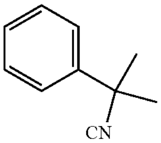
Iso20
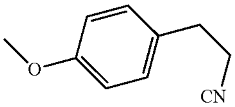
Iso21
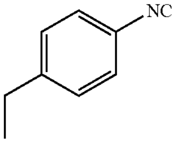
Iso22
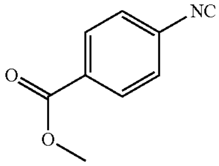
Iso23
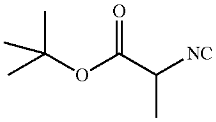
Iso24
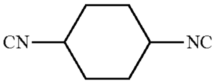

-continued

Iso25

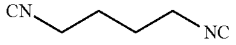

Iso26

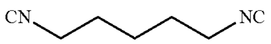

Iso27

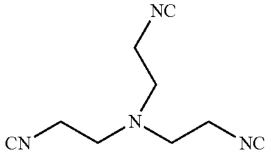

Iso28

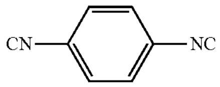

Iso29

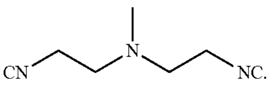

44. A modular lipid of Formula V, VI, VII, VIII, IX, or X:

V

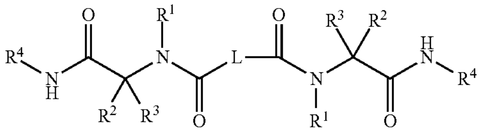

VI

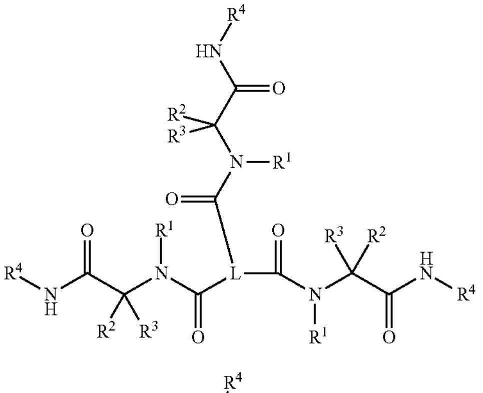

VII

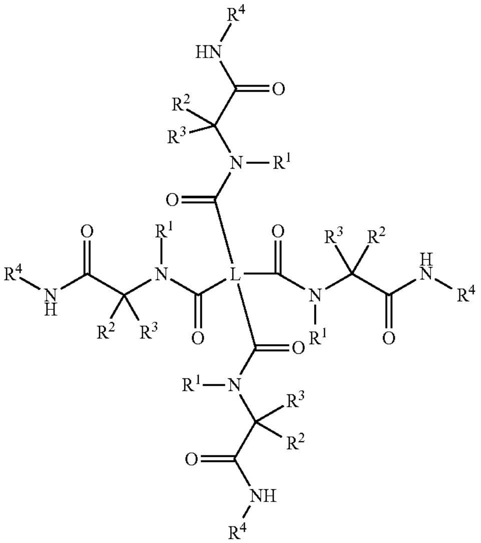

-continued

VIII

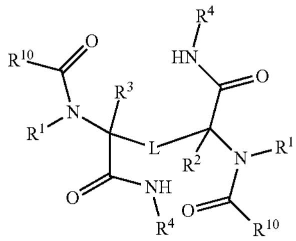

IX

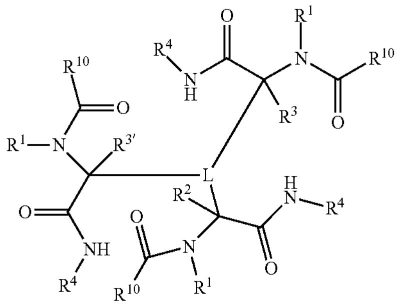

X

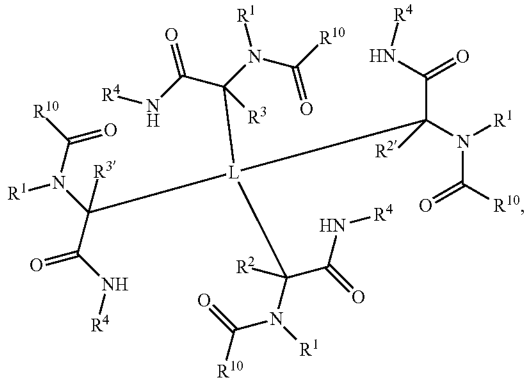

or a salt or isomer thereof, wherein each $R^1$, $R^4$, and $R^{10}$ is independently selected from $C_2$-$C_{24}$ alkyl, $C_2$-$C_{24}$ alkenyl, $C_2$-$C_{24}$ alkynyl, substituted $C_2$-$C_{24}$ alkyl, substituted alkenyl, substituted alkynyl, substituted acyl, substituted carbocyclyl, substituted heterocyclyl, substituted aryl, substituted heteroaryl; poly(ethylene glycol) (PEG),

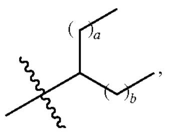

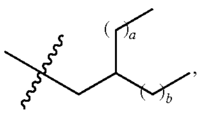

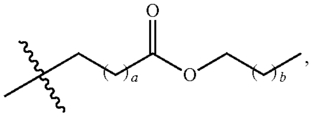

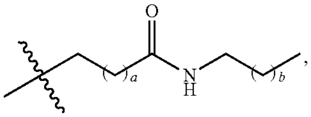

-continued
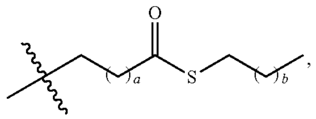
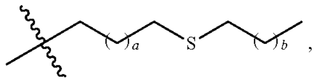
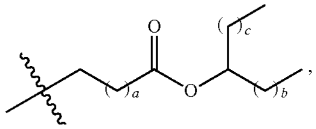
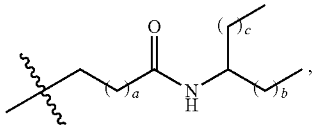
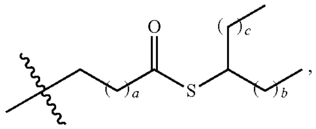
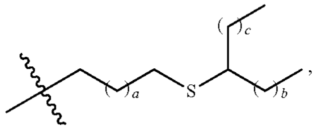
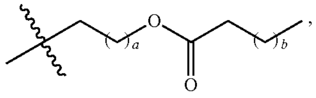
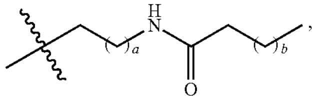
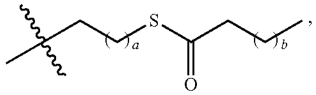
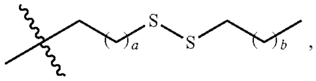
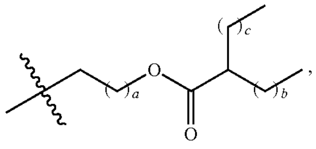
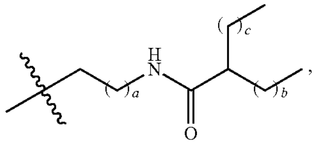
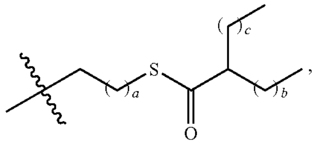
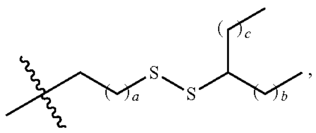
-continued
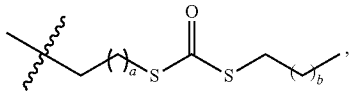
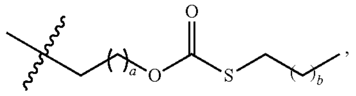
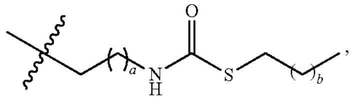
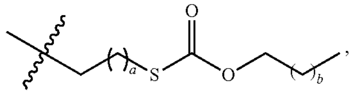
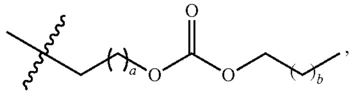
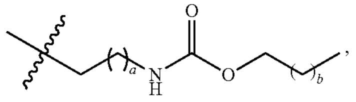
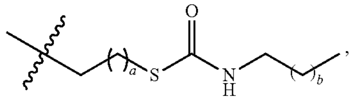
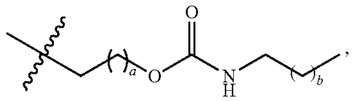
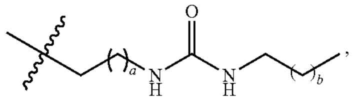
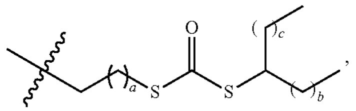
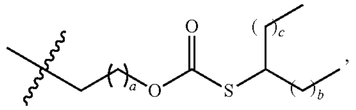
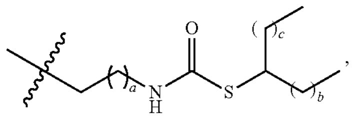
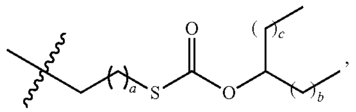
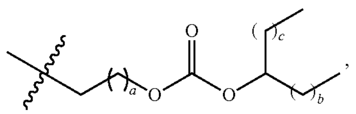
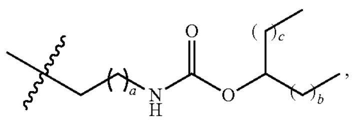
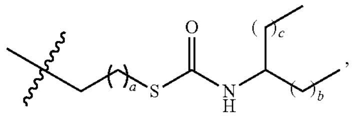

-continued
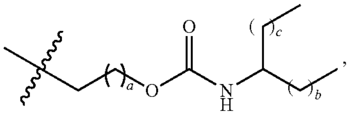
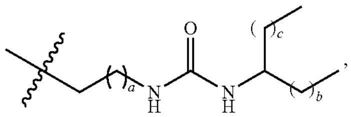
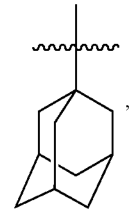
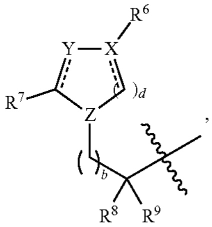
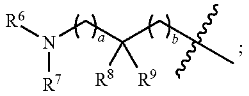
wherein each $R^2$, $R^{2'}$, $R^3$ and $R^{3'}$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl, poly(ethylene glycol) (PEG) and
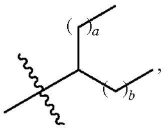
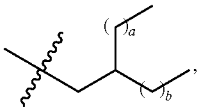
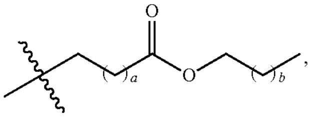
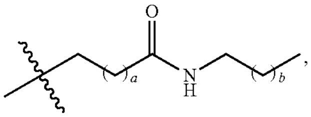
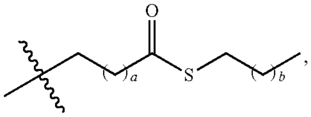
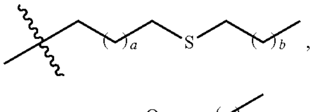
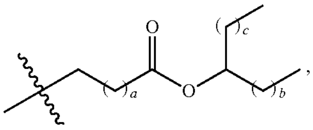
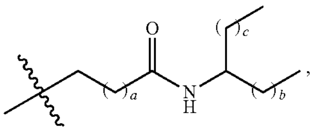
-continued
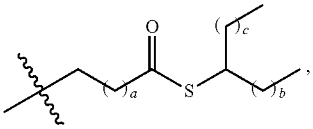
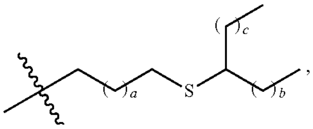
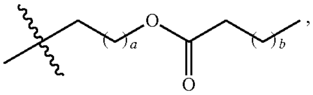
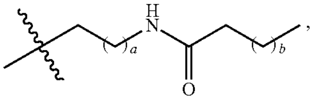
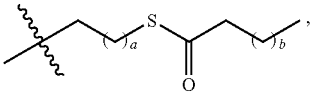
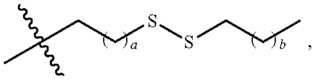
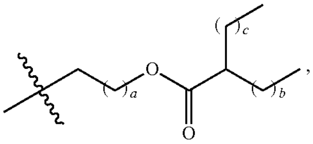
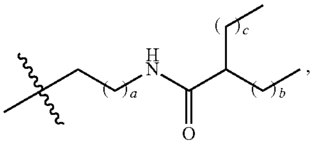
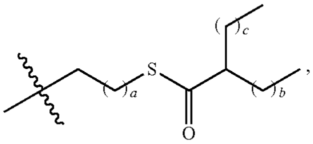
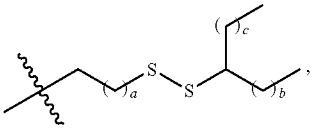
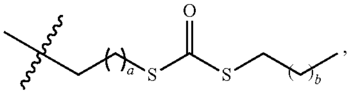
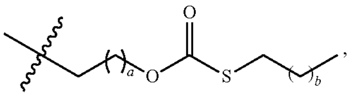
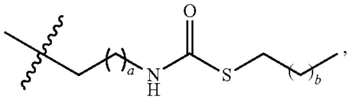
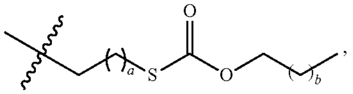
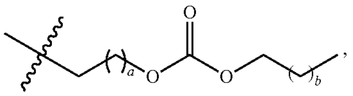

-continued
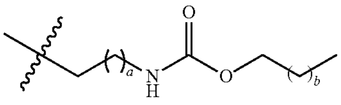,
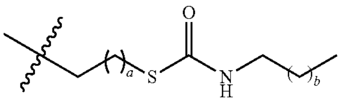,
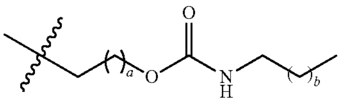,
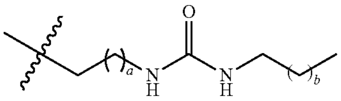,
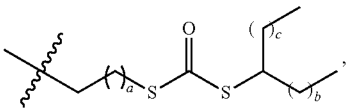,
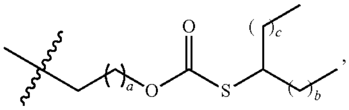,
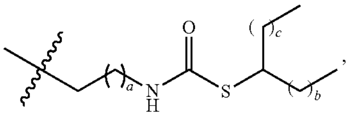,
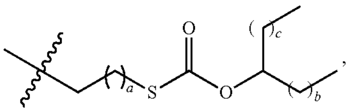,
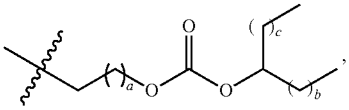,
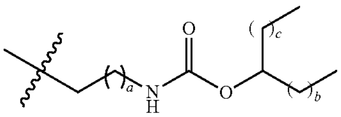,
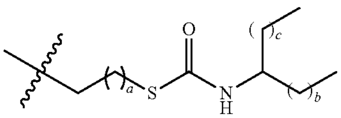,
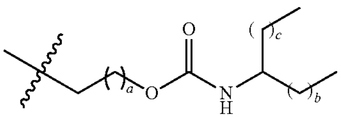,
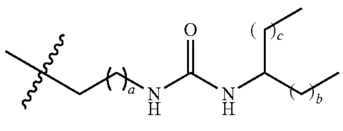, 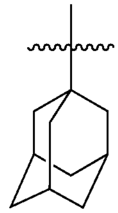,
-continued
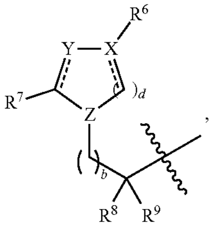, 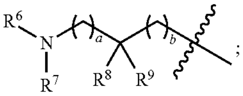;
wherein each L is independently selected from alkyl, alkenyl, alkynyl, substituted alkyl, substituted alkenyl, substituted alkynyl, substituted acyl, substituted carbocyclyl, substituted heterocyclyl, substituted aryl, substituted heteroaryl, poly(ethylene glycol) (PEG) and
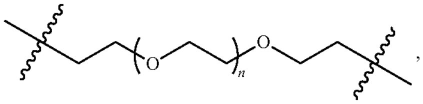,
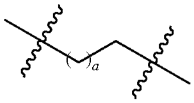, 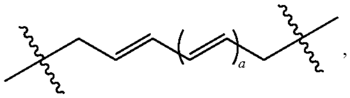,
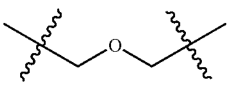, 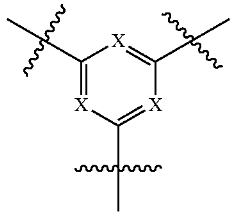,
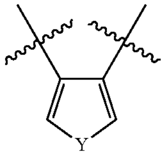, 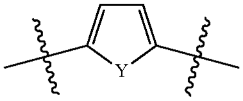,
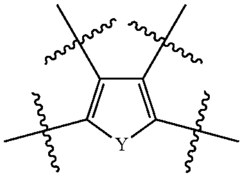, 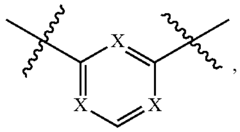,
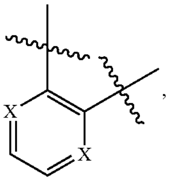, 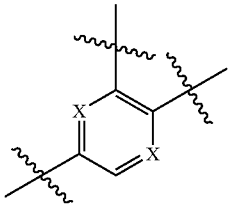,
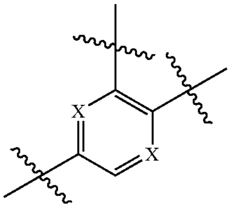, 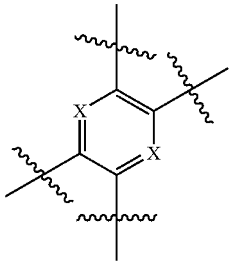, -continued

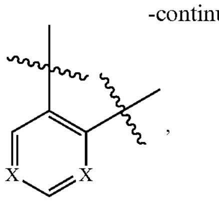,

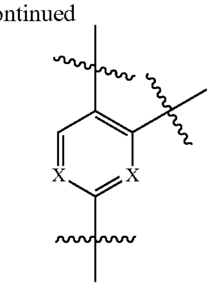,

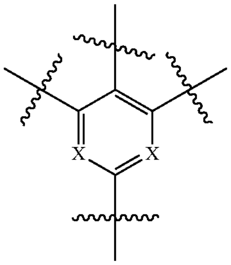,

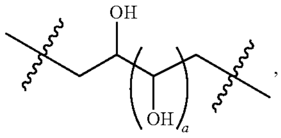,

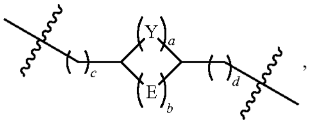,

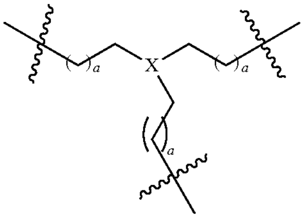,

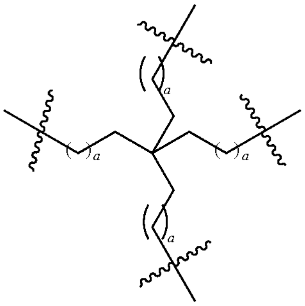,

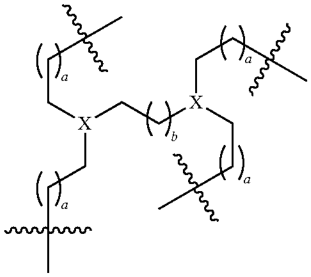,

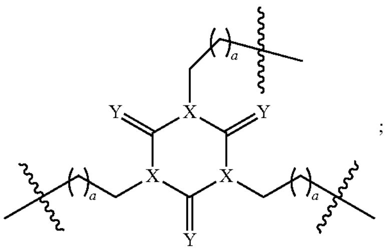;

wherein $R^6$, $R^7$, $R^8$ and $R^9$ are each independently selected from H, C1-C24 alkyl, C1-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl, substituted carbocyclyl, substituted heterocyclyl, substituted aryl, substituted heteroaryl,

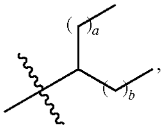,

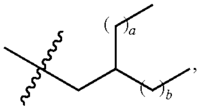,

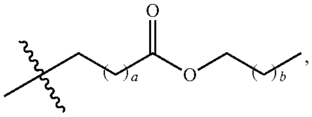,

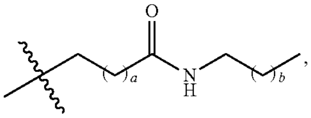,

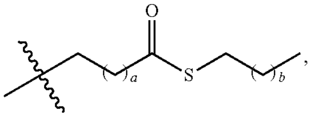,

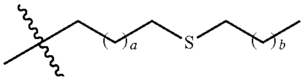,

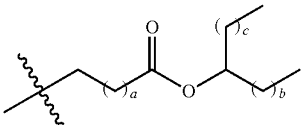,

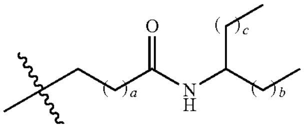,

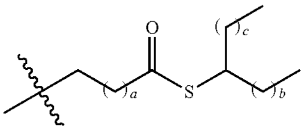,

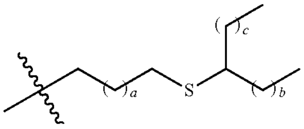,

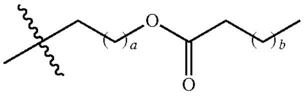,

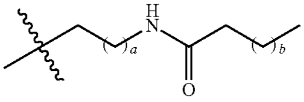,

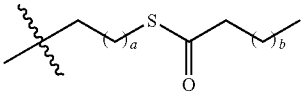,

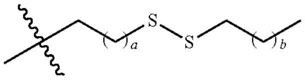,

-continued

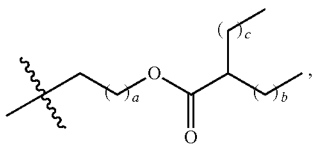

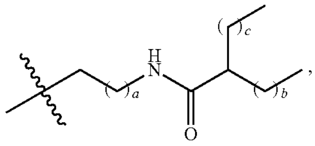

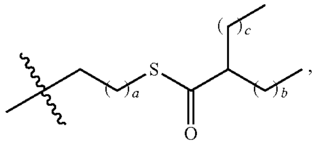

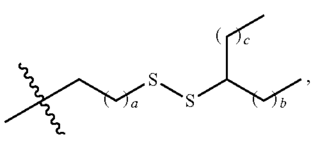

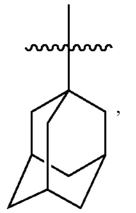

a, b, c and d are each independently an integer from 0-24;

each E is independently selected from $CH_2$, NH, O, or S;

each X is independently selected from CH or N;

each Y is independently selected from $CH_2$, NH, O, or S; and each Z is independently selected from CH or N.

45. A method for synthesizing a modular lipid of Formula V, VI and VII comprising performing the following four component reaction:

V

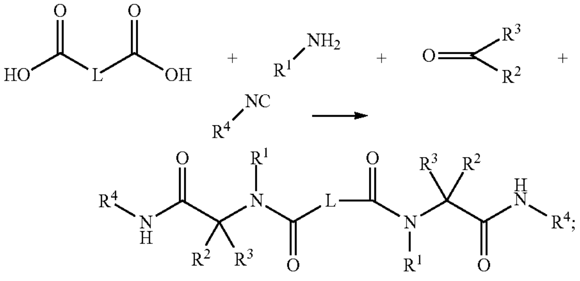

VI

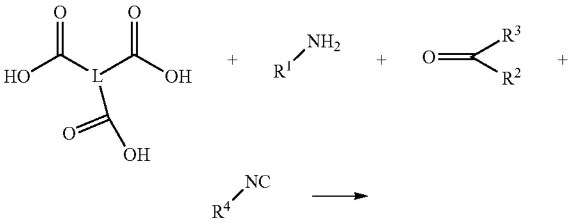

-continued

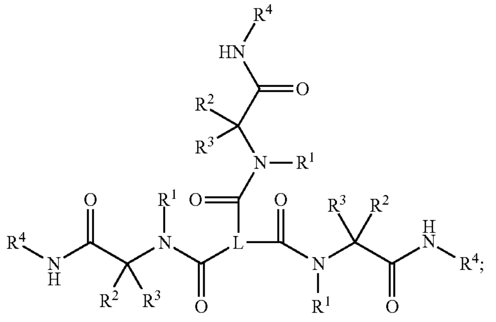

or

VII

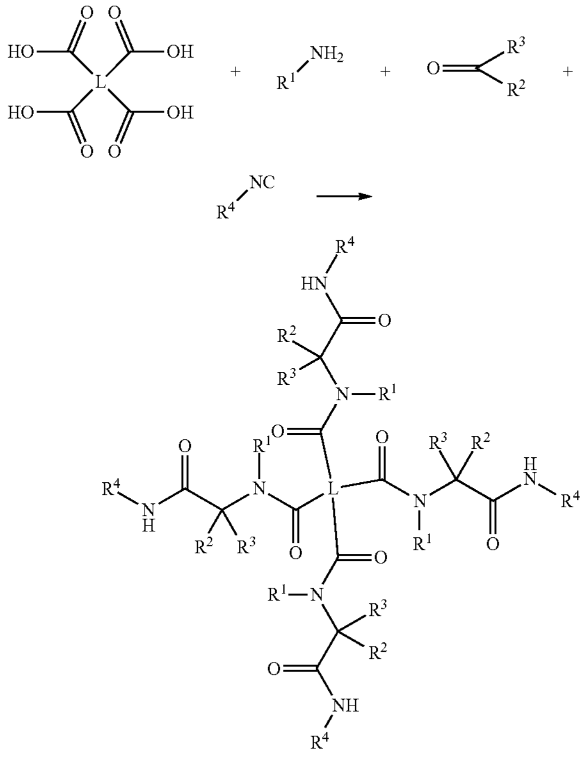

or a salt or isomer thereof, wherein wherein each $R^1$ and $R^4$ is independently selected from $C_2$-$C_{24}$ alkyl, $C_2$-$C_{24}$ alkenyl, $C_2$-$C_{24}$ alkynyl, substituted $C_2$-$C_{24}$ alkyl, substituted alkenyl, substituted alkynyl, substituted acyl, substituted carbocyclyl, substituted heterocyclyl, substituted aryl, substituted heteroaryl, poly(ethylene glycol) (PEG),

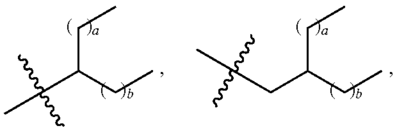

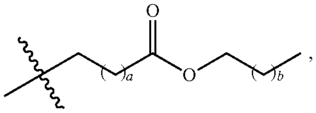

-continued
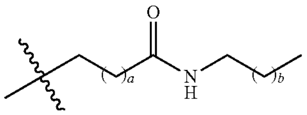
,
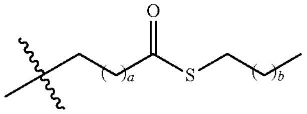
,
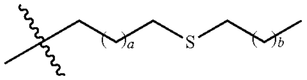
,
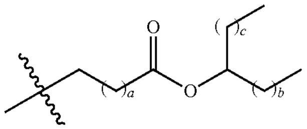
,
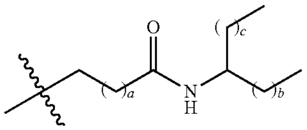
,
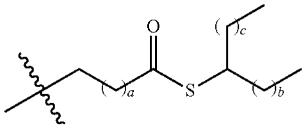
,
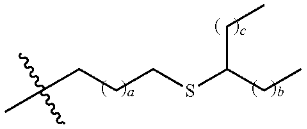
,
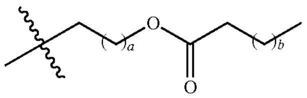
,
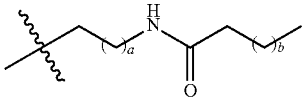
,
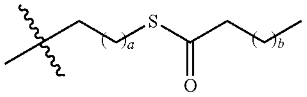
,
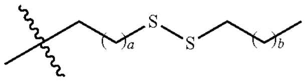
,
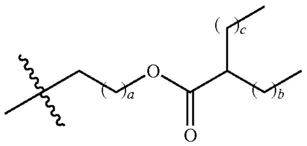
,
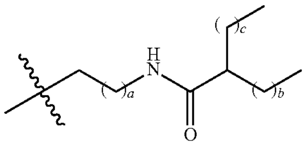
,
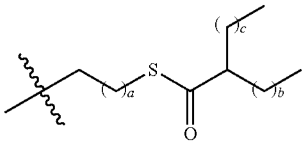
,
-continued
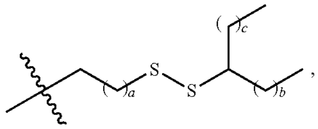
,
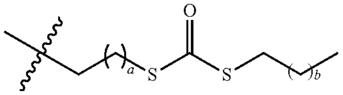
,
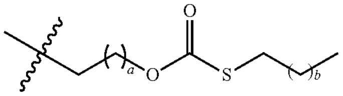
,
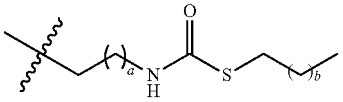
,
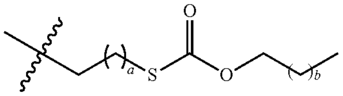
,
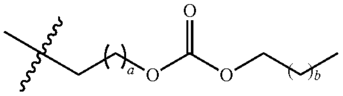
,
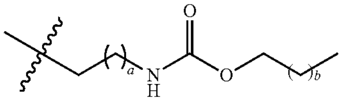
,
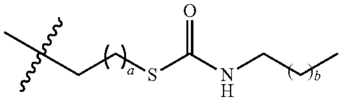
,
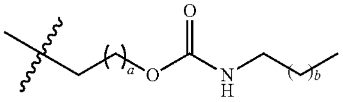
,
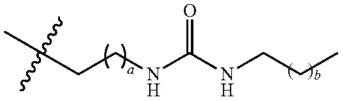
,
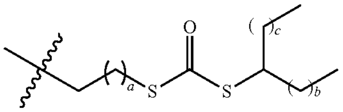
,
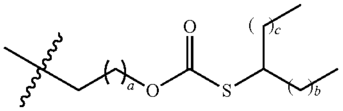
,
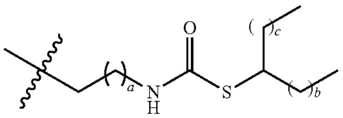
,
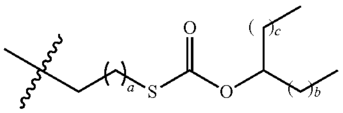
,
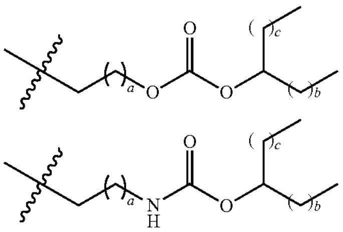
, -continued
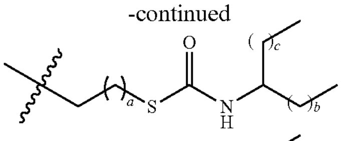
,
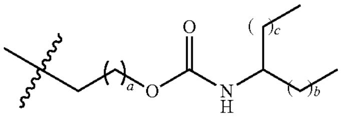
,
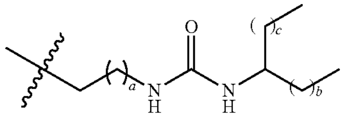
,
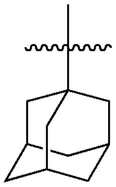
,
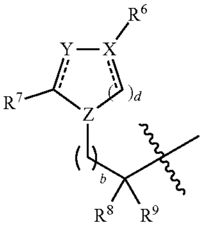
,
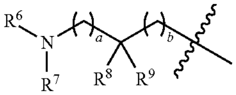
;
wherein each $R^2$ and $R^3$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl, poly(ethylene glycol) (PEG) and
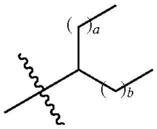
,
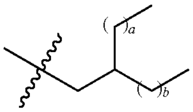
,
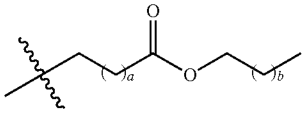
,
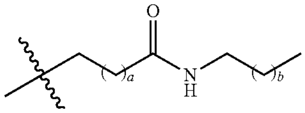
,
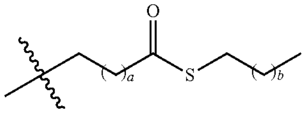
,
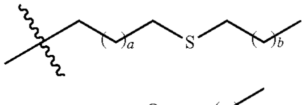
,
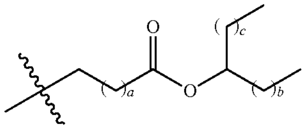
,
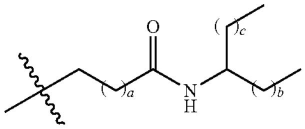
,
-continued
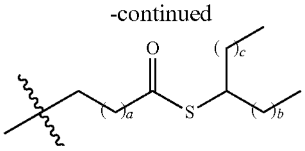
,
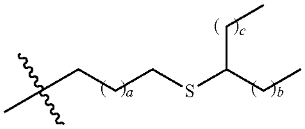
,
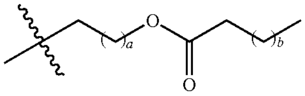
,
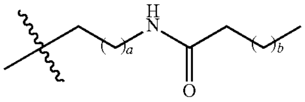
,
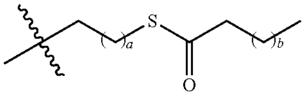
,
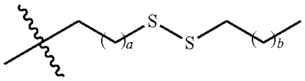
,
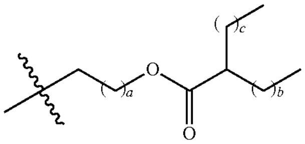
,
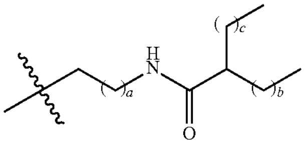
,
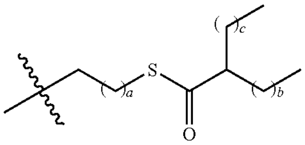
,
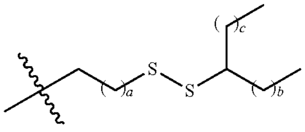
,
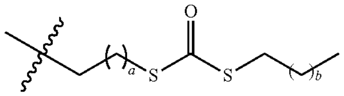
,
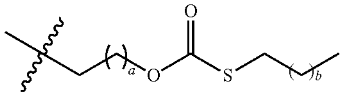
,
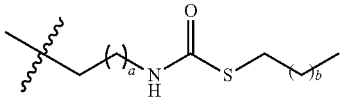
,
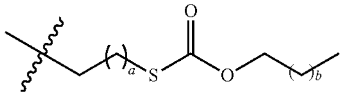
,
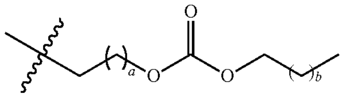
, -continued
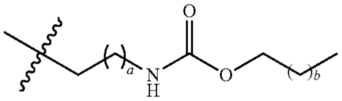,
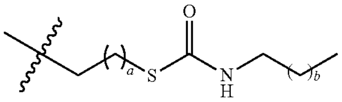,
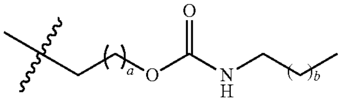,
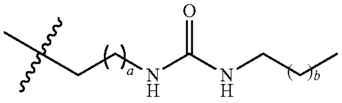,
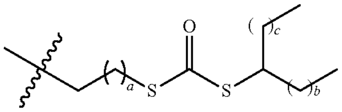,
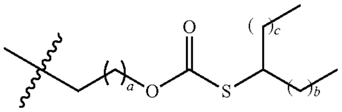,
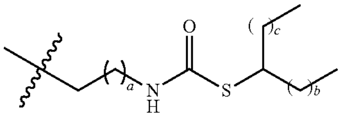,
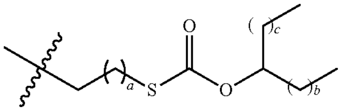,
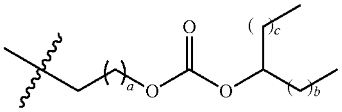,
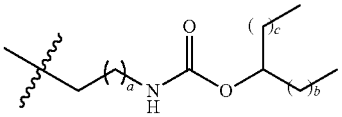,
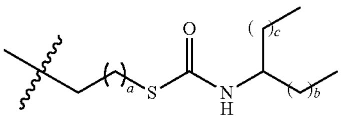,
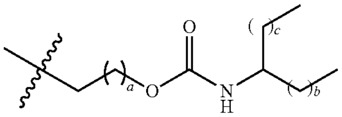,
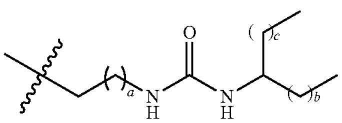, 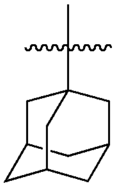,
-continued
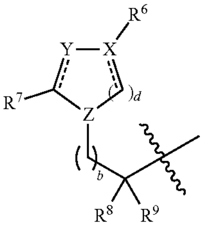, 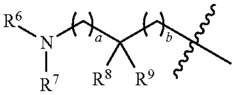;
wherein each L is independently selected from alkyl, alkenyl, alkynyl, substituted alkyl, substituted alkenyl, substituted alkynyl, substituted acyl, substituted carbocyclyl, substituted heterocyclyl, substituted aryl, substituted heteroaryl, poly(ethylene glycol) (PEG) and
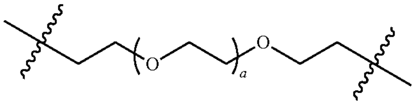,
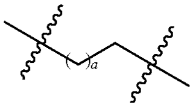, 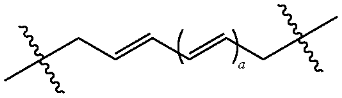,
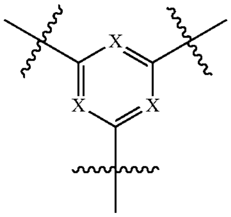,
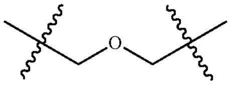,
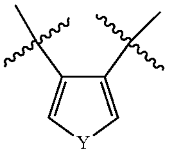, 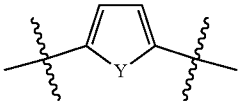,
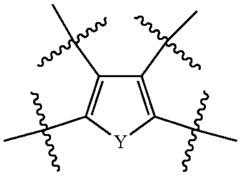, 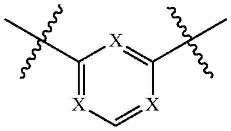,
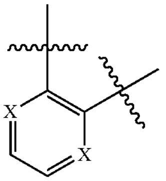, 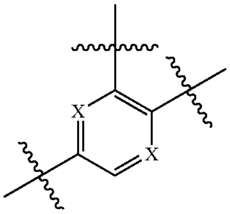,
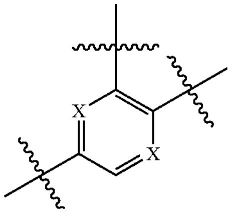, 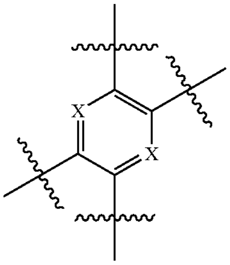

-continued

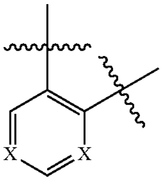,

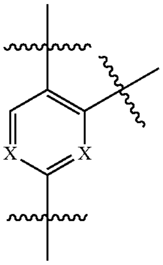,

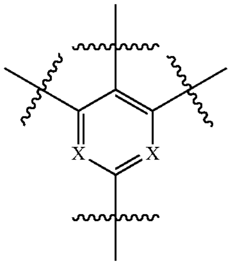,

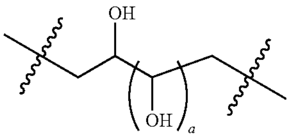,

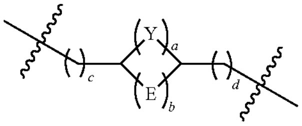,

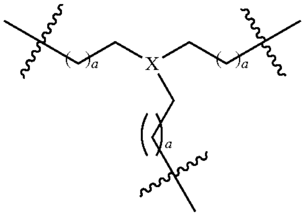,

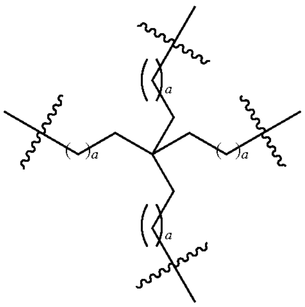,

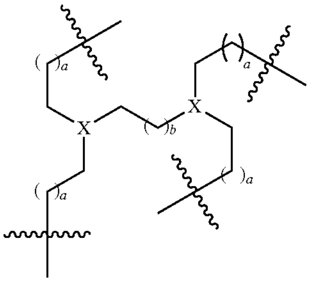,

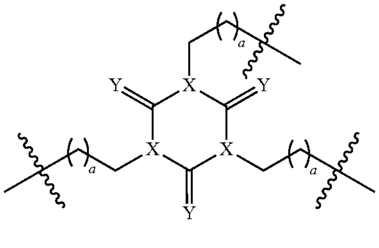;

wherein $R^6$, $R^7$, $R^8$ and $R^9$ are each independently selected from H, C1-C24 alkyl, C1-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl, substituted carbocyclyl, substituted heterocyclyl, substituted aryl, substituted heteroaryl,

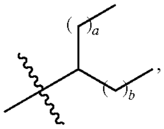,

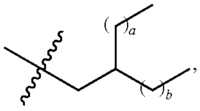,

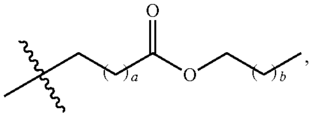,

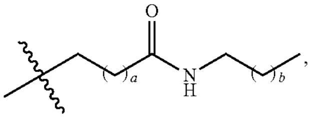,

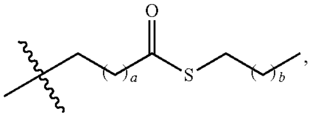,

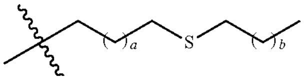,

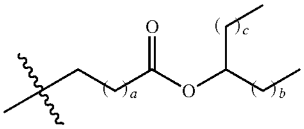,

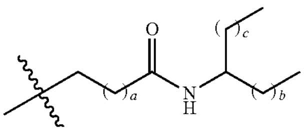,

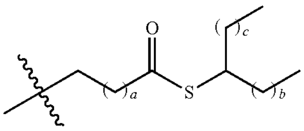,

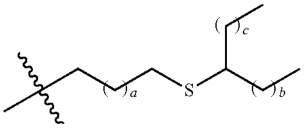,

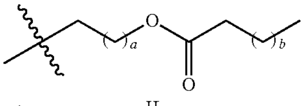,

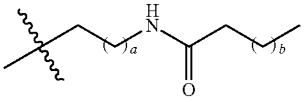,

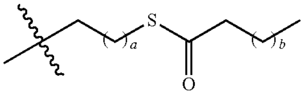,

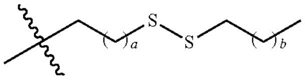,

-continued

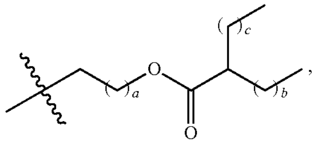

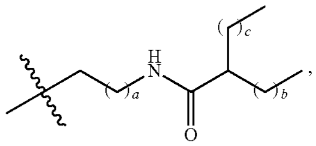

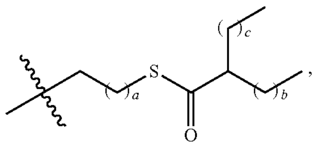

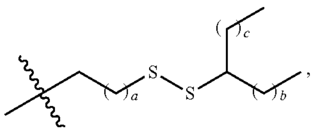

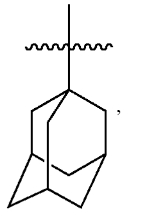

a, b, c and d are each independently an integer from 0-24;

each E is independently selected from $CH_2$, NH, O, or S;

each X is independently selected from CH or N;

each Y is independently selected from $CH_2$, NH, O, or S;

each Z is independently selected from CH or N.

46. A method for synthesizing a modular lipid of Formula VIII, IX and X comprising performing the following four component reaction:

VIII

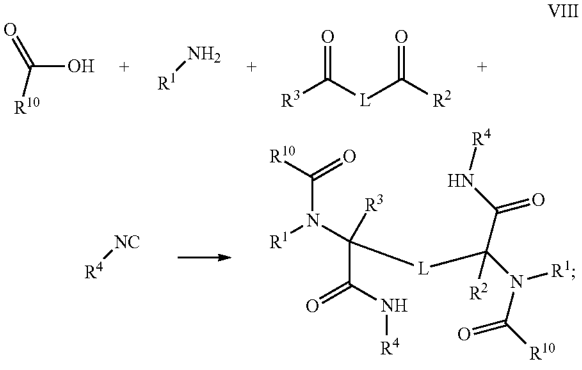

IX

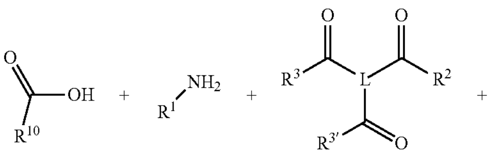

-continued

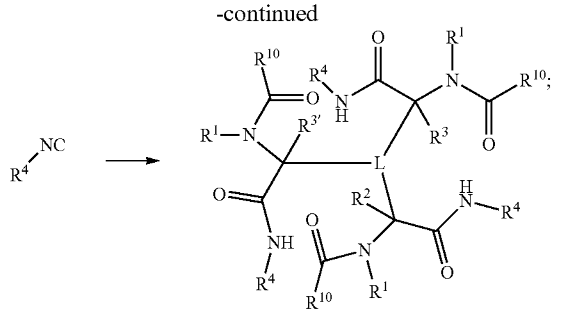

or

X

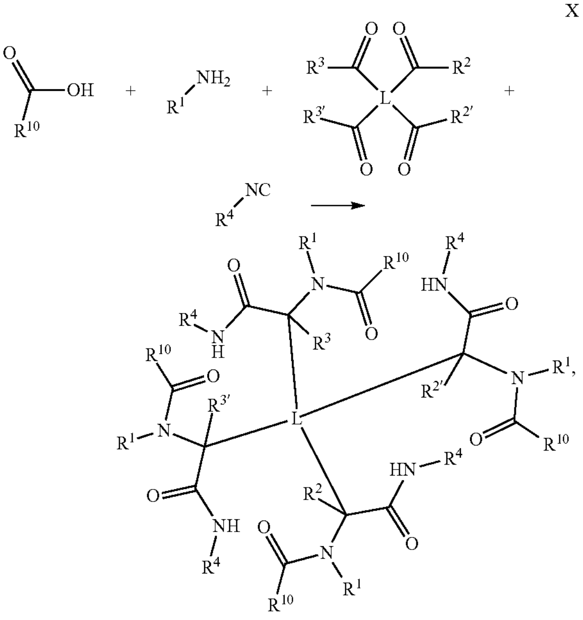

or a salt or isomer thereof, wherein each $R^1$, $R^4$ and $R^{10}$ is independently selected from $C_2$-$C_{24}$ alkyl, $C_2$-$C_{24}$ alkenyl, $C_2$-$C_{24}$ alkynyl, substituted $C_2$-$C_{24}$ alkyl, substituted alkenyl, substituted alkynyl, substituted acyl, substituted carbocyclyl, substituted heterocyclyl, substituted aryl, substituted heteroaryl, poly(ethylene glycol) (PEG),

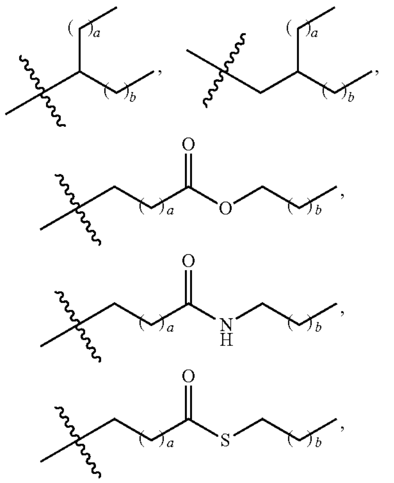

-continued
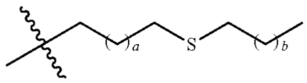,
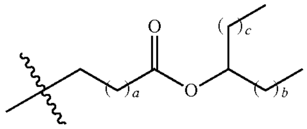,
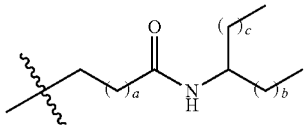,
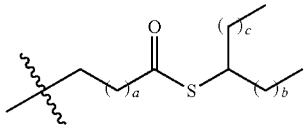,
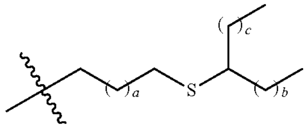,
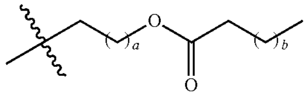,
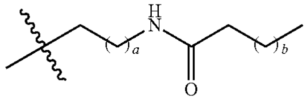,
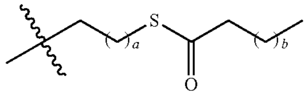,
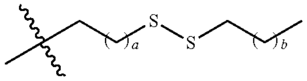,
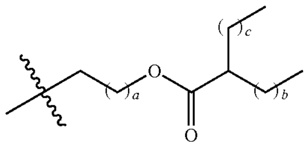,
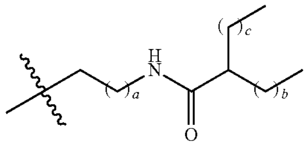,
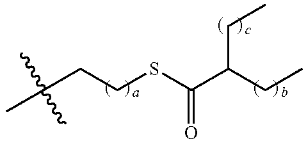,
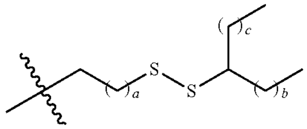,
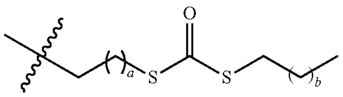,
-continued
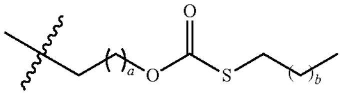,
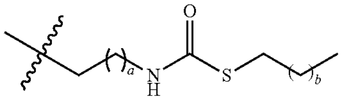,
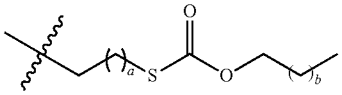,
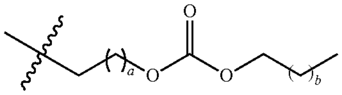,
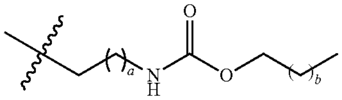,
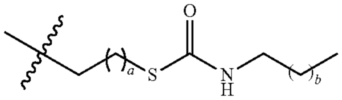,
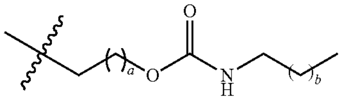,
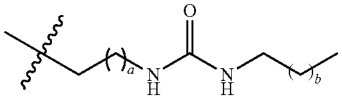,
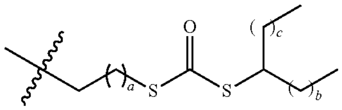,
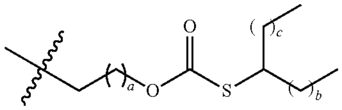,
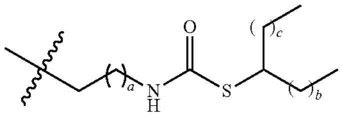,
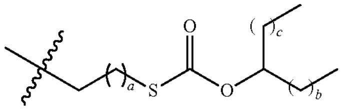,
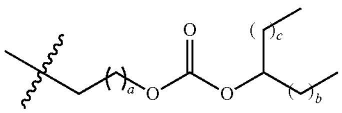,
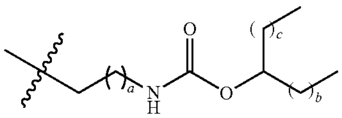,
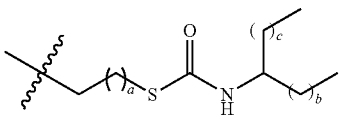,
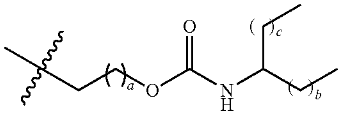, -continued
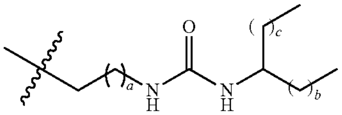
,
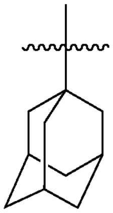
,
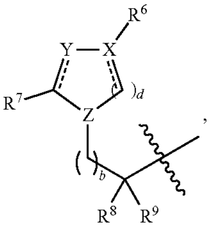
,
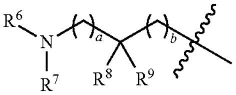
each $R^2$, $R^{2'}$, $R^3$ and $R^{3'}$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl, poly(ethylene glycol) (PEG) and
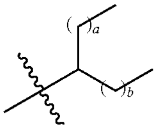
,
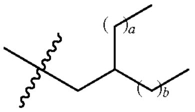
,
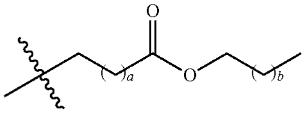
,
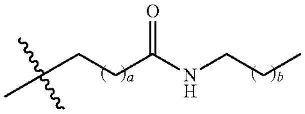
,
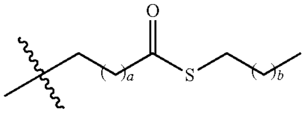
,
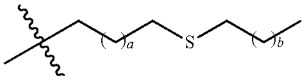
,
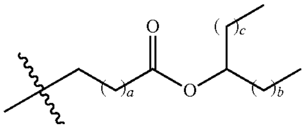
,
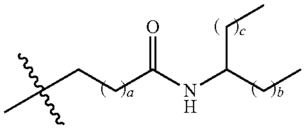
,
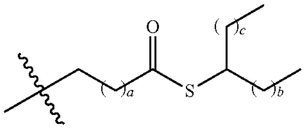
,
-continued
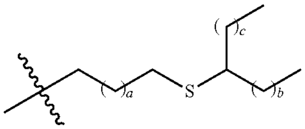
,
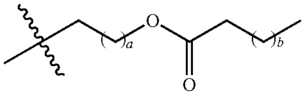
,
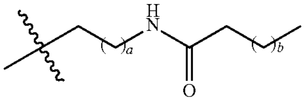
,
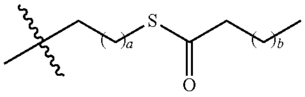
,
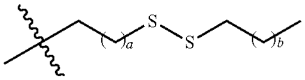
,
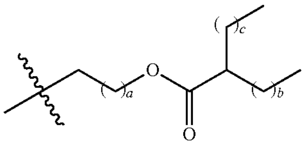
,
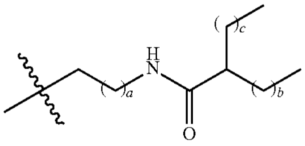
,
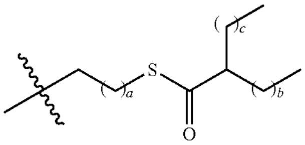
,
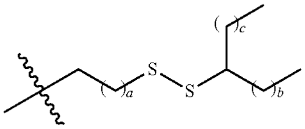
,
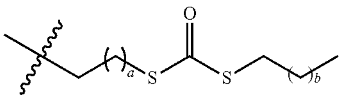
,
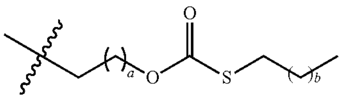
,
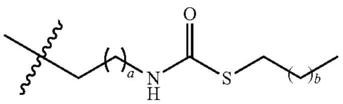
,
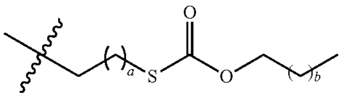
,
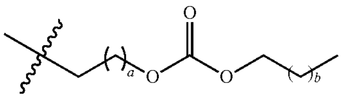
,
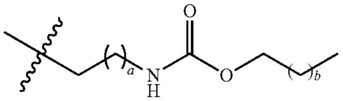
, -continued
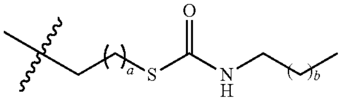 ,
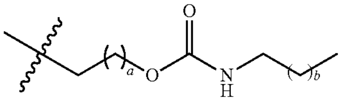 ,
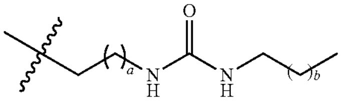 ,
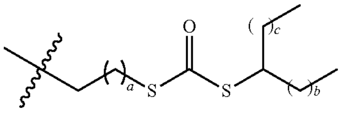 ,
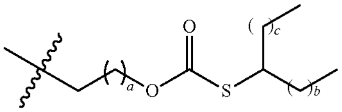 ,
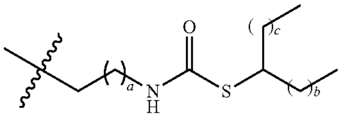 ,
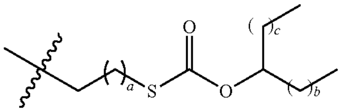 ,
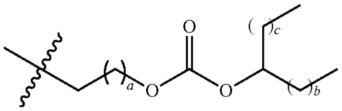 ,
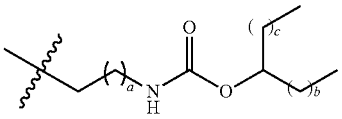 ,
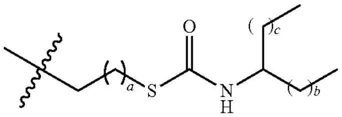 ,
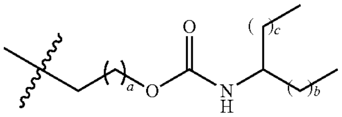 ,
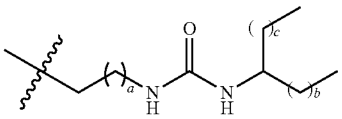 , 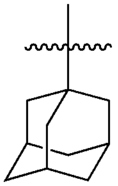 ,
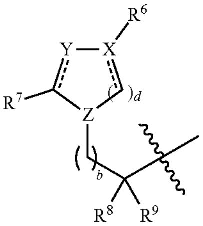 , 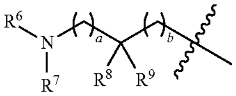 ;
each L is independently selected from alkyl, alkenyl, alkynyl, substituted alkyl, substituted alkenyl, substituted alkynyl, substituted acyl, substituted carbocyclyl, substituted heterocyclyl, substituted aryl, substituted heteroaryl, poly (ethylene glycol) (PEG) and
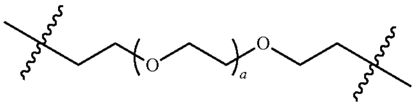 ,
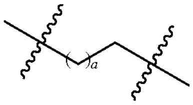 , 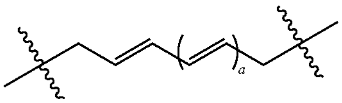 ,
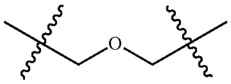 , 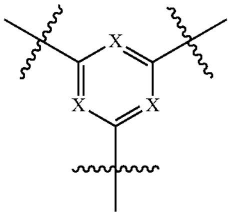 ,
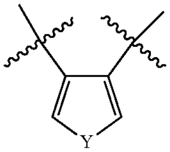 , 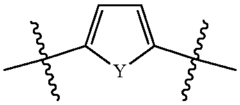 ,
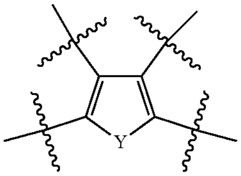 , 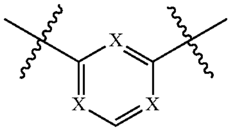 ,
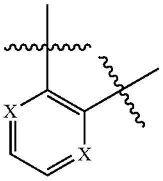 , 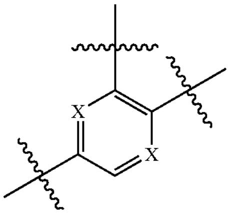 ,
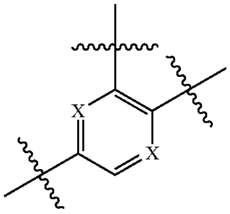 , 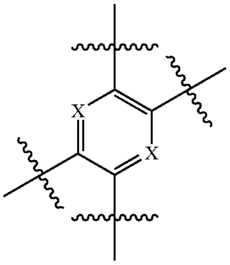 , -continued

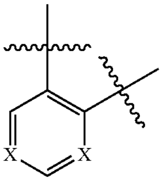,
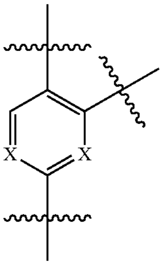,

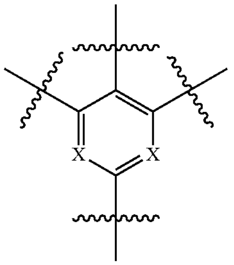,
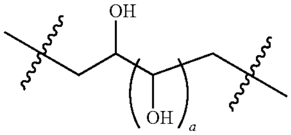,

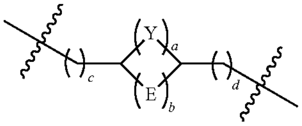,

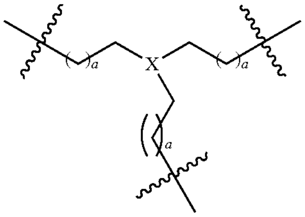,

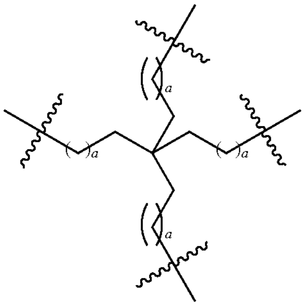,

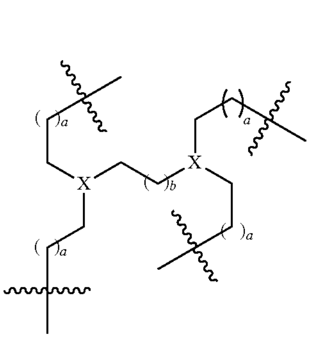,

-continued

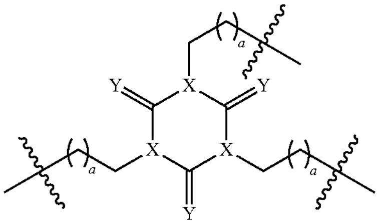;

wherein $R^6$, $R^7$, $R^8$ and $R^9$ are each independently selected from H, C1-C24 alkyl, C1-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl, substituted carbocyclyl, substituted heterocyclyl, substituted aryl, substituted heteroaryl,

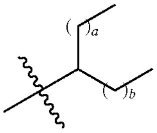,
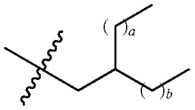,

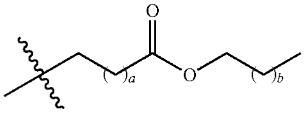,

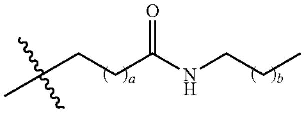,

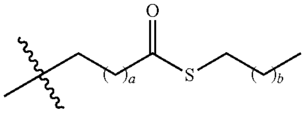,

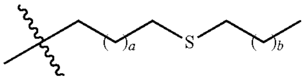,

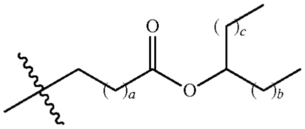,

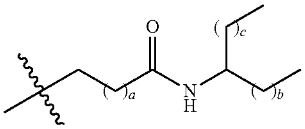,

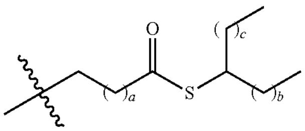,

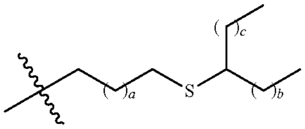,

-continued

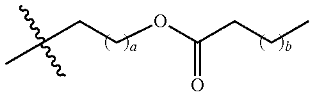
,

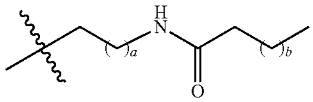
,

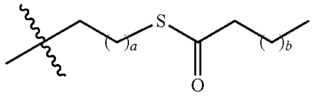
,

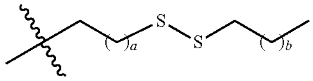
,

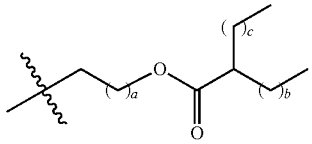
,

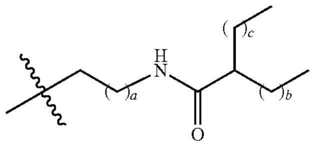
,

-continued

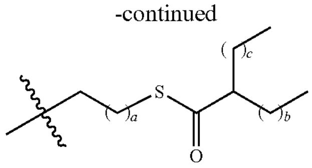
,

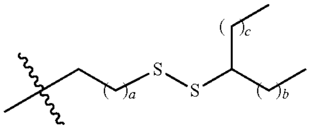
,
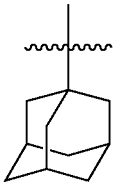
, a, b, c and d are each independently an integer from 0-24;

each E is independently selected from $CH_2$, NH, O, or S;

each X is independently selected from CH or N;

each Y is independently selected from $CH_2$, NH, O, or S; and each Z is independently selected from CH or N.

47. A modular lipid comprising two or more functional groups and at least one linker between at least two functional groups, wherein the functional groups are selected from a cationic or ionizable lipid, a phospholipid, a saccharide lipid, a lipid raft, a stabilizer lipid, a bipolar compound having hydrophobic and hydrophilic ends, a steric group, a sterol group, a sterol-containing group, a sterol derivative group, a folate-containing group, an N-acetylgalactosamine (GalNAc)-containing group, an oligopeptide group, an oligonucleotide group, or a combination thereof.

48. The modular lipid of item 47, wherein the lipid is:

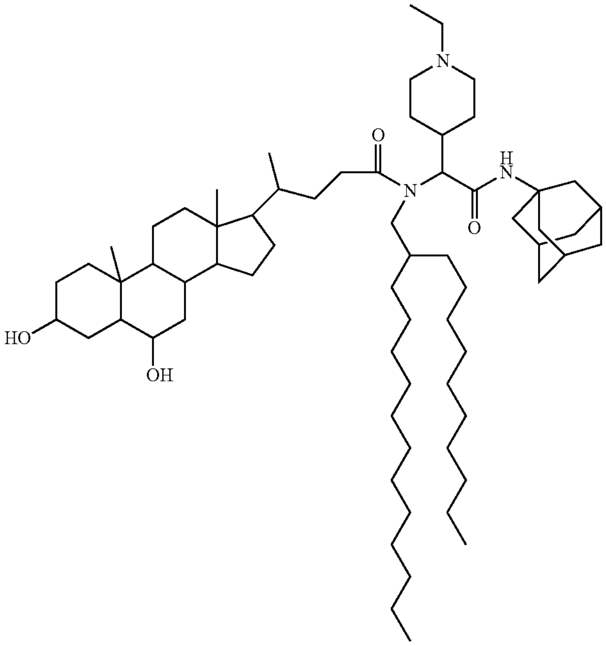

-continued
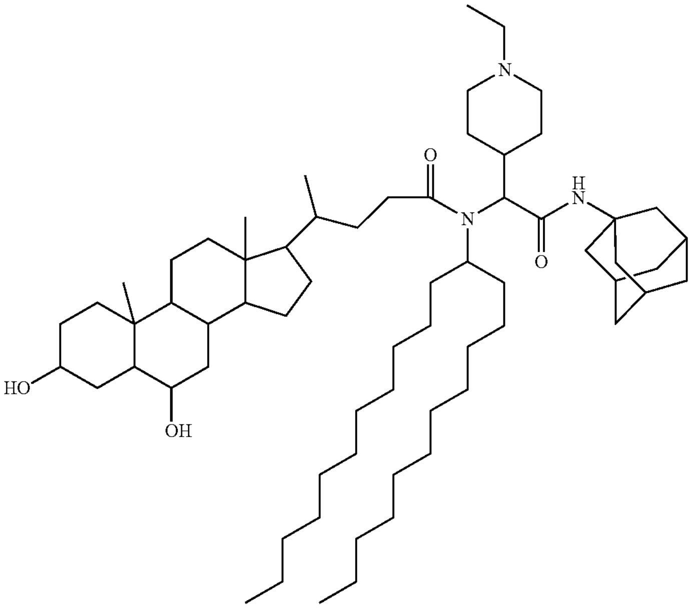
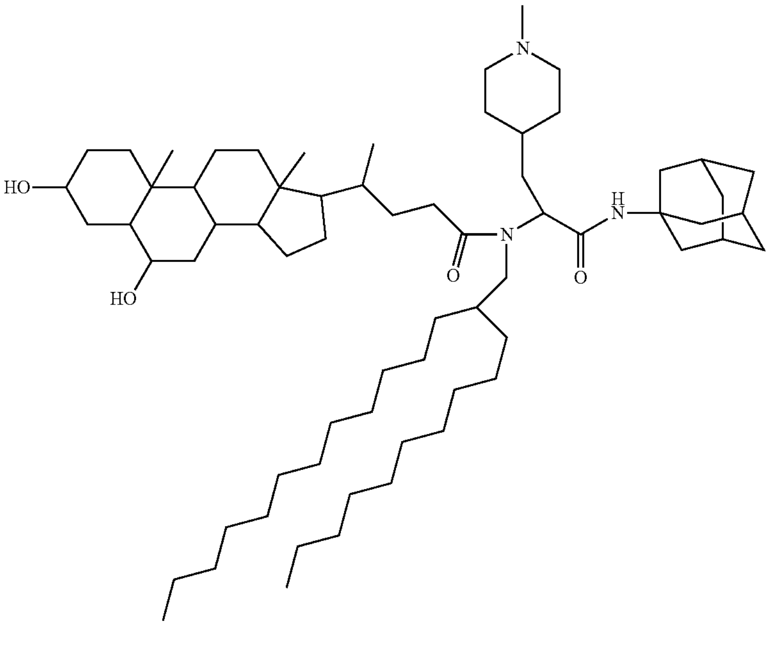

-continued
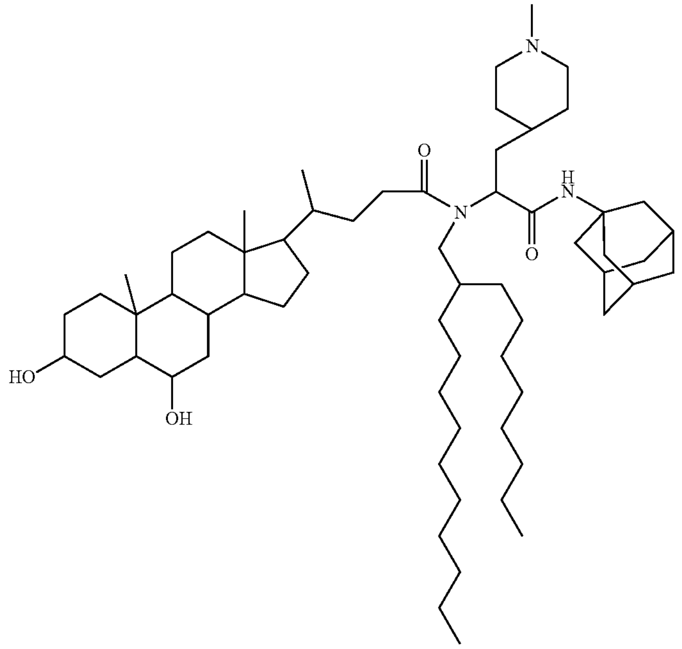
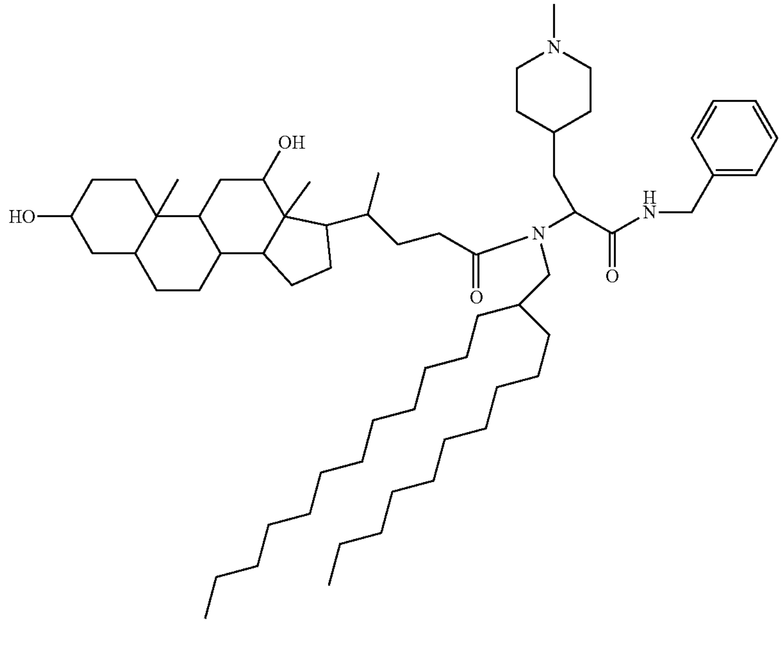

-continued
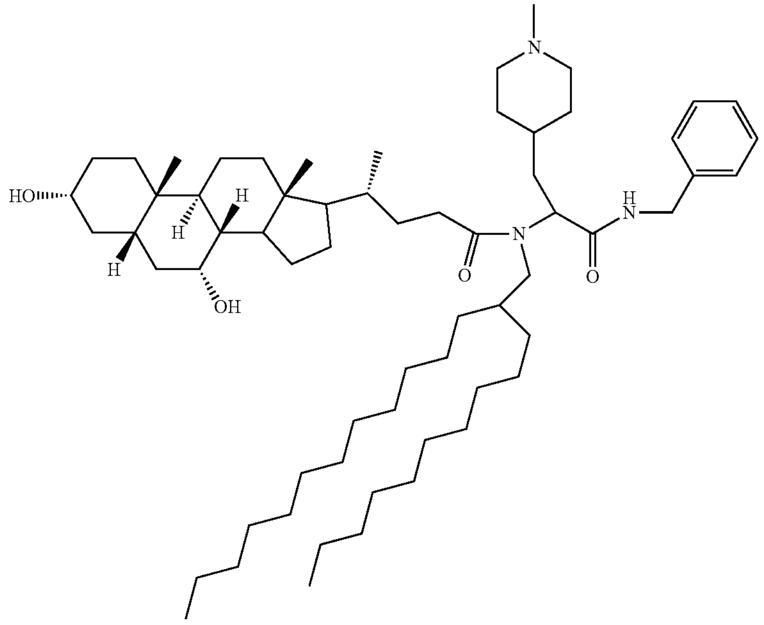
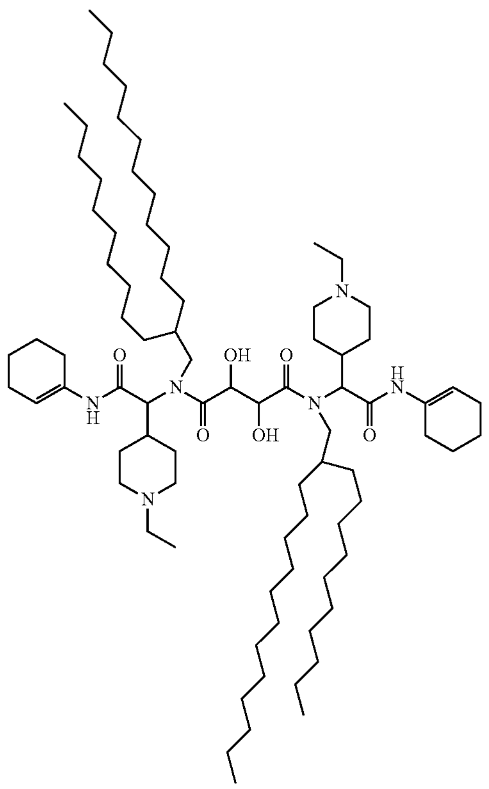

-continued
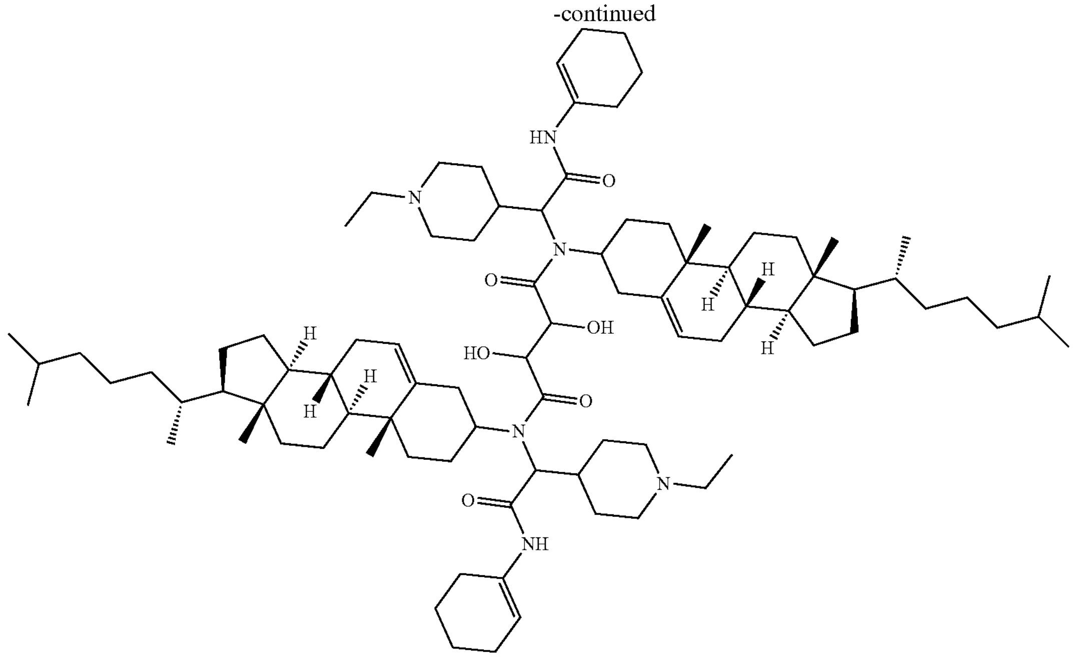
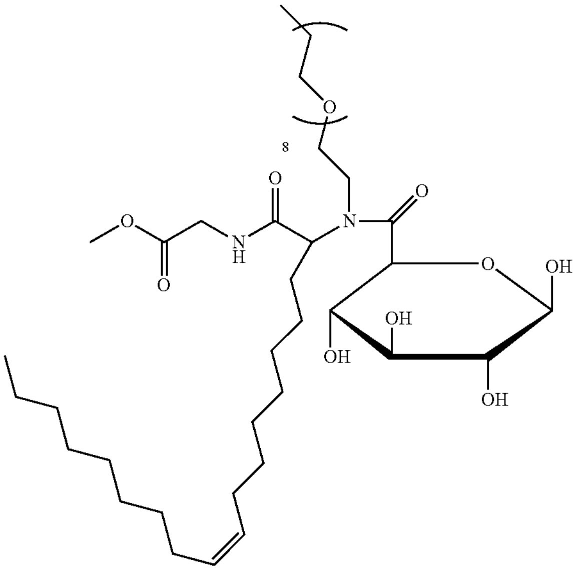
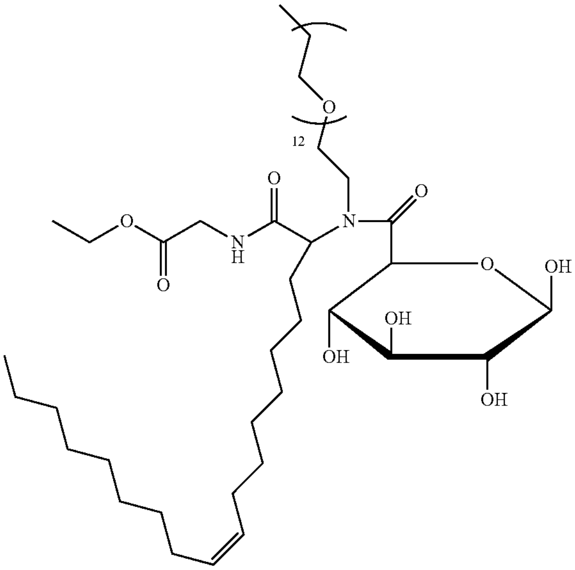
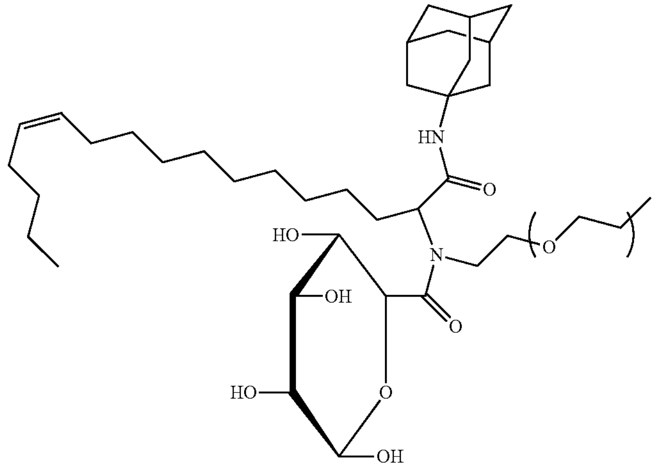

-continued
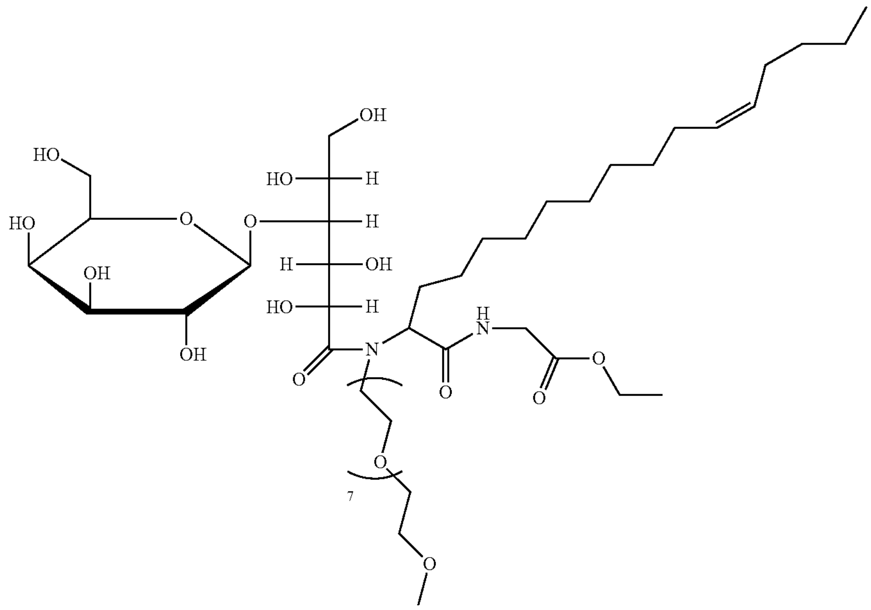
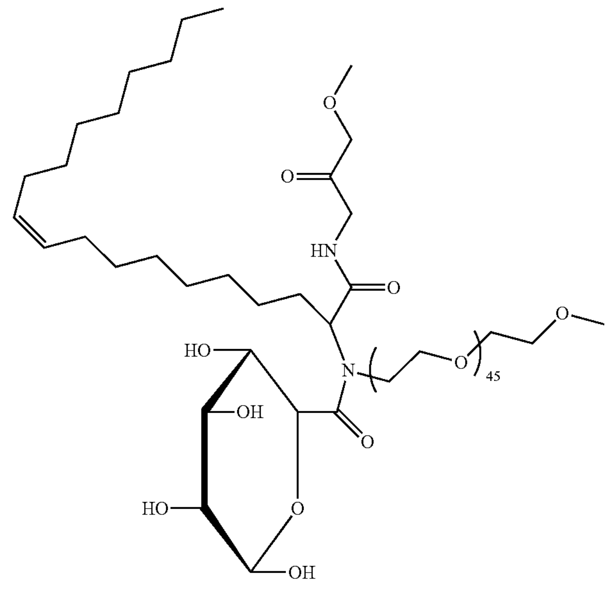

-continued
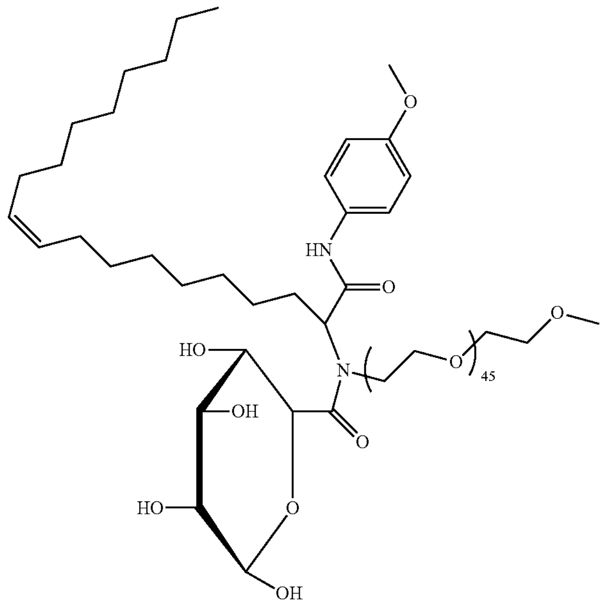
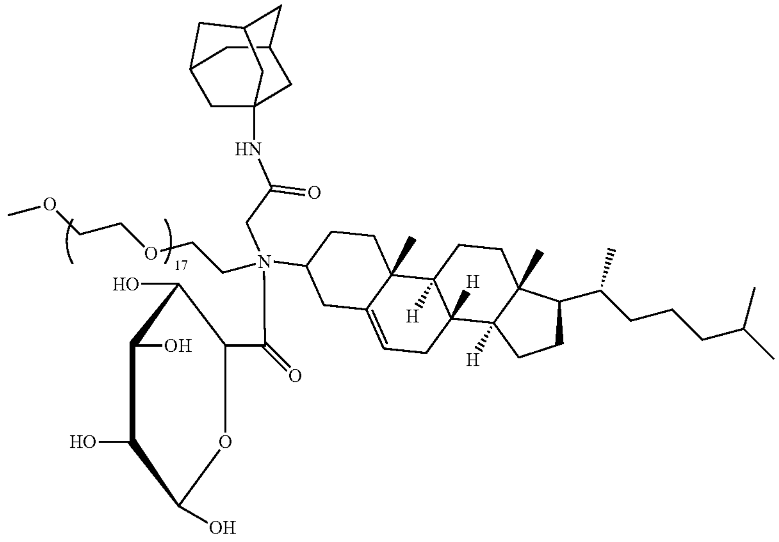
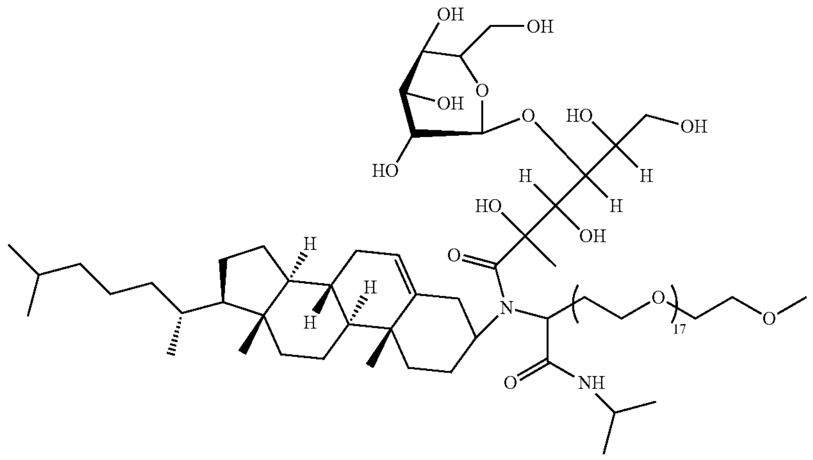

-continued
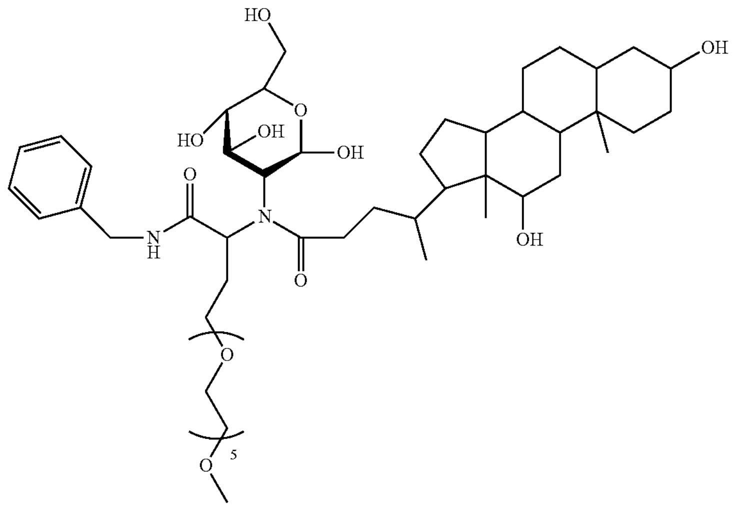
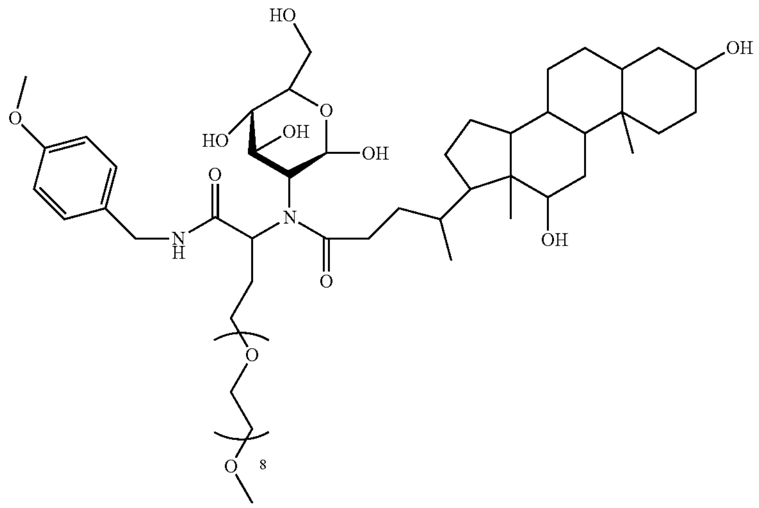
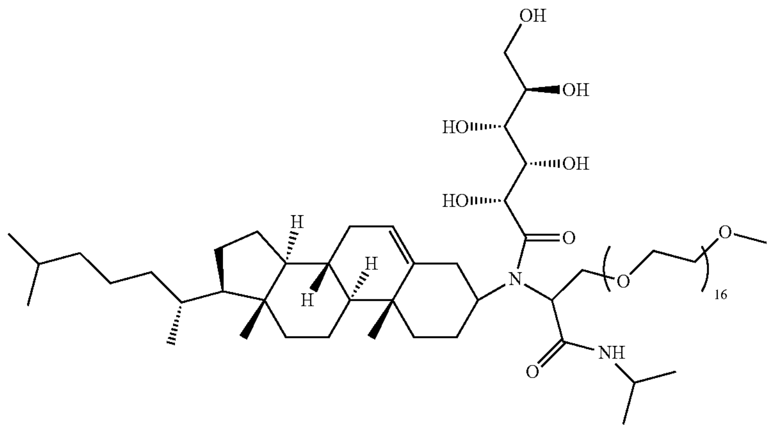

-continued
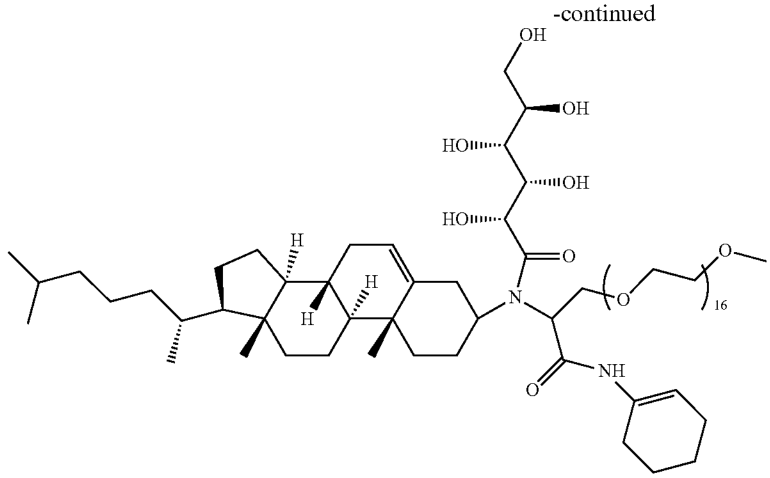
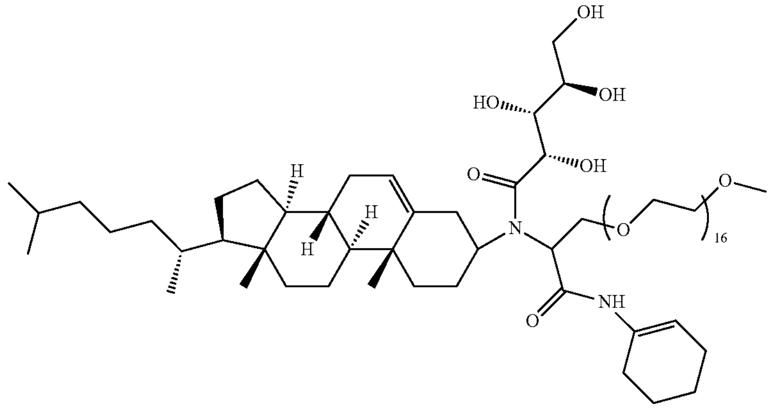
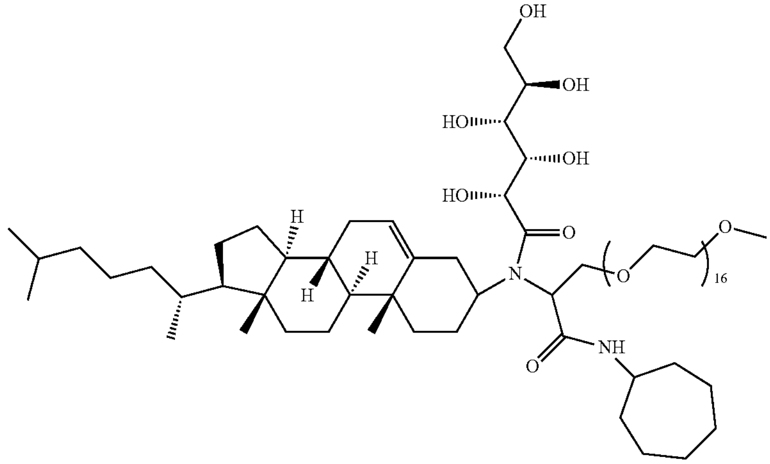

-continued

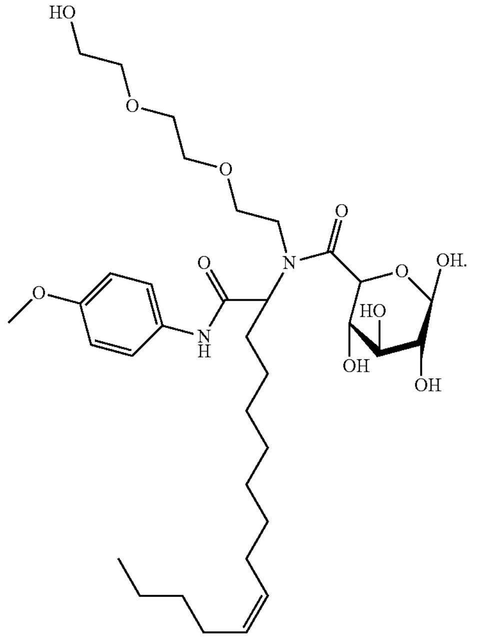

49. A nanoparticle composition comprising a lipid of any one of items 8-17 and 23-33 or any combination thereof.
50. The nanoparticle composition of item 49, further comprising a modular lipid component of any one of items 44 and 47-48.
51. The nanoparticle composition of item 49 or item 50, comprising a modular lipid component, a stabilizer lipid component, and/or a phospholipid component, optionally wherein the nanoparticle composition is a two-lipid composition or a three-lipid composition.
52. The nanoparticle composition of item 51, wherein the modular lipid component comprises a linker, a cationic ionizable group and a lipid raft group.
53. The nanoparticle composition of any one of items 49-52, wherein the stabilizer lipid component is the saccharide lipid compound of any one of items 8-17 and 23-32 or a PEG lipid.
54. The nanoparticle composition of any one of items 49-53, wherein the stabilizer lipid component is a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.
55. The nanoparticle composition of any one of items 49-54, wherein the phospholipid component comprise 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanol amine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, or a mixture thereof.
56. The nanoparticle composition of any one of items 1-7 or 49-55, wherein the nanoparticle composition further comprises a biologically active agent.
57. A pharmaceutical composition comprising the nanoparticle composition of any one of items 1-7 or 49-56 and a pharmaceutically acceptable carrier.
58. A method of delivering a biologically active agent to a cell, the method comprising administering to a subject the nanoparticle composition of any one of items 1-7 or 49-56, said administering comprising contacting the cell with the nanoparticle composition, whereby the biologically active agent is delivered to the cell.
59. A method of delivering a biologically active agent to a cell, the method comprising administering the pharmaceutical composition of item 57 to a subject.
60. A method of producing a polypeptide of interest in a cell, the method comprising contacting the cell with the nanoparticle composition of item 56, wherein the biologically active agent is a mRNA encoding the polypeptide of interest, whereby the mRNA is capable of being translated in the cell to produce the polypeptide of interest.
61. A method of modulating the expression of an endogenous nucleic acid in a cell, the method comprising contacting the cell with the nanoparticle composition of item 56, wherein the biologically active agent is a siRNA capable of binding to the endogenous nucleic acid, whereby the siRNA is capable of modulating the expression of the endogenous nucleic acid.

62. A method of modulating the expression of an endogenous nucleic acid in a cell, the method comprising contacting the cell with the nanoparticle composition of item 56, wherein the biologically active agent is an antisense RNA capable of binding to the endogenous nucleic acid, whereby the antisense RNA is capable of modulating the expression of the endogenous nucleic acid.
63. A method of treating a disease or disorder in a subject in need thereof, the method comprising administering to the subject a therapeutically effective amount of the nanoparticle composition of any one of items 1-7 or 49-56.
64. A method of formulating the nanoparticle composition of item 56, wherein the nucleic acid is dissolved in a first solution comprising an acidic buffer or neutral buffer and the lipid components are dissolved in a second solution comprising ethanol whereby the nanoparticle is formed by mixing said first solution with said second solution.
65. The method of item 64, wherein the acidic buffer is a citrate buffer.
66. The method of any one of items 64-65, wherein the acidic buffer has a pH of 3-6.
67. The method of any one of items 64-66, wherein the acidic buffer has a pH of 4.5.
68. The method of item 64, wherein the neutral buffer is a PBS.
69. The method of item 64 or item 68, wherein the neutral buffer has a pH of 7-8.
70. The method of any one of items 64 or 68-69, wherein the neutral buffer has a pH of 7.4.

EXAMPLES

Example 1: Saccharide Lipids

The saccharide lipids of the present disclosure were synthesized using four-component chemical reactions as part of a library with more than 10,000 saccharide-lipids. 96 different saccharide lipids, including (III)(a)-(IV)(c), were formulated into mLNPs by mixing the lipid-containing ethanol phase with a mRNA-containing aqueous phase using a pipette. The ethanol phase was prepared by mixing the ionizable lipids (I)b (or (II)e), 1,2-Dioleoyl-sn-glycero-3-phosphoethanolamine (DOPE), and saccharide-lipid at a predetermined molar ratio of 20 (or 30):30 (or 15):40 (or 50) in ethanol. The aqueous phase was prepared in citrate buffer (100 mM, pH 4.5) with GFP-mRNA. The aqueous and ethanol phases were mixed at 3:1 ratio with N:P at 8.4:1 (or 4.2:1) ratio. Transfection efficacy and cell cytotoxicity of the LNPs were assayed in 293 T cells. The LNPs of the present disclosure were found to be effectively transfected in to 293 T cells in vitro and GFP was expressed. The data demonstrated better or comparable transfection efficacies than LNPs currently approved by FDA.

FIG. 1 shows a heat map of high-throughput screening of percent transfection of GFP-self-amplifying mRNA (GFP-saRNA) in to 293T cells in a 96-well plate, wherein the GFP-saRNA was delivered using LNPs formulated with saccharide lipids and the ionizable lipid of Formula (Ib); compared to the percent transfection of GFP-saRNA delivered using 4 component LNPs comprising the ionizable lipid of Formula (I), a saccharide lipid, a phospholipid, and a PEG-lipid. The saccharide lipids of Formula (III) (a) corresponds to position E2 of the 96-well plate, the saccharide lipid of Formula (III) (b) corresponds to position F11, and the saccharide lipid of Formula (III) (c) corresponds to position C6.

Figure 2:
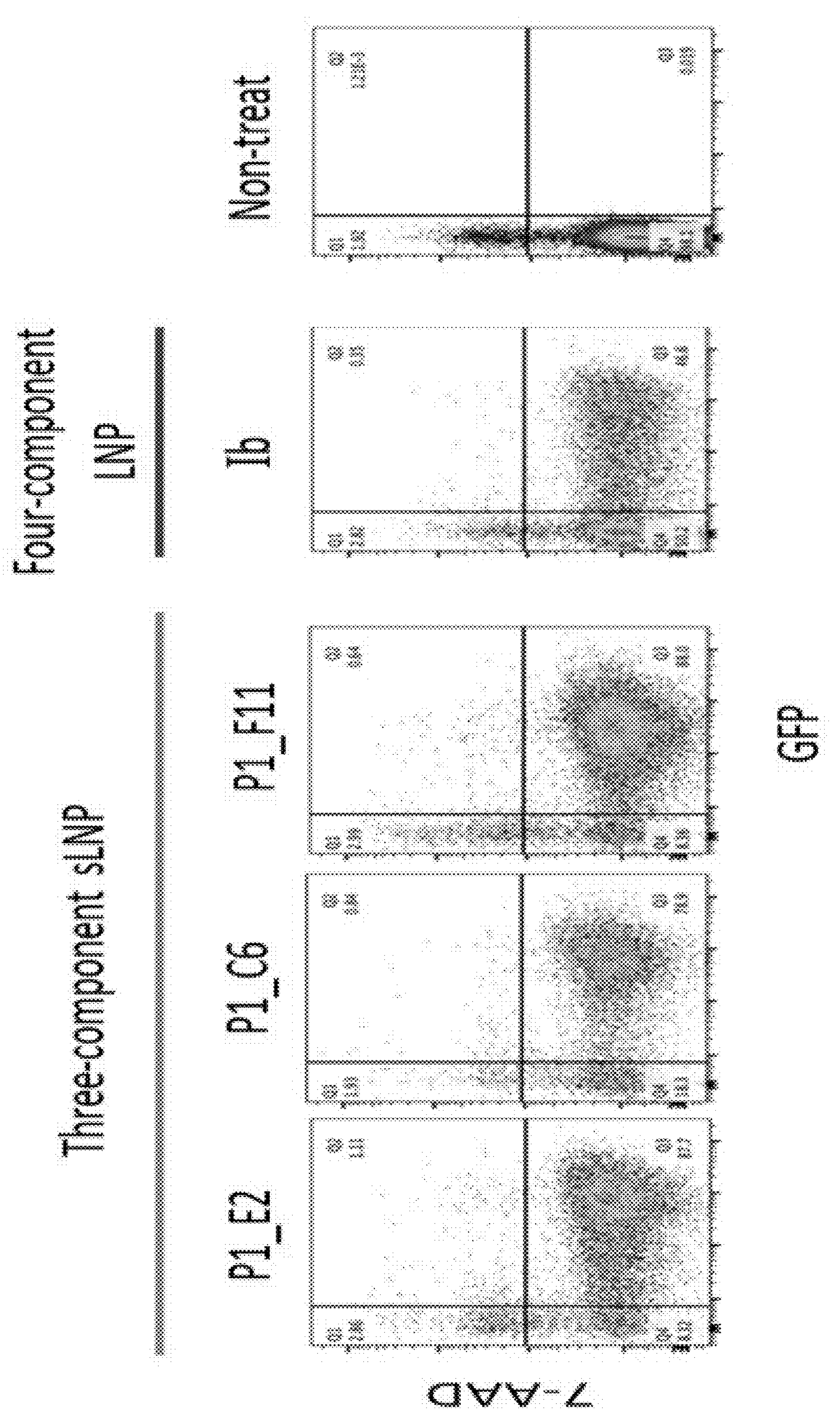
FIG. 2 shows in vitro expression of GFP-saRNA in 293T cells, which were transfected using mLNPs formulated with a saccharide lipid, including the saccharide lipids of Formula (III)(a) (also referred to as P1_E2), (III)(b) (also referred to as P1_F11) and (III)(c) (also referred to as P1_C6), and the ionizable lipid of Formula (Ib).

FIG. 2 shows in vitro expression of GFP-saRNA in 293T cells, which were transfected using LNPs formulated with a saccharide lipid, including the saccharide lipids of Formulae (III)(a) (P1_E2), (III)(b)(P1_F11) and (III)(c) (P1_C6), and the ionizable lipid of Formula (Ib).

Figure 3:
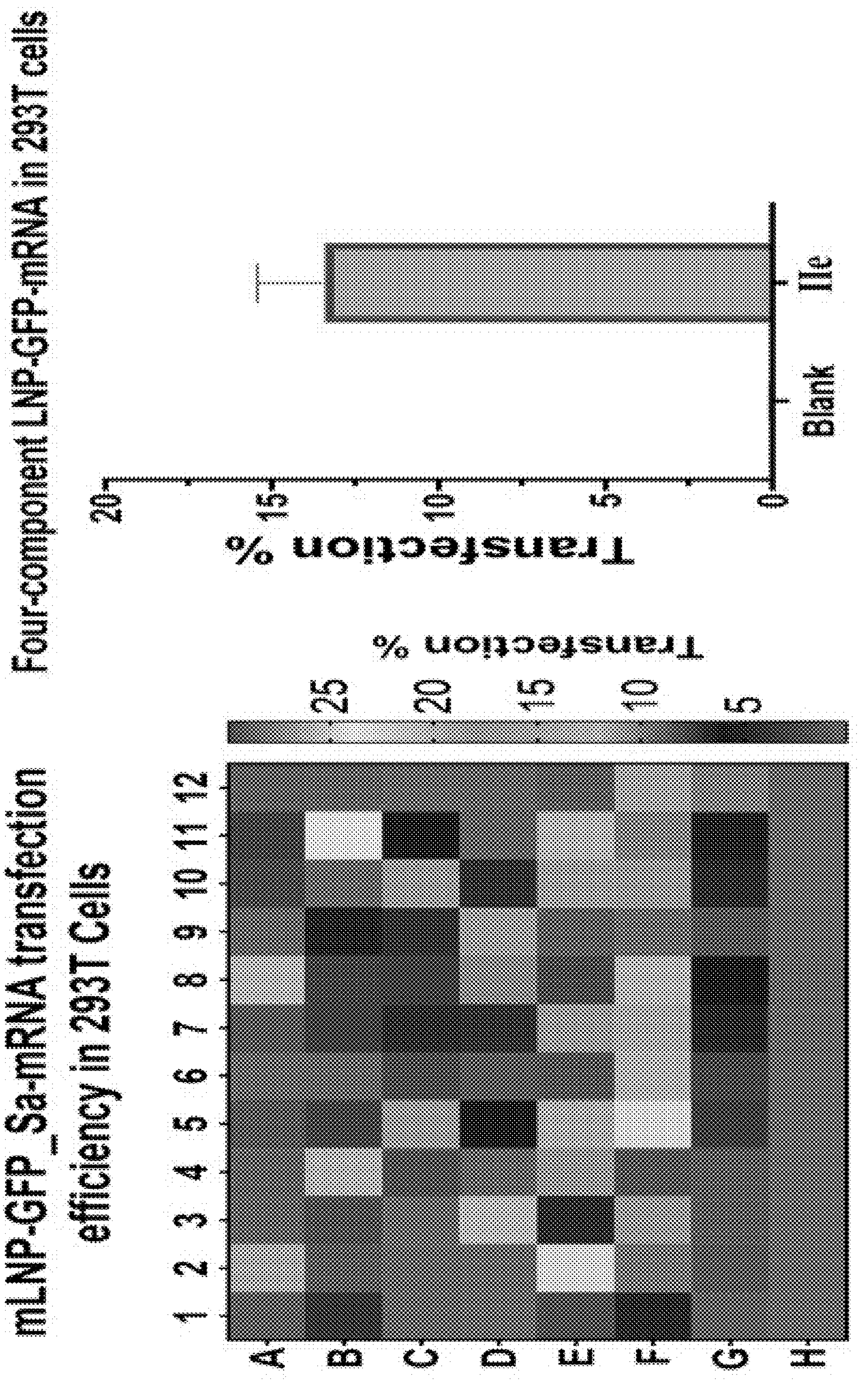
FIG. 3 shows a heat map of high-throughput screening of percent transfection of GFP-self-amplifying mRNA (GFP-saRNA) in to 293T cells in a 96-well plate, wherein the GFP-saRNA was delivered using mLNPs formulated with saccharide lipids and the ionizable lipid of Formula (IIe); compared to the percent transfection of GFP-saRNA delivered using 4 component LNPs comprising the ionizable lipid of Formula (IIe), a structural lipid, a phospholipid, and a PEG-lipid. The saccharide lipids of Formula (III)(d) corresponds to position E8 of the 96-well plate, the saccharide lipid of Formula (III)(e) corresponds to position D8, and the saccharide lipid of Formula (III)(f) corresponds to position D9.

FIG. 3 shows a heat map of high-throughput screening of percent transfection of GFP-self-amplifying mRNA (GFP-saRNA) in to 293T cells in a 96-well plate, wherein the GFP-saRNA was delivered using LNPs formulated with saccharide lipids and the ionizable lipid of Formula (IIe); compared to the percent transfection of GFP-saRNA delivered using 4 component LNPs comprising the ionizable lipid of Formula (IIe), a saccharide lipid, a phospholipid, and a PEG-lipid. The saccharide lipids of Formula (III)(c) corresponds to position E8 of the 96-well plate, the saccharide lipid of Formula (III)(e) corresponds to position D8, and the saccharide lipid of Formula (III)(f) corresponds to position D9.

Figure 4:
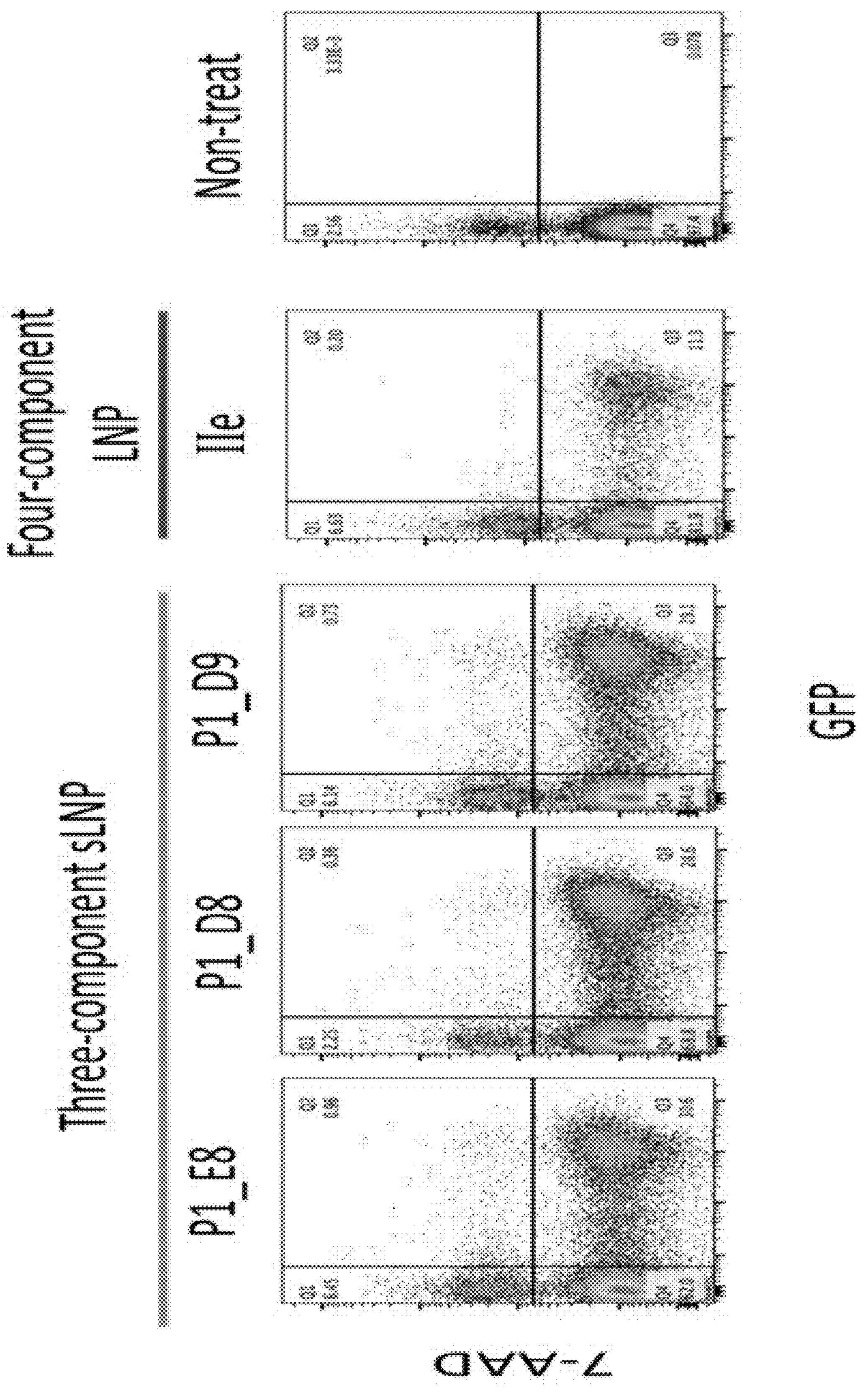
FIG. 4 shows in vitro expression of GFP-saRNA in 293T cells, which were transfected using mLNPs formulated with a saccharide lipid, including the saccharide lipids of Formulae (III)(d) (also referred to as P1_E8), (III)(e) (also referred to as P1_D8) and (III)(f) (also referred to as P1_D9), and the ionizable lipid of Formula (IIe).

FIG. 4 shows in vitro expression of GFP-saRNA in 293T cells, which were transfected using LNPs formulated with a saccharide lipid, including the saccharide lipids of Formulae (III)(d) (also referred to as P1_E8), (III)(e) (also referred to as P1_D8) and (III)(f) (also referred to as P1_D9), and the ionizable lipid of Formula (IIe).

Example 2: Nanoparticles Comprising Modular Lipids

Figure 5:
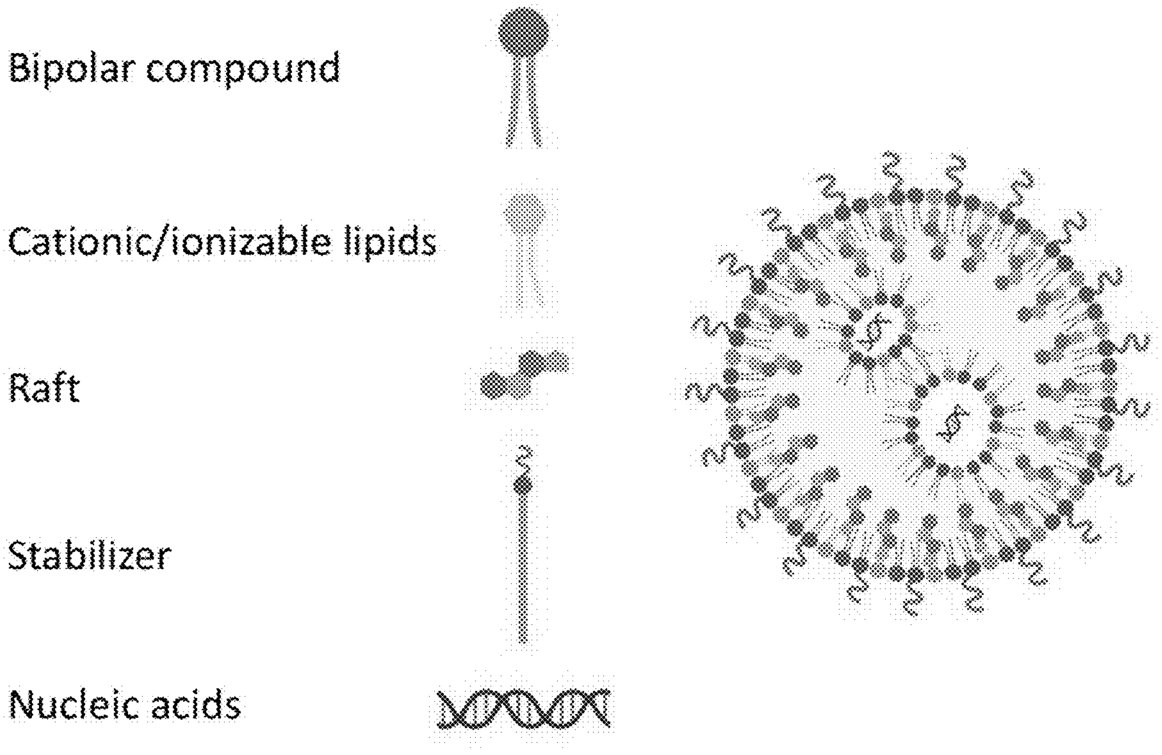
FIG. 5 shows a schematic of a four component nanoparticle comprising bipolar compounds, cationic ionizable lipids, lipid rafts, and stabilizers encapsulating a nucleic acid payload. The bipolar compound, such as a phospholipid or saccharide lipid, aids in nanoparticle formation in water or under physiological conditions, improving encapsulation of the payload, and aids in cellular delivery. Cationic ionizable lipids facilitate nucleic acid encapsulation and mediate endosomal membrane disruption to enable nucleic acid release to the cytosol. The lipid raft, such as a cholesterol or squalene, mediates nanoparticle formation and adjusts membrane fluidity. The stabilizer, such as a PEG-lipid, prevents particle aggregation; improves particle stability during preparation and storage; and modulates immune response against the nanoparticle. Further, some nanoparticles have functional ligands on the surface of the nanoparticles.
Figure 6:
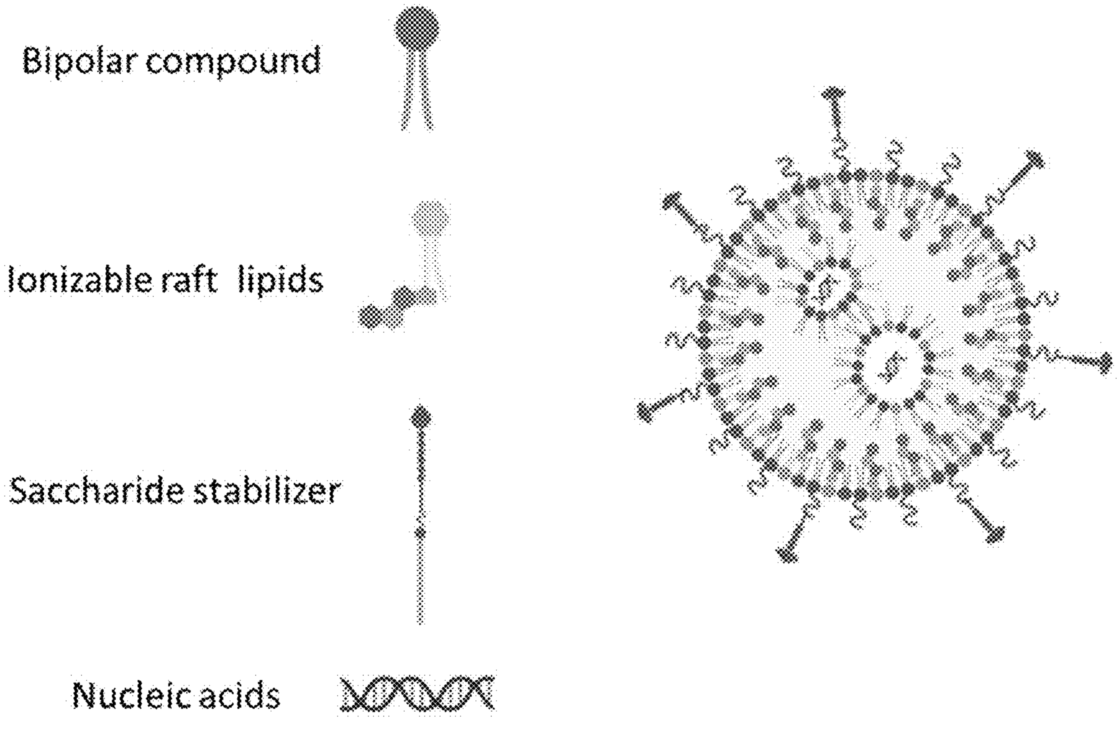
FIG. 6 shows a schematic of a nanoparticle comprising a bipolar compound; a modular lipid comprising a cationic ionizable group and a lipid raft group; a saccharide stabilizer, such as a saccharide lipid; nucleic acid payloads; and functional ligands on the surface of the nanoparticles.

LNPs of the present disclosure comprise a modular lipid, which integrates two or more functions of a traditional lipid component of an LNP as shown, for example, in FIG. 5. Modular lipids P161F5, P161F6, P161F10, P161F12, P287A12, and P287C12 of the disclosure comprise a sterol-containing or sterol derivatives group and a cationic ionizable group. Three component LNPs comprising a modular lipid (P161F5, P161F6, P161F10, P161F12, P287A12 or P287C12); a bipolar compound and a saccharide stabilizer lipid, as shown in FIG. 6 were made. Additionally two component LNPs were made using modular lipid P287A12 and DMG-PEG2000. Both types of LNPs showed effective transfection both in vivo and in vitro as described below.

The ionizable lipids used to formulate the LNPs of the disclosure were synthesized by two-step/one-pot reaction with a molar ratio of acid/amine/aldehyde/isocyanide at 1:1:1:1. Aldehyde (1 mmol) and amine (1 mmol) were mixed in 3 mL MeOH at room temperature (r.t.) and stirred for one hour, then isocyanide (1 mmol) and acid (1 mmol) were added. The resulting mixture was stirred further overnight. The solvent was removed with Rotary evaporator. Ethyl acetate (100 mL) was added and washed with brine (2×50 mL), dried over $MgSO_4$. Ethyl acetate was removed and the residue was purified by column chromatography using a Combi-Flash Rf system with a silica column (Redisep Gold Resolution, Teledyne, Isco) by gradient elution of CH2Cl2/methanol (0%-40% methanol). Ionizable lipid structure was confirmed by nuclear magnetic resonance spectra of 1H (Bruker AVANCE-400 NMR, Custom NMR Services, Inc.) and/or LC-Mass spectra (Agilent 1100 & 1200 HPLC/MS, Organix, Inc).

The modular lipids of the disclosure were mixed with at least one of ionizable lipid, DOPE, cholesterol (Chol), and/or DMG-PEG2000 in ethanol at a predetermined molar ratio. Ionizable lipid: SamRNA molar ratio of 6:1 was used to prepare an organic phase. SamRNA-LUC or SamRNA-GFP was diluted in 50 mM citrate buffer (pH 4.5, Fisher) or PBS (pH 7.4, Fisher) to prepare an aqueous phase. The SamRNA was stored at −80° C. and was thawed on ice prior to use. The ethanol and aqueous phases were mixed at a 1:3 ratio by pipette. The resultant LNPs were purified by ultra-filtration (100,000 cut-off, MilliporeSigma™ Amicon™ Ultra-15 Centrifugal Filter Units) at 4° C. prior to injection.

Reagents used in the reactions described above: Fetal bovine serum (FBS) and Ribogreen were purchased from Fisher Scientific. DOPE, DMG-PEG2000, and Cholesterol were purchased from Avanti Polar Lipids. The chemical reagents were purchased from Sigma-Aldrich, Millipore Sigma, Fisher Scientific, TCI America, Ambeed, Cayman-Chem, A2B Chem, BLD pharm, Aaron Chemicals, AAblocks, 1clickchemistry, Enamine, Aurum, Achemblock, BroadPharm, ChemShuttle, Biopharma PEG.

LNPs comprising modular lipids with a saccharide group were shown to have improved transfection efficiencies in Example 1 and LNPs comprising a ligand receptor functional group, such as GalNAc have improved targeting functions.

Example 3: Modular Lipid Library

Figure 7:
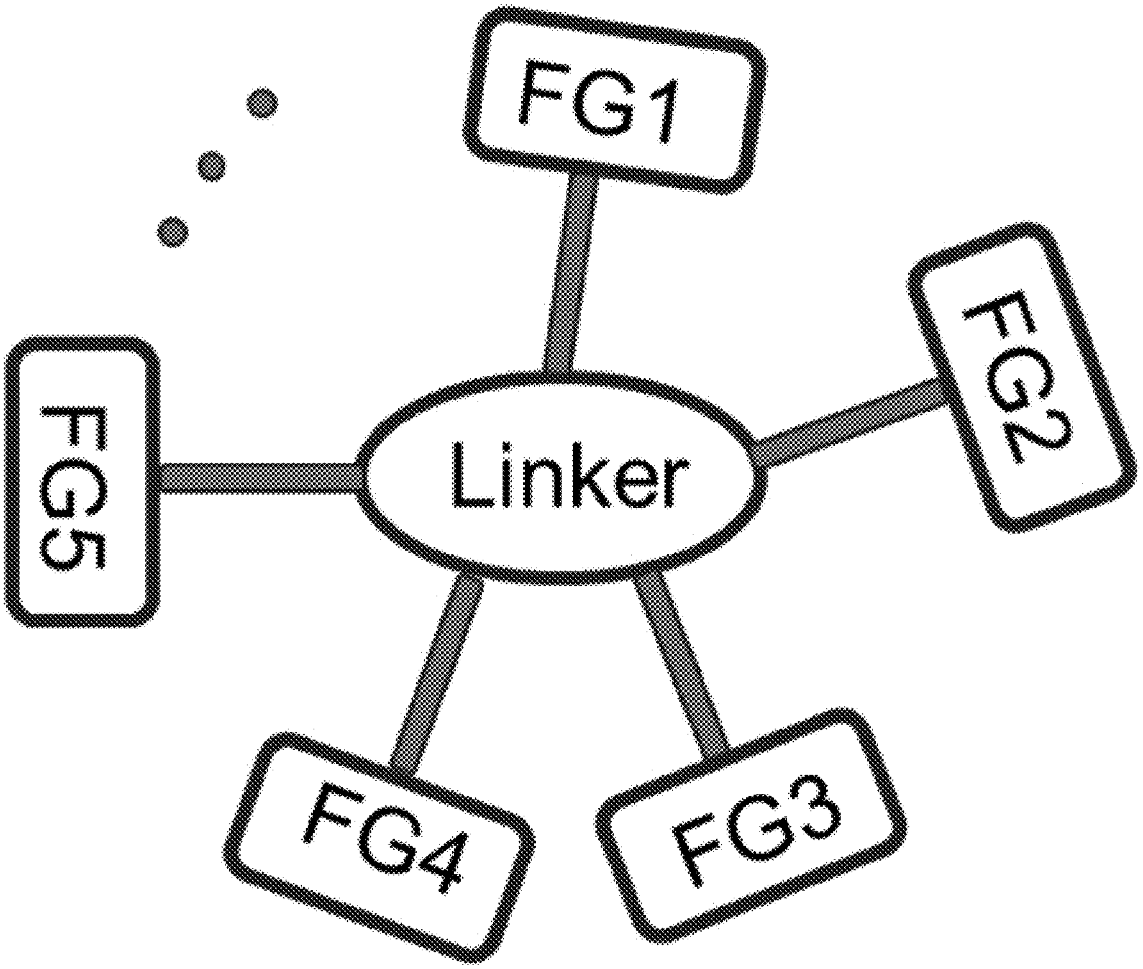
FIG. 7 shows a schematic of a modular lipid comprising one linker covalently linked to 5 functional groups. Functional groups include, but are not limited to lipid groups, cationic ionizable groups, steric groups, lipid raft groups, sterol groups, saccharide groups, folate groups, GalNAc groups, oligopeptide groups, oligonucleotide groups.

A multifunctional modular lipid library was designed. The modular lipids of the library combined two or more of the traditional LNP lipid components into one modular lipid. LNPs comprising modular lipids of the modular lipid library were formulated using with one or two additional components to deliver nucleic acids. The modular lipids of the disclosure contain two or more functional groups (FG) including but are not limited to lipid groups, cationic ionizable groups, steric groups, lipid raft groups, sterol groups, saccharide groups, folate groups, GalNAc groups, oligopeptide groups, and oligo nucleotide groups as shown in FIG. 7. The modular lipids of the multifunctional modular lipid library comprise over 1,000,000 modular lipids synthesized using the four component reaction of the disclosure:

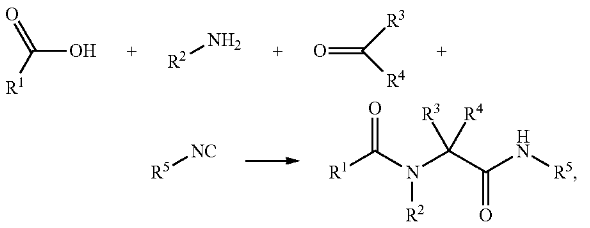

wherein

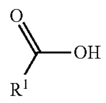

is an acid,

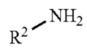

is an amine,

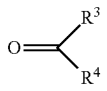

is an aldehyde or a ketone, and

is an isocyanide.

The synthesis reactions were carried out on 96-well plates with a glass insert (Analytical Sales and Services). The amine and aldehyde were first mixed and stirred at room temperature (r.t.), then the acid and isocyanide were added. The reaction was stirred at r.t. overnight. The lipid mixtures were directly used for in vitro high throughput screening of LNP delivery as described below.

Example 4: Transfection Efficiency In Vitro

LNPs containing SamRNA-GFP or SamRNA-LUC were added into 96-well plate at 100 ng/well pre-seeded with HEK293, C2C12 or MC38 cells. After a 24 hour incubation at 37° C. and 5% CO2, the SamRNA-LUC transfection efficiency was measured by plate reader (Perkin Elmer Envision 2104) and GFP SamRNA transfection efficiency was measured by flow cytometry (BD FACSymphony™ A5 SE Cell Analyzer).

Figure 8:
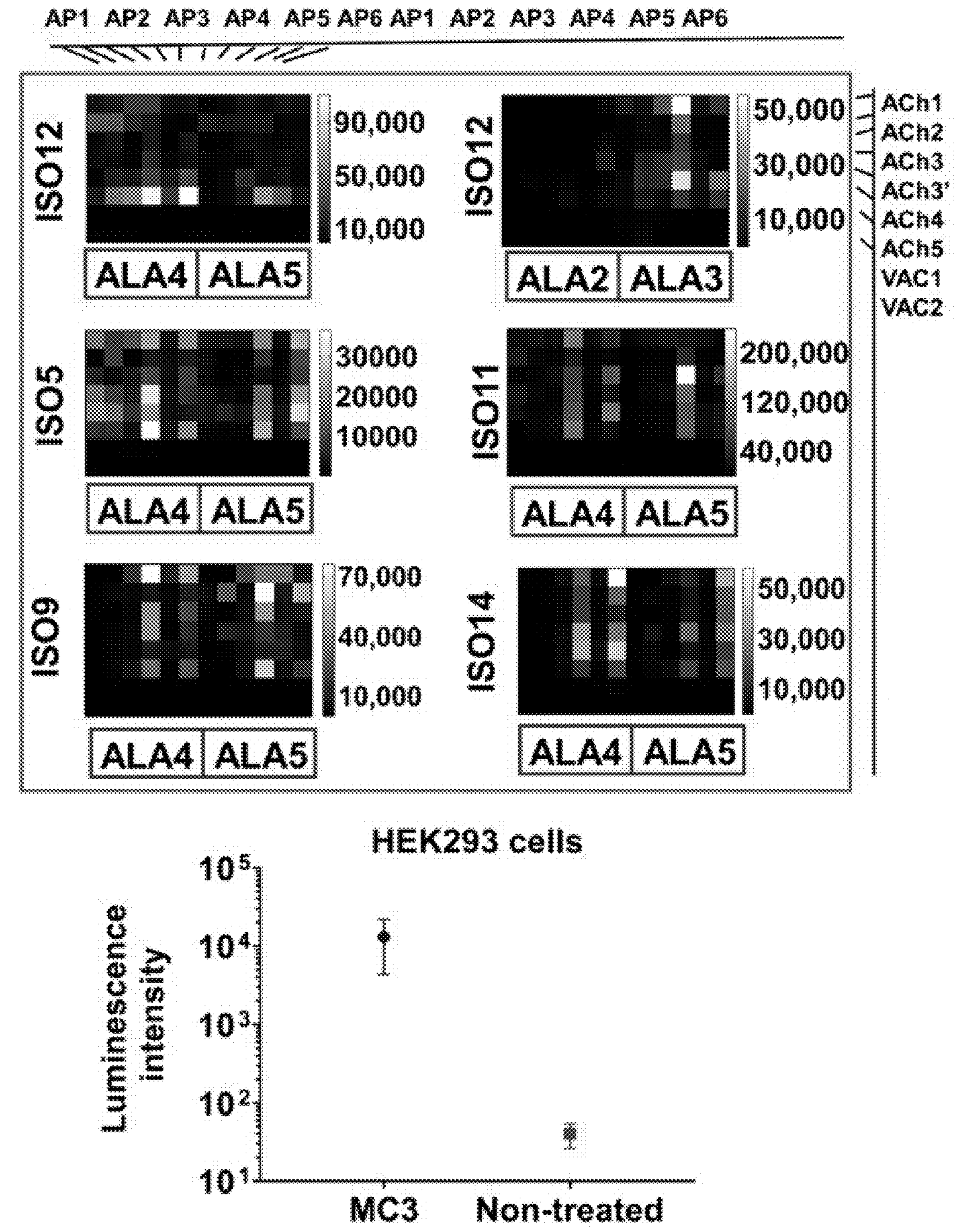
FIG. 8 shows the luminescence intensity of LNPs formulated using MC3 and modular lipids of the disclosure comprising a cationic ionizable group and a lipid raft group, in HEK293 cells shown in 96-well plates (top) or in a graph (bottom). The LNPs were formulated using a modular lipid (ionizable group and sterol derivatives group), DOPE, cholesterol and DMG-PEG2000 (50/38.5/10//1.5 mole ratio) encapsulating self-amplifying mRNA encoding the reporter gene firefly Luciferase (SamRNA-LUC). HEK293 cells were treated with 100 ng of SamRNA-LUC for 24 hours. Each LNP formulation was tested in triplicate and represented as the mean±SD.
Figure 9:
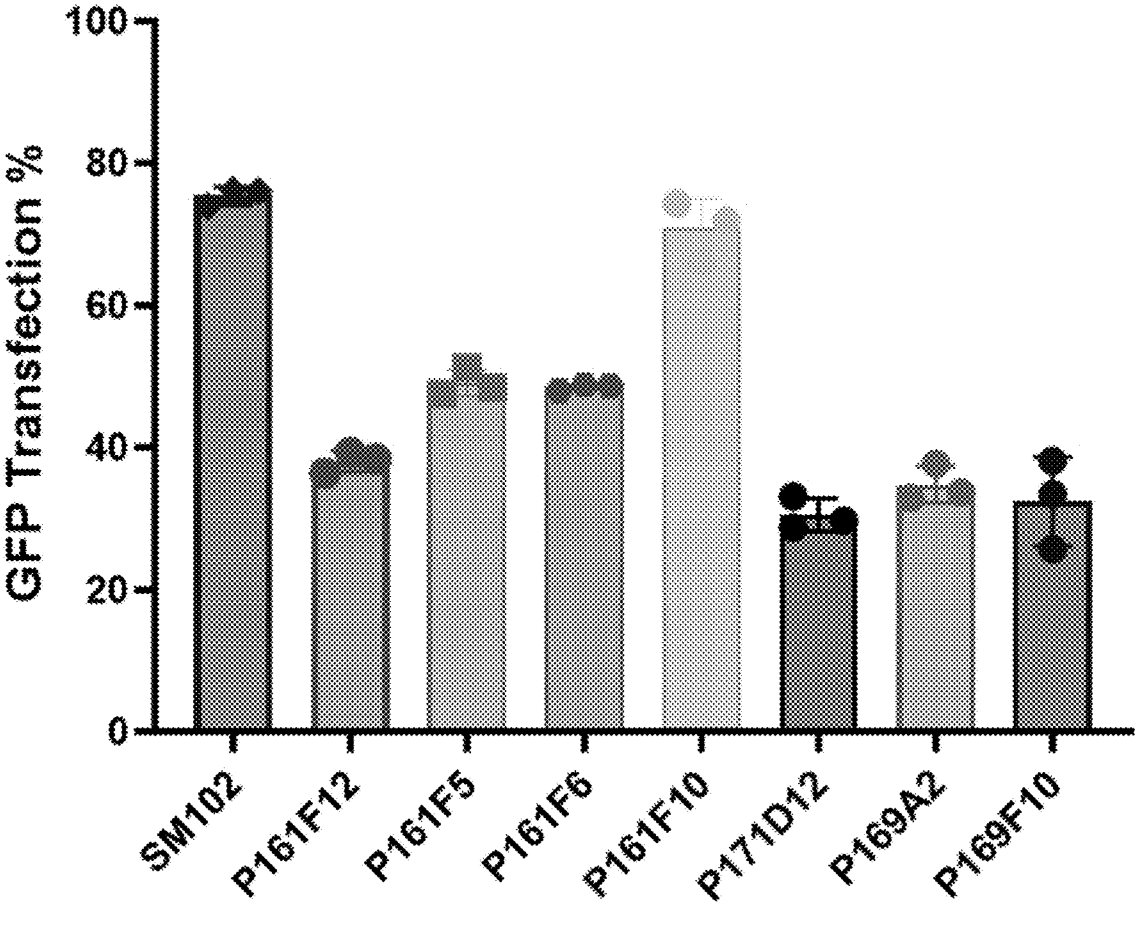
FIG. 9 shows GFP expression in HEK293T cells that were treated using LNPs of the disclosure for 24 hours. The cells were treated with LNPs formulated using a modular lipid of the disclosure comprising a cationic ionizable group, DOPE and DMG-PEG2000 encapsulating SamRNA-GFP. Four-component LNP containing SM102 was used as a control group. Each LNP formulation was tested in triplicate and represented as the mean±SD.

LNPs containing a modular lipid showed increased or comparable transfection efficiency in vitro compared to LNPs formulated using ionizable lipids used in FDA approved therapies ("FDA approved lipids"). Transfection efficacies of LNPs formulated using modular lipids comprising a cholesterol group and a cationic ionizable group were identified using HEK293 cells in 96-well plates. The LNPs (ionizable lipid-Chol/DOPE/DMG-PEG2000, 50-38.5/10/1.5 mole ratio) encapsulated SamRNA-LUC or SamRNA-GFP. HEK293 cells were treated with 100 ng of SamRNA-LUC or 100 ng of SamRNA-GFP for 24 hours. The transfection efficiency of LNP-SamRNA-GFP (FIG. 9) and LNP-SamRNA-LUC (FIG. 8) were determined by flow cytometry and plate reader. LNP formulated with FDA approved ionizable lipids MC3 (FIG. 8) and SM102 (FIG. 9) served as control. Data were collected in triplicate and represented as the mean+S D.

SamRNAs encoding with Firefly luciferase (SamRNA-LUC) and GFP (SamRNA-GFP) were synthesized by Sun-Vax mRNA Therapeutics.

Transfection efficacies of LNPs formulated using modular lipids comprising a sterol derivatives group, a saccharide group, and a PEG group were added into 96-well plates pre-seeded with HEK293 cells. The LNPs were formulated using a cationic ionizable lipid (P54B6, P38D8 or E6), DOPE and a modular lipid (35/40/15 mole ratio) encapsulated SamRNA-LUC or SamRNA-GFP. HEK293 cells were treated with 100 ng of SamRNA-LUC or SamRNA-GFP for 24 hours. The structures of the two of the ionizable lipids used to formulate the LNPs are shown below:

P38D8

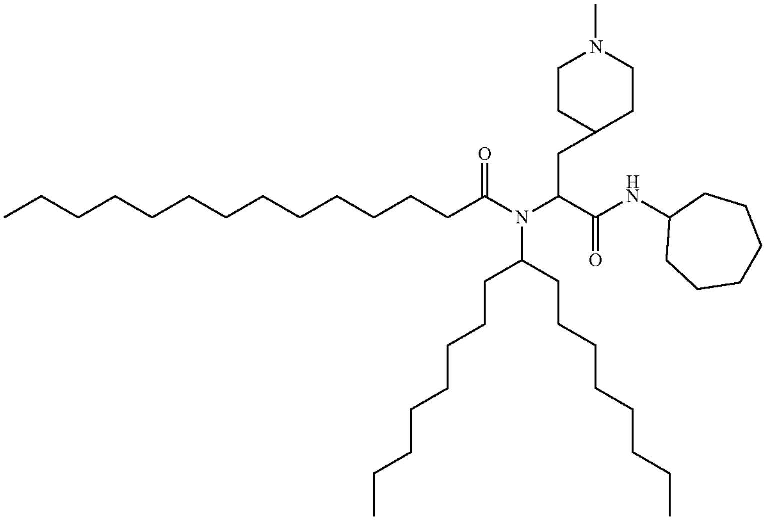

E6

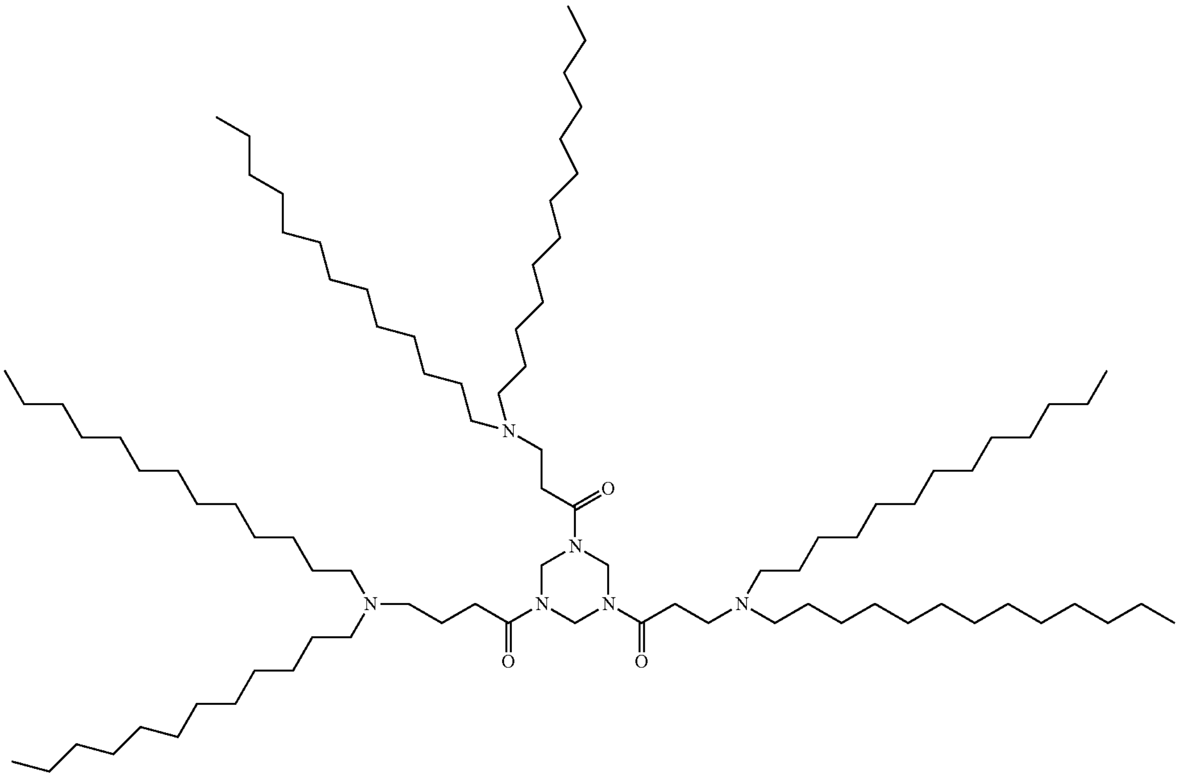

Figure 10:
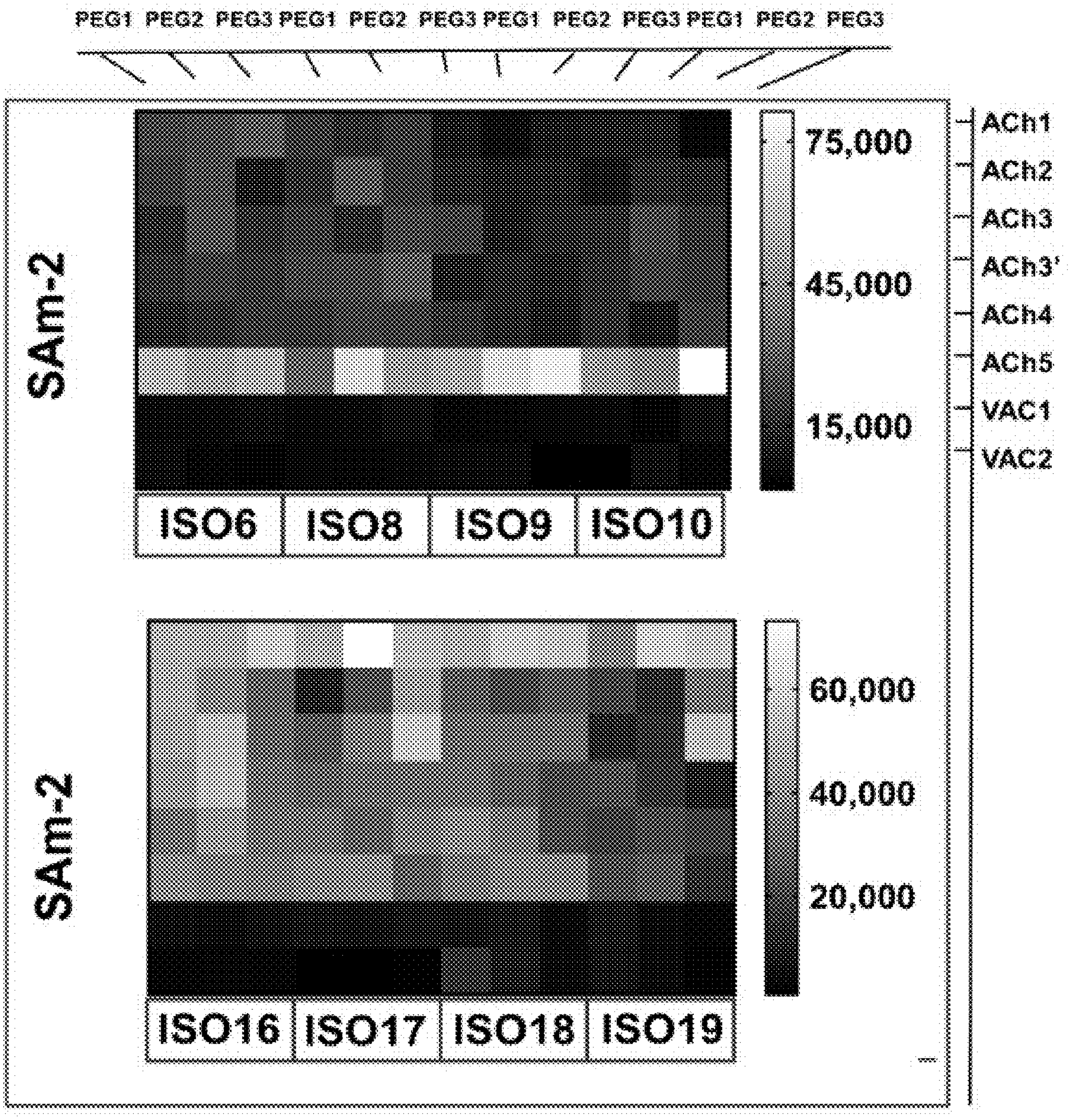
FIG. 10 shows the luminescence intensity of LNPs formulated using modular lipids of the disclosure comprising a sterol derivatives group, a saccharide group and a PEG group in HEK293T cells shown in 96-well plates (top) or in a graph (control group, bottom). The LNPs were formulated using a cationic ionizable lipid (P54B6, P38D8 or E6), DOPE and a modular lipid (35/40/15 mole ratio) encapsulating SamRNA-LUC. HEK293 cells were treated with 100 ng of SamRNA-LUC for 24 hours. Each LNP formulation was tested in triplicate and represented as the mean±SD.
Figure 10:
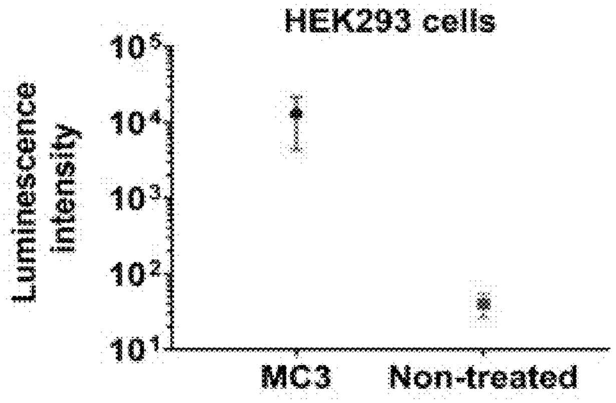
Figure 11:
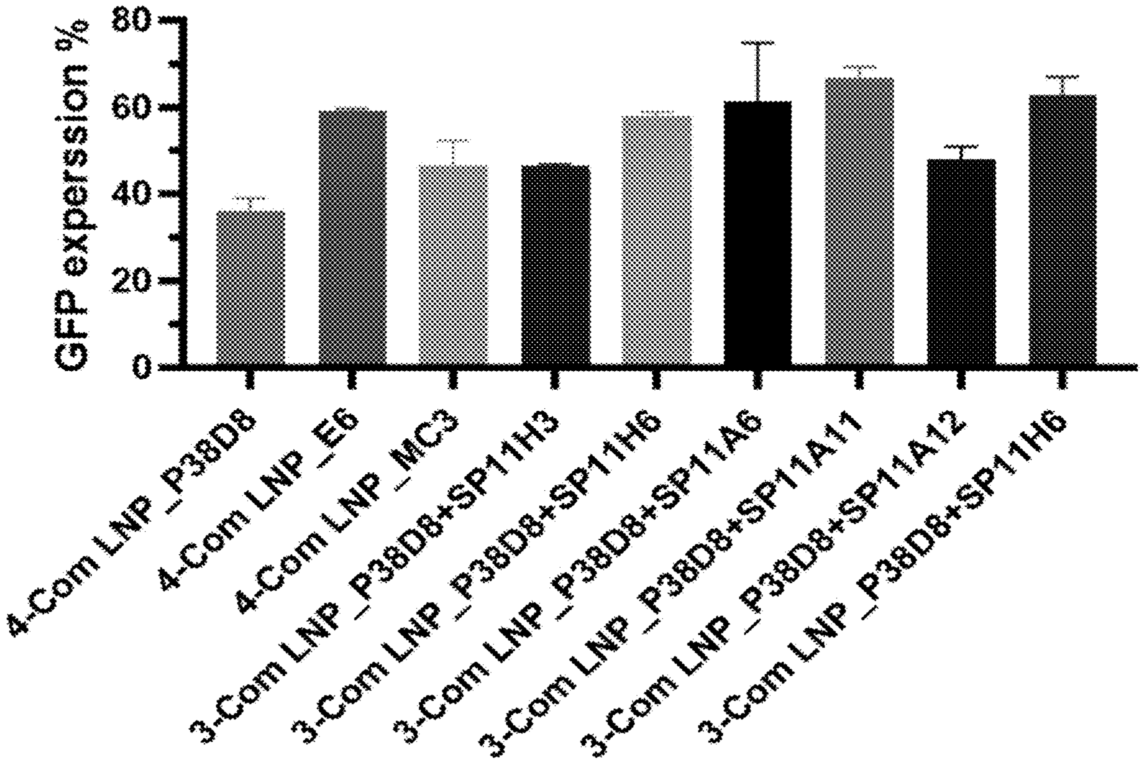
FIG. 11 shows GFP expression in HEK293 cells that were treated using LNPs of the disclosure for 24 hours. The three-component LNPs were formulated using a cationic ionizable lipid (P38D8), DOPE and a modular lipid (SP11H3, SP11A6, SP11A11, SP11A12 or SP11H6) (35/40/15 mole ratio) encapsulating SamRNA-GFP. Four-component LNPs containing P38D8, E6 or MC3 were used as control groups. Each LNP formulation was tested in triplicate and represented as the mean±SD. 4-Com LNP: Four-component LNP. 3-Com LNP: Three-component LNP.

The transfection efficiency of LNP-SamRNA-GFP (FIG. 11) and LNP-SamRNA-LUC (FIG. 10) were determined by flow cytometry and a plate reader. LNPs formulated with FDA approved ionizable lipids MC3 served as a control. Data were collected in triplicate and represented as the mean±S D.

Figure 12:
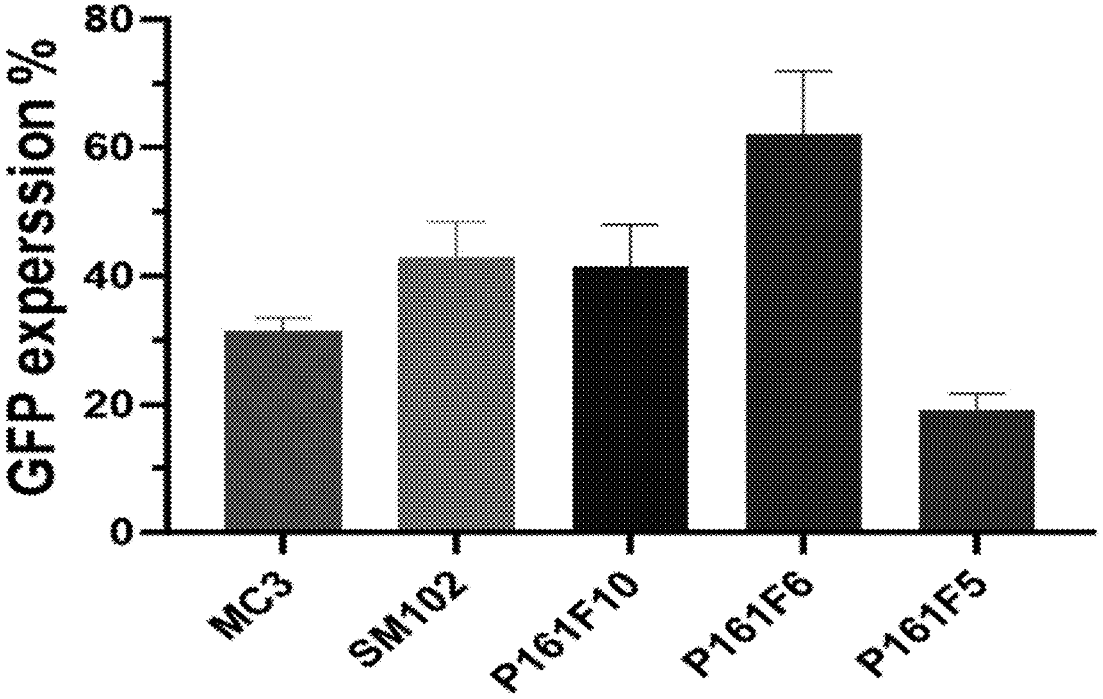
FIG. 12 shows GFP expression in HEK293 cells that were treated using LNPs of the disclosure for 24 hours. The LNPs were formulated using the modular lipid P161F5, P161F6 or P161F10; DOPE; and DMG-PEG2000 (40/10/2, mole ratio) encapsulating SamRNA-GFP. 100 ng RNA were incubated to a well of 96-well plate with 60-70% confluent of HEK293 cells. Each LNP formulation was tested in triplicate and represented as the mean±SD.

The transfection efficacy of LNPs formulated using modular lipids P161F5, P161F6 or P161F10; DOPE and DMG-$PEG_{2000}$ (modular lipid/DOPE/DMG-$PEG_{2000}$, 40/10/2 mole ratio) encapsulating LNP-SamRNA-GFP were studied using HEK293T cells in 96-well plates. 100 ng RNA were incubated with 60-70% confluent of HEK293T cells in a 96-well plate for 24 hours. The in vitro delivery efficiency of LNPs comprising modular lipid P161F6 and P161F10 (ionizable lipid/DOPE/DMG-$PEG_{2000}$ with 40/10/2, mole ratio) showed comparable or higher transfection efficiencies than four-component LNPs containing MC3 and SM102 as shown in FIG. 12. Data were collected in triplicate and represented as the mean±S D.

The transfection efficacy of LNPs formulated using modular lipid SP1F11; ionizable lipids P38D8, P40D7 or P1D4; and DOPE (ionizable lipid/DOPE/SP1F11, 40/60/15 mole ratio) encapsulating LNP-SamRNA-GFP were compared to four-component LNP control groups (ionizable lipid/DOPE/Cholesterol/DMP-PEG2000, 30/15/50/1.5 mole ratio). 100 ng RNA were incubated with 60-70% confluent of HEK293T cells in a 96-well plate for 24 hours. The structures of two of the ionizable lipids used to formulate the LNPs are shown below:

P1D4

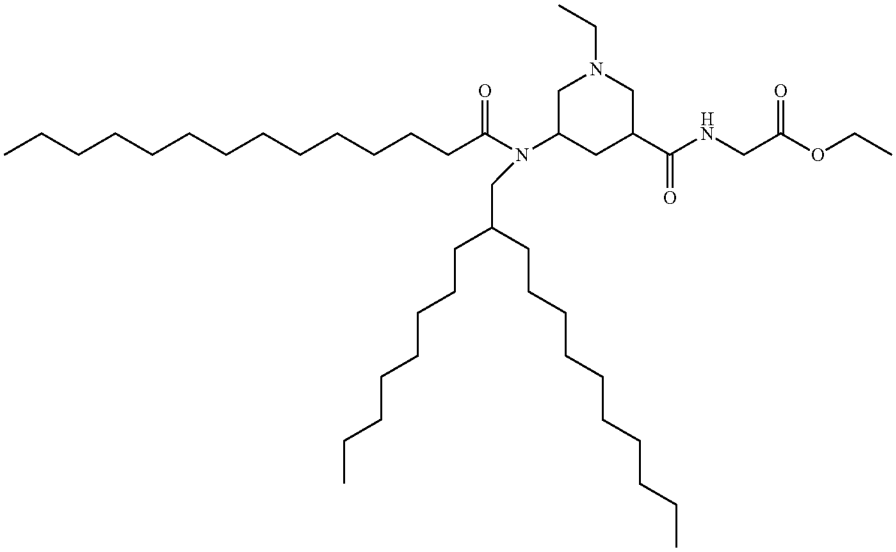

P40D7

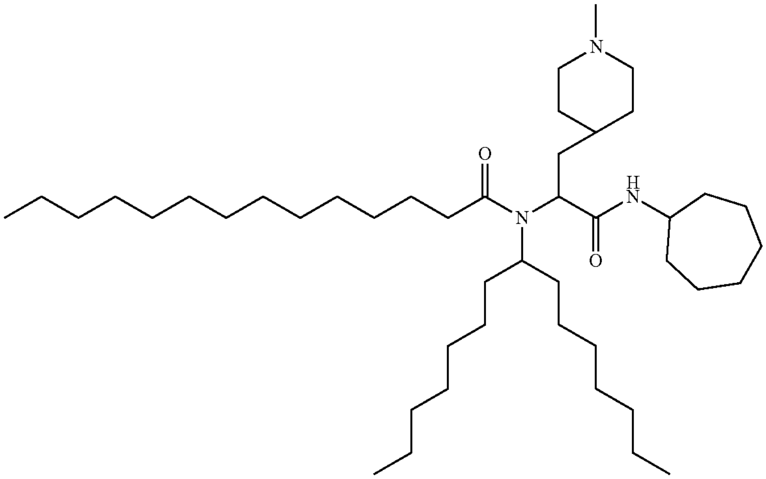

Figure 13:
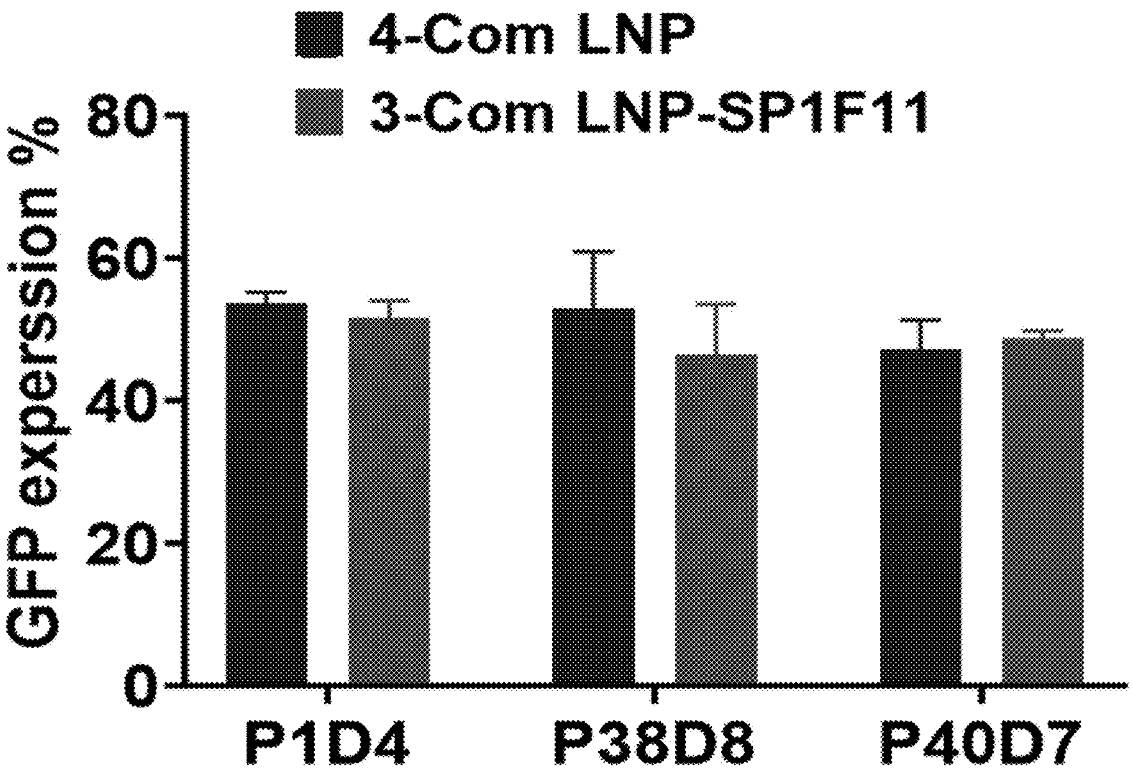
FIG. 13 shows GFP expression in HEK293T cells. The LNPs of the disclosure were formulated using P38D8, P40D7 or P1D4, DOPE and modular lipid SP1F11 (40/60/15, mole ratio). LNPs of the disclosure and four-component LNP control groups (ionizable lipid/DOPE/Cholesterol/DMP-PEG2000, 30/15/50/1.5 mole ratio) encapsulating SamRNA-GFP were applied to HEK293T cells for 24 hours. 100 ng mRNA were incubated to a well of a 96-well plate with 60-70% confluent of HEK293 cells. Each LNP formulation was tested in triplicate and represented as the mean±SD.

Approximately 50% of HEK293 cells were transfected by both four- and three-component LNPs as shown in FIG. 13. Data were collected in triplicate and represented as the mean±S D.

The transfection efficacy of LNPs formulated using ionizable lipids P54B6, SM102, MC3 or ALC0315; DOPE; and modular lipids SP2B12, SP11A6 or SP11A12 (35/40/20, mole ratio) encapsulating SamRNA-GFP were studied using HEK293T cells. 100 ng RNA were incubated with HEK293T cells for 24 hours. The structure of P54B6 is shown below:

P54B6

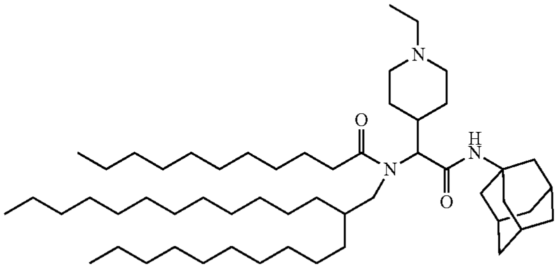

Figure 14:
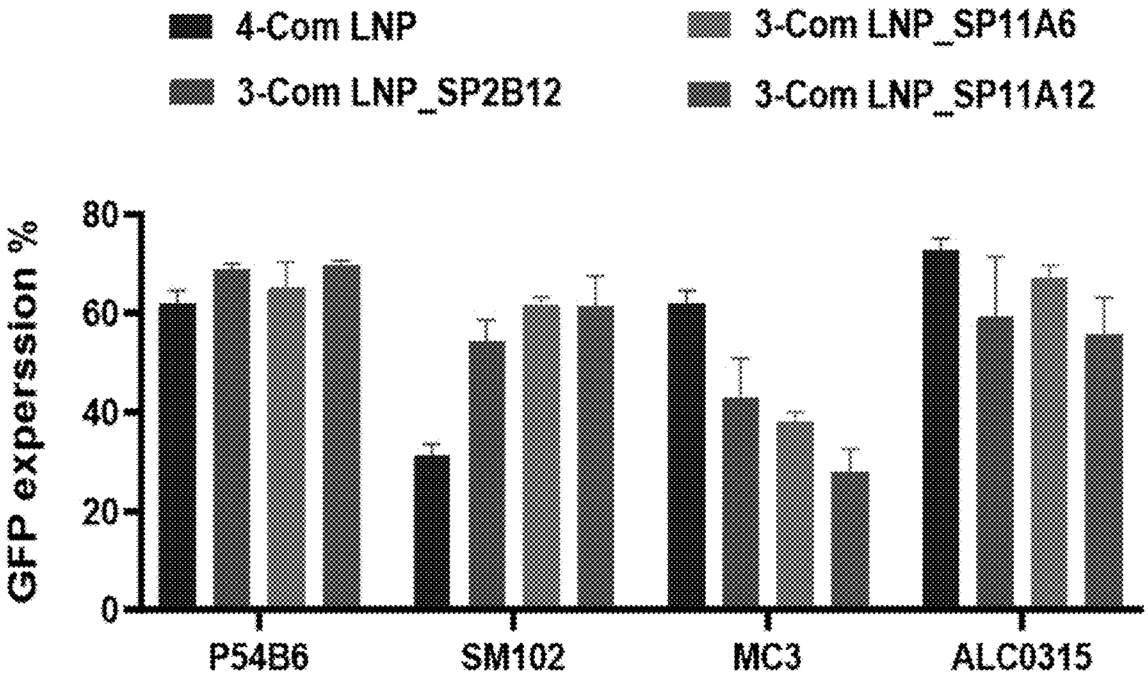
FIG. 14 shows GFP expression in HEK293T cells that were treated using LNPs of the disclosure for 24 hours. The LNPs were formulated using ionizable lipids P54B6, SM102, MC3 or ALC0315; DOPE; and the modular lipid SP2B12, SP11A6 or SP11A12 (35/40/20, mole ratio) encapsulating SamRNA-GFP. The four-component LNPs containing P54B6, SM102, MC3 or ALC0315 were used as control groups. The formulations containing 100 ng mRNA were incubated with cells for 24 hours. Each LNP formulation was tested in triplicate and represented as the mean±SD. From left to right, each set of four bars shows 4-component LNP, 3-component LNP_SP2B12, 3-component LNP_SP11A6, and 3-component LNP_SP11A12. 4-Com LNP: Four-component LNP. 3-Com LNP: Three-component LNP.

The in vitro delivery efficiency of modular lipid containing three-component LNPs showed comparable or higher than four-component LNPs as shown in FIG. 14. Data were collected in triplicate and represented as the mean±S D.

The transfection efficacy of LNPs formulated using P287A12, DOPE, DMG-PEG2000 (40/10/2, mole ratio) or P287A12 and DMG-PEG2000 (40/2, mole ratio) formulated in acidic buffer (citrate buffer, pH 4.5) and/or neutral buffer (PBS, pH 7.4) encapsulating SamRNA-GFP or modified mRNA-GFP were studied using HEK293 cells in 96-well plates.

Figure 15A:
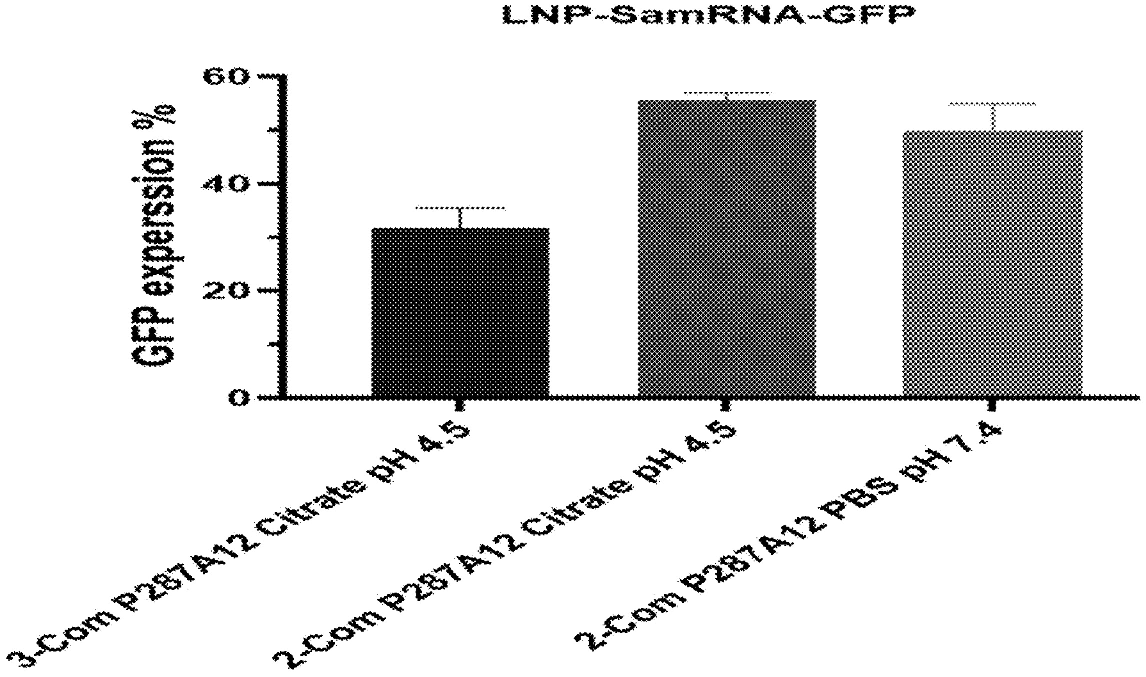
FIGS. 15A-15B show GFP expression in HEK293 cells that were treated using LNPs of the disclosure for 24 hours. The LNPs were formulated using P287A12, DOPE, DMG-PEG2000 (40/10/2, mole ratio) or P287A12 and DMG-PEG2000 (40/2, mole ratio) formulated in acidic buffer (citrate buffer, pH 4.5) and/or neutral buffer (PBS, pH 7.4) encapsulating SamRNA-GFP or modified mRNA-GFP. The formulations containing 100 ng of SamRNA-GFP (FIG. 15A) or 100 ng of modified mRNA-GFP (FIG. 15B) were incubated to a well of 96-well plate with 60-70% confluent of HEK293 cells. Each LNP formulation was tested in triplicate and represented as the mean±SD. 3-Com LNP: Three-component LNP. 2-Com LNP: Two-component LNP.
Figure 15B:
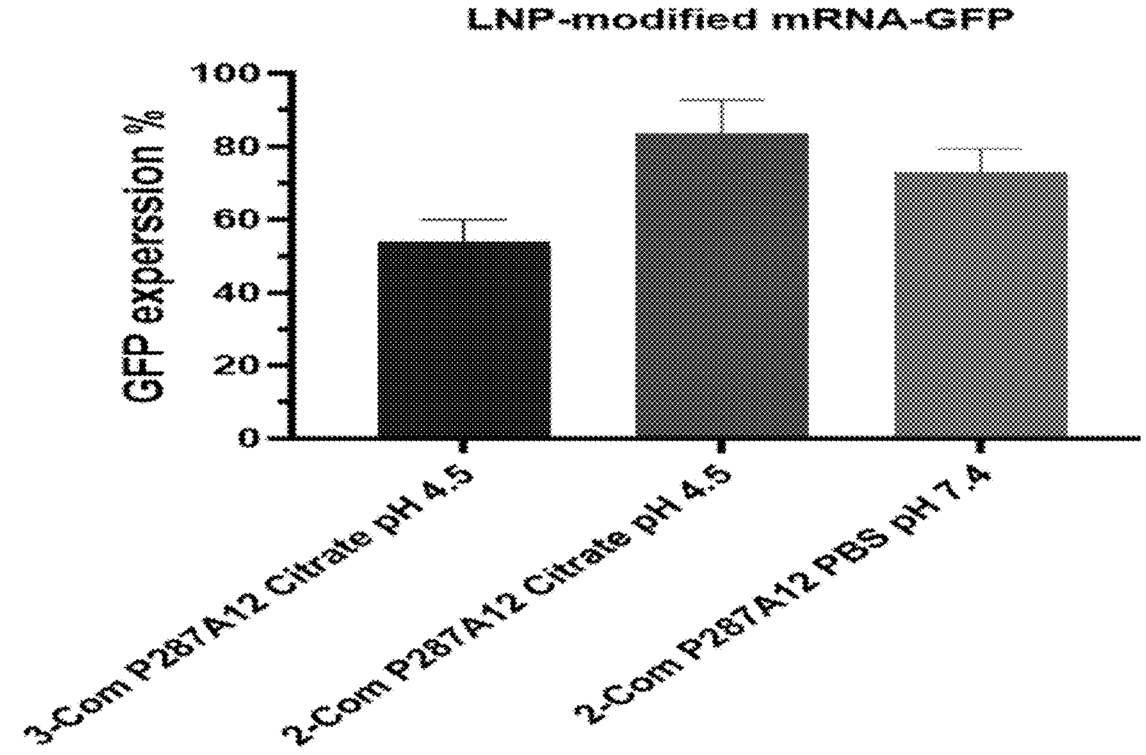

The LNPs were formulated in either an acidic buffer (citrate buffer, pH 4.5) or a neutral buffer (PBS, pH 7.4) and ethanol. The nucleic acid payload was dissolved in the buffer while the lipid components were dissolved in ethanol, and the LNPs of the disclosure were formed by mixing the two phases. 100 ng RNA was incubated with HEK293 cells for 24 hours using a neutral (PBS) or acidic (citric) buffer. There was no significant difference in in vitro delivery efficiency between the LNPs formulated in acidic buffer and neutral buffer as shown in FIGS. 15A and 15B. Citrate buffers are traditionally used in LNP formulation and has a low pH of approximately 4.5. PBS is a neutral buffer with a pH of approximately 7.4. Data were collected in triplicate and represented as the mean±S D.

Example 5: Modular Lipids

Modular lipids P161F5, P161F6, P161F10, P161F12, P287A12, P287C12, SP1E2, SP1F2, SP1F11, SP1E8, SP1E2K, SP1E2KI, SP2B12, SP2A3, SP11H3, SP11A6, SP11H6, SP11A12, and SP1E2-PEG3 were synthesized and confirmed by mass spectrometry.

N-(1-(((1s,3s)-adamantan-1-yl)amino)-3-(1-methylpiperidin-4-yl)-1-oxopropan-2-yl)-4-(3,6-dihydroxy-10,13-dimethylhexadecahydro-1H-cyclopenta[a]phenanthren-17-yl)-N-(2-octyldodecyl)pentanamide (P161F10): yield (51%). MS (APCI) m/z 974.9 [M+H]+.

N-(2-(((1s,3s)-adamantan-1-yl)amino)-1-(1-ethylpiperidin-4-yl)-2-oxoethyl)-N-(2-decyltetradecyl)-4-(3,6-dihydroxy-10,13-dimethylhexadecahydro-1H-cyclopenta[a]phenanthren-17-yl) pentanamide (P161F6): yield (57%). MS (APCI) m/z 1031.0 [M+H]+.

N-(2-(((1s,3s)-adamantan-1-yl)amino)-1-(1-ethylpiperidin-4-yl)-2-oxoethyl)-4-(3,6-dihydroxy-10,13-dimethylhexadecahydro-1H-cyclopenta[a]phenanthren-17-yl)-N-(tricosan-12-yl) pentanamide (P161F5): yield (61%). MS (APCI) m/z 1017.9 [M+H]+.

N-(1-(((3s,5s,7s)-adamantan-1-yl)amino)-3-(1-methylpiperidin-4-yl)-1-oxopropan-2-yl)-N-(2-decyltetradecyl)-4-(3,6-dihydroxy-10,13-dimethylhexadecahydro-1H-cyclopenta[a]phenanthren-17-yl) pentanamide (P161F5): yield (49%). MS (APCI) m/z 1030.9 [M+H]+.

N-(1-(benzylamino)-3-(1-methylpiperidin-4-yl)-1-oxopropan-2-yl)-N-(2-decyltetradecyl)-4-(3,12-dihydroxy-10,13-dimethylhexadecahydro-1H-cyclopenta[a]phenanthren-17-yl) pentanamide (P287A12): yield (42%). MS (APCI) m/z 986.8 [M+H]+.

(4R)—N-(1-(benzylamino)-3-(1-methylpiperidin-4-yl)-1-oxopropan-2-yl)-N-(2-decyltetradecyl)-4-((3R,5S,7R,8R,9S,10S,13R,17R)-3,7-dihydroxy-10,13-dimethylhexadecahydro-1H-cyclopenta[a]phenanthren-17-yl) pentanamide (P287C12): yield (40%). MS (APCI) m/z 986.8 [M+H]+.

(3S,4R,5S,6R)—N-(57-(((3R,5R,7R)-adamantan-1-yl)amino)-57-oxo-2,5,8,11,14,17,20,23,26,29,32,35,38,41,44,47,50,53-octadecaoxaheptapentacontan-56-yl)-N-((8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)-3,4,5,6-tetrahydroxytetrahydro-2H-pyran-2-carboxamide (SP2B12): yield (53%). MS (APCI) m/z 780.5 [M+2H]2+.

ethyl (141-((Z)-heptadec-8-en-1-yl)-140-((2S,3S,4S,5R,6R)-3,4,5,6-tetrahydroxytetrahydro-2H-pyran-2-carbonyl)-2,5,8,11,14,17,20,23,26,29,32,35,38,41,44,47,50,53,56,59,62,65,68,71,74,77,80,83,86,89,92,95,9 8,101,104,107,110,113,116,119,122,125,128,131,134,137-hexatetracontaoxa-140-azadotetracontahectan-142-oyl)glycinate (SP1E2K): yield (33%). MS (MALDI-TOF) m/z 2657.6 [M+K]+.

(3S,4R,5S,6R)-3,4,5,6-tetrahydroxy-N—((Z)-1-((4-methoxyphenyl)amino)-1-oxononadec-10-en-2-yl)-N-(2,5,8,11,14,17,20,23,26,29,32,35,38,41,44,47,50,53,56,59,62,65,68,71,74,77,80,83,86,89,92,95, 98,101,104,107,110,113,116,119,122,125,128,131,134,137-hexatetracontaoxanonatriacontahectan-139-yl)tetrahydro-2H-pyran-2-carboxamide (SP1E2KI): yield (40%). MS (MALDI-TOF) m/z 2657.6 [M+K]+.

N-(cyclohex-1-en-1-yl)-52-((2R,3S,4R,5R)—N-((8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)-2,3,4,5,6-pentahydroxyhexanamido)-2,5,8,11,14,17,20,23,26,29,32,35,38,41,44,47,50-heptadecaoxatripentacontan-53-amide (SP11H6): yield (54%). MS (MALDI-TOF) m/z 1473.9 [M+Na]+.

N-cycloheptyl-52-((2R,3S,4R,5R)—N-((8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)-2,3,4,5,6-pentahydroxyhexanamido)-2,5,8,11,14,17,20,23,26,29,32,35,38,41,44,47,50-heptadecaoxatripentacontan-53-amide (SP11A12): yield (54%). MS (MALDI-TOF) m/z 1489.9 [M+Na]+.

Example 6: Transfection Efficiency In Vivo

LNPs containing modular lipids showed higher or comparable transfection efficiency in vivo compared to traditional four-component LNPs. Transfection efficacies of LNPs formulated using P54B6 or P38D8; DOPE; Cholesterol; and DMG-PEG2000 (30/15/50/1.5, mole ratio); P54B6, DOPE and modular lipid SP2B12 (35/40/20, mole ratio); P161F5, DOPE, DMG-PEG2000 (40/10/2, mole ratio); P161F5, DOPE and SP1E2K (40/10/2, mole ratio); or P38D8, DOPE and SP1F11 (40/60/15, mole ratio) encapsulating SamRNA-LUC were studied in mice.

All animal procedures were performed with ethical compliance and approval by Institutional Animal Care and Use Committee (IACUC). Female Balb/c mice (6-8 weeks) were obtained from Charles River Laboratories Inc.

Figure 16:
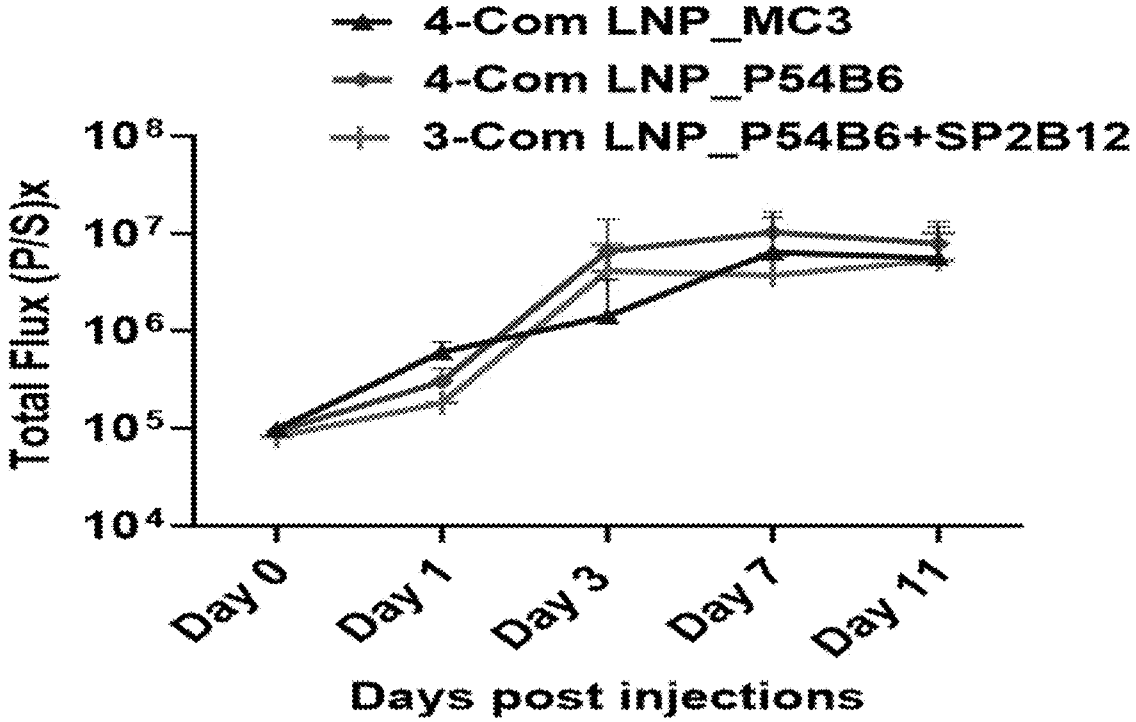
FIG. 16 shows in vivo bioluminescence intensity of metastatic sites in mice treated with LNPs of the disclosure measured using IVIS imaging system. The LNPs are formulated using ionizable lipid P54B6, DOPE, Cholesterol and DMG-PEG2000 (30/15/50/1.5, mole ratio); or ionizable lipid P54B6, DOPE and modular lipid SP2B12 (35/40/20, mole ratio). Four-component LNP containing MC3 was used as a control group. Each mouse was treated with 1 μg of SamRNA-LUC. Each LNP formulation was tested in 5 replicates and represented as the mean±SD. 4-Com LNP: Four-component LNP. 3-Com LNP: Three-component LNP.
Figure 17:
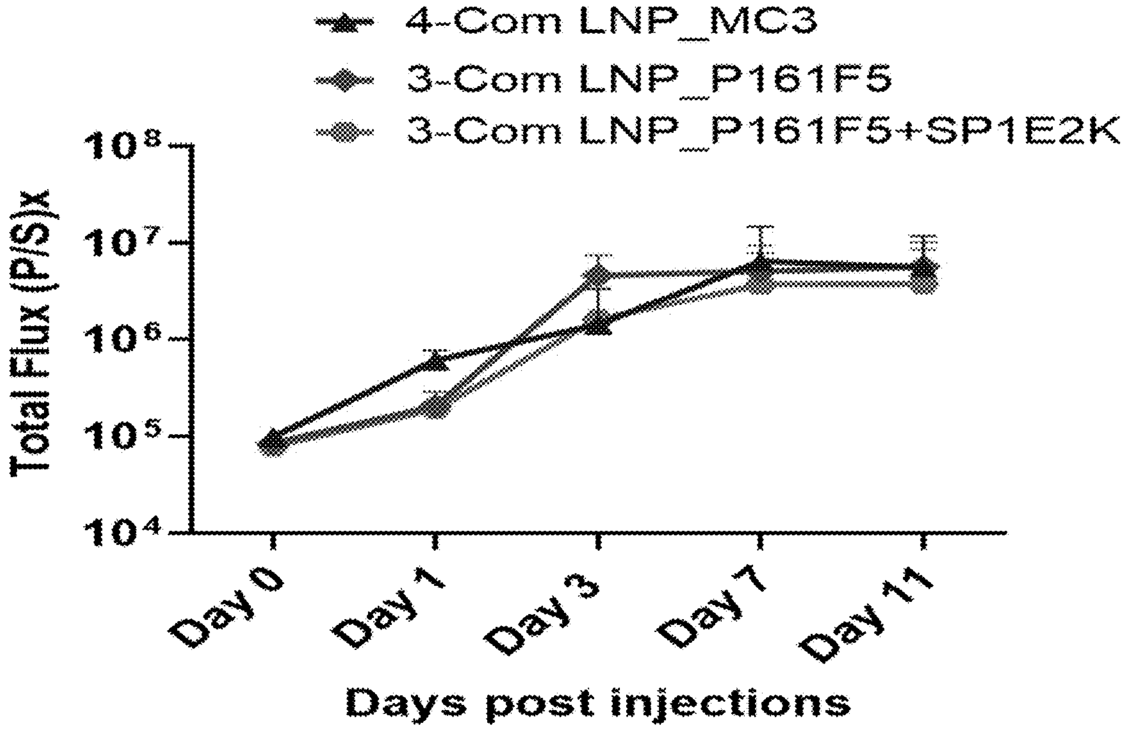
FIG. 17 shows in vivo bioluminescence intensity of metastatic sites in mice treated with LNPs of the disclosure measured using IVIS imaging system. The LNPs are formulated using P161F5, DOPE, DMG-PEG2000 (40/10/2, mole ratio); or P161F5, DOPE and SP1E2K (40/10/2, mole ratio). Four-component LNP containing MC3 was used as a control group. Each mouse was treated with 1 μg of SamRNA-LUC. Each LNP formulation was tested in 5 replicates and represented as the mean±SD. 4-Com LNP: Four-component LNP. 3-Com LNP: Three-component LNP.
Figure 18:
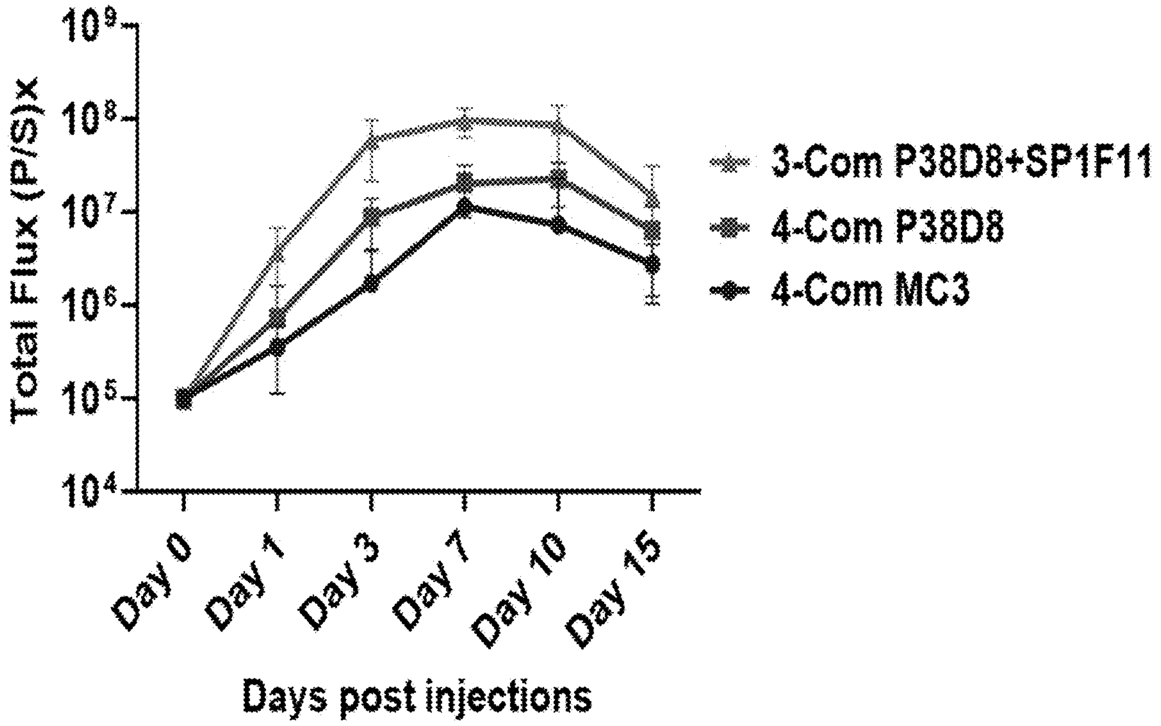
FIG. 18 shows in vivo bioluminescence intensities of metastatic sites in mice treated with LNPs of the disclosure measured using the IVIS imaging system. The LNPs are formulated using P38D8, DOPE, cholesterol and DMG-PEG2000 (30/15/50/1.5, mole ratio); or P38D8, DOPE and SP1F11 (40/60/15, mole ratio). Four-component LNP containing MC3 was used as a control group. Each mouse was treated with 1 μg of SamRNA-LUC. Each LNP formulation was tested in 5 replicates and represented as the mean±SD. 4-Com LNP: Four-component LNP. 3-Com LNP: Three-component LNP.

Mice were injected intramuscularly with 1 μg of LNPs. Subsequently, the mice were injected intraperitoneally with Luciferin (Perkin Elmer, 6 mg/mouse) and bioluminescence intensities were measured using the IVIS imaging system (IVIS, Perkin Elmer). As shown in FIGS. 16, 17 and 18, in vivo bioluminescence intensity of metastatic sites in mice treated with four-component LNPs were lower or comparable to LNPs comprising modular lipids of the disclosure. Notably, LNPs comprising P38D8, SP1F11 and DOPE showed higher transfection efficiency compared to the four component LNP comprising MC3. Data were collected in replicates of 5 and represented as the mean #S D.

Example 7: Characterization of Modular Lipids

Figure 19A:
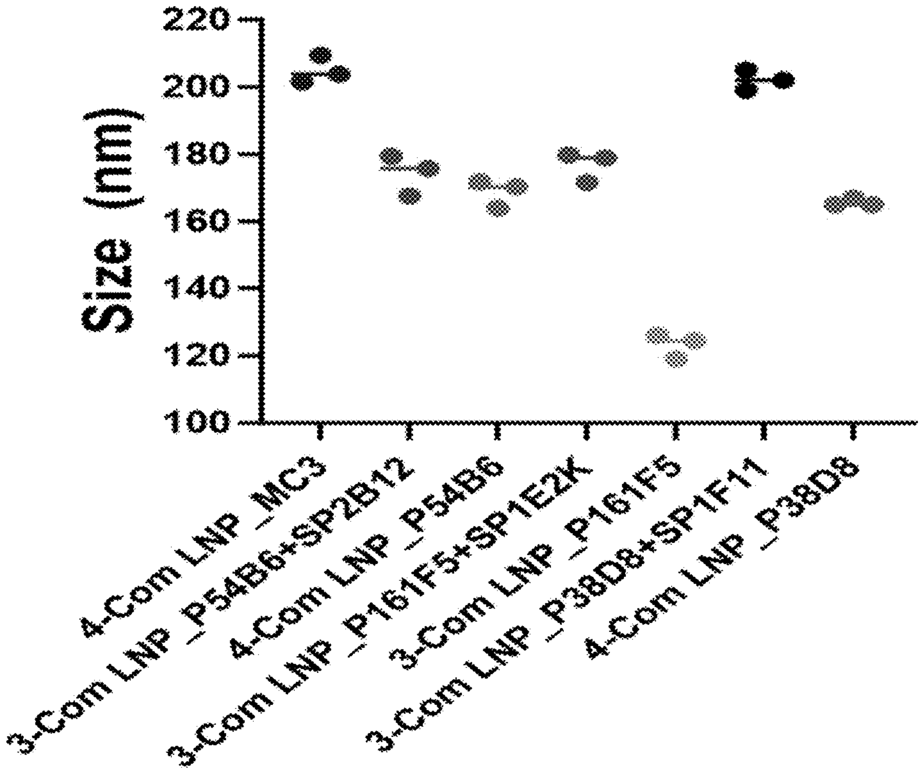
FIGS. 19A-19B show nanoparticles size (FIG. 19A) and polydispersity index (PDI) (FIG. 19B) of LNPs of the disclosure. 4-Com LNP: Four-component LNP. 3-Com LNP: Three-component LNP.
Figure 19B:
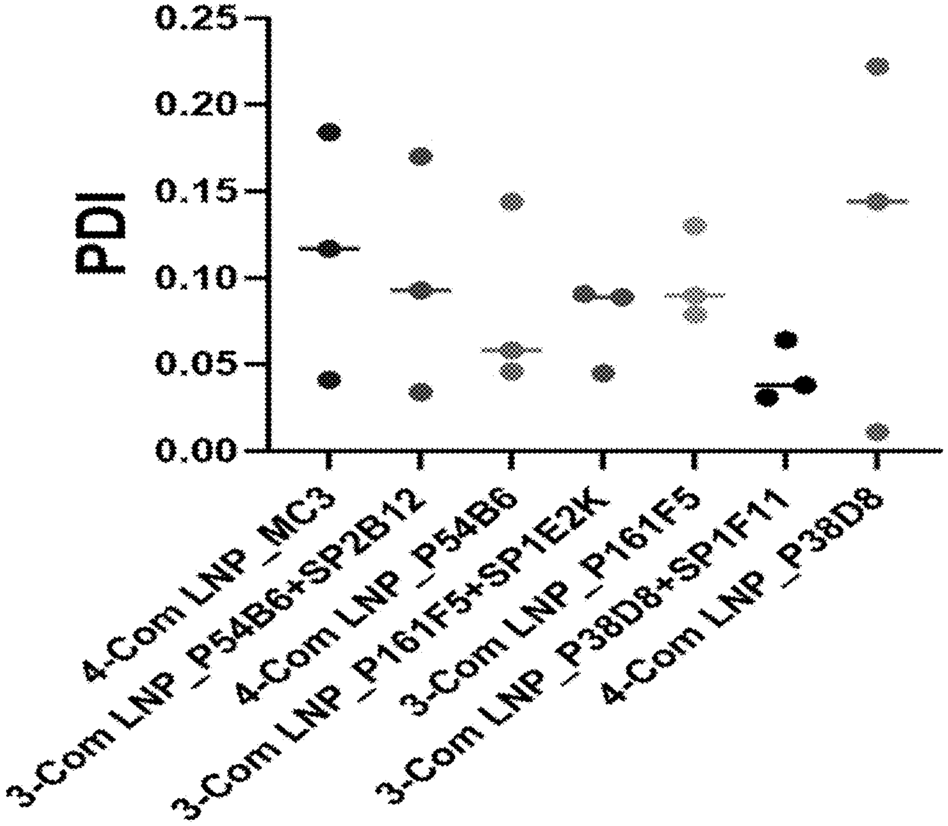

LNPs of the disclosure were characterized and the nanoparticle size (FIG. 19A) and PDI (FIG. 19B) are shown.

The size and polydispersity index (PDI) were measured by dynamic light scattering (SZ-100-Z2 (MTS), Horiba Scientific). Diameters are reported as the intensity mean peak average. The nucleic acid encapsulation efficiency was calculated by a modified Quant-iT RiboGreen RNA assay (Invitrogen).

In addition, it is to be understood that any particular embodiment of the present disclosure that falls within the prior art may be explicitly excluded from any one or more of the claims. Since such aspects are deemed to be known to one of ordinary skill in the art, they may be excluded even if the exclusion is not set forth explicitly herein.

It is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

The invention claimed is:
1. A modular lipid selected from:
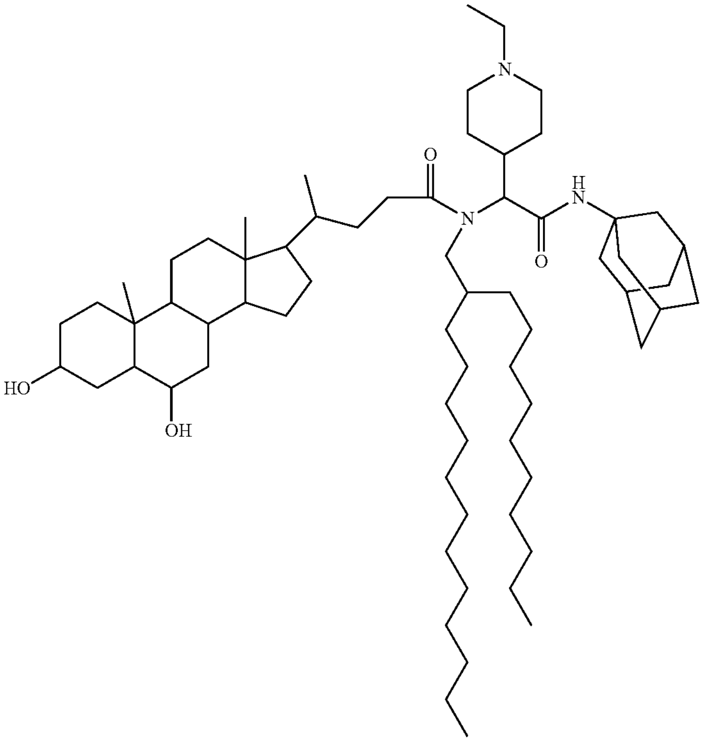
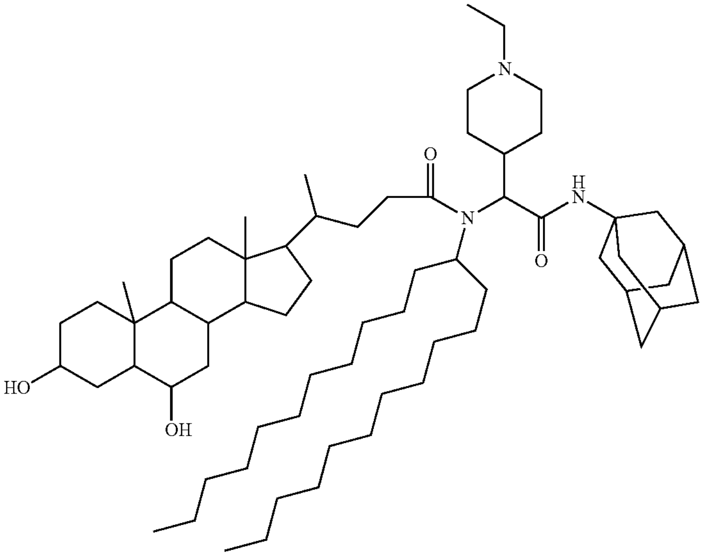

-continued
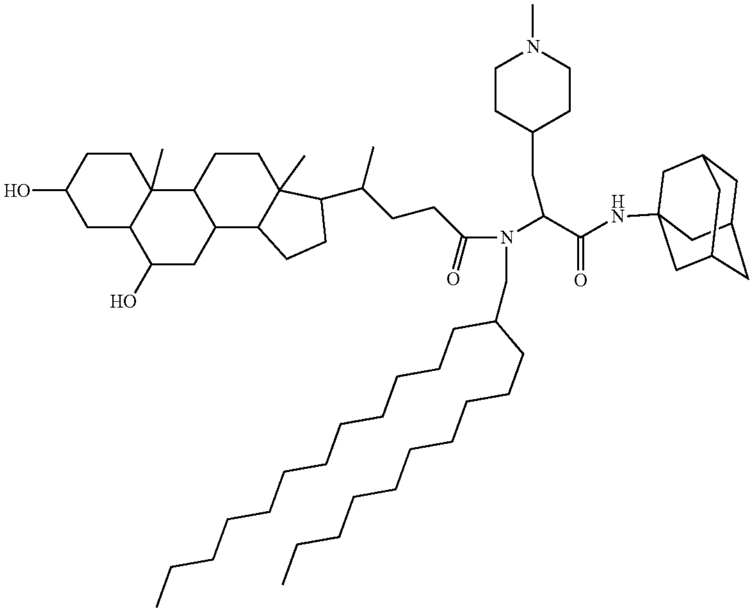
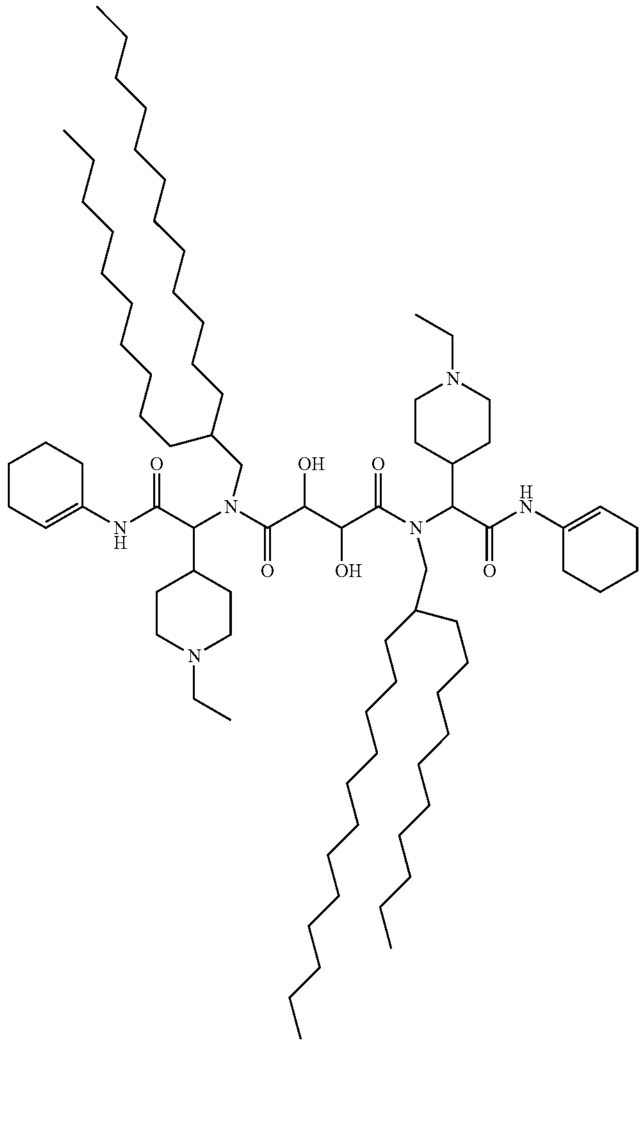

-continued
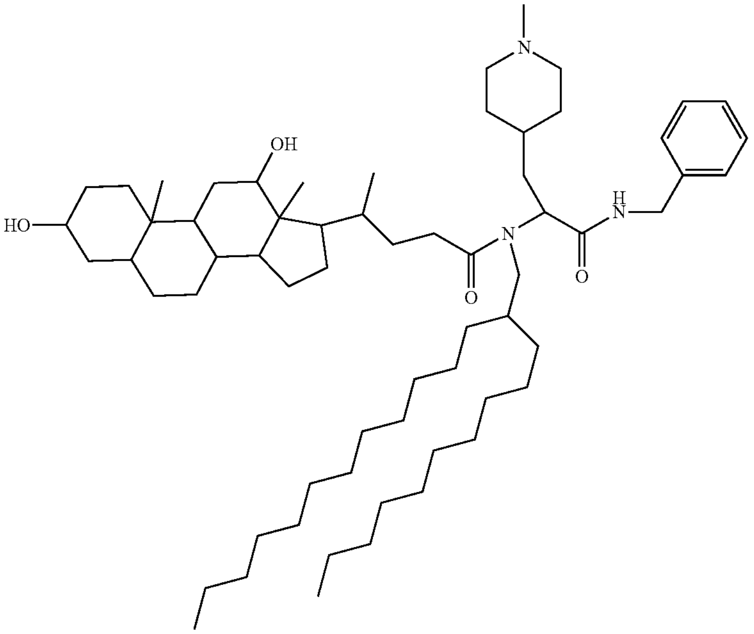
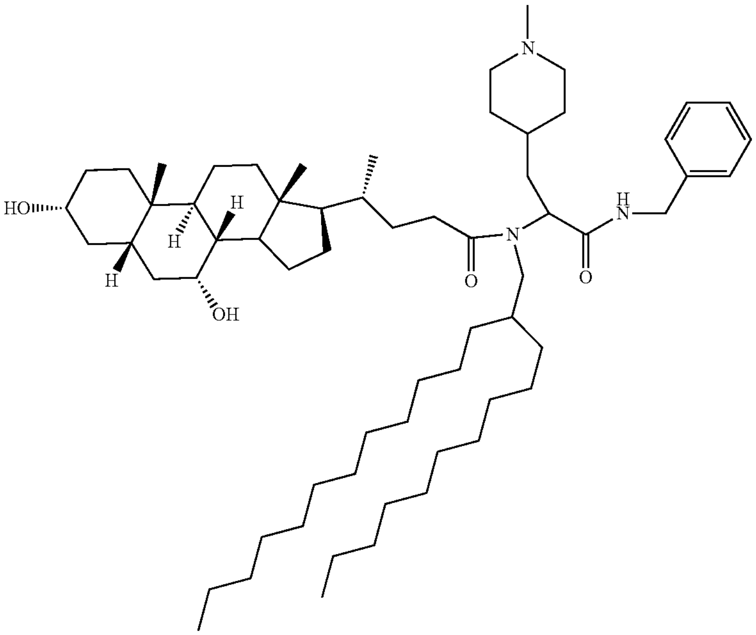

-continued
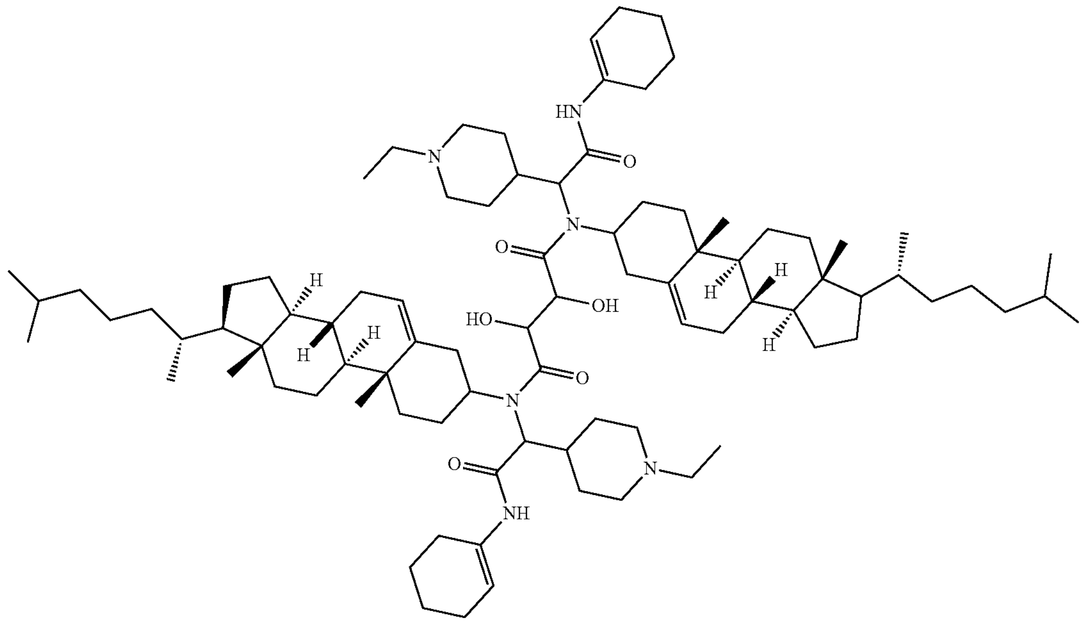
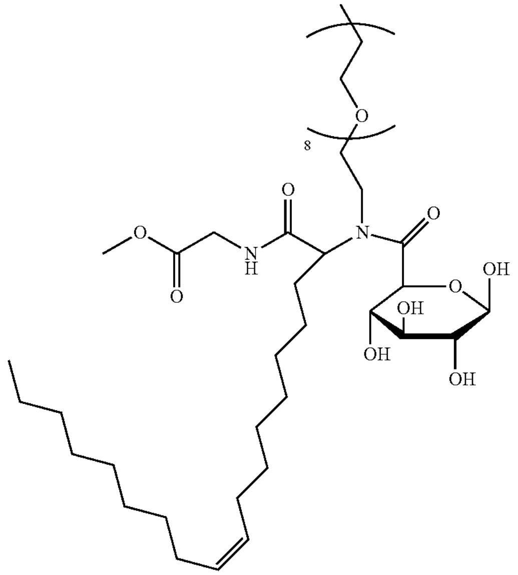

-continued
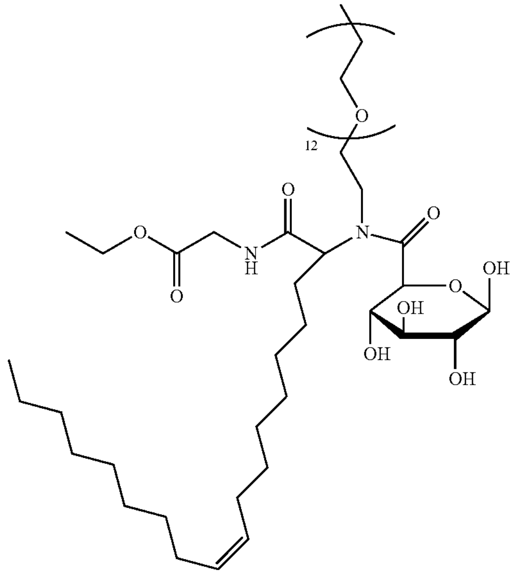
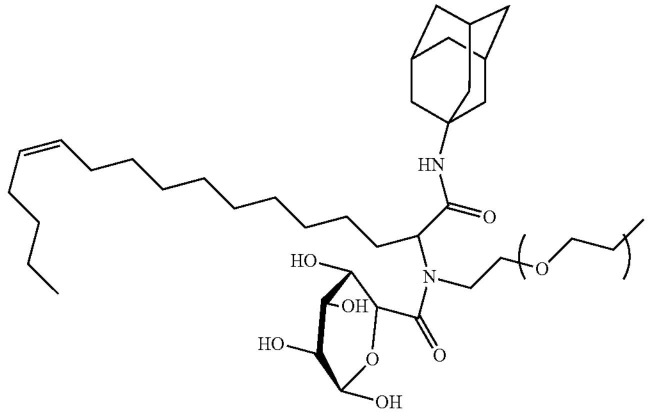
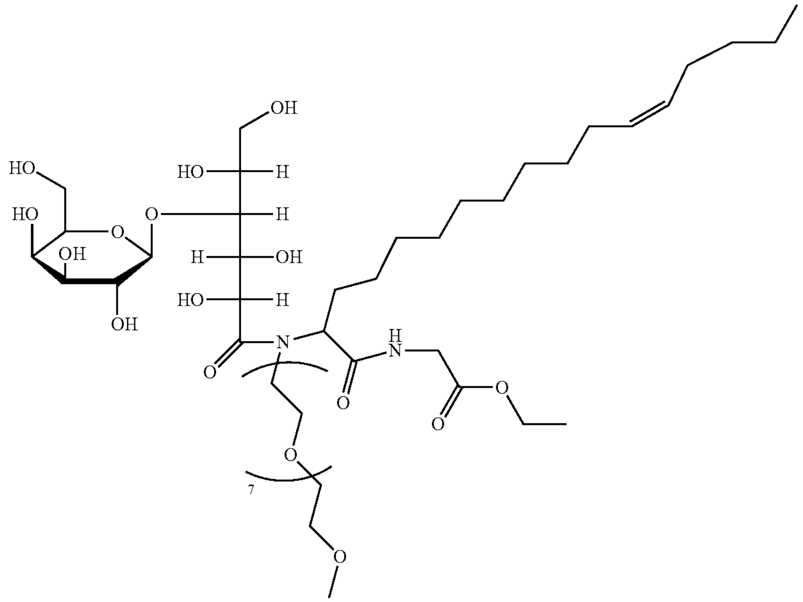

-continued
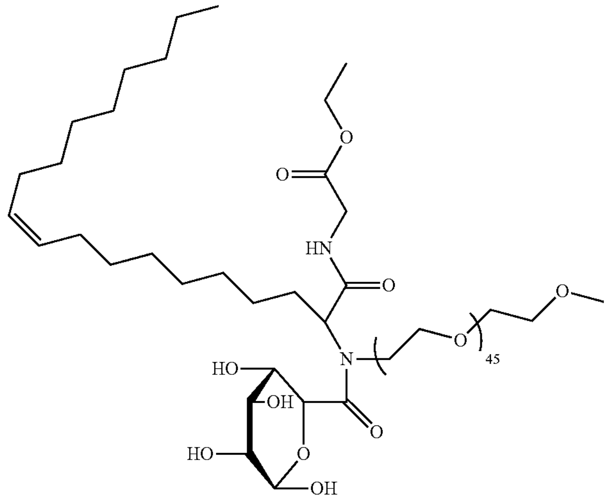
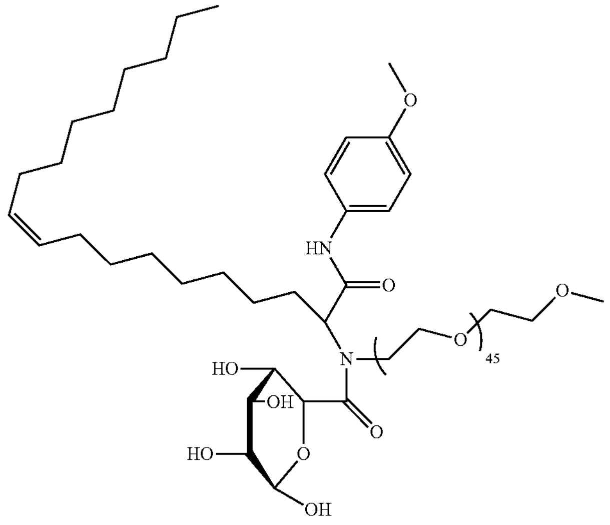
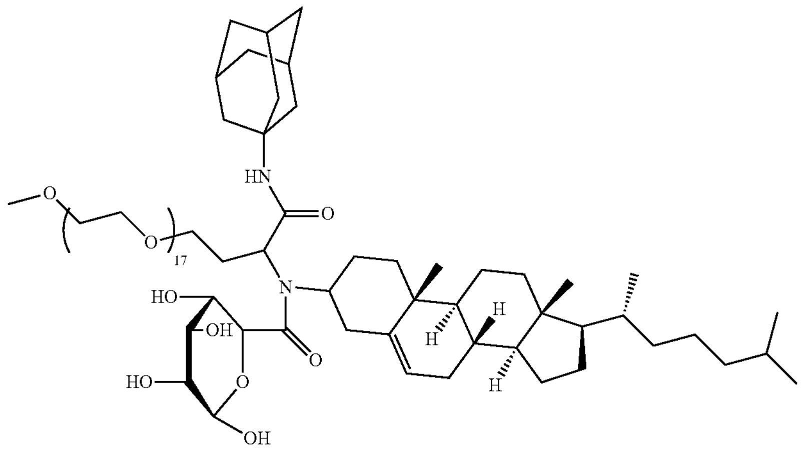

-continued
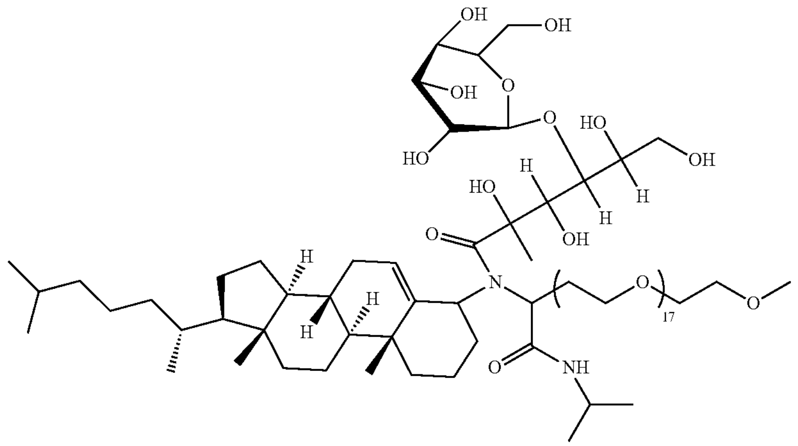
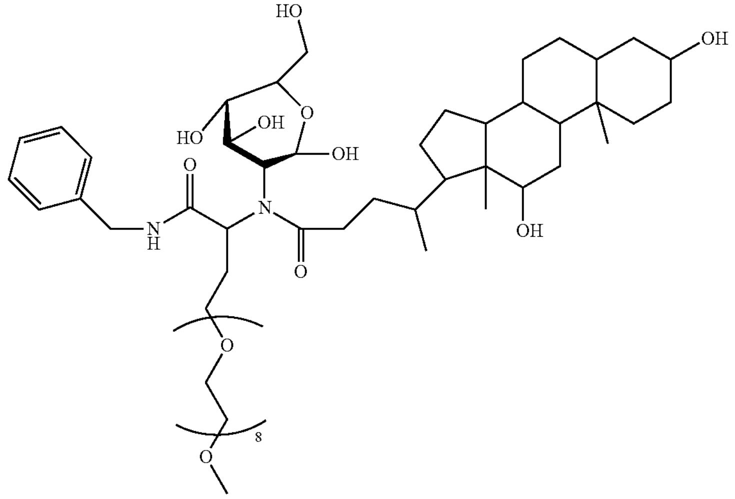
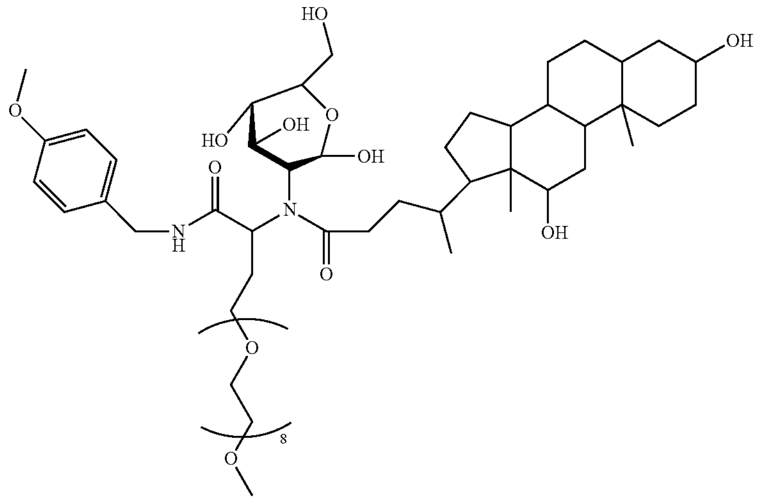

-continued
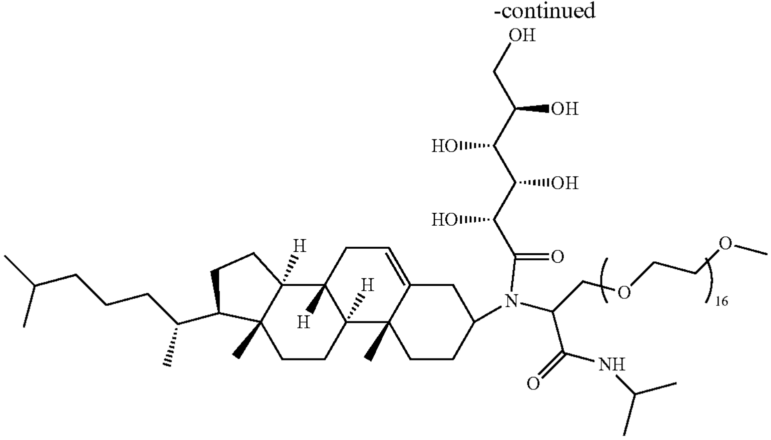
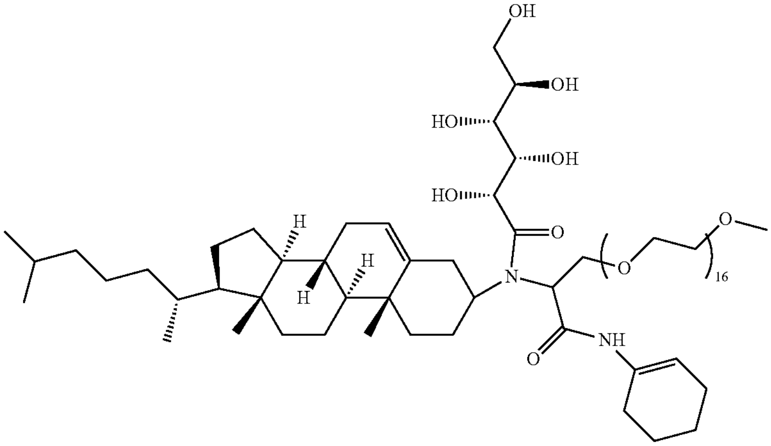
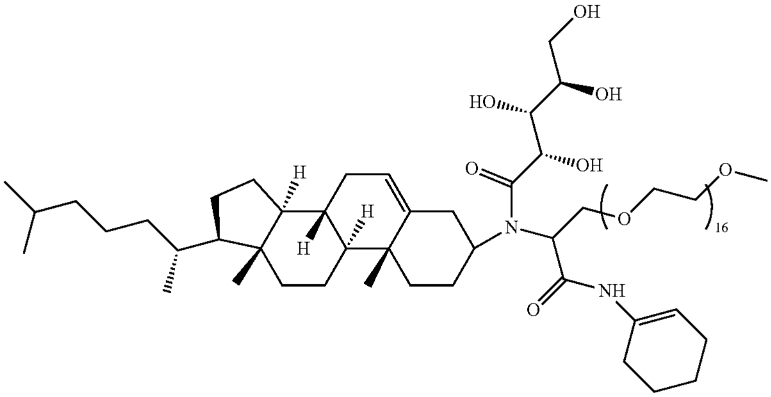
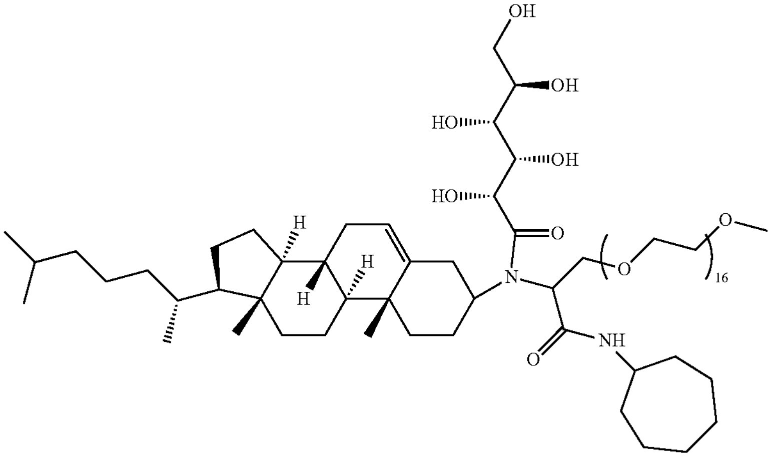

-continued
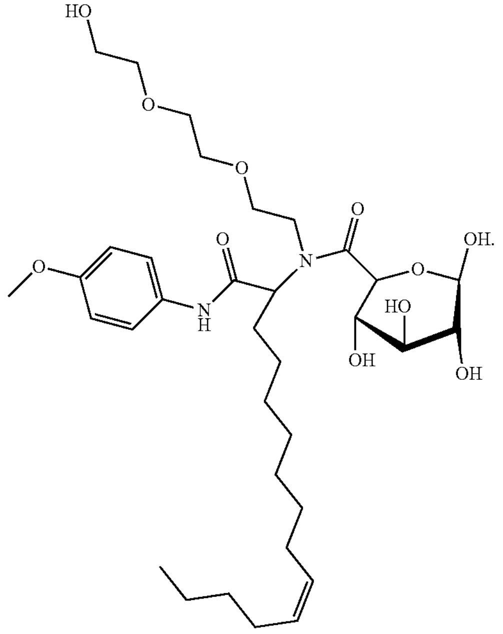
2. A compound selected from:
P83B4
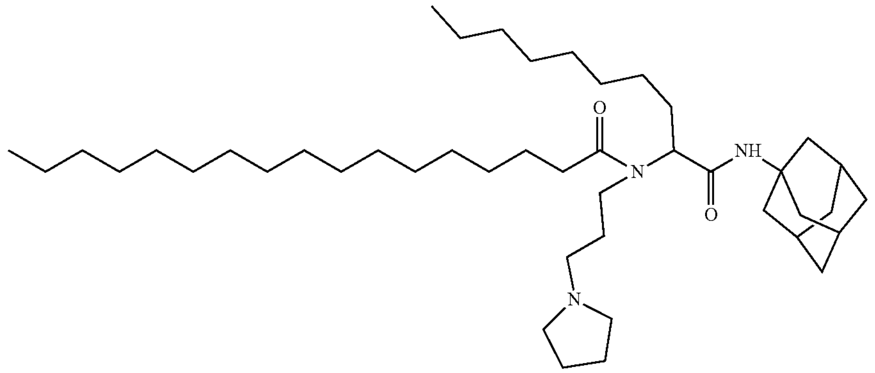
P83C4
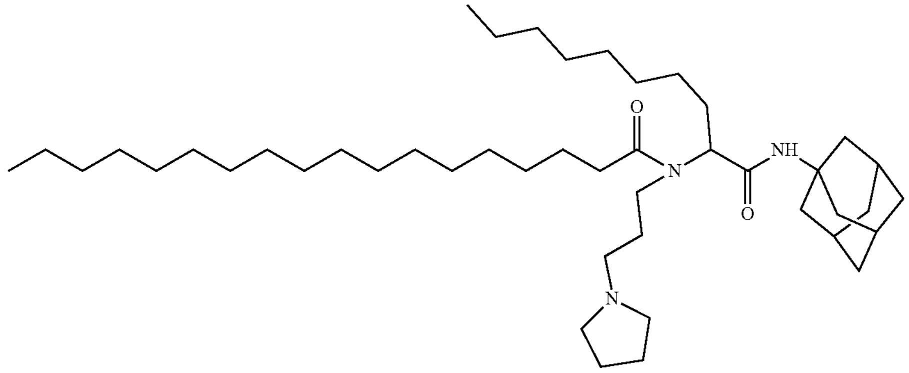

-continued
P83A4
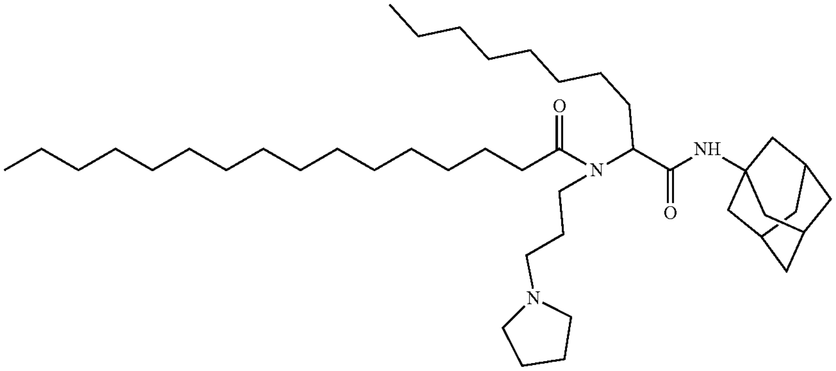
P94B4
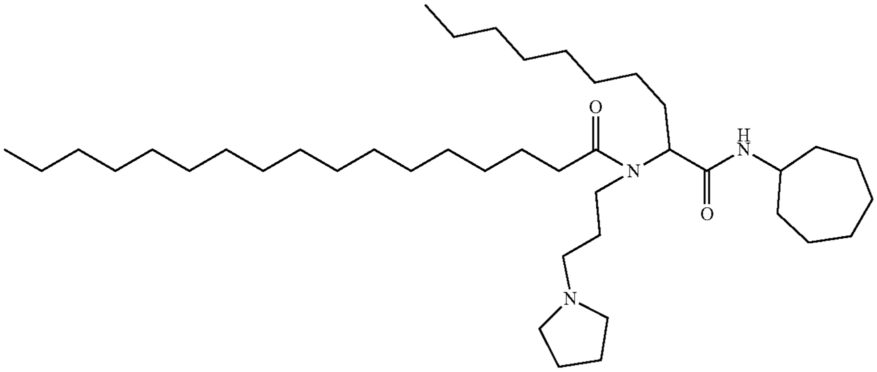
P94C4
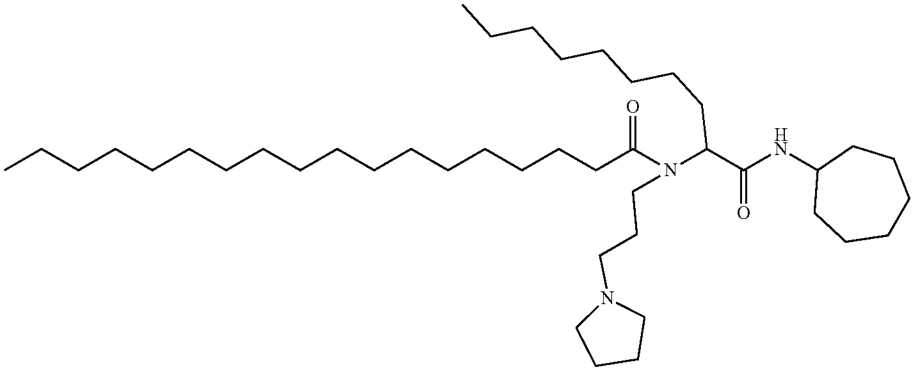
P95G12
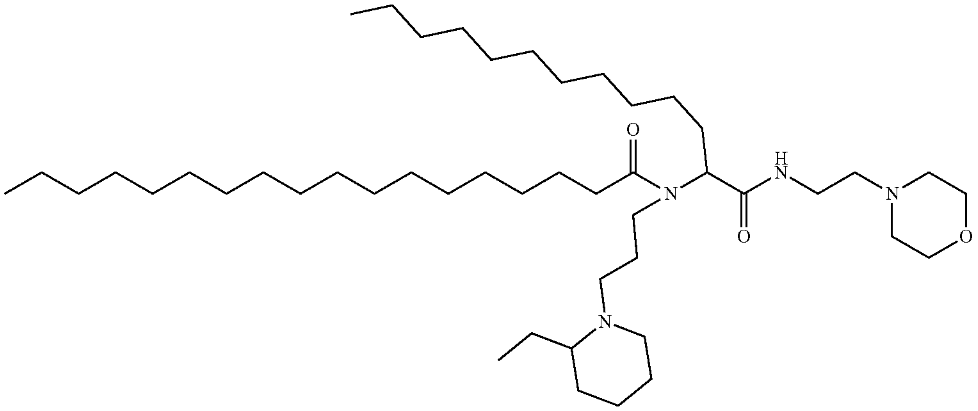

-continued
P110C10
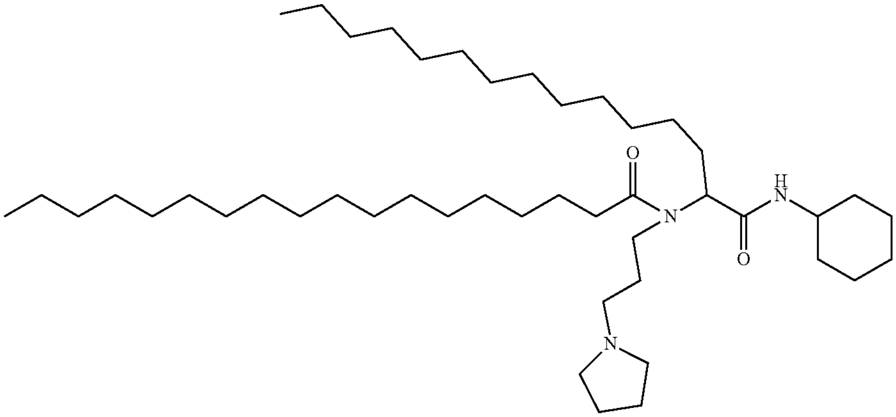
P366B5
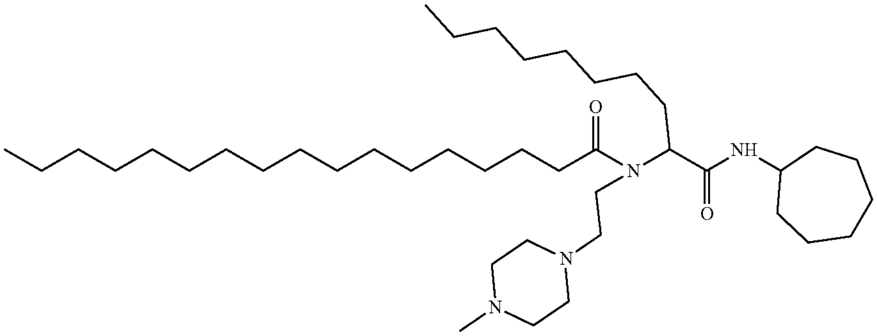
P366B6
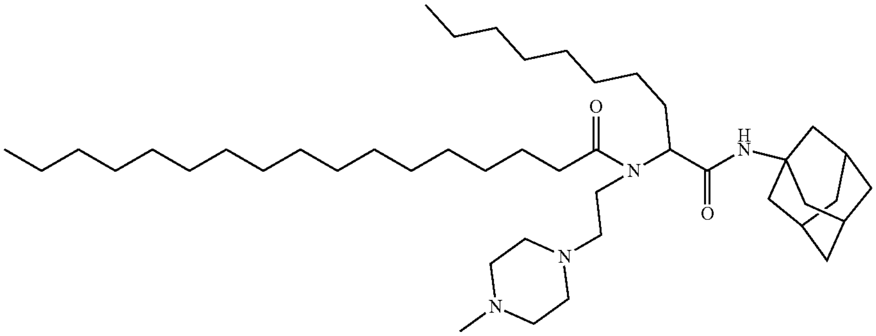
P366B12
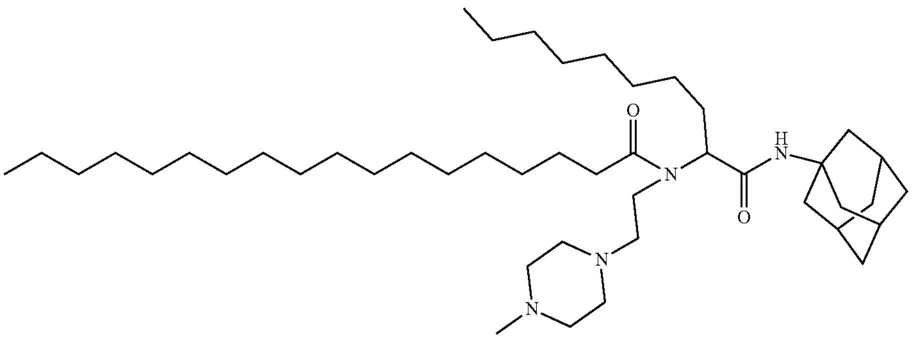

-continued
P366C1
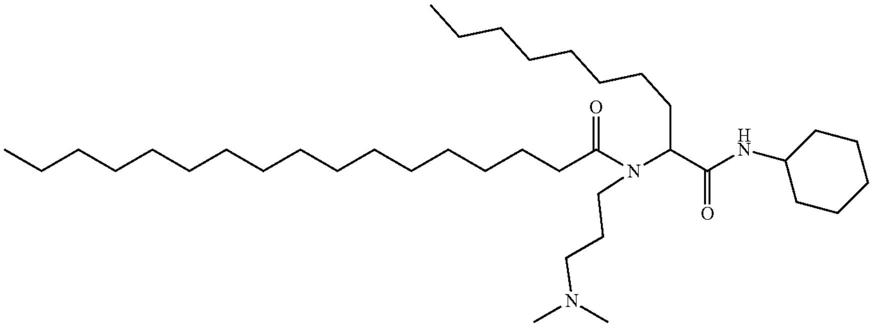
P366C4
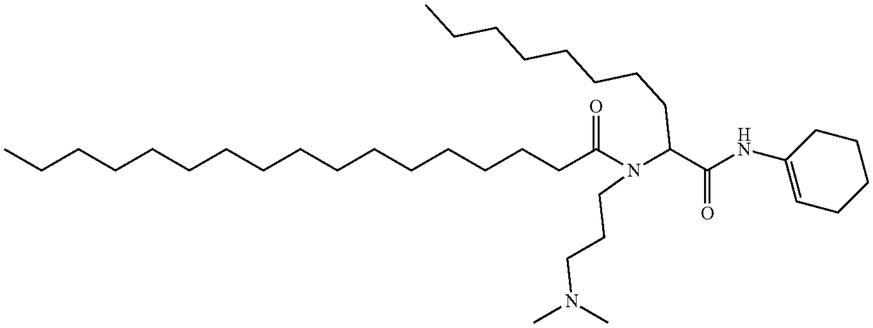
P366C6
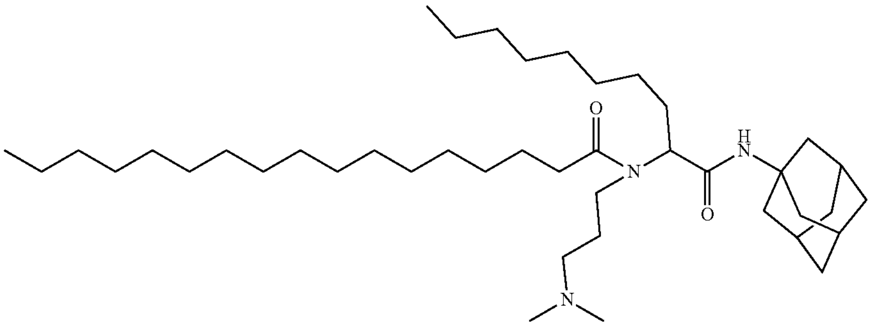
P366C7
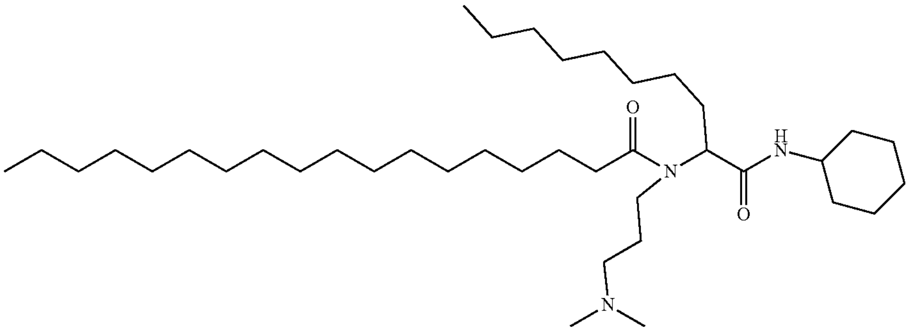

-continued
P366C11
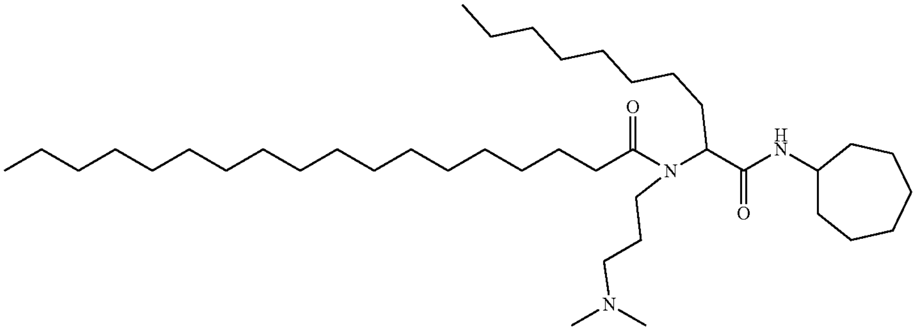
P366C12
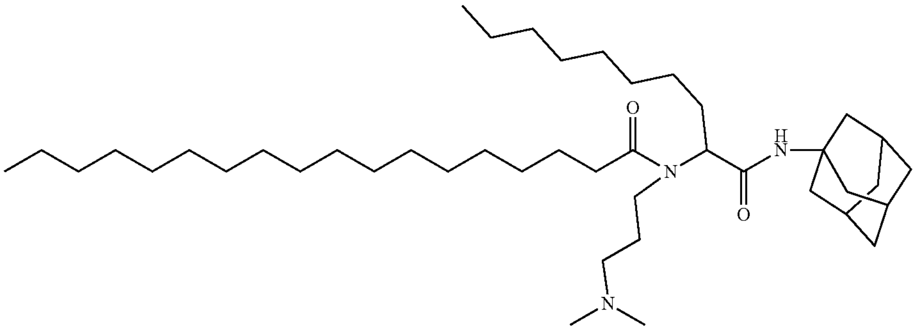
PC66D11
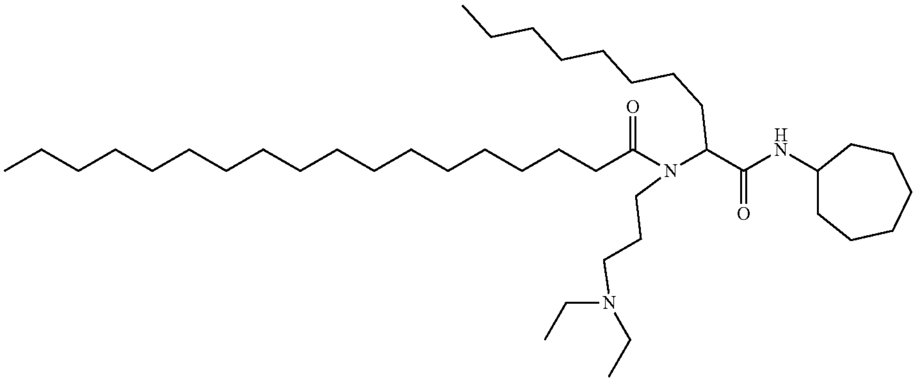
P366D12
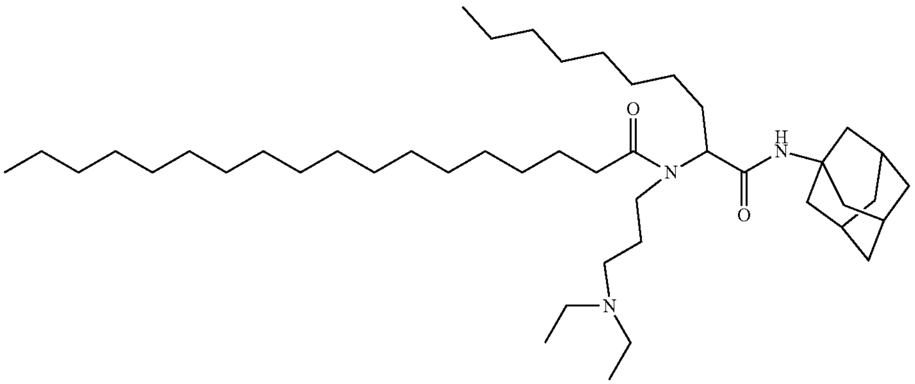

-continued
P368C5
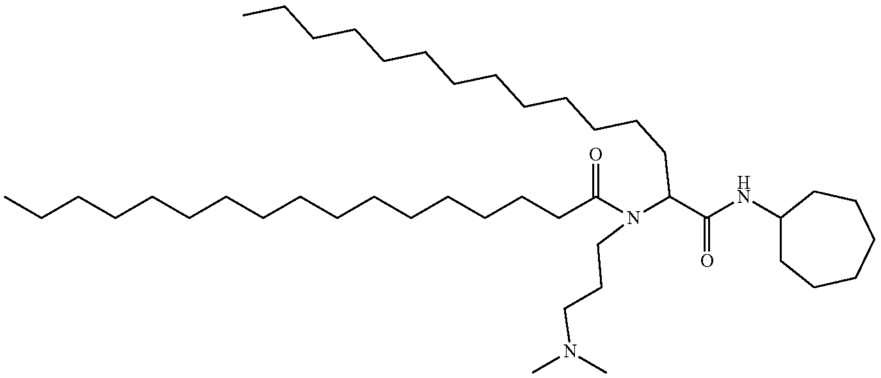
P368C12
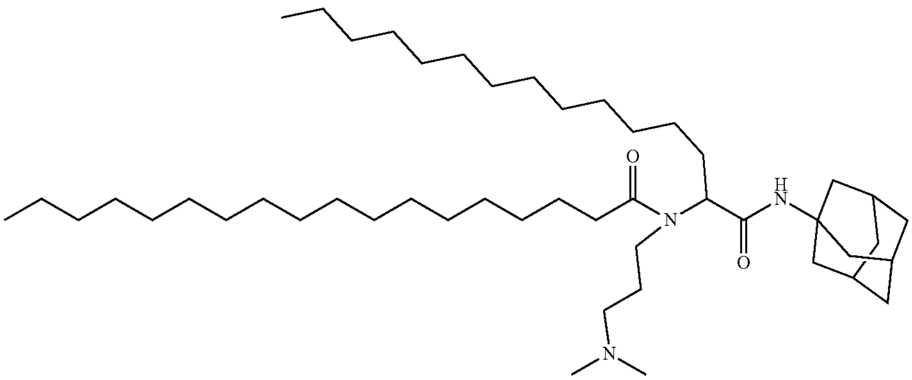
P368D12
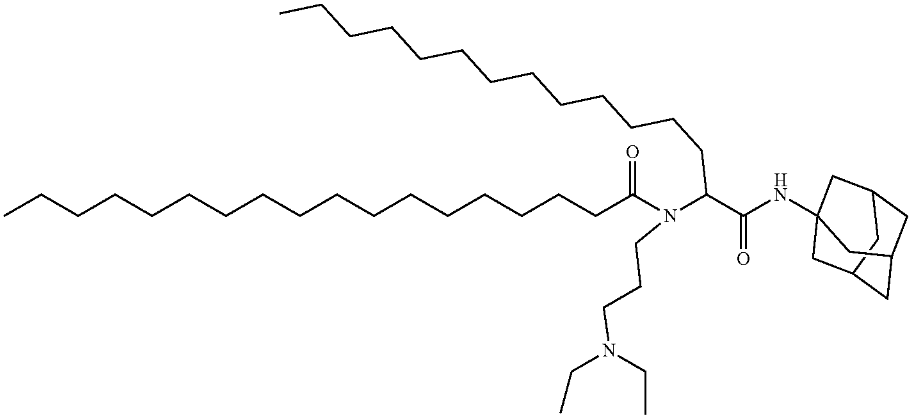
P370D6
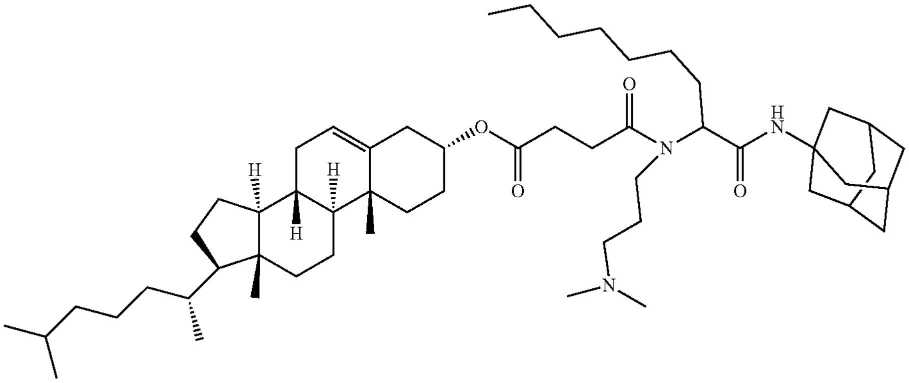

-continued
P371A6
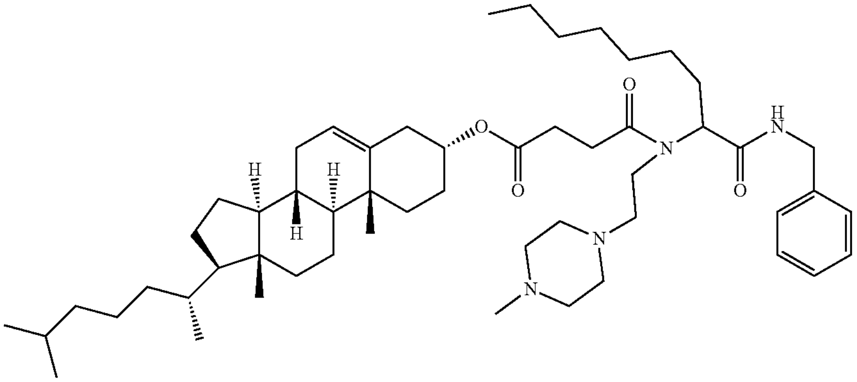
P371D6
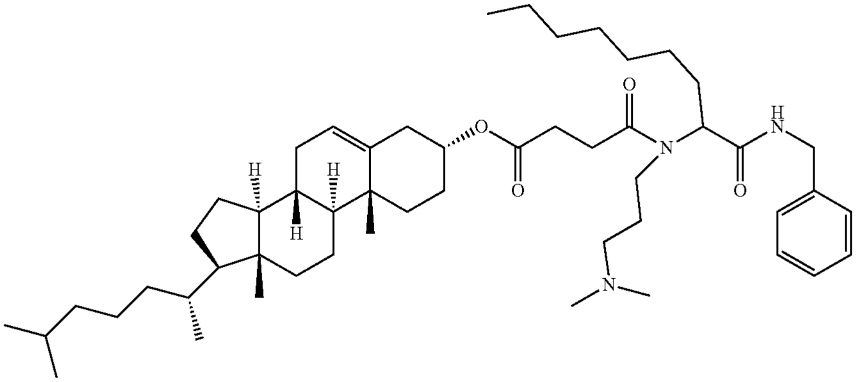
P374F7
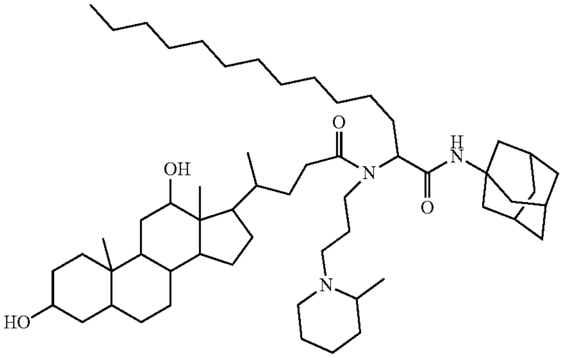
P376F1
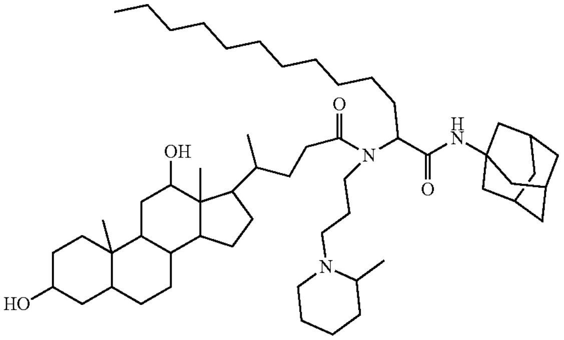
P380D1
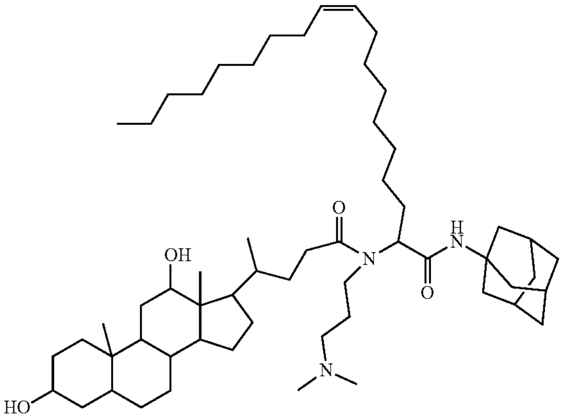
P380E1
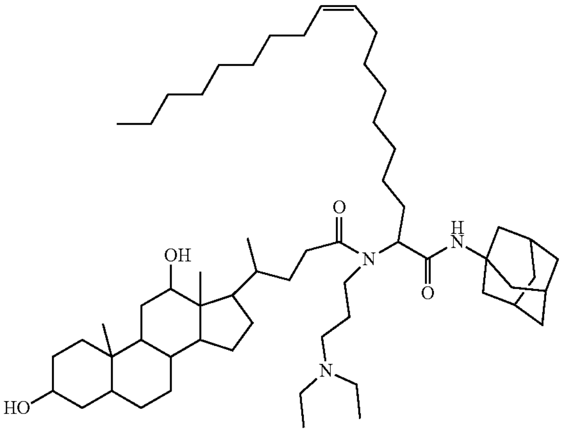

-continued
P380F1
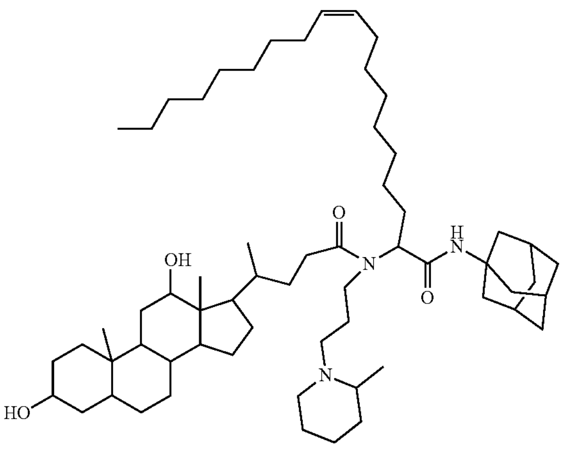
P380F4
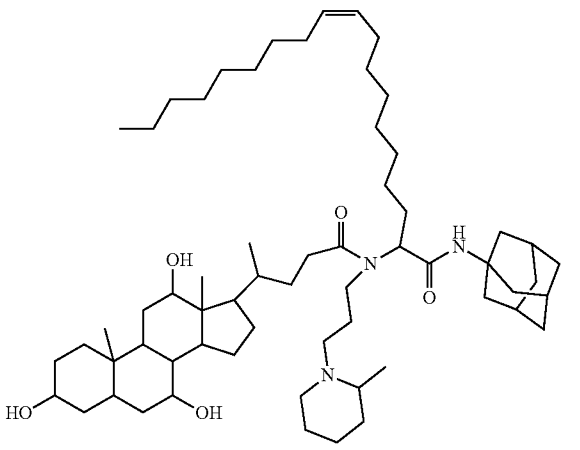
P381F1
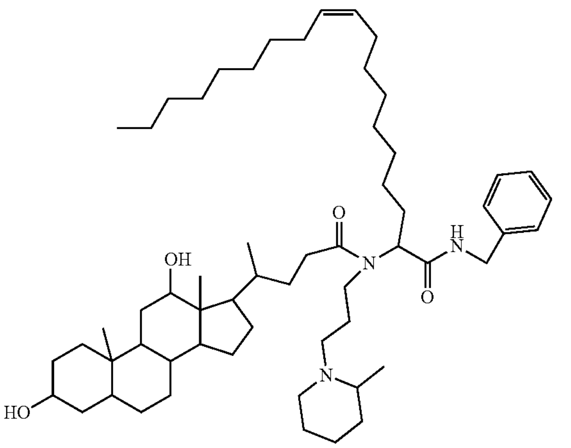
P383A9
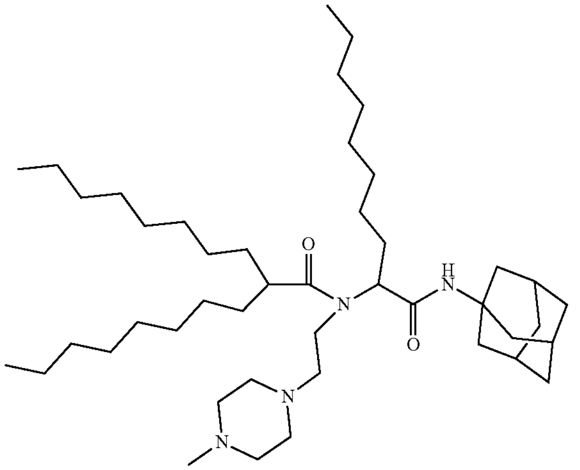
P383B10
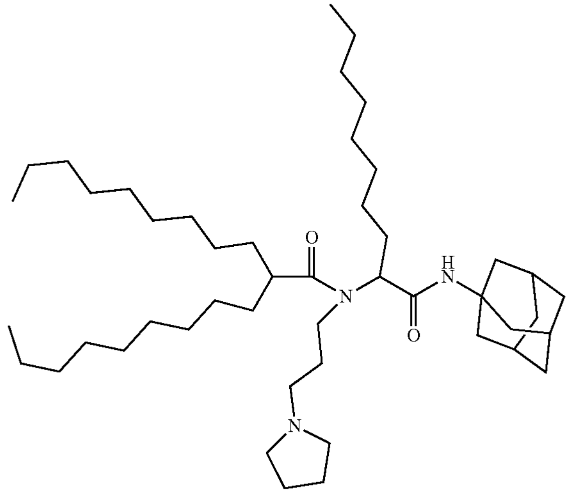
P386D12
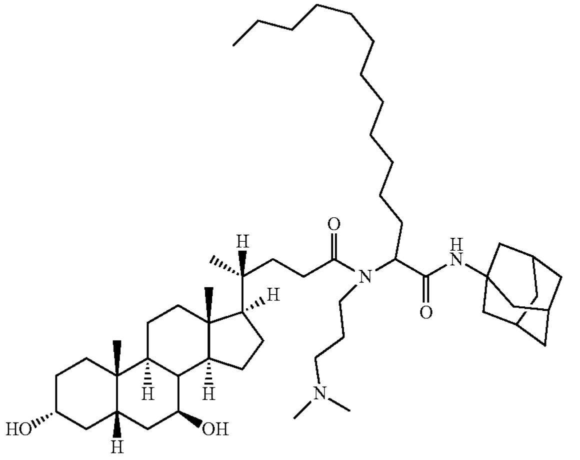

-continued
P387A2
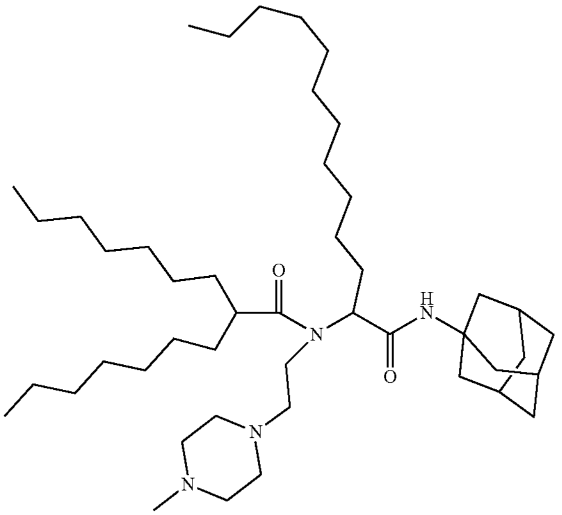
P390E12
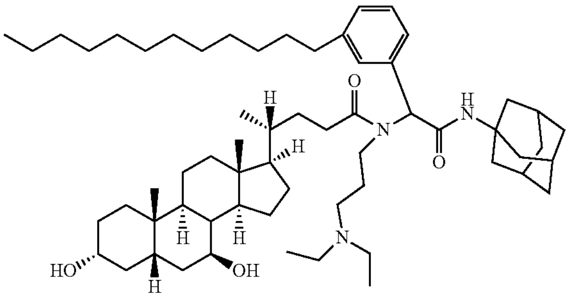
P394A7
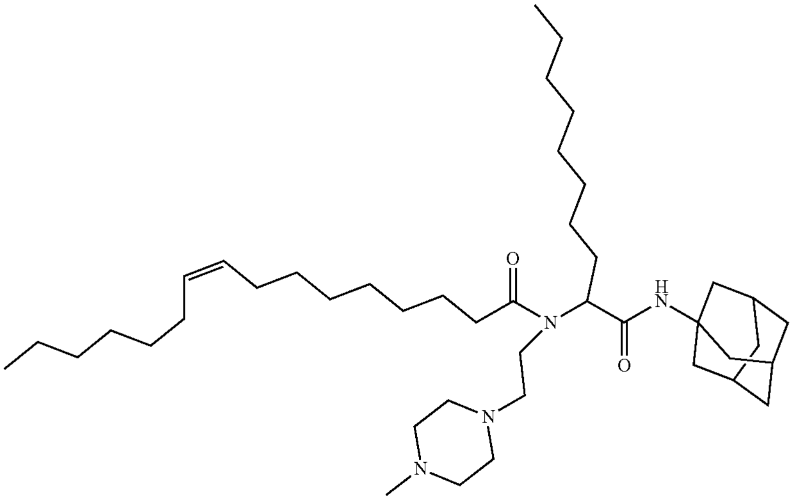
P394D7
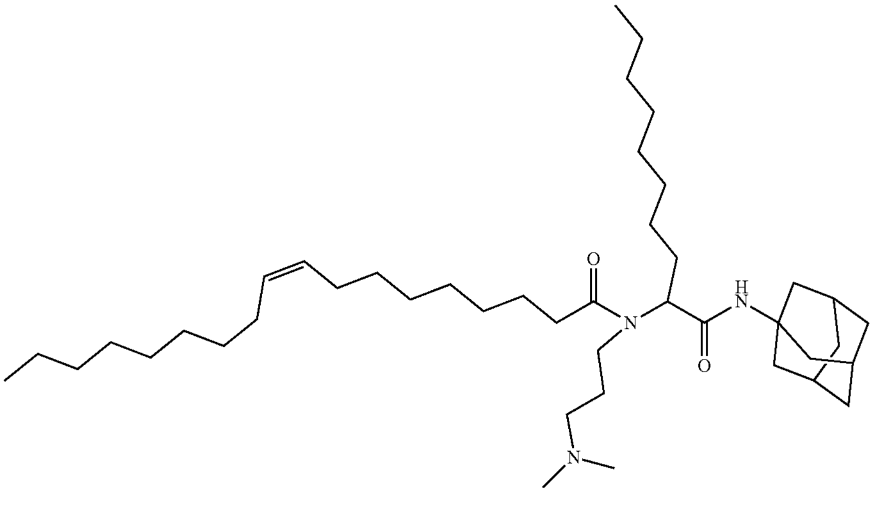

-continued
P394D12
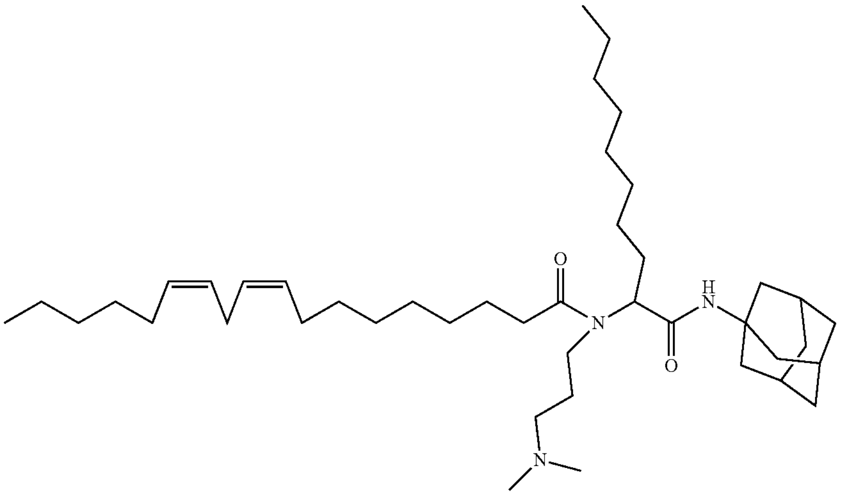
P394H8
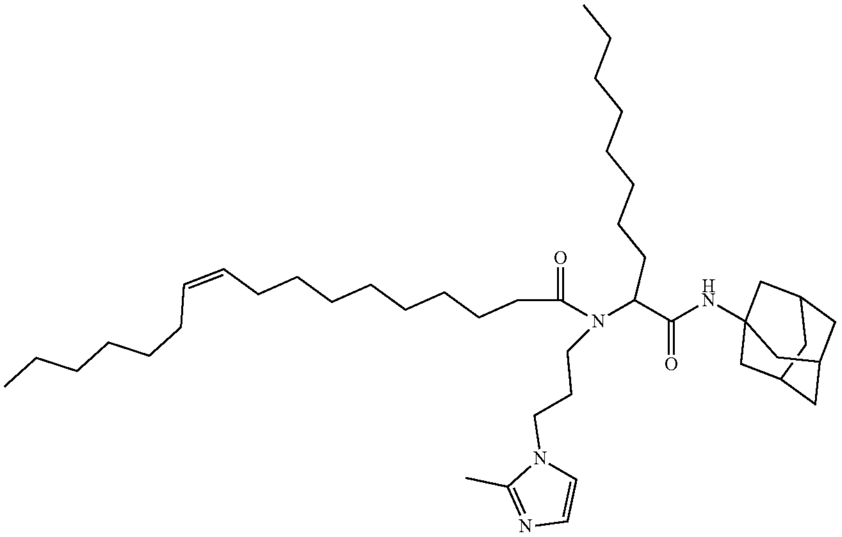
P394H9
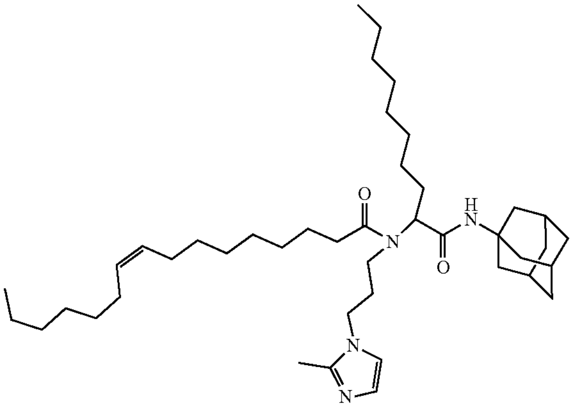
P398D1
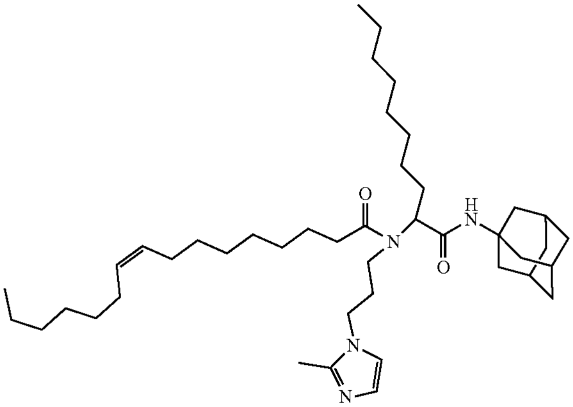

-continued
P398D6
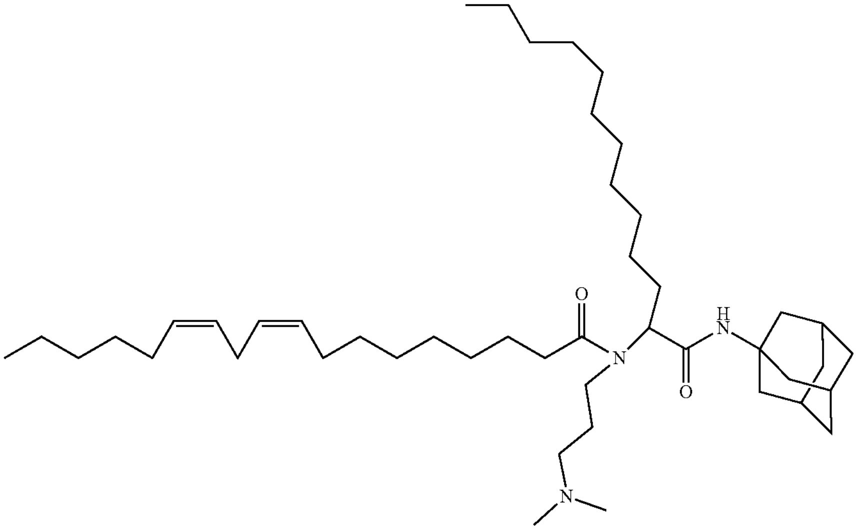
P398D7
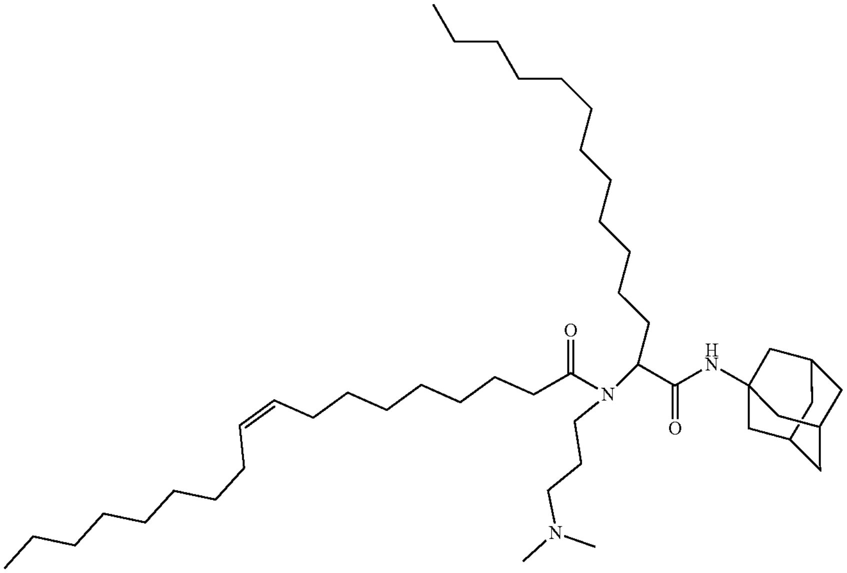

-continued
P398D8
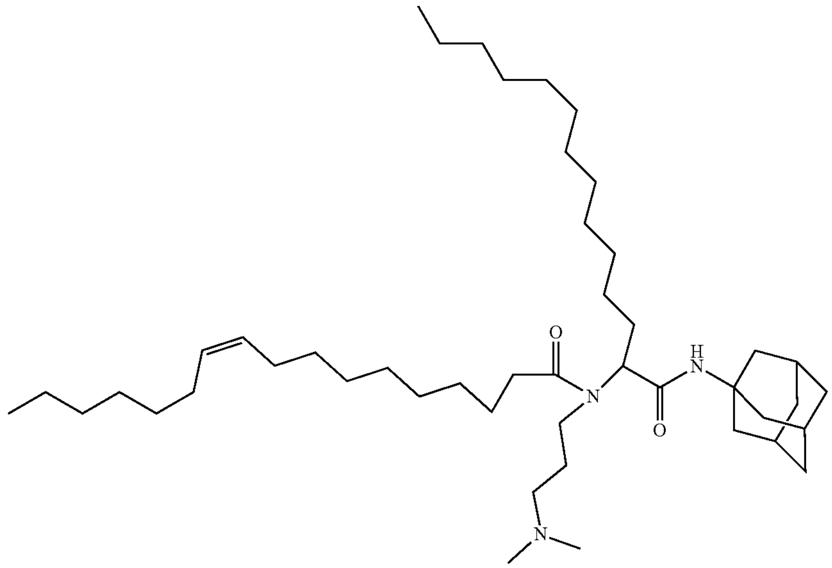
P398D9
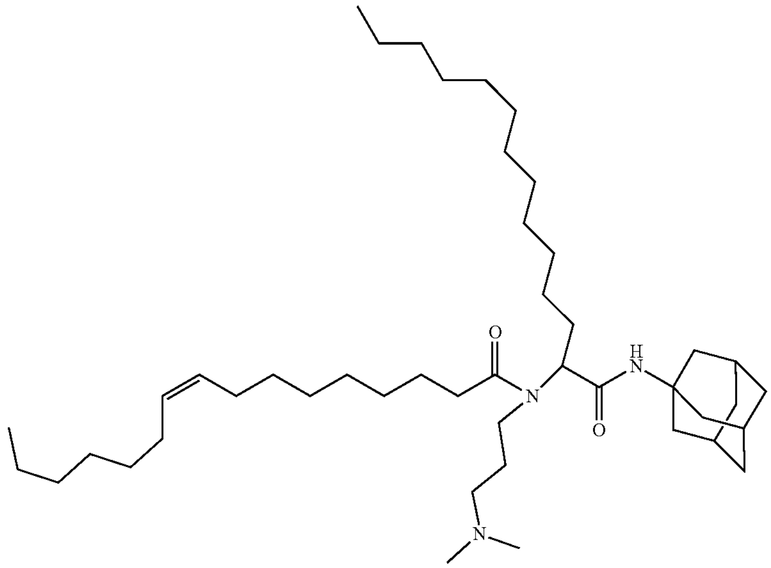

-continued
P398D12
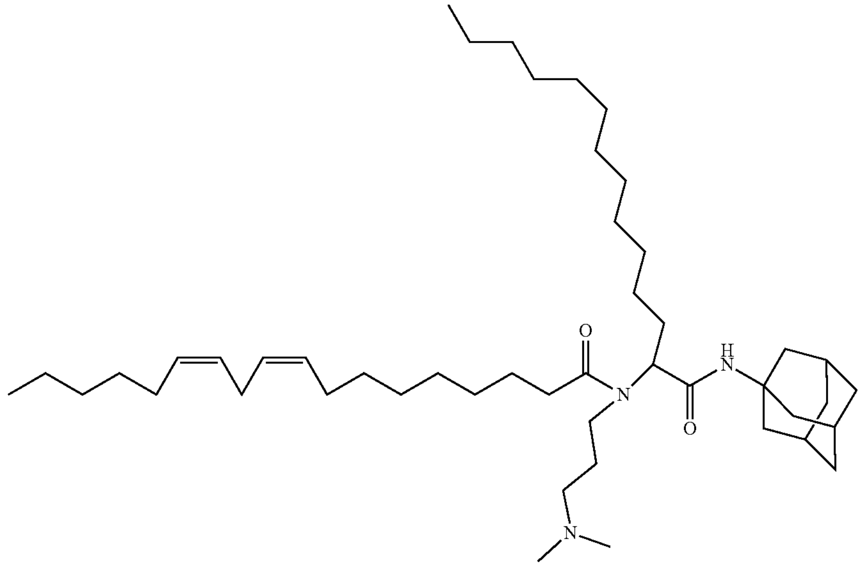
P398E1
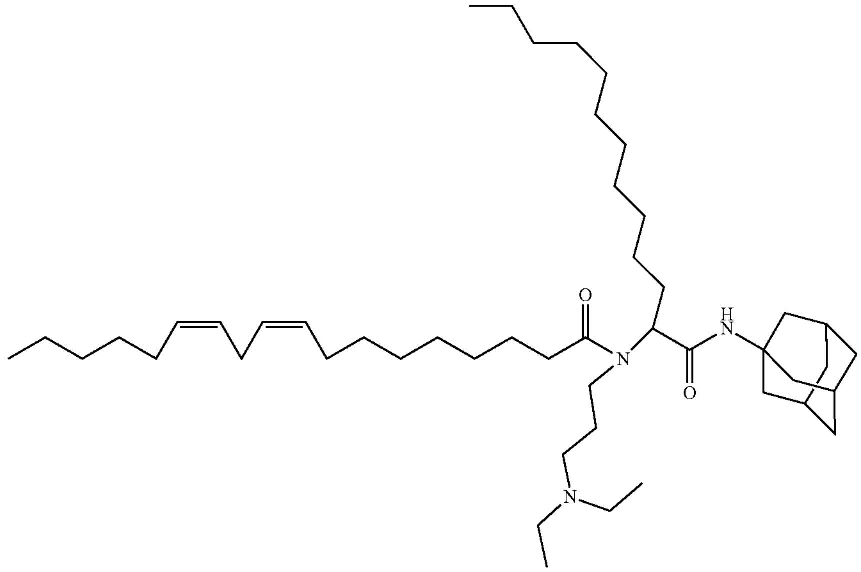

-continued
P399A1
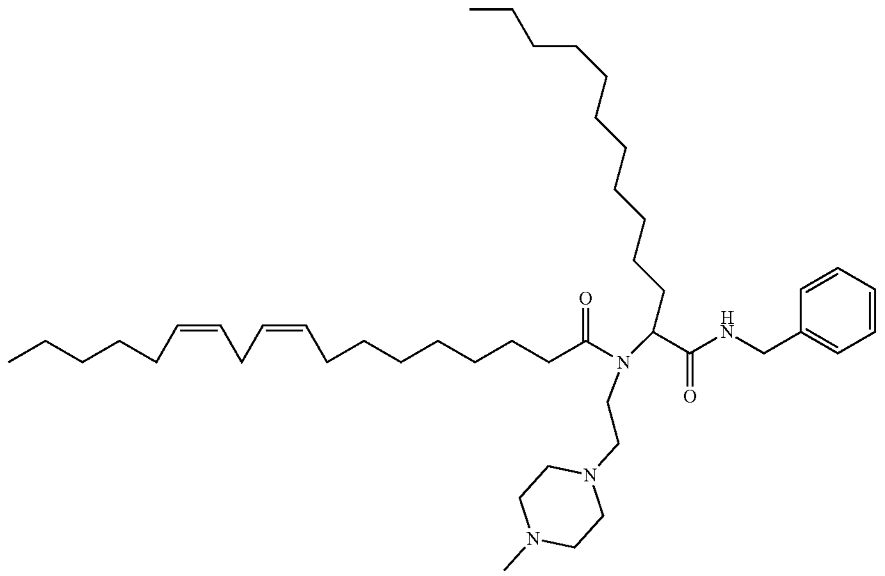
P399A9
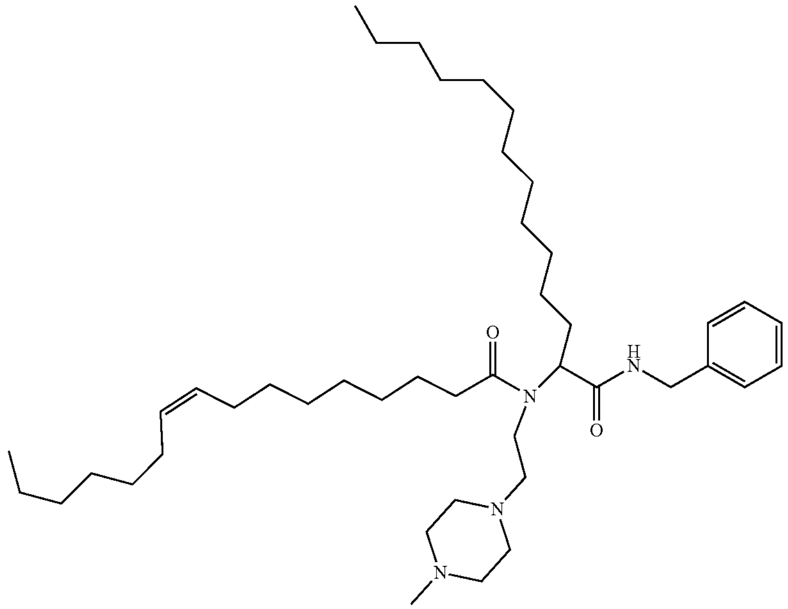

-continued
P399E1
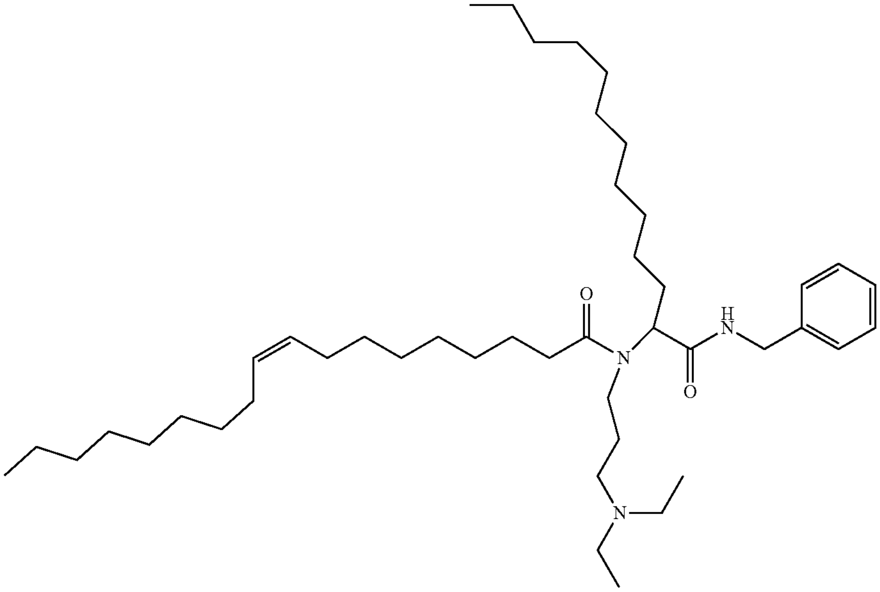
P399F1
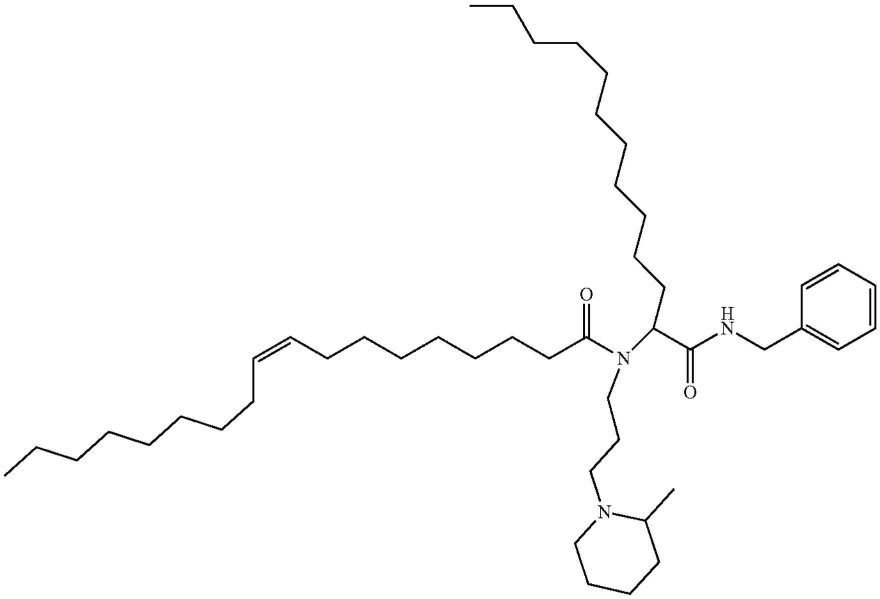

-continued
P39912
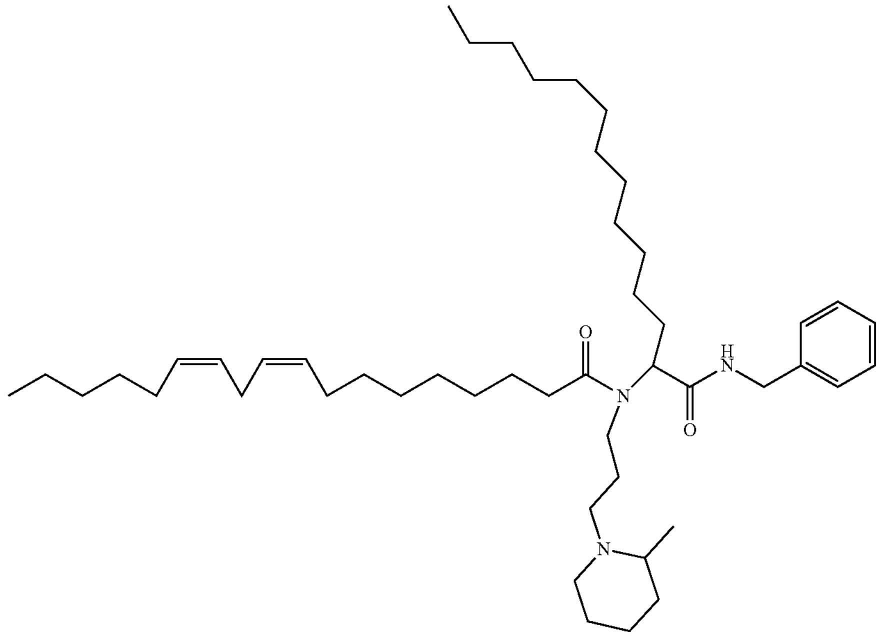
P399H1
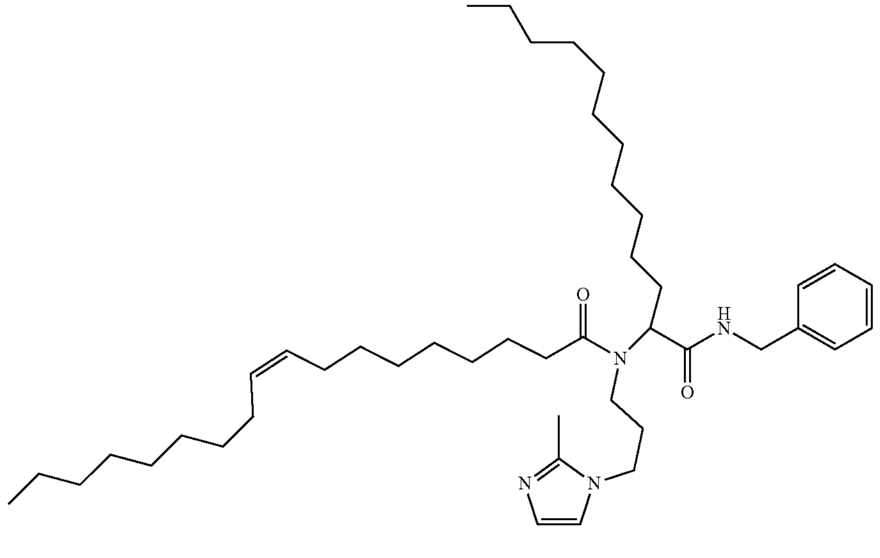

-continued
P399H3
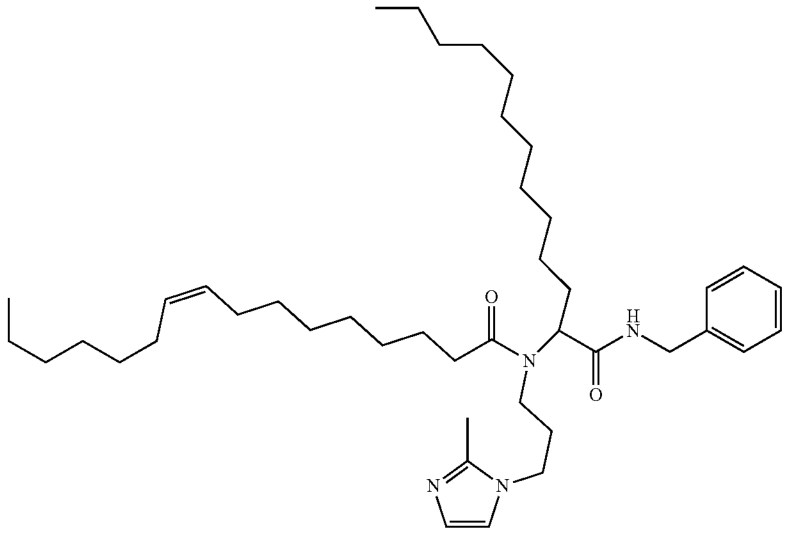
P400A3
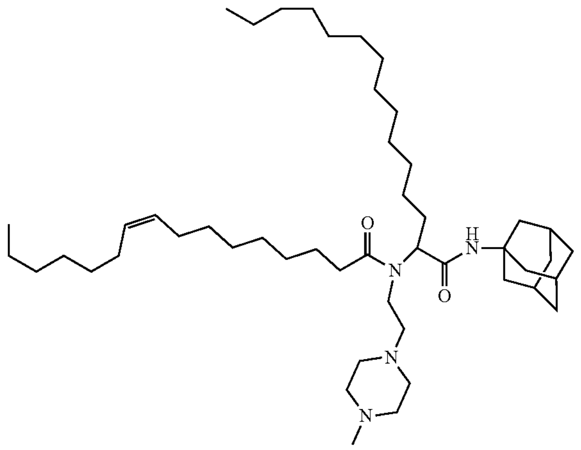
P400A4
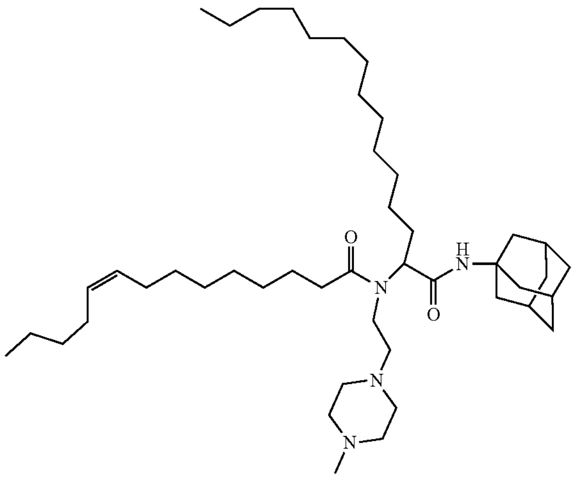
P400D12
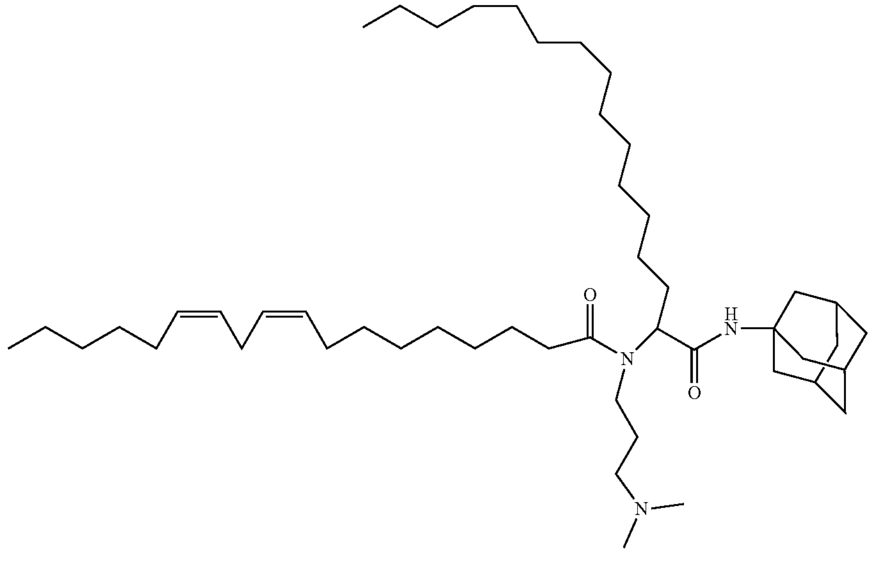

-continued
P401A3
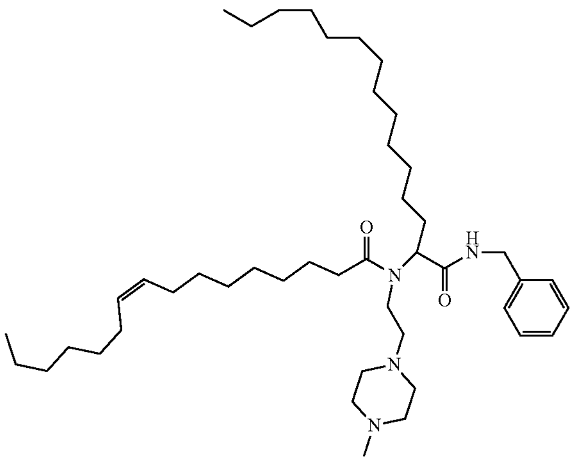
P401A4
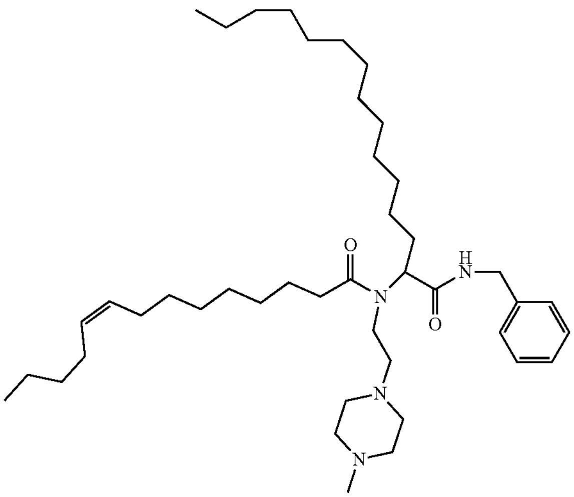
P401A6
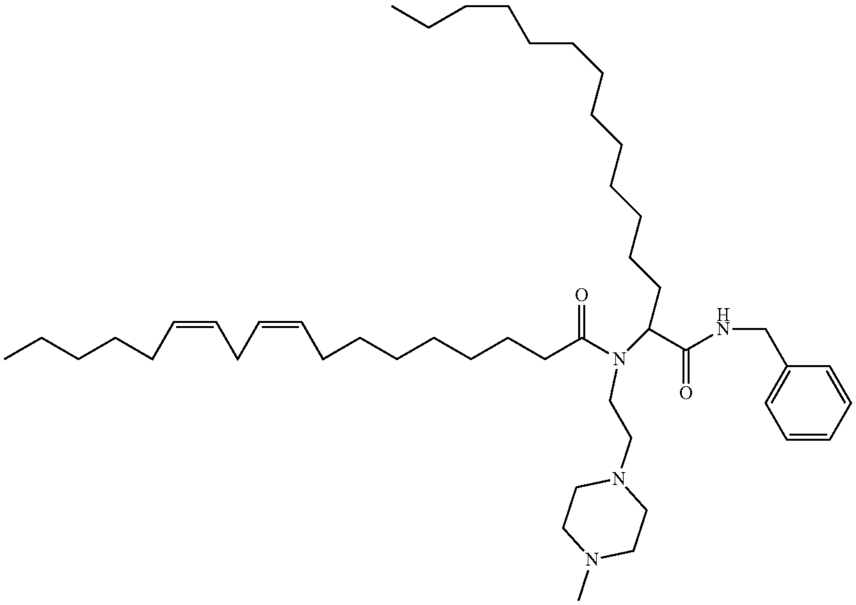
P401D1
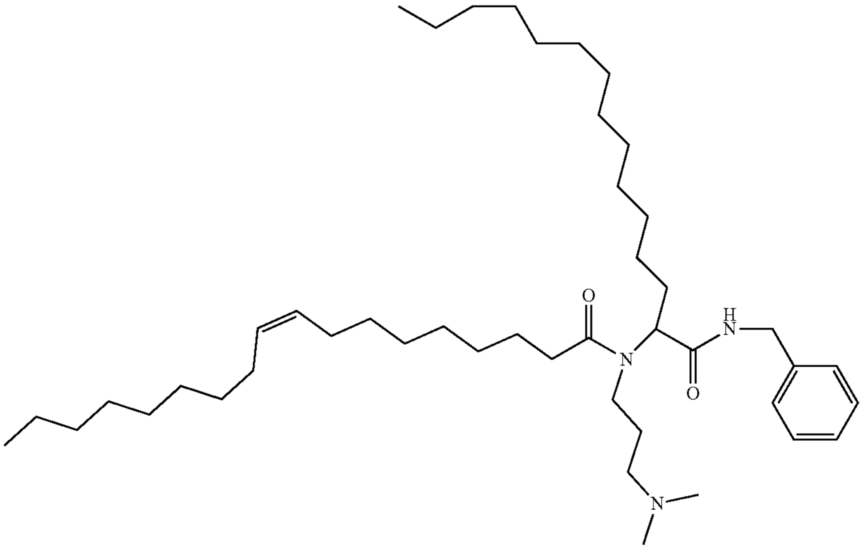

-continued
P401E1
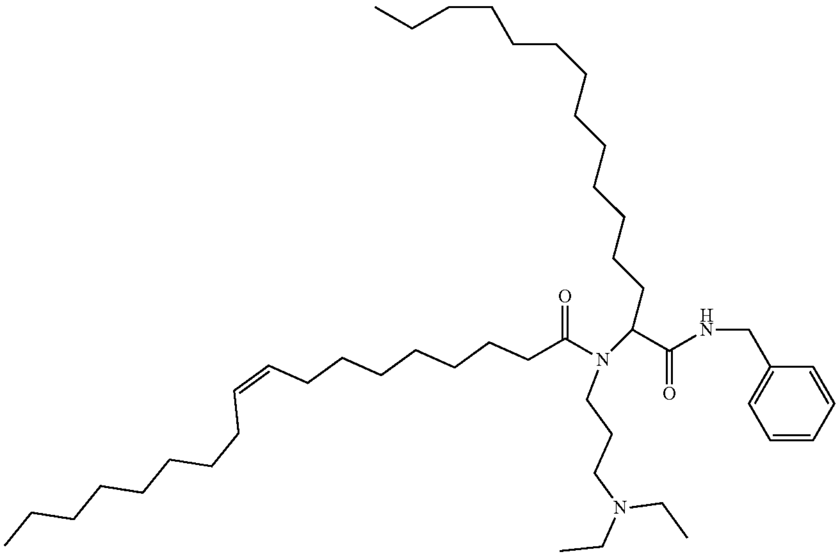
P401E9
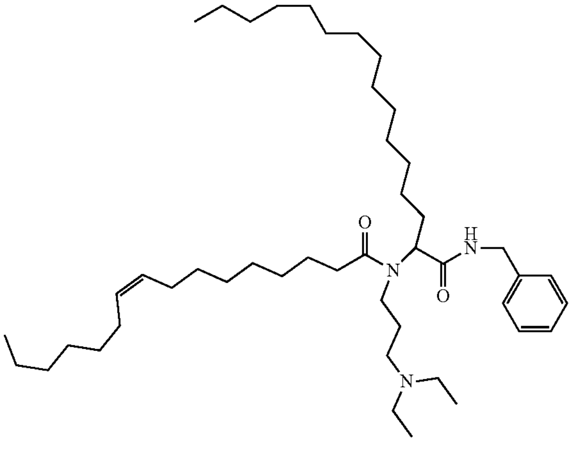
P401E10
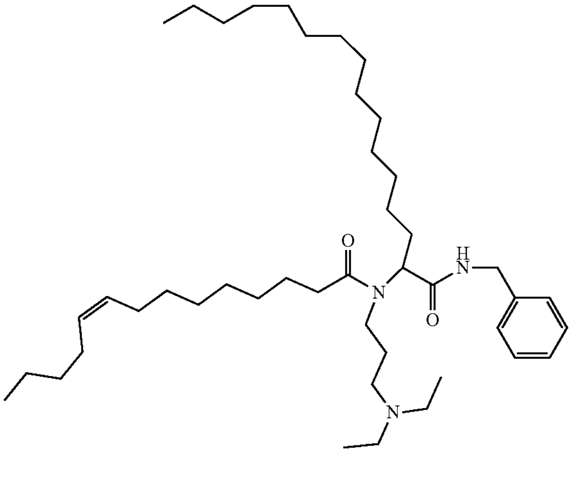

P401E12
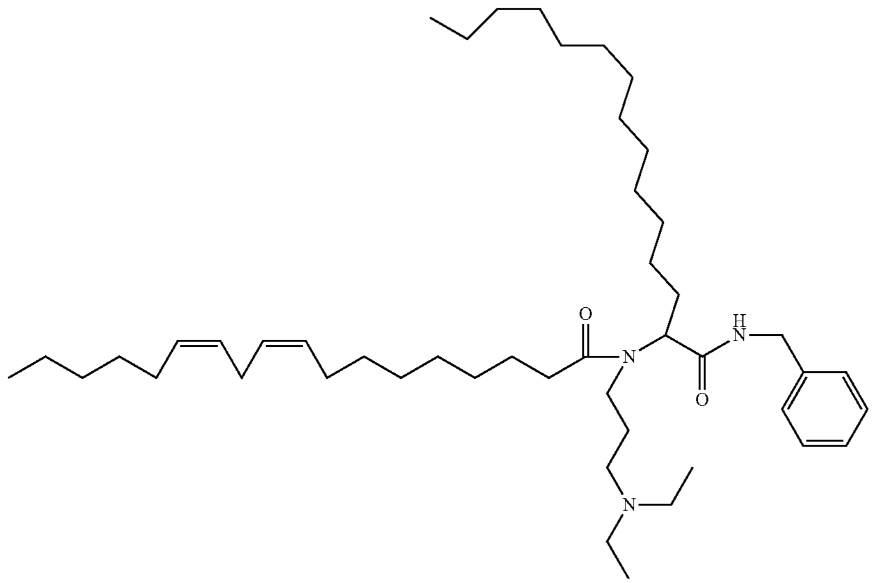
P401H12
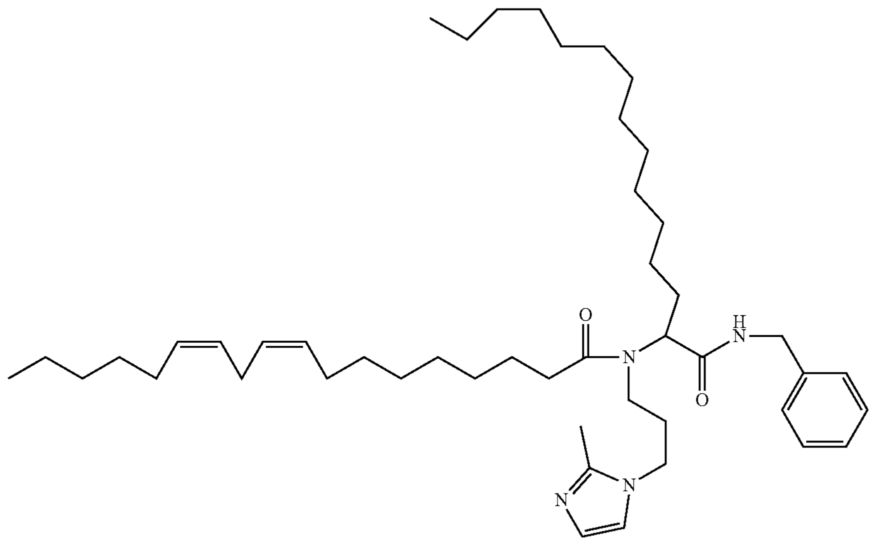
P402A7
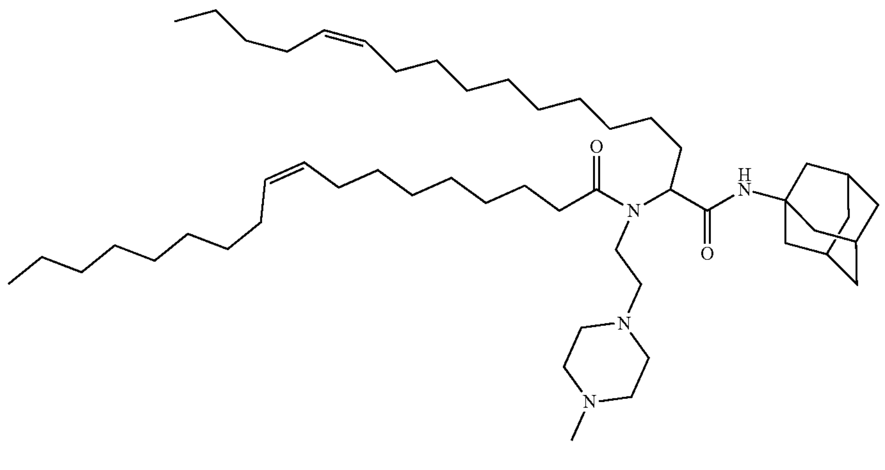

-continued
P402A9
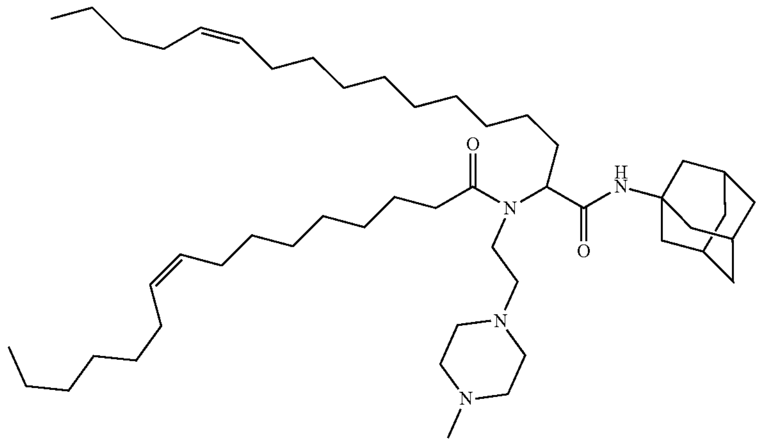
P402D7
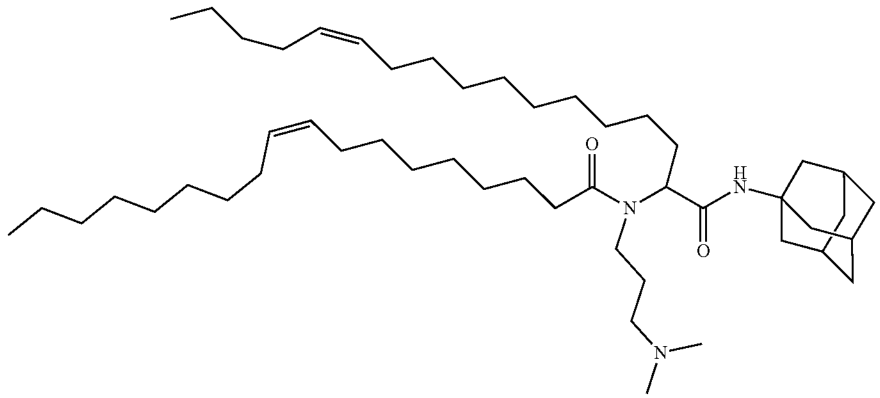
P402D9
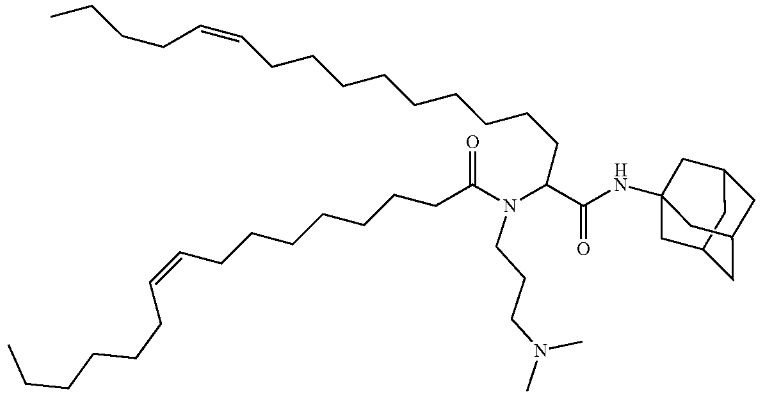
P402D12
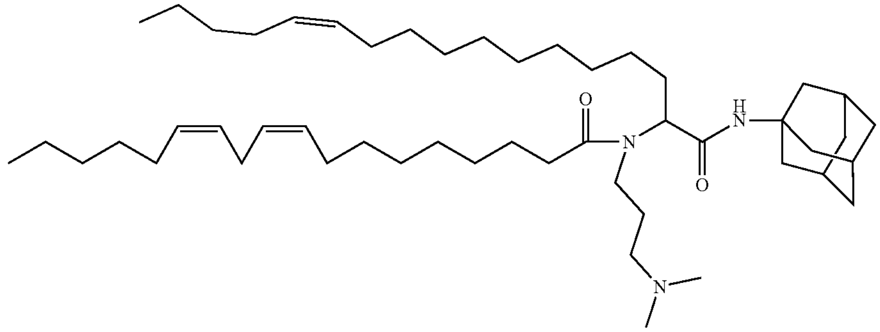

-continued
P402E12
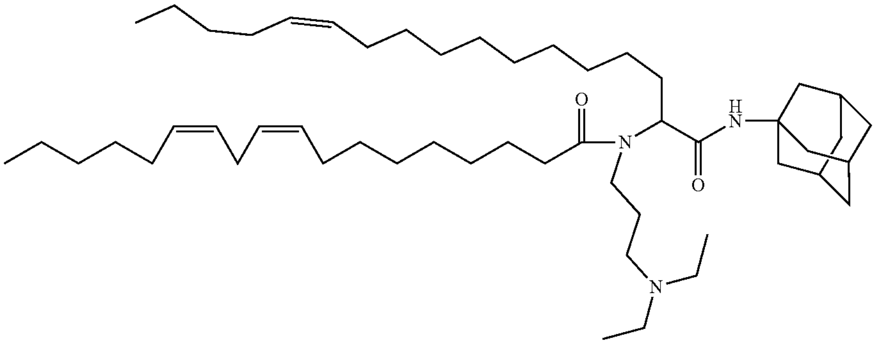
P403A7
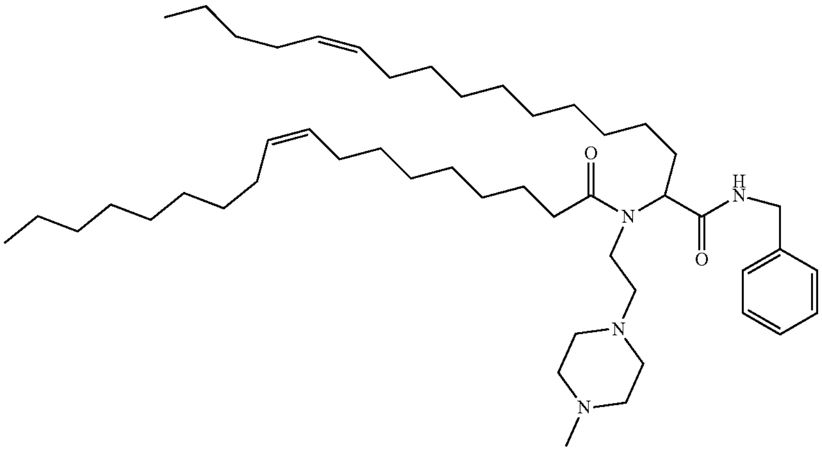
P403A9
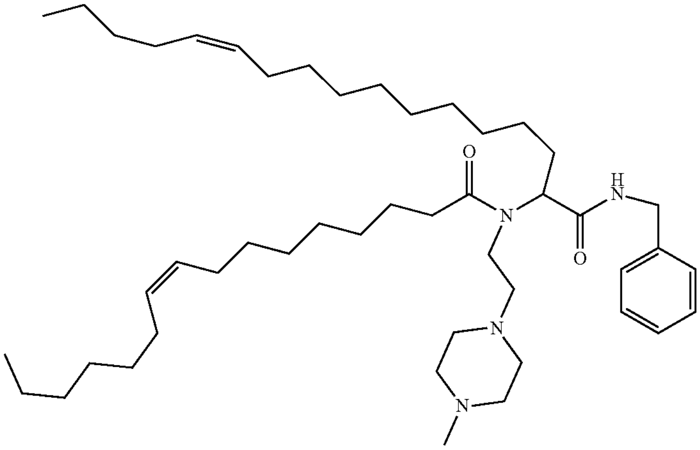
P403H7
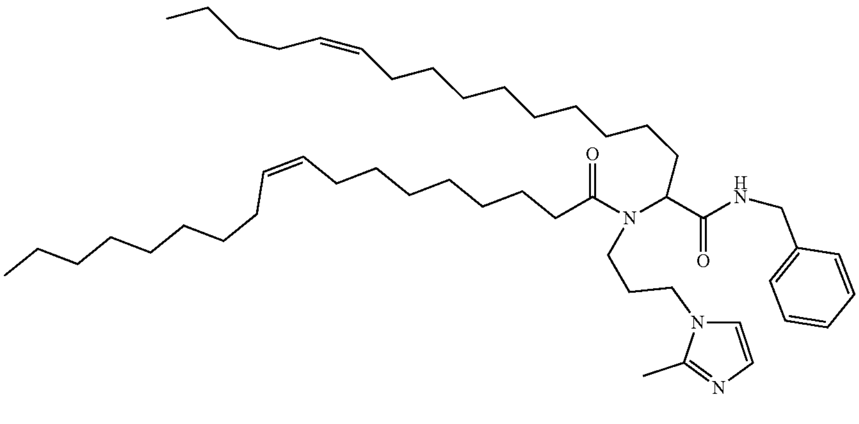

-continued
P403H10
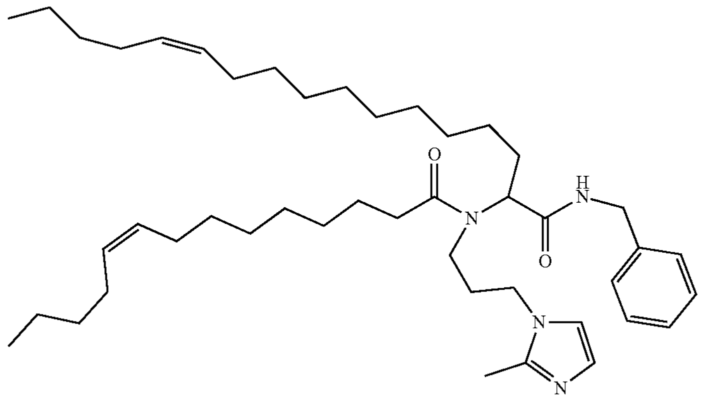
P404D1
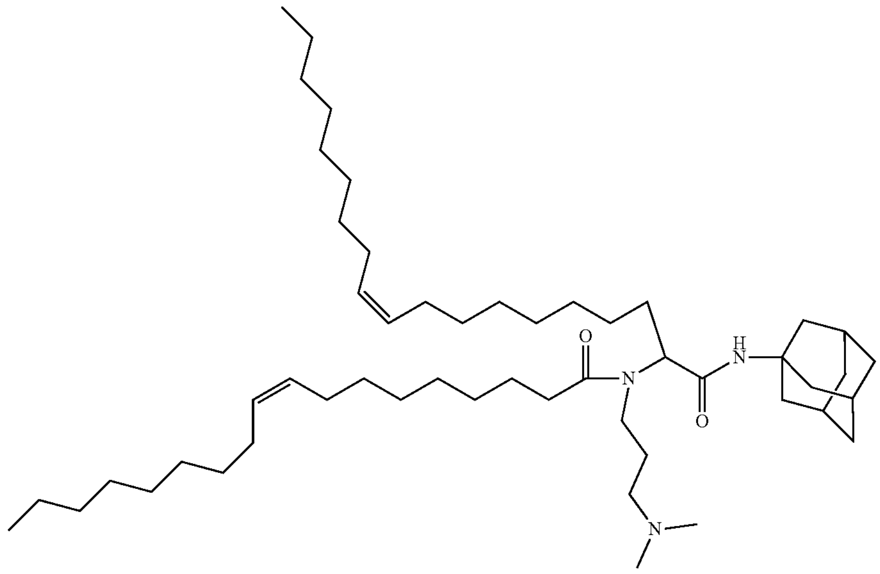
P404D3
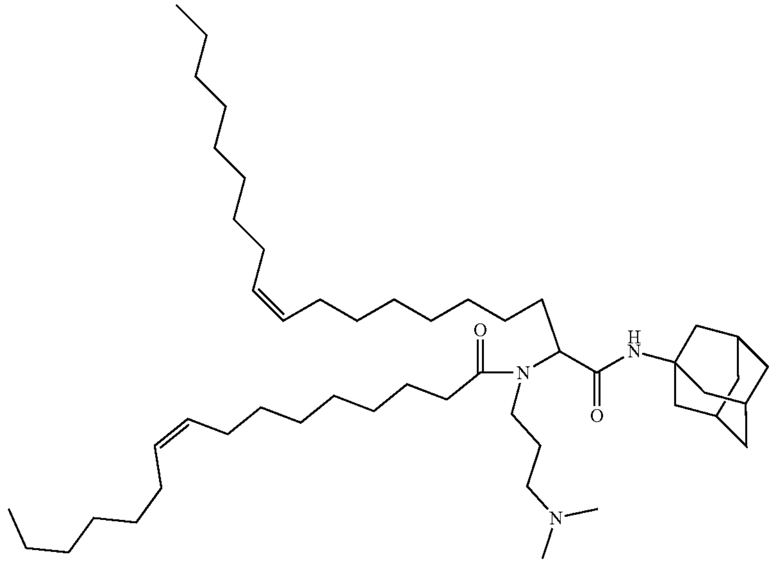

-continued
P404D6
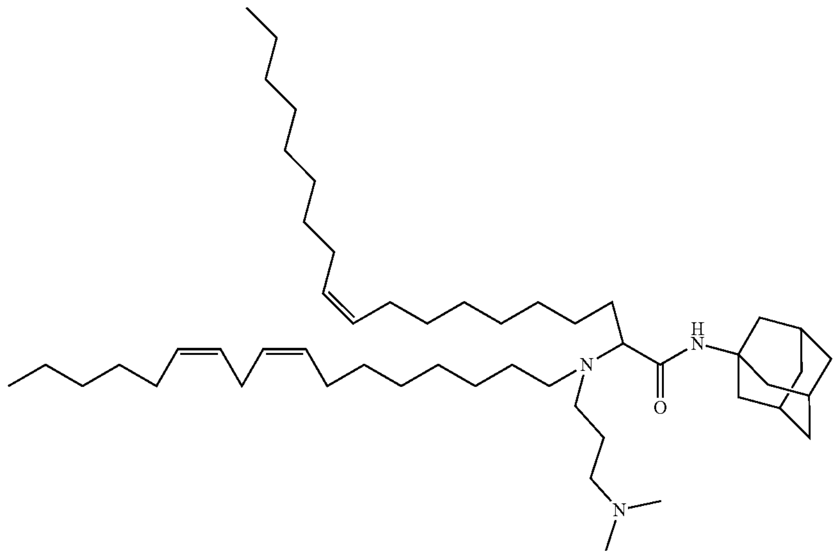
P404E1
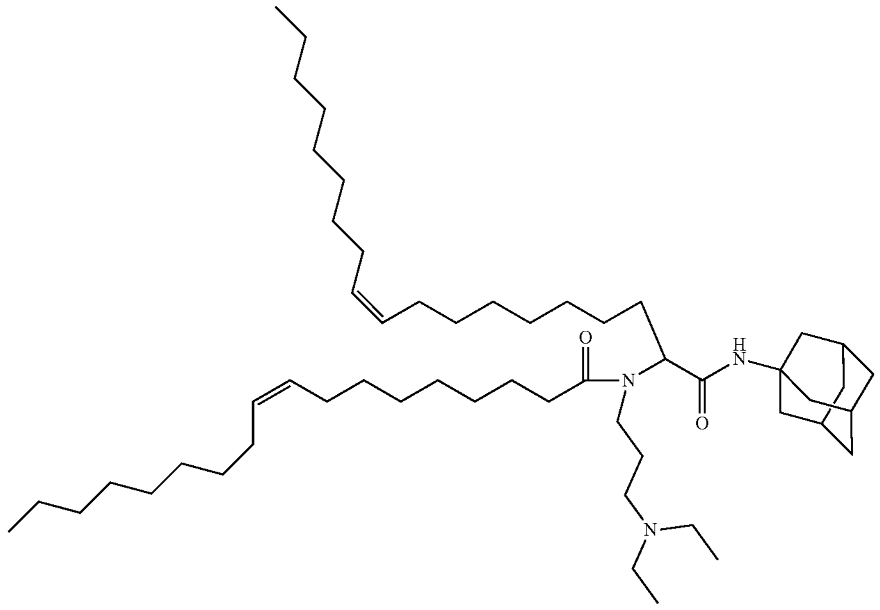

-continued
P405E3
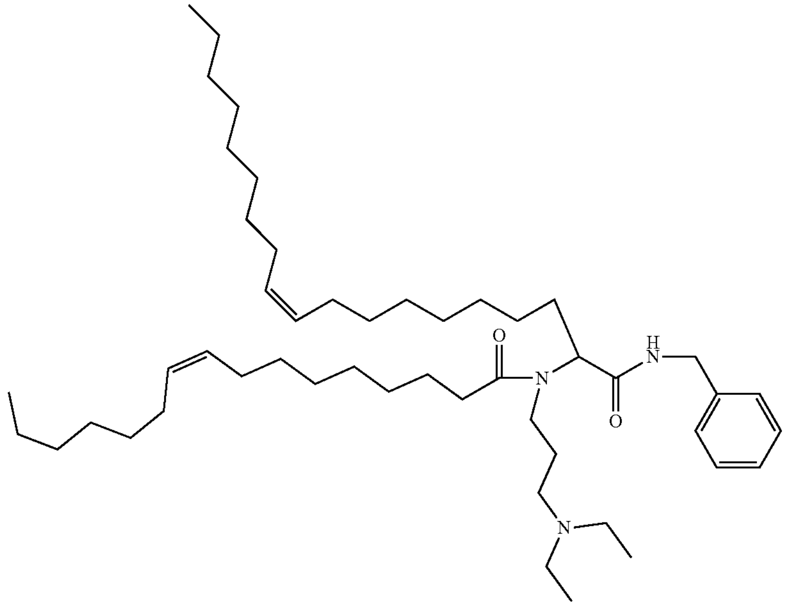
P406A6
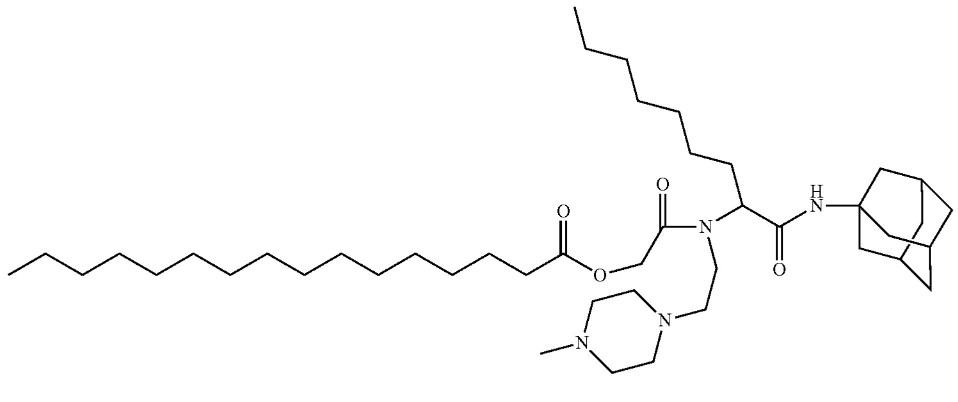
P406A12
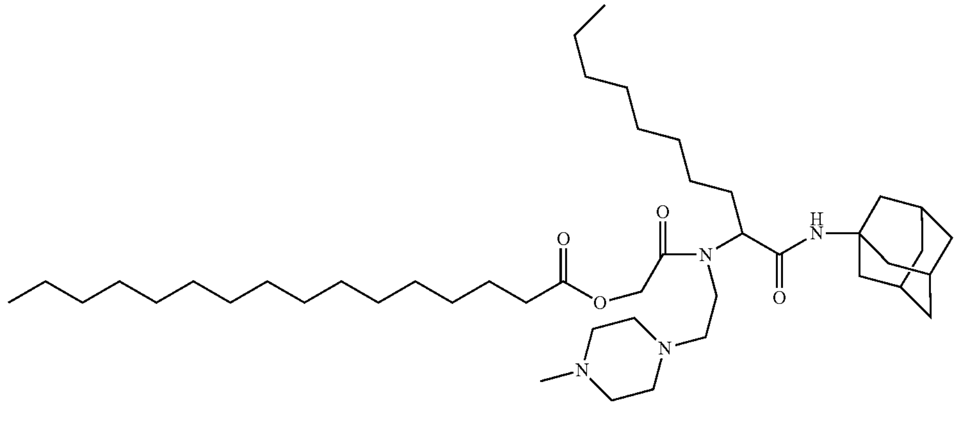

-continued
P406E12
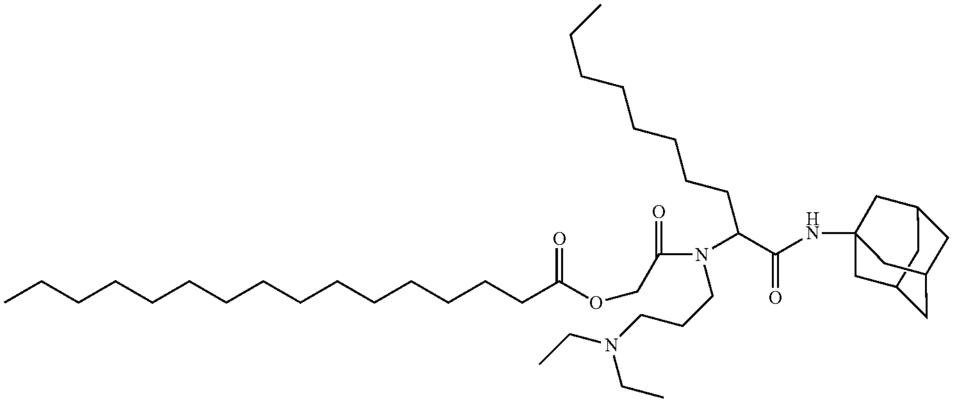
P406F12
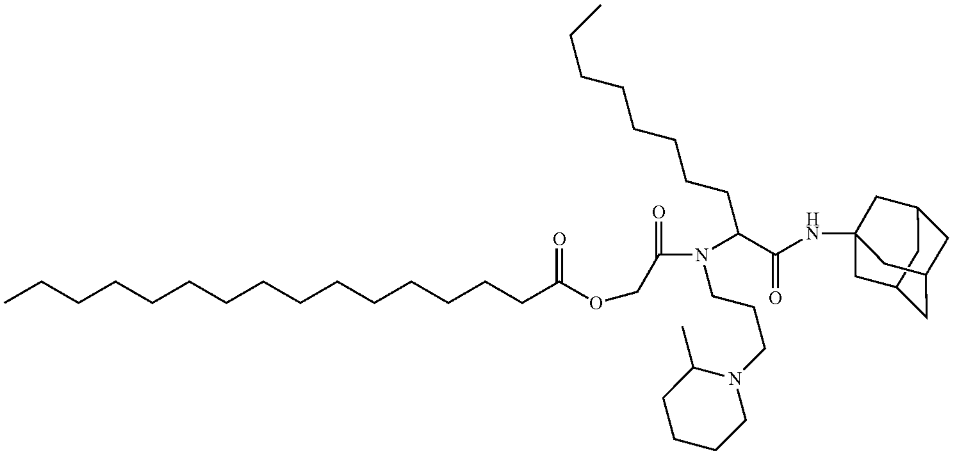
P406H6
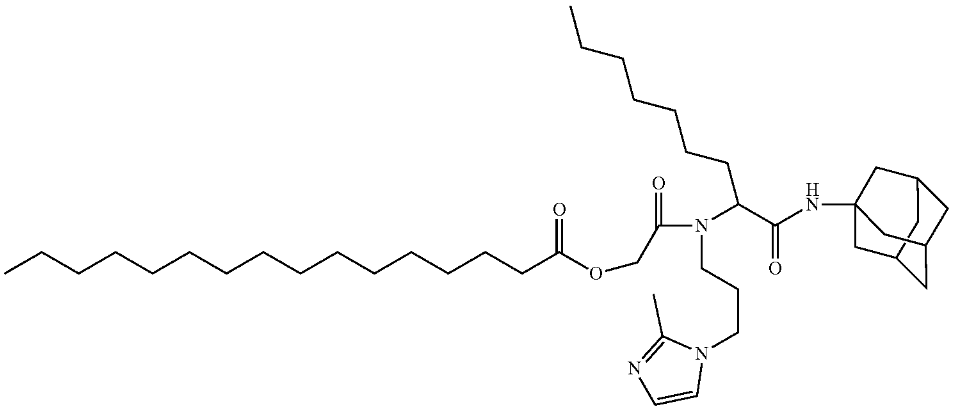

-continued
P406F10
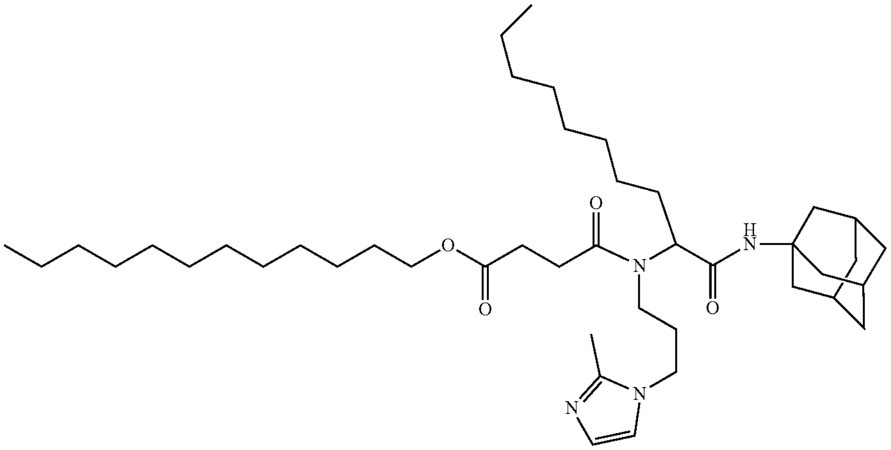
P406H12
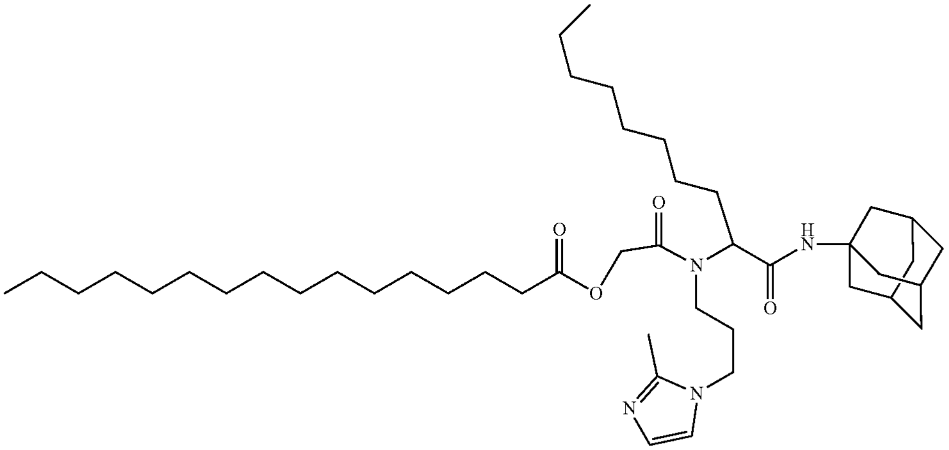
P407D12
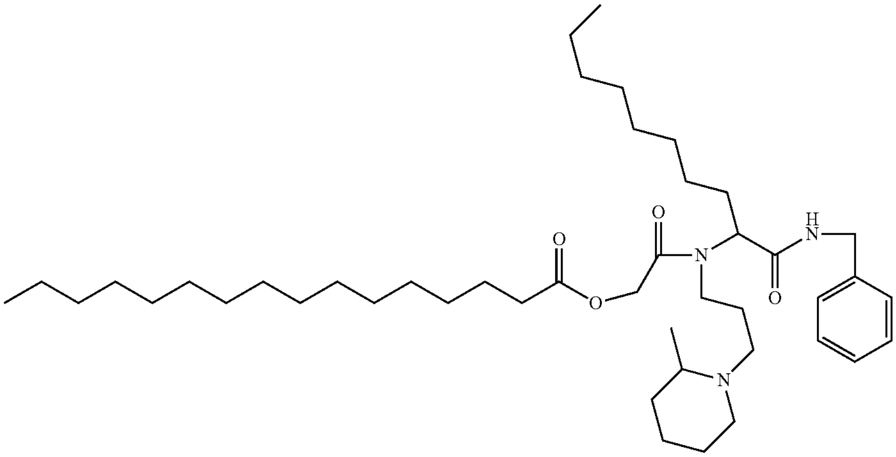

-continued
P407F12
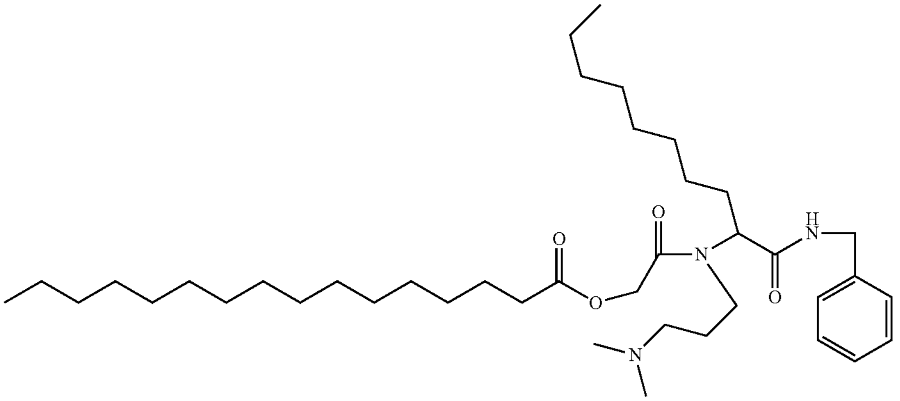
P408H4
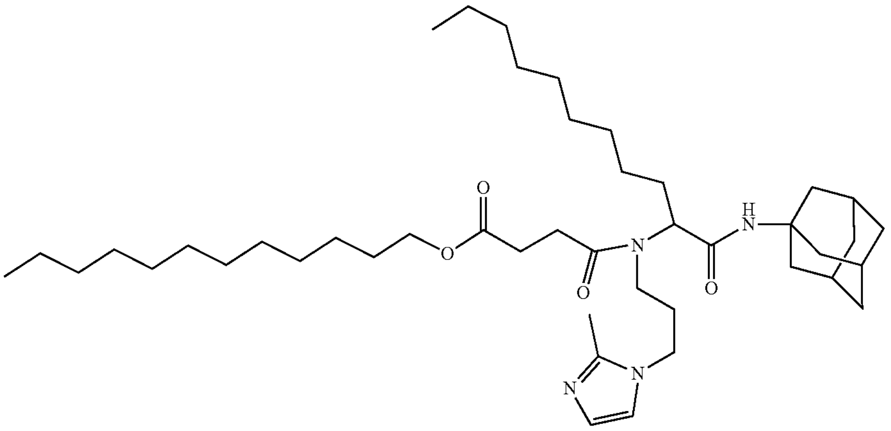
P410A6
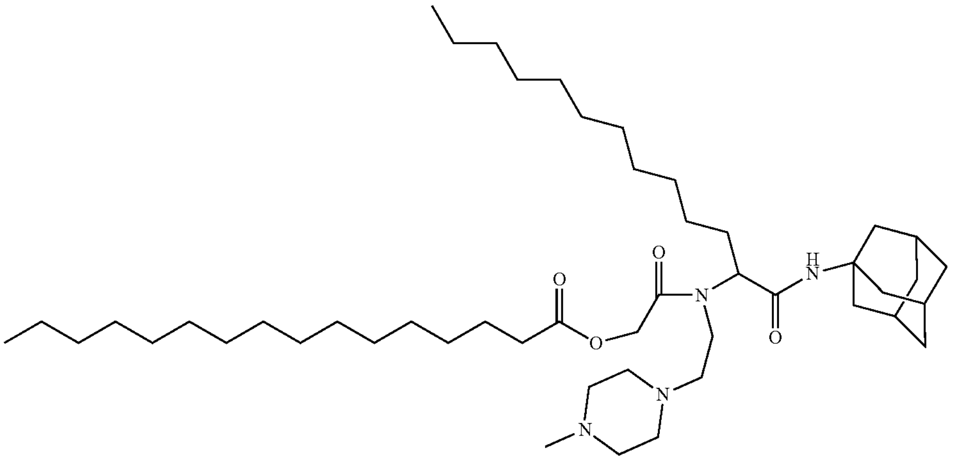

-continued
P410A10
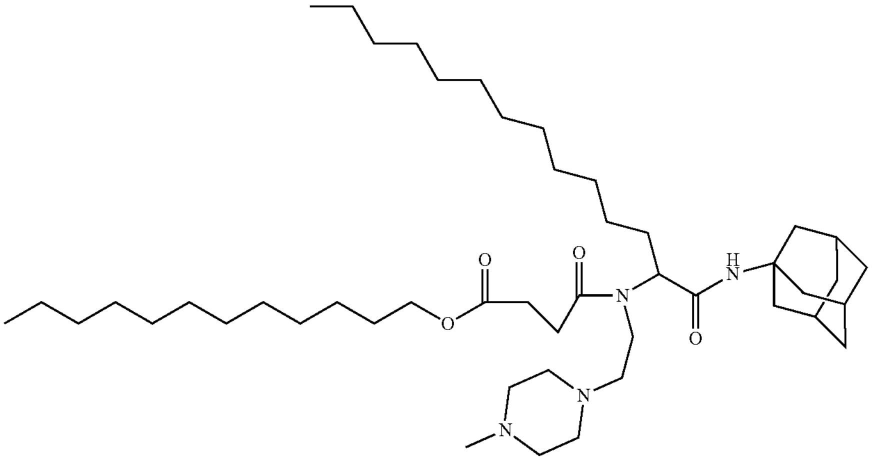
P410D4
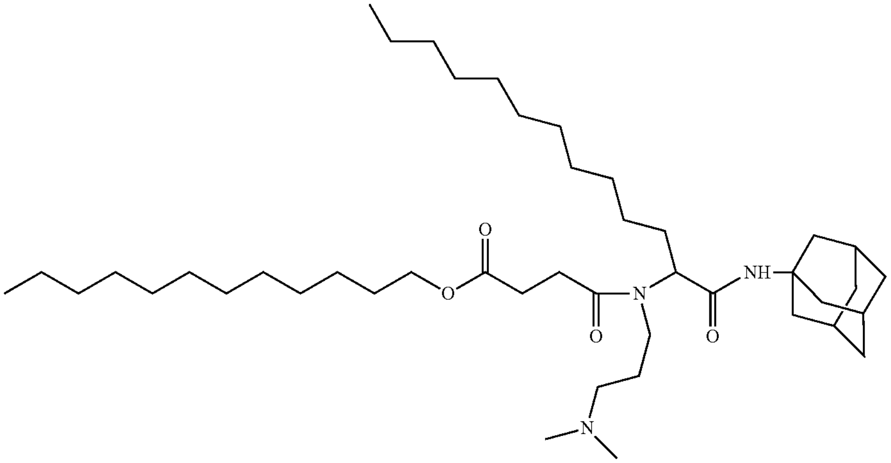
P410D12
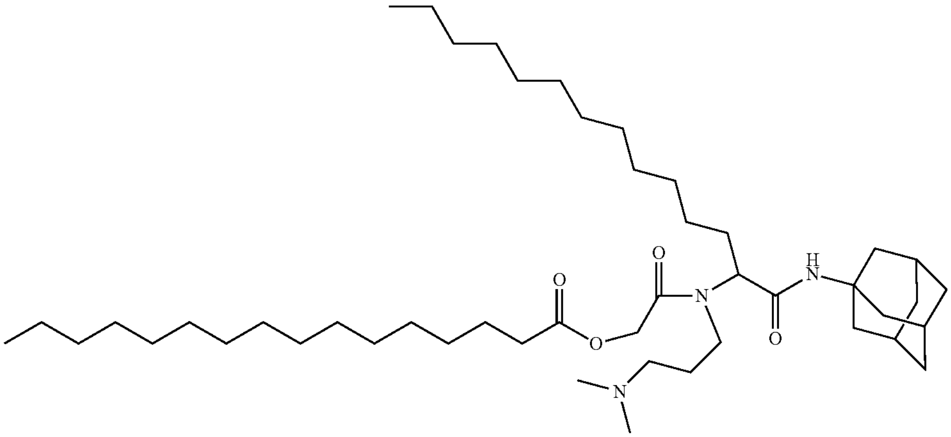

-continued
P410E12
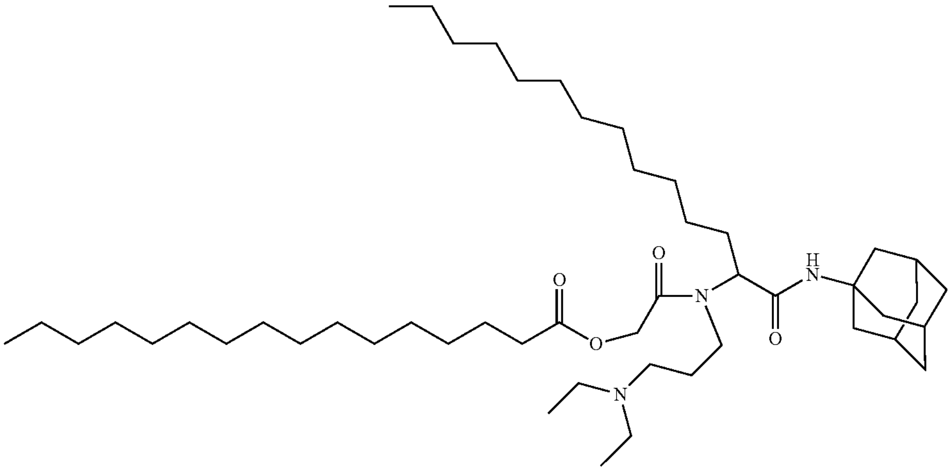
P410F12
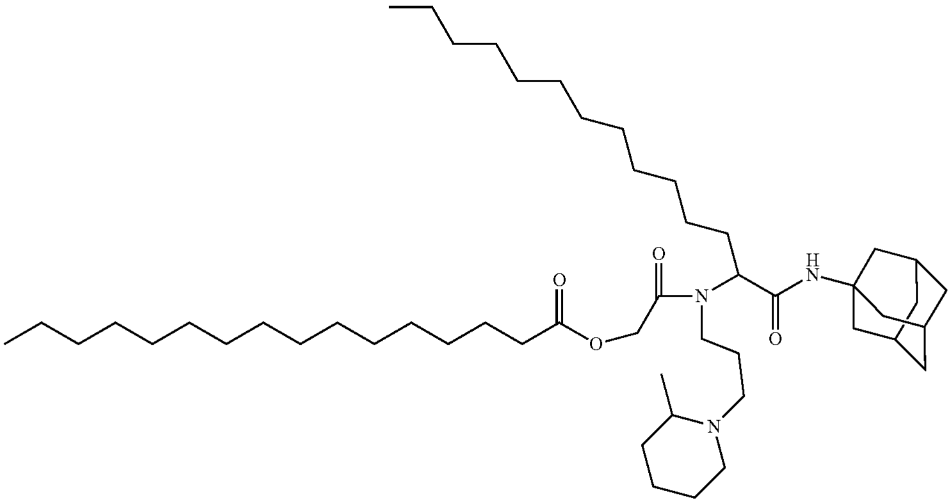
P410H4
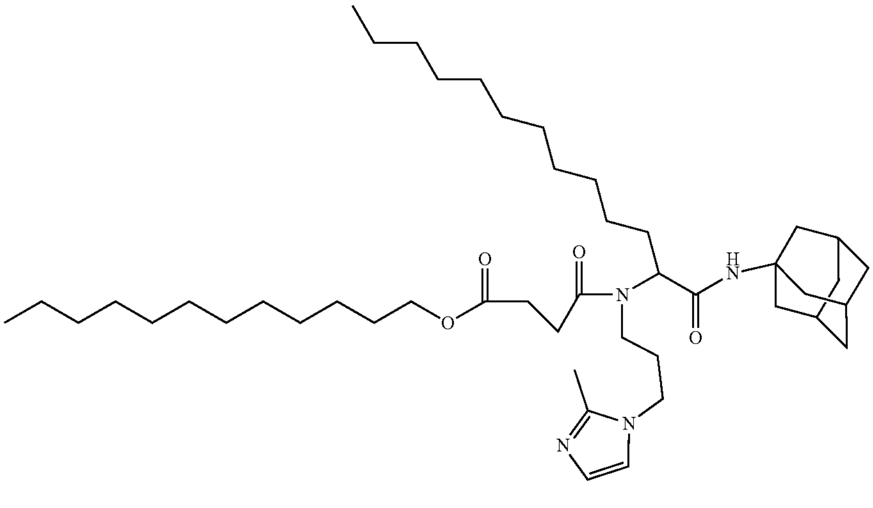

-continued
P410H6
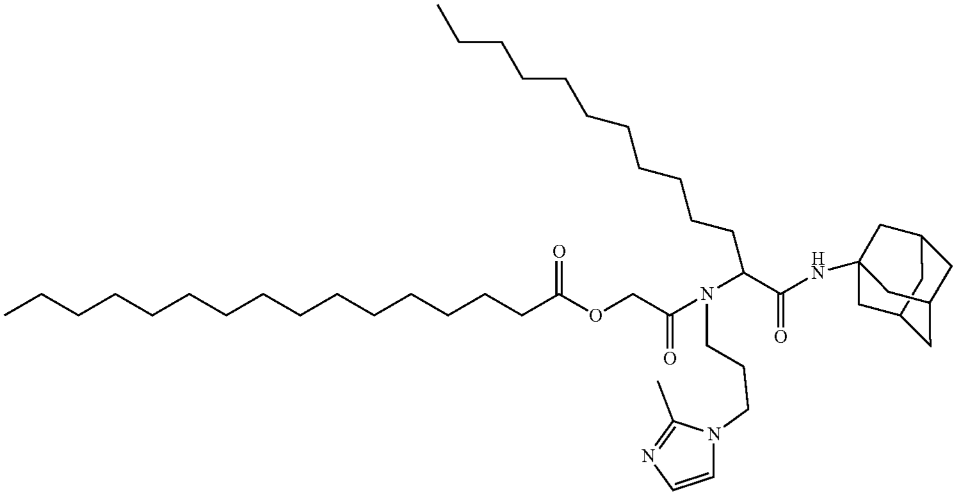
P410H8
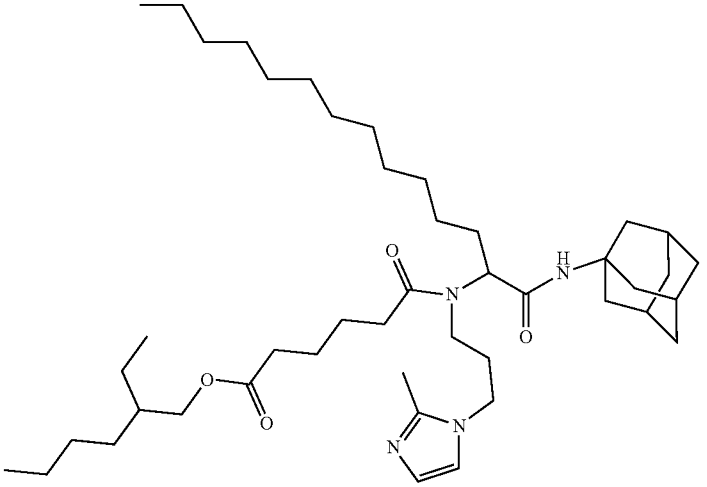
P410H10
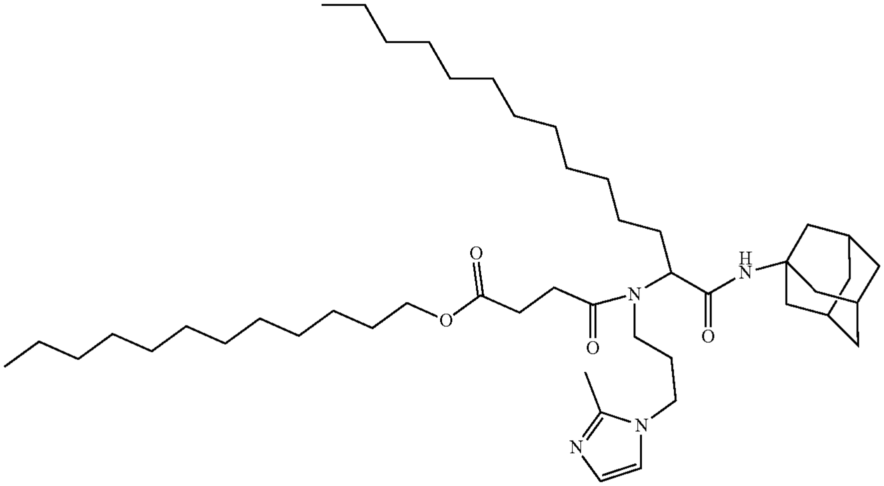

-continued
P411C6
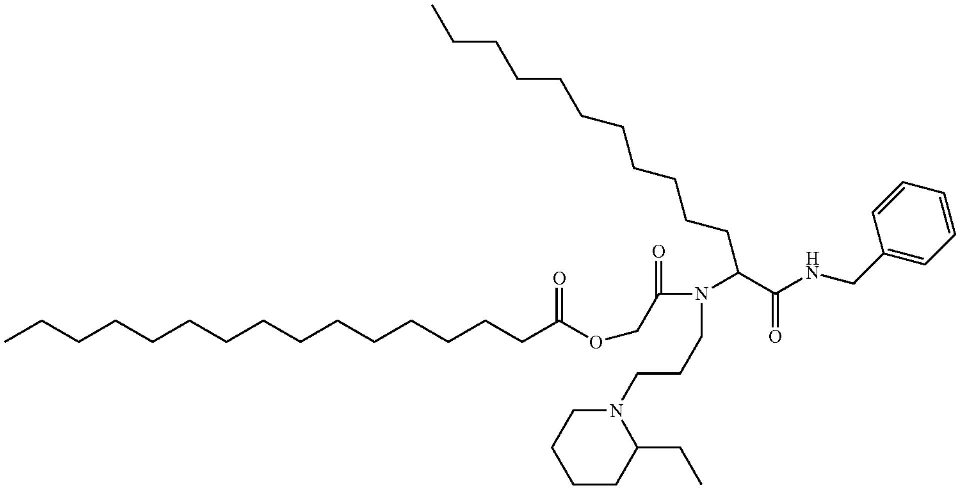
P411C12
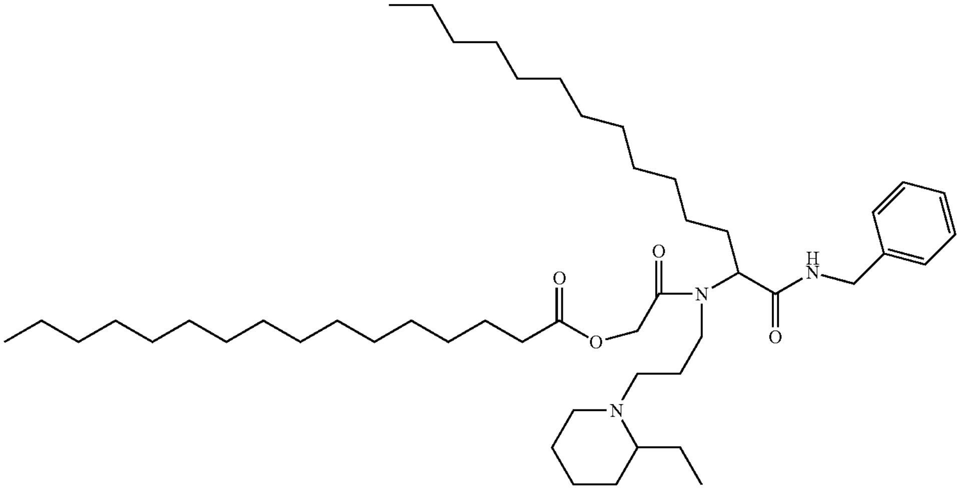
P411F12
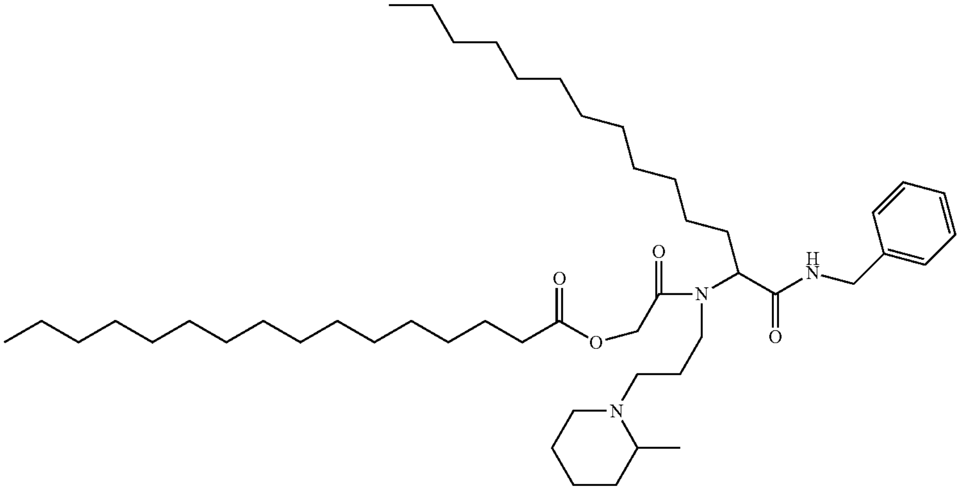

-continued
P411H6
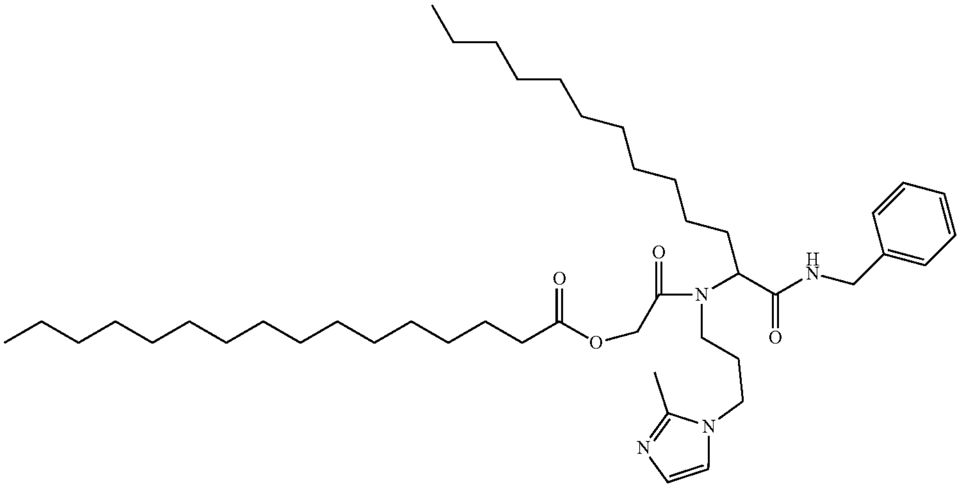
P411H10
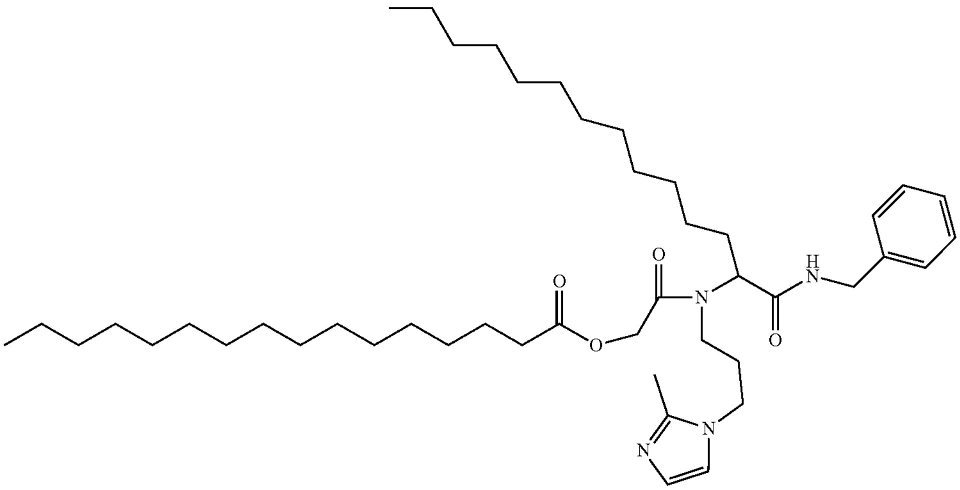
P411H12
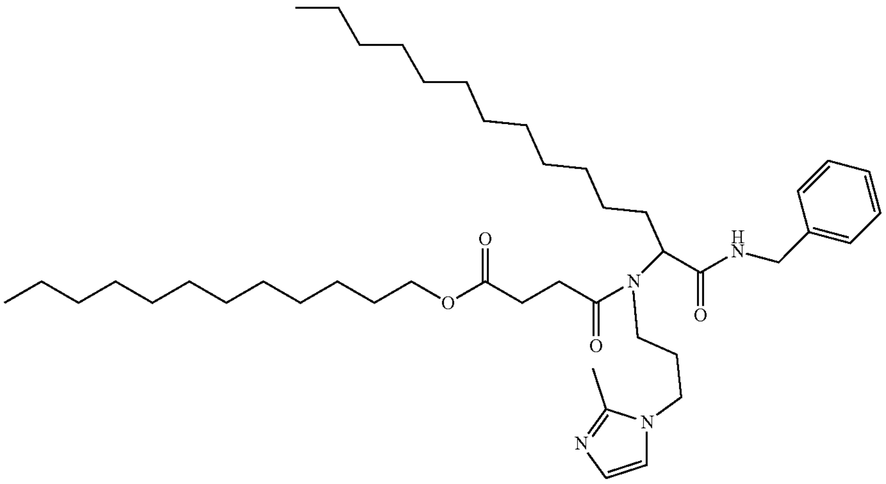

-continued
P412A6
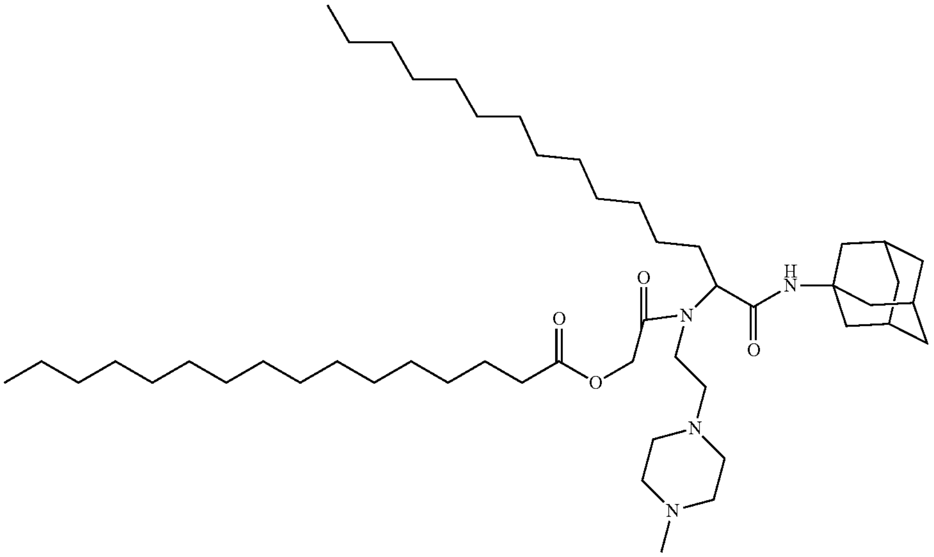
P412D6
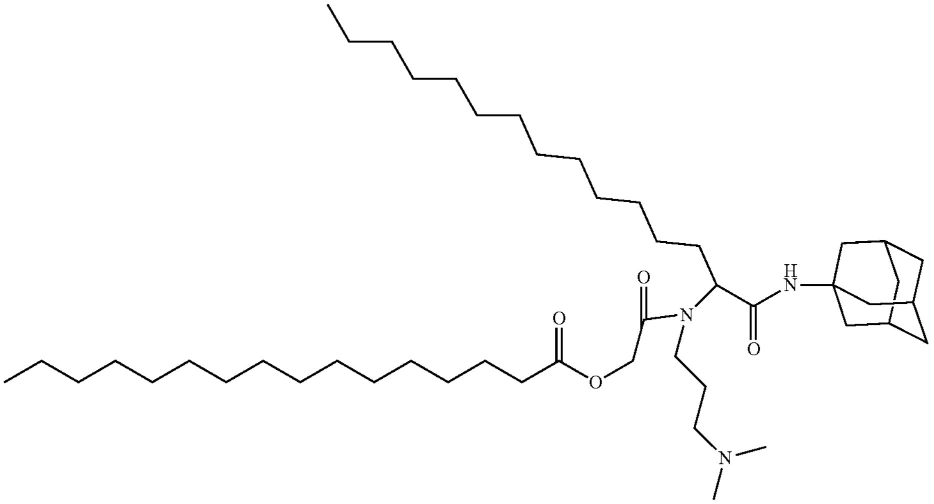
P412D10
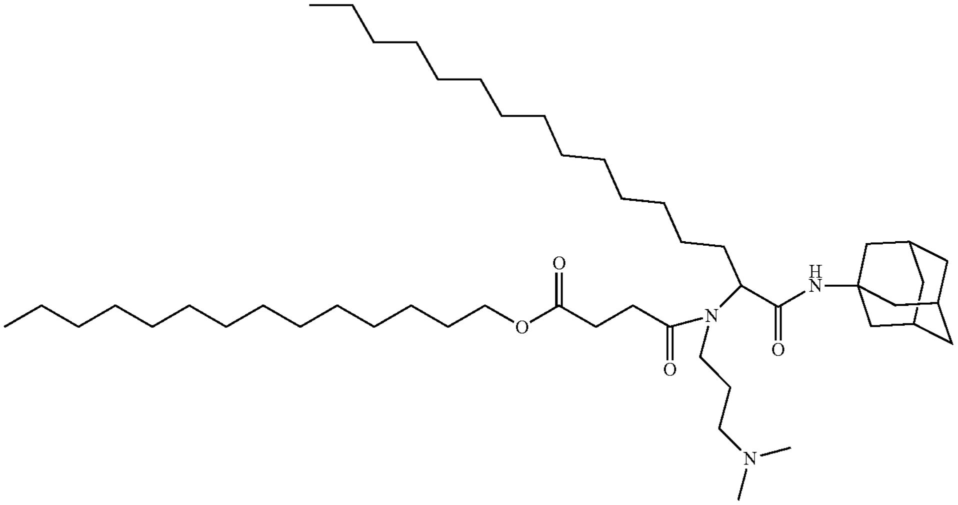

-continued
P412D12
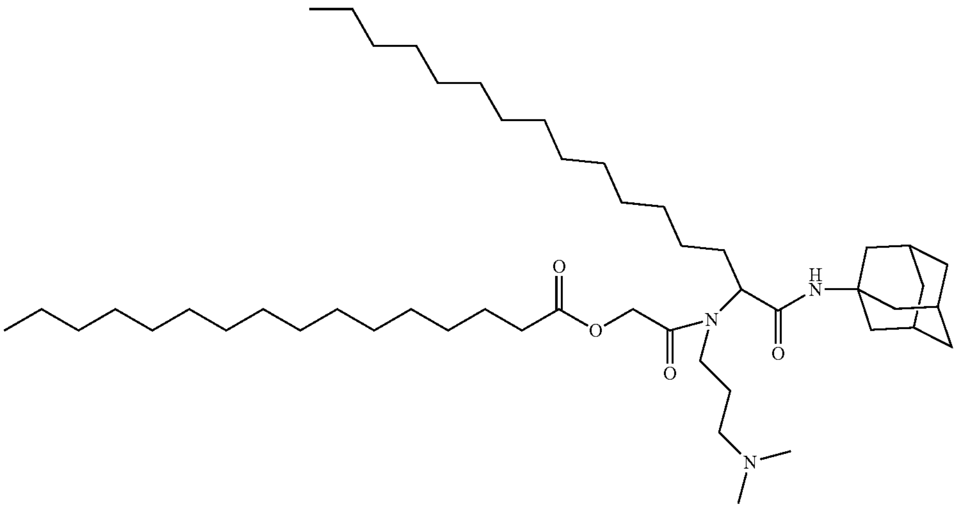
P412H2
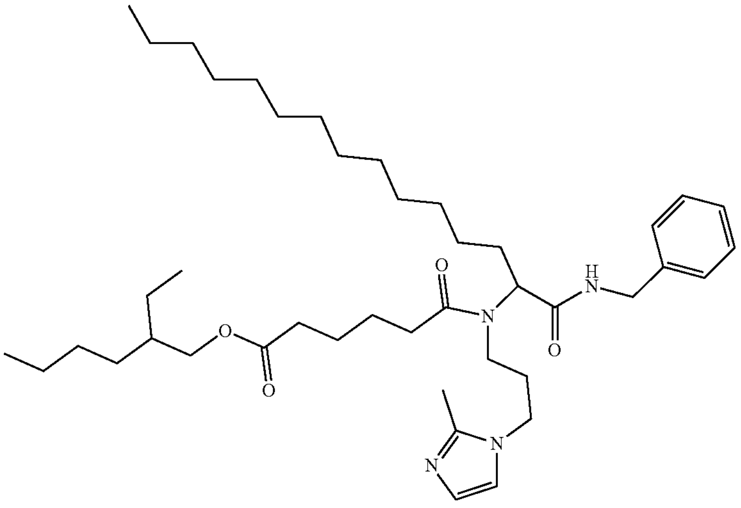
P412H4
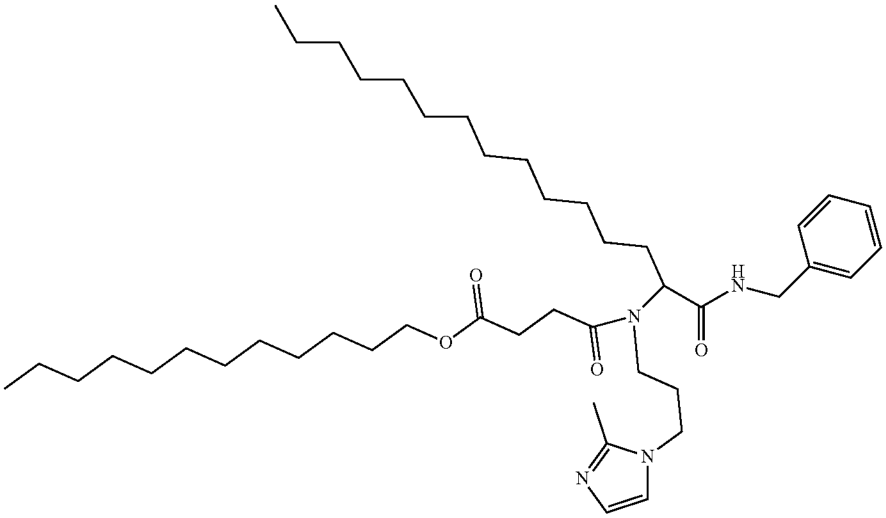

-continued
P412H6
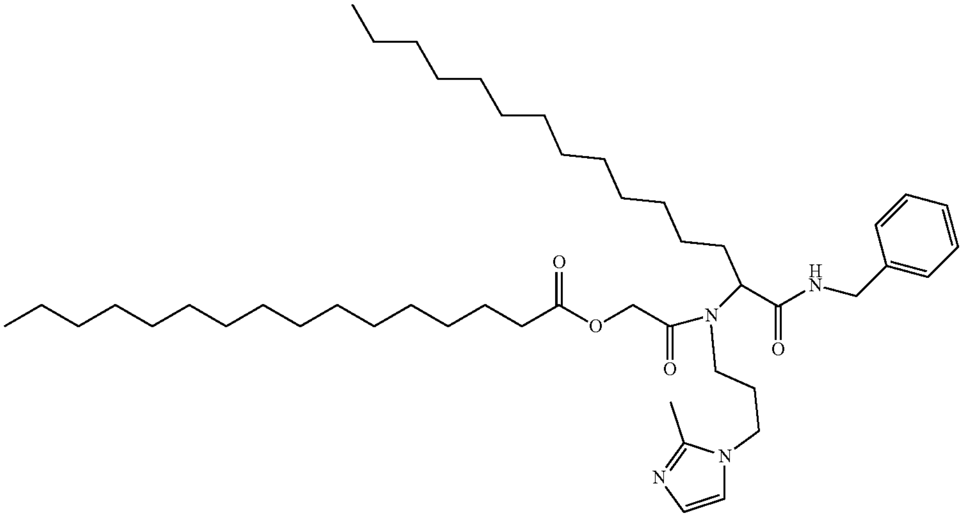
P412H10
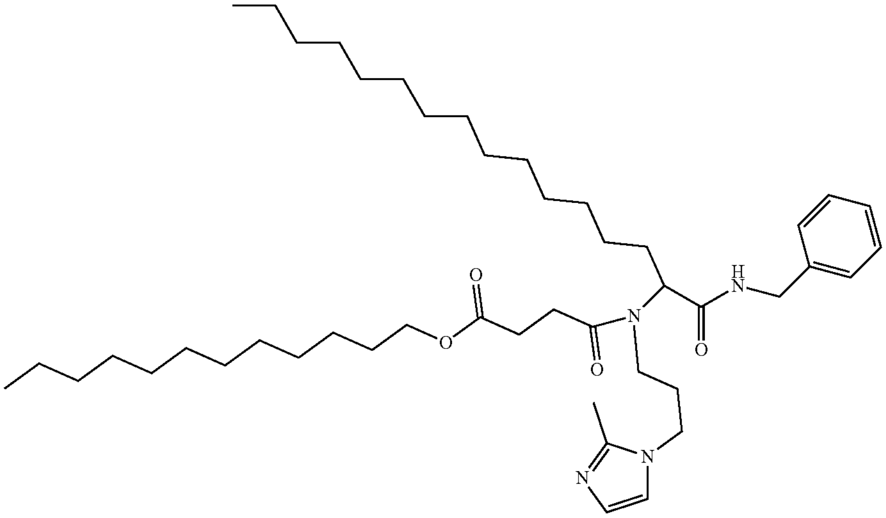
P414A10
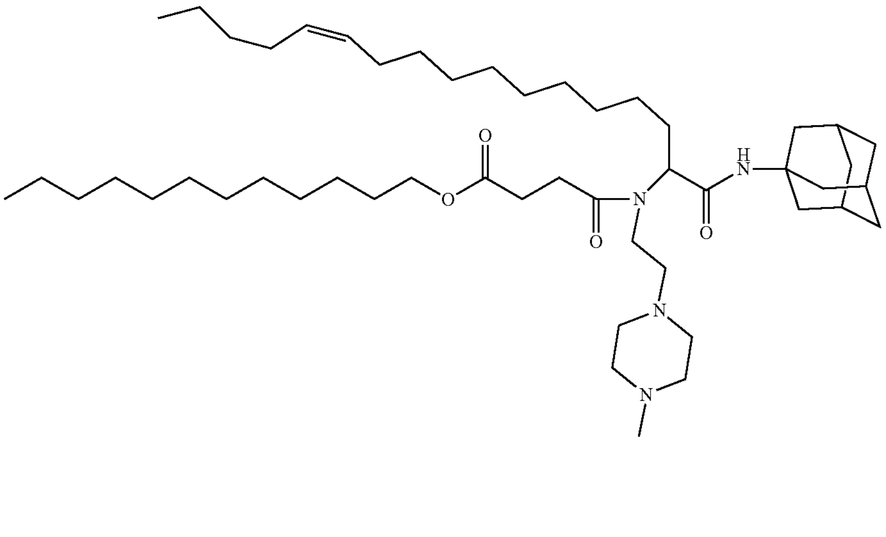

-continued
P414A11
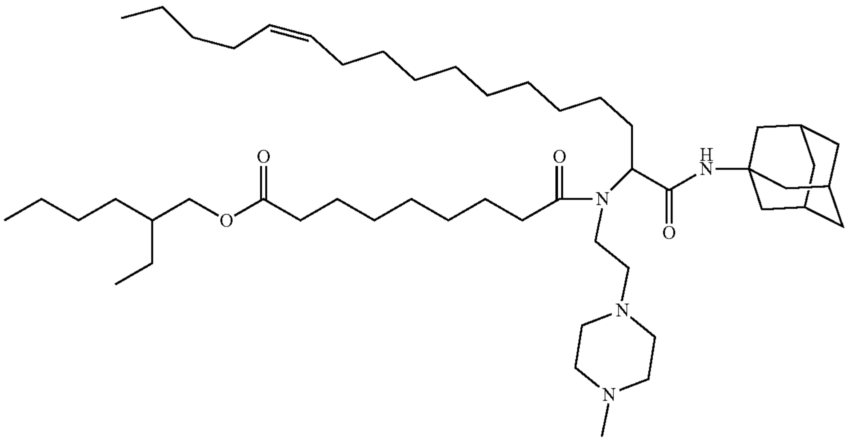
P414A12
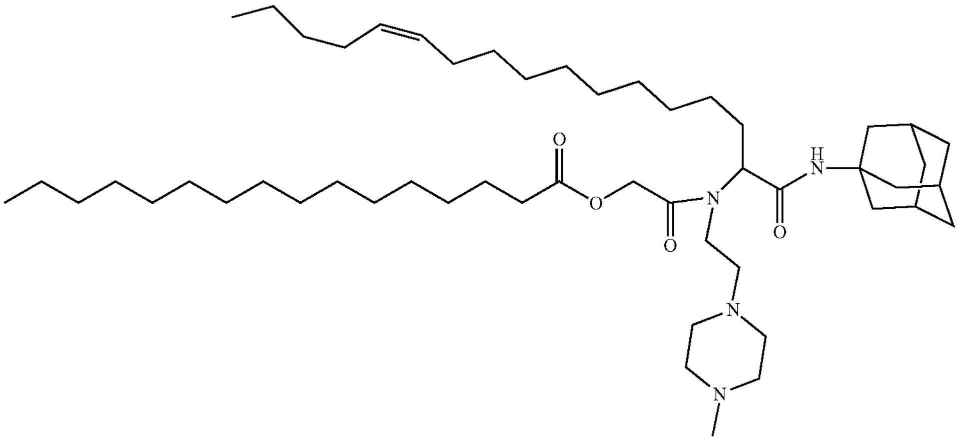
P414D12
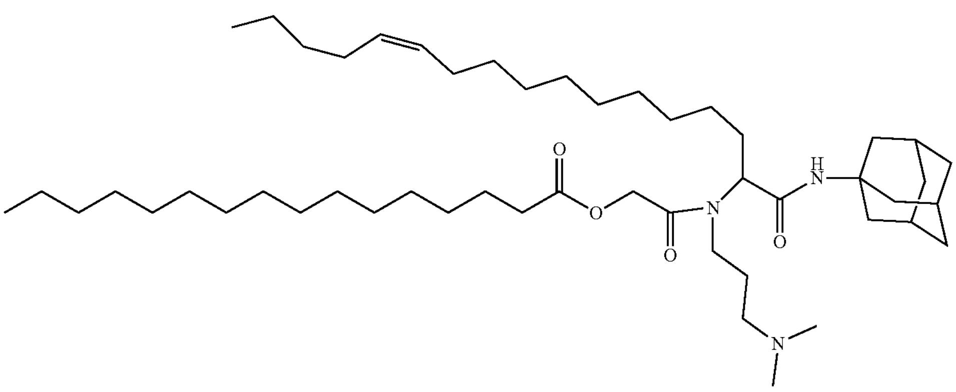

-continued
P414E12
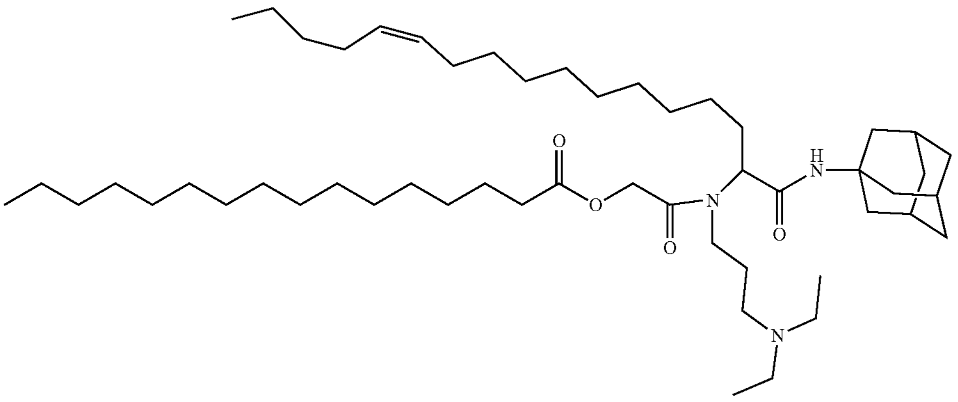
P414A12
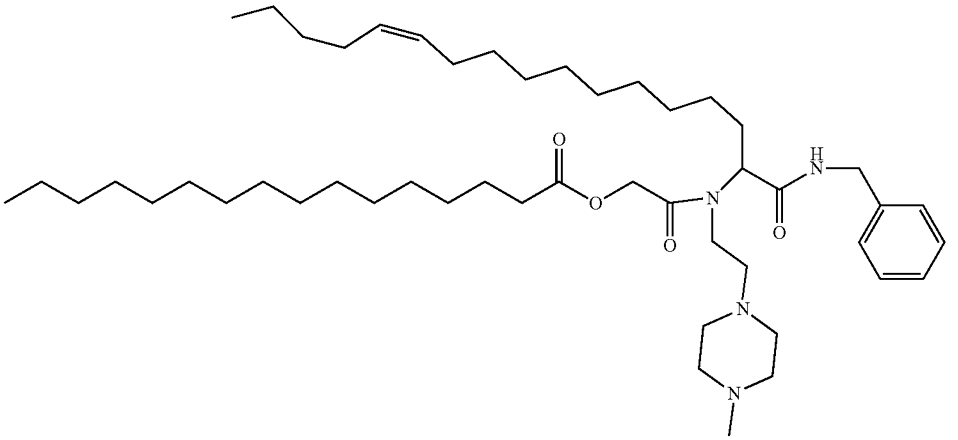
P415C12
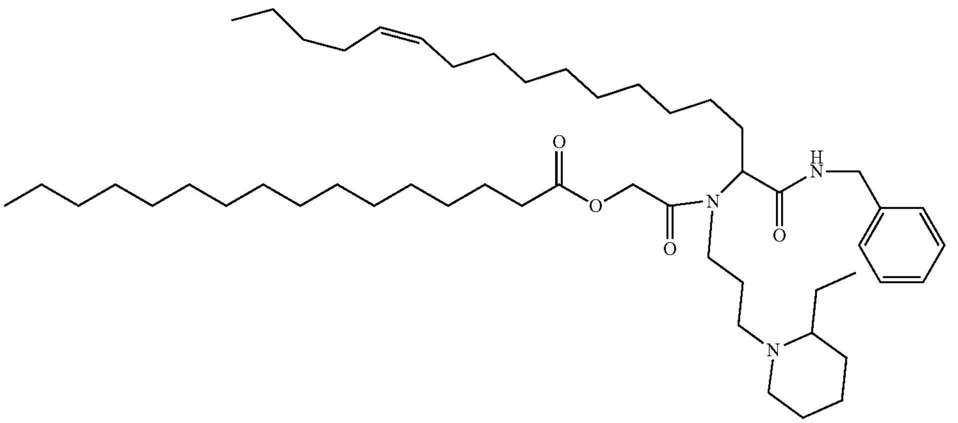

-continued
P415F12
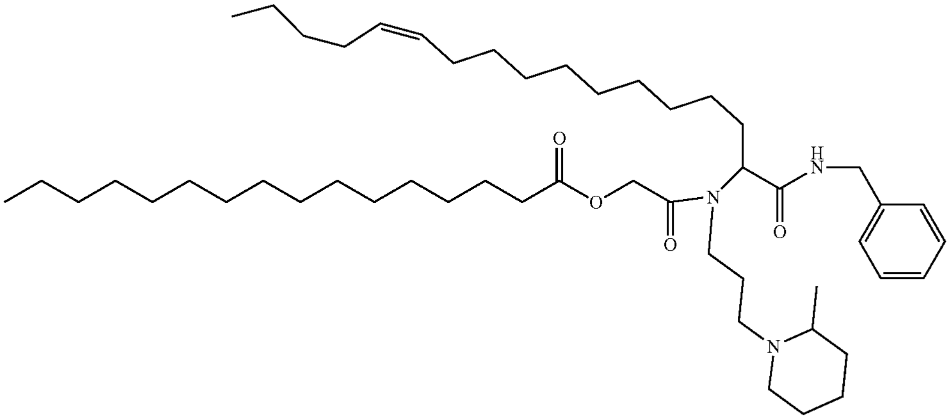
P416D4
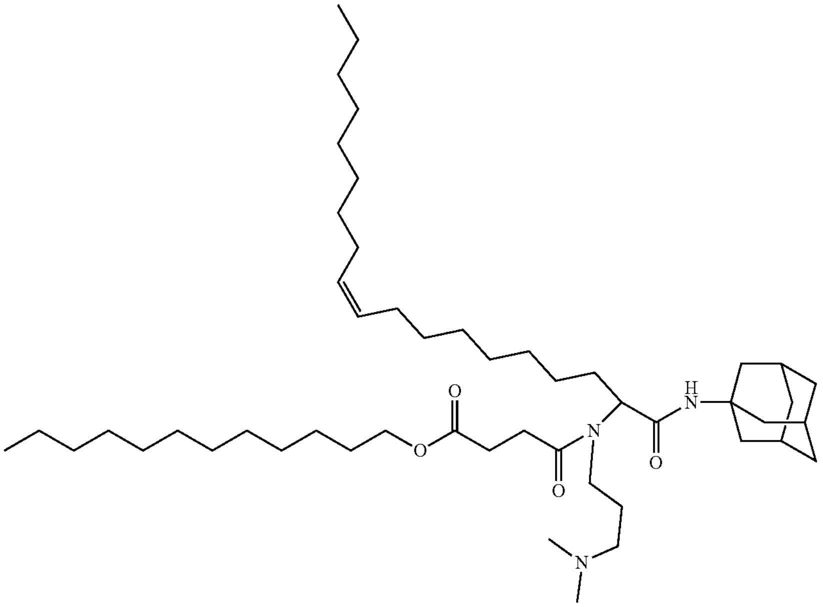
P416D6
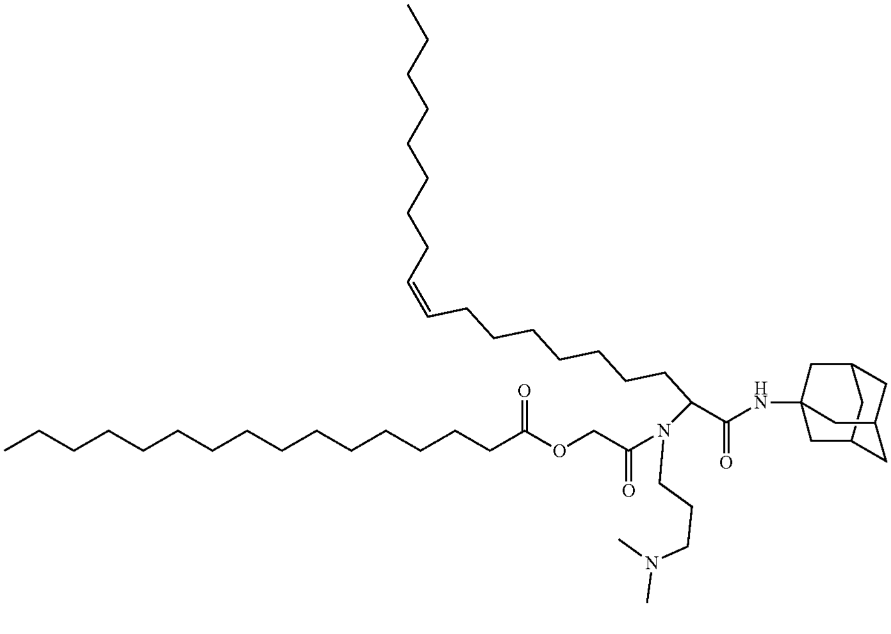

-continued
P416E4
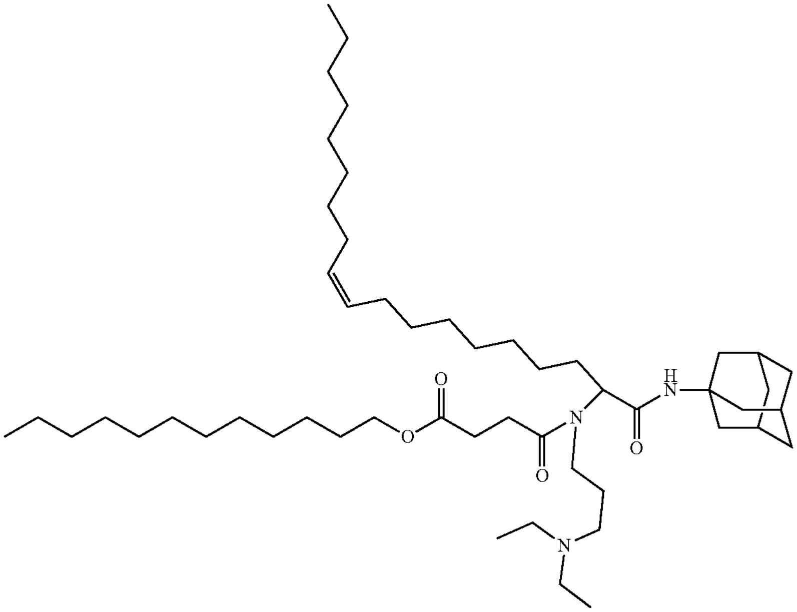
P416E6
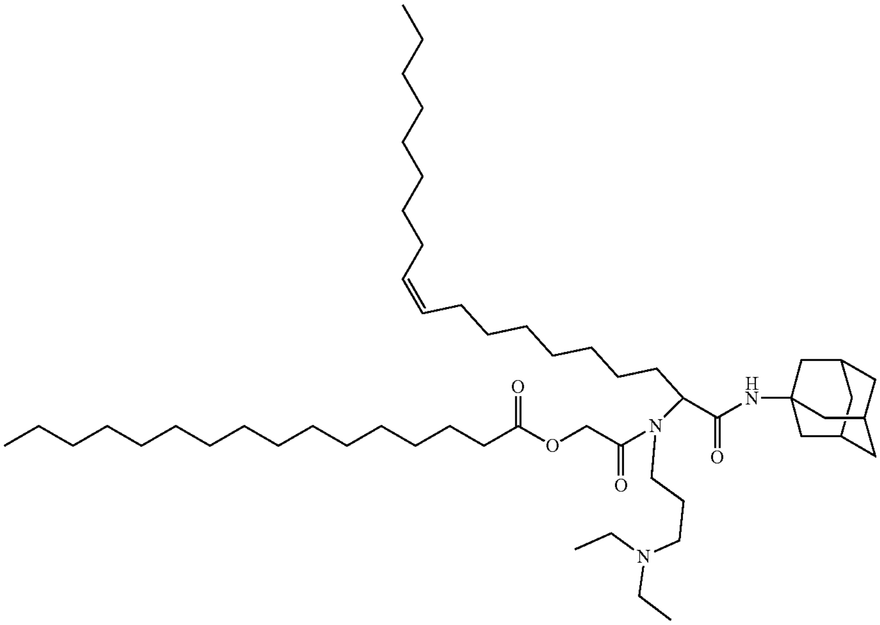

-continued
P417A4
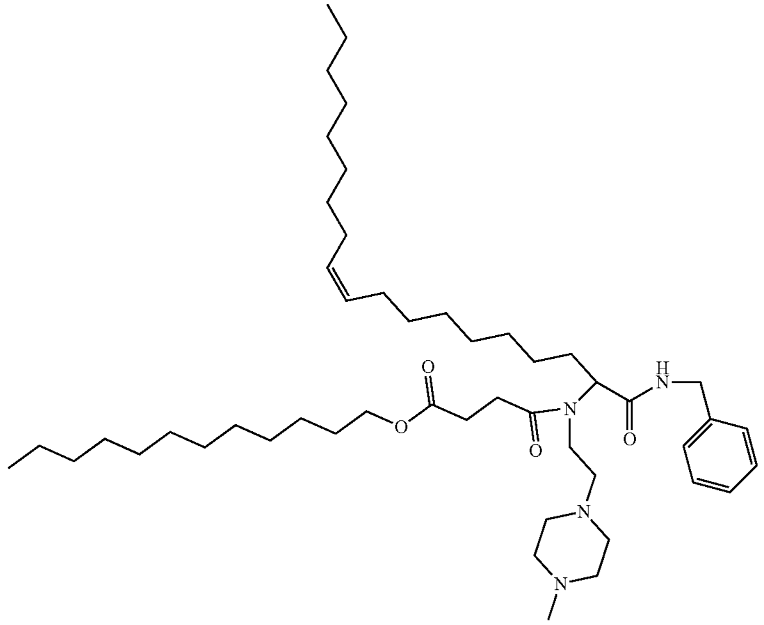
P417D6
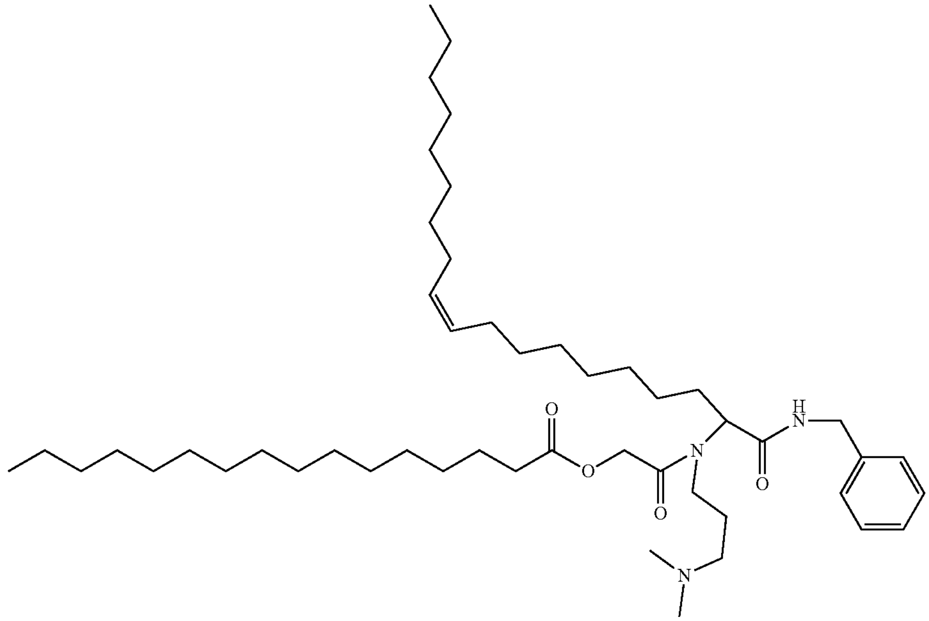

-continued
P417E4
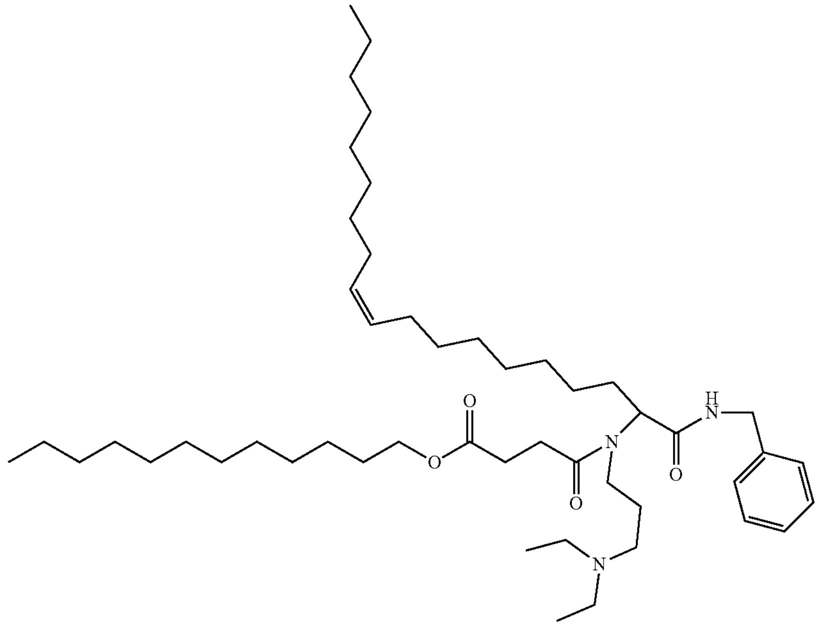
P417E6
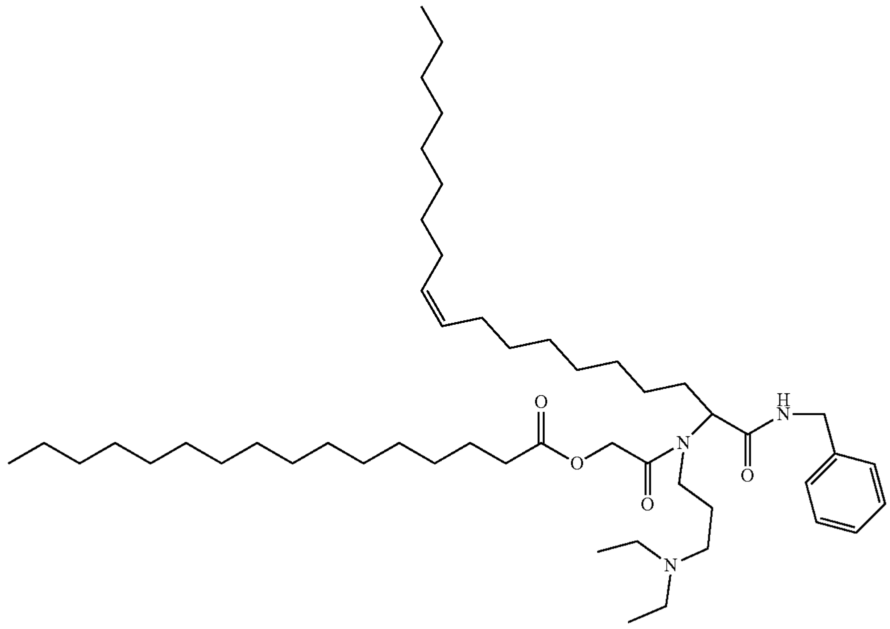

-continued
P417F4
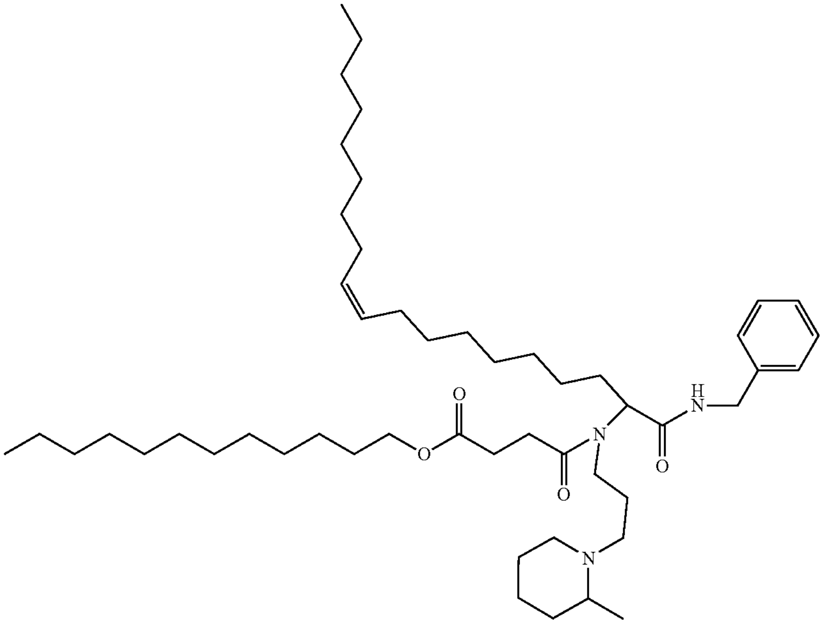
P417H2
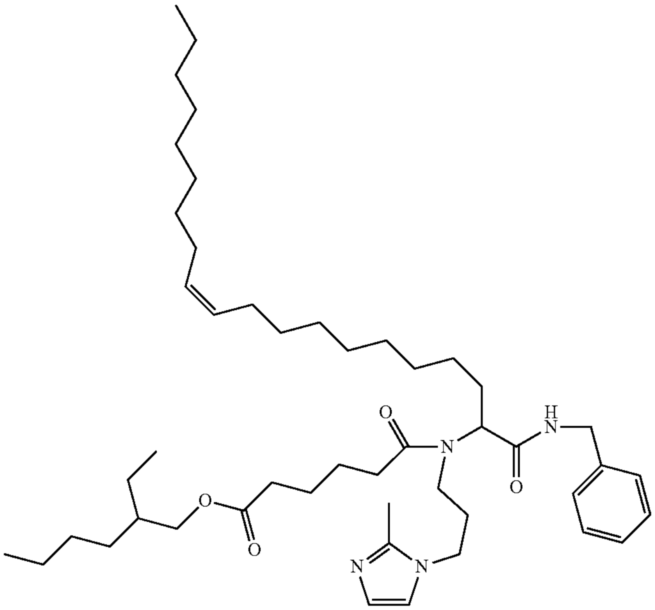

-continued
P417H4
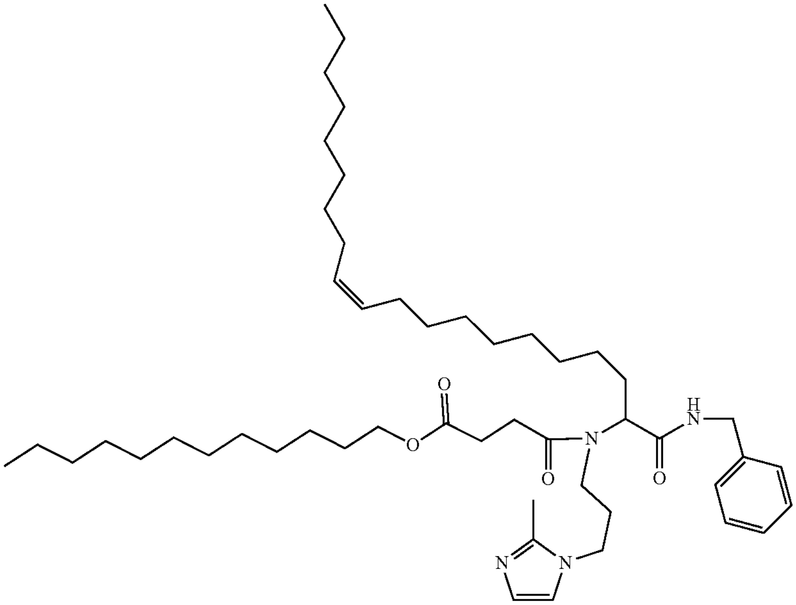
P417H6
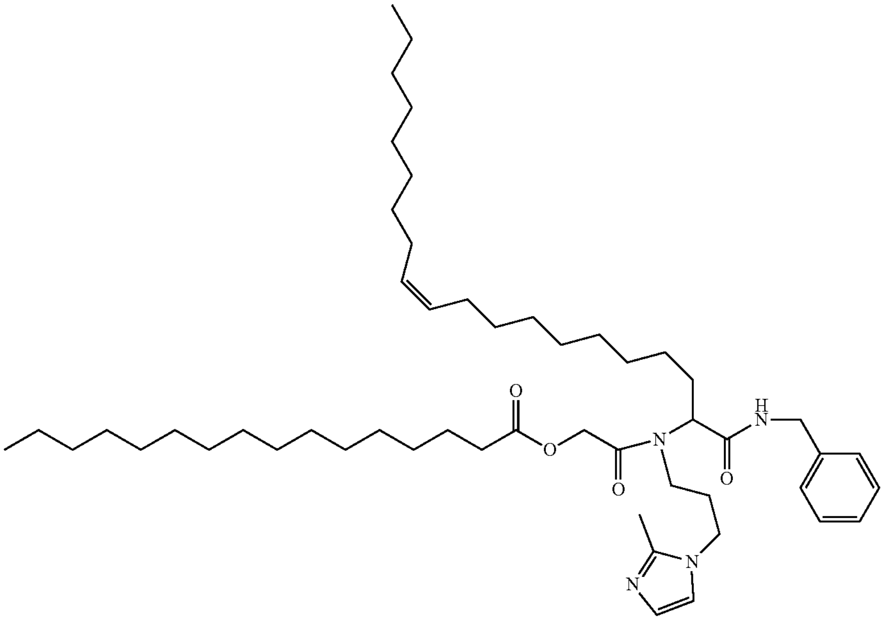
P432A2
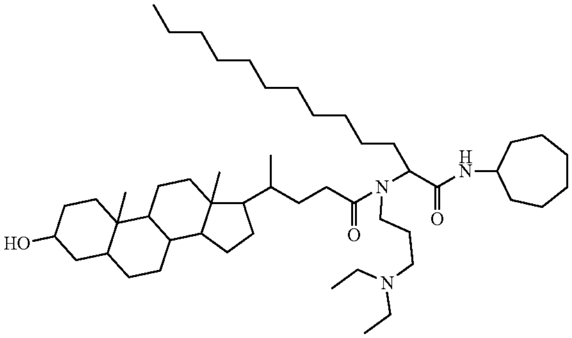
P423C7
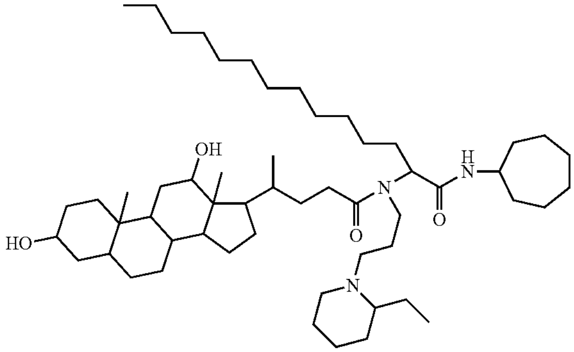

-continued
P429D1
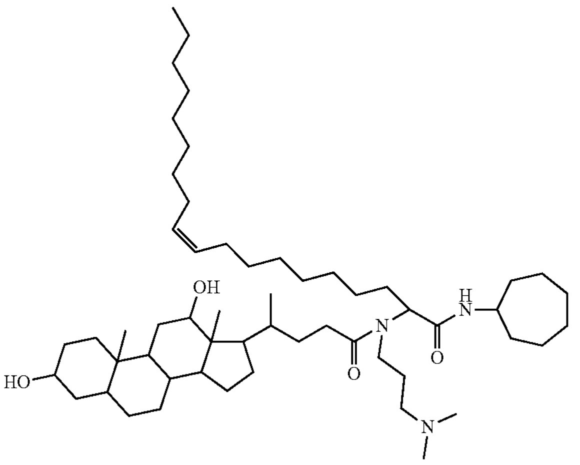
P441D1
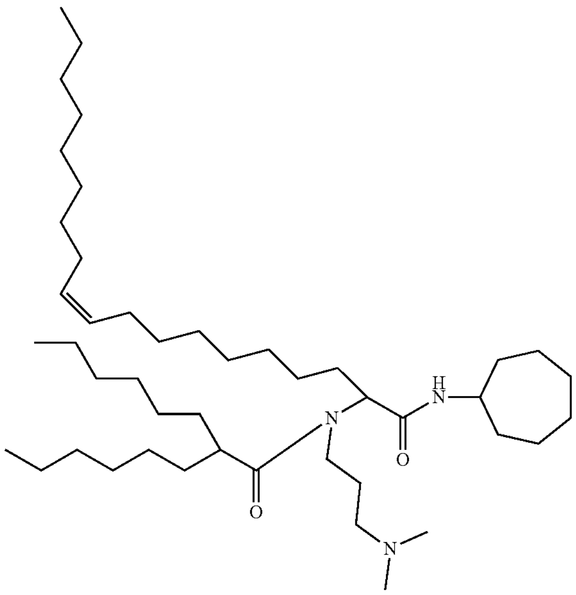
P442H1
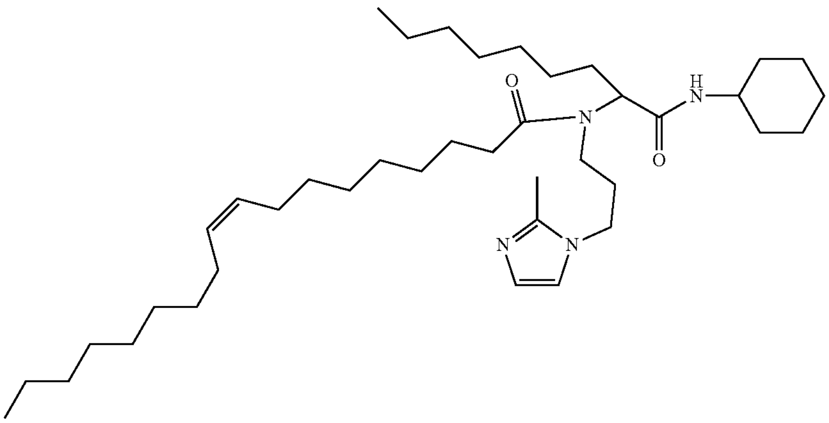
P442H7
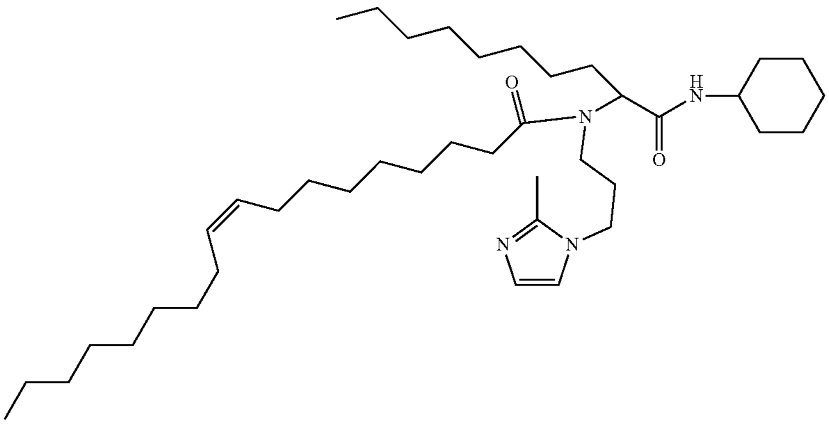

-continued
P443H1
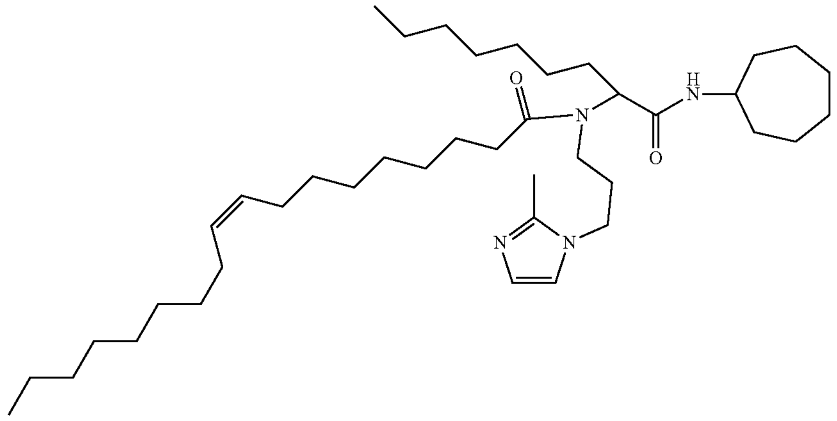
P443A1
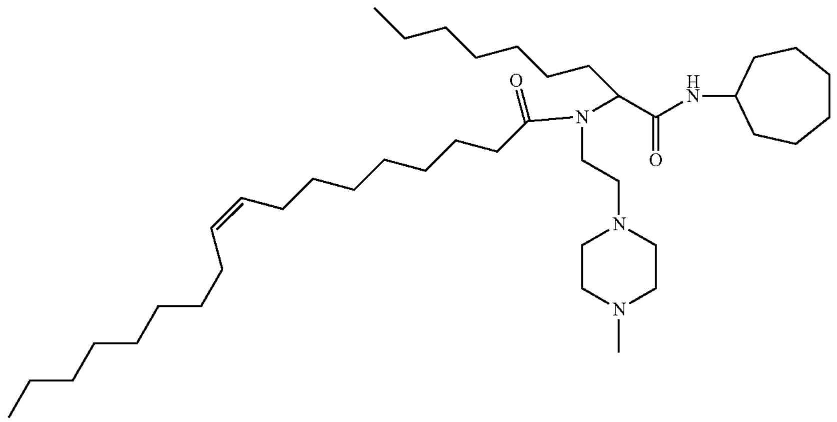
P443A7
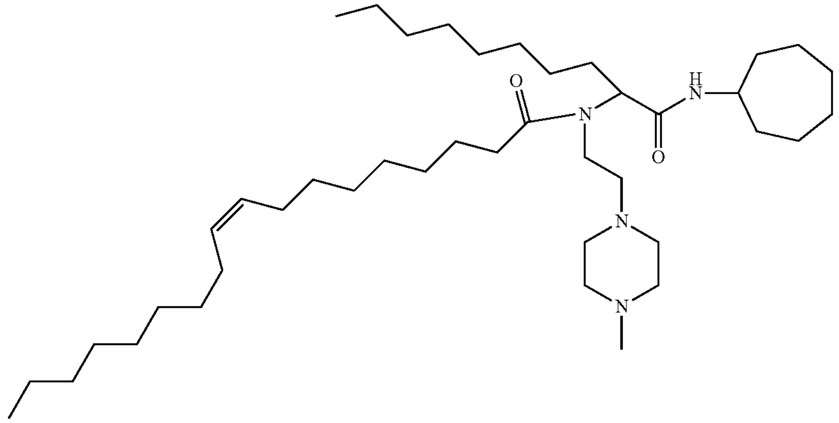

-continued
P446H7
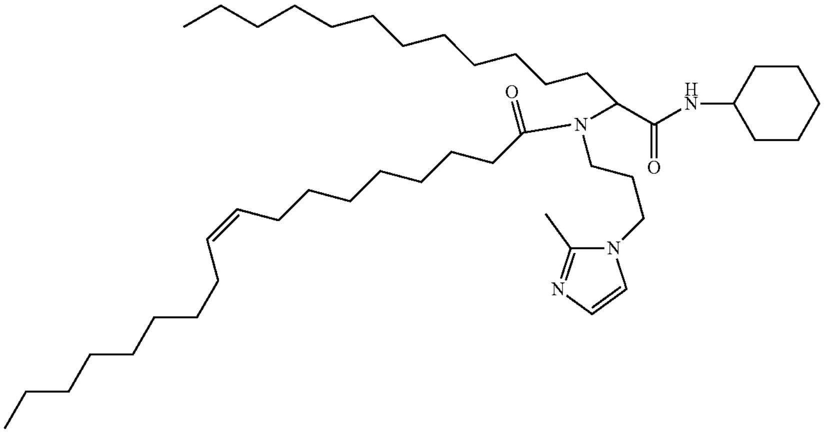
P446D7
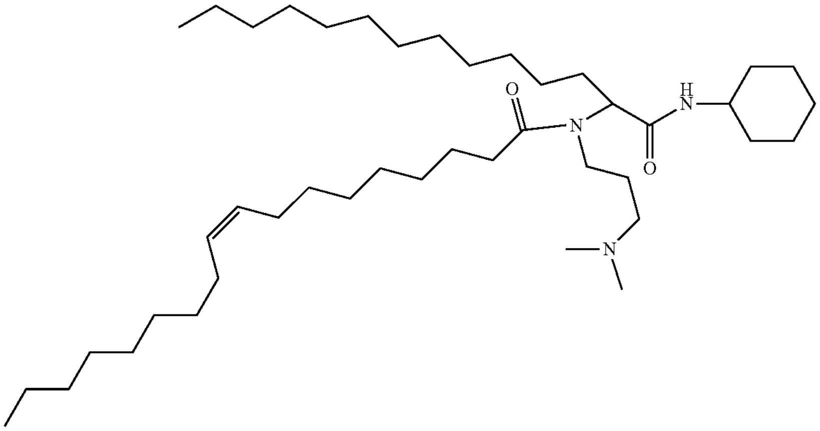
P446D12
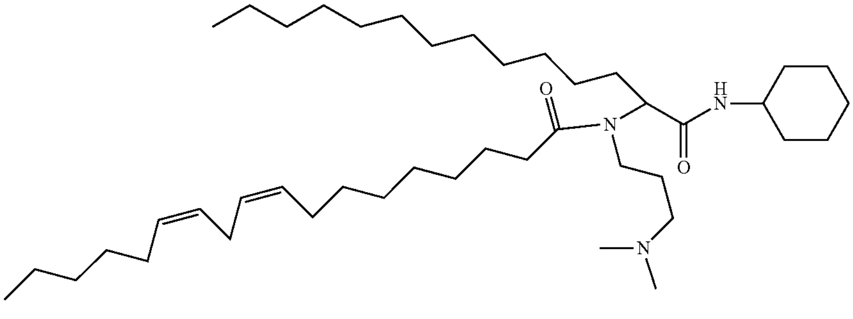
P447A1
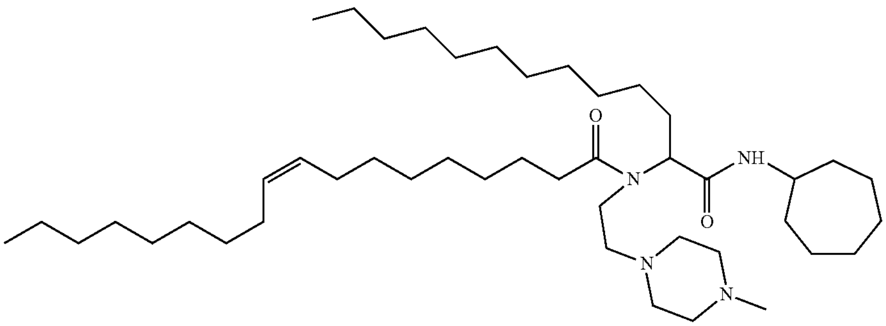

-continued
P447A6
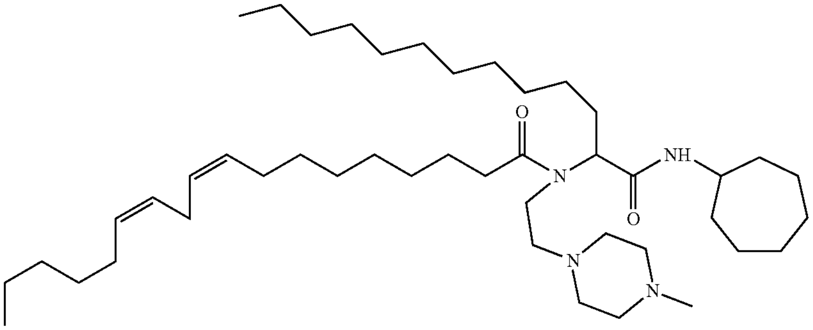
P447A7
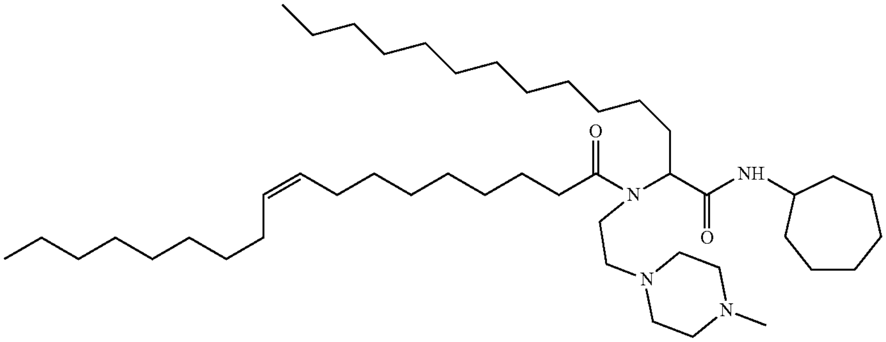
P447A9
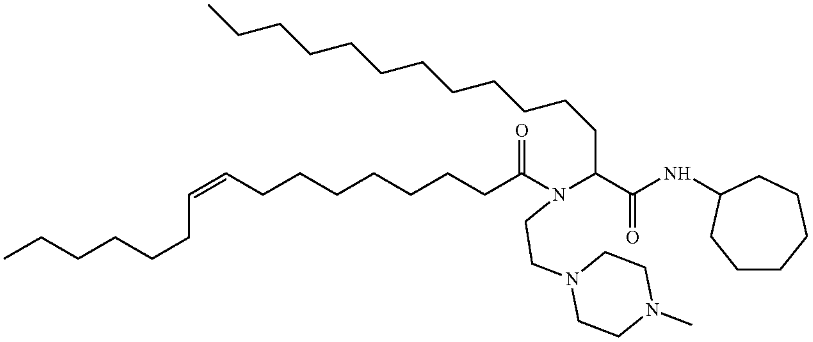
P447A12
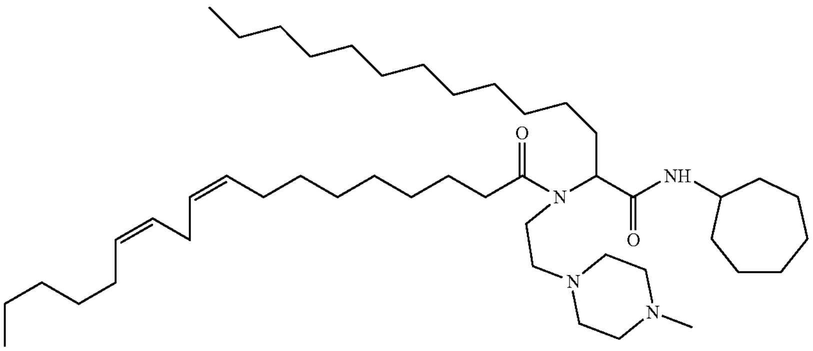

-continued
P447D1
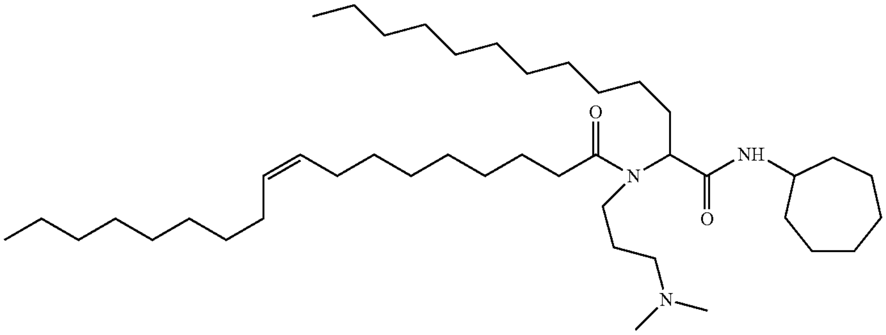
P447D6
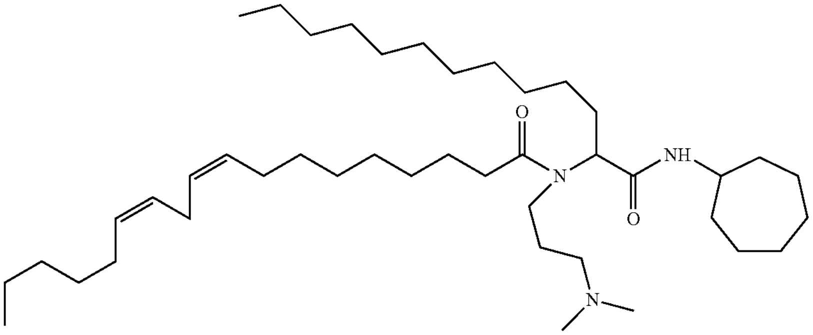
P447D7
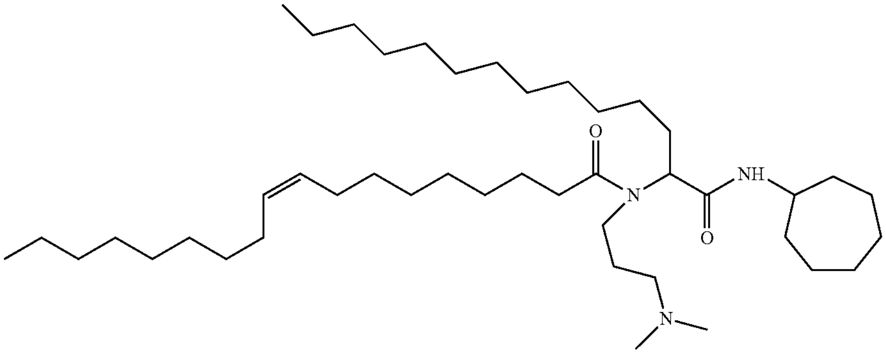
P447D12
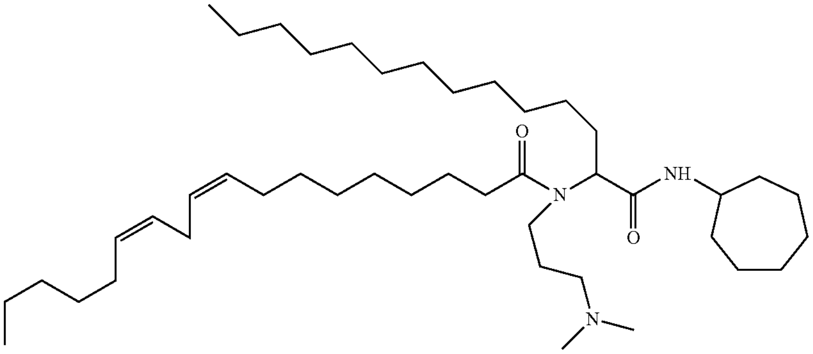

-continued
P447H1
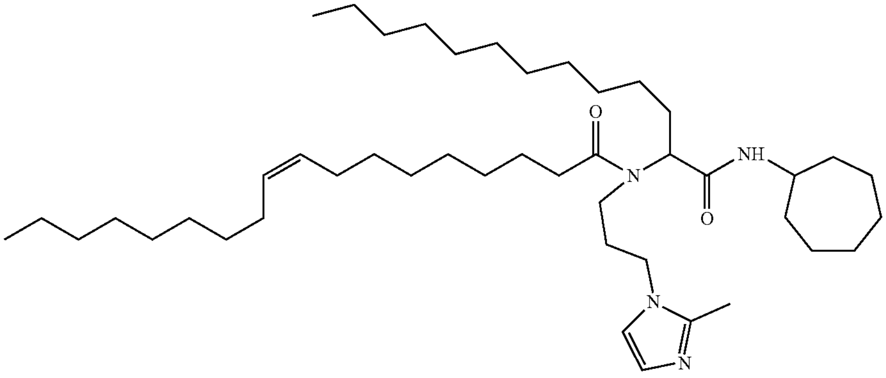
P447H3
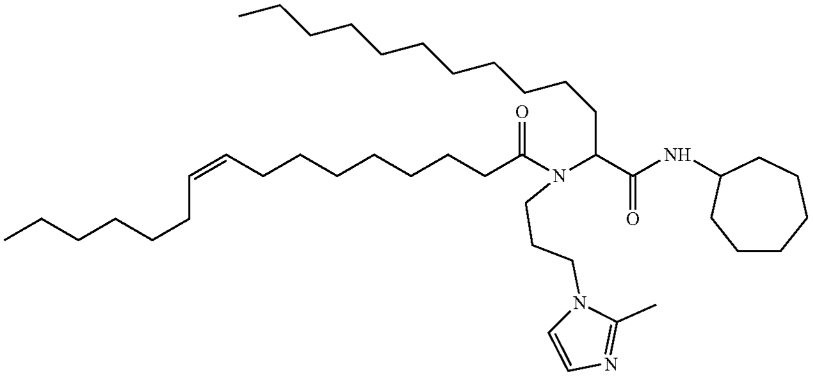
P447H7
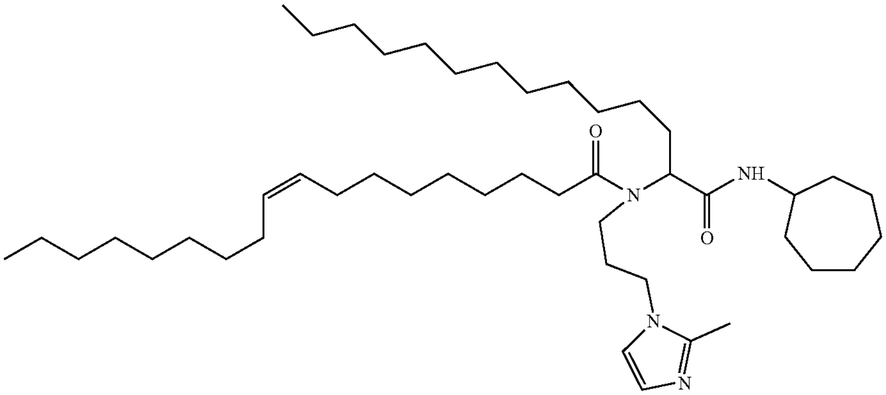
P447H9
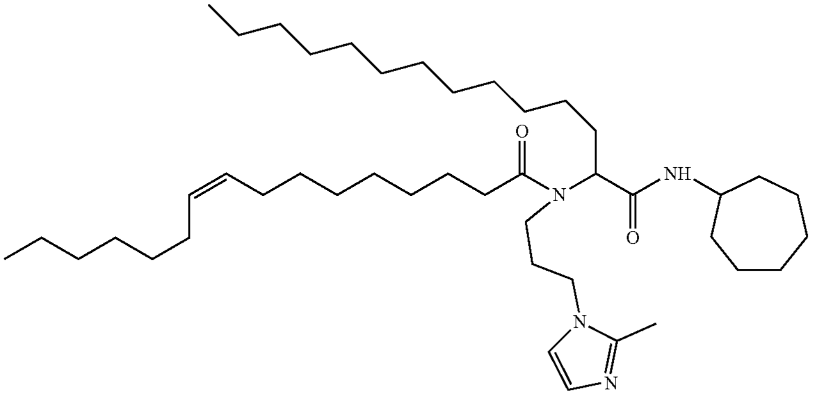

-continued
P447H10
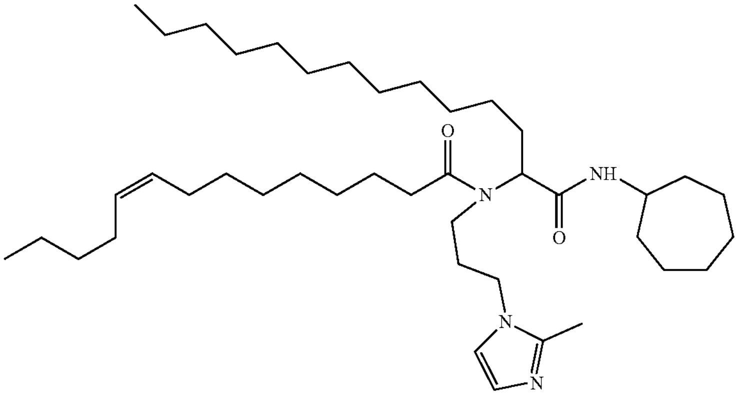
P447H12
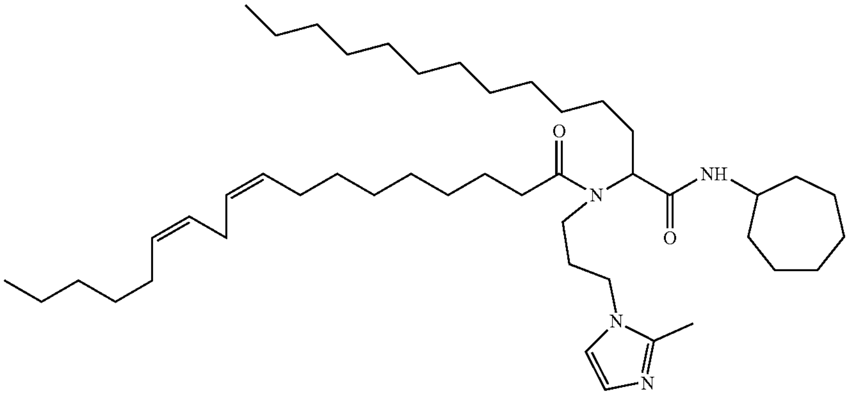
P448A1
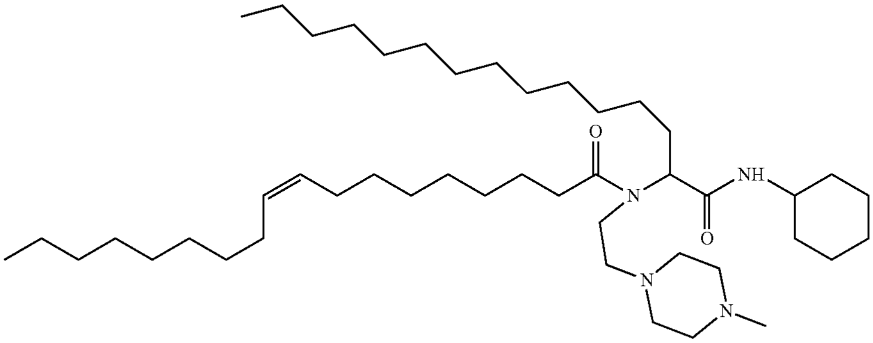
P448A6
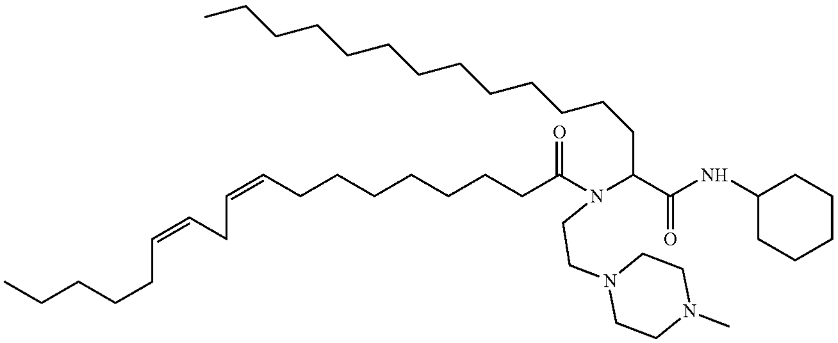

-continued
P448D7
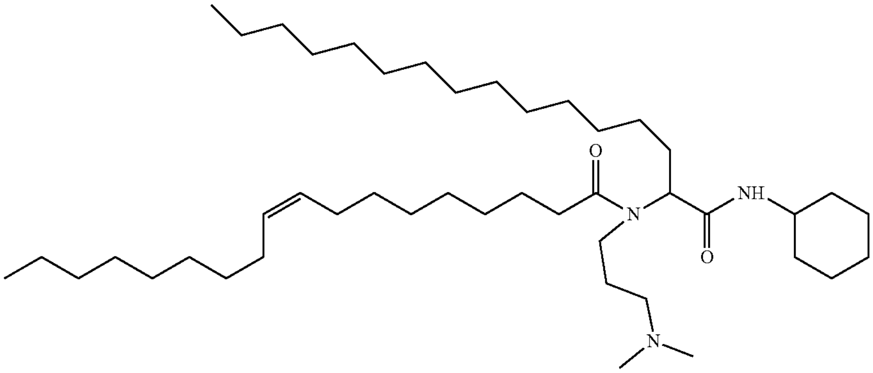
P448H7
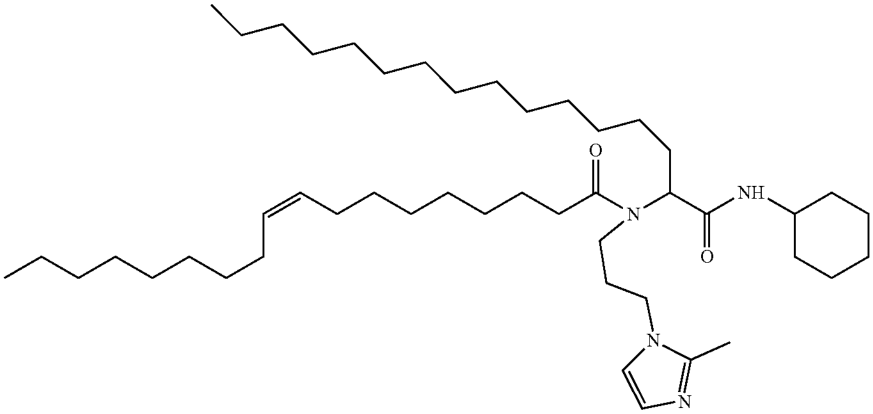
P448H9
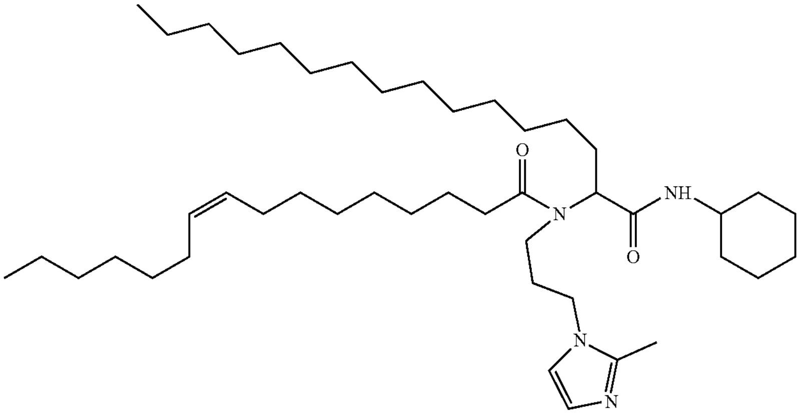
P449A3
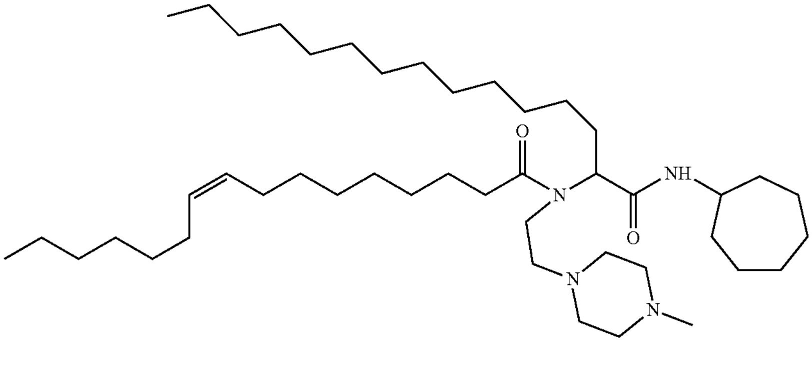

-continued
P449A6
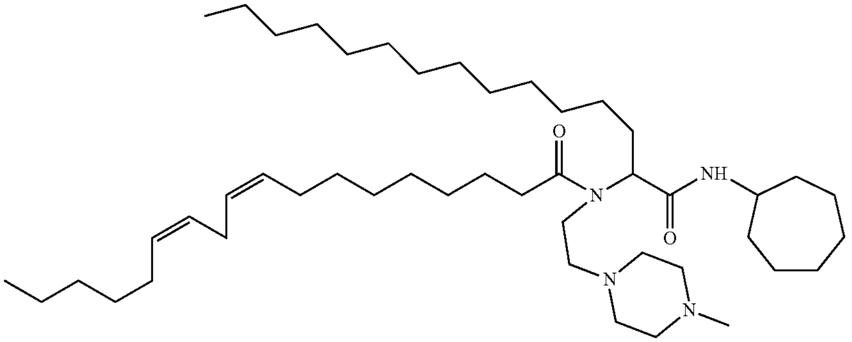
P449A12
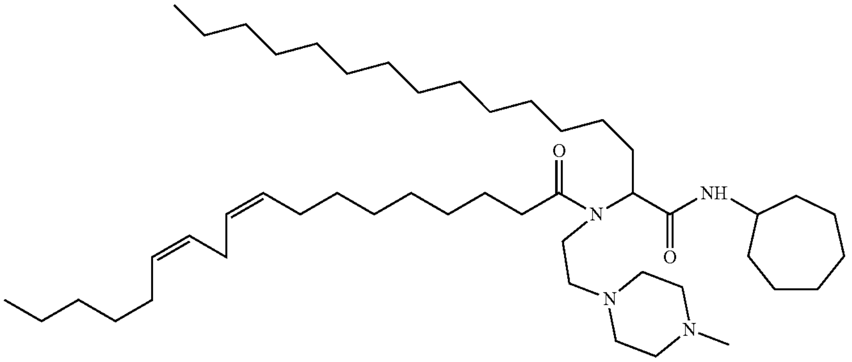
P449D1
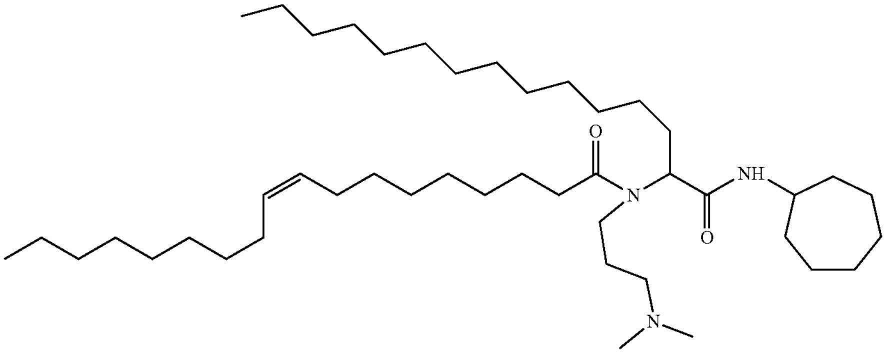
P448H7
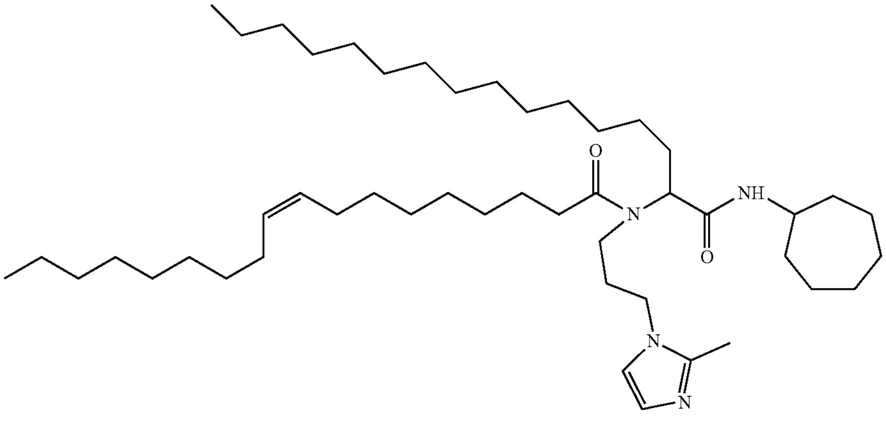

-continued
P451A7
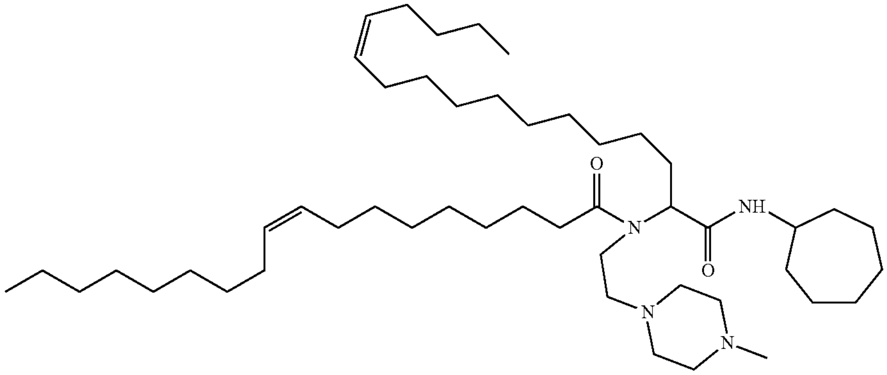
P451A9
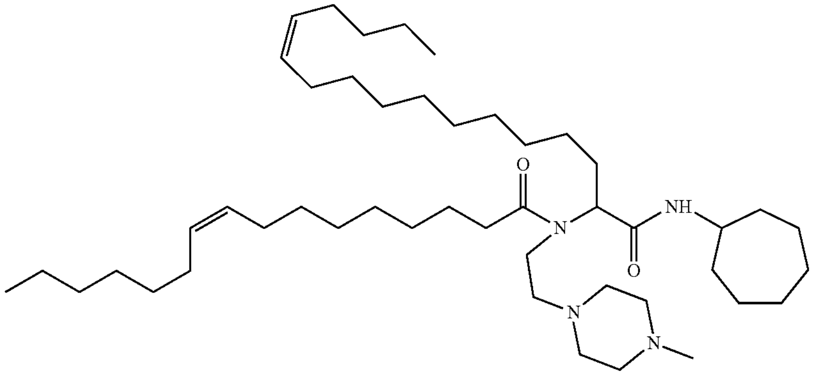
P451A10
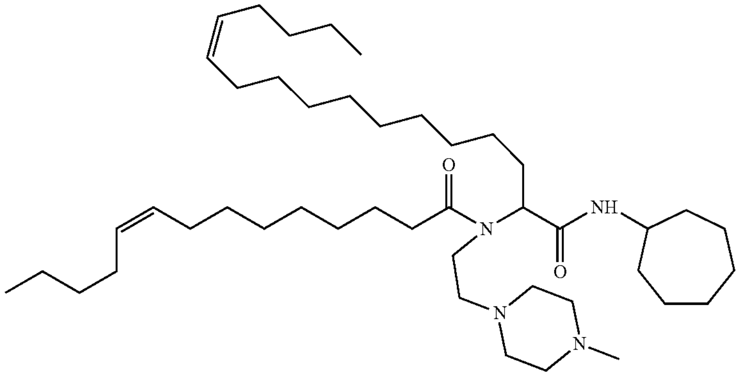
P451A12
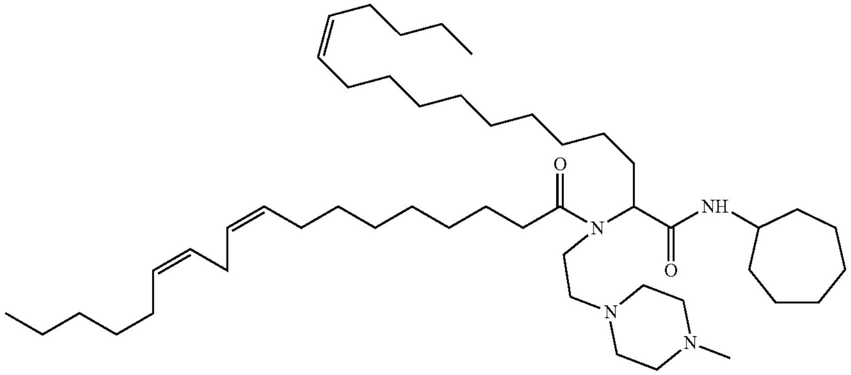

P451D12
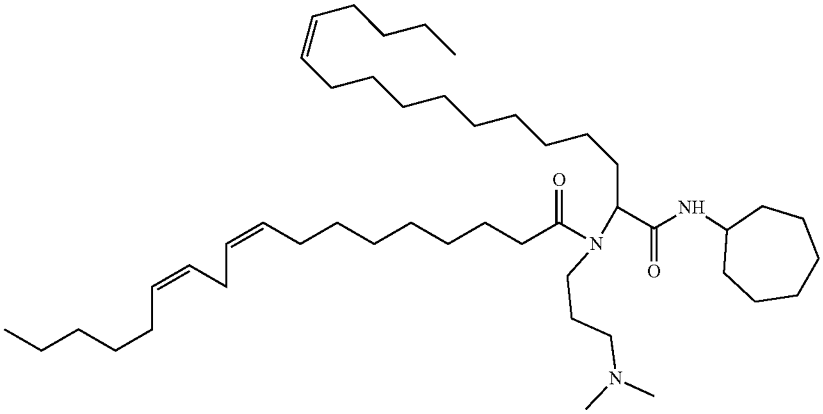
P451H7
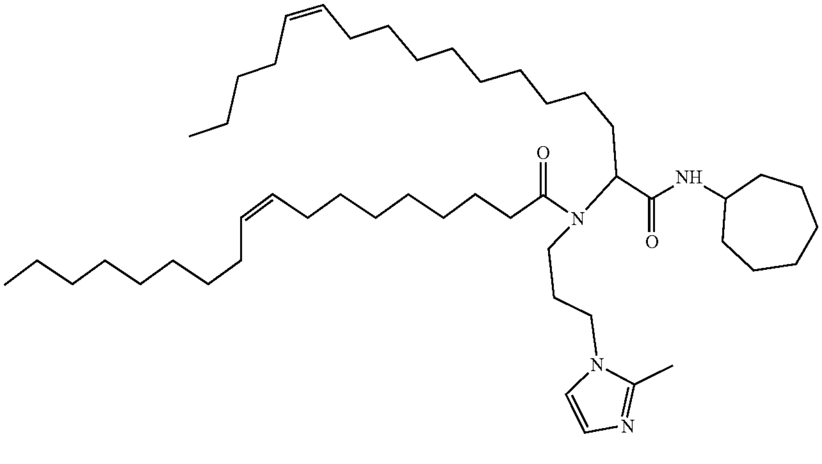
P451H9
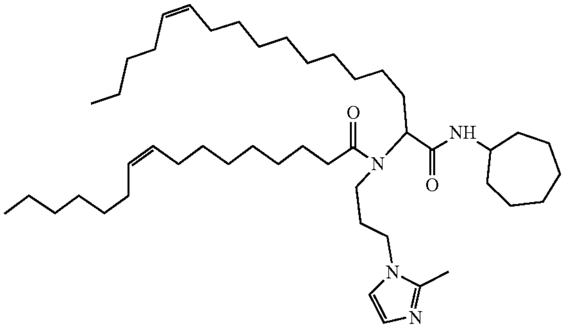
P453A4
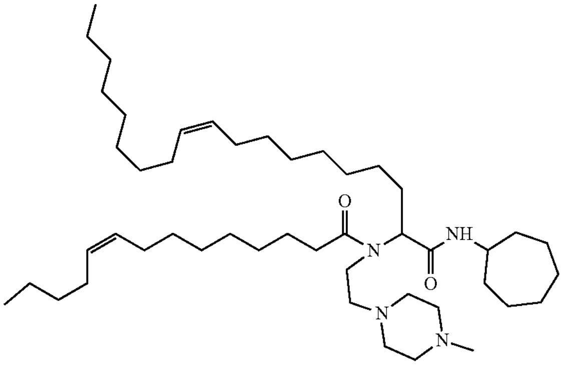

-continued
P453A6
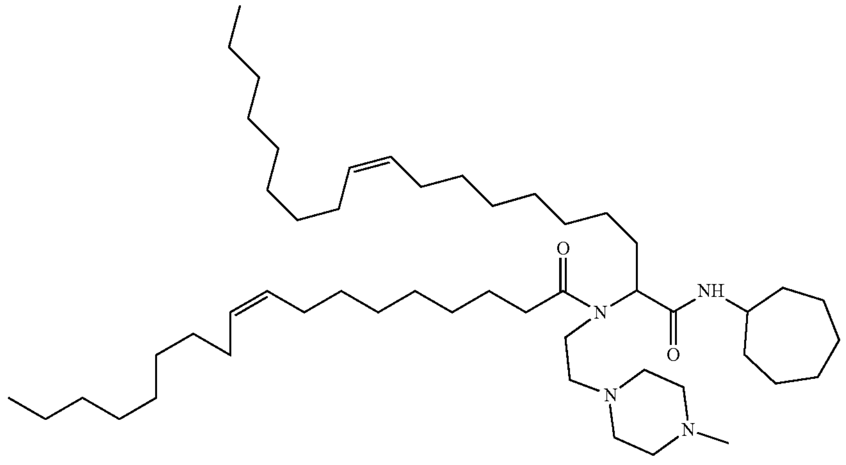
P453H1
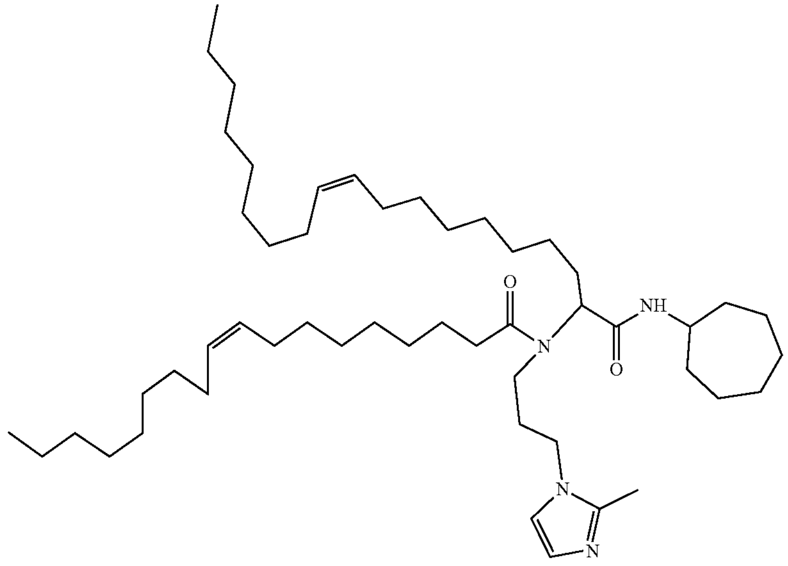
P453H3
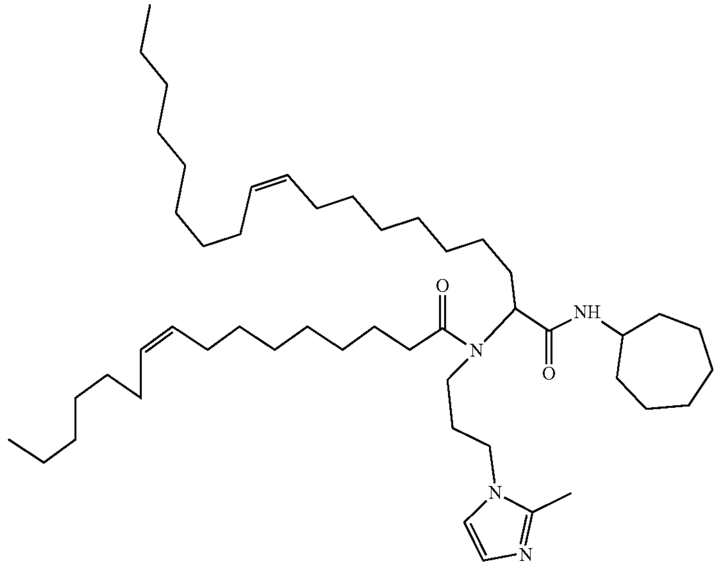

-continued
P454A6
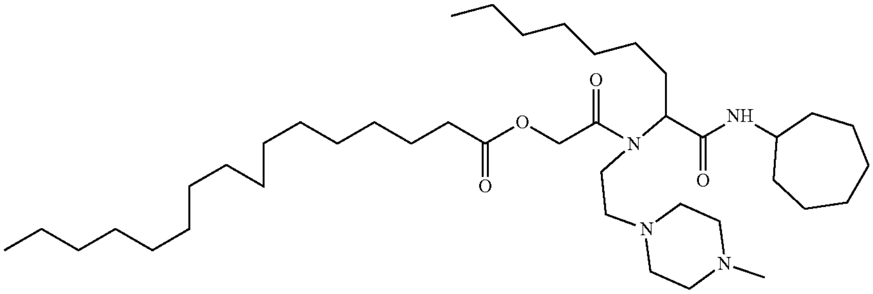
P454A12
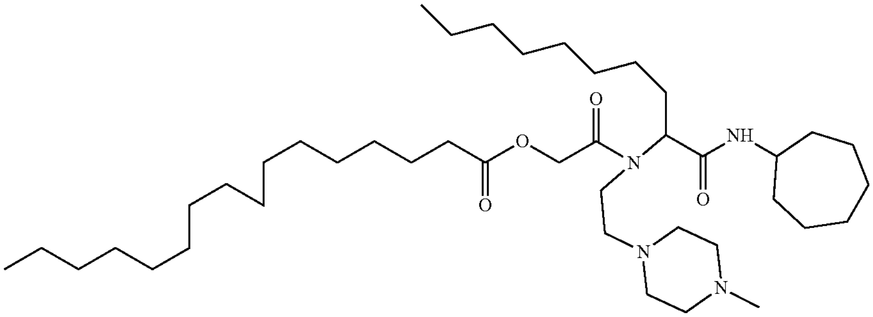
P454B12
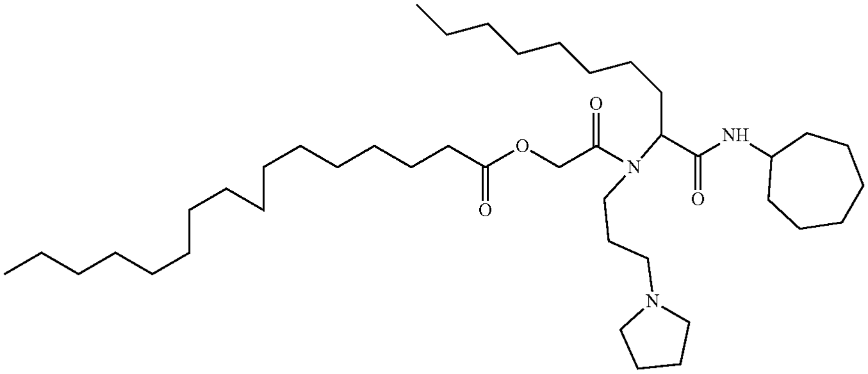
P454C12
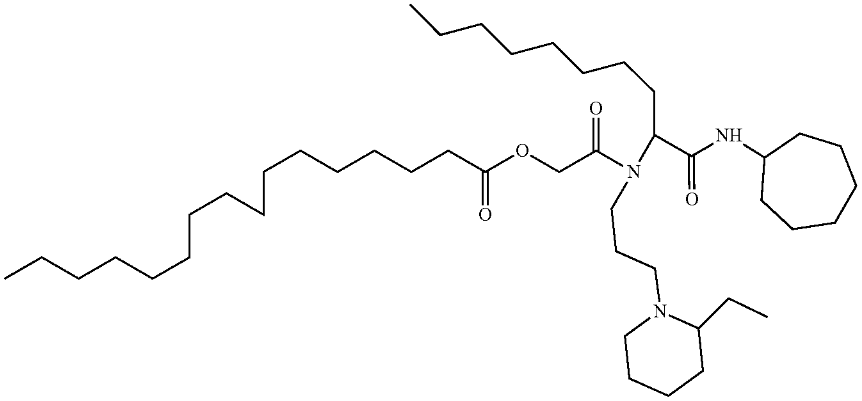

-continued
P454D12
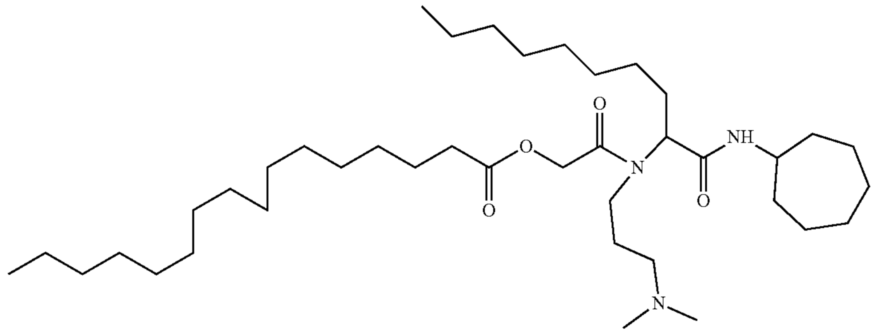
P454E12
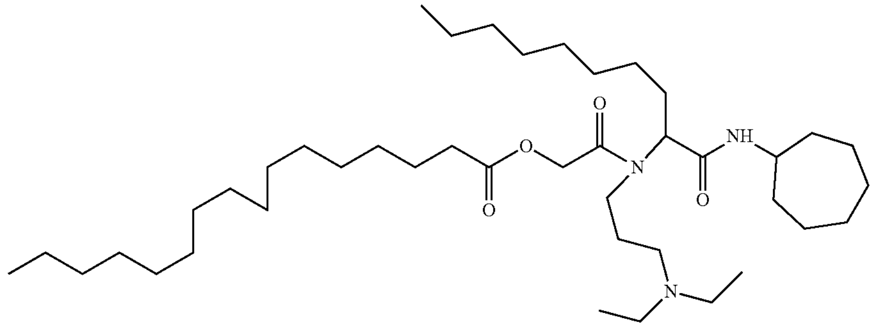
P454F12
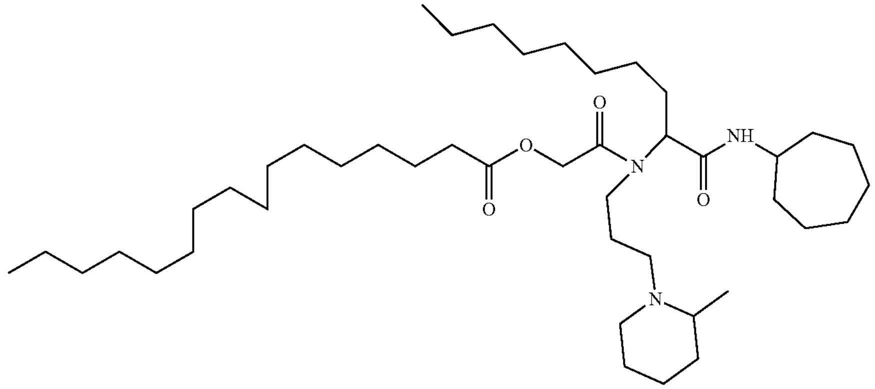
P454H6
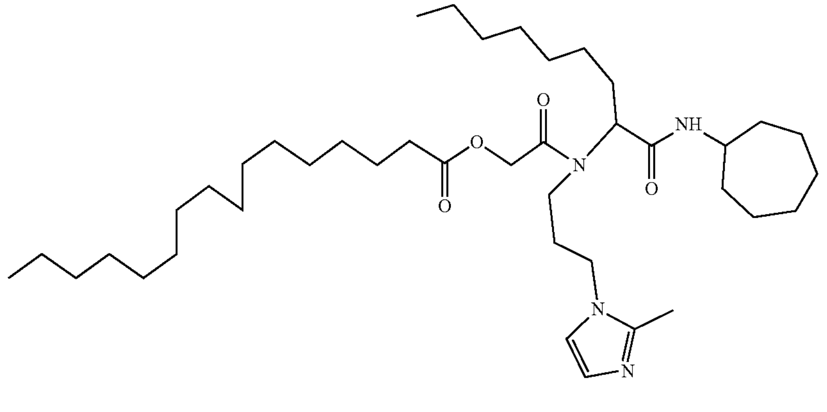

-continued
P455A6
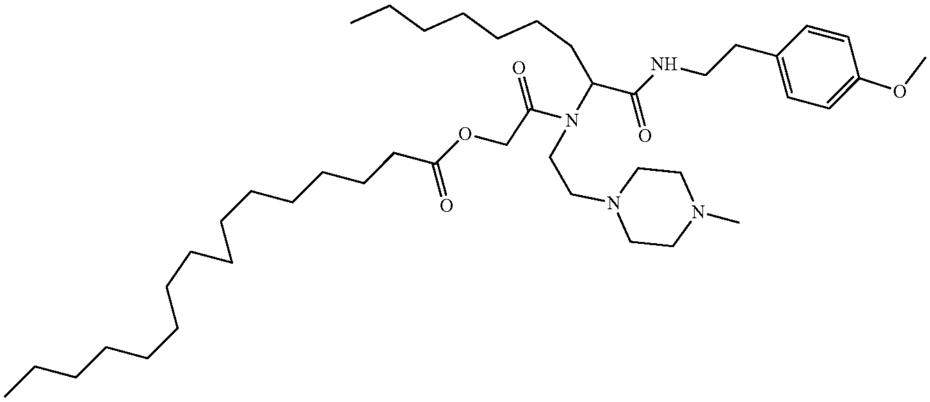
P455A12
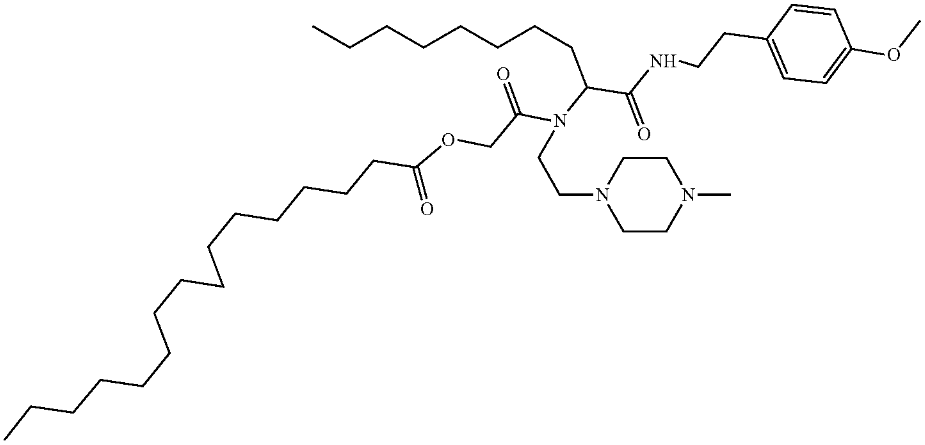
P455C12
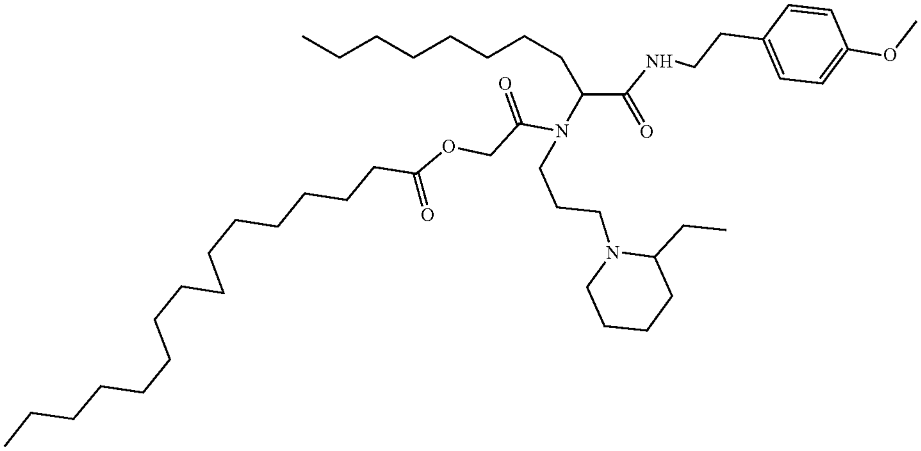
P455D12
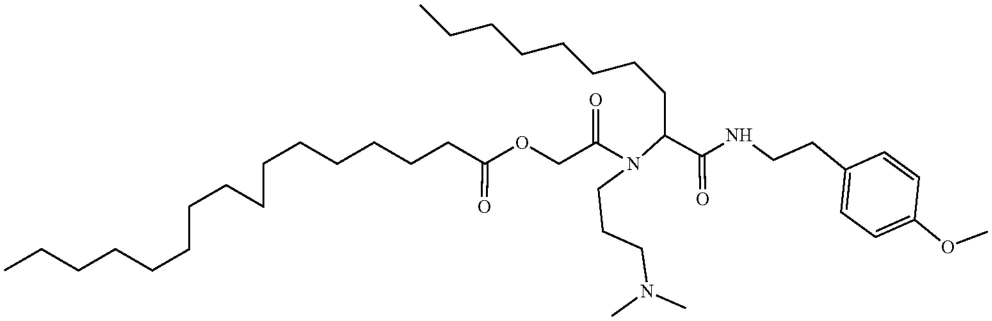

-continued
P455F12
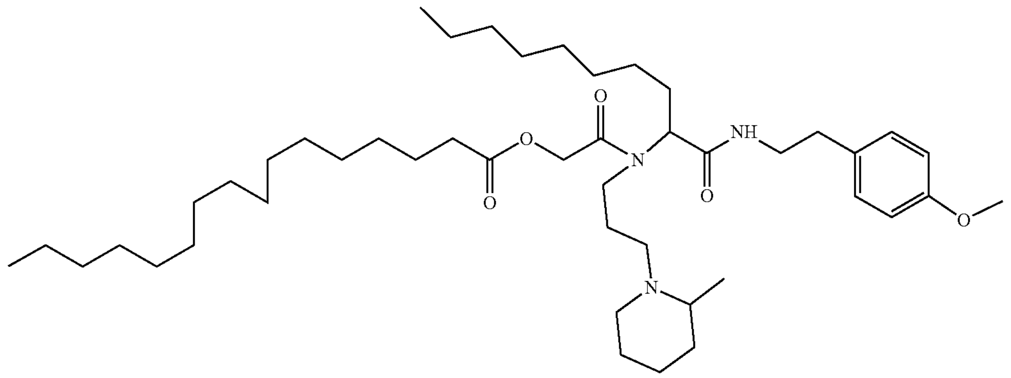
P458A10
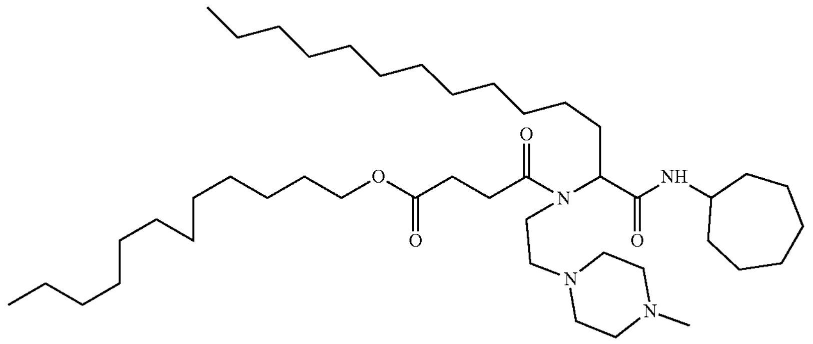
P458A11
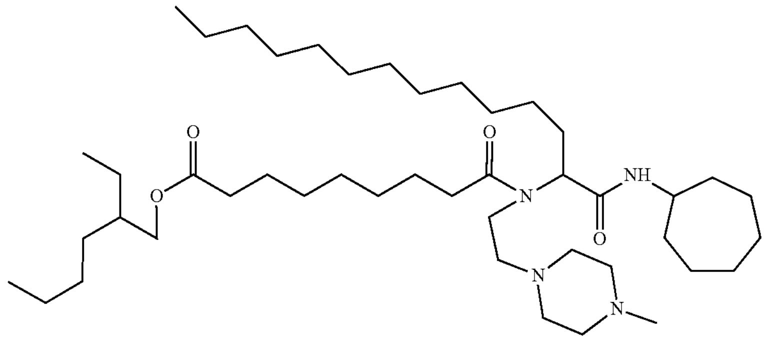
P458A12
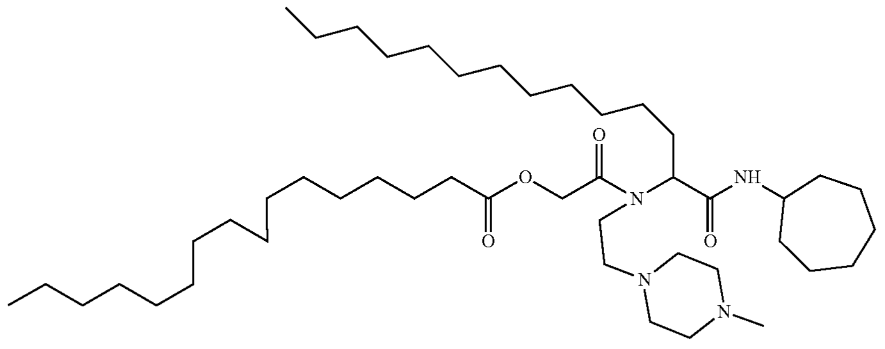

-continued
P458B12
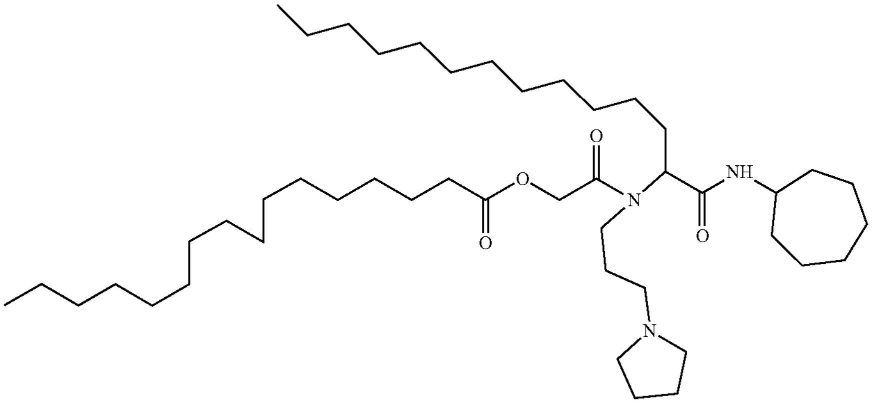
P458C12
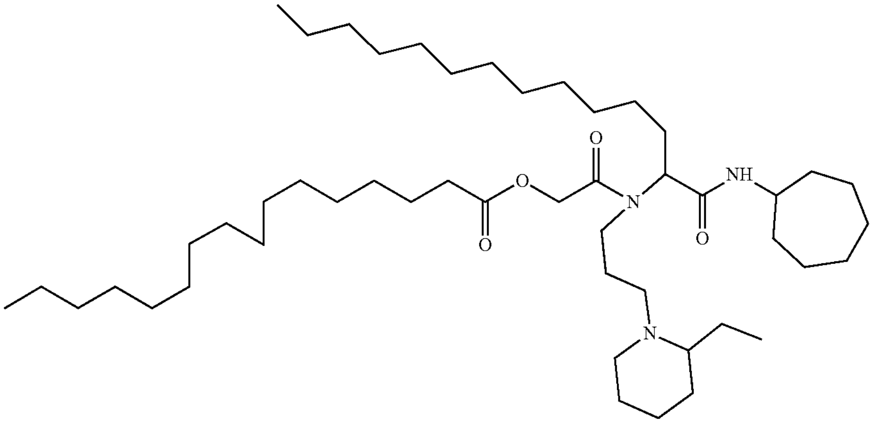
P458D12
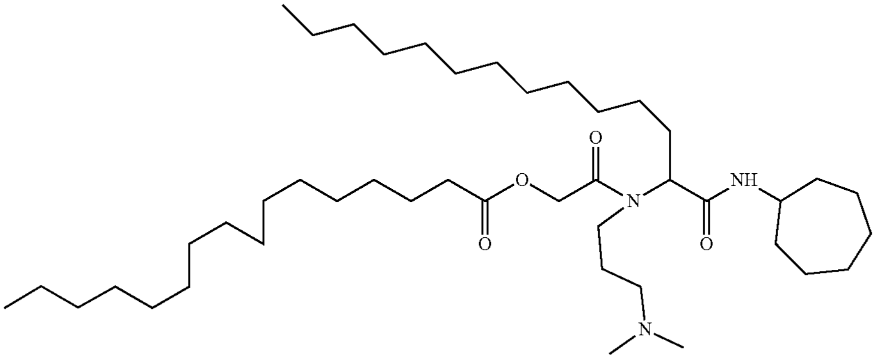
P458F12
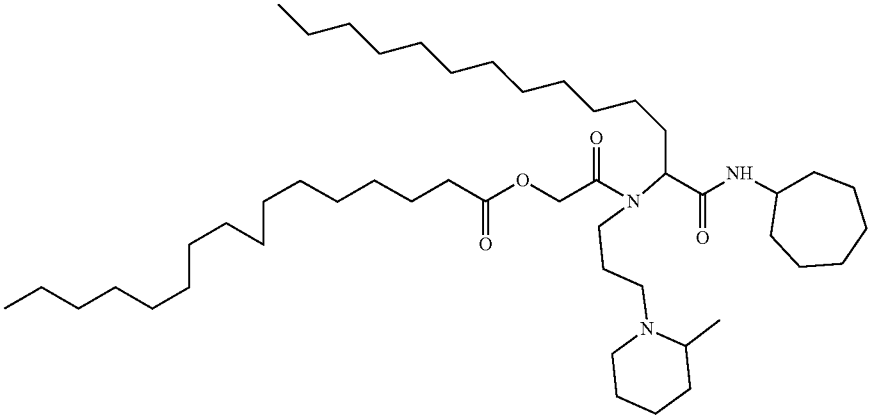

-continued
P459C6
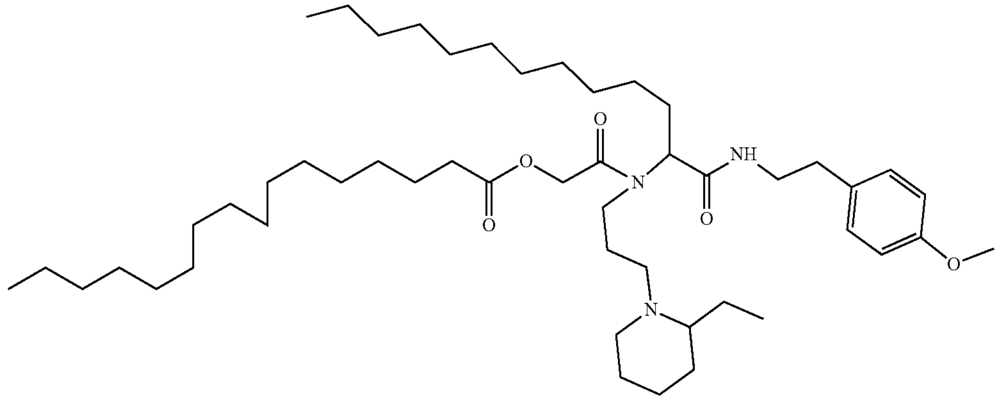
P459C12
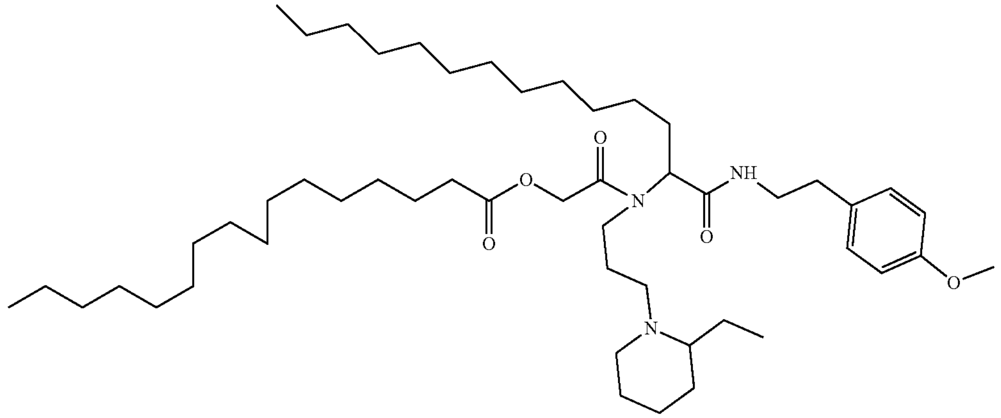
P459F4
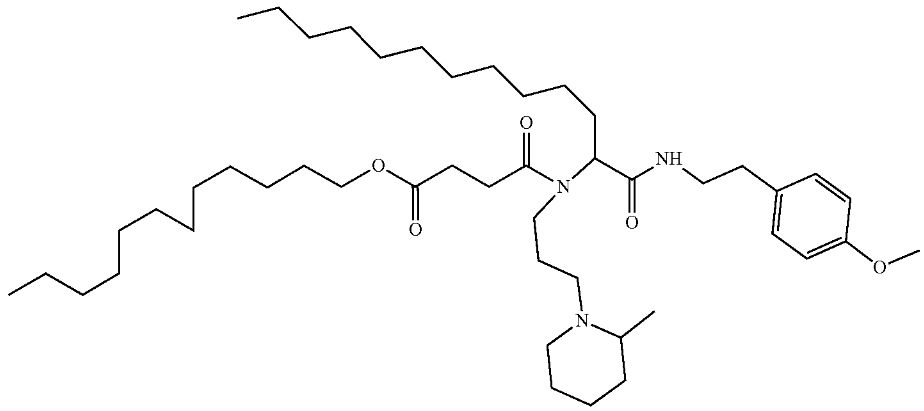
P459F6
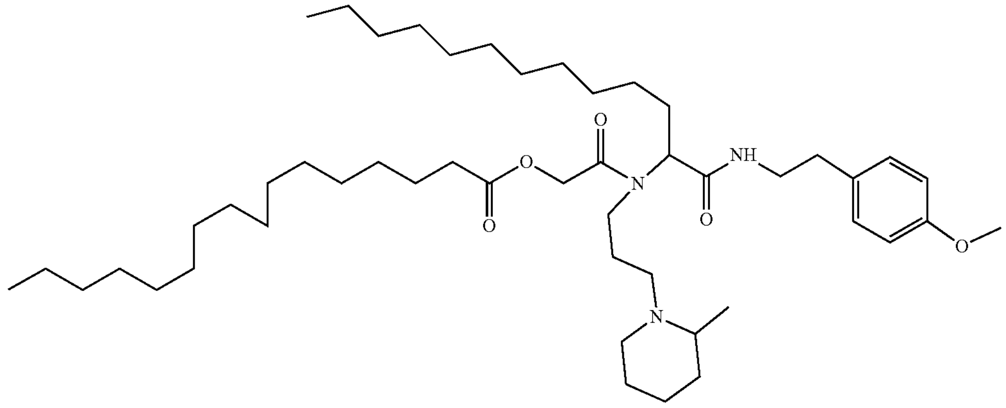

-continued
P460A5
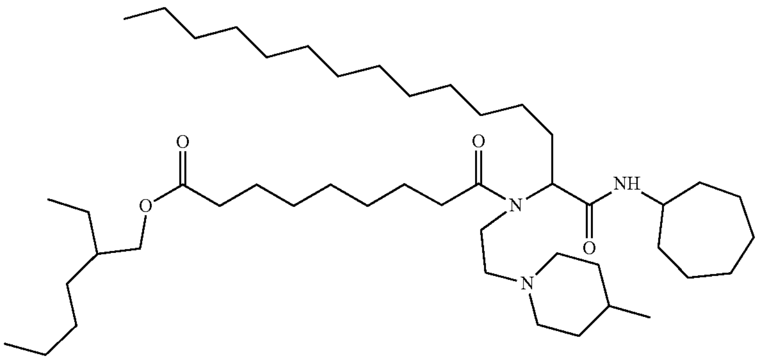
P460A6
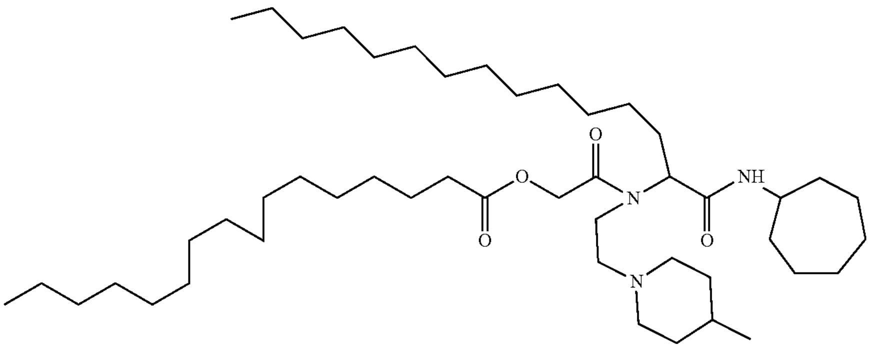
P460A11
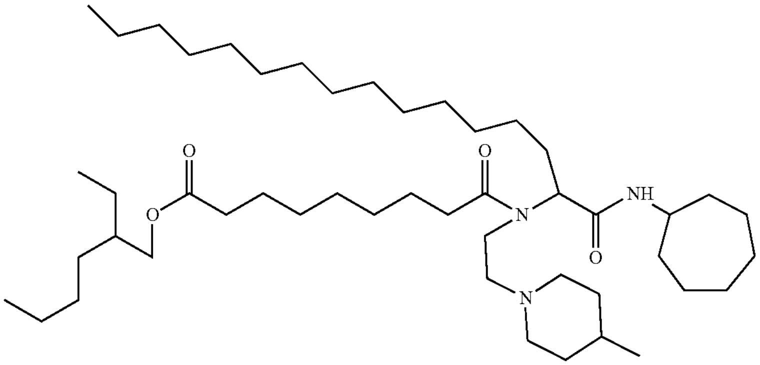
P461A2
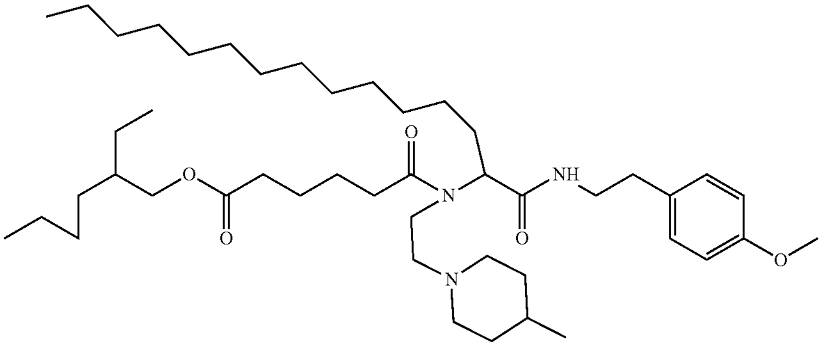

-continued
P461A5
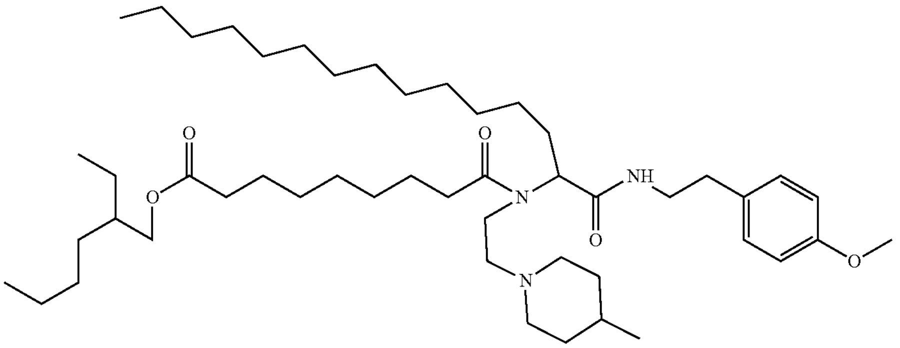
P461H6
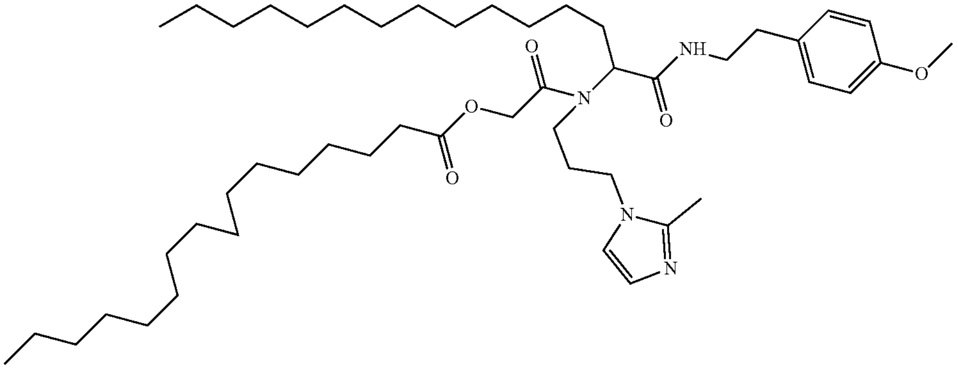
P461H12
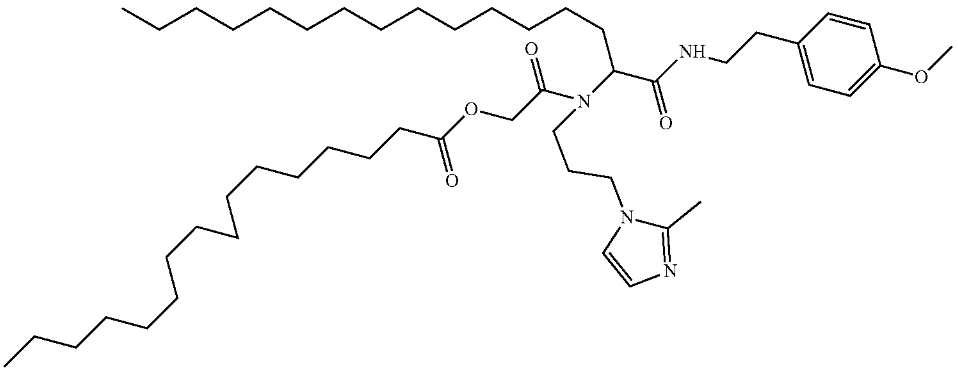
P462A10
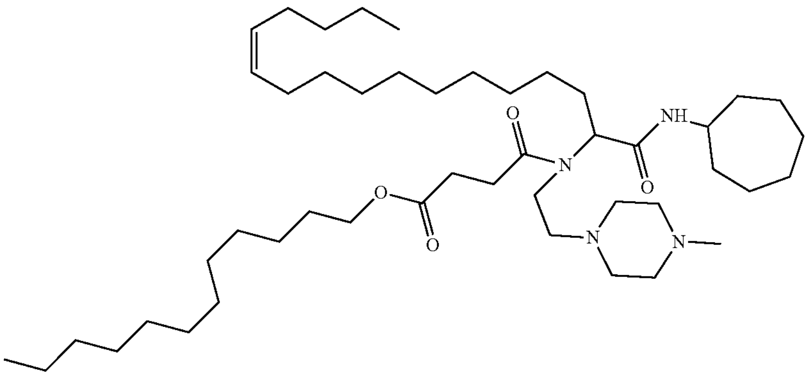

-continued
P462A11
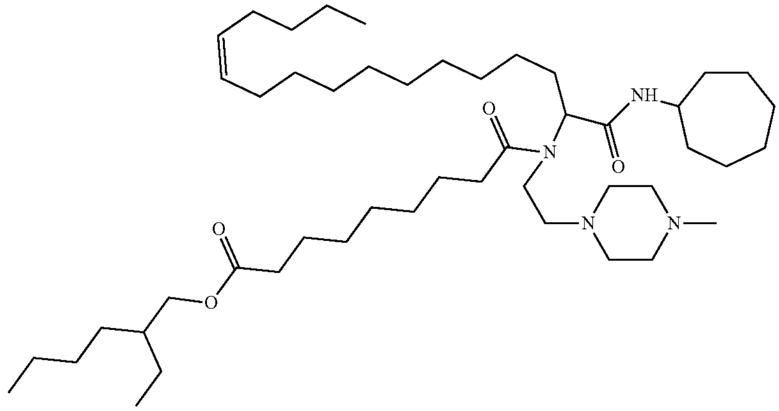
P462A12
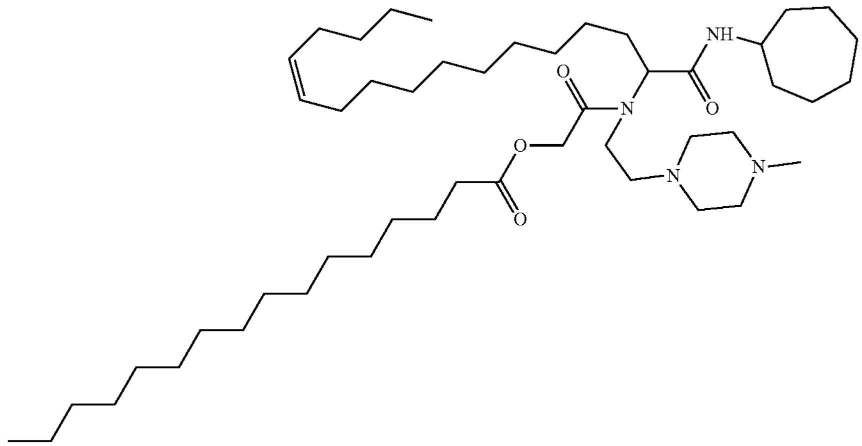
P462C12
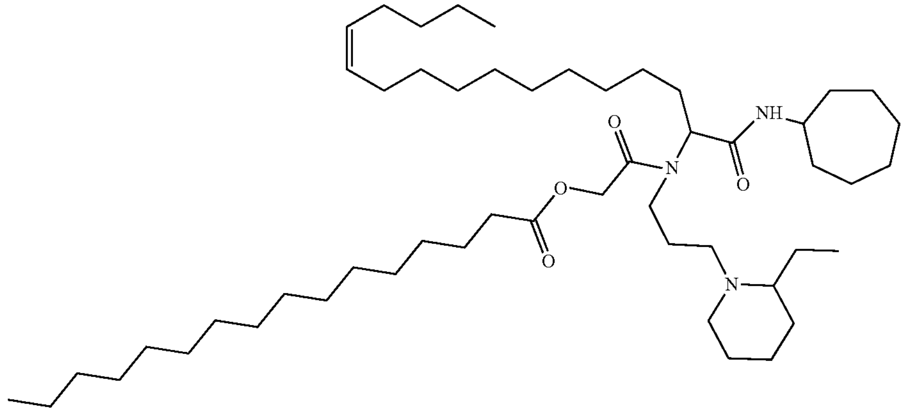

-continued
P462E10
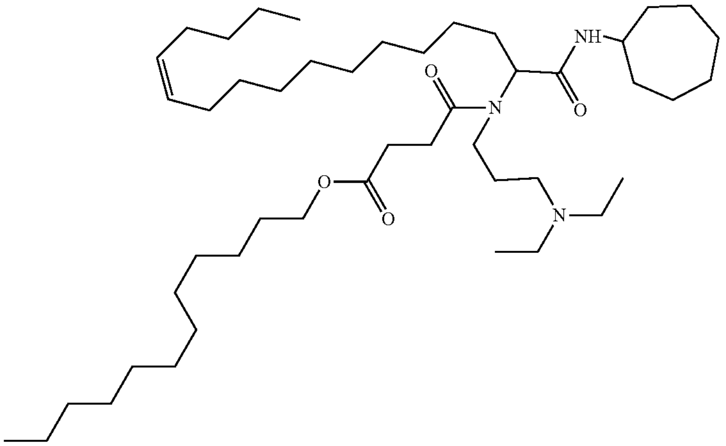
P462E11
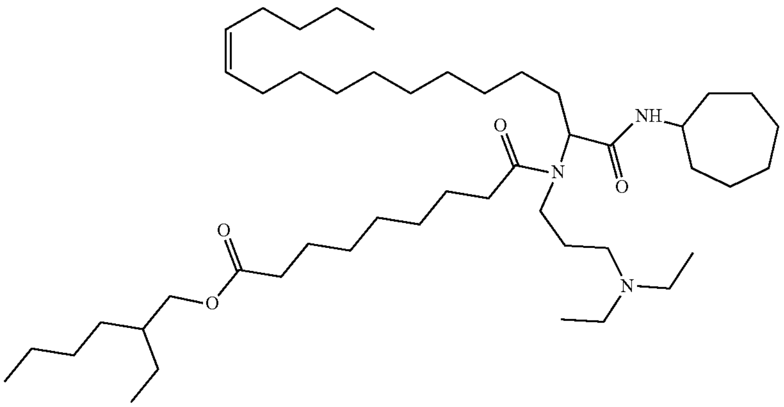
P462E12
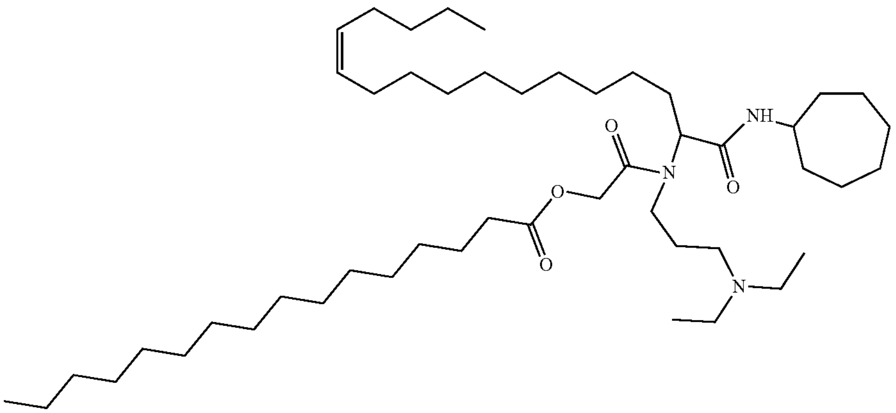

-continued
P462F12
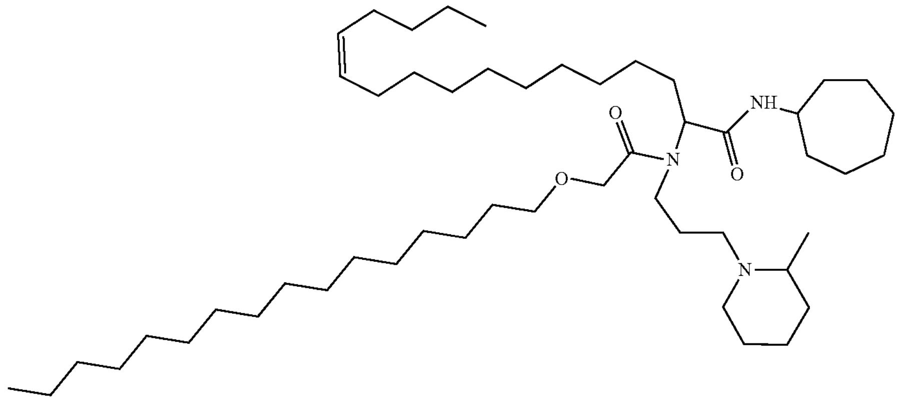
P463A8
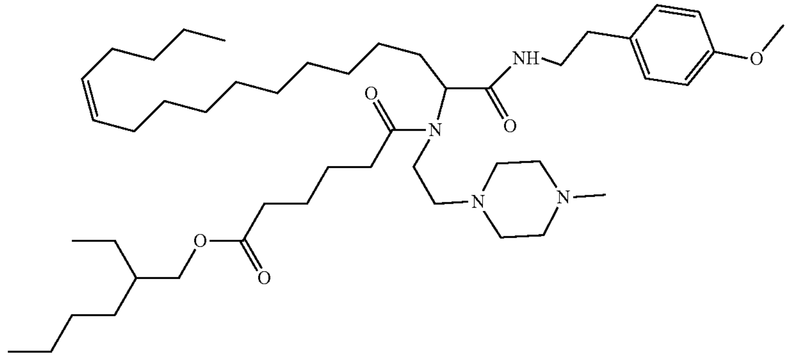
P463A9
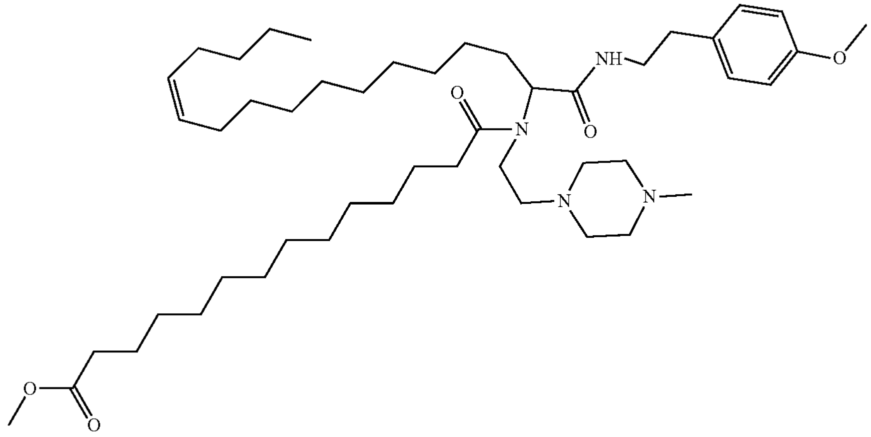
P463A10
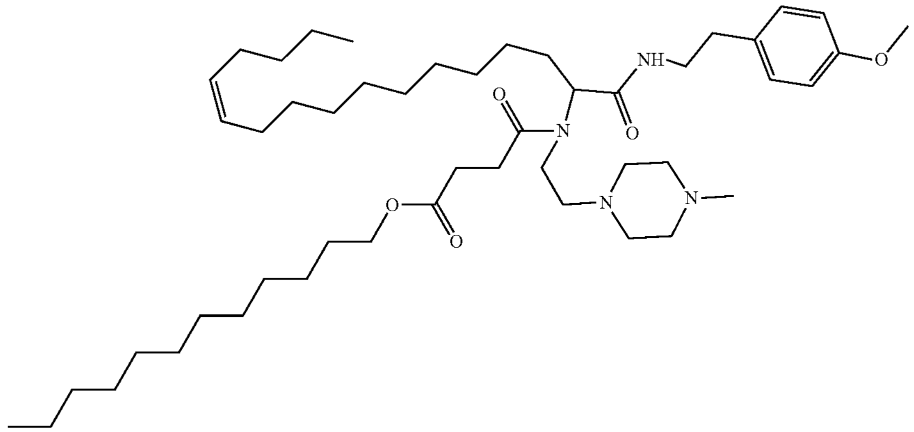

-continued
P463A11
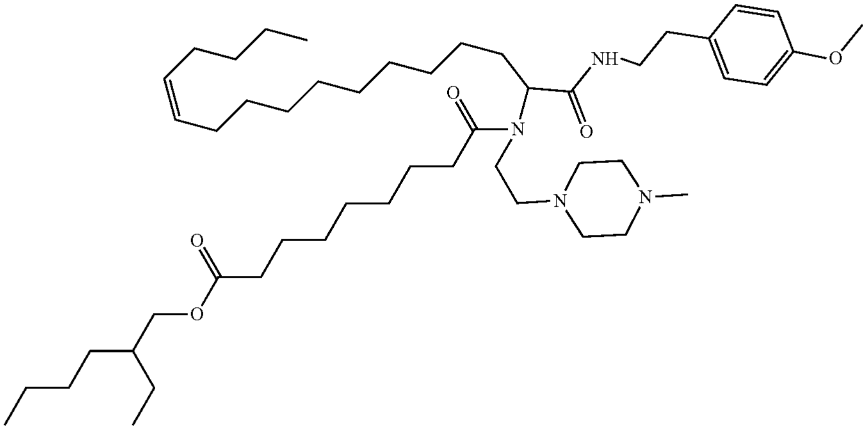
P463A12
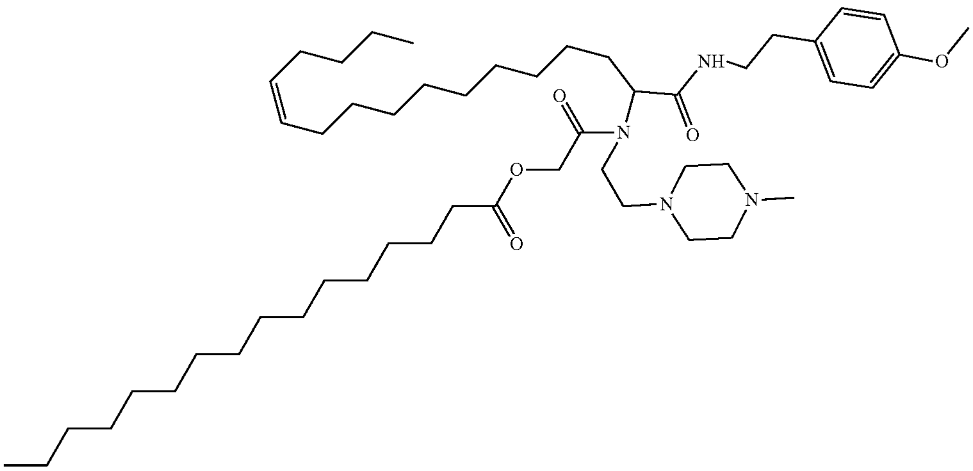
P463B10
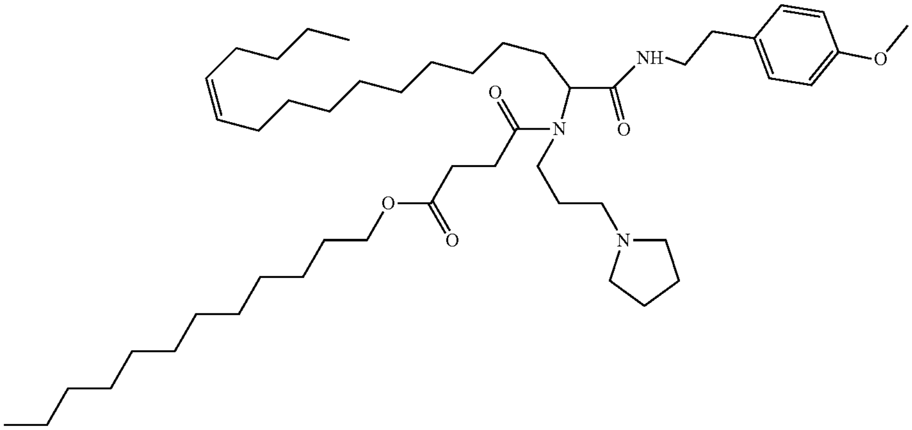

-continued
P463D8
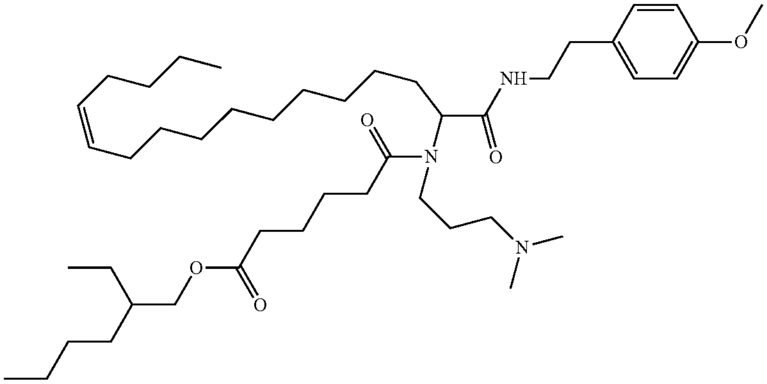
P463D10
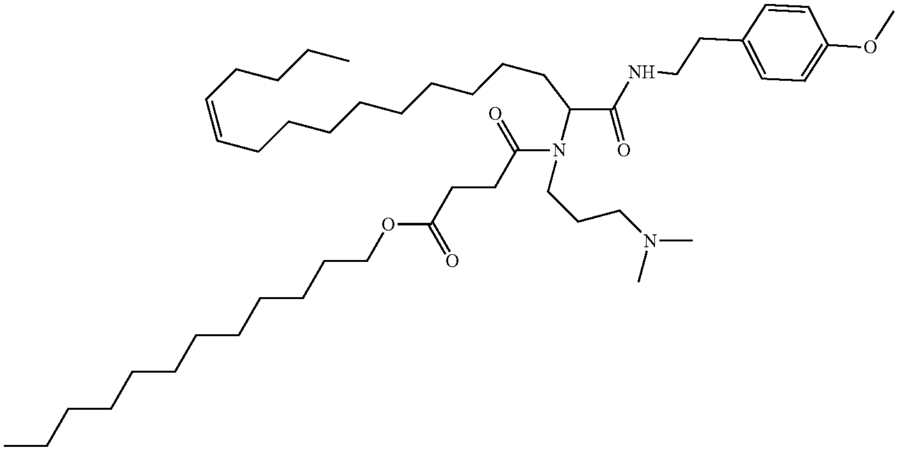
P463D12
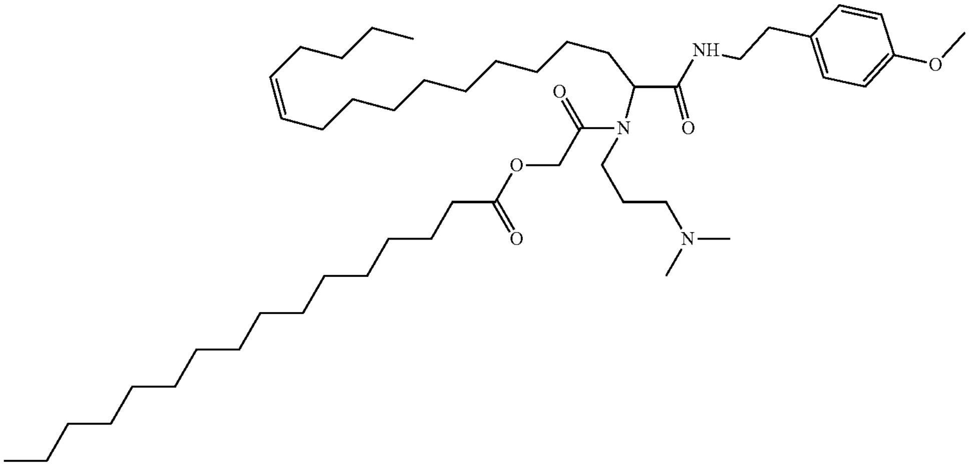

-continued
P464A4
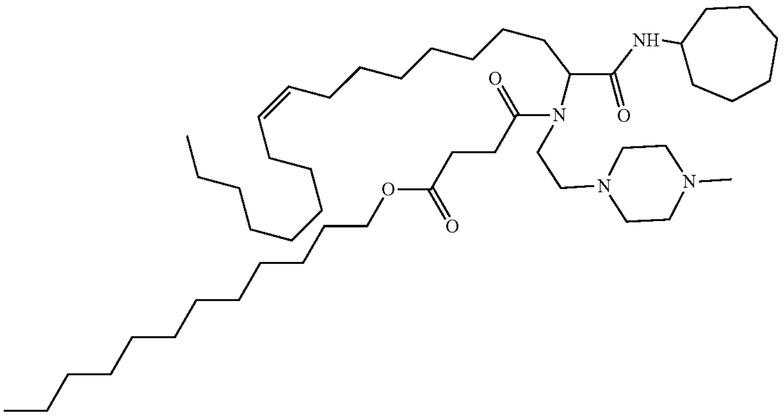
P464A5
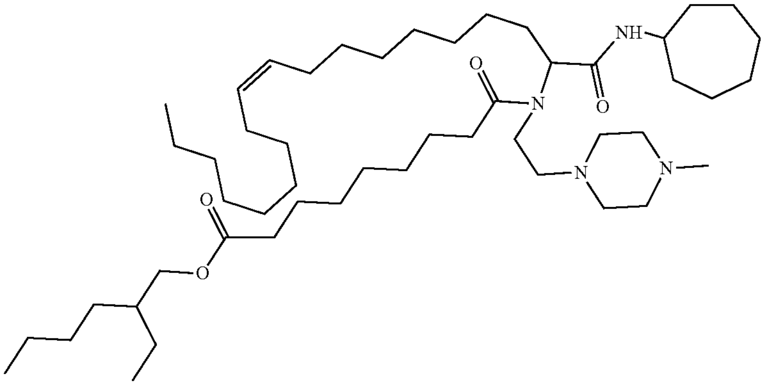
P464B6
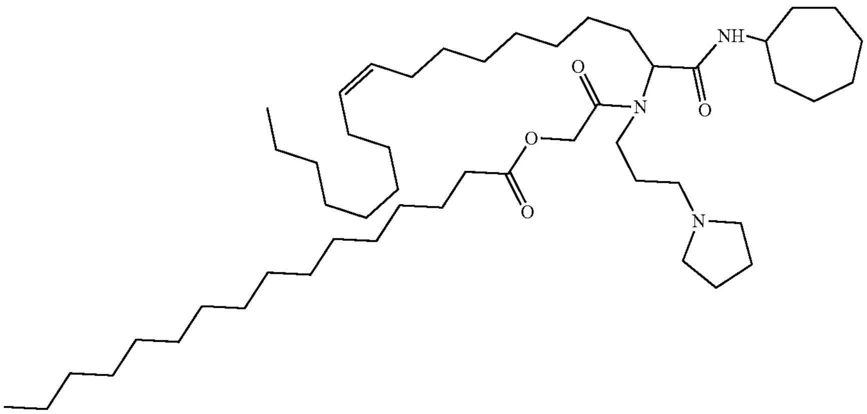
P464D6
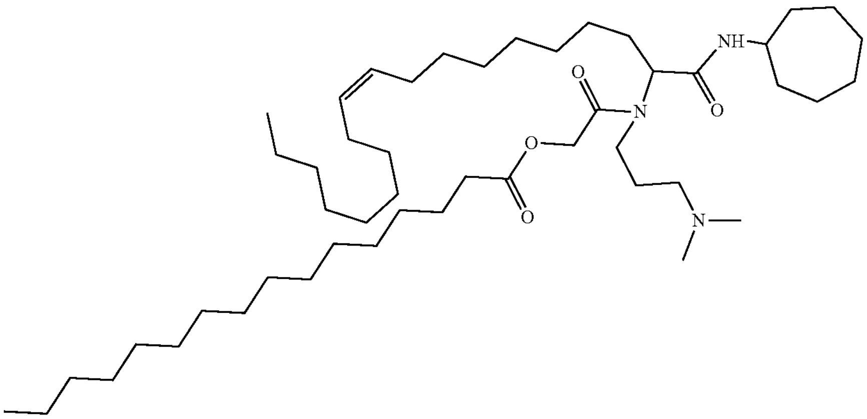

-continued
P464E6
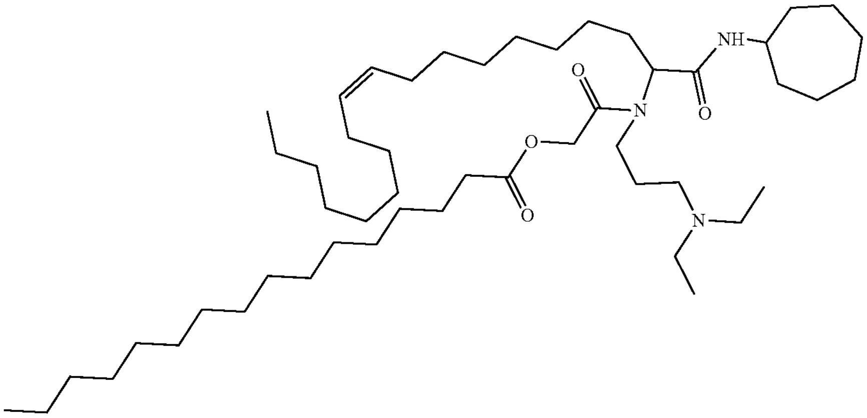
P465A2
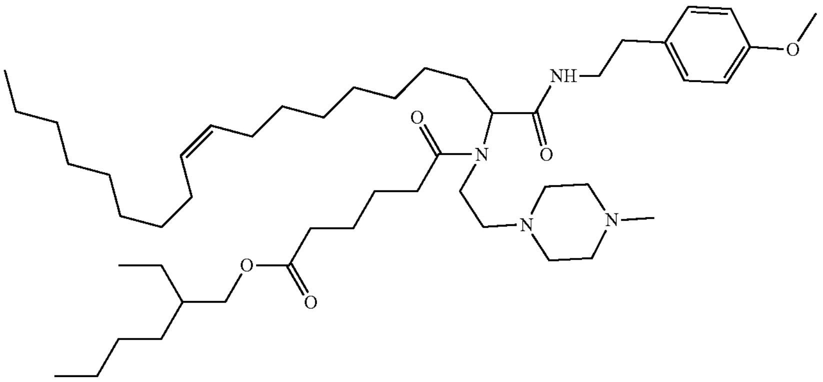
P465A5
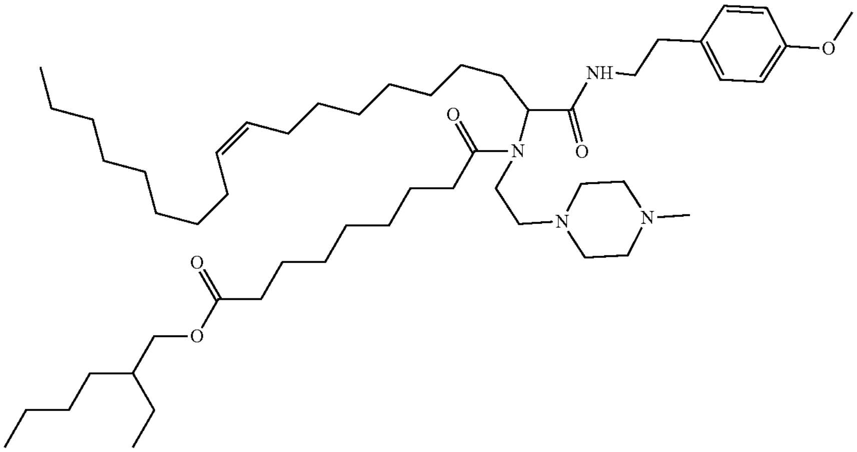

-continued
P465A6
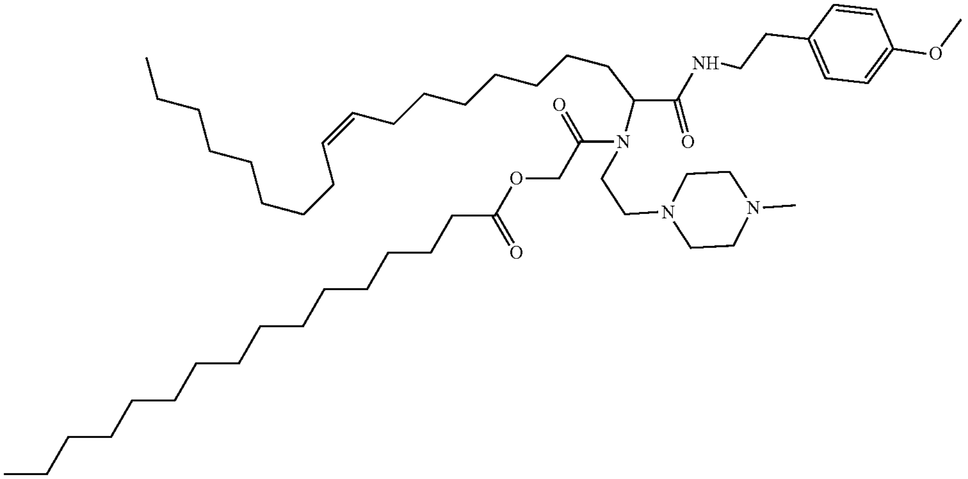
P465B4
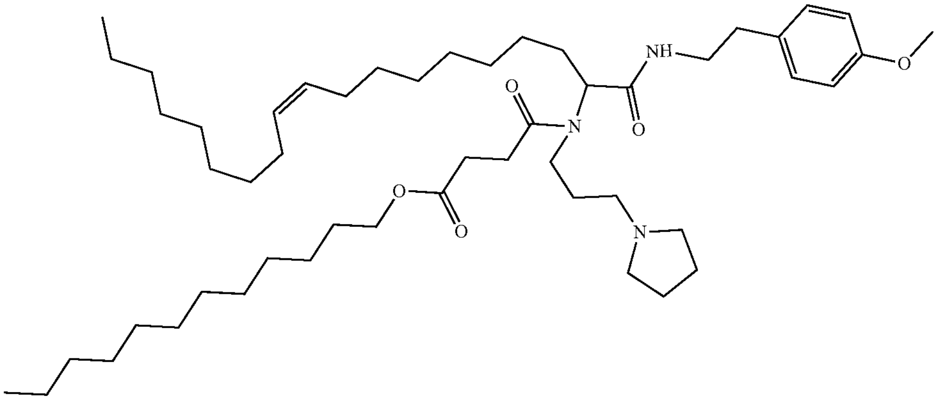
P465B10
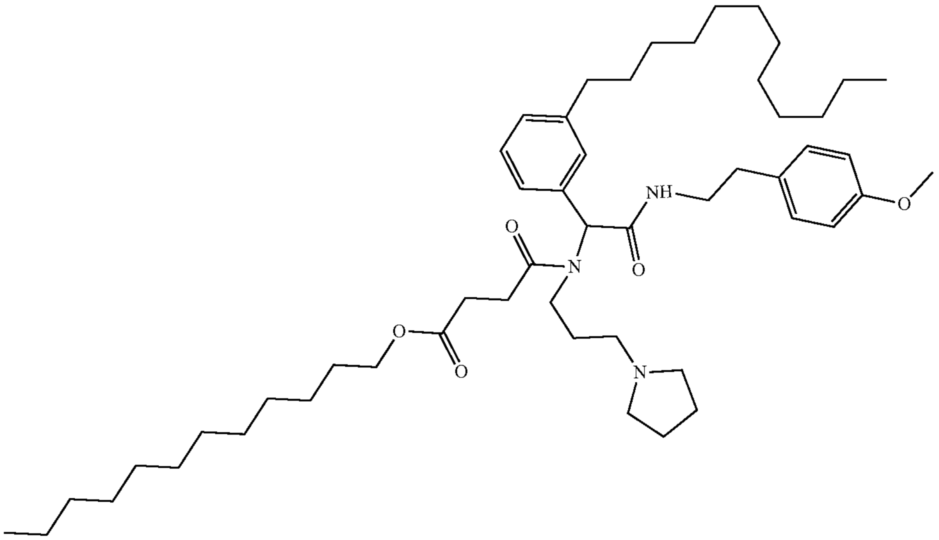

-continued
P465B12
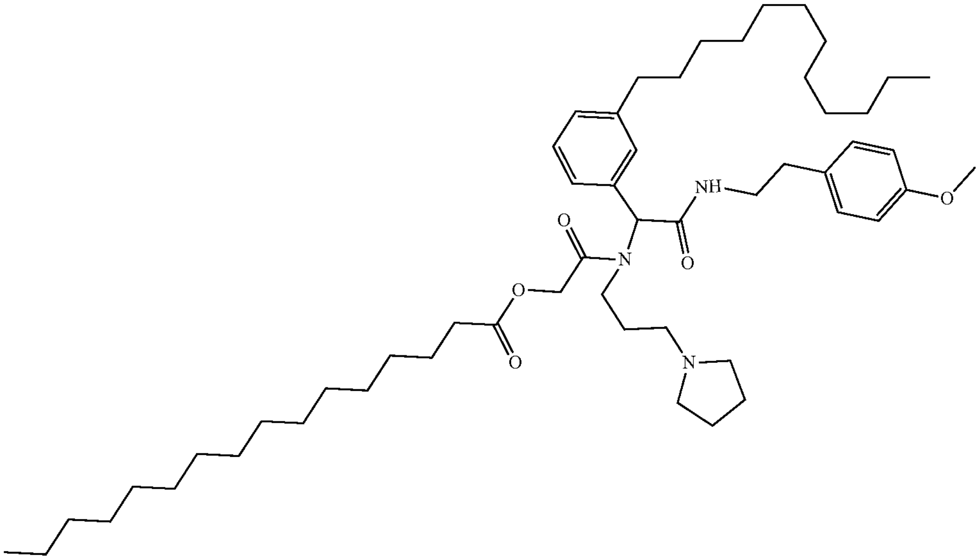
P465D10
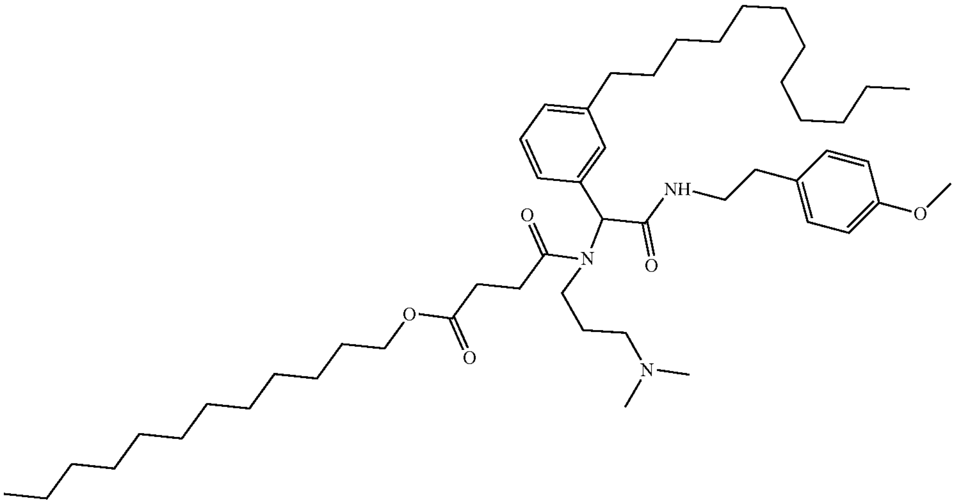
P470D7
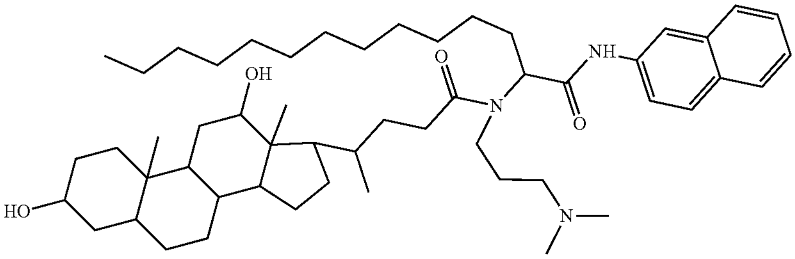

-continued
P500D6
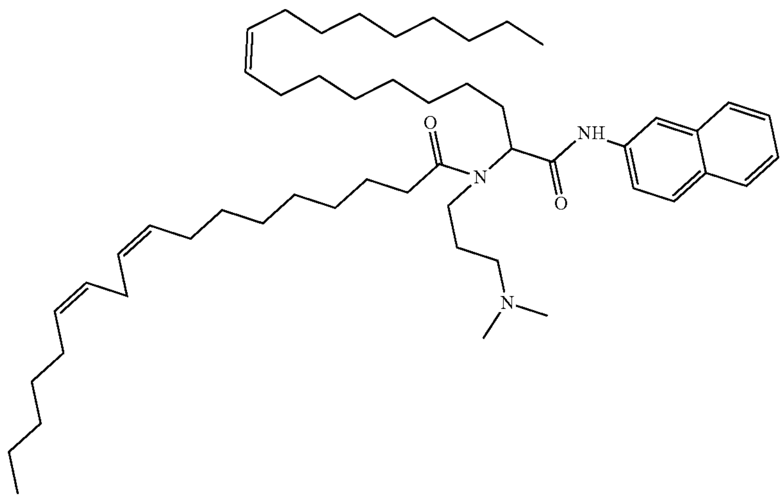
P56A7
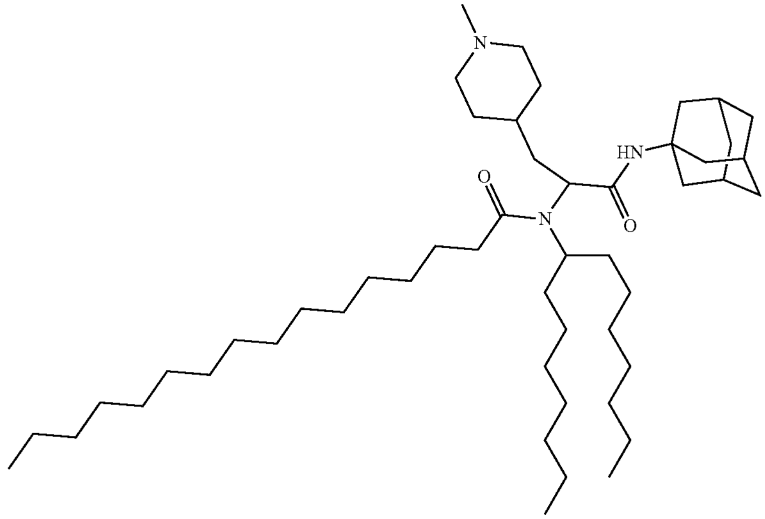
P319C8
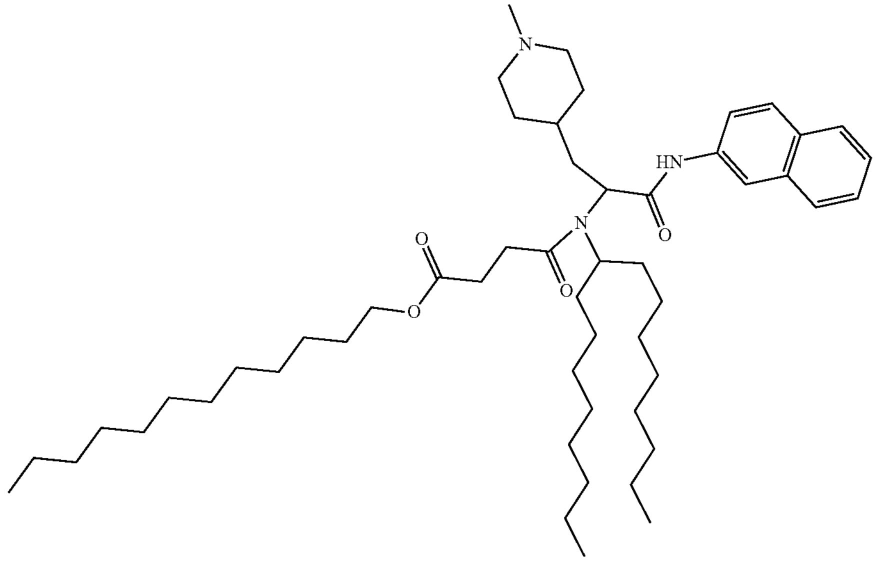

-continued
P363E8
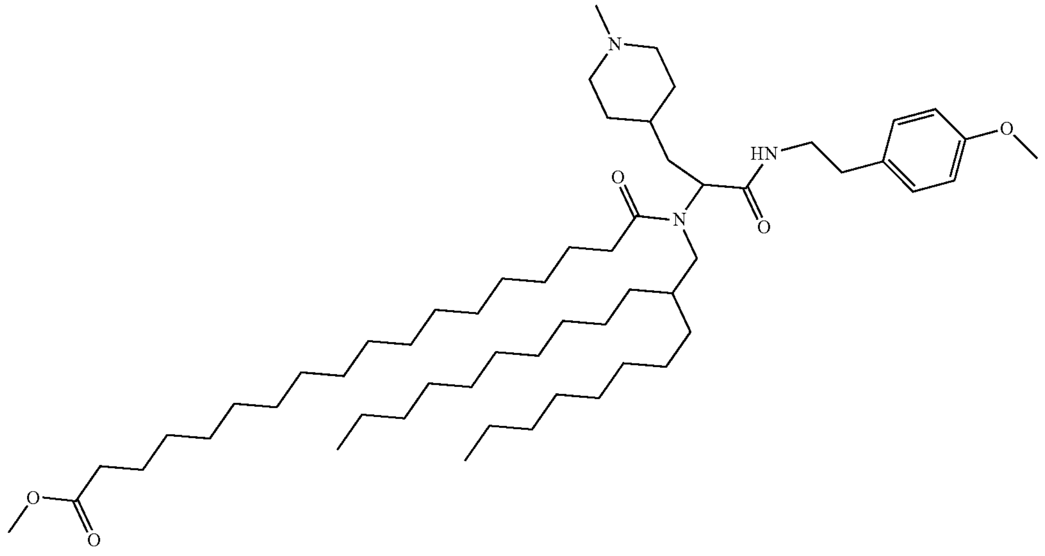
P56B9
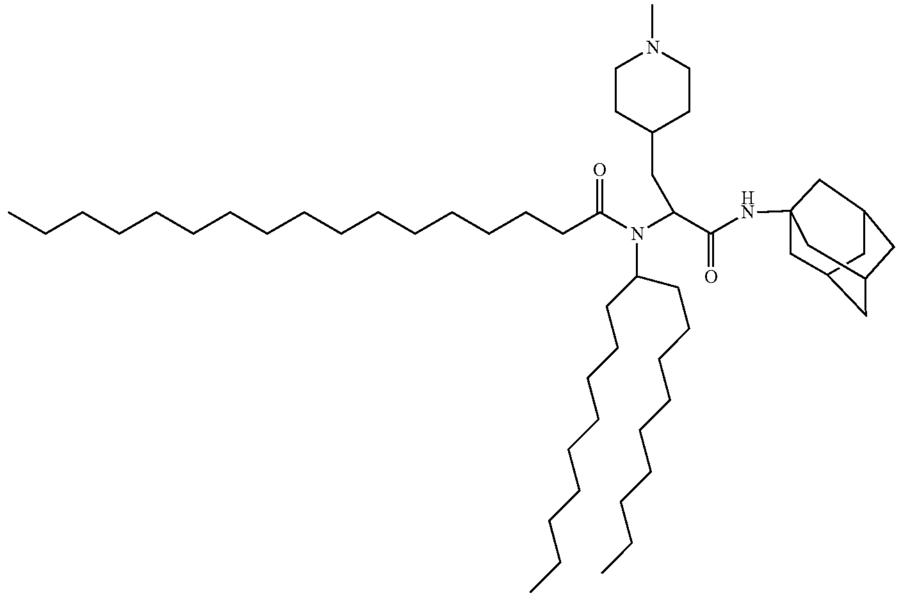

-continued
P313B7
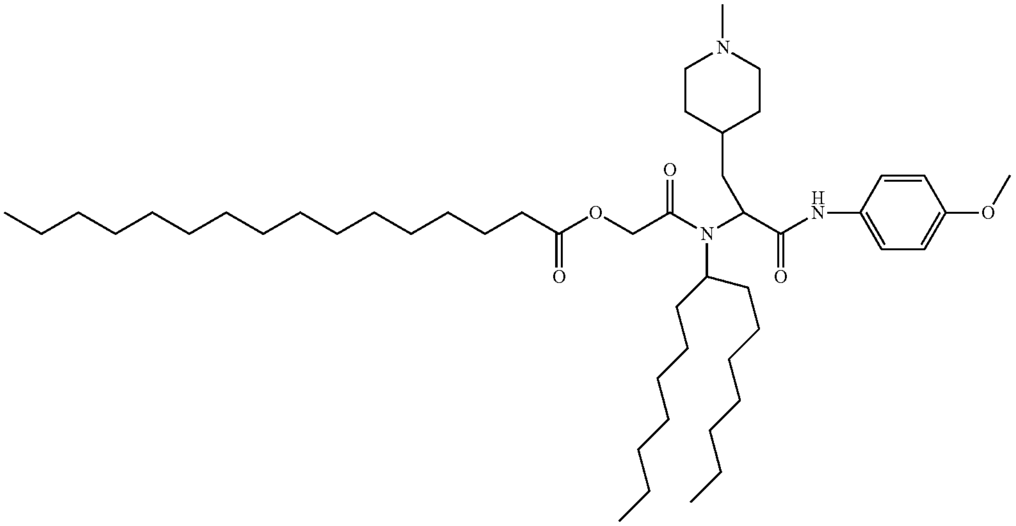
P331E4
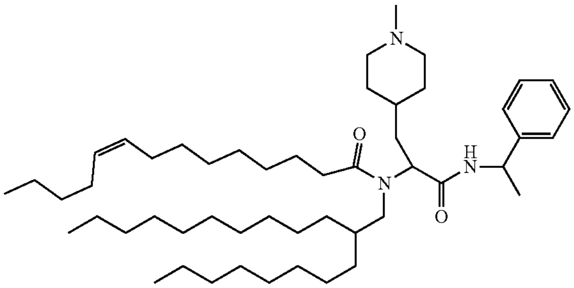
P149A3
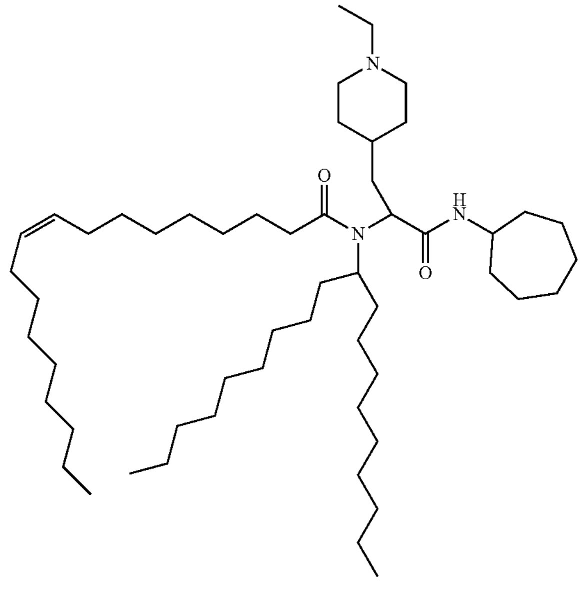

P149C1
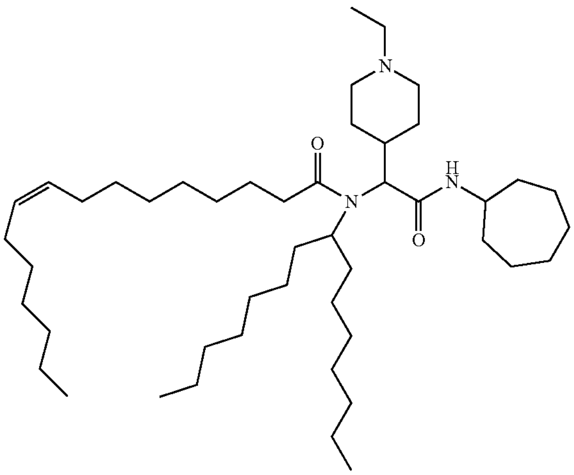
P149C2
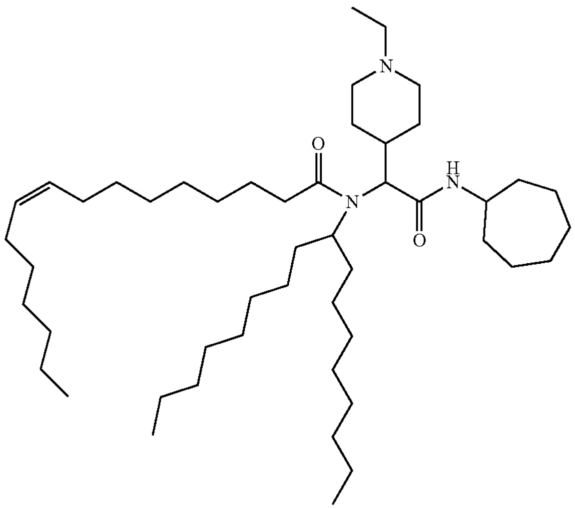
P149C3
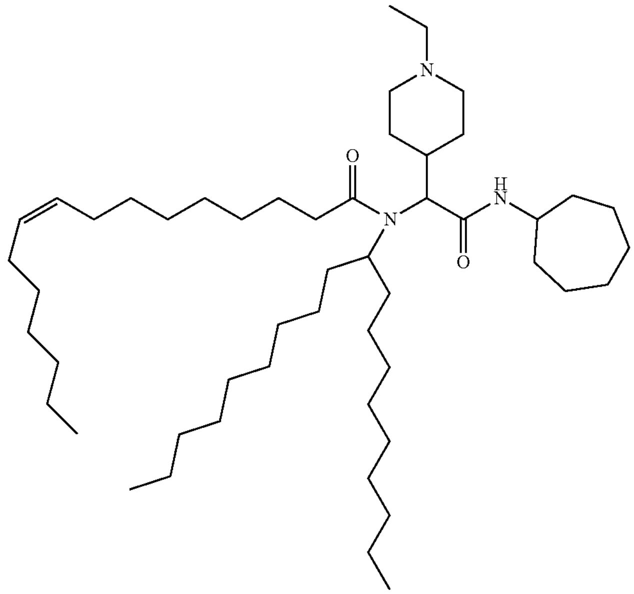
P313B6
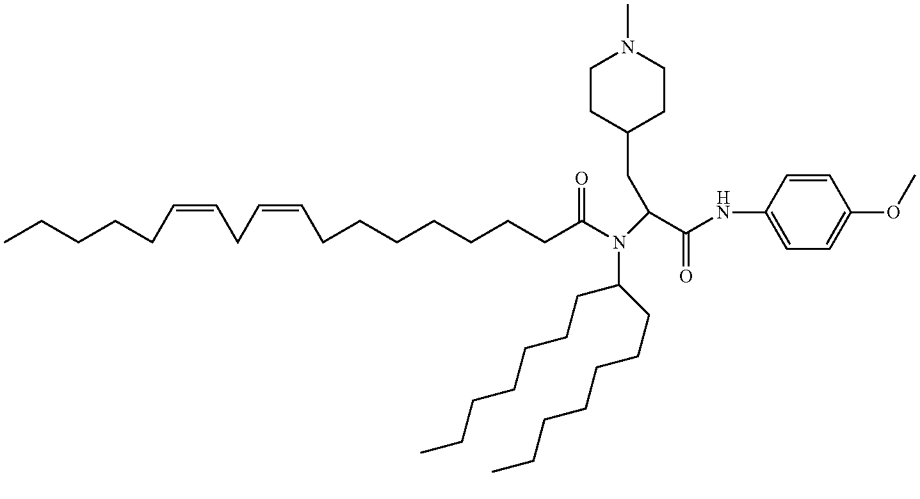

-continued
P319B6
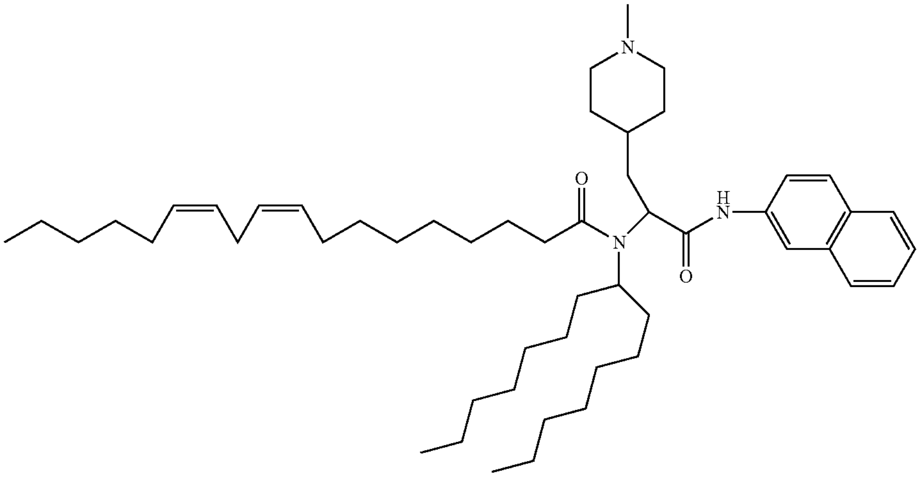
P343E5
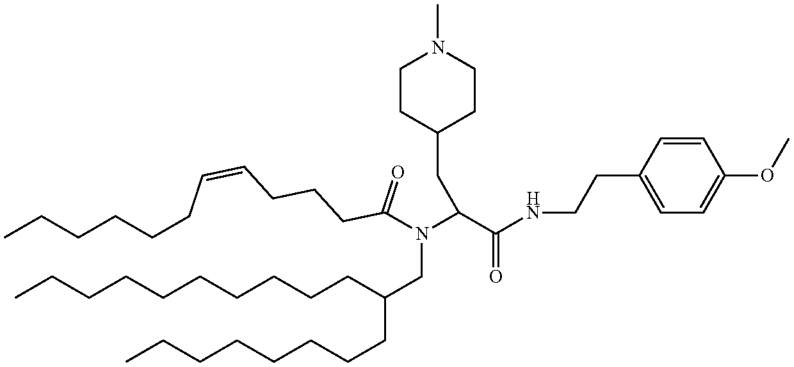
P343B1
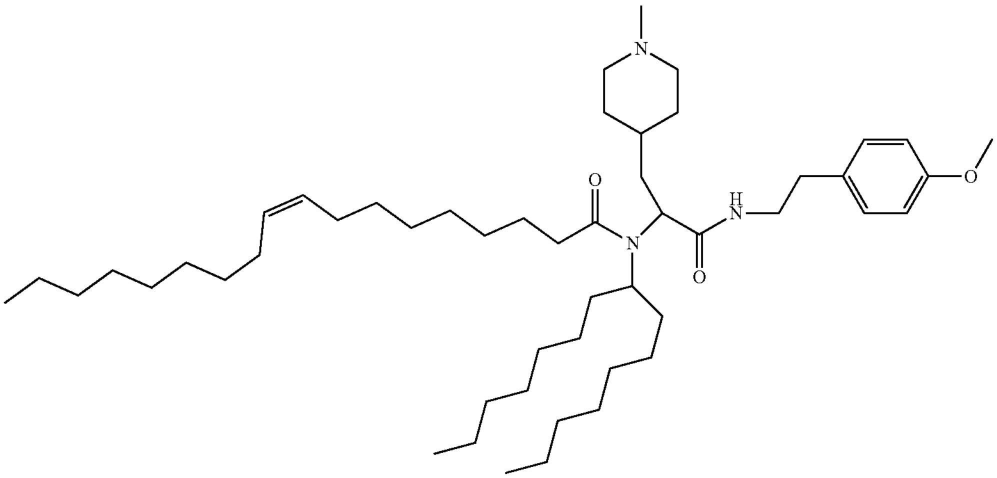

-continued
P363E10
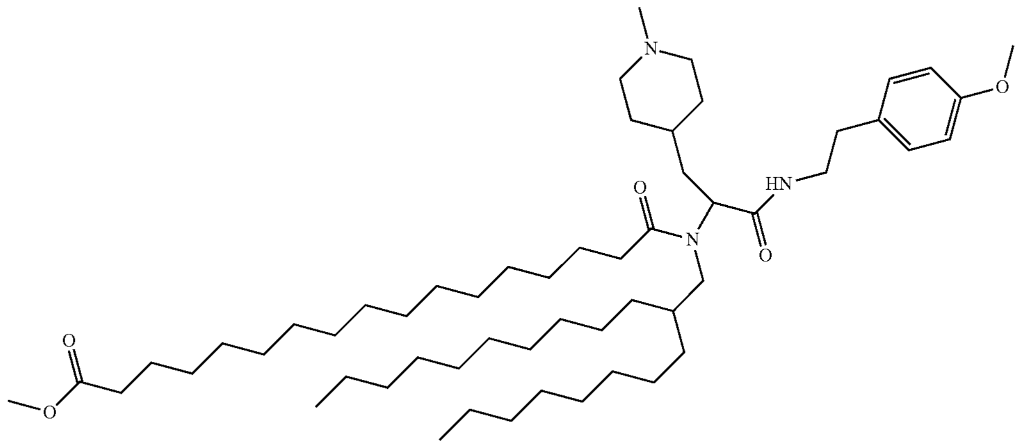
P341A10
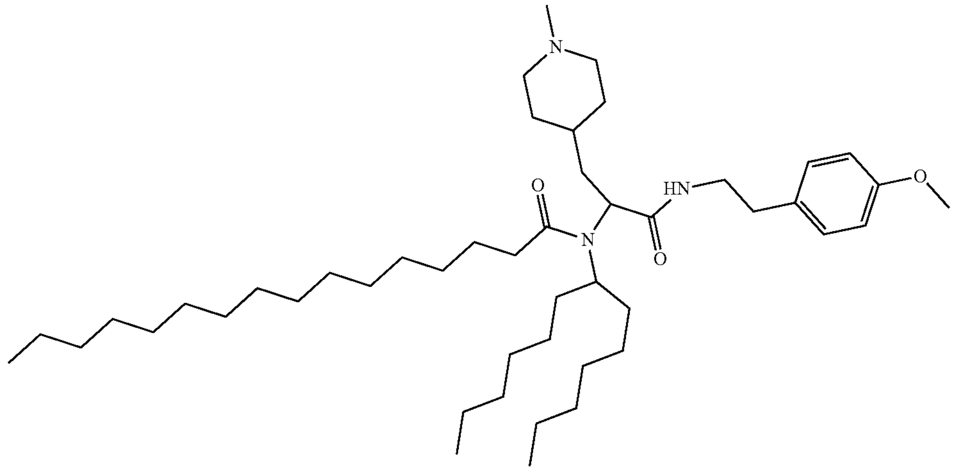
P363B8
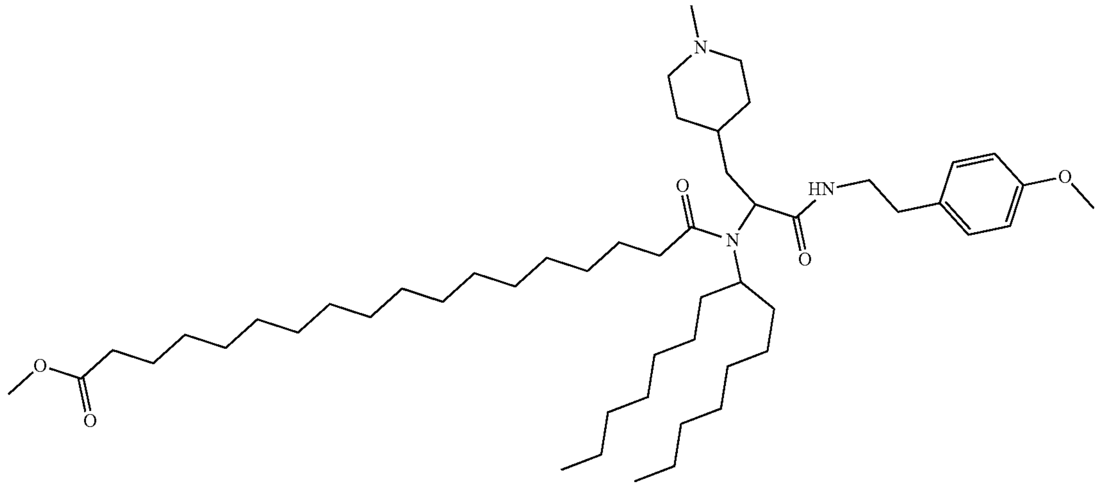

-continued
P343B6
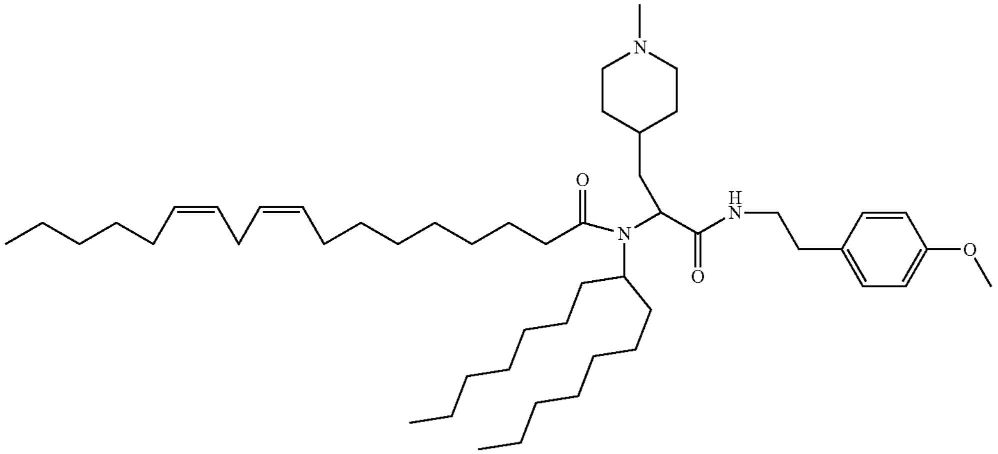
P343B8
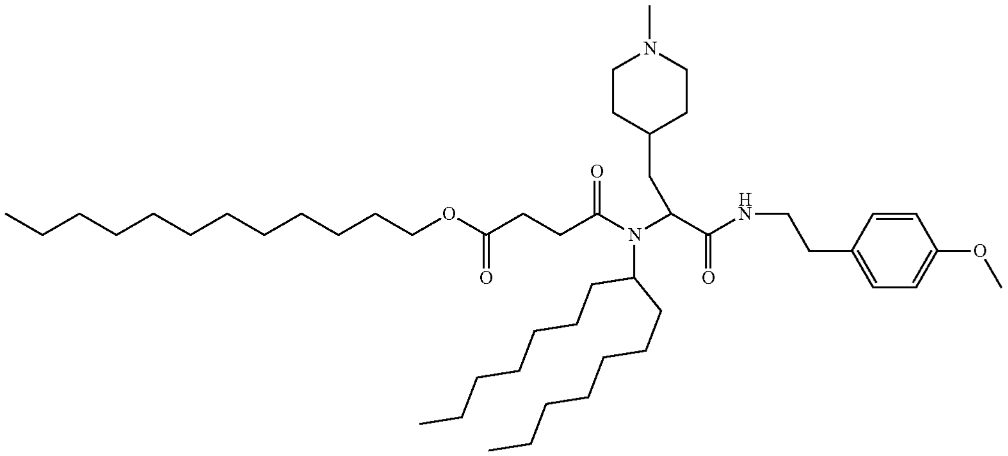
P153C1
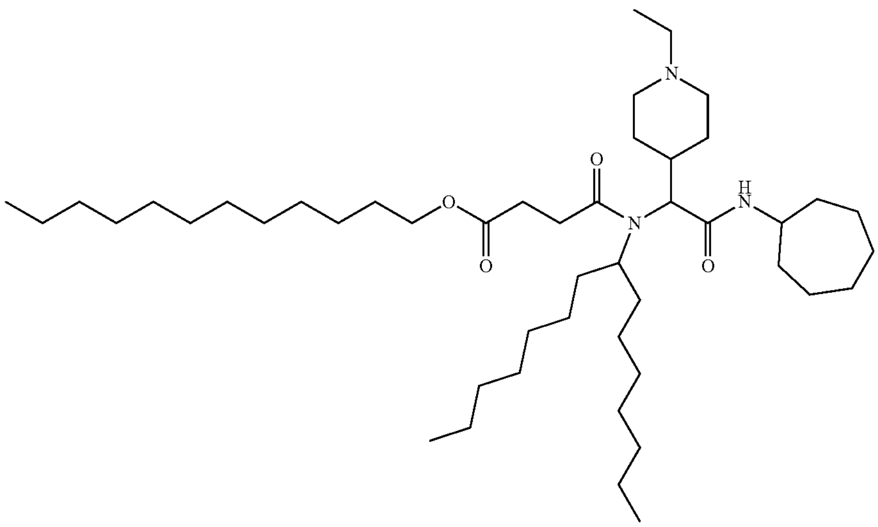

-continued
P153C2
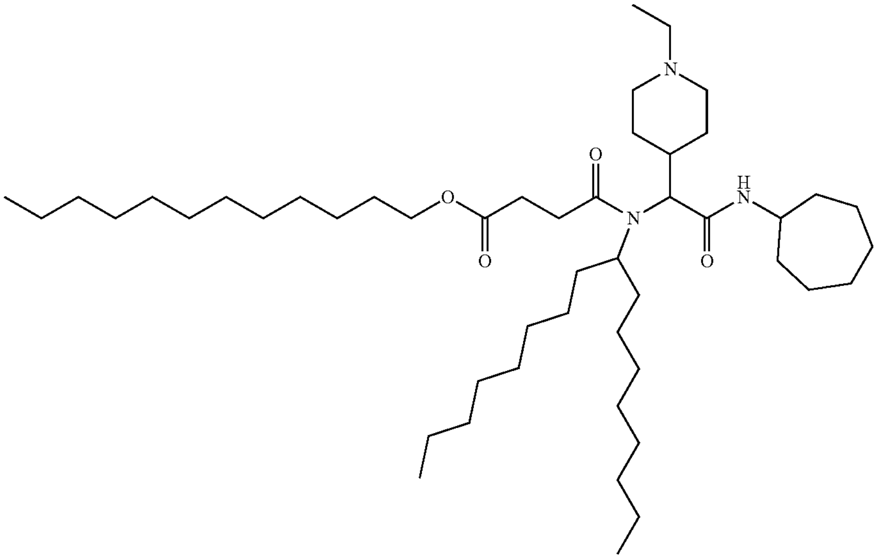
P153C3
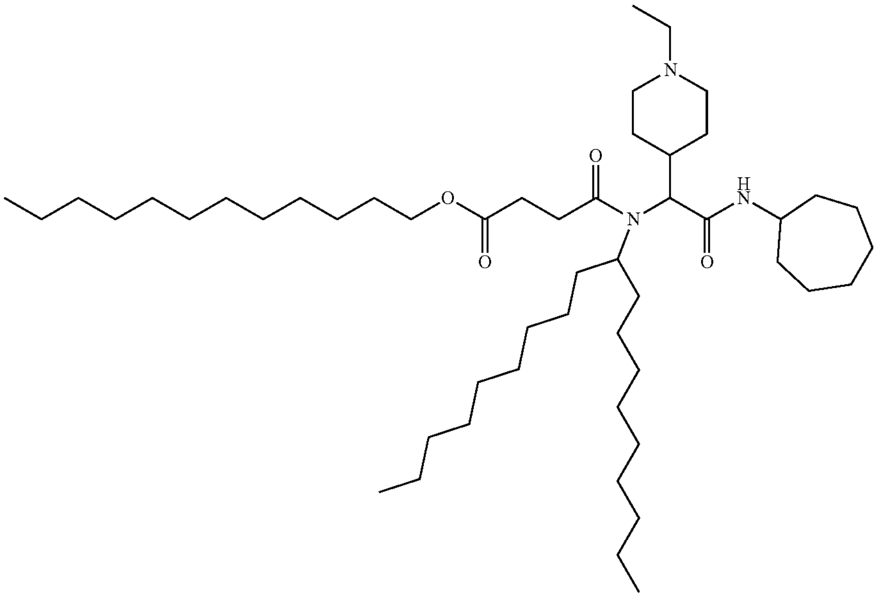

-continued
P153C5
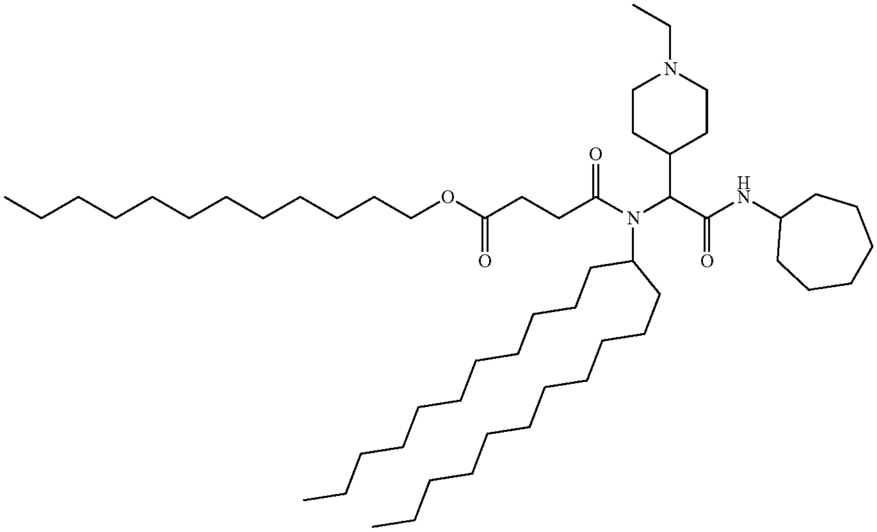
P56A3
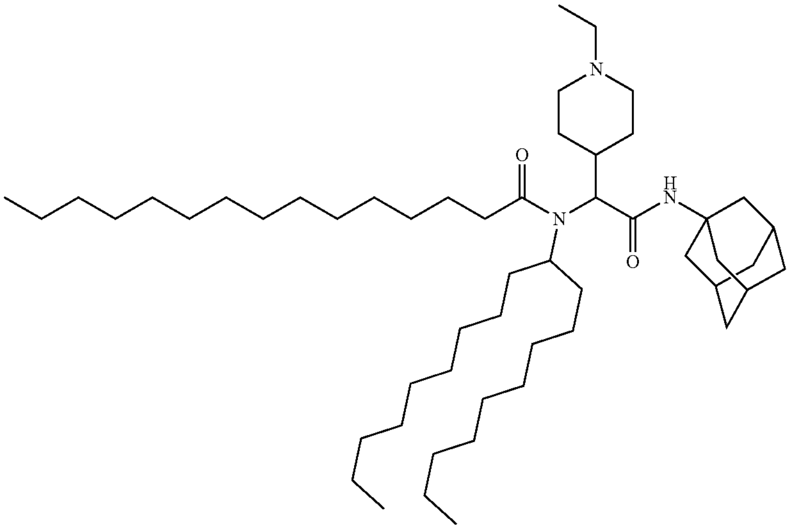
P56B3
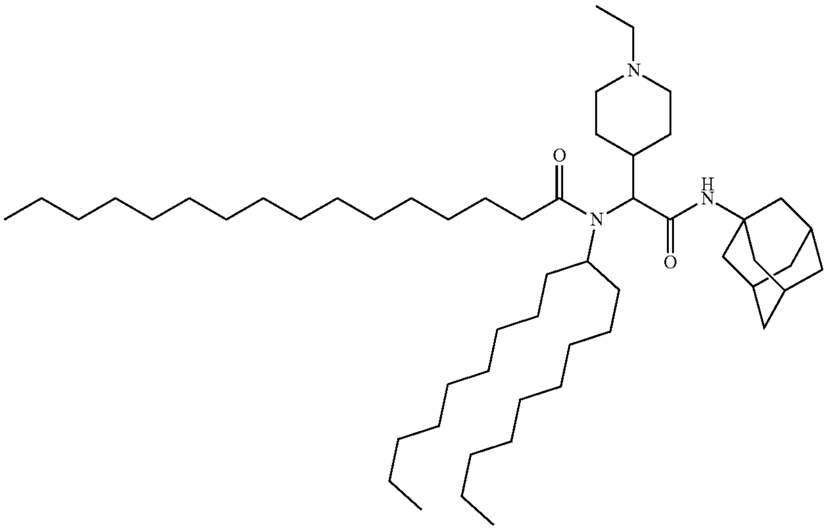

-continued
P56B7
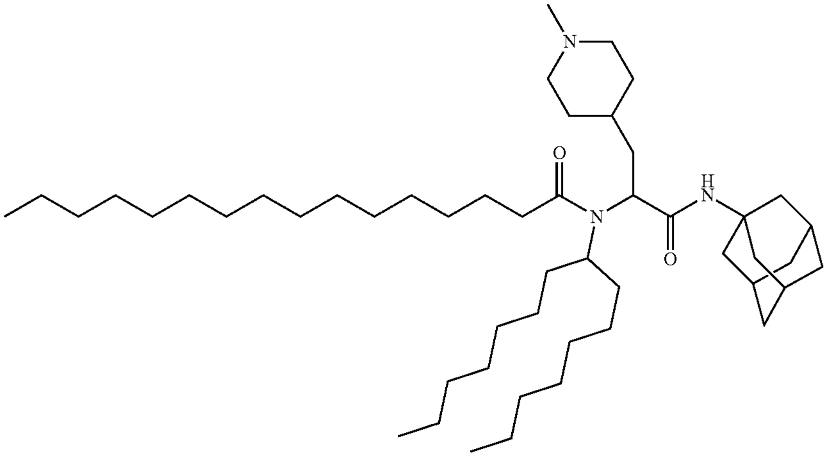
P56A8
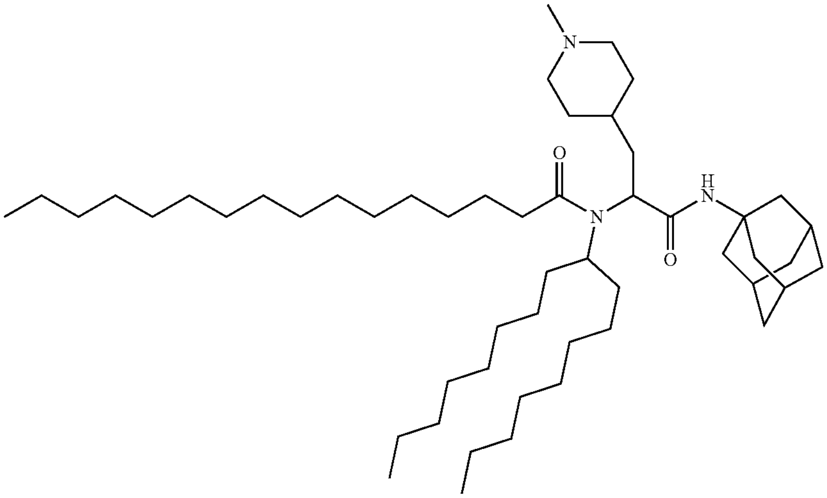
P56B8
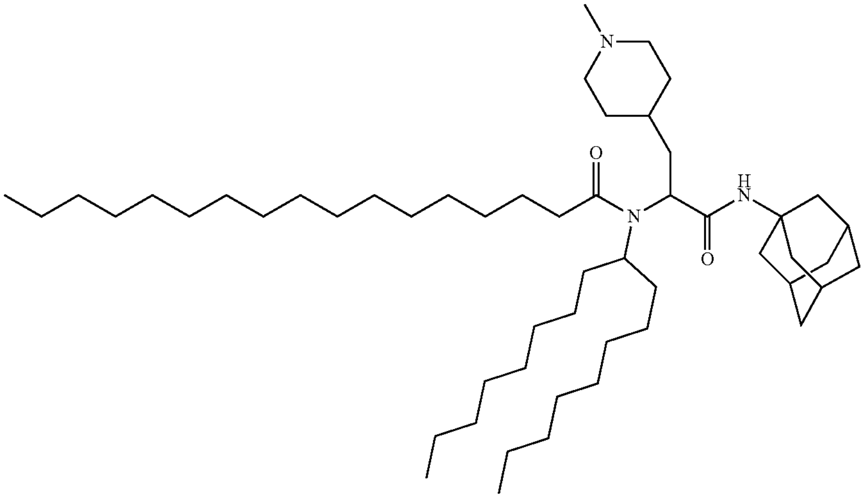

-continued
P56A9
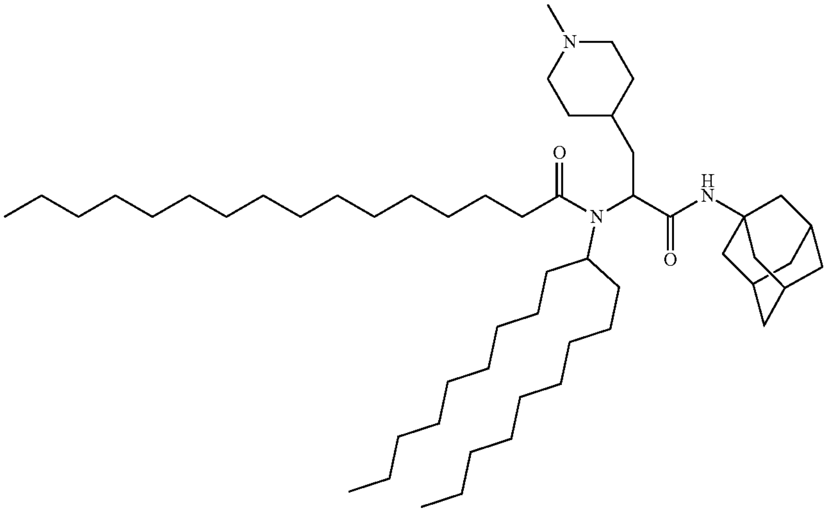
P55A6
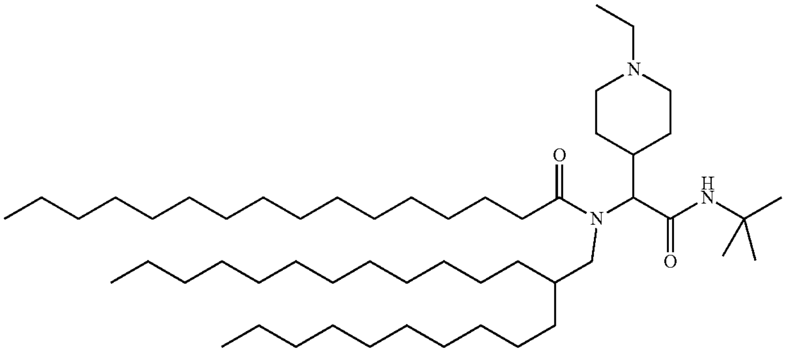
P55C12
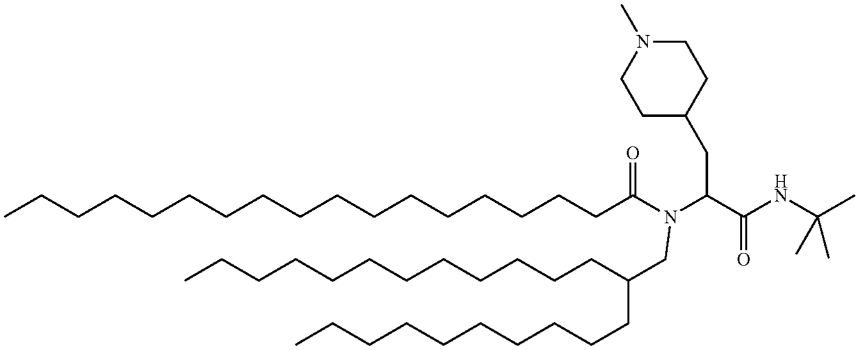
P54D6
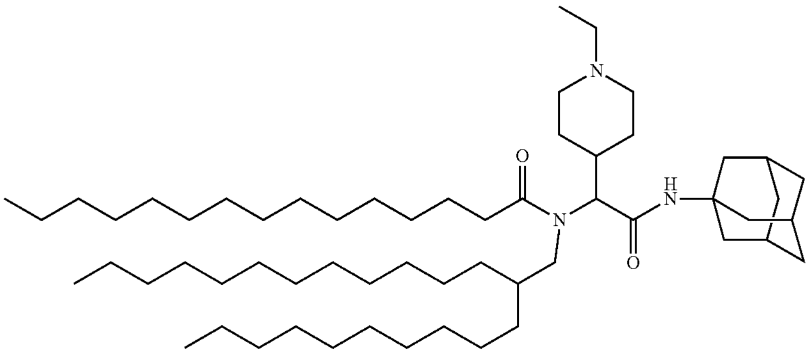

-continued
P54A10
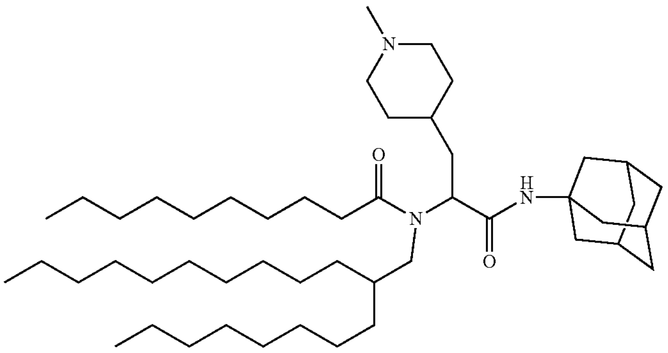
P54A12
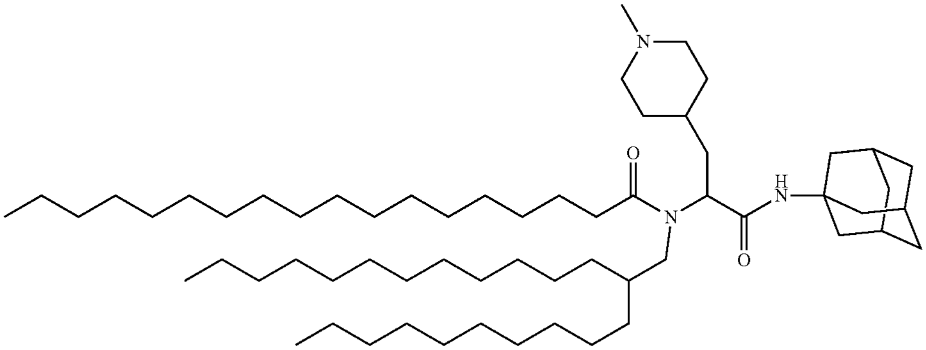
P53G11
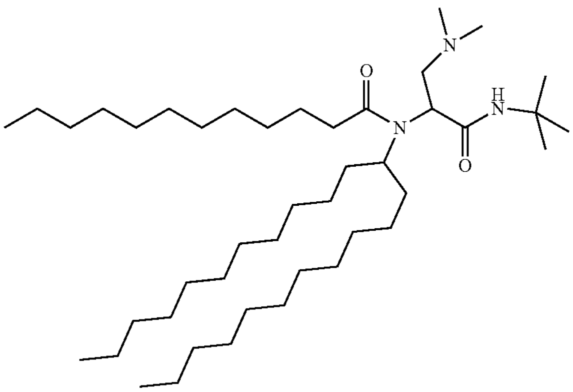
P53E12
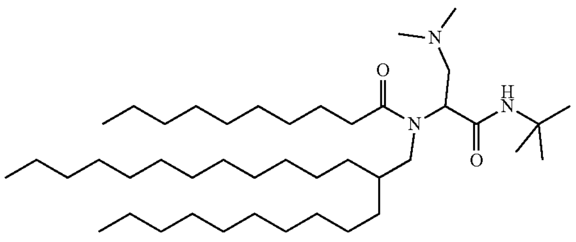

P52B5
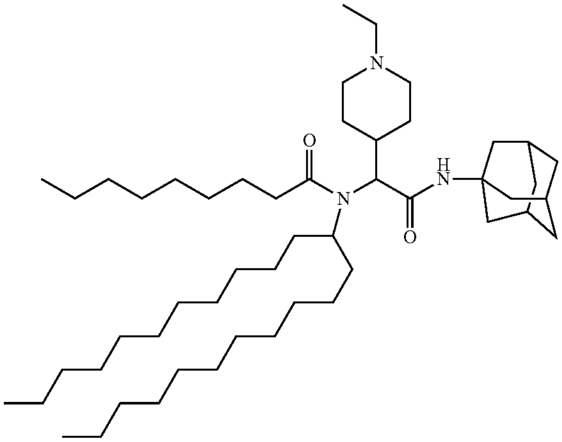
P52B6
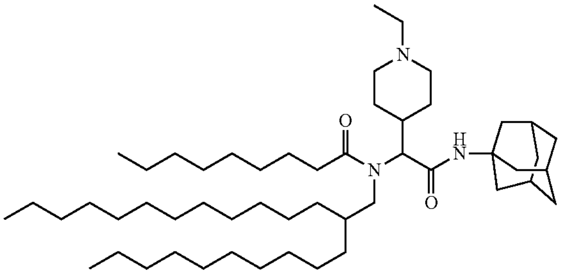
P52C6
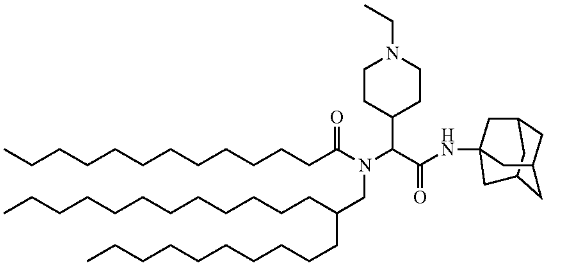
P52D6
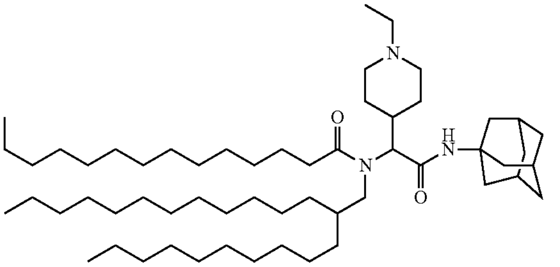
P52C12
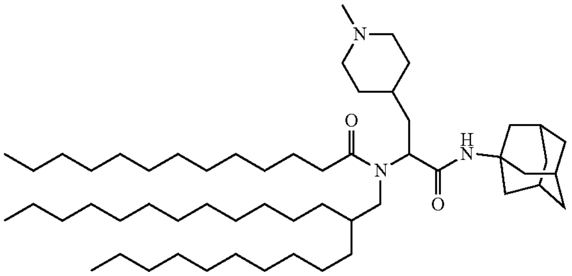
P51A12
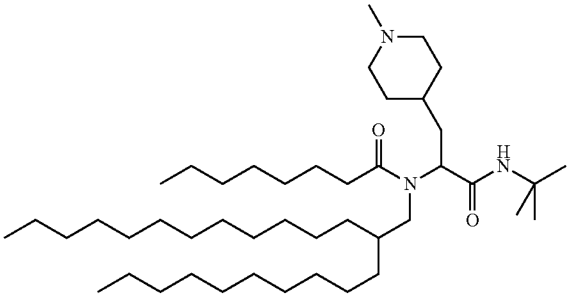
P51B12
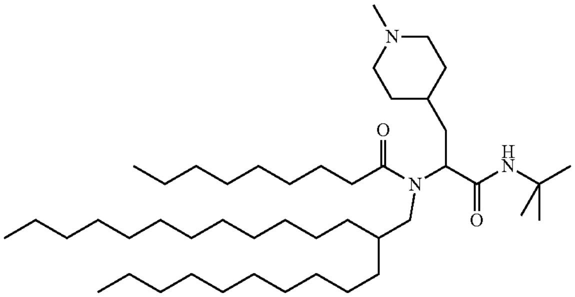
P51E12
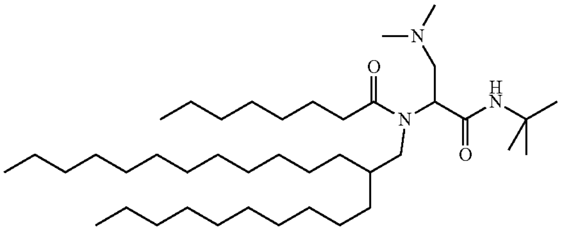

-continued
P42A4
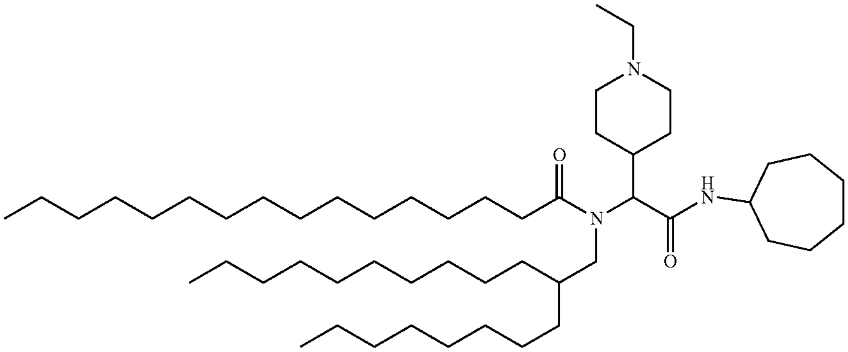
P42B4
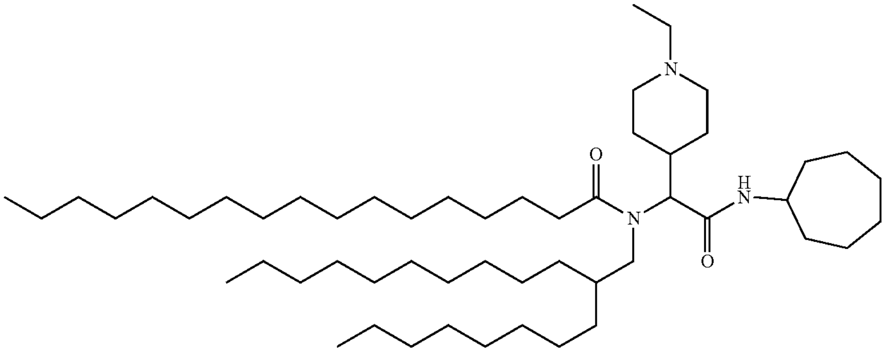
P40A10
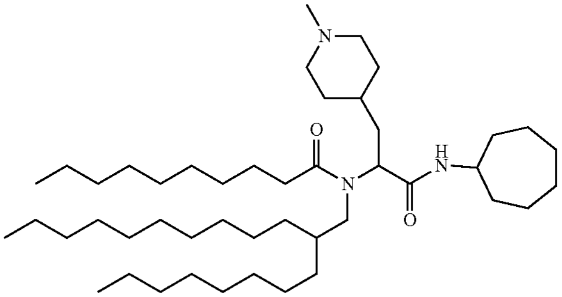
P40C12
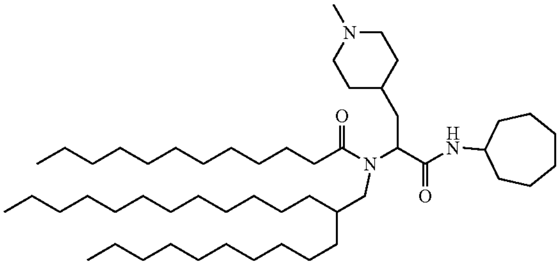
P40B2
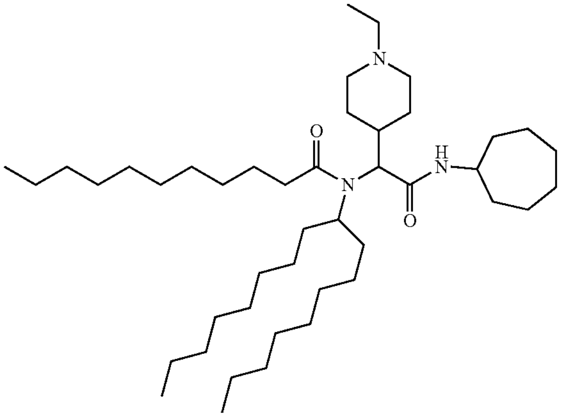
P40C2
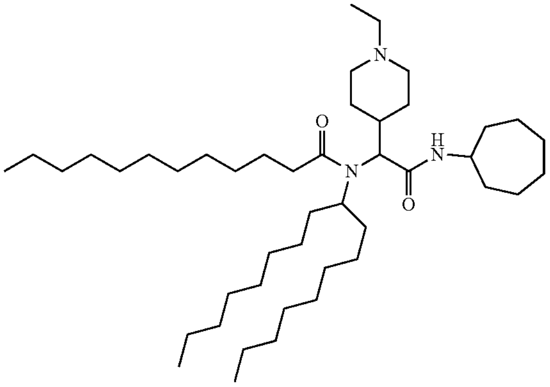

-continued
P40C4
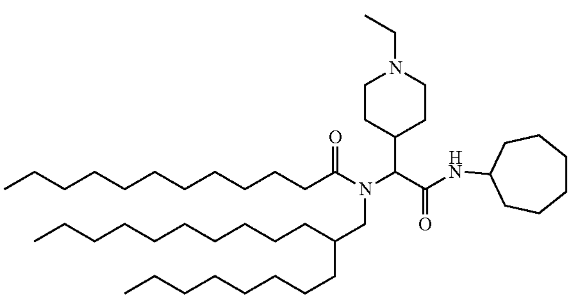
P38C3
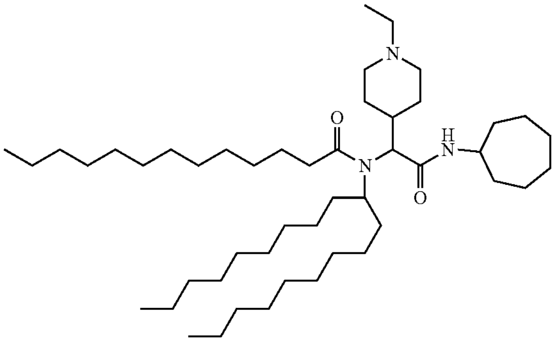
P38A6
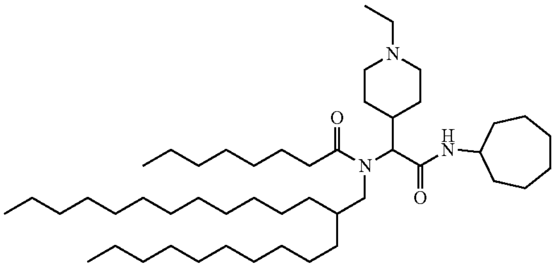
P38C8
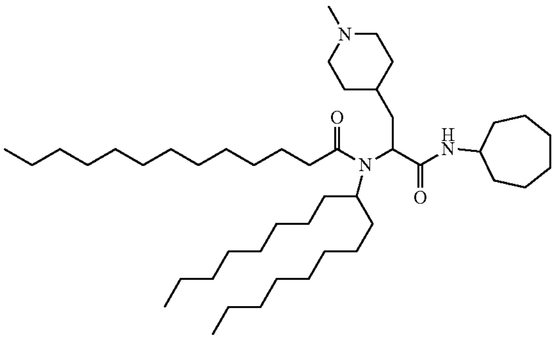
P40C4
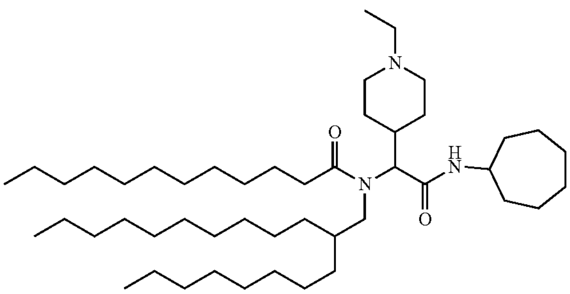
P38C4
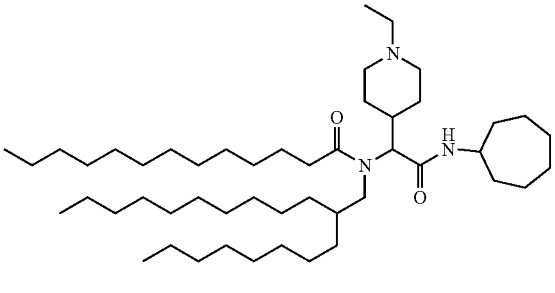
P38C7
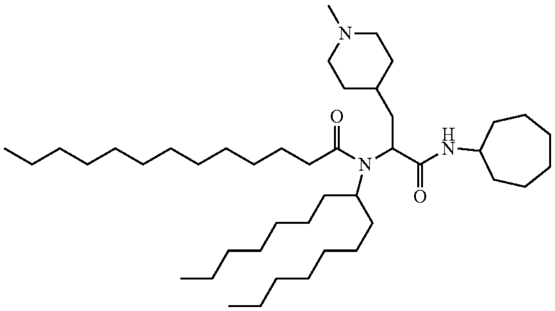
P36A9
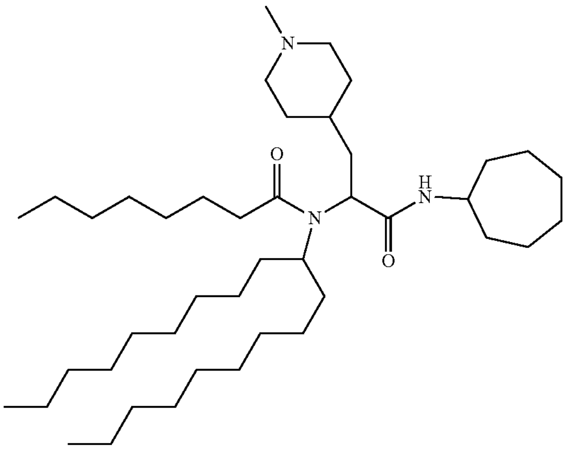

-continued
P38A10
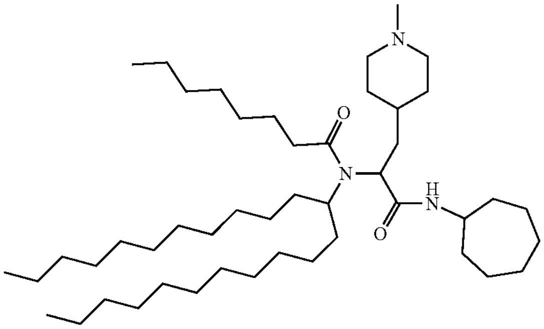
P38B10
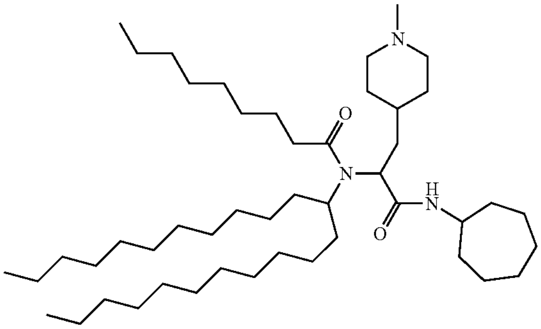
P38C10
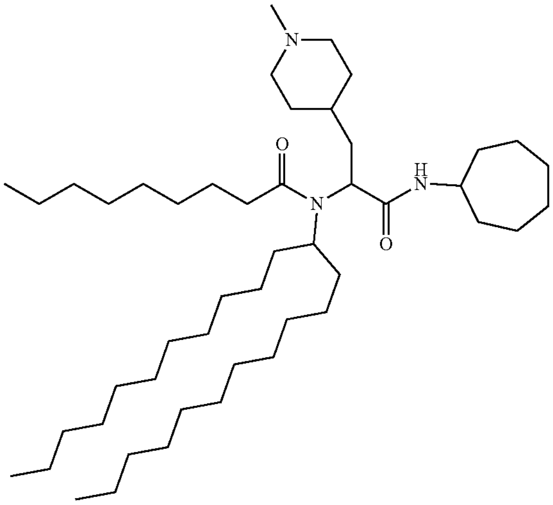
P38C1
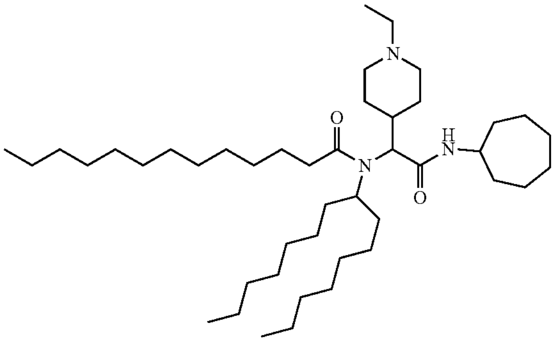
P38B2
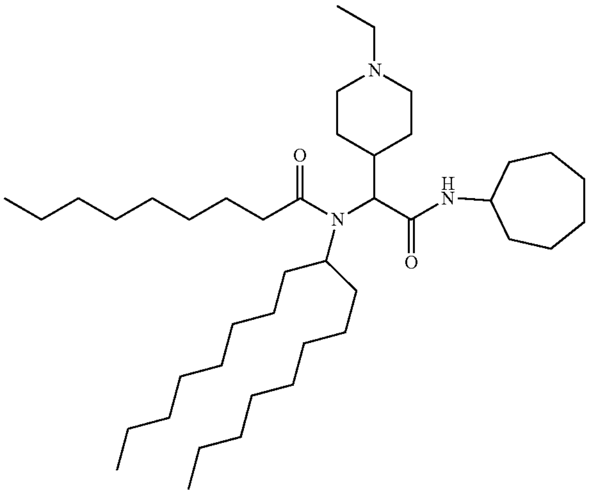

-continued
P28D10
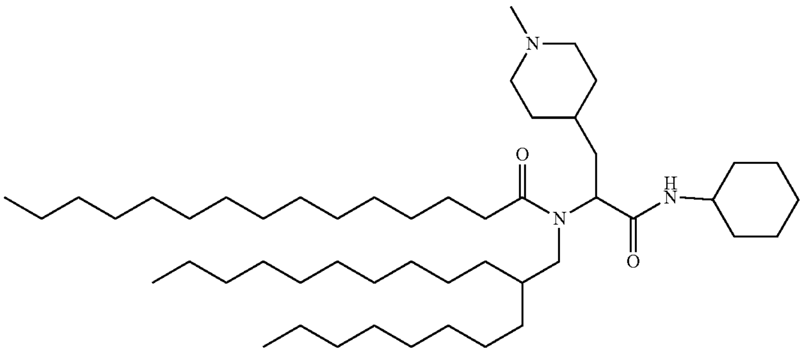
P30C4
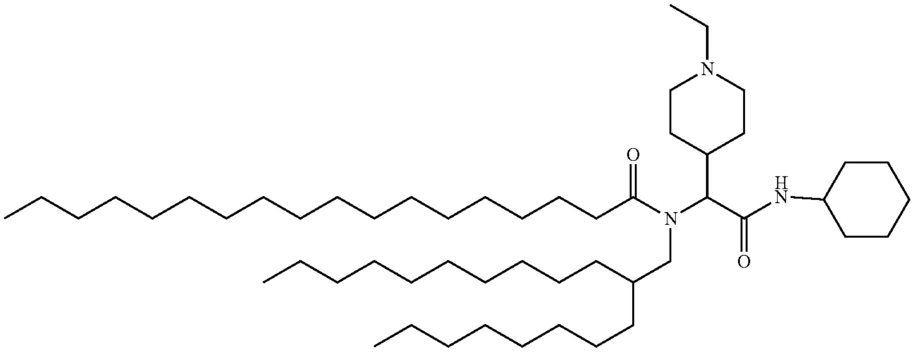
P30C1
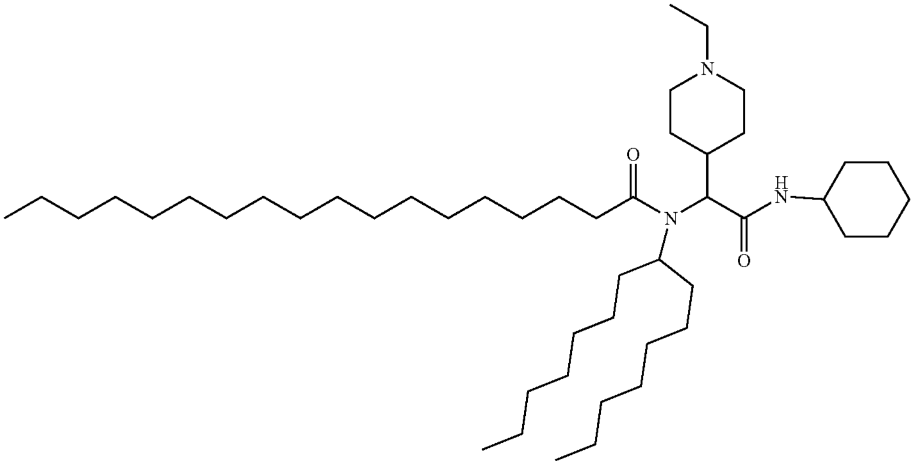
P26D4
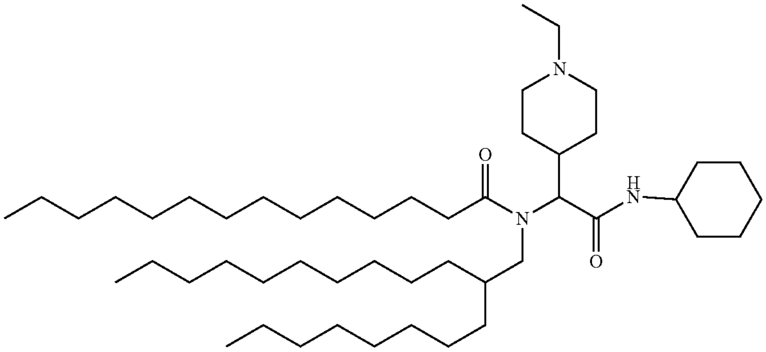

-continued
P1C4
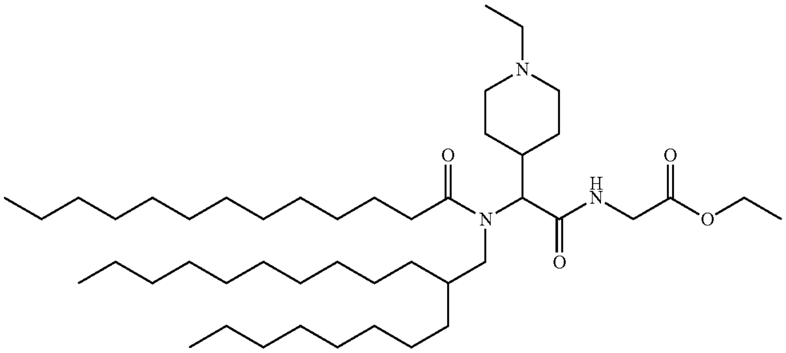
P43C10
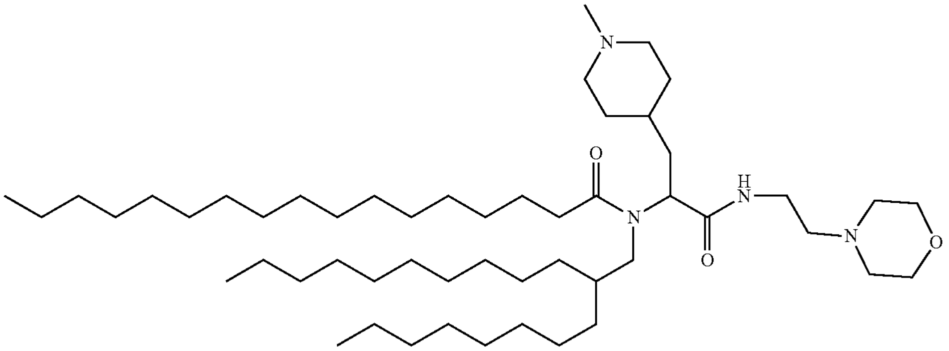
P43A12
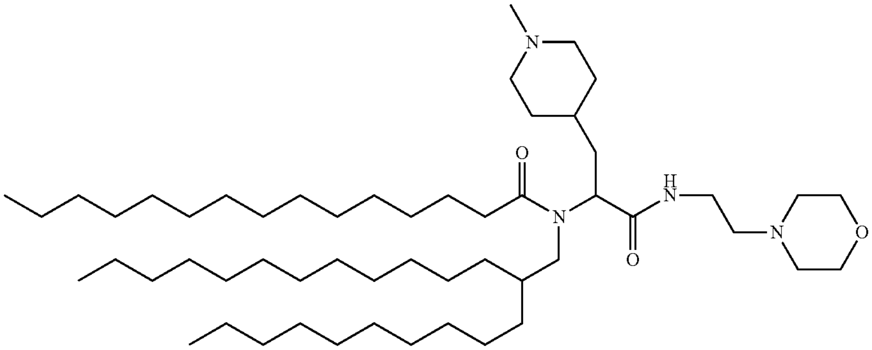
P43C12
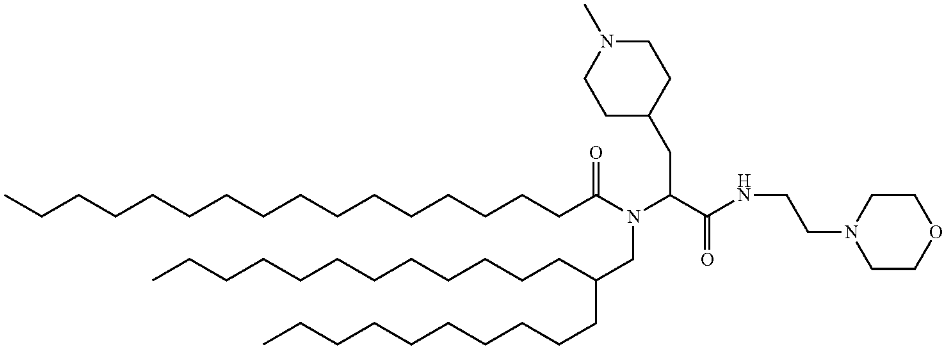

-continued
P41B4
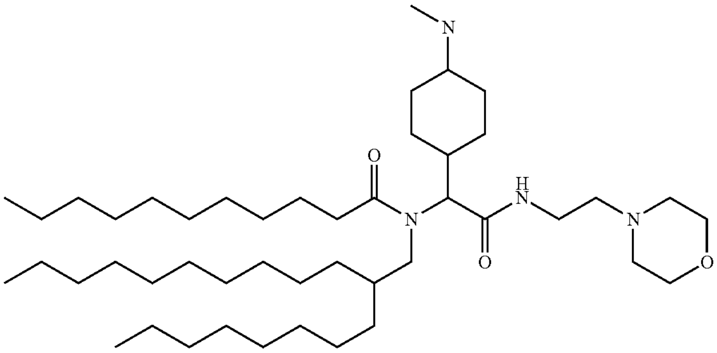
P41D4
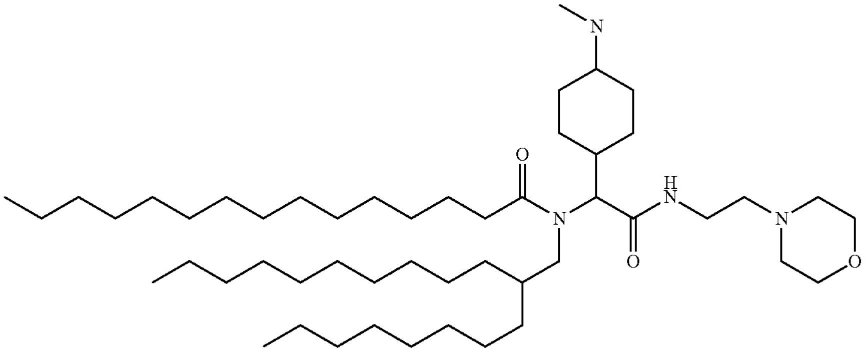
P41C6
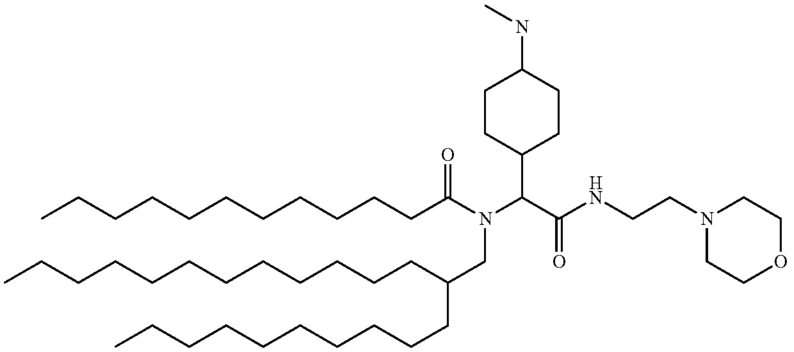
P41B10
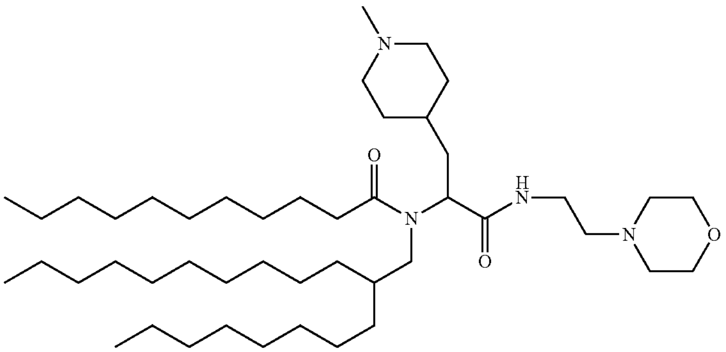

-continued
P41C10
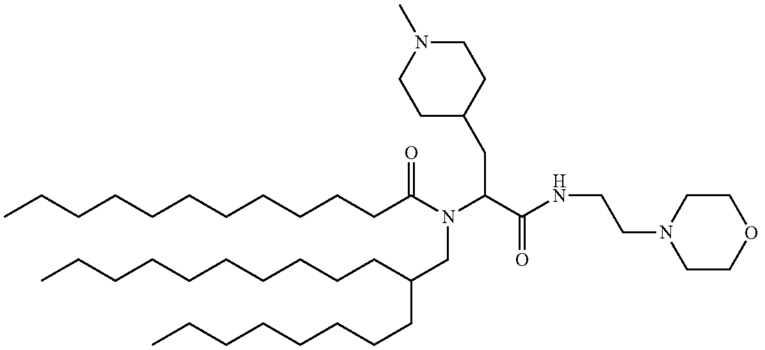
P41D10
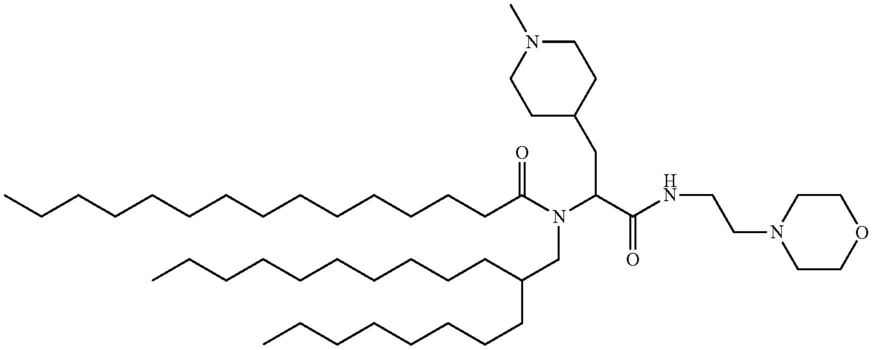
P41B12
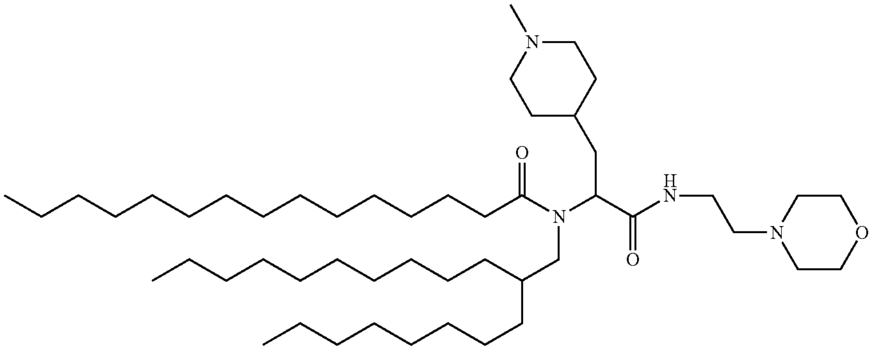
P39C10
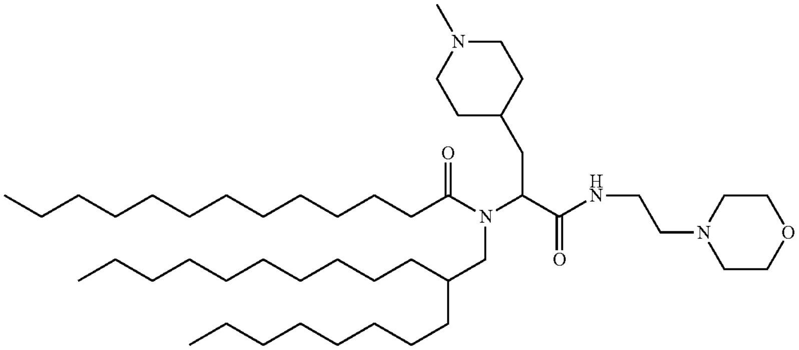

-continued
P39D10
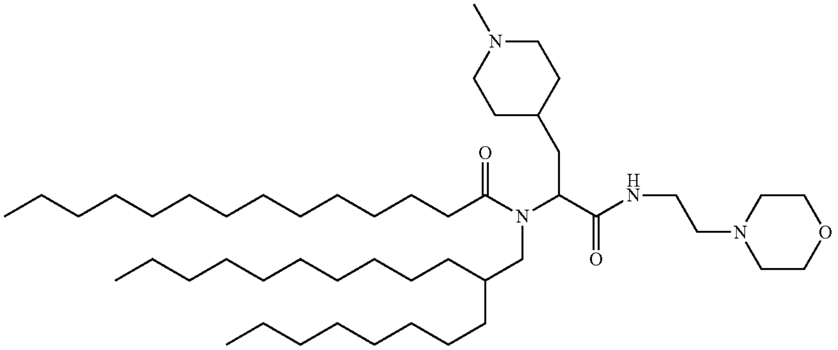
P39A12
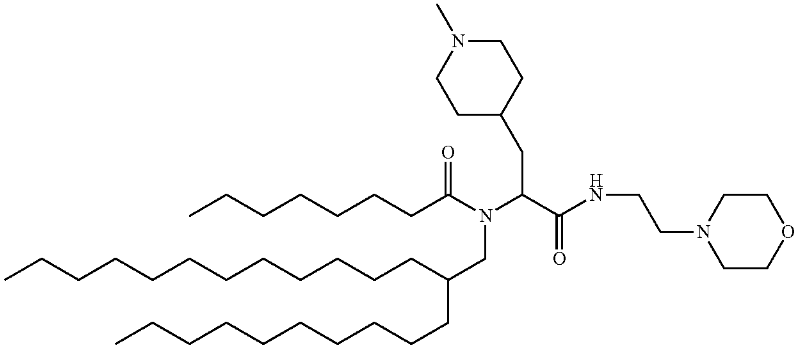
P39F12
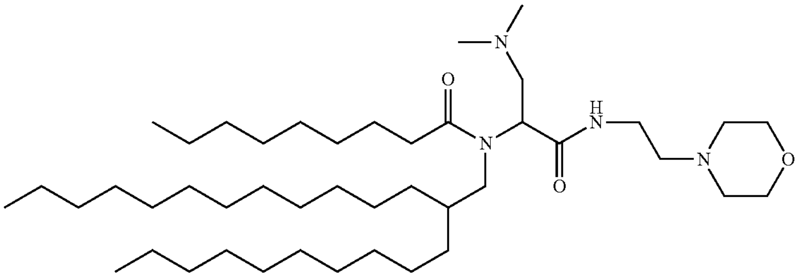
P39G12
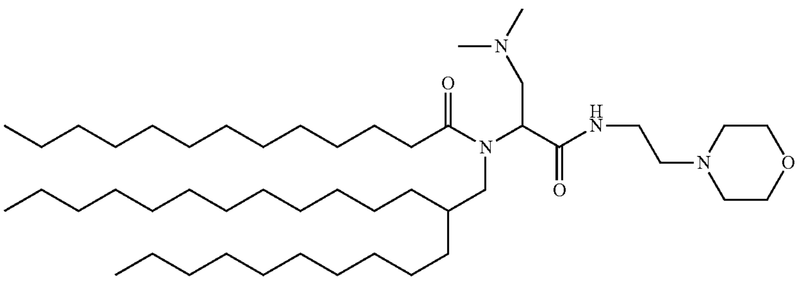

P39B12
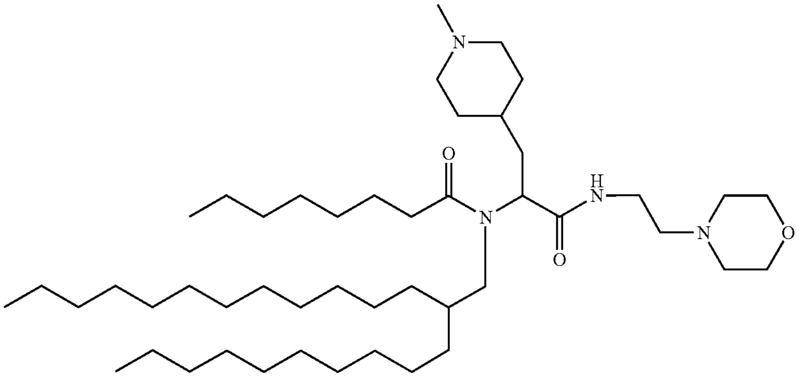
P39C12
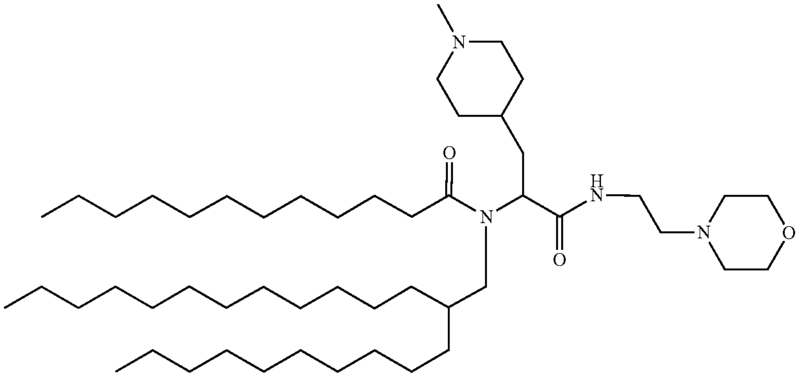
P39D4
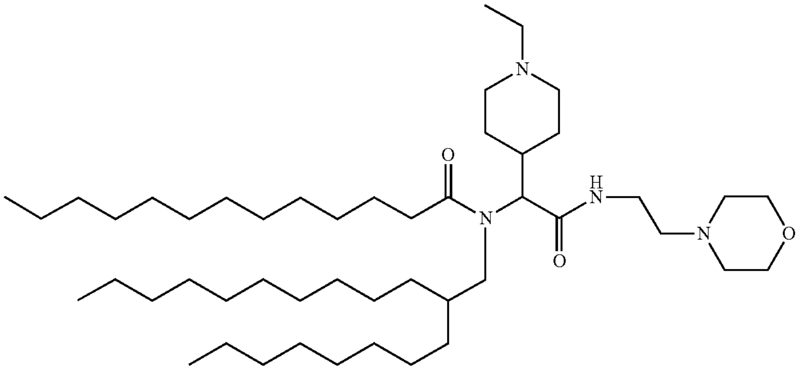
P39A6
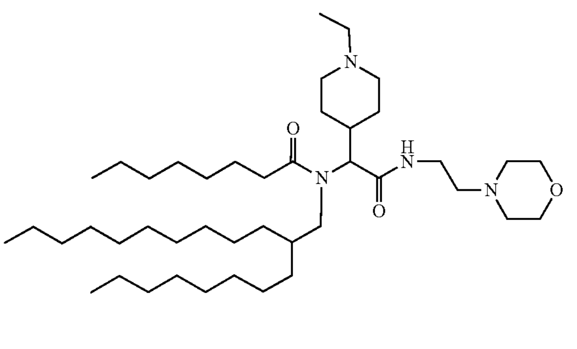
P38B12
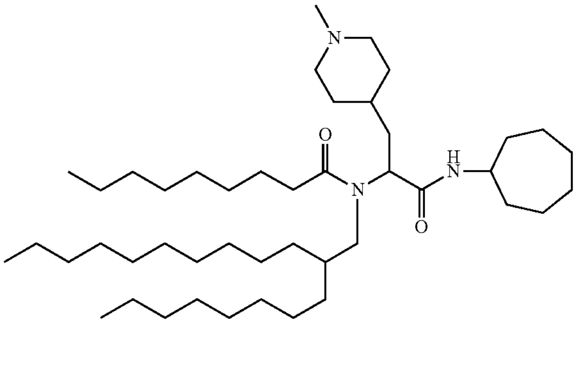

-continued
P38C12
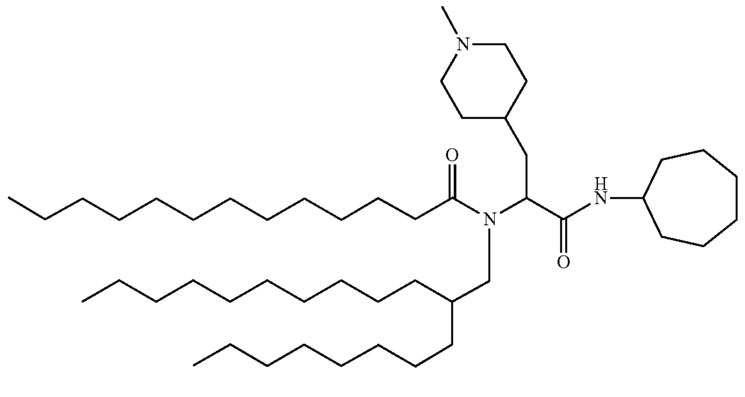
P143A7
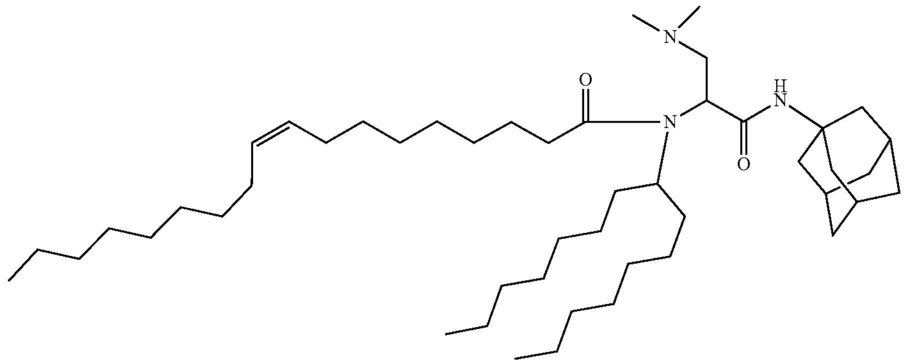
P143A9
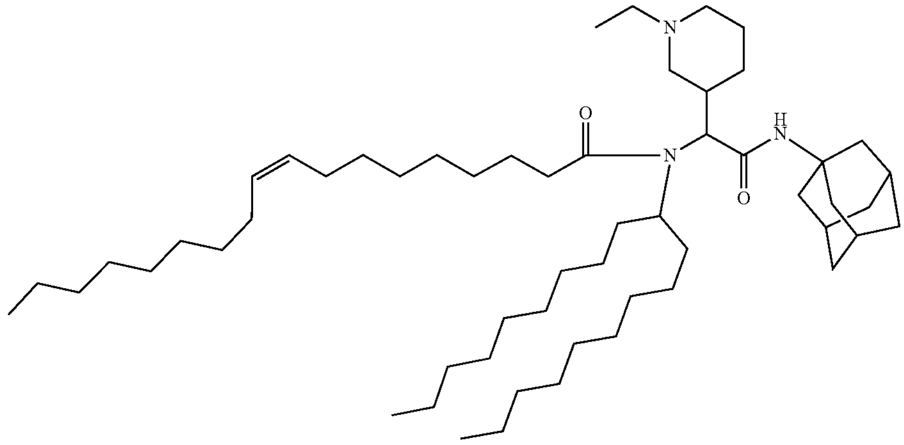
P143C7
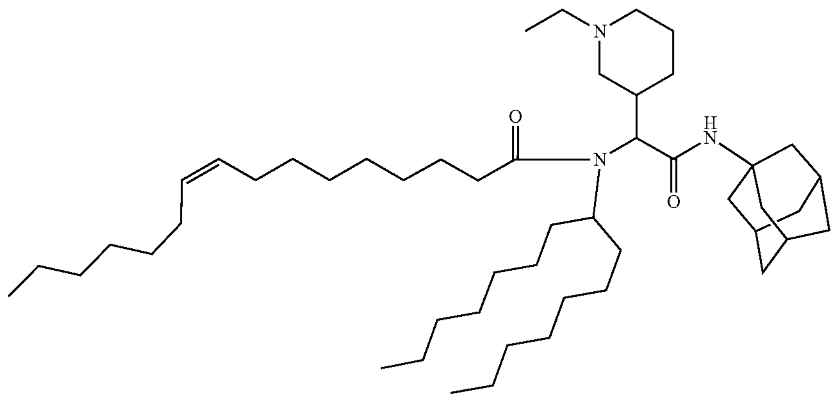

-continued
P143C9
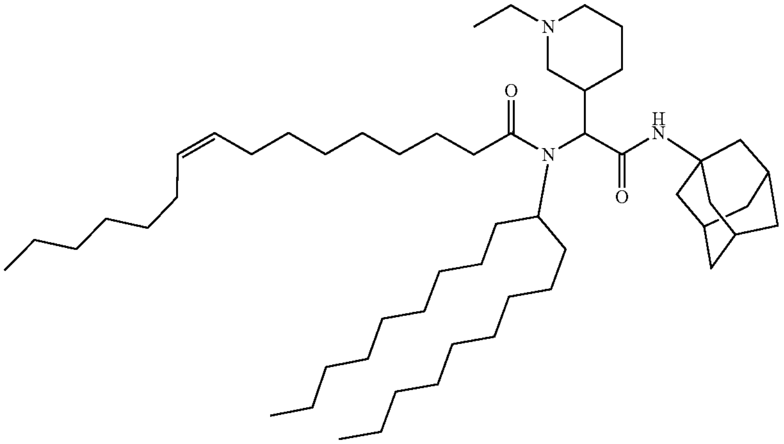
P143C10
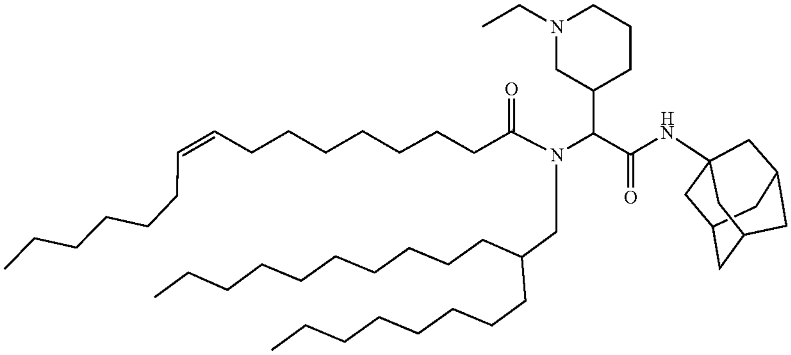
P143D10
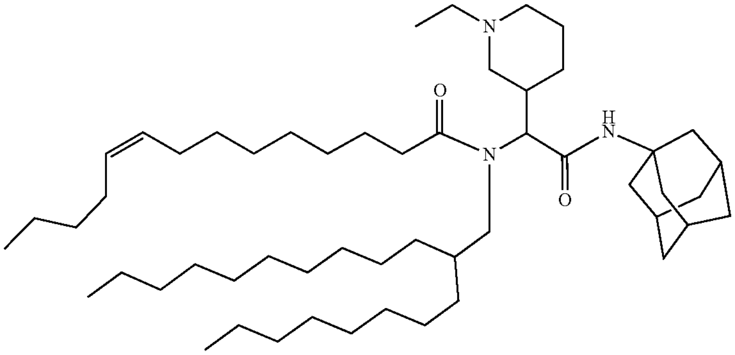
P147B10
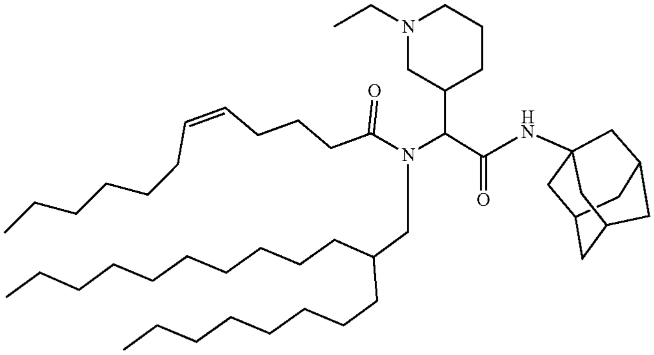

-continued
P147C7
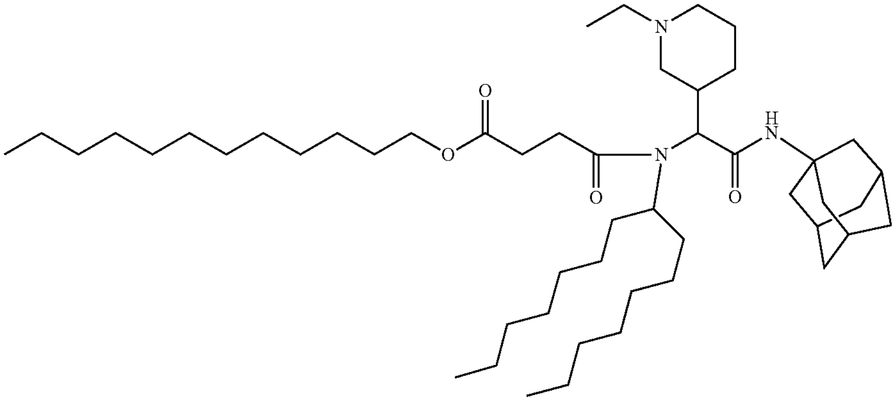
P147C8
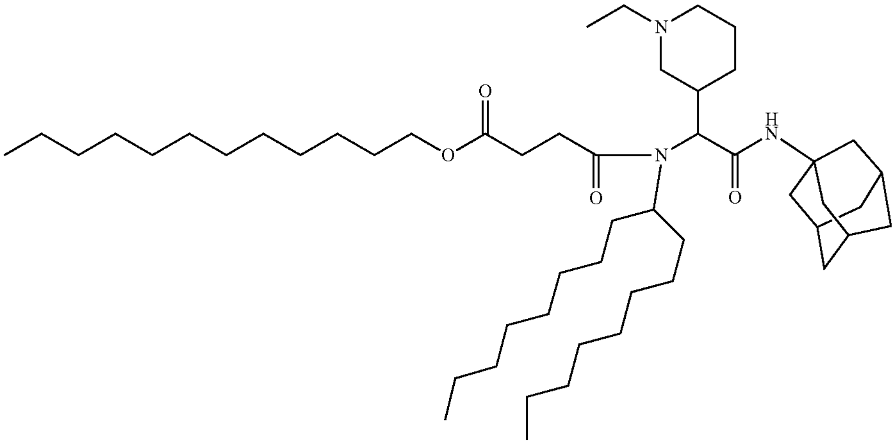
P147C9
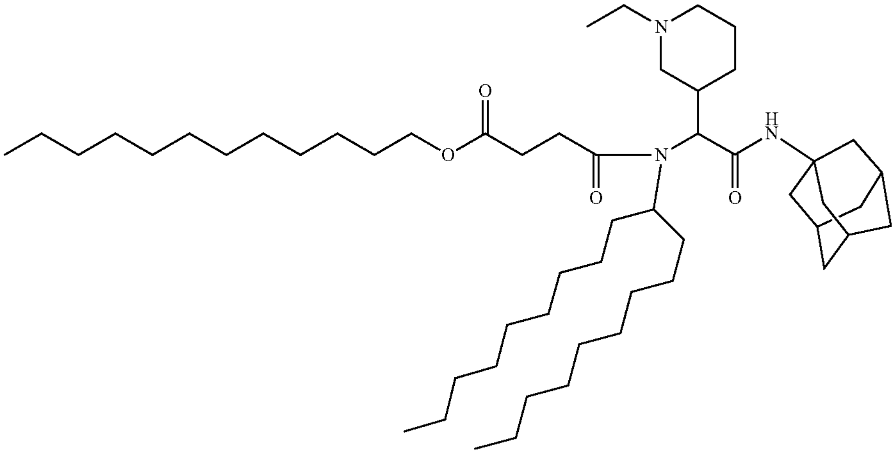
P147C10
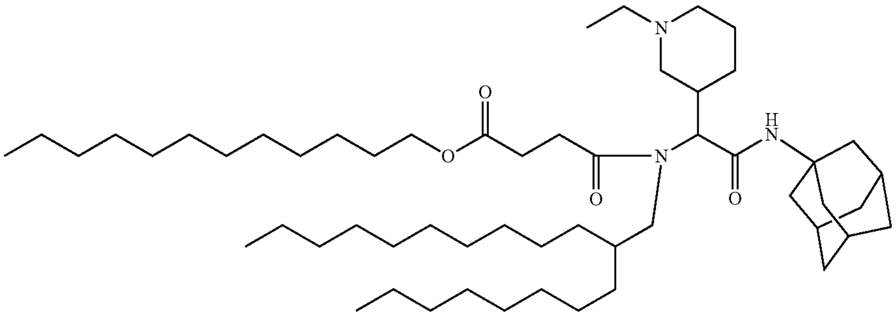

-continued
P147C12
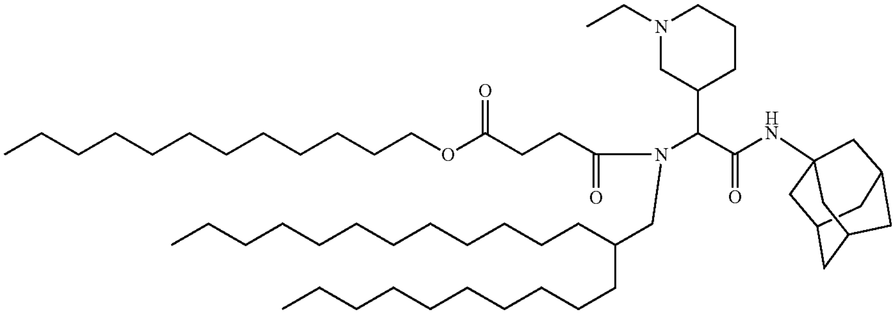
P147D10
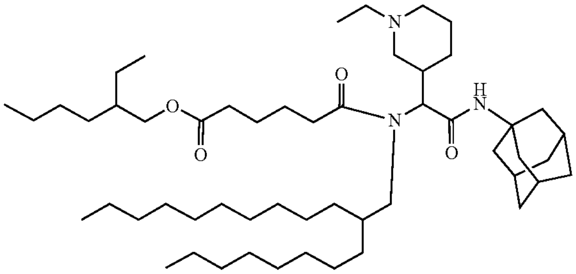
P147D12
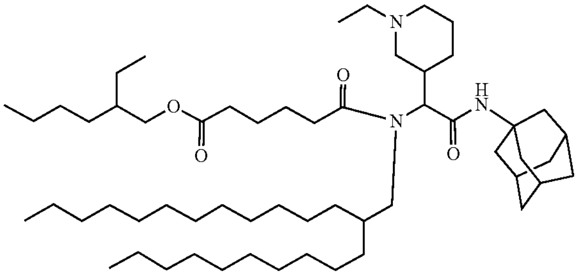
P150C2
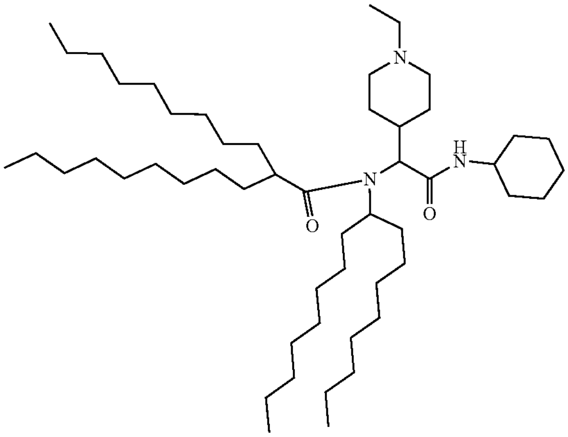
P149A4
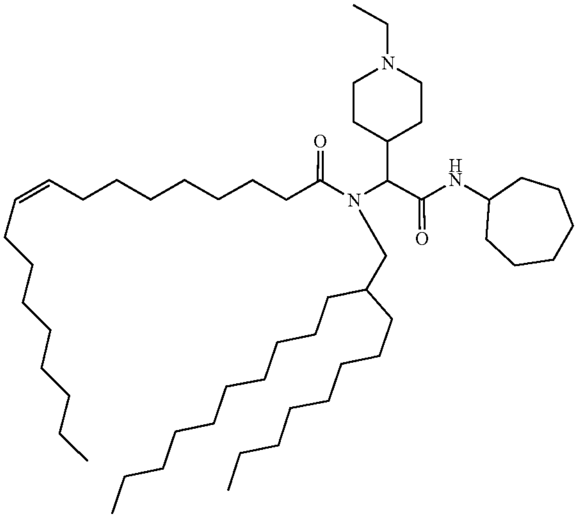

-continued
P149A7
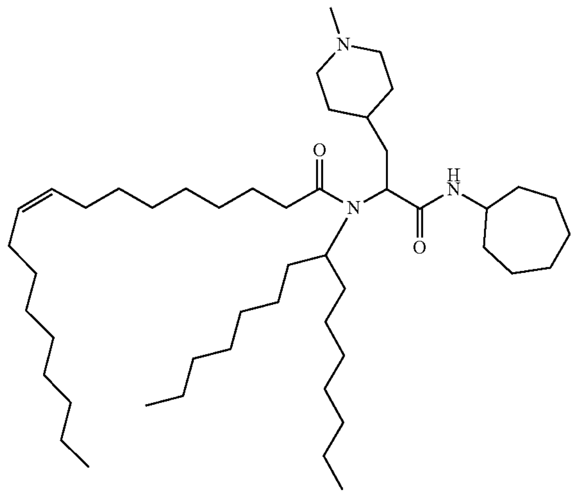
P149A8
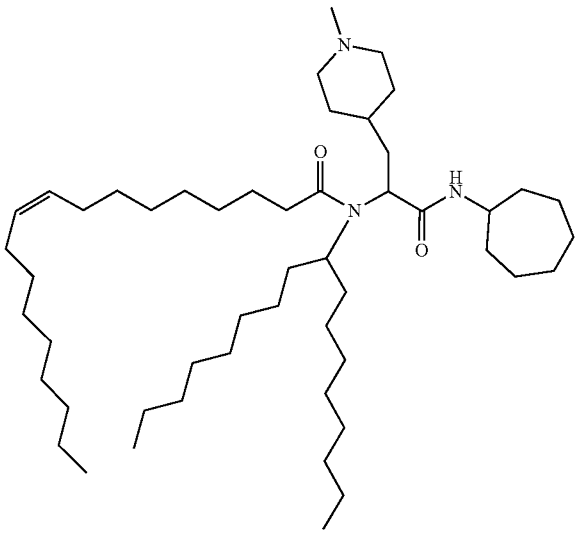
P148A1
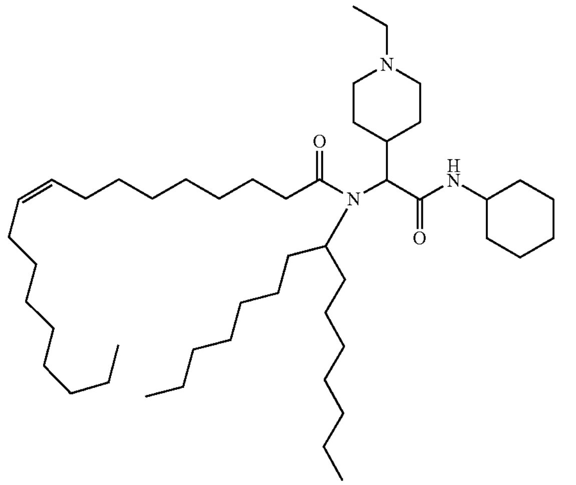
P148A2
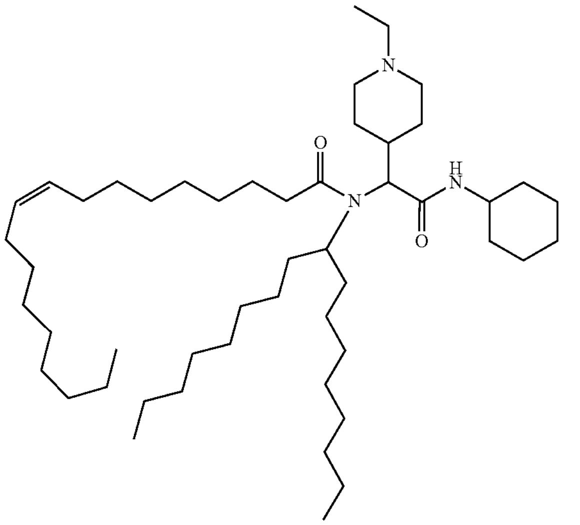
P148A3
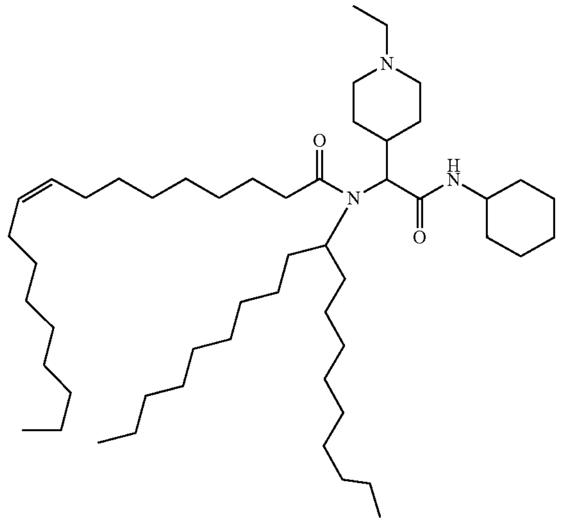
P148C1
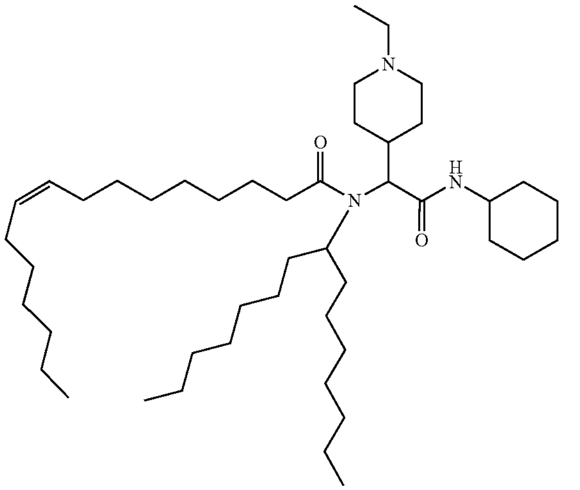

P148C2
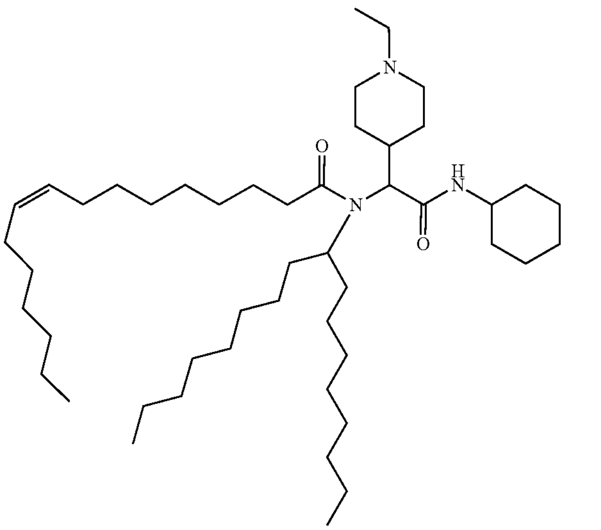
P148C3
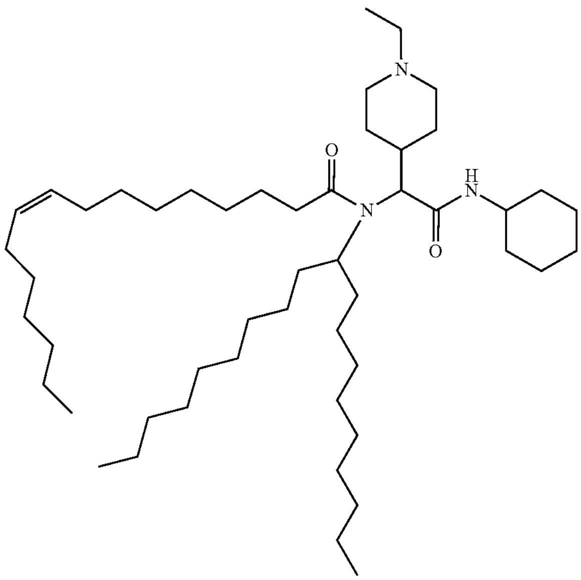
P153C4
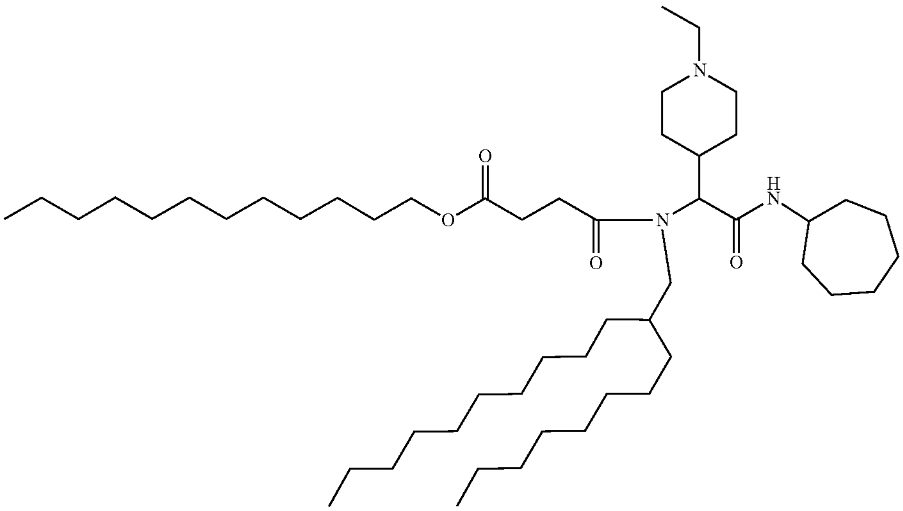
P153D10
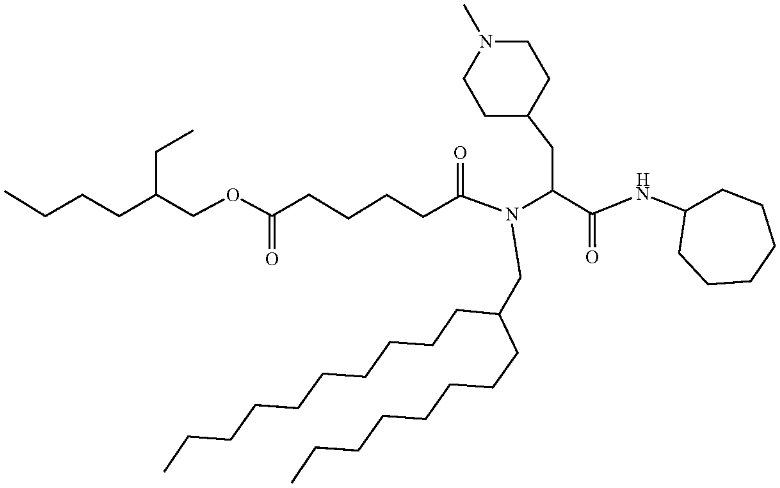

-continued
P153A1
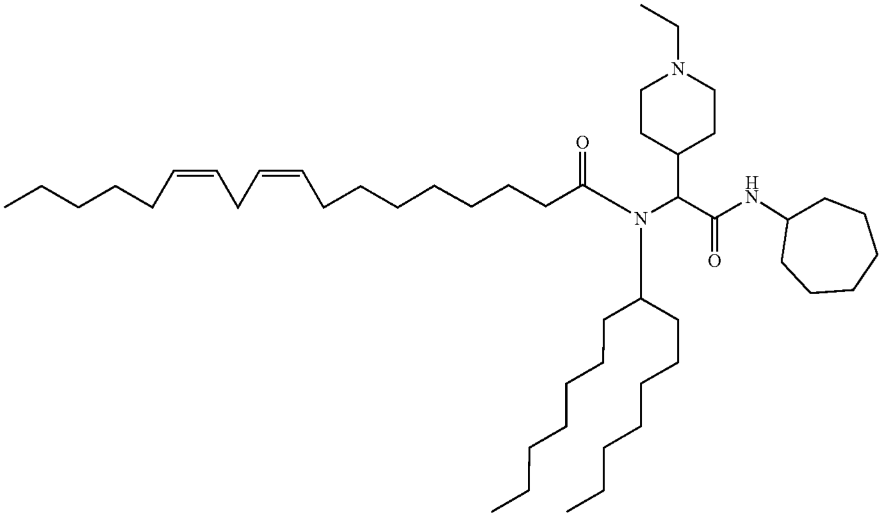
P153A2
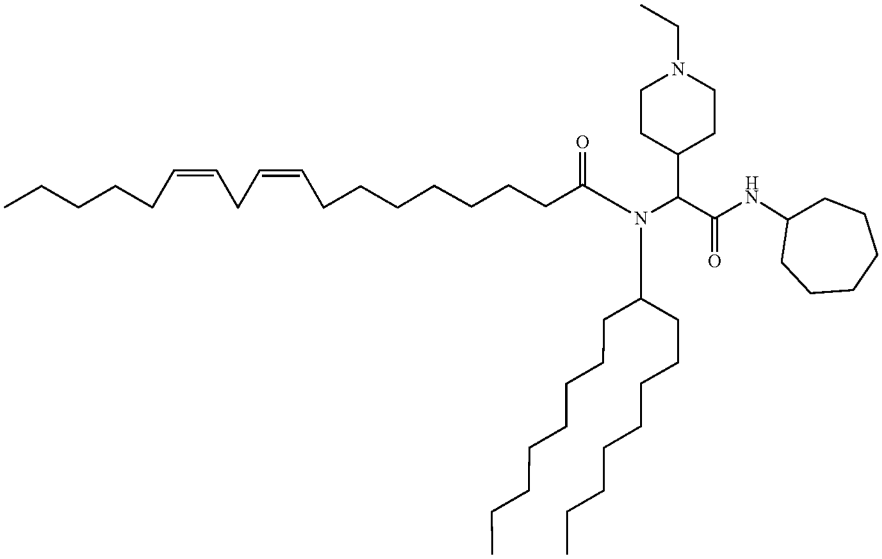
P153A3
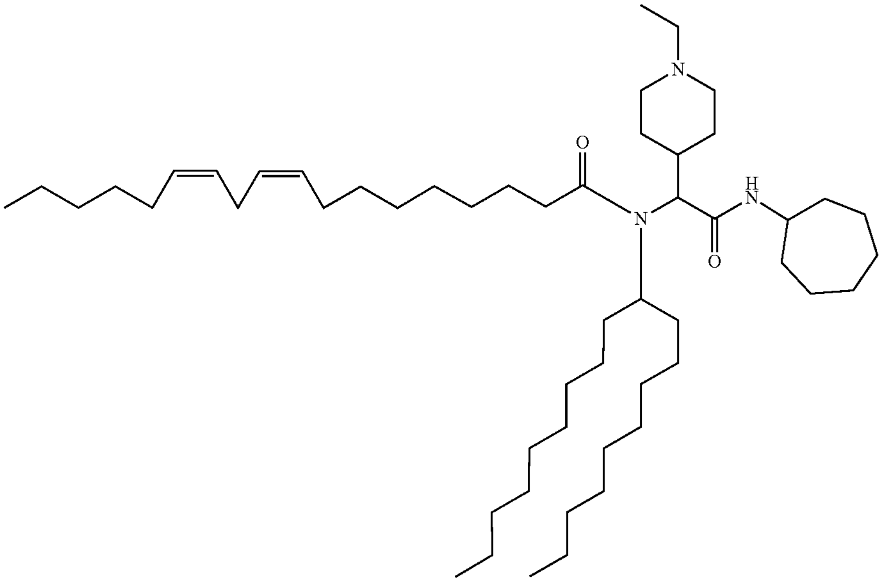

-continued
P153B10
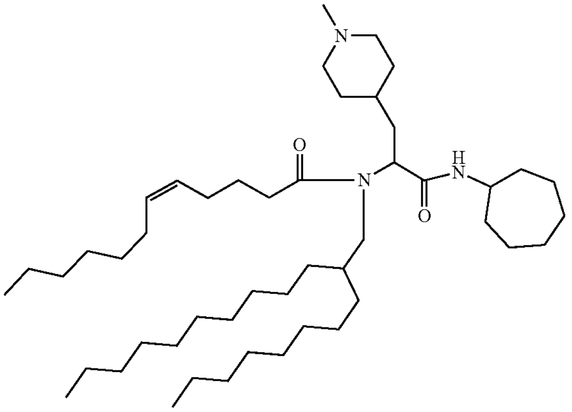
P152D10
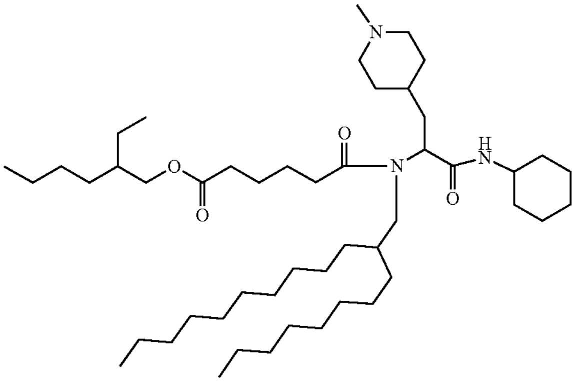
P152C1
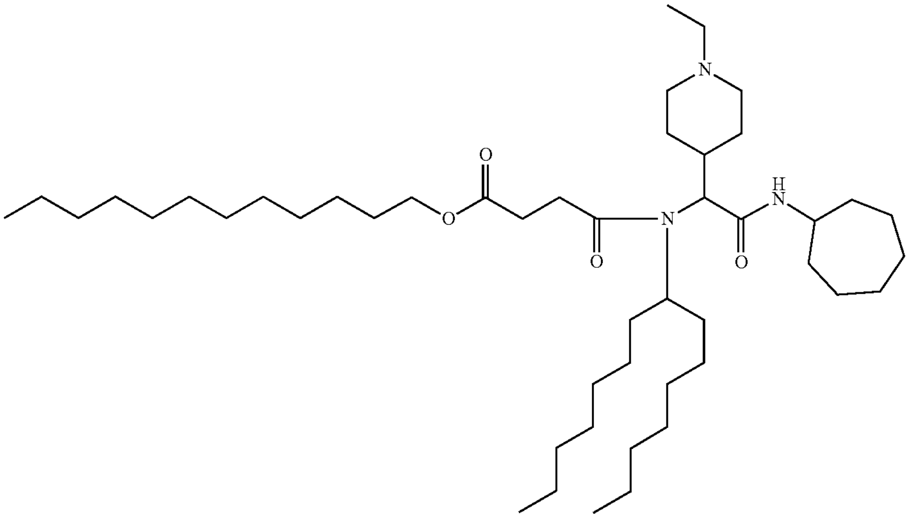
P152C2
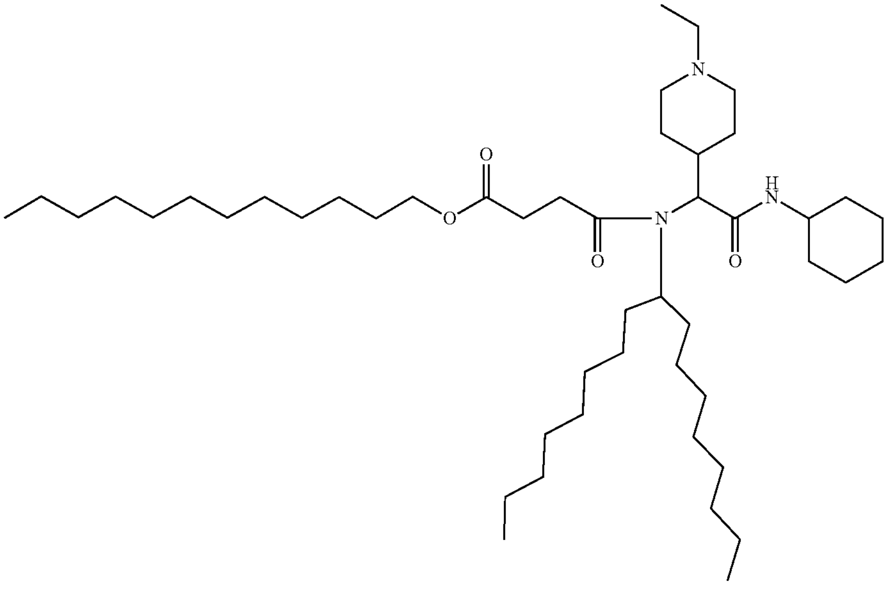

-continued
P151B3
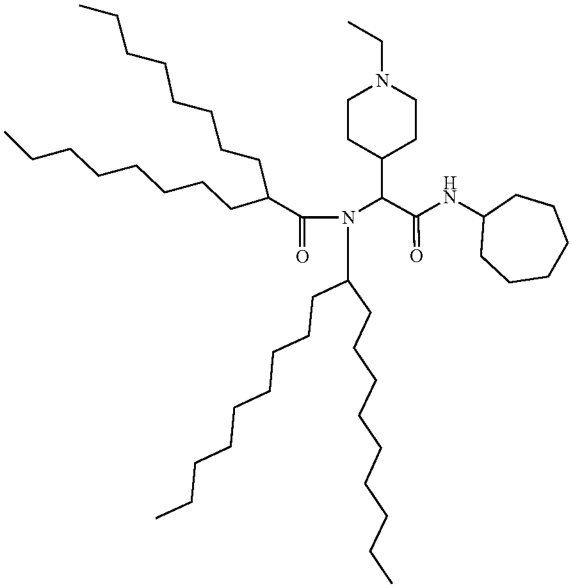
P151C2
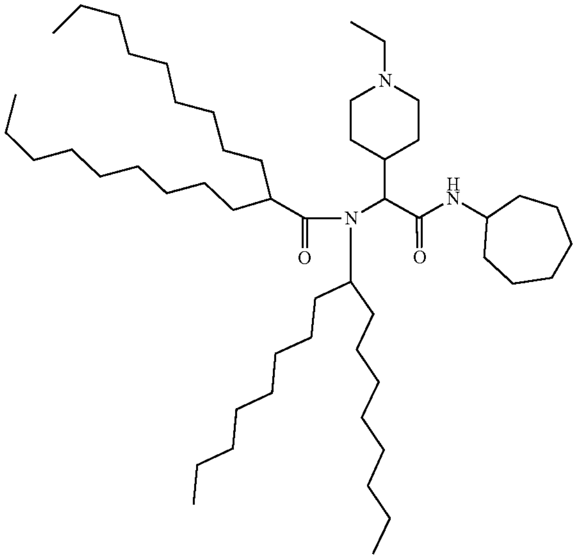
P154A10
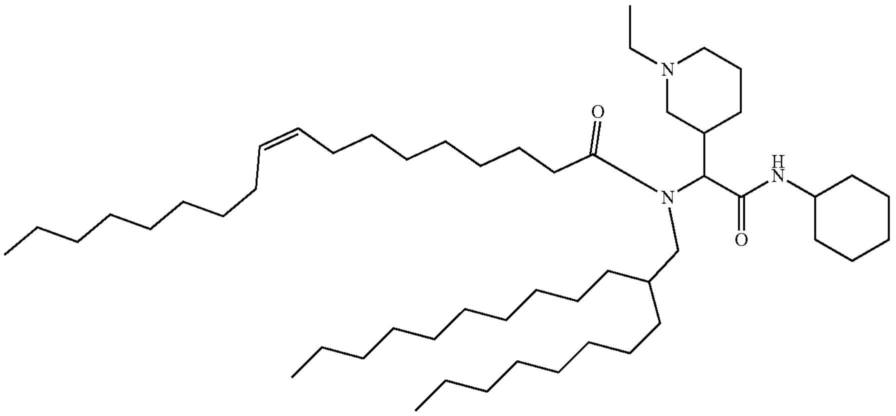
P154D10
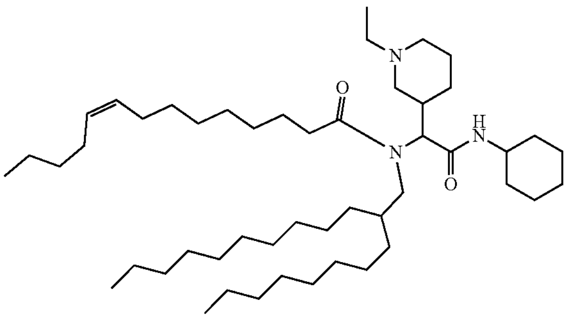
P160B4
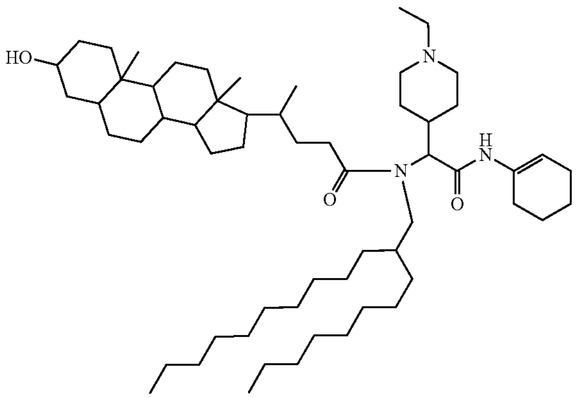

-continued
P161C4
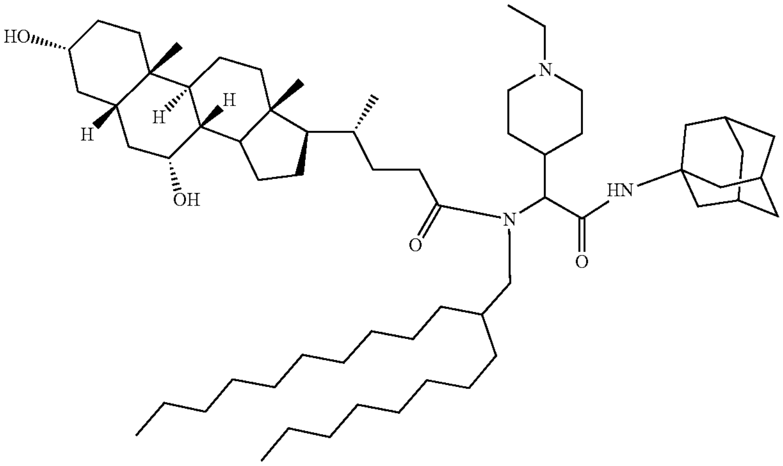
P161E4
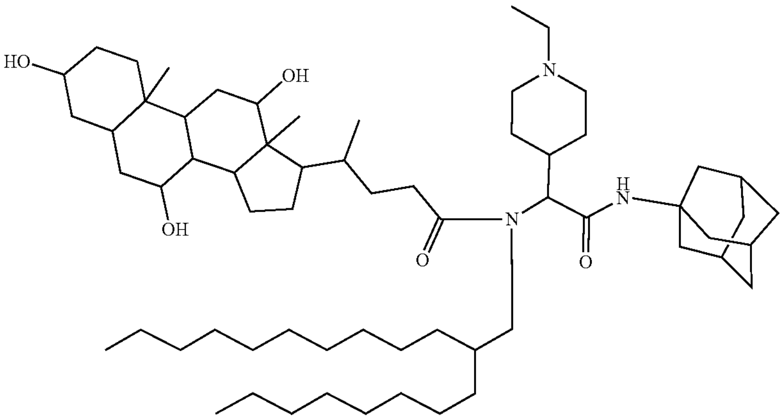
P160E6
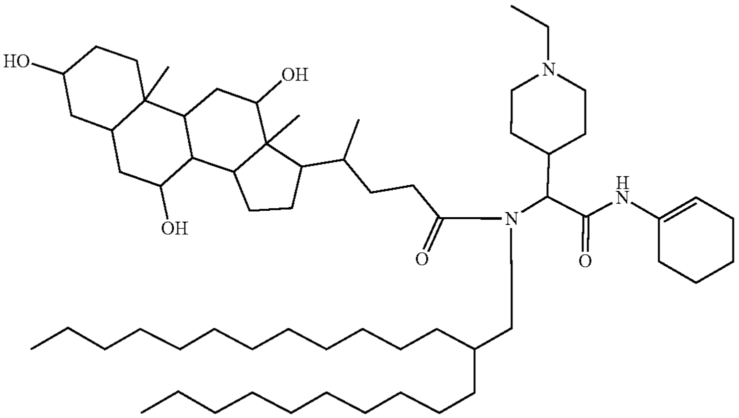

-continued
P161F4
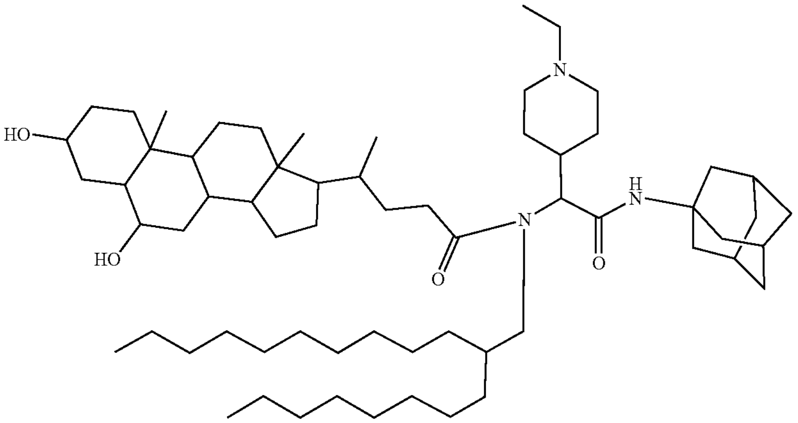
P161E6
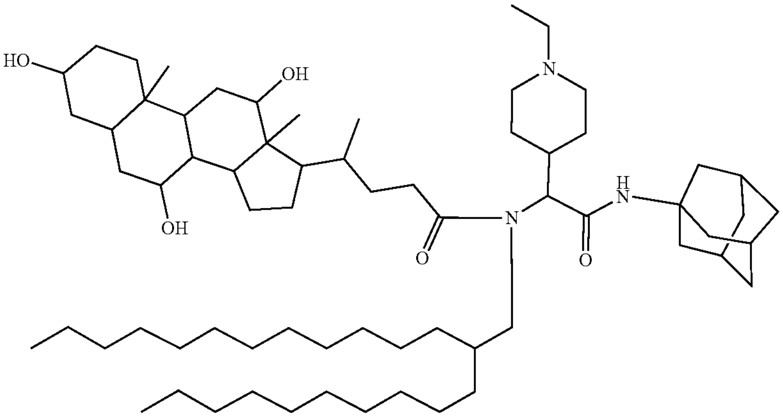
P363G10
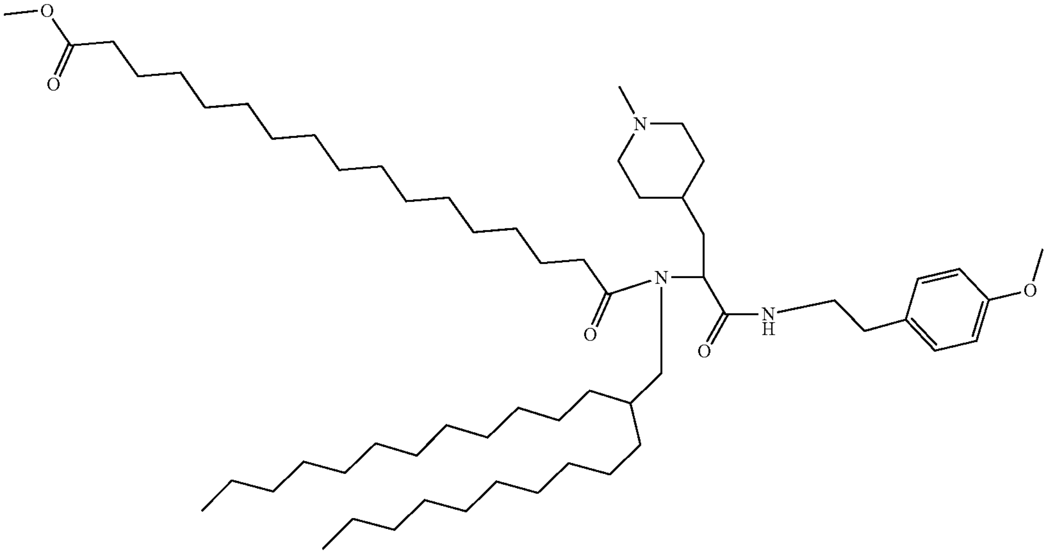

-continued
P165A10
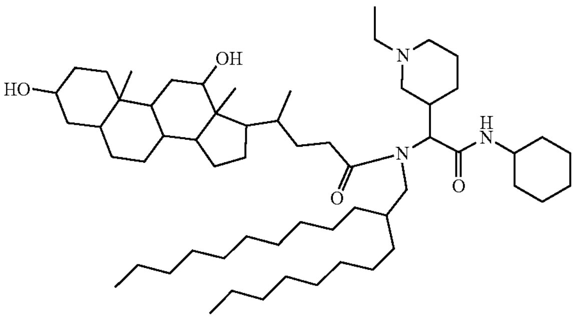
P165D10
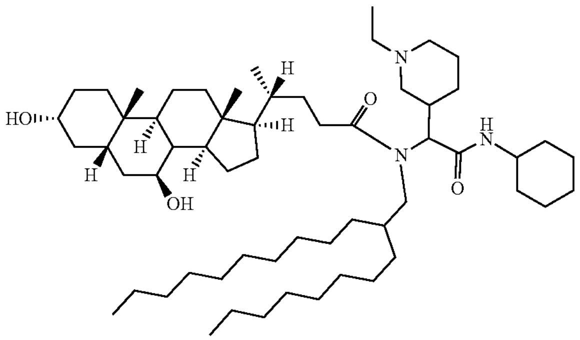
P165F10
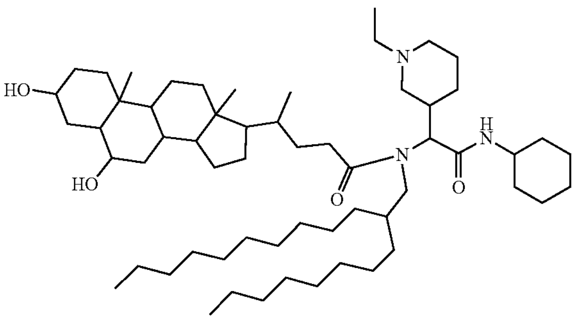
P165E12
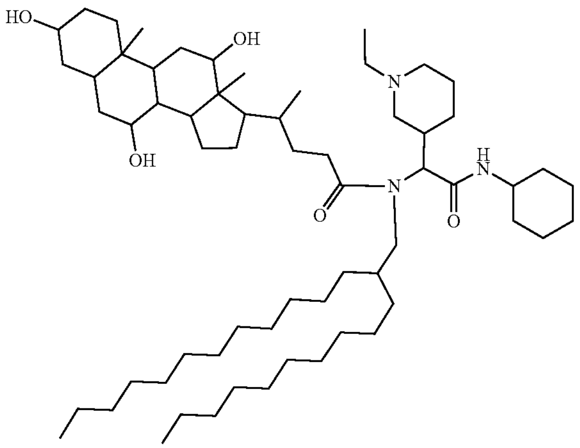
P169A2
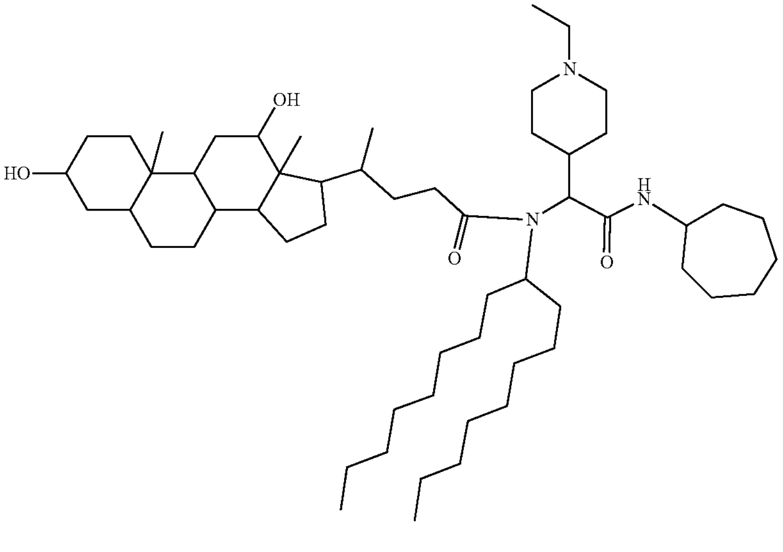

-continued
P169A8
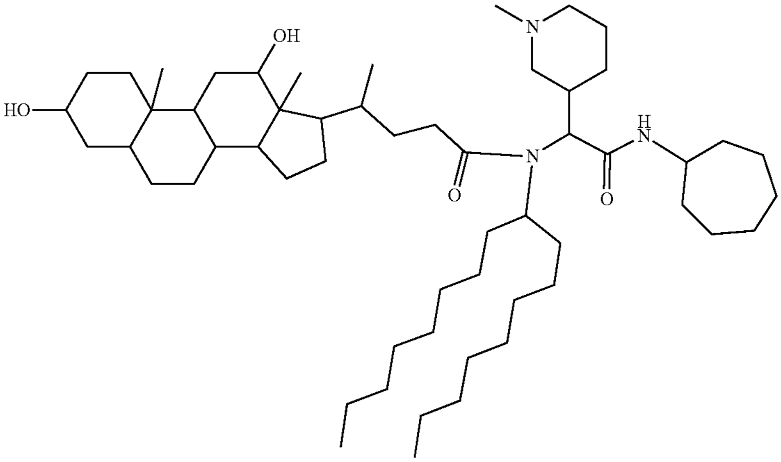
P169F10
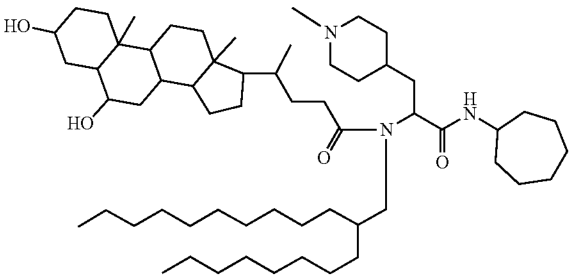
P169C10
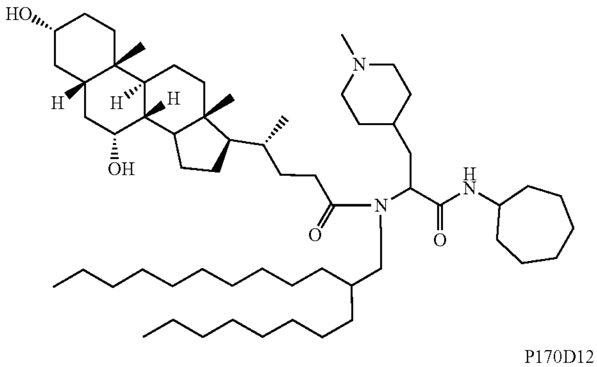
P169C12
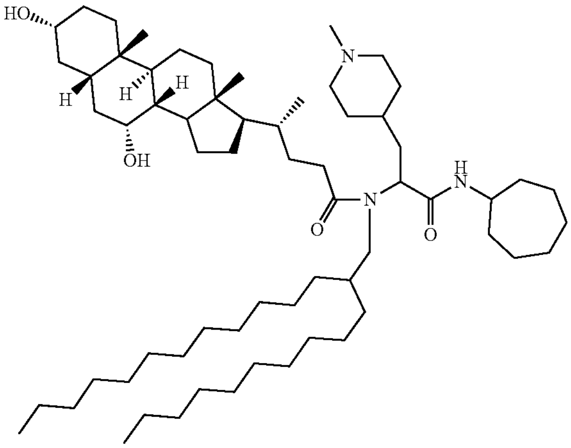
P170D12
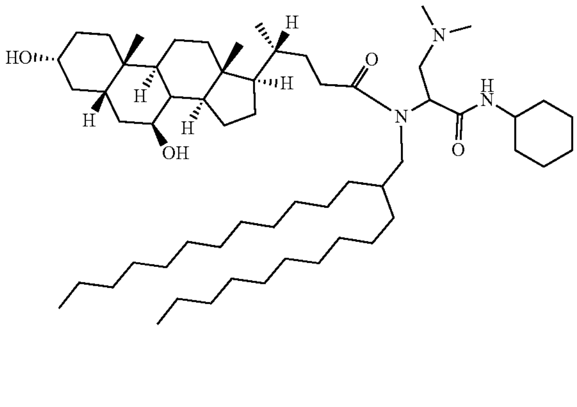
P171D12
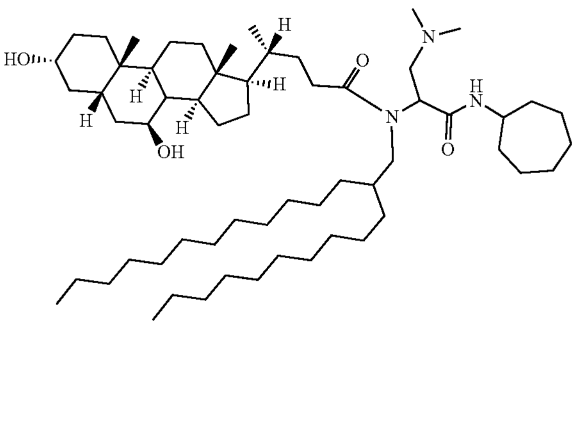
P173F10
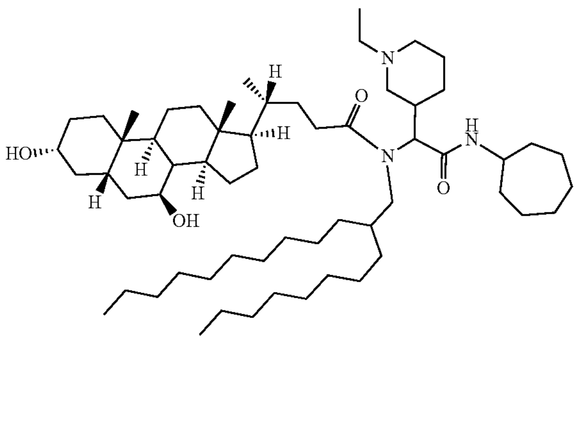

-continued
P177F6
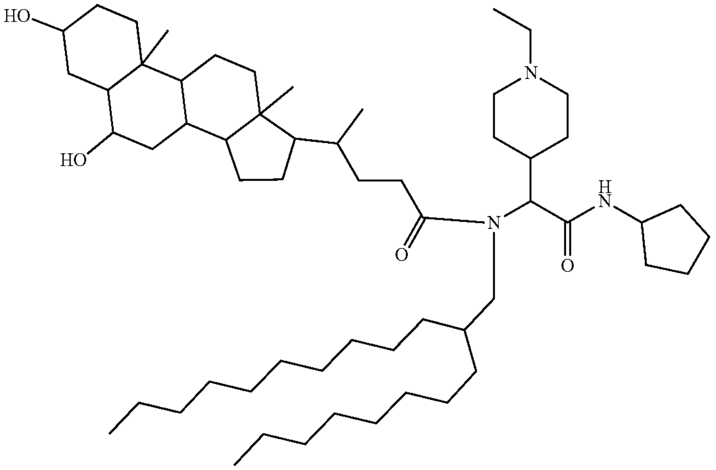
P235F9
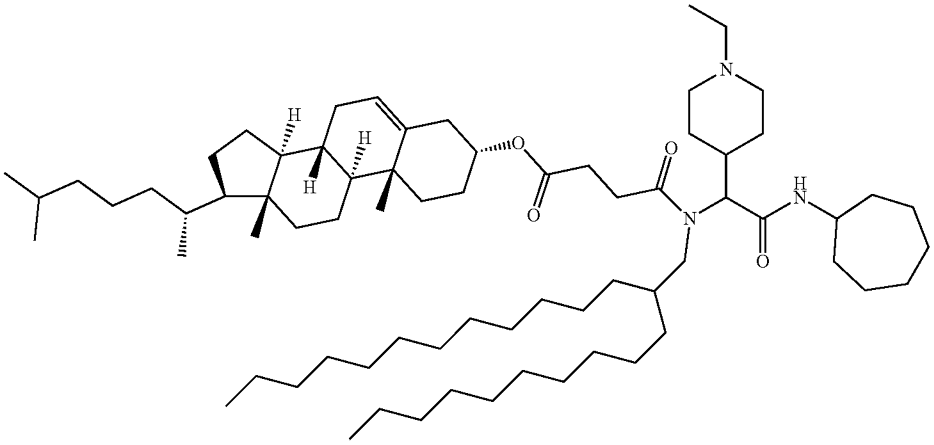
P235F11
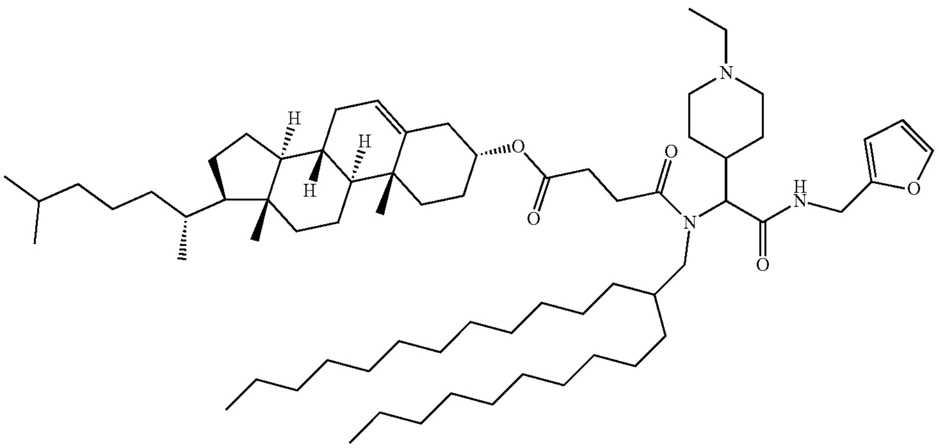

-continued
P235G10
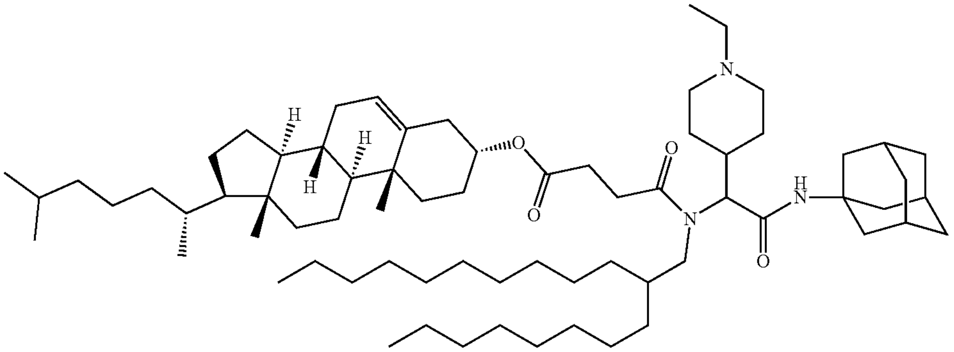
P235G11
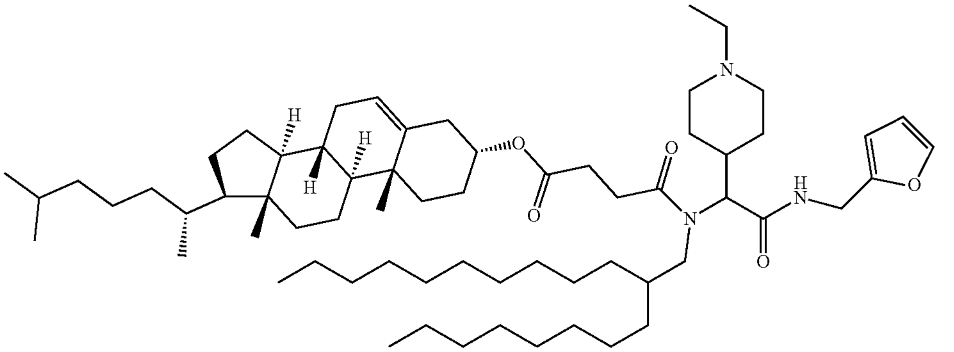
P235F7
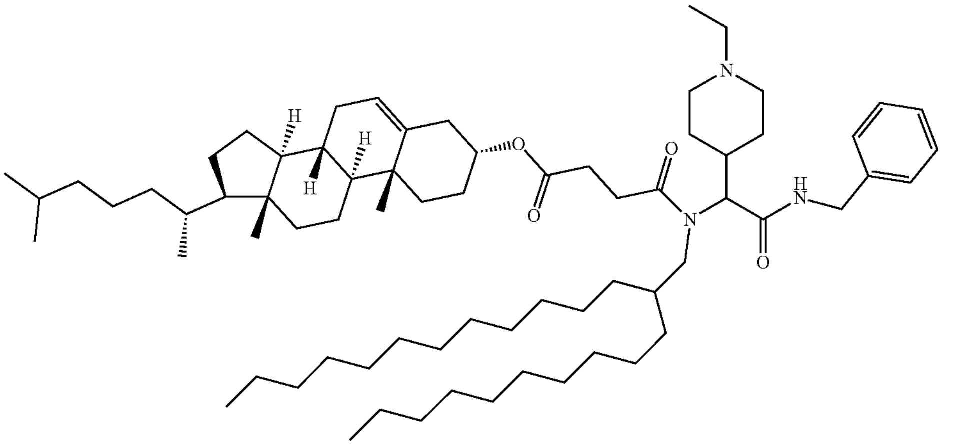

-continued
P245G8
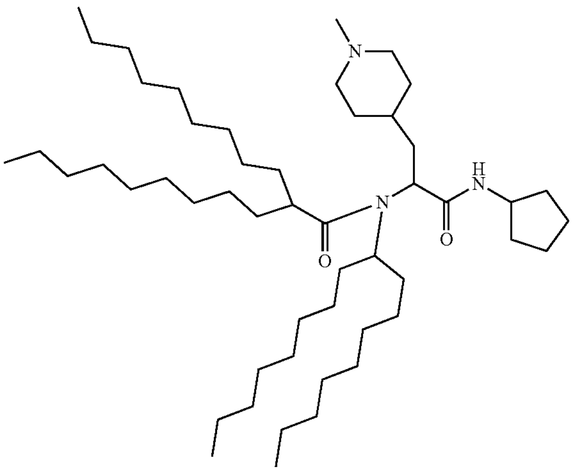
P245A4
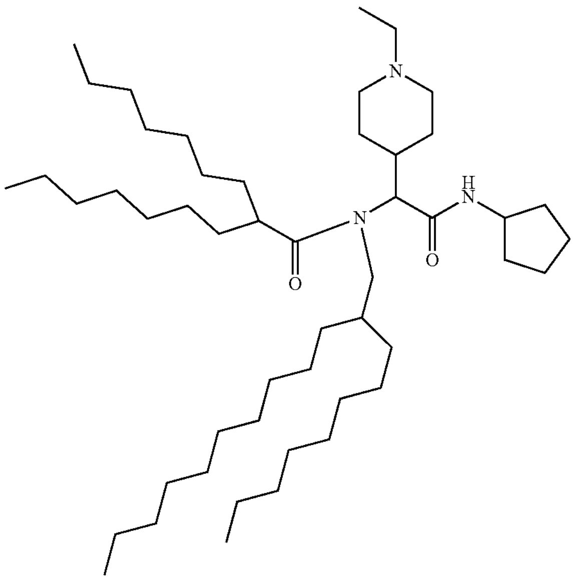
P247C4
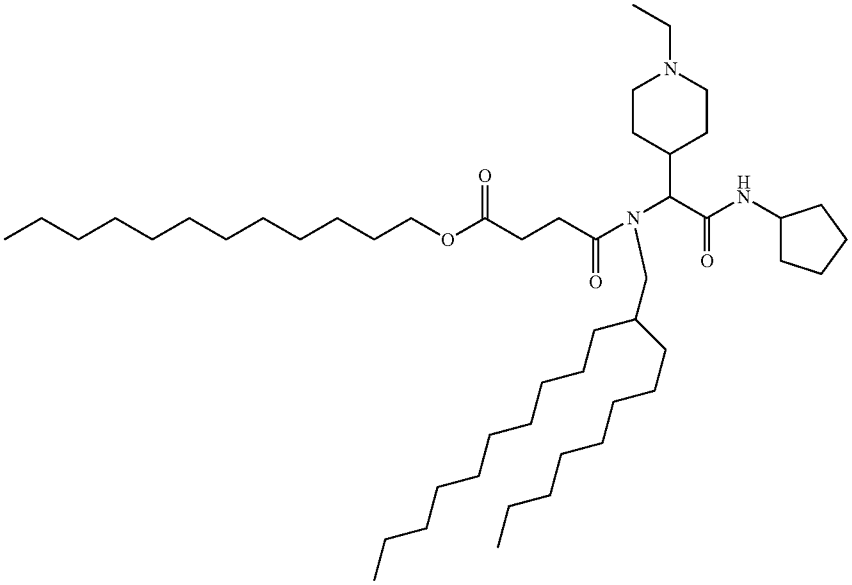
P247C6
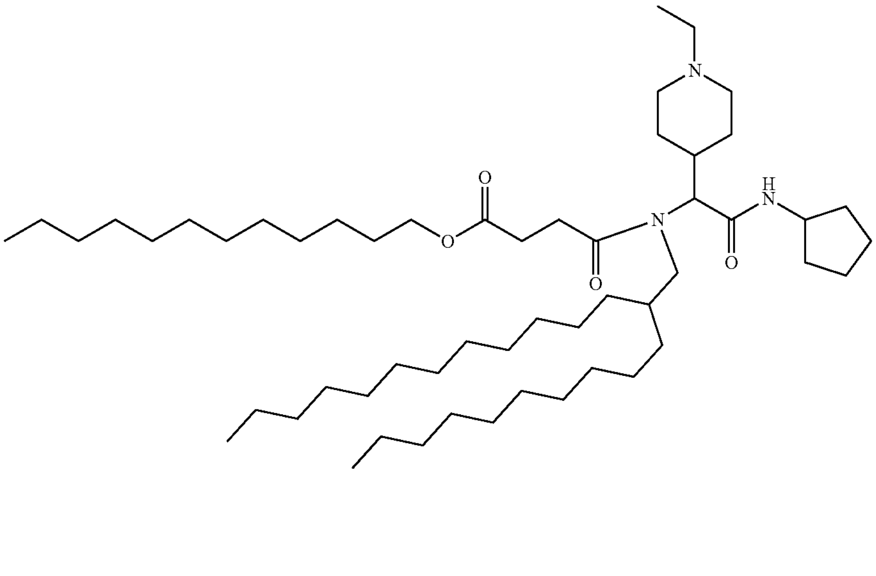

-continued
P247G12
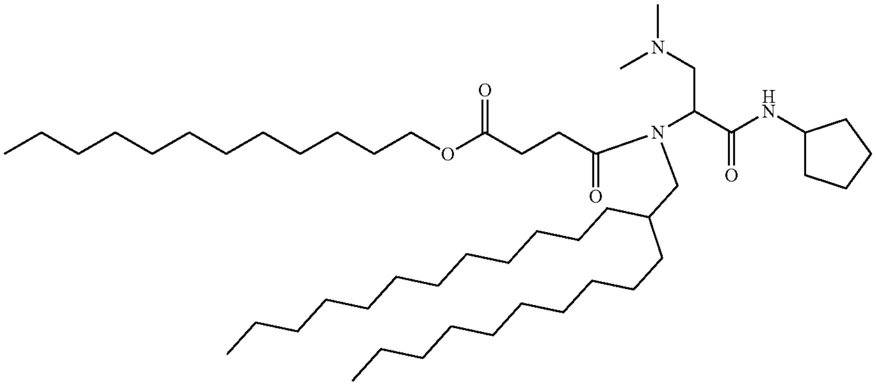
P254B10
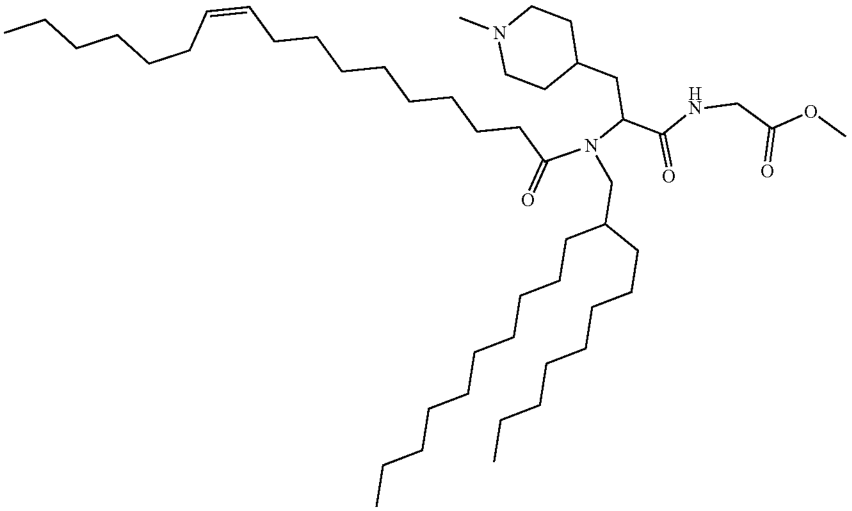
P255C6
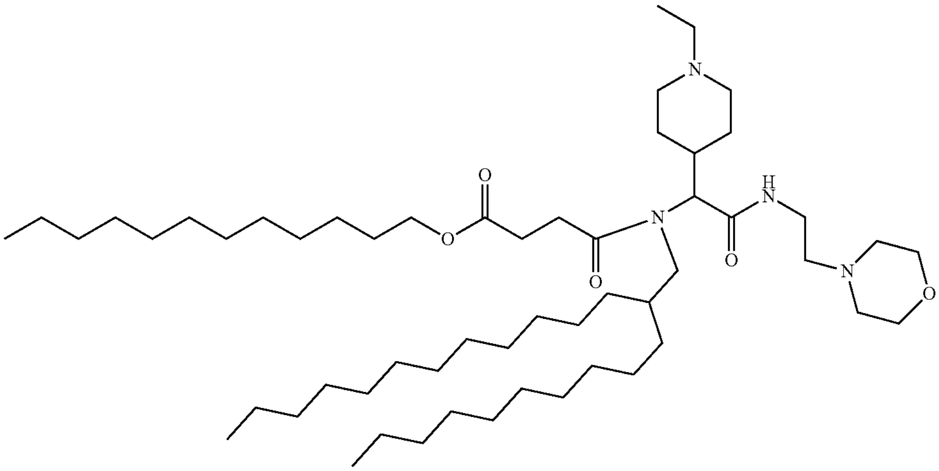

-continued
P255D6
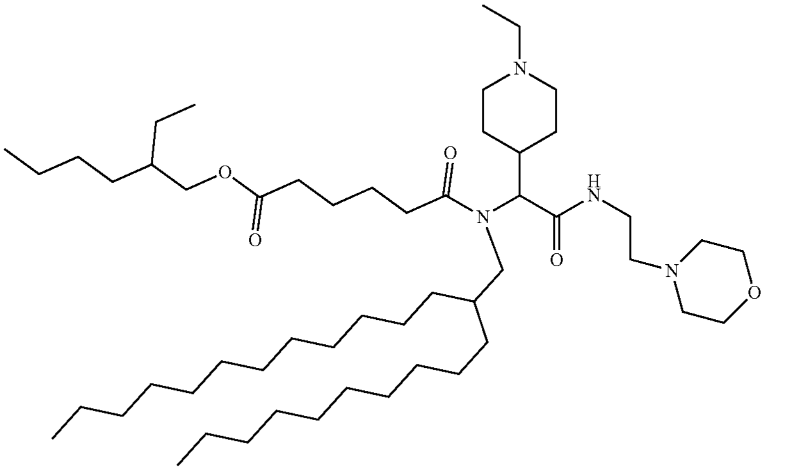
P256B4
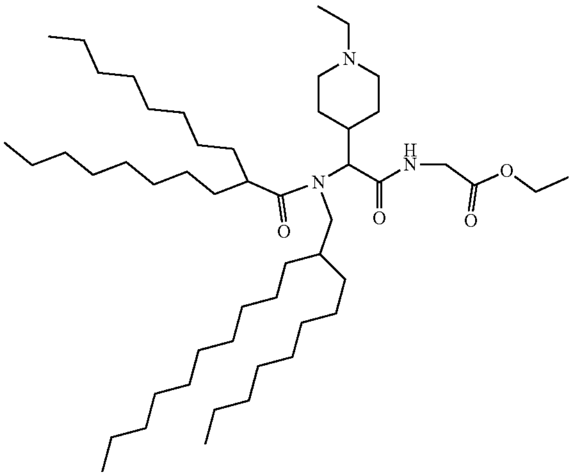
P256C4
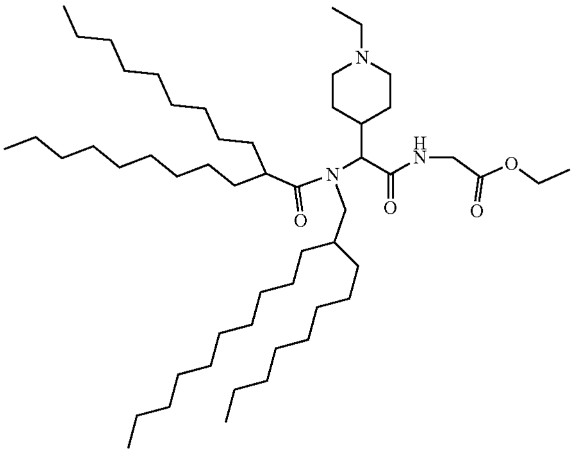
P256C6
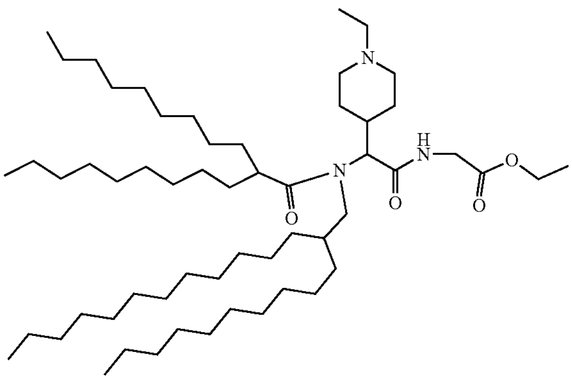
P257A6
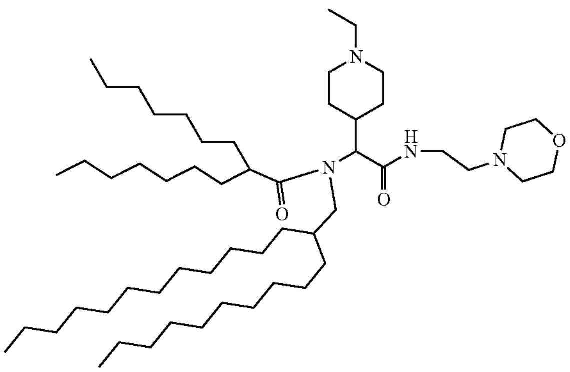

-continued
P258D6
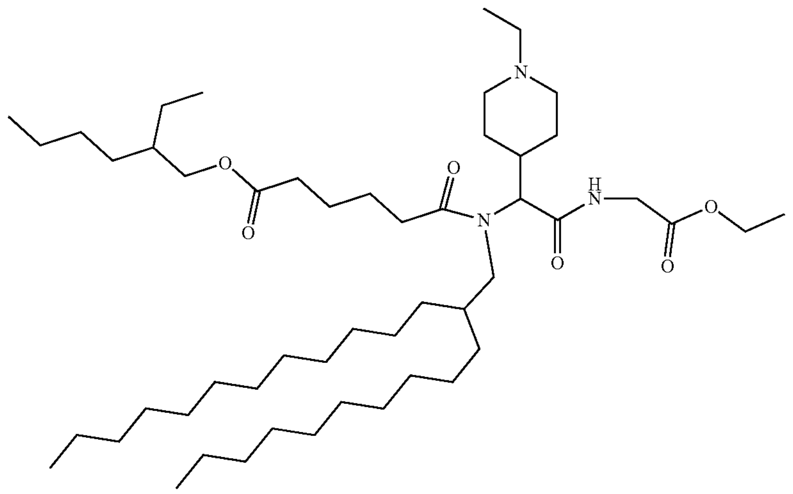
P258D10
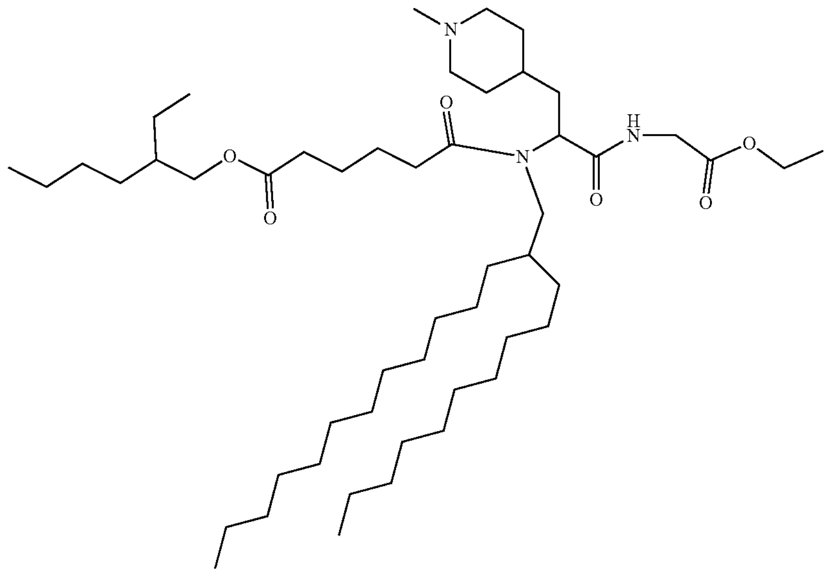
P258C12
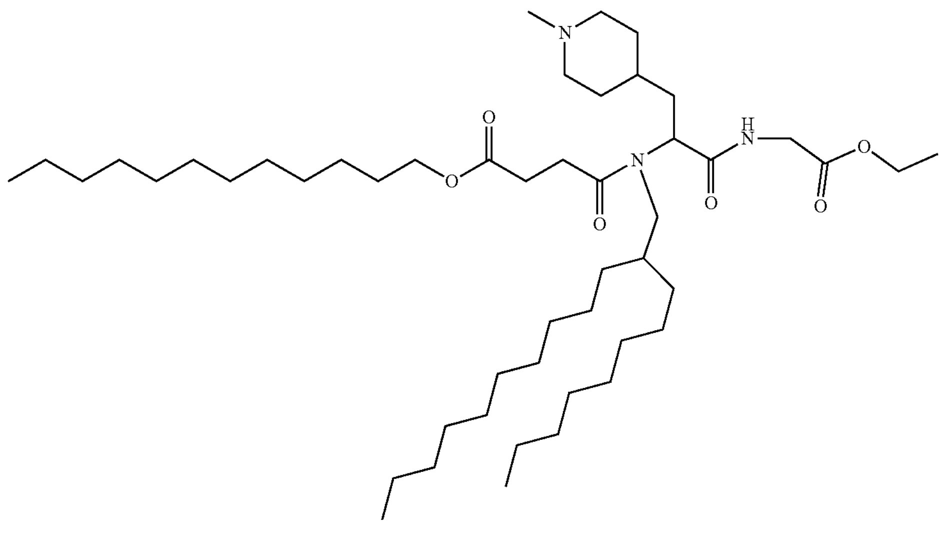

-continued
P259C4
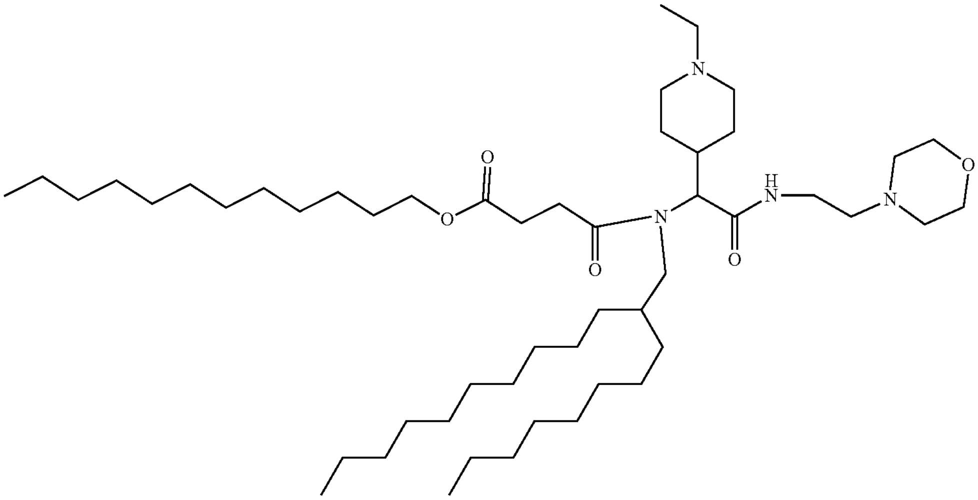
P259C6
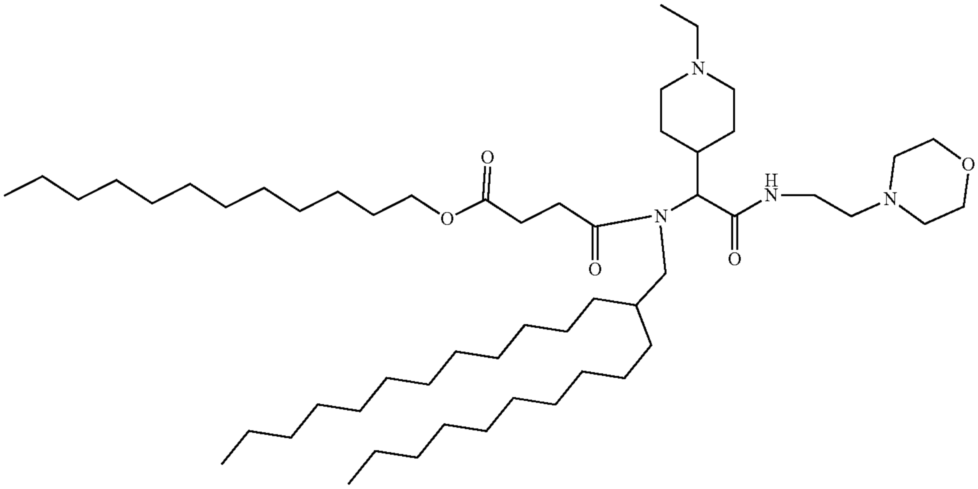
P259D6
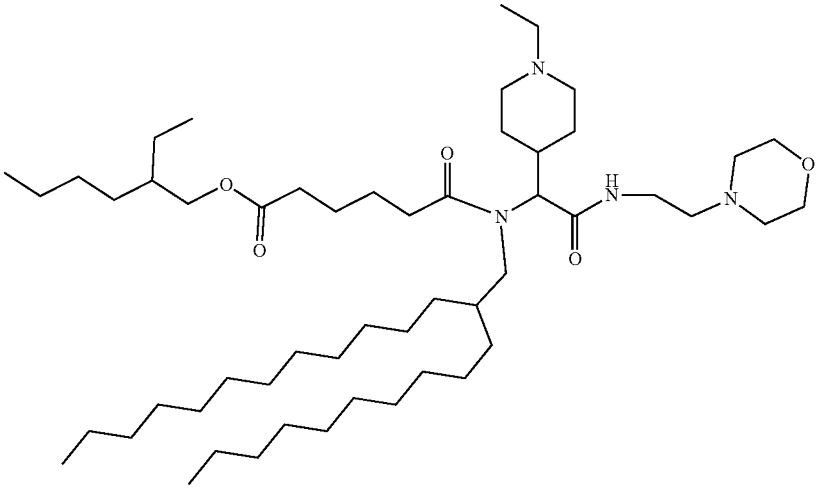

-continued
P259C12
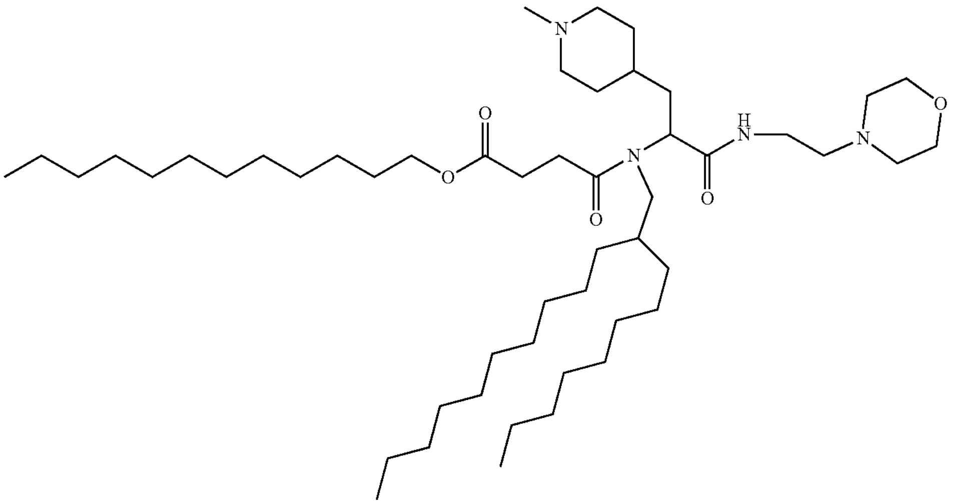
P265E6
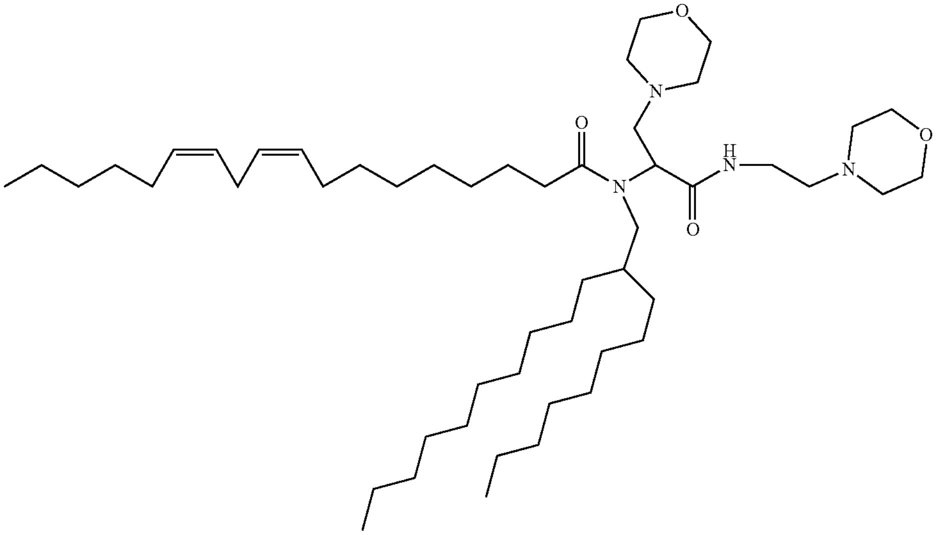
P266A1
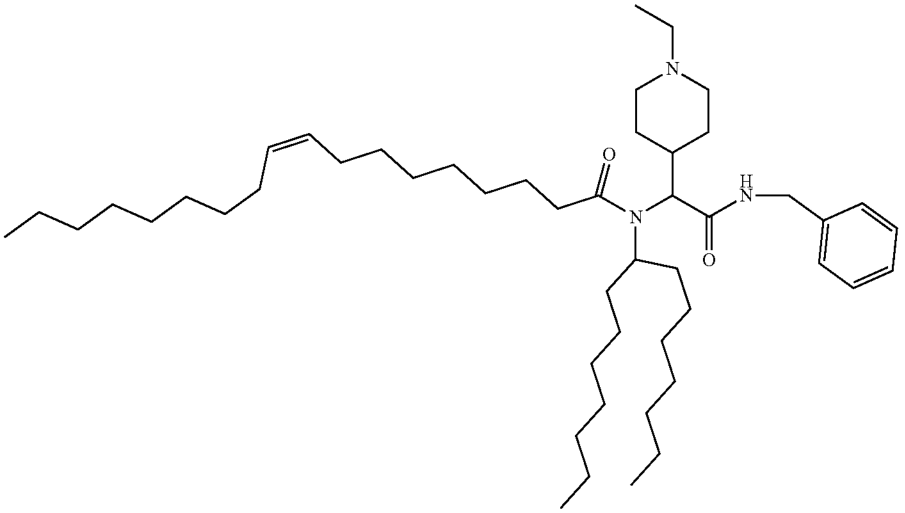

-continued
P266A2
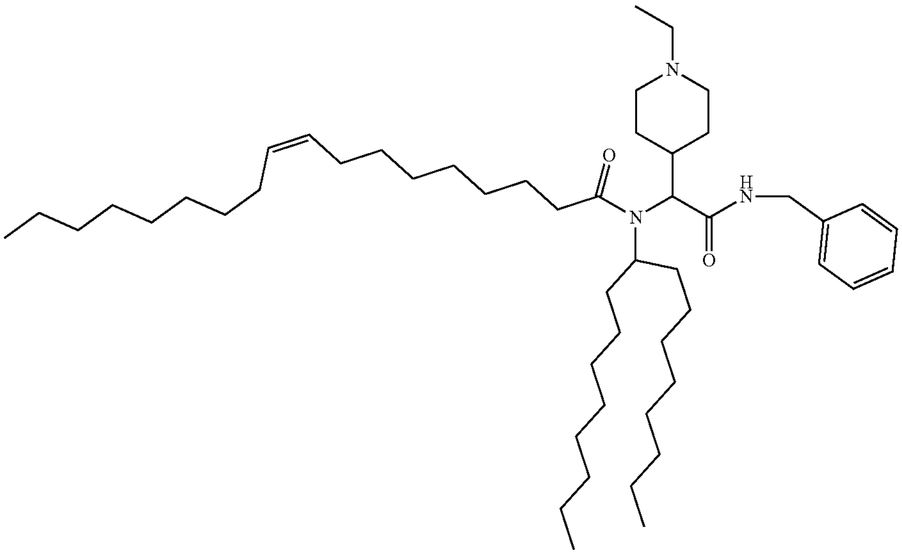
P266A3
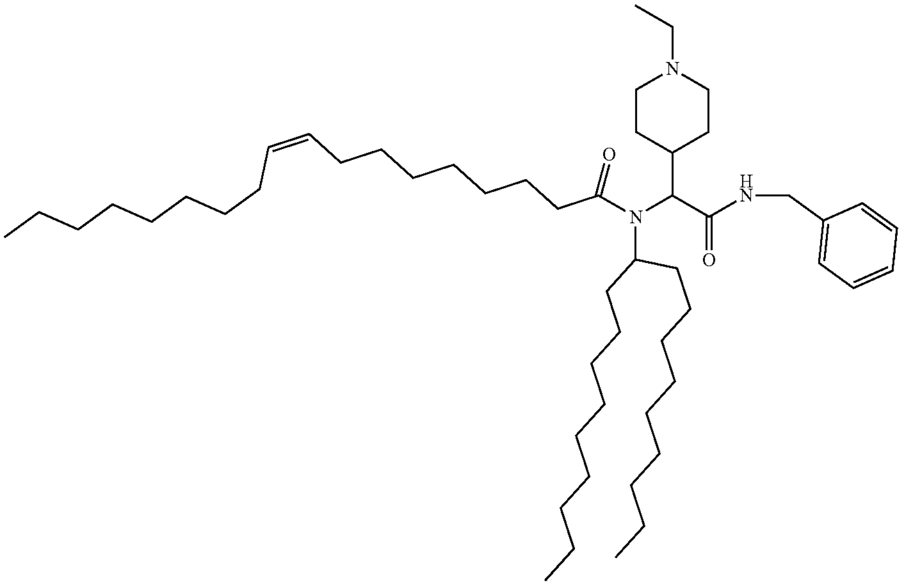

P266B2
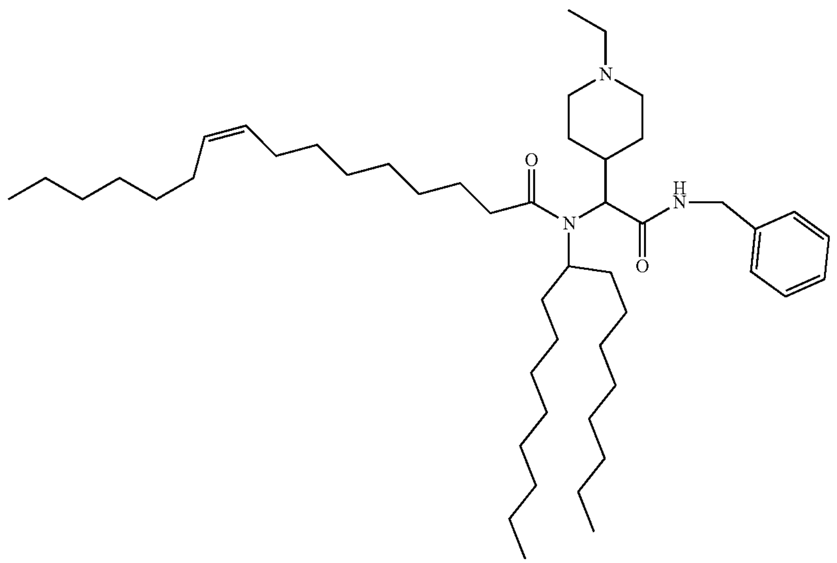
P266F1
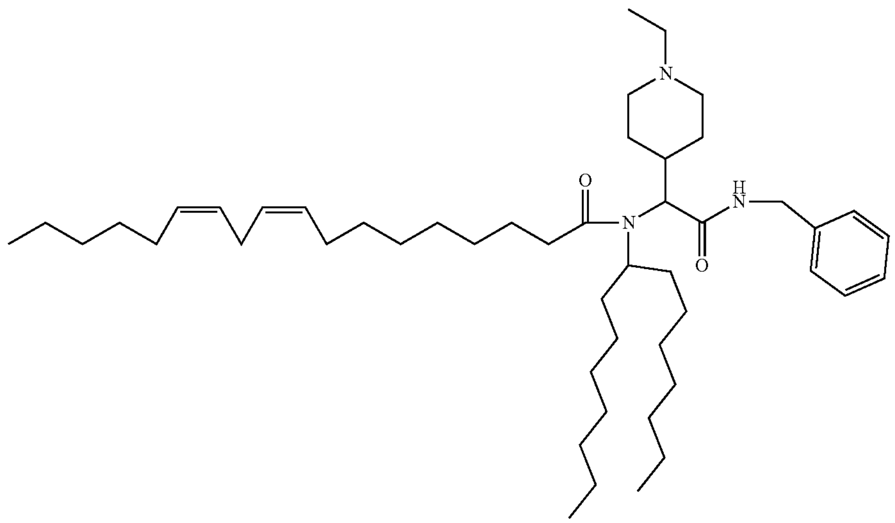
P266F2
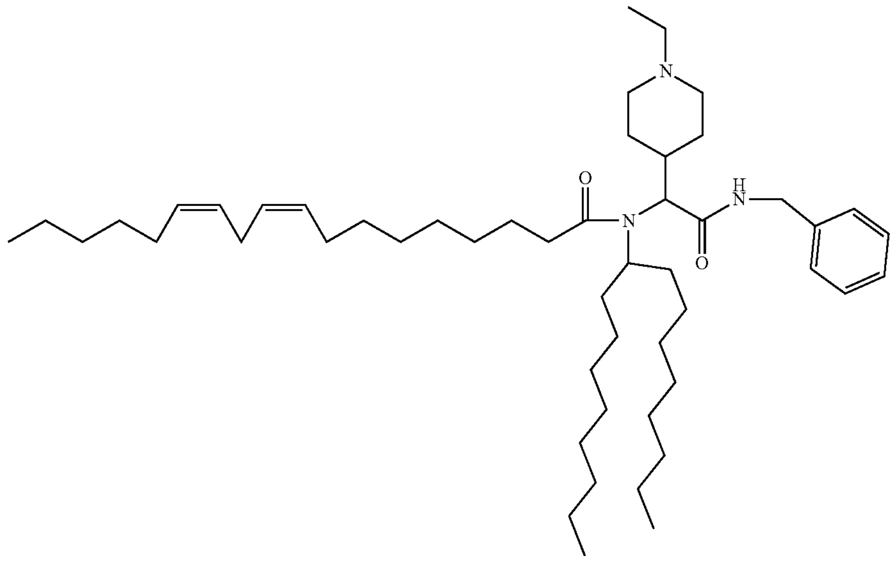

-continued
P266F3
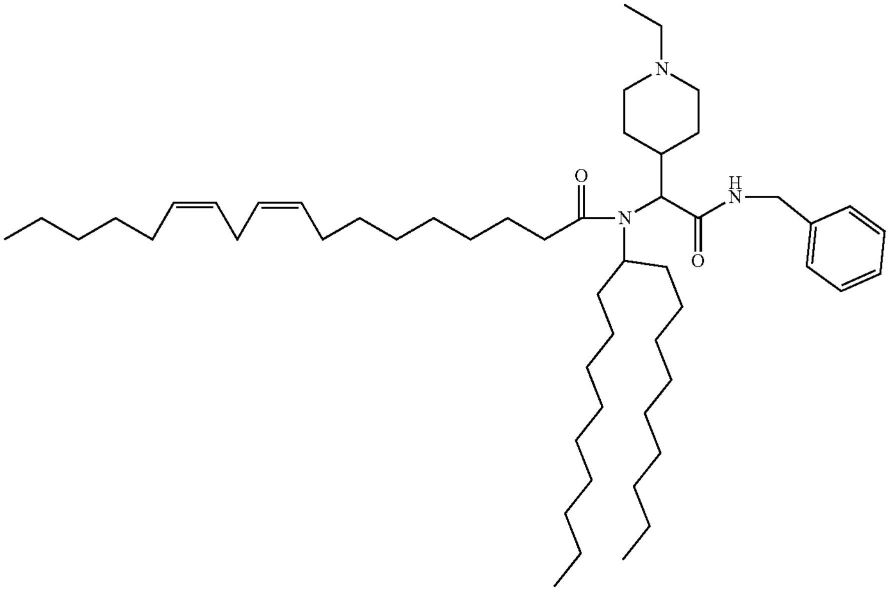
P266G1
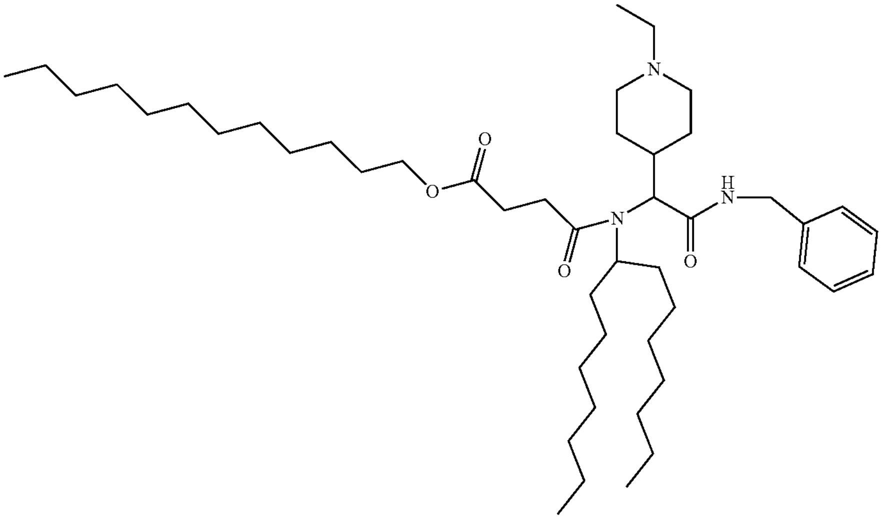

-continued
P266G2
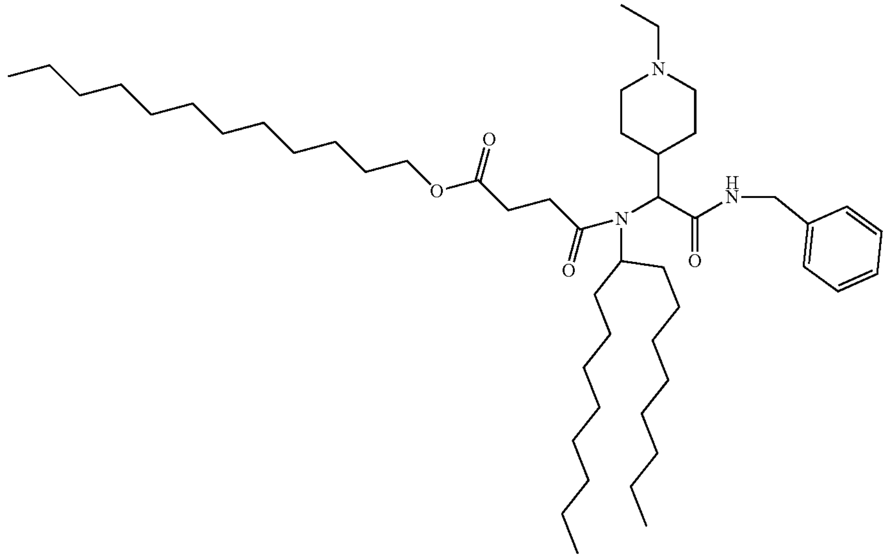
P266G3
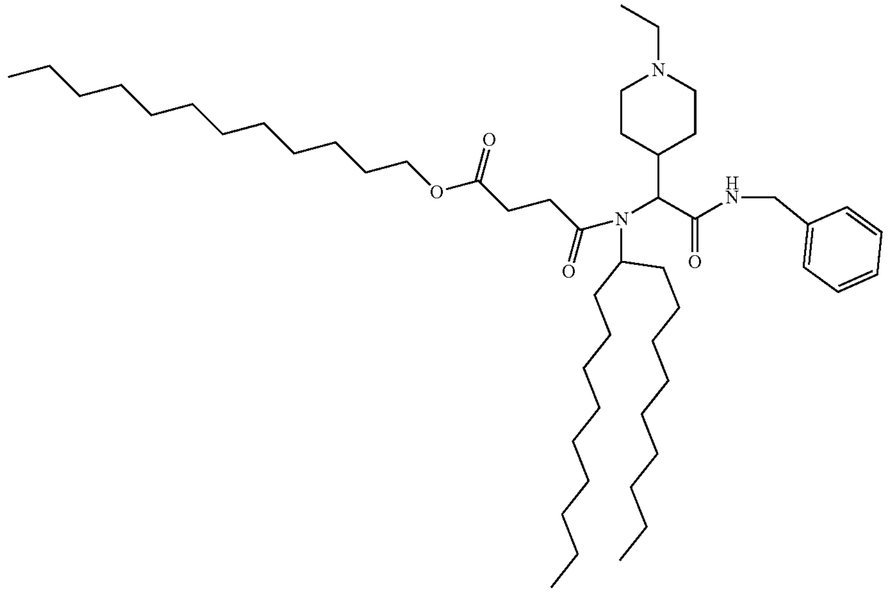

-continued
P266G5
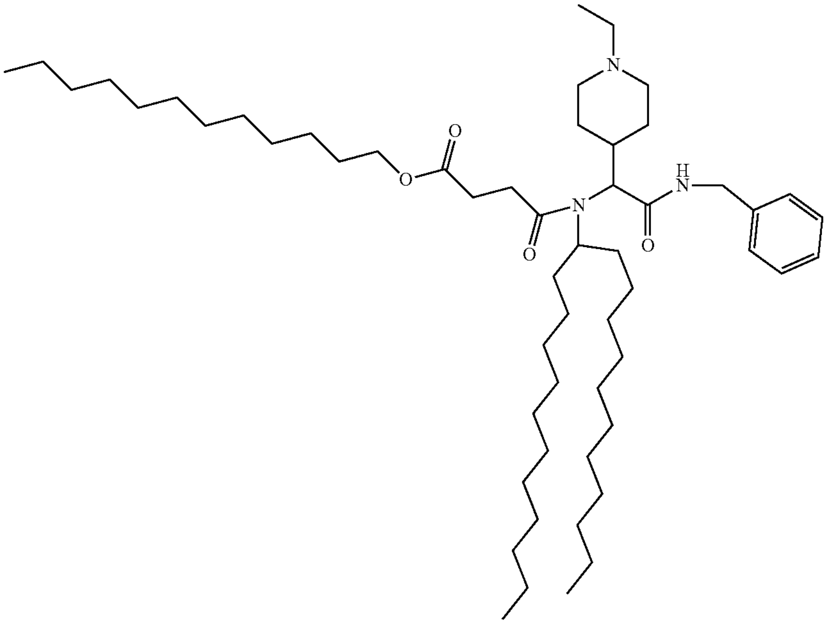
P267G2
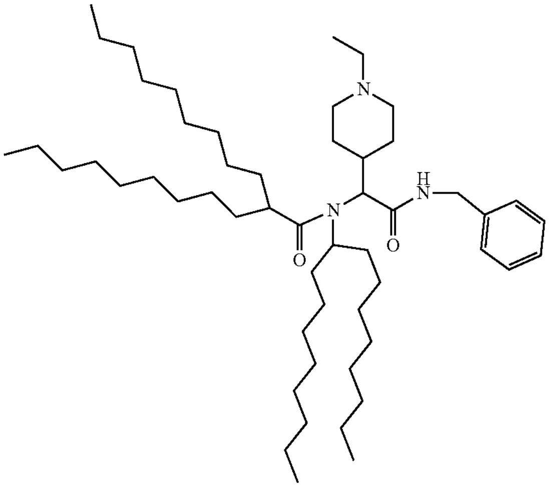
P268B2
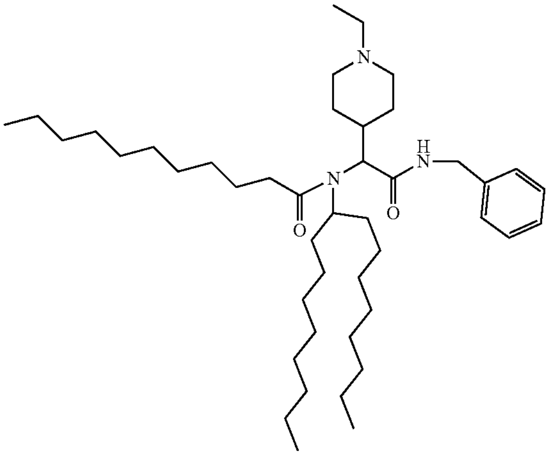
P269F1
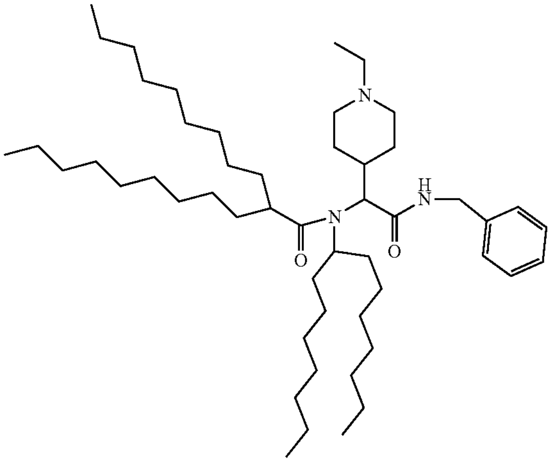
P287A6
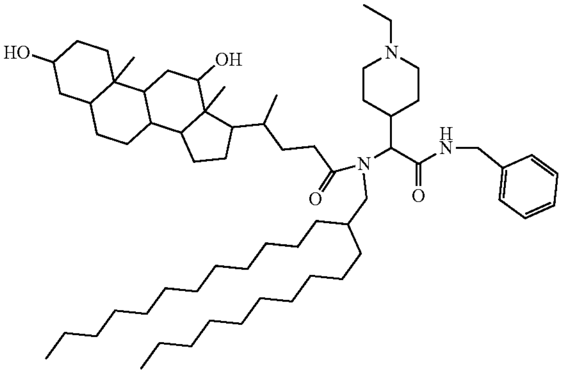

-continued
P287A10
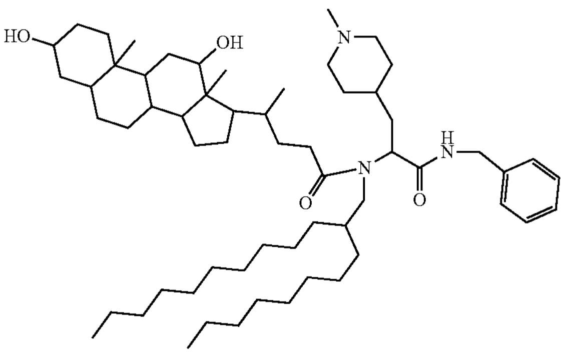
P287B10
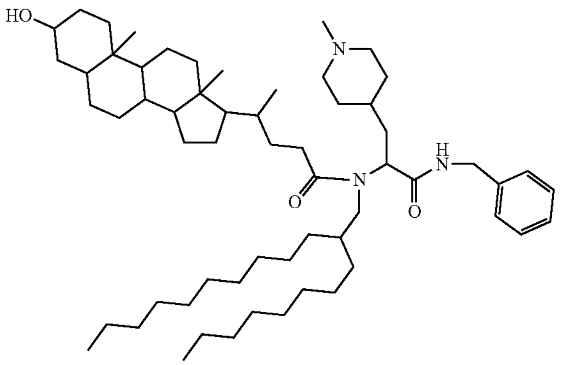
P287B12
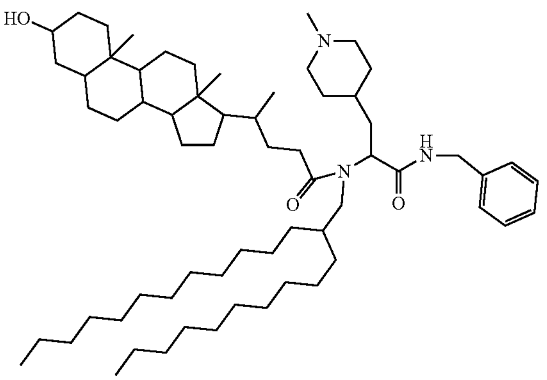
P287C4
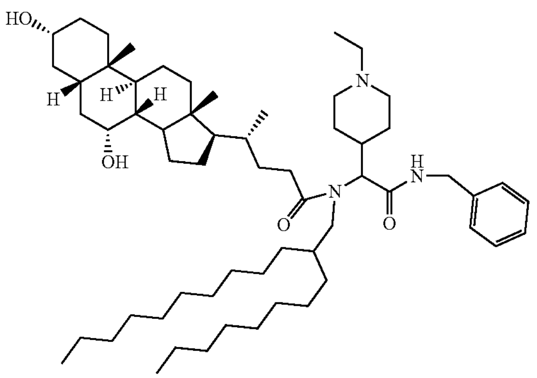
P287C6
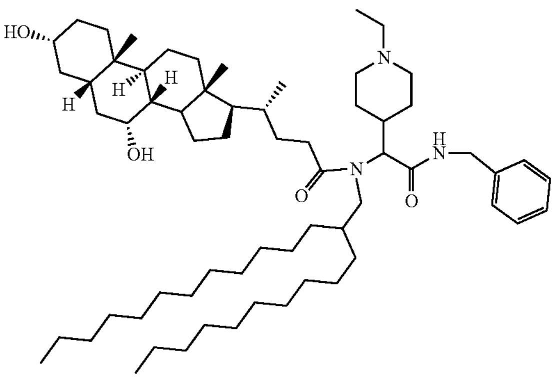
P287C10
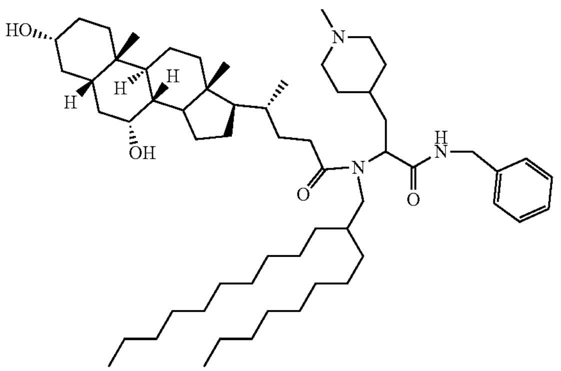
P287D10
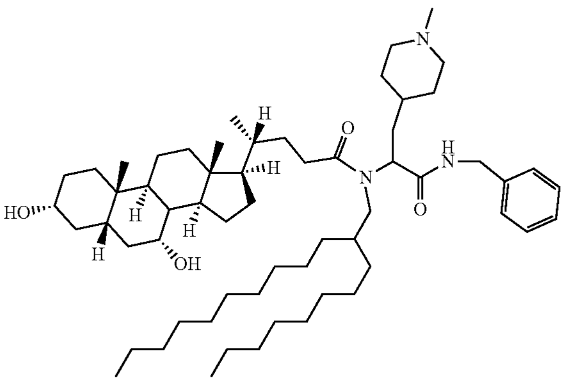
P287F4
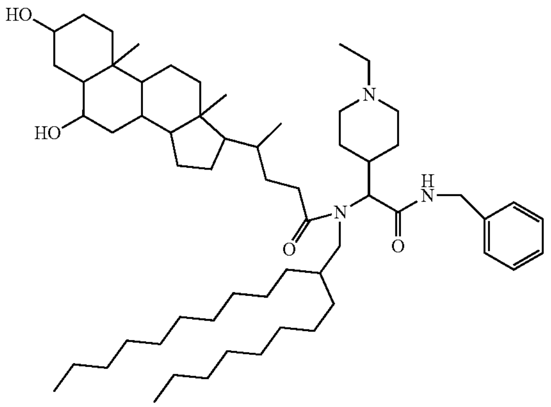

-continued
P287F6
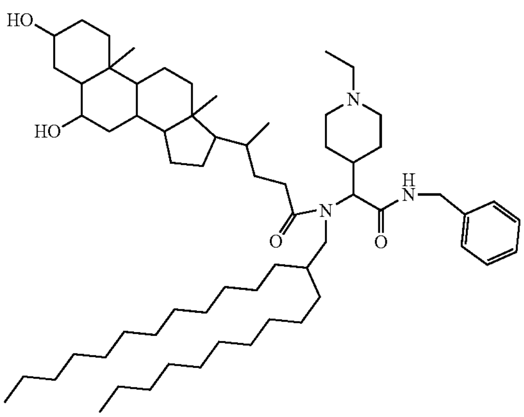
P287F10
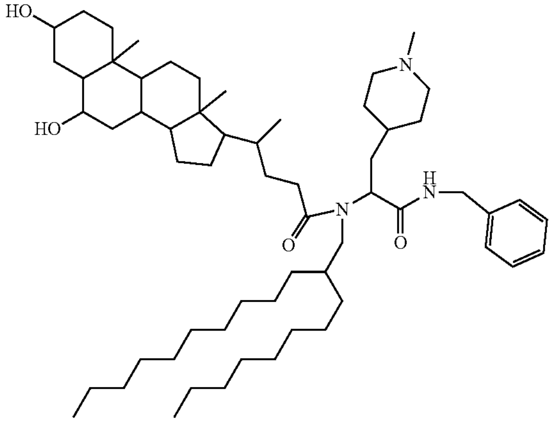
P287F12
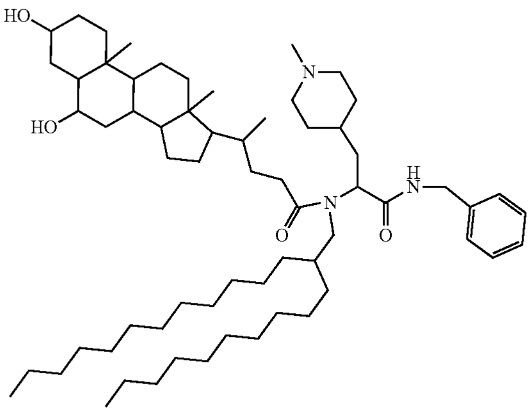
P294A6
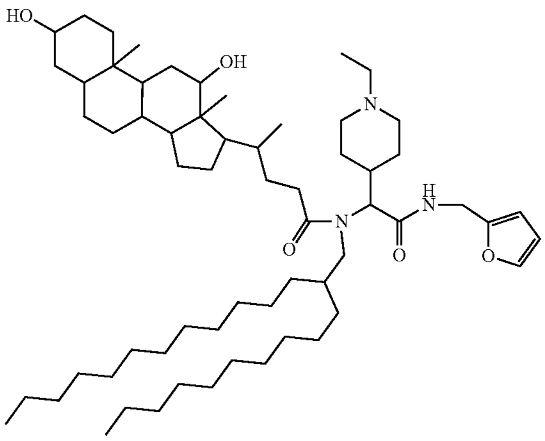
P310B10
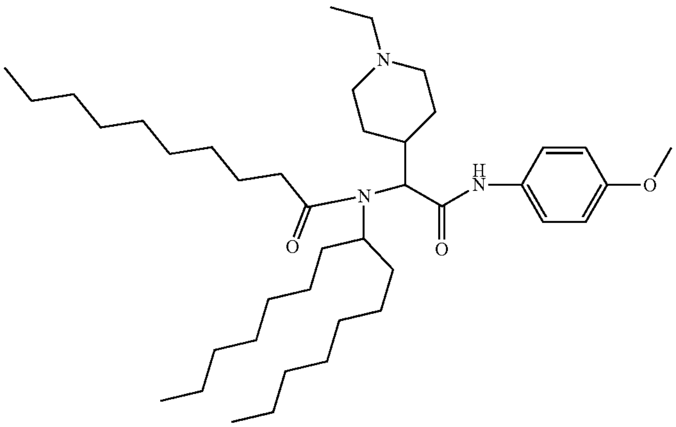

-continued
P310E12
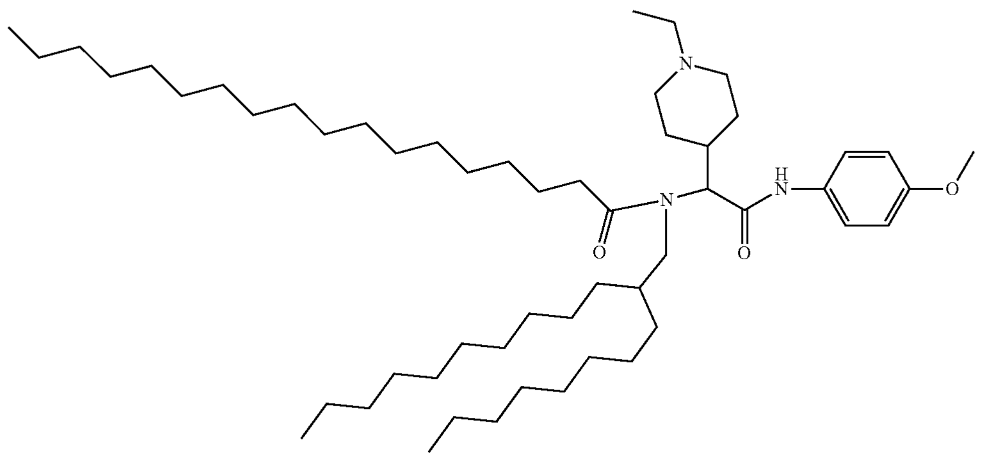
P312A1
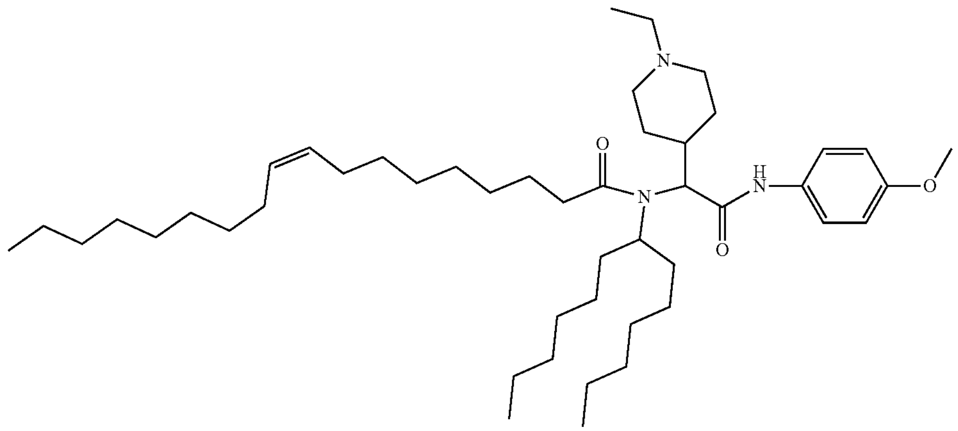
P312B1
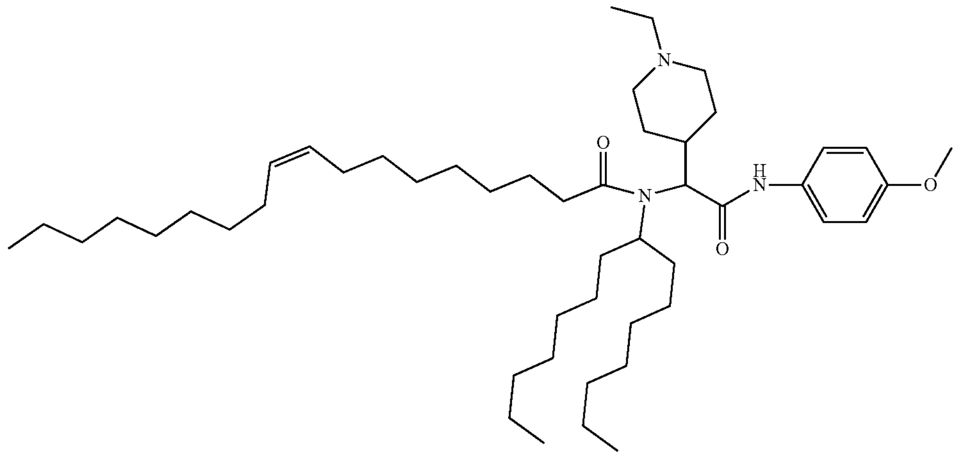

-continued
P312C1
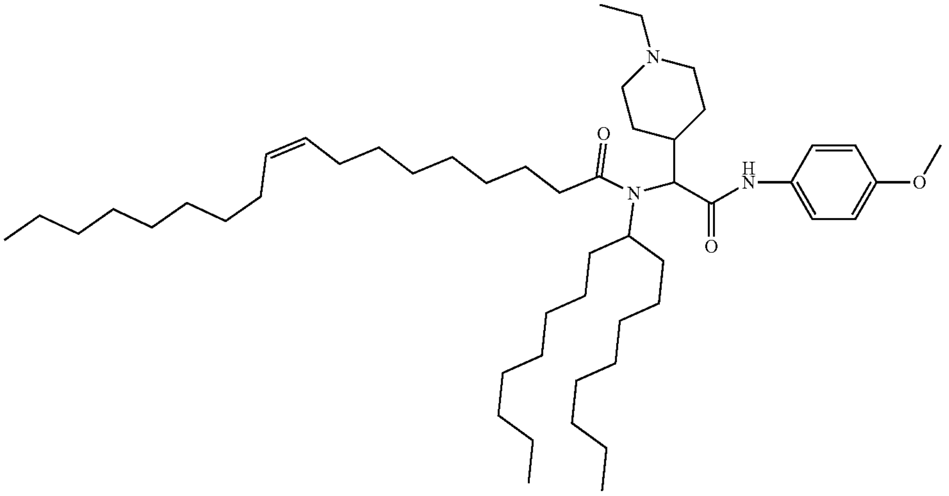
P312D1
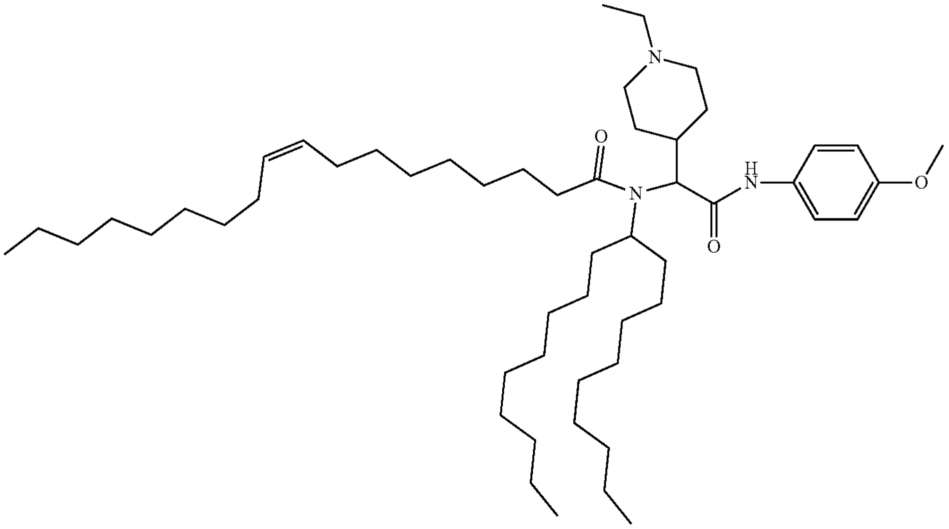
P312E1
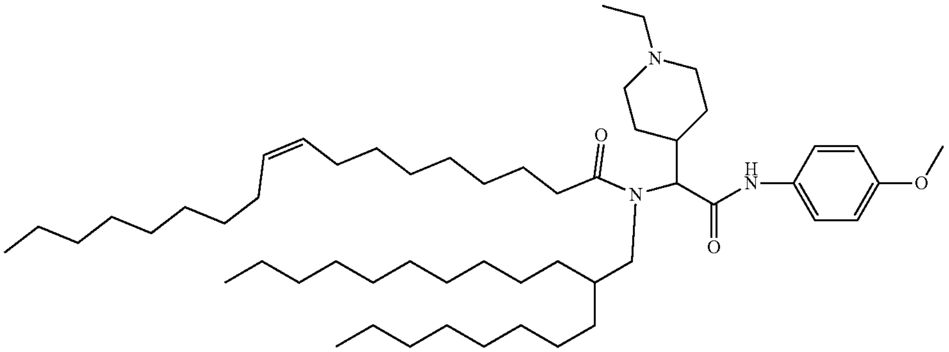

-continued
P312B3
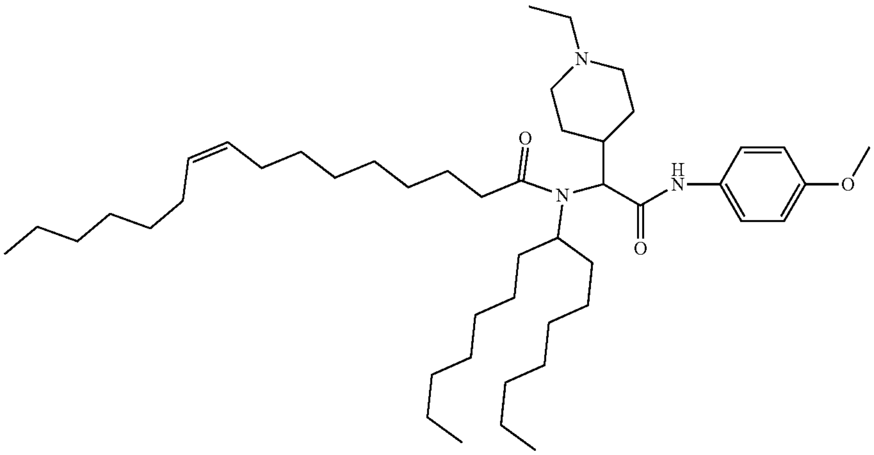
P312C3
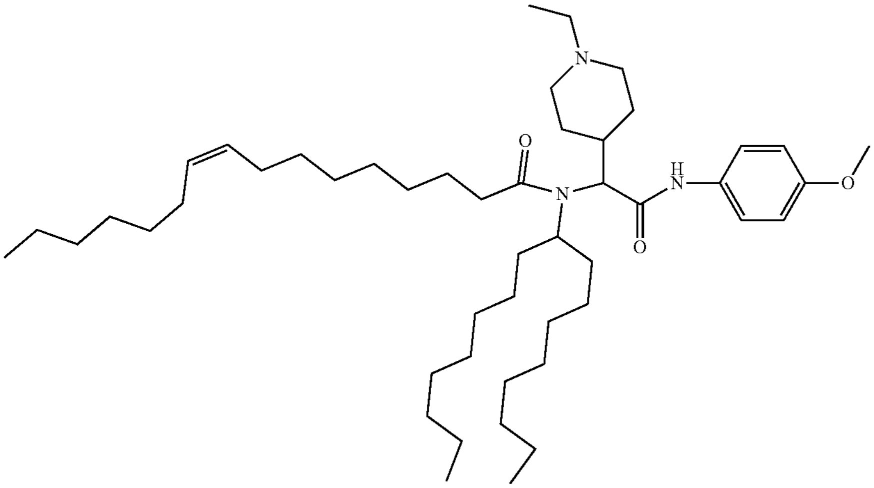
P312E3
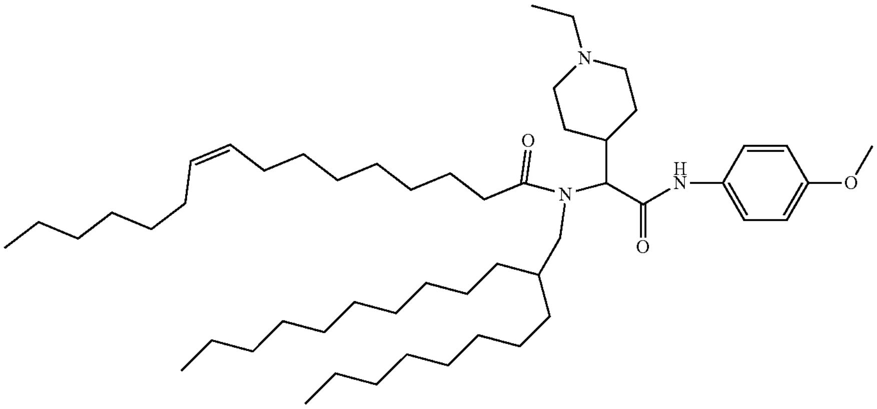

-continued
P312B6
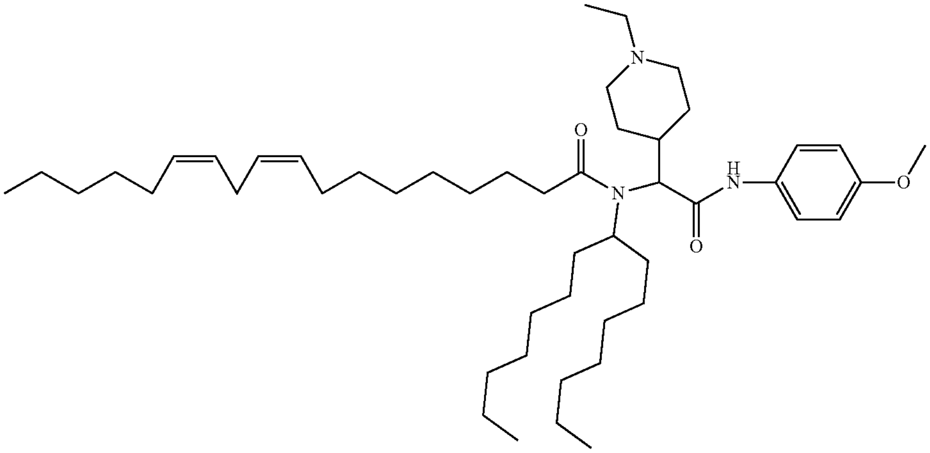
P312C6
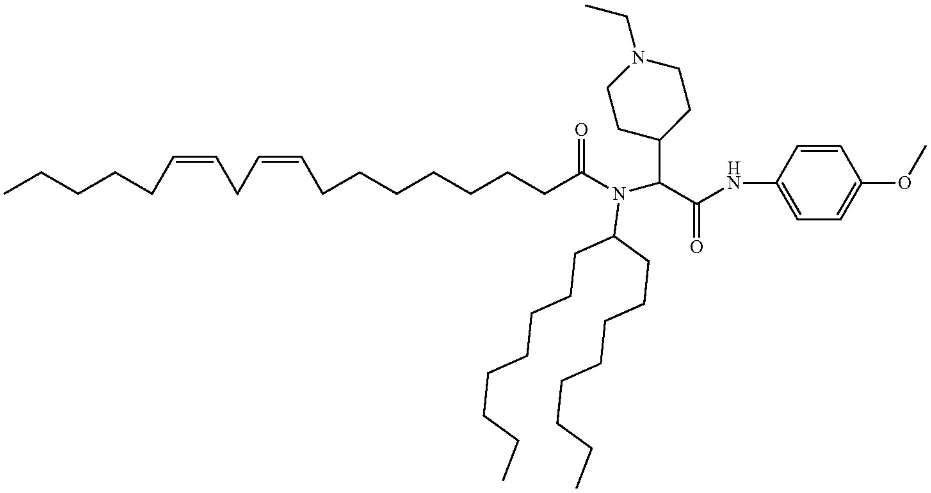
P312B7
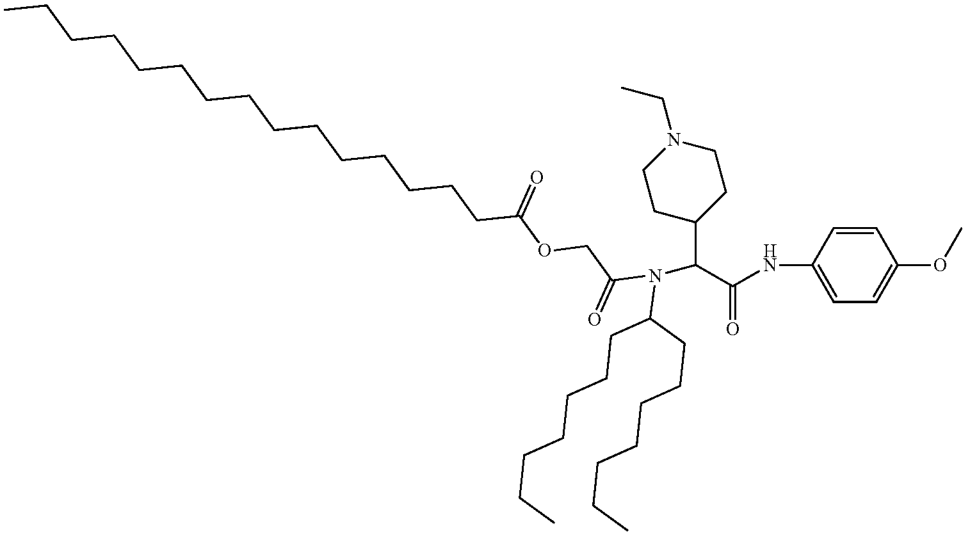

-continued
P312C7
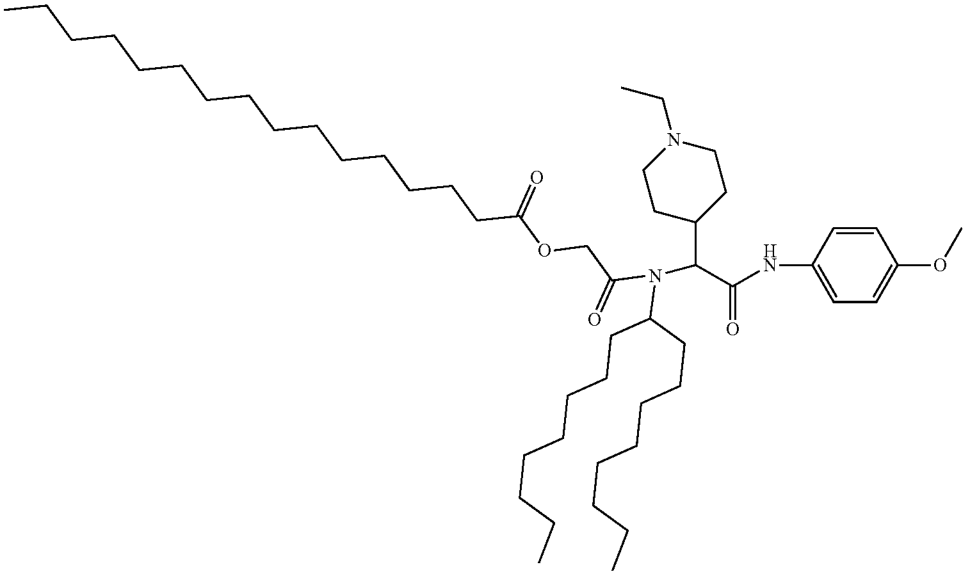
P312E7
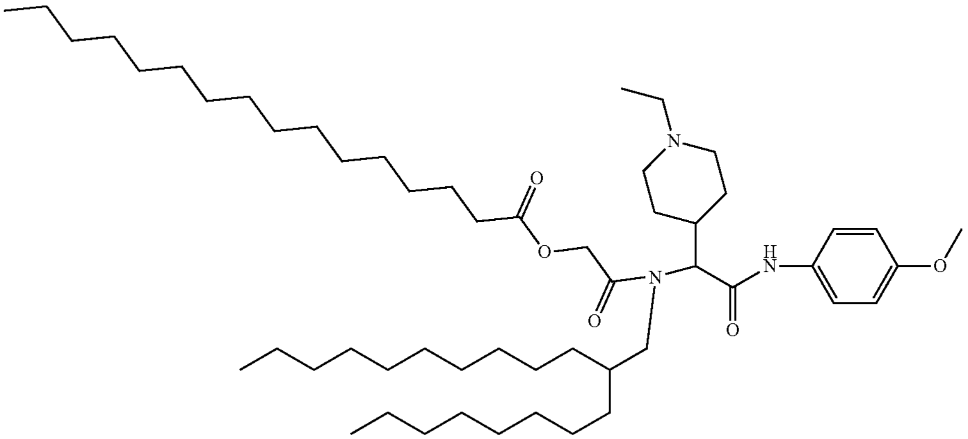
P313B1
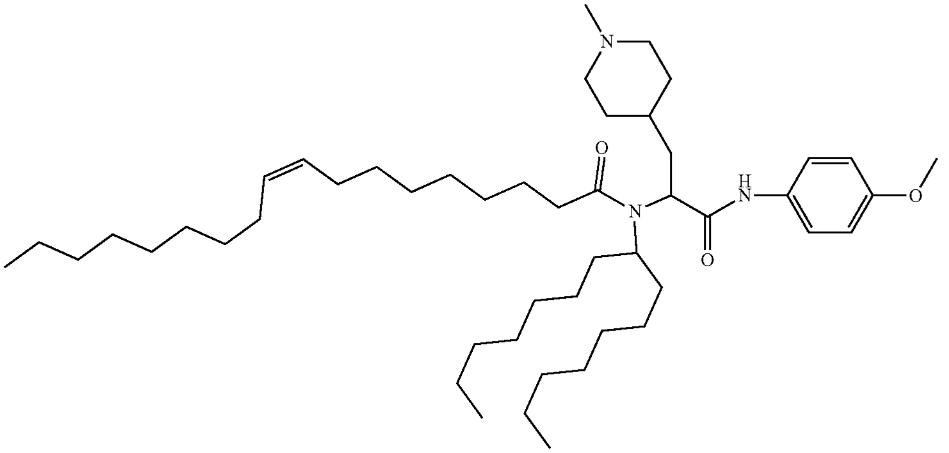

P313C1
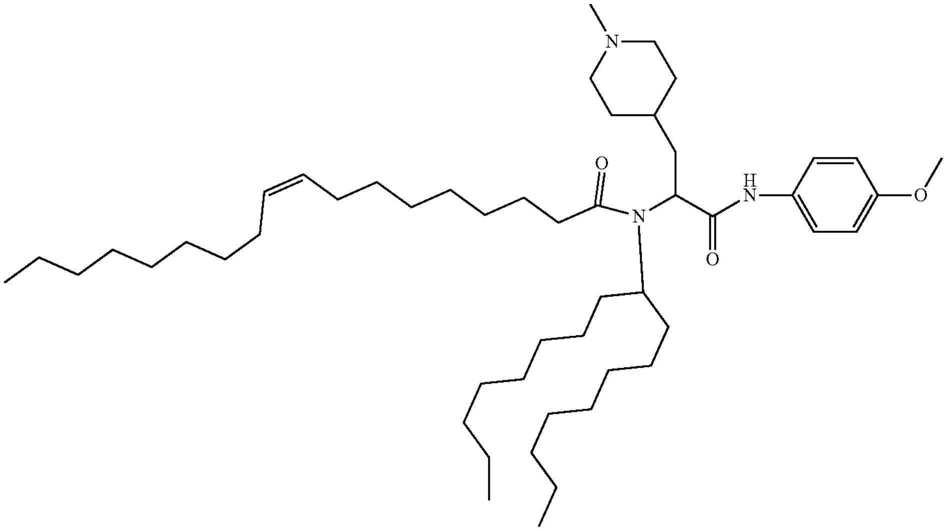
P313C6
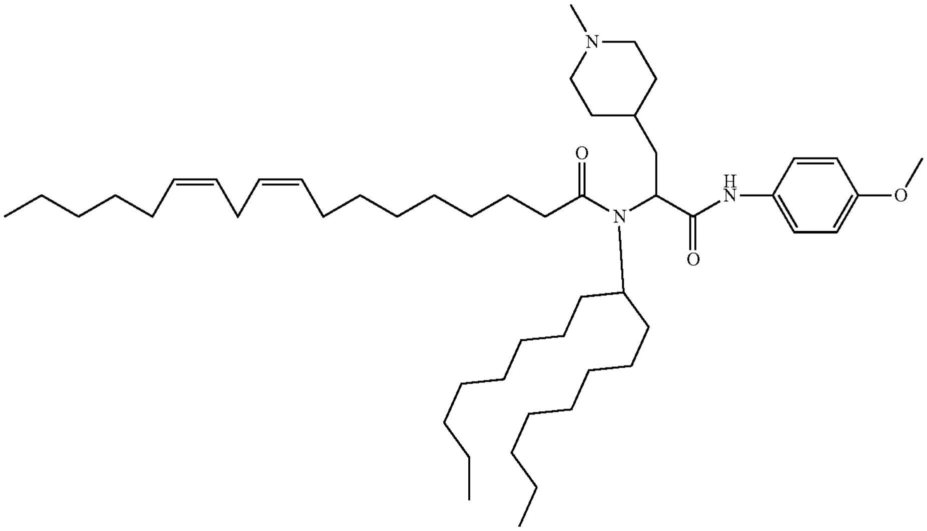
P313C7
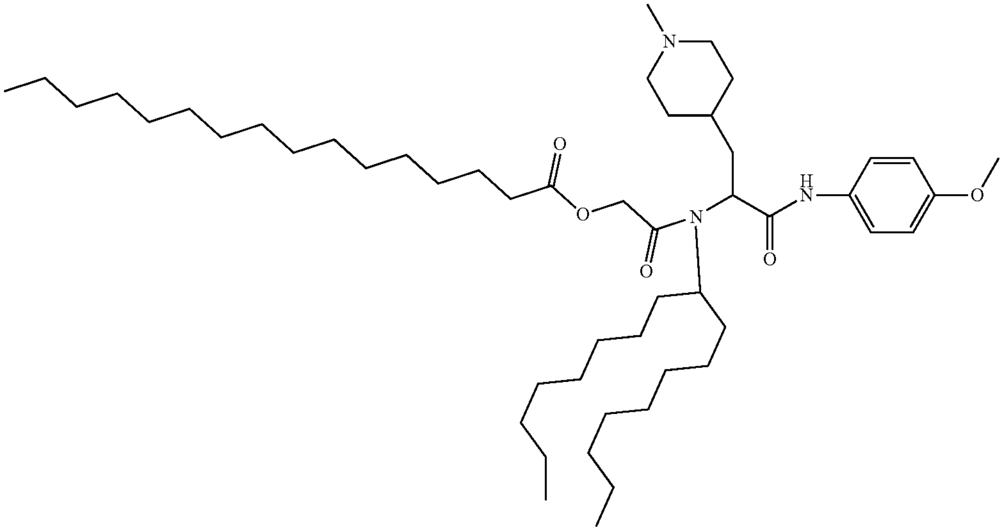

-continued
P313C8
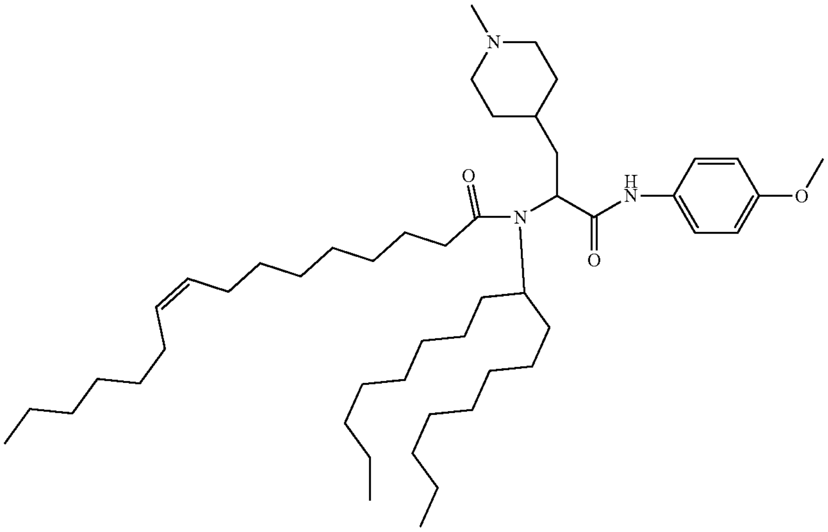
P314E1
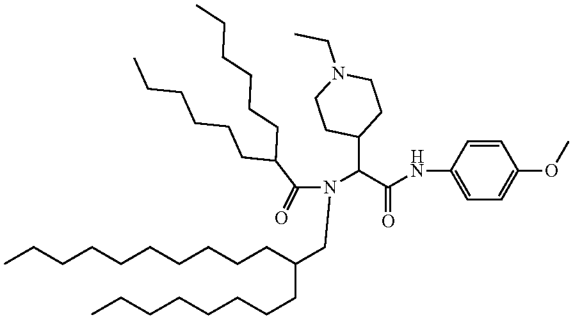
P314E3
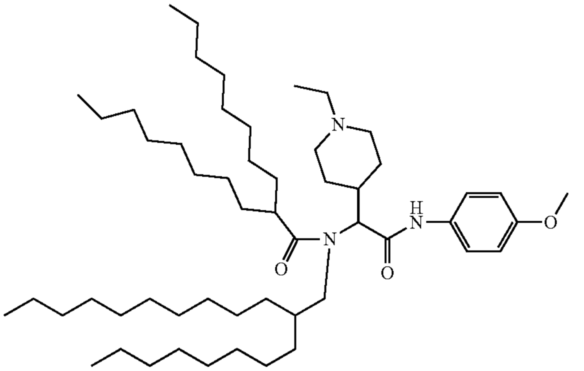
P314F1
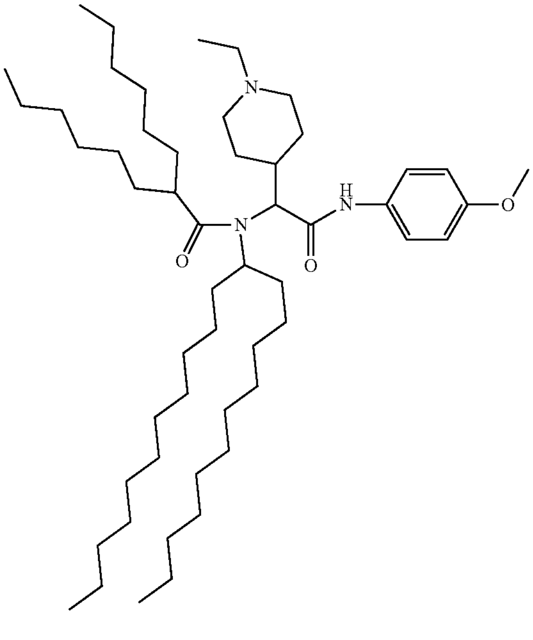
P314G1
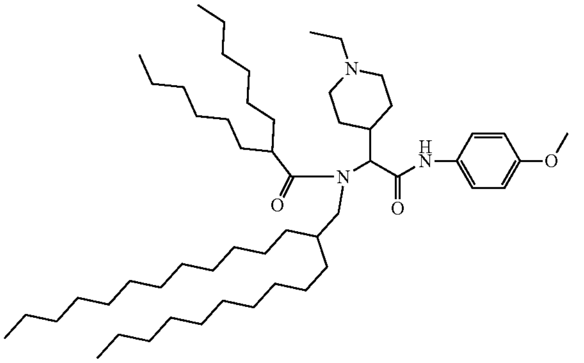

-continued
P316B6
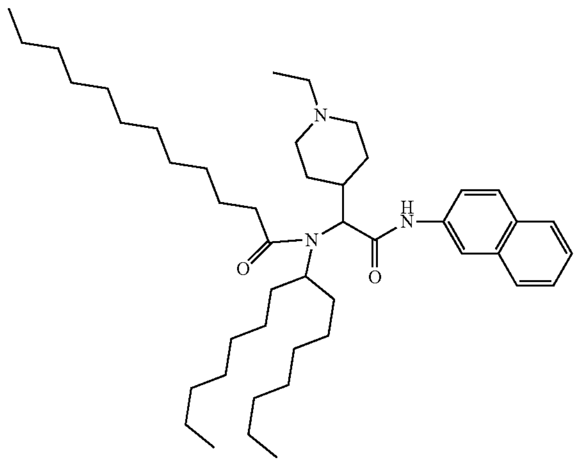
P316B7
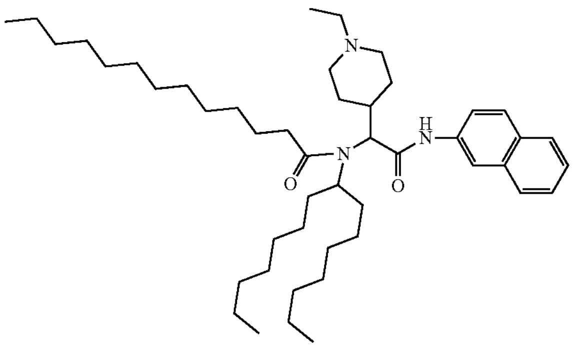
P316B8
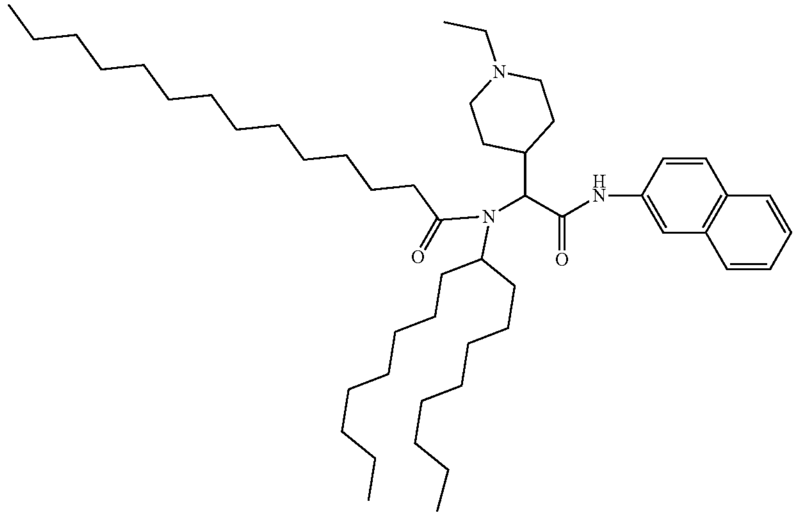
P316B10
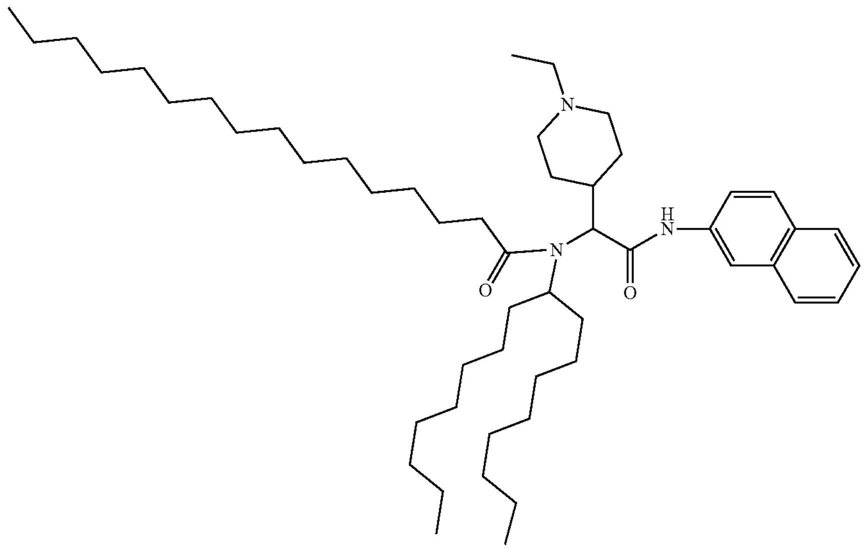

-continued
P316B11
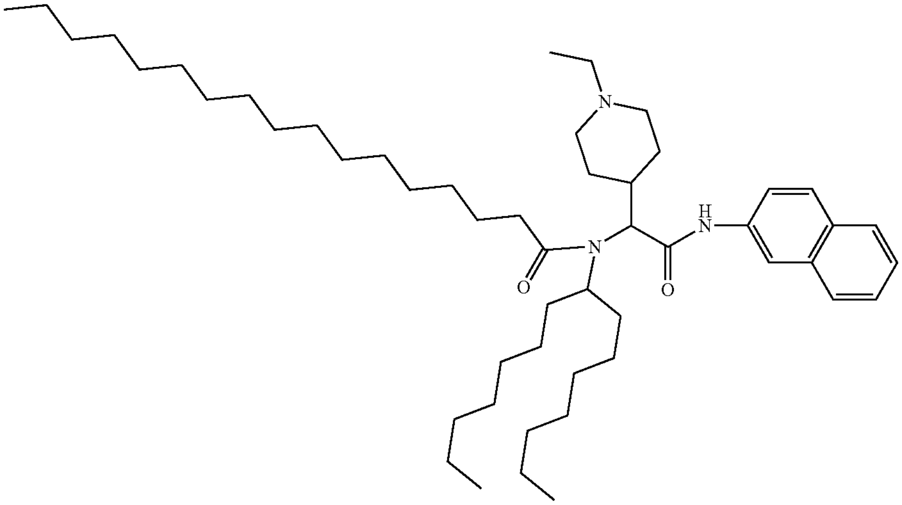
P316C8
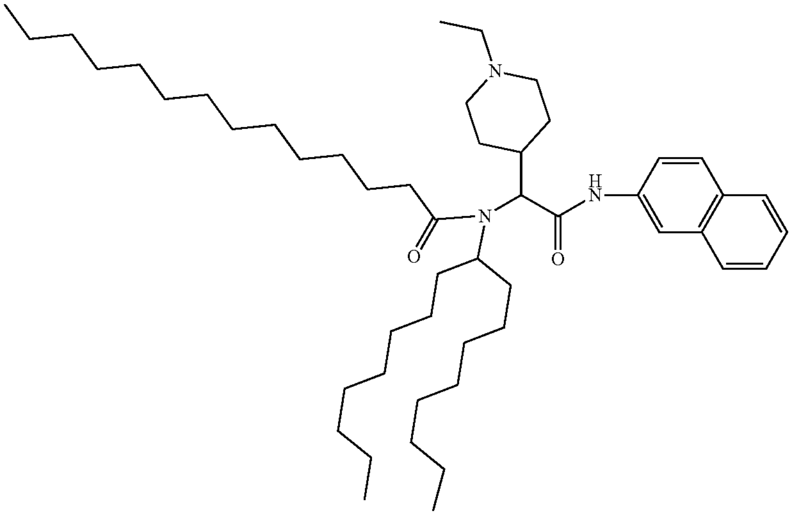
P316C11
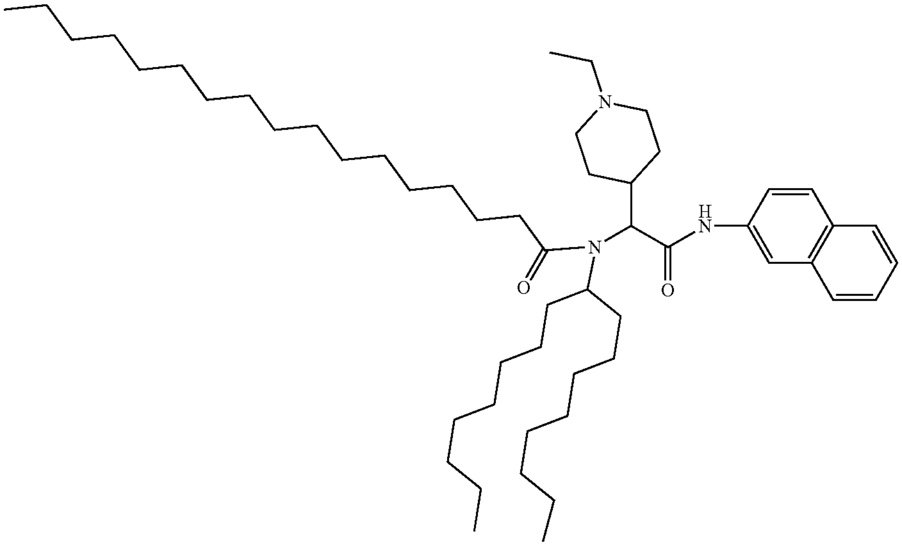

-continued
P316E1
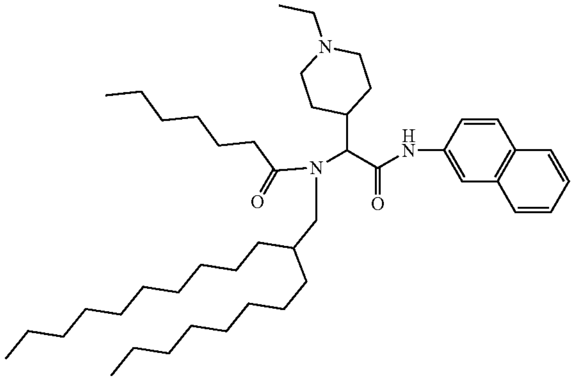
P316E5
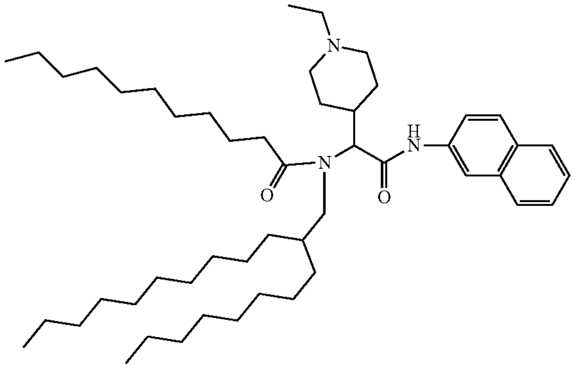
P316E6
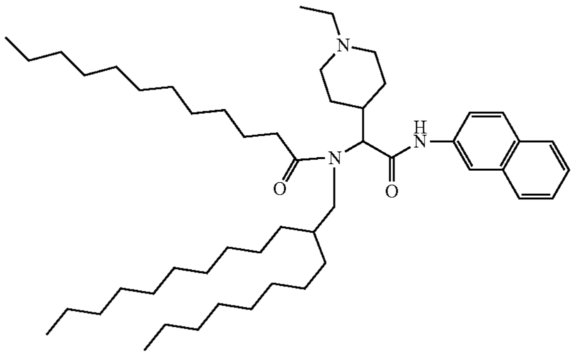
P316E7
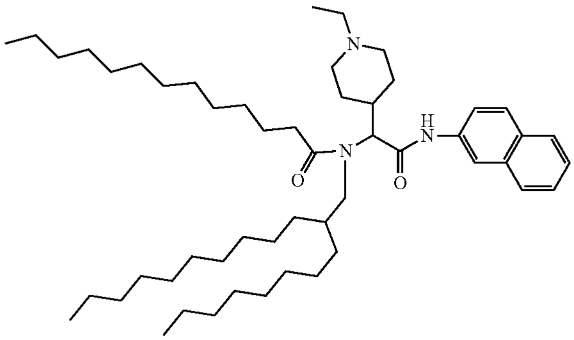
P316E8
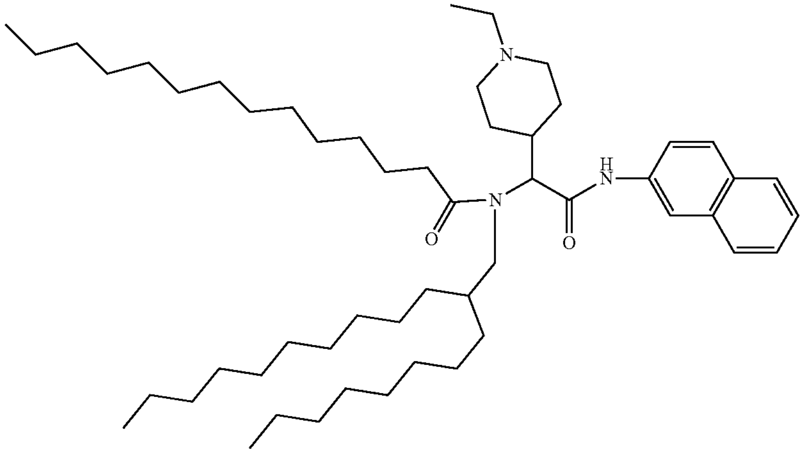

-continued
P316E10
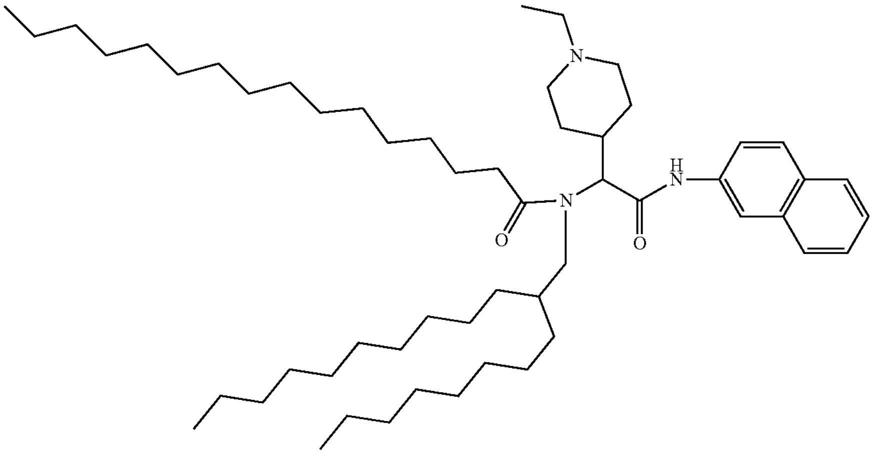
P316E11
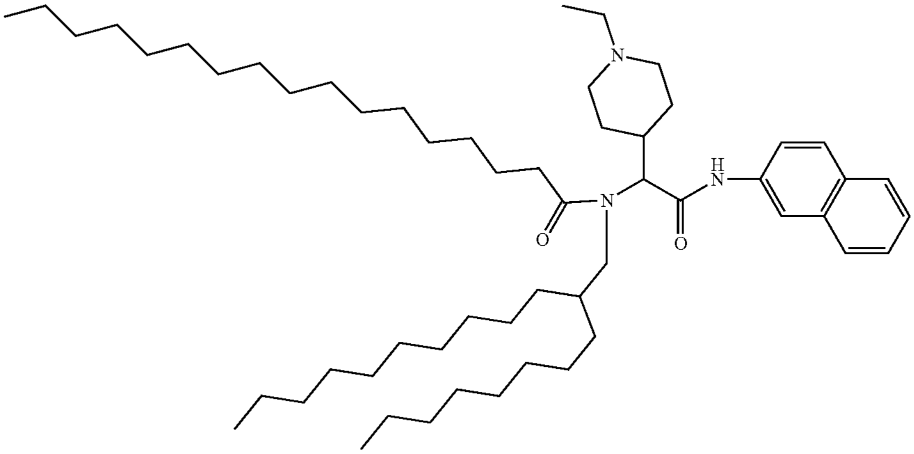
P316E12
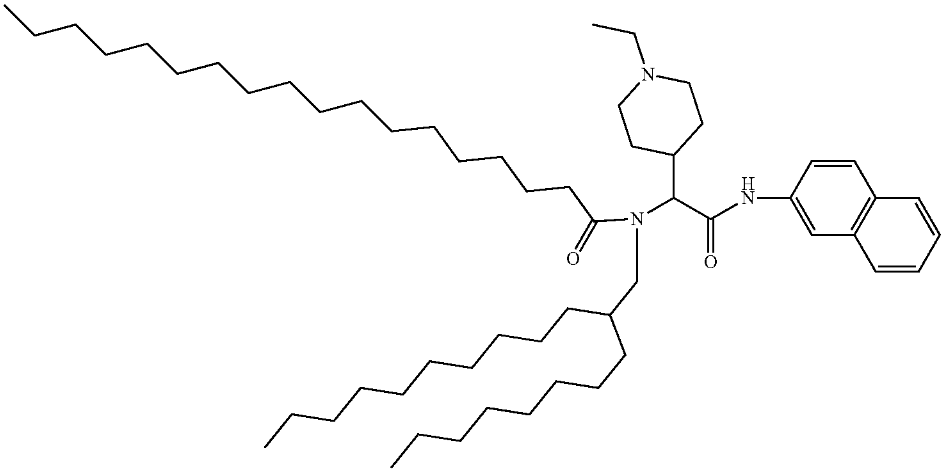

-continued
P318B1
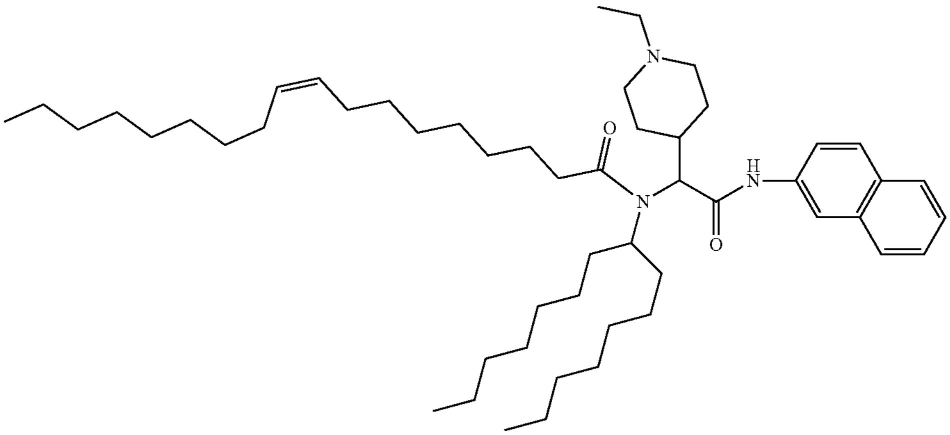
P318C1
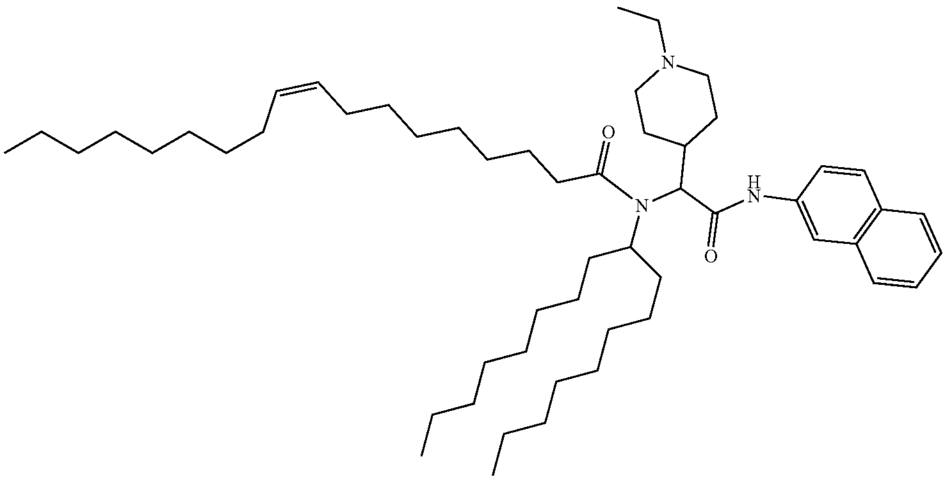
P318E1
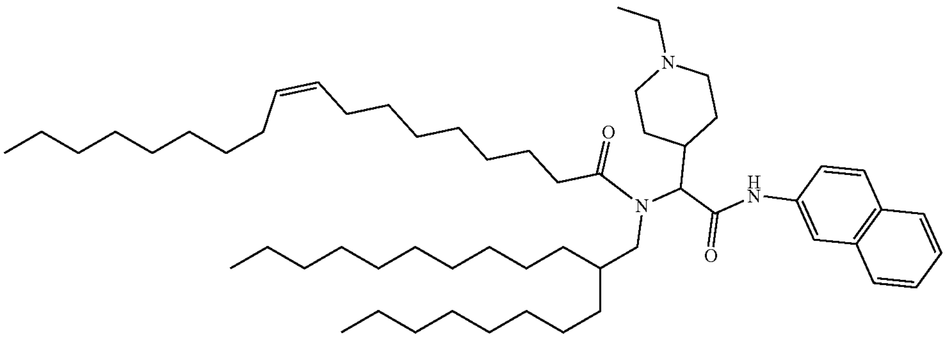

P318F1
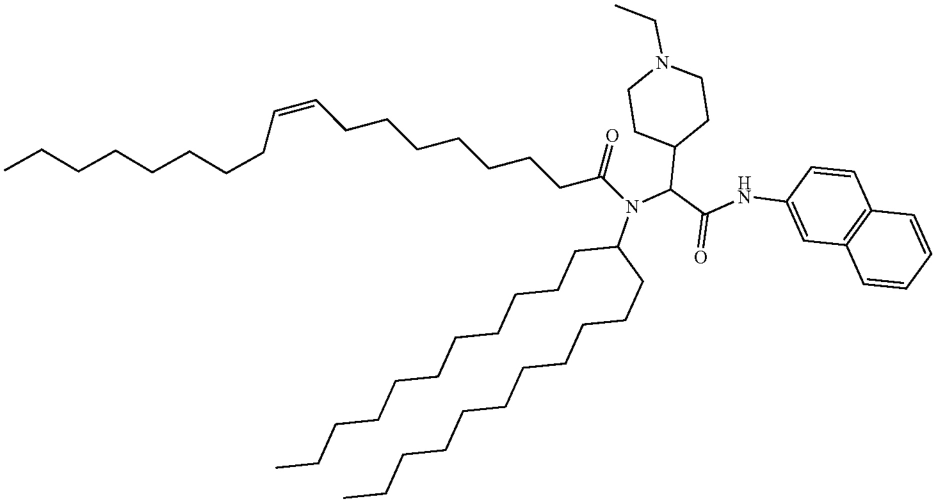
P318G1
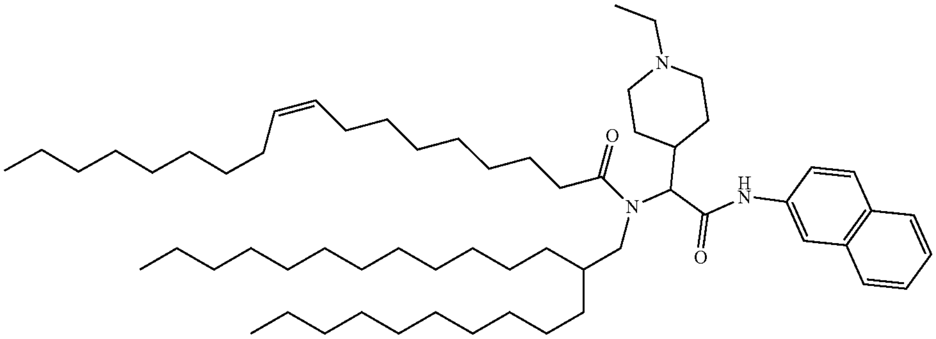
P318B3
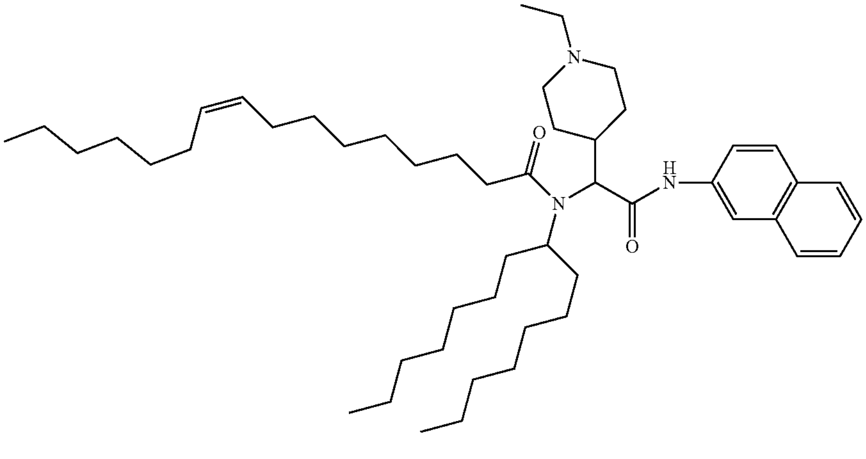

-continued
P318B6
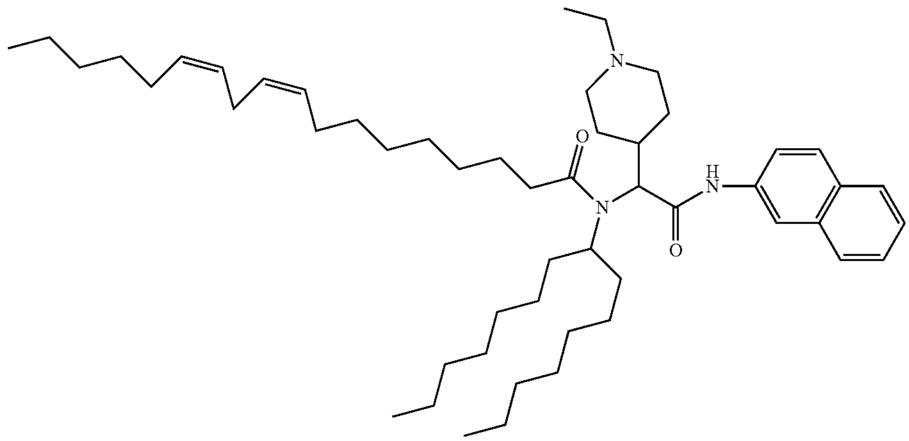
P318E6
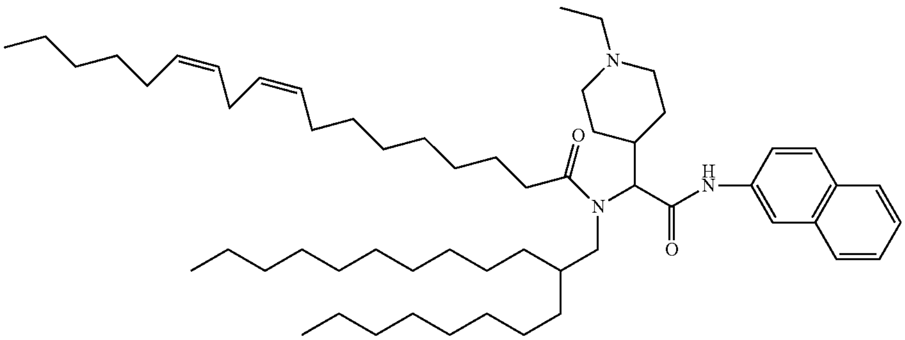
P318B7
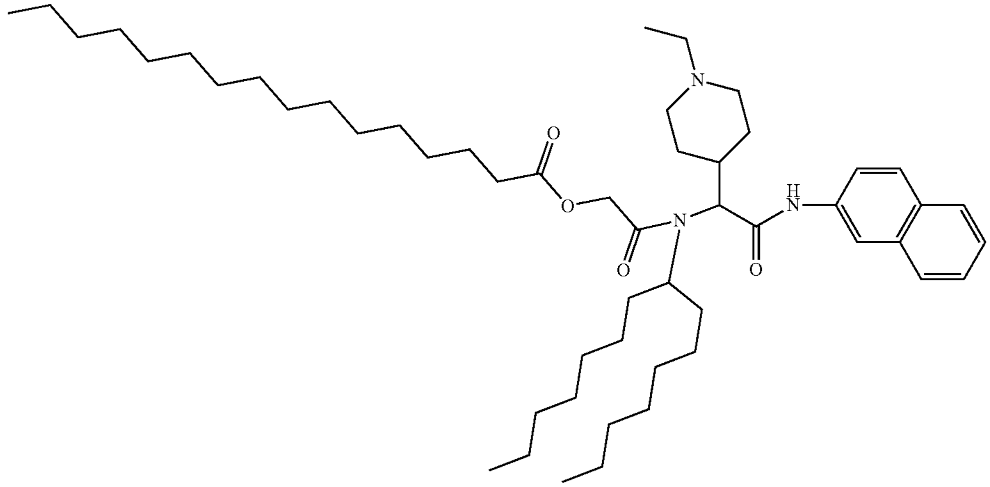

-continued
P318C7
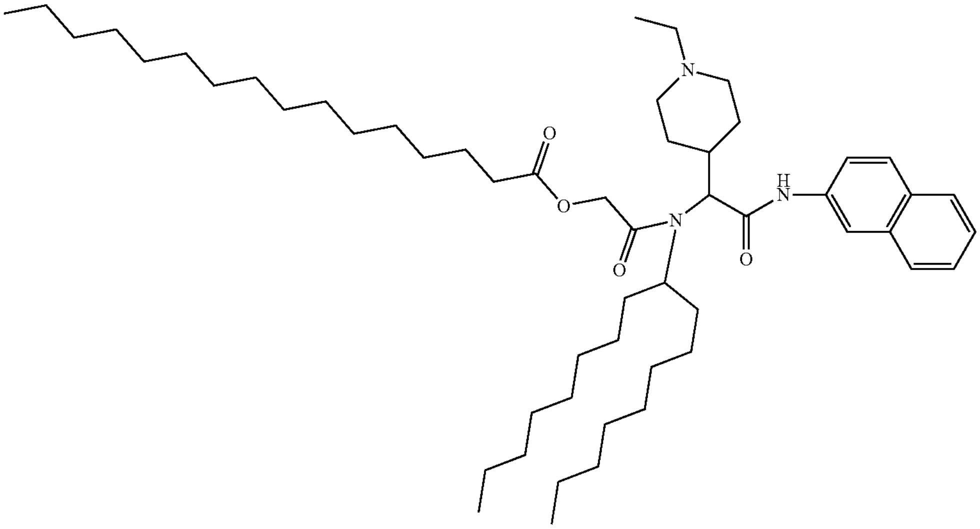
P318D7
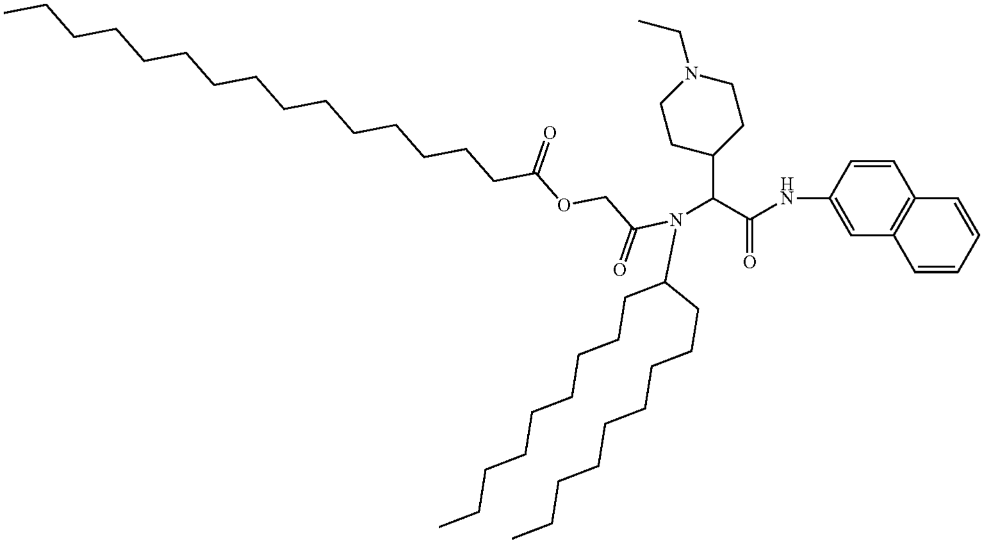
P318E7
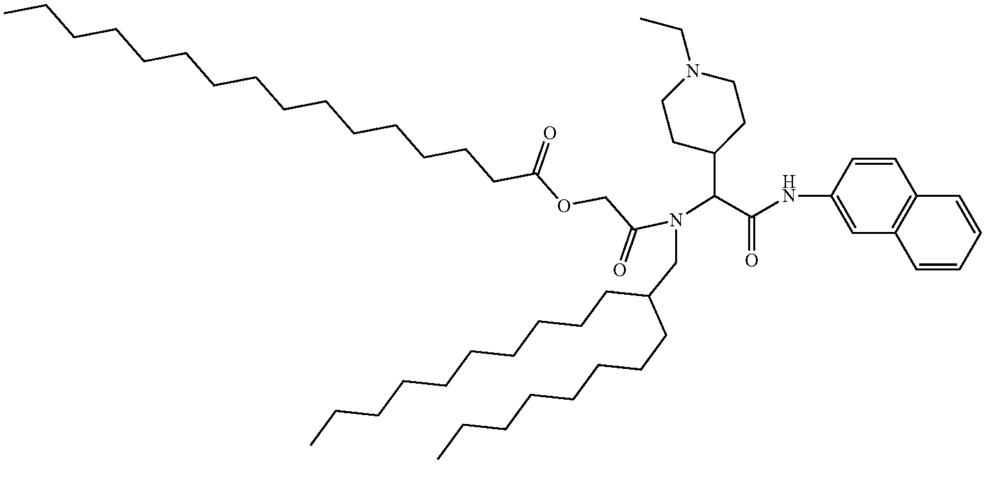

-continued
P318E10
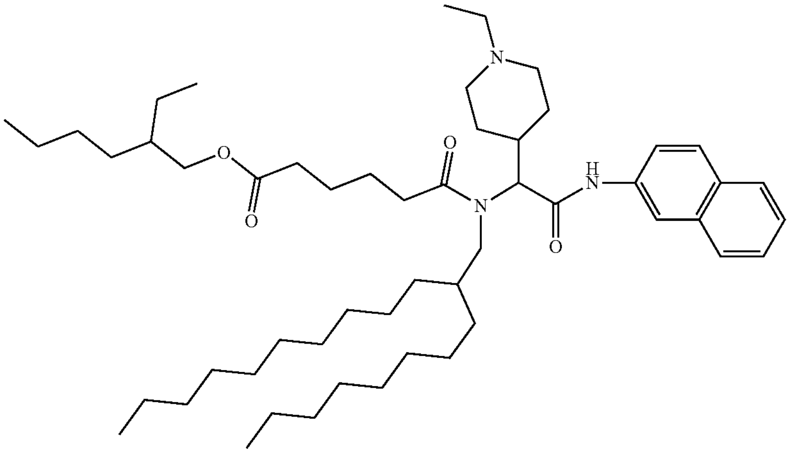
P318G10
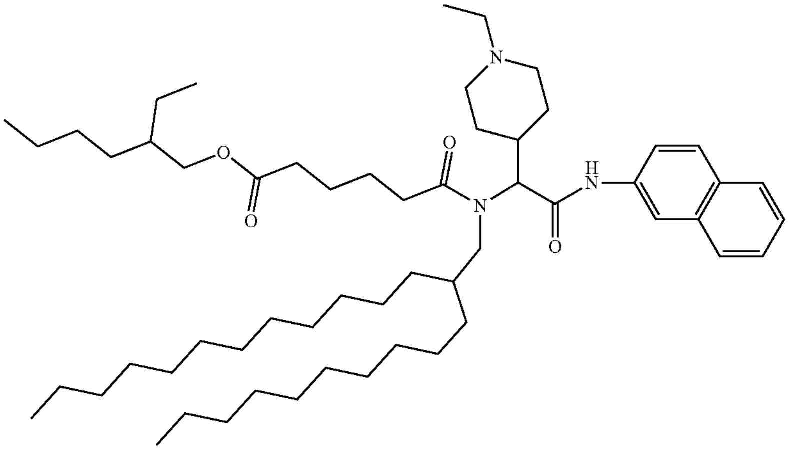
P318E12
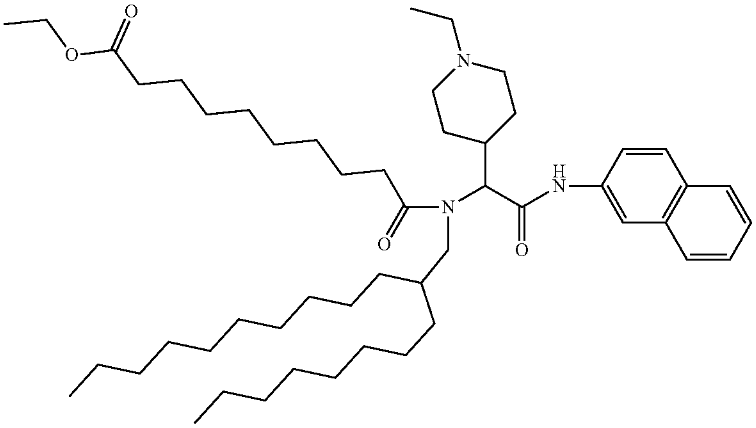

-continued
P319B7
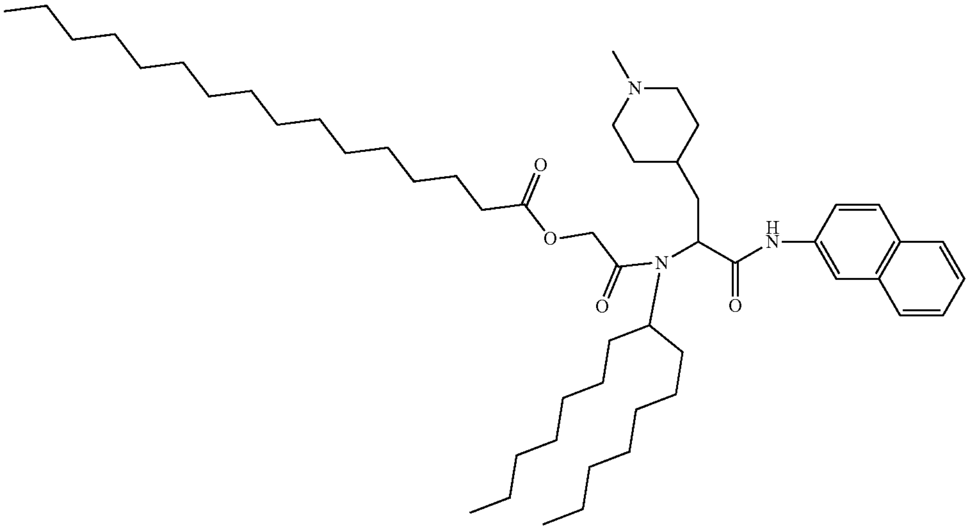
P319C1
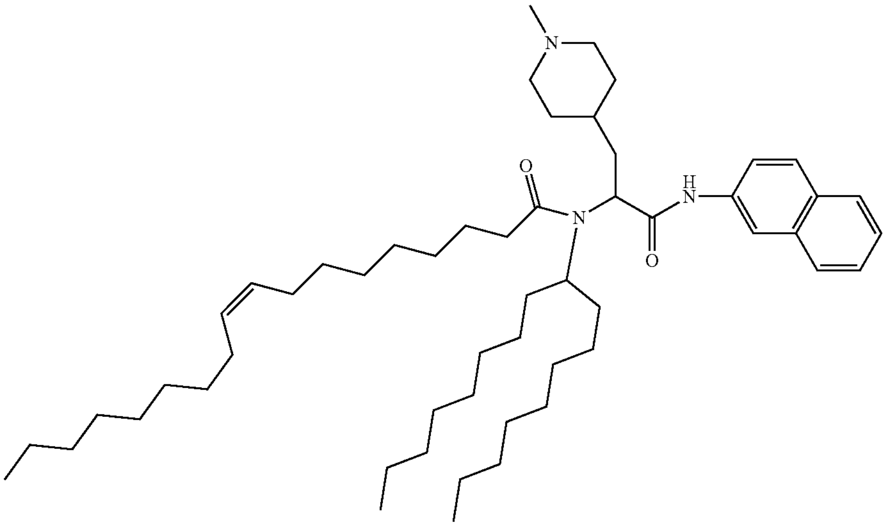
P320E1
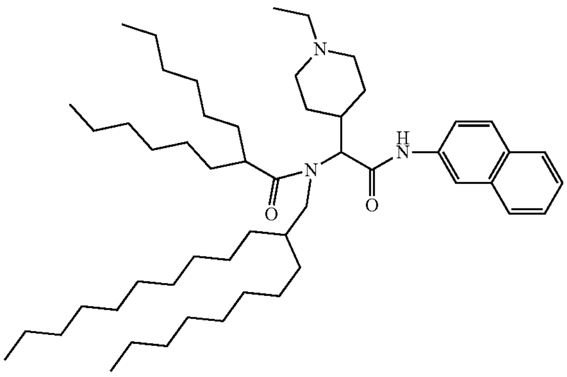
P320G1
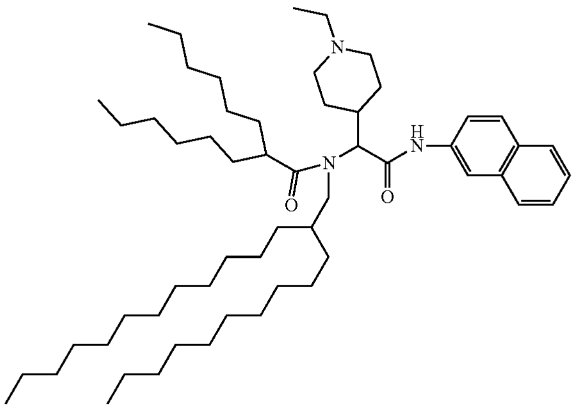

-continued
P320E2
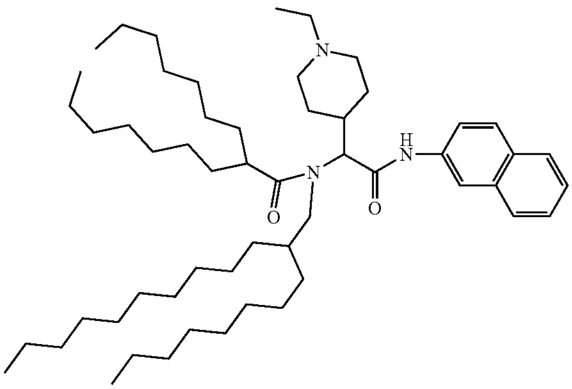
P320E3
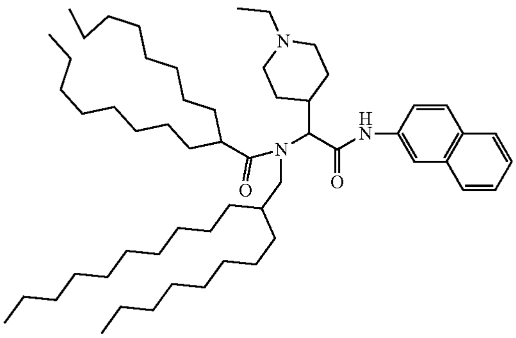
P320E7
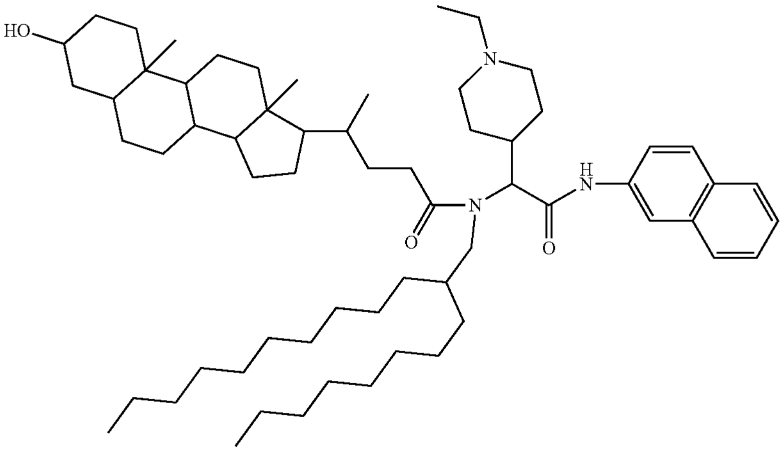
P321E1
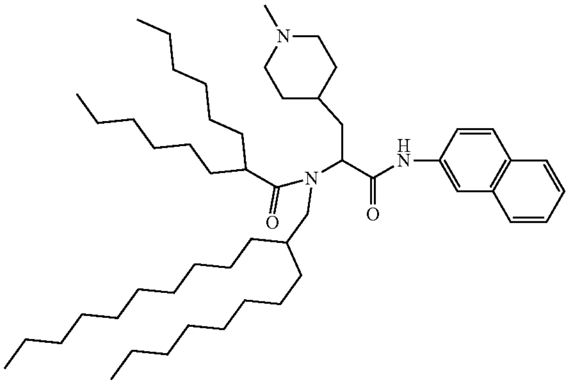
P321G1
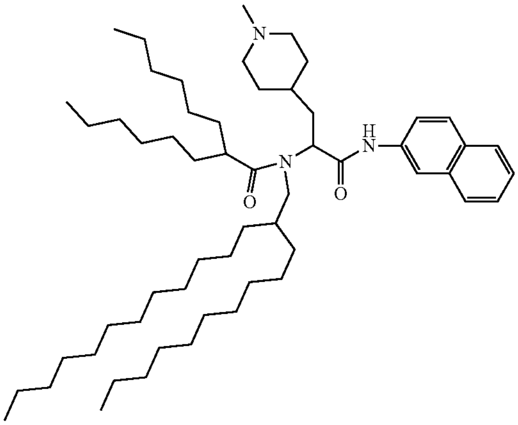

-continued
P328A10
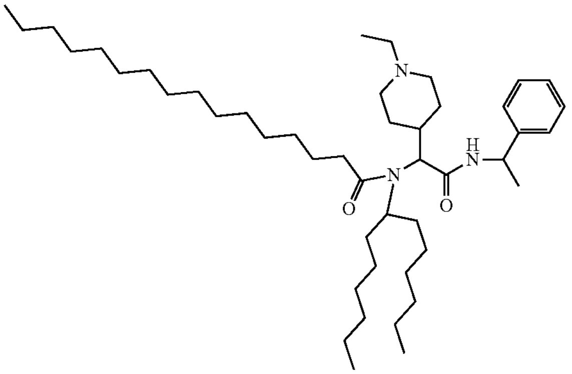
P328A11
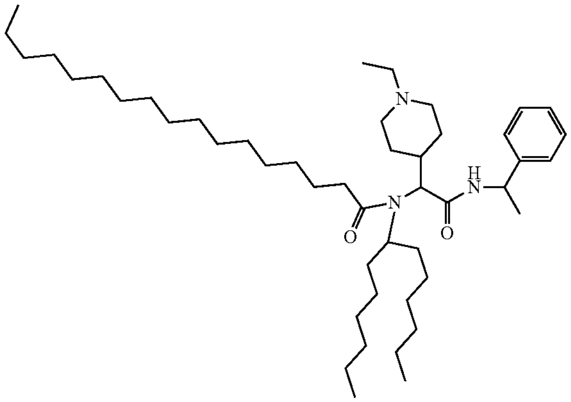
P329E7
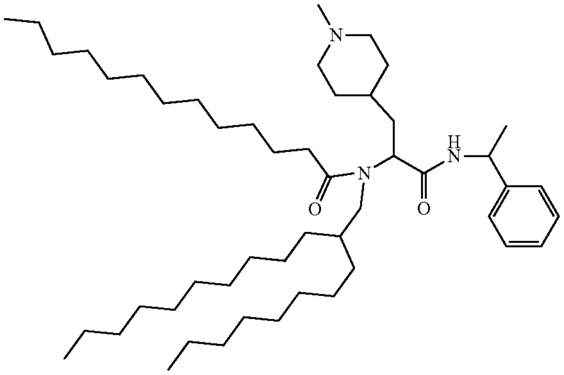
P329E8
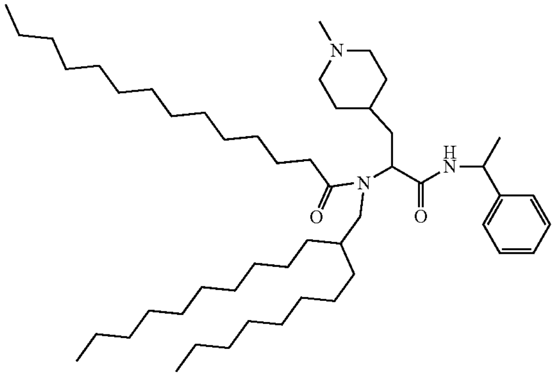
P329E10
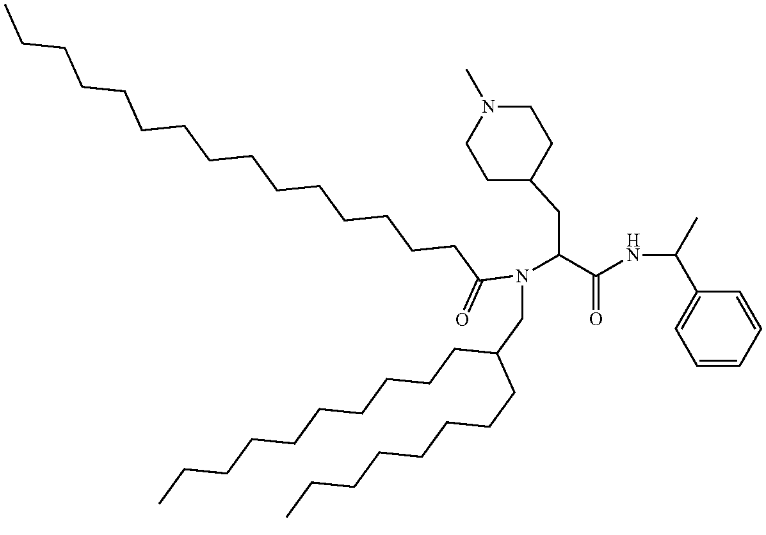

-continued
P329E11
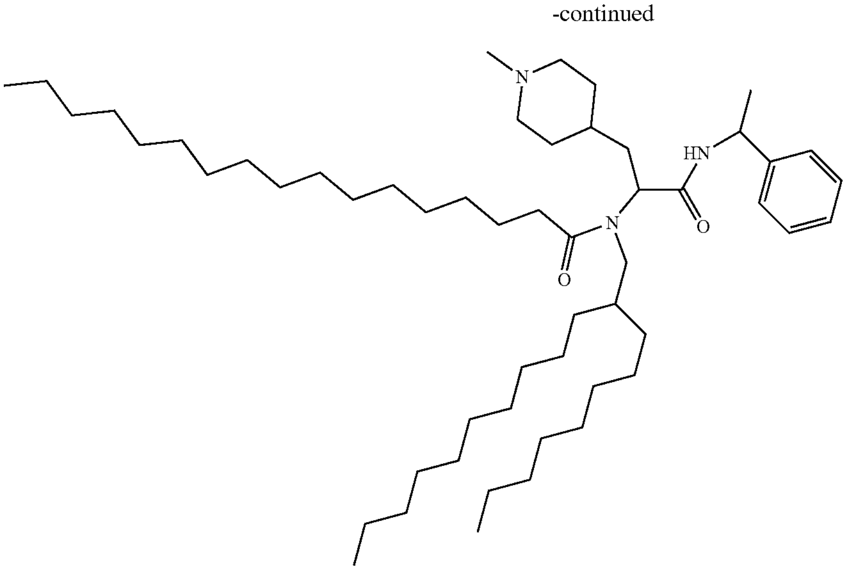
P329E12
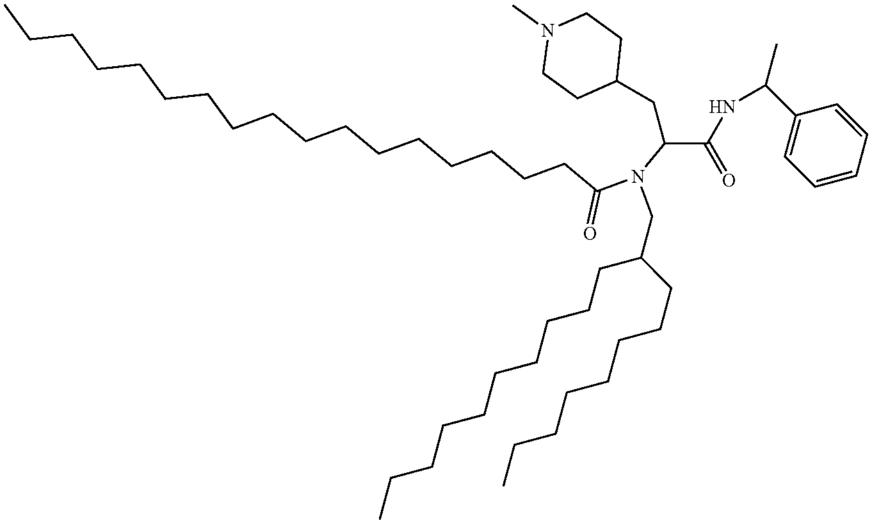
P330A1
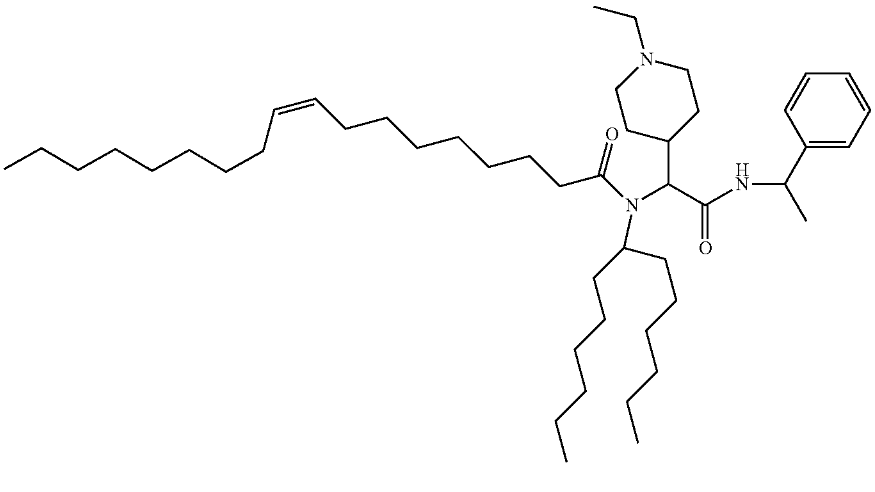

-continued
P330A7
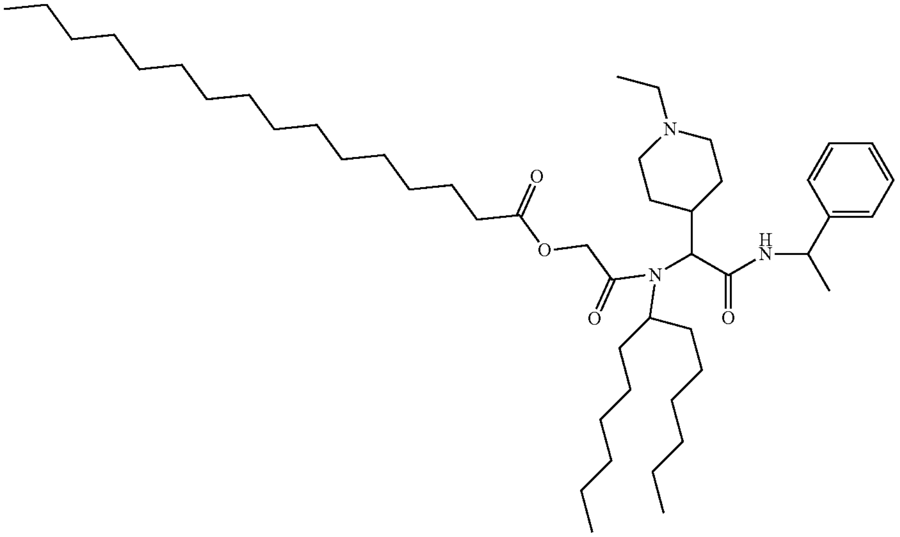
P330B1
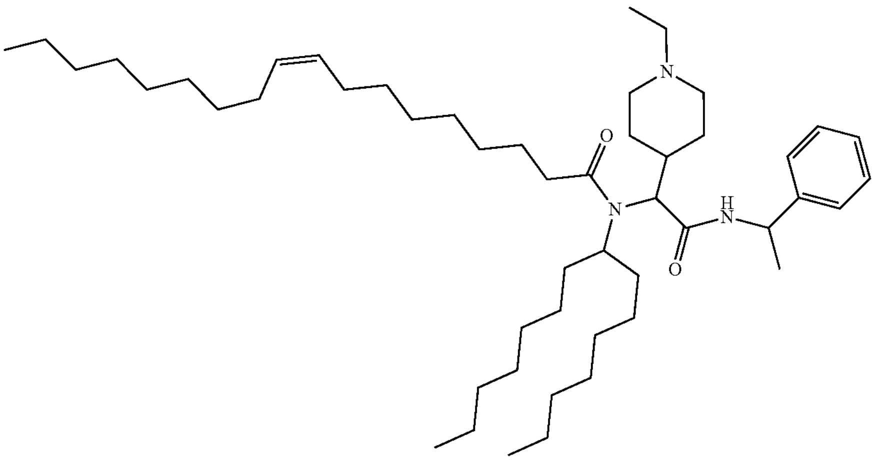
P330C1
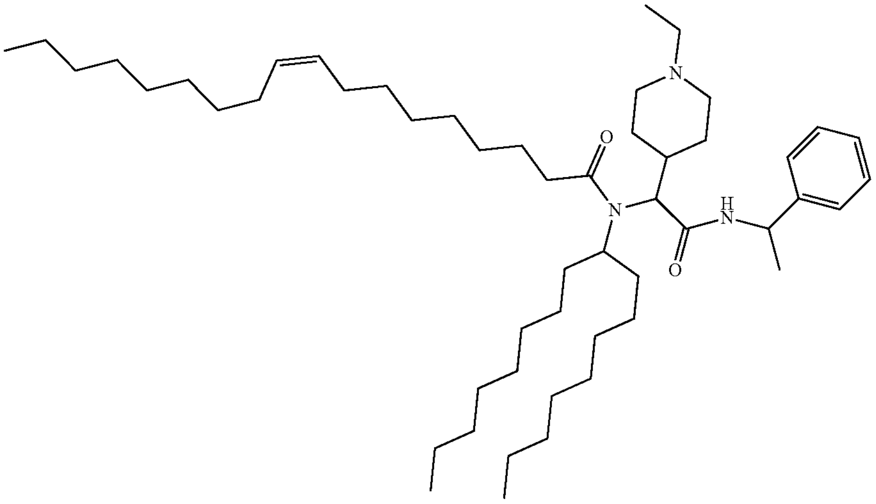

-continued
P330E1
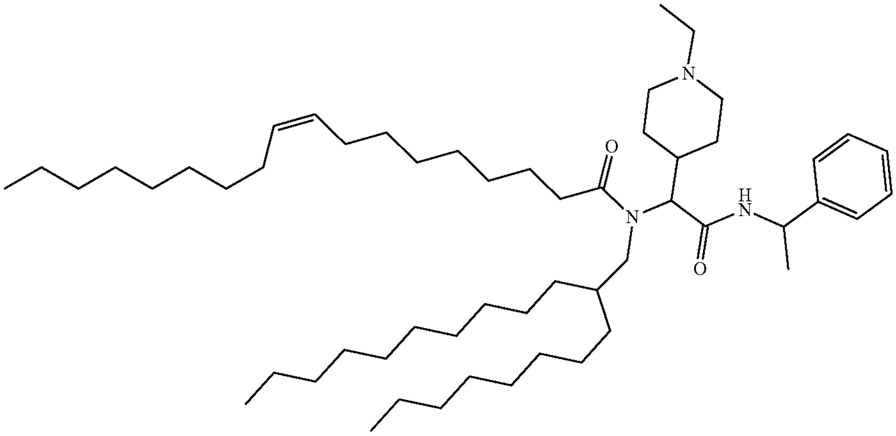
P330E6
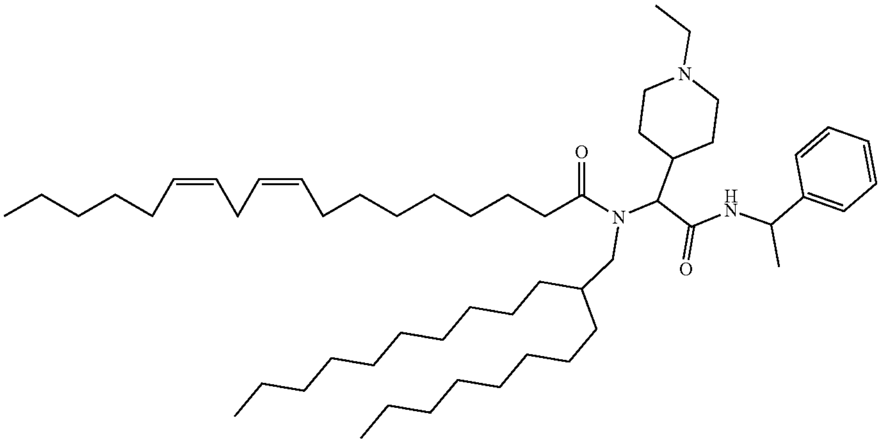
P330E8
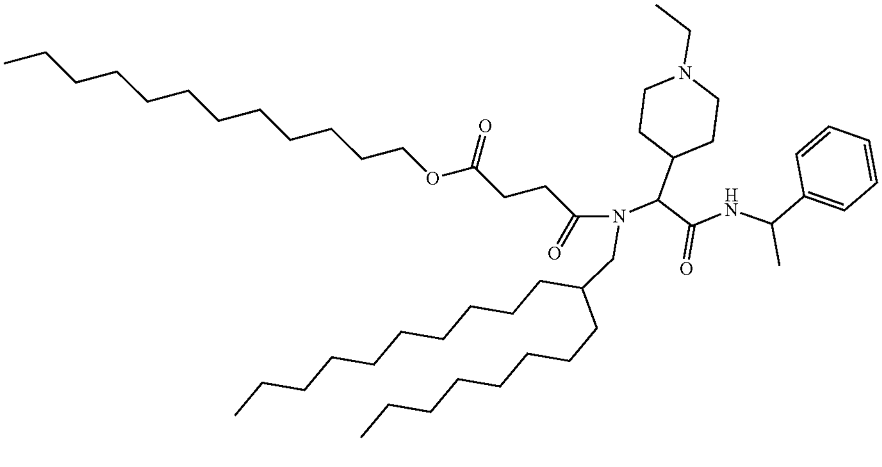

-continued
P331A1
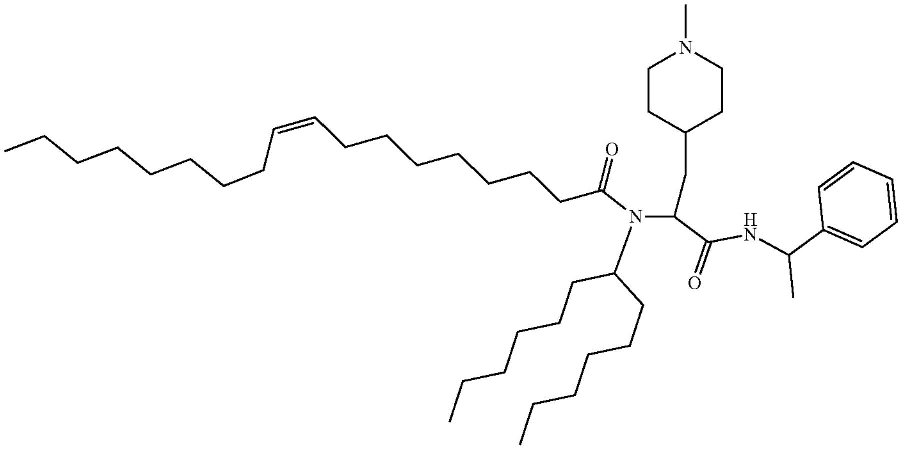
P331B1
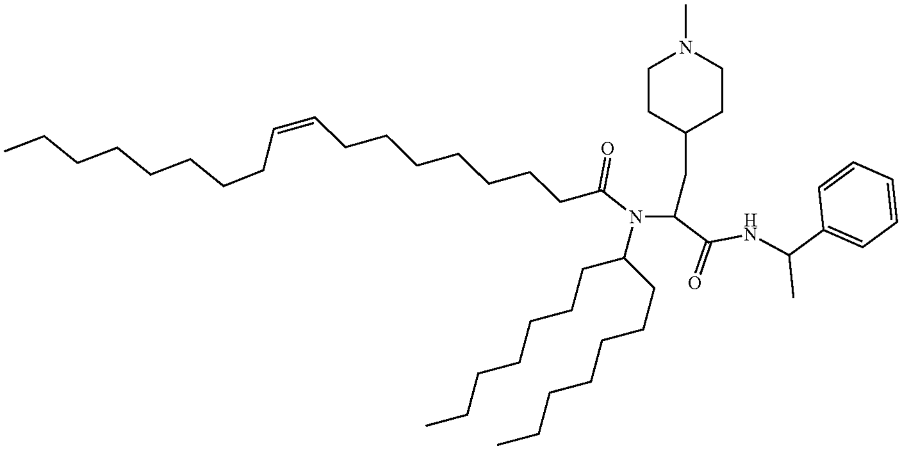
P331B3
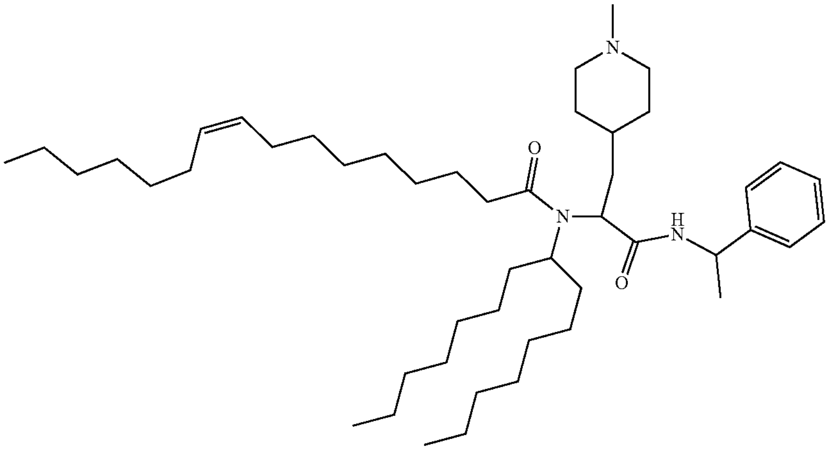

-continued
P331B6
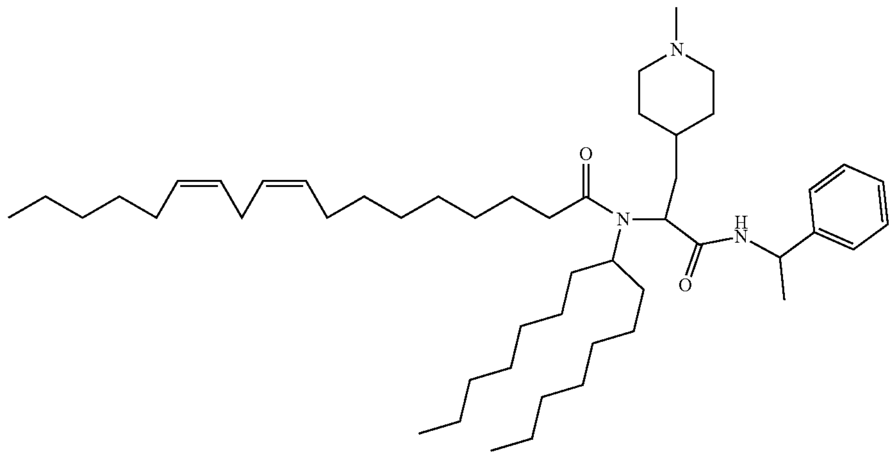
P331B8
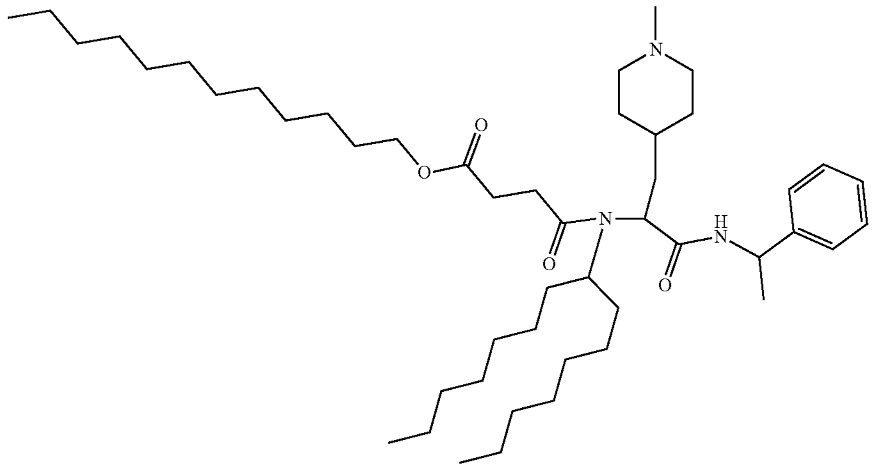
P331C1
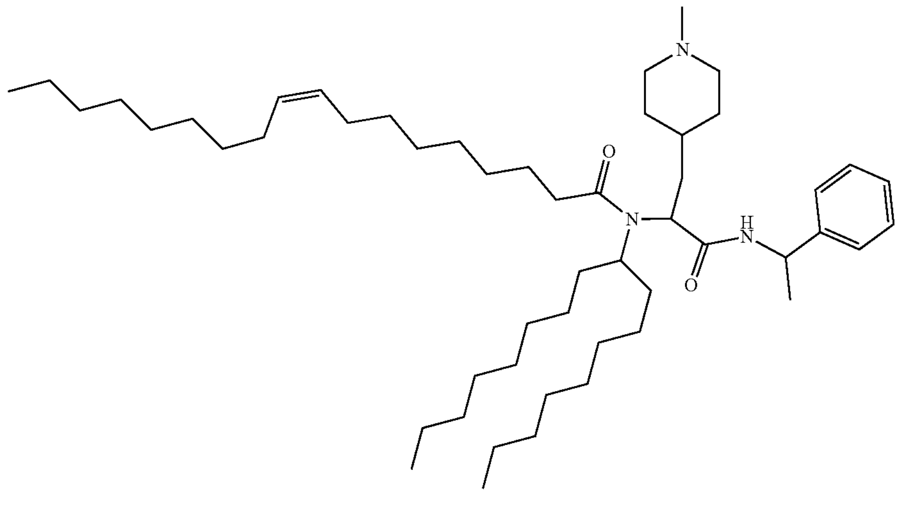

-continued
P331C4
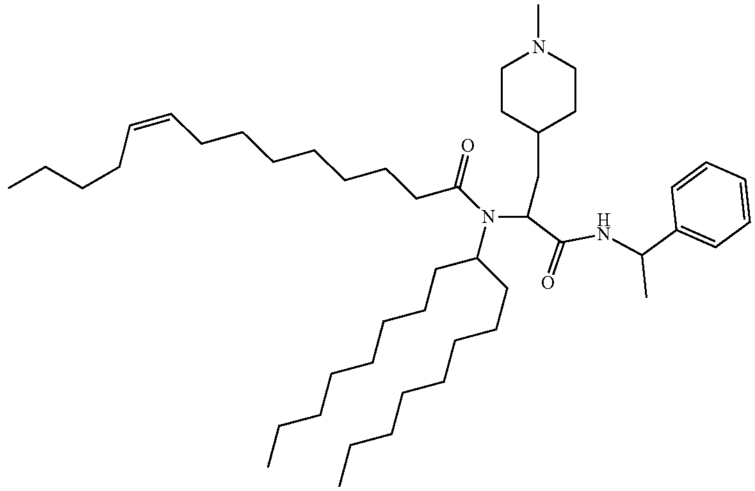
P331D1
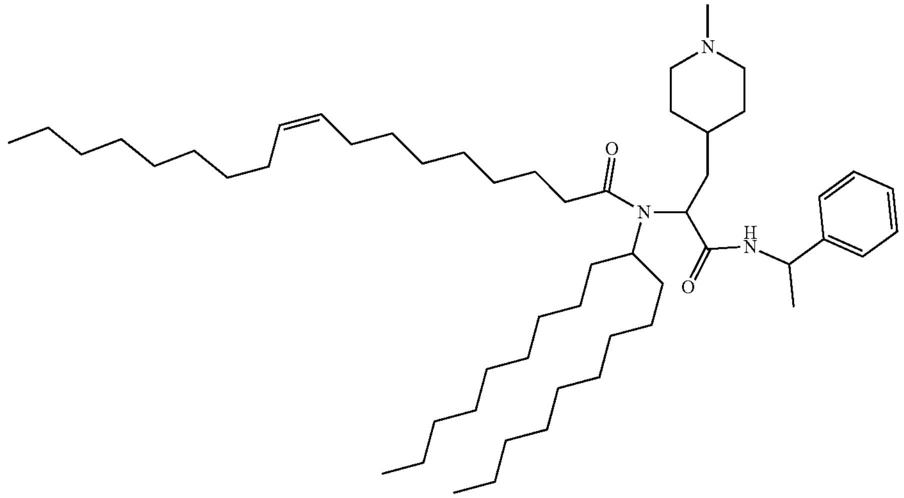
P331E1
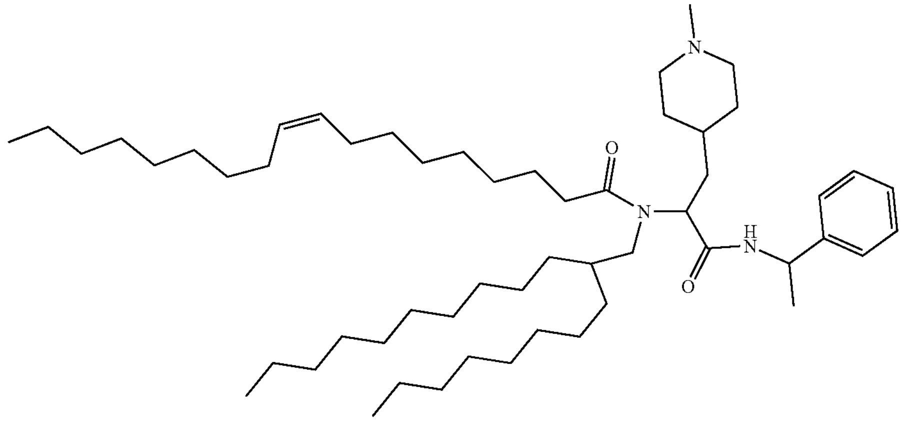

-continued
P331E6
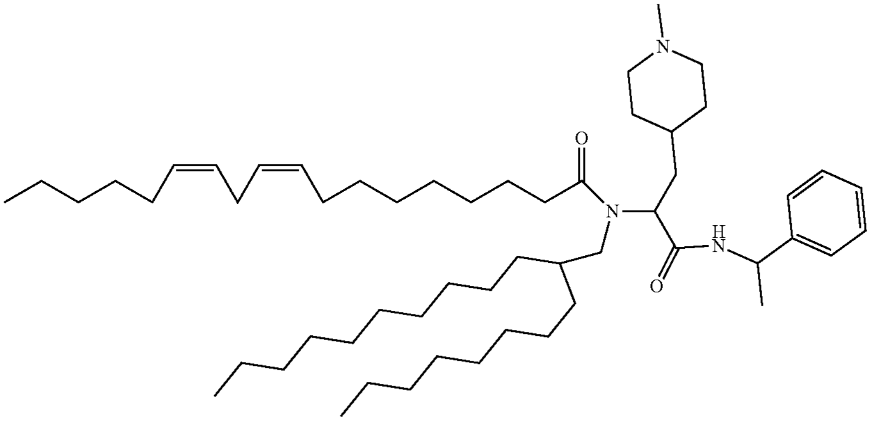
P332G1
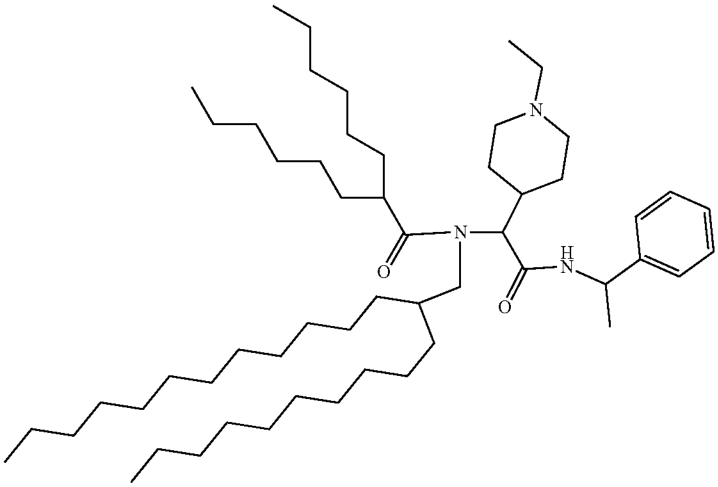
P341A9
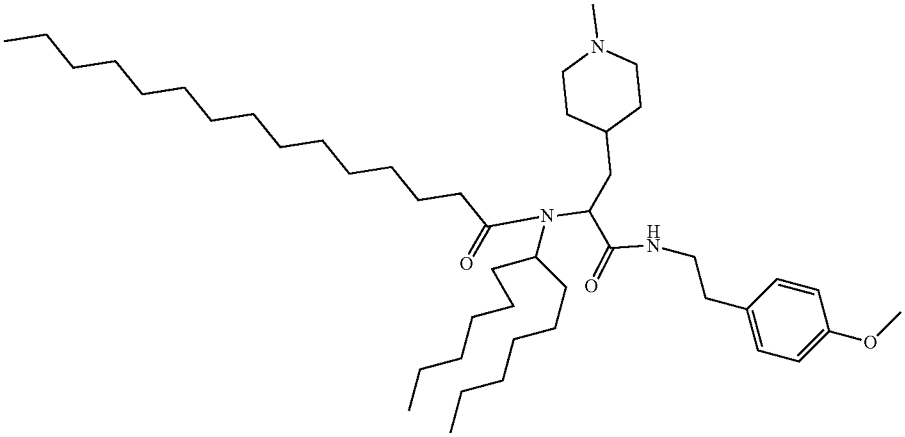

-continued
P341A11
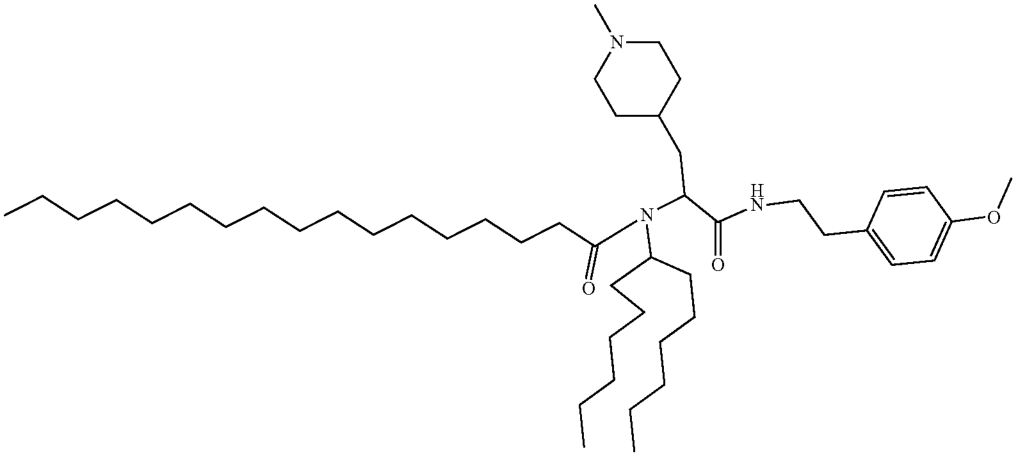
P341C9
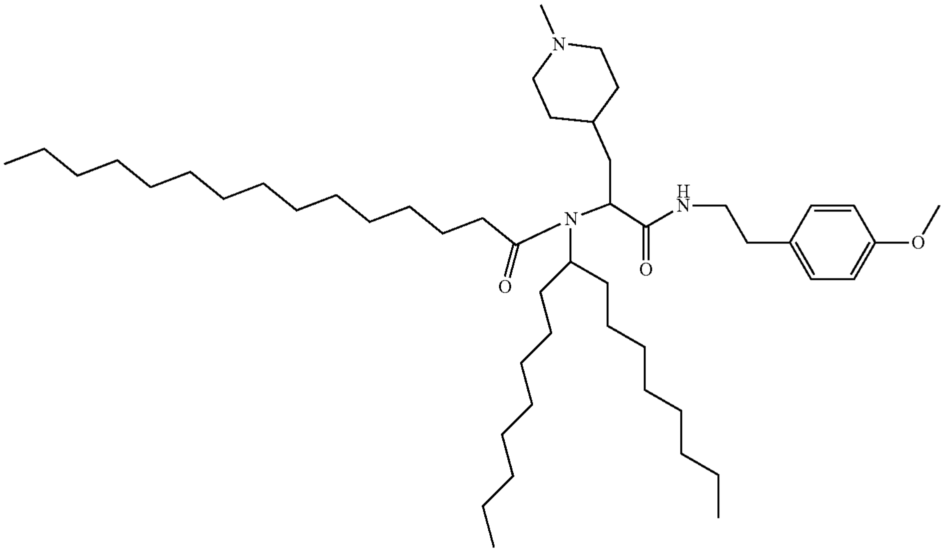
P341C11
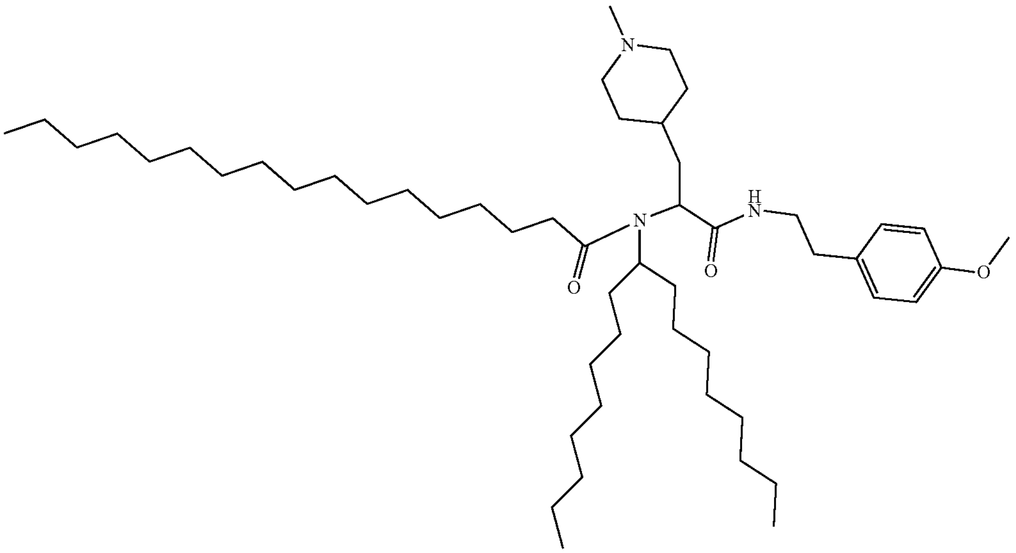

-continued
P341C12
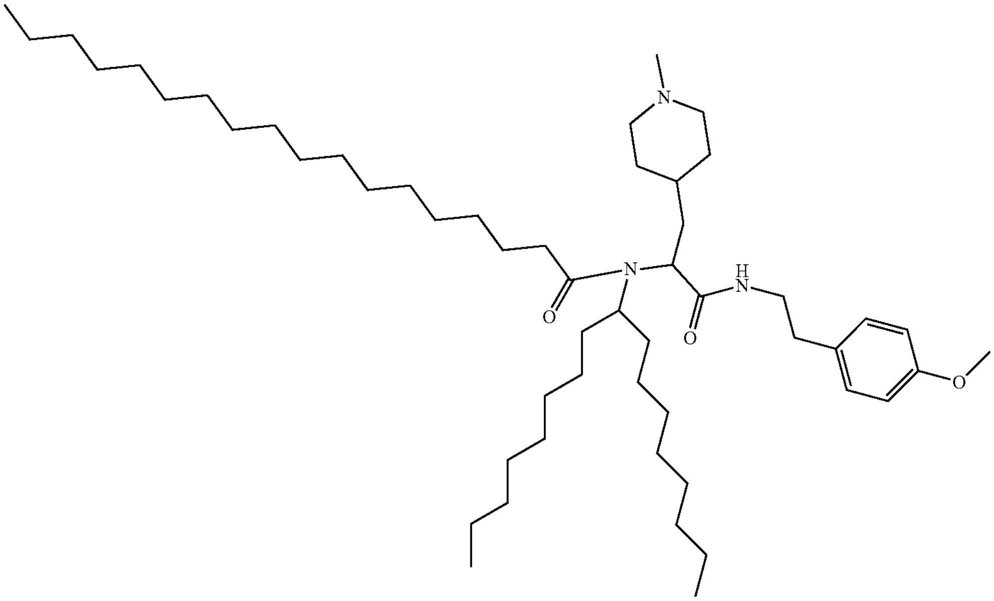
P341D11
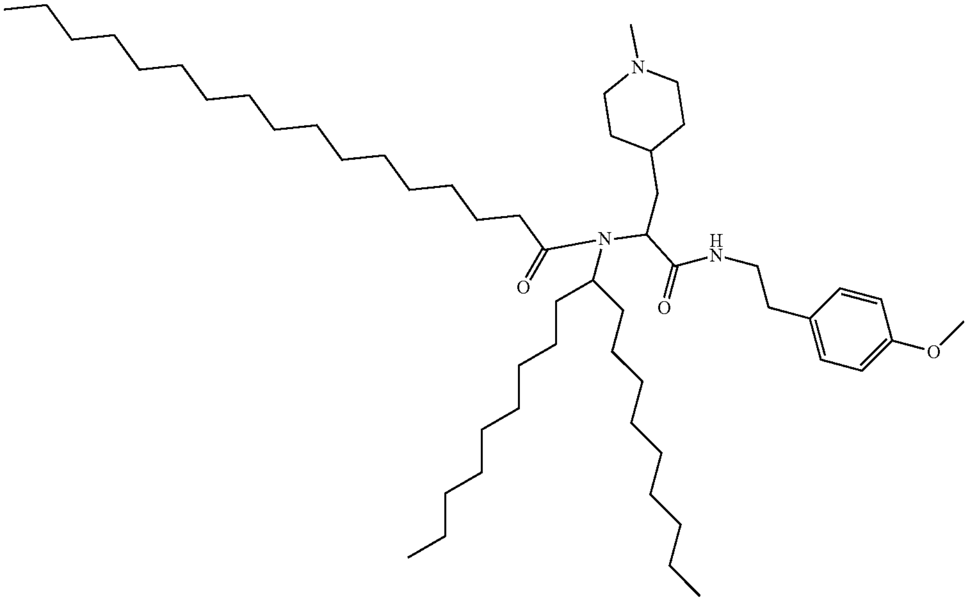
P341E1
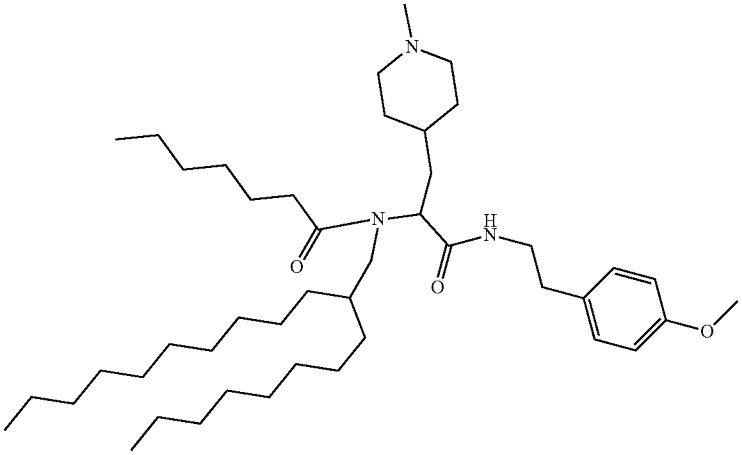

-continued
P341G11
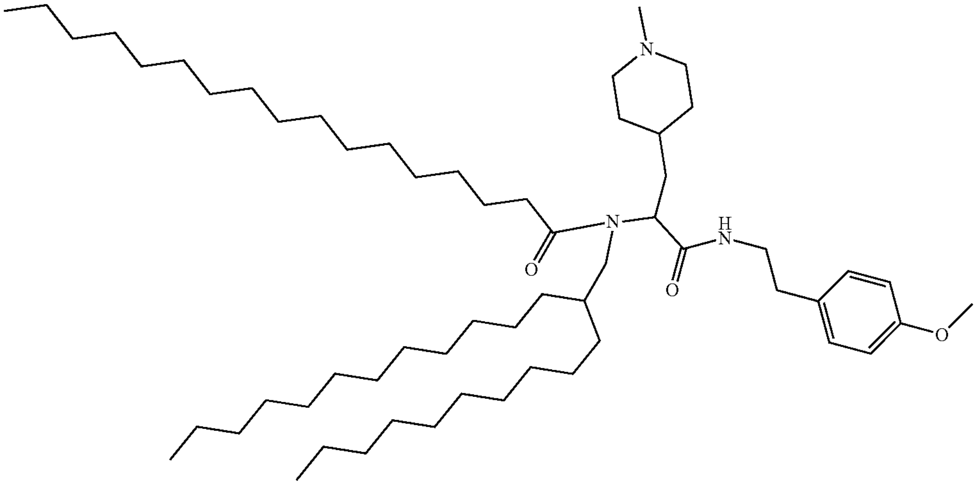
P342B1
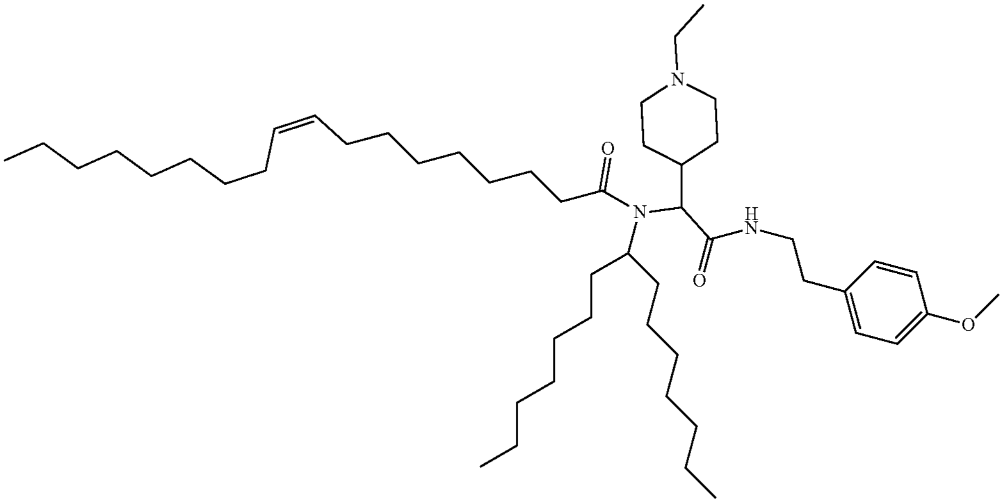
P342F1
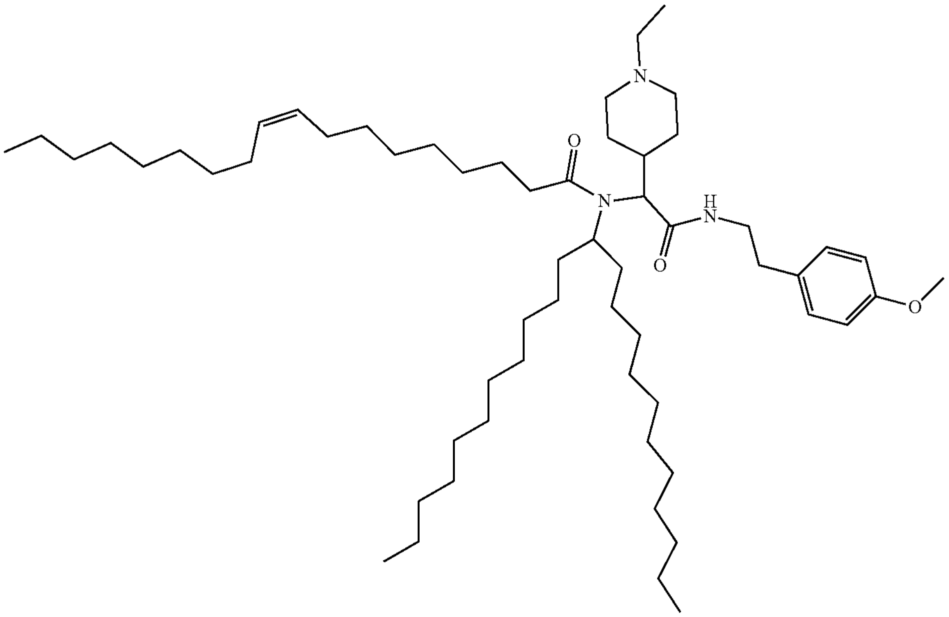

-continued
P342F8
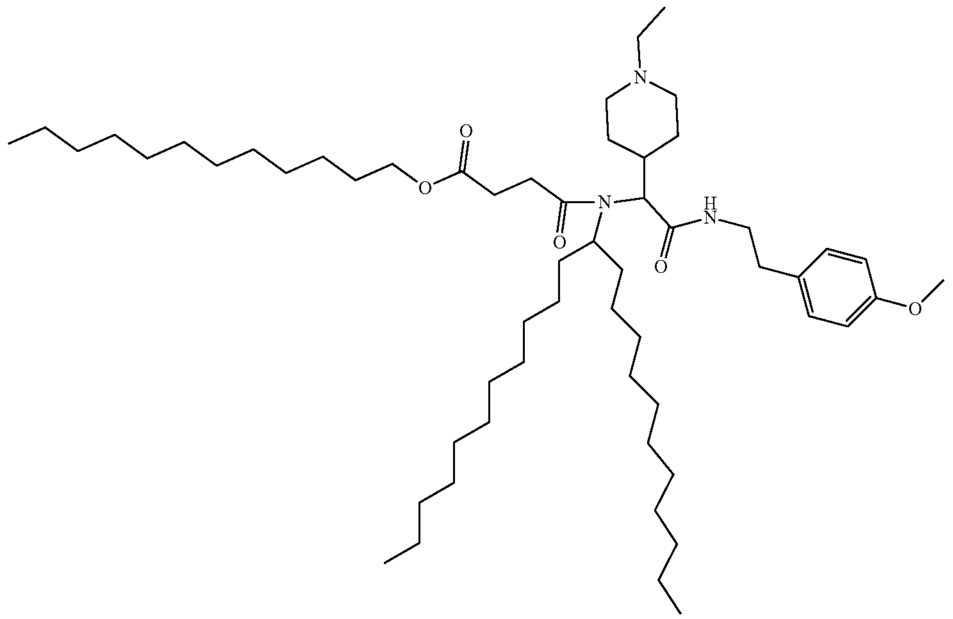
P34F12
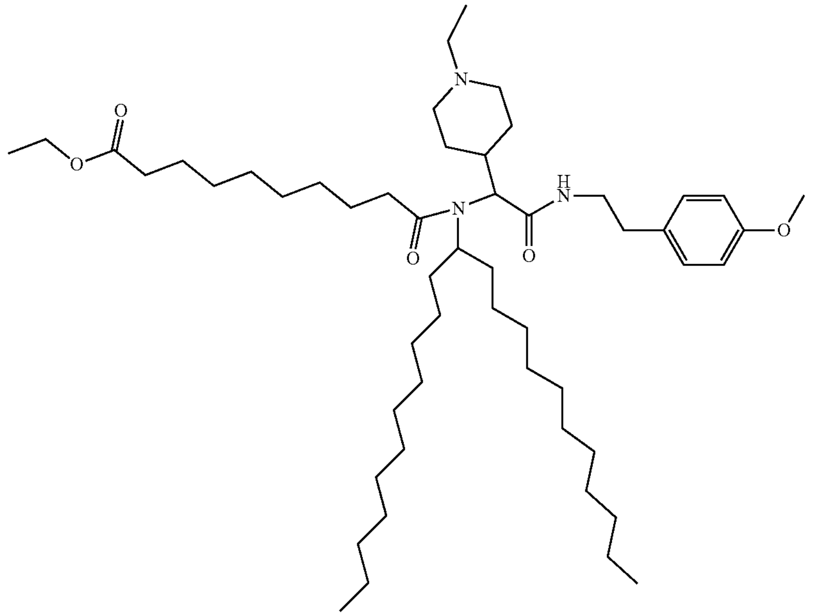

-continued
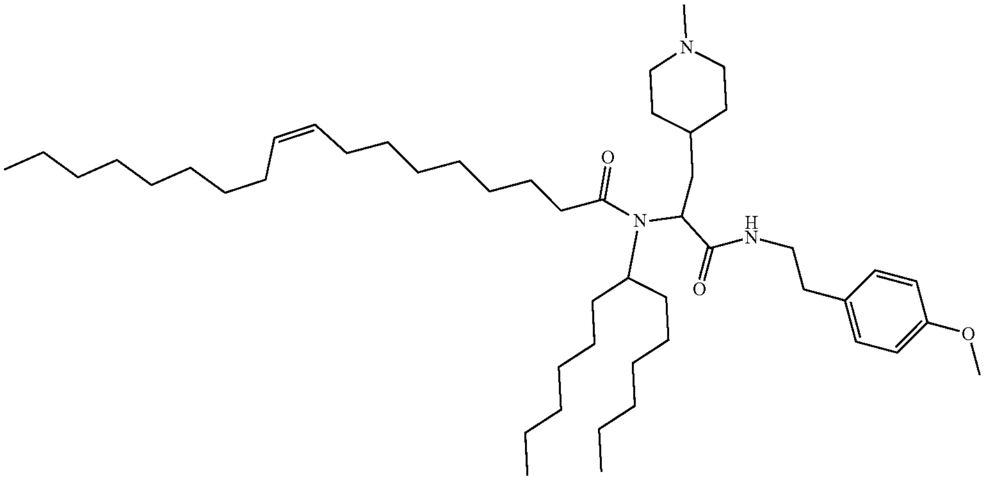
P343A1
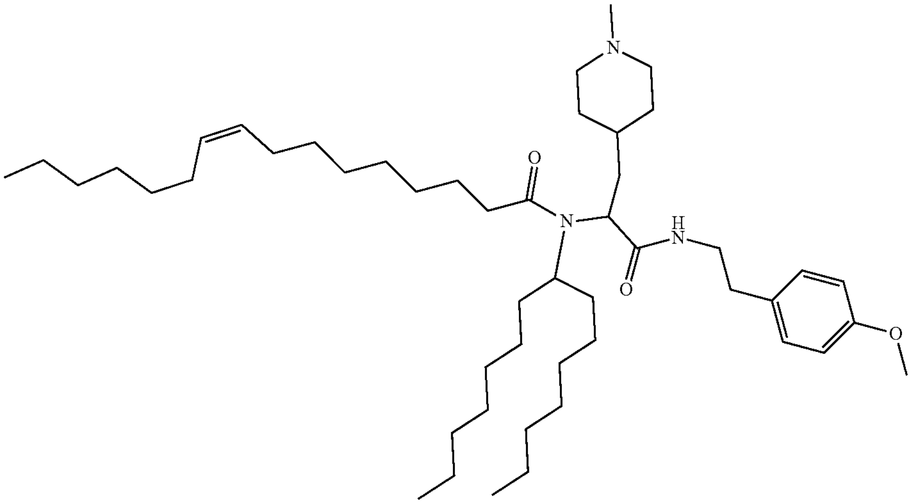
P343B3
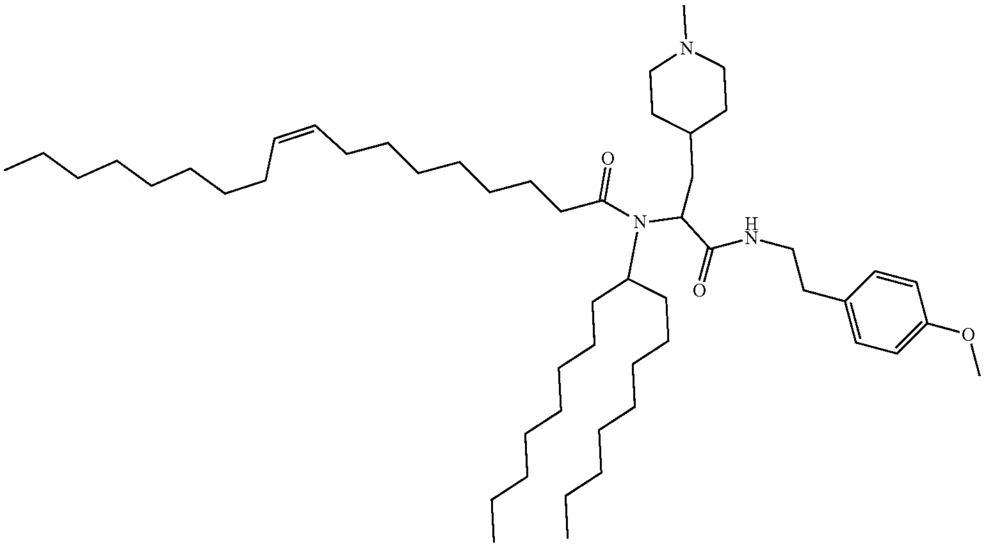
P343C1

-continued
P343C3
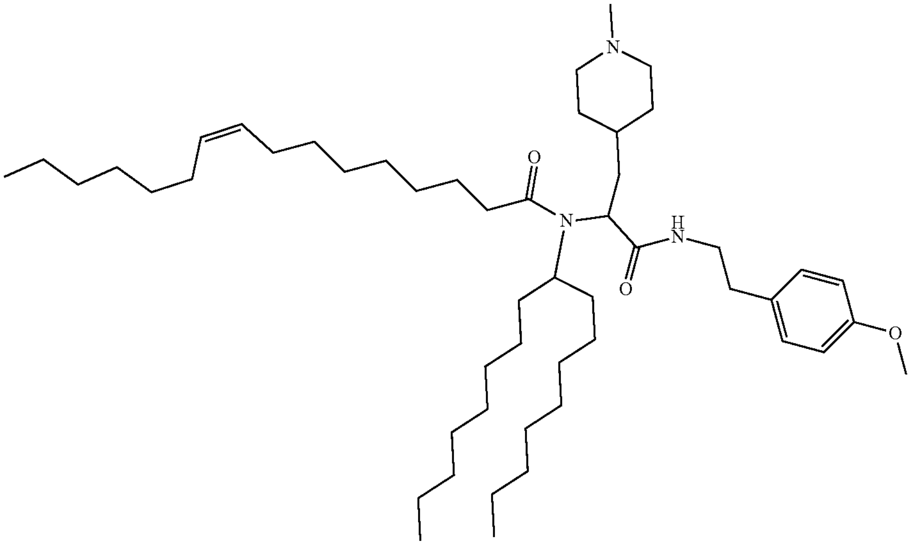
P343C6
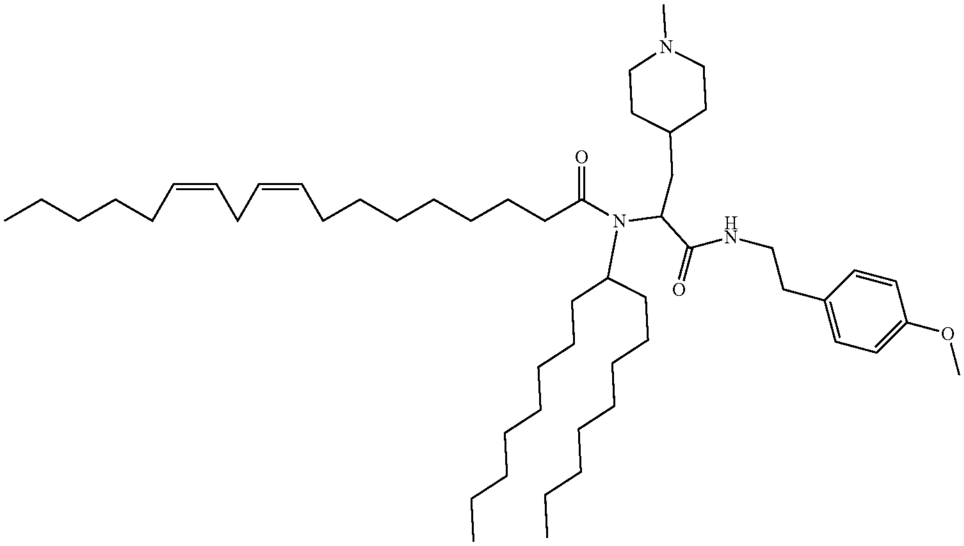
P343C8
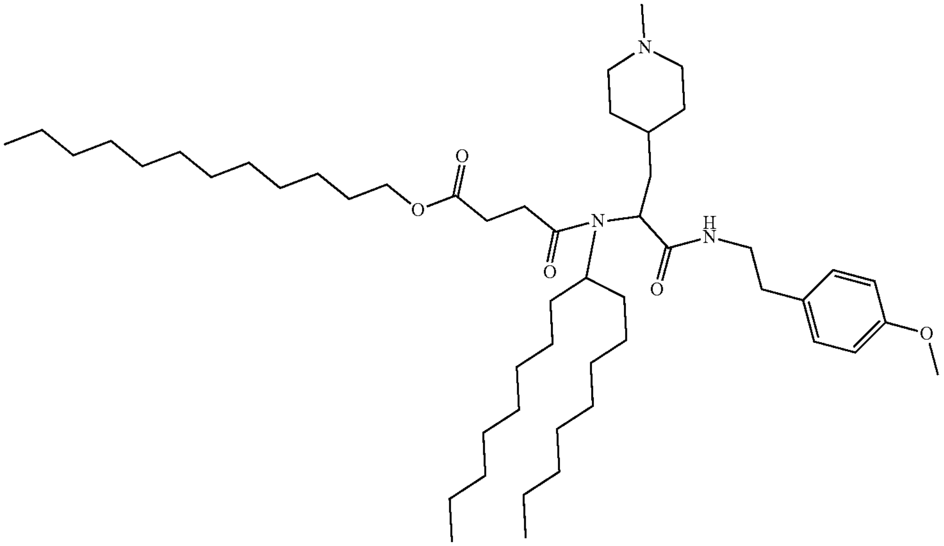

-continued
P343D1
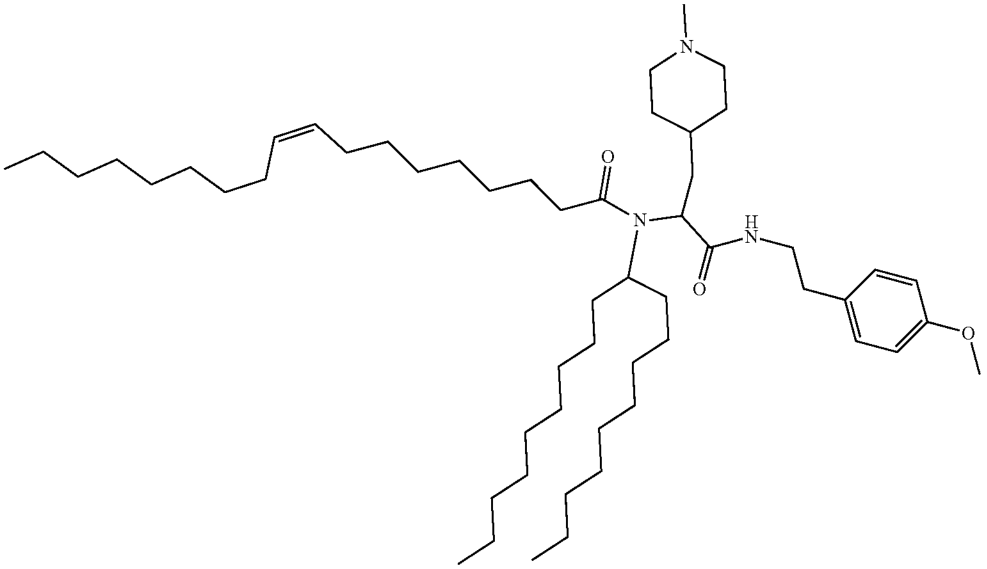
P343D3
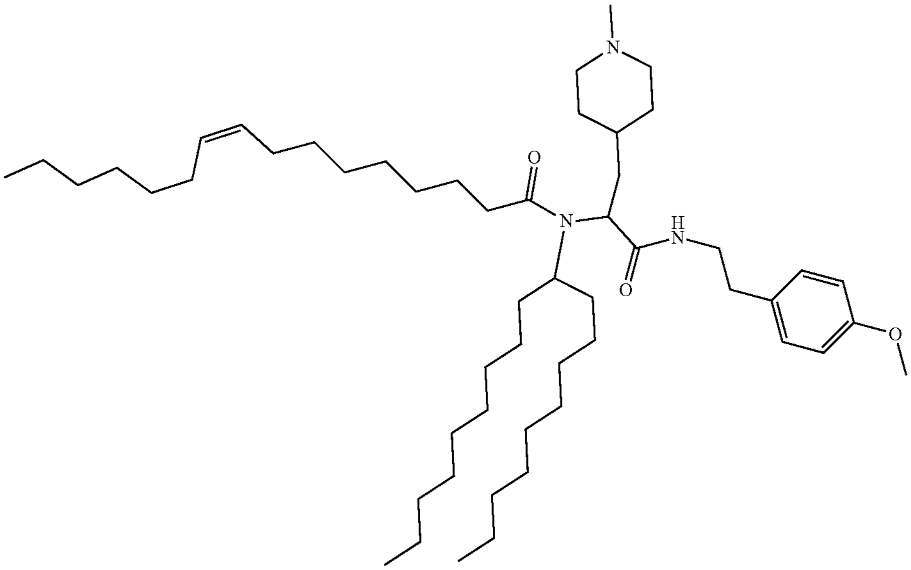

-continued
P343D7
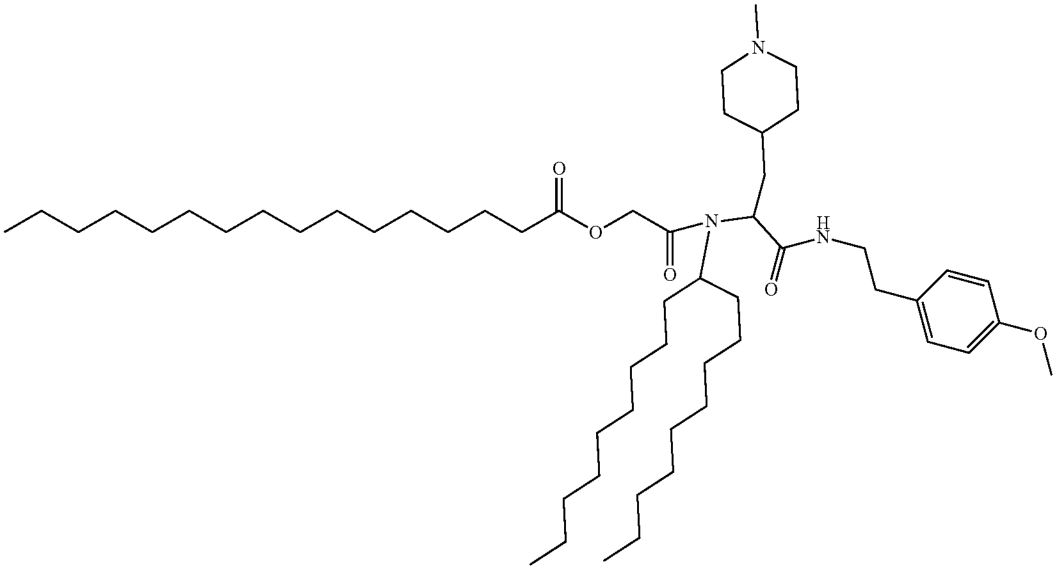
P343E1
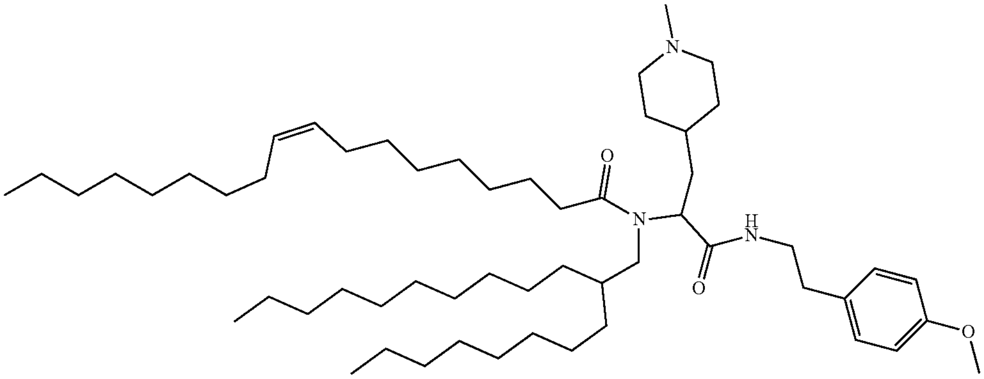
P344A3
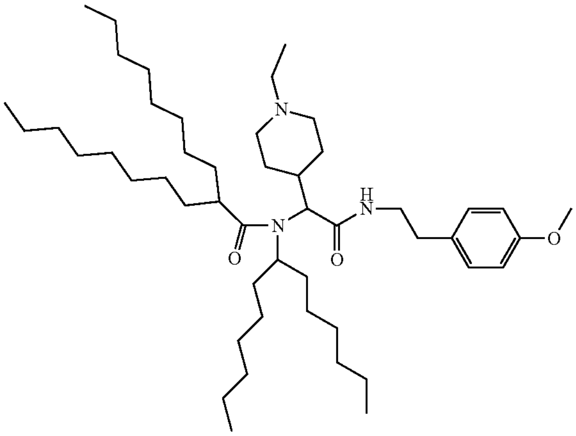
P344B5
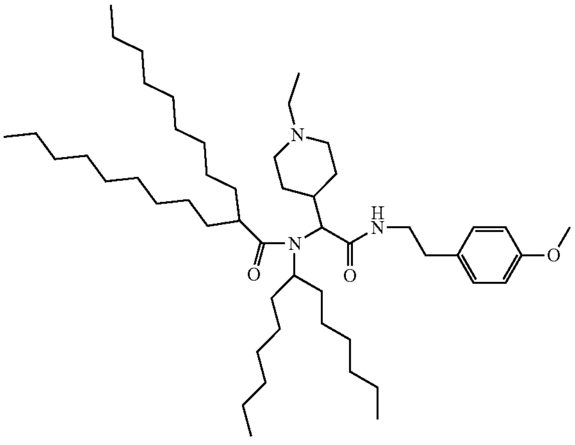

-continued
P344A4
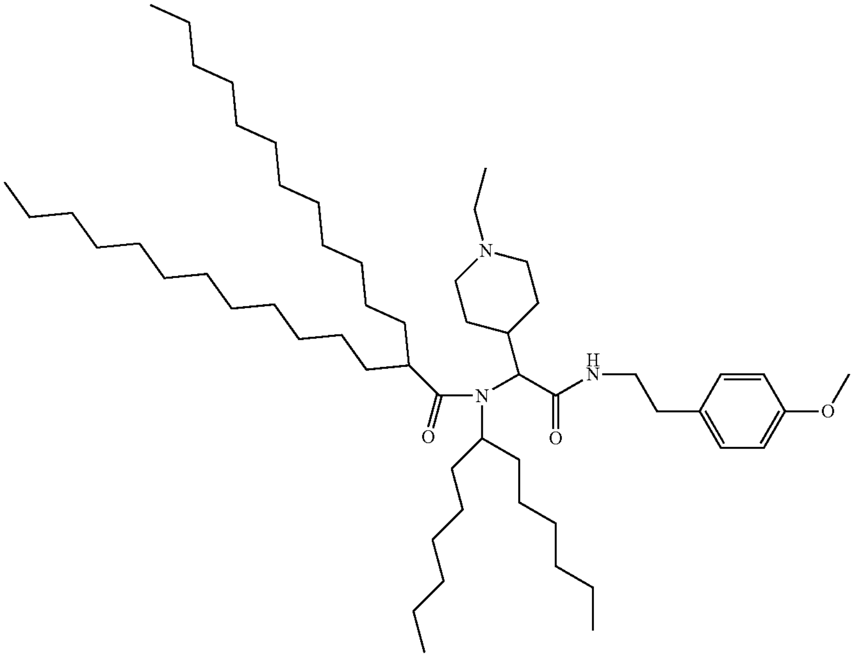
P344D3
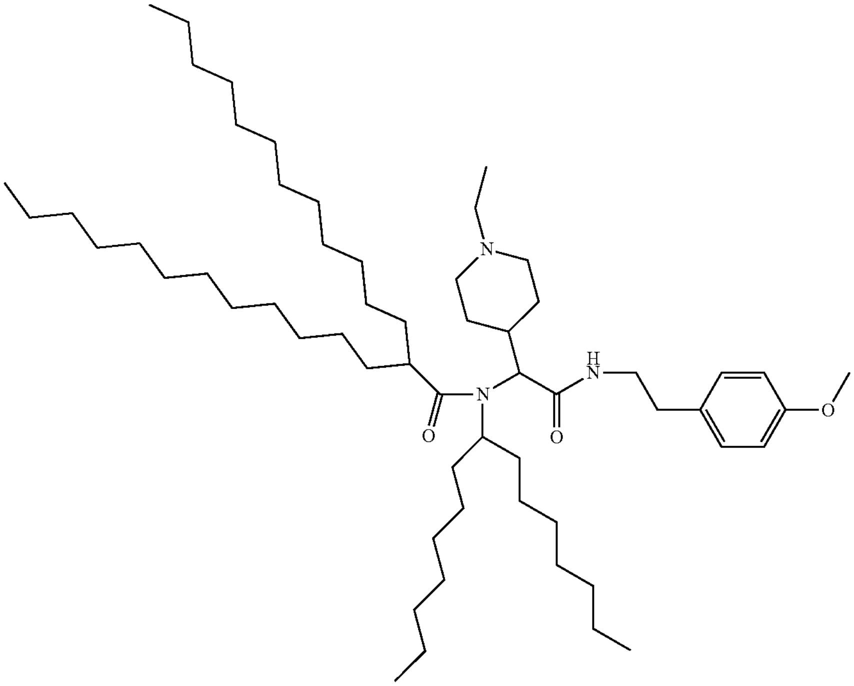

-continued
P344E2
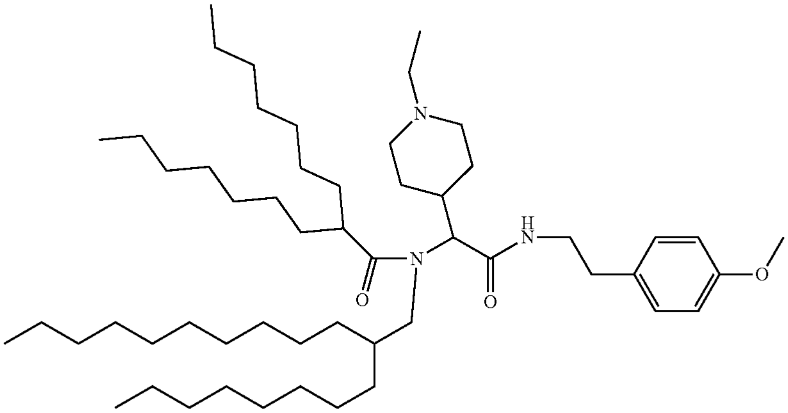
P345B2
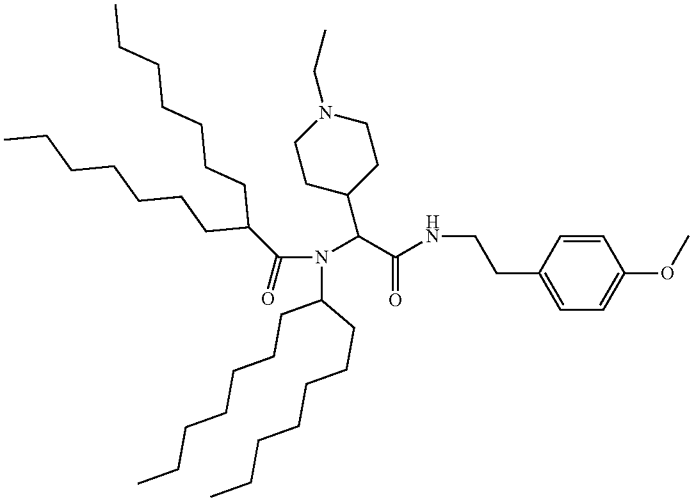
P345E1
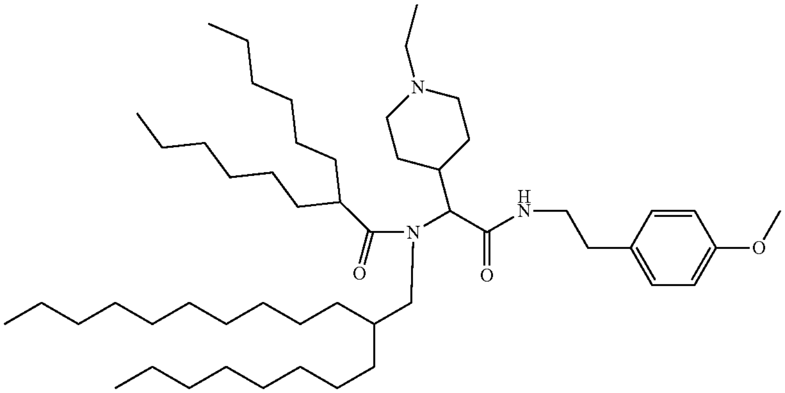

-continued
P345E7
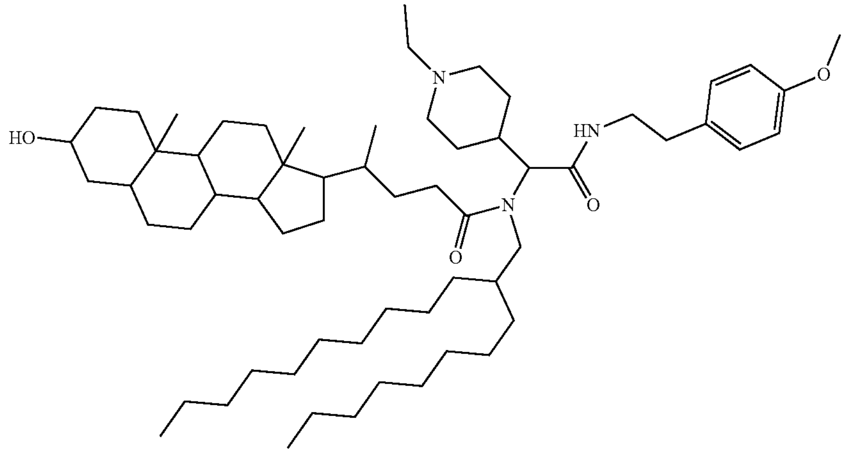
P345G7
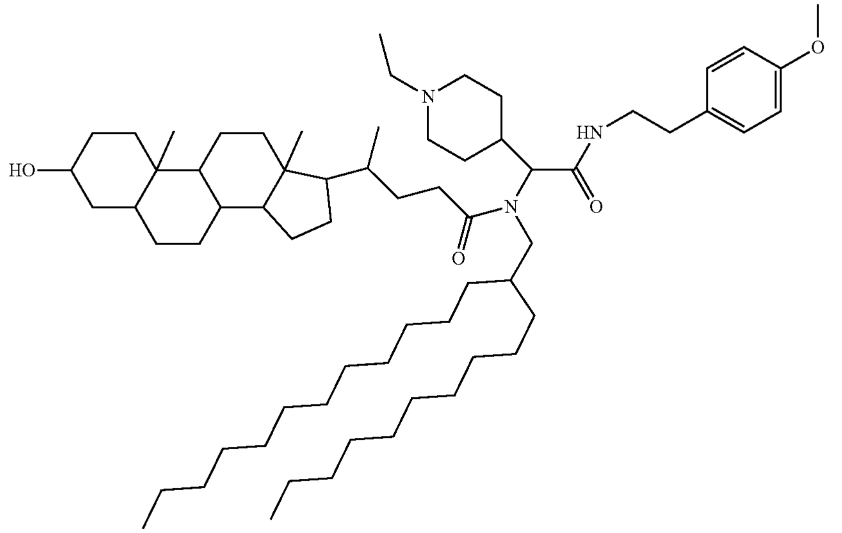
P359B2
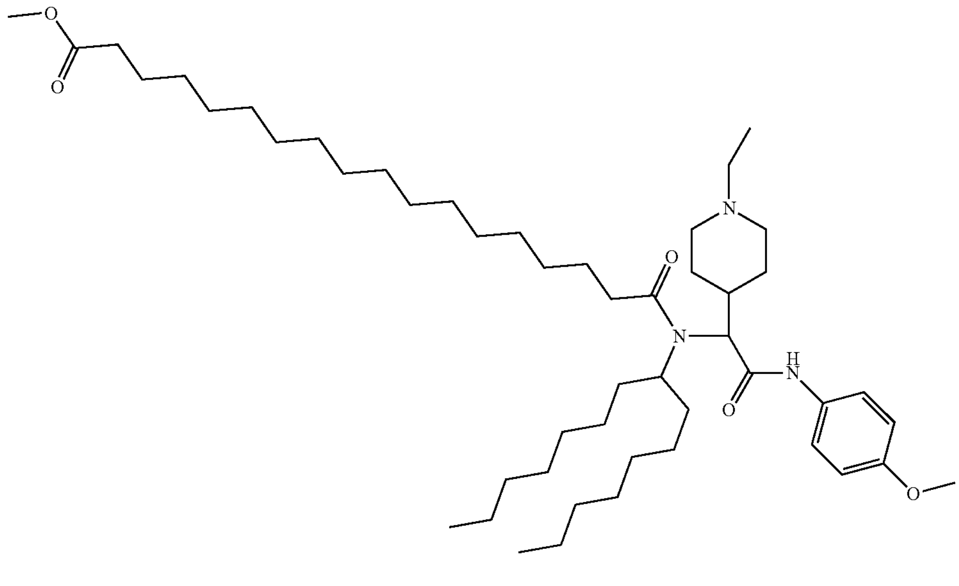

-continued
P359B4
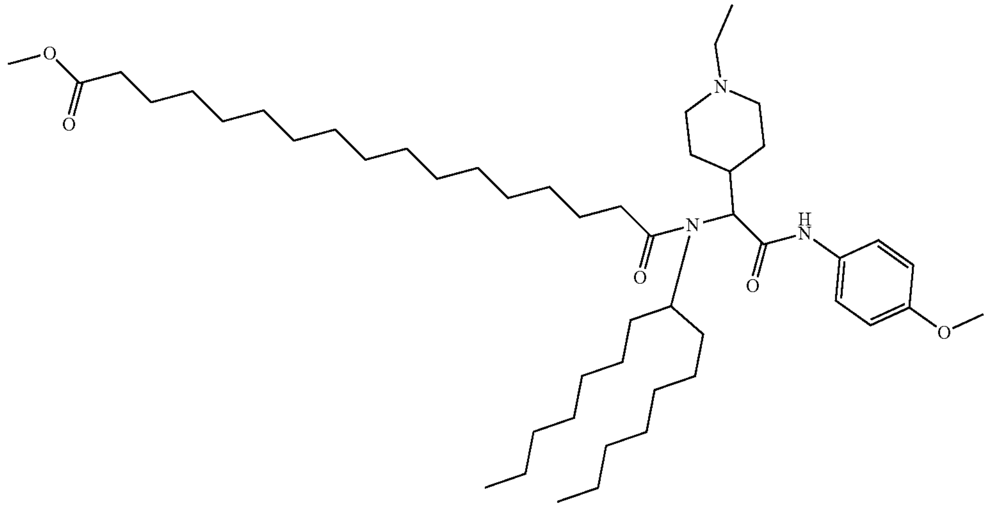
P359E4
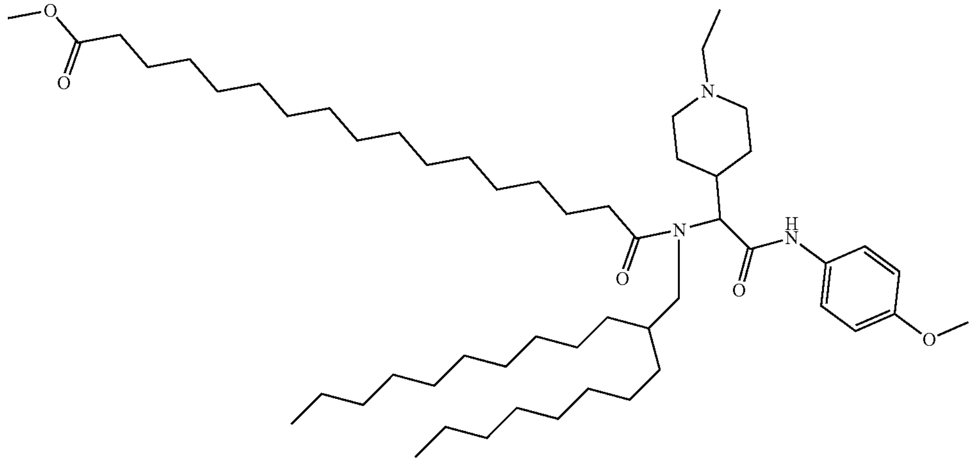
P360A4
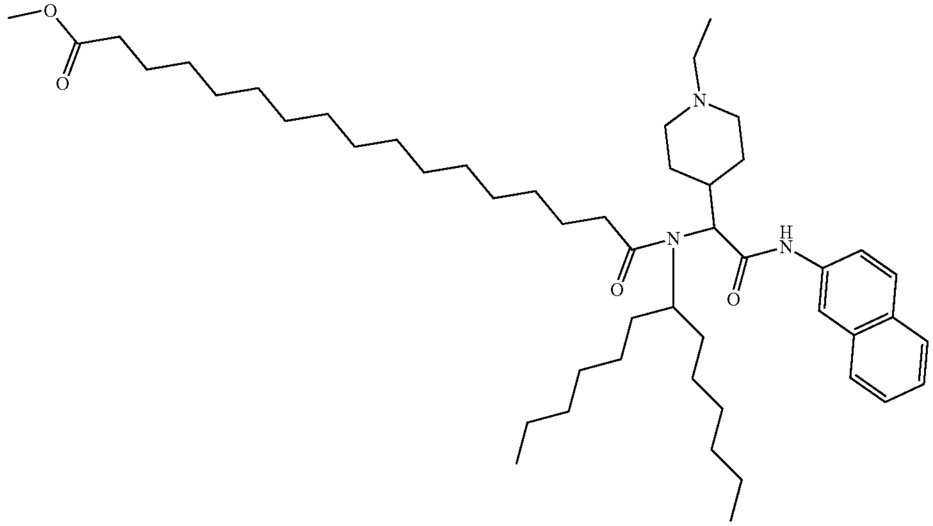

-continued
P360B2
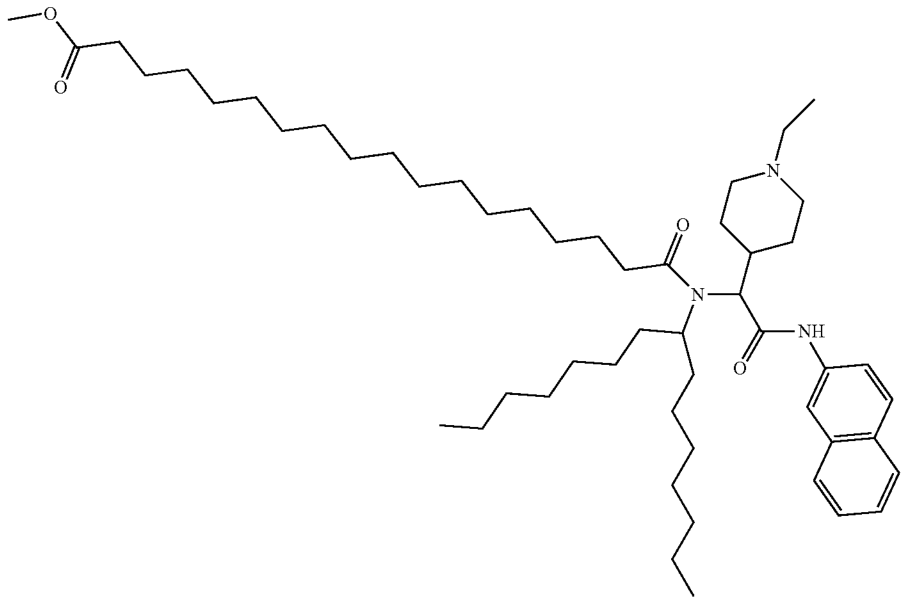
P360B9
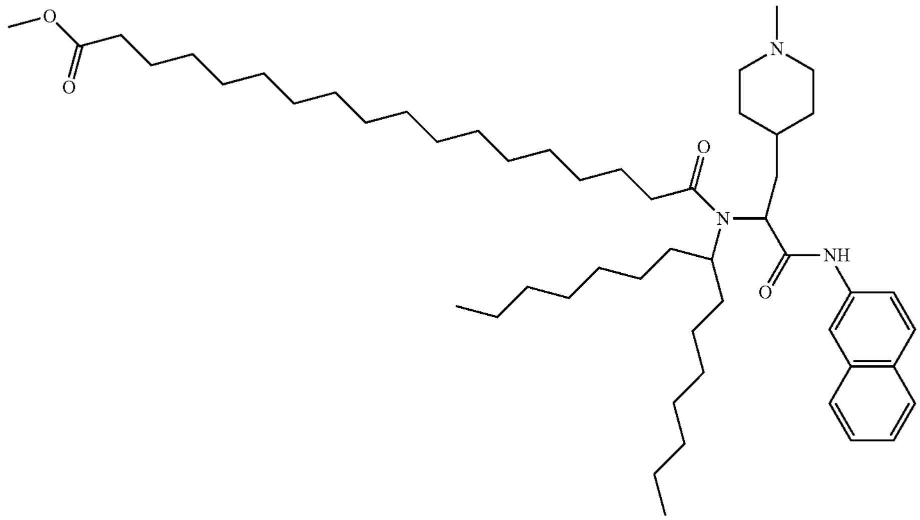
P360E3
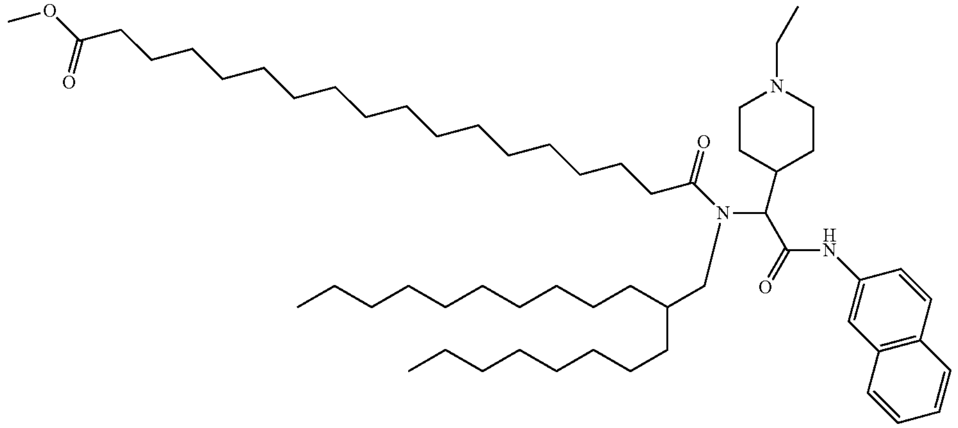

-continued
P362B2
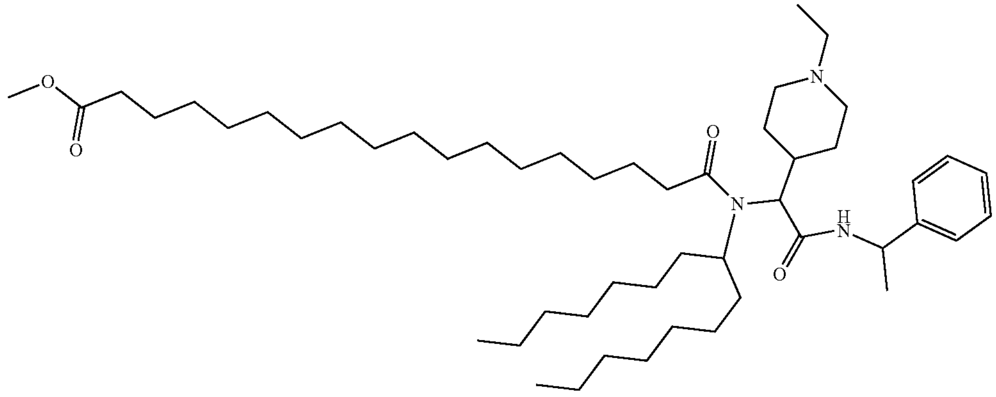
P362B3
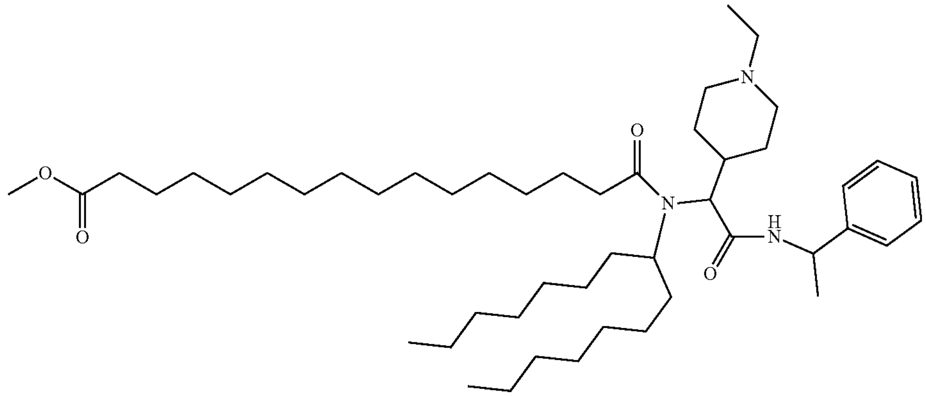
P362C3
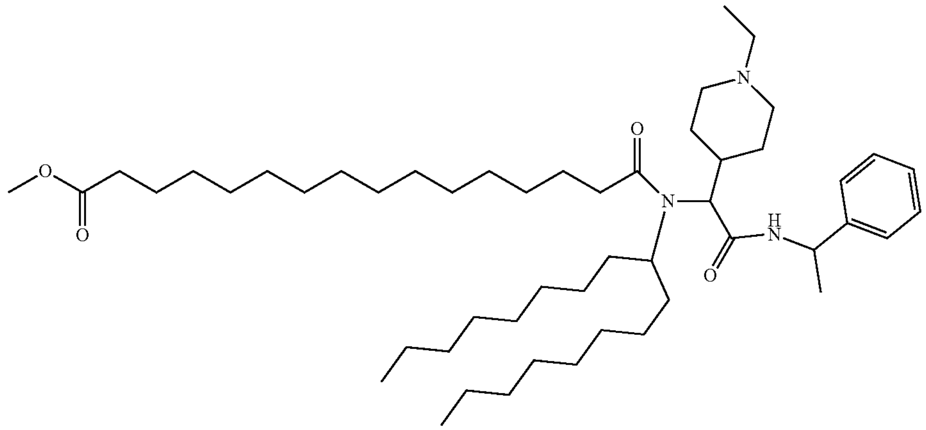

-continued
P362C4
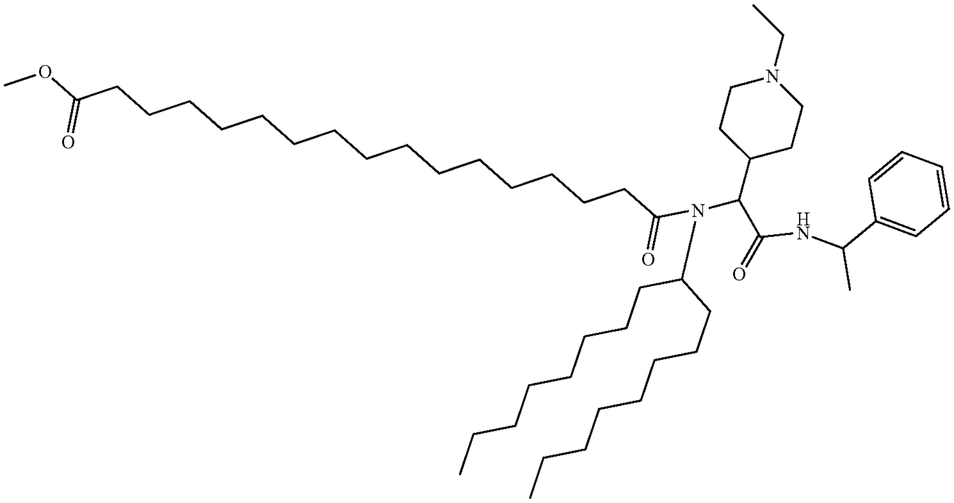
P362E3
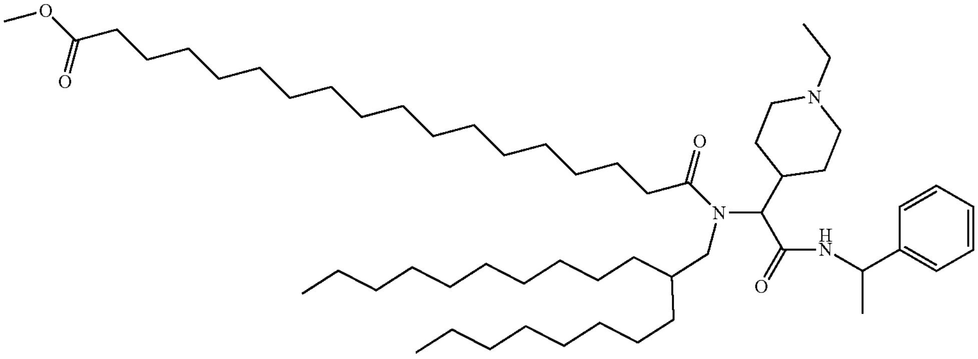
P363A2
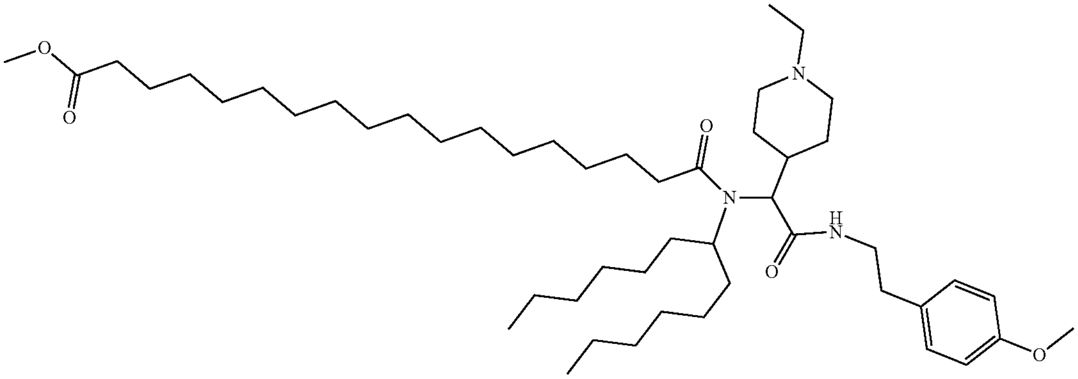
P363B2
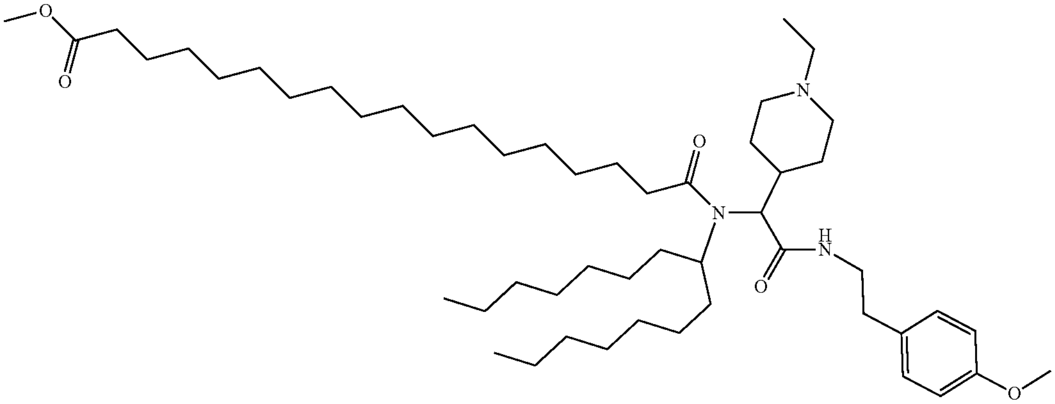

-continued
P363C3
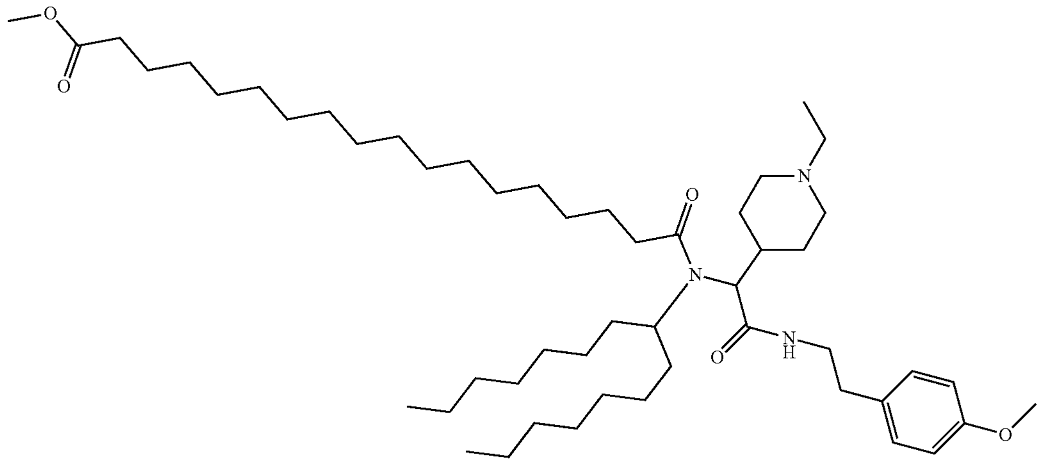
P363C10
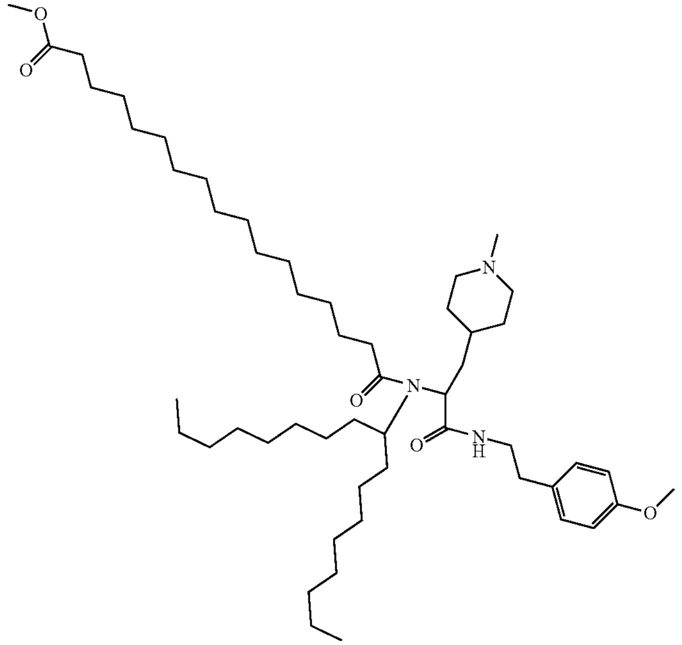

-continued
P363D9
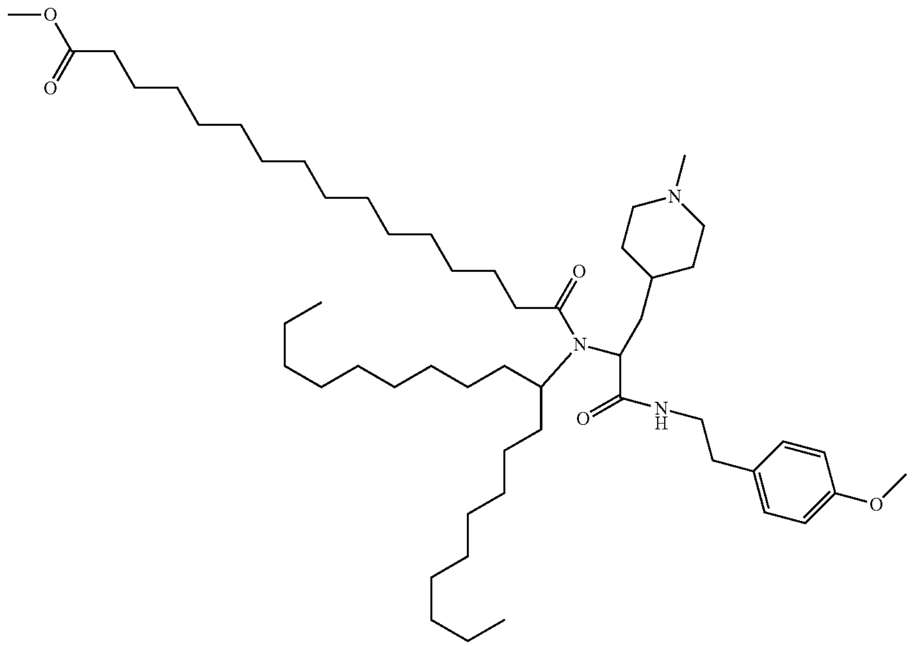
P363E2
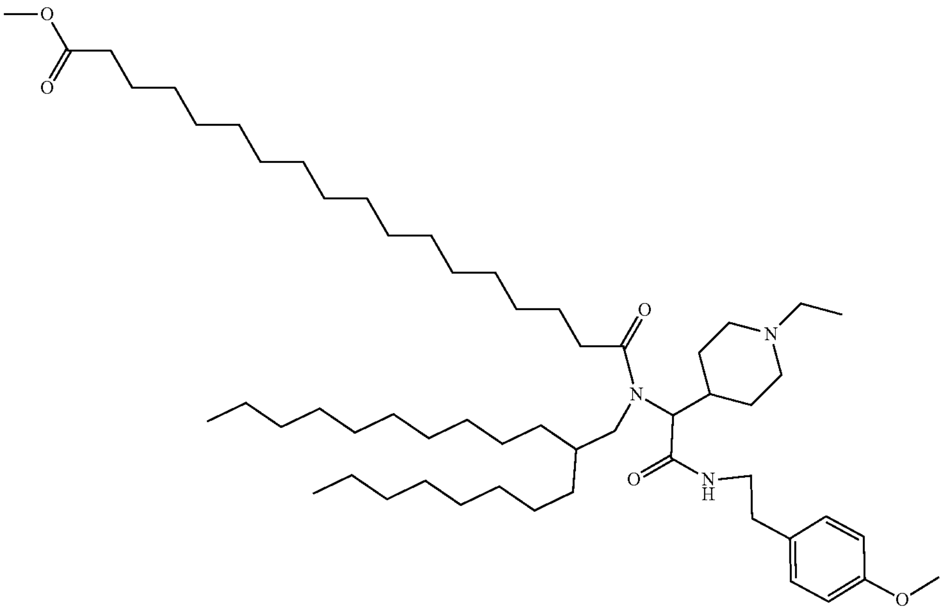

-continued
P363E3
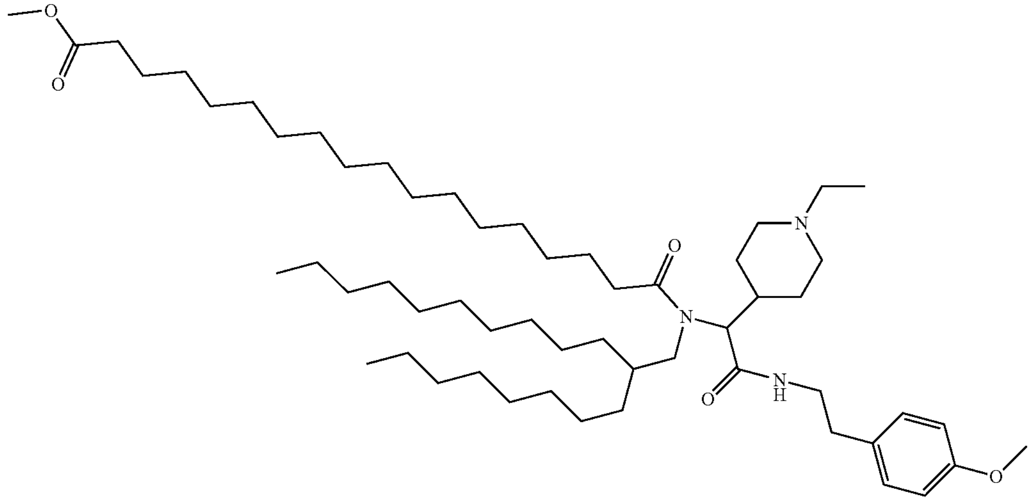
P363E4
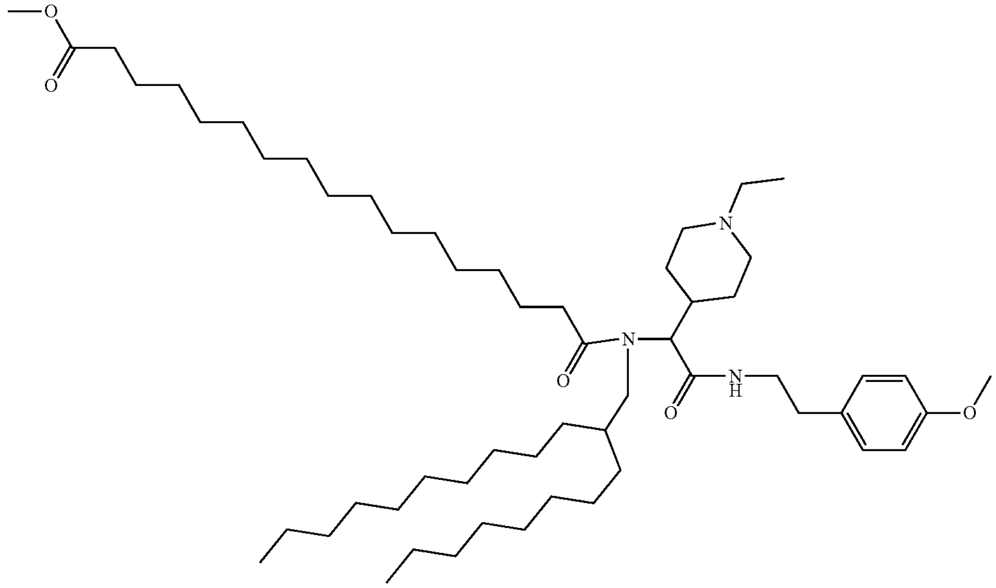
P363E12
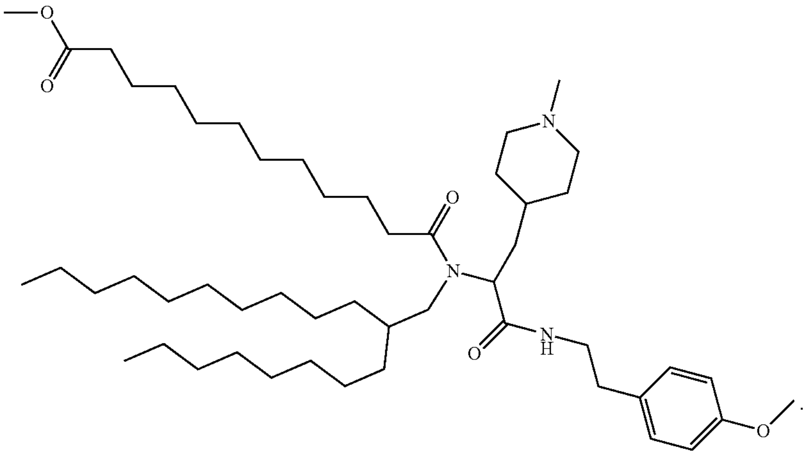

-continued
P149A1
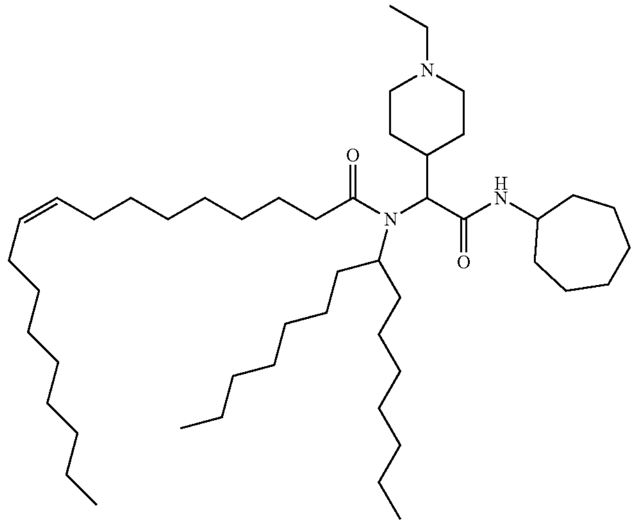
P56B2
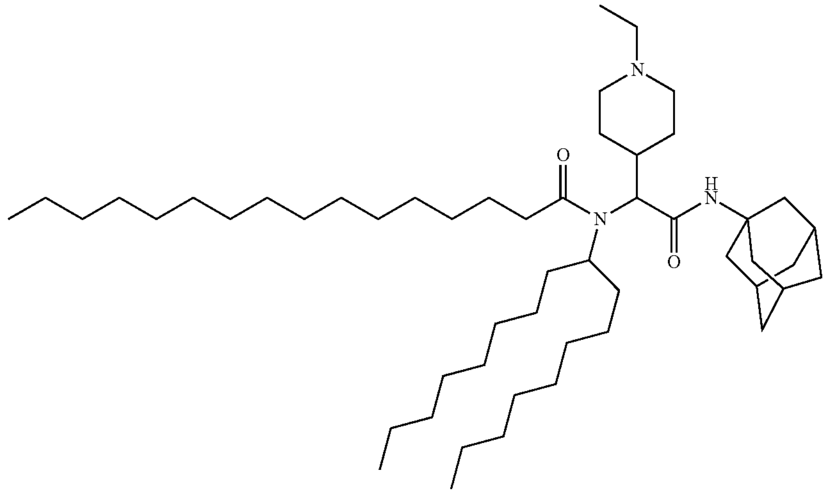
P30B1
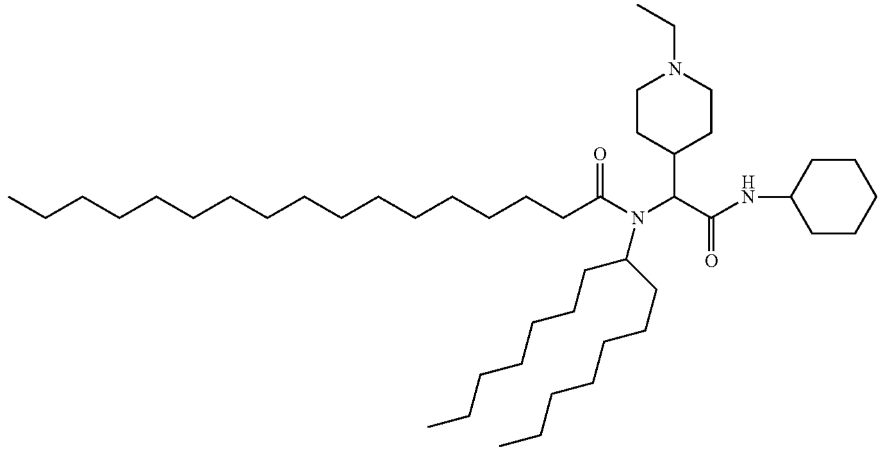

-continued

P53A12

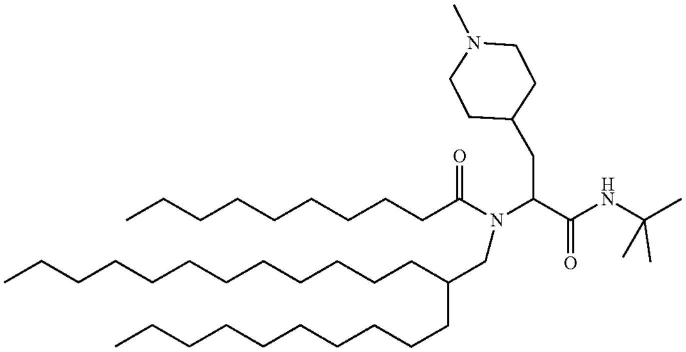

P158C10

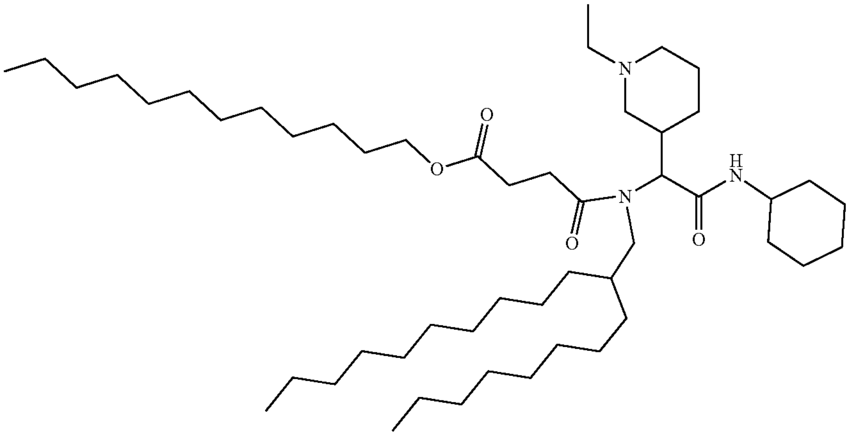

P161F5

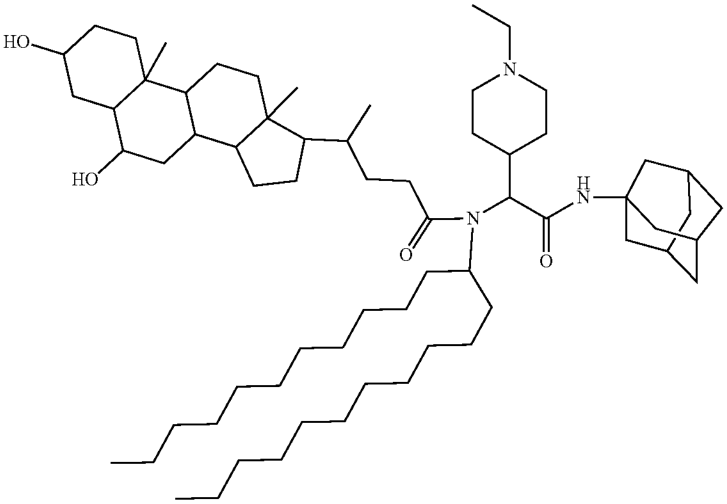

3. The lipid of claim 2, selected from P380D1, P380E1, P380F1, P380F4, and P381F1.

4. The lipid of claim 2, selected from P429D1.

5. The lipid of claim 2, selected from P374F7, P376F1, and P386D12.

6. The lipid of claim 2, selected from P423A2 and P423C7.

7. The lipid of claim 2, selected from P390E12.

8. The lipid of claim 2, selected from P160B4, P160E6, P161C4, P161E4, P161E6, P161F4, P161F5, P169A2, and P177F6.

9. The lipid of claim 2, selected from P287A6, P287C4, P287C6, P287F4, P287F6, and P294A6.

10. The lipid of claim 2, selected from P320E7, P345E7, and P345G7.

11. The lipid of claim 2, selected from P169A8, P169C10, P169C12, and P169F10.

12. The lipid of claim 2, selected from P287A10, P287B10, P287B12, P287C10, P287D10, and P287F10.

13. The lipid of claim 2, selected from P165A10, P165D10, P165E12, P165F10, and P173F10.

14. The lipid of claim 2, wherein the lipid is P171D12.

* * * * *